US012559508B2

(12) United States Patent
Reutershan et al.

(10) Patent No.: US 12,559,508 B2
(45) Date of Patent: Feb. 24, 2026

(54) SEMI-SATURATED BICYCLIC DERIVATIVES AND RELATED USES

(71) Applicant: MOMA Therapeutics, Inc., Cambridge, MA (US)

(72) Inventors: Michael H Reutershan, Acton, MA (US); Laurie B Schenkel, Belmont, MA (US); Meredeth A Mcgowan, Bedford, MA (US); Timothy J Guzi, Sudbury, MA (US); John R Butler, Thousand Oaks, CA (US); Haoxuan Wang, Somerville, MA (US); Cen Gao, Carmel, IN (US); Yonghong Bai, Lexington, MA (US)

(73) Assignee: MOMA Therapeutics, Inc., Cambridge, MA (US)

( * ) Notice: Subject to any disclaimer, the term of this patent is extended or adjusted under 35 U.S.C. 154(b) by 0 days.

(21) Appl. No.: 19/076,644

(22) Filed: Mar. 11, 2025

(65) Prior Publication Data

US 2025/0230171 A1 Jul. 17, 2025

Related U.S. Application Data

(63) Continuation of application No. PCT/US2024/023445, filed on Apr. 5, 2024.

(60) Provisional application No. 63/542,486, filed on Oct. 4, 2023, provisional application No. 63/457,353, filed on Apr. 5, 2023.

(51) Int. Cl.

| | |
|---|---|
| *C07D 513/04* | (2006.01) |
| *A61K 31/444* | (2006.01) |
| *A61K 31/497* | (2006.01) |
| *A61K 31/501* | (2006.01) |
| *A61K 31/506* | (2006.01) |
| *C07D 417/14* | (2006.01) |
| *C07D 519/00* | (2006.01) |

(52) U.S. Cl.

CPC .......... *C07D 513/04* (2013.01); *A61K 31/444* (2013.01); *A61K 31/497* (2013.01); *A61K 31/501* (2013.01); *A61K 31/506* (2013.01); *C07D 417/14* (2013.01); *C07D 519/00* (2013.01)

(58) Field of Classification Search

CPC .. C07D 513/04; C07D 417/14; C07D 519/00; A61K 31/444; A61K 31/497; A61K 31/501; A61K 31/506

USPC .................................................... 514/252.03

See application file for complete search history.

(56) References Cited

U.S. PATENT DOCUMENTS

| | | | |
|---|---|---|---|
| 4,613,598 | A | 9/1986 | Fukami et al. |
| 2005/0165028 | A1 | 7/2005 | Norman et al. |
| 2006/0058341 | A1 | 3/2006 | Connolly et al. |
| 2011/0071130 | A1 | 3/2011 | Cole et al. |
| 2012/0108591 | A1 | 5/2012 | Semple et al. |
| 2014/0221411 | A1 | 8/2014 | Kim et al. |
| 2017/0239225 | A1 | 8/2017 | Androphy et al. |
| 2018/0289676 | A1 | 10/2018 | Arnatt et al. |
| 2024/0327399 | A1 | 10/2024 | Botyanszki et al. |
| 2024/0327430 | A1 | 10/2024 | Corella et al. |

FOREIGN PATENT DOCUMENTS

| | | | |
|---|---|---|---|
| CN | 112237580 | A | 1/2021 |
| WO | WO-2005037845 | A1 | 4/2005 |
| WO | WO-2005044793 | A2 | 5/2005 |
| WO | WO-2005073224 | A2 | 8/2005 |
| WO | WO-2006099379 | A2 | 9/2006 |
| WO | WO-2009050228 | A2 | 4/2009 |
| WO | WO-2010024258 | A1 | 3/2010 |
| WO | WO-2011090738 | A2 | 7/2011 |
| WO | WO-2014138484 | A1 | 9/2014 |
| WO | WO-2014176258 | A1 | 10/2014 |
| WO | WO-2018017435 | A1 | 1/2018 |
| WO | WO-2018119263 | A1 | 6/2018 |
| WO | WO-2018157737 | A1 | 9/2018 |
| WO | WO-2018237370 | A1 | 12/2018 |
| WO | WO-2019037861 | A1 | 2/2019 |
| WO | WO-2019141980 | A1 | 7/2019 |
| WO | WO-2019191599 | A1 | 10/2019 |
| WO | WO-2020146858 | A1 | 7/2020 |
| WO | WO-2020176863 | A1 | 9/2020 |
| WO | WO-2020228649 | A1 | 11/2020 |

(Continued)

OTHER PUBLICATIONS

Adam, Salomé, et al. "The CIP2A-TOPBP1 axis safeguards chromosome stability and is a synthetic lethal target for BRCA-mutated cancer" Nature cancer (2021); 2(12):1357-1371.

(Continued)

*Primary Examiner* — Kahsay Habte

(74) *Attorney, Agent, or Firm* — Fenwick & West LLP; Heidi A. Erlacher; Christine E. McCain

(57) ABSTRACT

The present disclosure relates to pounds of Formula (I):

(I)

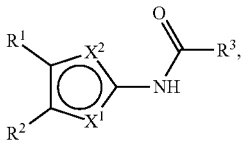

and to their prodrugs, pharmaceutically acceptable salts, pharmaceutical compositions, methods of use, and methods for their preparation. The compounds disclosed herein are useful for modulating DNA polymerase Θ activity and may be used in the treatment of disorders in which DNA polymerase Θ activity is implicated, such as cancer.

20 Claims, No Drawings

(56) References Cited

FOREIGN PATENT DOCUMENTS

| | | | |
|---|---|---|---|
| WO | WO-2020243459 | A1 | 12/2020 |
| WO | WO-2021086076 | A1 | 5/2021 |
| WO | WO-2021242955 | A1 | 12/2021 |
| WO | WO-2021256902 | A1 | 12/2021 |
| WO | WO-2021259208 | A1 | 12/2021 |
| WO | WO-2022118210 | A1 | 6/2022 |
| WO | WO-2022128851 | A1 | 6/2022 |
| WO | WO-2022259204 | A1 | 12/2022 |
| WO | WO-2023050007 | A1 | 4/2023 |
| WO | WO-2023061415 | A1 | 4/2023 |
| WO | WO-2023134708 | A1 | 7/2023 |
| WO | WO-2023134739 | A1 | 7/2023 |
| WO | WO-2023178035 | A1 | 9/2023 |
| WO | WO-2023205366 | A1 | 10/2023 |
| WO | WO-2023233295 | A1 | 12/2023 |
| WO | WO-2024069592 | A1 | 4/2024 |
| WO | WO-2024088407 | A1 | 5/2024 |
| WO | WO-2024099336 | A1 | 5/2024 |
| WO | WO-2024099337 | A1 | 5/2024 |
| WO | WO-2024121290 | A1 | 6/2024 |
| WO | WO-2024121753 | A1 | 6/2024 |
| WO | WO-2024147972 | A2 | 7/2024 |
| WO | WO-2024182380 | A2 | 9/2024 |
| WO | WO-2024182382 | A1 | 9/2024 |
| WO | WO-2024182384 | A1 | 9/2024 |
| WO | WO-2024189493 | A1 | 9/2024 |
| WO | WO-2024197401 | A1 | 10/2024 |
| WO | WO-2024197653 | A1 | 10/2024 |
| WO | WO-2024205311 | A1 | 10/2024 |
| WO | WO-2024211834 | A1 | 10/2024 |
| WO | WO-2024211836 | A2 | 10/2024 |
| WO | WO-2024213082 | A1 | 10/2024 |
| WO | WO-2024215870 | A2 | 10/2024 |
| WO | WO-2024230578 | A1 | 11/2024 |
| WO | WO-2024245310 | A1 | 12/2024 |
| WO | WO-2024259233 | A2 | 12/2024 |

OTHER PUBLICATIONS

Aguilera A. et al. "Causes of genome instability" Genetics (2013); 47:1-32.

Ames BN et al. "Methods for detecting carcinogens and mutagens with the Salmonella/mammalian-microsome mutagenicity test" Mutation Res. (1975); 31(6):347-364.

Babb et al. "Cancer phase I clinical trials: efficient dose escalation with overdose control" Statistics in medicine (1998); 17(10):1103-1120.

Belan, Ondrej et al. "POLQ seals post-replicative ssDNA gaps to maintain genome stability in BRCA-deficient cancer cells" Molecular cell (2022); 82(24):4664-4680.

Black, Samuel J., et al. "Molecular basis of microhomology-mediated end-joining by purified full-length Polθ" Nature communications (2019); 10(1):4423, 16 pages.

Brambati, Alessandra, et al. "RHINO directs MMEJ to repair DNA breaks in mitosis" Science (2023); 381(6658):653-660.

Bruin, Maaike AC, et al. "Pharmacokinetics and pharmacodynamics of PARP inhibitors in oncology" Clinical pharmacokinetics (2022); 61(12):1649-1675.

Bubenik et al. "Identification of RP-6685, an orally bioavailable compound that inhibits the DNA polymerase activity of Polθ" Journal of Medicinal Chemistry (2022); 65(19):13198-13215.

Caldecott KW "Causes and consequences of DNA single-strand breaks" Trends Biochem Sci (2024); 49:68-78.

Carvajal-Garcia, Juan, et al. "Mechanistic basis for microhomology identification and genome scarring by polymerase theta" Proceedings of the National Academy of Sciences (2020); 117(15):8476-8485.

CAS RN 1310260-23-1, entered Jun. 24, 2011, 1 page.

CAS RN 1596148-39-8, entered May 2, 2014, 1 page.

CAS RN 1596439-76-7, entered May 2, 2014, 1 page.

CAS RN 303788-46-7, entered Nov. 21, 2000, 1 page.

CAS RN 937995-81-8, entered Jun. 20, 2007, 1 page.

CAS RN 939926-94-0, entered Jun. 28, 2007, 1 page.

Ceccaldi, Raphael, et al. "Homologous-recombination-deficient tumours are dependent on Polθ-mediated repair" Nature (2015); 518(7538):258-262.

Celso De Oliveira Rezende et al. "Hit-to-lead optimization of a 2-aminobenzimidazole series as new candidates for chagas disease" European Journal of Medicinal Chemistry (2023); 246:114925, 10 pages.

Clinical Trial NCT06545942 "Study of Orally Administered MOMA-313 in Participants With Advanced or Metastatic Solid Tumors" First submitted Jul. 26, 2024, Last updated March, 3, 2025, 13 pages. https://clinicaltrials.gov/study/NCT06545942?lead=MOMA%20Therapeutics&rank=1.

Curtin NJ et al. "Poly(ADP-ribose) polymerase inhibition: past, present and future" Nat Rev Drug Discov. (2020); 19(10):711-736.

Disilvestro et al. "Overall survival with maintenance olaparib at a 7-year follow-up in patients with newly diagnosed advanced ovarian cancer and a BRCA mutation: the SOLO1/GOG 3004 trial" J Clin Oncol (2022); 41:609-617.

Eisenhauer EA et al. "New response evaluation criteria in solid tumours: revised RECIST guideline (version 1.1)" Eur J Cancer (2009); 45(2):228-247.

Evans, E. et al "MOMA-313 is a potent, selective Polθ inhibitor that enhances response to PARP inhibition in HR deficient tumor models" Poster of MOMA Therapeutics, Cambridge, Massachusetts, USA (2024); 1 page.

Farmer H. et al. Targeting the DNA repair defect in BRCA mutant cells as a therapeutic strategy. Nature. (2005); 434(7035):917-921.

Feng, Wanjuan, et al. "Genetic determinants of cellular addiction to DNA polymerase theta" Nature communications (2019); 10(1):4286, 13 pages.

Fizazi K. et al. "Rucaparib or physician's choice in metastatic prostate cancer" New Engl J Med (2023); 388:719-732.

Gelot, Camille, et al. "Polθ is phosphorylated by Polo-like kinase 1 (PLK1) to enable repair of DNA double strand breaks in mitosis" BioRxiv (2023); Mar. 2023, 26 pages.

Gonzalez-Martin et al. "Niraparib in patients with newly diagnosed ovarian cancer" New Engl J Med (2019); 381:2391-2402.

Greco WR et al. "The search for synergy: a critical review from a response surface perspective" Pharmacol Rev. (1995); 47(2):331-385.

Green et al. "Mutagen testing using trp+ reversion in *Escherichia coli*" Mutation Research/Environmental Mutagenesis and Related Subjects (1976); 38:3-32.

Harvey-Jones E. et al. "Longitudinal profiling identifies co-occurring BRCA1/2 reversions, TP53BP1, RIF1 and PAXIP1 mutations in PARP inhibitor-resistant advanced breast cancer" Ann Oncol. (2024); 35(4):364-380.

Heeke AL et al. "Prevalence of homologous recombination-related gene mutations across multiple cancer types" JCO Precis Oncol. (2018); 2:1-13.

Hoppe MM et al. "Biomarkers for homologous recombination deficiency in cancer" J Natl Cancer Inst. (2018); 110(7):704-713.

Hucl T et al. "A syngeneic variance library for functional annotation of human variation: application to BRCA2" Cancer Res. (2008); 68(13):5023-5030.

Illuzzi G et al. "Preclinical characterization of AZD5305, a next-generation, highly selective PARP1 inhibitor and trapper" Clin Cancer Res. (2022); 28(21):4724-4736.

International Conference on Harmonisation (ICH) of Technical Requirements for Registration of Pharmaceuticals for Human Use. ICH guideline S2 (R1) on genotoxicity testing and data interpretation for pharmaceuticals intended for human use. S2(R1) document recommended for adoption at step 4 of the ICH process on Nov. 9, 2011. Adopted at Step 5 in Europe by CHMP Dec. 2011 (issued as EMA/CHMP/ICH/126642/2008). Adopted at Step 5 in US by FDA on Jun. 7, 2012 (issued as 77 FR 33748 pp. 33748-33749). Adopted in Japan at Step 5 Sep. 20, 2012 (issued as PFSB/ELD Notification No. 0920-2), 30 pages.

Jasin M et al. "Repair of strand breaks by homologous recombination" Cold Spring Harb Perspect Biol. (2013); 5(11):a012740, 19 pages.

(56) References Cited

OTHER PUBLICATIONS

Jones RD et al. "PhRMA CPCDC initiative on predictive models of human pharmacokinetics, part 2: comparative assessment of prediction methods of human volume of distribution" J Pharm Sci. (2011); 100(10):4074-4089.
Jonsson P et al. "Tumour lineage shapes BRCA-mediated phenotypes" Nature (2019); 571(7766):576-579.
Kent, Tatiana, et al. "Mechanism of microhomology-mediated end-joining promoted by human DNA polymerase θ" Nature structural & molecular biology (2015); 22(3):230-237.
Kumar RJ et al. "Dual inhibition of DNA-PK and DNA polymerase theta overcomes radiation resistance induced by p53 deficiency" NAR Cancer (2020); 2(4):zcaa038, 15 pages.
Lai, Zhongwu, et al. "Landscape of homologous recombination deficiencies in solid tumours: analyses of two independent genomic datasets" BMC cancer (2022); 22:1-13.
Lehár J et al. "Synergistic drug combinations tend to improve therapeutically relevant selectivity" Nat Biotechnology (2009); 27(7):659-666.
Llorens-Agost, Marta, et al. "POLθ-mediated end joining is restricted by RAD52 and BRCA2 until the onset of mitosis" Nature cell biology (2021); 23(10):1095-1104.
Loehr, Andrea, et al. "Emergence of BRCA reversion mutations in patients with metastatic castration-resistant prostate cancer after treatment with rucaparib" European urology (2023); 83(3):200-209.
Loewe S. "The quantitative problems of pharmacology" Ergebnisse der Physiologie (1928); 27(1):47-187, with English translation, 284 pages.
Lombardo F. et al. "Comprehensive assessment of human pharmacokinetic prediction based on in vivo animal pharmacokinetic data, part 1: volume of distribution at steady state" J Clin Pharmacol. (2013b); 53(2):167-177.
Lombardo F. et al. "Comprehensive assessment of human pharmacokinetic prediction based on in vivo animal pharmacokinetic data, part 2: clearance" J Clin Pharmacol. (2013a); 53(2):178-191.
Lord CJ et al. "PARP inhibitors: synthetic lethality in the clinic" Science (2017); 355(6330):1152-1158.
Lynparza® (olaparib) tablets, for oral use, Tablets: 150 mg, 100 mg, Highlights of Prescribing Information / Package Insert / Label, Revised: Sep. 2023 (Sep. 2023), Initial U.S. Approval: 2014, Reference ID: 5242218, Distributed by: AstraZeneca Pharmaceuticals LP, Wilmington, DE 19850, USA, 60 pages.
Mann, Anjali, et al. "POLθ prevents MRE11-NBS1-CtIP-dependent fork breakage in the absence of BRCA2/RAD51 by filling lagging-strand gaps" Molecular cell (2022); 82(22):4218-4231.
Maron et al. "Revised Methods for the Salmonella Mutagenicity Test" Mutation Research (1983); 113:173-215.
Mateos-Gomez, Pedro A., et al. "Mammalian polymerase θ promotes alternative NHEJ and suppresses recombination" Nature (2015); 518(7538):254-257.
Mateos-Gomez, Pedro A., et al. "The helicase domain of Polθ counteracts RPA to promote alt-NHEJ" Nature structural & molecular biology (2017); 24(12):1116-1123.
Mccann, J. et al. "Detection of carcinogens as mutagens in the *Salmonella*/microsome test: assay of 300 chemicals: discussion" Proc. Natl. Acad. Sci. USA (1976); 73:950-954.
Mccann, J. et al. "Detection of carcinogens as mutagens in the *Salmonella*/microsome test: assay of 300 chemicals" Proc. Natl. Acad. Sci. USA (1975); 72:5135-5139.
Mengwasser, Kristen E., et al. "Genetic screens reveal FEN1 and APEX2 as BRCA2 synthetic lethal targets" Molecular cell (2019); 73(5):885-899.
Morgan, Ryan E. et al. "A multifactorial approach to hepatobiliary transporter assessment enables improved therapeutic compound development" Toxicological Sciences (2013); 136(1):216-241.
National Comprehensive Cancer Network. NCCN clinical practice guidelines in oncology (NCCN Guidelines) breast cancer. Mar. 11, 2024c. 256 pages. https://www.nccn.org/guidelines/guidelines-detail?category=1&id=1419.
National Comprehensive Cancer Network. NCCN clinical practice guidelines in oncology (NCCN Guidelines) ovarian cancer including fallopian tube cancer and primary peritoneal cancer. Jan. 17, 2024a. 241 pages. https://www.nccn.org/guidelines/guidelines-detail?category=1&id=1453.
National Comprehensive Cancer Network. NCCN clinical practice guidelines in oncology (NCCN Guidelines) pancreatic adenocarcinoma. Dec. 13, 2023. 174 pages. https://www.nccn.org/guidelines/guidelines-detail?category=1&id=1455.
National Comprehensive Cancer Network. NCCN clinical practice guidelines in oncology (NCCN Guidelines) prostate cancer. Mar 8, 2024b. 221 pages. https://www.nccn.org/guidelines/guidelines-detail?category=1&id=1459.
Neuenschwander et al. "Bayesian industry approach to phase I combination trials in oncology" Statistical methods in drug combination studies (2015); 2015:95-135.
Neuenschwander et al. "Critical aspects of the Bayesian approach to phase I cancer trials" Stat Med. (2008); 27(13):2420-2439.
Newman, Joseph A., et al. "Structure of the helicase domain of DNA polymerase theta reveals a possible role in the microhomology-mediated end-joining pathway" Structure (2015); 23(12):2319-2330.
Nguyen L. et al. "Pan-cancer landscape of homologous recombination deficiency" Nat Commun. (2020); 11(1):5584, 12 pages.
O'Connor MJ "Targeting the DNA damage response in cancer" Mol Cell (2015); 60:547-560.
OECD Guideline 471 (Genetic Toxicology: Bacterial Reverse Mutation Test), Ninth Addendum to the OECD Guidelines for the Testing of Chemicals, adopted Jul. 21, 1997 and corrected Jun. 26, 2020, 12 pages.
Oken MM et al. "Toxicity and response criteria of the Eastern Cooperative Oncology Group" Am J Clin Oncol. (1982); 5(6):649-655.
Pennington KP et al. "Germline and somatic mutations in homologous recombination genes predict platinum response and survival in ovarian, fallopian tube, and peritoneal carcinomas" Clin Cancer Res (2014); 20:764-775.
Pettitt, Stephen J., et al. "Clinical BRCA1/2 reversion analysis identifies hotspot mutations and predicted neoantigens associated with therapy resistance" Cancer discovery (2020); 10(10):1475-1488.
Pismataro, Maria Chiara, et al. "Small molecules targeting DNA polymerase theta (POLθ) as promising synthetic lethal agents for precision cancer therapy" Journal of medicinal chemistry (2023); 66(10):6498-6522.
Pujade-Lauraine et al. "Olaparib tablets as maintenance therapy in patients with platinum-sensitive, relapsed ovarian cancer and a BRCA1/2 mutation (SOLO2/ENGOT-Ov21): a double-blind, randomised, placebo-controlled, phase 3 trial" The lancet oncology (2017); 18(9):1274-1284.
Ramsden et al. "Mechanism, cellular functions and cancer roles of polymerase-theta-mediated DNA end joining" Nature reviews Molecular cell biology (2022); 23(2):125-140.
Riaz N. et al. "Pan-cancer analysis of bi-allelic alterations in homologous recombination DNA repair genes" Nat Commun. (2017); 8(1):857, 7 pages.
Ring et al. "PhRMA CPCDC initiative on predictive models of human pharmacokinetics, part 3: comparative assessment of prediction methods of human clearance" J Pharm Sci. (2011); 100(10):4090-4110.
Robson M. et al. "Olaparib for metastatic breast cancer in patients with a germline BRCA mutation" New Engl J Med (2017); 377:523-533.
Rose M. et al. "PARP Inhibitors: Clinical Relevance, Mechanisms of Action and Tumor Resistance" Front Cell Dev Biol. (2020); 8:564601, 22 pages.
RUBRACA® (rucaparib) tablets, for oral use, Tablets: 200 mg, 250 mg, and 300 mg, Highlights of Prescribing Information / Package Insert / Label, Revised: Sep. 2023 (Sep. 2023), Initial U.S. Approval: 2016, Manufactured for pharmaand GmbH, Taborstrasse 1, 1020 Vienna. Austria, Distributed by: Summit SD, LLC, 255 Northwest Victoria Drive, Suite A, Lee's Summit, MO 64086, USA, 18 pages.

(56) References Cited

OTHER PUBLICATIONS

Schaub et al. "Polymerase theta-helicase promotes end joining by stripping single-stranded DNA-binding proteins and bridging DNA ends" Nucleic acids research (2022); 50(7):3911-3921.

Schrempf et al. "Targeting the DNA repair enzyme polymerase θ in cancer therapy" Trends in Cancer (2021); 7(2):98-111.

Scully et al. "DNA double-strand break repair-pathway choice in somatic mammalian cells" Nat Rev Mol Cell Biol. (2019); 20(11):698-714.

Seki et al. "POLQ (Pol θ), a DNA polymerase and DNA-dependent ATPase in human cells" Nucleic acids research (2003); 31(21):6117-6126.

Shima N. et al. "Phenotype-based identification of mouse chromosome instability mutants" Genetics (2003); 163(3):1031-1040.

Shima N. et al. "The mouse genomic instability mutation chaos1 is an allele of Polq that exhibits genetic interaction with Atm" Mol Cell Biol. (2004); 24(23):10381-10389.

Silver, Daniel P., et al. "Efficacy of neoadjuvant Cisplatin in triple-negative breast cancer" Journal of clinical oncology (2010); 28(7):1145-1153.

Stockley, Martin L., et al. "Discovery, characterization, and structure-based optimization of small-molecule in vitro and in vivo probes for human DNA polymerase theta" Journal of medicinal chemistry (2022); 65(20):13879-13891.

Talzenna® (talazoparib) capsules, for oral use, Capsules: 0.1 mg, 0.25 mg, 0.35 mg, 0.5 mg, 0.75 mg, and 1 mg, Highlights of Prescribing Information / Package Insert / Label, Revised: Mar. 2024 (Mar. 2024), Initial U.S. Approval: 2018, Reference ID: 5342166, Distributed by: Pfizer Labs, Division of Pfizer Inc., New York, NY 10001, USA, 25 pages.

Tobalina, L., et al. "A meta-analysis of reversion mutations in BRCA genes identifies signatures of DNA end-joining repair mechanisms driving therapy resistance" Annals of Oncology (2021); 32(1):103-112.

Tutt, Andrew, et al. "Carboplatin in BRCA1/2-mutated and triple-negative breast cancer BRCAness subgroups: the TNT Trial" Nature medicine (2018); 24(5):628-637.

United States Food and Drug Administration. "S9 nonclinical evaluation for anticancer pharmaceuticals" Mar. 2010, 12 pages. https://www.fda.gov/regulatory-information/search-fda-guidance-documents/s9-nonclinical-evaluation-anticancer-pharmaceuticals.

United States Food and Drug Administration. "Drug development and drug interactions | table of substrates, inhibitors, and inducers" Updated Jun. 5, 2023. Accessed Apr. 9, 2025, 10 pages. https://www.fda.gov/drugs/drug-interactions-labeling/drug-development-and-drug-interactions-table-substrates-inhibitors-and-inducers.

United States Food and Drug Administration. "For healthcare professionals | FDA's examples of drugs that interact with CYP enzymes and transporter systems" Updated Jun. 24, 2024. Accessed Apr. 9, 2025, 9 pages. https://www.fda.gov/drugs/drug-interactions-labeling/healthcare-professionals-fdas-examples-drugs-interact-cyp-enzymes-and-transporter-systems.

United States Food and Drug Administration. In vitro drug interaction studies—cytochrome P450 enzyme- and transporter-mediated drug interactions guidance for industry. Jan. 2020. 46 pages. https://www.fda.gov/regulatory-information/search-fda-guidance-documents/in-vitro-drug-interaction-studies-cytochrome-p450-enzyme-and-transporter-mediated-drug-interactions.

United States Food and Drug Administration. "M12 drug interaction studies" Endorsed on May 24, 2022; updated as of Aug. 2, 2024, 79 pages. https://www.fda.gov/regulatory-information/search-fda-guidance-documents/m12-drug-interaction-studies.

Wood, Richard D. et al. "Genome protection by DNA polymerase θ" Annual review of genetics (2022); 56(1):207-228.

Wyatt, David W., et al. "Essential roles for polymerase θ-mediated end joining in the repair of chromosome breaks" Molecular cell (2016); 63(4):662-673.

Zatreanu, Diana, et al. "Polθ inhibitors elicit BRCA-gene synthetic lethality and target PARP inhibitor resistance" Nature communications (2021); 12(1):3636, 15 pages.

Zejula (niraparib) tablets, for oral use, Tablets: 100 mg, 200 mg, 300 mg, Highlights of Prescribing Information / Package Insert / Label, Revised: May 2024 (May 2024), Initial U.S. Approval: 2017, Manufactured for GlaxoSmithKline, Durham, NC 27701, USA, 31 pages.

Zhou, Jia, et al. "A first-in-class polymerase theta inhibitor selectively targets homologous-recombination-deficient tumors" Nature cancer (2021); 2(6):598-610.

SEMI-SATURATED BICYCLIC DERIVATIVES AND RELATED USES

RELATED APPLICATIONS

This application is a continuation of International PCT Patent Application No. PCT/US2024/023445, filed Apr. 5, 2024, which claims priority to, and the benefit of, U.S. Provisional Application No. 63/457,353, filed on Apr. 5, 2023; and U.S. Provisional Application No. 63/542,486, filed on Oct. 4, 2023, the entire contents of which are incorporated herein by reference.

BACKGROUND

The present disclosure relates to small molecule, antagonists of DNA polymerase Θ, designed for the treatment of cancer.

The proper repair of DNA double-strand breaks (DSBs) is essential for the maintenance of genome integrity. Inaccurate repair of DSBs can cause mutations in crucial coding or regulatory regions, while the accumulation of unrepaired DNA damage introduces mitotic stress that can lead to genomic alterations or cell death. In normal cells, DSBs are primarily repaired through two key mechanisms. DNA lesions that occur during DNA replication (S-phase) are typically repaired by homologous recombination (HR), which uses a replicated "sister chromatid" as a template for error-free repair. In contrast, non-homologous end-joining (NHEJ) is the primary repair process for DSBs when there is no DNA template available for templated repair. A third DSB repair pathway, termed alternative end-joining (Alt-EJ), microhomology-mediated end-joining (MMEJ), or theta-mediated end-joining (TMEJ), is executed by polymerase-theta (POLΘ). In contrast to NHEJ and HR, TMEJ is thought to play a limited role in heathy cells under normal conditions.

Some tumors harbor inactivating mutations in homologous repair genes, most commonly disabling the function of BRCA1 or BRCA2. As a result, these tumors are intrinsically sensitive to DNA damaging agents, as well as to inhibitors of specific DNA repair proteins. Accordingly, DNA cross-linking agents such as platinum-based chemotherapies are more effective in BRCA-mutant tumors than in tumors with intact BRCA function. Similarly, small molecule inhibitors of PARP1/2 are efficacious in BRCA1/2-deficient tumors, which rely on the PARP enzymes to repair single-strand DNA breaks and prevent their conversion to toxic DSBs that overwhelm the repair capacity of HR-deficient cells.

An alternative approach to therapeutically targeting HR-deficient tumors is through the inhibition of back-up repair pathways such as POLΘ-mediated TMEJ. Consistent with its role as a back-up DNA repair enzyme, ablation of the POLΘ gene locus is well tolerated in mouse models, causing only mild phenotypes characterized by micronuclei in reticulocytes and increased cellular (but not organismic) sensitivity to DNA cross-linking agents. In contrast, POLΘ DNA repair activity has been shown to be essential for cell survival when NHEJ or HR are inactivated, implicating POLΘ as a potential target for cancer therapy in specific mutational settings.

Unique in the human genome, POLΘ contains both an N-terminal SF2 DNA helicase domain and a C-terminal DNA polymerase domain. In the setting of chromosomal DSBs, these domains work in tandem to repair DSBs containing long Y-single-strand DNA overhangs. Specifically, the helicase domain is thought to strip the RPA protein complex from the overhangs and promote annealing to the opposite DNA end via a region of DNA microhomology. The annealed DNA then serves as a primer for the POLΘ polymerase domain, which extends the annealed DNA to fill in the single-strand DNA gap. Given the role of POLΘ catalytic activity in DNA repair processes that are crucial in HR-deficient tumors, POLΘ represents an attractive target for the development chemical inhibitors to exploit newly discovered functional dependencies.

The disclosure arises from a need to provide compounds for the modulation of DNA polymerase Θ activity with improved therapeutic potential. In particular, compounds with improved physicochemical, pharmacological and/or pharmaceutical properties.

SUMMARY

In some aspects, the present disclosure provides a compound of Formula (I):

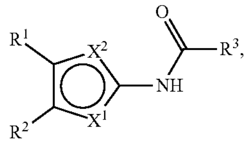

(I)

or a pharmaceutically acceptable salt, solvate, clathrate, hydrate, stereoisomer, or tautomer thereof, wherein:

$X^1$ is CH, S, or N;

$X^2$ is N, S, or O;

$R^1$ and $R^2$, together with the atoms to which they are attached, form a $C_5$-$C_{10}$ cycloalkyl or 5- to 10-membered heterocycloalkyl, wherein the $C_5$-$C_{10}$ cycloalkyl or 5- to 10-membered heterocycloalkyl is optionally substituted with one or more $R^a$;

each $R^a$ independently is oxo, halo, cyano, —$OR^{a1}$, —$N(R)_2$, —$C(O)R^{a1}$, —$C(O)N(R^{a1})_2$, —$C(O)OR^{a1}$, —$S(O)_2N(R^{a1})_2$, —$S(O)_2(R^{a1})$, $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, $C_6$-$C_{10}$ aryl, 5- to 10-membered heteroaryl, or 3- to 10-membered heterocycloalkyl, wherein the $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, $C_6$-$C_{10}$ aryl, 5- to 10-membered heteroaryl, or 3- to 10-membered heterocycloalkyl is optionally substituted with one or more $R^{a1}$;

each $R^{a1}$ independently is H, oxo, halo, cyano, —OH, —$NH_2$, —$C(O)(C_1$-$C_6$ alkyl), —$C(O)(C_3$-$C_{10}$ cycloalkyl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_{10}$ cycloalkyl, 3- to 10-membered heterocycloalkyl, $C_6$-$C_{10}$ aryl, or 5- to 10-membered heteroaryl, wherein the —$C(O)(C_3$-$C_{10}$ cycloalkyl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_{10}$ cycloalkyl, 3- to 10-membered heterocycloalkyl, $C_6$-$C_{10}$ aryl, or 5- to 10-membered heteroaryl is optionally substituted with one or more $R^{a2}$ each $R^{a2}$ independently is oxo, halo, cyano, —OH, —$NH_2$, —$NH(C_1$-$C_6$ alkyl), —$N(C_1$-$C_6$ alkyl$)_2$, $C_1$-$C_6$ alkyl optionally substituted with $C_1$-$C_6$ alkoxy or —OH. $C_3$-$C_{10}$ cycloalkyl, $C_1$-$C_6$ haloalkoxy, $C_1$-$C_6$ haloalkyl, $C_1$-$C_6$ alkoxy, 3- to 10-membered heterocycloalkyl optionally substituted with oxo, or 5- to 10-membered heteroaryl;

$R^3$ is $C_6$-$C_{10}$ aryl or 5- to 10-membered heteroaryl, wherein the $C_6$-$C_{10}$ aryl or 5- to 10-membered heteroaryl is substituted with one or more $R^{3a}$;

each $R^{3a}$ independently is halo, cyano, —OH, —$NH_2$, $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, 3- to 10-membered heterocycloalkyl, $C_6$-$C_{10}$ aryl, or 5- to 10-membered heteroaryl, wherein the $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, 3- to 10-membered heterocycloalkyl, $C_6$-$C_{10}$ aryl, or 5- to 10-membered heteroaryl is optionally substituted with one or more $R^{3a1}$ and each $R^{3a1}$ independently is oxo, halo, cyano, —OH, —C(O)($C_1$-$C_6$ alkyl), —C(O)(O—($C_1$-$C_6$ alkyl)), $C_1$-$C_6$ alkyl optionally substituted with $C_3$-$C_{10}$ cycloalkyl, $C_2$-$C_6$ alkenyl, $C_2$-$C_6$ alkynyl, $C_1$-$C_6$ haloalkyl, $C_1$-$C_6$ haloalkoxy. $C_1$-$C_6$ alkoxy, —O($C_1$-$C_6$haloalkyl), $C_3$-$C_{10}$ cycloalkyl, $C_6$-$C_{10}$ aryl, or 5- to 10-membered heteroaryl.

In some aspects, the present disclosure provides a compound obtainable by, or obtained by, a method for preparing a compound as described herein (e.g., a method comprising one or more steps described in Schemes 1-7).

In some aspects, the present disclosure provides a pharmaceutical composition comprising a compound of the present disclosure, or a pharmaceutically acceptable salt thereof, and a pharmaceutically acceptable diluent or carrier.

In some aspects, the present disclosure provides an intermediate as described herein, being suitable for use in a method for preparing a compound as described herein (e.g., the intermediate is selected from the intermediates described in Examples 1-753).

In some aspects, the present disclosure provides a method of modulating DNA polymerase Θ activity (e.g., in vitro or in vivo), comprising contacting a cell with an effective amount of a compound of the present disclosure or a pharmaceutically acceptable salt thereof.

In some aspects, the present disclosure provides a method of treating or preventing a disease or disorder disclosed herein in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating a disease or disorder disclosed herein in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a compound of the present disclosure or a pharmaceutically acceptable salt thereof for use in modulating DNA polymerase Θ activity (e.g., in vitro or in vivo).

In some aspects, the present disclosure provides a compound of the present disclosure or a pharmaceutically acceptable salt thereof for use in treating or preventing a disease or disorder disclosed herein.

In some aspects, the present disclosure provides a compound of the present disclosure or a pharmaceutically acceptable salt thereof for use in treating a disease or disorder disclosed herein.

In some aspects, the present disclosure provides use of a compound of the present disclosure or a pharmaceutically acceptable salt thereof in the manufacture of a medicament for modulating DNA polymerase Θ activity (e.g., in vitro or in vivo).

In some aspects, the present disclosure provides use of a compound of the present disclosure or a pharmaceutically acceptable salt thereof in the manufacture of a medicament for treating or preventing a disease or disorder disclosed herein.

In some aspects, the present disclosure provides use of a compound of the present disclosure or a pharmaceutically acceptable salt thereof in the manufacture of a medicament for treating a disease or disorder disclosed herein. In some aspects, modulation is inhibition.

In some aspects, the present disclosure provides a method of preparing a compound of the present disclosure.

In some aspects, the present disclosure provides a method of preparing a compound, comprising one or more steps described herein.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting. In the case of conflict between the chemical structures and names of the compounds disclosed herein, the chemical structures will control.

Other features and advantages of the disclosure will be apparent from the following detailed description and claims.

DETAILED DESCRIPTION

The present disclosure relates to semi-saturated bicyclic derivatives, prodrugs, and pharmaceutically acceptable salts thereof, which may modulate DNA polymerase Θ activity and are accordingly useful in methods of treatment of the human or animal body. The present disclosure also relates to processes for the preparation of these compounds, to pharmaceutical compositions comprising them and to their use in the treatment of disorders in which DNA polymerase Θ is implicated, such as cancer.

Definitions

Unless otherwise stated, the following terms used in the specification and claims have the following meanings set out below.

Without wishing to be limited by this statement, it is understood that, while various options for variables are described herein, the disclosure intends to encompass operable embodiments having combinations of the options. The disclosure may be interpreted as excluding the non-operable embodiments caused by certain combinations of the options. For example, while various options for variables $X^1$, $X^2$, $R^1$, $R^2$, $R^a$, $R^{a1}$, $R^{a2}$, $R^3$, $R^{3a}$, and $R^{3a1}$ are described herein, the disclosure may be interpreted as excluding structures for non-operable compound caused by certain combinations of variables $X^1$, $X^2$, $R^1$, $R^2$, $R^a$, $R^{a1}$, $R^{a2}$, $R^3$, $R^{3a}$, and $R^{3a1}$.

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl includes $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, i-pentyl, or n-hexyl. In some embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

As used herein, the term "alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

As used herein, the term "optionally substituted alkenyl" refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

As used herein, the term "alknyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms. As used herein, "$C_2$-$C_6$ alkenylene linker" or "$C_2$-$C_6$ alkynylene linker" is intended to include $C_2$, $C_3$, $C_4$, $C_5$ or $C_6$ chain (linear or branched) divalent unsaturated aliphatic hydrocarbon groups. For example, $C_2$-$C_6$ alkenylene linker is intended to include $C_2$, $C_3$, $C_4$, $C_5$ and $C_6$ alkenylene linker groups.

As used herein, the term "optionally substituted alkynyl" refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents. For example, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

As used herein, the term "cycloalkyl" refers to a saturated or partially unsaturated hydrocarbon monocyclic or polycyclic (e.g., fused, bridged, or spiro rings) system having 3 to 30 carbon atoms (e.g., $C_3$-$C_2$, $C_3$-$C_{10}$, or $C_3$-$C_8$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, 1,2,3,4-tetrahydronaphthalenyl, and adamantyl. In the case of polycyclic cycloalkyl, only one of the rings in the cycloalkyl needs to be non-aromatic.

As used herein, the term "heterocycloalkyl" refers to a saturated or partially unsaturated 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, P, or Se), e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur, unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, oxiranyl, azetidinyl, oxetanyl, thietanyl, 1,2,3,6-tetrahydropyridinyl, tetrahydropyranyl, dihydropyranyl, pyranyl, morpholinyl, tetrahydrothiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro

[3.3]heptanyl, 1,4-dioxa-8-azaspiro[4.5]decanyl, 1,4-dioxaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, 3'H-spiro[cyclohexane-1,1'-furo[3,4-c]pyridin]-yl, 3-azabicyclo[3.1.0]hexanyl, 3-azabicyclo[3.1.0]hexan-3-yl, 1,4,5,6-tetrahydropyrrolo[3,4-c]pyrazolyl, 3,4,5,6,7,8-hexahydropyrido[4,3-d]pyrimidinyl, 4,5,6,7-tetrahydro-1H-pyrazolo[3,4-c]pyridinyl, 5,6,7,8-tetrahydropyrido[4,3-d]pyrimidinyl, 2-azaspiro[3.3]heptanyl, 2-methyl-2-azaspiro[3.3]heptanyl, 2-azaspiro[3.5]nonanyl, 2-methyl-2-azaspiro[3.5]nonanyl, 2-azaspiro[4.5]decanyl, 2-methyl-2-azaspiro[4.5]decanyl, 2-oxa-azaspiro[3.4]octanyl, 2-oxa-azaspiro[3.4]octan-6-yl, 5,6-dihydro-4H-cyclopenta[b]thiophenyl, and the like. In the case of multicyclic heterocycloalkyl, only one of the rings in the heterocycloalkyl needs to be non-aromatic (e.g., 4,5,6,7-tetrahydrobenzo[c]isoxazolyl).

It is understood that when a variable has two attachments to the rest of the formula of the compound, the two attachments could be at the same atom or different atoms of the variable. For example, when a variable (e.g., variable X) is cycloalkyl or heterocycloalkyl, and has two attachments to the rest of the formula of the compound, the two attachments could be at the same atom or different atoms of the cycloalkyl or heterocycloalkyl.

As used herein, the term "aryl" includes groups with aromaticity, including "conjugated," or multicyclic systems with one or more aromatic rings and do not contain any heteroatom in the ring structure. The term aryl includes both monovalent species and divalent species. Examples of aryl groups include, but are not limited to, phenyl, biphenyl, naphthyl and the like.

As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidised (i.e., N→O and $S(O)_p$, where p=1 or 2). It is to be noted that total number of S and O atoms in the aromatic heterocycle is not more than 1. Examples of heteroaryl groups include pyrrole, furan, thiophene, thiazole, isothiazole, imidazole, triazole, tetrazole, pyrazole, oxazole, isoxazole, isothiazole, pyridine, pyrazine, pyridazine, pyrimidine, and the like. Heteroaryl groups can also be fused or bridged with alicyclic or heterocyclic rings, which are not aromatic so as to form a multicyclic system (e.g., 4,5,6,7-tetrahydrobenzo[c]isoxazolyl).

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, quinoline, isoquinoline, naphthrydine, indole, benzofuran, purine, benzofuran, deazapurine, indolizine.

When a ring is denoted with a circle and all ring members are carbon atoms (e.g., 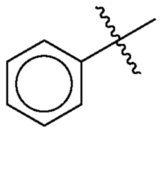), the ring is an aryl ring. When a ring is denoted with a circle and comprises at least one ring member that is a heteroatom (e.g., 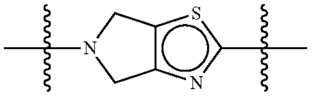), the ring is a heteroaryl ring. Multicyclic aryl or heteroaryl groups can be denoted with two or more circles (e.g., 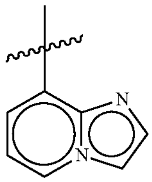).

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl such as benzo[d][1,3]dioxole-5-yl).

As used herein, the term "about" refers to a recited amount, value, or duration±10% or less of said amount, value, or duration. In some embodiments, "about" refers to a recited amount, value, or duration ±10%, ±8%, ±6%, ±5%, ±4%, ±2%, ±1%, or ±0.5%. In other embodiments, "about" refers to a recited amount, value, or duration ±10%, ±8%, ±6, ±5%, ±4%, or ±2%. In other embodiments, "about" refers to a recited amount, value, or duration ±5%. In some embodiments, "about" refers to a listed amount, value, or duration ±2% or ±1%. For example, in some embodiments, when the term "about" is used when reciting a temperature or temperature range, these terms refer to the recited temperature or temperature range ±5° C., ±2 CC, or ±1° C. In other embodiments, the term "about" refers to the recited temperature or temperature range ±2° C.

As used herein, the term "substituted," means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C═C, C═N or N═N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., R) occurs more than one time in any constituent or formula for a compound, its definition at each occurrence is independent of its definition at every other occurrence. Thus, for example, if a group is shown to be substituted with 0-2 R moieties, then the group may optionally be substituted with up to two R moieties and R at each occurrence is selected independently from the definition of R. Also, combinations of substituents and/or variables are permissible, but only if such combinations result in stable compounds.

As used herein, the term "hydroxy" or "hydroxyl" includes groups with an —OH or —O—.

As used herein, the term "halo" or "halogen" refers to fluoro, chloro, bromo and iodo.

The term "haloalkyl" or "haloalkoxyl" refers to an alkyl or alkoxyl substituted with one or more halogen atoms.

As used herein, the term "optionally substituted haloalkyl" refers to unsubstituted haloalkyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

As used herein, the term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

As used herein, the expressions "one or more of A, B, or C." "one or more A, B, or C," "one or more of A, B, and C," "one or more A, B, and C," "selected from the group consisting of A, B. and C", "selected from A, B, and C", and the like are used interchangeably and all refer to a selection from a group consisting of A, B, and/or C, i.e., one or more As, one or more Bs, one or more Cs, or any combination thereof, unless indicated otherwise.

It is to be understood that the present disclosure provides methods for the synthesis of the compounds of any of the Formulae described herein. The present disclosure also provides detailed methods for the synthesis of various disclosed compounds of the present disclosure according to the following schemes as well as those shown in the Examples.

It is to be understood that, throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps for performing certain actions is immaterial so long as the invention remains operable. Moreover, two or more steps or actions can be conducted simultaneously.

It is to be understood that the synthetic processes of the disclosure can tolerate a wide variety of functional groups, therefore various substituted starting materials can be used. The processes generally provide the desired final compound at or near the end of the overall process, although it may be desirable in certain instances to further convert the compound to a pharmaceutically acceptable salt thereof.

It is to be understood that compounds of the present disclosure can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms. and Structure,* 5$^{th}$ edition, John Wiley & Sons: New York, 2001; Greene, T. W., Wuts, P. G. M., *Protective Groups in Organic Synthesis,* 3$^{rd}$ edition, John Wiley & Sons: New York, 1999; R. Larock, *Comprehensive Organic Transformations*, VCH Publishers (1989); L. Fieser and M. Fieser, *Fieser and Fieser's Reagents for organic Synthesis*, John Wiley and Sons (1994); and L. Paquette, ed., *Encyclopedia of Reagents for organic Synthesis*. John Wiley and Sons (1995), incorporated by reference herein, are useful and recognized reference textbooks of organic synthesis known to those in the art.

One of ordinary skill in the art will note that, during the reaction sequences and synthetic schemes described herein, the order of certain steps may be changed, such as the introduction and removal of protecting groups. One of ordinary skill in the art will recognize that certain groups may require protection from the reaction conditions via the use of protecting groups. Protecting groups may also be used to differentiate similar functional groups in molecules. A list of protecting groups and how to introduce and remove these groups can be found in Greene, T. W., Wuts, P. G. M., *Protective Groups in Organic Synthesis,* $3^{rd}$ edition, John Wiley & Sons: New York, 1999.

It is to be understood that, unless otherwise stated, any description of a method of treatment or prevention includes use of the compounds to provide such treatment or prevention as is described herein. It is to be further understood, unless otherwise stated, any description of a method of treatment or prevention includes use of the compounds to prepare a medicament to treat or prevent such condition. The treatment or prevention includes treatment or prevention of human or non-human animals including rodents and other disease models.

It is to be understood that, unless otherwise stated, any description of a method of treatment includes use of the compounds to provide such treatment as is described herein. It is to be further understood, unless otherwise stated, any description of a method of treatment includes use of the compounds to prepare a medicament to treat such condition. The treatment includes treatment of human or non-human animals including rodents and other disease models.

As used herein, the term "subject" includes human and non-human animals, as well as cell lines, cell cultures, tissues, and organs. In some embodiments, the subject is a mammal. The mammal can be e.g., a human or appropriate non-human mammal, such as primate, mouse, rat, dog, cat, cow, horse, goat, camel, sheep or a pig. The subject can also be a bird or fowl. In some embodiments, the subject is a human.

As used herein, the term "subject in need thereof" refers to a subject having a disease or having an increased risk of developing the disease. A subject in need thereof can be one who has been previously diagnosed or identified as having a disease or disorder disclosed herein. A subject in need thereof can also be one who is suffering from a disease or disorder disclosed herein. Alternatively, a subject in need thereof can be one who has an increased risk of developing such disease or disorder relative to the population at large (i.e., a subject who is predisposed to developing such disorder relative to the population at large). A subject in need thereof can have a refractory or resistant a disease or disorder disclosed herein (i.e., a disease or disorder disclosed herein that does not respond or has not yet responded to treatment). The subject may be resistant at start of treatment or may become resistant during treatment. In some embodiments, the subject in need thereof received and failed all known effective therapies for a disease or disorder disclosed herein. In some embodiments, the subject in need thereof received at least one prior therapy.

As used herein, the term "treating" or "treat" describes the management and care of a patient for the purpose of combating a disease, condition, or disorder and includes the administration of a compound of the present disclosure, or a pharmaceutically acceptable salt, polymorph or solvate thereof, to alleviate the symptoms or complications of a disease, condition or disorder, or to eliminate the disease, condition or disorder. The term "treat" can also include treatment of a cell in vitro or an animal model. It is to be appreciated that references to "treating" or "treatment" include the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

It is to be understood that a compound of the present disclosure, or a pharmaceutically acceptable salt, polymorph or solvate thereof, can or may also be used to prevent a relevant disease, condition or disorder, or used to identify suitable candidates for such purposes.

As used herein, the term "preventing," "prevent," or "protecting against" describes reducing or eliminating the onset of the symptoms or complications of such disease, condition or disorder.

It is to be understood that one skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning. A Laboratory Manual* ($3^{rd}$ edition), Cold Spring Harbor Press, Cold Spring Harbor, New York (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, PA, $18^{th}$ edition (1990). These texts can, of course, also be referred to in making or using an aspect of the disclosure.

It is to be understood that the present disclosure also provides pharmaceutical compositions comprising any compound described herein in combination with at least one pharmaceutically acceptable excipient or carrier.

As used herein, the term "pharmaceutical composition" is a formulation containing the compounds of the present disclosure in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this disclosure include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the term "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

It is to be understood that a pharmaceutical composition of the disclosure is formulated to be compatible with its intended route of administration. Examples of routes of administration include parenteral, e.g., intravenous, intradermal, subcutaneous, oral (e.g., ingestion), inhalation, transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

It is to be understood that a compound or pharmaceutical composition of the disclosure can be administered to a subject in many of the well-known methods currently used for chemotherapeutic treatment. For example, a compound of the disclosure may be injected into the blood stream or body cavities or taken orally or applied through the skin with patches. The dose chosen should be sufficient to constitute effective treatment but not so high as to cause unacceptable side effects. The state of the disease condition (e.g., a disease or disorder disclosed herein) and the health of the patient should preferably be closely monitored during and for a reasonable period after treatment.

As used herein, the term "therapeutically effective amount," refers to an amount of a pharmaceutical agent to treat, ameliorate, and/or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

It is to be understood that, for any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present disclosure may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), cyclodextrins and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze drying that yields a powder of the active ingredient plus any additional desired ingredient from a previously sterile filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, capsules or sachets. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays, powders or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved.

In therapeutic applications, the dosages of the pharmaceutical compositions used in accordance with the disclosure vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the symptoms of the disease or disorder disclosed herein and also preferably causing complete regression of the disease or disorder. Dosages can range from about 0.01 mg/kg per day to about 5000 mg/kg per day. An effective amount of a pharmaceutical agent is that which provides an objectively identifiable improvement as noted by the clinician or other qualified observer. Improvement in survival and growth indicates regression. As used herein, the term “dosage effective manner” refers to amount of an active compound to produce the desired biological effect in a subject or cell.

It is to be understood that the pharmaceutical compositions can be included in a container, pack, or dispenser together with instructions for administration.

It is to be understood that, for the compounds of the present disclosure being capable of further forming salts, all of these forms are also contemplated within the scope of the claimed disclosure.

As used herein, the term “pharmaceutically acceptable salts” refer to derivatives of the compounds of the present disclosure wherein the parent compound is modified by making acid or base salts thereof. Examples of pharmaceutically acceptable salts include, but are not limited to, mineral organic acid salts of basic residues such as amines, alkali organic salts of acidic residues such as carboxylic acids, and the like. The pharmaceutically acceptable salts include the conventional non-toxic salts or the quaternary ammonium salts of the parent compound formed, for example, from non-toxic inorganic organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

In some embodiments, the pharmaceutically acceptable salt is a sodium salt, a potassium salt, a calcium salt, a magnesium salt, a diethylamine salt, a choline salt, a meglumine salt, a benzathine salt, a tromethamine salt, an ammonia salt, an arginine salt, or a lysine salt.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present disclosure also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ratio other than 1:1, e.g., 3:1, 2:1, 1:2, or 1:3.

It is to be understood that all references to pharmaceutically acceptable salts include solvent addition forms (solvates) or crystal forms (polymorphs) as defined herein, of the same salt.

The compounds, or pharmaceutically acceptable salts thereof, are administered orally, nasally, transdermally, pulmonary, inhalationally, buccally, sublingually, intraperitoneally, subcutaneously, intramuscularly, intravenously, rectally, intrapleurally, intrathecally and parenterally. In one embodiment, the compound is administered orally. One skilled in the art will recognise the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition. An ordinarily skilled physician or veterinarian can readily determine and prescribe the effective amount of the drug required to counter or arrest the progress of the condition.

Techniques for formulation and administration of the disclosed compounds of the disclosure can be found in *Remington: the Science and Practice of Pharmacy,* $19^{th}$ edition, Mack Publishing Co., Easton, PA (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous organic solutions. The compounds will be present in such pharmaceutical compositions in amounts sufficient to provide the desired dosage amount in the range described herein.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

In the synthetic schemes described herein, compounds may be drawn with one particular configuration for simplicity. Such particular configurations are not to be construed as limiting the disclosure to one or another isomer, tautomer, regioisomer or stereoisomer, nor does it exclude mixtures of isomers, tautomers, regioisomers or stereoisomers; however, it will be understood that a given isomer, tautomer, regioisomer or stereoisomer may have a higher level of activity than another isomer, tautomer, regioisomer or stereoisomer.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

As use herein, the phrase "compound of the disclosure" refers to those compounds which are disclosed herein, both generically and specifically.

Compounds of the Present Disclosure

In some aspects, the present disclosure provides a compound of Formula (I):

(I)

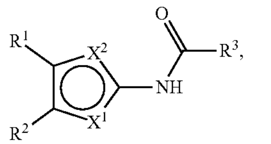

or a pharmaceutically acceptable salt, solvate, clathrate, hydrate, stereoisomer, or tautomer thereof, wherein:

$X^1$ is CH, S, or N;

$X^2$ is N, S, or O;

$R^1$ and $R^2$, together with the atoms to which they are attached, form a $C_5$-$C_{10}$ cycloalkyl or 5- to 10-membered heterocycloalkyl, wherein the $C_5$-$C_{10}$ cycloalkyl or 5- to 10-membered heterocycloalkyl is optionally substituted with one or more $R^a$;

each $R^a$ independently is oxo, halo, cyano. —$OR^{a1}$, —$N(R^{a1})_2$, —$C(O)R^{a1}$, —$C(O)N(R^{a1})_2$, —$C(O)OR^{a1}$, —$S(O)_2N(R^{a1})_2$, —$S(O)_2(R^{a1})$, $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, $C_6$-$C_{10}$ aryl, 5- to 10-membered heteroaryl, or 3- to 10-membered heterocycloalkyl, wherein the $C_1$-$C_6$ alkyl, $C_2$-$C_6$ alkenyl, $C_2$-$C_6$ alkynyl. $C_1$-$C_6$ haloalkyl, $C_3$-$C_{10}$ cycloalkyl, $C_6$-$C_{10}$ aryl, 5- to 10-membered heteroaryl, or 3- to 10-membered heterocycloalkyl is optionally substituted with one or more $R^{a1}$;

each $R^{a1}$ independently is H, oxo, halo, cyano. —OH, —$NH_2$, —$C(O)C_1$-$C_6$ alkyl), —$C(O)(C_3$-$C_{10}$ cycloalkyl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_{10}$ cycloalkyl, 3- to 10-membered heterocycloalkyl, $C_6$-$C_{10}$ aryl, or 5- to 10-membered heteroaryl, wherein the —$C(O)(C_3$-$C_{10}$ cycloalkyl), $C_1$-$C_6$ alkyl, $C_2$-$C_6$alkenyl, $C_2$-$C_6$ alkynyl, $C_1$-$C_6$ haloalkyl, $C_1$-$C_6$ alkoxy, $C_3$-$C_{10}$ cycloalkyl, 3- to 10-membered heterocycloalkyl, $C_6$-$C_{10}$ aryl, or 5- to 10-membered heteroaryl is optionally substituted with one or more $R^{a2}$ each $R^{a2}$ independently is oxo, halo, cyano, —OH, —$NH_2$, —$NH(C_1$-$C_6$ alkyl), —$N(C_1$-$C_6$ alkyl$)_2$, $C_1$-$C_6$ alkyl optionally substituted with $C_1$-$C_6$ alkoxy or —OH, $C_3$-$C_{10}$ cycloalkyl, $C_1$-$C_6$ haloalkoxy, $C_1$-$C_6$ haloalkyl, $C_1$-$C_6$ alkoxy, 3- to 10-membered heterocycloalkyl optionally substituted with oxo, or 5- to 10-membered heteroaryl;

$R^3$ is $C_6$-$C_{10}$ aryl or 5- to 10-membered heteroaryl, wherein the $C_6$-$C_{10}$ aryl or 5- to 10-membered heteroaryl is substituted with one or more $R^{3a}$;

each $R^{3a}$ independently is halo, cyano, —OH, —$NH_2$, $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, 3- to 10-membered heterocycloalkyl, $C_6$-$C_{10}$ aryl, or 5- to 10-membered heteroaryl, wherein the $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, 3- to 10-membered heterocycloalkyl, $C_6$-$C_{10}$ aryl, or 5- to 10-membered heteroaryl is optionally substituted with one or more $R^{3a1}$; and each $R^{3a1}$ independently is oxo, halo, cyano, —OH, —C(O)($C_1$-$C_6$ alkyl), —C(O)—($C_1$-$C_6$ alkyl)), $C_1$-$C_6$ alkyl optionally substituted with $C_3$-$C_{10}$ cycloalkyl, $C_2$-$C_6$ alkenyl, $C_2$-$C_6$ alkynyl, $C_1$-$C_6$ haloalkyl, $C_1$-$C_6$ haloalkoxy. $C_1$-$C_6$ alkoxy, —O($C_1$-$C_6$haloalkyl), $C_3$-$C_{10}$ cycloalkyl, $C_6$-$C_{10}$ aryl, or 5- to 10-membered heteroaryl.

In some aspects, the present disclosure provides a compound of Formula (I):

(I)

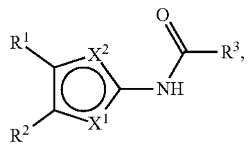

or a pharmaceutically acceptable salt, solvate, clathrate, hydrate, stereoisomer, or tautomer thereof, wherein:

$X^1$ is CH, S, or N;

$X^2$ is N, S, or O;

$R^1$ and $R^2$, together with the atoms to which they are attached, form a $C_5$-$C_{10}$ cycloalkyl or 5- to 10-membered heterocycloalkyl, wherein the $C_5$-$C_{10}$ cycloalkyl or 5- to 10-membered heterocycloalkyl is optionally substituted with one or more $R^a$;

each $R^a$ independently is oxo, halo, cyano, —$OR^{a1}$, —$N(R^{a1})_2$, —$C(O)R^{a1}$, —$C(O)N(R^{a1})_2$, —C(O)OR, —$S(O)_2N(R^{a1})_2$, —$S(O)_2(R^{a1})$, $C_1$-$C_6$ alkyl, $C_2$-$C_6$ alkenyl, $C_2$-$C_6$ alkynyl, $C_1$-$C_6$ haloalkyl. $C_3$-$C_{10}$ cycloalkyl, $C_6$-$C_{10}$ aryl, 5- to 10-membered heteroaryl, or 3- to 10-membered heterocycloalkyl, wherein the $C_1$-$C_6$ alkyl, $C_2$-$C_6$ alkenyl, $C_2$-$C_6$ alkynyl. $C_1$-$C_6$ haloalkyl, $C_3$-$C_{10}$ cycloalkyl, $C_6$-$C_{10}$ aryl, 5- to 10-membered heteroaryl, or 3- to 10-membered heterocycloalkyl is optionally substituted with one or more $R^{a1}$;

each $R^{a1}$ independently is H, oxo, halo, cyano, —OH, —$NH_2$, —C(O)($C_1$-$C_6$ alkyl), —C(O)($C_3$-$C_{10}$ cycloalkyl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_{10}$ cycloalkyl, 3- to 10-membered heterocycloalkyl, $C_6$-$C_{10}$ aryl, or 5- to 10-membered heteroaryl, wherein the —C(O)($C_3$-$C_{10}$ cycloalkyl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_{10}$ cycloalkyl, 3- to 10-membered heterocycloalkyl, $C_6$-$C_{10}$ aryl, or 5- to 10-membered heteroaryl is optionally substituted with one or more $R^{a2}$;

each $R^{a2}$ independently is oxo, halo, cyano, —OH, —$NH_2$, —NH($C_1$-$C_6$ alkyl), —N($C_1$-$C_6$ alkyl)$_2$, $C_1$-$C_6$ alkyl optionally substituted with $C_1$-$C_6$ alkoxy or —OH, $C_3$-$C_{10}$ cycloalkyl, $C_1$-$C_6$ haloalkoxy, $C_1$-$C_6$ haloalkyl, $C_1$-$C_6$ alkoxy, 3- to 10-membered heterocycloalkyl optionally substituted with oxo, or 5- to 10-membered heteroaryl;

$R^3$ is $C_6$-$C_{10}$ aryl or 5- to 10-membered heteroaryl, wherein the $C_6$-$C_{10}$ aryl or 5- to 10-membered heteroaryl is substituted with one or more $R^{3a}$;

each $R^{3a}$ independently is halo, cyano, —OH, —$NH_2$, $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, 3- to 10-membered heterocycloalkyl, $C_6$-$C_{10}$ aryl, or 5- to 10-membered heteroaryl, wherein the $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, 3- to 10-membered heterocycloalkyl, $C_6$-$C_{10}$ aryl, or 5- to 10-membered heteroaryl is optionally substituted with one or more $R^{3a1}$; and each $R^{3a1}$ independently is oxo, halo, cyano, —C(O)($C_1$-$C_6$alkyl), —C(O)O—($C_1$-$C_6$ alkyl)), $C_1$-$C_6$ alkyl optionally substituted with $C_3$-$C_{10}$ cycloalkyl, $C_2$-$C_6$ alkenyl, $C_2$-$C_6$ alkynyl, $C_1$-$C_6$ haloalkyl, $C_1$-$C_6$ alkoxy, —O($C_1$-$C_6$haloalkyl), $C_3$-$C_{10}$ cycloalkyl. $C_6$-$C_{10}$ aryl, or 5- to 10-membered heteroaryl.

It is understood that, for a compound of the present disclosure, variables $X^1$, $X^2$, $R^1$, $R^2$, $R^a$, $R^{a1}$, $R^{a2}$, $R^3$, $R^{3a}$, and $R^{3a1}$ can each be, where applicable, selected from the groups described herein, and any group described herein for any of variables $X^1$, $X^2$, $R^1$, $R^2$, $R^a$, $R^{a1}$, $R^{a2}$, $R^3$, $R^{3a}$, and $R^{3a1}$ can be combined, where applicable, with any group described herein for one or more of the remainder of variables $X^1$, $X^2$, $R^1$, $R^2$, $R^a$, $R^{a1}$, $R^{a2}$, $R^3$, $R^{3a}$, and $R^{3a1}$.

In some embodiments, $X^1$ is CH or S.

In some embodiments. $X^1$ is CH or N.

In some embodiments, $X^1$ is S or N.

In some embodiments, $X^1$ is CH. In some embodiments, $X^1$ is S. In some embodiments, $X^1$ is N.

In some embodiments, $X^2$ is N or S.

In some embodiments, $X^2$ is N or O.

In some embodiments. $X^2$ is O or S.

In some embodiments, $X^2$ is N. In some embodiments, $X^2$ is S. In some embodiments, $X^2$ is O.

In some embodiments, $R^1$ and $R^2$, together with the atoms to which they are attached, form a $C_5$-$C_6$ cycloalkyl or 5- to 6-membered heterocycloalkyl.

In some embodiments, $R^1$ and $R^2$, together with the atoms to which they are attached, form a $C_5$-$C_6$ cycloalkyl or 5- to 6-membered heterocycloalkyl, wherein the $C_5$-$C_6$ cycloalkyl or 5- to 6-membered heterocycloalkyl is optionally substituted with one or more $R^a$.

In some embodiments, $R^1$ and $R^2$, together with the atoms to which they are attached, form a $C_5$-$C_6$ cycloalkyl or 5- to 6-membered heterocycloalkyl, wherein the $C_5$-$C_6$ cycloalkyl or 5- to 6-membered heterocycloalkyl is substituted with one or more $R^a$.

In some embodiments, $R^1$ and $R^2$, together with the atoms to which they are attached, form a $C_5$-$C_{10}$ cycloalkyl.

In some embodiments, $R^1$ and $R^2$, together with the atoms to which they are attached, form a $C_5$-$C_{10}$ cycloalkyl optionally substituted with one or more $R^a$.

In some embodiments, $R^1$ and $R^2$, together with the atoms to which they are attached, form a $C_5$-$C_{10}$ cycloalkyl substituted with one or more $R^a$.

In some embodiments, $R^1$ and $R^2$, together with the atoms to which they are attached, form a $C_6$ cycloalkyl.

In some embodiments, $R^1$ and $R^2$, together with the atoms to which they are attached, form a $C_6$ cycloalkyl optionally substituted with one or more $R^a$.

In some embodiments, $R^1$ and $R^2$, together with the atoms to which they are attached, form a $C_6$ cycloalkyl substituted with one or more $R^a$.

In some embodiments, $R^1$ and $R^2$, together with the atoms to which they are attached, form a 5- to 10-membered heterocycloalkyl.

In some embodiments, $R^1$ and $R^2$, together with the atoms to which they are attached, form a 5- to 10-membered heterocycloalkyl optionally substituted with one or more $R^a$.

In some embodiments, $R^1$ and $R^2$, together with the atoms to which they are attached, form a 5- to 10-membered heterocycloalkyl substituted with one or more $R^a$.

In some embodiments, $R^1$ and $R^2$, together with the atoms to which they are attached, form a 5- to 7-membered heterocycloalkyl.

In some embodiments, $R^1$ and $R^2$, together with the atoms to which they are attached, form a 5- to 7-membered heterocycloalkyl optionally substituted with one or more $R^a$.

In some embodiments, $R^1$ and $R^2$, together with the atoms to which they are attached, form a 5- to 7-membered heterocycloalkyl substituted with one or more $R^a$.

In some embodiments, $R^1$ and $R^2$, together with the atoms to which they are attached, form a 5-membered heterocycloalkyl.

In some embodiments, $R^1$ and $R^2$, together with the atoms to which they are attached, form a 5-membered heterocycloalkyl optionally substituted with one or more RV.

In some embodiments, $R^1$ and $R^2$, together with the atoms to which they are attached, form a 5-membered heterocycloalkyl substituted with one or more $R^a$.

In some embodiments, $R^1$ and $R^2$, together with the atoms to which they are attached, form a 6-membered heterocycloalkyl.

In some embodiments, $R^1$ and $R^2$, together with the atoms to which they are attached, form a 6-membered heterocycloalkyl optionally substituted with one or more RV.

In some embodiments, $R^1$ and $R^2$, together with the atoms to which they are attached, form a 6-membered heterocycloalkyl substituted with one or more $R^a$.

In some embodiments, each $R^a$ independently is oxo, $—OR^{a1}$, $—N(R^{a1})_2$, $—C(O)R^{a1}$, $—C(O)N(R^{a1})_2$, $—C(O)OR^{a1}$, $—S(O)_2N(R^{a1})_2$, $—S(O)_2(R^{a1})$, $C_1$-$C_6$ alkyl, $C_3$-$C_{10}$ cycloalkyl, $C_6$-$C_{10}$ aryl, 5- to 10-membered heteroaryl, or 3- to 10-membered heterocycloalkyl.

In some embodiments, each $R^a$ independently is oxo, $—OR^{a1}$, $—N(R^{a1})_2$, $—C(O)R^{a1}$, $—C(O)N(R^{a1})_2$, $—C(O)OR^{a1}$, $—S(O)_2N(R^{a1})_2$, $—S(O)_2(R^{a1})$, $C_1$-$C_6$ alkyl, $C_3$-$C_{10}$ cycloalkyl, $C_6$-$C_{10}$ aryl, 5- to 10-membered heteroaryl, or 3- to 10-membered heterocycloalkyl, wherein the $C_1$-$C_6$ alkyl, $C_3$-$C_{10}$ cycloalkyl, $C_6$-$C_{10}$ aryl, 5- to 10-membered heteroaryl, or 3- to 10-membered heterocycloalkyl is optionally substituted with one or more $R^{a1}$.

In some embodiments, each $R^a$ independently is oxo, $—OR^{a1}$, $—N(R^{a1})_2$, $—C(O)R^{a1}$, $—C(O)N(R^{a1})_2$, $—C(O)OR^{a1}$, $—S(O)_2N(R^{a1})_2$, $—S(O)_2(R^{a1})$, $C_1$-$C_6$ alkyl, $C_3$-$C_{10}$ cycloalkyl, $C_6$-$C_{10}$ aryl, 5- to 10-membered heteroaryl, or 3- to 10-membered heterocycloalkyl, wherein the $C_1$-$C_6$ alkyl. $C_3$-$C_{10}$ cycloalkyl, $C_6$-$C_{10}$ aryl, 5- to 10-membered heteroaryl, or 3- to 10-membered heterocycloalkyl is substituted with one or more $R^{a1}$.

In some embodiments, each $R^a$ independently is oxo.

In some embodiments, each $R^a$ independently is halo.

In some embodiments, each $R^a$ independently is F, Cl, Br, or I. In some embodiments, each $R^a$ independently is F, Cl, or Br. In some embodiments, each $R^a$ independently is F or Cl.

In some embodiments, each $R^a$ independently is F. In some embodiments, each $R^a$ independently is Cl. In some embodiments, each Rh independently is Br. In some embodiments, each $R^a$ independently is I.

In some embodiments, each $R^a$ independently is cyano.

In some embodiments, each $R^a$ independently is $—OR^{a1}$.

In some embodiments, each $R^a$ independently is $—N(R^{a1})_2$.

In some embodiments, each $R^a$ independently is $—C(O)R^{a1}$.

In some embodiments, each $R^a$ independently is $—C(O)N(R^{a1})_2$.

In some embodiments, each $R^a$ independently is $—C(O)OR^{a1}$.

In some embodiments, each $R^a$ independently is $—S(O)_2N(R^{a1})_2$.

In some embodiments, each $R^a$ independently is $—S(O)_2(R^{a1})$.

In some embodiments, each $R^a$ independently is $C_1$-$C_6$ alkyl.

In some embodiments, each $R^a$ independently is $C_1$-$C_6$ alkyl optionally substituted with one or more $R^{a1}$.

In some embodiments, each $R^a$ independently is $C_1$-$C_6$ alkyl substituted with one or more R.

In some embodiments, each $R^a$ independently is methyl. In some embodiments, each $R^a$ independently is ethyl. In some embodiments, each $R^a$ independently is propyl. In some embodiments, each $R^a$ independently is butyl. In some embodiments, each $R^a$ independently is pentyl. In some embodiments, each $R^a$ independently is hexyl. In some embodiments, each $R^a$ independently is isopropyl. In some embodiments, each $R^a$ independently is isobutyl. In some embodiments, each $R^a$ independently is isopentyl. In some embodiments, each $R^a$ independently is isohexyl. In some embodiments, each $R^a$ independently is secbutyl. In some embodiments, each $R^a$ independently is secpentyl. In some embodiments, each $R^a$ independently is sechexyl. In some embodiments, each $R^a$ independently is tertbutyl.

In some embodiments, each $R^a$ independently is $C_2$-$C_6$ alkenyl.

In some embodiments, each $R^a$ independently is $C_2$-$C_6$ alkenyl optionally substituted with one or more $R^{a1}$.

In some embodiments, each $R^a$ independently is $C_2$-$C_6$ alkenyl substituted with one or more.

In some embodiments, each $R^a$ independently is $C_2$-$C_6$ alkynyl.

In some embodiments, each $R^a$ independently is $C_2$-$C_6$ alkynyl optionally substituted with one or more $R^{a1}$.

In some embodiments, each R independently is $C_2$-$C_6$ alkynyl substituted with one or more $R^{a1}$.

In some embodiments, each $R^a$ independently is $C_1$-$C_6$ haloalkyl.

In some embodiments, each $R^a$ independently is $C_1$-$C_6$ haloalkyl optionally substituted with one or more $R^{a1}$.

In some embodiments, each $R^a$ independently is halomethyl. In some embodiments, each $R^a$ independently is haloethyl. In some embodiments, each $R^a$ independently is halopropyl. In some embodiments, each $R^a$ independently is halobutyl. In some embodiments, each $R^a$ independently is halopentyl. In some embodiments, each $R^a$ independently is halohexyl.

In some embodiments, each $R^a$ independently is $C_3$-$C_{10}$ cycloalkyl.

In some embodiments, each $R^a$ independently is $C_3$-$C_{10}$ cycloalkyl optionally substituted with one or more $R^a$.

In some embodiments, each $R^a$ independently is $C_3$-$C_{10}$ cycloalkyl substituted with one or more $R^{a1}$.

In some embodiments, each $R^a$ independently is $C_3$-$C_7$ cycloalkyl.

In some embodiments, each $R^a$ independently is $C_3$-$C_7$ cycloalkyl optionally substituted with one or more $R^{a1}$.

In some embodiments, each $R^a$ independently is $C_3$-$C_7$ cycloalkyl substituted with one or more $R^{a1}$.

In some embodiments, each $R^a$ independently is $C_6$-$C_{10}$ aryl.

In some embodiments, each $R^a$ independently is $C_6$-$C_{10}$ aryl optionally substituted with one or more $R^{a1}$.

In some embodiments, each $R^a$ independently is $C_6$-$C_{10}$ aryl substituted with one or more $R^{a1}$.

In some embodiments, each $R^a$ independently is $C_6$ aryl.

In some embodiments, each $R^a$ independently is $C_6$ aryl optionally substituted with one or more $R^{a1}$.

In some embodiments, each $R^a$ independently is C aryl substituted with one or more $R^{a1}$.

In some embodiments, each $R^a$ independently is 5- to 10-membered heteroaryl.

In some embodiments, each $R^a$ independently is 5- to 10-membered heteroaryl optionally substituted with one or more $R^{a1}$.

In some embodiments, each $R^a$ independently is 5- to 10-membered heteroaryl substituted with one or more $R^{a1}$.

In some embodiments, each $R^a$ independently is 5- to 6-membered heteroaryl.

In some embodiments, each $R^a$ independently is 5- to 6-membered heteroaryl optionally substituted with one or more $R^{a1}$.

In some embodiments, each $R^a$ independently is 5- to 6-membered heteroaryl substituted with one or more $R^{a1}$.

In some embodiments, each $R^a$ independently is 3- to 10-membered heterocycloalkyl.

In some embodiments, each $R^a$ independently is 3- to 10-membered heterocycloalkyl optionally substituted with one or more $R^{a1}$.

In some embodiments, each $R^a$ independently is 3- to 10-membered heterocycloalkyl substituted with one or more $R^{a1}$.

In some embodiments, each $R^a$ independently is 3- to 7-membered heterocycloalkyl.

In some embodiments, each $R^a$ independently is 3- to 7-membered heterocycloalkyl optionally substituted with one or more $R^{a1}$.

In some embodiments, each $R^a$ independently is 3- to 7-membered heterocycloalkyl substituted with one or more $R^{a1}$.

In some embodiments, each $R^a$ independently is:

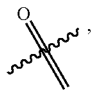
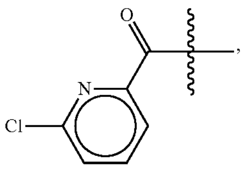
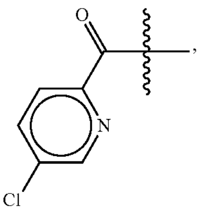
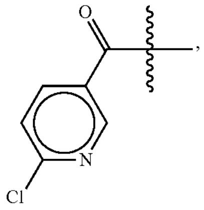
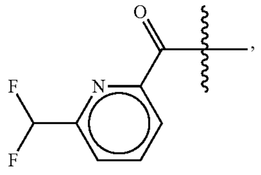

-continued

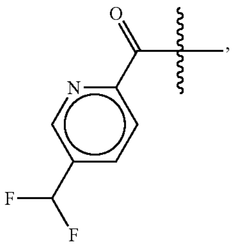
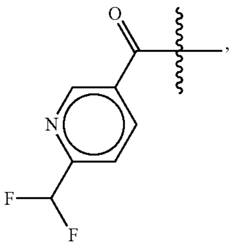
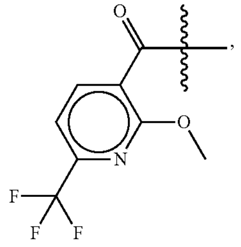
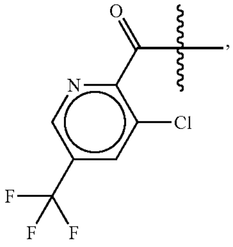
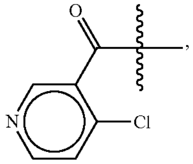
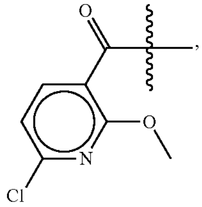
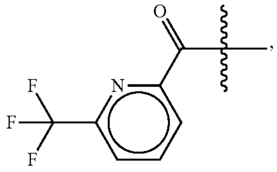
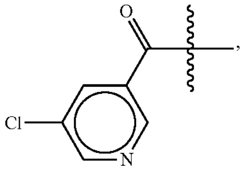
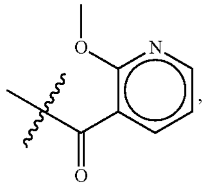
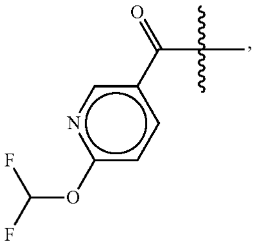
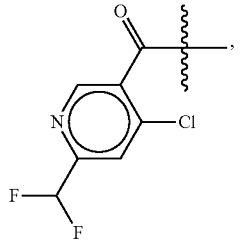
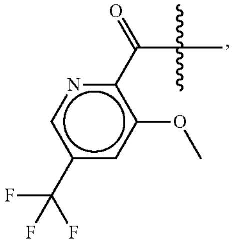
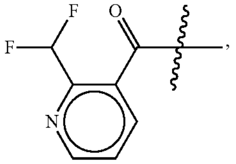
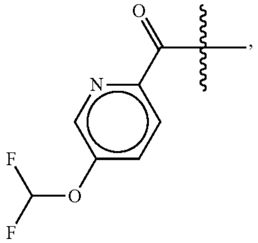

-continued
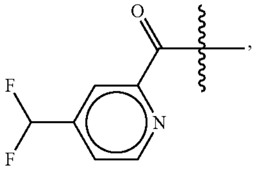, 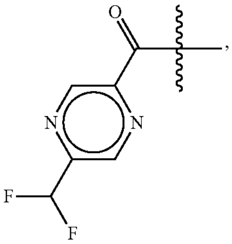,
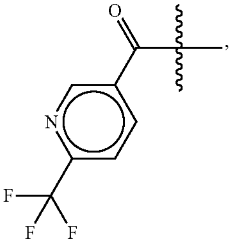, 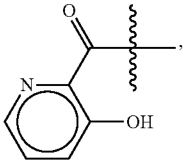,
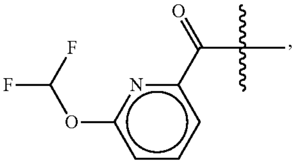, 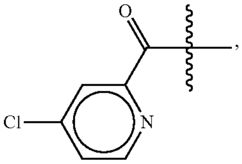,
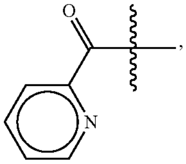, 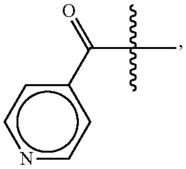,
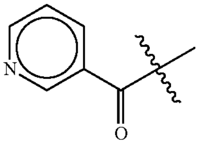, 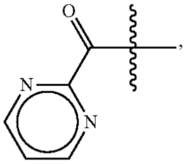,
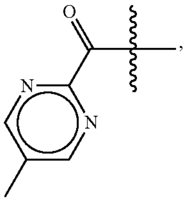, 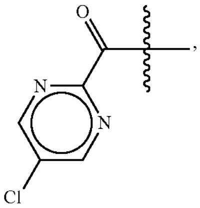,
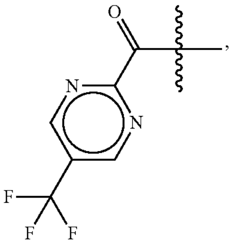, 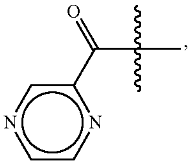,
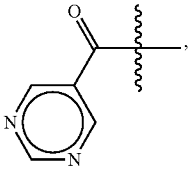, 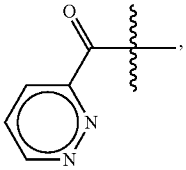,
-continued
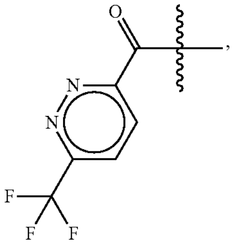, 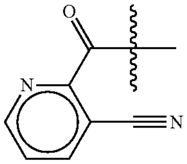,
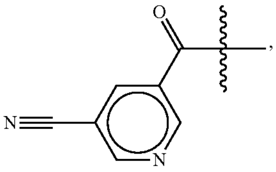, 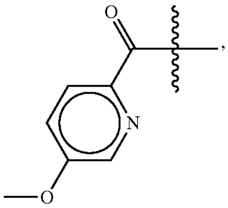,
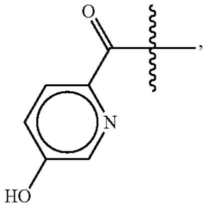, 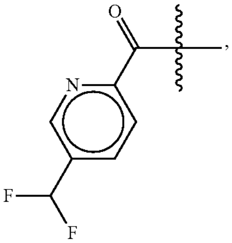,
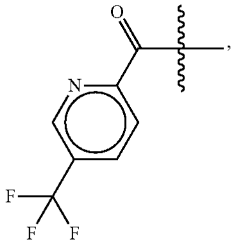, 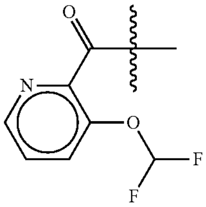,
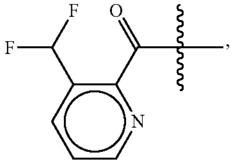, 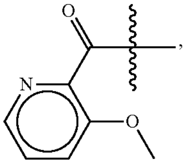,
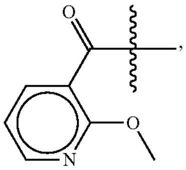, 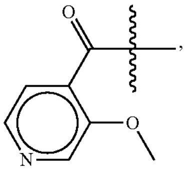,
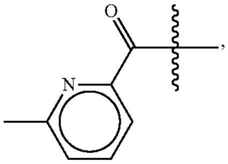, 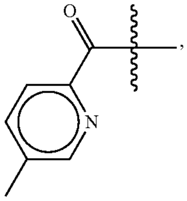,
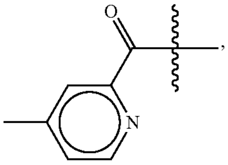, 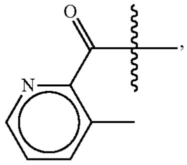, -continued
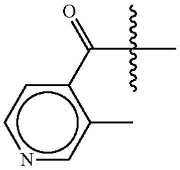, 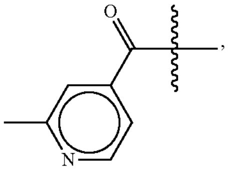,
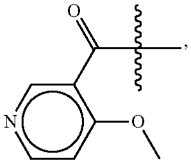, 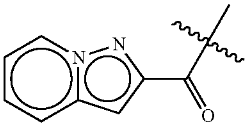,
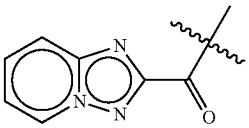, 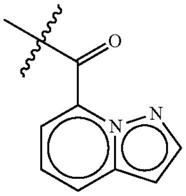,
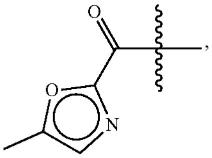, 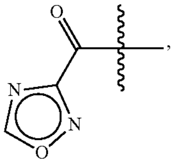,
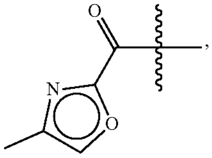, 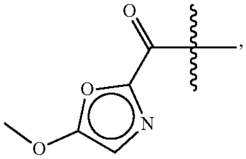,
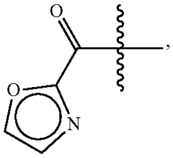, 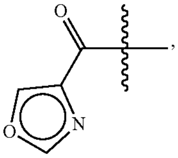, 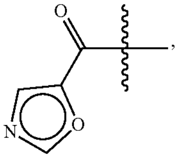,
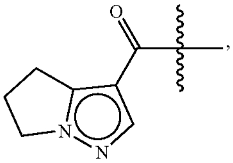, 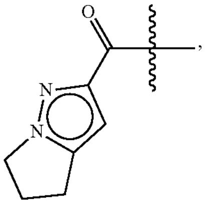,
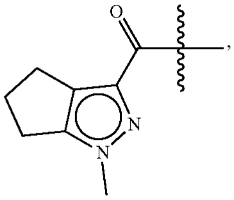, 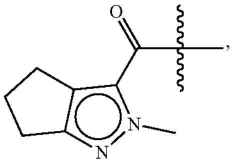,
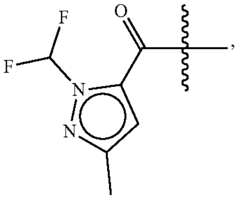, 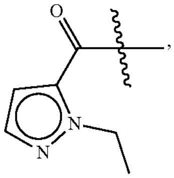,
-continued
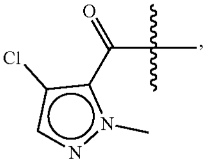, 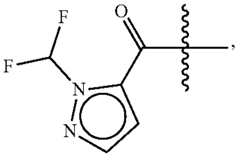,
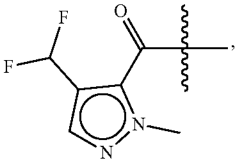, 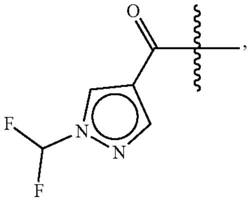,
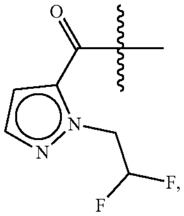 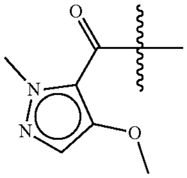,
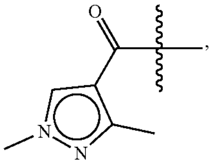, 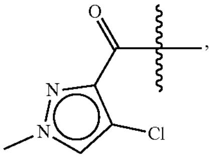,
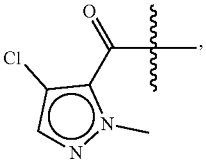, 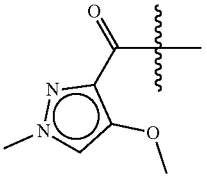,
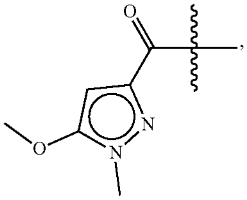, 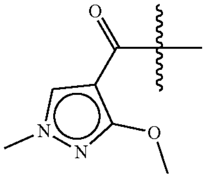,
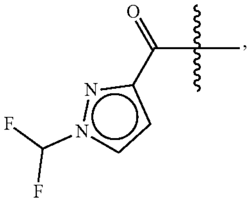, 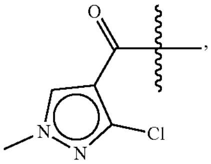,
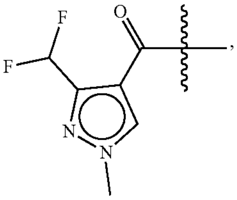, 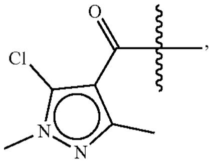,
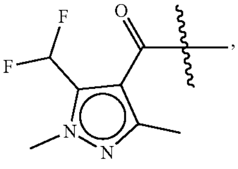, 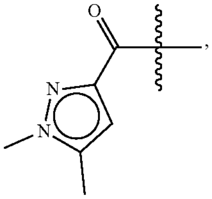, -continued
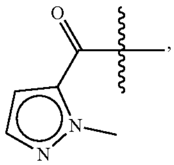,
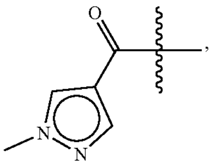,
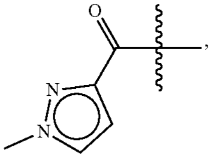,
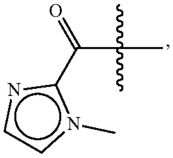,
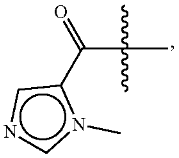,
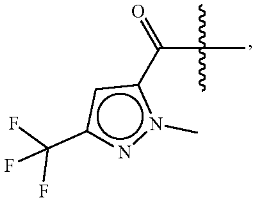,
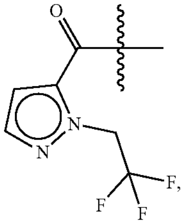
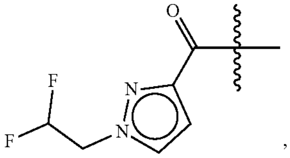,
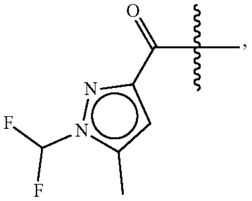,
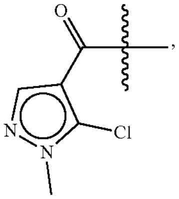,
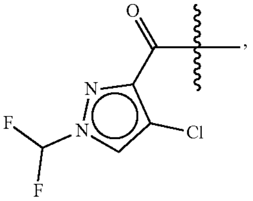,
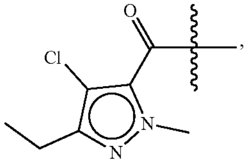,
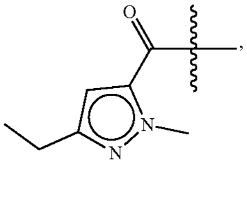,
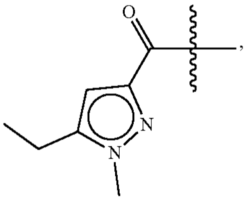,
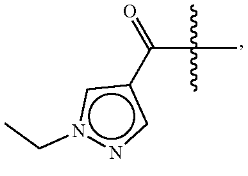,
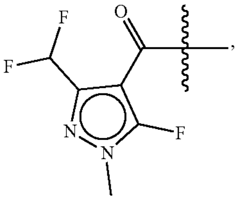,
-continued
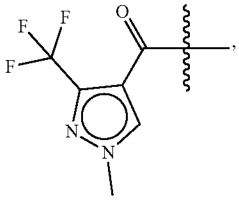,
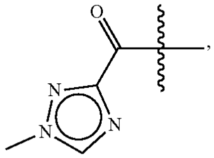,
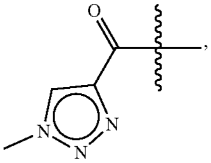,
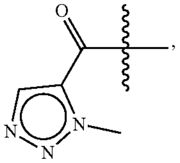,
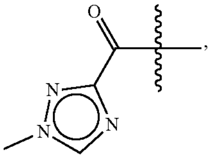,
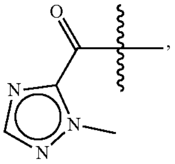,
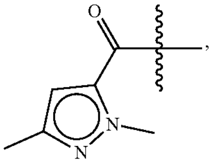,
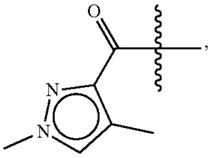,
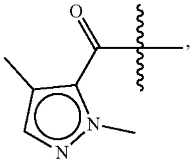,
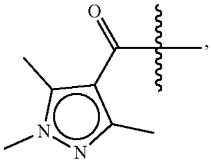,
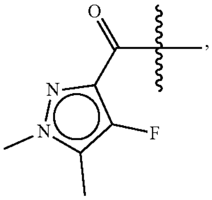,
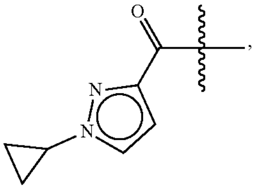,
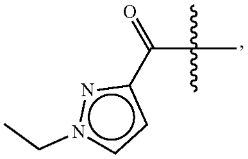,
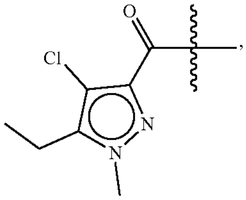,
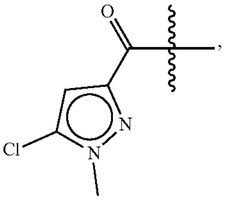,
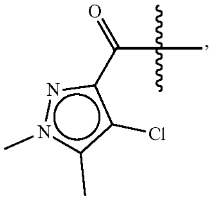,
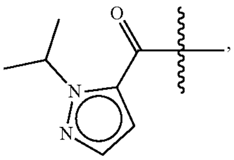,
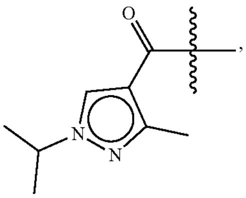, -continued
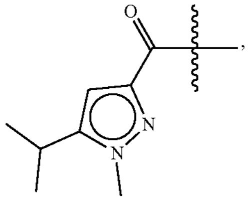,
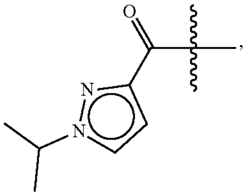,
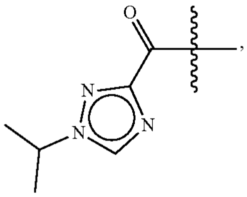,
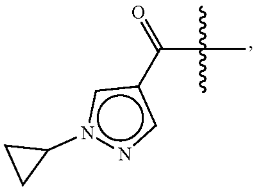,
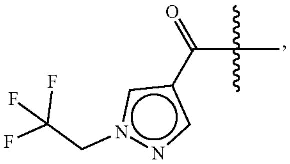,
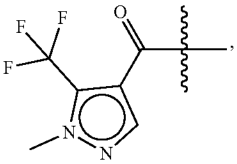,
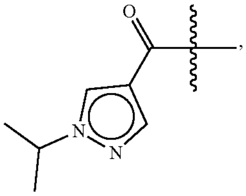,
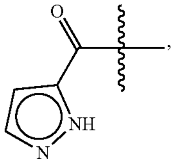,
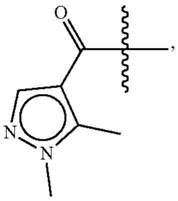,
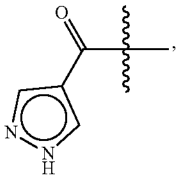,
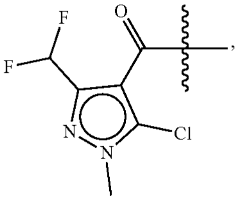,
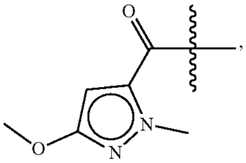,
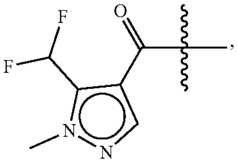,
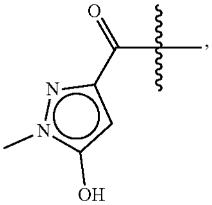,
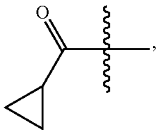,
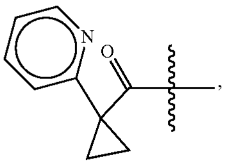,
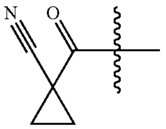,
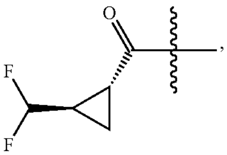,
-continued
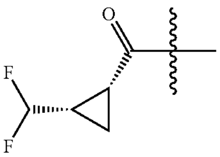,
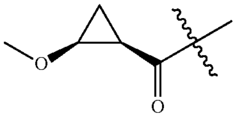,
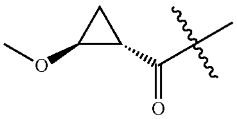,
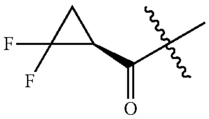,
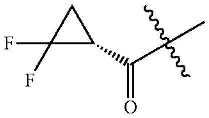,
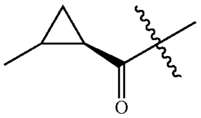,
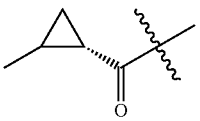,
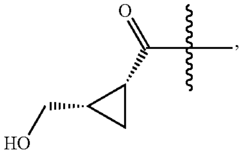,
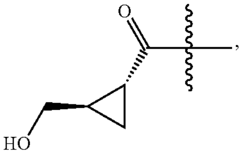,
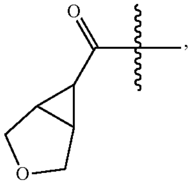,
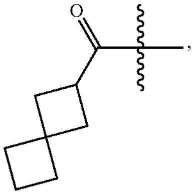,
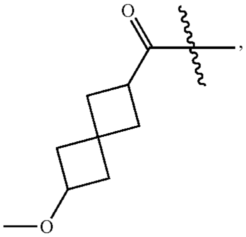,
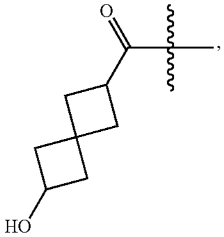,
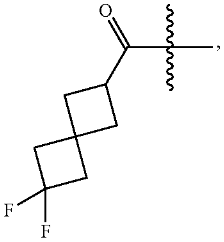,
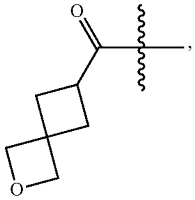,
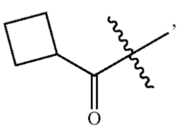,
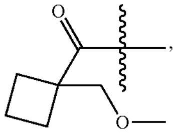,
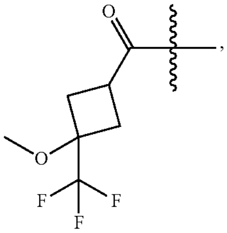, -continued
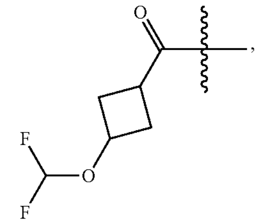
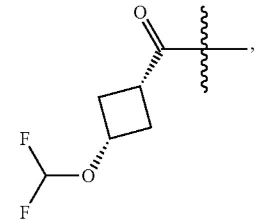
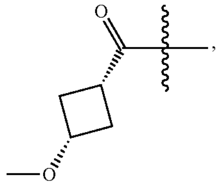
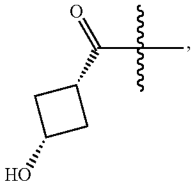
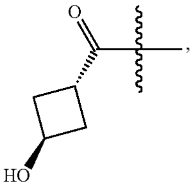
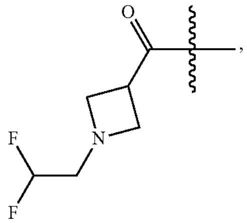
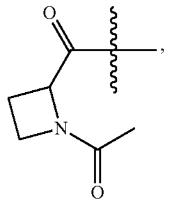
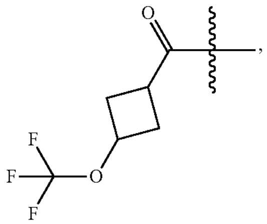
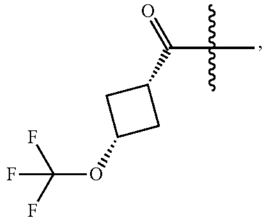
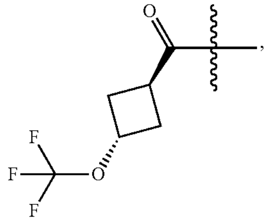
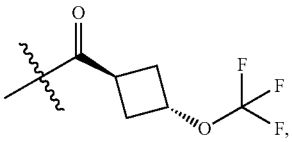
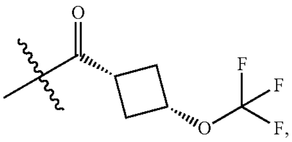
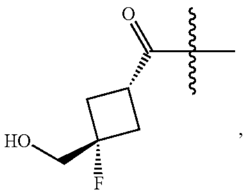
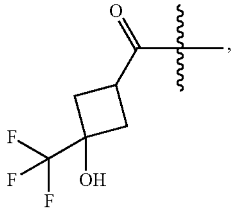
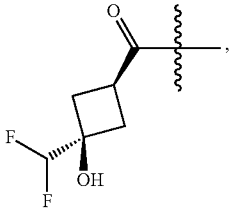
-continued
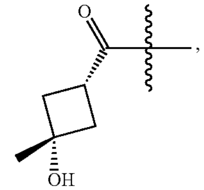
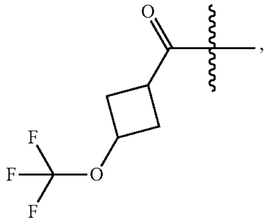
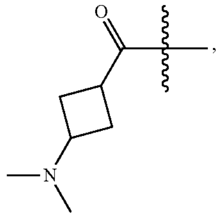
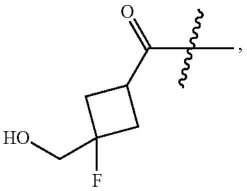
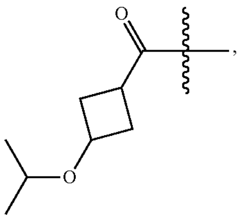
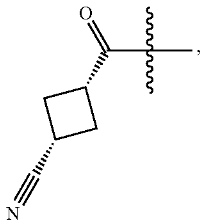
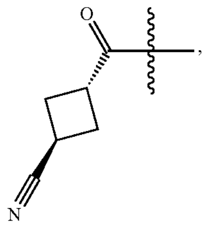
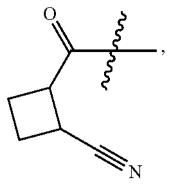
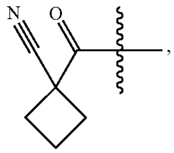
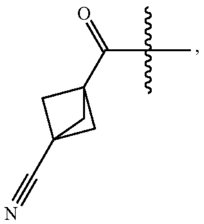
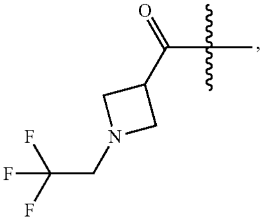
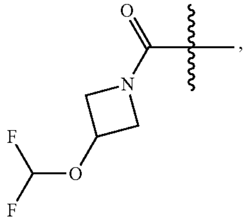
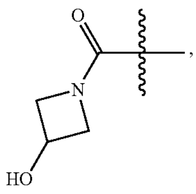
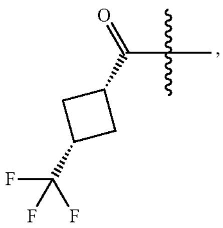

-continued
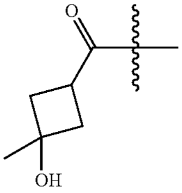,
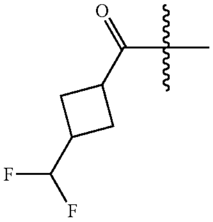,
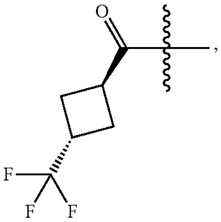,
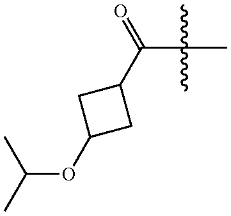,
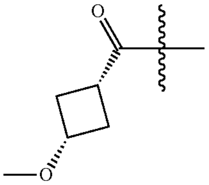,
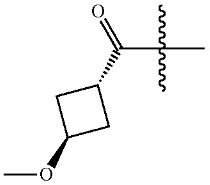,
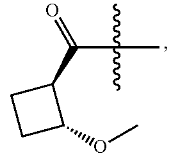,
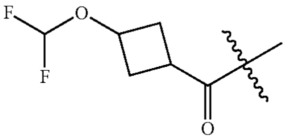,
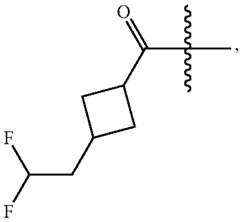,
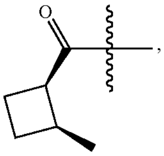,
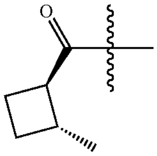,
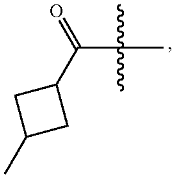,
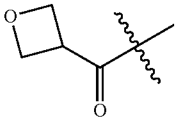,
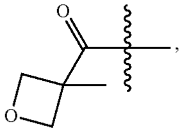,
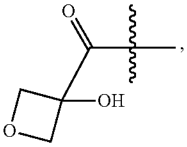,
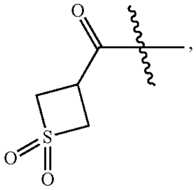,
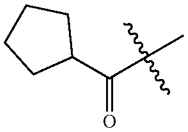,
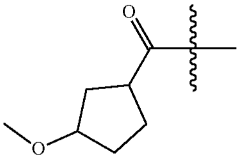,
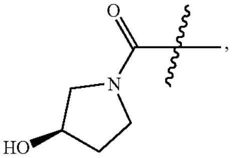,
-continued
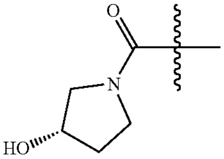,
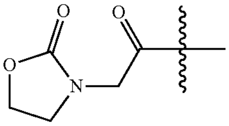,
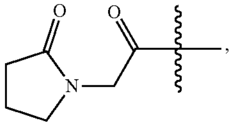,
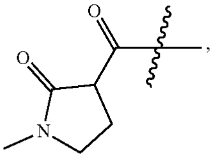,
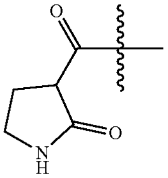,
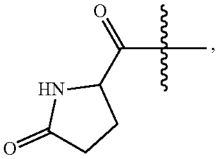,
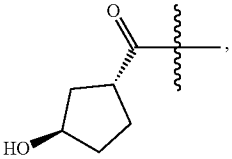,
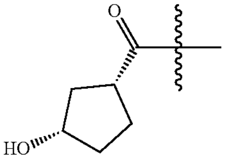,
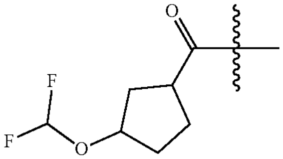,
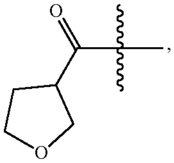,
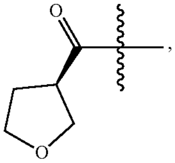,
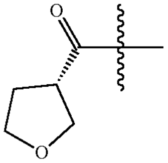,
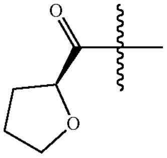,
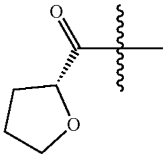,
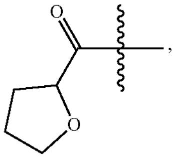,
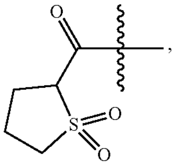,
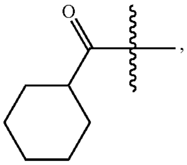,
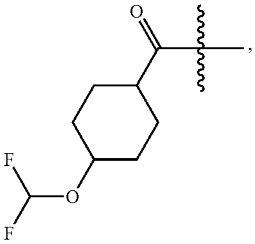,
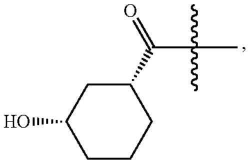,
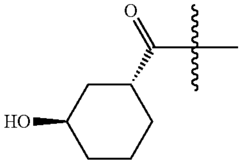, -continued
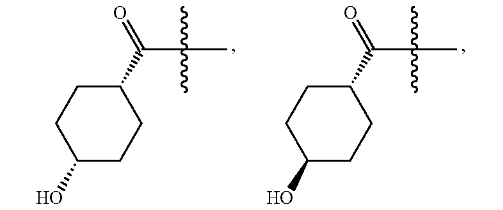
, ,
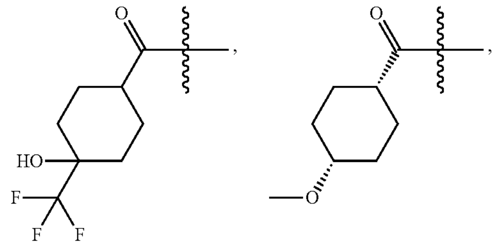
, ,
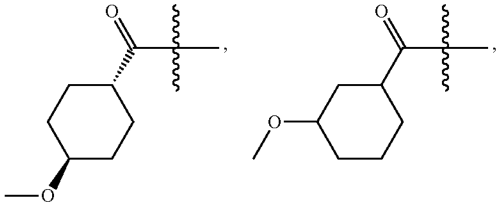
, ,
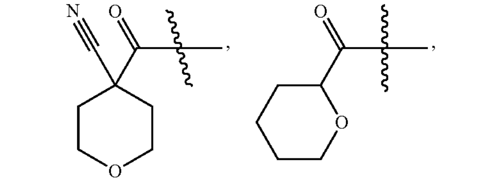
, ,
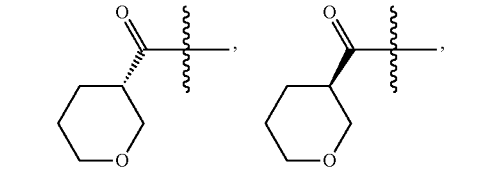
, ,
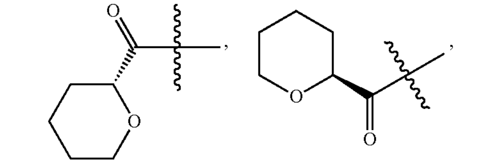
, ,
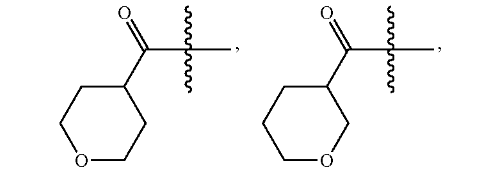
, ,
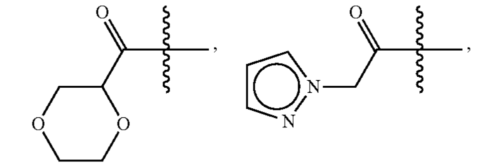
, ,
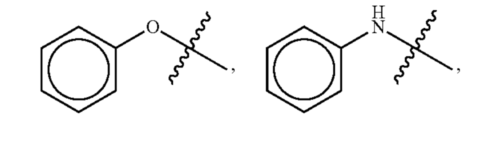
, ,
-continued
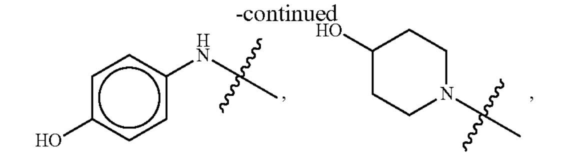
, ,
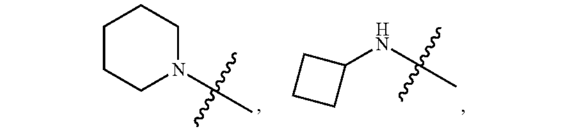
, ,
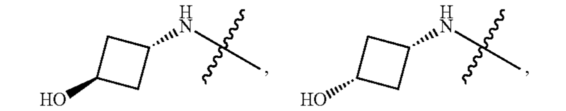
, ,
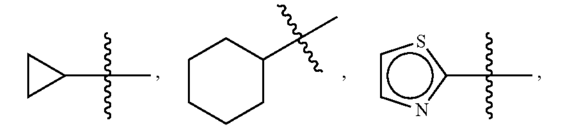
, , ,
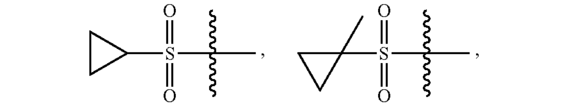
, ,
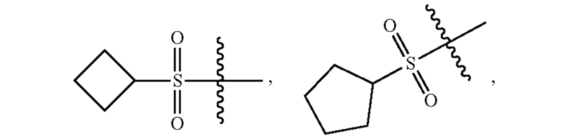
, ,
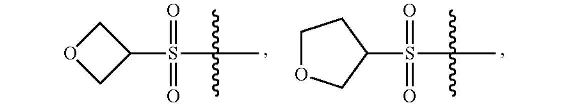
, ,
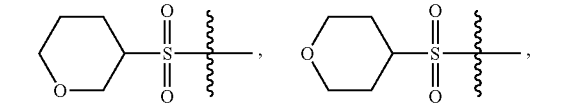
, ,
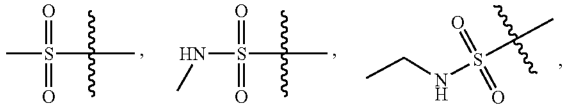
, , ,
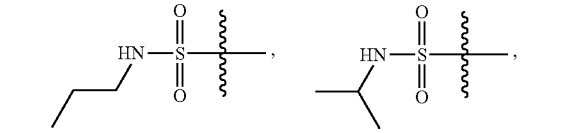
, ,
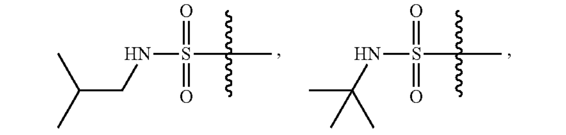
, ,
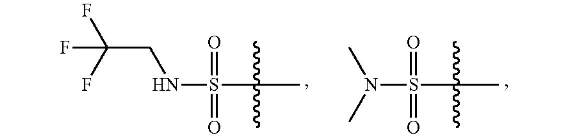
, ,
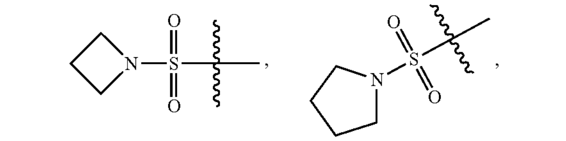
, ,
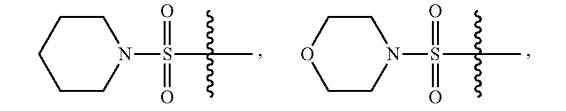
, , -continued
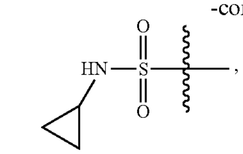, 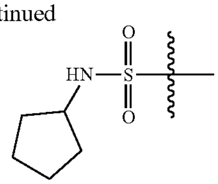,
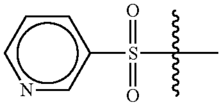, 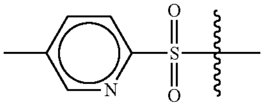,
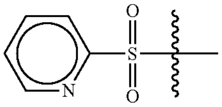, 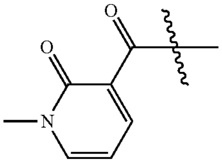,
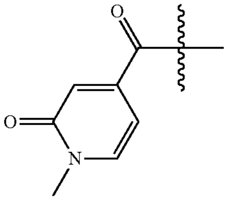, 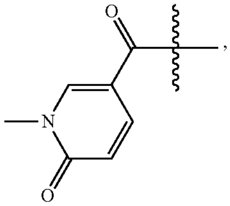,
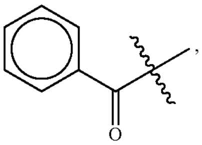, 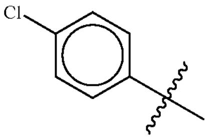,
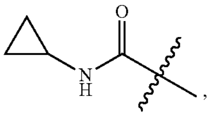, 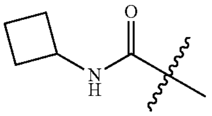,
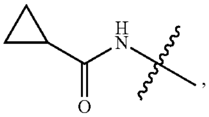, 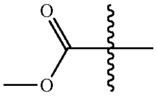,
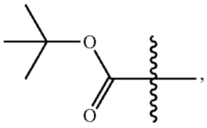, 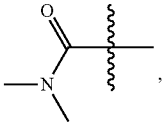,
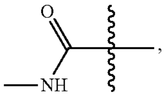, 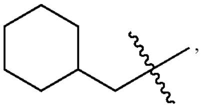,
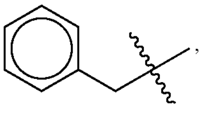, 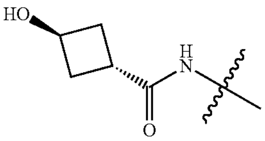,
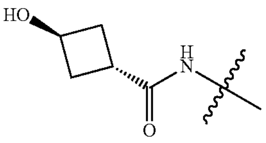, and
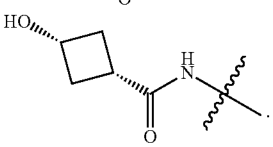.
In some embodiments, each $R^a$ independently is selected from:
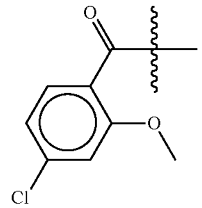, 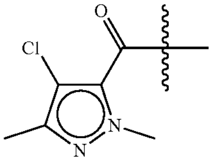,
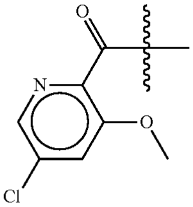, 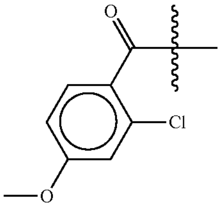,
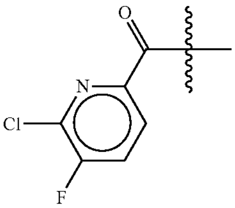, 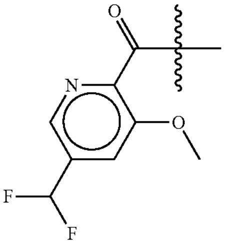,
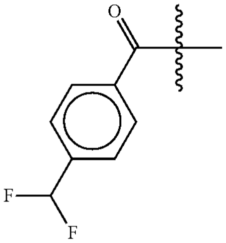, 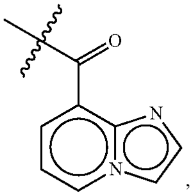,
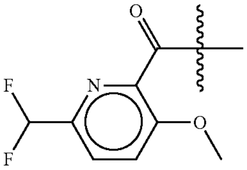, 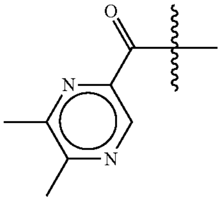,
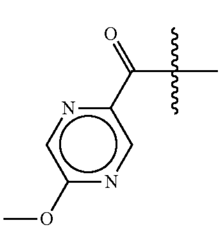, 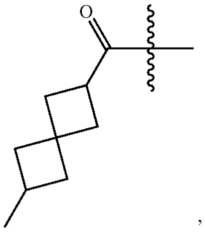,
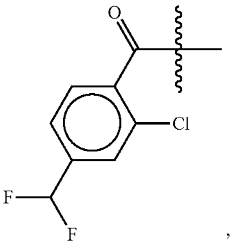, 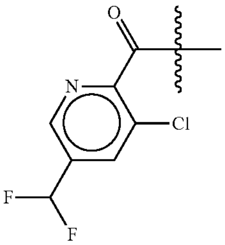, -continued
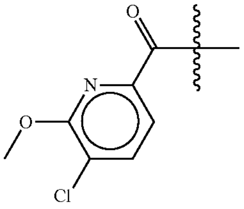,
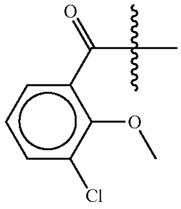,
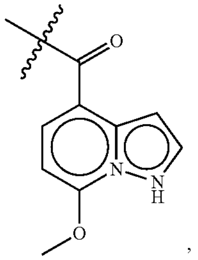,
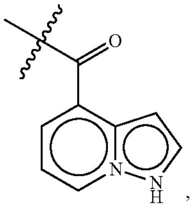,
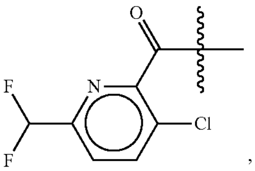,
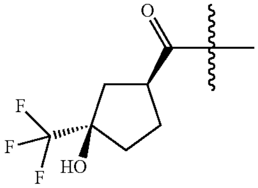,
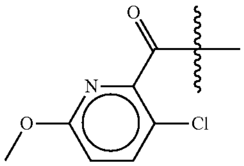,
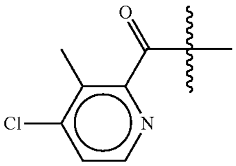,
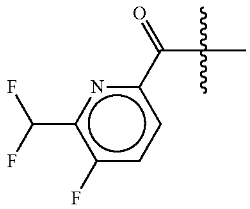,
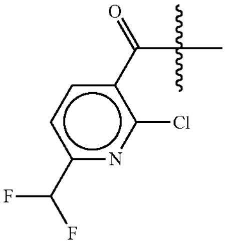,
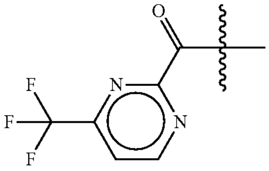,
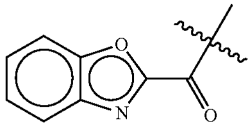,
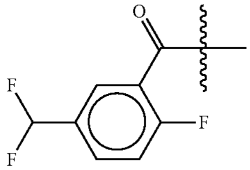,
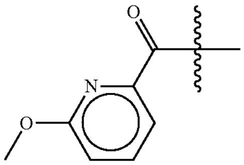,
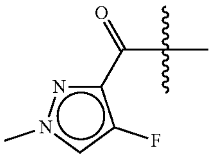,
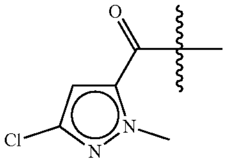,
-continued
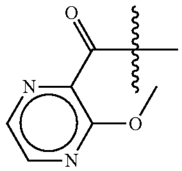,
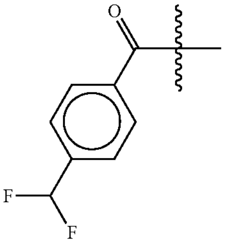,
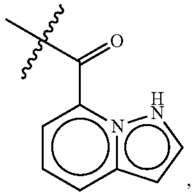,
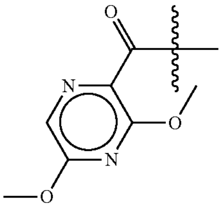,
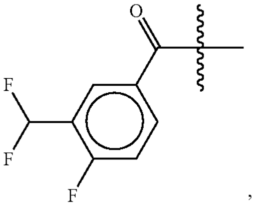,
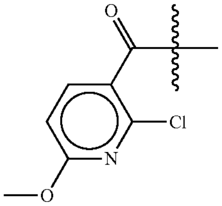,
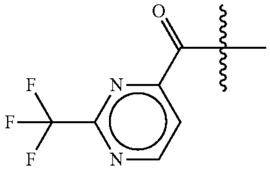,
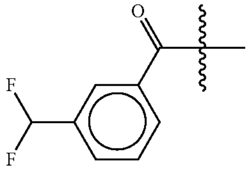,
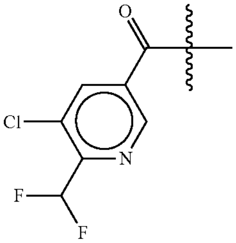,
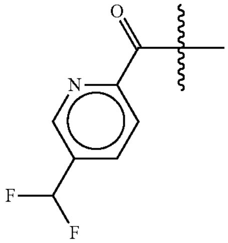,
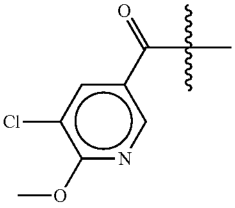,
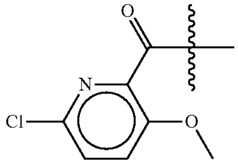,
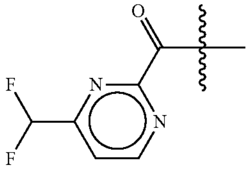,
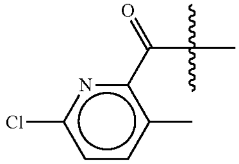,
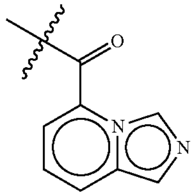,
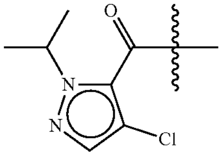, -continued
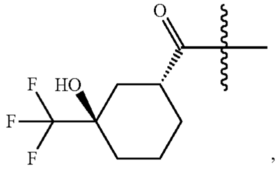,
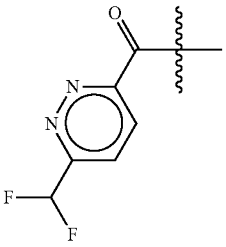,
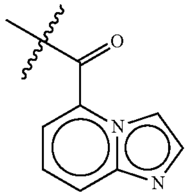,
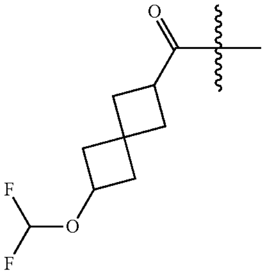,
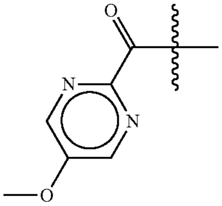,
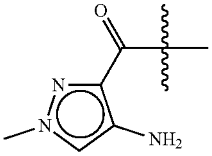,
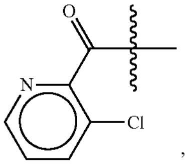,
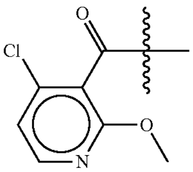,
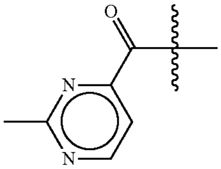,
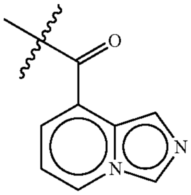,
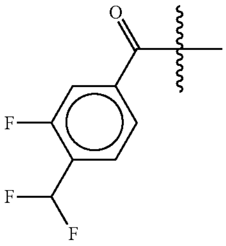,
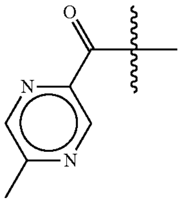,
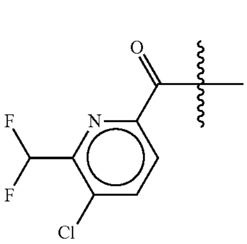,
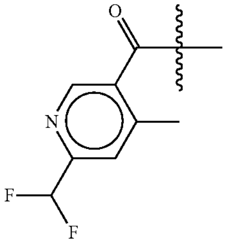,
-continued
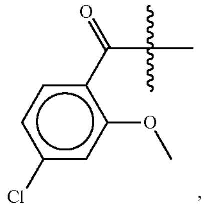,
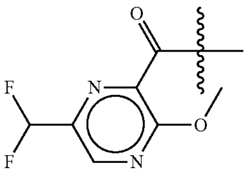,
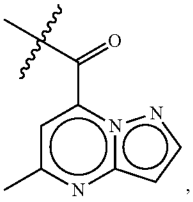,
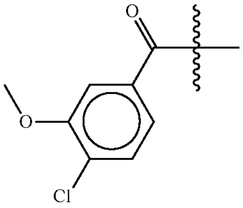,
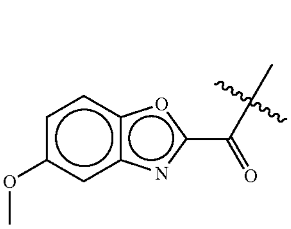,
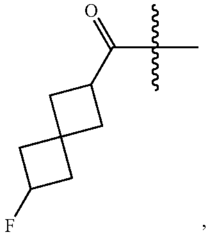,
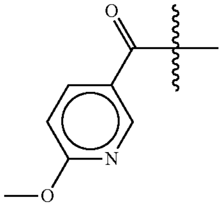,
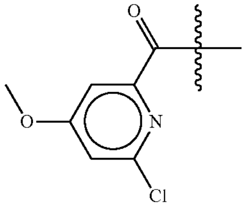,
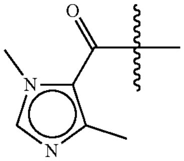,
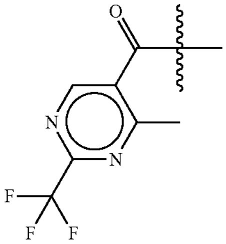,
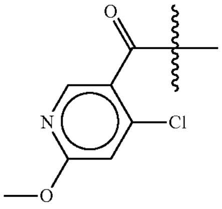,
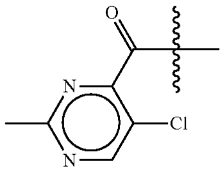,
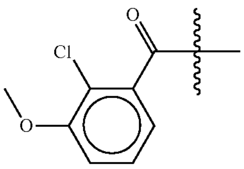,
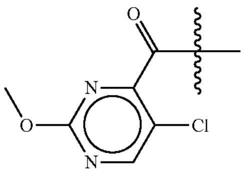,
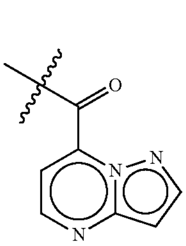,
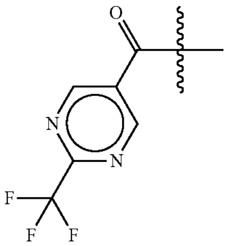, -continued
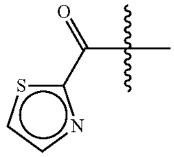,
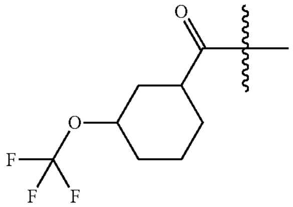,
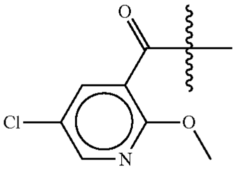,
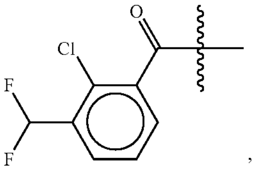,
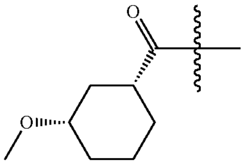,
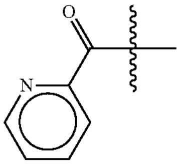,
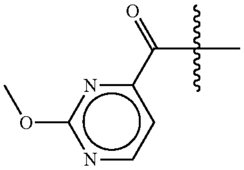,
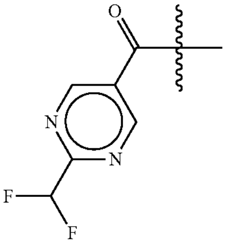,
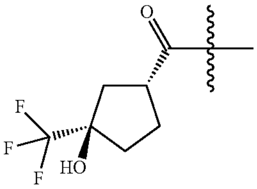,
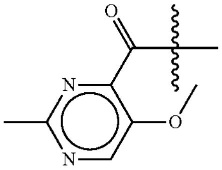,
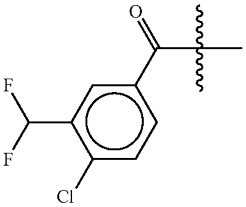,
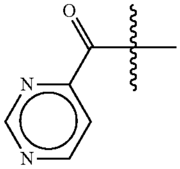,
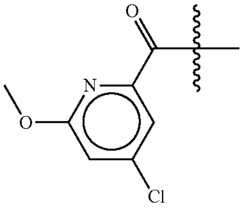,
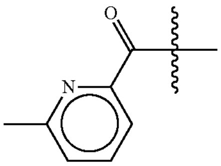,
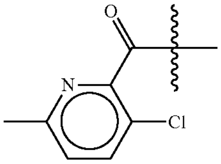,
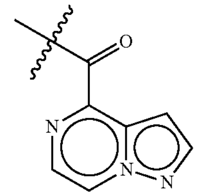,
-continued
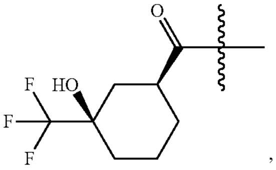,
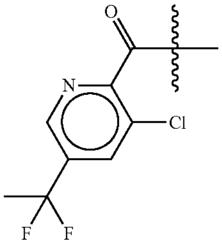,
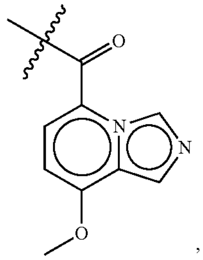,
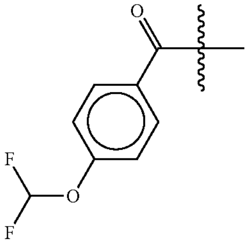,
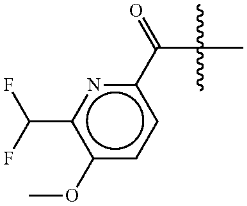,
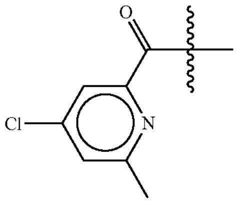,
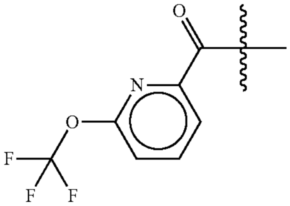,
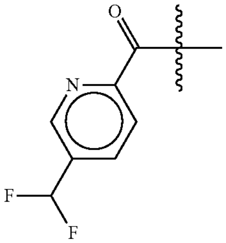,
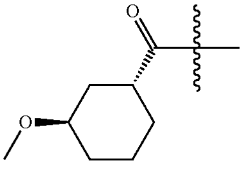,
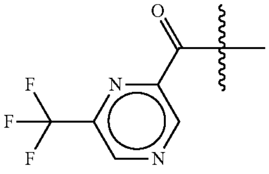,
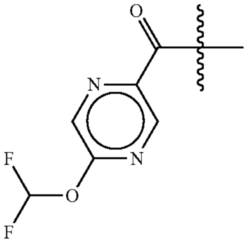,
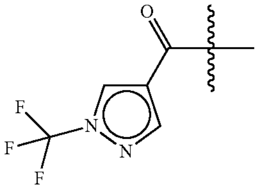,
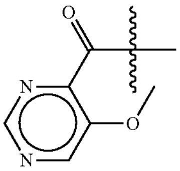,
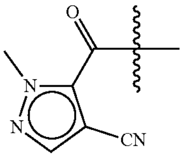, -continued
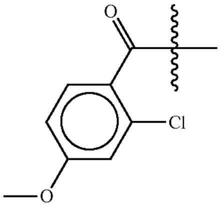,
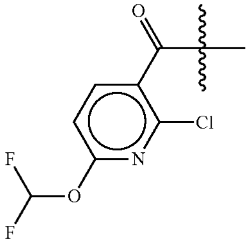,
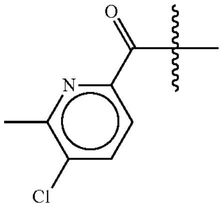,
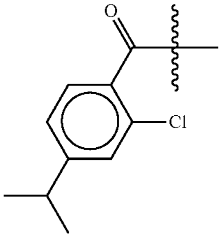,
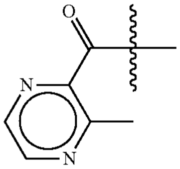,
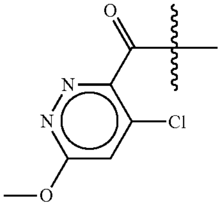,
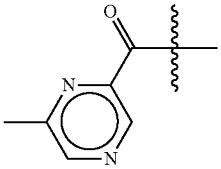,
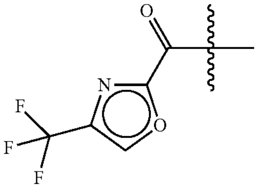,
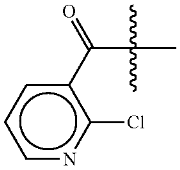,
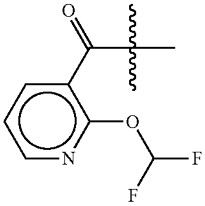,
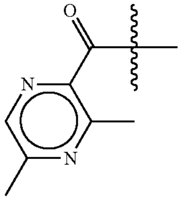,
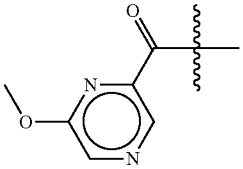,
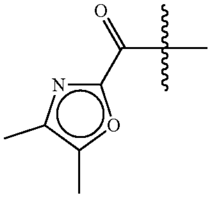,
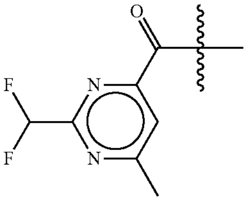,
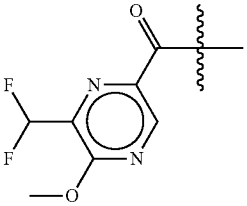,
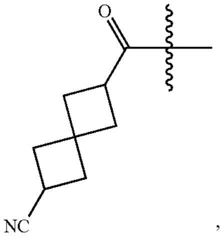,
-continued
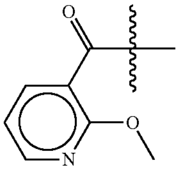,
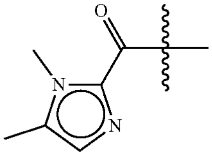,
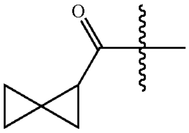,
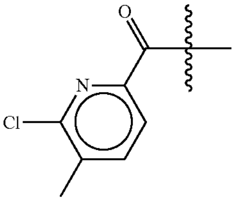,
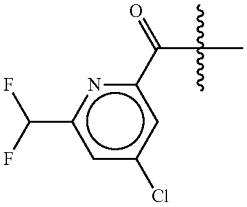,
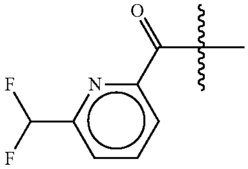,
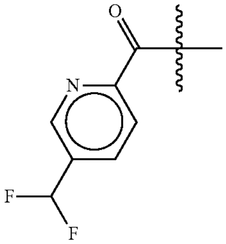,
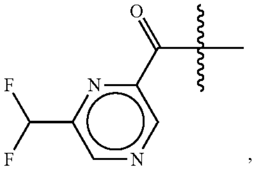,
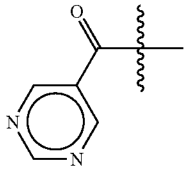,
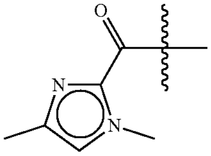,
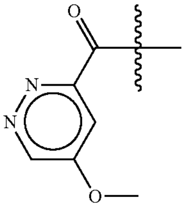,
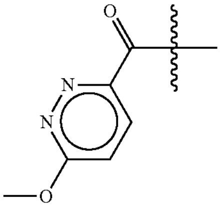,
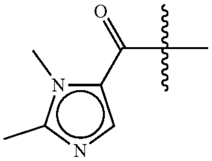,
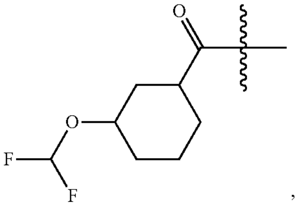,
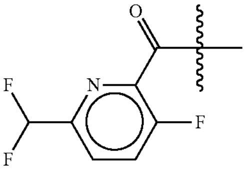,
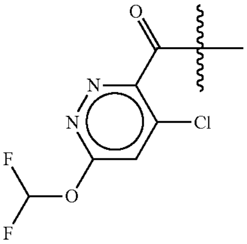, -continued
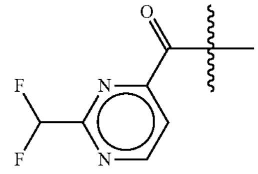
,
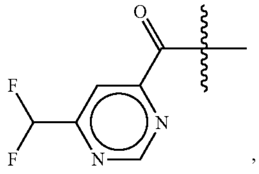
,
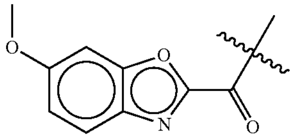
,
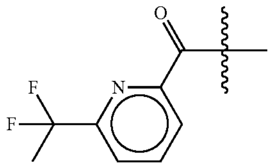
,
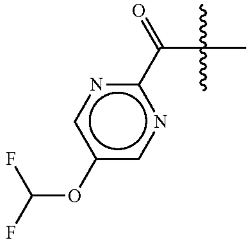
,
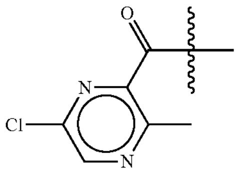
,
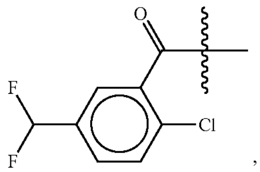
,
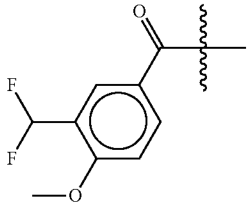
,
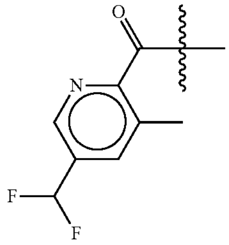
,
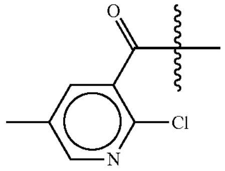
,
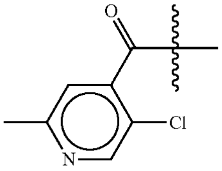
,
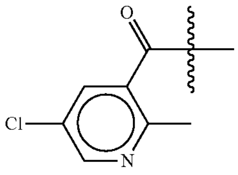
,
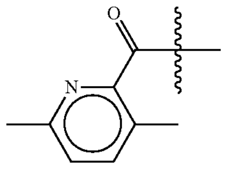
,
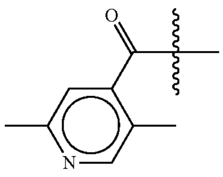
,
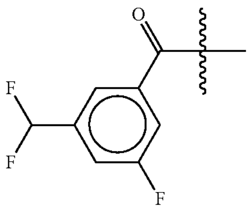
,
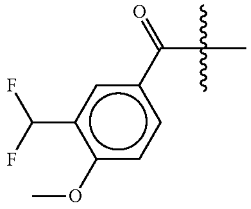
,
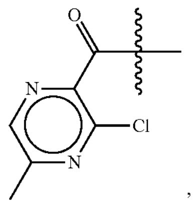
,
-continued
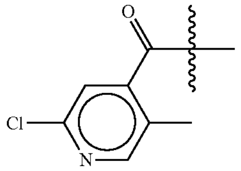
,
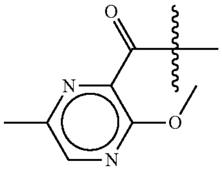
,
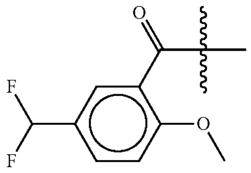
,
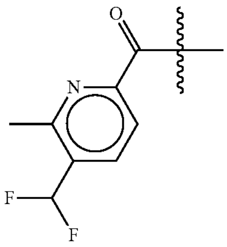
,
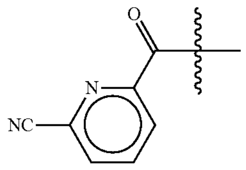
,
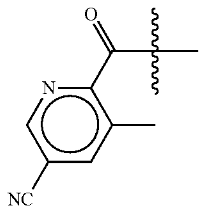
,
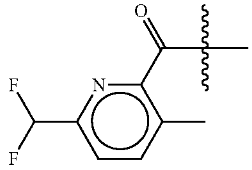
,
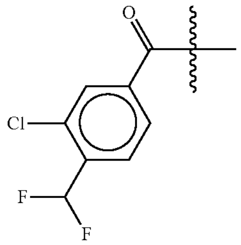
,
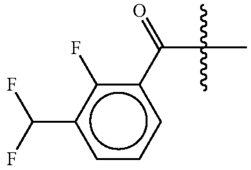
,
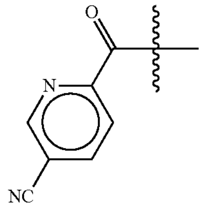
,
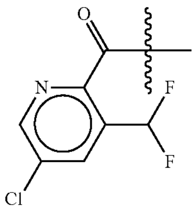
,
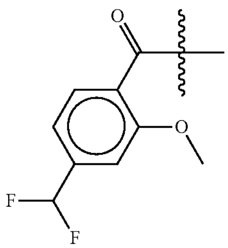
,
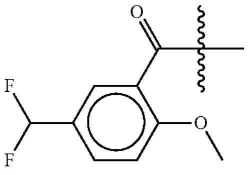
,
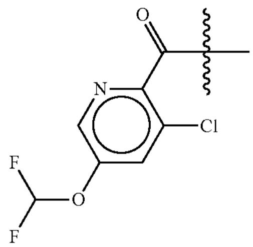
, -continued
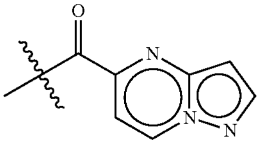, 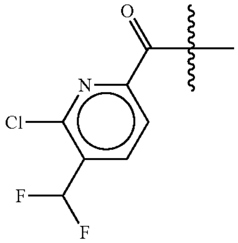,
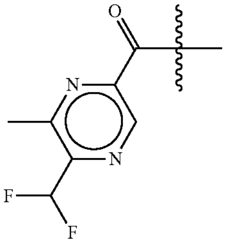, 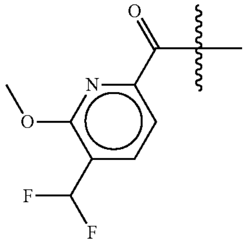,
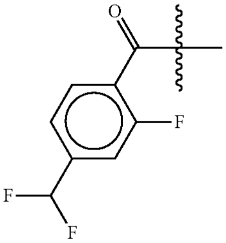, 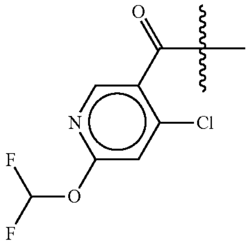,
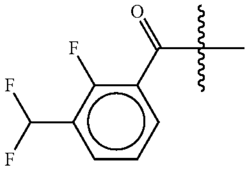, 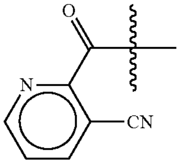,
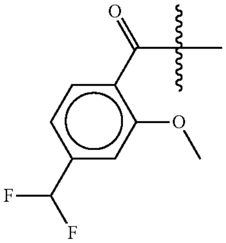, 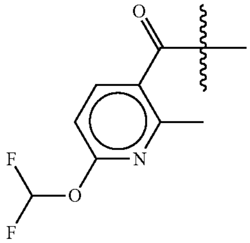,
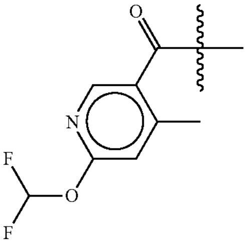, 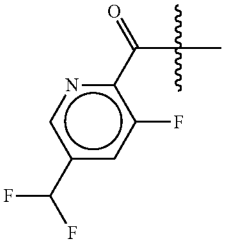,
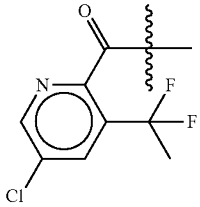, 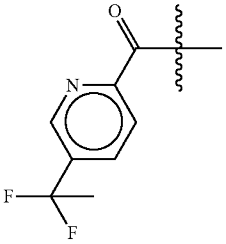,
-continued
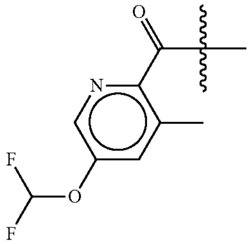, 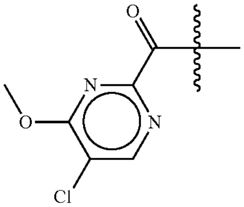,
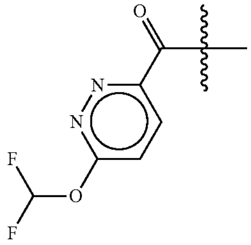, 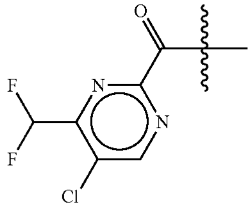,
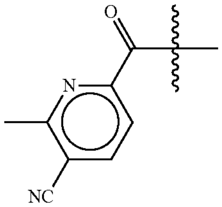, 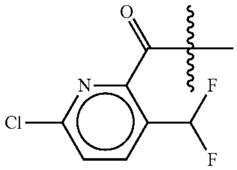,
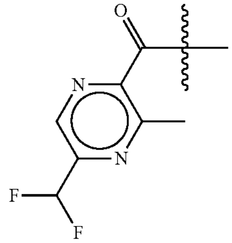, 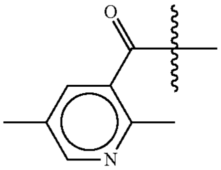,
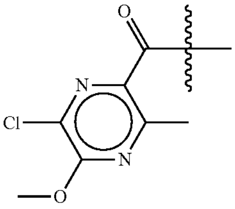, 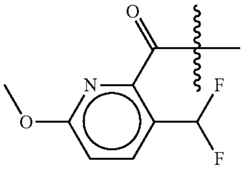,
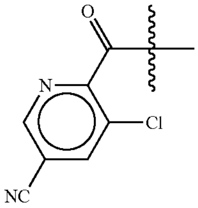, 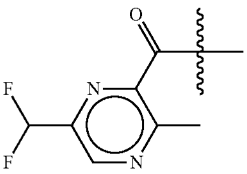,
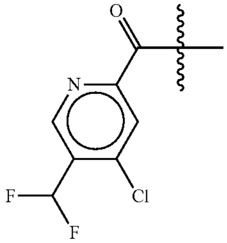, 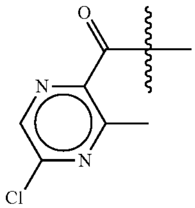, -continued
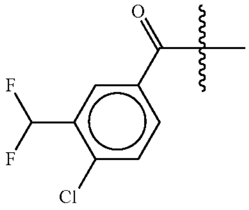,
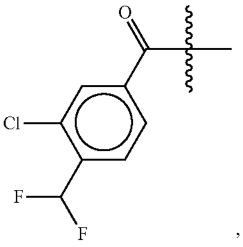,
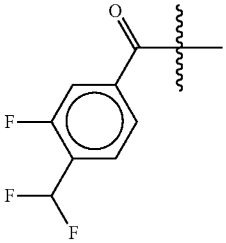,
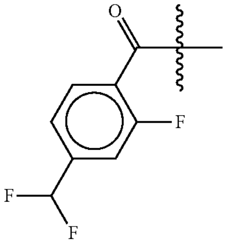,
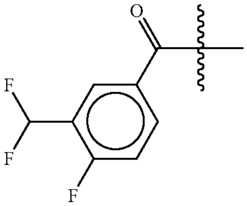,
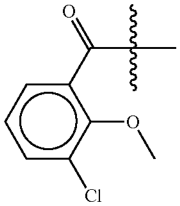,
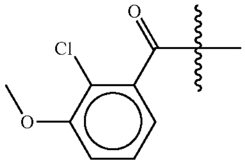,
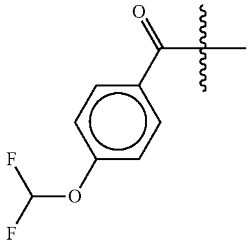,
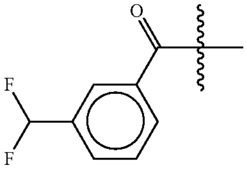,
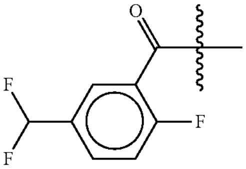,
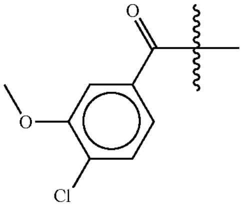,
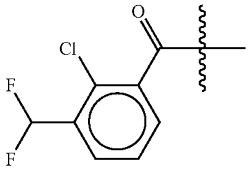,
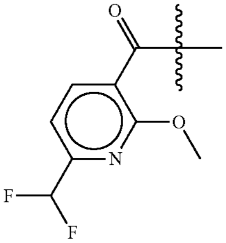,
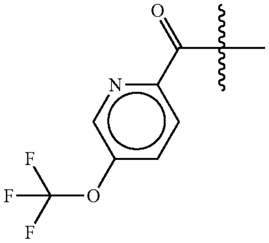,
-continued
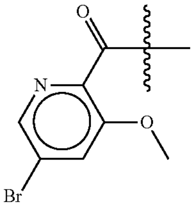,
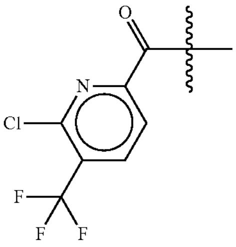,
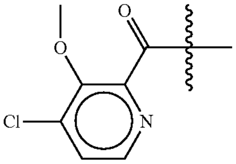,
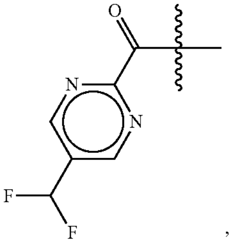,
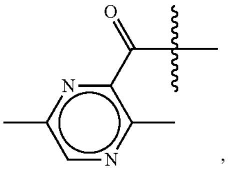,
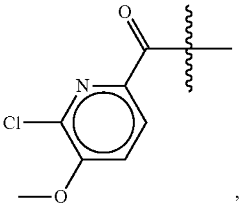,
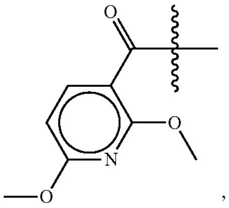,
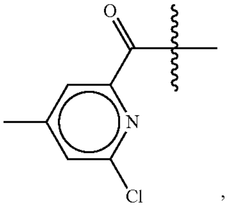,
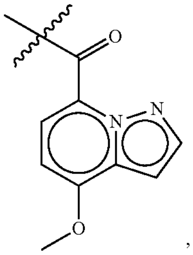,
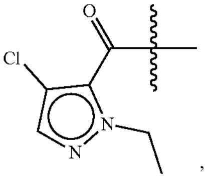,
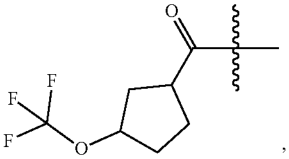,
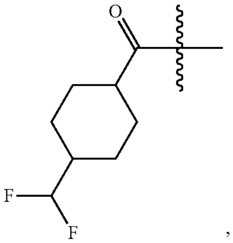, and
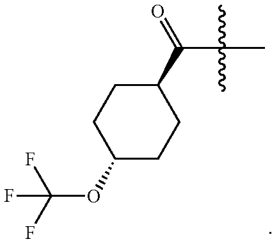.
In some embodiments, each $R^a$ independently is selected from:

-continued
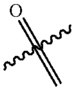,
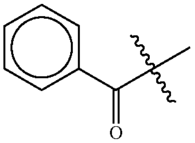,
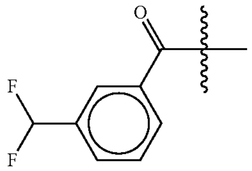,
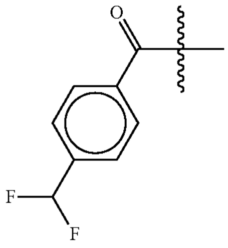,
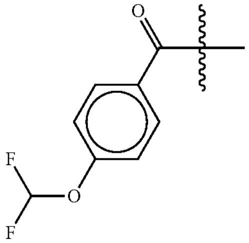,
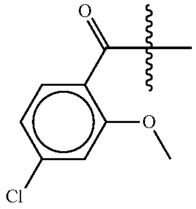,
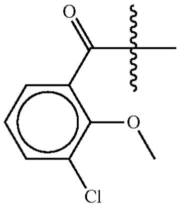,
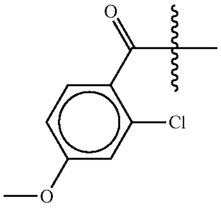,
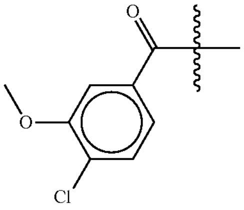,
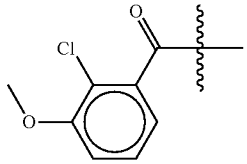,
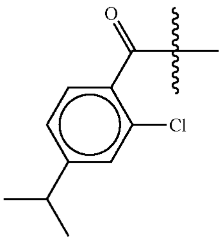,
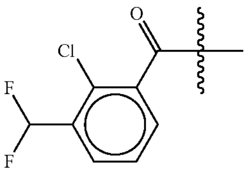,
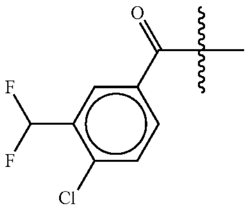,
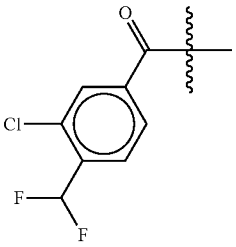,
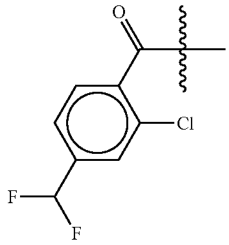,
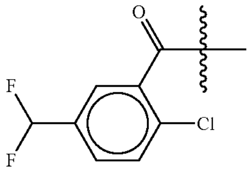,
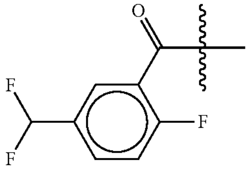,
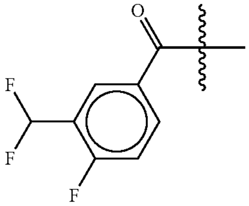,
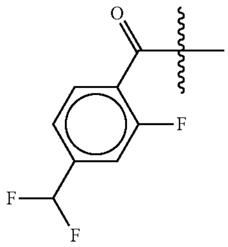,
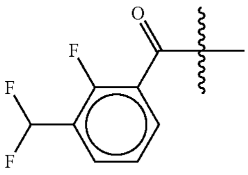,
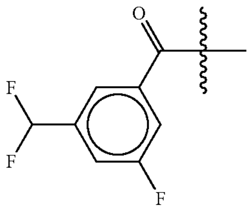,
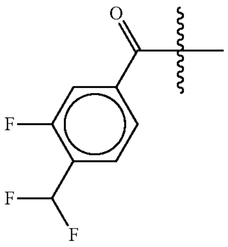,
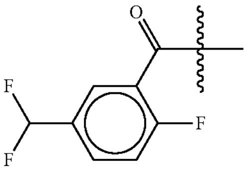,
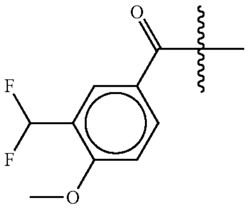,
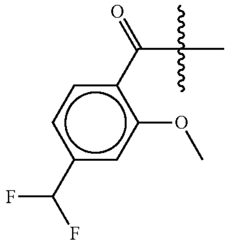,
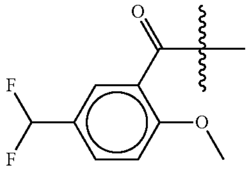,
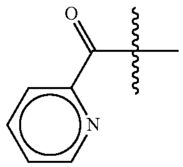,
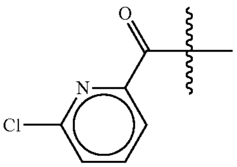, -continued
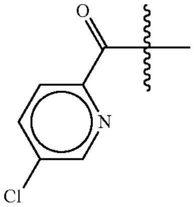,
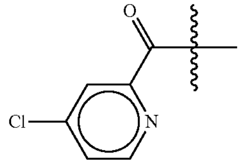,
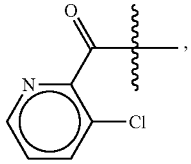,
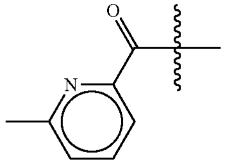,
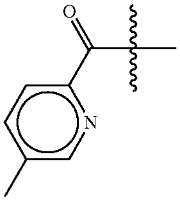,
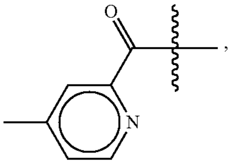,
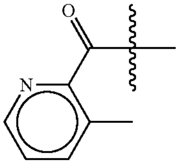,
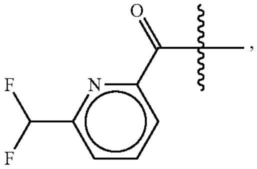,
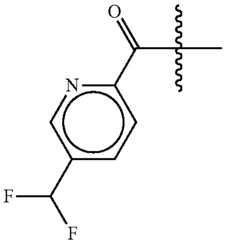,
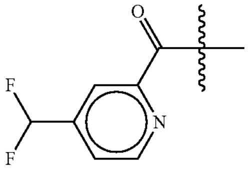,
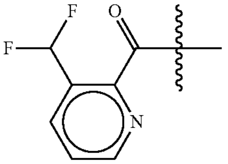,
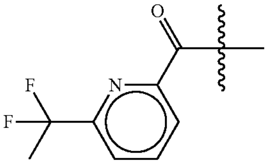,
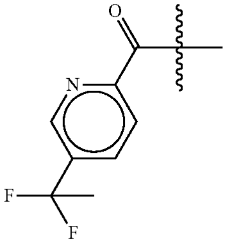,
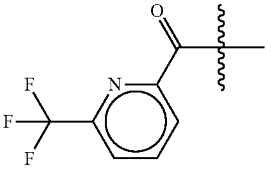,
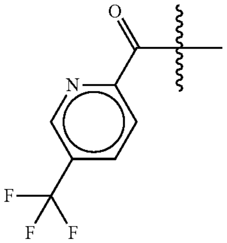,
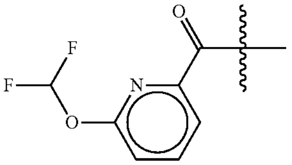,
-continued
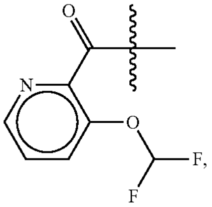,
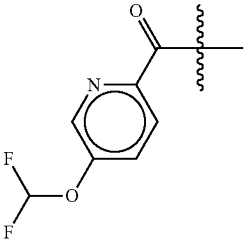,
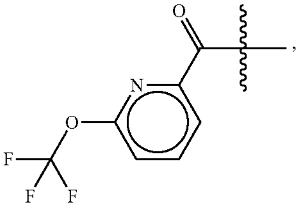,
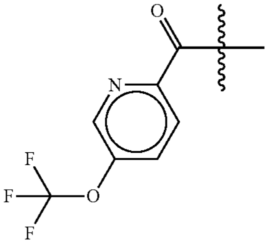,
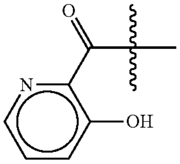,
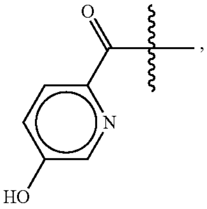,
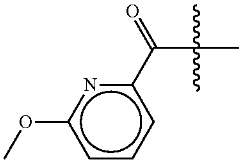,
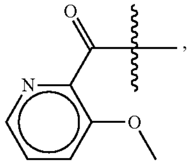,
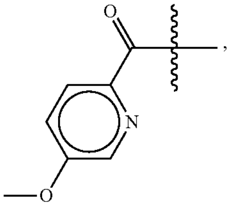,
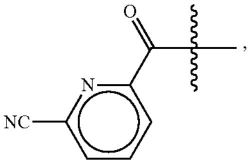,
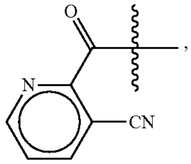,
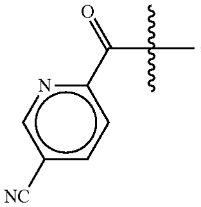,
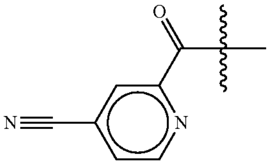,
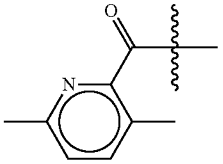,
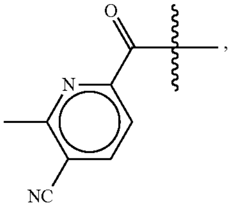, -continued
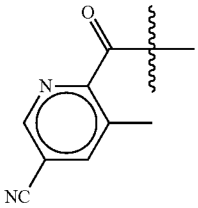,
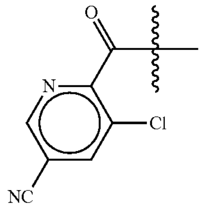,
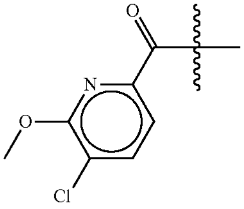,
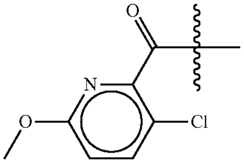,
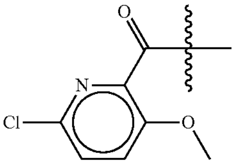,
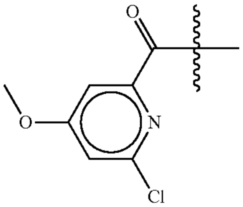,
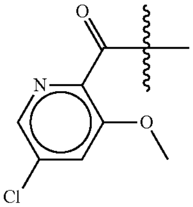,
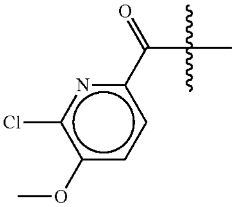,
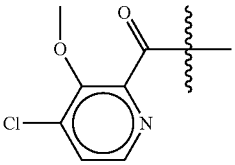,
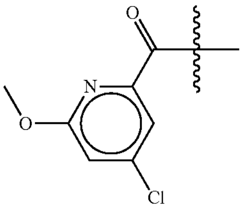,
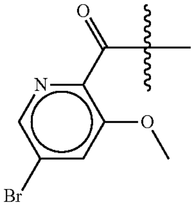,
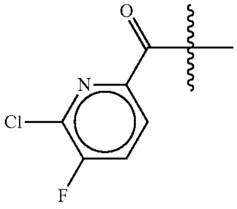,
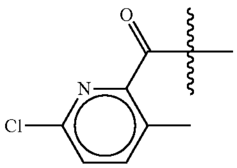,
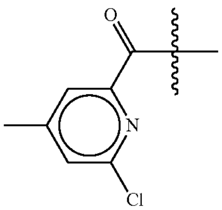,
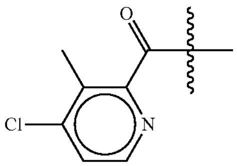,
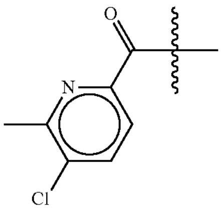,
-continued
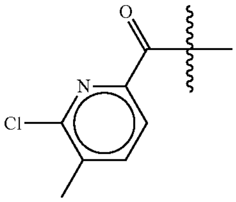,
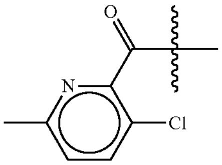,
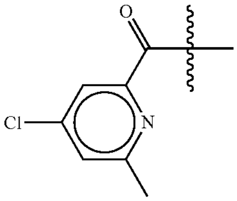,
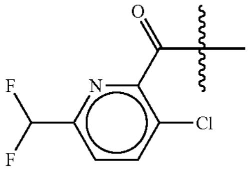,
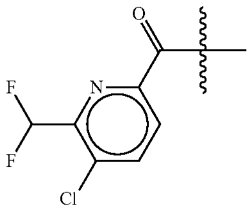,
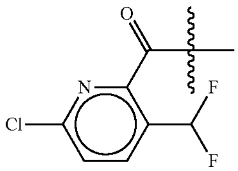,
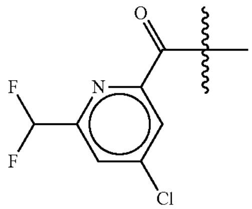,
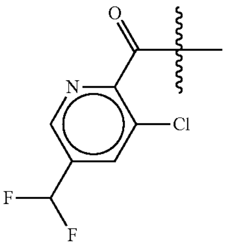,
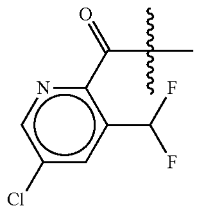,
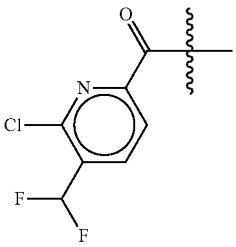,
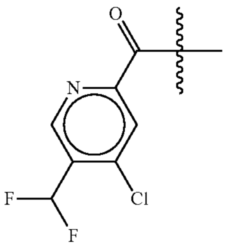,
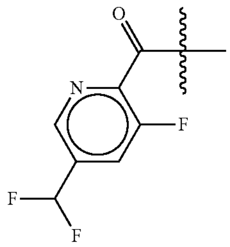,
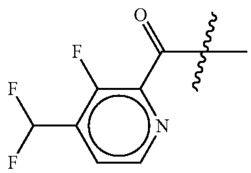,
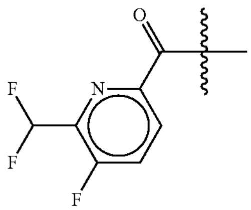, -continued
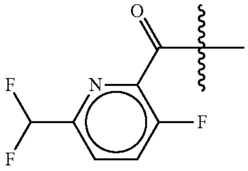,
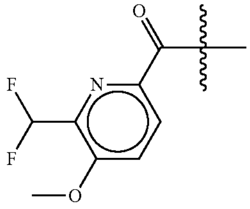,
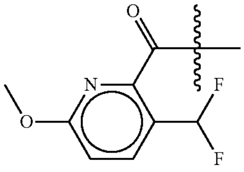,
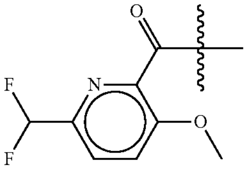,
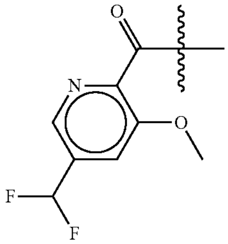,
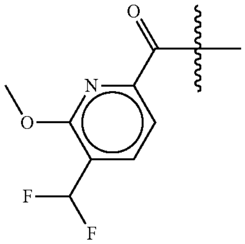,
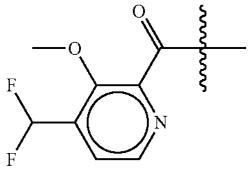,
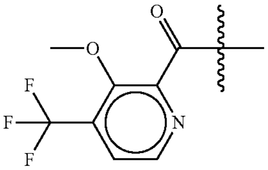,
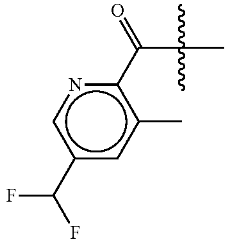,
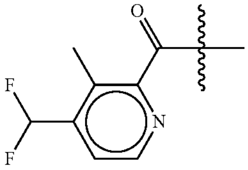,
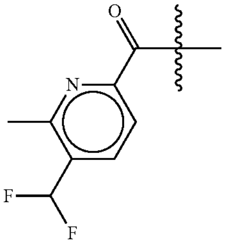,
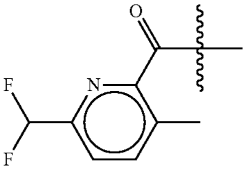,
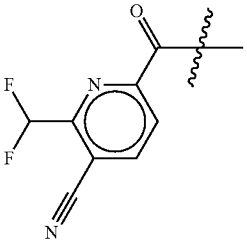,
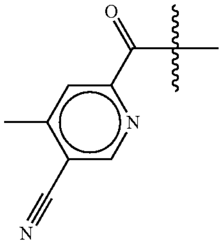,
-continued
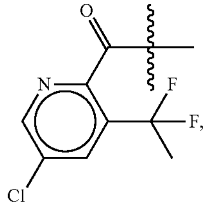
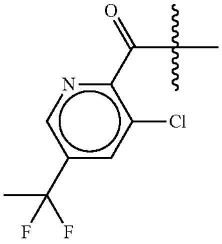,
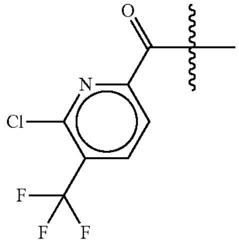,
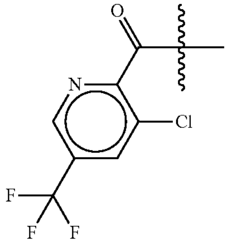,
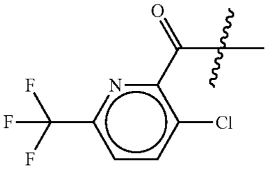,
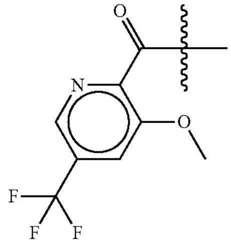,
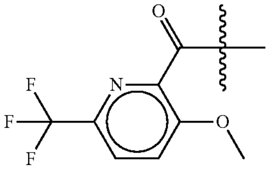,
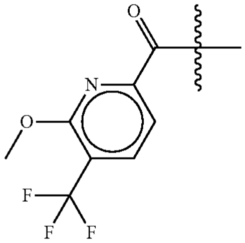,
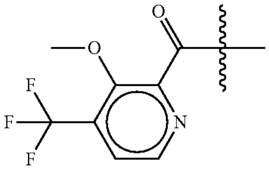,
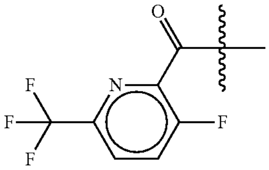,
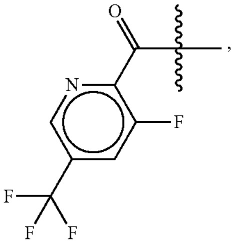,
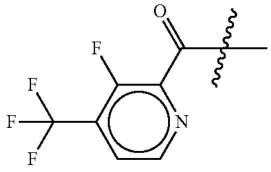,
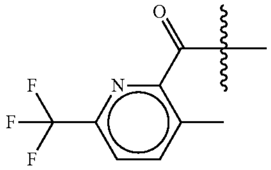,
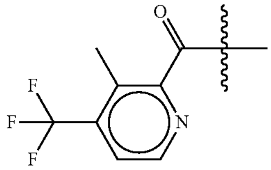, -continued
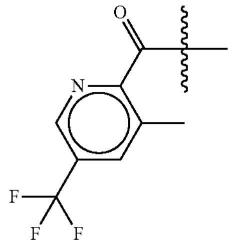,
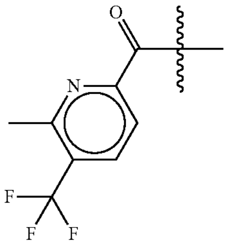,
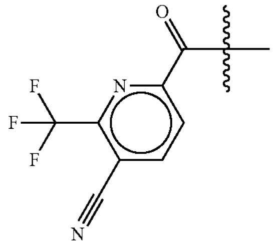,
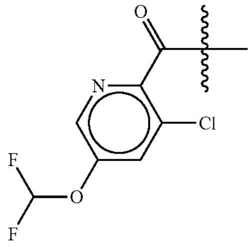,
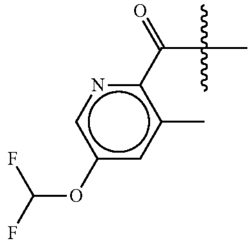,
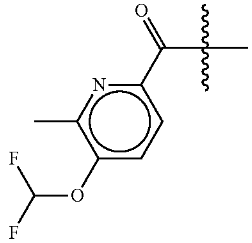,
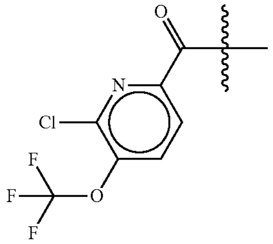,
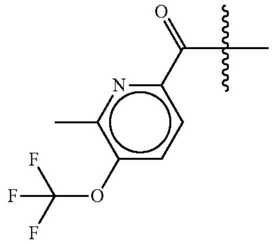,
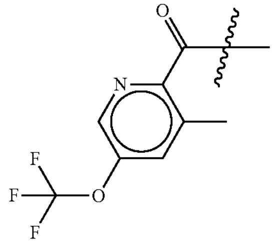,
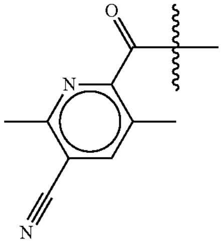,
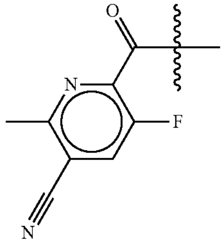,
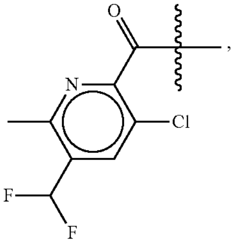,
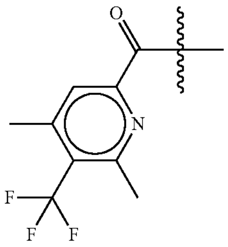,
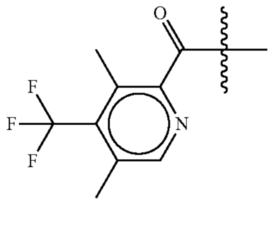,
-continued
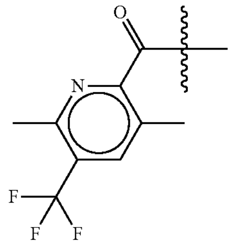,
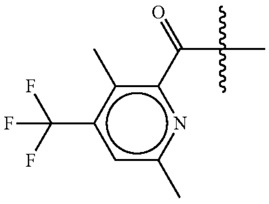,
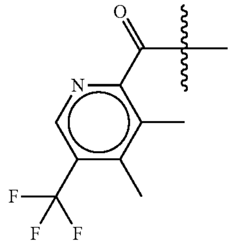,
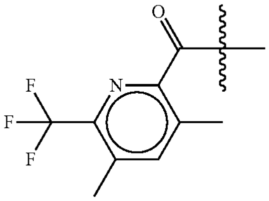,
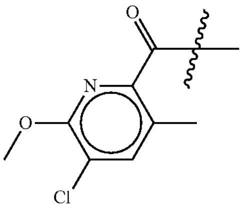,
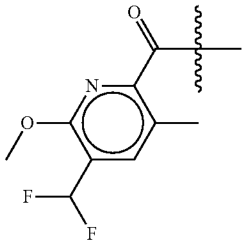,
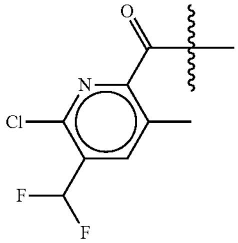,
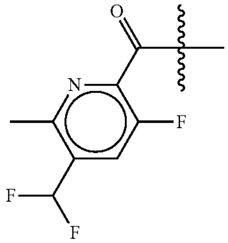,
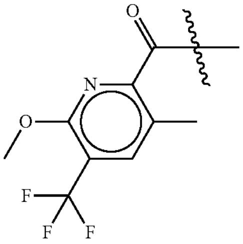,
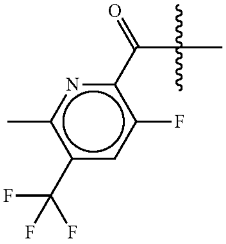,
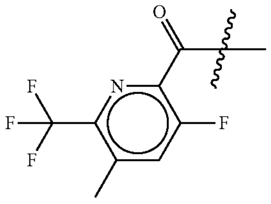,
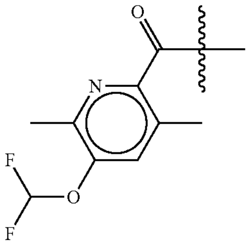,
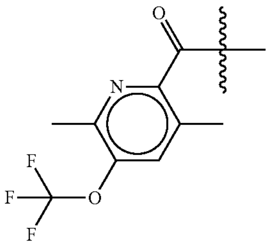,
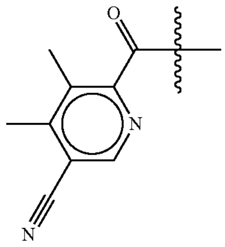, -continued
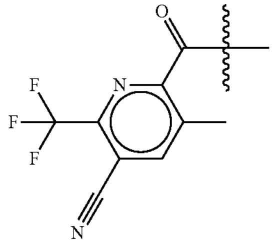
,
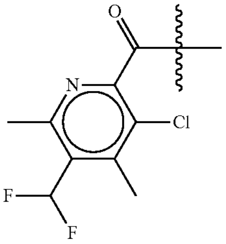
,
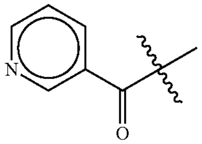
,
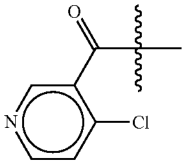
,
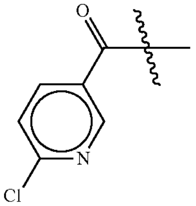
,
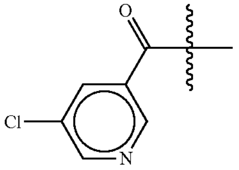
,
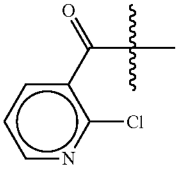
,
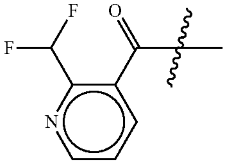
,
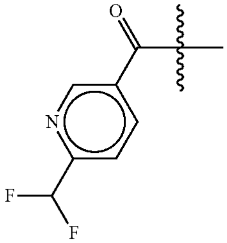
,
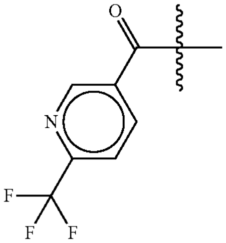
,
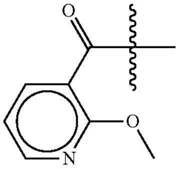
,
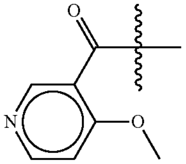
,
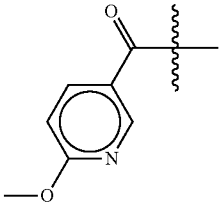
,
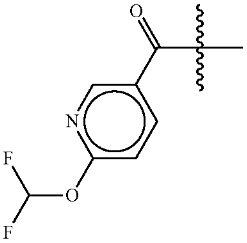
,
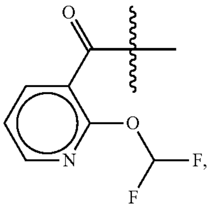
,
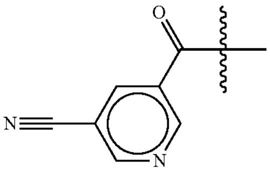
,
-continued
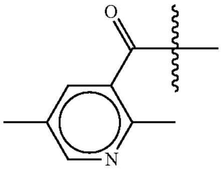
,
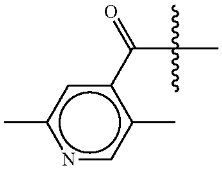
,
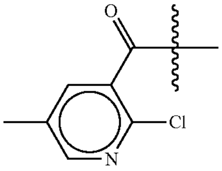
,
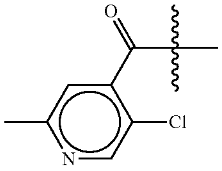
,
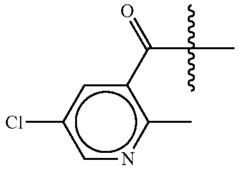
,
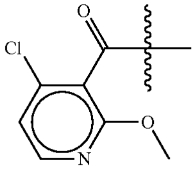
,
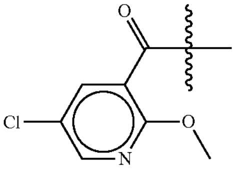
,
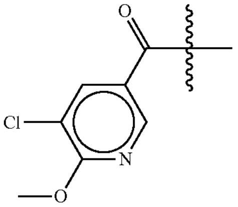
,
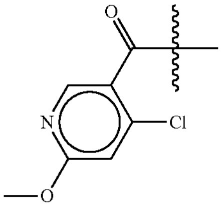
,
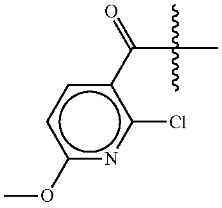
,
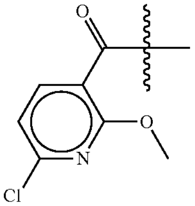
,
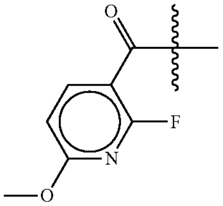
,
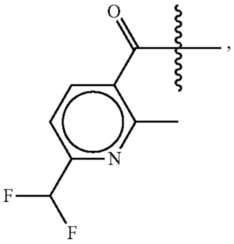
,
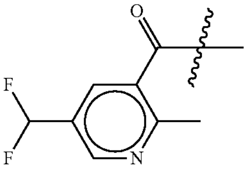
,
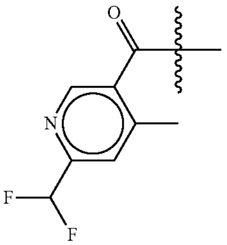
,
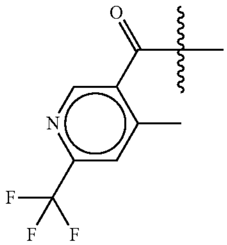
,

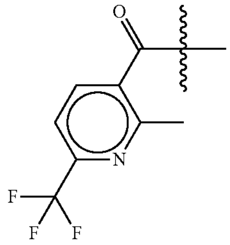,
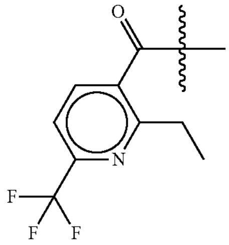,
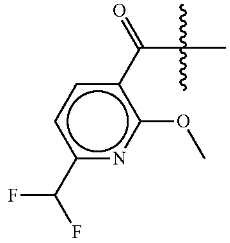,
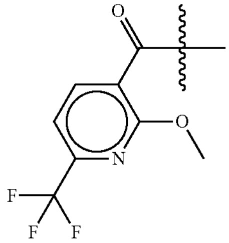,
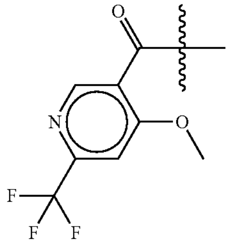,
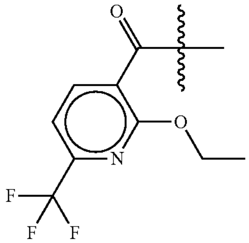,
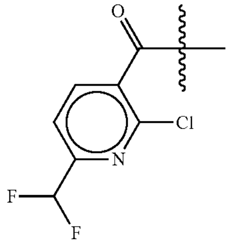,
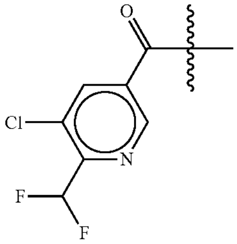,
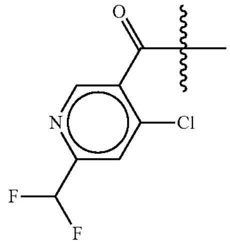,
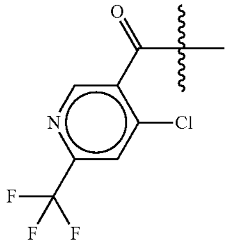,
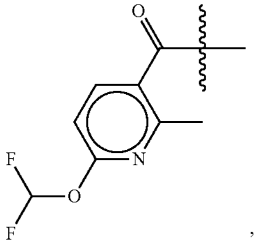,
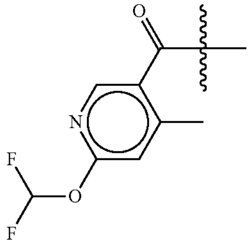,
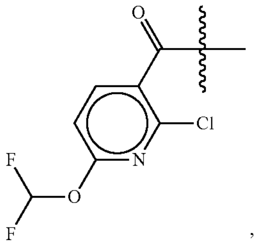,
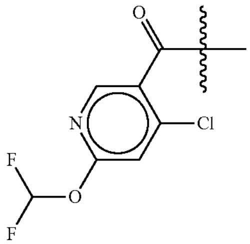,
-continued
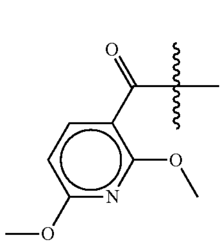,
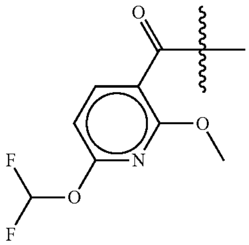,
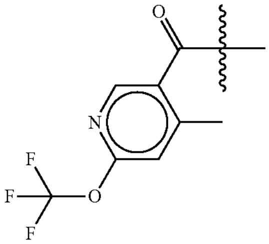,
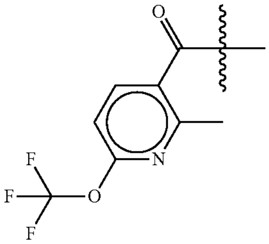,
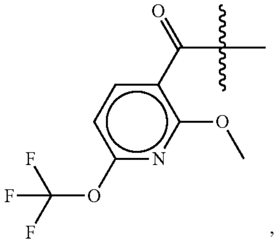,
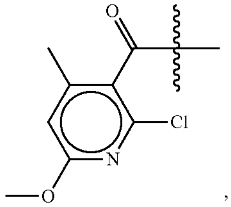,
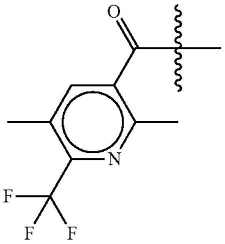,
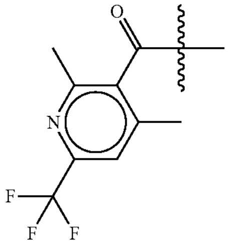,
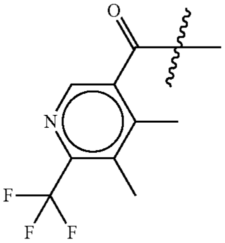,
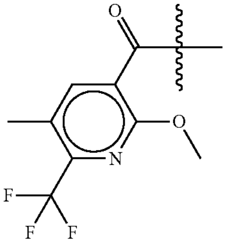,
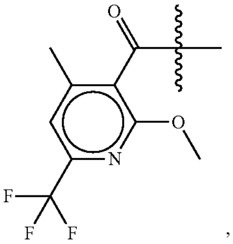,
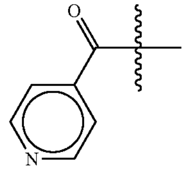,
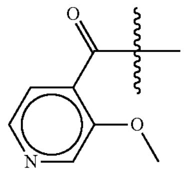,
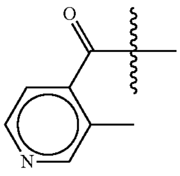, -continued
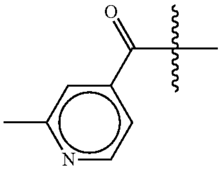,
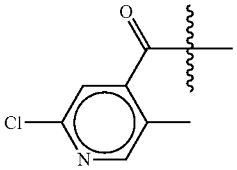,
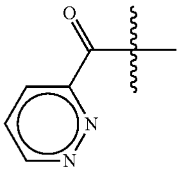,
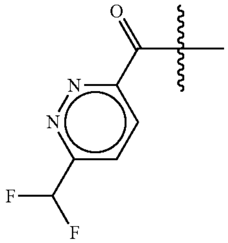,
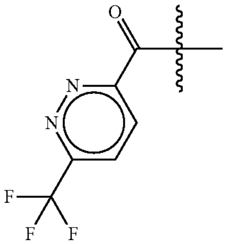,
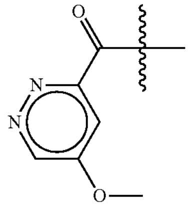,
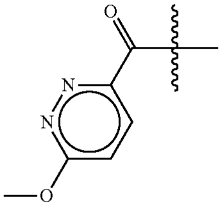,
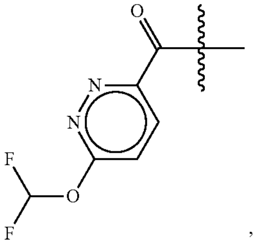,
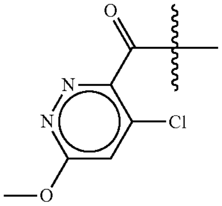,
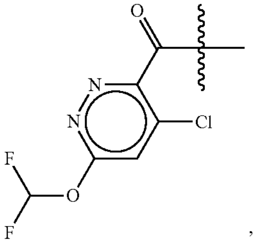,
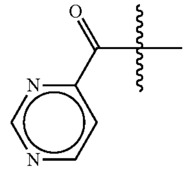,
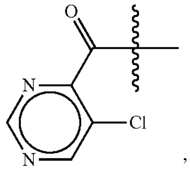,
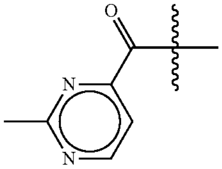,
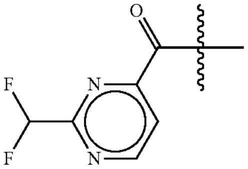,
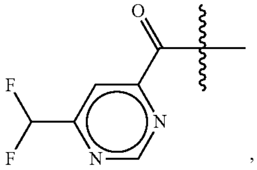,
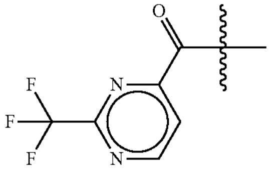,
-continued
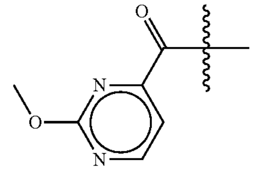,
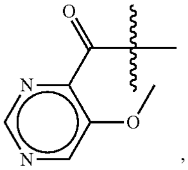,
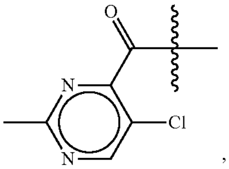,
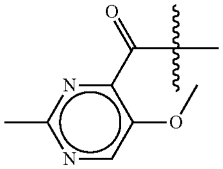,
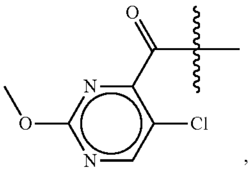,
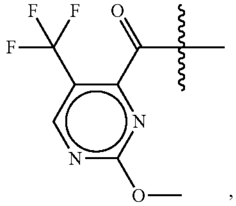,
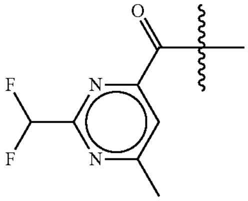,
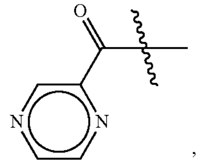,
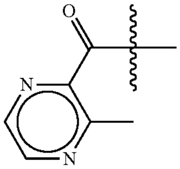,
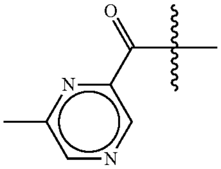,
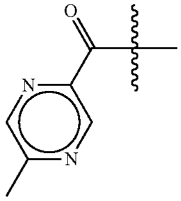,
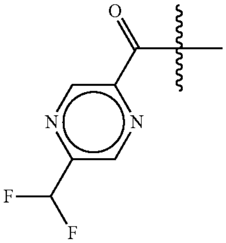,
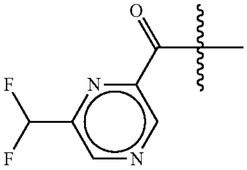,
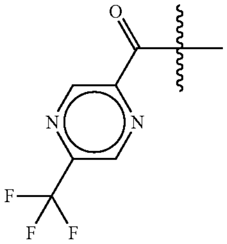,
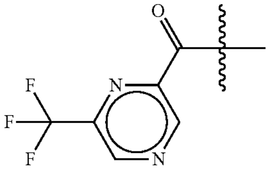,
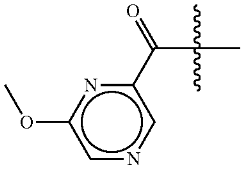, -continued
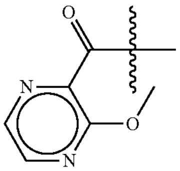,
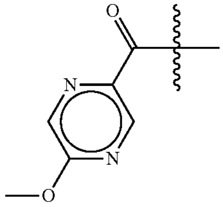,
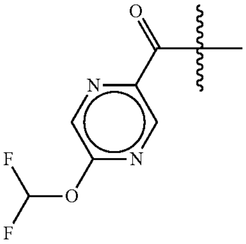,
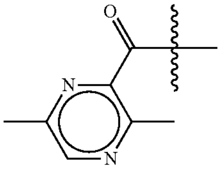,
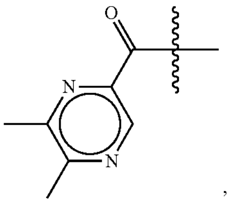,
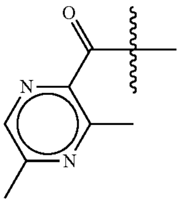,
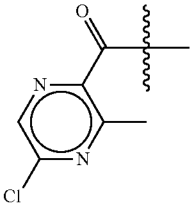,
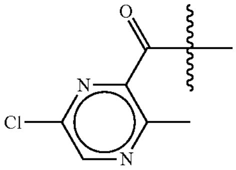,
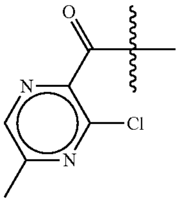,
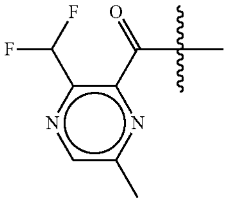,
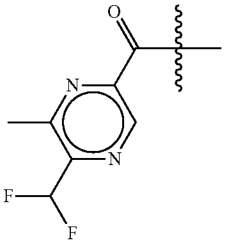,
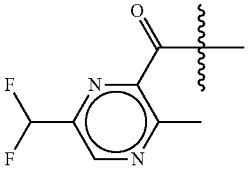,
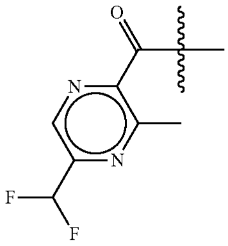,
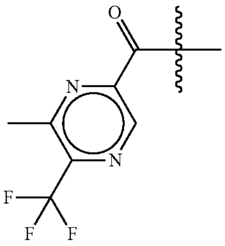,
-continued
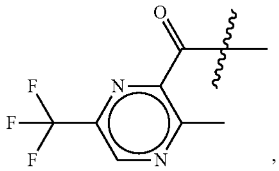,
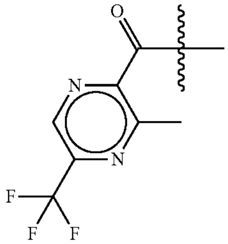,
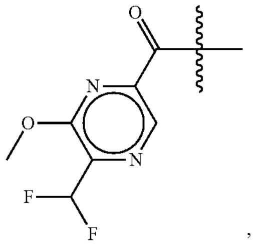,
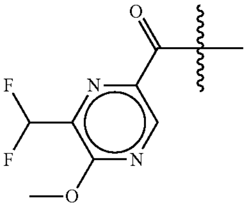,
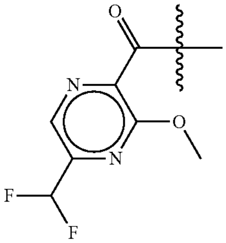,
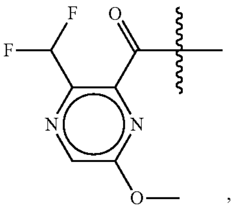,
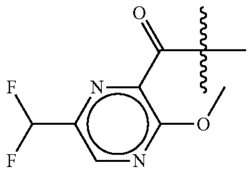,
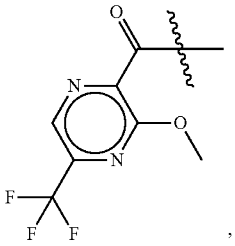,
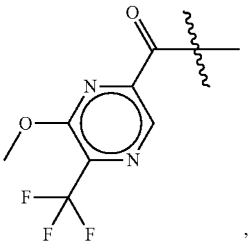,
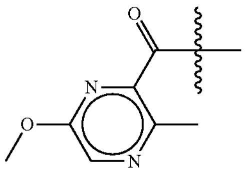,
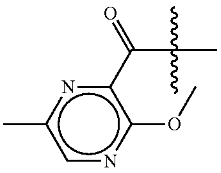,
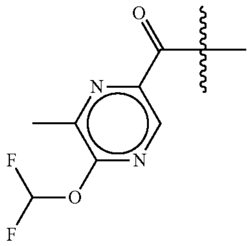,
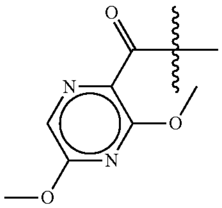,
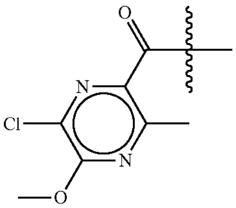,

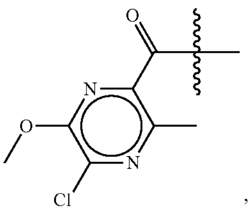,
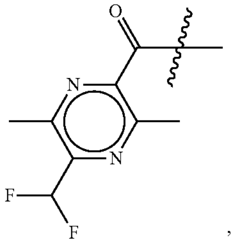,
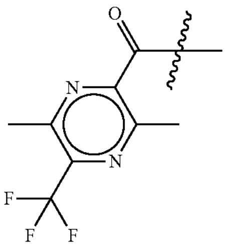,
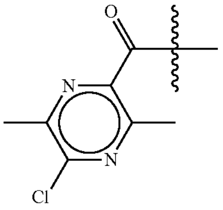,
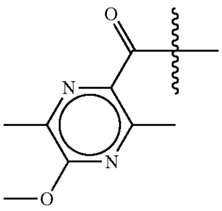,
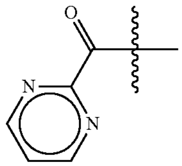,
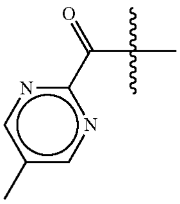,
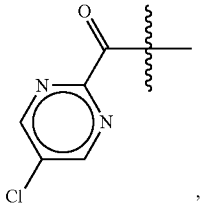,
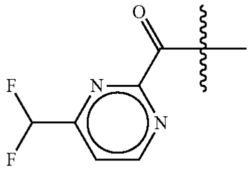,
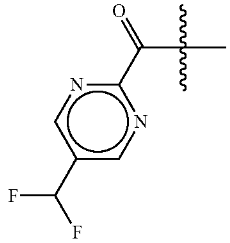,
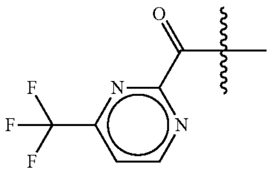,
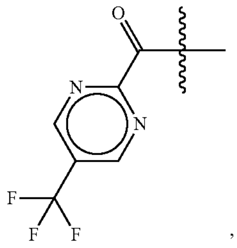,
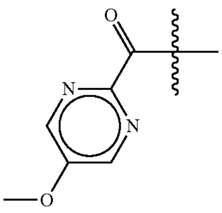,
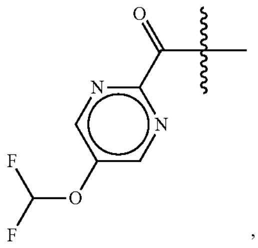,
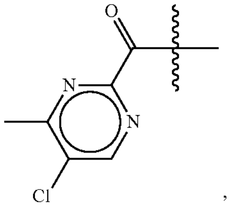,
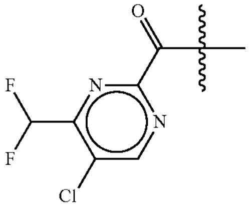,
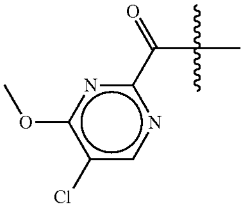,
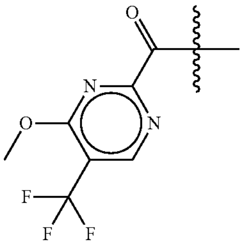,
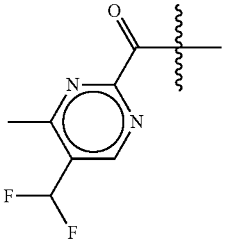,
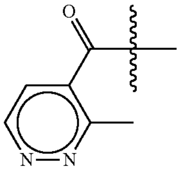,
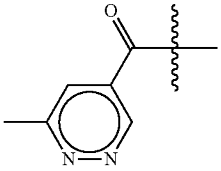,
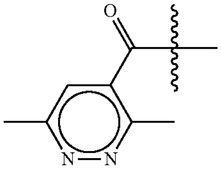,
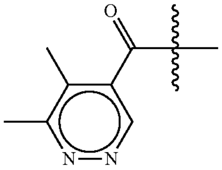,
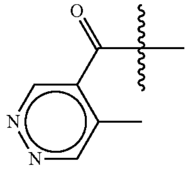,
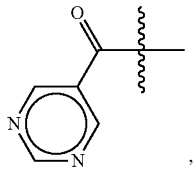,
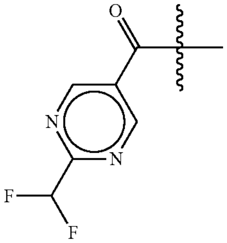,
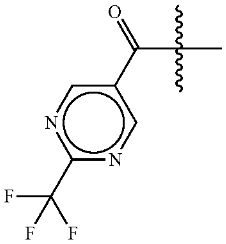,
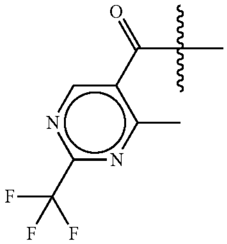,
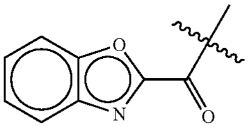,
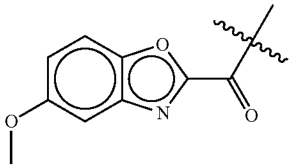, -continued
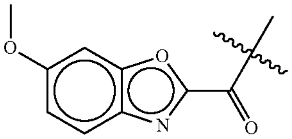 , 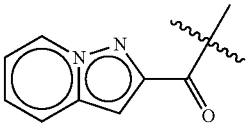 ,
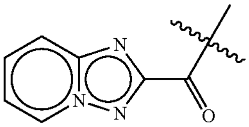 , 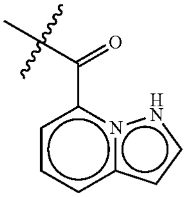 ,
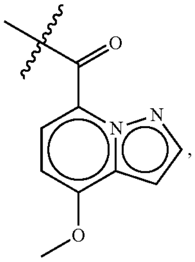 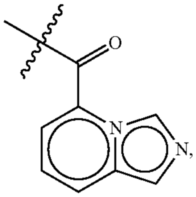
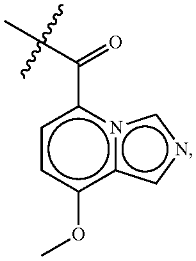 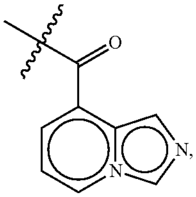
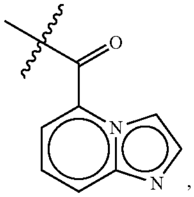 , 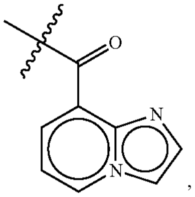 ,
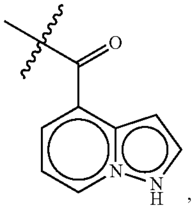 , 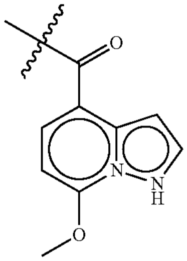 ,
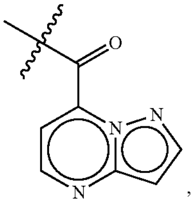 , 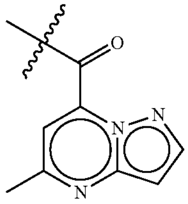 ,
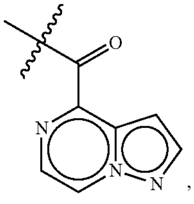 , 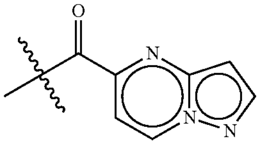 ,
-continued
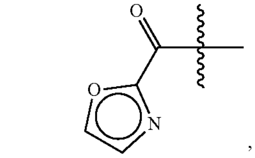 , 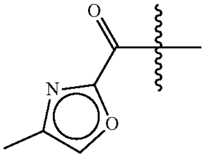 ,
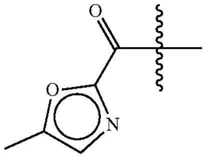 , 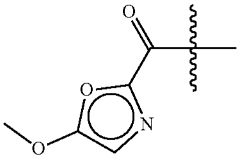 ,
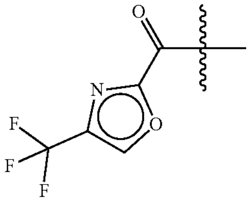 , 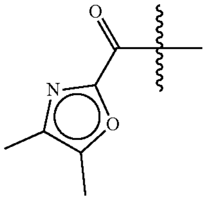 ,
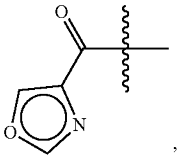 , 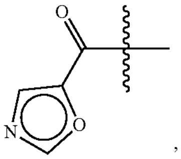 , 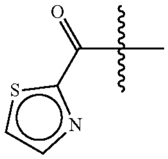 ,
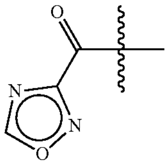 , 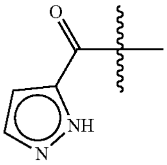 , 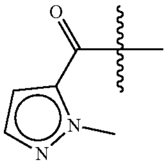 ,
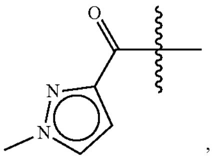 , 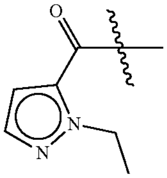 ,
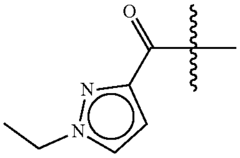 , 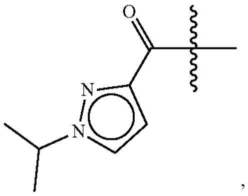 ,
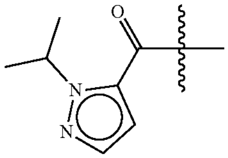 , 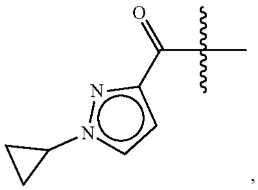 ,
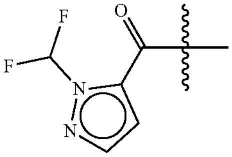 , 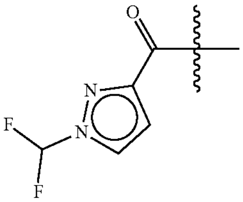 , -continued
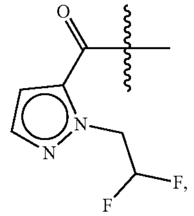
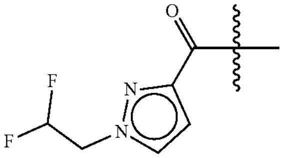
,
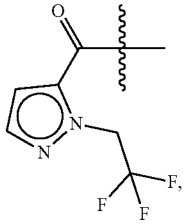
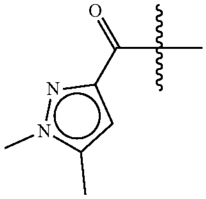
,
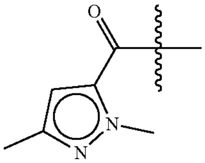
,
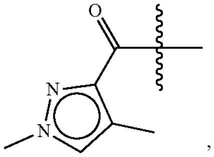
,
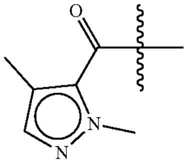
,
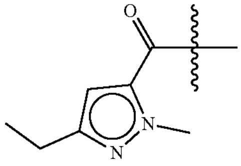
,
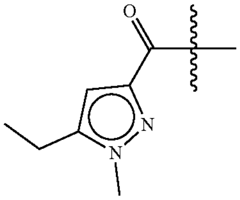
,
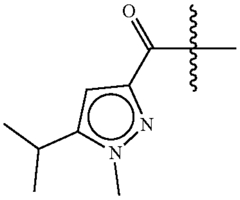
,
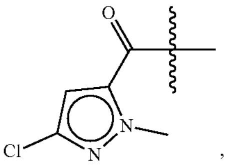
,
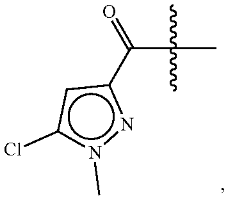
,
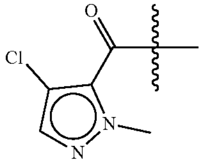
,
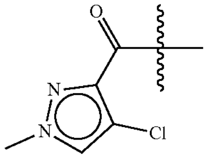
,
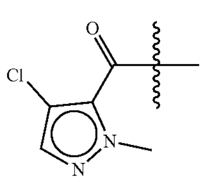
,
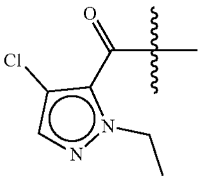
,
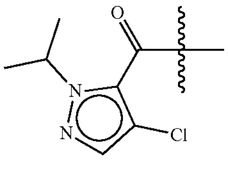
,
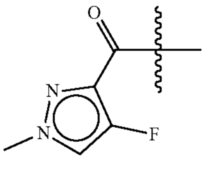
,
-continued
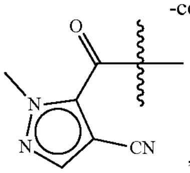
,
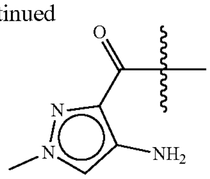
,
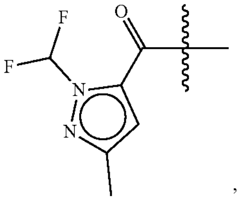
,
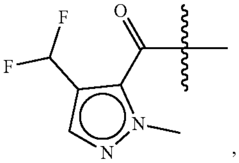
,
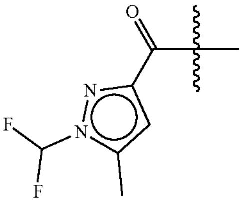
,
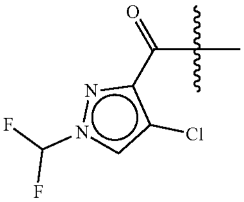
,
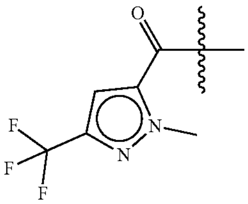
,
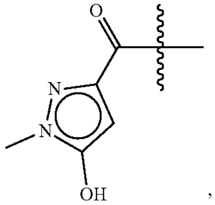
,
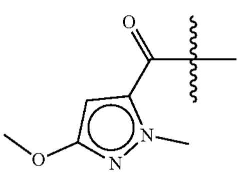
,
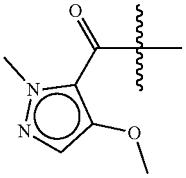
,
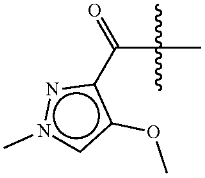
,
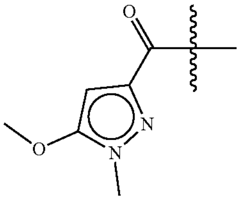
,
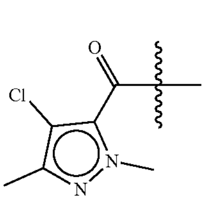
,
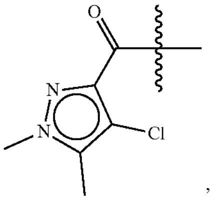
,
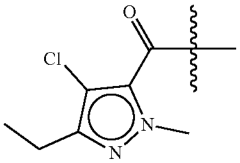
,
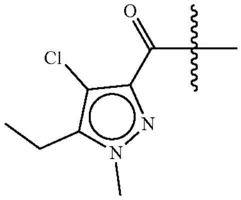
,
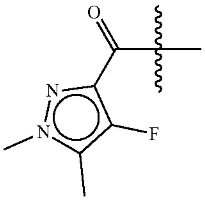
,
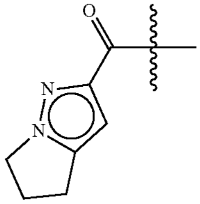
, -continued
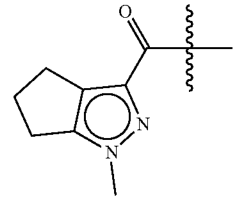,
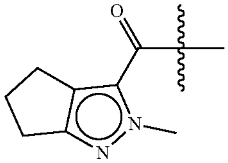,
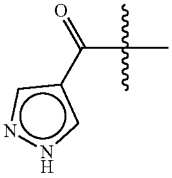,
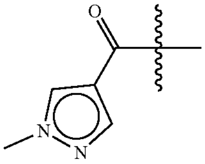,
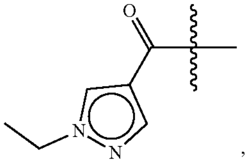,
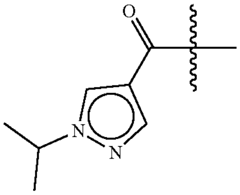,
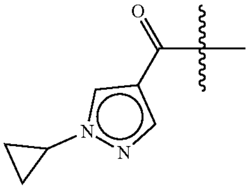,
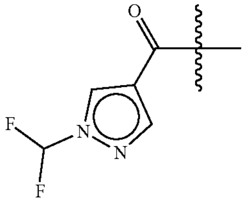,
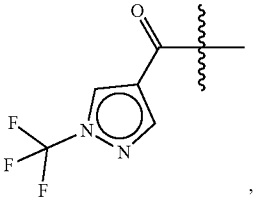,
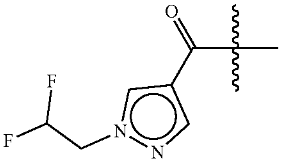,
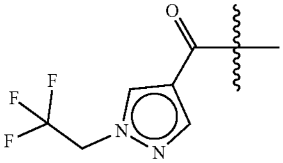,
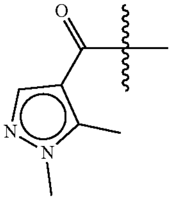,
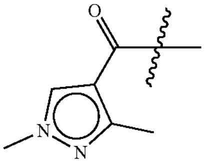,
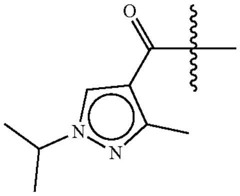,
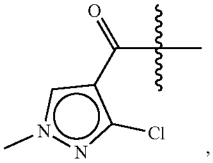,
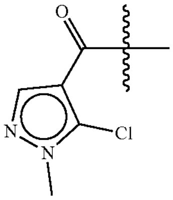,
-continued
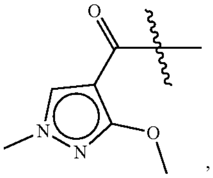,
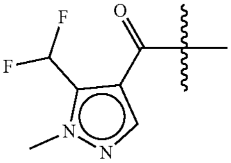,
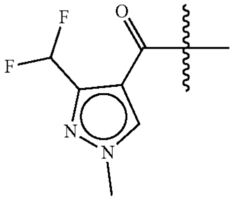,
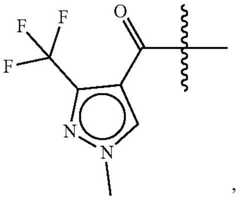,
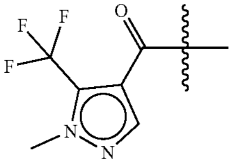,
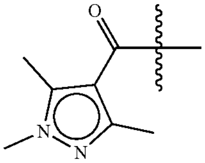,
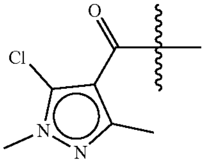,
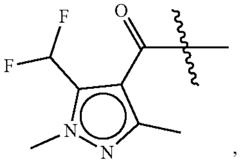,
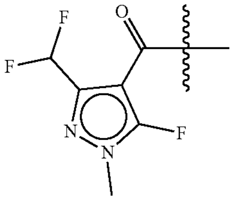,
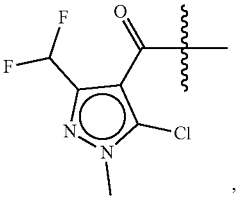,
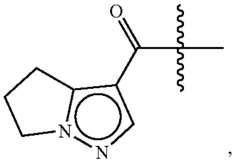,
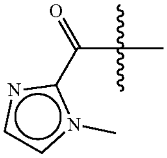,
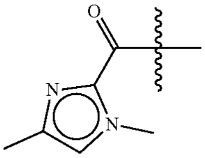,
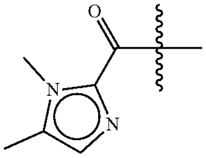,
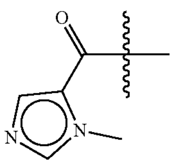,
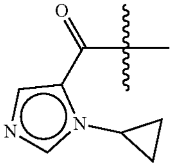,
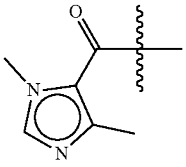,
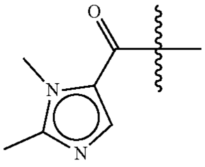,

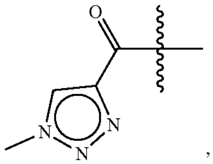 , 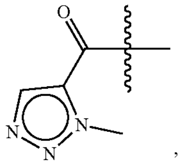 ,
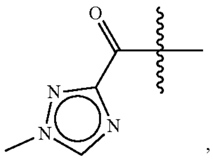 , 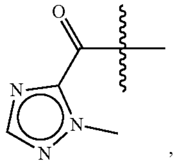 ,
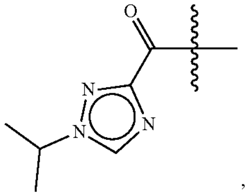 , 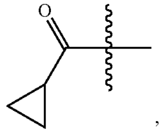 ,
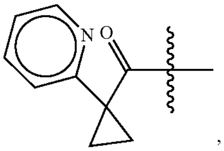 , 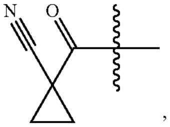 ,
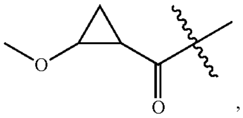 , 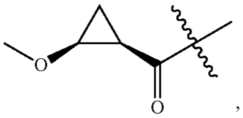 ,
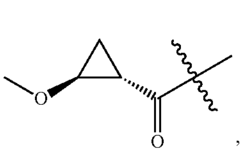 , 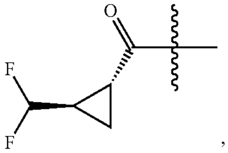 ,
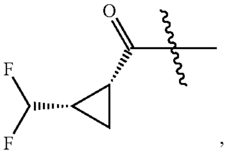 , 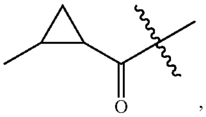 ,
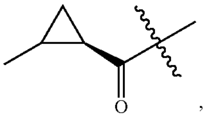 , 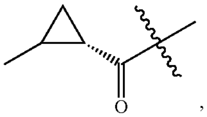 ,
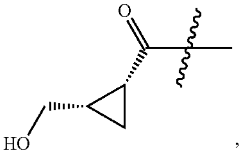 , 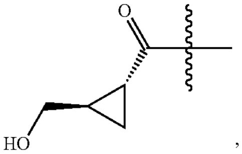 ,
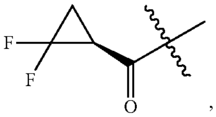 , 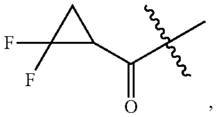 ,
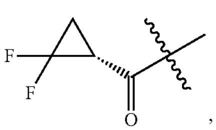 , 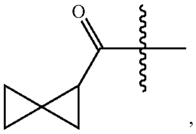 ,
-continued
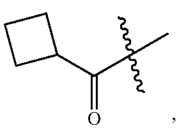 , 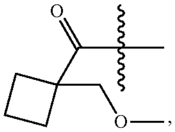 ,
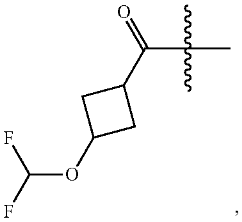 , 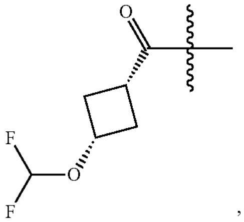 ,
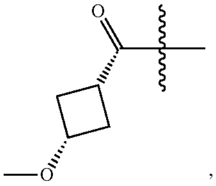 , 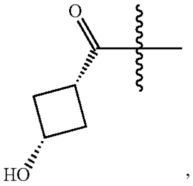 ,
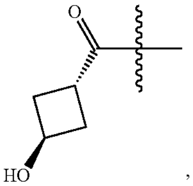 , 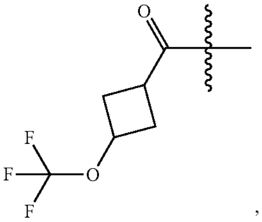 ,
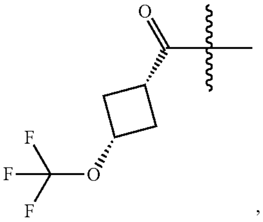 , 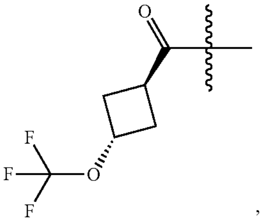 ,
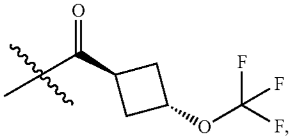
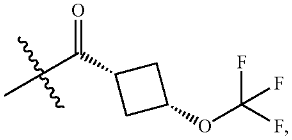 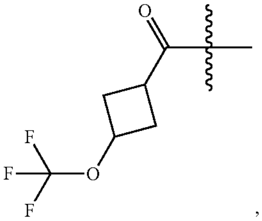 ,
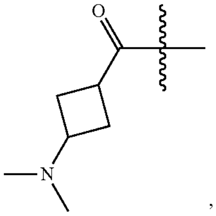 , 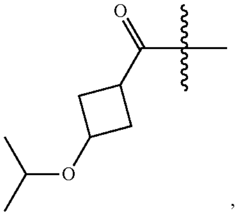 , -continued
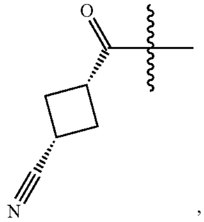, 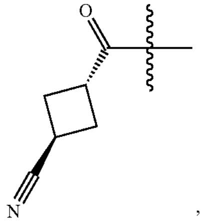, 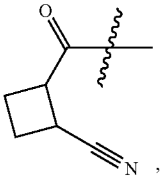, 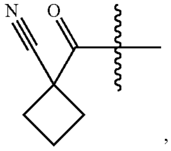, 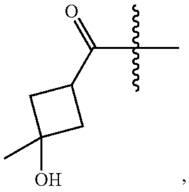, 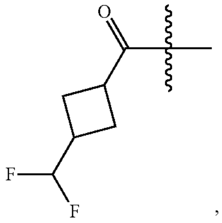, 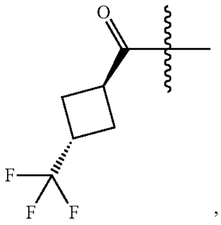, 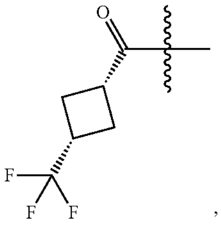, 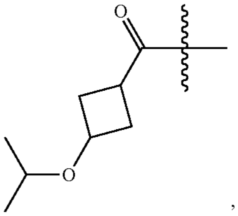, 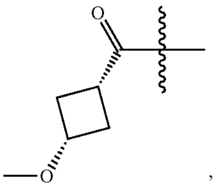, 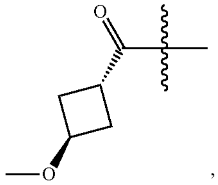, 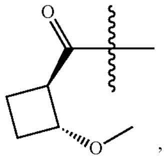, 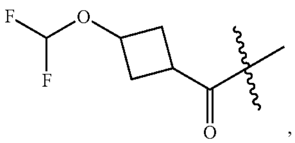, 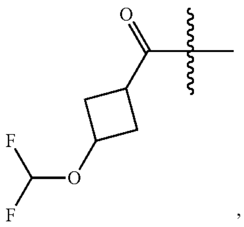, 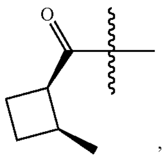, 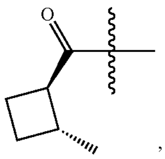, 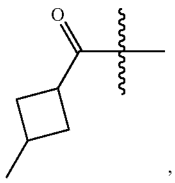,
-continued
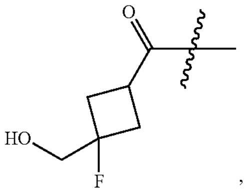, 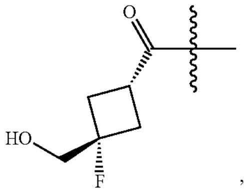, 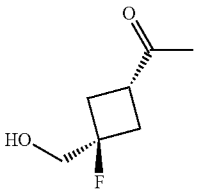, 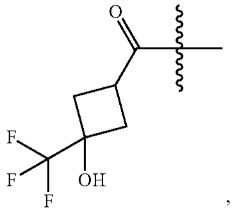, 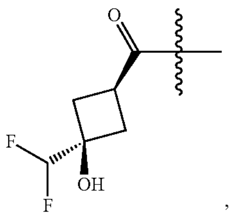, 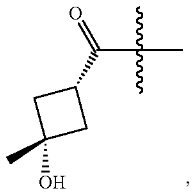, 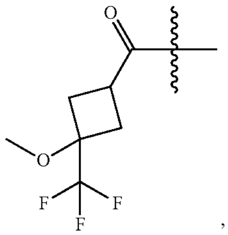, 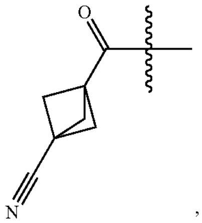, 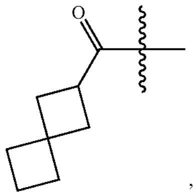, 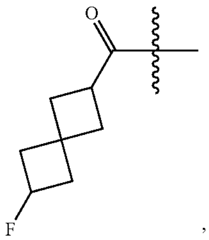, 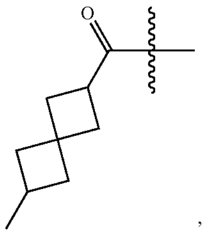, 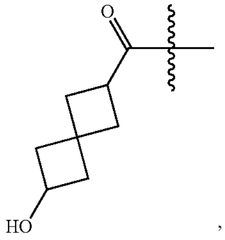, 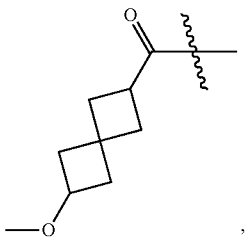, 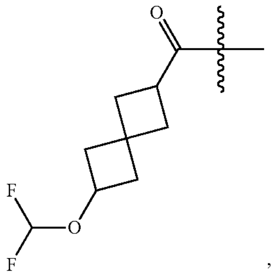, -continued
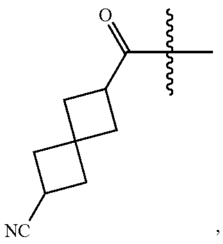,
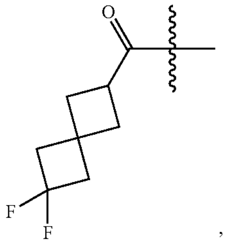,
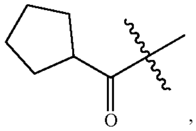,
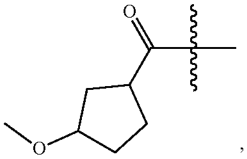,
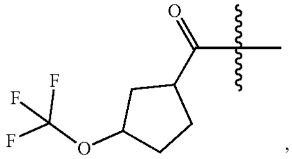,
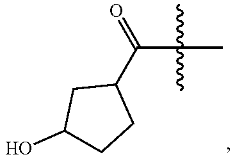,
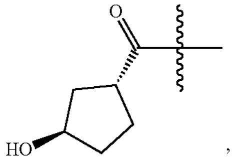,
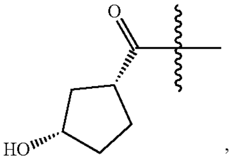,
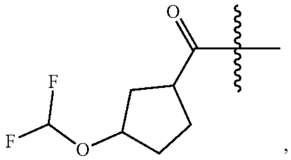,
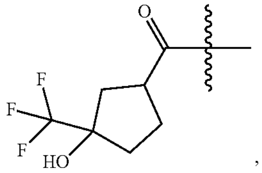,
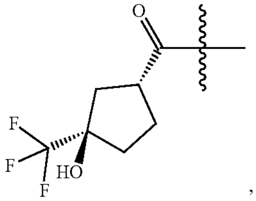,
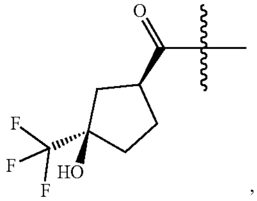,
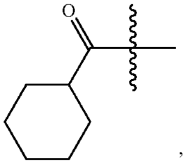,
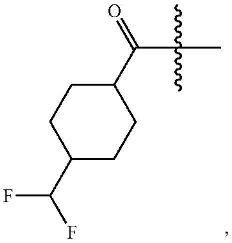,
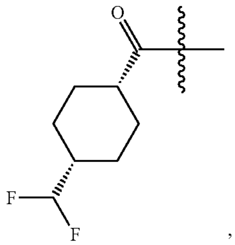,
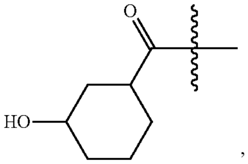,
-continued
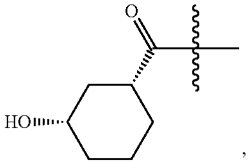,
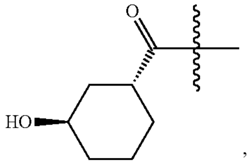,
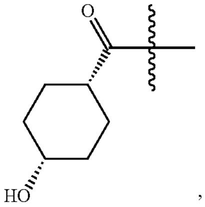,
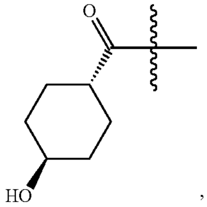,
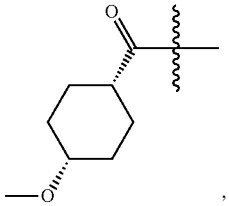,
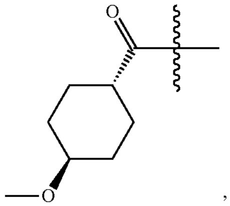,
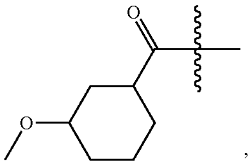,
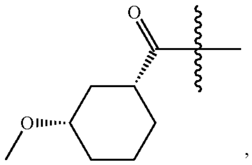,
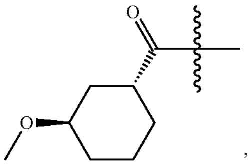,
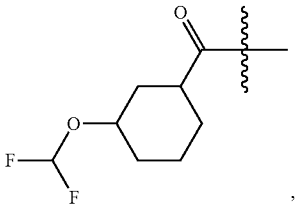,
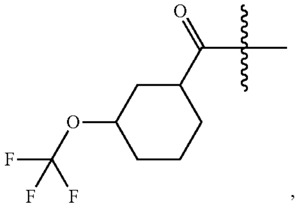,
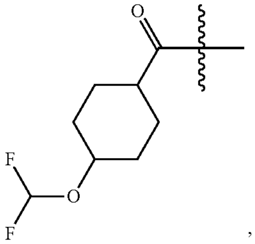,
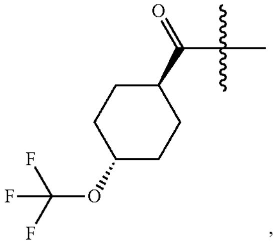,
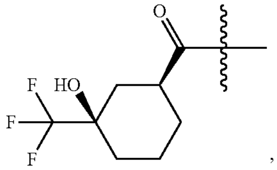,
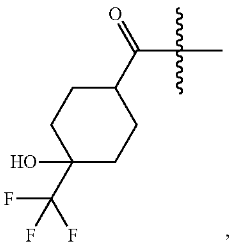,
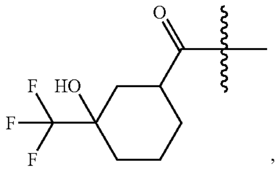, -continued
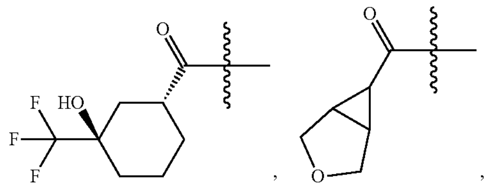
, ,
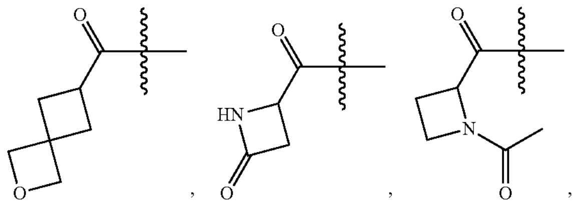
, , ,
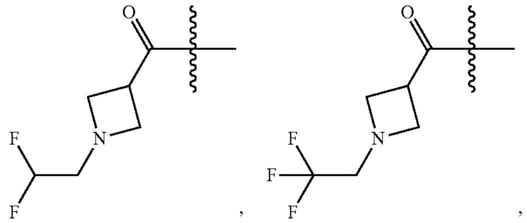
, ,
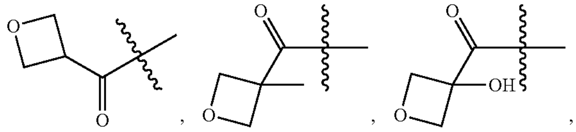
, , ,
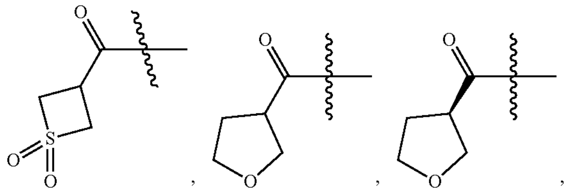
, , ,
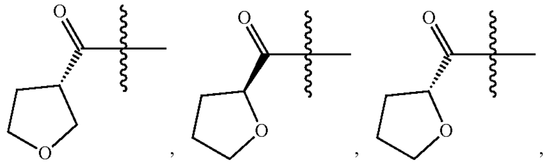
, , ,
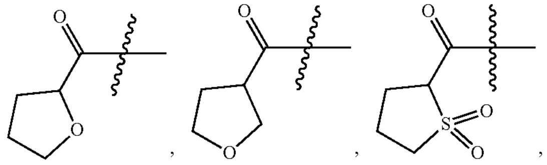
, , ,
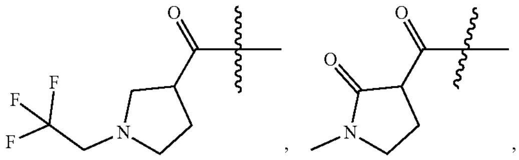
, ,
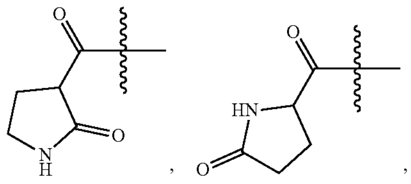
, ,
-continued
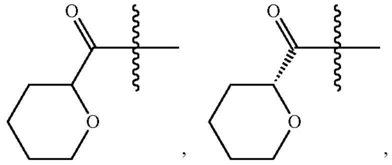
, ,
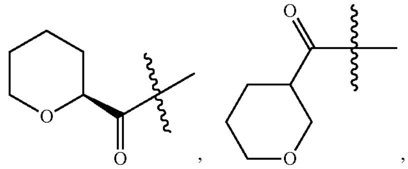
, ,
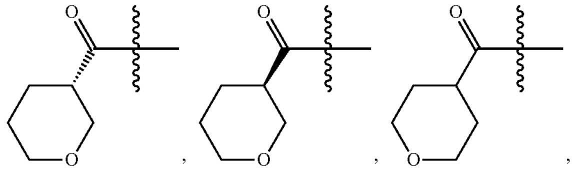
, , ,
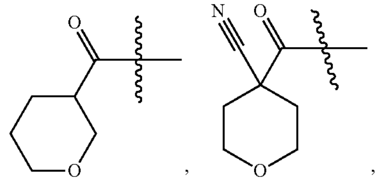
, ,
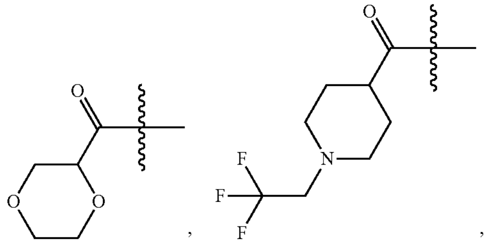
, ,
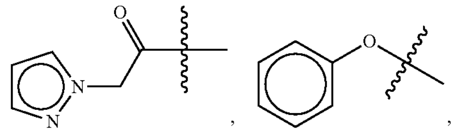
, ,
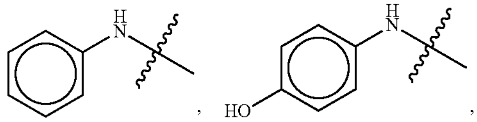
, ,
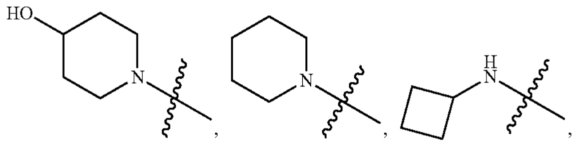
, , ,
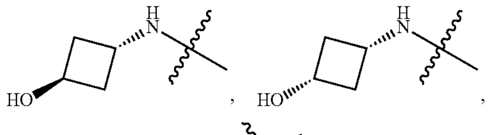
, ,
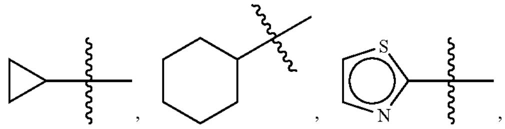
, , ,
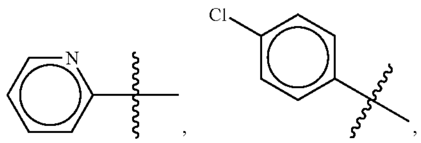
, , -continued
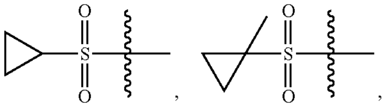, ,
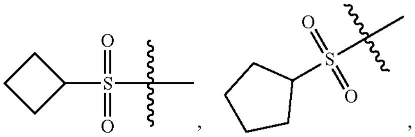, ,
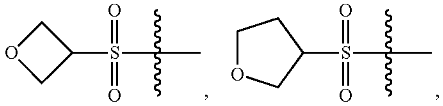, ,
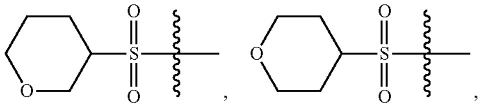, ,
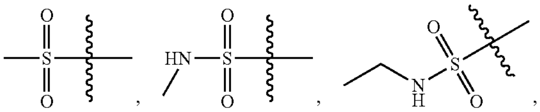, , ,
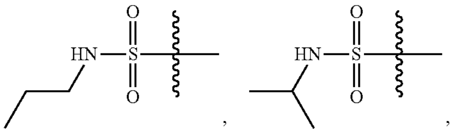, ,
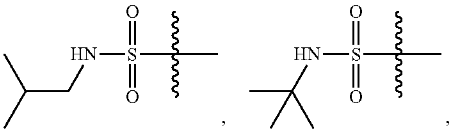, ,
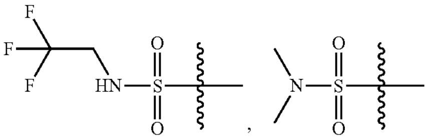, ,
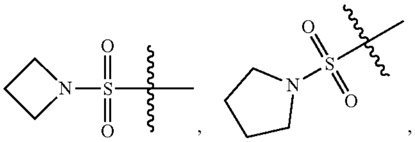, ,
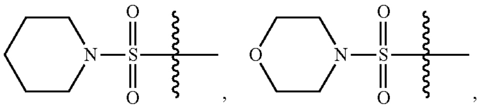, ,
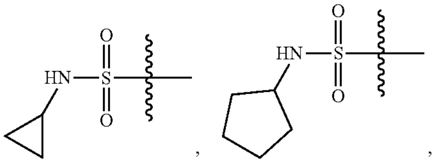, ,
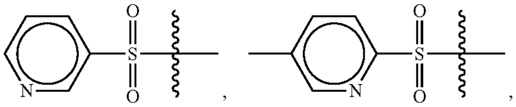, ,
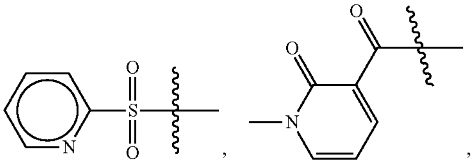, ,
-continued
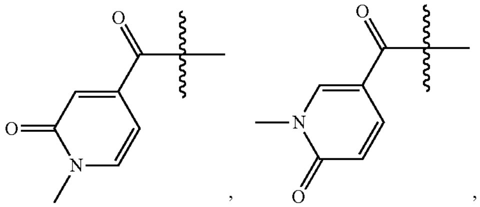, ,
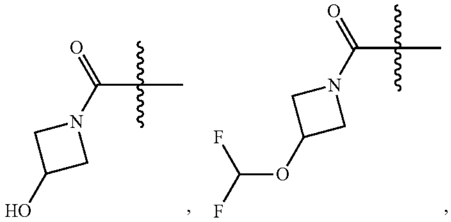, ,
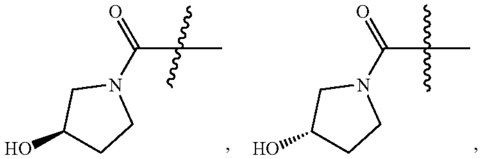, ,
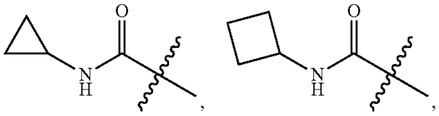, ,
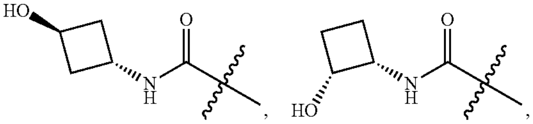, ,
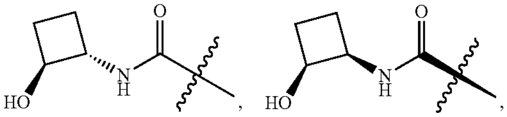, ,
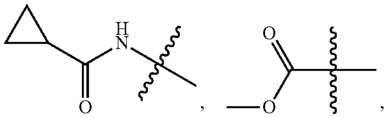, ,
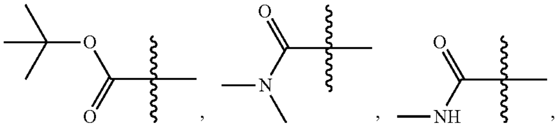, , ,
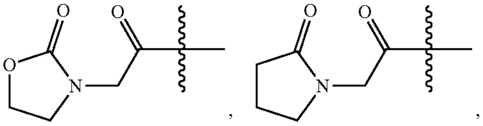, ,
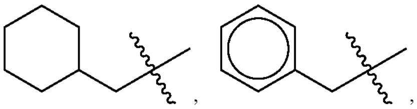, ,
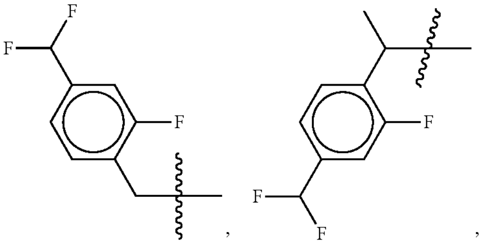, , -continued

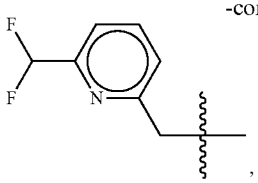,

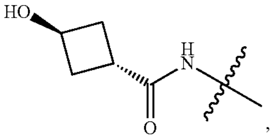,

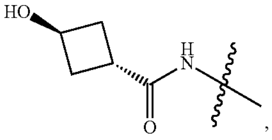, and

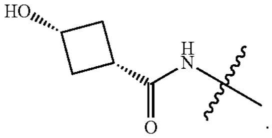.

In some embodiments, each $R^{a1}$ independently is H, halo, cyano, —C(O)($C_1$-$C_6$ alkyl), —C(O)($C_3$-$C_{10}$ cycloalkyl), $C_1$-$C_6$ alkyl. $C_3$-$C_{10}$ cycloalkyl, 3- to 10-membered heterocycloalkyl. $C_6$-$C_{10}$ aryl, or 5- to 10-membered heteroaryl.

In some embodiments, each $R^{a1}$ independently is H, halo, cyano, —C(O)($C_1$-$C_6$ alkyl), —C(O)($C_3$-$C_{10}$ cycloalkyl), $C_1$-$C_6$ alkyl, $C_3$-$C_{10}$ cycloalkyl, 3- to 10-membered heterocycloalkyl, $C_6$-$C_{10}$ aryl, or 5- to 10-membered heteroaryl, wherein the —C(O)($C_3$-$C_{10}$ cycloalkyl), $C_1$-$C_6$ alkyl. $C_3$-$C_{10}$ cycloalkyl, 3- to 10-membered heterocycloalkyl, $C_6$-$C_{10}$ aryl, or 5- to 10-membered heteroaryl is optionally substituted with one or more $R^{a2}$.

In some embodiments, each $R^{a1}$ independently is H, halo, cyano, —C(O)($C_1$-$C_6$ alkyl), —C(O)($C_3$-$C_{10}$ cycloalkyl). $C_1$-$C_6$ alkyl, $C_3$-$C_{10}$ cycloalkyl, 3- to 10-membered heterocycloalkyl, $C_6$-$C_{10}$ aryl, or 5- to 10-membered heteroaryl, wherein the —C(O)($C_3$-$C_{10}$ cycloalkyl), $C_1$-$C_6$ alkyl, $C_3$-$C_{10}$ cycloalkyl, 3- to 10-membered heterocycloalkyl, $C_6$-$C_{10}$ aryl, or 5- to 10-membered heteroaryl is substituted with one or more $R^1$.

In some embodiments, each $R^{a1}$ independently is H.

In some embodiments, each $R^{a1}$ independently is oxo.

In some embodiments, each $R^{a1}$ independently is halo.

In some embodiments, each $R^a$ independently is F, Cl, Br, or I. In some embodiments, each $R^{a1}$ independently is F, Cl, or Br. In some embodiments, each $R^{a1}$ independently is F or Cl.

In some embodiments, each $R^{a1}$ independently is F. In some embodiments, each $R^{a1}$ independently is Cl. In some embodiments, each $R^{a1}$ independently is Br. In some embodiments, each $R^{a1}$ independently is I.

In some embodiments, each $R^{a1}$ independently is cyano.

In some embodiments, each $R^{a1}$ independently is —OH.

In some embodiments, each $R^{a1}$ independently is —$NH_2$.

In some embodiments, each $R^{a1}$ independently is —C(O)($C_1$-$C_6$ alkyl).

In some embodiments, each $R^{a1}$ independently is —C(O)($C_3$-$C_{10}$ cycloalkyl).

In some embodiments, each $R^{a1}$ independently is —C(O)($C_3$-$C_{10}$ cycloalkyl) optionally substituted with one or more $R^{a2}$.

In some embodiments, each $R^{a1}$ independently is —C(O)($C_3$-$C_{10}$ cycloalkyl) substituted with one or more $R^{a2}$.

In some embodiments, each $R^{a1}$ independently is $C_1$-$C_6$ alkyl.

In some embodiments, each $R^{a1}$ independently is $C_1$-$C_6$ alkyl optionally substituted with one or more $R^{a2}$.

In some embodiments, each $R^{a1}$ independently is $C_1$-$C_6$ alkyl substituted with one or more R.

In some embodiments, each $R^{a1}$ independently is methyl. In some embodiments, each $R^{a1}$ independently is ethyl. In some embodiments, each $R^{a1}$ independently is propyl. In some embodiments, each $R^{a1}$ independently is butyl. In some embodiments, each R independently is pentyl. In some embodiments, each $R^{a1}$ independently is hexyl. In some embodiments, each $R^{a1}$ independently is isopropyl. In some embodiments, each $R^{a1}$ independently is isobutyl. In some embodiments, each $R^{a1}$ independently is isopentyl. In some embodiments, each $R^{a1}$ independently is isohexyl. In some embodiments, each $R^{a1}$ independently is secbutyl. In some embodiments, each $R^{a1}$ independently is secpentyl. In some embodiments, each $R^{a1}$ independently is sechexyl. In some embodiments, each $R^{a1}$ independently is tertbutyl.

In some embodiments, each $R^{a1}$ independently is $C_2$-$C_6$ alkenyl.

In some embodiments, each $R^{a1}$ independently is $C_2$-$C_6$ alkenyl optionally substituted with one or more R.

In some embodiments, each $R^{a1}$ independently is $C_2$-$C_6$ alkenyl substituted with one or more $R^{a2}$.

In some embodiments, each $R^{a1}$ independently is $C_2$-$C_6$ alkynyl.

In some embodiments, each $R^{a1}$ independently is $C_2$-$C_6$ alkynyl optionally substituted with one or more $R^{a2}$.

In some embodiments, each $R^{a1}$ independently is $C_2$-$C_6$ alkynyl substituted with one or more $R^{a2}$.

In some embodiments, each $R^{a1}$ independently is $C_1$-$C_6$ haloalkyl.

In some embodiments, each $R^{a1}$ independently is $C_1$-$C_6$ haloalkyl optionally substituted with one or more $R^{a2}$.

In some embodiments, each $R^{a1}$ independently is $C_1$-$C_6$ haloalkyl substituted with one or more $R^{a2}$.

In some embodiments, each $R^{a1}$ independently is halomethyl. In some embodiments, each $R^{a1}$ independently is haloethyl. In some embodiments, each $R^{a1}$ independently is halopropyl. In some embodiments, each $R^{a1}$ independently is halobutyl. In some embodiments, each $R^{a1}$ independently is halopentyl. In some embodiments, each $R^{a1}$ independently is halohexyl.

In some embodiments, each $R^{a1}$ independently is $C_1$-$C_6$ alkoxy.

In some embodiments, each R independently is $C_1$-$C_6$ alkoxy optionally substituted with one or more $R^{a2}$.

In some embodiments, each $R^{a1}$ independently is $C_1$-$C_6$ alkoxy substituted with one or more $R^2$.

In some embodiments, each $R^{a1}$ independently is $C_3$-$C_{10}$ cycloalkyl.

In some embodiments, each $R^{a1}$ independently is $C_3$-$C_{10}$ cycloalkyl optionally substituted with one or more $R^{a2}$.

In some embodiments, each R independently is $C_3$-$C_{10}$ cycloalkyl substituted with one or more $R^{a2}$.

In some embodiments, each $R^{a1}$ independently is $C_3$-$C_7$ cycloalkyl.

In some embodiments, each $R^{a1}$ independently is $C_3$-$C_7$ cycloalkyl optionally substituted with one or more $R^{a2}$.

In some embodiments, each Rai independently is $C_3$-$C_7$ cycloalkyl substituted with one or more $R^{a2}$.

In some embodiments, each $R^{a1}$ independently 3- to 10-membered heterocycloalkyl.

In some embodiments, each $R^1$ independently is 3- to 10-membered heterocycloalkyl optionally substituted with one or more $R^{a2}$.

In some embodiments, each $R^{a1}$ independently is 3- to 10-membered heterocycloalkyl substituted with one or more $R^{a2}$.

In some embodiments, each $R^{a1}$ independently 3- to 7-membered heterocycloalkyl.

In some embodiments, each $R^{a1}$ independently is 3- to 7-membered heterocycloalkyl optionally substituted with one or more $R^{a2}$.

In some embodiments, each $R^{a1}$ independently is 3- to 7-membered heterocycloalkyl substituted with one or more $R^{a2}$.

In some embodiments, each $R^{a1}$ independently is $C_6$-$C_{10}$ aryl.

In some embodiments, each $R^{a1}$ independently is $C_6$-$C_{10}$ aryl optionally substituted with one or more $R^{a2}$.

In some embodiments, each $R^{a1}$ independently is $C_6$-$C_{10}$ aryl substituted with one or more R.

In some embodiments, each $R^{a1}$ independently is $C_6$ aryl.

In some embodiments, each $R^{a1}$ independently is $C_6$ aryl optionally substituted with one or more $R^{a2}$.

In some embodiments, each $R^{a1}$ independently is $C_6$ aryl substituted with one or more $R^{a2}$.

In some embodiments, each $R^{a1}$ independently is 5- to 10-membered heteroaryl.

In some embodiments, each $R^{a1}$ independently is 5- to 10-membered heteroaryl optionally substituted with one or more $R^{a2}$.

In some embodiments, each $R^{a1}$ independently is 5- to 10-membered heteroaryl substituted with one or more $R^{a2}$.

In some embodiments, each $R^{a1}$ independently is 5- to 6-membered heteroaryl.

In some embodiments, each $R^{a1}$ independently is 5- to 6-membered heteroaryl optionally substituted with one or more $R^{a2}$.

In some embodiments, each $R^{a1}$ independently is 5- to 6-membered heteroaryl substituted with one or more $R^{a2}$.

In some embodiments, each $R^{a1}$ independently is:

H, —OH, —$CH_3$,

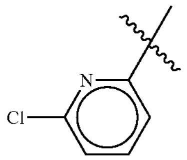,
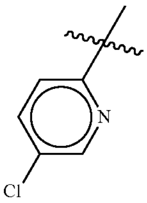,
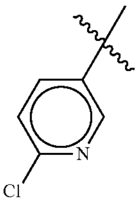,
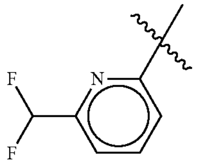,
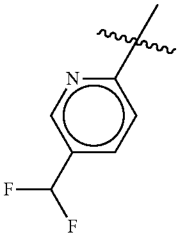,
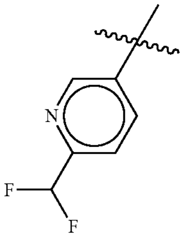,
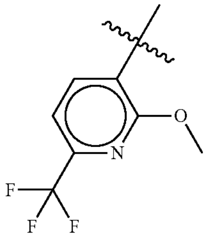, -continued

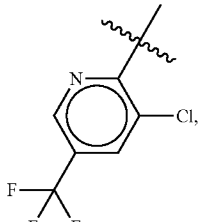
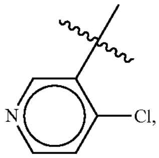
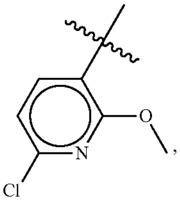,
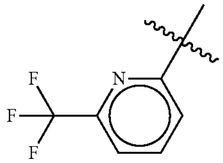,
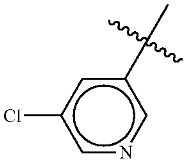,
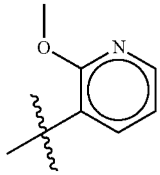,
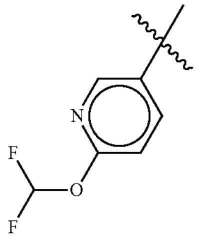,
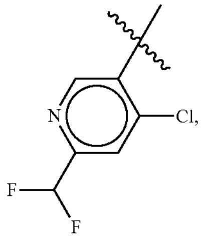
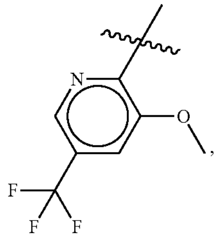,
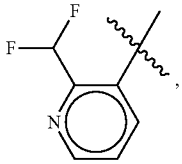,
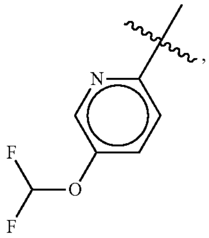,
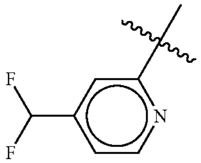,
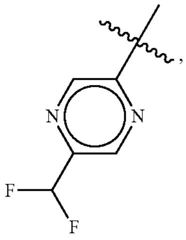,
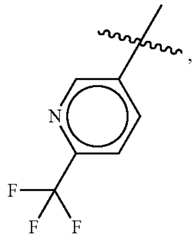,
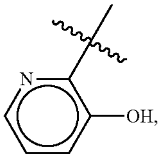
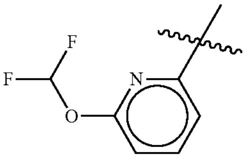, -continued
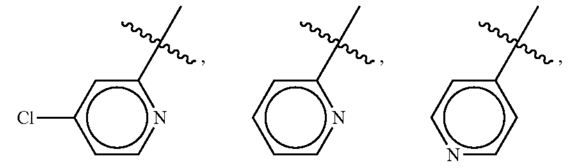
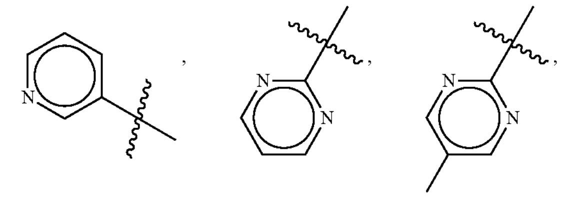
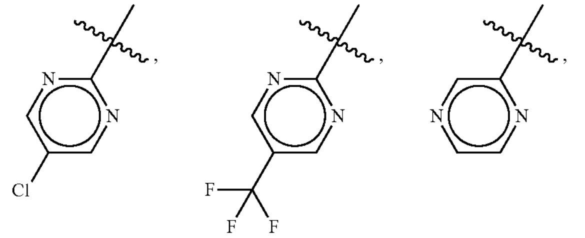
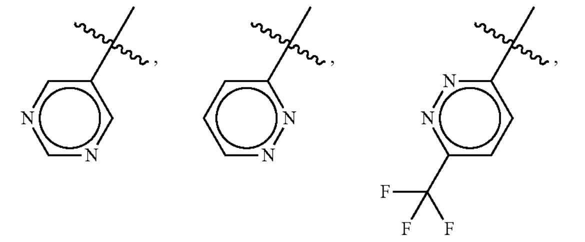
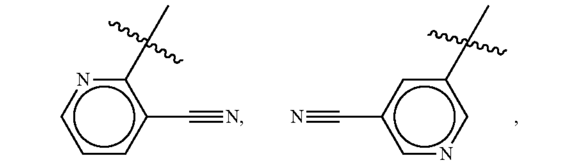
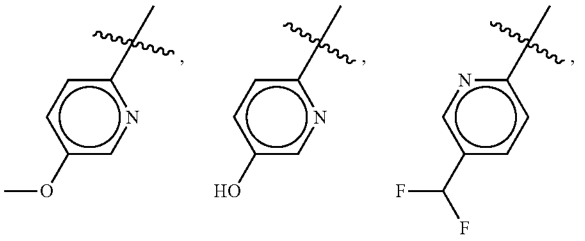
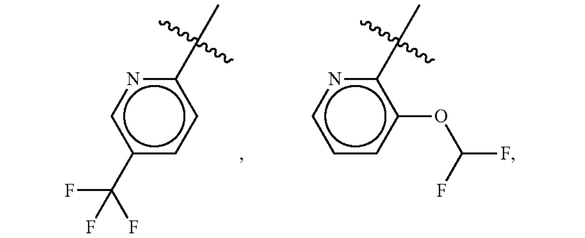
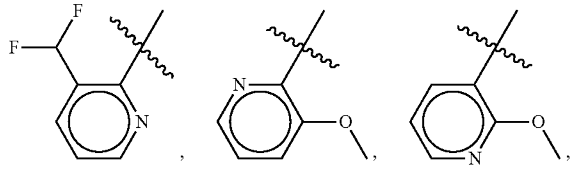
-continued
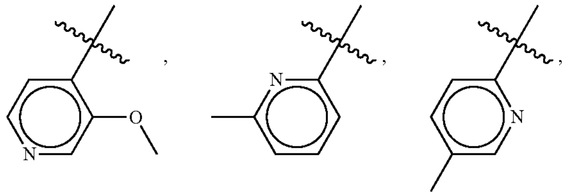
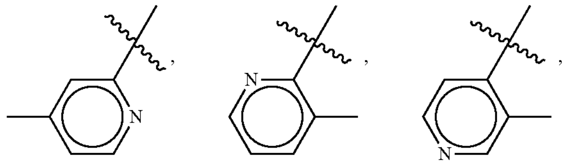
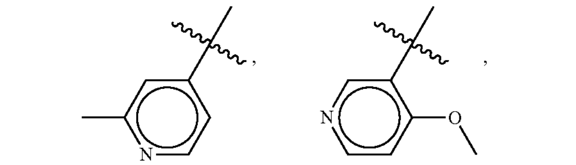
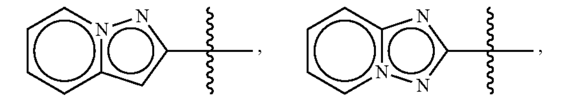
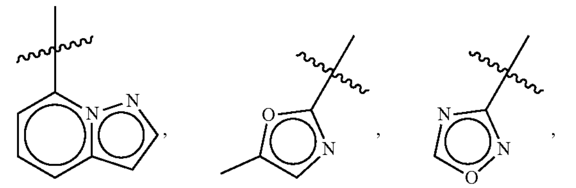
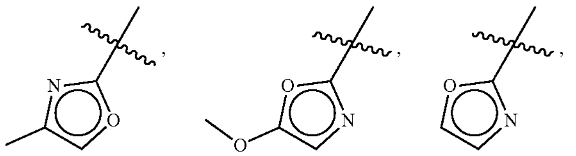
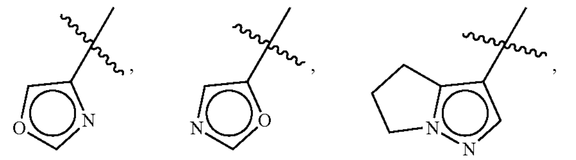
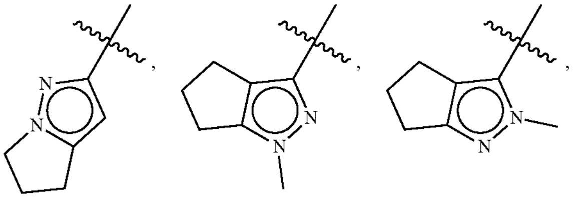
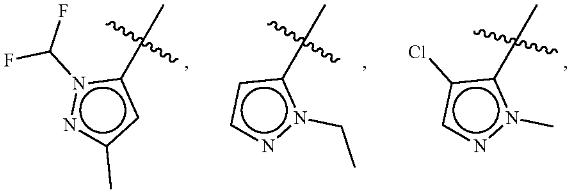
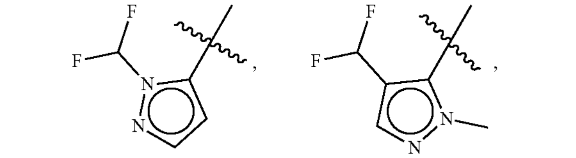

-continued
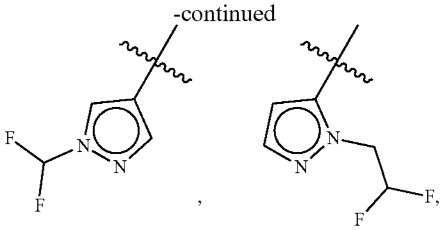
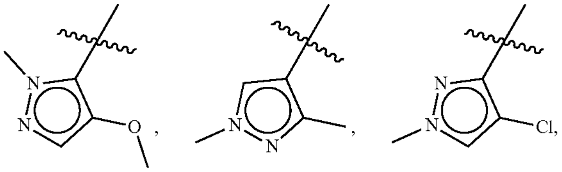
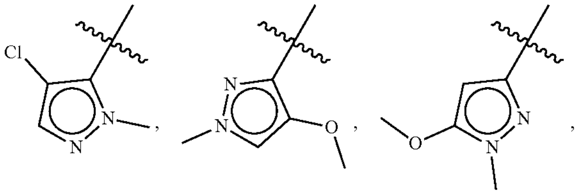
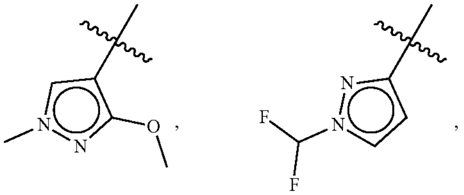
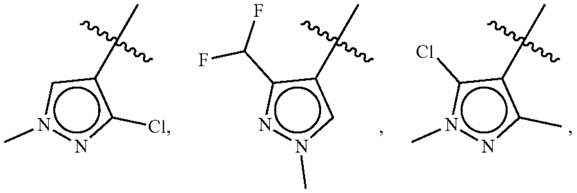
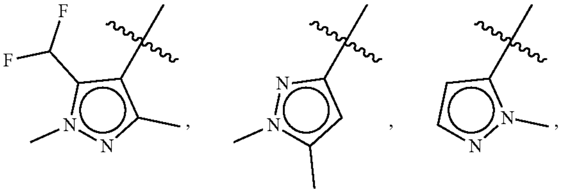
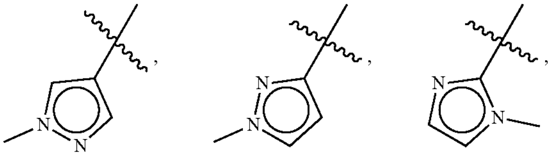
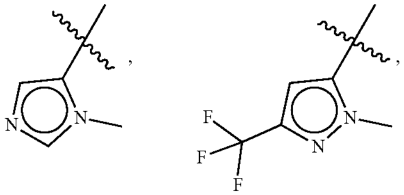
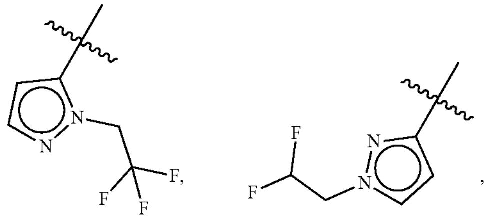
-continued
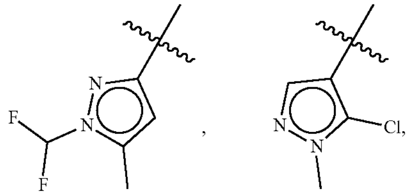
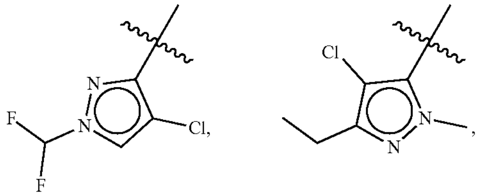
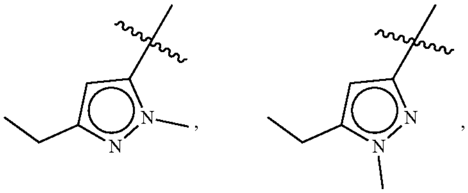
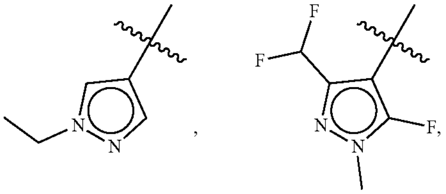
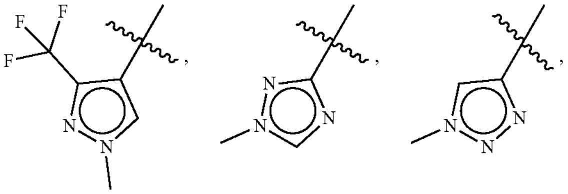
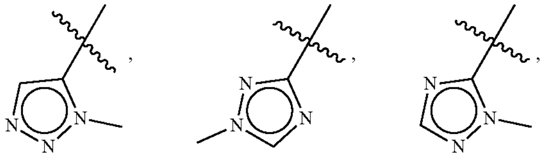
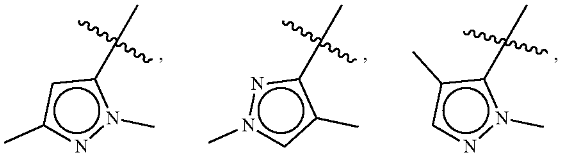
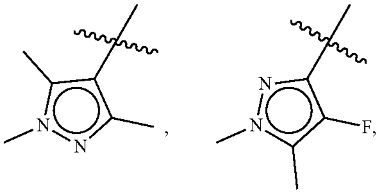
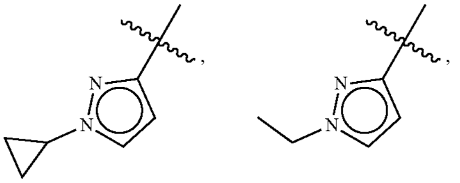

-continued
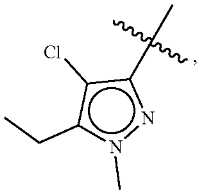,
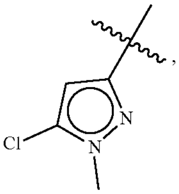,
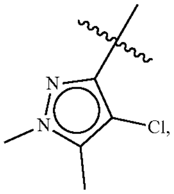
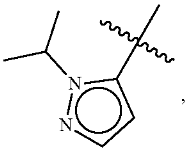,
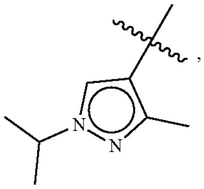,
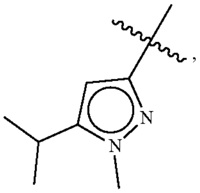,
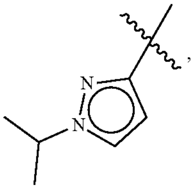,
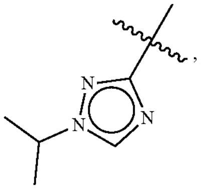,
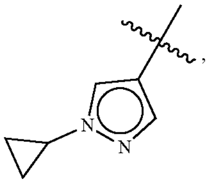,
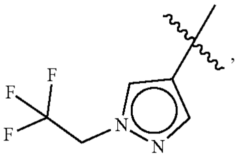,
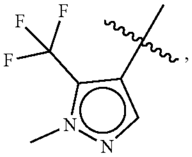,
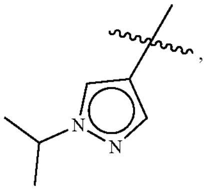,
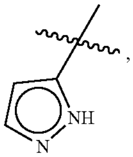,
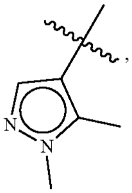,
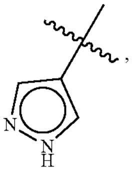,
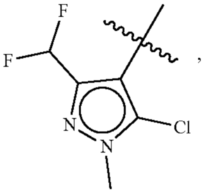,
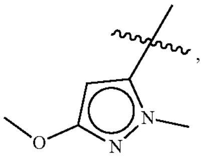,
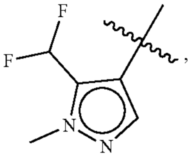,
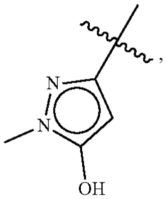,
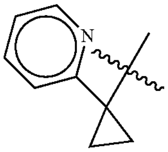,
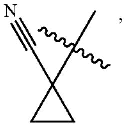,
-continued
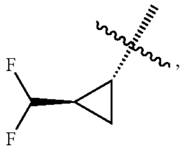,
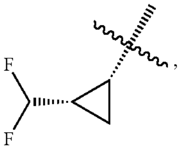,
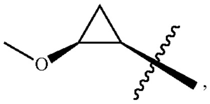,
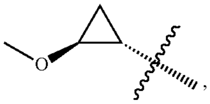,
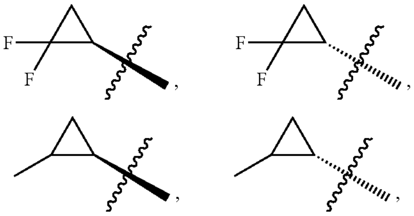,
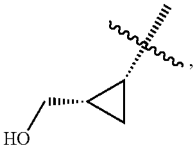,
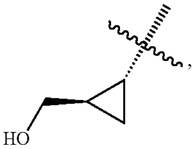,
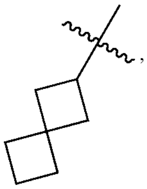,
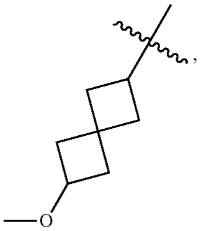,
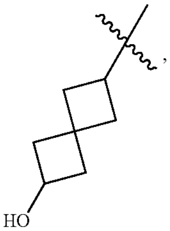,
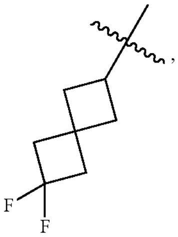,
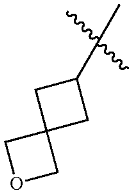,
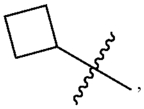,
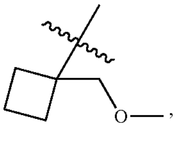,
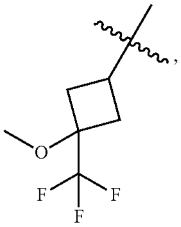,
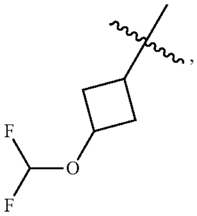,
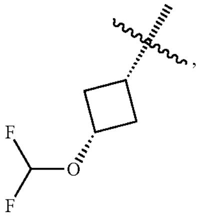,
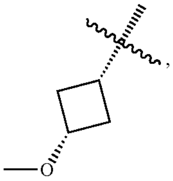,
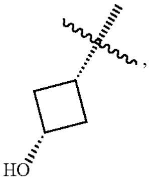, -continued
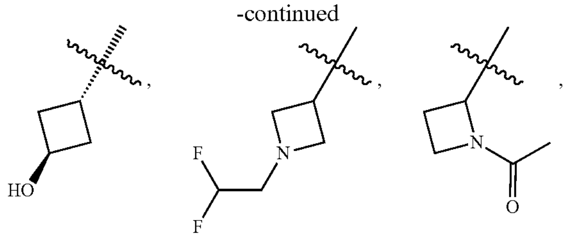
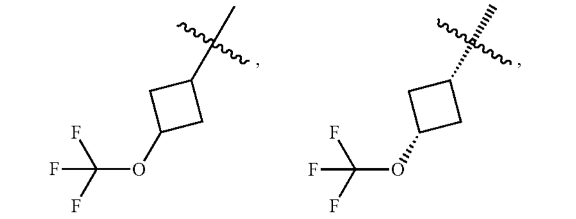
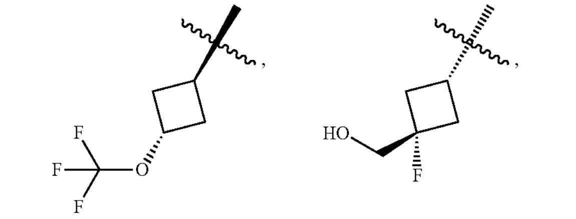
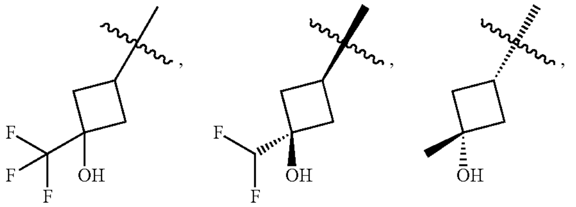
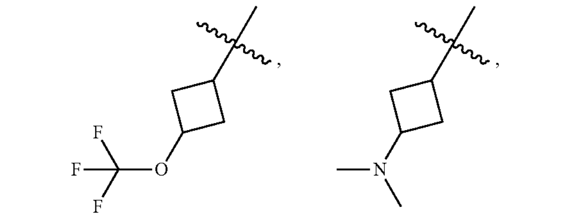
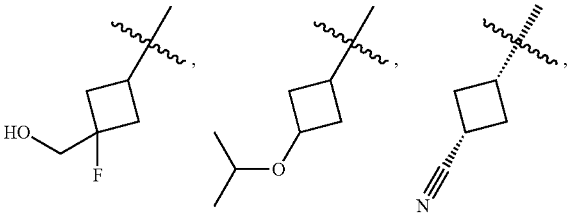
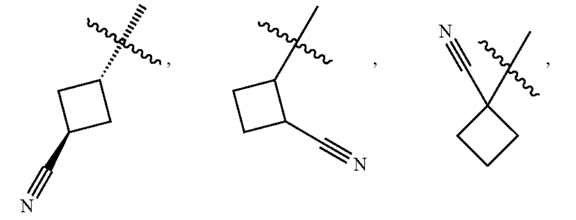
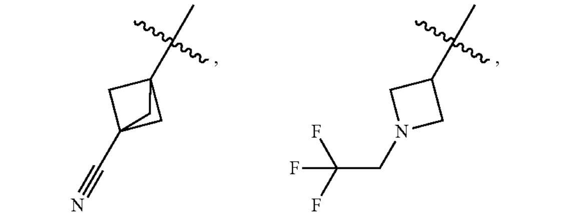
-continued
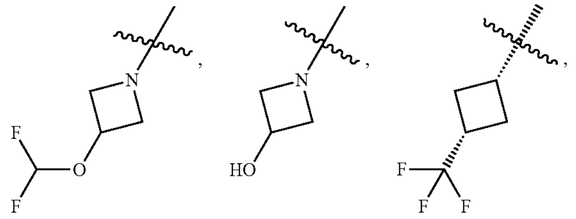
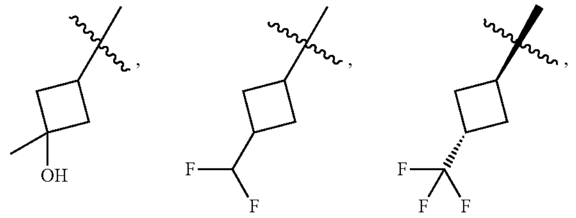
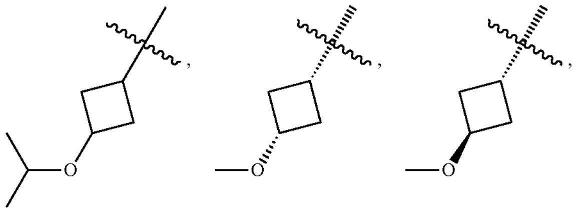
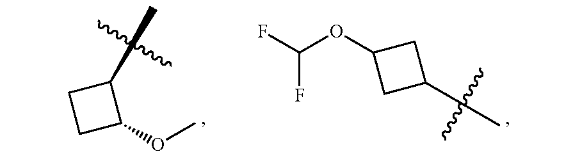
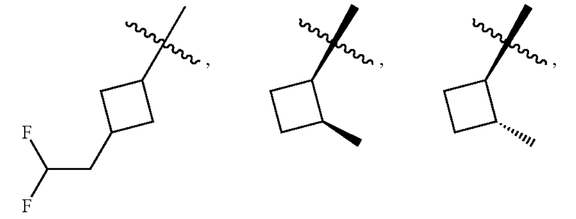
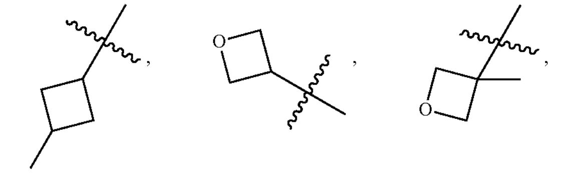
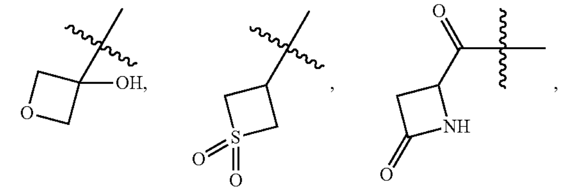
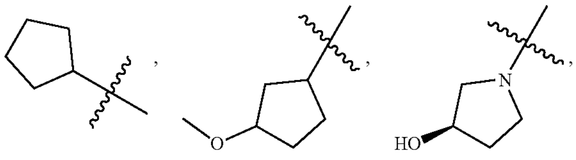
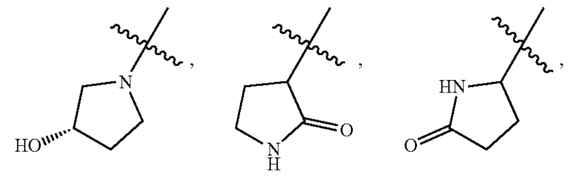

-continued
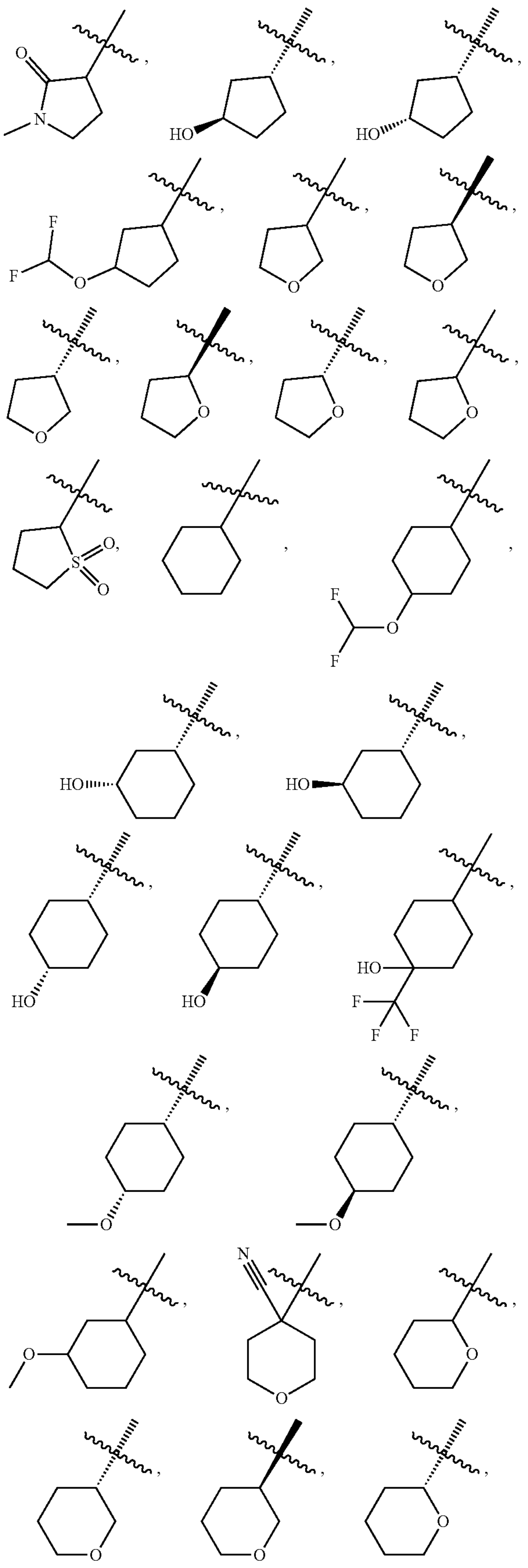
-continued
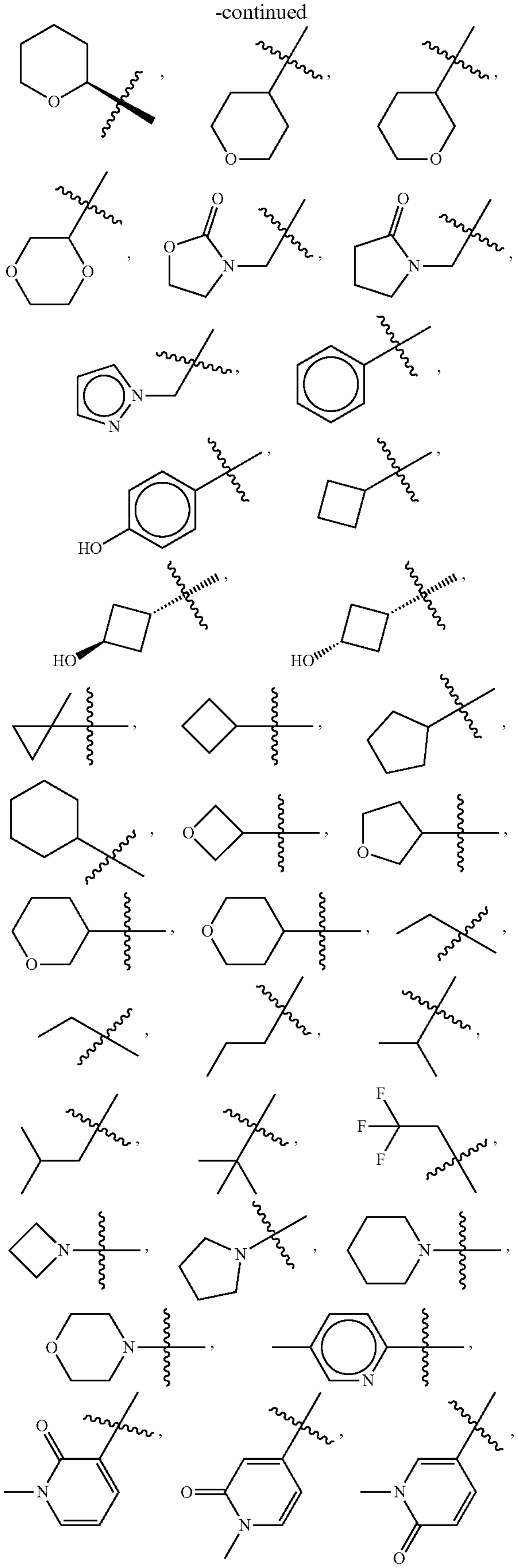

-continued

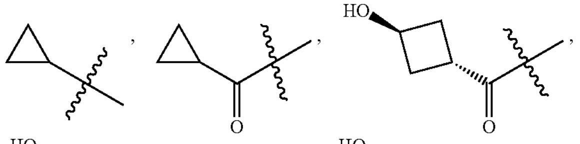

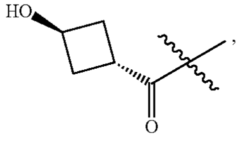

or

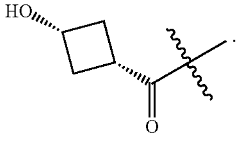

In some embodiments, each $R^{a2}$ independently is oxo, cyano, —OH, —$N(C_1$-$C_6$ alkyl$)_2$, $C_1$-$C_6$ alkyl, $C_3$-$C_{10}$ cycloalkyl. $C_1$-$C_6$ haloalkoxy, $C_1$-$C_6$ haloalkyl, $C_1$-$C_6$ alkoxy, 3- to 10-membered heterocycloalkyl optionally substituted with oxo, or 5- to 10-membered heteroaryl.

In some embodiments, each $R^{a2}$ independently is oxo, cyano, —OH, —$N(C_1$-$C_6$ alkyl$)_2$, $C_1$-$C_6$ alkyl optionally substituted with $C_1$-$C_6$ alkoxy or —OH, $C_3$-$C_{10}$ cycloalkyl, $C_1$-$C_6$ haloalkoxy, $C_1$-$C_6$ haloalkyl, $C_1$-$C_6$ alkoxy, 3- to 10-membered heterocycloalkyl optionally substituted with oxo, or 5- to 10-membered heteroaryl.

In some embodiments, each $R^{a2}$ independently is oxo, cyano, —OH, —$N(C_1$-$C_6$ alkyl$)_2$, $C_1$-$C_6$ alkyl substituted with $C_1$-$C_6$ alkoxy or —OH, $C_3$-$C_{10}$ cycloalkyl, $C_1$-$C_6$ haloalkoxy, $C_1$-$C_6$ haloalkyl, $C_1$-$C_6$ alkoxy, 3- to 10-membered heterocycloalkyl optionally substituted with oxo, or 5- to 10-membered heteroaryl.

In some embodiments, each $R^{a2}$ independently is oxo.

In some embodiments, each $R^{a2}$ independently is halo.

In some embodiments, each $R^{a2}$ independently is F, Cl, Br, or I. In some embodiments, each $R^{a2}$ independently is F, Cl, or Br. In some embodiments, each $R^{a2}$ independently is F or Cl.

In some embodiments, each $R^{a2}$ independently is F. In some embodiments, each $R^{a2}$ independently is Cl. In some embodiments, each $R^{a2}$ independently is Br. In some embodiments, each $R^{a2}$ independently is I.

In some embodiments, each $R^{a2}$ independently is cyano.

In some embodiments, each $R^{a2}$ independently is —OH.

In some embodiments, each $R^{a2}$ independently is —$NH_2$.

In some embodiments, each $R^{a2}$ independently is —NH($C_1$-$C_6$ alkyl).

In some embodiments, each $R^{a2}$ independently is —$N(C_1$-$C_6$ alkyl$)_2$.

In some embodiments, each $R^{a2}$ independently is $C_1$-$C_6$ alkyl.

In some embodiments, each $R^{a2}$ independently is $C_1$-$C_6$ alkyl optionally substituted with $C_1$-$C_6$ alkoxy or —OH.

In some embodiments, each $R^{a2}$ independently is $C_1$-$C_6$ alkyl substituted with $C_1$-$C_6$ alkoxy or —OH.

In some embodiments, each $R^{a2}$ independently is $C_1$-$C_6$ alkyl optionally substituted with $C_1$-$C_6$ alkoxy.

In some embodiments, each $R^{a2}$ independently is $C_1$-$C_6$ alkyl substituted with $C_1$-$C_6$ alkoxy.

In some embodiments, each $R^{a2}$ independently is $C_1$-$C_6$ alkyl optionally substituted with —OH.

In some embodiments, each $R^{a2}$ independently is $C_1$-$C_6$ alkyl substituted with —OH.

In some embodiments, each $R^2$ independently is methyl. In some embodiments, each $R^{a2}$ independently is ethyl. In some embodiments, each $R^{a2}$ independently is propyl. In some embodiments, each $R^{a2}$ independently is butyl. In some embodiments, each $R^{a2}$ independently is pentyl. In some embodiments, each $R^{a2}$ independently is hexyl. In some embodiments, each $R^{a2}$ independently is isopropyl. In some embodiments, each $R^{a2}$ independently is isobutyl. In some embodiments, each $R^{a2}$ independently is isopentyl. In some embodiments, each $R^{a2}$ independently is isohexyl. In some embodiments, each $R^{a2}$ independently is secbutyl. In some embodiments, each $R^{a2}$ independently is secpentyl. In some embodiments, each $R^{a2}$ independently is sechexyl. In some embodiments, each $R^{a2}$ independently is tertbutyl.

In some embodiments, each $R^{a2}$ independently is $C_3$-$C_{10}$ cycloalkyl.

In some embodiments, each $R^{a2}$ independently is $C_3$-$C_2$ cycloalkyl.

In some embodiments, each $R^{a2}$ independently is $C_1$-$C_6$, haloalkoxy.

In some embodiments, each $R^{a2}$ independently is $C_1$-$C_6$ haloalkyl.

In some embodiments, each $R^{a2}$ independently is $C_1$-$C_6$ alkoxy.

In some embodiments, each $R^{a2}$ independently is 3- to 10-membered heterocycloalkyl.

In some embodiments, each $R^{a2}$ independently is 3- to 10-membered heterocycloalkyl optionally substituted with oxo.

In some embodiments, each $R^{a2}$ independently is 3- to 10-membered heterocycloalkyl substituted with oxo.

In some embodiments, each $R^{a2}$ independently is 3- to 7-membered heterocycloalkyl.

In some embodiments, each $R^2$ independently is 3- to 7-membered heterocycloalkyl optionally substituted with oxo.

In some embodiments, each $R^{a2}$ independently is 3- to 7-membered heterocycloalkyl substituted with oxo.

In some embodiments, each $R^{a2}$ independently is 5- to 10-membered heteroaryl.

In some embodiments, each $R^{a2}$ independently is 5- to 6-membered heteroaryl.

In some embodiments, each $R^{a2}$ independently is oxo, —$CH_3$, —$CH_2CH_3$, —$CH(CH_3)_2$, —Cl, —F, —CN, —$CHF_2$, —$OCH_3$, —$CF_3$, —$OCHF_2$, —OH, —$CH_2CHF_2$, —$CH_2CF_3$, —$CH_2OH$, —$CH_2OCH_3$, —$OCF_3$, —$N(CH_3)_2$, —$OCH(CH_3)_2$,

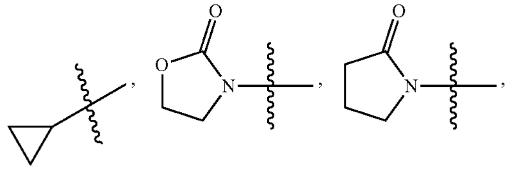

or

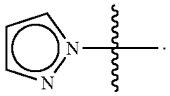

In some embodiments, $R^3$ is $C_6$-$C_{10}$ aryl.

In some embodiments. $R^3$ is $C_6$-$C_{10}$ aryl optionally substituted with one or more $R^{3a}$.

In some embodiments, $R^3$ is $C_6$-$C_{10}$ aryl substituted with one or more $R^{3a}$.

In some embodiments, $R^3$ is $C_6$ aryl.

In some embodiments. $R^3$ is $C_6$ aryl optionally substituted with one or more $R^{3a}$.

In some embodiments, $R^3$ is $C_6$ aryl substituted with one or more $R^{3a}$.

In some embodiments, $R^3$ is 5- to 10-membered heteroaryl.

In some embodiments, $R^3$ is 5- to 10-membered heteroaryl optionally substituted with one or more $R^{3a}$.

In some embodiments, $R^3$ is 5- to 10-membered heteroaryl substituted with one or more $R^{3a}$.

In some embodiments, $R^3$ is 5- to 10-membered heteroaryl optionally substituted with one $R^{3a}$.

In some embodiments, $R^3$ is 5- to 10-membered heteroaryl substituted with one $R^{3a}$.

In some embodiments, $R^3$ is 5- to 6-membered heteroaryl.

In some embodiments, $R^3$ is 5- to 6-membered heteroaryl optionally substituted with one or more $R^3$.

In some embodiments, $R^3$ is 5- to 6-membered heteroaryl substituted with one or more $R^{3a}$.

In some embodiments, $R^3$ is 5- to 6-membered heteroaryl optionally substituted with one $R^{3a}$.

In some embodiments, $R^3$ is 5- to 6-membered heteroaryl substituted with one $R^{3a}$.

In some embodiments, $R^3$ is:

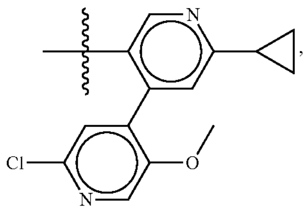,

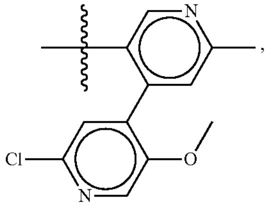,

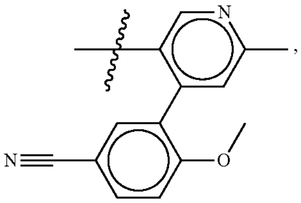, 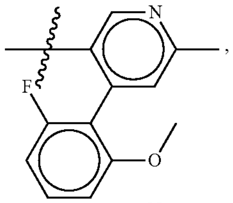,

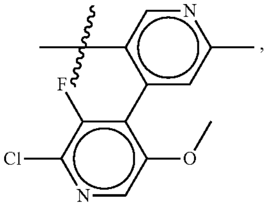, 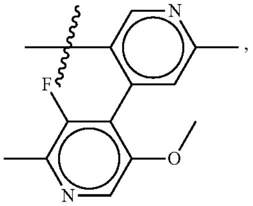,

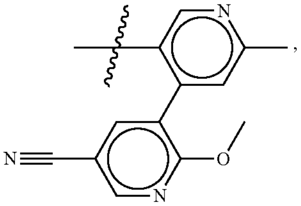,

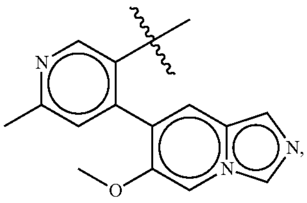, 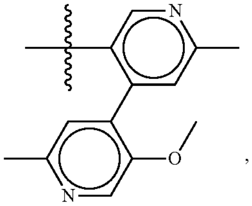,

-continued

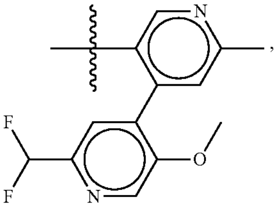, 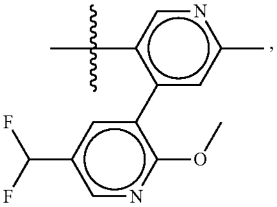,

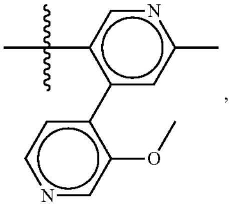, 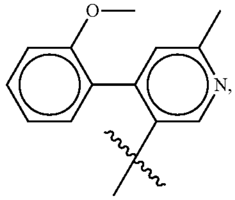,

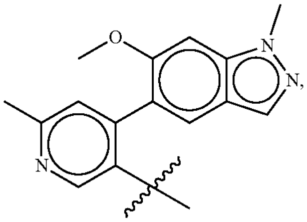,

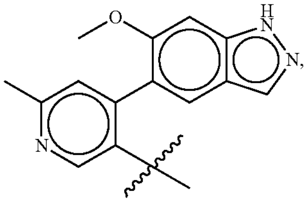,

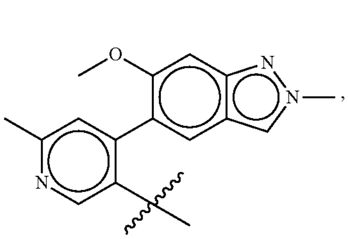, 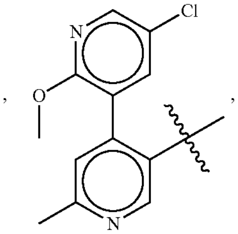,

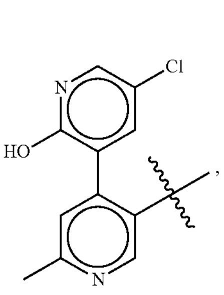, 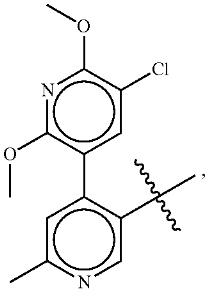,

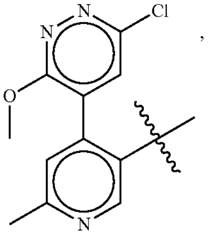, 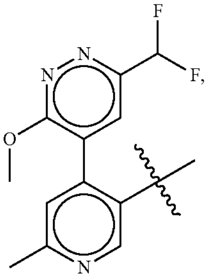,

-continued
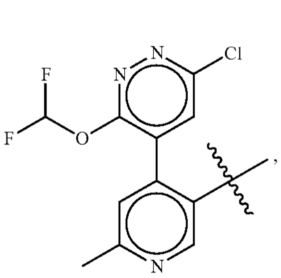
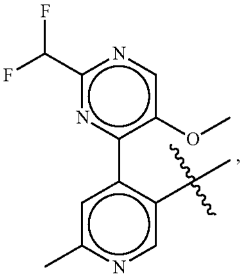
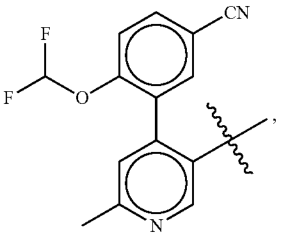
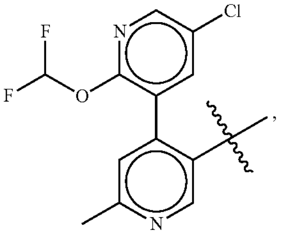
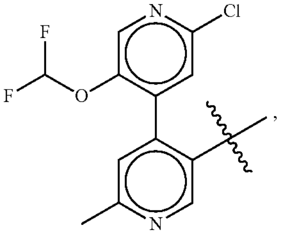
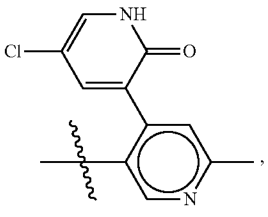
or
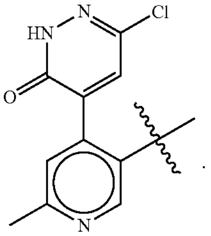
In some embodiments, $R^3$ is:
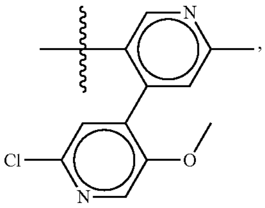
-continued
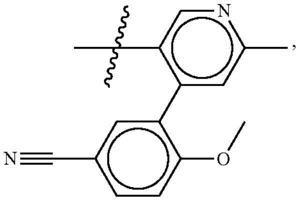
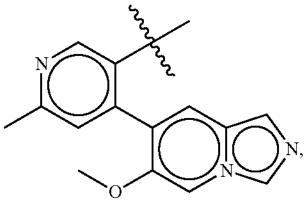
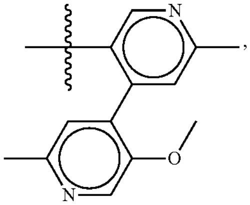
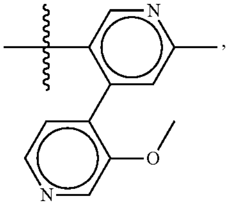
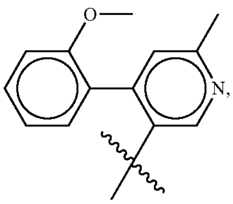
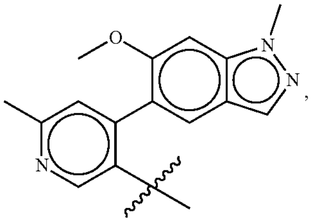
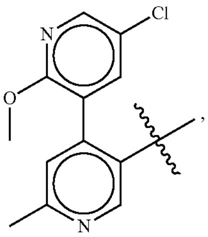
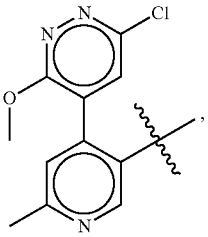
or
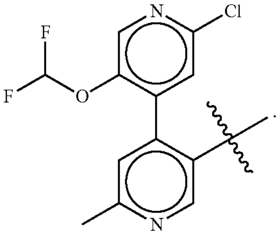
In some embodiments, $R^3$ is:
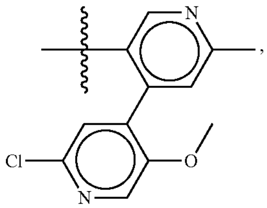

-continued

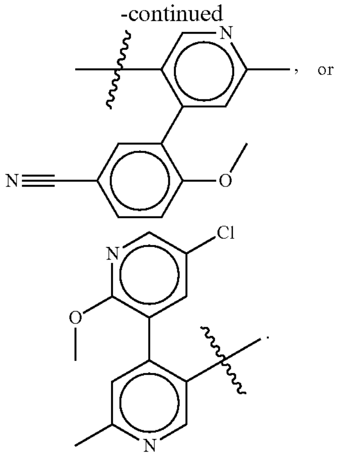

In some embodiments, each $R^{3a}$ independently is halo.

In some embodiments, each $R^{3a}$ independently is F, Cl, Br, or I. In some embodiments, each $R^{3a}$ independently is F, Cl, or Br. In some embodiments, each $R^{3a}$ independently is F or Cl.

In some embodiments, each $R^{3a}$ independently is F. In some embodiments, each $R^{3a}$ independently is Cl. In some embodiments, each $R^{3a}$ independently is Br. In some embodiments, each $R^{3a}$ independently is I.

In some embodiments, each $R^{3a}$ independently is cyano.

In some embodiments, each $R^{3a}$ independently $R^{3a}$ is —OH.

In some embodiments, each $R^{3a}$ independently is —$NH_2$.

In some embodiments, each $R^{3a}$ independently is $C_1$-$C_6$ alkyl.

In some embodiments, each $R^{3a}$ independently is $C_1$-$C_6$ alkyl optionally substituted with one or more $R^{3a1}$.

In some embodiments, each $R^{3a}$ independently is $C_1$-$C_6$ alkyl substituted with one or more $R^{3a1}$.

In some embodiments, each $R^{3a}$ independently is methyl. In some embodiments, each $R^{3a}$ independently is ethyl. In some embodiments, each $R^{3a}$ independently is propyl. In some embodiments, each $R^{3a}$ independently is butyl. In some embodiments, each $R^{3a}$ independently is pentyl. In some embodiments, each $R^{3a}$ independently is hexyl. In some embodiments, each $R^{3a}$ independently is isopropyl. In some embodiments, each $R^{3a}$ independently is isobutyl. In some embodiments, each $R^{3a}$ independently is isopentyl. In some embodiments, each $R^{3a}$ independently is isohexyl. In some embodiments, each $R^{3a}$ independently is secbutyl. In some embodiments, each $R^{3a}$ independently is secpentyl. In some embodiments, each $R^{3a}$ independently is sechexyl. In some embodiments, each $R^{3a}$ independently is tertbutyl.

In some embodiments, each $R^{3a}$ independently is $C_2$-$C_6$ alkenyl.

In some embodiments, each $R^{3a}$ independently is $C_2$-$C_6$ alkenyl optionally substituted with one or more $R^{3a1}$.

In some embodiments, each $R^{3a}$ independently is $C_2$-$C_6$ alkenyl substituted with one or more $R^{3a1}$.

In some embodiments, each $R^{3a}$ independently is $C_2$-$C_6$ alkynyl.

In some embodiments, each $R^{3a}$ independently is $C_2$-$C_6$ alkynyl optionally substituted with one or more $R^{3a1}$.

In some embodiments, each $R^{3a}$ independently is $C_2$-$C_6$ alkynyl substituted with one or more $R^{3a1}$.

In some embodiments, each $R^{3a}$ independently is $C_1$-$C_6$ haloalkyl.

In some embodiments, each $R^{3a}$ independently is $C_1$-$C_6$ haloalkyl optionally substituted with one or more $R^{3a1}$.

In some embodiments, each $R^{3a}$ independently is $C_1$-$C_6$ haloalkyl substituted with one or more $R^{3a1}$.

In some embodiments, each $R^{3a}$ independently is halomethyl. In some embodiments, each $R^{3a}$ independently is haloethyl. In some embodiments, each $R^{3a}$ independently is halopropyl. In some embodiments, each $R^{3a}$ independently is halobutyl. In some embodiments, each $R^{3a}$ independently is halopentyl. In some embodiments, each $R^{3a}$ independently is halohexyl.

In some embodiments, each $R^{3a}$ independently is $C_3$-$C_{10}$ cycloalkyl.

In some embodiments, each $R^{3a}$ independently is $C_3$-$C_{10}$ cycloalkyl optionally substituted with one or more $R^{3a1}$.

In some embodiments, each $R^{3a}$ independently is $C_3$-$C_{10}$ cycloalkyl substituted with one or more $R^{3a1}$.

In some embodiments, each $R^{3a}$ independently is $C_3$-$C_7$ cycloalkyl.

In some embodiments, each $R^{3a}$ independently is $C_3$-$C_7$ cycloalkyl optionally substituted with one or more $R^{3a1}$.

In some embodiments, each $R^{3a}$ independently is $C_3$-$C_7$ cycloalkyl substituted with one or more $R^{3a1}$.

In some embodiments, each $R^{3a}$ independently is 3- to 10-membered heterocycloalkyl.

In some embodiments, each $R^{3a}$ independently is 3- to 10-membered heterocycloalkyl optionally substituted with one or more $R^{3a1}$.

In some embodiments, each $R^{3a}$ independently is 3- to 10-membered heterocycloalkyl substituted with one or more $R^{3a1}$.

In some embodiments, each $R^{3a}$ independently is 3- to 7-membered heterocycloalkyl.

In some embodiments, each $R^{3a}$ independently is 3- to 7-membered heterocycloalkyl optionally substituted with one or more $R^{3a1}$.

In some embodiments, each $R^{3a}$ independently is 3- to 7-membered heterocycloalkyl substituted with one or more $R^{3a1}$.

In some embodiments, each $R^{3a}$ independently is $C_6$-$C_{10}$ aryl.

In some embodiments, each $R^{3a}$ independently is $C_6$-$C_{10}$ aryl optionally substituted with one or more $R^{3a1}$.

In some embodiments, each $R^{3a}$ independently is $C_6$-$C_{10}$ aryl substituted with one or more $R^{3a1}$.

In some embodiments, each $R^{3a}$ independently is $C_6$ aryl.

In some embodiments, each $R^{3a}$ independently is $C_6$ aryl optionally substituted with one or more $R^{3a1}$.

In some embodiments, each $R^{3a}$ independently is $C_6$ aryl substituted with one or more $R^{3a1}$.

In some embodiments, $R^{3a}$ is $C_6$-$C_{10}$ aryl.

In some embodiments, $R^{3a}$ is $C_6$-$C_{10}$ aryl optionally substituted with one or more $R^{3a1}$.

In some embodiments, $R^{3a}$ is $C_6$-$C_{10}$ aryl substituted with one or more $R^{3a1}$.

In some embodiments, $R^{3a}$ is $C_6$ aryl.

In some embodiments, $R^{3a}$ is $C_6$ aryl optionally substituted with one or more $R^{3a1}$.

In some embodiments, $R^{3a}$ is $C_6$ aryl substituted with one or more $R^{3a1}$.

In some embodiments, each $R^{3a}$ independently is 5- to 10-membered heteroaryl.

In some embodiments, each $R^{3a}$ independently is 5- to 10-membered heteroaryl optionally substituted with one or more $R^{3a1}$.

In some embodiments, each $R^{3a}$ independently is 5- to 10-membered heteroaryl substituted with one or more $R^{3a1}$.

In some embodiments, each $R^{3a}$ independently is 5- to 6-membered heteroaryl.

In some embodiments, each $R^{3a}$ independently is 5- to 6-membered heteroaryl optionally substituted with one or more $R^{3a1}$.

In some embodiments, each $R^{3a}$, independently is 5- to 6-membered heteroaryl substituted with one or more $R^{3a1}$.

In some embodiments, each $R^{3a}$ is $—CH_3$, cyclopropyl,

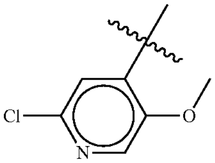,
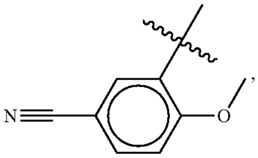,
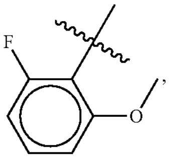,
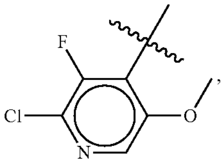,
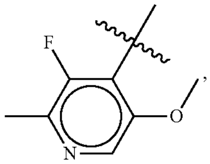,
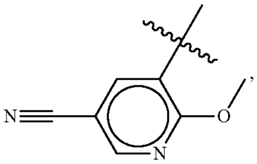,
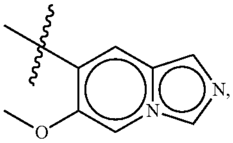,
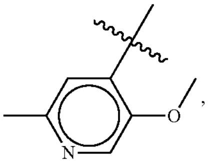,
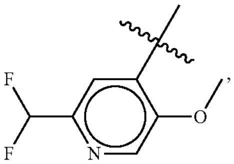,
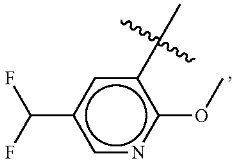,
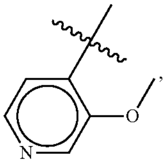,
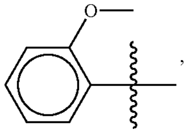,
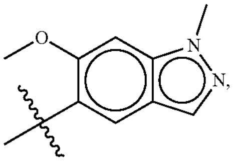,
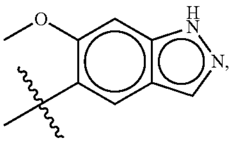,
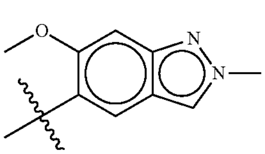,
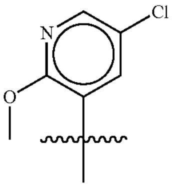, -continued

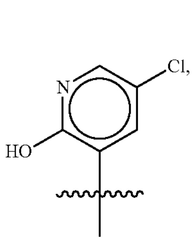
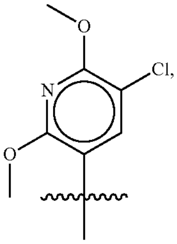
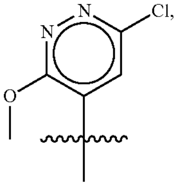
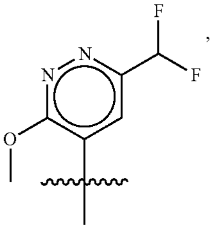,
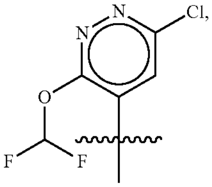
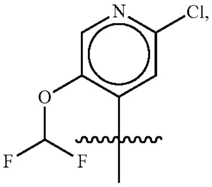
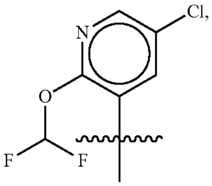
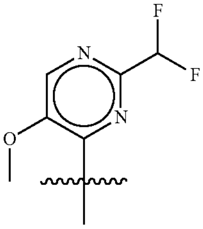,
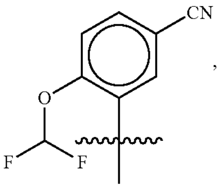,
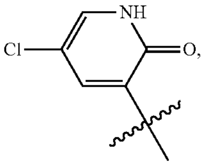 or
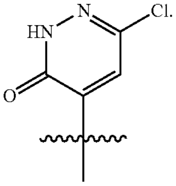

In some embodiments, each $R^{3a}$ is $—CH_3$,

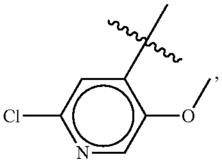
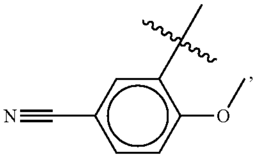
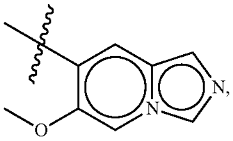
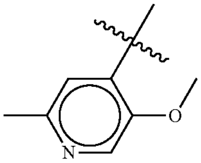

-continued

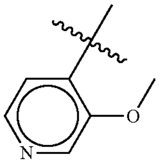,

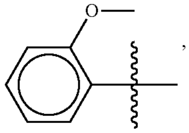,

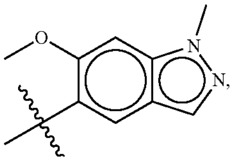,

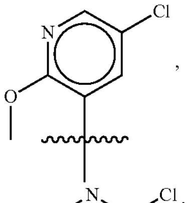,

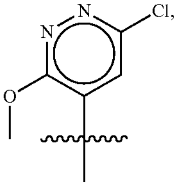 or

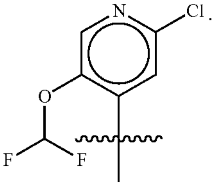.

In some embodiments, each $R^{3a}$ is —$CH_3$,

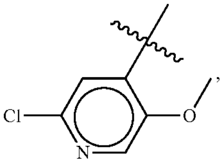,

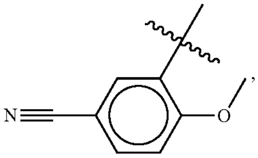, or

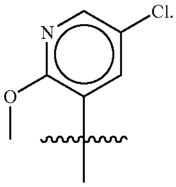.

In some embodiments, each $R^{3a1}$ independently is oxo.

In some embodiments, each $R^{3a1}$ independently is halo.

In some embodiments, each $R^{3a1}$ independently is F, Cl, Br, or I. In some embodiments, each $R^{3a}$ independently is F, Cl, or Br. In some embodiments, each $R^{3a1}$ independently is F or Cl.

In some embodiments, each $R^{3a1}$ independently is F. In some embodiments, each $R^{3a1}$ independently is Cl. In some embodiments, each $R^{3a1}$ independently is Br. In some embodiments, each $R^{3a1}$ independently is I.

In some embodiments, each $R^{3a1}$ independently is cyano.

In some embodiments, each $R^{3a1}$ independently is —OH.

In some embodiments, each $R^{3a1}$ independently is —C(O)($C_1$-$C_6$ alkyl).

In some embodiments, each $R^{3a1}$ independently is —C(O)(O—($C_1$-$C_6$ alkyl)).

In some embodiments, each $R^{3a1}$ independently is $C_1$-$C_6$ alkyl.

In some embodiments, each $R^{3a1}$ independently is $C_1$-$C_6$alkyl optionally substituted with $C_3$-$C_{10}$ cycloalkyl.

In some embodiments, each $R^{3a1}$ independently is $C_1$-$C_6$ alkyl substituted with $C_3$-$C_{10}$ cycloalkyl.

In some embodiments, each $R^{3a1}$ independently is methyl. In some embodiments, each $R^{3a1}$ independently is ethyl. In some embodiments, each $R^{3a1}$ independently is propyl. In some embodiments, each $R^{3a1}$ independently is butyl. In some embodiments, each $R^{3a1}$ independently is pentyl. In some embodiments, each $R^{3a1}$ independently is hexyl. In some embodiments, each $R^{3a1}$ independently is isopropyl. In some embodiments, each $R^{3a1}$ independently is isobutyl. In some embodiments, each $R^{3a1}$ independently is isopentyl. In some embodiments, each $R^{3a1}$ independently is isohexyl. In some embodiments, each $R^{3a1}$ independently is secbutyl. In some embodiments, each $R^{3a1}$ independently is secpentyl. In some embodiments, each $R^{3a1}$ independently is sechexyl. In some embodiments, each $R^{3a1}$ independently is tertbutyl.

In some embodiments, each $R^{3a1}$ independently is $C_2$-$C_6$ alkenyl.

In some embodiments, each $R^{3a1}$ independently is $C_2$-$C_6$ alkynyl.

In some embodiments, each $R^{3a1}$ independently is $C_1$-$C_6$ haloalkyl.

In some embodiments, each $R^{3a1}$ independently is halomethyl. In some embodiments, each $R^{3a1}$ independently is haloethyl. In some embodiments, each $R^{3a1}$ independently is halopropyl. In some embodiments, each $R^{3a1}$ independently is halobutyl. In some embodiments, each $R^{3a1}$ independently is halopentyl. In some embodiments, each $R^{3a1}$ independently is halohexyl.

In some embodiments, each $R^{3a1}$ independently is $C_1$-$C_6$ haloalkoxy.

In some embodiments, each $R^{3a1}$ independently is $C_1$-$C_6$ alkoxy.

In some embodiments, each $R^{3a1}$ independently is —O($C_1$-$C_6$ haloalkyl).

In some embodiments, each $R^{3a1}$ independently is $C_3$-$C_{10}$ cycloalkyl.

In some embodiments, each $R^{3a1}$ independently is $C_3$-$C_7$ cycloalkyl.

In some embodiments, each $R^{3a1}$ independently is $C_6$-$C_{10}$ aryl.

In some embodiments, each $R^{3a1}$ independently is $C_6$ aryl.

In some embodiments, each $R^{3a1}$ independently is 5- to 10-membered heteroaryl.

In some embodiments, each $R^{3a1}$ independently is 5- to 6-membered heteroaryl.

In some embodiments, each $R^{3a1}$ independently is cyano or $C_1$-$C_6$ alkoxy.

In some embodiments, each $R^{3a1}$ independently is methyl, cyano, —Cl, or —$OCH_3$.

In some embodiments, each $R^{3a1}$ independently is oxo, methyl, —$CF_2H$, cyano, —F, —Cl, —OH, —$OCF_2H$, or —$OCH_3$.

In some embodiments, the compound is of Formula (I), wherein:

$X^1$ is CH, S, or N;

$X^2$ is N, S, or O;

$R^1$ and $R^2$, together with the atoms to which they are attached, form a $C_5$-$C_{10}$ cycloalkyl or 5- to 10-membered heterocycloalkyl, wherein the $C_5$-$C_{10}$ cycloalkyl or 5- to 10-membered heterocycloalkyl is optionally substituted with one or more $R^a$;

each $R^a$ independently is oxo, halo, cyano, —$OR^{a1}$, —N(R)$_2$, —C(O)$R^{a1}$, —C(O)N($R^{a1}$)$_2$, —C(O)O$R^{a1}$, —S(O)$_2$N($R^{a1}$)$_2$, —S(O)$_2$($R^{a1}$), $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, $C_6$-$C_{10}$ aryl, 5- to 10-membered heteroaryl, or 3- to 10-membered heterocycloalkyl, wherein the $C_1$-$C_6$ alkyl, $C_2$-$C_6$ alkenyl, $C_2$-$C_6$ alkynyl, $C_6$-$C_{10}$ haloalkyl, $C_3$-$C_{10}$ cycloalkyl, $C_6$-$C_{10}$ aryl, 5- to 10-membered heteroaryl, or 3- to 10-membered heterocycloalkyl is optionally substituted with one or more $R^{a1}$;

each $R^{a1}$ independently is H, oxo, halo, cyano, —OH, —$NH_2$, —C(O)($C_1$-$C_6$ alkyl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_{10}$ cycloalkyl, 3- to 10-membered heterocycloalkyl, $C_6$-$C_{10}$ aryl, or 5- to 10-membered heteroaryl, wherein the $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_{10}$ cycloalkyl, 3- to 10-membered heterocycloalkyl, $C_6$-$C_{10}$ aryl, or 5- to 10-membered heteroaryl is optionally substituted with one or more $R^{a2}$;

each $R^{a2}$ independently is oxo, halo, cyano, —OH, —$NH_2$, $C_1$-$C_6$ alkyl optionally substituted with $C_1$-$C_6$ alkoxy, $C_1$-$C_6$ haloalkoxy, 3- to 10-membered heterocycloalkyl optionally substituted with oxo, or 5- to 10-membered heteroaryl;

$R^3$ is $C_6$-$C_{10}$ aryl or 5- to 10-membered heteroaryl, wherein the $C_6$-$C_{10}$ aryl or 5- to 10-membered heteroaryl is substituted with one or more $R^{3a}$;

each $R^{3a}$ independently is halo, cyano, —OH, —$NH_2$. $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, 3- to 10-membered heterocycloalkyl, $C_6$-$C_{10}$ aryl, or 5- to 10-membered heteroaryl, wherein the $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, 3- to 10-membered heterocycloalkyl, $C_6$-$C_{10}$ aryl, or 5- to 10-membered heteroaryl is optionally substituted with one or more $R^{3a1}$; and each $R^{3a1}$ independently is oxo, halo, cyano, —C(O)($C_1$-$C_6$alkyl), —C(O)O—($C_1$-$C_6$ alkyl)), $C_1$-$C_6$ alkyl optionally substituted with $C_3$-$C_{10}$ cycloalkyl, $C_2$-$C_6$ alkenyl, $C_2$-$C_6$ alkynyl, $C_1$-$C_6$ haloalkyl, $C_1$-$C_6$ alkoxy, —O($C_1$-$C_6$haloalkyl), $C_3$-$C_{10}$ cycloalkyl, $C_6$-$C_{10}$ aryl, or 5- to 10-membered heteroaryl.

In some embodiments, the compound is of Formula (I), wherein:

$X^1$ is S or N;

$X^2$ is N or S;

$R^1$ and $R^2$, together with the atoms to which they are attached, form a $C_5$-$C_6$ cycloalkyl or 5- to 6-membered heterocycloalkyl, wherein the $C_5$-$C_6$ cycloalkyl or 5- to 6-membered heterocycloalkyl is optionally substituted with one or more $R^a$:

each $R^a$ independently is oxo, —$OR^{a1}$, —$N(R^{a1})_2$, —C(O)$R^{a1}$, —C(O)$N(R^{a1})_2$, —C(O)$OR^{a1}$, —$S(O)_2N(R^{a1})_2$, —$S(O)_2(R^{a1})$, $C_1$-$C_6$ alkyl, $C_3$-$C_{10}$ cycloalkyl, $C_6$-$C_{10}$ aryl, 5- to 10-membered heteroaryl, or 3- to 10-membered heterocycloalkyl, wherein the $C_1$-$C_6$ alkyl, $C_3$-$C_{10}$ cycloalkyl, $C_6$-$C_{10}$ aryl, 5- to 10-membered heteroaryl, or 3- to 10-membered heterocycloalkyl is optionally substituted with one or more $R^{a1}$;

each $R^{a1}$ independently is H, halo, cyano. —C(O)($C_1$-$C_6$ alkyl), —C(O)($C_3$-$C_{10}$ cycloalkyl), $C_1$-$C_6$ alkyl, $C_1$-$C_6$ haloalkyl, $C_3$-$C_{10}$ cycloalkyl, 3- to 10-membered heterocycloalkyl, $C_6$-$C_{10}$ aryl, or 5- to 10-membered heteroaryl, wherein the —C(O)($C_3$-$C_{10}$ cycloalkyl), $C_1$-$C_6$ alkyl, $C_1$-$C_6$ haloalkyl, $C_3$-$C_{10}$ cycloalkyl, 3- to 10-membered heterocycloalkyl, $C_6$-$C_{10}$ aryl, or 5- to 10-membered heteroaryl is optionally substituted with one or more $R^{a2}$.

each $R^{a2}$ independently is oxo, cyano, —OH, —N($C_1$-$C_6$ alkyl)$_2$, $C_1$-$C_6$ alkyl optionally substituted with $C_1$-$C_6$ alkoxy or —OH, $C_3$-$C_{10}$ cycloalkyl, $C_1$-$C_6$ haloalkoxy, $C_1$-$C_6$ haloalkyl, $C_1$-$C_6$ alkoxy, 3- to 10-membered heterocycloalkyl optionally substituted with oxo, or 5- to 10-membered heteroaryl;

$R^3$ is 5- to 10-membered heteroaryl substituted with one $R^{3a}$;

$R^{3a}$ is $C_6$-$C_{10}$ aryl optionally substituted with one or more $R^{3a1}$; and each $R^{3a}$ independently is cyano or $C_1$-$C_6$ alkoxy.

In some embodiments, the compound is of Formula (I-A):

(I-A)

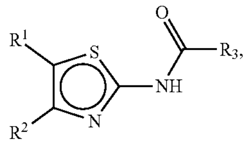

or a pharmaceutically acceptable salt, solvate, clathrate, hydrate, stereoisomer, or tautomer thereof.

In some embodiments, the compound is of Formula (I-B), (I-C), (I-D), or (I-E):

(I-B)

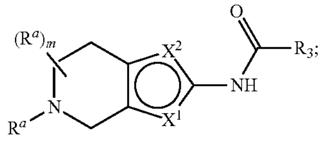

(I-C)

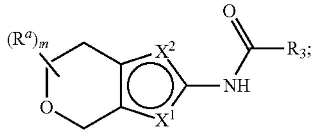

(I-D)

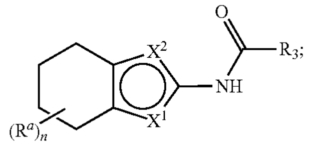

or (I-E)

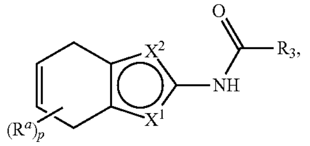

or a pharmaceutically acceptable salt, solvate, clathrate, hydrate, stereoisomer, or tautomer thereof, wherein m is 0 to 6, n is 0 to 8, and p is 0 to 6.

In some embodiments, the compound is of Formula (I-F):

(I-F)

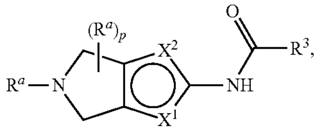

or a pharmaceutically acceptable salt, solvate, clathrate, hydrate, stereoisomer, or tautomer thereof, wherein p is 0 to 4.

In some embodiments, the compound is of Formula (I-Fa):

(I-Fa)

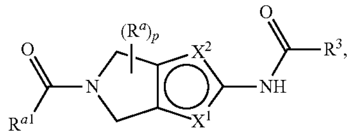

or a pharmaceutically acceptable salt, solvate, clathrate, hydrate, stereoisomer, or tautomer thereof, wherein p is 0 to 4.

In some embodiments, the compound is of Formula (I-Fb):

(I-Fb)

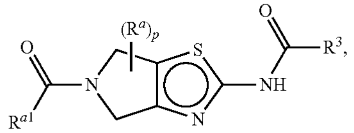

or a pharmaceutically acceptable salt, solvate, clathrate, hydrate, stereoisomer, or tautomer thereof, wherein p is 0 to 4.

In some embodiments, the compound is of Formula (I-Fb'):

(I-Fb')

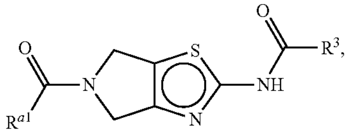

or a pharmaceutically acceptable salt, solvate, clathrate, hydrate, stereoisomer, or tautomer thereof.

In some embodiments, the compound is of Formula (I-Fc):

(I-Fc)

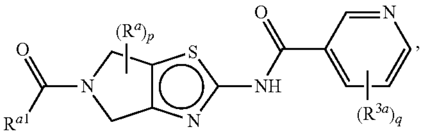

or a pharmaceutically acceptable salt, solvate, clathrate, hydrate, stereoisomer, or tautomer thereof, wherein p is 0 to 4 and q is 1 to 4.

In some embodiments, the compound is of Formula (I-Fc'):

(I-Fc')

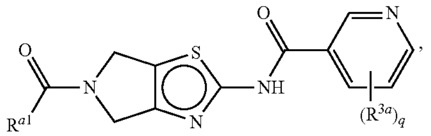

or a pharmaceutically acceptable salt, solvate, clathrate, hydrate, stereoisomer, or tautomer thereof, wherein q is 1 to 4.

In some embodiments, the compound is of Formula (I-Fd):

(I-Fd)

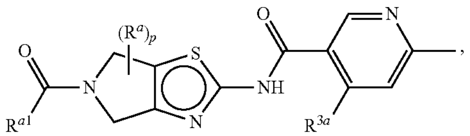

or a pharmaceutically acceptable salt, solvate, clathrate, hydrate, stereoisomer, or tautomer thereof, wherein p is 0 to 4.

In some embodiments, the compound is of Formula (I-Fd'):

(I-Fd')

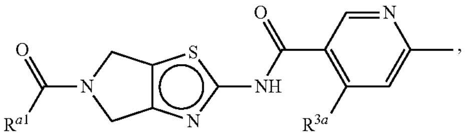

or a pharmaceutically acceptable salt, solvate, clathrate, hydrate, stereoisomer, or tautomer thereof.

In some embodiments, the compound is of Formula (I-G):

(I-G)

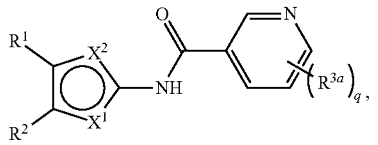

or a pharmaceutically acceptable salt, solvate, clathrate, hydrate, stereoisomer, or tautomer thereof, wherein q is 1 to 4.

In some embodiments, the compound is of Formula (I-Ga):

(I-Ga)

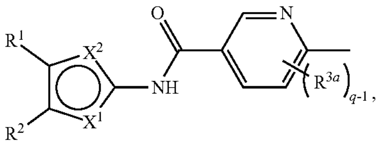

or a pharmaceutically acceptable salt, solvate, clathrate, hydrate, stereoisomer, or tautomer thereof, wherein q is 1 to 4.

In some embodiments, the compound is of Formula (I-Ga'):

(I-Ga')

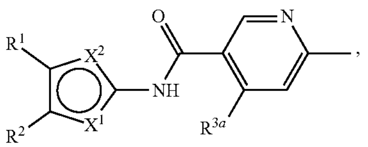

or a pharmaceutically acceptable salt, solvate, clathrate, hydrate, stereoisomer, or tautomer thereof.

In some embodiments, the compound is a compound described in Table 1, or a prodrug or pharmaceutically acceptable salt thereof.

In some embodiments, the compound is a compound described in Table 1, or a pharmaceutically acceptable salt thereof.

In some embodiments, the compound is a prodrug of a compound described in Table 1, or a pharmaceutically acceptable salts thereof.

In some embodiments, the compound is a compound described in Table 1.

In some embodiments, the compound is a compound described in Table 2, or a prodrug or pharmaceutically acceptable salt thereof.

In some embodiments, the compound is a compound described in Table 2, or a pharmaceutically acceptable salt thereof.

In some embodiments, the compound is a prodrug of a compound described in Table 2, or a pharmaceutically acceptable salts thereof.

In some embodiments, the compound is a compound described in Table 2.

In some embodiments, the compound is a compound described in Table 3, or a prodrug or pharmaceutically acceptable salt thereof.

In some embodiments, the compound is a compound described in Table 3, or a pharmaceutically acceptable salt thereof.

In some embodiments, the compound is a prodrug of a compound described in Table 3, or a pharmaceutically acceptable salts thereof.

In some embodiments, the compound is a compound described in Table 3.

Compounds in Tables 1-3 are each assigned a compound number, and any alternative compound numbers are indicated in parentheses. For compounds with two compound numbers, both compound numbers may be used interchangeably to refer to the same compound.

TABLE 1

| Compound No. | Name | Structure |
|---|---|---|
| 1 | (Racemic) 2'-chloro-N-(5-(3-(difluoromethoxy)cyclopentane-1-carbonyl)-5,6-dihydro-4H-pyrrolo[3,4-d]thiazol-2-yl)-5'-methoxy-6-methyl-[4,4'-bipyridine]-3-carboxamide | 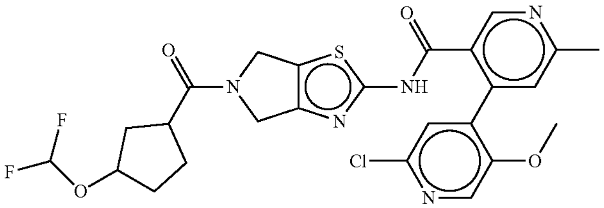 |
| 2 | (Cis and Trans) 2'-chloro-N-(5-(4-(difluoromethoxy)cyclohexane-1-carbonyl)-5,6-dihydro-4H-pyrrolo[3,4-d]thiazol-2-yl)-5'-methoxy-6-methyl-[4,4'-bipyridine]-3-carboxamide | 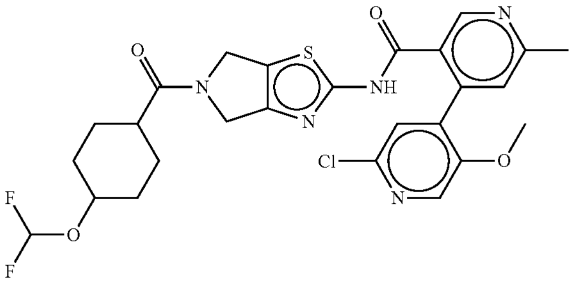 |
| 3 | 2'-chloro-N-(5-((1R,2R)-2-(difluoromethyl)cyclopropane-1-carbonyl)-5,6-dihydro-4H-pyrrolo[3,4-d]thiazol-2-yl)-5'-methoxy-6-methyl-[4,4'-bipyridine]-3-carboxamide | 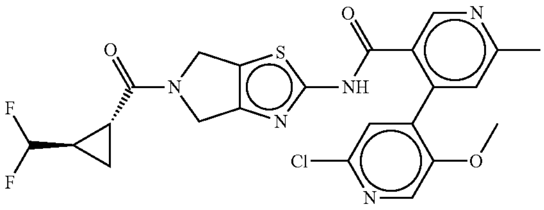 |
| 4 | 2'-chloro-N-(5-(5,6-dihydro-4H-pyrrolo[1,2-b]pyrazole-3-carbonyl)-5,6-dihydro-4H-pyrrolo[3,4-d]thiazol-2-yl)-5'-methoxy-6-methyl-[4,4'-bipyridine]-3-carboxamide | 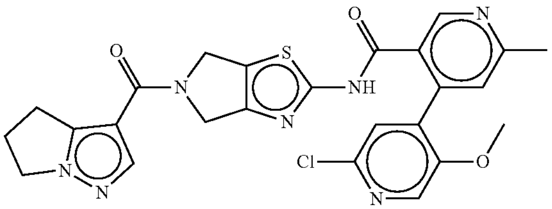 |

TABLE 1-continued

| Compound No. | Name | Structure |
|---|---|---|
| 5 | 2'-chloro-N-(5-(5-chloro-1,3-dimethyl-1H-pyrazole-4-carbonyl)-5,6-dihydro-4H-pyrrolo[3,4-d]thiazol-2-yl)-5'-methoxy-6-methyl-[4,4'-bipyridine]-3-carboxamide | 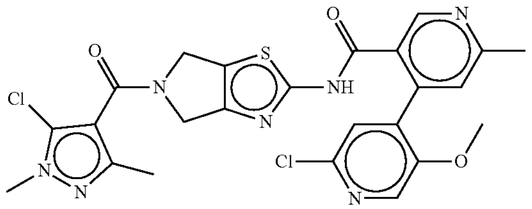 |
| 6 | 2'-chloro-N-(5-(5-(difluoromethyl)-1,3-dimethyl-1H-pyrazole-4-carbonyl)-5,6-dihydro-4H-pyrrolo[3,4-d]thiazol-2-yl)-5'-methoxy-6-methyl-[4,4'-bipyridine]-3-carboxamide | 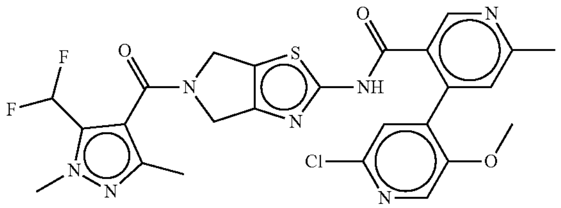 |
| 7 | 2'-chloro-N-(5-(6-chloropicolinoyl)-5,6-dihydro-4H-pyrrolo[3,4-d]thiazol-2-yl)-5'-methoxy-6-methyl-[4,4'-bipyridine]-3-carboxamide | 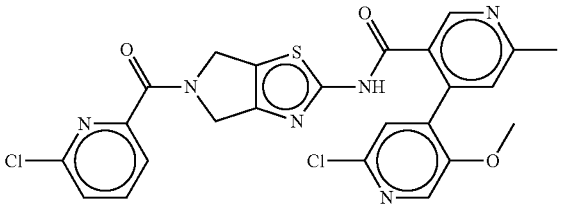 |
| 8 | 2'-chloro-5'-methoxy-6-methyl-N-(5-(spiro[3.3]heptane-2-carbonyl)-5,6-dihydro-4H-pyrrolo[3,4-d]thiazol-2-yl)-[4,4'-bipyridine]-3-carboxamide | 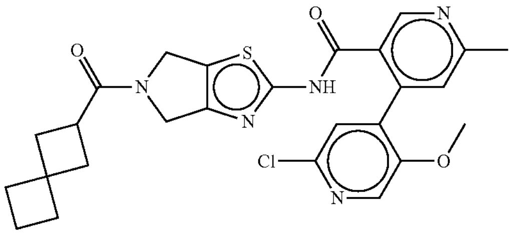 |
| 9 | 2'-chloro-N-(5-(5-(difluoromethyl)picolinoyl)-5,6-dihydro-4H-pyrrolo[3,4-d]thiazol-2-yl)-5'-methoxy-6-methyl-[4,4'-bipyridine]-3-carboxamide | 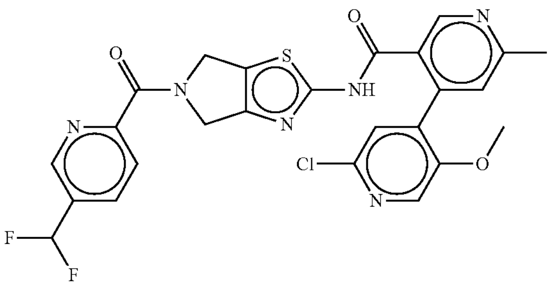 |
| 10 | 2'-chloro-N-(5-((1s,3s)-3-(difluoromethoxy)cyclobutane-1-carbonyl)-5,6-dihydro-4H-pyrrolo[3,4-d]thiazol-2-yl)-5'-methoxy-6-methyl-[4,4'-bipyridine]-3-carboxamide | 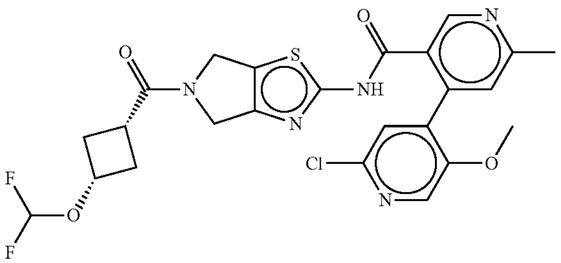 |

TABLE 1-continued

| Compound No. | Name | Structure |
|---|---|---|
| 11 | 2'-chloro-N-(5-(5-chloropicolinoyl)-5,6-dihydro-4H-pyrrolo[3,4-d]thiazol-2-yl)-5'-methoxy-6-methyl-[4,4'-bipyridine]-3-carboxamide | 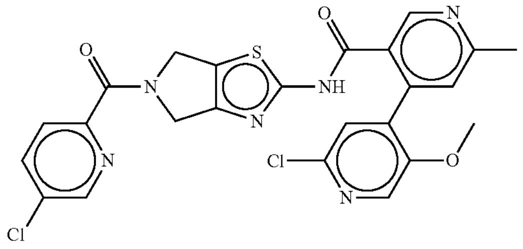 |
| 12 | 2'-chloro-N-(5-(6-(difluoromethyl)nicotinoyl)-5,6-dihydro-4H-pyrrolo[3,4-d]thiazol-2-yl)-5'-methoxy-6-methyl-[4,4'-bipyridine]-3-carboxamide | 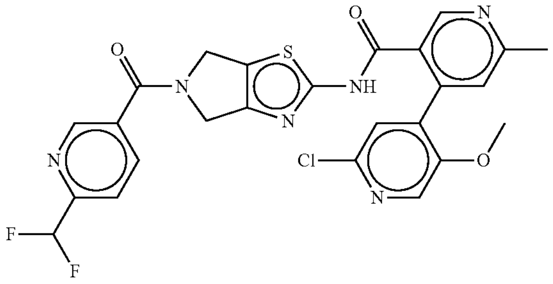 |
| 13 | 2'-chloro-N-(5-(6-chloronicotinoyl)-5,6-dihydro-4H-pyrrolo[3,4-d]thiazol-2-yl)-5'-methoxy-6-methyl-[4,4'-bipyridine]-3-carboxamide | 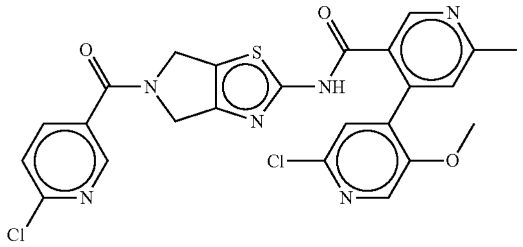 |
| 14 | 2'-chloro-5'-methoxy-6-methyl-N-(5-(6-(trifluoromethyl)pyridazine-3-carbonyl)-5,6-dihydro-4H-pyrrolo[3,4-d]thiazol-2-yl)-[4,4'-bipyridine]-3-carboxamide | 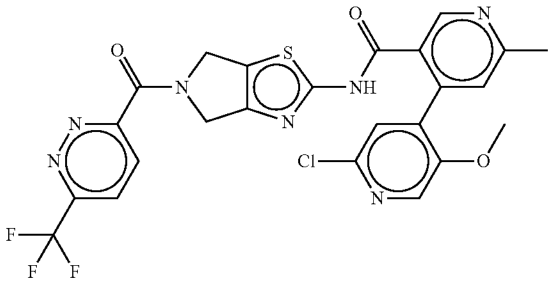 |
| 15 | 2'-chloro-5'-methoxy-N-(5-(2-methoxy-6-(trifluoromethyl)nicotinoyl)-5,6-dihydro-4H-pyrrolo[3,4-d]thiazol-2-yl)-6-methyl-[4,4'-bipyridine]-3-carboxamide | 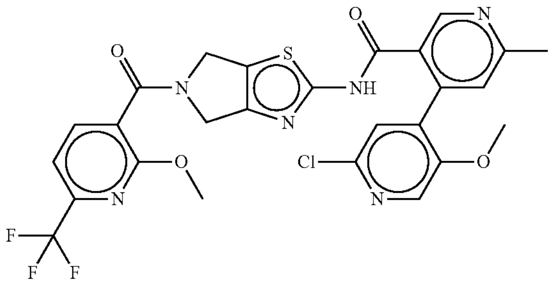 |

TABLE 1-continued

| Compound No. | Name | Structure |
|---|---|---|
| 16 | 2'-chloro-N-(5-(3-chloro-5-(trifluoromethyl)picolinoyl)-5,6-dihydro-4H-pyrrolo[3,4-d]thiazol-2-yl)-5'-methoxy-6-methyl-[4,4'-bipyridine]-3-carboxamide | 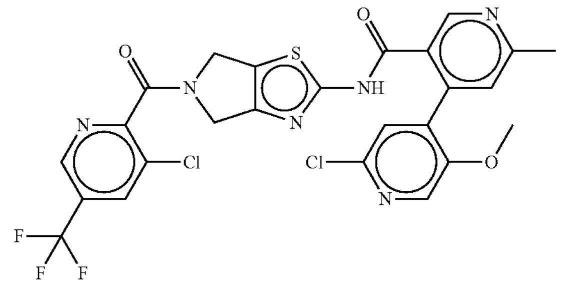 |
| 17 | 2'-chloro-N-(5-(1,5-dimethyl-1H-pyrazole-3-carbonyl)-5,6-dihydro-4H-pyrrolo[3,4-d]thiazol-2-yl)-5'-methoxy-6-methyl-[4,4'-bipyridine]-3-carboxamide | 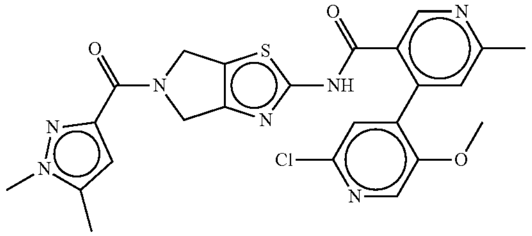 |
| 18 | 2'-chloro-N-(5-(6-(difluoromethyl)picolinoyl)-5,6-dihydro-4H-pyrrolo[3,4-d]thiazol-2-yl)-5'-methoxy-6-methyl-[4,4'-bipyridine]-3-carboxamide | 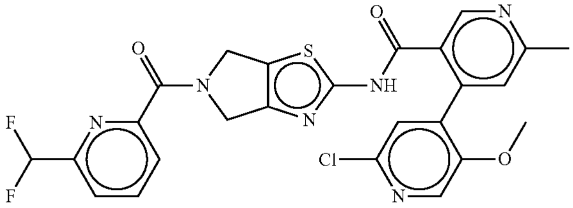 |
| 19 | 2'-chloro-N-(5-(4-chloronicotinoyl)-5,6-dihydro-4H-pyrrolo[3,4-d]thiazol-2-yl)-5'-methoxy-6-methyl-[4,4'-bipyridine]-3-carboxamide | 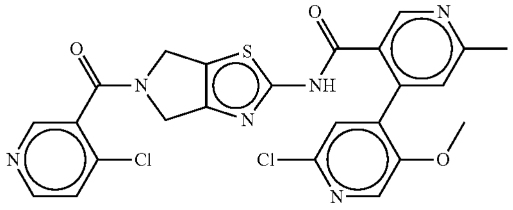 |
| 20 | 2'-chloro-N-(5-(6-chloro-2-methoxynicotinoyl)-5,6-dihydro-4H-pyrrolo[3,4-d]thiazol-2-yl)-5'-methoxy-6-methyl-[4,4'-bipyridine]-3-carboxamide | 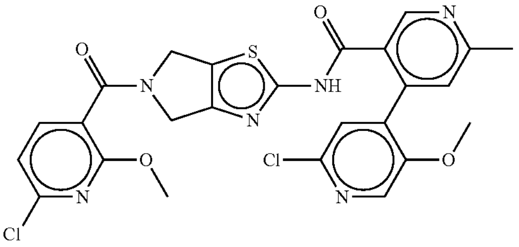 |
| 21 | 2'-chloro-5'-methoxy-6-methyl-N-(5-(6-(trifluoromethyl)picolinoyl)-5,6-dihydro-4H-pyrrolo[3,4-d]thiazol-2-yl)-[4,4'-bipyridine]-3-carboxamide | 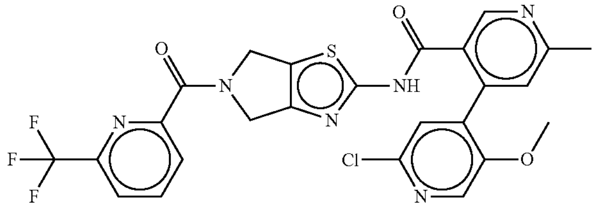 |

TABLE 1-continued

| Compound No. | Name | Structure |
|---|---|---|
| 22 | 4-(6-methoxyimidazo[1,5-a]pyridin-7-yl)-6-methyl-N-(5-((1r,3r)-3-(trifluoromethoxy)cyclobutane-1-carbonyl)-5,6-dihydro-4H-pyrrolo[3,4-d]thiazol-2-yl)nicotinamide | 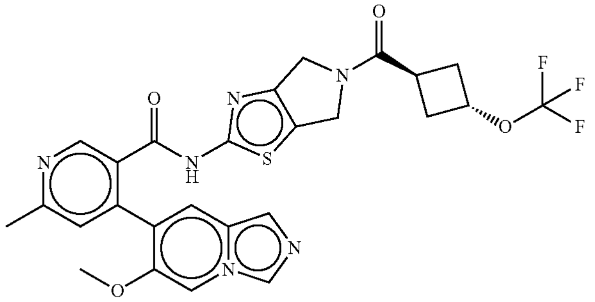 |
| 23 | 2'-chloro-5'-methoxy-6-methyl-N-(5-(1-methyl-1H-imidazole-2-carbonyl)-5,6-dihydro-4H-pyrrolo[3,4-d]thiazol-2-yl)-[4,4'-bipyridine]-3-carboxamide | 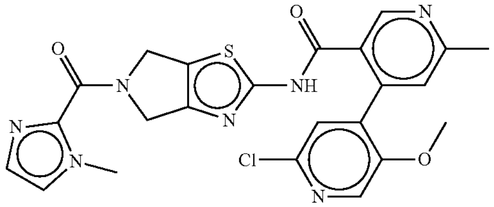 |
| 24 | 2'-chloro-N-(5-(1-(2,2-difluoroethyl)azetidine-3-carbonyl)-5,6-dihydro-4H-pyrrolo[3,4-d]thiazol-2-yl)-5'-methoxy-6-methyl-[4,4'-bipyridine]-3-carboxamide | 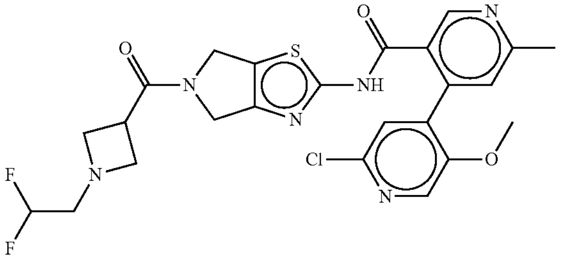 |
| 25 | 2'-chloro-5'-methoxy-6-methyl-N-(5-((1s,3s)-3-(trifluoromethoxy)cyclobutane-1-carbonyl)-5,6-dihydro-4H-pyrrolo[3,4-d]thiazol-2-yl)-[4,4'-bipyridine]-3-carboxamide | 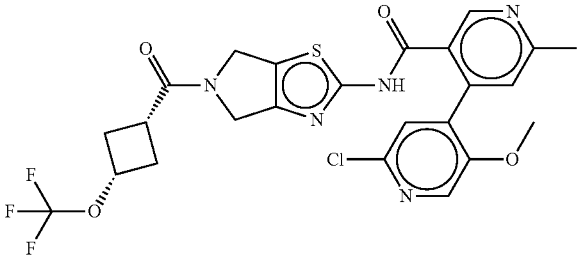 |
| 26 | 2'-chloro-5'-methoxy-6-methyl-N-(5-((1r,3r)-3-(trifluoromethoxy)cyclobutane-1-carbonyl)-5,6-dihydro-4H-pyrrolo[3,4-d]thiazol-2-yl)-[4,4'-bipyridine]-3-carboxamide | 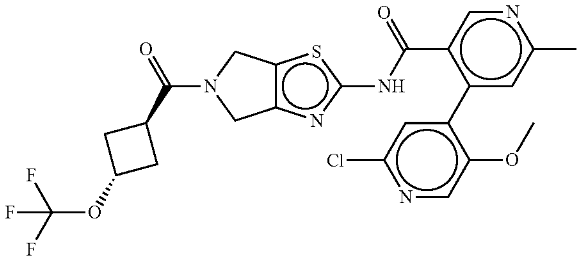 |
| 27 | (R or S)-2-(2'-chloro-5'-methoxy-6-methyl-[4,4'-bipyridine]-3-carboxamido)-N-cyclobutyl-4,5,6,7-tetrahydrobenzo[d]thiazole-6-carboxamide | 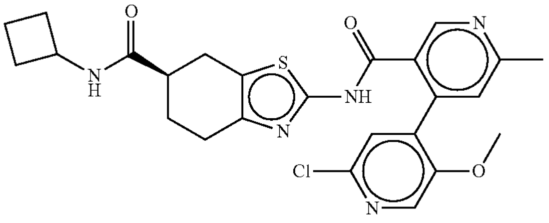 |

TABLE 1-continued

| Compound No. | Name | Structure |
|---|---|---|
| 28 | 2'-chloro-N-(5-(5-chloronicotinoyl)-5,6-dihydro-4H-pyrrolo[3,4-d]thiazol-2-yl)-5'-methoxy-6-methyl-[4,4'-bipyridine]-3-carboxamide | 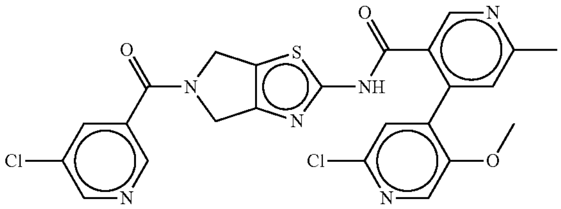 |
| 29 | (S or R)-2-(2'-chloro-5'-methoxy-6-methyl-[4,4'-bipyridine]-3-carboxamido)-N-cyclobutyl-4,5,6,7-tetrahydrobenzo[d]thiazole-6-carboxamide | 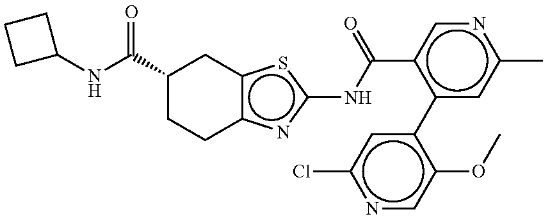 |
| 30 | 2'-chloro-5'-methoxy-6-methyl-N-(5-(1-methyl-1H-imidazole-5-carbonyl)-5,6-dihydro-4H-pyrrolo[3,4-d]thiazol-2-yl)-[4,4'-bipyridine]-3-carboxamide | 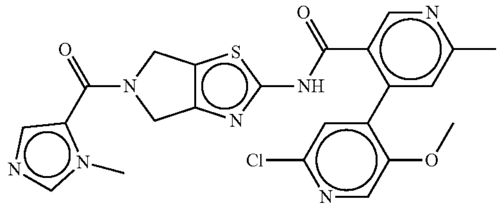 |
| 31 | 4-(6-methoxy-1-methyl-1H-indazol-5-yl)-N-(5-(2-methoxynicotinoyl)-5,6-dihydro-4H-pyrrolo[3,4-d]thiazol-2-yl)-6-methylnicotinamide | 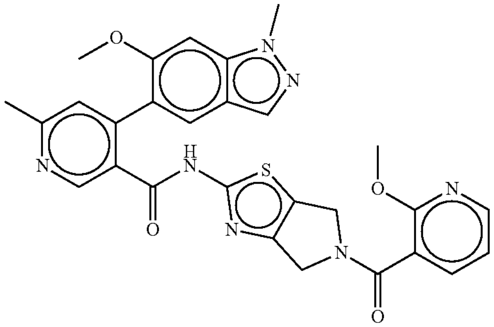 |
| 32 | 2'-chloro-N-(5-(6-(difluoromethoxy)nicotinoyl)-5,6-dihydro-4H-pyrrolo[3,4-d]thiazol-2-yl)-5'-methoxy-6-methyl-[4,4'-bipyridine]-3-carboxamide | 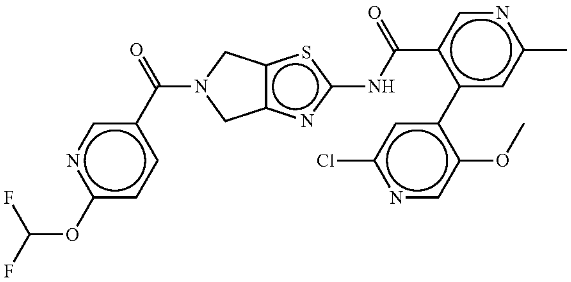 |
| 33 | 2'-chloro-5'-methoxy-6-methyl-N-(5-(pyridazine-3-carbonyl)-5,6-dihydro-4H-pyrrolo[3,4-d]thiazol-2-yl)-[4,4'-bipyridine]-3-carboxamide | 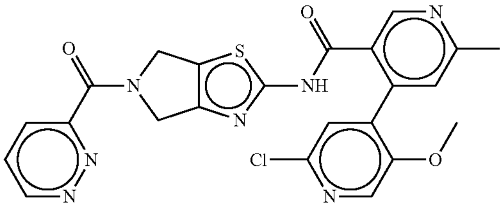 |

TABLE 1-continued

| Compound No. | Name | Structure |
|---|---|---|
| 34 | 2'-chloro-5'-methoxy-6-methyl-N-(5-(5-methylpyrimidine-2-carbonyl)-5,6-dihydro-4H-pyrrolo[3,4-d]thiazol-2-yl)-[4,4'-bipyridine]-3-carboxamide | 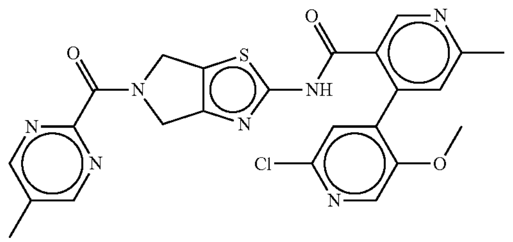 |
| 35 | 2'-chloro-N-(5-(5-chloropyrimidine-2-carbonyl)-5,6-dihydro-4H-pyrrolo[3,4-d]thiazol-2-yl)-5'-methoxy-6-methyl-[4,4'-bipyridine]-3-carboxamide | 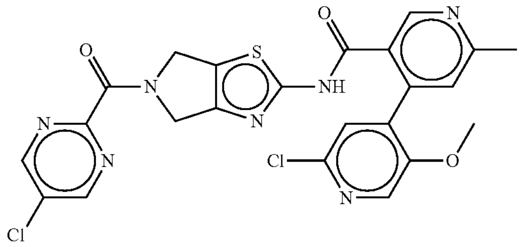 |
| 36 | 2'-chloro-N-(5-(4-chloro-6-(difluoromethyl)nicotinoyl)-5,6-dihydro-4H-pyrrolo[3,4-d]thiazol-2-yl)-S'-methoxy-6-methyl-[4,4'-bipyridine]-3-carboxamide | 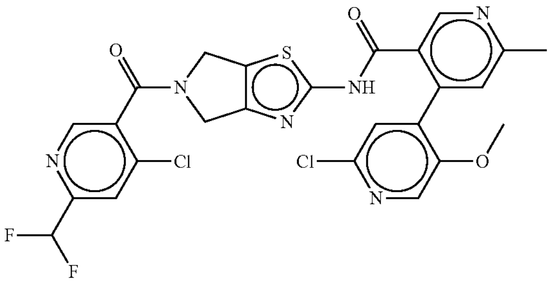 |
| 37 | 2'-chloro-5'-methoxy-6-methyl-N-(5-(5-(trifluoromethyl)pyrimidine-2-carbonyl)-5,6-dihydro-4H-pyrrolo[3,4-d]thiazol-2-yl)-[4,4'-bipyridine]-3-carboxamide | 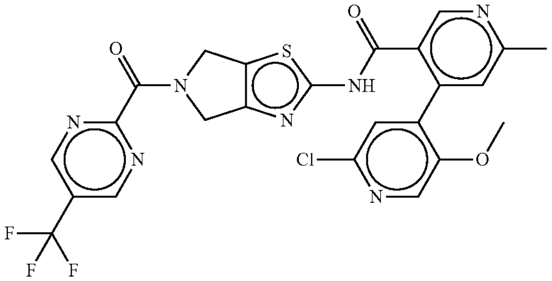 |
| 38 | 2'-chloro-5'-methoxy-N-(5-(3-methoxy-5-(trifluoromethyl)picolinoyl)-5,6-dihydro-4H-pyrrolo[3,4-d]thiazol-2-yl)-6-methyl-[4,4'-bipyridine]-3-carboxamide | 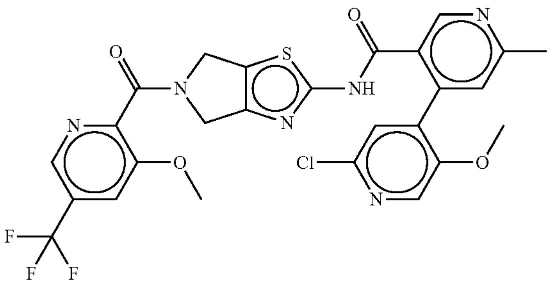 |
| 39 | 2'-chloro-N-(5-(2-(difluoromethyl)nicotinoyl)-5,6-dihydro-4H-pyrrolo[3,4-d]thiazol-2-yl)-5'-methoxy-6-methyl-[4,4'-bipyridine]-3-carboxamide | 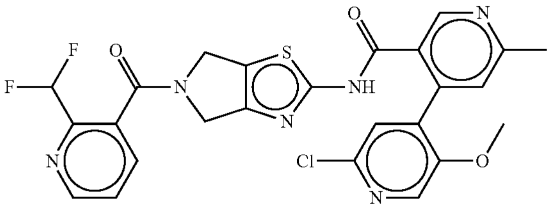 |

TABLE 1-continued

| Compound No. | Name | Structure |
|---|---|---|
| 40 | 2'-chloro-N-(5-(5-(difluoromethyl)pyrazine-2-carbonyl)-5,6-dihydro-4H-pyrrolo[3,4-d]thiazol-2-yl)-5'-methoxy-6-methyl-[4,4'-bipyridine]-3-carboxamide | 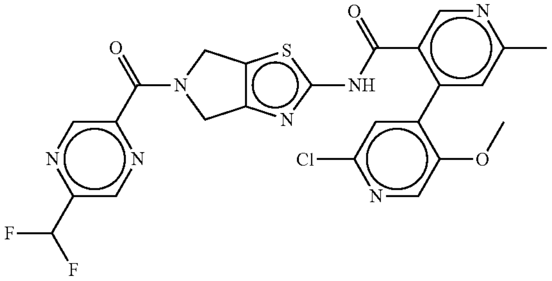 |
| 41 | 2'-chloro-5'-methoxy-6-methyl-N-(5-(pyrazine-2-carbonyl)-5,6-dihydro-4H-pyrrolo[3,4-d]thiazol-2-yl)-[4,4'-bipyridine]-3-carboxamide | 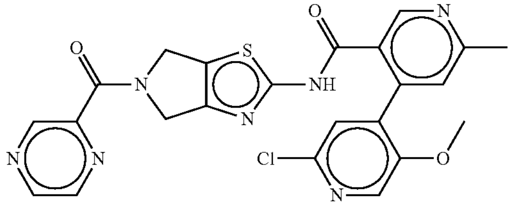 |
| 42 | 2'-chloro-5'-methoxy-6-methyl-N-(5-(6-(trifluoromethyl)nicotinoyl)-5,6-dihydro-4H-pyrrolo[3,4-d]thiazol-2-yl)-[4,4'-bipyridine]-3-carboxamide | 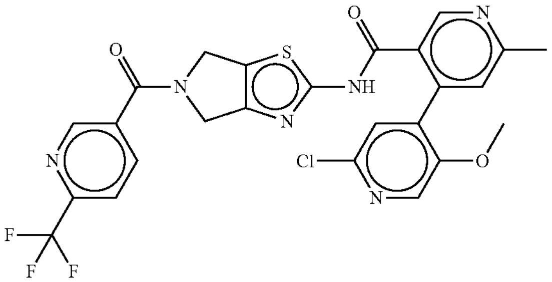 |
| 43 | 2'-chloro-N-(5-(3-(dimethylamino)cyclobutane-1-carbonyl)-5,6-dihydro-4H-pyrrolo[3,4-d]thiazol-2-yl)-5'-methoxy-6-methyl-[4,4'-bipyridine]-3-carboxamide | 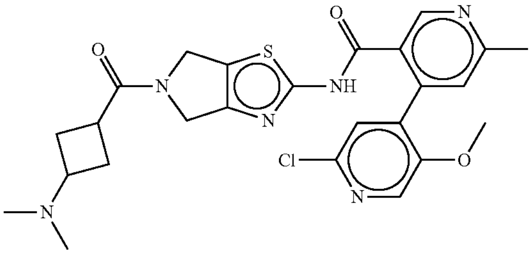 |
| 44 | 2'-chloro-5'-methoxy-6-methyl-N-(5-(1-methyl-3-(trifluoromethyl)-1H-pyrazole-5-carbonyl)-5,6-dihydro-4H-pyrrolo[3,4-d]thiazol-2-yl)-[4,4'-bipyridine]-3-carboxamide | 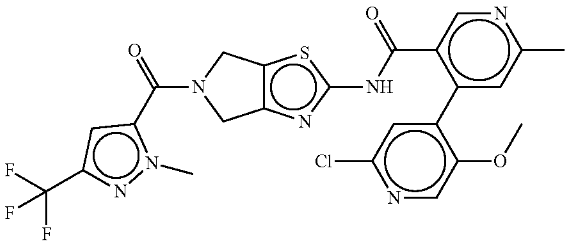 |
| 45 | 2'-chloro-5'-methoxy-6-methyl-N-(5-(5-methyloxazole-2-carbonyl)-5,6-dihydro-4H-pyrrolo[3,4-d]thiazol-2-yl)-[4,4'-bipyridine]-3-carboxamide | 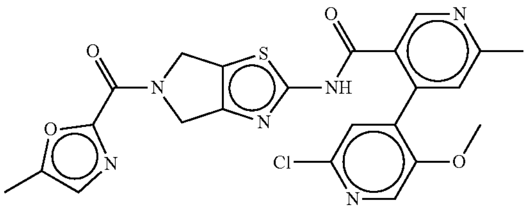 |

TABLE 1-continued

| Compound No. | Name | Structure |
|---|---|---|
| 46 | 2'-chloro-5'-methoxy-6-methyl-N-(5-(1-(2,2,2-trifluoroethyl)-1H-pyrazole-5-carbonyl)-5,6-dihydro-4H-pyrrolo[3,4-d]thiazol-2-yl)-[4,4'-bipyridine]-3-carboxamide | 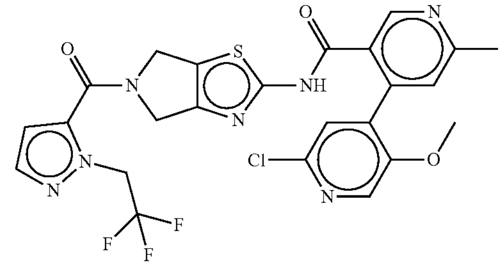 |
| 47 | 2'-chloro-5'-methoxy-6-methyl-N-(5-(1-methyl-1,4,5,6-tetrahydrocyclopenta[c]pyrazole-3-carbonyl)-5,6-dihydro-4H-pyrrolo[3,4-d]thiazol-2-yl)-[4,4'-bipyridine]-3-carboxamide | 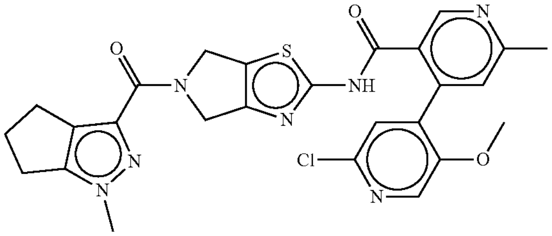 |
| 48 | 2'-chloro-5'-methoxy-N-(5-((1s,4s)-4-methoxycyclohexane-1-carbonyl)-5,6-dibydro-4H-pyrrolo[3,4-d]thiazol-2-yl)-6-methyl-[4,4'-bipyridine]-3-carboxamide | 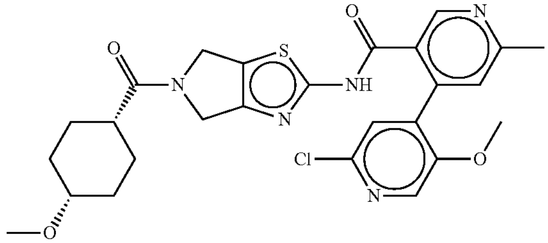 |
| 49 | 2'-chloro-N-(5-(1,3-dimethyl-1H-pyrazole-5-carbonyl)-5,6-dihydro-4H-pyrrolo[3,4-d]thiazol-2-yl)-5'-methoxy-6-methyl-[4,4'-bipyridine]-3-carboxamide | 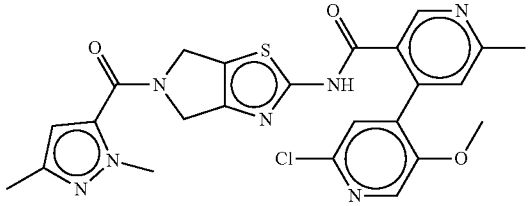 |
| 50 | 2'-chloro-5'-methoxy-6-methyl-N-(5-(1-methyl-1H-1,2,4-triazole-3-carbonyl)-5,6-dihydro-4H-pyrrolo[3,4-d]thiazol-2-yl)-[4,4'-bipyridine]-3-carboxamide | 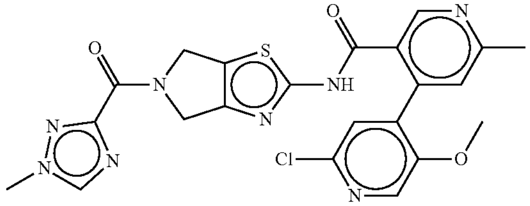 |
| 51 | 2'-chloro-N-(5-(1-(2,2-difluoroethyl)-1H-pyrazole-3-carbonyl)-5,6-dihydro-4H-pyrrolo[3,4-d]thiazol-2-yl)-5'-methoxy-6-methyl-[4,4'-bipyridine]-3-carboxamide | 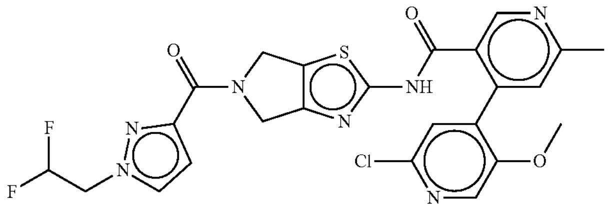 |

TABLE 1-continued

| Compound No. | Name | Structure |
|---|---|---|
| 52 | 2'-chloro-N-(5-(1-(difluoromethyl)-5-methyl-1H-pyrazole-3-carbonyl)-5,6-dihydro-4H-pyrrolo[3,4-d]thiazol-2-yl)-5'-methoxy-6-methyl-[4,4'-bipyridine]-3-carboxamide | 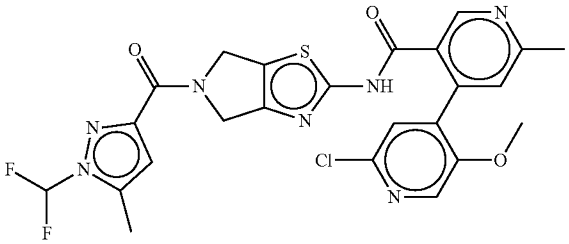 |
| 53 | 2'-chloro-N-(5-(5-chloro-1-methyl-1H-pyrazole-4-carbonyl)-5,6-dihydro-4H-pyrrolo[3,4-d]thiazol-2-yl)-5'-methoxy-6-methyl-[4,4'-bipyridine]-3-carboxamide | 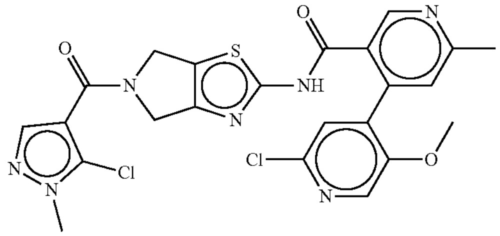 |
| 54 | 2'-chloro-5'-methoxy-6-methyl-N-(5-(2-methyl-2,4,5,6-tetrahydrocyclopenta[c]pyrazole-3-carbonyl)-5,6-dihydro-4H-pyrrolo[3,4-d]thiazol-2-yl)-[4,4'-bipyridine]-3-carboxamide | 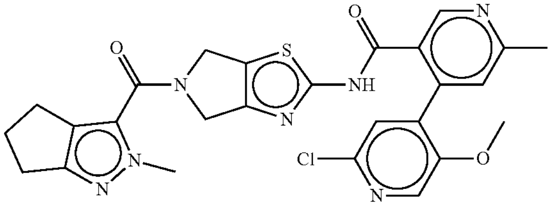 |
| 55 | 2'-chloro-N-(5-(4-chloro-1-(difluoromethyl)-1H-pyrazole-3-carbonyl)-5,6-dihydro-4H-pyrrolo[3,4-d]thiazol-2-yl)-5'-methoxy-6-methyl-[4,4'-bipyridine]-3-carboxamide | 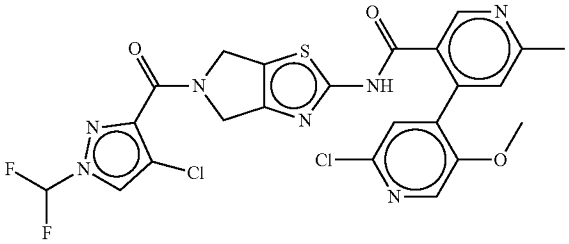 |
| 56 | 2'-chloro-N-(5-(4-chloro-3-ethyl-1-methyl-1H-pyrazole-5-carbonyl)-5,6-dihydro-4H-pyrrolo[3,4-d]thiazol-2-yl)-5'-methoxy-6-methyl-[4,4'-bipyridine]-3-carboxamide | 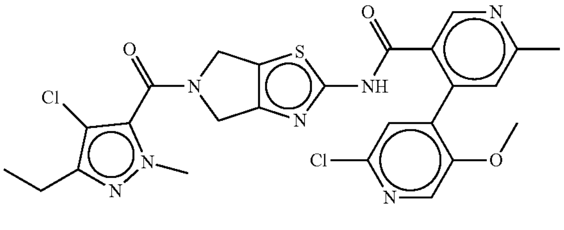 |
| 57 | 2'-chloro-N-(5-(3-ethyl-1-methyl-1H-pyrazole-5-carbonyl)-5,6-dihydro-4H-pyrrolo[3,4-d]thiazol-2-yl)-5'-methoxy-6-methyl-[4,4'-bipyridine]-3-carboxamide | 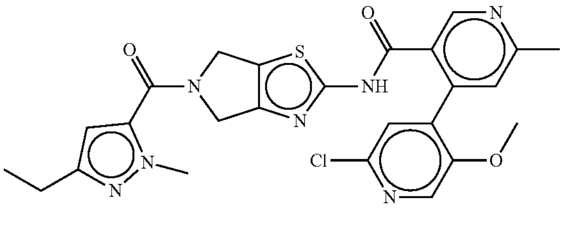 |

TABLE 1-continued

| Compound No. | Name | Structure |
|---|---|---|
| 58 | 2'-chloro-N-(5-(5-ethyl-1-methyl-1H-pyrazole-3-carbonyl)-5,6-dihydro-4H-pyrrolo[3,4-d]thiazol-2-yl)-5'-methoxy-6-methyl-[4,4'-bipyridine]-3-carboxamide | 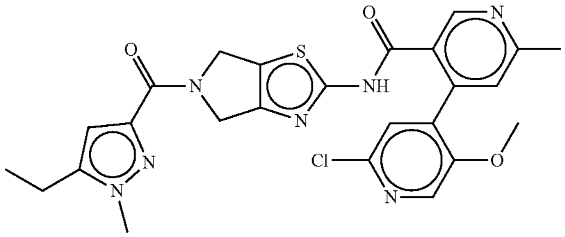 |
| 59 | 2'-chloro-N-(5-(3-(difluoromethyl)-5-fluoro-1-methyl-1H-pyrazole-4-carbonyl)-5,6-dihydro-4H-pyrrolo[3,4-d]thiazol-2-yl)-5'-methoxy-6-methyl-[4,4'-bipyridine]-3-carboxamide | 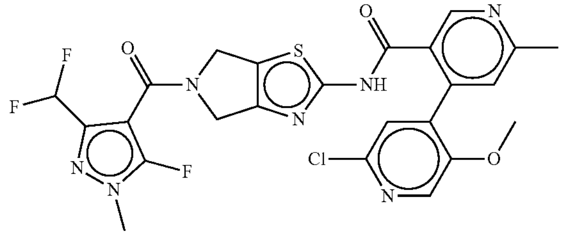 |
| 60 | N-(5-(1,2,4-oxadiazole-3-carbonyl)-5,6-dihydro-4H-pyrrolo[3,4-d]thiazol-2-yl)-2'-chloro-5'-methoxy-6-methyl-[4,4'-bipyridine]-3-carboxamide | 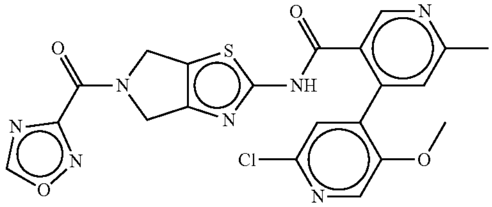 |
| 61 | 2'-chloro-5'-methoxy-6-methyl-N-(5-(1-methyl-3-(trifluoromethyl)-1H-pyrazole-4-carbonyl)-5,6-dihydro-4H-pyrrolo[3,4-d]thiazol-2-yl)-[4,4'-bipyridine]-3-carboxamide | 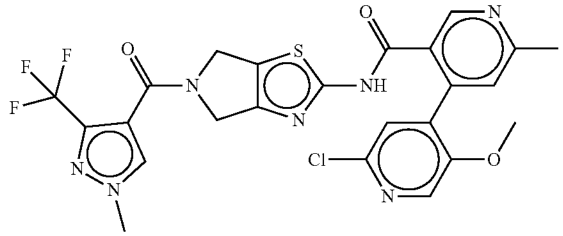 |
| 62 | 2'-chloro-N-(5-(1-ethyl-1H-pyrazole-4-carbonyl)-5,6-dihydro-4H-pyrrolo[3,4-d]thiazol-2-yl)-5'-methoxy-6-methyl-[4,4'-bipyridine]-3-carboxamide | 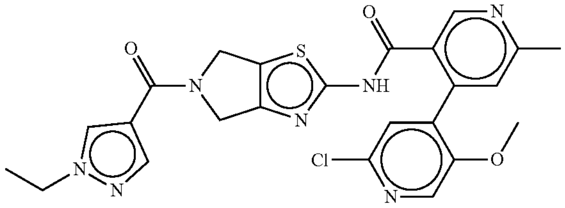 |
| 63 | 2'-chloro-N-(5-(5,6-dihydro-4H-pyrrolo[1,2-b]pyrazole-2-carbonyl)-5,6-dihydro-4H-pyrrolo[3,4-d]thiazol-2-yl)-5'-methoxy-6-methyl-[4,4'-bipyridine]-3-carboxamide | 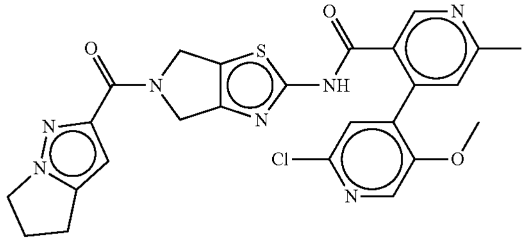 |

TABLE 1-continued

| Compound No. | Name | Structure |
|---|---|---|
| 64 | 2'-chloro-N-(5-(6,6-difluorospiro[3.3]heptane-2-carbonyl)-5,6-dihydro-4H-pyrrolo[3,4-d]thiazol-2-yl)-5'-methoxy-6-methyl-[4,4'-bipyridine]-3-carboxamide | 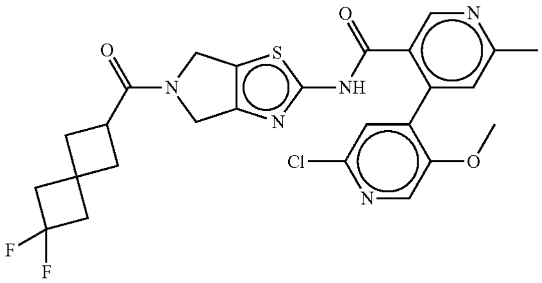 |
| 65 | 2'-chloro-N-(5-(1,4-dimethyl-1H-pyrazole-3-carbonyl)-5,6-dihydro-4H-pyrrolo[3,4-d]thiazol-2-yl)-5'-methoxy-6-methyl-[4,4'-bipyridine]-3-carboxamide | 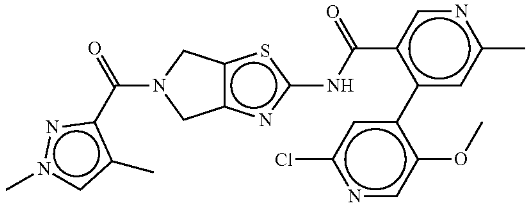 |
| 66 | 2'-chloro-N-(S-(4-fluoro-1,5-dimethyl-1H-pyrazole-3-carbonyl)-5,6-dihydro-4H-pyrrolo[3,4-d]thiazol-2-y])-5'-methoxy-6-methyl-[4,4'-bipyridine]-3-carboxamide | 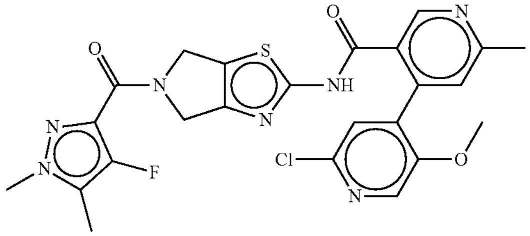 |
| 67 | 2'-chloro-5'-methoxy-6-methyl-N-(5-(4-methyloxazole-2-carbonyl)-5,6-dihydro-4H-pyrrolo[3,4-d]thiazol-2-yl)-[4,4'-bipyridine]-3-carboxamide | 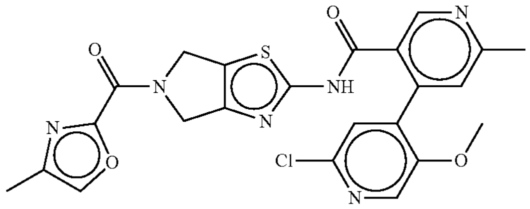 |
| 68 | 2'-chloro-N-(5-(1-cyclopropyl-1H-pyrazole-3-carbonyl)-5,6-dihydro-4H-pyrrolo[3,4-d]thiazol-2-yl)-5'-methoxy-6-methyl-[4,4'-bipyridine]-3-carboxamide | 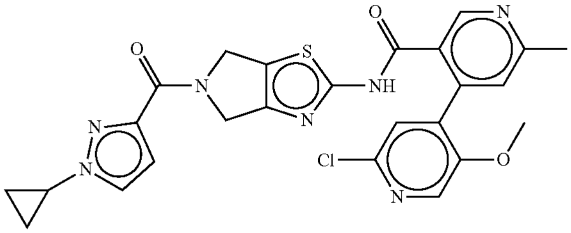 |
| 69 | 2'-chloro-N-(5-(1-ethyl-1H-pyrazole-3-carbonyl)-5,6-dihydro-4H-pyrrolo[3,4-d]thiazol-2-yl)-5'-methoxy-6-methyl-[4,4'-bipyridine]-3-carboxamide | 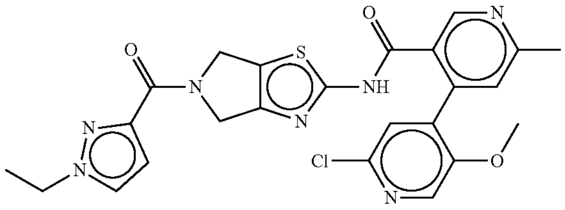 |

TABLE 1-continued

| Compound No. | Name | Structure |
|---|---|---|
| 70 | 2'-chloro-N-(5-(4-chloro-5-ethyl-1-methyl-1H-pyrazole-3-carbonyl)-5,6-dihydro-4H-pyrrolo[3,4-d]thiazol-2-yl)-5'-methoxy-6-methyl-[4,4'-bipyridine]-3-carboxamide | 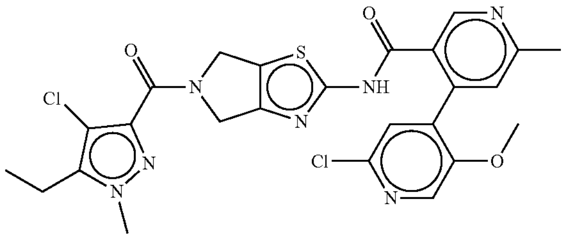 |
| 71 | 2'-chloro-N-(5-(3-hydroxypicolinoyl)-5,6-dihydro-4H-pyrrolo[3,4-d]thiazol-2-yl)-5'-methoxy-6-methyl-[4,4'-bipyridine]-3-carboxamide | 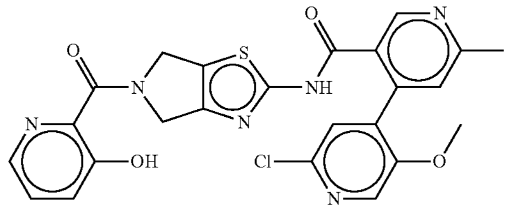 |
| 72 | 2'-chloro-N-(5-(6-(difluoromethoxy)picolinoyl)-5,6-dihydro-4H-pyrrolo[3,4-d]thiazol-2-yl)-5'-methoxy-6-methyl-[4,4'-bipyridine]-3-carboxamide | 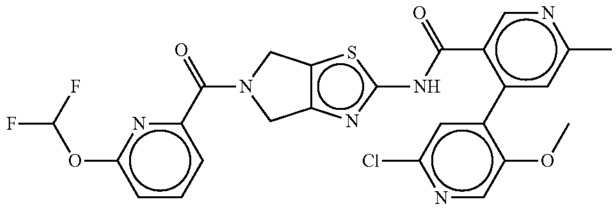 |
| 73 | 2'-chloro-N-(5-(5-chloro-1-methyl-1H-pyrazole-3-carbonyl)-5,6-dihydro-4H-pyrrolo[3,4-d]thiazol-2-yl)-5'-methoxy-6-methyl-[4,4'-bipyridine]-3-carboxamide | 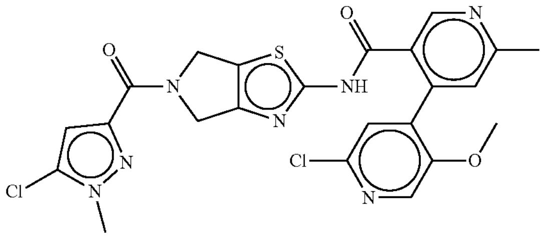 |
| 74 | 2'-chloro-N-(5-(4-chloro-1,5-dimethyl-1H-pyrazole-3-carbonyl)-5,6-dihydro-4H-pyrrolo[3,4-d]thiazol-2-yl)-5'-methoxy-6-methyl-[4,4'-bipyridine]-3-carboxamide | 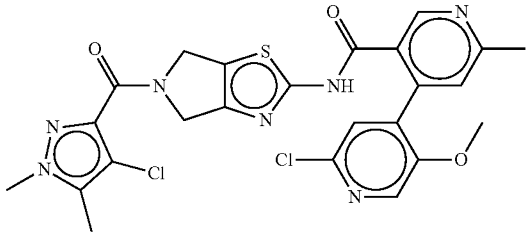 |
| 75 | 2'-chloro-N-(5-(1-isopropyl-1H-pyrazole-5-carbonyl)-5,6-dihydro-4H-pyrrolo[3,4-d]thiazol-2-yl)-5'-methoxy-6-methyl-[4,4'-bipyridine]-3-carboxamide | 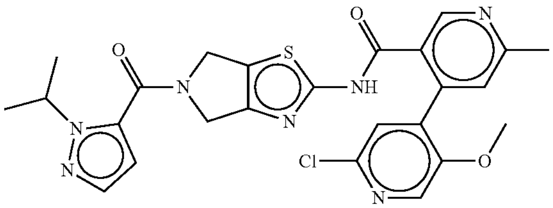 |

TABLE 1-continued

| Compound No. | Name | Structure |
|---|---|---|
| 76 | 2'-chloro-5'-methoxy-6-methyl-N-(5-(1,3,5-trimethyl-1H-pyrazole-4-carbonyl)-5,6-dihydro-4H-pyrrolo[3,4-d]thiazol-2-yl)-[4,4'-bipyridine]-3-carboxamide | 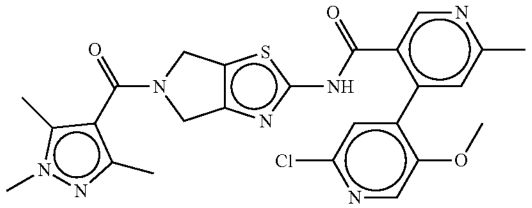 |
| 77 | 2'-chloro-N-(5-(1-isopropyl-1H-1,2,4-triazole-3-carbonyl)-5,6-dihydro-4H-pyrrolo[3,4-d]thiazol-2-yl)-5'-methoxy-6-methyl-[4,4'-bipyridine]-3-carboxamide | 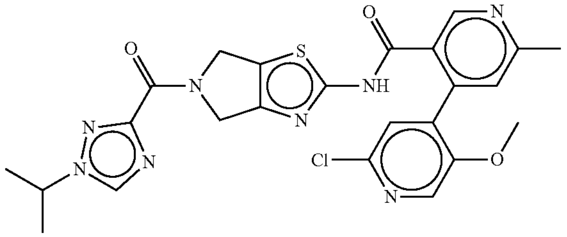 |
| 78 | 2'-chloro-N-(5-(4-chloropicolinoyl)-5,6-dihydro-4H-pyrrolo[3,4-d]thiazol-2-yl)-5'-methoxy-6-methyl-[4,4'-bipyridine]-3-carboxamide | 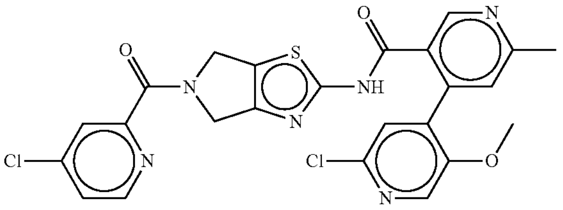 |
| 79 | 2'-chloro-5'-methoxy-N-(5-(5-methoxyoxazole-2-carbonyl)-5,6-dihydro-4H-pyrrolo[3,4-d]thiazol-2-yl)-6-methyl-[4,4'-bipyridine]-3-carboxamide | 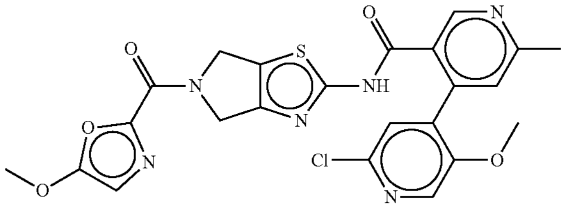 |
| 80 | 2'-chloro-N-(5-(1-cyclopropyl-1H-pyrazole-4-carbonyl)-5,6-dihydro-4H-pyrrolo[3,4-d]thiazol-2-yl)-5'-methoxy-6-methyl-[4,4'-bipyridine]-3-carboxamide | 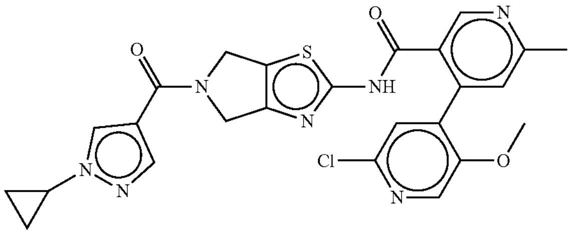 |
| 81 | 2'-chloro-N-(5-(1,4-dimethyl-1H-pyrazole-5-carbonyl)-5,6-dihydro-4H-pyrrolo[3,4-d]thiazol-2-yl)-5'-methoxy-6-methyl-[4,4'-bipyridine]-3-carboxamide | 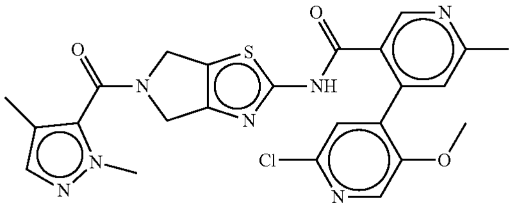 |

TABLE 1-continued

| Compound No. | Name | Structure |
|---|---|---|
| 82 | 2'-chloro-N-(5-(1-isopropyl-1H-pyrazole-3-carbonyl)-5,6-dihydro-4H-pyrrolo[3,4-d]thiazol-2-yl)-5'-methoxy-6-methyl-[4,4'-bipyridine]-3-carboxamide | 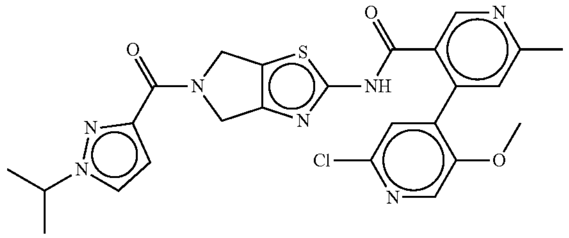 |
| 83 | 2'-chloro-5'-methoxy-6-methyl-N-(5-(1-(2,2,2-trifluoroethyl)-1H-pyrazole-4-carbonyl)-5,6-dihydro-4H-pyrrolo[3,4-d]thiazol-2-yl)-[4,4'-bipyridine]-3-carboxamide | 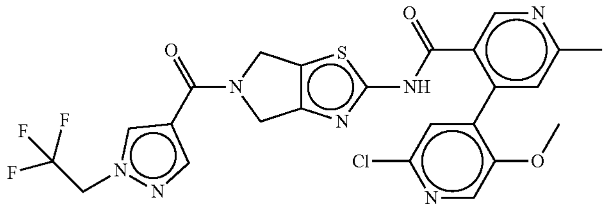 |
| 84 | 2'-chloro-5'-methoxy-6-methyl-N-(5-(1-methyl-5-(trifluoromethyl)-1H-pyrazole-4-carbonyl)-5,6-dihydro-4H-pyrrolo[3,4-d]thiazol-2-yl)-[4,4'-bipyridine]-3-carboxamide | 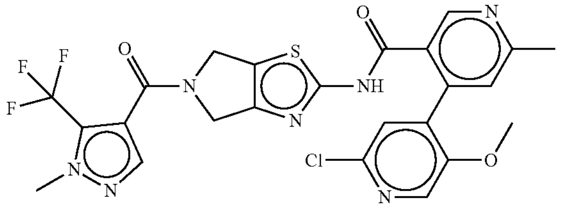 |
| 85 | 2'-chloro-N-(5-(1-isopropyl-1H-pyrazole-4-carbonyl)-5,6-dihydro-4H-pyrrolo[3,4-d]thiazol-2-yl)-5'-methoxy-6-methyl-[4,4'-bipyridine]-3-carboxamide | 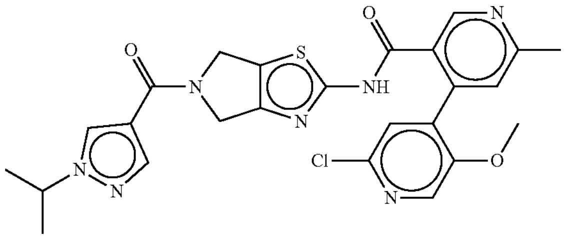 |
| 86 | N-(5-(1H-pyrazole-5-carbonyl)-5,6-dihydro-4H-pyrrolo[3,4-d]thiazol-2-yl)-2'-chloro-5'-methoxy-6-methyl-[4,4'-bipyridine]-3-carboxamide | 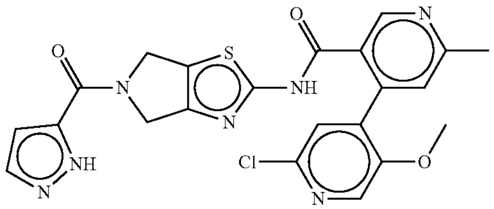 |
| 87 | 2'-chloro-N-(5-(1,5-dimethyl-1H-pyrazole-4-carbonyl)-5,6-dihydro-4H-pyrrolo[3,4-d]thiazol-2-yl)-5'-methoxy-6-methyl-[4,4'-bipyridine]-3-carboxamide | 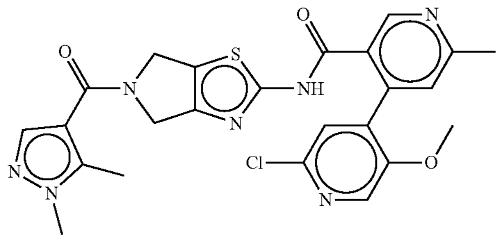 |

TABLE 1-continued

| Compound No. | Name | Structure |
|---|---|---|
| 88 | N-(5-(1H-pyrazole-4-carbonyl)-5,6-dihydro-4H-pyrrolo[3,4-d]thiazol-2-yl)-2'-chloro-5'-methoxy-6-methyl-[4,4'-bipyridine]-3-carboxamide | 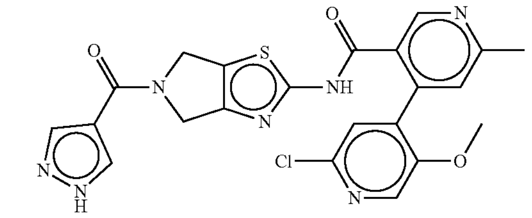 |
| 89 | 2'-chloro-N-(5-(5-chloro-3-(difluoromethyl)-1-methyl-1H-pyrazole-4-carbonyl)-5,6-dihydro-4H-pyrrolo[3,4-d]thiazol-2-yl)-5'-methoxy-6-methyl-[4,4'-bipyridine]-3-carboxamide | 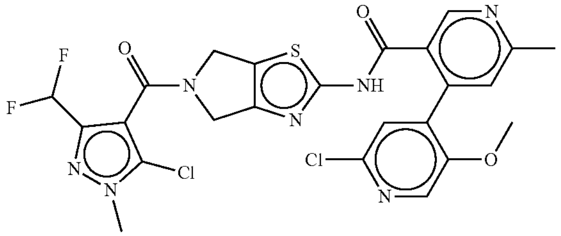 |
| 90 | 2'-chloro-5'-methoxy-N-(5-(3-methoxy-1-methyl-1H-pyrazole-5-carbonyl)-5,6-dihydro-4H-pyrrolo[3,4-d]thiazol-2-yl)-6-methyl-[4,4'-bipyridine]-3-carboxamide | 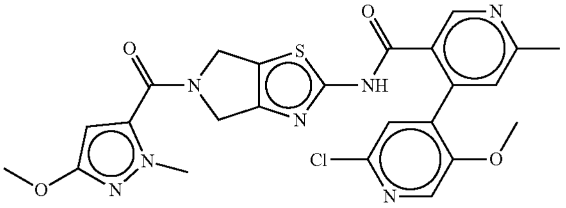 |
| 91 | 2'-chloro-N-(5-(5-(difluoromethyl)-1-methyl-1H-pyrazole-4-carbonyl)-5,6-dihydro-4H-pyrrolo[3,4-d]thiazol-2-yl)-5'-methoxy-6-methyl-[4,4'-bipyridine]-3-carboxamide | 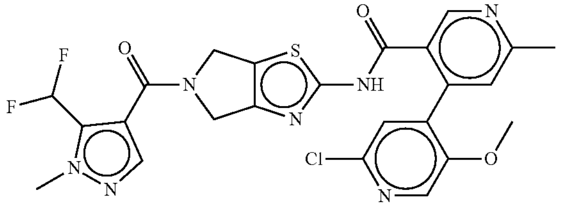 |
| 92 | 2'-chloro-N-(5-(5-hydroxy-1-methyl-1H-pyrazole-3-carbonyl)-5,6-dihydro-4H-pyrrolo[3,4-d]thiazol-2-yl)-5'-methoxy-6-methyl-[4,4'-bipyridine]-3-carboxamide | 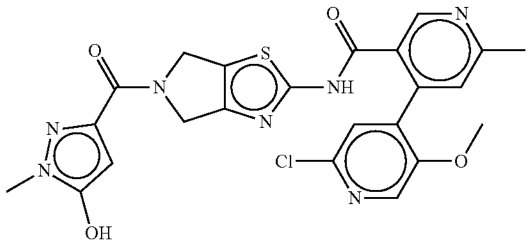 |
| 93 | 2'-chloro-N-(5-(5-(difluoromethoxy)picolinoyl)-5,6-dihydro-4H-pyrrolo[3,4-d]thiazol-2-yl)-5'-methoxy-6-methyl-[4,4'-bipyridine]-3-carboxamide | 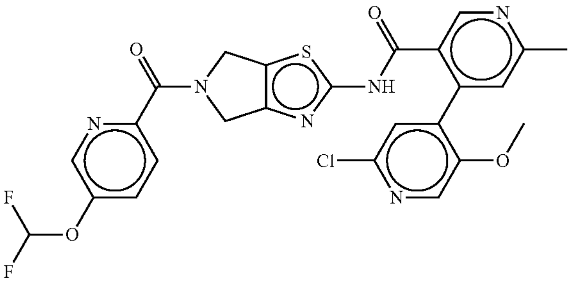 |

TABLE 1-continued

| Compound No. | Name | Structure |
|---|---|---|
| 94 | 2'-chloro-N-(5-(4-(difluoromethyl)picolinoyl)-5,6-dihydro-4H-pyrrolo[3,4-d]thiazol-2-yl)-5'-methoxy-6-methyl-[4,4'-bipyridine]-3-carboxamide | 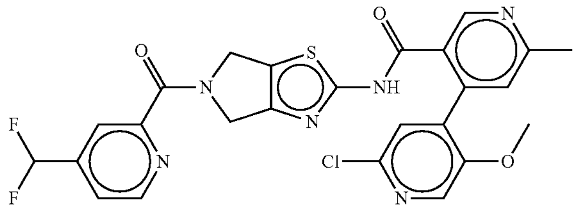 |
| 95 | 2'-chloro-N-(5-(5-isopropyl-1-methyl-1H-pyrazole-3-carbonyl)-5,6-dihydro-4H-pyrrolo[3,4-d]thiazol-2-yl)-5'-methoxy-6-methyl-[4,4'-bipyridine]-3-carboxamide | 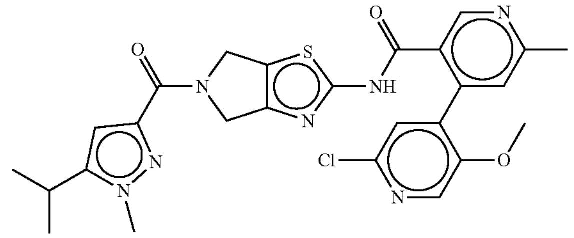 |
| 96 | 2'-chloro-N-(5-((1r,4r)-4-hydroxycyclohexane-1-carbonyl)-5,6-dihydro-4H-pyrrolo[3,4-d]thiazol-2-yl)-5'-methoxy-6-methyl-[4,4'-bipyridine]-3-carboxamide | 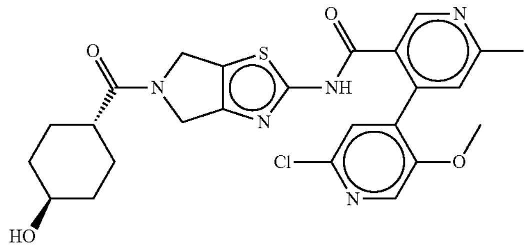 |
| 97 | 4-(6-methoxyimidazo[1,5-a]pyridin-7-yl)-6-methyl-N-(5-((1s,3s)-3-(trifluoromethoxy)cyclobutane-1-carbonyl)-5,6-dihydro-4H-pyrrolo[3,4-d]thiazol-2-yl)nicotinamide | 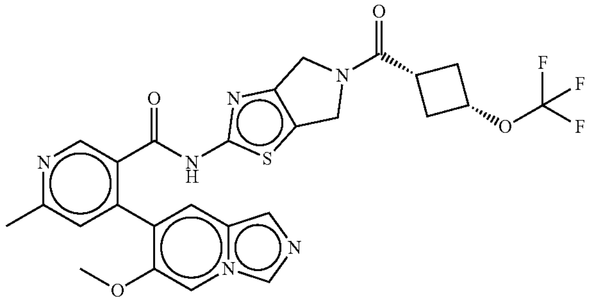 |
| 98 | 3'-methoxy-6-methyl-N-(5-picolinoyl-5,6-dihydro-4H-pyrrolo[3,4-d]thiazol-2-yl)-[4,4'-bipyridine]-3-carboxamide | 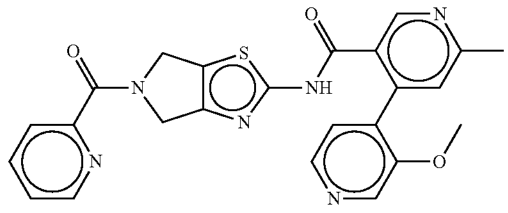 |
| 99 | 2'-chloro-N-(6-(((1s,3s)-3-hydroxycyclobutyl)amino)-4,5,6,7-tetrahydrobenzo[d]thiazol-2-yl)-5'-methoxy-6-methyl-[4,4'-bipyridine]-3-carboxamide | 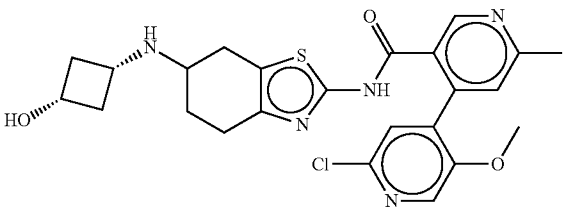 |

TABLE 1-continued

| Compound No. | Name | Structure |
|---|---|---|
| 100 | 2'-chloro-5'-methoxy-6-methyl-N-(5-(pyrimidine-2-carbonyl)-5,6-dihydro-4H-pyrrolo[3,4-d]thiazol-2-yl)-[4,4'-bipyridine]-3-carboxamide | 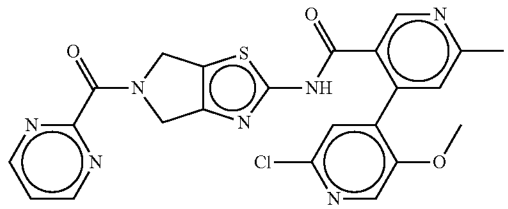 |
| 101 | (Racemic)-2'-chloro-5'-methoxy-N-(5-(3-methoxycyclopentane-1-carbonyl)-5,6-dihydro-4H-pyrrolo[3,4-d]thiazol-2-yl)-6-methyl-[4,4'-bipyridine]-3-carboxamide | 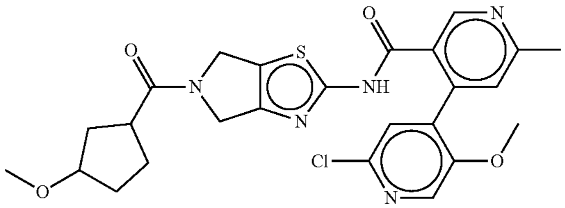 |
| 102 | 2'-chloro-N-(5-((1R,2R)-2-(hydroxymethyl)cyclopropane-1-carbonyl)-5,6-dihydro-4H-pyrrolo[3,4-d]thiazol-2-yl)-5'-methoxy-6-methyl-[4,4'-bipyridine]-3-carboxamide | 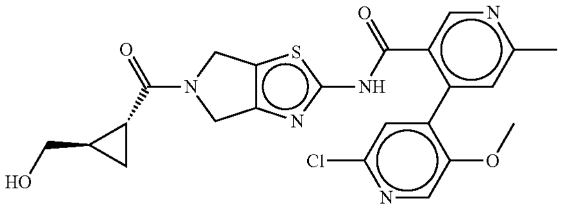 |
| 103 | (Racemic)-2'-chloro-5'-methoxy-N-(5-(3-methoxy-3-(trifluoromethyl)cyclobutane-1-carbonyl)-5,6-dihydro-4H-pyrrolo[3,4-d]thiazol-2-yl)-6-methyl-[4,4'-bipyridine]-3-carboxamide | 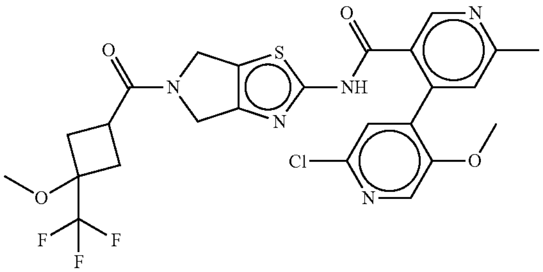 |
| 104 | 2'-chloro-N-(5-((1R,2S)-2-(difluoromethyl)cyclopropane-1-carbonyl)-5,6-dihydro-4H-pyrrolo[3,4-d]thiazol-2-yl)-5'-methoxy-6-methyl-[4,4'-bipyridine]-3-carboxamide | 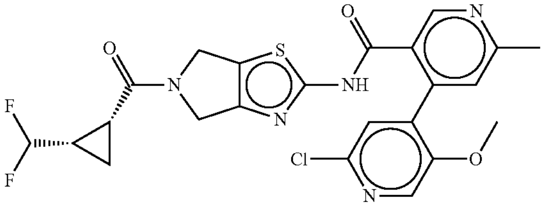 |
| 105 | 2'-chloro-N-(5-((1s,3s)-3-fluoro-3-(hydroxymethyl)cyclobutane-1-carbonyl)-5,6-dihydro-4H-pyrrolo[3,4-d]thiazol-2-yl)-5'-methoxy-6-methyl-[4,4'-bipyridine]-3-carboxamide | 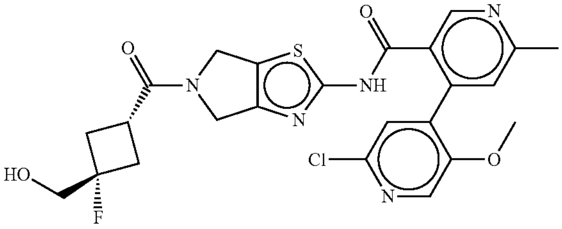 |

TABLE 1-continued

| Compound No. | Name | Structure |
|---|---|---|
| 106 | 2'-chloro-N-(5-((1r,3r)-3-fluoro-3-(hydroxymethyl)cyclobutane-1-carbonyl)-5,6-dihydro-4H-pyrrolo[3,4-d]thiazol-2-yl)-5'-methoxy-6-methyl-[4,4'-bipyridine]-3-carboxamide | 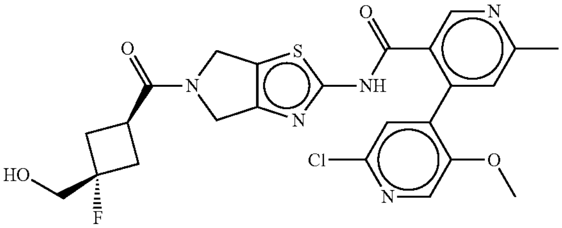 |
| 107 | 2'-chloro-N-(5-((1R,2S)-2-(hydroxymethyl)cyclopropane-1-carbonyl)-5,6-dihydro-4H-pyrrolo[3,4-d]thiazol-2-yl)-5'-methoxy-6-methyl-[4,4'-bipyridine]-3-carboxamide | 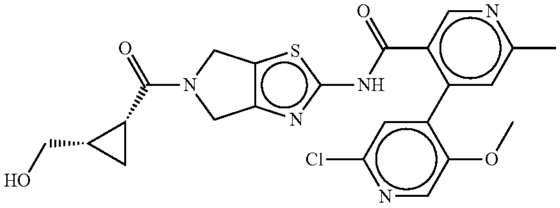 |
| 108 | 5'-methoxy-2',6-dimethyl-N-(5-picolinoyl-5,6-dihydro-4H-pyrrolo[3,4-d]thiazol-2-yl)-[4,4'-bipyridine]-3-carboxamide | 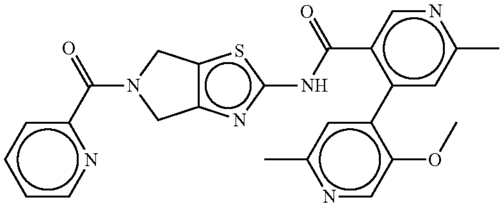 |
| 109 | (Racemic)-2'-chloro-N-(6-(4-hydroxypiperidin-1-yl)-4,5,6,7-tetrahydrobenzo[d]thiazol-2-yl)-5'-methoxy-6-methyl-[4,4'-bipyridine]-3-carboxamide | 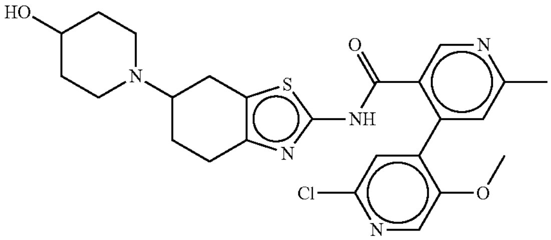 |
| 110 | (Racemic)-2'-chloro-5'-methoxy-6-methyl-N-(6-(piperidin-1-yl)-4,5,6,7-tetrahydrobenzo[d]thiazol-2-yl)-[4,4'-bipyridine]-3-carboxamide | 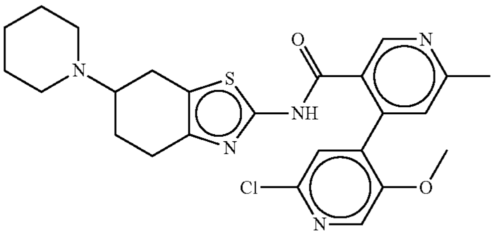 |
| 111 | 2'-chloro-N-(6-(((1r,3r)-3-hydroxycyclobutyl)amino)-4,5,6,7-tetrahydrobenzo[d]thiazol-2-yl)-5'-methoxy-6-methyl-[4,4'-bipyridine]-3-carboxamide | 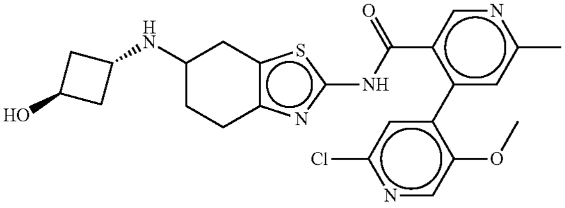 |

TABLE 1-continued

| Compound No. | Name | Structure |
|---|---|---|
| 112 | 2'-chloro-N-(5-(4-hydroxy-4-(trifluoromethyl)cyclohexane-1-carbonyl)-5,6-dihydro-4H-pyrrolo[3,4-d]thiazol-2-yl)-5'-methoxy-6-methyl-[4,4'-bipyridine]-3-carboxamide | 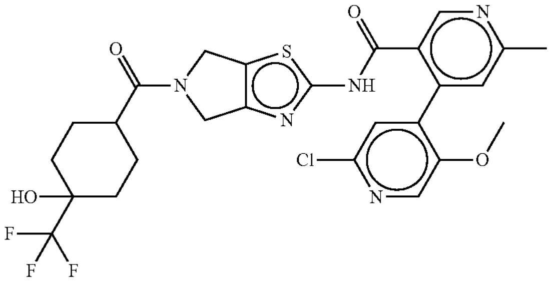 |
| 113 | 2'-chloro-5'-methoxy-N-(5-((1r,4r)-4-methoxycyclohexane-1-carbonyl)-5,6-dihydro-4H-pyrrolo[3,4-d]thiazol-2-yl)-6-methyl-[4,4'-bipyridine]-3-carboxamide | 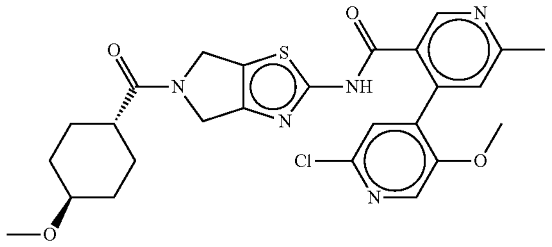 |
| 114 | 2'-chloro-N-(5-(1-(difluoromethyl)-3-methyl-1H-pyrazole-5-carbonyl)-5,6-dihydro-4H-pyrrolo[3,4-d]thiazol-2-yl)-5'-methoxy-6-methyl-[4,4'-bipyridine]-3-carboxamide | 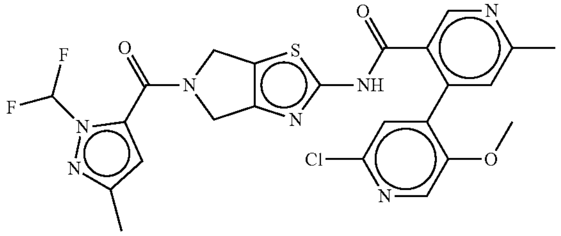 |
| 115 | 2'-chloro-N-(5-((1s,4s)-4-hydroxycyclohexane-1-carbonyl)-5,6-dihydro-4H-pyrrolo[3,4-d]thiazol-2-yl)-5'-methoxy-6-methyl-[4,4'-bipyridine]-3-carboxamide | 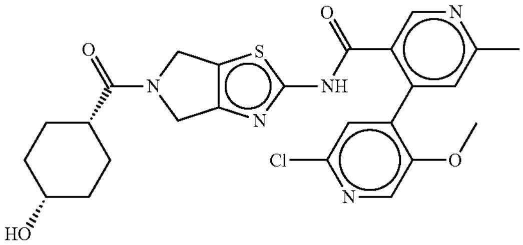 |
| 116 | 2'-chloro-N-(5-(1-ethyl-1H-pyrazole-5-carbonyl)-5,6-dihydro-4H-pyrrolo[3,4-d]thiazol-2-yl)-5'-methoxy-6-methyl-[4,4'-bipyridine]-3-carboxamide | 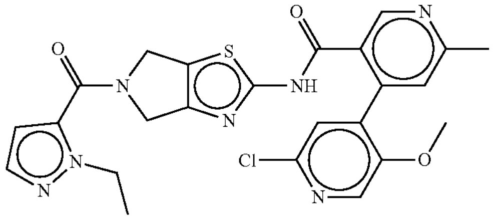 |
| 117 | N-(5-(5-(difluoromethyl)picolinoyl)-5,6-dihydro-4H-pyrrolo[3,4-d]thiazol-2-yl)-4-(6-methoxyimidazo[1,5-a]pyridin-7-yl)-6-methylnicotinamide | 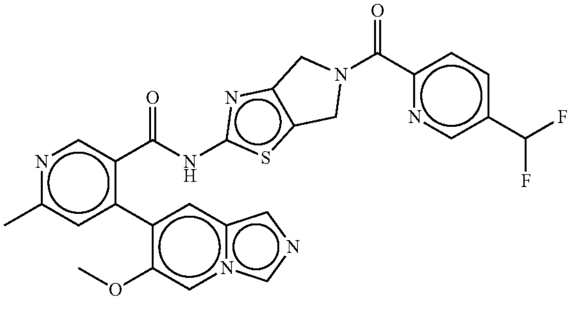 |

TABLE 1-continued

| Compound No. | Name | Structure |
| --- | --- | --- |
| 118 | 5-chloro-2-methoxy-6'-methyl-N-(5-picolinoyl-5,6-dihydro-4H-pyrrolo[3,4-d]thiazol-2-yl)-[3,4'-bipyridine]-3'-carboxamide | 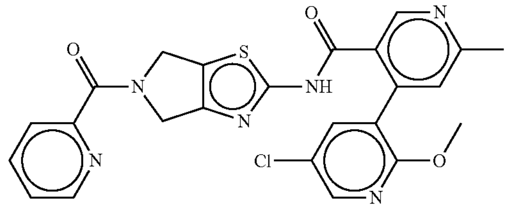 |
| 119 | (Cis and Trans) 2'-chloro-N-(5-(3-isopropoxycyclobutane-1-carbonyl)-5,6-dihydro-4H-pyrrolo[3,4-d]thiazol-2-yl)-5'-methoxy-6-methyl-[4,4'-bipyridine]-3-carboxamide | 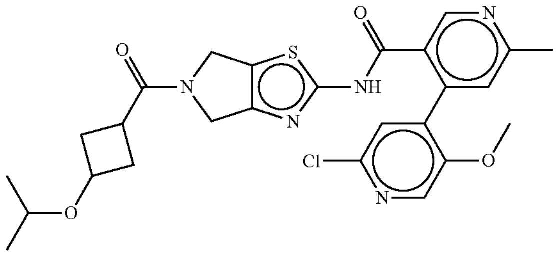 |
| 120 | 2'-chloro-5'-methoxy-6-methyl-N-(5-(1-(2,2,2-trifluoroethyl)azetidine-3-carbonyl)-5,6-dihydro-4H-pyrrolo[3,4-d]thiazol-2-yl)-[4,4'-bipyridine]-3-carboxamide | 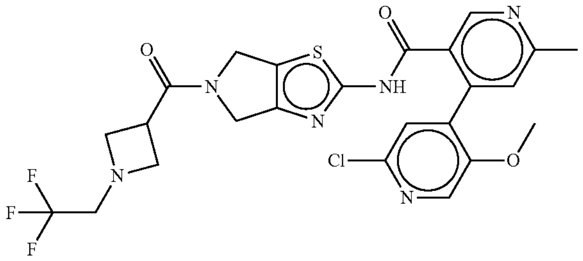 |
| 121 | 2'-chloro-5'-methoxy-N-(5-(5-methoxypicolinoyl)-5,6-dihydro-4H-pyrrolo[3,4-d]thiazol-2-yl)-6-methyl-[4,4'-bipyridine]-3-carboxamide | 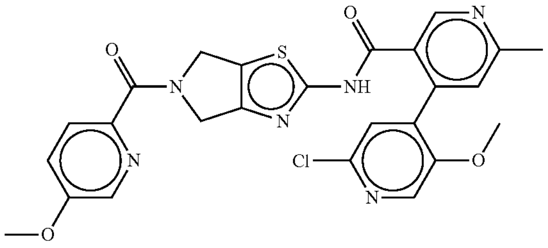 |
| 122 | 4-(5-cyano-2-methoxyphenyl)-N-(5-(5-(difluoromethyl)picolinoyl)-5,6-dihydro-4H-pyrrolo[3,4-d]thiazol-2-yl)-6-methylnicotinamide | 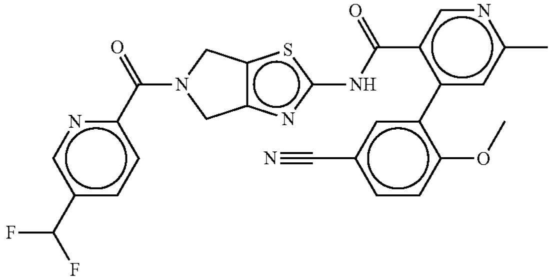 |
| 123 | N-(5-(4-chloro-1-methyl-1H-pyrazole-5-carbonyl)-5,6-dihydro-4H-pyrrolo[3,4-d]thiazol-2-yl)-4-(5-cyano-2-methoxyphenyl)-6-methylnicotinamide | 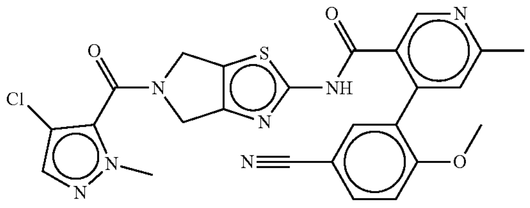 |

TABLE 1-continued

| Compound No. | Name | Structure |
|---|---|---|
| 124 | 4-(6-methoxyimidazo[1,5-a]pyridin-7-yl)-N-(5-(2-methoxynicotinoyl)-5,6-dihydro-4H-pyrrolo[3,4-d]thiazol-2-yl)-6-methylnicotinamide | 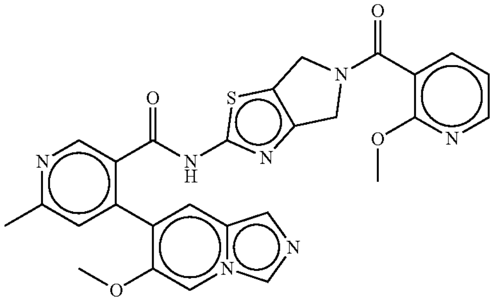 |
| 125 | N-(5-(4-chloro-1-methyl-1H-pyrazole-5-carbonyl)-5,6-dihydro-4H-pyrrolo[3,4-d]thiazol-2-yl)-4-(6-methoxyimidazo[1,5-a]pyridin-7-yl)-6-methylnicotinamide | 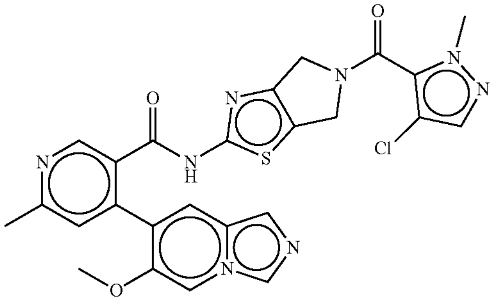 |
| 126 | 2'-chloro-N-(5-(3-(difluoromethoxy)azetidine-1-carbonyl)-5,6-dihydro-4H-pyrrolo[3,4-d]thiazol-2-yl)-5'-methoxy-6-methyl-[4,4'-bipyridine]-3-carboxamide | 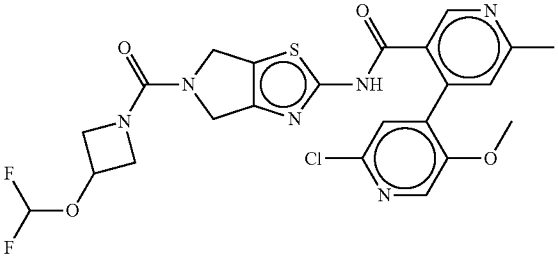 |
| 127 | 4-(5-cyano-2-methoxyphenyl)-N-(5-(2-methoxynicotinoyl)-5,6-dihydro-4H-pyrrolo[3,4-d]thiazol-2-yl)-6-methylnicotinamide | 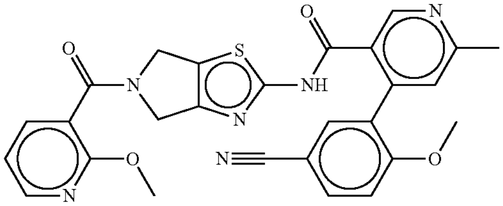 |
| 128 | (Racemic) 2'-chloro-5'-methoxy-N-(5-(3-methoxycyclohexane-1-carbonyl)-5,6-dihydro-4H-pyrrolo[3,4-d]thiazol-2-yl)-6-methyl-[4,4'-bipyridine]-3-carboxamide | 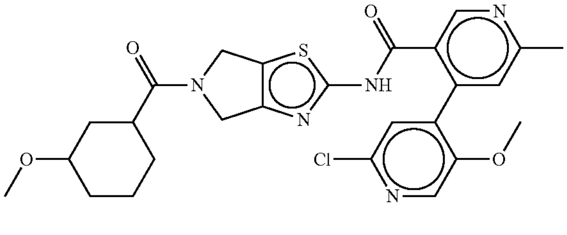 |
| 129 | (R)-2'-chloro-N-(5-(3-hydroxypyrrolidine-1-carbonyl)-5,6-dihydro-4H-pyrrolo[3,4-d]thiazol-2-yl)-5'-methoxy-6-methyl-[4,4'-bipyridine]-3-carboxamide | 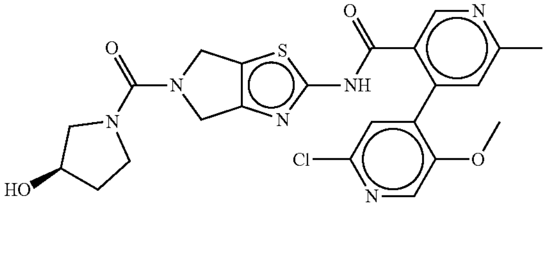 |

TABLE 1-continued

| Compound No. | Name | Structure |
| --- | --- | --- |
| 130 | 2'-chloro-N-((S)-6-((1r,3S)-3-hydroxycyclobutane-1-carboxamido)-4,5,6,7-tetrahydrobenzo[d]thiazol-2-yl)-5'-methoxy-6-methyl-[4,4'-bipyridine]-3-carboxamide | 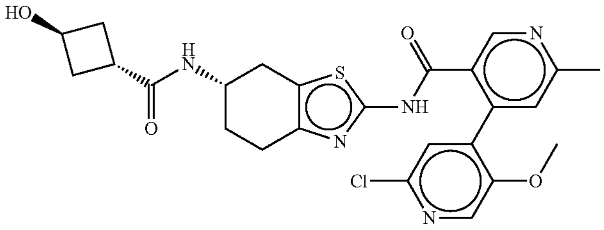 |
| 131 | 2'-chloro-N-(5-(1-(2,2-difluoroethyl)-1H-pyrazole-4-carbonyl)-5,6-dihydro-4H-pyrrolo[3,4-d]thiazol-2-yl)-5'-methoxy-6-methyl-[4,4'-bipyridine]-3-carboxamide | 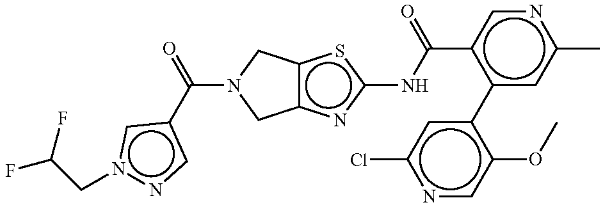 |
| 132 | 2'-chloro-5'-methoxy-6-methyl-N-(5-(5-(trifluoromethyl)picolinoyl)-5,6-dihydro-4H-pyrrolo[3,4-d]thiazol-2-yl)-[4,4'-bipyridine]-3-carboxamide | 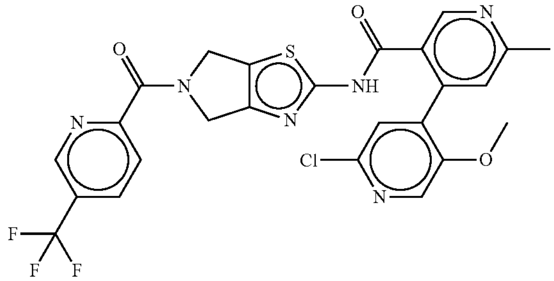 |
| 133 | (Racemic) 2'-chloro-5'-methoxy-6-methyl-N-(6-(phenylamino)-4,5,6,7-tetrahydrobenzo[d]thiazol-2-yl)-[4,4'-bipyridine]-3-carboxamide | 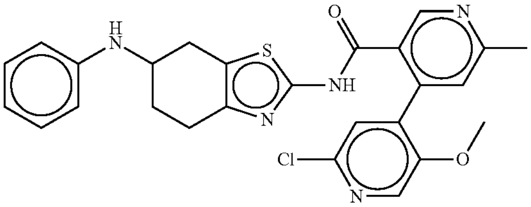 |
| 134 | (Racemic) 2'-chloro-N-(6-(cyclobutylamino)-4,5,6,7-tetrahydrobenzo[d]thiazol-2-yl)-5'-methoxy-6-methyl-[4,4'-bipyridine]-3-carboxamide | 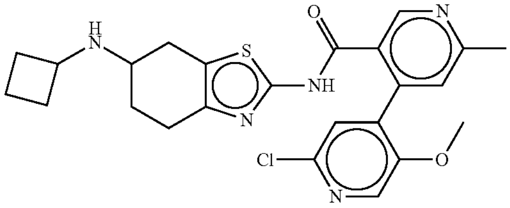 |
| 135 | (Racemic) 2'-chloro-N-(6-((4-hydroxyphenyl)amino)-4,5,6,7-tetrahydrobenzo[d]thiazol-2-yl)-5'-methoxy-6-methyl-[4,4'-bipyridine]-3-carboxamide | 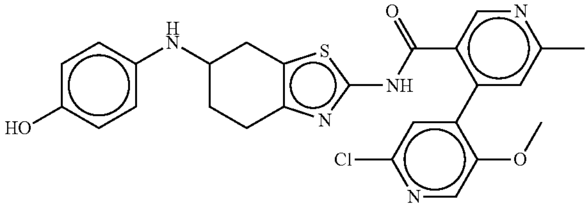 |

TABLE 1-continued

| Compound No. | Name | Structure |
|---|---|---|
| 136 | 2'-chloro-N-((S)-6-((1s,3R)-3-hydroxycyclobutane-1-carboxamido)-4,5,6,7-tetrahydrobenzo[d]thiazol-2-yl)-5'-methoxy-6-methyl-[4,4'-bipyridine]-3-carboxamide | 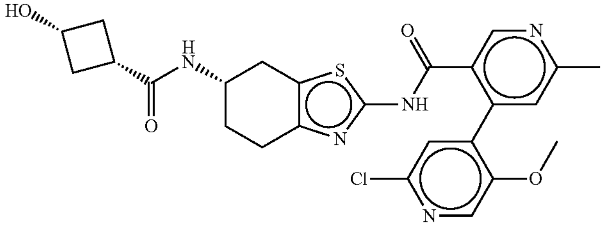 |
| 137 | 2'-chloro-N-(5-(1-(difluoromethyl)-1H-pyrazole-5-carbonyl)-5,6-dihydro-4H-pyrrolo[3,4-d]thiazol-2-yl)-5'-methoxy-6-methyl-[4,4'-bipyridine]-3-carboxamide | 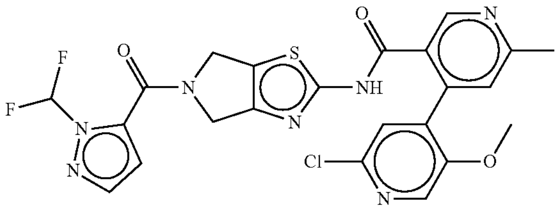 |
| 138 | 2'-chloro-N-(5-(4-(difluoromethyl)-1-methyl-1H-pyrazole-5-carbonyl)-5,6-dihydro-4H-pyrrolo[3,4-d]thiazol-2-yl)-5'-methoxy-6-methyl-[4,4'-bipyridine]-3-carboxamide | 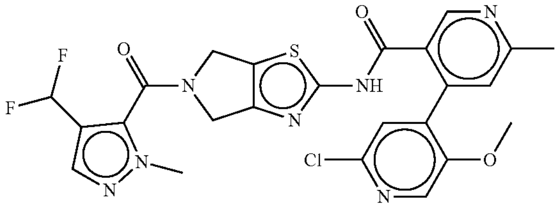 |
| 139 | 2'-chloro-N-(5-(1-(difluoromethyl)-1H-pyrazole-4-carbonyl)-5,6-dihydro-4H-pyrrolo[3,4-d]thiazol-2-yl)-5'-methoxy-6-methyl-[4,4'-bipyridine]-3-carboxamide | 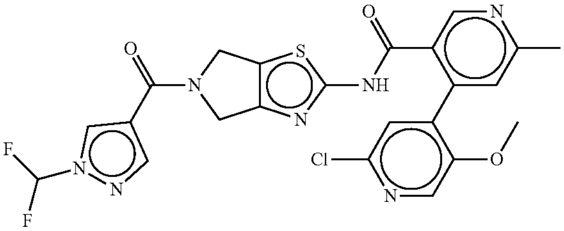 |
| 140 | 2'-chloro-5'-methoxy-N-(5-(6-methoxyspiro[3.3]heptane-2-carbonyl)-5,6-dihydro-4H-pyrrolo[3,4-d]thiazol-2-yl)-6-methyl-[4,4'-bipyridine]-3-carboxamide | 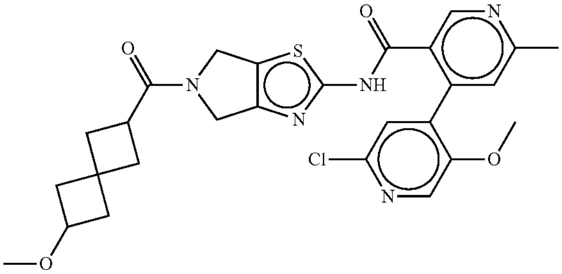 |
| 141 | 2'-chloro-N-(5-((1R or S,3S and R OR 1R and S,3S or R)-3-hydroxycyclohexane-1-carbonyl)-5,6-dihydro-4H-pyrrolo[3,4-d]thiazol-2-yl)-5'-methoxy-6-methyl-[4,4'-bipyridine]-3-carboxamide | 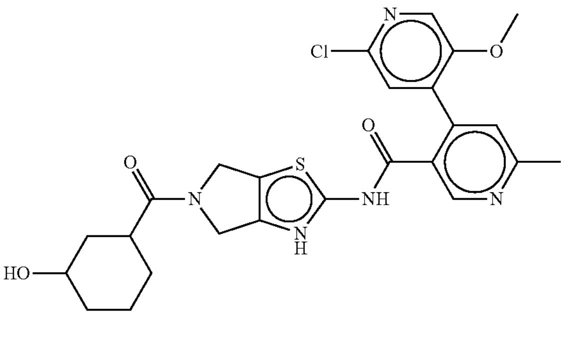 |

TABLE 1-continued

| Compound No. | Name | Structure |
|---|---|---|
| 142 | 2'-chloro-N-(5-((1R and S,3S or R OR 1R or S,3S and R)-3-hydroxycyclohexane-1-carbonyl)-5,6-dihydro-4H-pyrrolo[3,4-d]thiazol-2-yl)-5'-methoxy-6-methyl-[4,4'-bipyridine]-3-carboxamide | 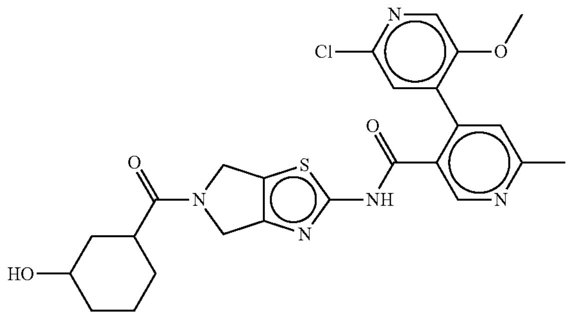 |
| 143 | 2'-chloro-N-(5-(1-(2,2-difluoroethyl)-1H-pyrazole-5-carbonyl)-5,6-dihydro-4H-pyrrolo[3,4-d]thiazol-2-yl)-5'-methoxy-6-methyl-[4,4'-bipyridine]-3-carboxamide | 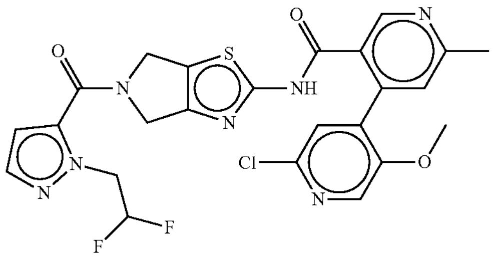 |
| 144 | 2'-chloro-N-((R)-6-((1s,3S)-3-hydroxycyclobutane-1-carboxamido)-4,5,6,7-tetrahydrobenzo[d]thiazol-2-yl)-5'-methoxy-6-methyl-[4,4'-bipyridine]-3-carboxamide | 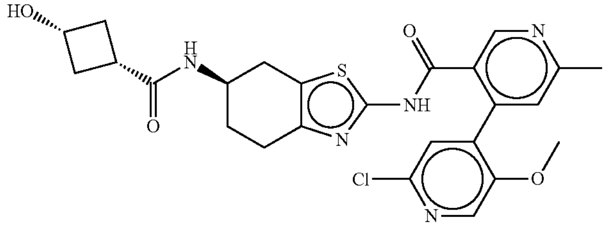 |
| 145 | 2'-chloro-N-(5-(3-(difluoromethoxy)picolinoyl)-5,6-dihydro-4H-pyrrolo[3,4-d]thiazol-2-yl)-5'-methoxy-6-methyl-[4,4'-bipyridine]-3-carboxamide | 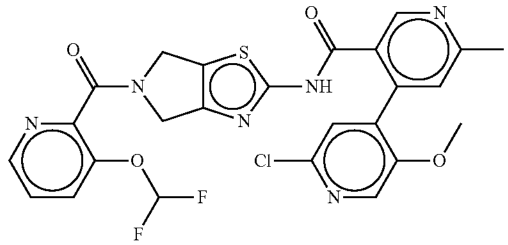 |
| 146 | 2'-chloro-5'-methoxy-N-(5-(4-methoxy-1-methyl-1H-pyrazole-5-carbonyl)-5,6-dihydro-4H-pyrrolo[3,4-d]thiazol-2-yl)-6-methyl-[4,4'-bipyridine]-3-carboxamide | 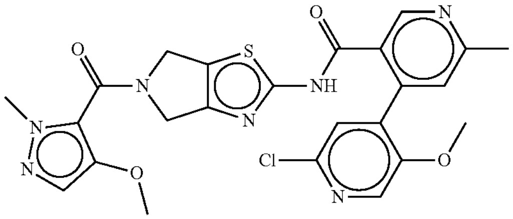 |
| 147 | 2'-chloro-N-((R)-6-((1r,3R)-3-hydroxycyclobutane-1-carboxamido)-4,5,6,7-tetrahydrobenzo[d]thiazol-2-yl)-5'-methoxy-6-methyl-[4,4'-bipyridine]-3-carboxamide | 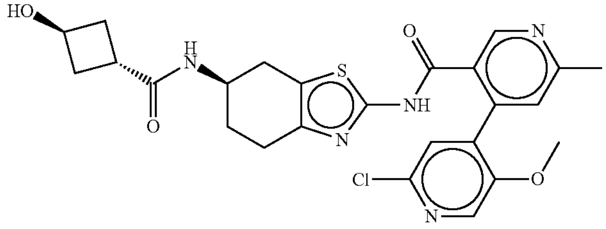 |

TABLE 1-continued

| Compound No. | Name | Structure |
|---|---|---|
| 148 | 2'-chloro-N-(5-(6-hydroxyspiro[3.3]heptane-2-carbonyl)-5,6-dihydro-4H-pyrrolo[3,4-d]thiazol-2-yl)-5'-methoxy-6-methyl-[4,4'-bipyridine]-3-carboxamide | 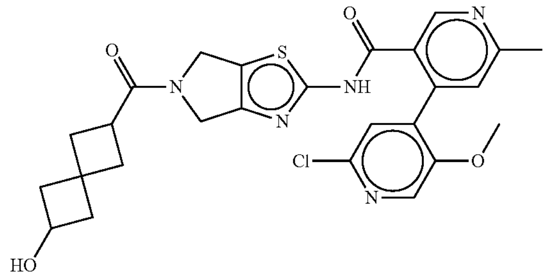 |
| 149 | 2'-chloro-N-(5-(3-hydroxyazetidine-1-carbonyl)-5,6-dihydro-4H-pyrrolo[3,4-d]thiazol-2-yl)-5'-methoxy-6-methyl-[4,4'-bipyridine]-3-carboxamide | 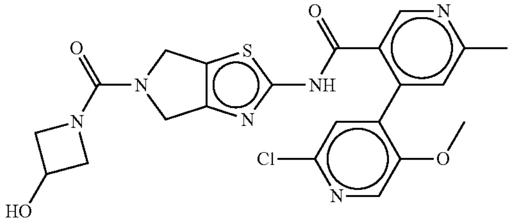 |
| 150 | (S)-2'-chloro-N-(5-(3-hydroxypyrrolidine-1-carbonyl)-5,6-dihydro-4H-pyrrolo[3,4-d]thiazol-2-yl)-5'-methoxy-6-methyl-[4,4'-bipyridine]-3-carboxamide | 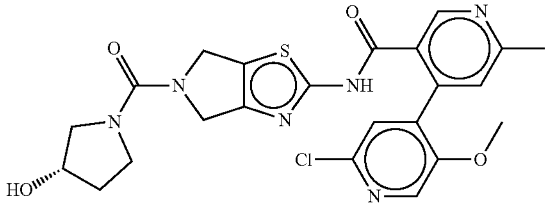 |
| 151 | 2'-chloro-N-(5-(1,3-dimethyl-1H-pyrazole-4-carbonyl)-5,6-dihydro-4H-pyrrolo[3,4-d]thiazol-2-yl)-5'-methoxy-6-methyl-[4,4'-bipyridine]-3-carboxamide | 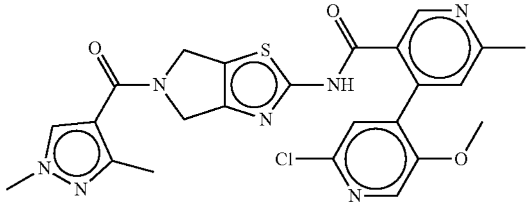 |
| 152 | 2'-chloro-N-(5-(4-chloro-1-methyl-1H-pyrazole-3-carbonyl)-5,6-dihydro-4H-pyrrolo[3,4-d]thiazol-2-yl)-5'-methoxy-6-methyl-[4,4'-bipyridine]-3-carboxamide | 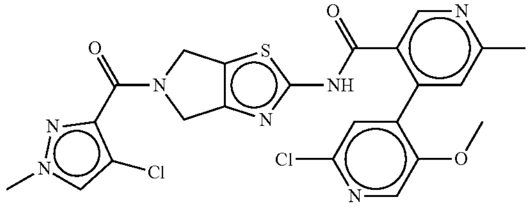 |
| 153 | (Racemic Trans)-2'-chloro-N-(5-(3-hydroxycyclopentane-1-carbonyl)-5,6-dihydro-4H-pyrrolo[3,4-d]thiazol-2-yl)-5'-methoxy-6-methyl-[4,4'-bipyridine]-3-carboxamide | 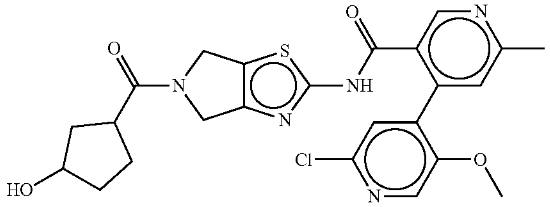 |

TABLE 1-continued

| Compound No. | Name | Structure |
| --- | --- | --- |
| 154 | (S or R)-2-(2'-chloro-5'-methoxy-6-methyl-[4,4'-bipyridine]-3-carboxamido)-N-cyclopropyl-4,5,6,7-tetrahydrobenzo[d]thiazole-6-carboxamide | 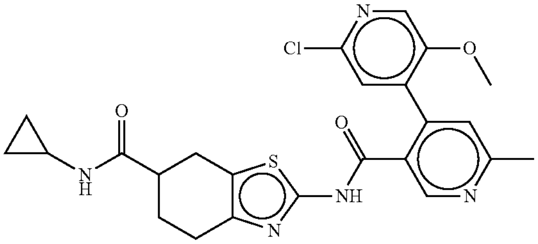 |
| 155 | 2'-chloro-5'-methoxy-N-(5-(4-methoxynicotinoyl)-5,6-dihydro-4H-pyrrolo[3,4-d]thiazol-2-yl)-6-methyl-[4,4'-bipyridine]-3-carboxamide | 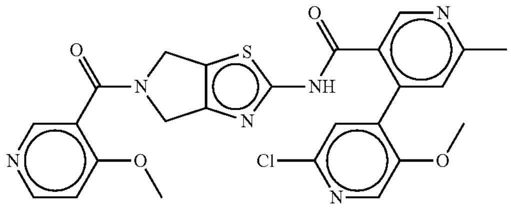 |
| 156 | 2'-chloro-N-(5-(4-chloro-1-methyl-1H-pyrazole-5-carbonyl)-5,6-dihydro-4H-pyrrolo[3,4-d]thiazol-2-yl)-5'-methoxy-6-methyl-[4,4'-bipyridine]-3-carboxamide | 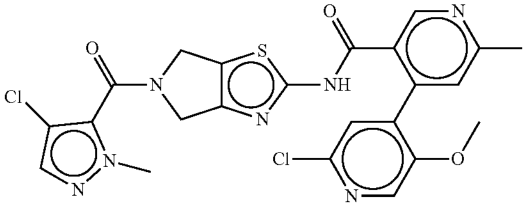 |
| 157 | 2'-chloro-5'-methoxy-N-(5-(4-methoxy-1-methyl-1H-pyrazole-3-carbonyl)-5,6-dihydro-4H-pyrrolo[3,4-d]thiazol-2-yl)-6-methyl-[4,4'-bipyridine]-3-carboxamide | 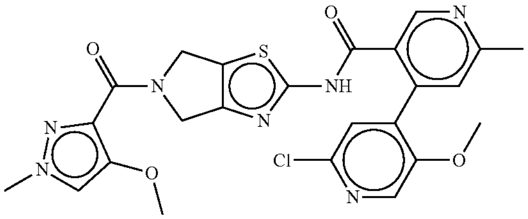 |
| 158 | 2'-chloro-N-(5-(3-(difluoromethyl)picolinoyl)-5,6-dihydro-4H-pyrrolo[3,4-d]thiazol-2-yl)-5'-methoxy-6-methyl-[4,4'-bipyridine]-3-carboxamide | 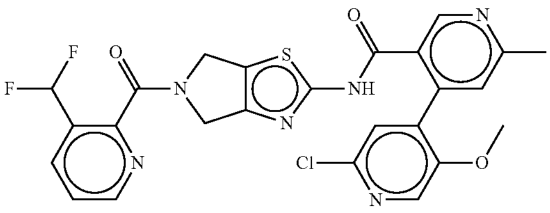 |
| 159 | 2'-chloro-N-(5-(1-(difluoromethyl)-1H-pyrazole-3-carbonyl)-5,6-dihydro-4H-pyrrolo[3,4-d]thiazol-2-yl)-5'-methoxy-6-methyl-[4,4'-bipyridine]-3-carboxamide | 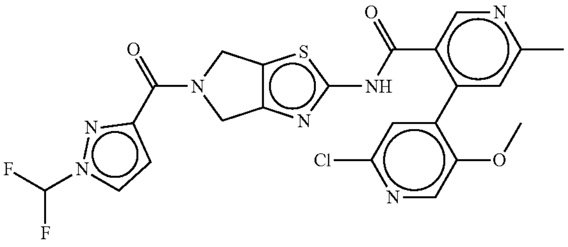 |

TABLE 1-continued

| Compound No. | Name | Structure |
|---|---|---|
| 160 | 2'-chloro-5'-methoxy-6-methyl-N-(5-((1s,3s)-3-(trifluoromethyl)cyclobutane-1-carbonyl)-5,6-dihydro-4H-pyrrolo[3,4-d]thiazol-2-yl)-[4,4'-bipyridine]-3-carboxamide | 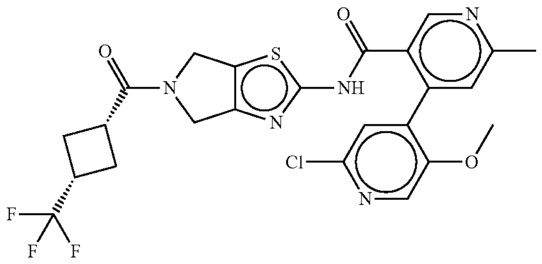 |
| 161 | 2'-chloro-N-(5-(3-chloro-1-methyl-1H-pyrazole-4-carbonyl)-5,6-dihydro-4H-pyrrolo[3,4-d]thiazol-2-yl)-5'-methoxy-6-methyl-[4,4'-bipyridine]-3-carboxamide | 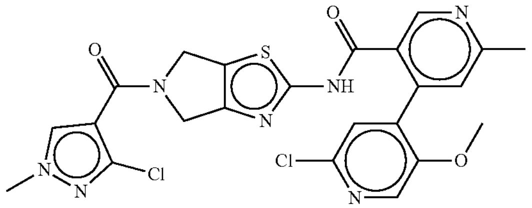 |
| 162 | (R or S)-2-(2'-chloro-5'-methoxy-6-methyl-[4,4'-bipyridine]-3-carboxamido)-N-cyclopropyl-4,5,6,7-tetrahydrobenzo[d]thiazole-6-carboxamide | 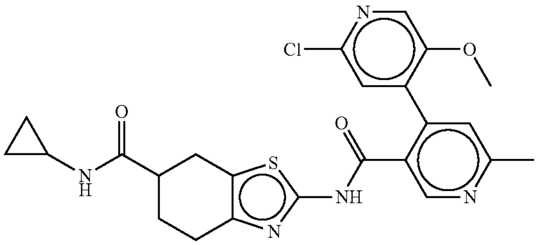 |
| 163 | (Cis and Trans)-2'-chloro-N-(5-(3-hydroxy-3-methylcyclobutane-1-carbonyl)-5,6-dihydro-4H-pyrrolo[3,4-d]thiazol-2-yl)-5'-methoxy-6-methyl-[4,4'-bipyridine]-3-carboxamide | 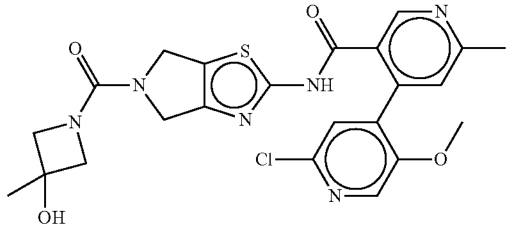 |
| 164 | 2'-chloro-5'-methoxy-6-methyl-N-(5-((1r,3r)-3-(trifluoromethyl)cyclobutane-1-carbonyl)-5,6-dihydro-4H-pyrrolo[3,4-d]thiazol-2-yl)-[4,4'-bipyridine]-3-carboxamide | 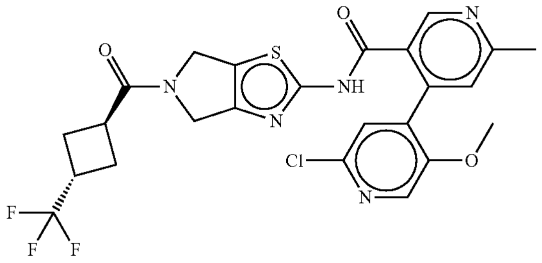 |
| 165 | 4-(5-cyano-2-methoxyphenyl)-N-(5-cyclopropyl-5,6-dihydro-4H-pyrrolo[3,4-d]thiazol-2-yl)-6-methylnicotinamide | 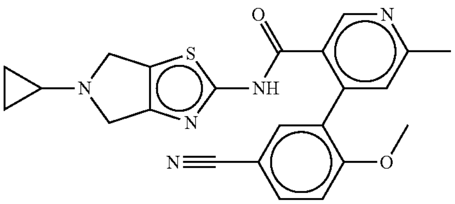 |

TABLE 1-continued

| Compound No. | Name | Structure |
|---|---|---|
| 166 | (Cis and Trans)-4-(5-cyano-2-methoxyphenyl)-N-(5-(3-isopropoxycyclobutane-1-carbonyl)-5,6-dihydro-4H-pyrrolo[3,4-d]thiazol-2-yl)-6-methylnicotinamide | 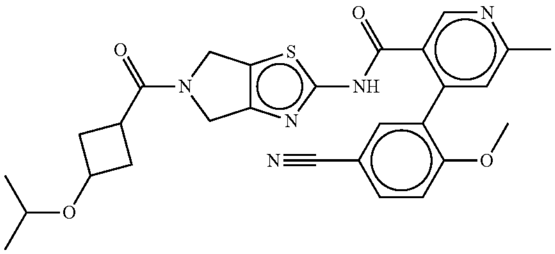 |
| 167 | (Racemic)-2-(2'-chloro-5'-methoxy-6-methyl-[4,4'-bipyridine]-3-carboxamido)-N-cyclopropyl-4,5,6,7-tetrahydrobenzo[d]thiazole-6-carboxamide | 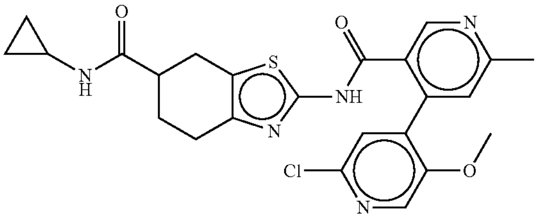 |
| 168 | 2'-chloro-5'-methoxy-N-(5-(3-methoxyisonicotinoyl)-5,6-dihydro-4H-pyrrolo[3,4-d]thiazol-2-yl)-6-methyl-[4,4'-bipyridine]-3-carboxamide | 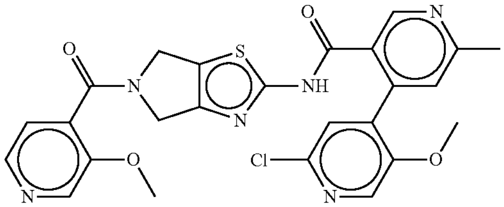 |
| 169 | 2'-chloro-5'-methoxy-N-(5-(3-methoxypicolinoyl)-5,6-dihydro-4H-pyrrolo[3,4-d]thiazol-2-yl)-6-methyl-[4,4'-bipyridine]-3-carboxamide | 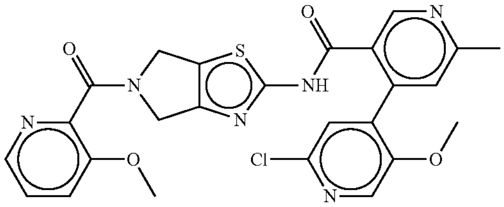 |
| 170 | 2'-chloro-5'-methoxy-6-methyl-N-(5-(1-methyl-1H-pyrazole-5-carbonyl)-5,6-dihydro-4H-pyrrolo[3,4-d]thiazol-2-yl)-[4,4'-bipyridine]-3-carboxamide | 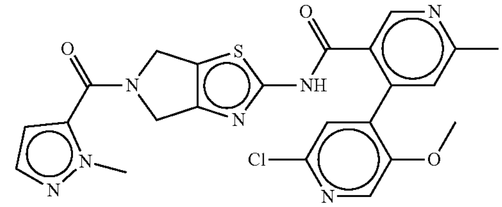 |
| 171 | 2'-chloro-5'-methoxy-N-(5-((1s,3s)-3-methoxycyclobutane-1-carbonyl)-5,6-dihydro-4H-pyrrolo[3,4-d]thiazol-2-yl)-6-methyl-[4,4'-bipyridine]-3-carboxamide | 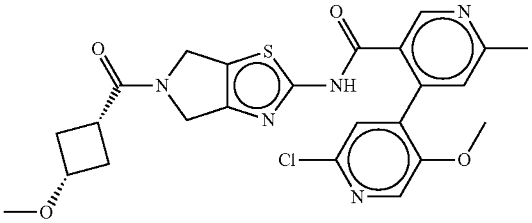 |
| 172 | 2'-chloro-5'-methoxy-N-(5-(2-methoxynicotinoyl)-5,6-dihydro-4H-pyrrolo[3,4-d]thiazol-2-yl)-6-methyl-[4,4'-bipyridine]-3-carboxamide | 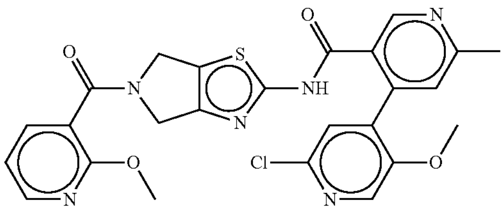 |

TABLE 1-continued

| Compound No. | Name | Structure |
| --- | --- | --- |
| 173 | 2'-chloro-N-(5-(3-(difluoromethyl)-1-methyl-1H-pyrazole-4-carbonyl)-5,6-dihydro-4H-pyrrolo[3,4-d]thiazol-2-yl)-5'-methoxy-6-methyl-[4,4'-bipyridine]-3-carboxamide | 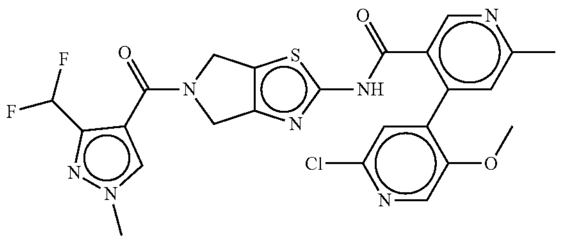 |
| 174 | 2'-chloro-N-(5-(5-hydroxypicolinoyl)-5,6-dihydro-4H-pyrrolo[3,4-d]thiazol-2-yl)-5'-methoxy-6-methyl-[4,4'-bipyridine]-3-carboxamide | 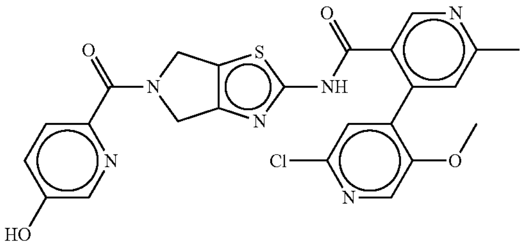 |
| 175 | 2'-chloro-N-(5-(1-isopropyl-3-methyl-1H-pyrazole-4-carbonyl)-5,6-dihydro-4H-pyrrolo[3,4-d]thiazol-2-yl)-5'-methoxy-6-methyl-[4,4'-bipyridine]-3-carboxamide | 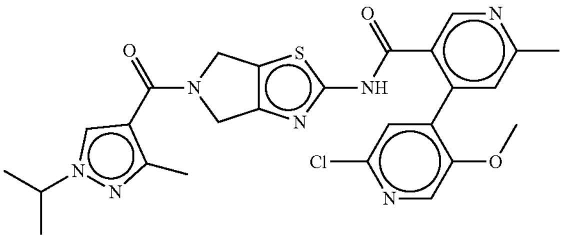 |
| 176 | (Cis and Trans)-4-(5-cyano-2-methoxyphenyl)-N-(5-(3-(difluoromethoxy)cyclobutane-1-carbonyl)-4,5,6,7-tetrahydrothiazolo[5,4-c]pyridin-2-yl)-6-methylnicotinamide | 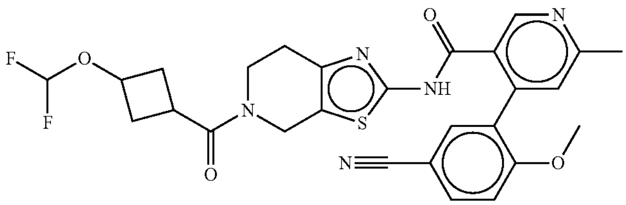 |
| 177 | (Cis and Trans)-2'-chloro-N-(5-(3-(2,2-difluoroethyl)cyclobutane-1-carbonyl)-5,6-dihydro-4H-pyrrolo[3,4-d]thiazol-2-yl)-5'-methoxy-6-methyl-[4,4'-bipyridine]-3-carboxamide | 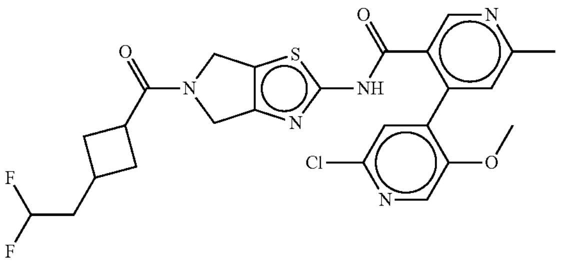 |
| 178 | (Cis and Trans)-2'-chloro-N-(5-(3-(difluoromethoxy)cyclobutane-1-carbonyl)-5,6-dihydro-4H-pyrrolo[3,4-d]thiazol-2-yl)-5'-methoxy-6-methyl-[4,4'-bipyridine]-3-carboxamide | 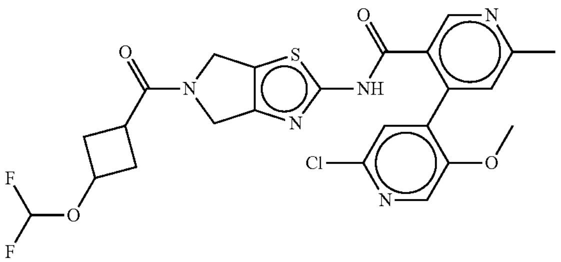 |

TABLE 1-continued

| Compound No. | Name | Structure |
|---|---|---|
| 179 | (Cis and Trans)-4-(5-cyano-2-methoxyphenyl)-N-(5-(3-(difluoromethoxy)cyclobutane-1-carbonyl)-5,6-dihydro-4H-pyrrolo[3,4-d]thiazol-2-yl)-6-methylnicotinamide | 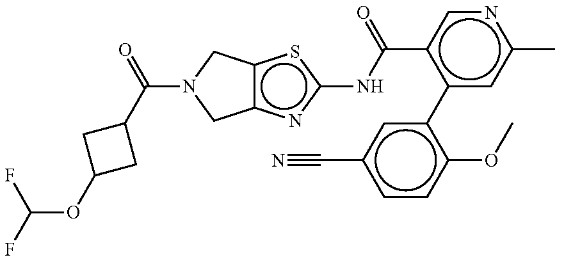 |
| 180 | (Racemic Cis)-2'-chloro-N-(5-(3-hydroxycyclopentane-1-carbonyl)-5,6-dihydro-4H-pyrrolo[3,4-d]thiazol-2-yl)-5'-methoxy-6-methyl-[4,4'-bipyridine]-3-carboxamide | 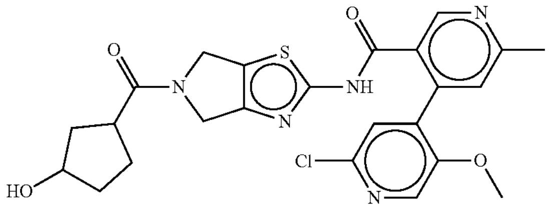 |
| 181 | (R)-2'-chloro-5'-methoxy-6-methyl-N-(5-(tetrahydrofuran-3-carbonyl)-5,6-dihydro-4H-pyrrolo[3,4-d]thiazol-2-yl)-[4,4'-bipyridine]-3-carboxamide | 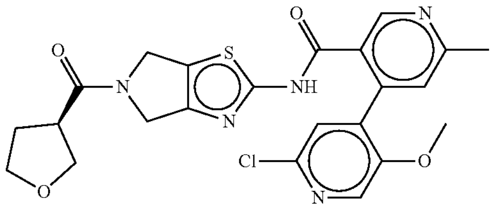 |
| 182 | 2'-chloro-5'-methoxy-6-methyl-N-(5-(oxazole-2-carbonyl)-5,6-dihydro-4H-pyrrolo[3,4-d]thiazol-2-yl)-[4,4'-bipyridine]-3-carboxamide | 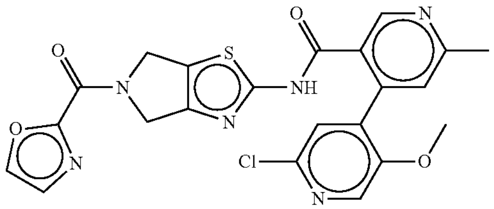 |
| 183 | (S)-2'-chloro-5'-methoxy-6-methyl-N-(5-(tetrahydro-2H-pyran-3-carbonyl)-5,6-dihydro-4H-pyrrolo[3,4-d]thiazol-2-yl)-[4,4'-bipyridine]-3-carboxamide | 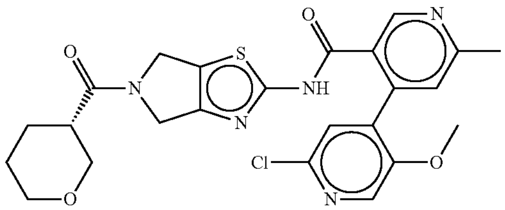 |
| 184 | 2'-chloro-5'-methoxy-6-methyl-N-(5-(tetrahydro-2H-pyran-4-carbonyl)-5,6-dihydro-4H-pyrrolo[3,4-d]thiazol-2-yl)-[4,4'-bipyridine]-3-carboxamide | 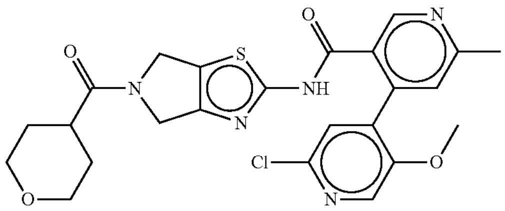 |
| 185 | 2'-chloro-N-(5-((1s,3s)-3-hydroxycyclobutane-1-carbonyl)-5,6-dihydro-4H-pyrrolo[3,4-d]thiazol-2-yl)-5'-methoxy-6-methyl-[4,4'-bipyridine]-3-carboxamide | 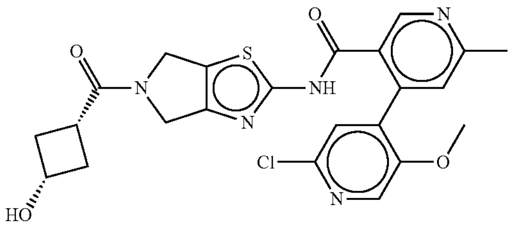 |

TABLE 1-continued

| Compound No. | Name | Structure |
|---|---|---|
| 186 | (R)-2'-chloro-5'-methoxy-6-methyl-N-(5-(tetrahydro-2H-pyran-2-carbonyl)-5,6-dihydro-4H-pyrrolo[3,4-d]thiazol-2-yl)-[4,4'-bipyridine]-3-carboxamide | 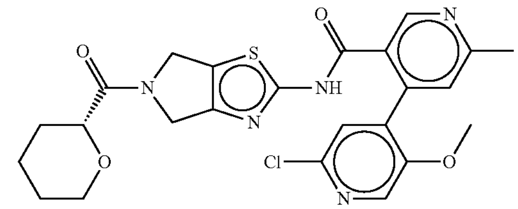 |
| 187 | 2'-chloro-N-(5-((1r,3r)-3-hydroxycyclobutane-1-carbonyl)-5,6-dihydro-4H-pyrrolo[3,4-d]thiazol-2-yl)-5'-methoxy-6-methyl-[4,4'-bipyridine]-3-carboxamide | 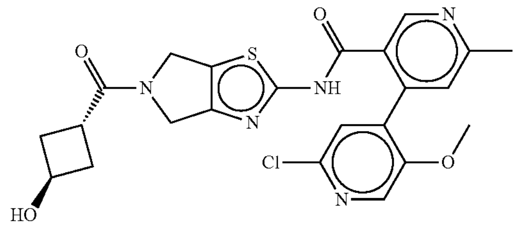 |
| 188 | (R)-2'-chloro-N-(6-(cyclopropanecarboxamido)-4,5,6,7-tetrahydrobenzo[d]thiazol-2-yl)-5'-methoxy-6-methyl-[4,4'-bipyridine]-3-carboxamide | 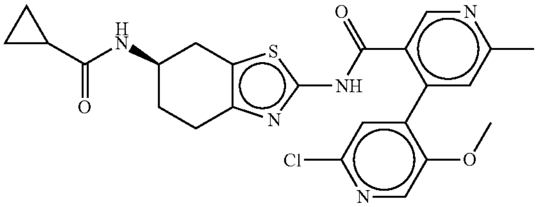 |
| 189 | (Cis and trans) 4-(5-cyano-2-methoxyphenyl)-6-methyl-N-(5-(3-methylcyclobutane-1-carbonyl)-5,6-dihydro-4H-pyrrolo[3,4-d]thiazol-2-yl)nicotinamide | 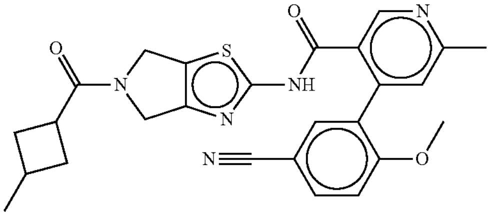 |
| 190 | 2'-chloro-N-(5-((1s,3s)-3-cyanocyclobutane-1-carbonyl)-5,6-dihydro-4H-pyrrolo[3,4-d]thiazol-2-yl)-5'-methoxy-6-methyl-[4,4'-bipyridine]-3-carboxamide | 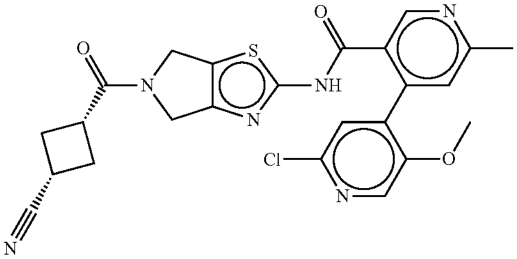 |
| 191 | (S)-2'-chloro-5'-methoxy-6-methyl-N-(5-(tetrahydrofuran-2-carbonyl)-5,6-dihydro-4H-pyrrolo[3,4-d]thiazol-2-yl)-[4,4'-bipyridine]-3-carboxamide | 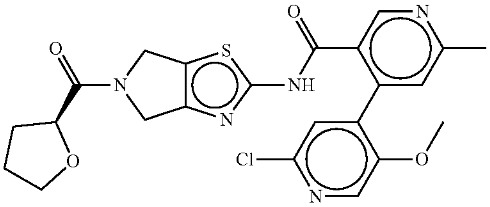 |

TABLE 1-continued

| Compound No. | Name | Structure |
|---|---|---|
| 192 | N-(5-(2-oxaspiro[3.3]heptane-6-carbonyl)-5,6-dihydro-4H-pyrrolo[3,4-d]thiazol-2-yl)-2'-chloro-5'-methoxy-6-methyl-[4,4'-bipyridine]-3-carboxamide | 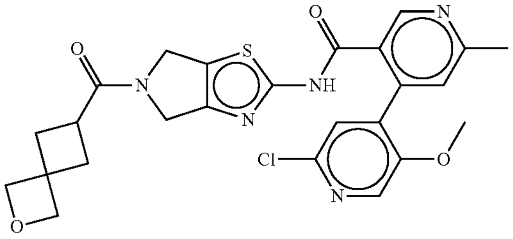 |
| 193 | 2'-chloro-N-(5-((1s,3s)-3-hydroxy-3-methylcyclobutane-1-carbonyl)-5,6-dihydro-4H-pyrrolo[3,4-d]thiazol-2-yl)-5'-methoxy-6-methyl-[4,4'-bipyridine]-3-carboxamide | 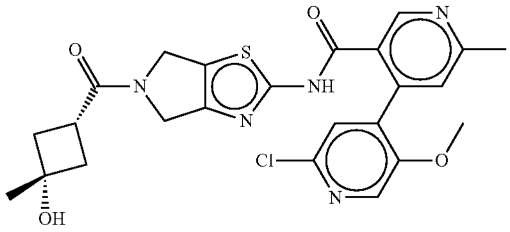 |
| 194 | 2'-chloro-5'-methoxy-6-methyl-N-(5-(2-methylisonicotinoyl)-5,6-dihydro-4H-pyrrolo[3,4-d]thiazol-2-yl)-[4,4'-bipyridine]-3-carboxamide | 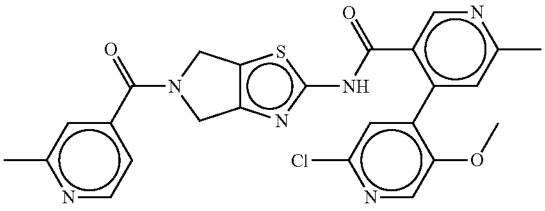 |
| 195 | 2'-chloro-N-(5-((1s,3s)-3-(difluoromethyl)-3-hydroxycyclobutane-1-carbonyl)-5,6-dihydro-4H-pyrrolo[3,4-d]thiazol-2-yl)-5'-methoxy-6-methyl-[4,4'-bipyridine]-3-carboxamide | 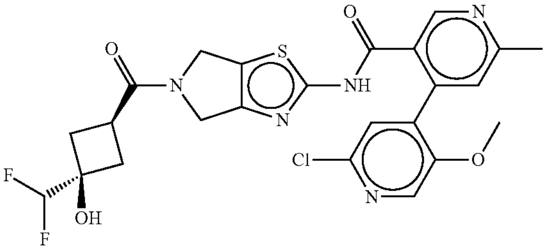 |
| 196 | (Cis and Trans)-2'-chloro-5'-methoxy-6-methyl-N-(5-(3-(trifluoromethoxy)cyclobutane-1-carbonyl)-5,6-dihydro-4H-pyrrolo[3,4-d]thiazol-2-yl)-[4,4'-bipyridine]-3-carboxamide | 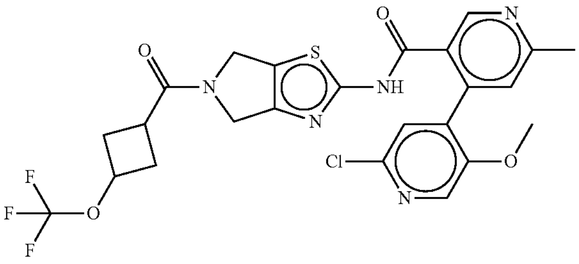 |
| 197 | 2'-chloro-5'-methoxy-6-methyl-N-(5-(1-methyl-1H-pyrazole-3-carbonyl)-5,6-dihydro-4H-pyrrolo[3,4-d]thiazol-2-yl)-[4,4'-bipyridine]-3-carboxamide | 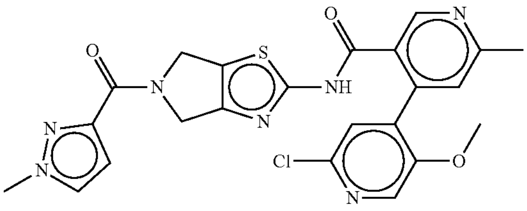 |

TABLE 1-continued

| Compound No. | Name | Structure |
|---|---|---|
| 198 | (R)-2'-chloro-5'-methoxy-6-methyl-N-(5-(tetrahydro-2H-pyran-3-carbonyl)-5,6-dihydro-4H-pyrrolo[3,4-d]thiazol-2-yl)-[4,4'-bipyridine]-3-carboxamide | 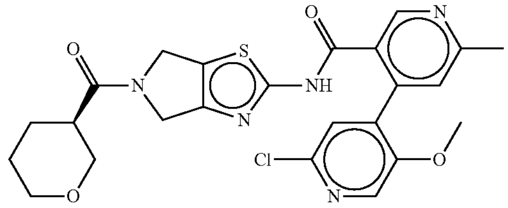 |
| 199 | 2'-chloro-5'-methoxy-6-methyl-N-(5-(5-methylpicolinoyl)-5,6-dihydro-4H-pyrrolo[3,4-d]thiazol-2-yl)-[4,4'-bipyridine]-3-carboxamide | 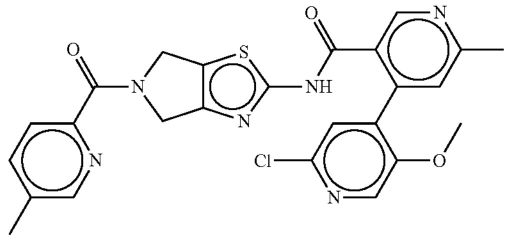 |
| 200 | (S)-2'-chloro-N-(6-(cyclopropanecarboxamido)-4,5,6,7-tetrahydrobenzo[d]thiazol-2-yl)-5'-methoxy-6-methyl-[4,4'-bipyridine]-3-carboxamide | 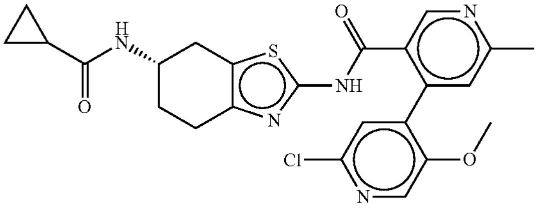 |
| 201 | (Cis and Trans)-2'-chloro-N-(5-(3-(difluoromethyl)cyclobutane-1-carbonyl)-5,6-dihydro-4H-pyrrolo[3,4-d]thiazol-2-yl)-5'-methoxy-6-methyl-[4,4'-bipyridine]-3-carboxamide | 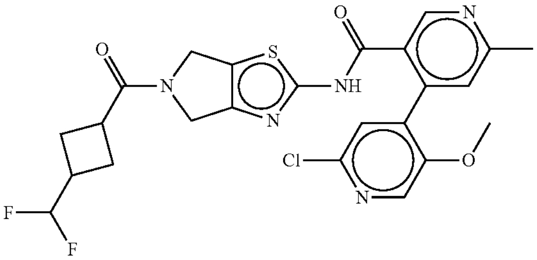 |
| 202 | (R)-2'-chloro-5'-methoxy-6-methyl-N-(5-(tetrahydrofuran-2-carbonyl)-5,6-dihydro-4H-pyrrolo[3,4-d]thiazol-2-yl)-[4,4'-bipyridine]-3-carboxamide | 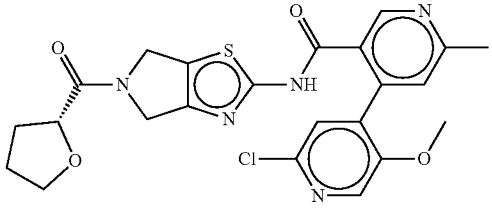 |
| 203 | 2'-chloro-N-(5-(cyclopropanecarbonyl)-5,6-dihydro-4H-pyrrolo[3,4-d]thiazol-2-yl)-5'-methoxy-6-methyl-[4,4'-bipyridine]-3-carboxamide | 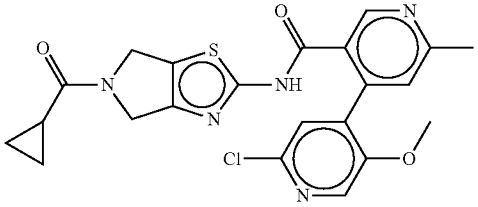 |

TABLE 1-continued

| Compound No. | Name | Structure |
|---|---|---|
| 204 | (Cis and Trans)-2'-chloro-N-(5-(3-hydroxy-3-(trifluoromethyl)cyclobutane-1-carbonyl)-5,6-dihydro-4H-pyrrolo[3,4-d]thiazol-2-yl)-5'-methoxy-6-methyl-[4,4'-bipyridine]-3-carboxamide | 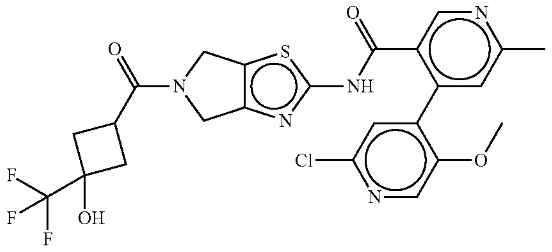 |
| 205 | (S)-2'-chloro-5'-methoxy-6-methyl-N-(5-(tetrahydrofuran-3-carbonyl)-5,6-dihydro-4H-pyrrolo[3,4-d]thiazol-2-yl)-[4,4'-bipyridine]-3-carboxamide | 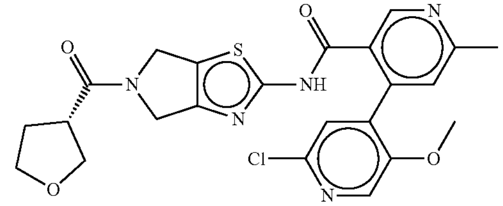 |
| 206 | 2'-chloro-N-(5-isonicotinoyl-5,6-dihydro-4H-pyrrolo[3,4-d]thiazol-2-yl)-5'-methoxy-6-methyl-[4,4'-bipyridine]-3-carboxamide | 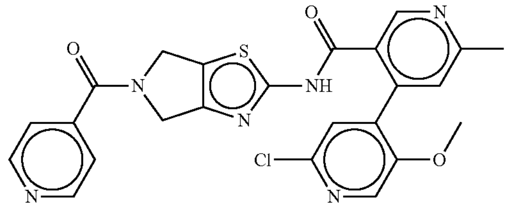 |
| 207 | 4-(5-cyano-2-methoxyphenyl)-N-(5-(2-methoxycyclopropane-1-carbonyl)-4,5,6,7-tetrahydrothiazolo[5,4-c]pyridin-2-yl)-6-methylnicotinamide<br>Mixture of isomers | 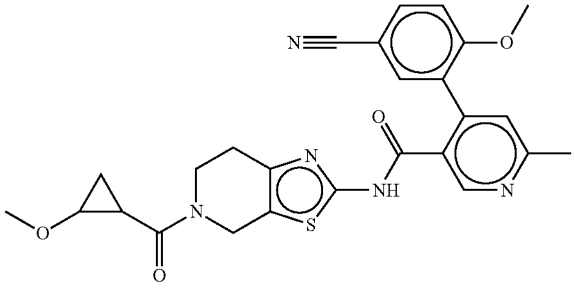 |
| 208 | (R or S) 4-(5-cyano-2-methoxyphenyl)-6-methyl-N-(5-(tetrahydro-2H-pyran-2-carbonyl)-4,5,6,7-tetrahydrothiazolo[5,4-c]pyridin-2-yl)nicotinamide | 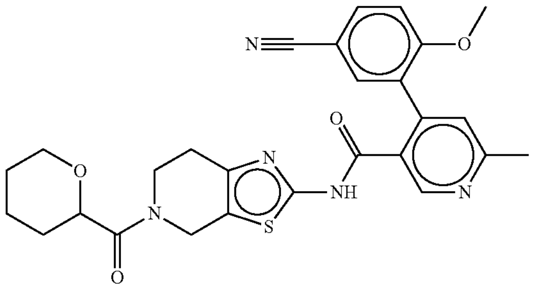 |
| 209 | (R or S) 4-(5-cyano-2-methoxyphenyl)-N-(5-(2,2-difluorocyclopropane-1-carbonyl)-4,5,6,7-tetrahydrothiazolo[5,4-c]pyridin-2-yl)-6-methylnicotinamide | 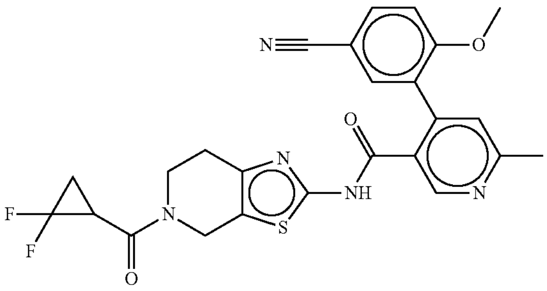 |

TABLE 1-continued

| Compound No. | Name | Structure |
|---|---|---|
| 210 | (S or R) 4-(5-cyano-2-methoxyphenyl)-N-(5-(2,2-difluorocyclopropane-1-carbonyl)-4,5,6,7-tetrahydrothiazolo[5,4-c]pyridin-2-yl)-6-methylnicotinamide | 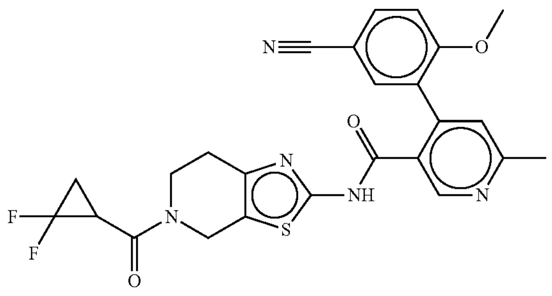 |
| 211 | 4-(5-cyano-2-methoxyphenyl)-6-methyl-N-(5-(2-methylcyclopropane-1-carbonyl)-4,5,6,7-tetrahydrothiazolo[5,4-c]pyridin-2-yl)nicotinamide Mixture of isomers | 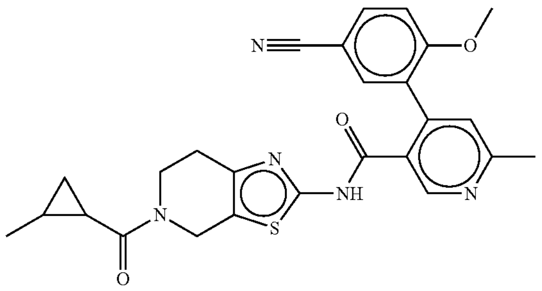 |
| 212 | 4-(5-cyano-2-methoxyphenyl)-6-methyl-N-(5-(2-methylcyclopropane-1-carbonyl)-4,5,6,7-tetrahydrothiazolo[5,4-c]pyridin-2-yl)nicotinamide Mixture of isomers | 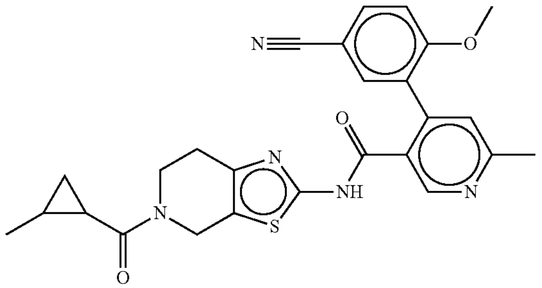 |
| 213 | 4-(5-cyano-2-methoxyphenyl)-N-(5-isonicotinoyl-4,5,6,7-tetrahydrothiazolo[5,4-c]pyridin-2-yl)-6-methylnicotinamide | 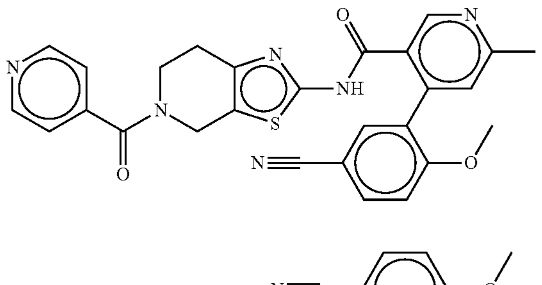 |
| 214 | 4-(5-cyano-2-methoxyphenyl)-N-(5-(2-methoxycyclopropane-1-carbonyl)-4,5,6,7-tetrahydrothiazolo[5,4-c]pyridin-2-yl)-6-methylnicotinamide Mixture of isomers | 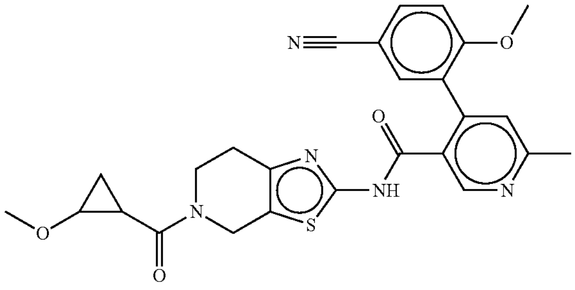 |

TABLE 1-continued

| Compound No. | Name | Structure |
|---|---|---|
| 215 | (S or R) 4-(5-cyano-2-methoxyphenyl)-6-methyl-N-(5-(tetrahydro-2H-pyran-2-carbonyl)-4,5,6,7-tetrahydrothiazolo[5,4-c]pyridin-2-yl)nicotinamide | 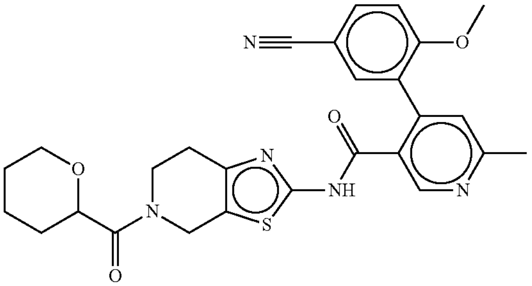 |
| 216 | (S) 2'-chloro-5'-methoxy-6-methyl-N-(5-(tetrahydro-2H-pyran-2-carbonyl)-5,6-dihydro-4H-pyrrolo[3,4-d]thiazol-2-yl)-[4,4'-bipyridine]-3-carboxamide | 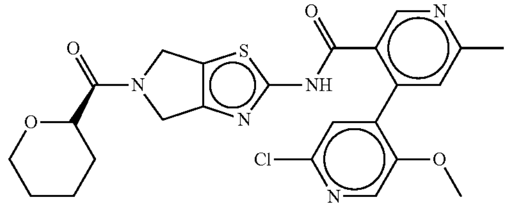 |
| 217 | 4-(5-cyano-2-methoxyphenyl)-6-methyl-N-(5-(oxetan-3-ylsulfonyl)-5,6-dihydro-4H-pyrrolo[3,4-d]thiazol-2-yl)nicotinamide | 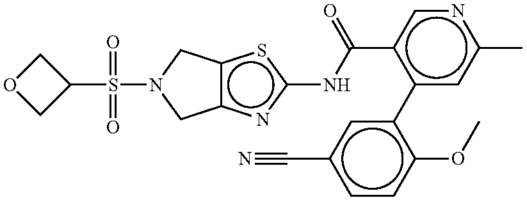 |
| 218 | N-(5-(azetidin-1-ylsulfonyl)-5,6-dihydro-4H-pyrrolo[3,4-d]thiazol-2-yl)-4-(5-cyano-2-methoxyphenyl)-6-methylnicotinamide | 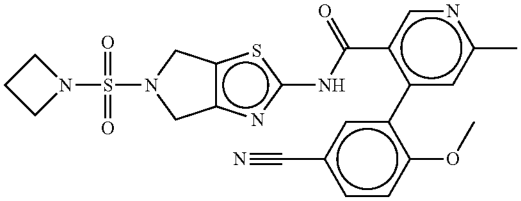 |
| 219 | 4-(5-cyano-2-methoxyphenyl)-6-methyl-N-(5-((1R,2S)-2-methylcyclobutane-1-carbonyl)-5,6-dihydro-4H-pyrrolo[3,4-d]thiazol-2-yl)nicotinamide<br>Mixture of cis isomers | 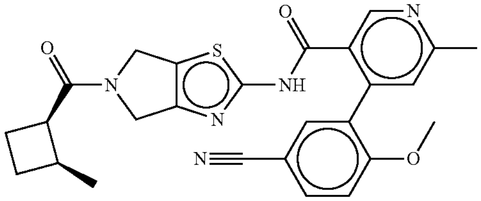 |
| 220 | 4-(5-cyano-2-methoxyphenyl)-6-methyl-N-(5-((1R,2R)-2-methylcyclobutane-1-carbonyl)-5,6-dihydro-4H-pyrrolo[3,4-d]thiazol-2-yl)nicotinamide<br>Mixture of trans isomers | 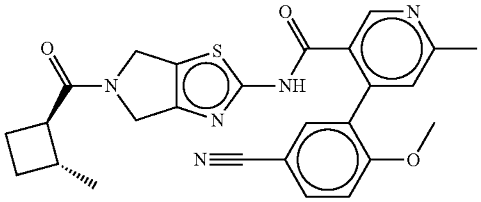 |
| 221 | 4-(5-cyano-2-methoxyphenyl)-N-(5-((1r,3r)-3-methoxycyclobutane-1-carbonyl)-5,6-dihydro-4H-pyrrolo[3,4-d]thiazol-2-yl)-6-methylnicotinamide | 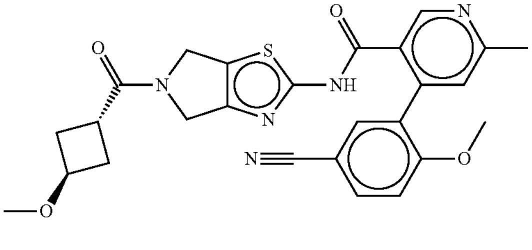 |

TABLE 1-continued

| Compound No. | Name | Structure |
|---|---|---|
| 222 | (R or S) 4-(5-cyano-2-methoxyphenyl)-6-methyl-N-(5-(tetrahydro-2H-pyran-3-carbonyl)-4,5,6,7-tetrahydrothiazolo[5,4-c]pyridin-2-yl)nicotinamide | 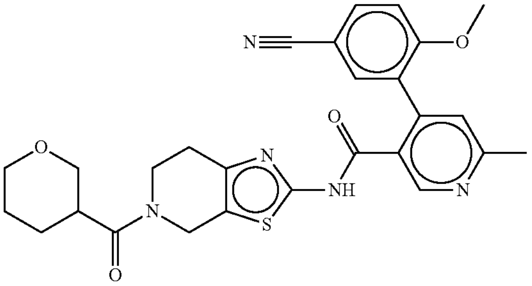 |
| 223 | (S or R) 4-(5-cyano-2-methoxyphenyl)-6-methyl-N-(5-(tetrahydro-2H-pyran-3-carbonyl)-4,5,6,7-tetrahydrothiazolo[5,4-c]pyridin-2-yl)nicotinamide | 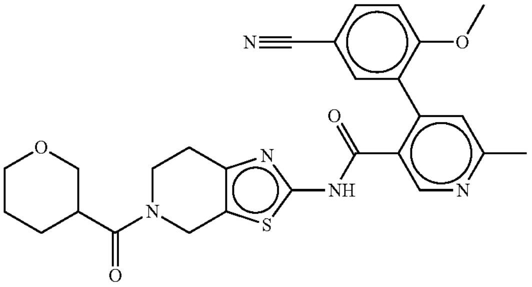 |
| 224 | 4-(5-cyano-2-methoxyphenyl)-N-(5-(cyclobutanecarbonyl)-4,5,6,7-tetrahydrothiazolo[5,4-c]pyridin-2-yl)-6-methylnicotinamide | 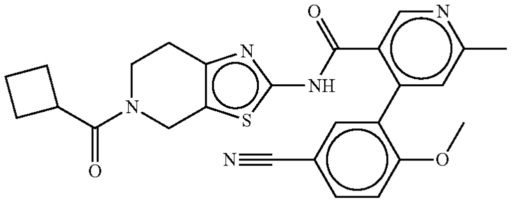 |
| 225 | (S) 4-(5-cyano-2-methoxyphenyl)-6-methyl-N-(5-(tetrahydrofuran-2-carbonyl)-4,5,6,7-tetrahydrothiazolo[5,4-c]pyridin-2-yl)nicotinamide | 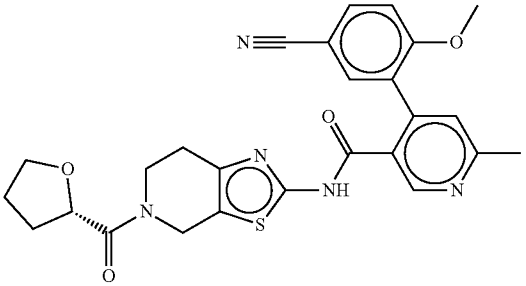 |
| 226 | 4-(5-cyano-2-methoxyphenyl)-6-methyl-N-(5-(pyrrolidin-1-ylsulfonyl)-4,5,6,7-tetrahydrothiazolo[5,4-c]pyridin-2-yl)nicotinamide | 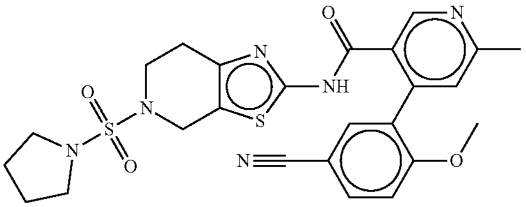 |
| 227 | (R)-4-(5-cyano-2-methoxyphenyl)-6-methyl-N-(5-(tetrahydrofuran-2-carbonyl)-4,5,6,7-tetrahydrothiazolo[5,4-c]pyridin-2-yl)nicotinamide | 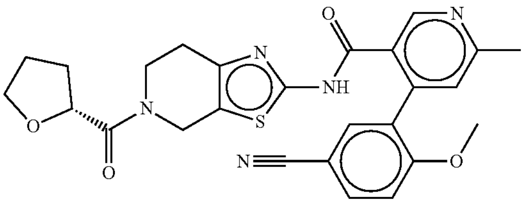 |

TABLE 1-continued

| Compound No. | Name | Structure |
|---|---|---|
| 228 | 4-(5-cyano-2-methoxyphenyl)-6-methyl-N-(5-(oxetane-3-carbonyl)-4,5,6,7-tetrahydrothiazolo[5,4-c]pyridin-2-yl)nicotinamide | 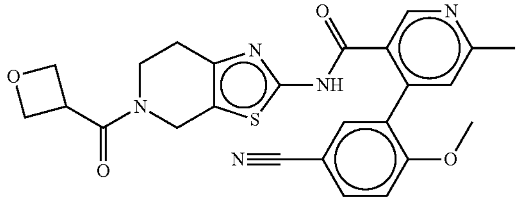 |
| 229 | 4-(5-cyano-2-methoxyphenyl)-N-(5-(cyclopentanecarbonyl)-4,5,6,7-tetrahydrothiazolo[5,4-c]pyridin-2-yl)-6-methylnicotinamide | 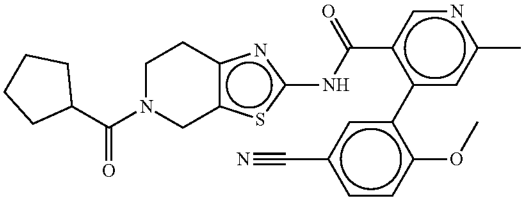 |
| 230 | 4-(5-cyano-2-methoxyphenyl)-N-(5-(N-cyclopentylsulfamoyl)-5,6-dihydro-4H-pyrrolo[3,4-d]thiazol-2-yl)-6-methylnicotinamide | 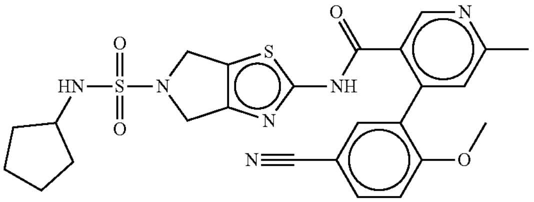 |
| 231 | (Cis and Trans) 4-(5-cyano-2-methoxyphenyl)-6-methyl-N-(5-(3-(trifluoromethoxy)cyclobutane-1-carbonyl)-5,6-dihydro-4H-pyrrolo[3,4-d]thiazol-2-yl)nicotinamide | 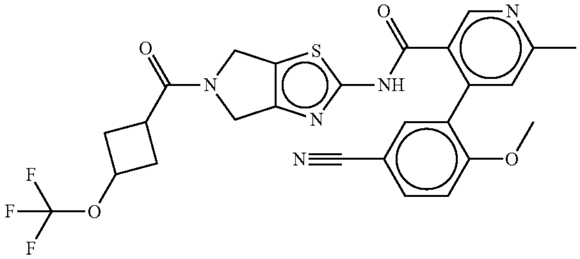 |
| 232 | 2'-chloro-5'-methoxy-N-(5-(3-methoxy-1-methyl-1H-pyrazole-4-carbonyl)-5,6-dihydro-4H-pyrrolo[3,4-d]thiazol-2-yl)-6-methyl-[4,4'-bipyridine]-3-carboxamide | 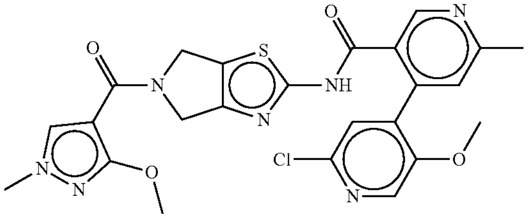 |
| 233 | (Racemic) 4-(5-cyano-2-methoxyphenyl)-6-methyl-N-(5-((tetrahydro-2H-pyran-3-yl)sulfonyl)-5,6-dihydro-4H-pyrrolo[3,4-d]thiazol-2-yl)nicotinamide | 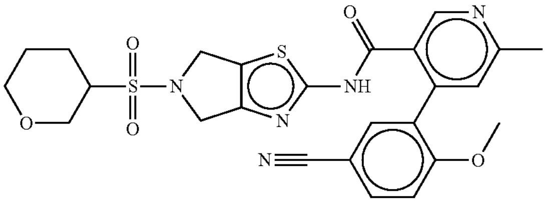 |
| 234 | 2'-chloro-N-(5-(cyclopropylsulfonyl)-5,6-dihydro-4H-pyrrolo[3,4-d]thiazol-2-yl)-5'-methoxy-6-methyl-[4,4'-bipyridine]-3-carboxamide | 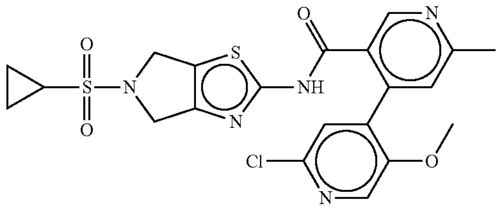 |

TABLE 1-continued

| Compound No. | Name | Structure |
|---|---|---|
| 235 | 4-(5-cyano-2-methoxyphenyl)-N-(5-((1R,2R)-2-methoxycyclobutane-1-carbonyl)-5,6-dihydro-4H-pyrrolo[3,4-d]thiazol-2-yl)-6-methylnicotinamide Mixture of trans isomers | 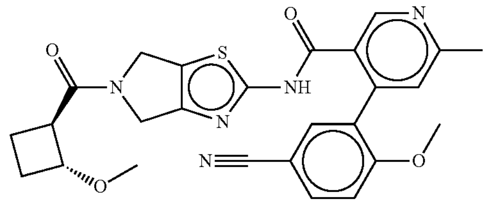 |
| 236 | (R or S) 4-(5-cyano-2-methoxyphenyl)-6-methyl-N-(5-(tetrahydrofuran-3-carbonyl)-4,5,6,7-tetrahydrothiazolo[5,4-c]pyridin-2-yl)nicotinamide | 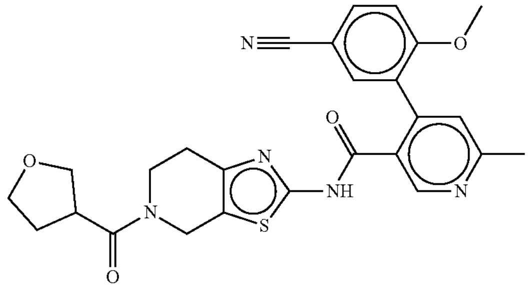 |
| 237 | 4-(5-cyano-2-methoxyphenyl)-6-methyl-N-(5-(tetrahydro-2H-pyran-4-carbonyl)-4,5,6,7-tetrahydrothiazolo[5,4-c]pyridin-2-yl)nicotinamide | 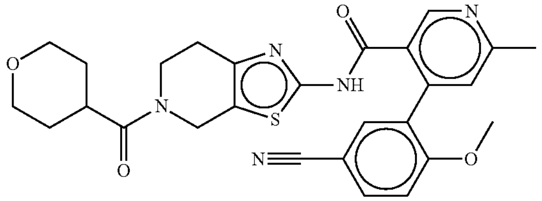 |
| 238 | 4-(5-cyano-2-methoxyphenyl)-6-methyl-N-(5-nicotinoyl-4,5,6,7-tetrahydrothiazolo[5,4-c]pyridin-2-yl)nicotinamide | 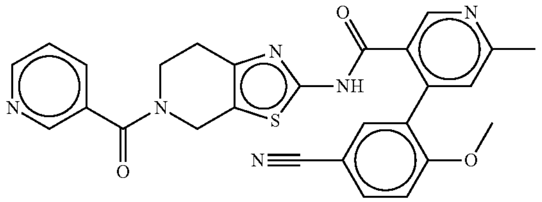 |
| 239 | (S or R) 4-(5-cyano-2-methoxyphenyl)-6-methyl-N-(5-(tetrahydrofuran-3-carbonyl)-4,5,6,7-tetrahydrothiazolo[5,4-c]pyridin-2-yl)nicotinamide | 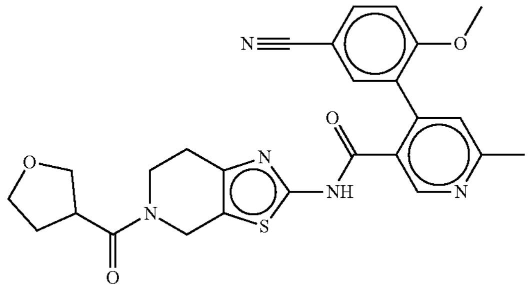 |
| 240 | 4-(5-cyano-2-methoxyphenyl)-N-(5-(N-cyclopropylsulfamoyl)-5,6-dihydro-4H-pyrrolo[3,4-d]thiazol-2-yl)-6-methylnicotinamide | 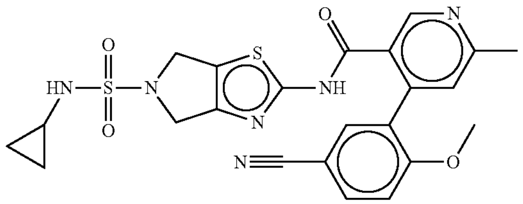 |

TABLE 1-continued

| Compound No. | Name | Structure |
| --- | --- | --- |
| 241 | (Cis and trans) 4-(5-cyano-2-methoxyphenyl)-N-(5-(3-(2,2-difluoroethyl)cyclobutane-1-carbonyl)-5,6-dihydro-4H-pyrrolo[3,4-d]thiazol-2-yl)-6-methylnicotinamide | 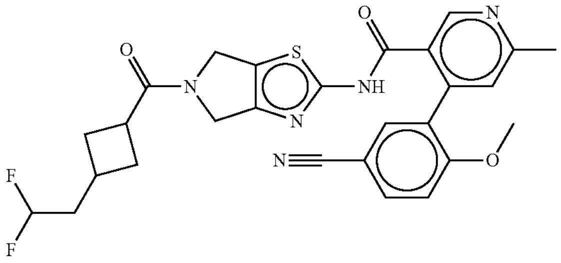 |
| 242 | 4-(5-cyano-2-methoxyphenyl)-6-methyl-N-(5-((5-methylpyridin-2-yl)sulfonyl)-5,6-dihydro-4H-pyrrolo[3,4-d]thiazol-2-yl)nicotinamide | 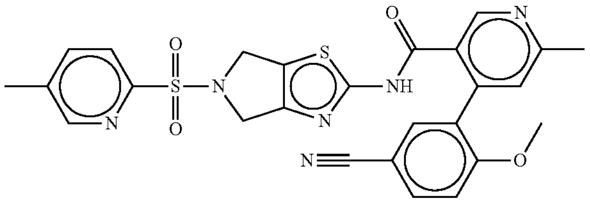 |
| 243 | 4-(5-cyano-2-methoxyphenyl)-N-(5-((1s,3s)-3-cyanocyclobutane-1-carbonyl)-5,6-dihydro-4H-pyrrolo[3,4-d]thiazol-2-yl)-6-methylnicotinamide | 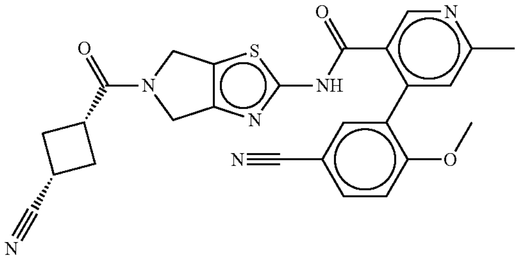 |
| 244 | (Cis and trans) 4-(5-cyano-2-methoxyphenyl)-N-(5-(3-(difluoromethyl)cyclobutane-1-carbonyl)-5,6-dihydro-4H-pyrrolo[3,4-d]thiazol-2-yl)-6-methylnicotinamide | 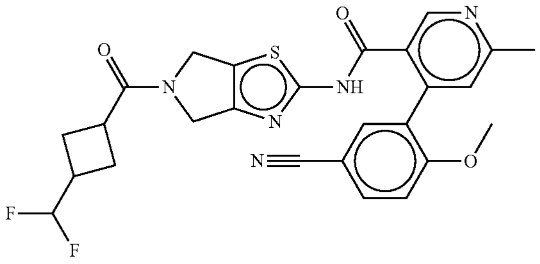 |
| 245 | 4-(5-cyano-2-methoxyphenyl)-N-(5-((1r,3r)-3-cyanocyclobutane-1-carbonyl)-5,6-dihydro-4H-pyrrolo[3,4-d]thiazol-2-yl)-6-methylnicotinamide | 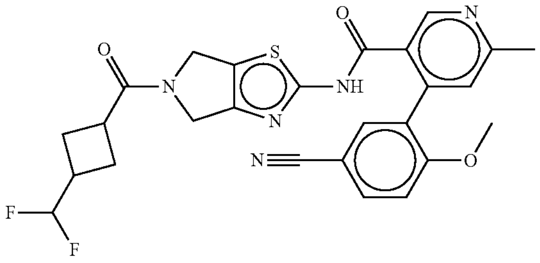 298 |
| 246 | (Racemic) 4-(5-cyano-2-methoxyphenyl)-6-methyl-N-(5-((tetrahydrofuran-3-yl)sulfonyl)-5,6-dihydro-4H-pyrrolo[3,4-d]thiazol-2-yl))nicotinamide | 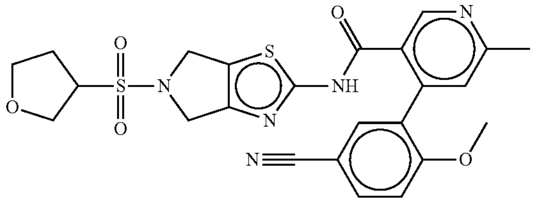 |

TABLE 1-continued

| Compound No. | Name | Structure |
|---|---|---|
| 247 | 4-(5-cyano-2-methoxyphenyl)-6-methyl-N-(5-picolinoyl-4,5,6,7-tetrahydrothiazolo[5,4-c]pyridin-2-yl)nicotinamide | 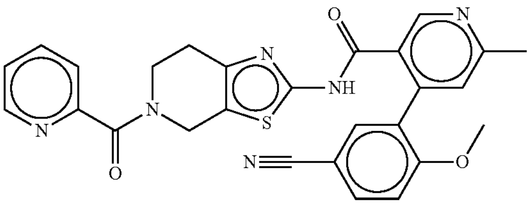 |
| 248 | 4-(5-cyano-2-methoxyphenyl)-N-(5-(cyclopentylsulfonyl)-4,5,6,7-tetrahydrothiazolo[5,4-c]pyridin-2-yl)-6-methylnicotinamide | 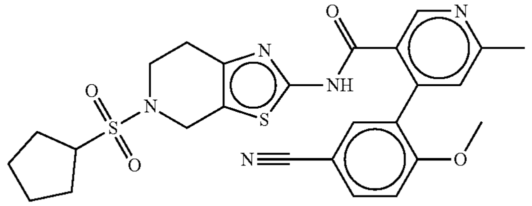 |
| 249 | 4-(5-cyano-2-methoxyphenyl)-N-(5-(N-ethylsulfamoyl)-4,5,6,7-tetrahydrothiazolo[5,4-c]pyridin-2-yl)-6-methylnicotinamide | 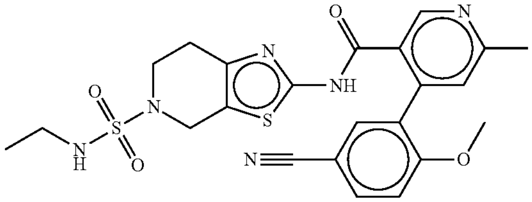 |
| 250 | N-(5-(1,2,4-oxadiazole-3-carbonyl)-5,6-dihydro-4H-pyrrolo[3,4-d]thiazol-2-yl)-4-(2-methoxyphenyl)-6-methylnicotinamide | 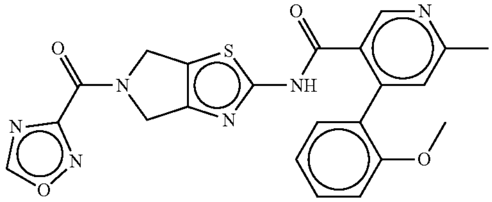 |
| 251 | N-(5-(3-hydroxyoxetane-3-carbonyl)-5,6-dihydro-4H-pyrrolo[3,4-d]thiazol-2-yl)-4-(2-methoxyphenyl)-6-methylnicotinamide | 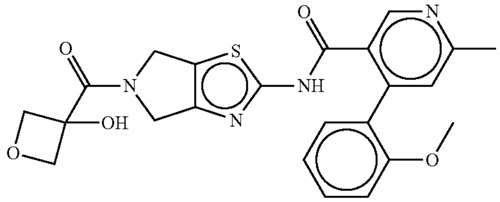 |
| 252 | N-(5-([1,2,4]triazolo[1,5-a]pyridine-2-carbonyl)-5,6-dihydro-4H-pyrrolo[3,4-d]thiazol-2-yl)-4-(2-methoxyphenyl)-6-methylnicotinamide | 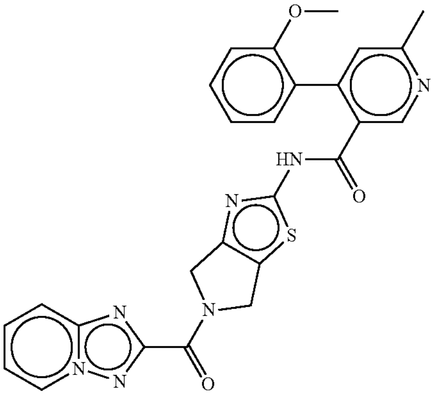 |

TABLE 1-continued

| Compound No. | Name | Structure |
|---|---|---|
| 253 | 4-(2-methoxyphenyl)-6-methyl-N-(5-(pyrazolo[1,5-a]pyridine-7-carbonyl)-5,6-dihydro-4H-pyrrolo[3,4-d]thiazol-2-yl)nicotinamide | 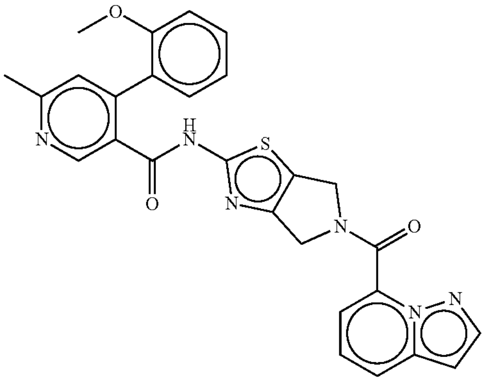 |
| 254 | 4-(2-methoxyphenyl)-6-methyl-N-(5-(1-methyl-2-oxo-1,2-dihydropyridine-3-carbonyl)-5,6-dihydro-4H-pyrrolo[3,4-d]thiazol-2-yl)nicotinamide | 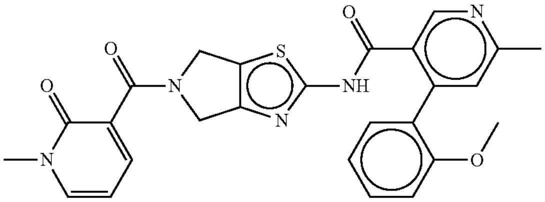 |
| 255 | 4-(2-methoxyphenyl)-6-methyl-N-(5-(1-methyl-1H-1,2,4-triazole-3-carbonyl)-5,6-dihydro-4H-pyrrolo[3,4-d]thiazol-2-yl)nicotinamide | 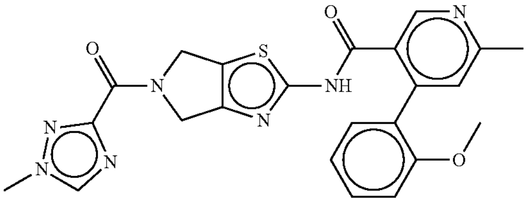 |
| 256 | 4-(2-methoxyphenyl)-6-methyl-N-(5-(oxetane-3-carbonyl)-5,6-dihydro-4H-pyrrolo[3,4-d]thiazol-2-yl)nicotinamide | 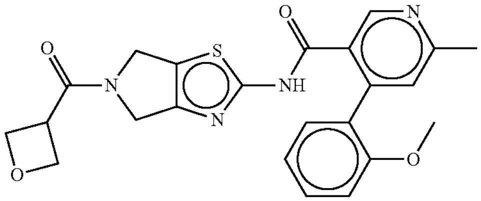 |
| 257 | 4-(5-cyano-2-methoxyphenyl)-N-(5-(cyclopentanecarbonyl)-5,6-dihydro-4H-pyrrolo[3,4-d]thiazol-2-yl)-6-methylnicotinamide | 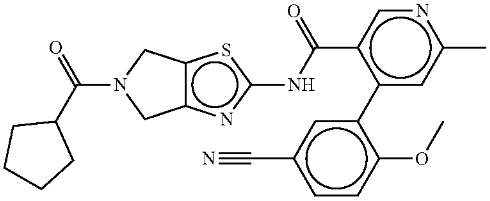 |
| 258 | 4-(5-cyano-2-methoxyphenyl)-N-(5-((1s,3s)-3-methoxycyclobutane-1-carbonyl)-5,6-dihydro-4H-pyrrolo[3,4-d]thiazol-2-yl)-6-methylnicotinamide | 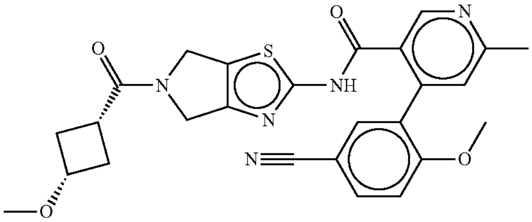 |

TABLE 1-continued

| Compound No. | Name | Structure |
|---|---|---|
| 259 | 4-(5-cyano-2-methoxyphenyl)-6-methyl-N-(5-(morpholinosulfonyl)-5,6-dihydro-4H-pyrrolo[3,4-d]thiazol-2-yl)nicotinamide | 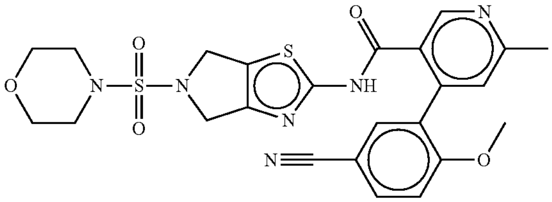 |
| 260 | 4-(5-cyano-2-methoxyphenyl)-6-methyl-N-(5-(pyrrolidin-1-ylsulfony])-5,6-dihydro-4H-pyrrolo[3,4-d]thiazol-2-yl)nicotinamide | 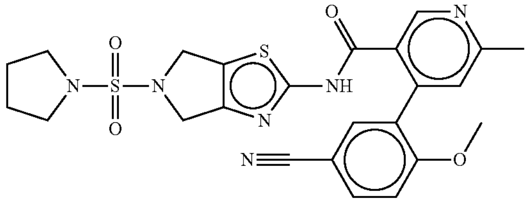 |
| 261 | (S)-4-(5-cyano-2-methoxyphenyl)-6-methyl-N-(5-(tetrahydrofuran-2-carbonyl)-5,6-dihydro-4H-pyrrolo[3,4-d]thiazol-2-yl)nicotinamide | 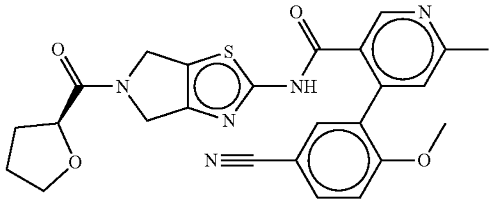 |
| 262 | 4-(5-cyano-2-methoxyphenyl)-N-(5-isonicotinoyl-5,6-dihydro-4H-pyrrolo[3,4-d]thiazol-2-yl)-6-methylnicotinamide | 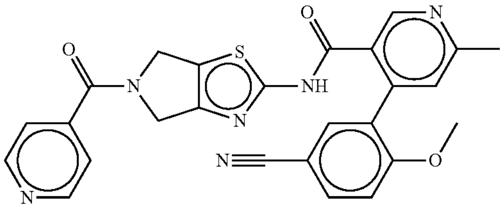 |
| 263 | 4-(5-cyano-2-methoxyphenyl)-6-methyl-N-(5-((1-methylcyclopropyl)sulfonyl)-5,6-dihydro-4H-pyrrolo[3,4-d]thiazol-2-yl)nicotinamide | 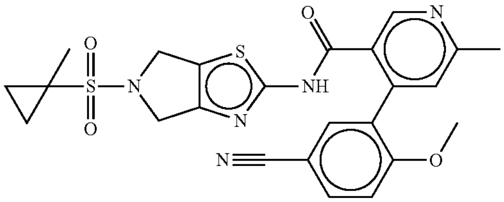 |
| 264 | 4-(5-cyano-2-methoxyphenyl)-N-(5-(cyclobutanecarbonyl)-5,6-dihydro-4H-pyrrolo[3,4-d]thiazol-2-yl)-6-methylnicotinamide | 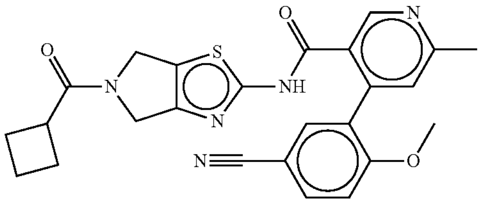 |
| 265 | 4-(5-cyano-2-methoxyphenyl)-6-methyl-N-(5-(piperidin-1-ylsulfony])-5,6-dihydro-4H-pyrrolo[3,4-d]thiazol-2-yl)nicotinamide | 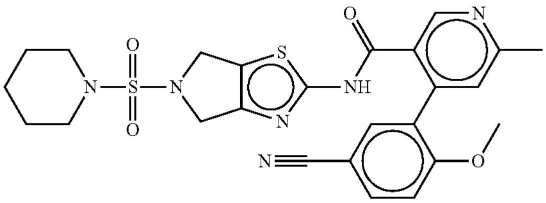 |

TABLE 1-continued

| Compound No. | Name | Structure |
|---|---|---|
| 266 | 4-(5-cyano-2-methoxyphenyl)-N-(5-(cyclobutylsulfonyl)-5,6-dihydro-4H-pyrrolo[3,4-d]thiazol-2-yl)-6-methylnicotinamide | 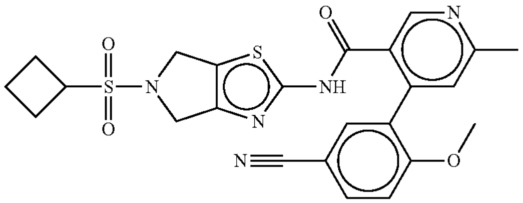 |
| 267 | 4-(5-cyano-2-methoxyphenyl)-6-methyl-N-(5-(3-methylisonicotinoyl)-5,6-dihydro-4H-pyrrolo[3,4-d]thiazol-2-yl)nicotinamide | 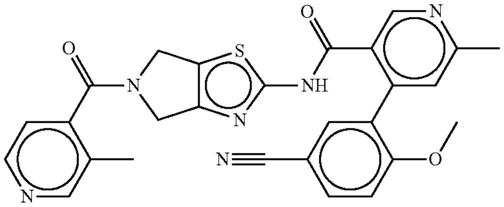 |
| 268 | (R)-4-(5-cyano-2-methoxyphenyl)-6-methyl-N-(5-(tetrahydrofuran-2-carbonyl)-5,6-dihydro-4H-pyrrolo[3,4-d]thiazol-2-yl)nicotinamide | 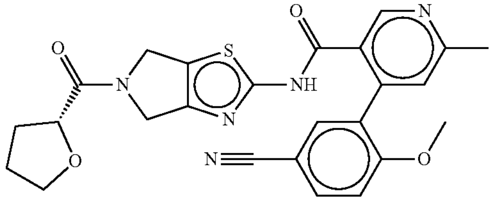 |
| 269 | 4-(5-cyano-2-methoxyphenyl)-N-(5-(N-isopropylsulfamoyl)-5,6-dihydro-4H-pyrrolo[3,4-d]thiazol-2-yl)-6-methylnicotinamide | 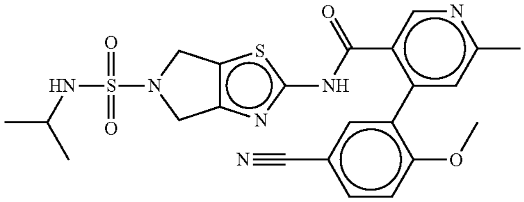 |
| 270 | 4-(5-cyano-2-methoxyphenyl)-6-methyl-N-(5-(N-propylsulfamoyl)-5,6-dihydro-4H-pyrrolo[3,4-d]thiazol-2-yl)nicotinamide | 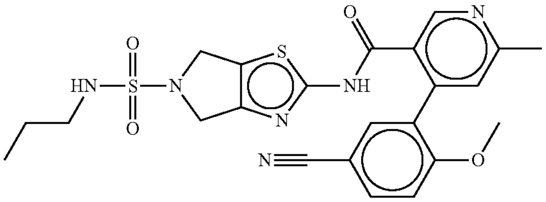 |
| 271 | 4-(5-cyano-2-methoxyphenyl)-6-methyl-N-(5-(2-methylisonicotinoyl)-5,6-dihydro-4H-pyrrolo[3,4-d]thiazol-2-yl)nicotinamide | 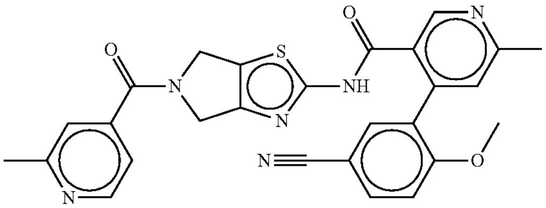 |
| 272 | 4-(5-cyano-2-methoxyphenyl)-6-methyl-N-(5-(N-(2,2,2-trifluoroethyl)sulfamoyl)-5,6-dihydro-4H-pyrrolo[3,4-d]thiazol-2-yl)nicotinamide | 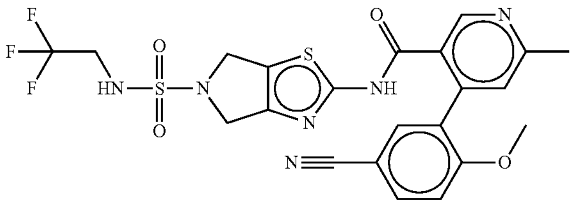 |

TABLE 1-continued

| Compound No. | Name | Structure |
|---|---|---|
| 273 | 4-(S-cyano-2-methoxyphenyl)-N-(5-(cyclohexanecarbonyl)-5,6-dihydro-4H-pyrrolo[3,4-d]thiazol-2-yl)-6-methylnicotinamide | 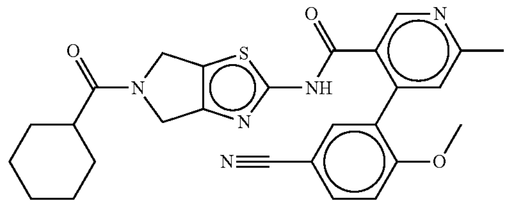 |
| 274 | 4-(5-cyano-2-methoxyphenyl)-N-(5-(cyclopropylsulfonyl)-5,6-dihydro-4H-pyrrolo[3,4-d]thiazol-2-yl)-6-methylnicotinamide | 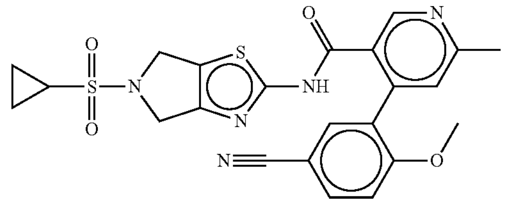 |
| 275 | N-(5-(N-(tert-butyl)sulfamoyl)-5,6-dihydro-4H-pyrrolo[3,4-d]thiazol-2-yl)-4-(5-cyano-2-methoxyphenyl)-6-methylnicotinamide | 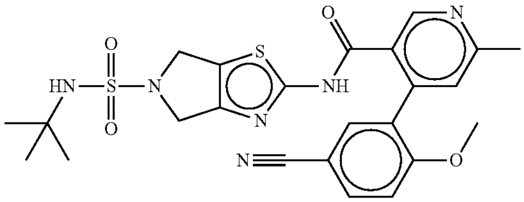 |
| 276 | 4-(5-cyano-2-methoxyphenyl)-6-methyl-N-(S-picolinoyl-5,6-dihydro-4H-pyrrolo[3,4-d]thiazol-2-yl)nicotinamide | 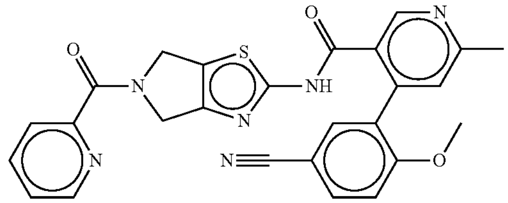 |
| 277 | 4-(5-cyano-2-methoxyphenyl)-6-methyl-N-(5-(3-methylpicolinoyl)-5,6-dihydro-4H-pyrrolo[3,4-d]thiazol-2-yl)nicotinamide | 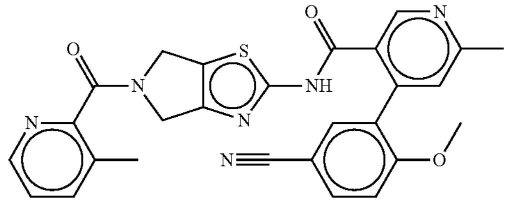 |
| 278 | 2'-chloro-5'-methoxy-6-methyl-N-(5-picolinoyl-5,6-dihydro-4H-pyrrolo[3,4-d]thiazol-2-yl)-[4,4'-bipyridine]-3-carboxamide | 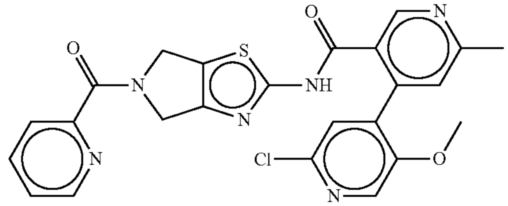 |
| 279 | N-(5-(cyclobutylsulfonyl)-5,6-dihydro-4H-pyrrolo[3,4-d]thiazol-2-yl)-4-(2-methoxyphenyl)-6-methylnicotinamide | 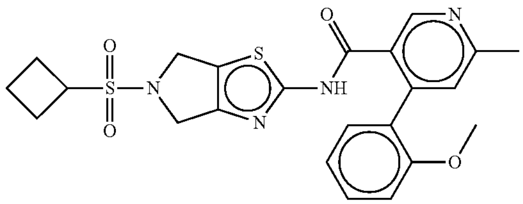 |

TABLE 1-continued

| Compound No. | Name | Structure |
|---|---|---|
| 280 | N-(5-(N-isopropylsulfamoyl)-5,6-dihydro-4H-pyrrolo[3,4-d]thiazol-2-yl)-4-(2-methoxyphenyl)-6-methylnicotinamide | 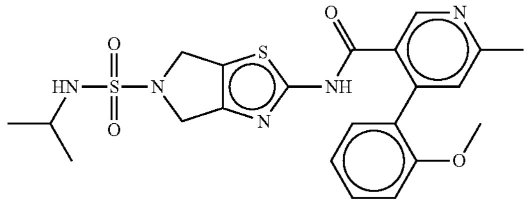 |
| 281 | 4-(5-cyano-2-methoxyphenyl)-6-methyl-N-(5-(pyridin-3-ylsulfonyl)-5,6-dihydro-4H-pyrrolo[3,4-d]thiazol-2-yl)nicotinamide | 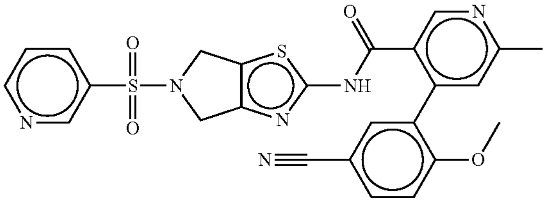 |
| 282 | 4-(5-cyano-2-methoxyphenyl)-6-methyl-N-(5-(4-methylpicolinoyl)-5,6-dihydro-4H-pyrrolo[3,4-d]thiazol-2-yl)nicotinamide | 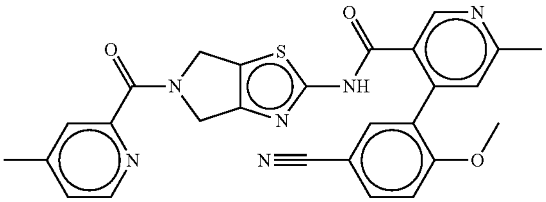 |
| 283 | 4-(2-methoxyphenyl)-6-methyl-N-(5-(oxazole-4-carbonyl)-5,6-dihydro-4H-pyrrolo[3,4-d]thiazol-2-yl)nicotinamide | 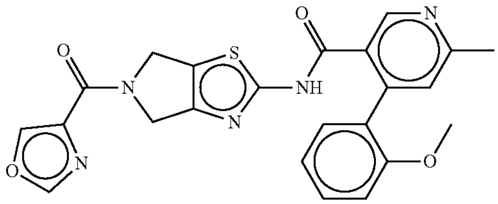 |
| 284 | 4-(2-methoxyphenyl)-6-methyl-N-(5-(1-methyl-1H-1,2,3-triazole-5-carbonyl)-5,6-dihydro-4H-pyrrolo[3,4-d]thiazol-2-yl)nicotinamide | 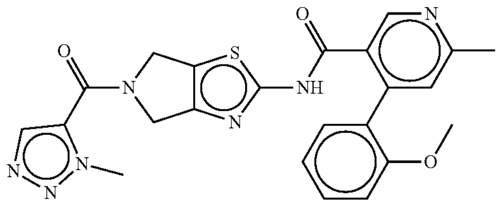 |
| 285 | 4-(2-methoxyphenyl)-6-methyl-N-(5-(1-methyl-2-oxo-1,2-dihydropyridine-4-carbonyl)-5,6-dihydro-4H-pyrrolo[3,4-d]thiazol-2-yl)nicotinamide | 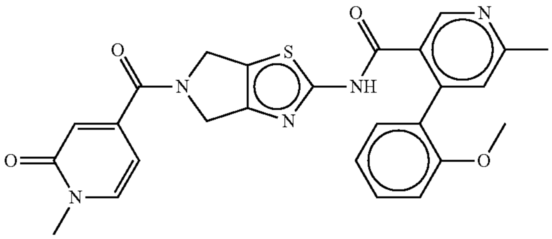 |
| 286 | 4-(2-methoxyphenyl)-6-methyl-N-(5-(1-methyl-1H-1,2,4-triazole-5-carbonyl)-5,6-dihydro-4H-pyrrolo[3,4-d]thiazol-2-yl)nicotinamide | 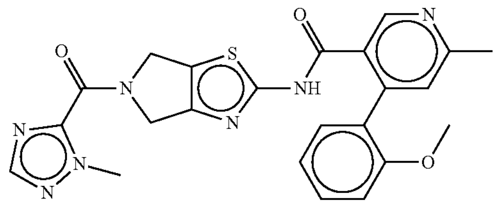 |

TABLE 1-continued

| Compound No. | Name | Structure |
|---|---|---|
| 287 | 4-(2-methoxyphenyl)-6-methyl-N-(5-(1-methyl-1H-pyrazole-5-carbonyl)-5,6-dihydro-4H-pyrrolo[3,4-d]thiazol-2-yl)nicotinamide | 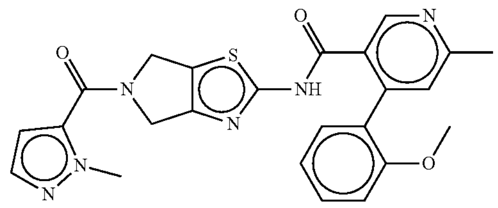 |
| 288 | 4-(2-methoxyphenyl)-6-methyl-N-(5-(1-methyl-6-oxo-1,6-dihydropyridine-3-carbonyl)-5,6-dihydro-4H-pyrrolo[3,4-d]thiazol-2-yl)nicotinamide | 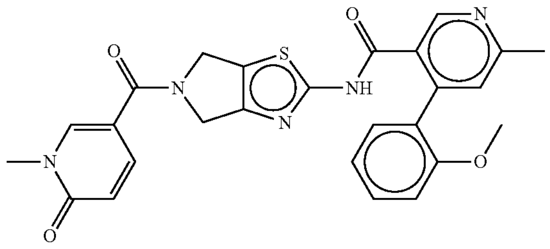 |
| 289 | 4-(2-methoxyphenyl)-6-methyl-N-(5-(1-methyl-1H-pyrazole-3-carbonyl)-5,6-dihydro-4H-pyrrolo[3,4-d]thiazol-2-yl)nicotinamide | 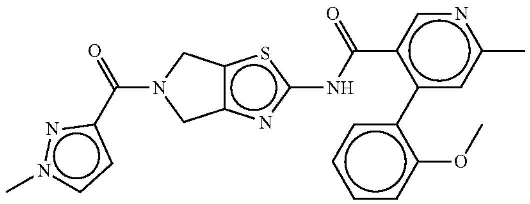 |
| 290 | N-(5-(3-cyanopicolinoyl)-5,6-dihydro-4H-pyrrolo[3,4-d]thiazol-2-yl)-4-(2-methoxyphenyl)-6-methylnicotinamide | 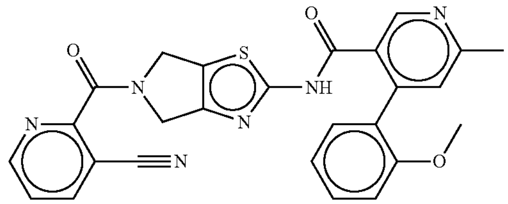 |
| 291 | N-(5-(3-methoxy-1-methyl-1H-pyrazole-4-carbonyl)-5,6-dihydro-4H-pyrrolo[3,4-d]thiazol-2-yl)-4-(2-methoxyphenyl)-6-methylnicotinamide | 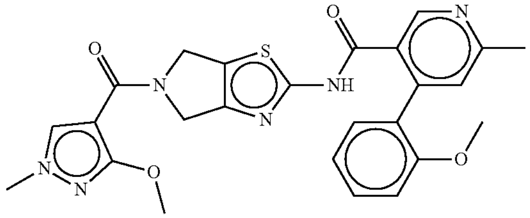 |
| 292 | N-(5-(2-(1H-pyrazol-1-yl)acetyl)-5,6-dihydro-4H-pyrrolo[3,4-d]thiazol-2-yl)-4-(2-methoxyphenyl)-6-methylnicotinamide | 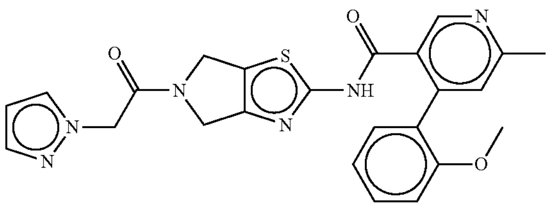 |
| 293 | 4-(2-methoxyphenyl)-6-methyl-N-(5-(1-methyl-1H-pyrazole-4-carbonyl)-5,6-dihydro-4H-pyrrolo[3,4-d]thiazol-2-yl)nicotinamide | 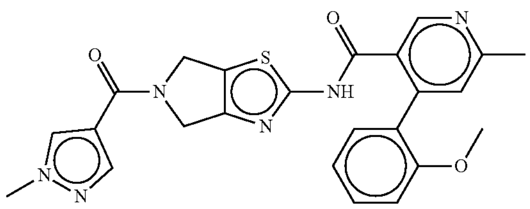 |

TABLE 1-continued

| Compound No. | Name | Structure |
|---|---|---|
| 294 | 4-(2-methoxyphenyl)-6-methyl-N-(5-(oxazole-2-carbonyl)-5,6-dihydro-4H-pyrrolo[3,4-d]thiazol-2-yl)nicotinamide | 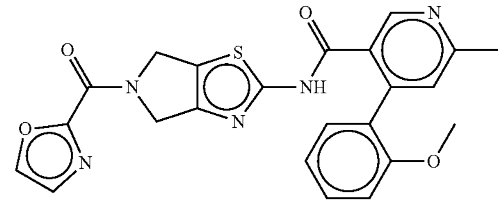 |
| 295 | 4-(2-methoxyphenyl)-6-methyl-N-(5-(oxazole-5-carbonyl)-5,6-dihydro-4H-pyrrolo[3,4-d]thiazol-2-yl)nicotinamide | 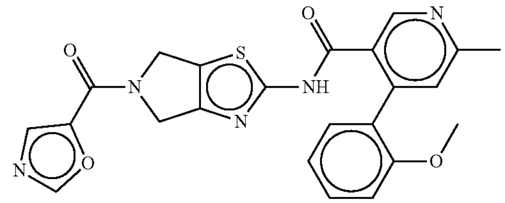 |
| 296 | 4-(2-methoxyphenyl)-6-methyl-N-(5-(1-methyl-1H-1,2,3-triazole-4-carbonyl)-5,6-dihydro-4H-pyrrolo[3,4-d]thiazol-2-yl)nicotinamide | 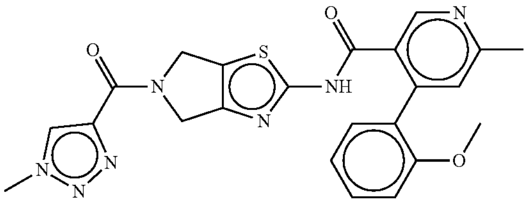 |
| 297 | N-(5-(5-methoxy-1-methyl-1H-pyrazole-3-carbonyl)-5,6-dihydro-4H-pyrrolo[3,4-d]thiazol-2-yl)-4-(2-methoxyphenyl)-6-methylnicotinamide | 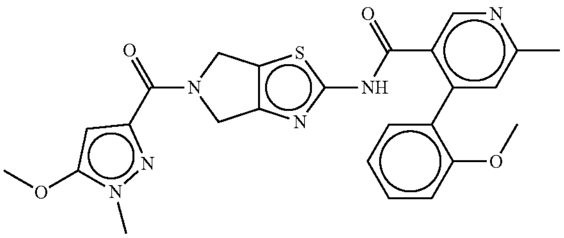 |
| 298 | 4-(2-methoxyphenyl)-6-methyl-N-(5-(pyrazolo[1,5-a]pyridine-2-carbonyl)-5,6-dihydro-4H-pyrrolo[3,4-d]thiazol-2-yl)nicotinamide | 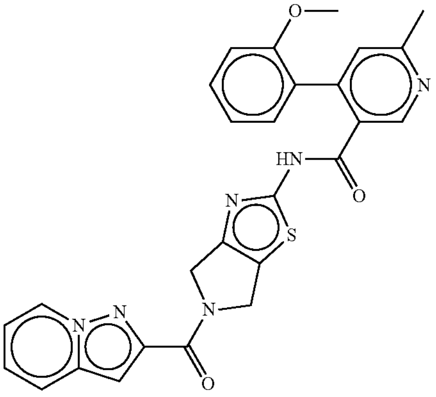 |
| 299 | 4-(5-cyano-2-methoxyphenyl)-N-(5-(N-ethylsulfamoyl)-5,6-dihydro-4H-pyrrolo[3,4-d]thiazol-2-yl)-6-methylnicotinamide | 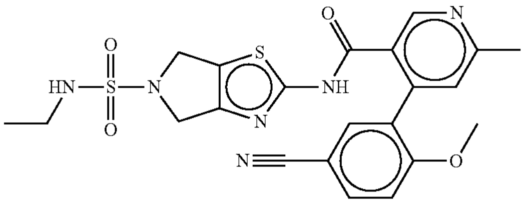 |

TABLE 1-continued

| Compound No. | Name | Structure |
|---|---|---|
| 300 | 4-(2-methoxyphenyl)-6-methyl-N-(5-(thiazol-2-yl)-5,6-dihydro-4H-pyrrolo[3,4-d]thiazol-2-yl)nicotinamide | 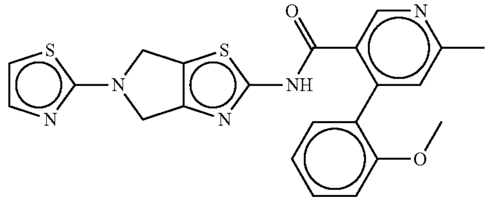 |
| 301 | N-(5-(N-isobutylsulfamoyl)-5,6-dihydro-4H-pyrrolo[3,4-d]thiazol-2-yl)-4-(2-methoxyphenyl)-6-methylnicotinamide | 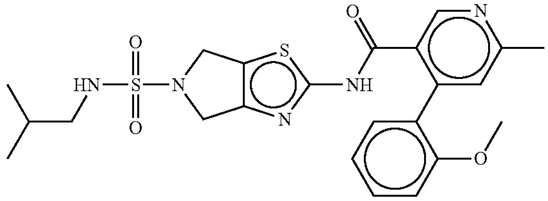 |
| 302 | 4-(5-cyano-2-methoxyphenyl)-N-(5-(N-isobutylsulfamoyl)-5,6-dihydro-4H-pyrrolo[3,4-d]thiazol-2-yl)-6-methylnicotinamide | 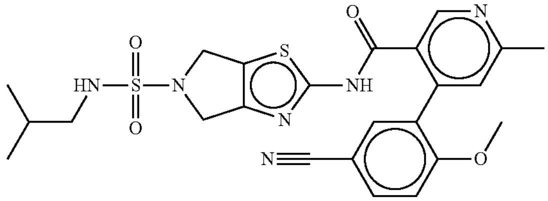 |
| 303 | 4-(5-cyano-2-methoxyphenyl)-6-methyl-N-(5-((tetrahydro-2H-pyran-4-yl)sulfonyl)-5,6-dihydro-4H-pyrrolo[3,4-d]thiazol-2-yl)nicotinamide | 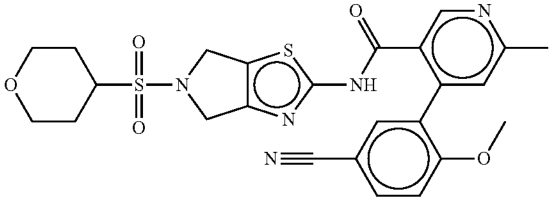 |
| 304 | 4-(5-cyano-2-methoxyphenyl)-6-methyl-N-(S-(5-methylpicolinoyl)-5,6-dihydro-4H-pyrrolo[3,4-d]thiazol-2-yl)nicotinamide | 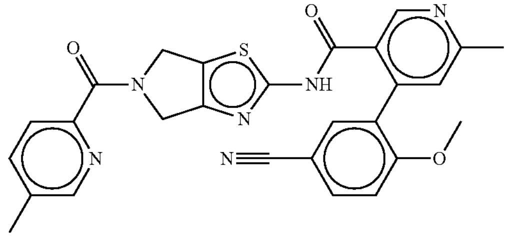 |
| 305 | (Racemic) 4-(5-cyano-2-methoxyphenyl)-6-methyl-N-(6-(phenylamino)-4,5,6,7-tetrahydrobenzo[d]thiazol-2-yl)nicotinamide | 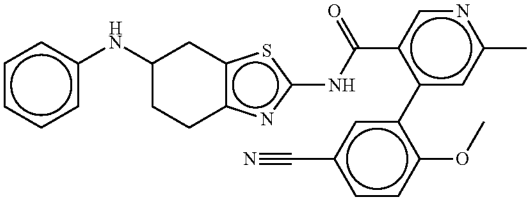 |
| 306 | (Cis and trans) N-(5-(3-(difluoromethoxy)cyclobutane-1-carbonyl)-5,6-dihydro-4H-pyrrolo[3,4-d]thiazol-2-yl)-4-(2-methoxyphenyl)-6-methylnicotinamide | 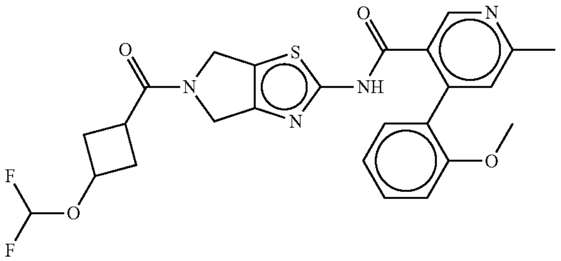 |

TABLE 1-continued

| Compound No. | Name | Structure |
|---|---|---|
| 307 | 4-(5-cyano-2-methoxyphenyl)-6-methyl-N-(5-(6-methylpicolinoyl)-5,6-dihydro-4H-pyrrolo[3,4-d]thiazol-2-yl)nicotinamide | 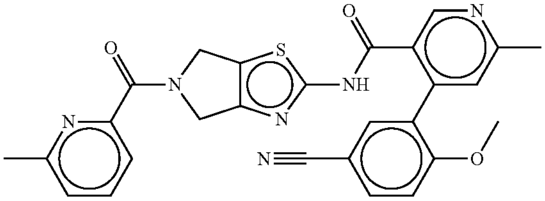 |
| 308 | 4-(5-cyano-2-methoxyphenyl)-6-methyl-N-(5-(pyridin-2-ylsulfonyl)-5,6-dihydro-4H-pyrrolo[3,4-d]thiazol-2-yl)nicotinamide | 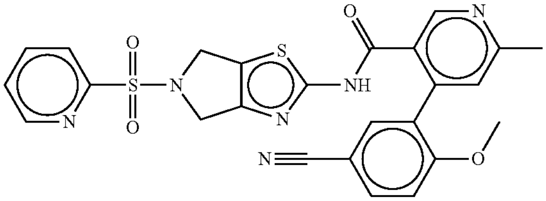 |
| 309 | N-(5-(N-ethylsulfamoyl)-5,6-dihydro-4H-pyrrolo[3,4-d]thiazol-2-yl)-4-(2-methoxyphenyl)-6-methylnicotinamide | 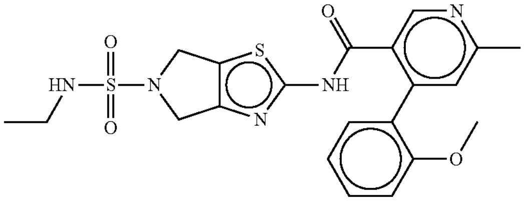 |
| 310 | 4-(2-methoxyphenyl)-6-methyl-N-(5-(morpholinosulfonyl)-5,6-dihydro-4H-pyrrolo[3,4-d]thiazol-2-yl)nicotinamide | 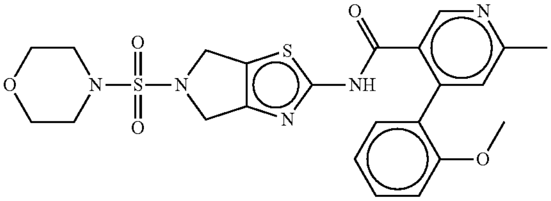 |
| 311 | 4-(2-methoxyphenyl)-6-methyl-N-(5-(pyrrolidin-1-ylsulfonyl)-5,6-dihydro-4H-pyrrolo[3,4-d]thiazol-2-yl)nicotinamide | 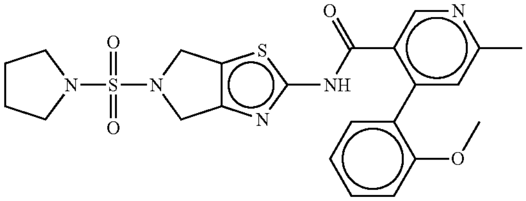 |
| 312 | (R or S) 4-(2-methoxyphenyl)-6-methyl-N-(6-(phenylamino)-4,5,6,7-tetrahydrobenzo[d]thiazol-2-yl)nicotinamide | 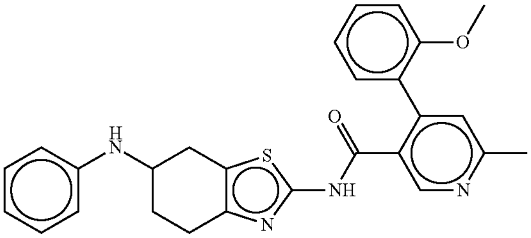 |
| 313 | N-(5-isonicotinoyl-5,6-dihydro-4H-pyrrolo[3,4-d]thiazol-2-yl)-4-(2-methoxyphenyl)-6-methylnicotinamide | 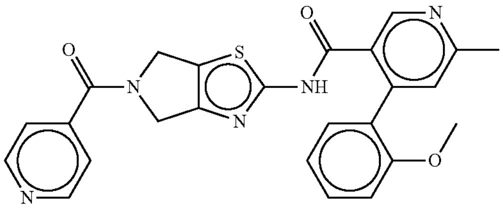 |

TABLE 1-continued

| Compound No. | Name | Structure |
|---|---|---|
| 314 | tert-butyl 2-(4-(2-methoxyphenyl)-6-methylnicotinamido)-4,6-dihydro-5H-pyrrolo[3,4-d]thiazole-5-carboxylate | 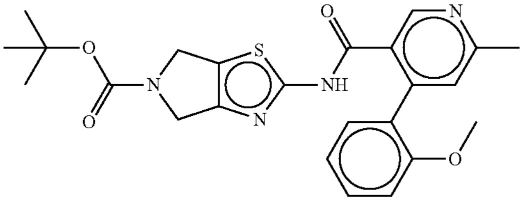 |
| 315 | 4-(2-methoxyphenyl)-6-methyl-N-(5-(1-(pyridin-2-yl)cyclopropane-1-carbonyl)-5,6-dihydro-4H-pyrrolo[3,4-d]thiazol-2-yl)nicotinamide | 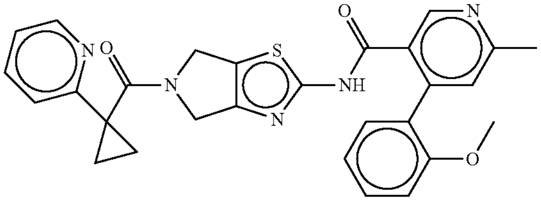 |
| 316 | 4-(2-methoxyphenyl)-6-methyl-N-(5-(N-methylsulfamoyl)-5,6-dihydro-4H-pyrrolo[3,4-d]thiazol-2-yl)nicotinamide | 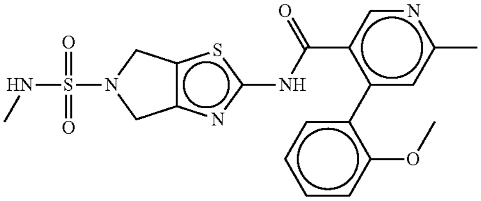 |
| 317 | N-(5-(cyclobutanecarbonyl)-5,6-dihydro-4H-pyrrolo[3,4-d]thiazol-2-yl)-4-(2-methoxyphenyl)-6-methylnicotinamide | 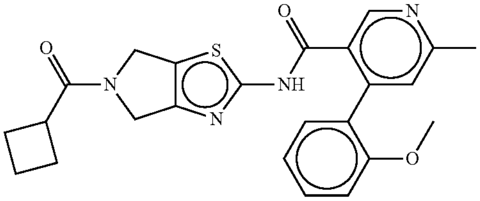 |
| 318 | (Racemic)-4-(2-methoxyphenyl)-6-methyl-N-(6-(phenylamino)-4,5,6,7-tetrahydrobenzo[d]thiazol-2-yl)nicotinamide | 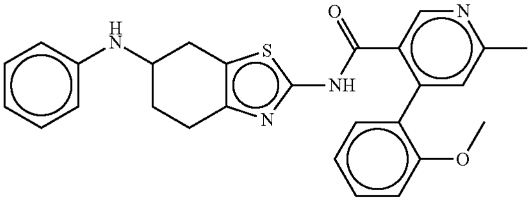 |
| 319 | 4-(2-methoxyphenyl)-6-methyl-N-(5-nicotinoyl-5,6-dihydro-4H-pyrrolo[3,4-d]thiazol-2-yl)nicotinamide | 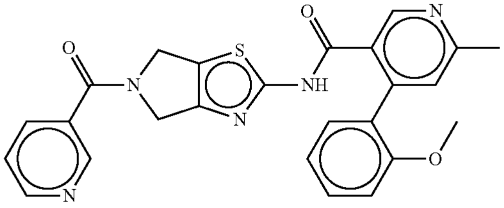 |
| 320 | N-(5-(2-oxaspiro[3.3]heptane-6-carbonyl)-5,6-dihydro-4H-pyrrolo[3,4-d]thiazol-2-yl)-4-(2-methoxyphenyl)-6-methylnicotinamide | 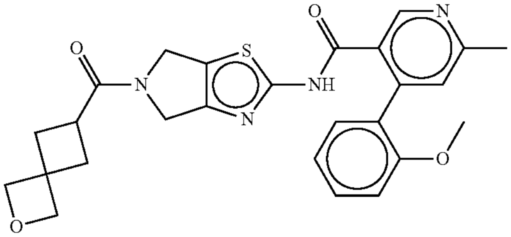 |

TABLE 1-continued

| Compound No. | Name | Structure |
|---|---|---|
| 321 | (R and S) N-(6-(4-chlorophenyl)-4,5,6,7-tetrahydrobenzo[d]thiazol-2-yl)-4-(2-methoxyphenyl)-6-methylnicotinamide | 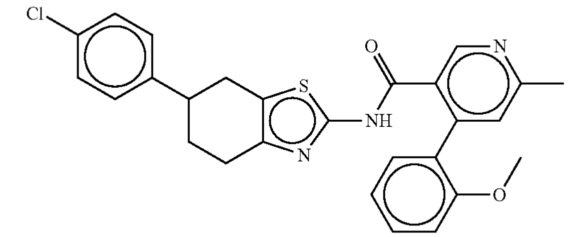 |
| 322 | N-(5-(5-cyanonicotinoyl)-5,6-dihydro-4H-pyrrolo[3,4-d]thiazol-2-yl)-4-(2-methoxyphenyl)-6-methylnicotinamide | 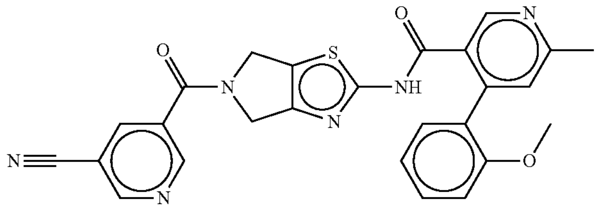 |
| 323 | 4-(2-methoxyphenyl)-6-methyl-N-(5-picolinoyl-5,6-dihydro-4H-pyrrolo[3,4-d]thiazol-2-yl)nicotinamide | 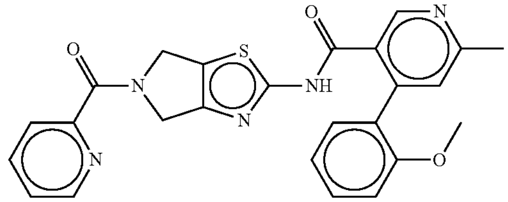 |
| 324 | (Racemic) 4-(2-methoxyphenyl)-6-methyl-N-(5-(tetrahydro-2H-pyran-2-carbonyl)-5,6-dihydro-4H-pyrrolo[3,4-d]thiazol-2-yl)nicotinamide | 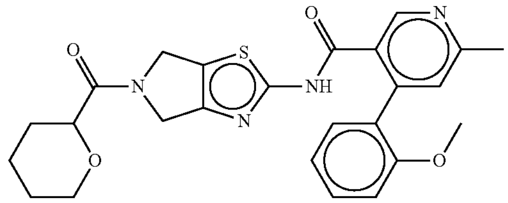 |
| 325 | (S or R) N-(6-(4-chlorophenyl)-4,5,6,7-tetrahydrobenzo[d]thiazol-2-yl)-4-(2-methoxyphenyl)-6-methylnicotinamide | 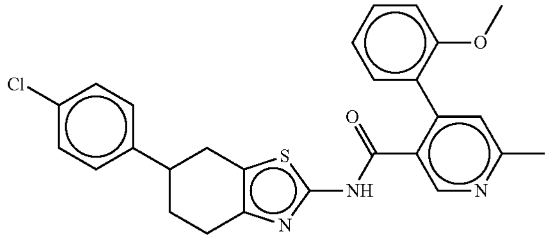 |
| 326 | 4-(2-methoxyphenyl)-6-methyl-N-(5-(tetrahydro-2H-pyran-4-carbonyl)-5,6-dihydro-4H-pyrrolo[3,4-d]thiazol-2-yl)nicotinamide | 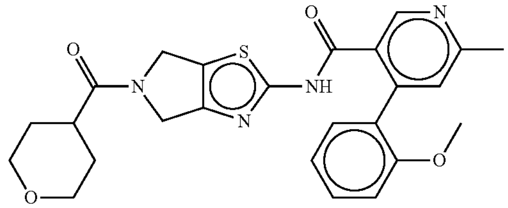 |
| 327 | 4-(2-methoxyphenyl)-6-methyl-N-(5-(pyrazine-2-carbonyl)-5,6-dihydro-4H-pyrrolo[3,4-d]thiazol-2-yl)nicotinamide | 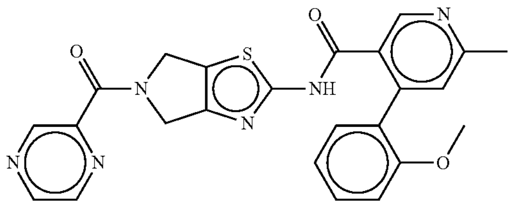 |

TABLE 1-continued

| Compound No. | Name | Structure |
|---|---|---|
| 328 | N-(6-(4-chlorophenyl)-4,7-dihydrobenzo[d]thiazol-2-yl)-4-(2-methoxyphenyl)-6-methylnicotinamide | 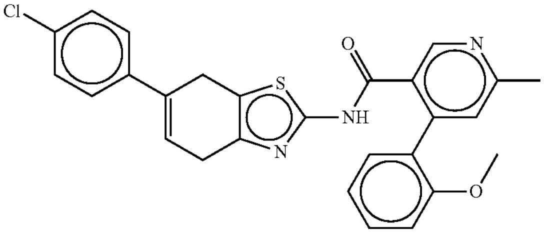 |
| 329 | (Racemic) 4-(2-methoxyphenyl)-6-methyl-N-(5-(tetrahydro-2H-pyran-3-carbonyl)-5,6-dihydro-4H-pyrrolo[3,4-d]thiazol-2-yl)nicotinamide | 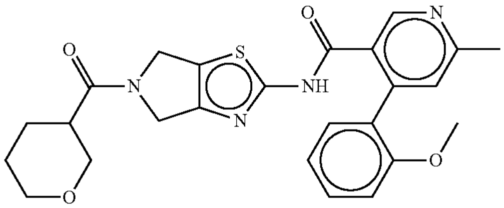 |
| 330 | N-(5-(3-oxabicyclo[3.1.0]hexane-6-carbonyl)-5,6-dihydro-4H-pyrrolo[3,4-d]thiazol-2-yl)-4-(2-methoxyphenyl)-6-methylnicotinamide | 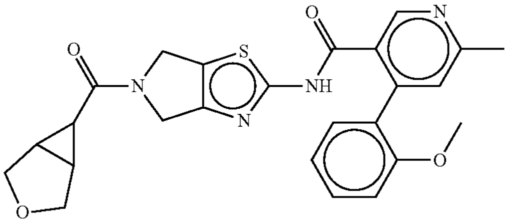 |
| 331 | N-(5-(N,N-dimethylsulfamoyl)-5,6-dihydro-4H-pyrrolo[3,4-d]thiazol-2-yl)-4-(2-methoxyphenyl)-6-methylnicotinamide | 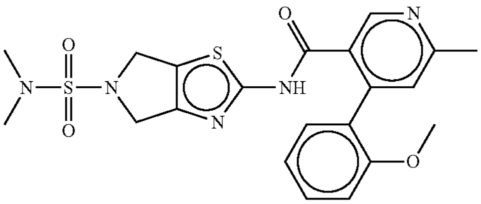 |
| 332 | (Racemic) 4-(2-methoxyphenyl)-6-methyl-N-(5-(tetrahydrofuran-2-carbonyl)-5,6-dihydro-4H-pyrrolo[3,4-d]thiazol-2-yl)nicotinamide | 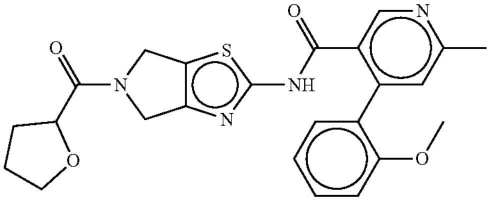 |
| 333 | methyl 2-(4-(2-methoxyphenyl)-6-methylnicotinamido)-4,6-dihydro-5H-pyrrolo[3,4-d]thiazole-5-carboxylate | 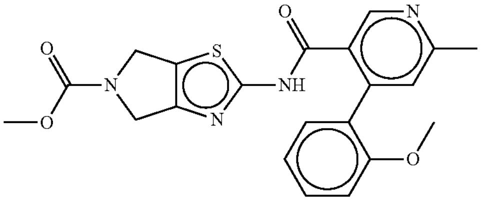 |
| 334 | N-(5-(1-(methoxymethyl)cyclobutane-1-carbonyl)-5,6-dihydro-4H-pyrrolo[3,4-d]thiazol-2-yl)-4-(2-methoxyphenyl)-6-methylnicotinamide | 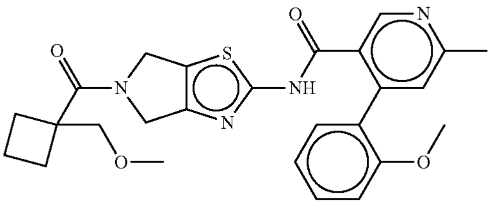 |

TABLE 1-continued

| Compound No. | Name | Structure |
| --- | --- | --- |
| 335 | tert-butyl 2-(4-(2-methoxyphenyl)-6-methylnicotinamido)-6,7-dihydrothiazolo[5,4-c]pyridine-5(4H)-carboxylate | 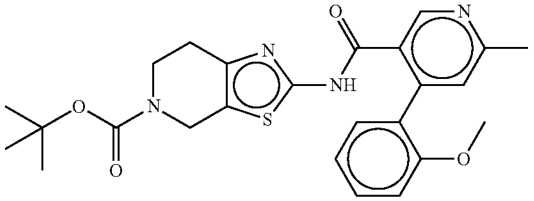 |
| 336 | (Racemic) 4-(2-methoxyphenyl)-6-methyl-N-(5-(tetrahydrofuran-3-carbonyl)-5,6-dihydro-4H-pyrrolo[3,4-d]thiazol-2-yl)nicotinamide | 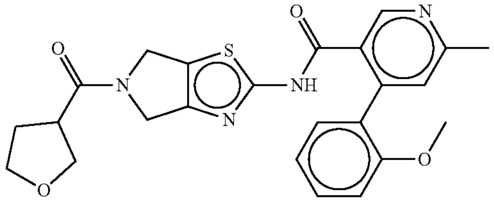 |
| 337 | 4-(2-methoxyphenyl)-6-methyl-N-(5-(methylsulfonyl)-5,6-dihydro-4H-pyrrolo[3,4-d]thiazol-2-yl)nicotinamide | 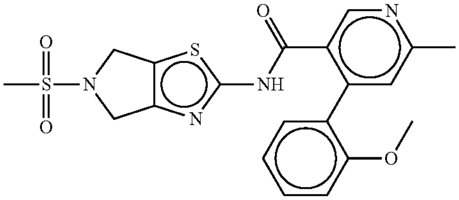 |
| 338 | (R or S) N-(6-(4-chlorophenyl)-4,5,6,7-tetrahydrobenzo[d]thiazol-2-yl)-4-(2-methoxyphenyl)-6-methylnicotinamide | 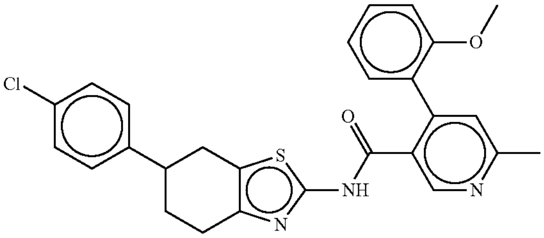 |
| 339 | (Racemic) N-(5-(1,4-dioxane-2-carbonyl)-5,6-dihydro-4H-pyrrolo[3,4-d]thiazol-2-yl)-4-(2-methoxyphenyl)-6-methylnicotinamide | 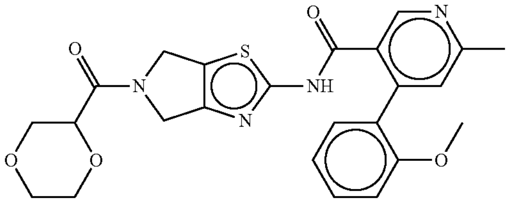 |
| 340 | N-(5-(cyclopropanecarbonyl)-5,6-dihydro-4H-pyrrolo[3,4-d]thiazol-2-yl)-4-(2-methoxyphenyl)-6-methylnicotinamide | 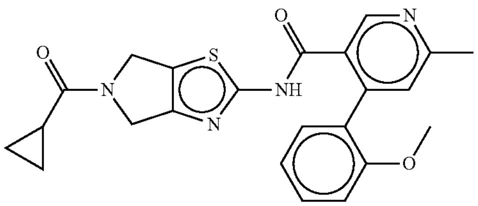 |
| 341 | 4-(2-methoxyphenyl)-6-methyl-N-(5-(pyrimidine-5-carbonyl)-5,6-dihydro-4H-pyrrolo[3,4-d]thiazol-2-yl)nicotinamide | 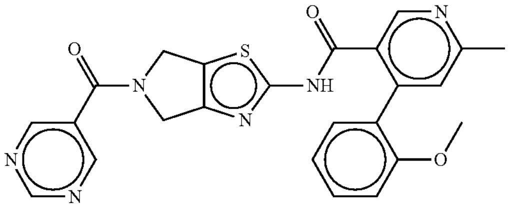 |

TABLE 1-continued

| Compound No. | Name | Structure |
|---|---|---|
| 342 | 4-(2-methoxyphenyl)-6-methyl-N-(5-(pyridazine-3-carbonyl)-5,6-dihydro-4H-pyrrolo[3,4-d]thiazol-2-yl)nicotinamide | 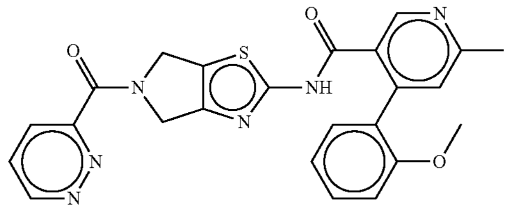 |
| 343 | N-(5-(1,1-dioxidothietane-3-carbonyl)-5,6-dihydro-4H-pyrrolo[3,4-d]thiazol-2-yl)-4-(2-methoxyphenyl)-6-methylnicotinamide | 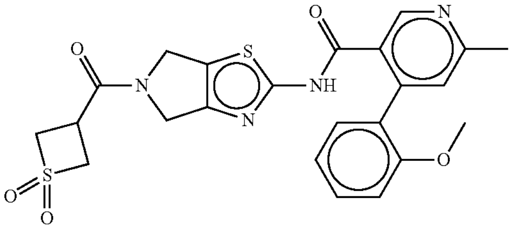 |
| 344 | N-(5-(cyclopropanecarbonyl)-4,5,6,7-tetrahydrothiazolo[5,4-c]pyridin-2-yl)-4-(2-methoxyphenyl)-6-methylnicotinamide | 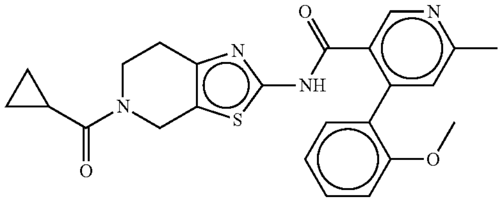 |
| 345 | (Racemic) 4-(2-methoxyphenyl)-6-methyl-N-(5-(2-oxopyrrolidine-3-carbonyl)-5,6-dihydro-4H-pyrrolo[3,4-d]thiazol-2-yl)nicotinamide | 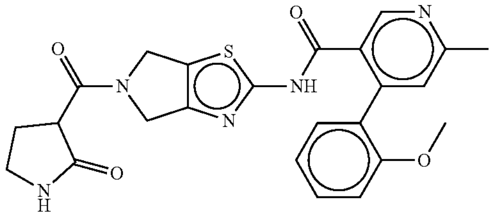 |
| 346 | (Racemic) N-(5-(2-cyanocyclobutane-1-carbonyl)-5,6-dihydro-4H-pyrrolo[3,4-d]thiazol-2-yl)-4-(2-methoxyphenyl)-6-methylnicotinamide | 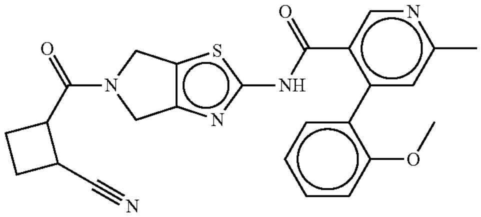 |
| 347 | N-(5-(1-cyanocyclobutane-1-carbonyl)-5,6-dihydro-4H-pyrrolo[3,4-d]thiazol-2-yl)-4-(2-methoxyphenyl)-6-methylnicotinamide | 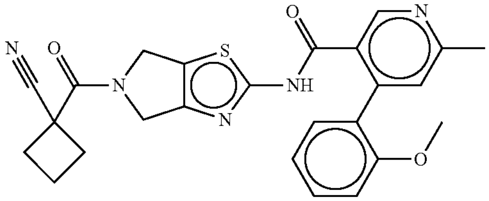 |
| 348 | (Racemic) 4-(2-methoxyphenyl)-6-methyl-N-(5-(5-oxopyrrolidine-2-carbonyl)-5,6-dihydro-4H-pyrrolo[3,4-d]thiazol-2-yl)nicotinamide | 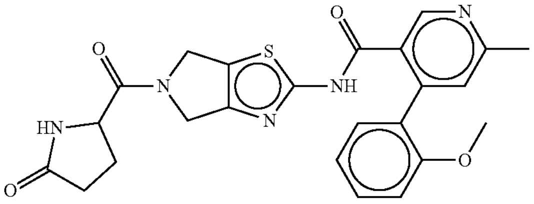 |

TABLE 1-continued

| Compound No. | Name | Structure |
|---|---|---|
| 349 | N-(5-(3-cyanobicyclo[1.1.1]pentane-1-carbonyl)-5,6-dihydro-4H-pyrrolo[3,4-d]thiazol-2-yl)-4-(2-methoxyphenyl)-6-methylnicotinamide | 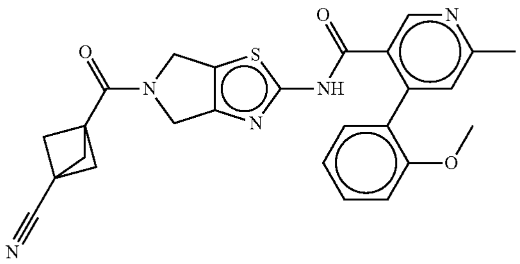 |
| 350 | (Racemic) 4-(2-methoxyphenyl)-6-methyl-N-(5-(4-oxoazetidine-2-carbonyl)-5,6-dihydro-4H-pyrrolo[3,4-d]thiazol-2-yl)nicotinamide | 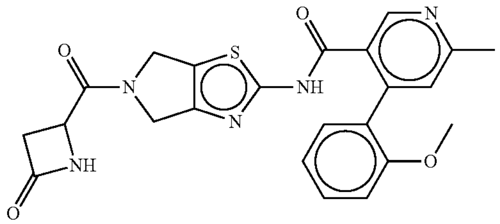 |
| 351 | 2-(4-(2-methoxyphenyl)-6-methylnicotinamido)-N,N-dimethyl-4,6-dihydro-5H-pyrrolo[3,4-d]thiazole-5-carboxamide | 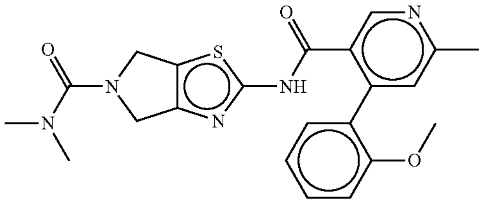 |
| 352 | N-(5-cyclopropyl-4-oxo-5,6-dihydro-4H-pyrrolo[3,4-d]thiazol-2-yl)-4-(2-methoxyphenyl)-6-methylnicotinamide | 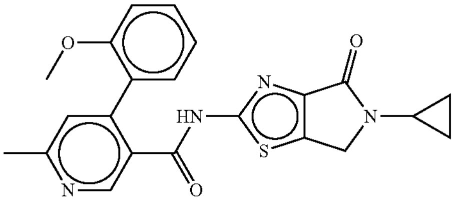 |
| 353 | (R and S) 4-(2-methoxyphenyl)-6-methyl-N-(6-phenoxy-4,5,6,7-tetrahydrobenzo[d]thiazol-2-yl)nicotinamide | 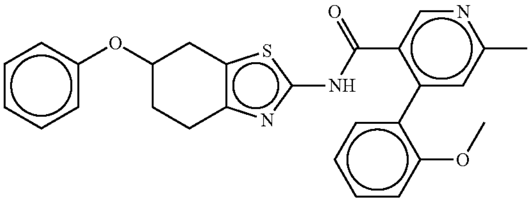 |
| 354 | 4-(2-methoxyphenyl)-6-methyl-N-(5-(3-methyloxetane-3-carbonyl)-5,6-dihydro-4H-pyrrolo[3,4-d]thiazol-2-yl)nicotinamide | 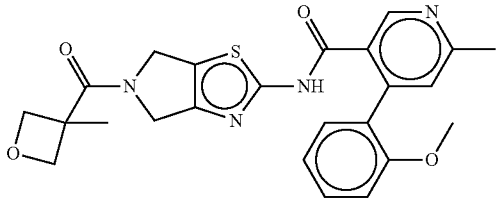 |
| 355 | N-(5-(1-cyanocyclopropane-1-carbonyl)-5,6-dihydro-4H-pyrrolo[3,4-d]thiazol-2-yl)-4-(2-methoxyphenyl)-6-methylnicotinamide | 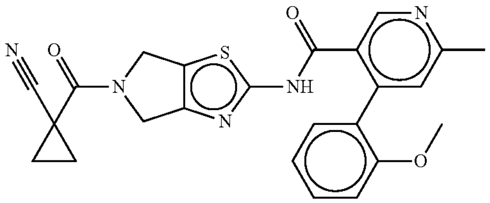 |

TABLE 1-continued

| Compound No. | Name | Structure |
|---|---|---|
| 356 | N-(5-cyclopropyl-6-oxo-5,6-dihydro-4H-pyrrolo[3,4-d]thiazol-2-yl)-4-(2-methoxyphenyl)-6-methylnicotinamide | 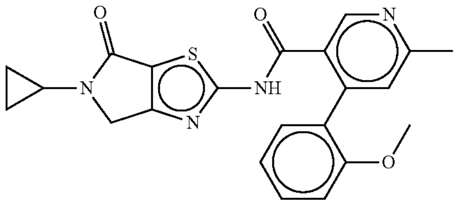 |
| 357 | N-(5-(4-chlorophenyl)-4,5,6,7-tetrahydrothiazolo[5,4-c]pyridin-2-yl)-4-(2-methoxyphenyl)-6-methylnicotinamide | 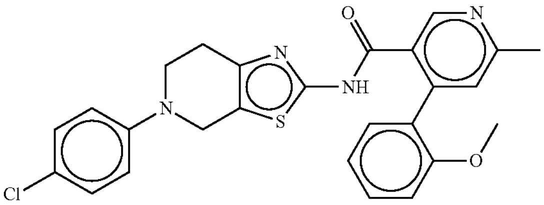 |
| 358 | N-(5-(cyclohexylmethyl)-4,5,6,7-tetrahydrothiazolo[5,4-c]pyridin-2-yl)-4-(2-methoxyphenyl)-6-methylnicotinamide | 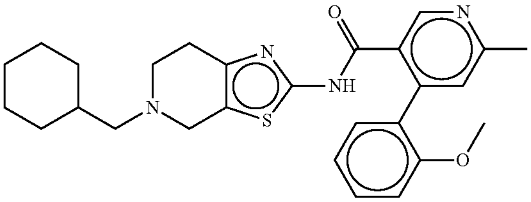 |
| 359 | 4-(2-methoxyphenyl)-6-methyl-N-(5-(2-(2-oxooxazolidin-3-yl)acetyl)-5,6-dihydro-4H-pyrrolo[3,4-d]thiazol-2-yl)nicotinamide | 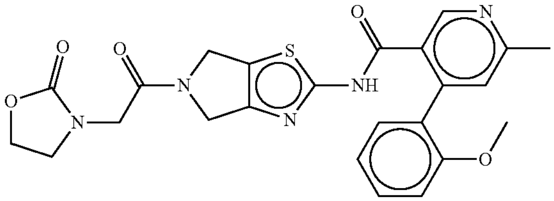 |
| 360 | N-(5-(4-cyanotetrahydro-2H-pyran-4-carbonyl)-5,6-dihydro-4H-pyrrolo[3,4-d]thiazol-2-yl)-4-(2-methoxyphenyl)-6-methylnicotinamide | 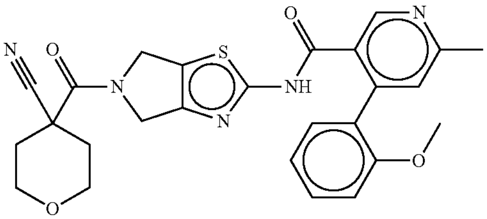 |
| 361 | 4-(2-methoxyphenyl)-6-methyl-N-(4,5,6,7-tetrahydrobenzo[d]thiazol-2-yl)nicotinamide | 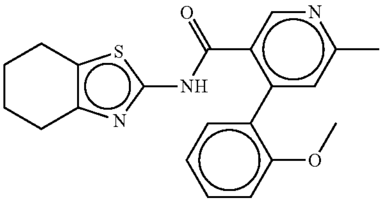 |
| 362 | N-(5-(cyclohexanecarbonyl)-4,5,6,7-tetrahydrothiazolo[5,4-c]pyridin-2-yl)-4-(2-methoxyphenyl)-6-methylnicotinamide | 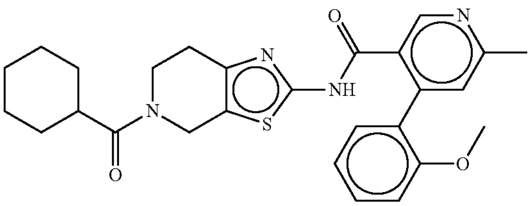 |

TABLE 1-continued

| Compound No. | Name | Structure |
|---|---|---|
| 363 | 4-(2-methoxyphenyl)-6-methyl-N-(5-(2-(2-oxopyrrolidin-1-yl)acetyl)-5,6-dihydro-4H-pyrrolo[3,4-d]thiazol-2-yl)nicotinamide | 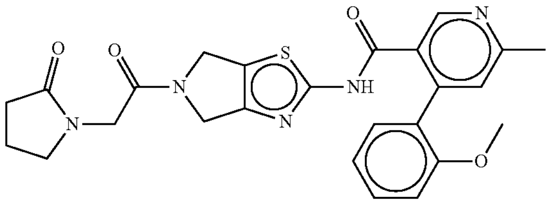 |
| 364 | (Racemic) 4-(2-methoxyphenyl)-6-methyl-N-(5-(1-methyl-2-oxopyrrolidine-3-carbonyl)-5,6-dihydro-4H-pyrrolo[3,4-d]thiazol-2-yl)nicotinamide | 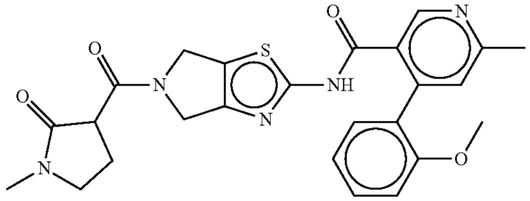 |
| 365 | (Racemic) N-(5-(1-acetylazetidine-2-carbonyl)-5,6-dihydro-4H-pyrrolo[3,4-d]thiazol-2-yl)-4-(2-methoxyphenyl)-6-methylnicotinamide | 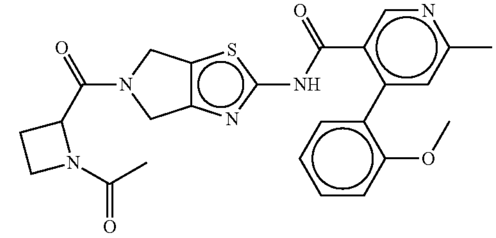 |
| 366 | (S or R) 4-(2-methoxyphenyl)-6-methyl-N-(6-(phenylamino)-4,5,6,7-tetrahydrobenzo[d]thiazol-2-yl)nicotinamide | 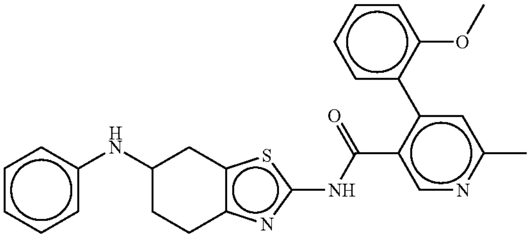 |
| 367 | 4-(2-methoxyphenyl)-6-methyl-N-(5-(pyridin-2-yl)-5,6-dihydro-4H-pyrrolo[3,4-d]thiazol-2-yl)nicotinamide | 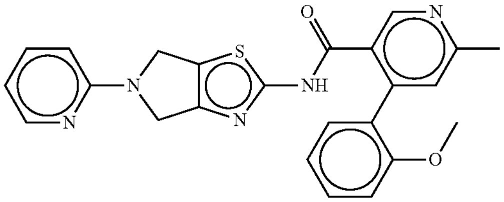 |
| 368 | N-(5,6-dihydro-4H-pyrrolo[3,4-d]thiazol-2-yl)-4-(2-methoxyphenyl)-6-methylnicotinamide | 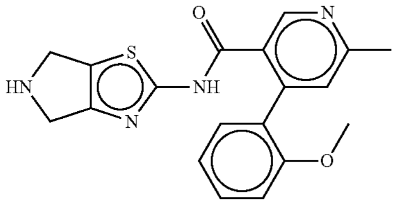 |
| 369 | N-(5-benzoyl-4,5,6,7-tetrahydrothiazolo[5,4-c]pyridin-2-yl)-4-(2-methoxyphenyl)-6-methylnicotinamide | 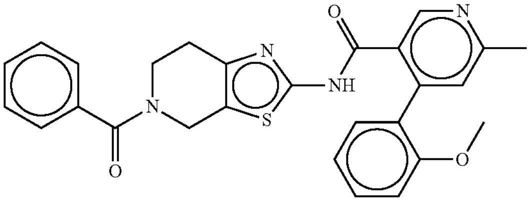 |

TABLE 1-continued

| Compound No. | Name | Structure |
|---|---|---|
| 370 | (Racemic) N-(5-(1,1-dioxidotetrahydrothiophene-2-carbonyl)-5,6-dihydro-4H-pyrrolo[3,4-d]thiazol-2-yl)-4-(2-methoxyphenyl)-6-methylnicotinamide | 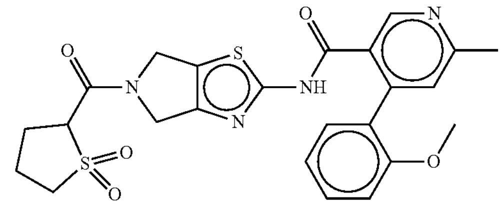 |
| 371 | 2-(4-(2-methoxyphenyl)-6-methylnicotinamido)-N-methyl-4,6-dihydro-5H-pyrrolo[3,4-d]thiazole-5-carboxamide | 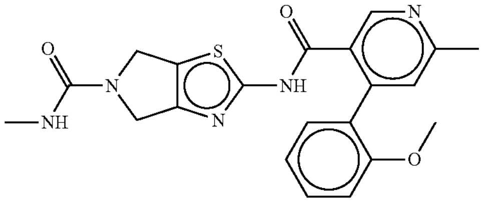 |
| 372 | N-(5-benzyl-4,5,6,7-tetrahydrothiazolo[5,4-c]pyridin-2-yl)-4-(2-methoxyphenyl)-6-methylnicotinamide | 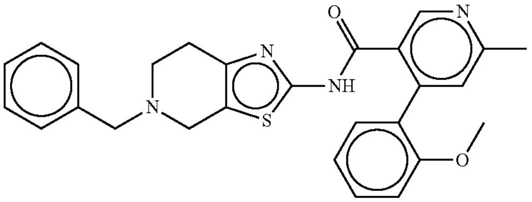 |
| 373 | 4-(2-methoxyphenyl)-6-methyl-N-(6-oxo-4,5,6,7-tetrahydrobenzo[d]thiazol-2-yl)nicotinamide | 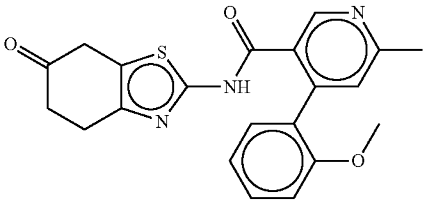 |
| 374 | N-(5-cyclohexyl-4,5,6,7-tetrahydrothiazolo[5,4-c]pyridin-2-yl)-4-(2-methoxyphenyl)-6-methylnicotinamide | 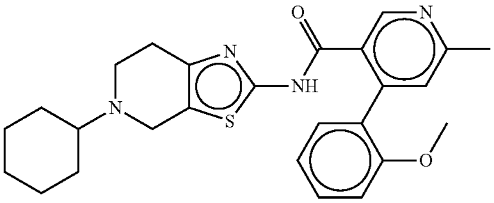 |
| 375 | 4-(2-methoxyphenyl)-6-methyl-N-(4-oxo-4,5,6,7-tetrahydrothiazolo[5,4-c]pyridin-2-yl)nicotinamide | 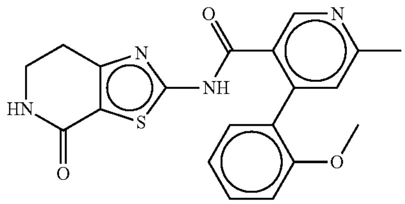 |
| 376 | N-(6,7-dihydro-4H-pyrano[4,3-d]thiazol-2-yl)-4-(2-methoxyphenyl)-6-methylnicotinamide | 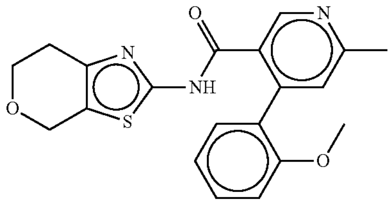 |

TABLE 1-continued

| Compound No. | Name | Structure |
|---|---|---|
| 377 | 4-(2-methoxyphenyl)-6-methyl-N-(4,5,6,7-tetrahydrothiazolo[5,4-c]pyridin-2-yl)nicotinamide | 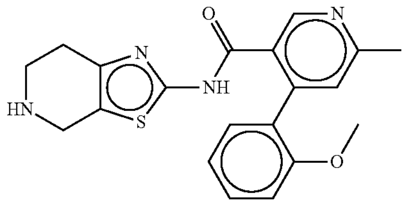 |
| 378 | tert-butyl 2-(4-(2-methoxyphenyl)-6-methylnicotinamido)-6,7-dihydrothiazolo[4,5-c]pyridine-5(4H)-carboxylate | 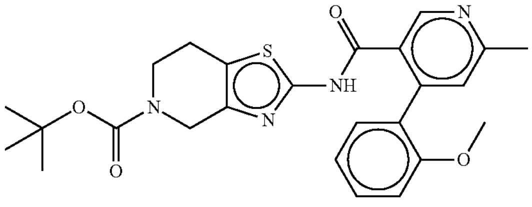 |
| 379 (739) | 2'-chloro-5'-methoxy-6-methyl-N-(5-(5-(trifluoromethyl)pyrazine-2-carbonyl)-5,6-dihydro-4H-pyrrolo[3,4-d]thiazol-2-yl)-[4,4'-bipyridine]-3-carboxamide | 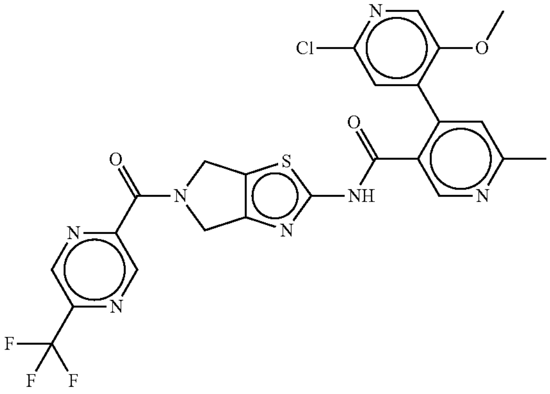 |
| 380 (834) | 2'-chloro-N-(5-(4-chloro-3-(difluoromethyl)benzoyl)-5,6-dihydro-4H-pyrrolo[3,4-d]thiazol-2-yl)-5'-methoxy-6-methyl-[4,4'-bipyridine]-3-carboxamide | 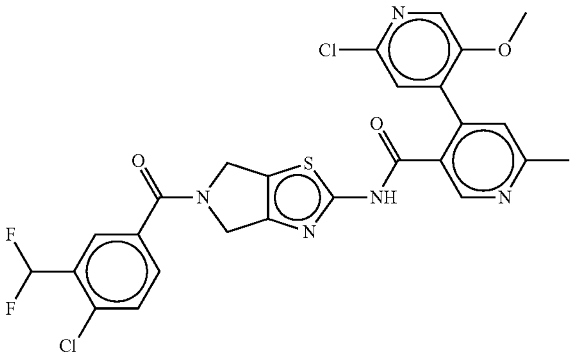 |
| 381 (831) | 2'-chloro-N-(5-(3-chloro-4-(difluoromethyl)benzoyl)-5,6-dihydro-4H-pyrrolo[3,4-d]thiazol-2-yl)-5'-methoxy-6-methyl-[4,4'-bipyridine]-3-carboxamide | 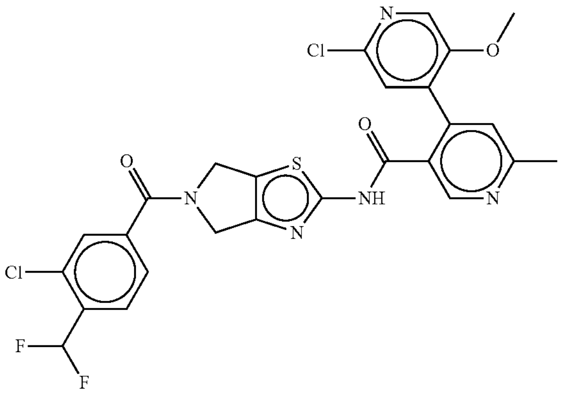 |

TABLE 1-continued

| Compound No. | Name | Structure |
| --- | --- | --- |
| 382 (828) | 2'-chloro-N-(5-(4-(difluoromethyl)-2-fluorobenzoyl)-5,6-dihydro-4H-pyrrolo[3,4-d]thiazol-2-yl)-5'-methoxy-6-methyl-[4,4'-bipyridine]-3-carboxamide | 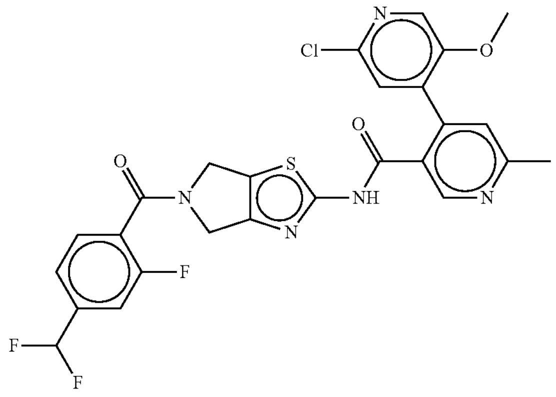 |
| 383 (826) | 2'-chloro-N-(5-(3-(difluoromethyl)-4-fluorobenzoyl)-5,6-dihydro-4H-pyrrolo[3,4-d]thiazol-2-yl)-5'-methoxy-6-methyl-[4,4'-bipyridine]-3-carboxamide | 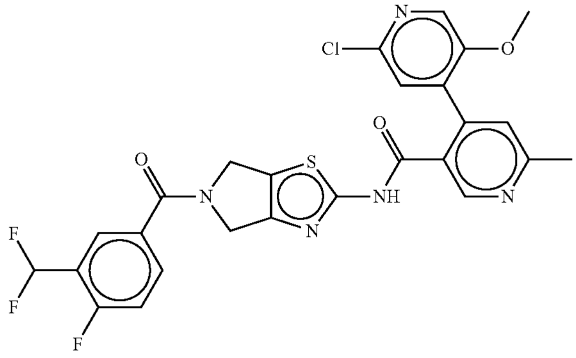 |
| 384 (820) | 2'-chloro-N-(5-(6-(difluoromethyl)-2-methoxynicotinoyl)-5,6-dihydro-4H-pyrrolo[3,4-d]thiazol-2-yl)-5'-methoxy-6-methyl-[4,4'-bipyridine]-3-carboxamide | 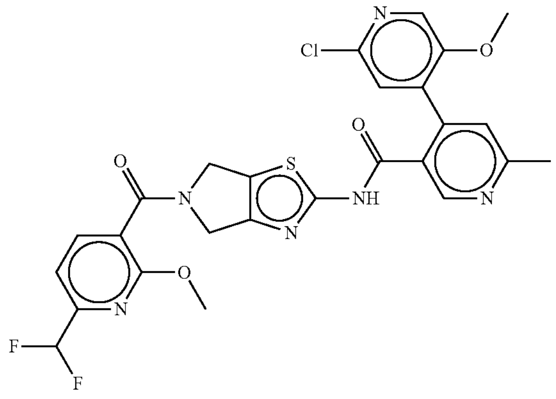 |
| 385 (785) | 2'-chloro-N-(5-(3-chloro-2-methoxybenzoyl)-5,6-dihydro-4H-pyrrolo[3,4-d]thiazol-2-yl)-5'-methoxy-6-methyl-[4,4'-bipyridine]-3-carboxamide | 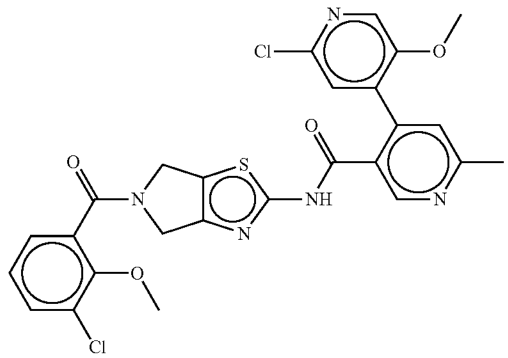 |

TABLE 1-continued

| Compound No. | Name | Structure |
|---|---|---|
| 386 (768) | 2'-chloro-N-(5-(4-(difluoromethoxy)benzoyl)-5,6-dihydro-4H-pyrrolo[3,4-d]thiazol-2-yl)-5'-methoxy-6-methyl-[4,4'-bipyridine]-3-carboxamide | 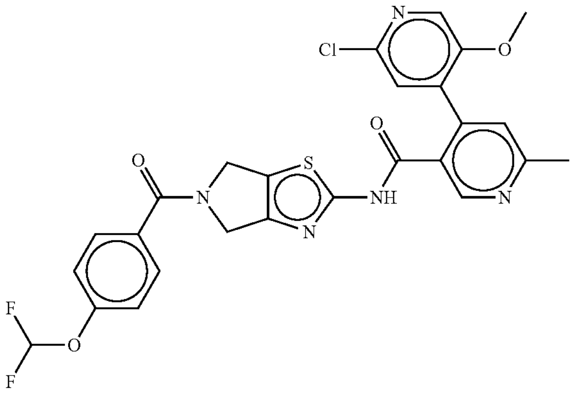 |
| 387 (765) | 2'-chloro-N-(5-(3-(difluoromethyl)benzoyl)-5,6-dihydro-4H-pyrrolo[3,4-d]thiazol-2-y])-5'-methoxy-6-methyl-[4,4'-bipyridine]-3-carboxamide | 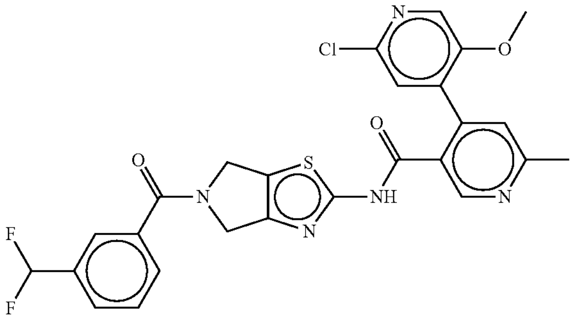 |
| 388 (764) | 2'-chloro-N-(5-(4-chloro-3-methoxybenzoyl)-5,6-dihydro-4H-pyrrolo[3,4-d]thiazol-2-yl)-5'-methoxy-6-methyl-[4,4'-bipyridine]-3-carboxamide | 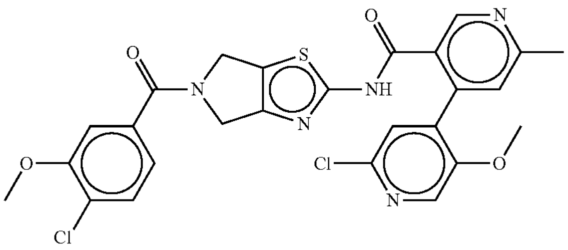 |
| 389 (749) | 2'-chloro-N-(5-(6-chloro-5-(trifluoromethyl)picolinoyl)-5,6-dihydro-4H-pyrrolo[3,4-d]thiazol-2-yl)-5'-methoxy-6-methyl-[4,4'-bipyridine]-3-carboxamide | 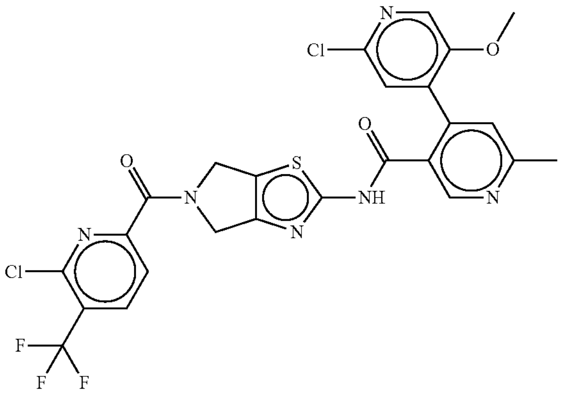 |

TABLE 1-continued

| Compound No. | Name | Structure |
| --- | --- | --- |
| 390 (730) | 2'-chloro-5'-methoxy-6-methyl-N-(5-((1r,4r)-4-(trifluoromethoxy)cyclohexane-1-carbonyl)-5,6-dihydro-4H-pyrrolo[3,4-d]thiazol-2-yl)-[4,4'-bipyridine]-3-carboxamide | 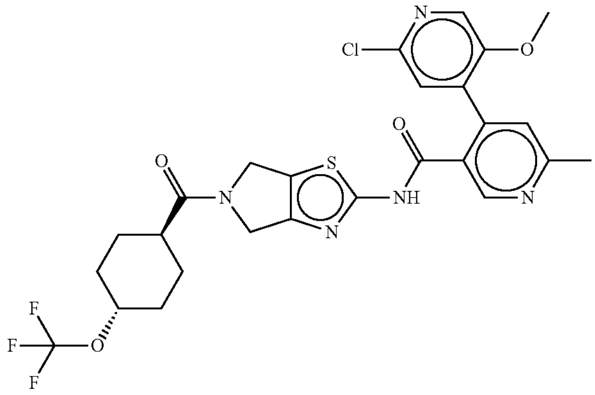 |
| 391 (672) | 2'-chloro-N-(5-(2,6-dimethoxynicotinoyl)-5,6-dihydro-4H-pyrrolo[3,4-d]thiazol-2-yl)-5'-methoxy-6-methyl-[4,4'-bipyridine]-3-carboxamide | 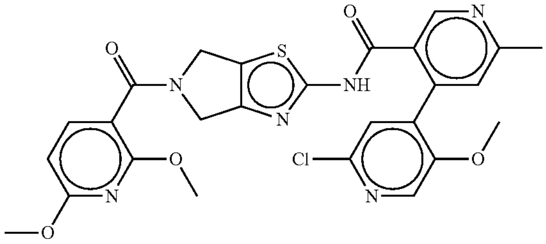 |
| 392 (762) | 2'-chloro-N-(5-(6-chloro-4-methylpicolinoyl)-5,6-dihydro-4H-pyrrolo[3,4-d]thiazol-2-yl)-5'-methoxy-6-methyl-[4,4'-bipyridine]-3-carboxamide | 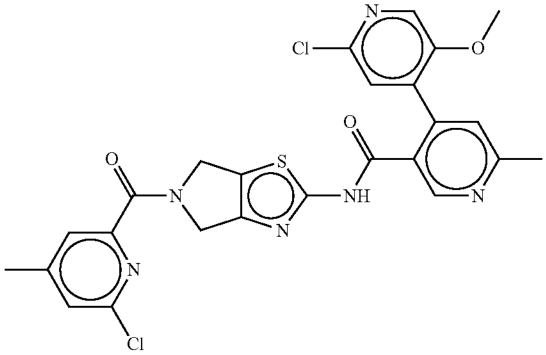 |
| 393 (701) | 2'-chloro-N-(5-(4-chloro-1-ethyl-1H-pyrazole-5-carbonyl)-5,6-dihydro-4H-pyrrolo[3,4-d]thiazol-2-yl)-5'-methoxy-6-methyl-[4,4'-bipyridine]-3-carboxamide | 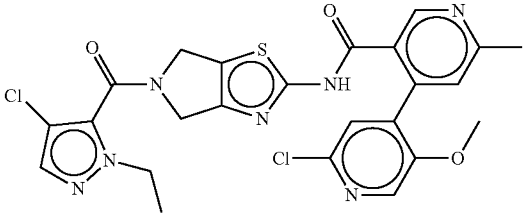 |

TABLE 1-continued

| Compound No. | Name | Structure |
| --- | --- | --- |
| 394 (657) | 2'-chloro-5'-methoxy-6-methyl-N-(5-(5-(trifluoromethoxy)picolinoyl)-5,6-dihydro-4H-pyrrolo[3,4-d]thiazol-2-yl)-[4,4'-bipyridine]-3-carboxamide | 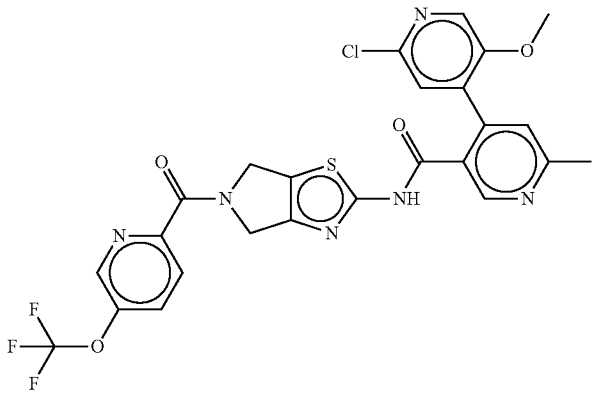 |
| 395 (737) | 2'-chloro-N-(5-(6-chloro-5-methoxypicolinoyl)-5,6-dihydro-4H-pyrrolo[3,4-d]thiazol-2-yl)-5'-methoxy-6-methyl-[4,4'-bipyridine]-3-carboxamide | 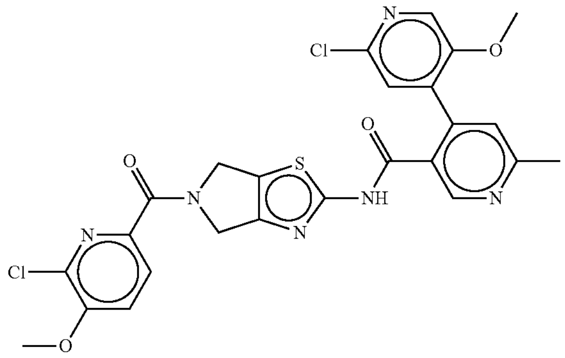 |
| 396 (767) | 2'-chloro-N-(5-(2-chloro-3-methoxybenzoyl)-5,6-dihydro-4H-pyrrolo[3,4-d]thiazol-2-yl)-5'-methoxy-6-methyl-[4,4'-bipyridine]-3-carboxamide | 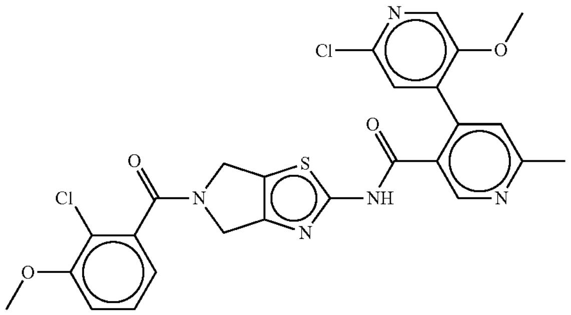 |
| 397 (735) | (Racemic) 2'-chloro-5'-methoxy-6-methyl-N-(5-(3-(trifluoromethoxy)cyclopentane-1-carbonyl)-5,6-dihydro-4H-pyrrolo[3,4-d]thiazol-2-yl)-[4,4'-bipyridine]-3-carboxamide | 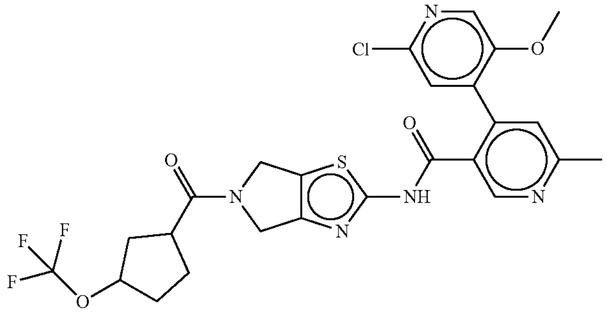 |

TABLE 1-continued

| Compound No. | Name | Structure |
| --- | --- | --- |
| 398 (810) | 2'-chloro-N-(5-(5-(difluoromethyl)-2-fluorobenzoyl)-5,6-dihydro-4H-pyrrolo[3,4-d]thiazol-2-yl)-5'-methoxy-6-methyl-[4,4'-bipyridine]-3-carboxamide | 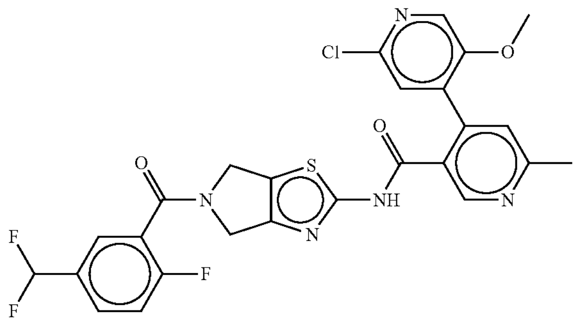 |
| 399 (663) | 2'-chloro-N-(5-(4-chloro-3-methoxypicolinoyl)-5,6-dihydro-4H-pyrrolo[3,4-d]thiazol-2-yl)-5'-methoxy-6-methyl-[4,4'-bipyridine]-3-carboxamide | 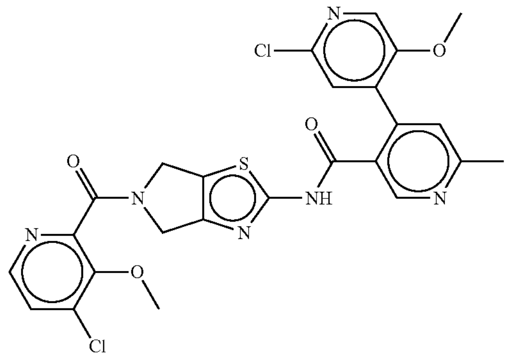 |
| 400 (805) | 2'-chloro-N-(5-(5-(difluoromethyl)pyrimidine-2-carbonyl)-5,6-dihydro-4H-pyrrolo[3,4-d]thiazol-2-yl)-5'-methoxy-6-methyl-[4,4'-bipyridine]-3-carboxamide | 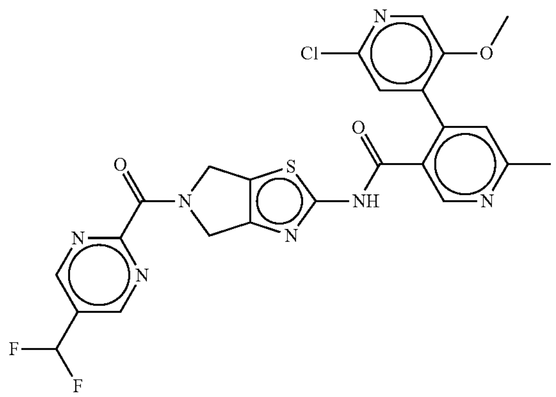 |
| 401 (813) | 2'-chloro-N-(5-(2-chloro-3-(difluoromethyl)benzoyl)-5,6-dihydro-4H-pyrrolo[3,4-d]thiazol-2-yl)-5'-methoxy-6-methyl-[4,4'-bipyridine]-3-carboxamide | 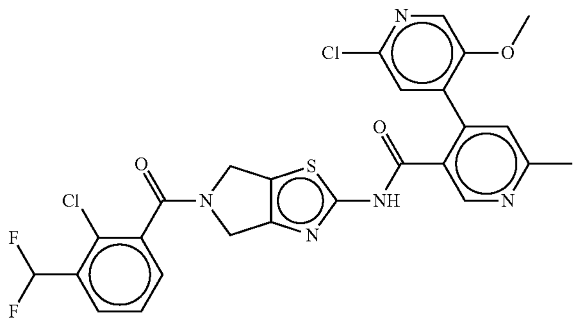 |

TABLE 1-continued

| Compound No. | Name | Structure |
| --- | --- | --- |
| 402 (653) | 2'-chloro-5'-methoxy-N-(5-(4-methoxypyrazolo[1,5-a]pyridine-7-carbonyl)-5,6-dihydro-4H-pyrrolo[3,4-d]thiazol-2-yl)-6-methyl-[4,4'-bipyridine]-3-carboxamide | 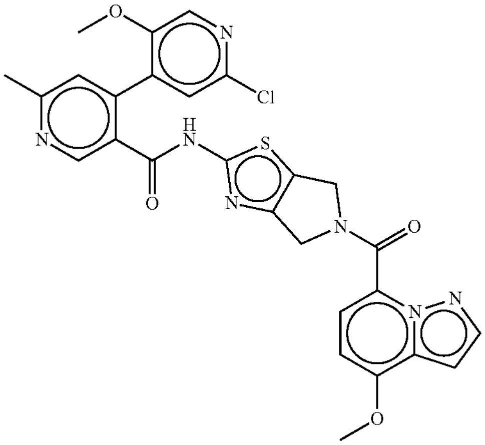 |
| 403 (812) | 2'-chloro-N-(5-(4-(difluoromethyl)-3-fluorobenzoyl)-5,6-dihydro-4H-pyrrolo[3,4-d]thiazol-2-yl)-5'-methoxy-6-methyl-[4,4'-bipyridine]-3-carboxamide | 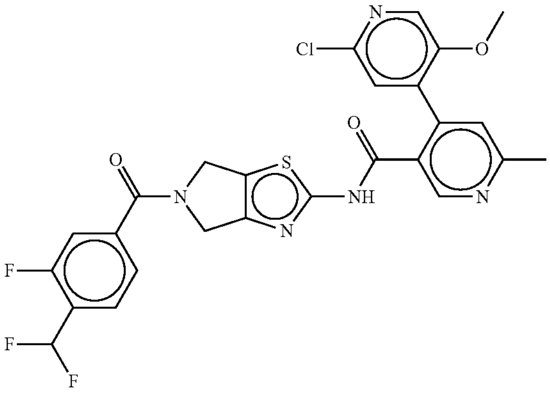 |
| 404 (763) | 2'-chloro-N-(5-(3,6-dimethylpyrazine-2-carbonyl)-5,6-dihydro-4H-pyrrolo[3,4-d]thiazol-2-yl)-5'-methoxy-6-methyl-[4,4'-bipyridine]-3-carboxamide | 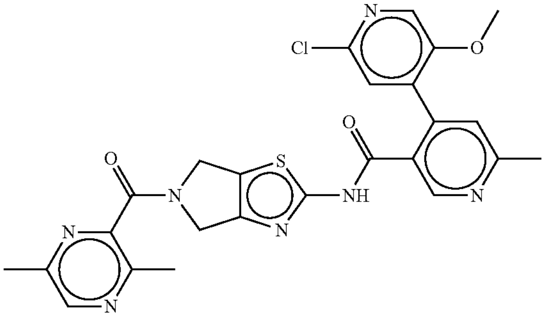 |
| 405 (819) | N-(5-(5-bromo-3-methoxypicolinoyl)-5,6-dihydro-4H-pyrrolo[3,4-d]thiazol-2-yl)-2'-chloro-5'-methoxy-6-methyl-[4,4'-bipyridine]-3-carboxamide | 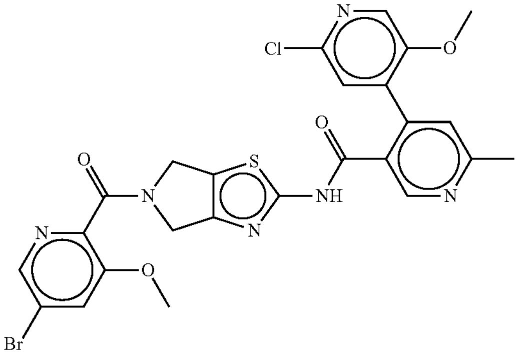 |

TABLE 1-continued

| Compound No. | Name | Structure |
|---|---|---|
| 406 (759) | (Cis and trans) 2'-chloro-N-(5-(4-(difluoromethyl)cyclohexane-1-carbonyl)-5,6-dihydro-4H-pyrrolo[3,4-d]thiazol-2-yl)-5'-methoxy-6-methyl-[4,4'-bipyridine]-3-carboxamide | 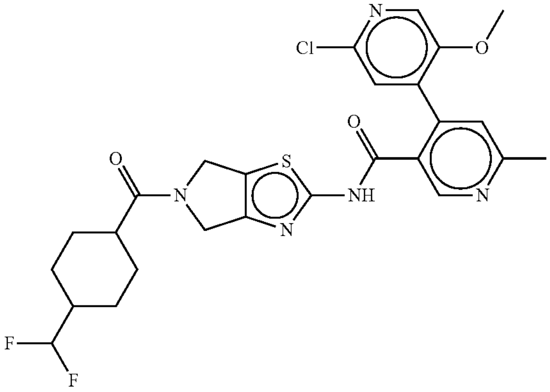 |
| 407 (773) | 2'-chloro-N-(5-(4-chloro-2-methoxybenzoyl)-5,6-dihydro-4H-pyrrolo[3,4-d]thiazol-2-yl)-5'-methoxy-6-methyl-[4,4'-bipyridine]-3-carboxamide | 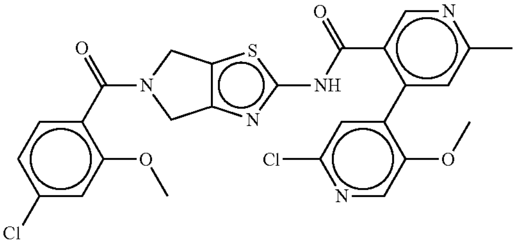 |
| 408 (652) | 2'-chloro-N-(5-(4-chloro-1,3-dimethyl-1H-pyrazole-5-carbonyl)-5,6-dihydro-4H-pyrrolo[3,4-d]thiazol-2-yl)-5'-methoxy-6-methyl-[4,4'-bipyridine]-3-carboxamide | 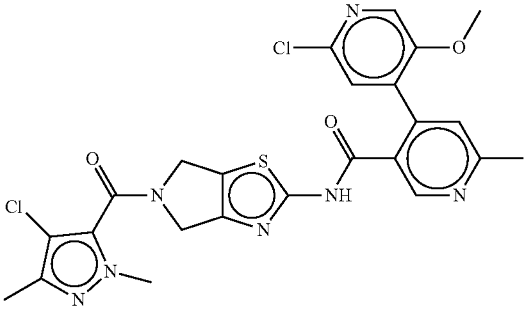 |
| 409 (654) | 2'-chloro-N-(5-(5-chloro-3-methoxypicolinoyl)-5,6-dihydro-4H-pyrrolo[3,4-d]thiazol-2-yl)-5'-methoxy-6-methyl-[4,4'-bipyridine]-3-carboxamide | 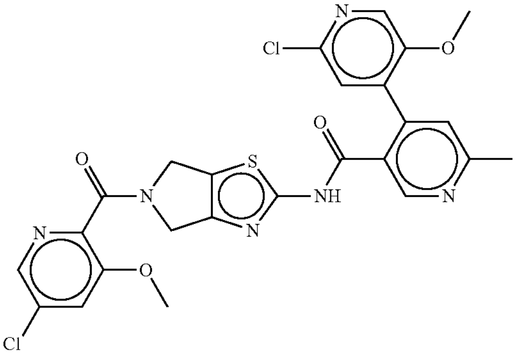 |
| 410 (772) | 2'-chloro-N-(5-(2-chloro-4-methoxybenzoyl)-5,6-dihydro-4H-pyrrolo[3,4-d]thiazol-2-yl)-5'-methoxy-6-methyl-[4,4'-bipyridine]-3-carboxamide | 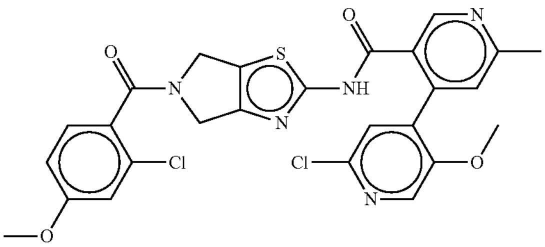 |

TABLE 1-continued

| Compound No. | Name | Structure |
|---|---|---|
| 411 (754) | 2'-chloro-N-(5-(6-chloro-5-fluoropicolinoyl)-5,6-dihydro-4H-pyrrolo[3,4-d]thiazol-2-yl)-5'-methoxy-6-methyl-[4,4'-bipyridine]-3-carboxamide | 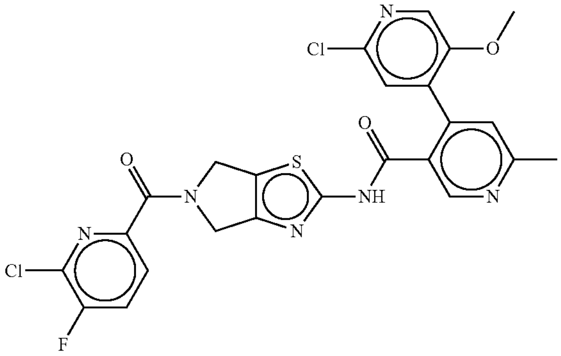 |
| 412 (660) | 2'-chloro-N-(5-(5-(difluoromethyl)-3-methoxypicolinoyl)-5,6-dihydro-4H-pyrrolo[3,4-d]thiazol-2-yl)-5'-methoxy-6-methyl-[4,4'-bipyridine]-3-carboxamide | 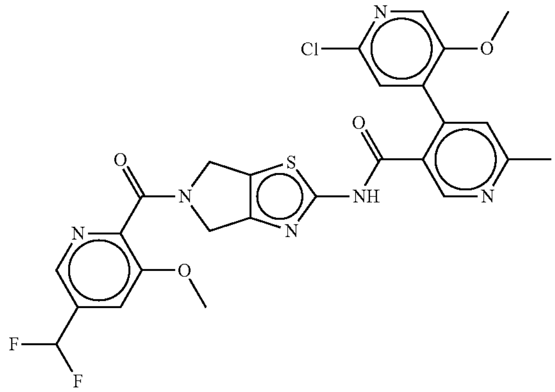 |
| 413 (770) | 2'-chloro-N-(5-(4-(difluoromethyl)benzoyl)-5,6-dihydro-4H-pyrrolo[3,4-d]thiazol-2-yl)-5'-methoxy-6-methyl-[4,4'-bipyridine]-3-carboxamide | 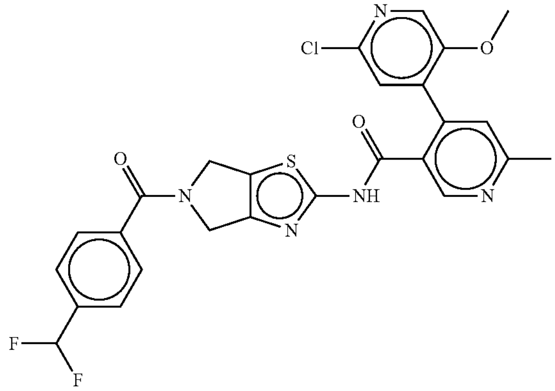 |
| 414 (775) | 2'-chloro-N-(5-(imidazo[1,2-a]pyridine-8-carbonyl)-5,6-dihydro-4H-pyrrolo[3,4-d]thiazol-2-yl)-5'-methoxy-6-methyl-[4,4'-bipyridine]-3-carboxamide | 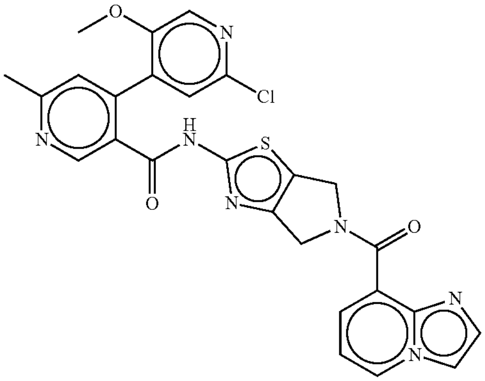 |

TABLE 1-continued

| Compound No. | Name | Structure |
|---|---|---|
| 415 (822) | 2'-chloro-N-(5-(6-(difluoromethyl)-3-methoxypicolinoyl)-5,6-dihydro-4H-pyrrolo[3,4-d]thiazol-2-yl)-5'-methoxy-6-methyl-[4,4'-bipyridine]-3-carboxamide | 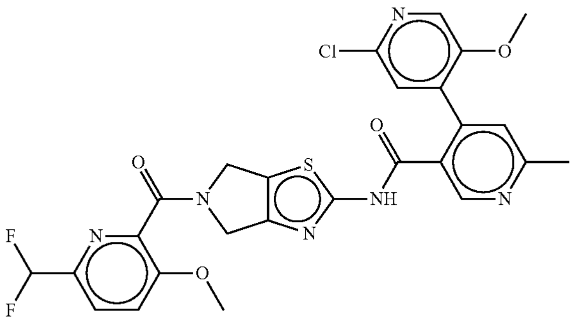 |
| 416 (750) | 2'-chloro-N-(5-(5,6-dimethylpyrazine-2-carbonyl)-5,6-dihydro-4H-pyrrolo[3,4-d]thiazol-2-yl)-5'-methoxy-6-methyl-[4,4'-bipyridine]-3-carboxamide | 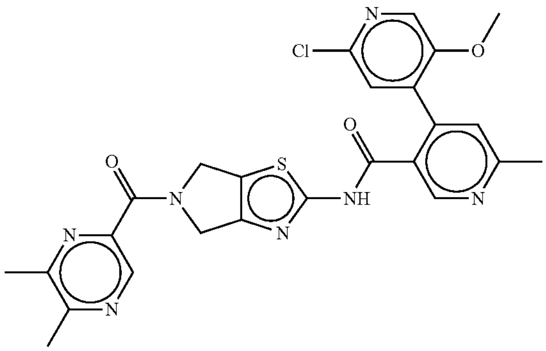 |
| 417 (748) | 2'-chloro-5'-methoxy-N-(5-(5-methoxypyrazine-2-carbonyl)-5,6-dihydro-4H-pyrrolo[3,4-d]thiazol-2-yl)-6-methyl-[4,4'-bipyridine]-3-carboxamide | 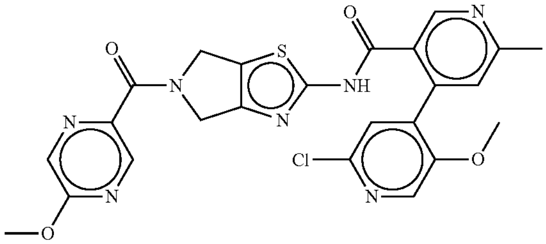 |
| 418 (727) | 2'-chloro-5'-methoxy-6-methyl-N-(5-(6-methylspiro[3.3]heptane-2-carbonyl)-5,6-dihydro-4H-pyrrolo[3,4-d]thiazol-2-yl)-[4,4'-bipyridine]-3-carboxamide | 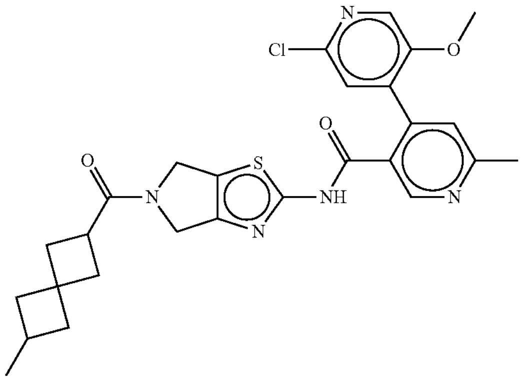 |

TABLE 1-continued

| Compound No. | Name | Structure |
|---|---|---|
| 419 (811) | 2'-chloro-N-(5-(2-chloro-4-(difluoromethyl)benzoyl)-5,6-dihydro-4H-pyrrolo[3,4-d]thiazol-2-yl)-5'-methoxy-6-methyl-[4,4'-bipyridine]-3-carboxamide | 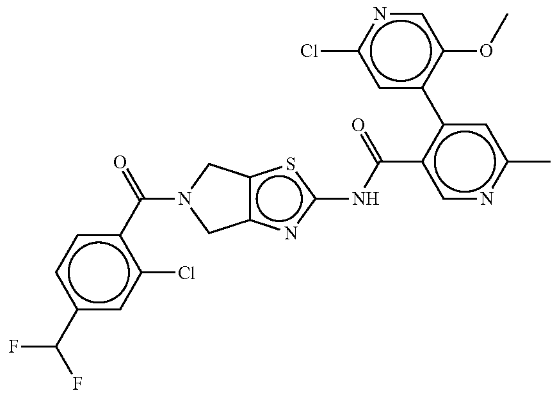 |
| 420 (662) | 2'-chloro-N-(5-(3-chloro-5-(difluoromethyl)picolinoyl)-5,6-dihydro-4H-pyrrolo[3,4-d]thiazol-2-yl)-5'-methoxy-6-methyl-[4,4'-bipyridine]-3-carboxamide | 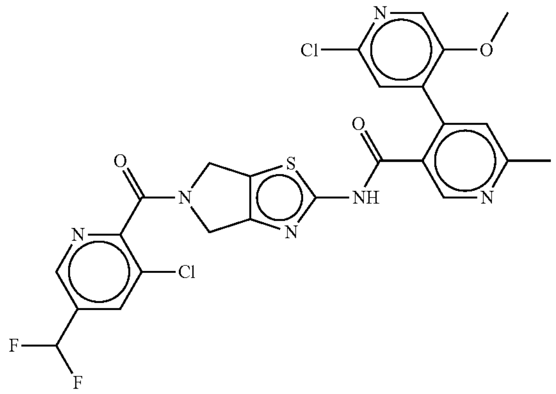 |
| 421 (719) | 2'-chloro-N-(5-(5-chloro-6-methoxypicolinoyl)-5,6-dihydro-4H-pyrrolo[3,4-d]thiazol-2-yl)-5'-methoxy-6-methyl-[4,4'-bipyridine]-3-carboxamide | 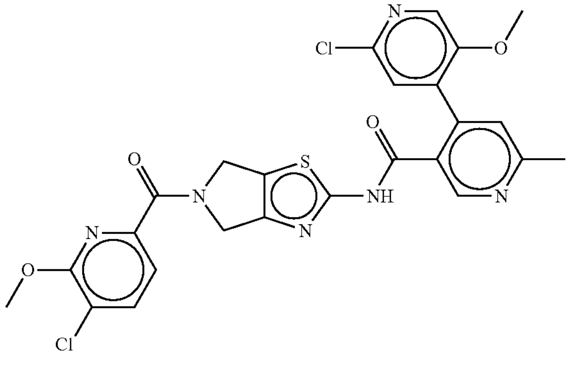 |
| 422 (783) | N-(5-(3-chloro-2-methoxybenzoyl)-5,6-dihydro-4H-pyrrolo[3,4-d]thiazol-2-yl)-4-(5-cyano-2-methoxyphenyl)-6-methylnicotinamide | 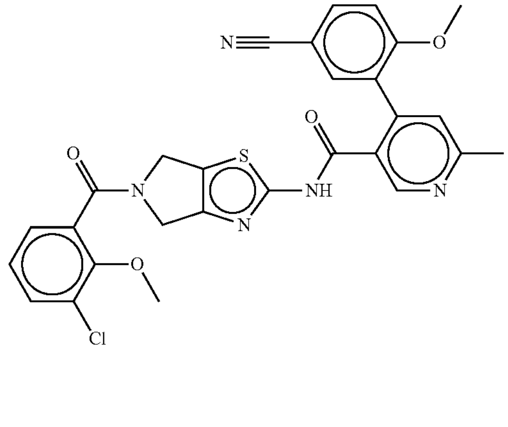 |

TABLE 1-continued

| Compound No. | Name | Structure |
|---|---|---|
| 423 (818) | 2'-chloro-5'-methoxy-N-(5-(7-methoxypyrazolo[1,5-alpyridine-4-carbonyl)-5,6-dihydro-4H-pyrrolo[3,4-d]thiazol-2-yl)-6-methyl-[4,4'-bipyridine]-3-carboxamide | 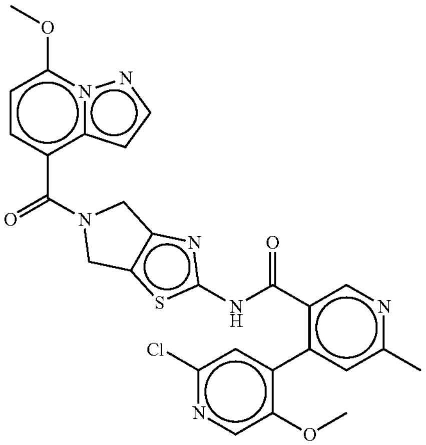 |
| 424 (760) | 2'-chloro-5'-methoxy-6-methyl-N-(5-(pyrazolo[1,5-a]pyridine-4-carbonyl)-5,6-dihydro-4H-pyrrolo[3,4-d]thiazol-2-yl)-[4,4'-bipyridine]-3-carboxamide | 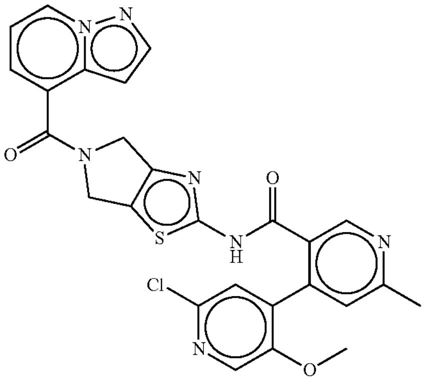 |
| 425 (801) | 2'-chloro-N-(5-(3-chloro-6-(difluoromethyl)picolinoyl)-5,6-dihydro-4H-pyrrolo[3,4-d]thiazol-2-yl)-5'-methoxy-6-methyl-[4,4'-bipyridine]-3-carboxamide | 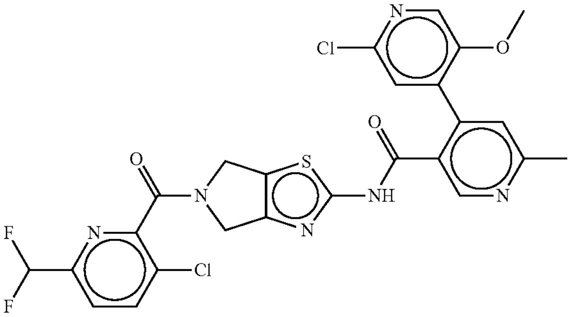 |
| 426 | 2'-chloro-N-(5-((1S or R,3R and S OR 1S and R,3R or S)-3-hydroxy-3-(trifluoromethyl)cyclopentane-1-carbonyl)-5,6-dihydro-4H-pyrrolo[3,4-d]thiazol-2-yl)-5'-methoxy-6-methyl-[4,4'-bipyridine]-3-carboxamide | 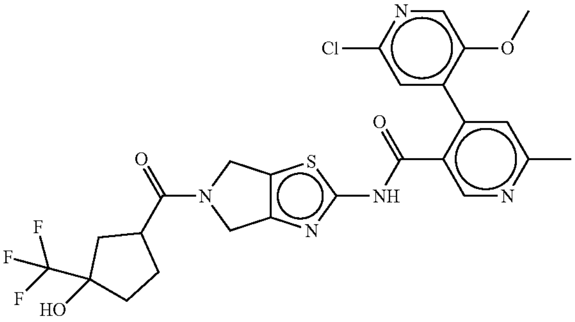 |

TABLE 1-continued

| Compound No. | Name | Structure |
|---|---|---|
| 427 (724) | 2'-chloro-N-(5-(3-chloro-6-methoxypicolinoyl)-5,6-dihydro-4H-pyrrolo[3,4-d]thiazol-2-yl)-5'-methoxy-6-methyl-[4,4'-bipyridine]-3-carboxamide | 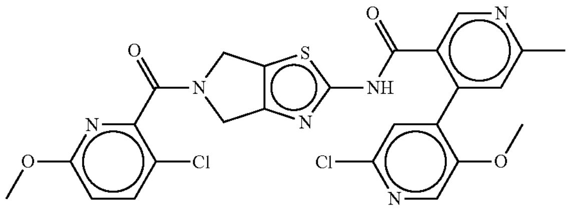 |
| 428 (814) | 2'-chloro-N-(5-(4-chloro-3-methylpicolinoyl)-5,6-dihydro-4H-pyrrolo[3,4-d]thiazol-2-yl)-5'-methoxy-6-methyl-[4,4'-bipyridine]-3-carboxamide | 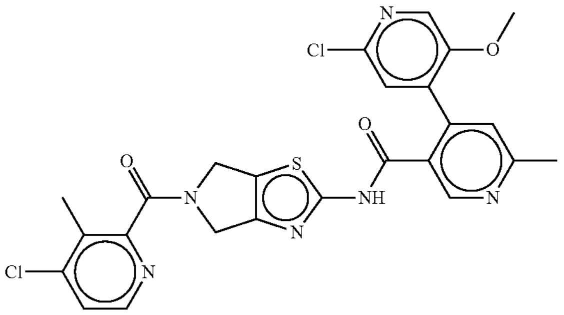 |
| 429 (698) | 2'-chloro-N-(5-(6-(difluoromethyl)-5-fluoropicolinoyl)-5,6-dihydro-4H-pyrrolo[3,4-d]thiazol-2-yl)-5'-methoxy-6-methyl-[4,4'-bipyridine]-3-carboxamide | 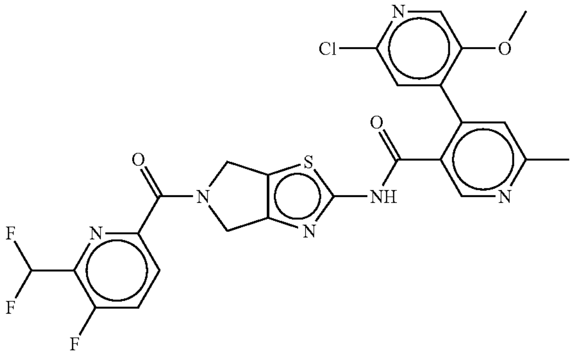 |
| 430 (695) | 2'-chloro-N-(5-(2-chloro-6-(difluoromethyl)nicotinoyl)-5,6-dihydro-4H-pyrrolo[3,4-d]thiazol-2-yl)-5'-methoxy-6-methyl-[4,4'-bipyridine]-3-carboxamide | 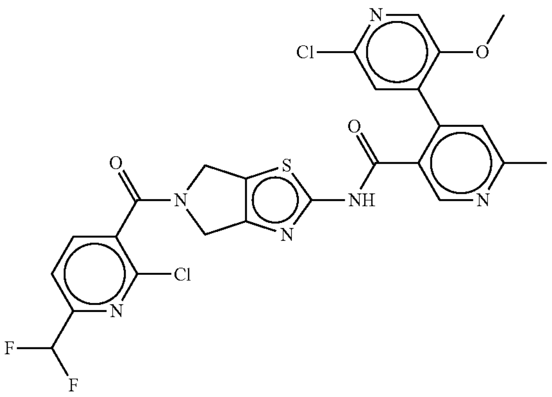 |

TABLE 1-continued

| Compound No. | Name | Structure |
|---|---|---|
| 431 (755) | 2'-chloro-5'-methoxy-6-methyl-N-(5-(4-(trifluoromethyl)pyrimidine-2-carbonyl)-5,6-dihydro-4H-pyrrolo[3,4-d]thiazol-2-yl)-[4,4'-bipyridine]-3-carboxamide | 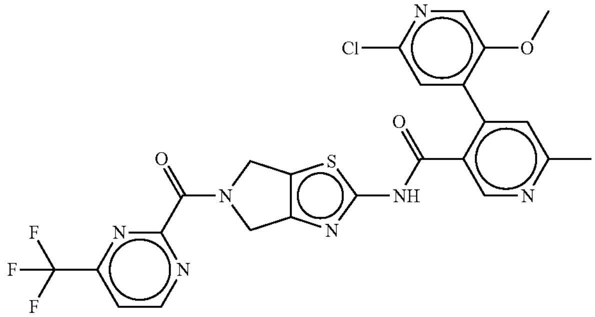 |
| 432 (793) | N-(5-(benzo[d]oxazole-2-carbonyl)-5,6-dihydro-4H-pyrrolo[3,4-d]thiazol-2-yl)-2'-chloro-5'-methoxy-6-methyl-[4,4'-bipyridine]-3-carboxamide | 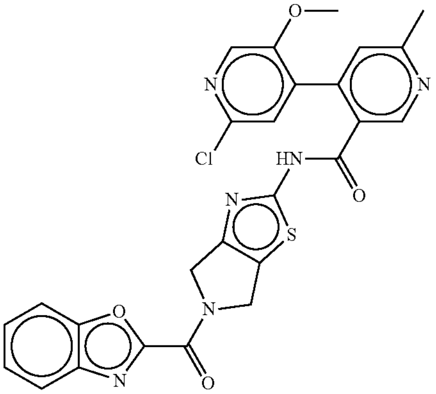 |
| 433 (833) | 4-(5-cyano-2-methoxyphenyl)-N-(5-(5-(difluoromethyl)-2-fluorobenzoyl)-5,6-dihydro-4H-pyrrolo[3,4-d]thiazol-2-yl)-6-methylnicotinamide | 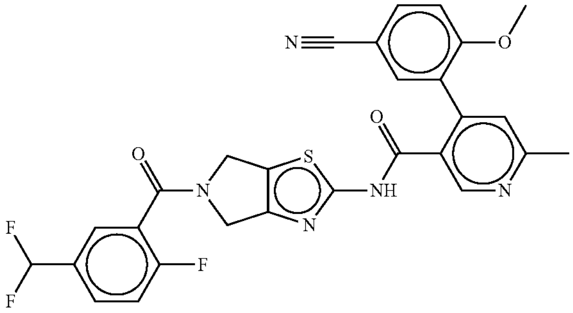 |
| 434 (687) | 2'-chloro-5'-methoxy-N-(5-(6-methoxypicolinoyl)-5,6-dihydro-4H-pyrrolo[3,4-d]thiazol-2-yl)-6-methyl-[4,4'-bipyridine]-3-carboxamide | 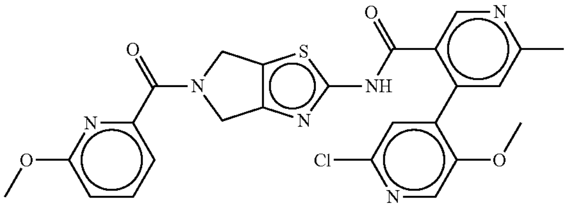 |
| 435 (708) | 2'-chloro-N-(5-(4-fluoro-1-methyl-1H-pyrazole-3-carbonyl)-5,6-dihydro-4H-pyrrolo[3,4-d]thiazol-2-yl)-5'-methoxy-6-methyl-[4,4'-bipyridine]-3-carboxamide | 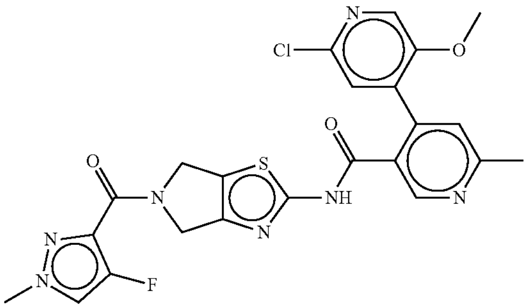 |

TABLE 1-continued

| Compound No. | Name | Structure |
|---|---|---|
| 436 (706) | 2'-chloro-N-(5-(3-chloro-1-methyl-1H-pyrazole-5-carbonyl)-5,6-dihydro-4H-pyrrolo[3,4-d]thiazol-2-yl)-5'-methoxy-6-methyl-[4,4'-bipyridine]-3-carboxamide | 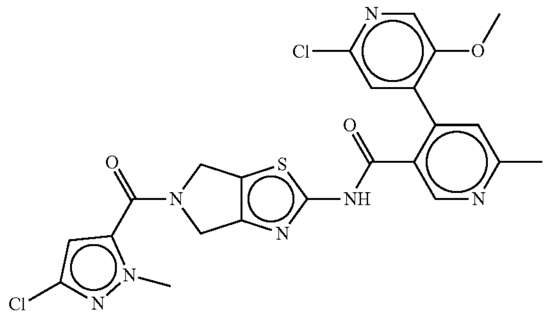 |
| 437 (744) | 2'-chloro-5'-methoxy-N-(5-(3-methoxypyrazine-2-carbonyl)-5,6-dihydro-4H-pyrrolo[3,4-d]thiazol-2-yl)-6-methyl-[4,4'-bipyridine]-3-carboxamide | 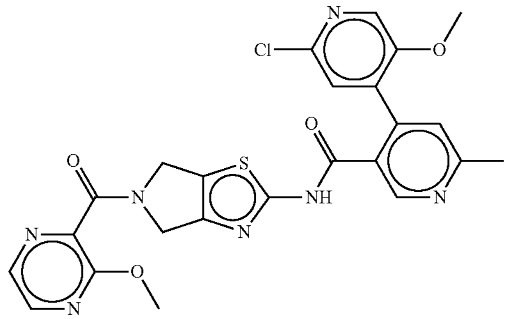 |
| 438 (782) | 4-(5-cyano-2-methoxyphenyl)-N-(5-(4-(difluoromethyl)benzoyl)-5,6-dihydro-4H-pyrrolo[3,4-d]thiazol-2-yl)-6-methylnicotinamide | 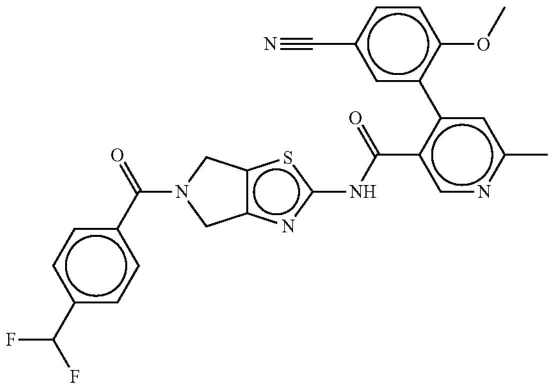 |
| 439 (655) | 2'-chloro-5'-methoxy-6-methyl-N-(5-(pyrazolo[1,5-a]pyridine-7-carbonyl)-5,6-dihydro-4H-pyrrolo[3,4-d]thiazol-2-yl)-[4,4'-bipyridine]-3-carboxamide | 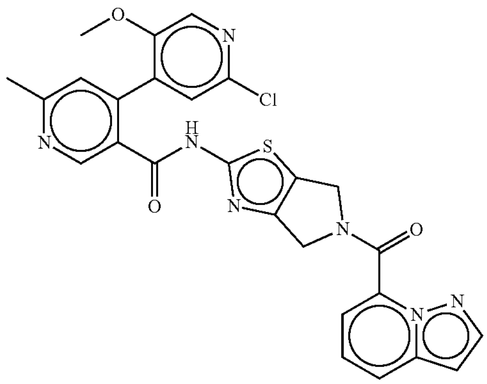 |

TABLE 1-continued

| Compound No. | Name | Structure |
|---|---|---|
| 440 (794) | 2'-chloro-N-(5-(3,5-dimethoxypyrazine-2-carbonyl)-5,6-dihydro-4H-pyrrolo[3,4-d]thiazol-2-yl)-5'-methoxy-6-methyl-[4,4'-bipyridine]-3-carboxamide | 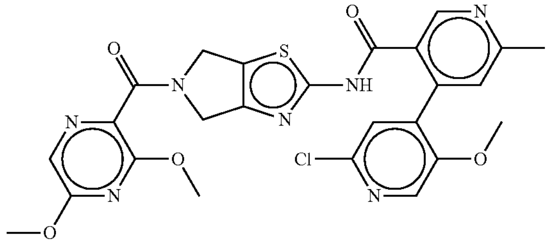 |
| 441 (827) | 4-(5-cyano-2-methoxyphenyl)-N-(5-(3-(difluoromethyl)-4-fluorobenzoyl)-5,6-dihydro-4H-pyrrolo[3,4-d]thiazol-2-yl)-6-methylnicotinamide | 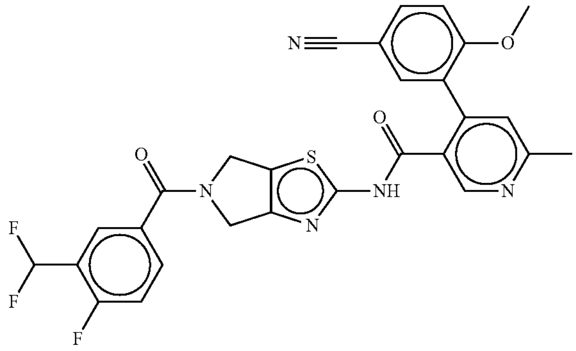 |
| 442 (688) | 2'-chloro-N-(5-(2-chloro-6-methoxynicotinoyl)-5,6-dihydro-4H-pyrrolo[3,4-d]thiazol-2-yl)-5'-methoxy-6-methyl-[4,4'-bipyridine]-3-carboxamide | 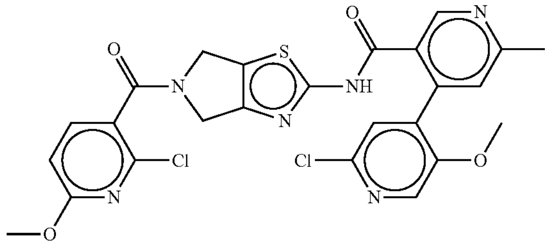 |
| 443 (699) | 2'-chloro-5'-methoxy-6-methyl-N-(5-(2-(trifluoromethyl)pyrimidine-4-carbonyl)-5,6-dihydro-4H-pyrrolo[3,4-d]thiazol-2-yl)-[4,4'-bipyridine]-3-carboxamide | 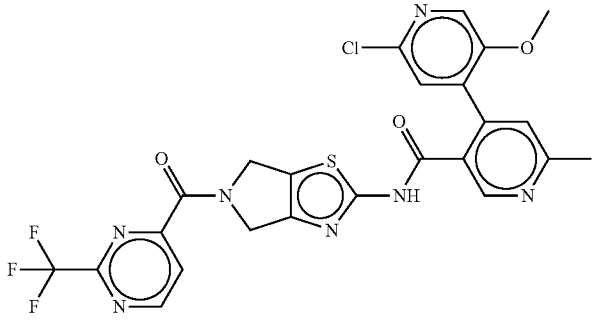 |
| 444 (778) | 4-(5-cyano-2-methoxyphenyl)-N-(5-(3-(difluoromethyl)benzoyl)-5,6-dihydro-4H-pyrrolo[3,4-d]thiazol-2-yl)-6-methylnicotinamide | 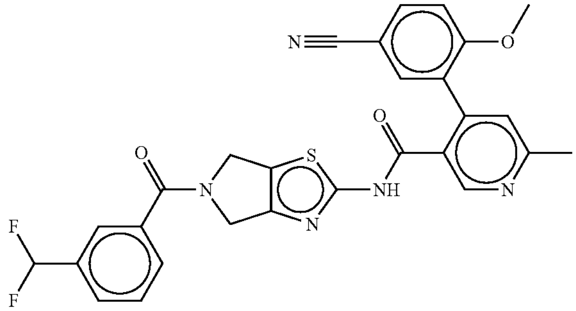 |

TABLE 1-continued

| Compound No. | Name | Structure |
| --- | --- | --- |
| 445 (799) | 2'-chloro-N-(5-(5-chloro-6-(difluoromethyl)nicotinoyl)-5,6-dihydro-4H-pyrrolo[3,4-d]thiazol-2-yl)-5'-methoxy-6-methyl-[4,4'-bipyridine]-3-carboxamide | 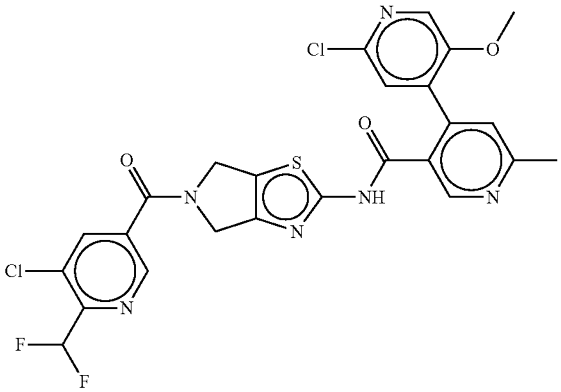 |
| 446 (800) | 5-chloro-N-(5-(5-(difluoromethyl)picolinoyl)-5,6-dihydro-4H-pyrrolo[3,4-d]thiazol-2-yl)-2-methoxy-6'-methyl-[3,4'-bipyridine]-3'-carboxamide | 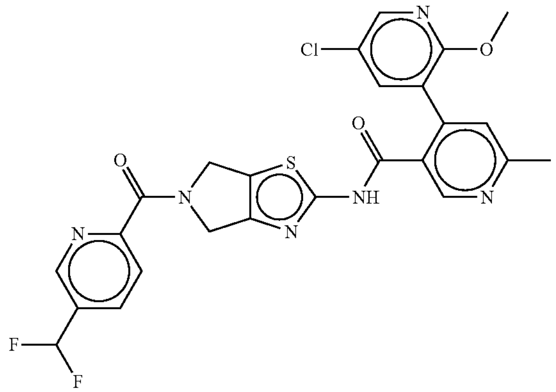 |
| 447 (678) | 2'-chloro-N-(5-(5-chloro-6-methoxynicotinoyl)-5,6-dihydro-4H-pyrrolo[3,4-d]thiazol-2-yl)-5'-methoxy-6-methyl-[4,4'-bipyridine]-3-carboxamide | 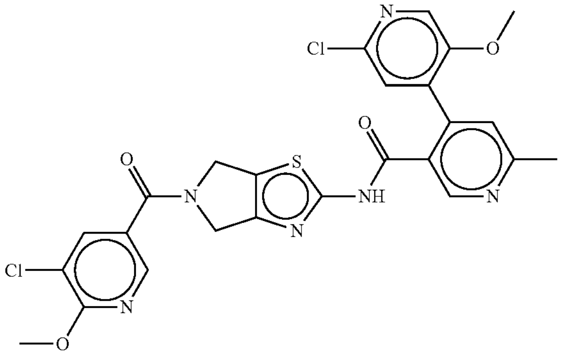 |
| 448 (733) | 2'-chloro-N-(5-(6-chloro-3-methoxypicolinoyl)-5,6-dihydro-4H-pyrrolo[3,4-d]thiazol-2-yl)-5'-methoxy-6-methyl-[4,4'-bipyridine]-3-carboxamide | 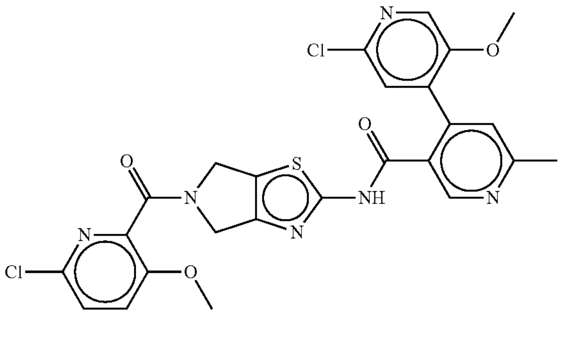 |

TABLE 1-continued

| Compound No. | Name | Structure |
|---|---|---|
| 449 (725) | 2'-chloro-N-(5-(4-(difluoromethyl)pyrimidine-2-carbonyl)-5,6-dihydro-4H-pyrrolo[3,4-d]thiazol-2-yl)-5'-methoxy-6-methyl-[4,4'-bipyridine]-3-carboxamide | 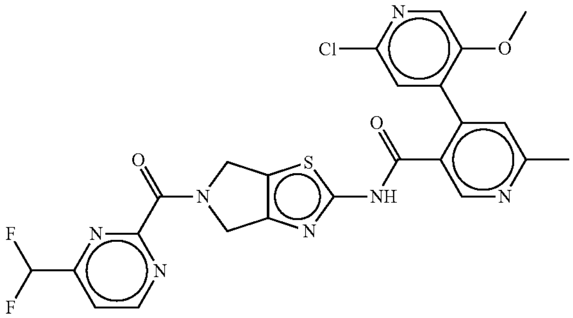 |
| 450 (742) | 2'-chloro-N-(5-(6-chloro-3-methylpicolinoyl)-5,6-dihydro-4H-pyrrolo[3,4-d]thiazol-2-yl)-5'-methoxy-6-methyl-[4,4'-bipyridine]-3-carboxamide | 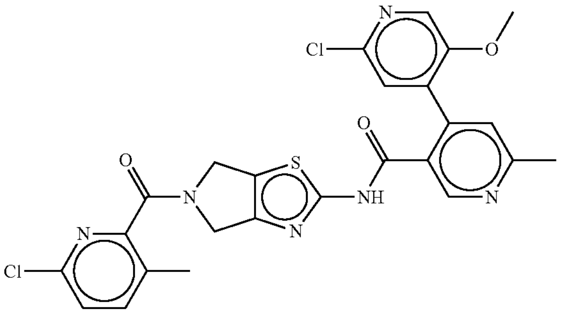 |
| 451 (776) | 2'-chloro-N-(5-(imidazo[1,5-a]pyridine-5-carbonyl)-5,6-dihydro-4H-pyrrolo[3,4-d]thiazol-2-yl)-5'-methoxy-6-methyl-[4,4'-bipyridine]-3-carboxamide | 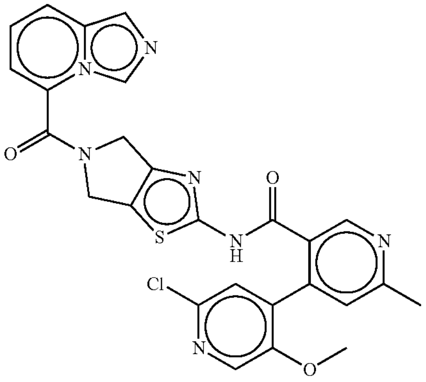 |
| 452 (661) | 2'-chloro-N-(5-(4-chloro-1-isopropyl-1H-pyrazole-5-carbonyl)-5,6-dihydro-4H-pyrrolo[3,4-d]thiazol-2-yl)-5'-methoxy-6-methyl-[4,4'-bipyridine]-3-carboxamide | 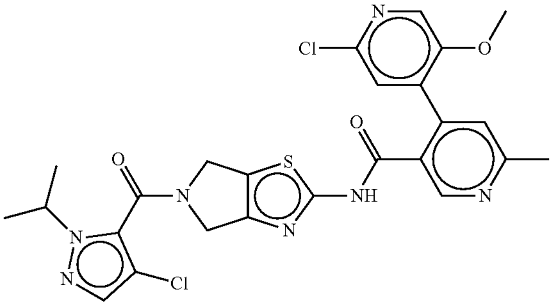 |

TABLE 1-continued

| Compound No. | Name | Structure |
|---|---|---|
| 453 | 2'-chloro-N-(5-((1S or R,3R and S OR 1S and R,3R or S)-3-hydroxy-3-(trifluoromethyl)cyclohexane-1-carbonyl)-5,6-dihydro-4H-pyrrolo[3,4-d]thiazol-2-yl)-5'-methoxy-6-methyl-[4,4'-bipyridine]-3-carboxamide | 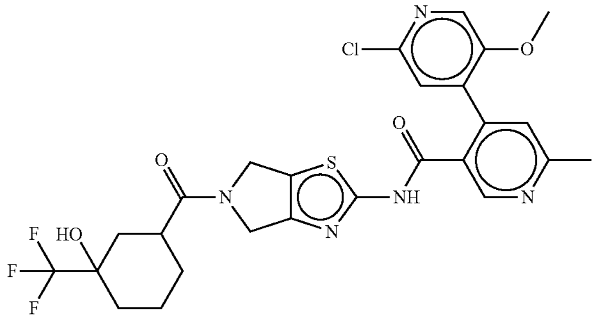 |
| 454 (824) | 2'-chloro-N-(5-(6-(difluoromethyl)pyridazine-3-carbonyl)-5,6-dihydro-4H-pyrrolo[3,4-d]thiazol-2-yl)-5'-methoxy-6-methyl-[4,4'-bipyridine]-3-carboxamide | 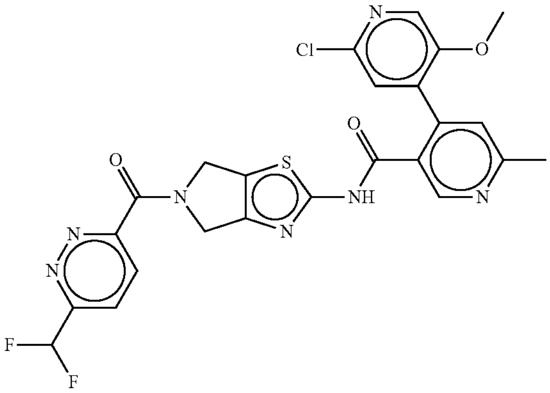 |
| 455 (777) | 2'-chloro-N-(5-(imidazo[1,2-a]pyridine-5-carbonyl)-5,6-dihydro-4H-pyrrolo[3,4-d]thiazol-2-yl)-5'-methoxy-6-methyl-[4,4'-bipyridine]-3-carboxamide | 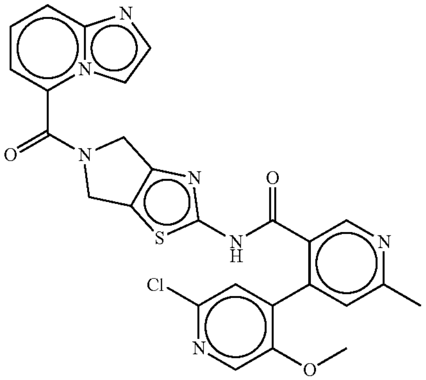 |
| 456 (738) | 2'-chloro-N-(5-(6-(difluoromethoxy)spiro[3.3]heptane-2-carbonyl)-5,6-dihydro-4H-pyrrolo[3,4-d]thiazol-2-yl)-5'-methoxy-6-methyl-[4,4'-bipyridine]-3-carboxamide | 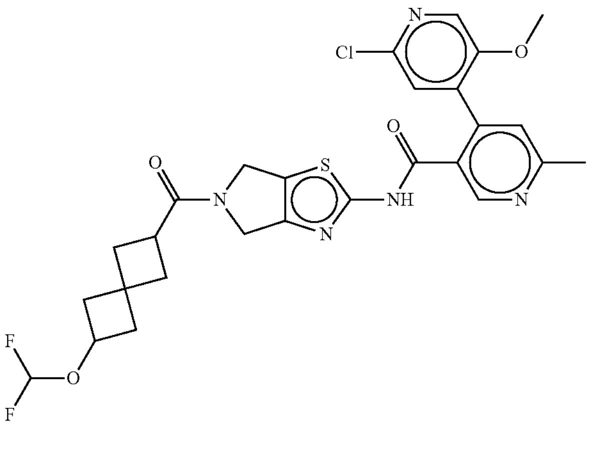 |

TABLE 1-continued

| Compound No. | Name | Structure |
|---|---|---|
| 457 (803) | 2'-chloro-5'-methoxy-N-(5-(5-methoxypyrimidine-2-carbonyl)-5,6-dihydro-4H-pyrrolo[3,4-d]thiazol-2-yl)-6-methyl-[4,4'-bipyridine]-3-carboxamide | 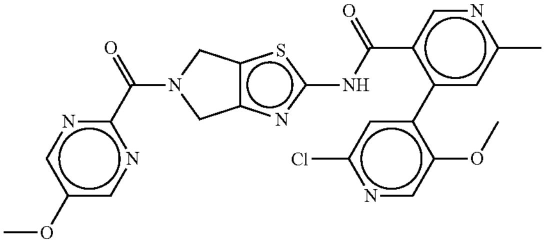 |
| 458 (705) | N-(5-(4-amino-1-methyl-1H-pyrazole-3-carbonyl)-5,6-dihydro-4H-pyrrolo[3,4-d]thiazol-2-yl)-2'-chloro-5'-methoxy-6-methyl-[4,4'-bipyridine]-3-carboxamide | 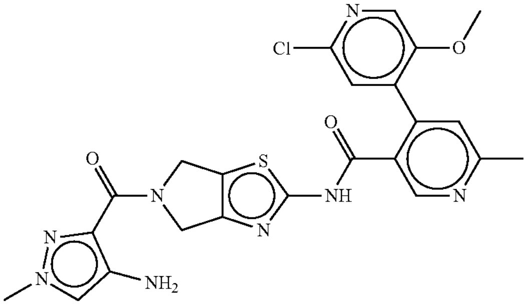 |
| 459 (707) | 2'-chloro-N-(5-(3-chloropicolinoyl)-5,6-dihydro-4H-pyrrolo[3,4-d]thiazol-2-yl)-5'-methoxy-6-methyl-[4,4'-bipyridine]-3-carboxamide | 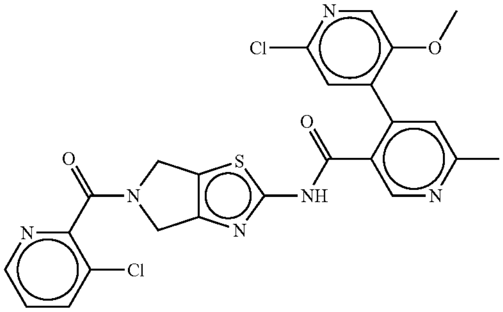 |
| 460 (684) | 2'-chloro-N-(5-(4-chloro-2-methoxynicotinoyl)-5,6-dihydro-4H-pyrrolo[3,4-d]thiazol-2-yl)-5'-methoxy-6-methyl-[4,4'-bipyridine]-3-carboxamide | 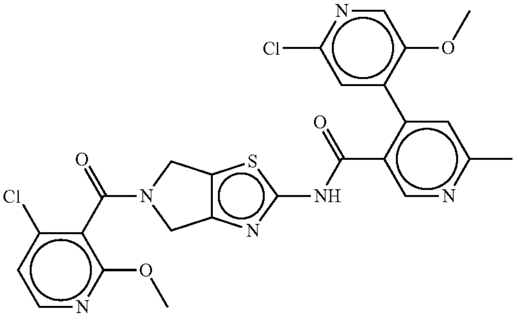 |
| 461 (715) | 2'-chloro-5'-methoxy-6-methyl-N-(5-(2-methylpyrimidine-4-carbonyl)-5,6-dihydro-4H-pyrrolo[3,4-d]thiazol-2-yl)-[4,4'-bipyridine]-3-carboxamide | 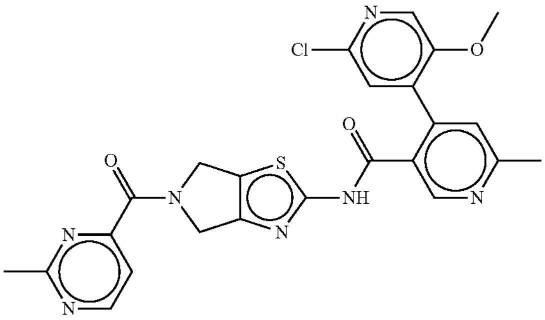 |

TABLE 1-continued

| Compound No. | Name | Structure |
|---|---|---|
| 462 (758) | 2'-chloro-N-(5-(imidazo[1,5-a]pyridine-8-carbonyl)-5,6-dihydro-4H-pyrrolo[3,4-d]thiazol-2-yl)-5'-methoxy-6-methyl-[4,4'-bipyridine]-3-carboxamide | 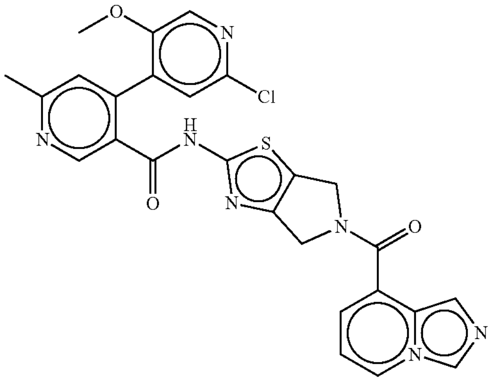 |
| 463 (816) | 4-(5-cyano-2-methoxyphenyl)-N-(5-(4-(difluoromethyl)-3-fluorobenzoyl)-5,6-dihydro-4H-pyrrolo[3,4-d]thiazol-2-yl)-6-methylnicotinamide | 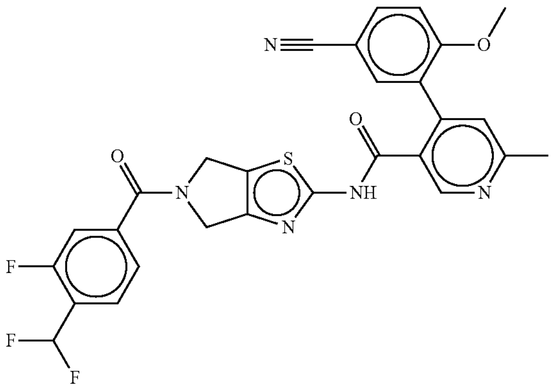 |
| 464 (745) | 2'-chloro-5'-methoxy-6-methyl-N-(5-(5-methylpyrazine-2-carbonyl)-5,6-dihydro-4H-pyrrolo[3,4-d]thiazol-2-yl)-[4,4'-bipyridine]-3-carboxamide | 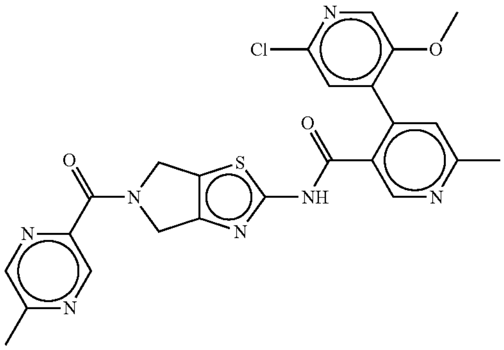 |
| 465 (781) | 2'-chloro-N-(5-(5-chloro-6-(difluoromethyl)picolinoyl)-5,6-dihydro-4H-pyrrolo[3,4-d]thiazol-2-yl)-5'-methoxy-6-methyl-[4,4'-bipyridine]-3-carboxamide | 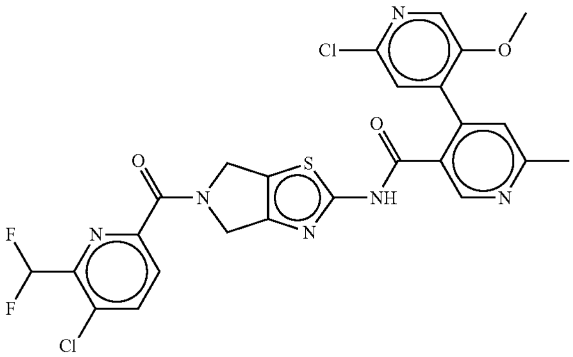 |

TABLE 1-continued

| Compound No. | Name | Structure |
| --- | --- | --- |
| 466 (656) | 2'-chloro-N-(5-(6-(difluoromethyl)-4-methylnicotinoyl)-5,6-dihydro-4H-pyrrolo[3,4-d]thiazol-2-yl)-5'-methoxy-6-methyl-[4,4'-bipyridine]-3-carboxamide | 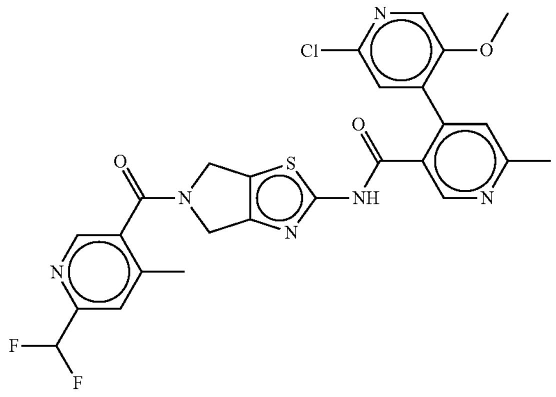 |
| 467 (780) | N-(5-(4-chloro-2-methoxybenzoyl)-5,6-dihydro-4H-pyrrolo[3,4-d]thiazol-2-yl)-4-(5-cyano-2-methoxyphenyl)-6-methylnicotinamide | 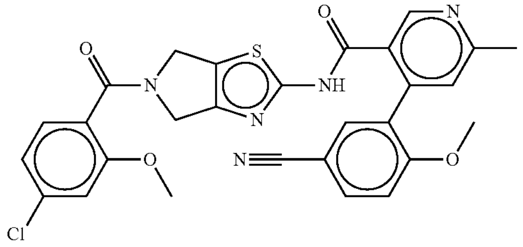 |
| 468 (835) | 2'-chloro-N-(5-(6-(difluoromethyl)-3-methoxypyrazine-2-carbonyl)-5,6-dihydro-4H-pyrrolo[3,4-d]thiazol-2-yl)-5'-methoxy-6-methyl-[4,4'-bipyridine]-3-carboxamide | 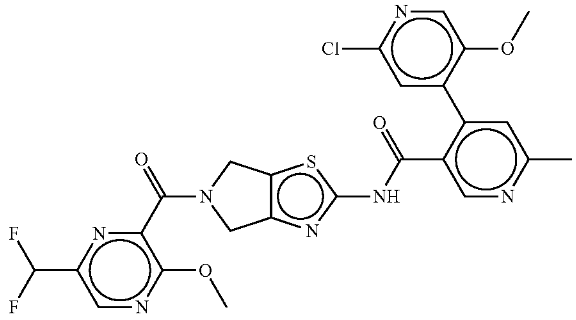 |
| 469 (789) | 2'-chloro-5'-methoxy-6-methyl-N-(5-(5-methylpyrazolo[1,5-a]pyrimidine-7-carbonyl)-5,6-dihydro-4H-pyrrolo[3,4-d]thiazol-2-yl)-[4,4'-bipyridine]-3-carboxamide | 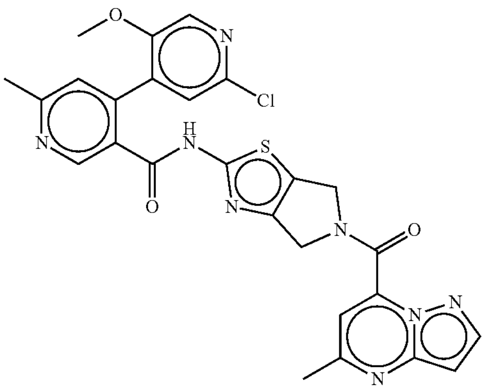 |

TABLE 1-continued

| Compound No. | Name | Structure |
|---|---|---|
| 470 (784) | N-(5-(4-chloro-3-methoxybenzoyl)-5,6-dihydro-4H-pyrrolo[3,4-d]thiazol-2-yl)-4-(5-cyano-2-methoxyphenyl)-6-methylnicotinamide | 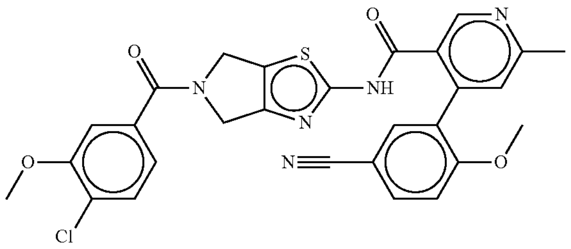 |
| 471 (667) | 4-(6-methoxy-1H-indazol-5-yl)-N-(5-(2-methoxynicotinoyl)-5,6-dihydro-4H-pyrrolo[3,4-d]thiazol-2-yl)-6-methylnicotinamide | 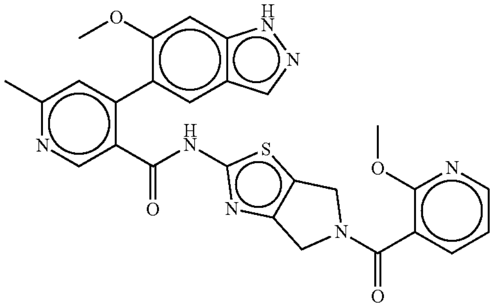 |
| 472 (804) | 2'-chloro-5'-methoxy-N-(5-(5-methoxybenzo[d]oxazole-2-carbonyl)-5,6-dihydro-4H-pyrrolo[3,4-d]thiazol-2-yl)-6-methyl-[4,4'-bipyridine]-3-carboxamide | 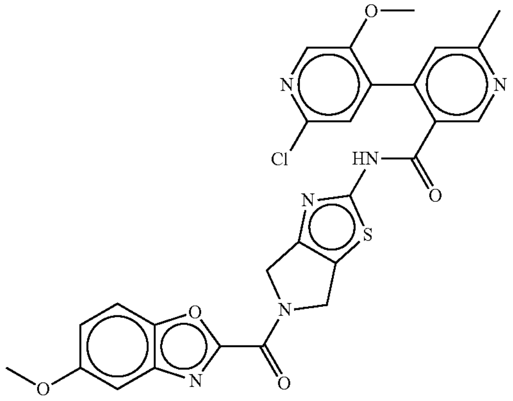 |
| 473 (691) | 2'-chloro-N-(5-(6-fluorospiro[3.3]heptane-2-carbonyl)-5,6-dihydro-4H-pyrrolo[3,4-d]thiazol-2-yl)-5'-methoxy-6-methyl-[4,4'-bipyridine]-3-carboxamide | 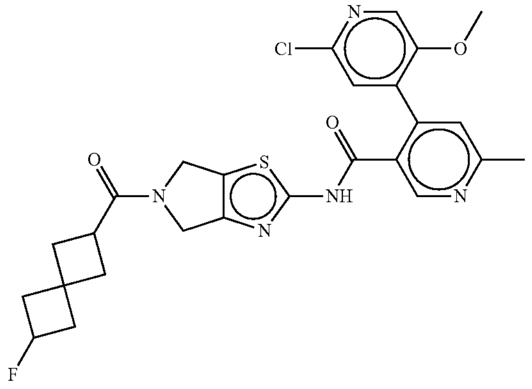 |

TABLE 1-continued

| Compound No. | Name | Structure |
| --- | --- | --- |
| 474 (671) | 2'-chloro-5'-methoxy-N-(5-(6-methoxynicotinoyl)-5,6-dihydro-4H-pyrrolo[3,4-d]thiazol-2-yl)-6-methyl-[4,4'-bipyridine]-3-carboxamide | 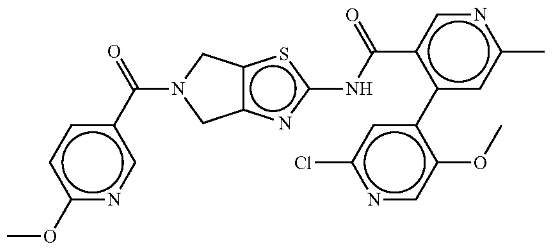 |
| 475 (752) | 2'-chloro-N-(5-(6-chloro-4-methoxypicolinoyl)-5,6-dihydro-4H-pyrrolo[3,4-d]thiazol-2-yl)-5'-methoxy-6-methyl-[4,4'-bipyridine]-3-carboxamide | 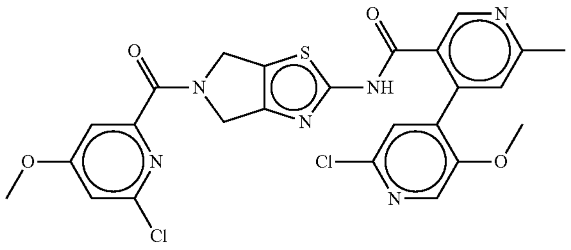 |
| 476 (693) | 2'-chloro-N-(5-(1,4-dimethyl-1H-imidazole-5-carbonyl)-5,6-dihydro-4H-pyrrolo[3,4-d]thiazol-2-yl)-5'-methoxy-6-methyl-[4,4'-bipyridine]-3-carboxamide | 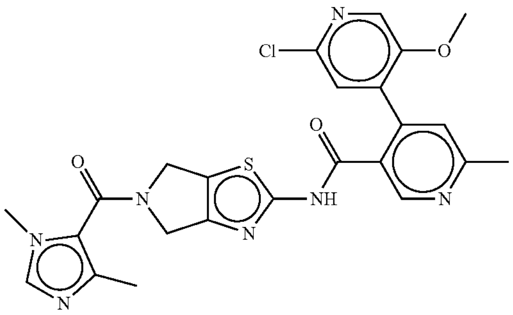 |
| 477 (702) | 2'-chloro-5'-methoxy-6-methyl-N-(5-(4-methyl-2-(trifluoromethyl)pyrimidine-5-carbonyl)-5,6-dihydro-4H-pyrrolo[3,4-d]thiazol-2-yl)-[4,4'-bipyridine]-3-carboxamide | 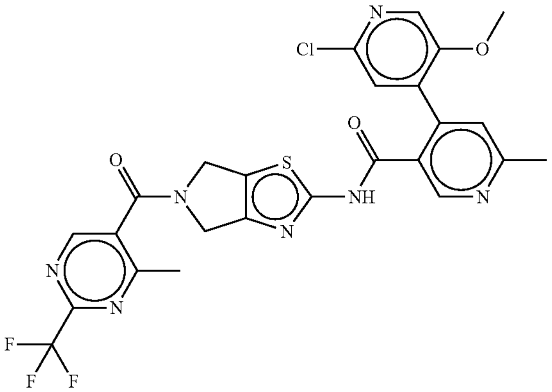 |
| 478 (670) | 2'-chloro-N-(5-(4-chloro-6-methoxynicotinoyl)-5,6-dihydro-4H-pyrrolo[3,4-d]thiazol-2-yl)-5'-methoxy-6-methyl-[4,4'-bipyridine]-3-carboxamide | 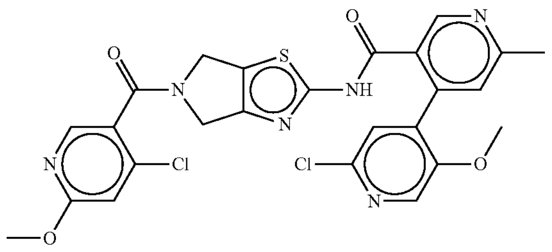 |

TABLE 1-continued

| Compound No. | Name | Structure |
|---|---|---|
| 479 (716) | 2'-chloro-N-(5-(5-chloro-2-methylpyrimidine-4-carbonyl)-5,6-dihydro-4H-pyrrolo[3,4-d]thiazol-2-yl)-5'-methoxy-6-methyl-[4,4'-bipyridine]-3-carboxamide | 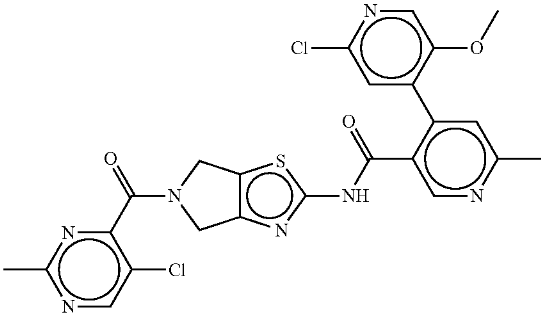 |
| 480 (779) | N-(5-(2-chloro-3-methoxybenzoyl)-5,6-dihydro-4H-pyrrolo[3,4-d]thiazol-2-yl)-4-(5-cyano-2-methoxyphenyl)-6-methylnicotinamide | 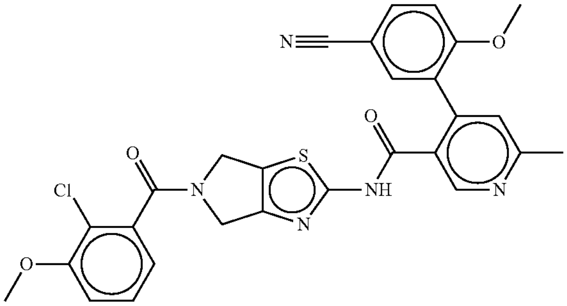 |
| 481 (713) | 2'-chloro-N-(5-(5-chloro-2-methoxypyrimidine-4-carbonyl)-5,6-dihydro-4H-pyrrolo[3,4-d]thiazol-2-yl)-5'-methoxy-6-methyl-[4,4'-bipyridine]-3-carboxamide | 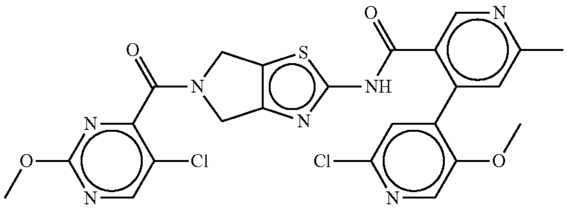 |
| 482 (791) | 2'-chloro-5'-methoxy-6-methyl-N-(5-(pyrazolo[1,5-a]pyrimidine-7-carbonyl)-5,6-dihydro-4H-pyrrolo[3,4-d]thiazol-2-yl)-[4,4'-bipyridine]-3-carboxamide | 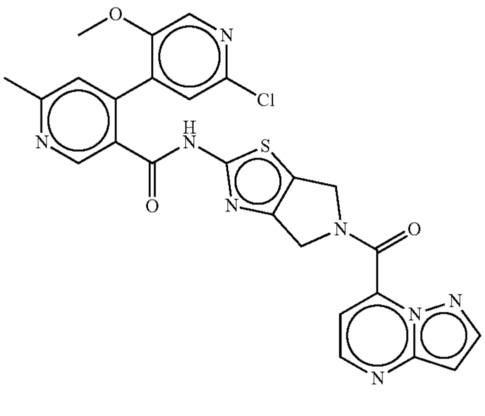 |

TABLE 1-continued

| Compound No. | Name | Structure |
|---|---|---|
| 483 (703) | 2'-chloro-5'-methoxy-6-methyl-N-(5-(2-(trifluoromethyl)pyrimidine-5-carbonyl)-5,6-dihydro-4H-pyrrolo[3,4-d]thiazol-2-yl)-[4,4'-bipyridine]-3-carboxamide | 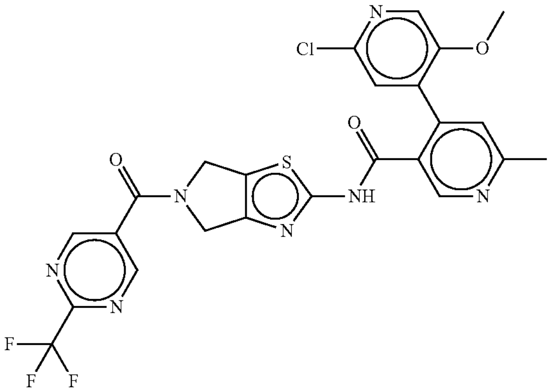 |
| 484 (774) | 2'-chloro-5'-methoxy-6-methyl-N-(5-(thiazole-2-carbonyl)-5,6-dihydro-4H-pyrrolo[3,4-d]thiazol-2-yl)-[4,4'-bipyridinel-3-carboxamide | 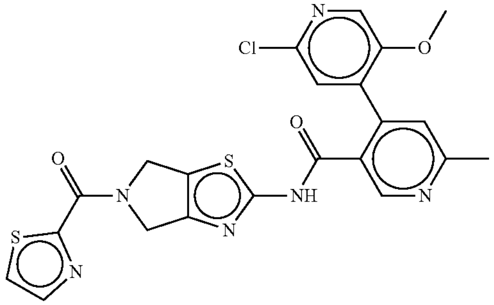 |
| 485 (731) | (Racemic) 2'-chloro-5'-methoxy-6-methyl-N-(5-(3-(trifluoromethoxy)cyclohexane-1-carbonyl)-5,6-dihydro-4H-pyrrolo[3,4-d]thiazol-2-yl)-[4,4'-bipyridine]-3-carboxamide | 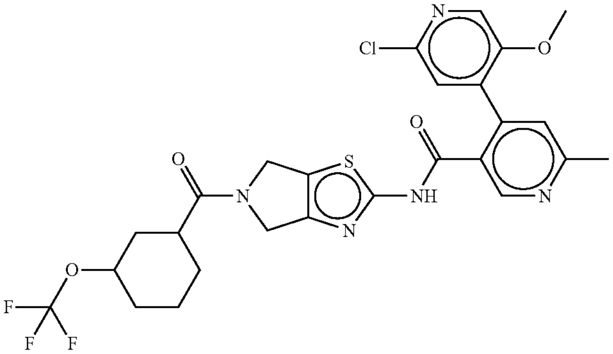 |
| 486 (679) | 2'-chloro-N-(5-(5-chloro-2-methoxynicotinoyl)-5,6-dihydro-4H-pyrrolo[3,4-d]thiazol-2-yl)-5'-methoxy-6-methyl-[4,4'-bipyridine]-3-carboxamide | 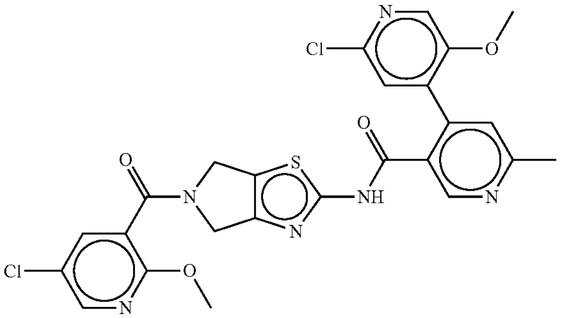 |

TABLE 1-continued

| Compound No. | Name | Structure |
|---|---|---|
| 487 (809) | N-(5-(2-chloro-3-(difluoromethyl)benzoyl)-5,6-dihydro-4H-pyrrolo[3,4-d]thiazol-2-yl)-4-(5-cyano-2-methoxyphenyl)-6-methylnicotinamide | 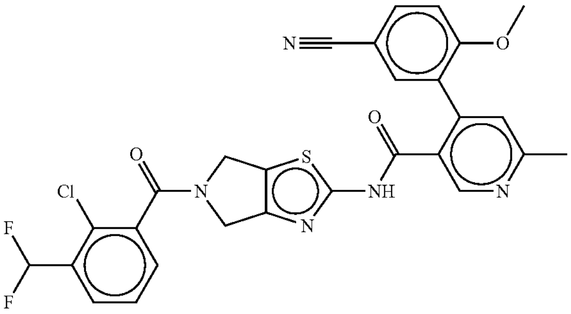 |
| 488 | 2'-chloro-5'-methoxy-N-(5-((1R or S,3S and R OR 1R and S,3S or R)-3-methoxycyclohexane-1-carbonyl)-5,6-dihydro-4H-pyrrolo[3,4-d]thiazol-2-yl)-6-methyl-[4,4'-bipyridine]-3-carboxamide Mixture of diastereomers | 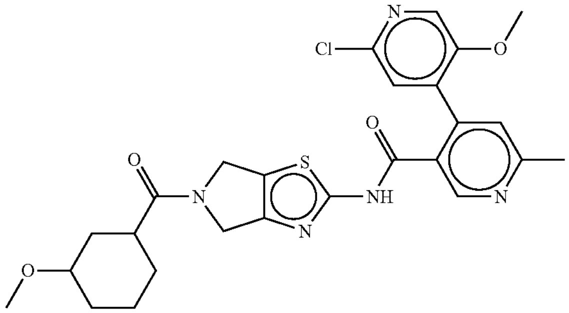 |
| 489 (728) | 2'-(difluoromethyl)-5'-methoxy-6-methyl-N-(5-picolinoyl-5,6-dihydro-4H-pyrrolo[3,4-d]thiazol-2-yl)-[4,4'-bipyridine]-3-carboxamide | 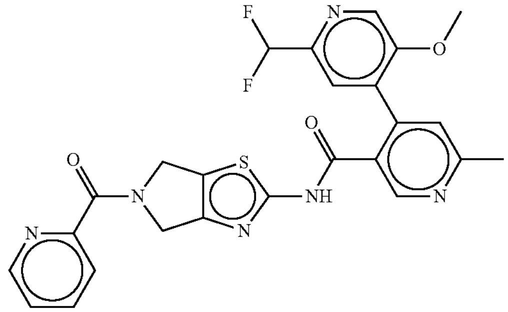 |
| 490 (717) | 2'-chloro-5'-methoxy-N-(5-(2-methoxypyrimidine-4-carbonyl)-5,6-dihydro-4H-pyrrolo[3,4-d]thiazol-2-yl)-6-methyl-[4,4'-bipyridine]-3-carboxamide | 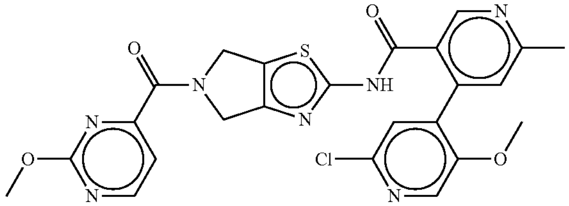 |
| 491 (704) | 2'-chloro-N-(5-(2-(difluoromethyl)pyrimidine-5-carbonyl)-5,6-dihydro-4H-pyrrolo[3,4-d]thiazol-2-yl)-5'-methoxy-6-methyl-[4,4'-bipyridine]-3-carboxamide | 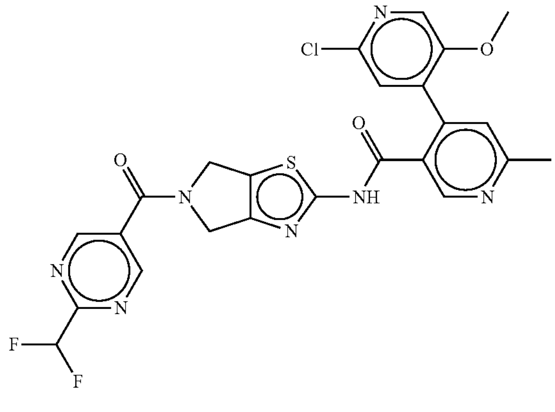 |

TABLE 1-continued

| Compound No. | Name | Structure |
|---|---|---|
| 492 | 2'-chloro-N-(5-((1R or S,3R and S OR 1R and S,3R or S)-3-hydroxy-3-(trifluoromethyl)cyclopentane-1-carbonyl)-5,6-dihydro-4H-pyrrolo[3,4-d]thiazol-2-yl)-5'-methoxy-6-methyl-[4,4'-bipyridine]-3-carboxamide | 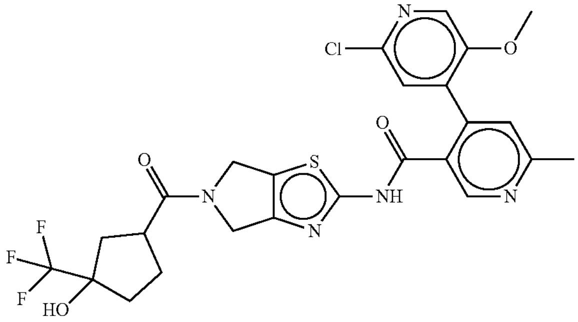 |
| 493 (732) | 2'-chloro-5'-methoxy-N-(5-(5-methoxy-2-methylpyrimidine-4-carbonyl)-5,6-dihydro-4H-pyrrolo[3,4-d]thiazol-2-yl)-6-methyl-[4,4'-bipyridine]-3-carboxamide | 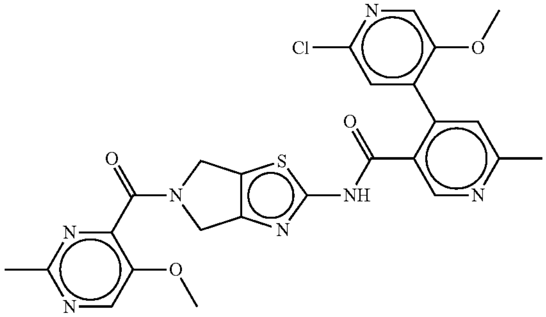 |
| 494 (830) | N-(5-(4-chloro-3-(difluoromethyl)benzoyl)-5,6-dihydro-4H-pyrrolo[3,4-d]thiazol-2-yl)-4-(5-cyano-2-methoxyphenyl)-6-methylnicotinamide | 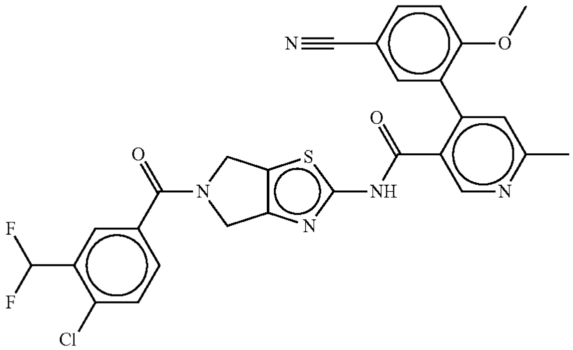 |
| 495 (697) | 2'-chloro-5'-methoxy-6-methyl-N-(5-(pyrimidine-4-carbonyl)-5,6-dihydro-4H-pyrrolo[3,4-d]thiazol-2-yl)-[4,4'-bipyridine]-3-carboxamide | 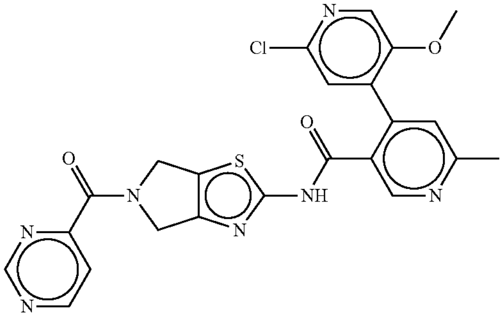 |
| 496 (721) | 2'-chloro-N-(5-(4-chloro-6-methoxypicolinoyl)-5,6-dihydro-4H-pyrrolo[3,4-d]thiazol-2-yl)-5'-methoxy-6-methyl-[4,4'-bipyridine]-3-carboxamide | 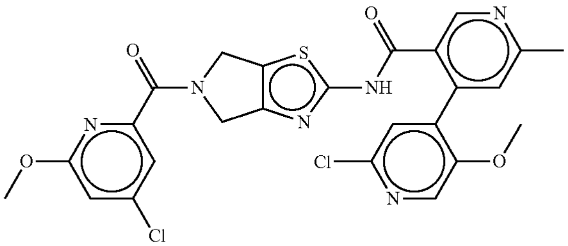 |

TABLE 1-continued

| Compound No. | Name | Structure |
|---|---|---|
| 497 (726) | 2'-chloro-5'-methoxy-6-methyl-N-(5-(6-methylpicolinoyl)-5,6-dihydro-4H-pyrrolo[3,4-d]thiazol-2-yl)-[4,4'-bipyridine]-3-carboxamide | 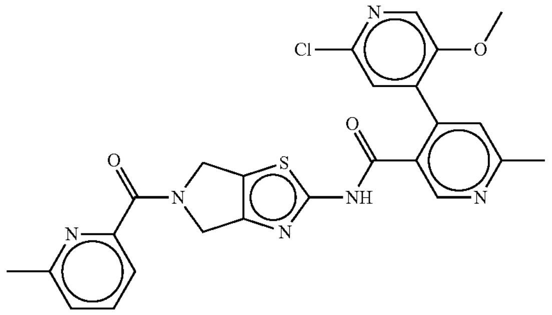 |
| 498 (720) | 2'-chloro-N-(5-(3-chloro-6-methylpicolinoyl)-5,6-dihydro-4H-pyrrolo[3,4-d]thiazol-2-yl)-5'-methoxy-6-methyl-[4,4'-bipyridine]-3-carboxamide | 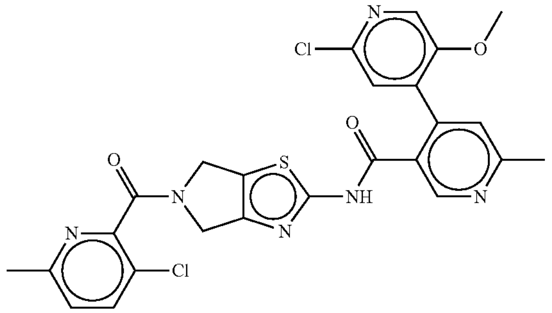 |
| 499 (792) | 2'-chloro-5'-methoxy-6-methyl-N-(5-(pyrazolo[1,5-a]pyrazine-4-carbonyl)-5,6-dihydro-4H-pyrrolo[3,4-d]thiazol-2-yl)-[4,4'-bipyridine]-3-carboxamide | 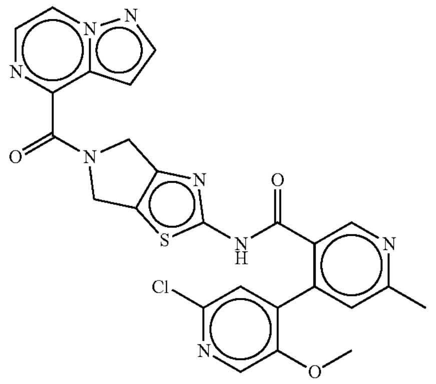 |
| 500 | 2'-chloro-N-(5-((1R or S,3R and S OR 1R and S, 3R or S)-3-hydroxy-3-(trifluoromethyl)cyclohexane-1-carbonyl)-5,6-dihydro-4H-pyrrolo[3,4-d]thiazol-2-yl)-5'-methoxy-6-methyl-[4,4'-bipyridine]-3-carboxamide | 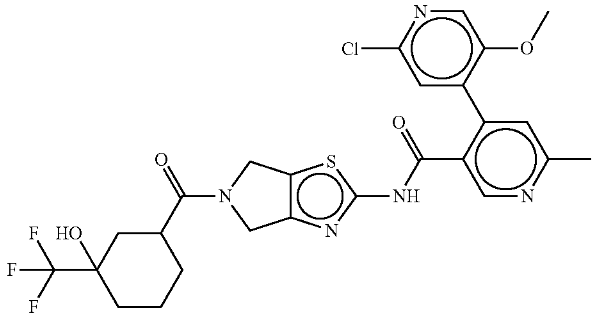 |

TABLE 1-continued

| Compound No. | Name | Structure |
|---|---|---|
| 501 (821) | 2'-chloro-N-(5-(3-chloro-5-(1,1-difluoroethyl)picolinoyl)-5,6-dihydro-4H-pyrrolo[3,4-d]thiazol-2-yl)-5'-methoxy-6-methyl-[4,4'-bipyridine]-3-carboxamide | 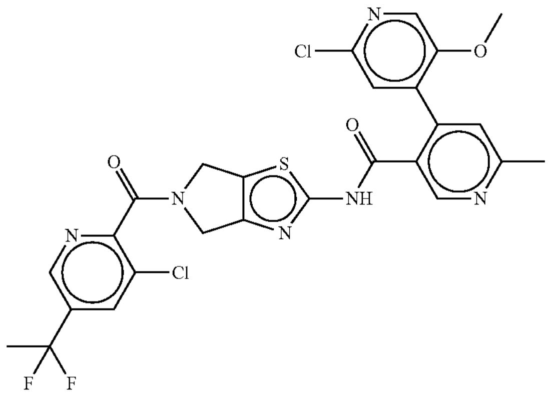 |
| 502 (823) | 2'-chloro-5'-methoxy-N-(5-(8-methoxyimidazo[1,5-a]pyridine-5-carbonyl)-5,6-dihydro-4H-pyrrolo[3,4-d]thiazol-2-yl)-6-methyl-[4,4'-bipyridine]-3-carboxamide | 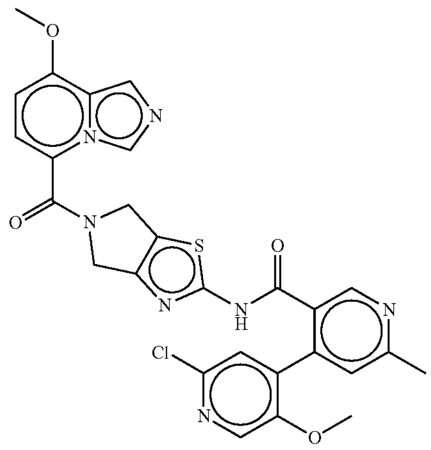 |
| 503 (787) | 4-(5-cyano-2-methoxyphenyl)-N-(5-(4-(difluoromethoxy)benzoyl)-5,6-dihydro-4H-pyrrolo[3,4-d]thiazol-2-yl)-6-methylnicotinamide | 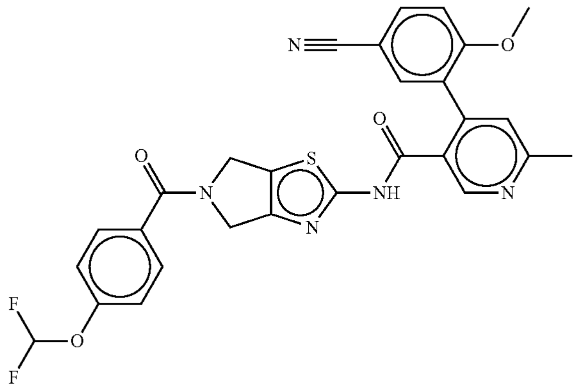 |
| 504 (802) | 2'-chloro-N-(5-(6-(difluoromethyl)-5-methoxypicolinoyl)-5,6-dihydro-4H-pyrrolo[3,4-d]thiazol-2-yl)-5'-methoxy-6-methyl-[4,4'-bipyridine]-3-carboxamide | 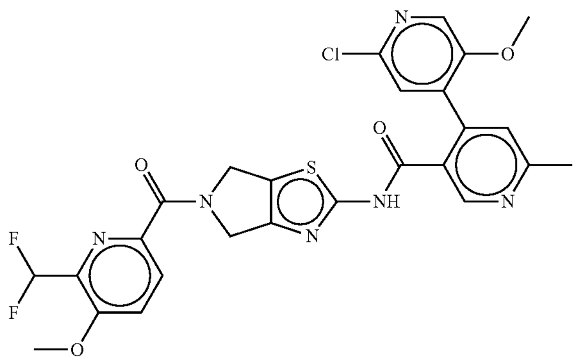 |

TABLE 1-continued

| Compound No. | Name | Structure |
|---|---|---|
| 505 (723) | 2'-chloro-N-(5-(4-chloro-6-methylpicolinoyl)-5,6-dihydro-4H-pyrrolo[3,4-d]thiazol-2-yl)-5'-methoxy-6-methyl-[4,4'-bipyridine]-3-carboxamide | 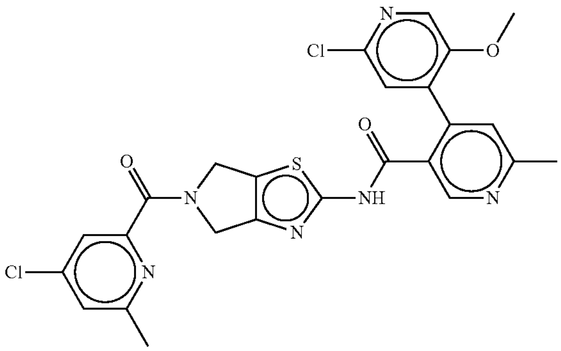 |
| 506 (700) | 2'-chloro-5'-methoxy-6-methyl-N-(5-(6-(trifluoromethoxy)picolinoyl)-5,6-dihydro-4H-pyrrolo[3,4-d]thiazol-2-yl)-[4,4'-bipyridine]-3-carboxamide | 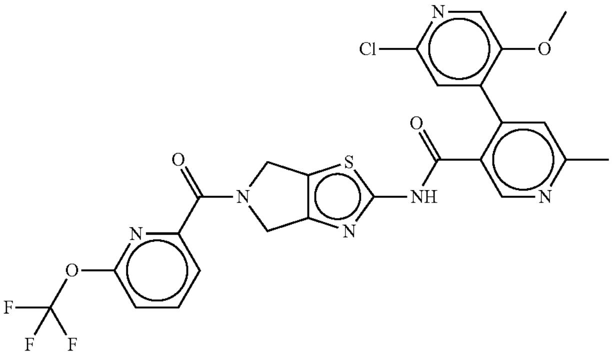 |
| 507 (714) | 2'-chloro-5'-methoxy-6-methyl-N-(5-(pyridin-2-ylsulfonyl)-5,6-dihydro-4H-pyrrolo[3,4-d]thiazol-2-yl)-[4,4'-bipyridine]-3-carboxamide | 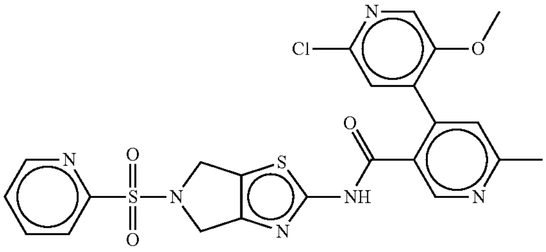 |
| 508 (790) | 4-(6-chloro-3-methoxypyridazin-4-yl)-N-(5-(5-(difluoromethyl)picolinoyl)-5,6-dihydro-4H-pyrrolo[3,4-d]thiazol-2-yl)-6-methylnicotinamide | 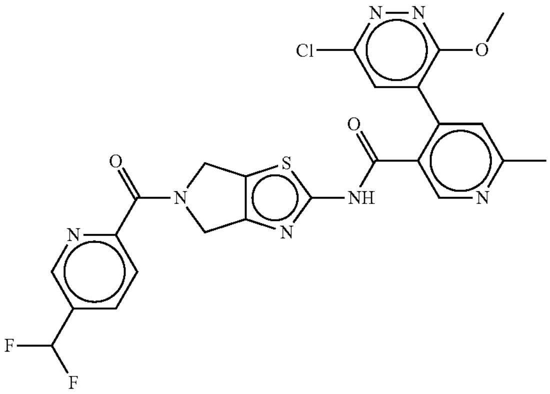 |

TABLE 1-continued

| Compound No. | Name | Structure |
|---|---|---|
| 509 | 2'-chloro-5'-methoxy-N-(5-((1R or S,3R and S OR 1R and S,3R or S)-3-methoxycyclohexane-1-carbonyl)-5,6-dihydro-4H-pyrrolo[3,4-d]thiazol-2-yl)-6-methyl-[4,4'-bipyridine]-3-carboxamide Mixture of diastereomers | 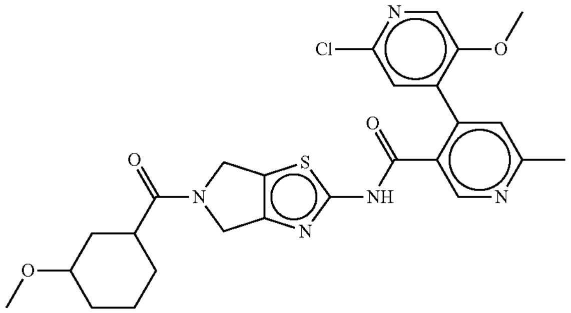 |
| 510 (751) | 2'-chloro-5'-methoxy-6-methyl-N-(5-(6-(trifluoromethyl)pyrazine-2-carbonyl)-5,6-dihydro-4H-pyrrolo[3,4-d]thiazol-2-yl)-[4,4'-bipyridine]-3-carboxamide | 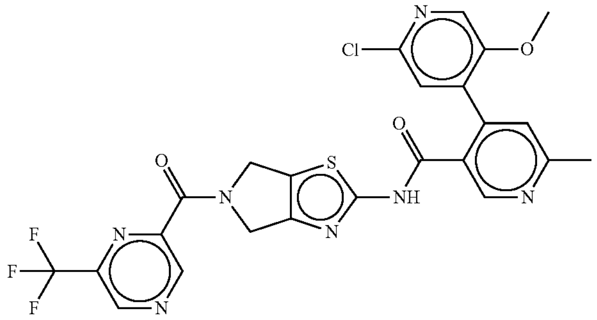 |
| 511 (815) | 2'-chloro-N-(5-(5-(difluoromethoxy)pyrazine-2-carbonyl)-5,6-dihydro-4H-pyrrolo[3,4-d]thiazol-2-yl)-5'-methoxy-6-methyl-[4,4'-bipyridine]-3-carboxamide | 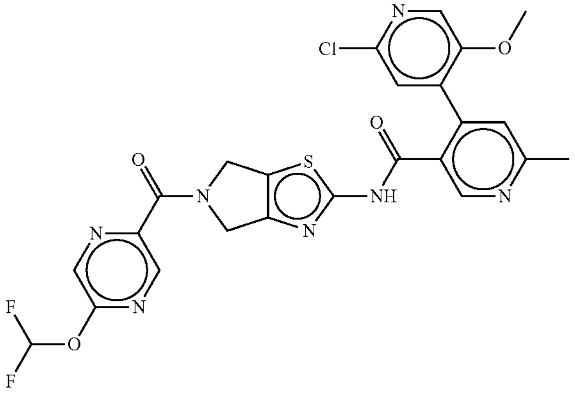 |
| 512 (712) | 2'-chloro-N-(5-(5-chloropyrimidine-4-carbonyl)-5,6-dihydro-4H-pyrrolo[3,4-d]thiazol-2-yl)-5'-methoxy-6-methyl-[4,4'-bipyridine]-3-carboxamide | 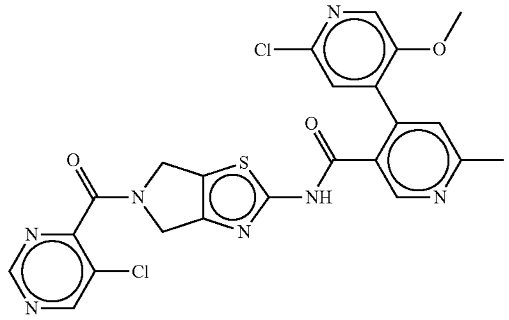 |

TABLE 1-continued

| Compound No. | Name | Structure |
| --- | --- | --- |
| 513 (710) | 2'-chloro-5'-methoxy-6-methyl-N-(5-(1-(trifluoromethyl)-1H-pyrazole-4-carbonyl)-5,6-dihydro-4H-pyrrolo[3,4-d]thiazol-2-yl)-[4,4'-bipyridine]-3-carboxamide | 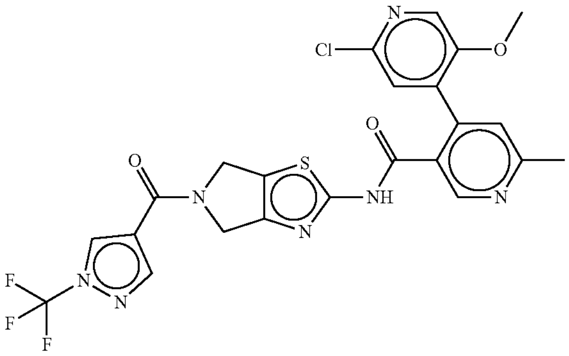 |
| 514 (718) | 2'-chloro-5'-methoxy-N-(5-(5-methoxypyrimidine-4-carbonyl)-5,6-dihydro-4H-pyrrolo[3,4-d]thiazol-2-yl)-6-methyl-[4,4'-bipyridine]-3-carboxamide | 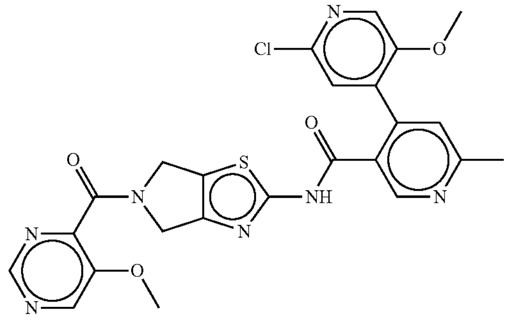 |
| 515 (680) | 2'-chloro-N-(5-(4-cyano-1-methyl-1H-pyrazole-5-carbonyl)-5,6-dihydro-4H-pyrrolo[3,4-d]thiazol-2-yl)-5'-methoxy-6-methyl-[4,4'-bipyridine]-3-carboxamide | 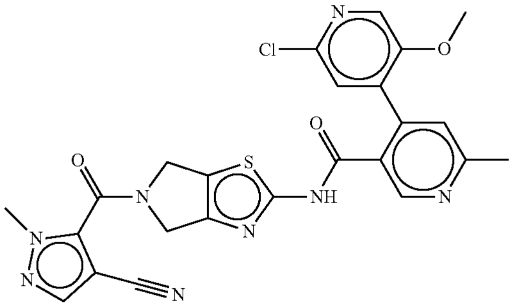 |
| 516 (786) | N-(5-(2-chloro-4-methoxybenzoyl)-5,6-dihydro-4H-pyrrolo[3,4-d]thiazol-2-yl)-4-(5-cyano-2-methoxyphenyl)-6-methylnicotinamide | 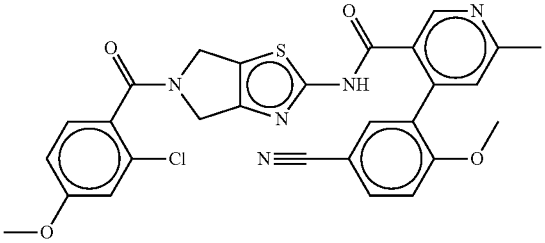 |

TABLE 1-continued

| Compound No. | Name | Structure |
|---|---|---|
| 517 (808) | 2'-chloro-N-(5-(2-chloro-6-(difluoromethoxy)nicotinoyl)-5,6-dihydro-4H-pyrrolo[3,4-d]thiazol-2-yl)-5'-methoxy-6-methyl-[4,4'-bipyridine]-3-carboxamide | 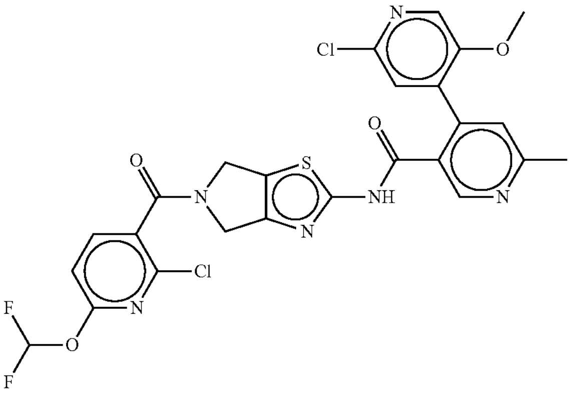 |
| 518 (771) | 2'-chloro-N-(S-(5-chloro-6-methylpicolinoyl)-5,6-dihydro-4H-pyrrolo[3,4-d]thiazol-2-yl)-5'-methoxy-6-methyl-[4,4'-bipyridine]-3-carboxamide | 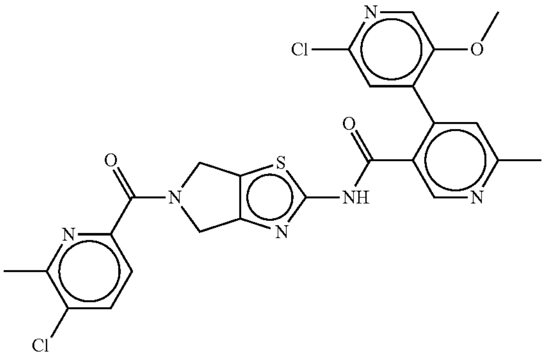 |
| 519 (817) | N-(5-(2-chloro-4-(difluoromethyl)benzoyl)-5,6-dihydro-4H-pyrrolo[3,4-d]thiazol-2-yl)-4-(5-cyano-2-methoxyphenyl)-6-methylnicotinamide | 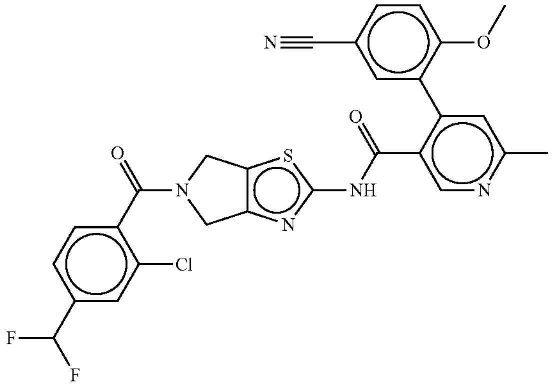 |
| 520 (743) | 2'-chloro-5'-methoxy-6-methyl-N-(5-(3-methylpyrazine-2-carbonyl)-5,6-dihydro-4H-pyrrolo[3,4-d]thiazol-2-yl)-[4,4'-bipyridine]-3-carboxamide | 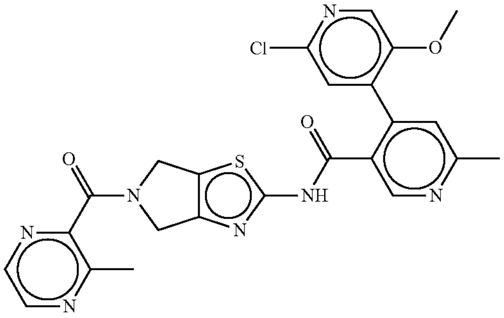 |

TABLE 1-continued

| Compound No. | Name | Structure |
|---|---|---|
| 521 (825) | 2'-chloro-N-(5-(4-chloro-6-methoxypyridazine-3-carbonyl)-5,6-dihydro-4H-pyrrolo[3,4-d]thiazol-2-yl)-5'-methoxy-6-methyl-[4,4'-bipyridine]-3-carboxamide | 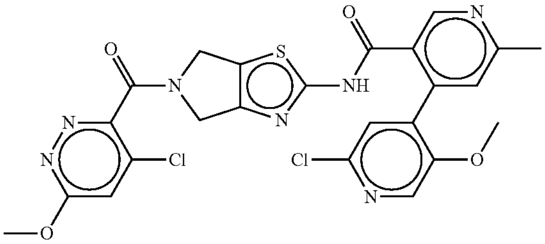 |
| 522 (753) | 2'-chloro-5'-methoxy-6-methyl-N-(5-(6-methylpyrazine-2-carbonyl)-5,6-dihydro-4H-pyrrolo[3,4-d]thiazol-2-yl)-[4,4'-bipyridine]-3-carboxamide | 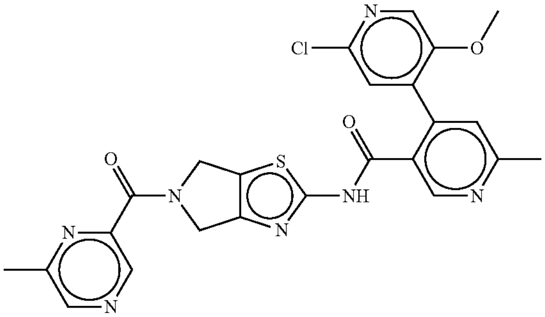 |
| 523 (709) | 2'-chloro-5'-methoxy-6-methyl-N-(5-(4-(trifluoromethyl)oxazole-2-carbonyl)-5,6-dihydro-4H-pyrrolo[3,4-d]thiazol-2-yl)-[4,4'-bipyridine]-3-carboxamide | 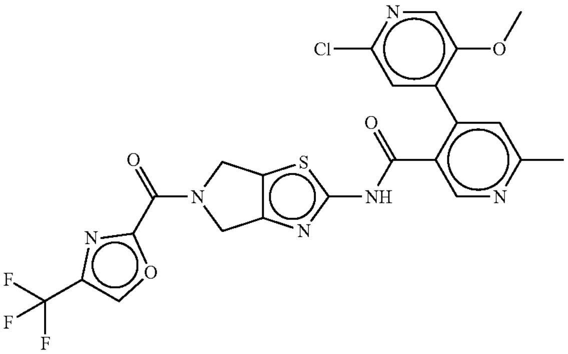 |
| 524 (690) | 2'-chloro-N-(5-(2-chloronicotinoyl)-5,6-dihydro-4H-pyrrolo[3,4-d]thiazol-2-yl)-5'-methoxy-6-methyl-[4,4'-bipyridine]-3-carboxamide | 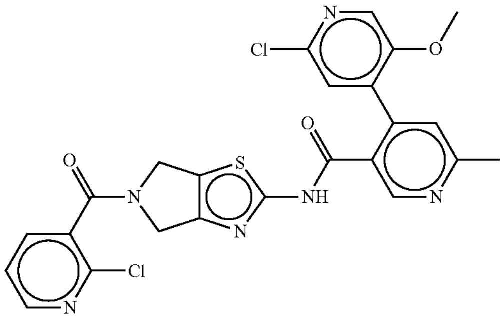 |

TABLE 1-continued

| Compound No. | Name | Structure |
|---|---|---|
| 525 (741) | 2'-chloro-N-(5-(2-(difluoromethoxy)nicotinoyl)-5,6-dihydro-4H-pyrrolo[3,4-d]thiazol-2-yl)-5'-methoxy-6-methyl-[4,4'-bipyridine]-3-carboxamide | 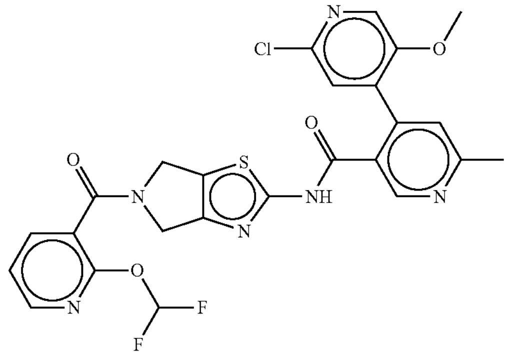 |
| 526 (740) | 2'-chloro-N-(5-(3,5-dimethylpyrazine-2-carbonyl)-5,6-dihydro-4H-pyrrolo[3,4-d]thiazol-2-yl)-5'-methoxy-6-methyl-[4,4'-bipyridine]-3-carboxamide | 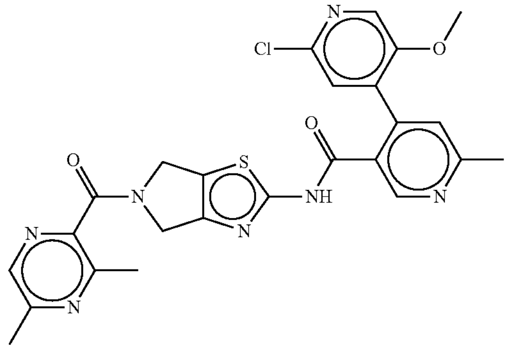 |
| 527 (796) | 2'-chloro-N-(5-(1-cyclopropyl-1H-imidazole-5-carbonyl)-5,6-dihydro-4H-pyrrolo[3,4-d]thiazol-2-yl)-5'-methoxy-6-methyl-[4,4'-bipyridine]-3-carboxamide | 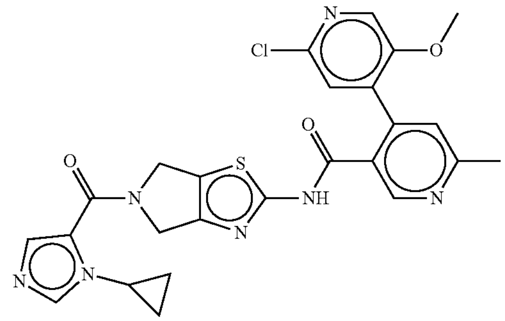 |
| 528 (747) | 2'-chloro-5'-methoxy-N-(5-(6-methoxypyrazine-2-carbonyl)-5,6-dihydro-4H-pyrrolo[3,4-d]thiazol-2-yl)-6-methyl-[4,4'-bipyridine]-3-carboxamide | 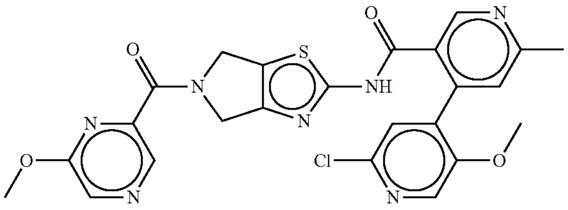 |

TABLE 1-continued

| Compound No. | Name | Structure |
|---|---|---|
| 529 (788) | 2'-chloro-N-(5-(4,5-dimethyloxazole-2-carbonyl)-5,6-dihydro-4H-pyrrolo[3,4-d]thiazol-2-yl)-5'-methoxy-6-methyl-[4,4'-bipyridine]-3-carboxamide | 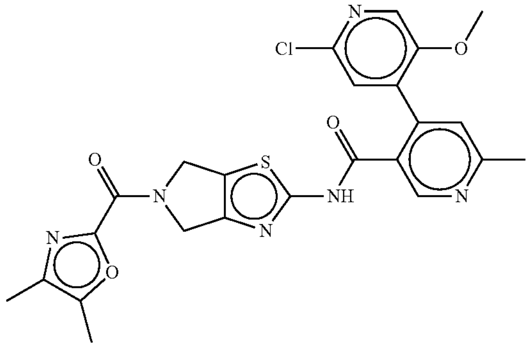 |
| 530 (711) | 2'-chloro-N-(5-(2-(difluoromethyl)-6-methylpyrimidine-4-carbonyl)-5,6-dihydro-4H-pyrrolo[3,4-d]thiazol-2-yl)-5'-methoxy-6-methyl-[4,4'-bipyridine]-3-carboxamide | 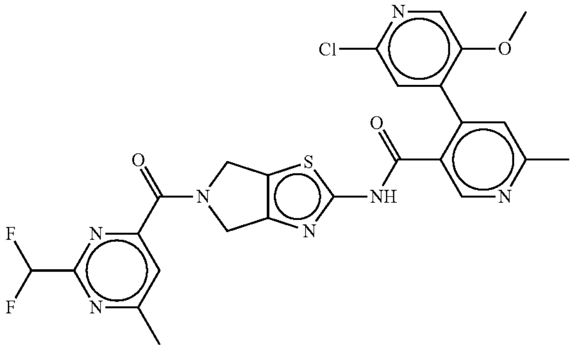 |
| 531 (832) | 2'-chloro-N-(5-(6-(difluoromethyl)-5-methoxypyrazine-2-carbonyl)-5,6-dihydro-4H-pyrrolo[3,4-d]thiazol-2-yl)-5'-methoxy-6-methyl-[4,4'-bipyridine]-3-carboxamide | 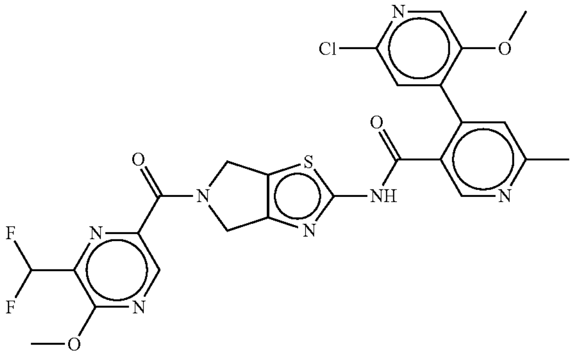 |
| 532 (722) | 2'-chloro-N-(5-(6-cyanospiro[3.3]heptane-2-carbonyl)-5,6-dihydro-4H-pyrrolo[3,4-d]thiazol-2-yl)-5'-methoxy-6-methyl-[4,4'-bipyridine]-3-carboxamide | 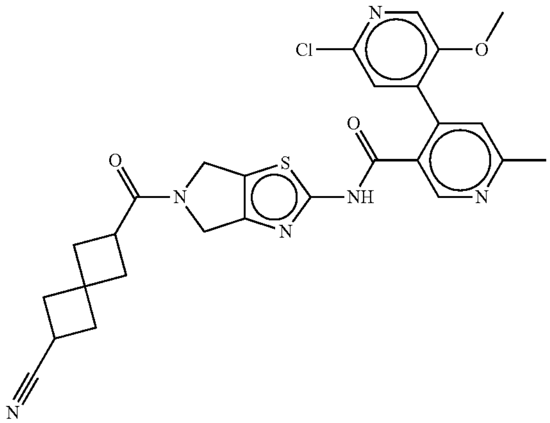 |

TABLE 1-continued

| Compound No. | Name | Structure |
|---|---|---|
| 533 (675) | 4-(6-methoxy-2-methyl-2H-indazol-5-yl)-N-(5-(2-methoxynicotinoyl)-5,6-dihydro-4H-pyrrolo[3,4-d]thiazol-2-yl)-6-methylnicotinamide | 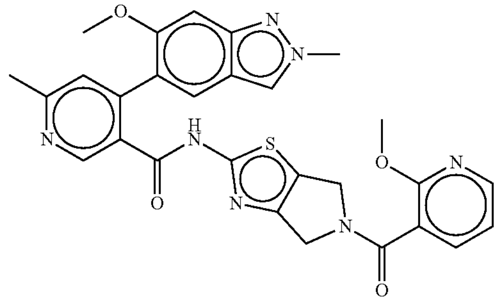 |
| 534 (729) | 2'-chloro-N-(5-(1,5-dimethyl-1H-imidazole-2-carbonyl)-5,6-dihydro-4H-pyrrolo[3,4-d]thiazol-2-yl)-5'-methoxy-6-methyl-[4,4'-bipyridine]-3-carboxamide | 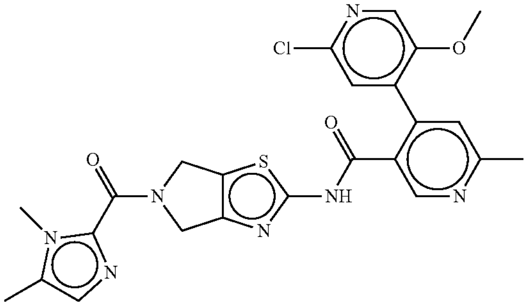 |
| 535 (673) | (Racemic) 2'-chloro-5'-methoxy-6-methyl-N-(5-(spiro[2.2]pentane-1-carbonyl)-5,6-dihydro-4H-pyrrolo[3,4-d]thiazol-2-yl)-[4,4'-bipyridine]-3-carboxamide | 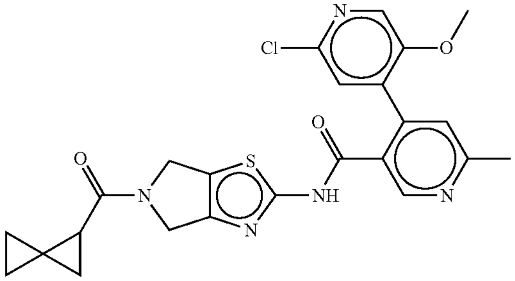 |
| 536 (769) | 2'-chloro-N-(5-(6-chloro-5-methylpicolinoyl)-5,6-dihydro-4H-pyrrolo[3,4-d]thiazol-2-yl)-5'-methoxy-6-methyl-[4,4'-bipyridine]-3-carboxamide | 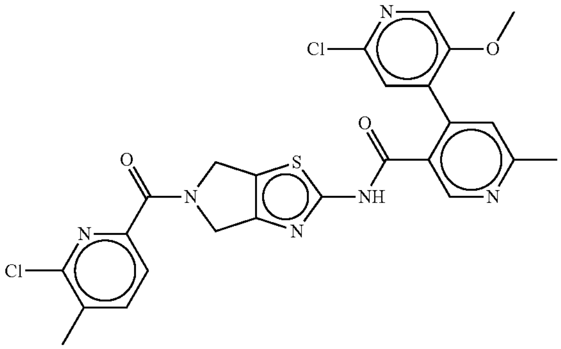 |

TABLE 1-continued

| Compound No. | Name | Structure |
|---|---|---|
| 537 (766) | 2'-chloro-N-(5-(4-chloro-6-(difluoromethyl)picolinoyl)-5,6-dihydro-4H-pyrrolo[3,4-d]thiazol-2-yl)-5'-methoxy-6-methyl-[4,4'-bipyridine]-3-carboxamide | 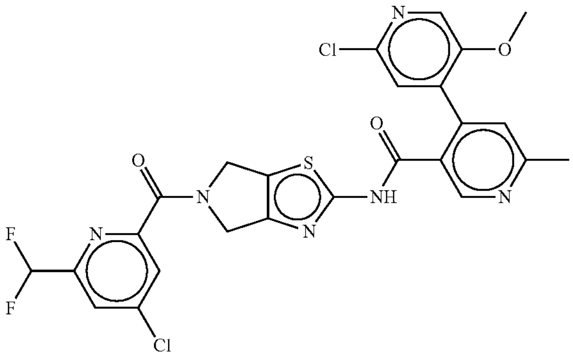 |
| 538 (797) | 4-(5-cyano-2-methoxyphenyl)-N-(5-(6-(difluoromethyl)picolinoyl)-5,6-dihydro-4H-pyrrolo[3,4-d]thiazol-2-yl)-6-methylnicotinamide | 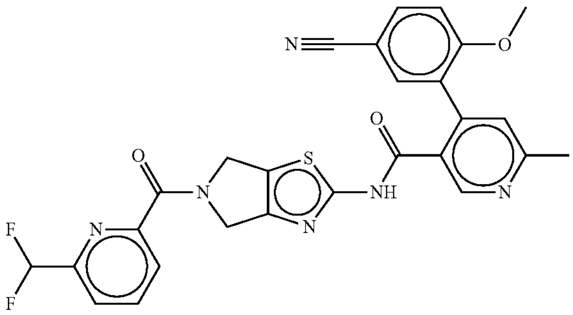 |
| 539 (795) | 5-chloro-N-(5-(6-(difluoromethyl)picolinoyl)-5,6-dihydro-4H-pyrrolo[3,4-d]thiazol-2-yl)-2-methoxy-6'-methyl-[3,4'-bipyridine]-3'-carboxamide | 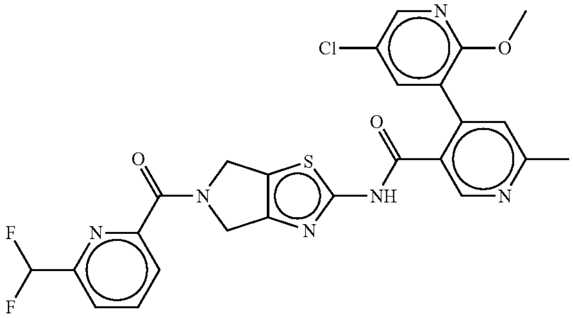 |
| 540 (829) | 5-cyano-N-(5-(5-(difluoromethyl)picolinoyl)-5,6-dihydro-4H-pyrrolo[3,4-d]thiazol-2-yl)-2-methoxy-6'-methyl-[3,4'-bipyridine]-3'-carboxamide | 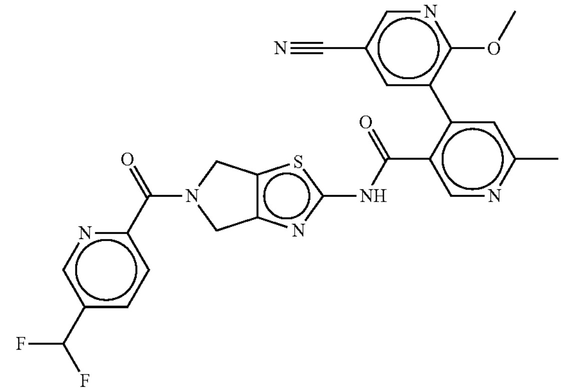 |

TABLE 1-continued

| Compound No. | Name | Structure |
| --- | --- | --- |
| 541 (798) | 2'-chloro-N-(5-(6-(difluoromethyl)pyrazine-2-carbonyl)-5,6-dihydro-4H-pyrrolo[3,4-d]thiazol-2-yl)-5'-methoxy-6-methyl-[4,4'-bipyridine]-3-carboxamide | 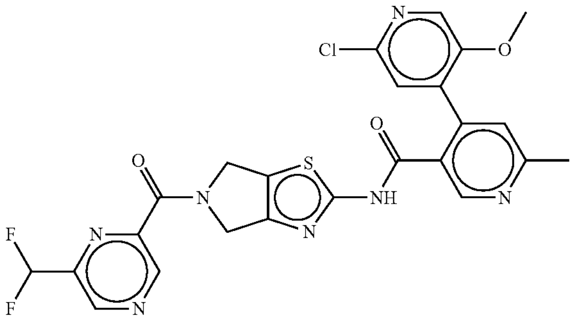 |
| 542 (696) | 2'-chloro-5'-methoxy-6-methyl-N-(5-(pyrimidine-5-carbonyl)-5,6-dihydro-4H-pyrrolo[3,4-d]thiazol-2-y])-[4,4'-bipyridine]-3-carboxamide | 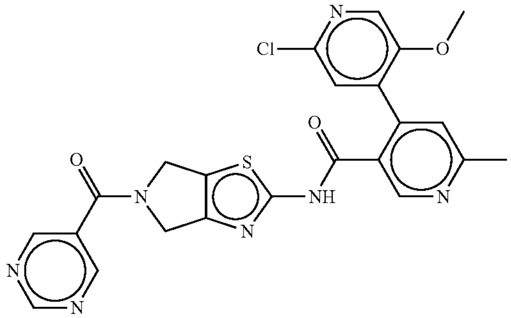 |
| 543 (746) | 2'-chloro-N-(5-(1,4-dimethyl-1H-imidazole-2-carbonyl)-5,6-dihydro-4H-pyrrolo[3,4-d]thiazol-2-yl)-5'-methoxy-6-methyl-[4,4'-bipyridine]-3-carboxamide | 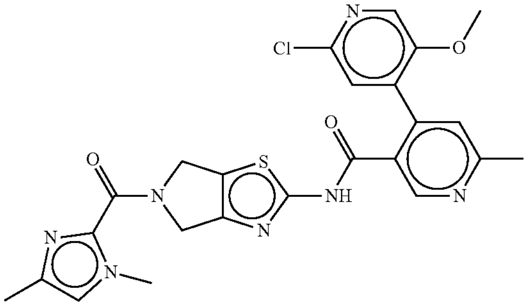 |
| 544 (806) | 2'-chloro-5'-methoxy-N-(5-(5-methoxypyridazine-3-carbonyl)-5,6-dihydro-4H-pyrrolo[3,4-d]thiazol-2-yl)-6-methyl-[4,4'-bipyridine]-3-carboxamide | 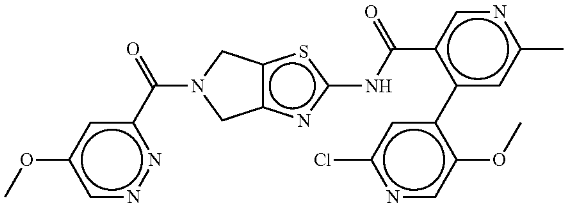 |
| 545 (807) | 2'-chloro-5'-methoxy-N-(5-(6-methoxypyridazine-3-carbonyl)-5,6-dihydro-4H-pyrrolo[3,4-d]thiazol-2-yl)-6-methyl-[4,4'-bipyridine]-3-carboxamide | 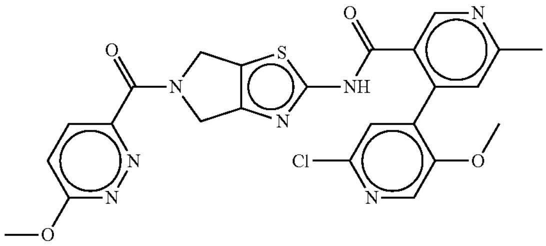 |

TABLE 1-continued

| Compound No. | Name | Structure |
|---|---|---|
| 546 (694) | 2'-chloro-N-(5-(1,2-dimethyl-1H-imidazole-5-carbonyl)-5,6-dihydro-4H-pyrrolo[3,4-d]thiazol-2-yl)-5'-methoxy-6-methyl-[4,4'-bipyridine]-3-carboxamide | 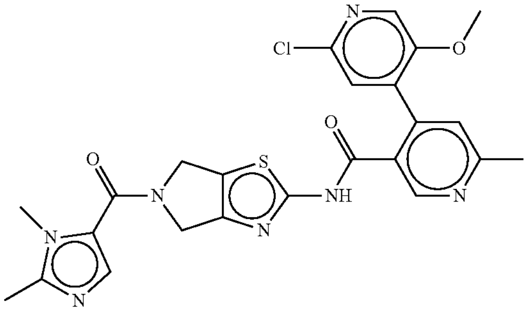 |
| 547 (757) | (Racemic) 2'-chloro-N-(5-(3-(difluoromethoxy)cyclohexane-1-carbonyl)-5,6-dihydro-4H-pyrrolo[3,4-d]thiazol-2-yl)-5'-methoxy-6-methyl-[4,4'-bipyridine]-3-carboxamide | 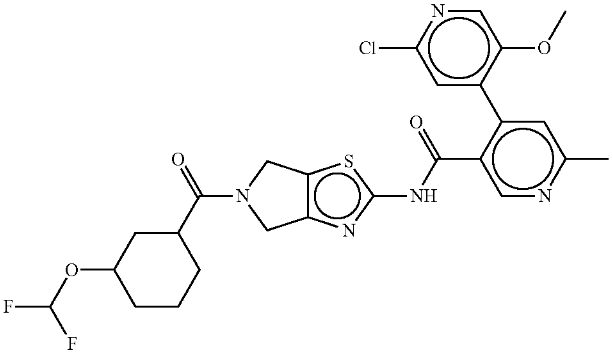 |
| 548 (886) | 2'-chloro-N-(5-(6-(difluoromethyl)-3-fluoropicolinoyl)-5,6-dihydro-4H-pyrrolo[3,4-d]thiazol-2-yl)-5'-methoxy-6-methyl-[4,4'-bipyridine]-3-carboxamide | 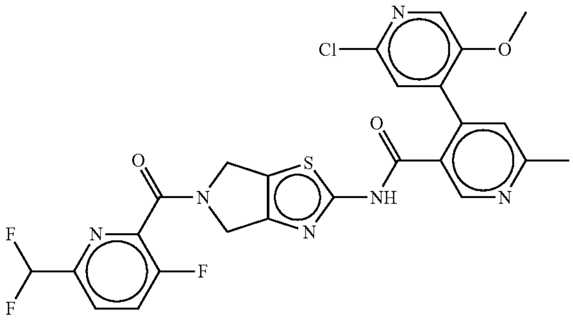 |
| 549 (885) | 2'-chloro-N-(5-(4-chloro-6-(difluoromethoxy)pyridazine-3-carbonyl)-5,6-dihydro-4H-pyrrolo[3,4-d]thiazol-2-yl)-5'-methoxy-6-methyl-[4,4'-bipyridine]-3-carboxamide | 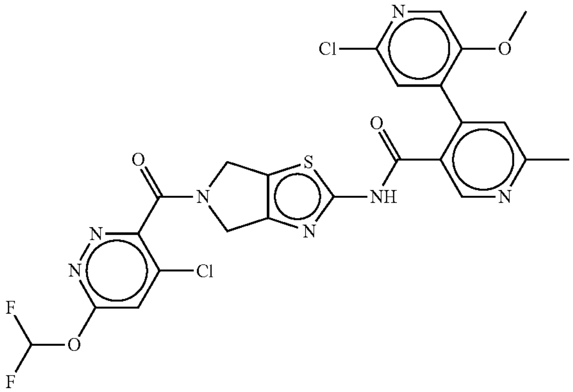 |

TABLE 1-continued

| Compound No. | Name | Structure |
|---|---|---|
| 550 (884) | 2'-chloro-N-(5-(2-(difluoromethyl)pyrimidine-4-carbonyl)-5,6-dihydro-4H-pyrrolo[3,4-d]thiazol-2-yl)-5'-methoxy-6-methyl-[4,4'-bipyridine]-3-carboxamide | 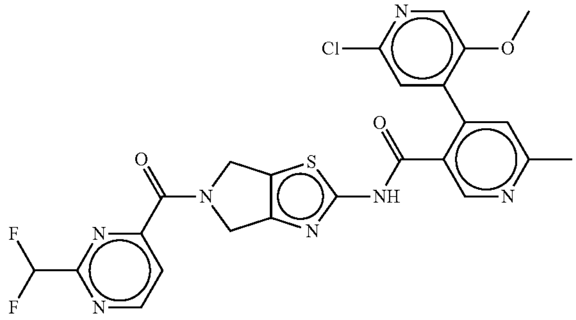 |
| 551 (883) | 2'-chloro-N-(5-(6-(difluoromethyl)pyrimidine-4-carbonyl)-5,6-dihydro-4H-pyrrolo[3,4-d]thiazol-2-yl)-5'-methoxy-6-methyl-[4,4'-bipyridine]-3-carboxamide | 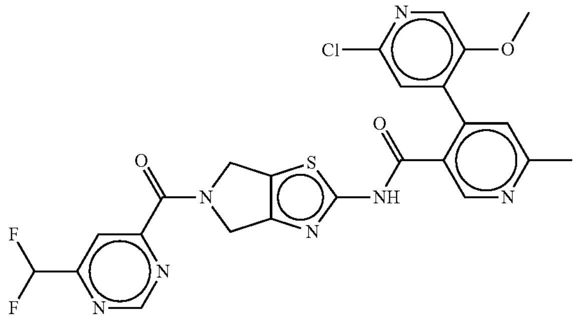 |
| 552 (882) | 2'-chloro-5'-methoxy-N-(5-(6-methoxybenzo[d]oxazole-2-carbonyl)-5,6-dihydro-4H-pyrrolo[3,4-d]thiazol-2-yl)-6-methyl-[4,4'-bipyridine]-3-carboxamide | 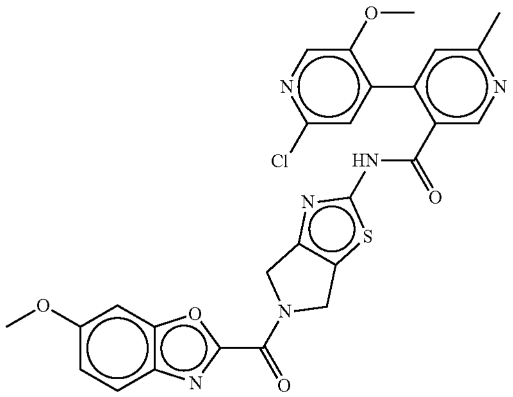 |
| 553 (881) | 2'-chloro-N-(5-(6-(1,1-difluoroethyl)picolinoyl)-5,6-dihydro-4H-pyrrolo[3,4-d]thiazol-2-yl)-5'-methoxy-6-methyl-[4,4'-bipyridine]-3-carboxamide | 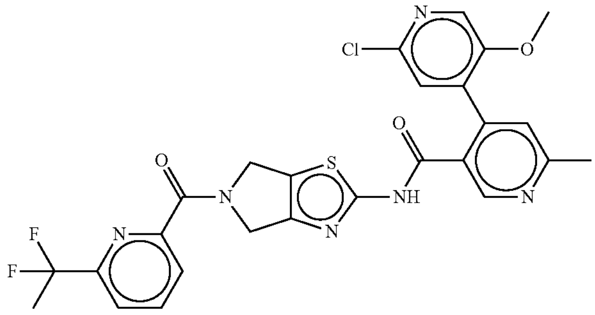 |

TABLE 1-continued

| Compound No. | Name | Structure |
|---|---|---|
| 554 (880) | 2'-chloro-N-(5-(5-(difluoromethoxy)pyrimidine-2-carbonyl)-5,6-dihydro-4H-pyrrolo[3,4-d]thiazol-2-yl)-5'-methoxy-6-methyl-[4,4'-bipyridine]-3-carboxamide | 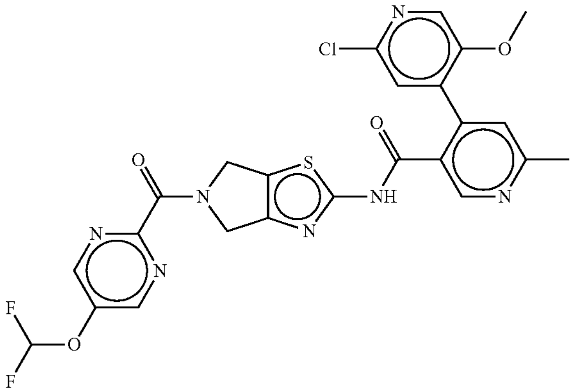 |
| 555 (879) | 2'-chloro-N-(5-(6-chloro-3-methylpyrazine-2-carbonyl)-5,6-dihydro-4H-pyrrolo[3,4-d]thiazol-2-yl)-5'-methoxy-6-methyl-[4,4'-bipyridine]-3-carboxamide | 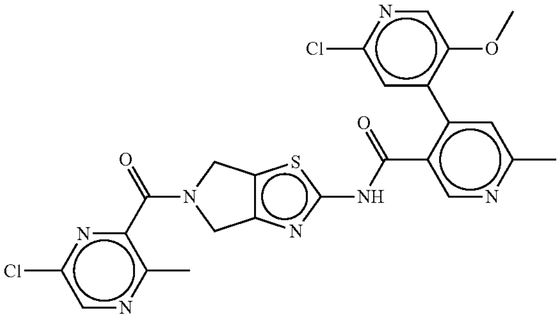 |
| 556 (878) | 2'-chloro-N-(5-(2-chloro-5-(difluoromethyl)benzoyl)-5,6-dihydro-4H-pyrrolo[3,4-d]thiazol-2-yl)-5'-methoxy-6-methyl-[4,4'-bipyridine]-3-carboxamide | 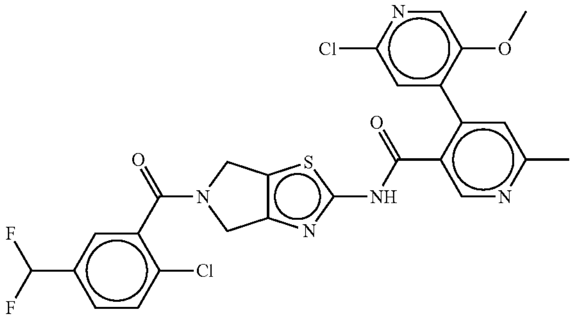 |
| 557 (877) | 2'-chloro-N-(5-(3-(difluoromethyl)-4-methoxybenzoyl)-5,6-dihydro-4H-pyrrolo[3,4-d]thiazol-2-yl)-5'-methoxy-6-methyl-[4,4'-bipyridine]-3-carboxamide | 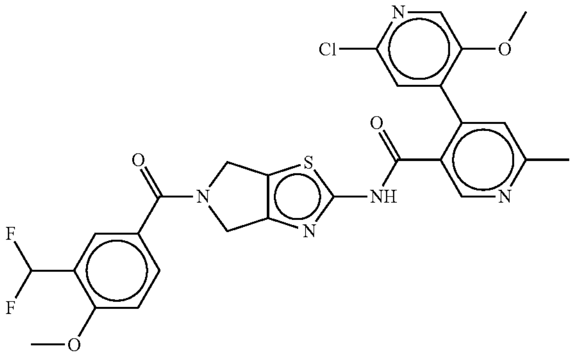 |

TABLE 1-continued

| Compound No. | Name | Structure |
|---|---|---|
| 558 (876) | N-(5-(2-chloro-5-(difluoromethyl)benzoyl)-5,6-dihydro-4H-pyrrolo[3,4-d]thiazol-2-yl)-4-(5-cyano-2-methoxyphenyl)-6-methylnicotinamide | 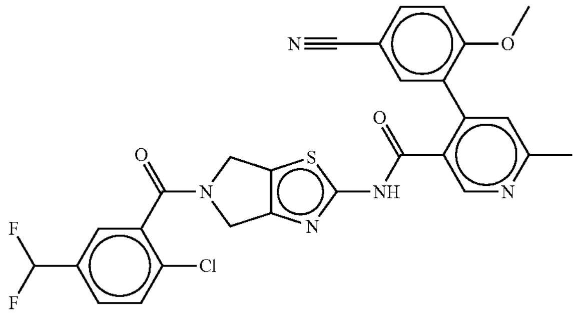 |
| 559 (875) | 2'-chloro-N-(5-(5-(difluoromethyl)-3-methylpicolinoyl)-5,6-dihydro-4H-pyrrolo[3,4-d]thiazol-2-yl)-5'-methoxy-6-methyl-[4,4'-bipyridine]-3-carboxamide | 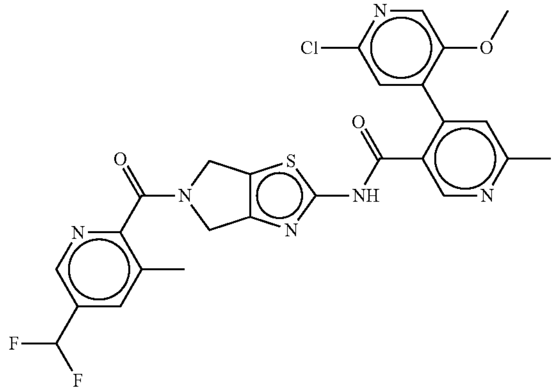 |
| 560 (874) | 2'-chloro-N-(5-(2-chloro-5-methylnicotinoyl)-5,6-dihydro-4H-pyrrolo[3,4-d]thiazol-2-yl)-5'-methoxy-6-methyl-[4,4'-bipyridine]-3-carboxamide | 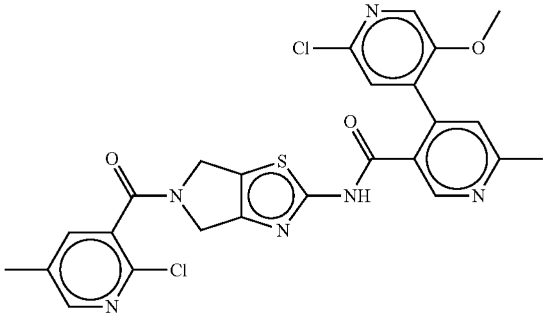 |
| 561 (873) | 2'-chloro-N-(5-(5-chloro-2-methylisonicotinoyl)-5,6-dihydro-4H-pyrrolo[3,4-d]thiazol-2-yl)-5'-methoxy-6-methyl-[4,4'-bipyridine]-3-carboxamide | 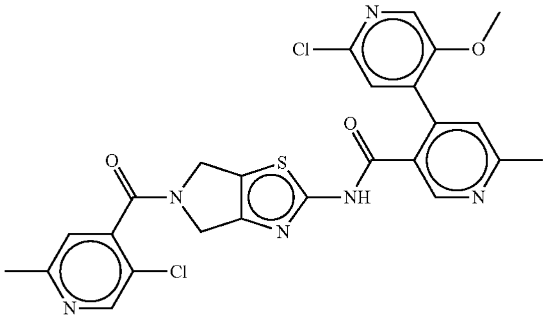 |

TABLE 1-continued

| Compound No. | Name | Structure |
|---|---|---|
| 562 (872) | 2'-chloro-N-(5-(5-chloro-2-methylnicotinoyl)-5,6-dihydro-4H-pyrrolo[3,4-d]thiazol-2-yl)-5'-methoxy-6-methyl-[4,4'-bipyridine]-3-carboxamide | 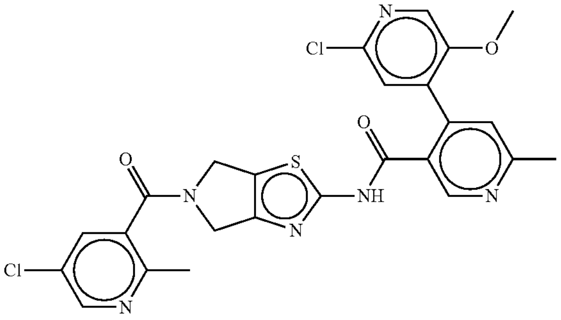 |
| 563 (871) | 2'-chloro-N-(5-(3,6-dimethylpicolinoyl)-5,6-dihydro-4H-pyrrolo[3,4-d]thiazol-2-yl)-5'-methoxy-6-methyl-[4,4'-bipyridine]-3-carboxamide | 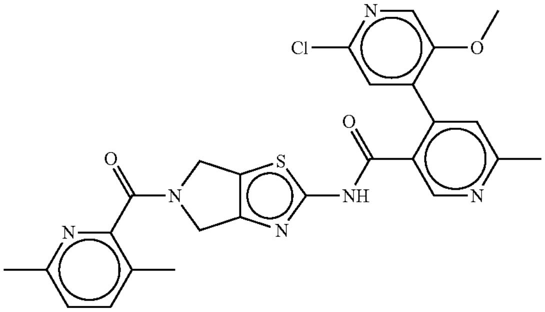 |
| 564 (870) | 2'-chloro-N-(5-(2,5-dimethylisonicotinoyl)-5,6-dihydro-4H-pyrrolo[3,4-d]thiazol-2-yl)-5'-methoxy-6-methyl-[4,4'-bipyridine]-3-carboxamide | 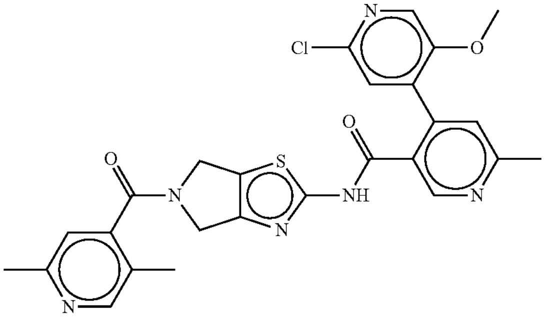 |
| 565 (869) | 2'-chloro-N-(5-(3-(difluoromethyl)-5-fluorobenzoyl)-5,6-dihydro-4H-pyrrolo[3,4-d]thiazol-2-yl)-5'-methoxy-6-methyl-[4,4'-bipyridine]-3-carboxamide | 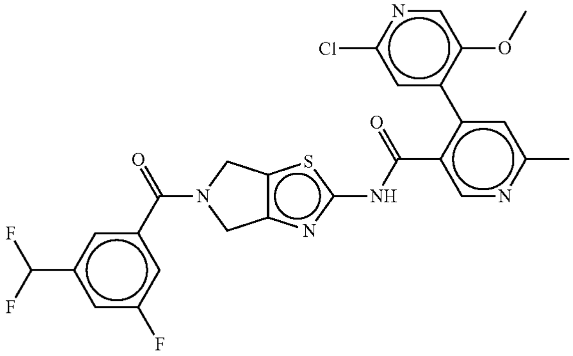 |

TABLE 1-continued

| Compound No. | Name | Structure |
|---|---|---|
| 566 (868) | 4-(5-cyano-2-methoxyphenyl)-N-(5-(3-(difluoromethyl)-4-methoxybenzoyl)-5,6-dihydro-4H-pyrrolo[3,4-d]thiazol-2-yl)-6-methylnicotinamide | 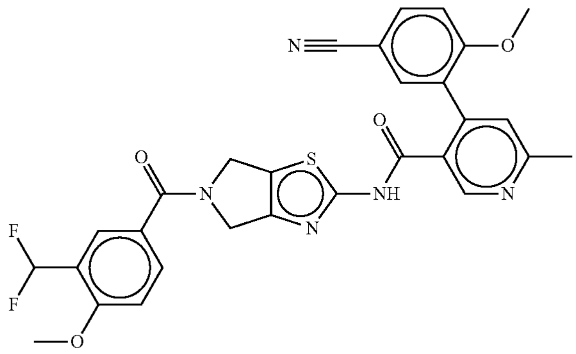 |
| 567 (867) | 2'-chloro-N-(5-(3-chloro-5-methylpyrazine-2-carbonyl)-5,6-dihydro-4H-pyrrolo[3,4-d]thiazol-2-yl)-5'-methoxy-6-methyl-[4,4'-bipyridine]-3-carboxamide | 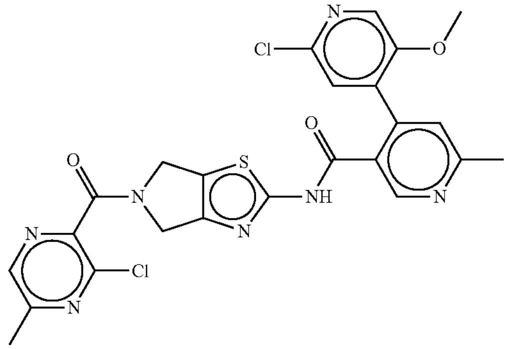 |
| 568 (866) | 2'-chloro-N-(5-(2-chloro-5-methylisonicotinoyl)-5,6-dihydro-4H-pyrrolo[3,4-d]thiazol-2-yl)-5'-methoxy-6-methyl-[4,4'-bipyridine]-3-carboxamide | 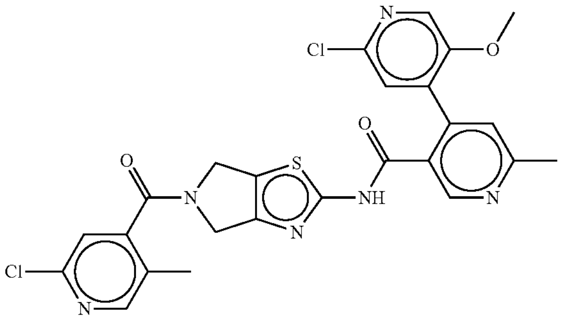 |
| 569 (865) | 2'-chloro-5'-methoxy-N-(5-(3-methoxy-6-methylpyrazine-2-carbonyl)-5,6-dihydro-4H-pyrrolo[3,4-d]thiazol-2-yl)-6-methyl-[4,4'-bipyridine]-3-carboxamide | 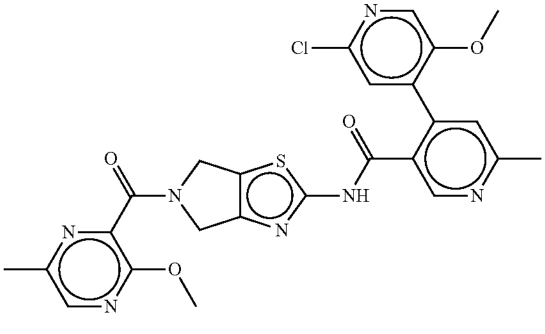 |
| 570 (864) | 4-(5-cyano-2-methoxyphenyl)-N-(5-(5-(difluoromethyl)-2-methoxybenzoyl)-5,6-dihydro-4H-pyrrolo[3,4-d]thiazol-2-yl)-6-methylnicotinamide | 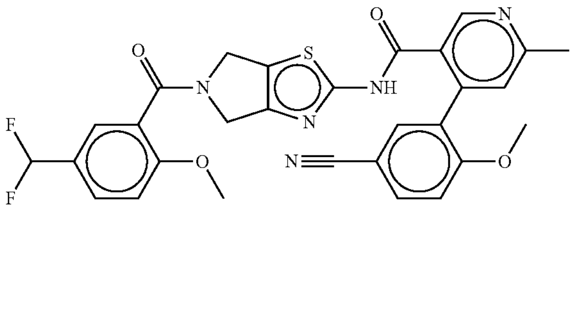 |

TABLE 1-continued

| Compound No. | Name | Structure |
|---|---|---|
| 571 (863) | 2'-chloro-N-(5-(5-(difluoromethyl)-6-methylpicolinoyl)-5,6-dihydro-4H-pyrrolo[3,4-d]thiazol-2-yl)-5'-methoxy-6-methyl-[4,4'-bipyridine]-3-carboxamide | 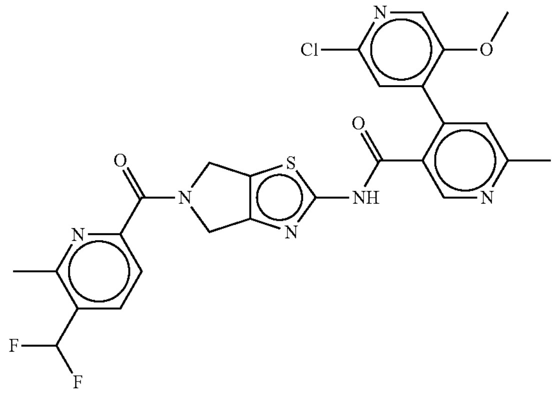 |
| 572 (862) | 4-(5-cyano-2-methoxyphenyl)-N-(5-(3-(difluoromethyl)-5-fluorobenzoyl)-5,6-dihydro-4H-pyrrolo[3,4-d]thiazol-2-yl)-6-methylnicotinamide | 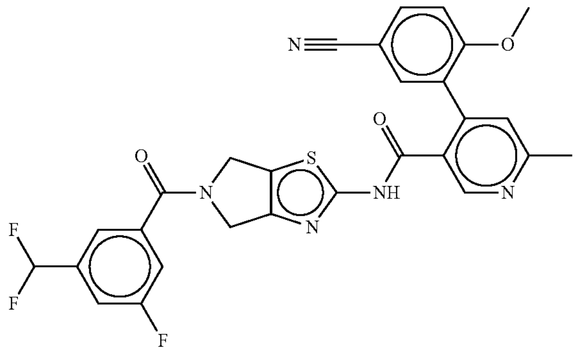 |
| 573 (861) | 2'-chloro-N-(5-(6-cyanopicolinoyl)-5,6-dihydro-4H-pyrrolo[3,4-d]thiazol-2-yl)-5'-methoxy-6-methyl-[4,4'-bipyridine]-3-carboxamide | 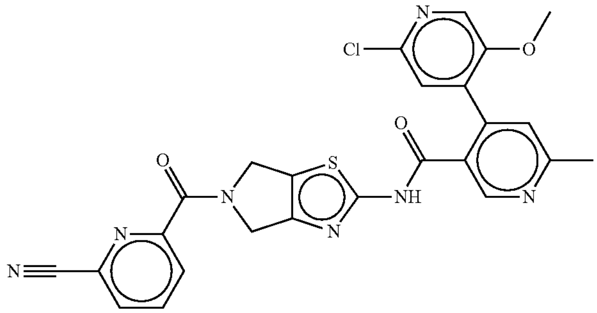 |
| 574 (860) | 2'-chloro-N-(5-(5-cyano-3-methylpicolinoyl)-5,6-dihydro-4H-pyrrolo[3,4-d]thiazol-2-yl)-5'-methoxy-6-methyl-[4,4'-bipyridine]-3-carboxamide | 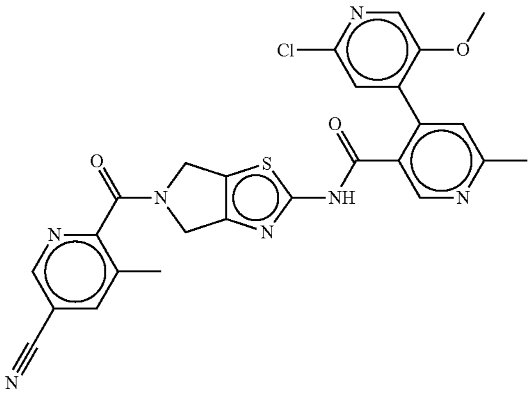 |

TABLE 1-continued

| Compound No. | Name | Structure |
|---|---|---|
| 575 (859) | 2'-chloro-N-(5-(6-(difluoromethyl)-3-methylpicolinoyl)-5,6-dihydro-4H-pyrrolo[3,4-d]thiazol-2-yl)-5'-methoxy-6-methyl-[4,4'-bipyridine]-3-carboxamide | 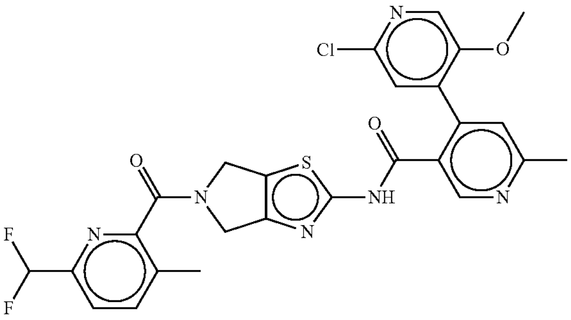 |
| 576 (858) | N-(5-(3-chloro-4-(difluoromethyl)benzoyl)-5,6-dihydro-4H-pyrrolo[3,4-d]thiazol-2-yl)-4-(5-cyano-2-methoxyphenyl)-6-methylnicotinamide | 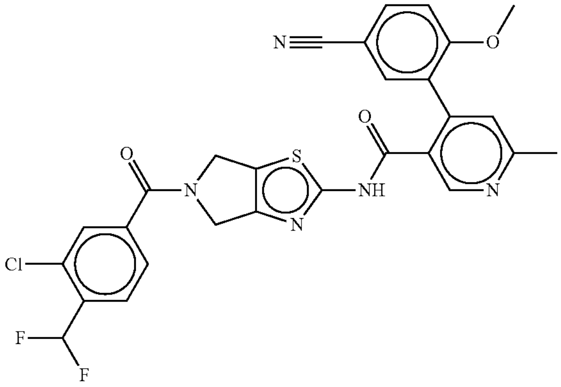 |
| 577 (857) | 2'-chloro-N-(5-(3-(difluoromethyl)-2-fluorobenzoyl)-5,6-dihydro-4H-pyrrolo[3,4-d]thiazol-2-yl)-5'-methoxy-6-methyl-[4,4'-bipyridine]-3-carboxamide | 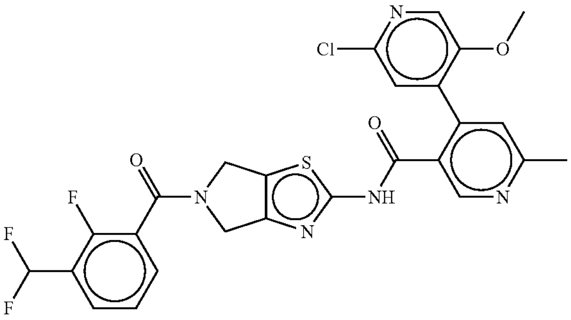 |
| 578 (856) | 2'-chloro-N-(5-(5-cyanopicolinoyl)-5,6-dihydro-4H-pyrrolo[3,4-d]thiazol-2-yl)-5'-methoxy-6-methyl-[4,4'-bipyridine]-3-carboxamide | 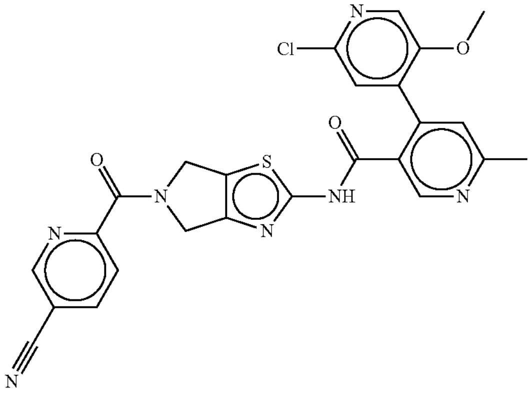 |

TABLE 1-continued

| Compound No. | Name | Structure |
|---|---|---|
| 579 (855) | 2'-chloro-N-(5-(5-chloro-3-(difluoromethyl)picolinoyl)-5,6-dihydro-4H-pyrrolo[3,4-d]thiazol-2-yl)-5'-methoxy-6-methyl-[4,4'-bipyridine]-3-carboxamide | 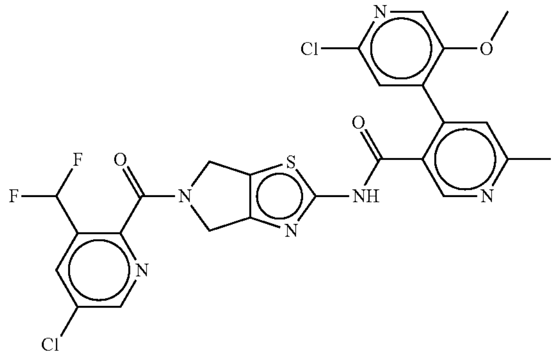 |
| 580 (854) | 4-(S-cyano-2-methoxyphenyl)-N-(5-(4-(difluoromethyl)-2-methoxybenzoyl)-5,6-dihydro-4H-pyrrolo[3,4-d]thiazol-2-yl)-6-methylnicotinamide | 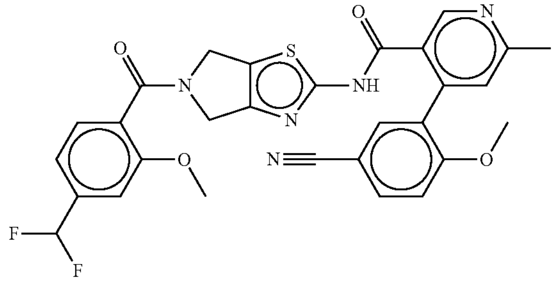 |
| 581 (853) | 2'-chloro-N-(5-(5-(difluoromethyl)-2-methoxybenzoyl)-5,6-dihydro-4H-pyrrolo[3,4-d]thiazol-2-yl)-5'-methoxy-6-methyl-[4,4'-bipyridine]-3-carboxamide | 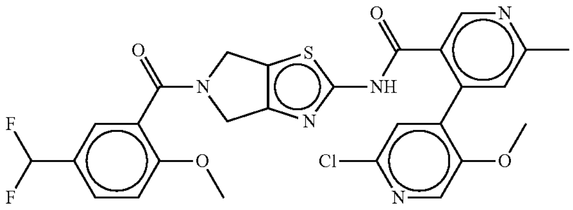 |
| 582 (852) | 2'-chloro-N-(5-(3-chloro-5-(difluoromethoxy)picolinoyl)-5,6-dihydro-4H-pyrrolo[3,4-d]thiazol-2-yl)-5'-methoxy-6-methyl-[4,4'-bipyridine]-3-carboxamide | 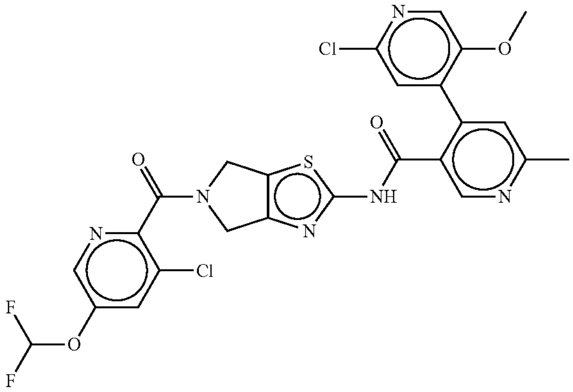 |
| 583 (851) | 2'-chloro-5'-methoxy-6-methyl-N-(5-(pyrazolo[1,5-a]pyrimidine-5-carbonyl)-5,6-dihydro-4H-pyrrolo[3,4-d]thiazol-2-yl)-[4,4'-bipyridine]-3-carboxamide | 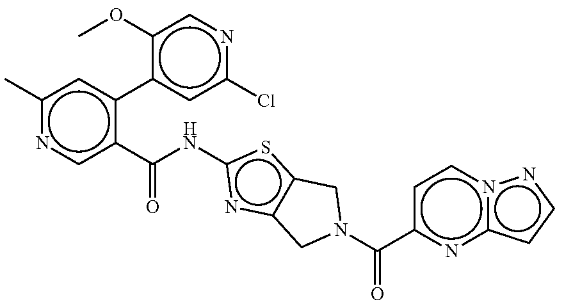 |

TABLE 1-continued

| Compound No. | Name | Structure |
|---|---|---|
| 584 (850) | 2'-chloro-N-(5-(6-chloro-5-(difluoromethyl)picolinoyl)-5,6-dihydro-4H-pyrrolo[3,4-d]thiazol-2-yl)-5'-methoxy-6-methyl-[4,4'-bipyridine]-3-carboxamide | 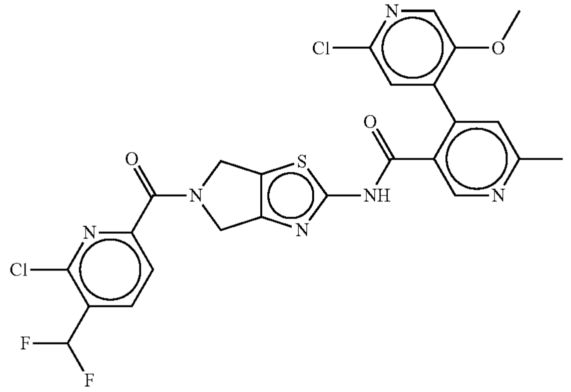 |
| 585 (849) | 2'-chloro-N-(5-(5-(difluoromethyl)-6-methylpyrazine-2-carbonyl)-5,6-dihydro-4H-pyrrolo[3,4-d]thiazol-2-yl)-5'-methoxy-6-methyl-[4,4'-bipyridine]-3-carboxamide | 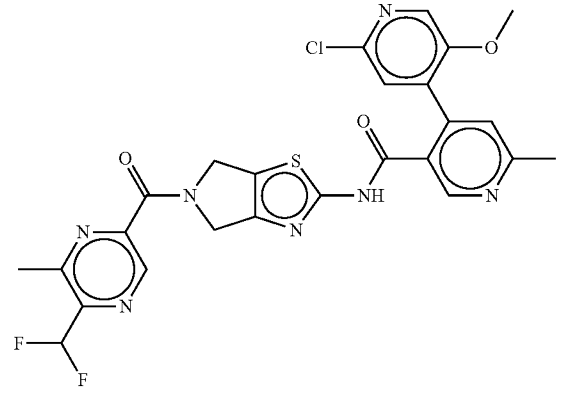 |
| 586 (848) | 2'-chloro-N-(5-(5-(difluoromethyl)-6-methoxypicolinoyl)-5,6-dihydro-4H-pyrrolo[3,4-d]thiazol-2-yl)-5'-methoxy-6-methyl-[4,4'-bipyridine]-3-carboxamide | 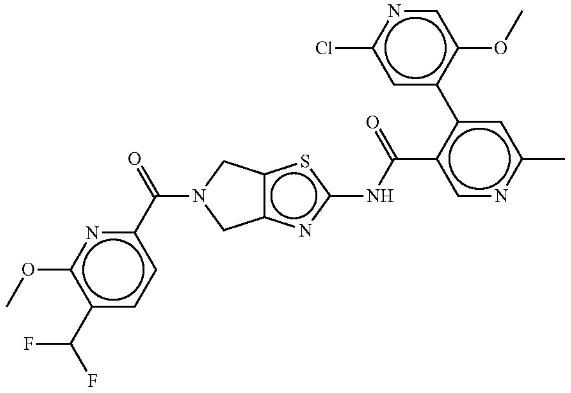 |
| 587 (847) | 4-(5-cyano-2-methoxyphenyl)-N-(5-(4-(difluoromethyl)-2-fluorobenzoyl)-5,6-dihydro-4H-pyrrolo[3,4-d]thiazol-2-yl)-6-methylnicotinamide | 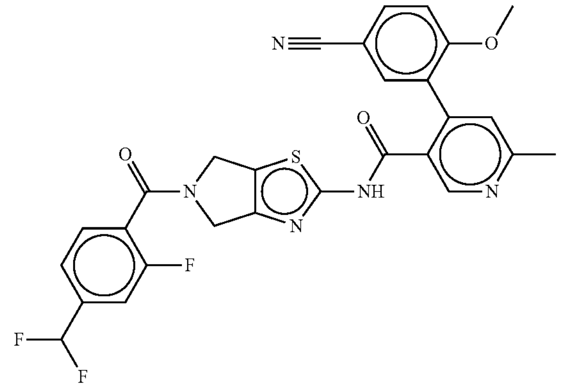 |

TABLE 1-continued

| Compound No. | Name | Structure |
|---|---|---|
| 588 (846) | 2'-chloro-N-(5-(4-chloro-6-(difluoromethoxy)nicotinoyl)-5,6-dihydro-4H-pyrrolo[3,4-d]thiazol-2-yl)-5'-methoxy-6-methyl-[4,4'-bipyridine]-3-carboxamide | 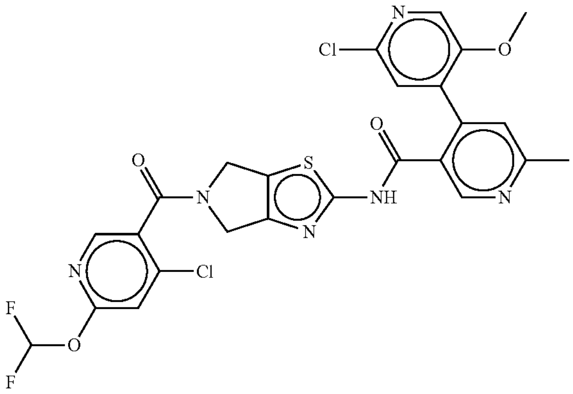 |
| 589 (845) | 4-(5-cyano-2-methoxyphenyl)-N-(5-(3-(difluoromethyl)-2-fluorobenzoyl)-5,6-dihydro-4H-pyrrolo[3,4-d]thiazol-2-yl)-6-methylnicotinamide | 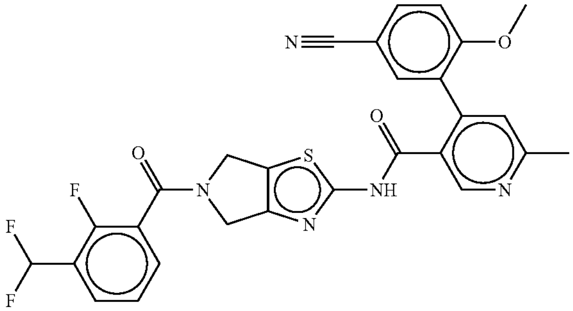 |
| 590 (844) | 2'-chloro-N-(5-(3-cyanopicolinoyl)-5,6-dihydro-4H-pyrrolo[3,4-d]thiazol-2-yl)-5'-methoxy-6-methyl-[4,4'-bipyridine]-3-carboxamide | 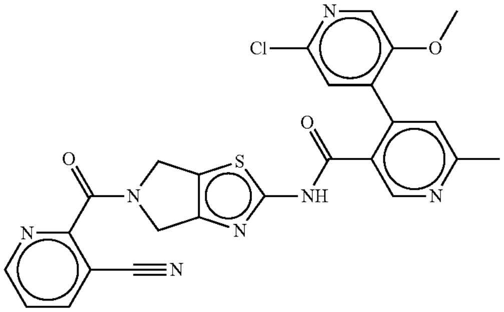 |
| 591 (843) | 2'-chloro-N-(5-(4-(difluoromethyl)-2-methoxybenzoyl)-5,6-dihydro-4H-pyrrolo[3,4-d]thiazol-2-yl)-5'-methoxy-6-methyl-[4,4'-bipyridine]-3-carboxamide | 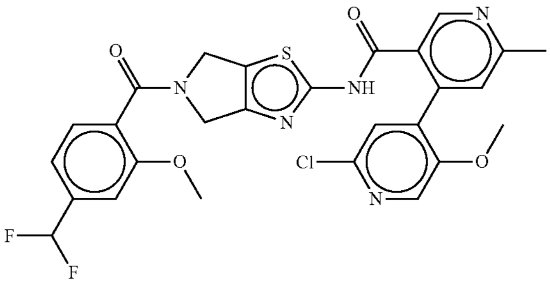 |

TABLE 1-continued

| Compound No. | Name | Structure |
|---|---|---|
| 592 (842) | 2'-chloro-N-(5-(6-(difluoromethoxy)-2-methylnicotinoyl)-5,6-dihydro-4H-pyrrolo[3,4-d]thiazol-2-yl)-5'-methoxy-6-methyl-[4,4'-bipyridine]-3-carboxamide | 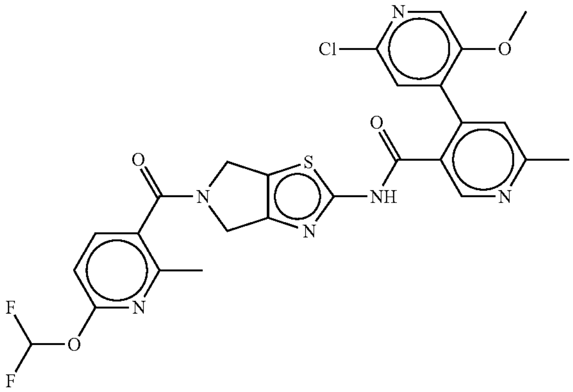 |
| 593 (841) | 2'-chloro-N-(5-(6-(difluoromethoxy)-4-methylnicotinoyl)-5,6-dihydro-4H-pyrrolo[3,4-d]thiazol-2-yl)-5'-methoxy-6-methyl-[4,4'-bipyridine]-3-carboxamide | 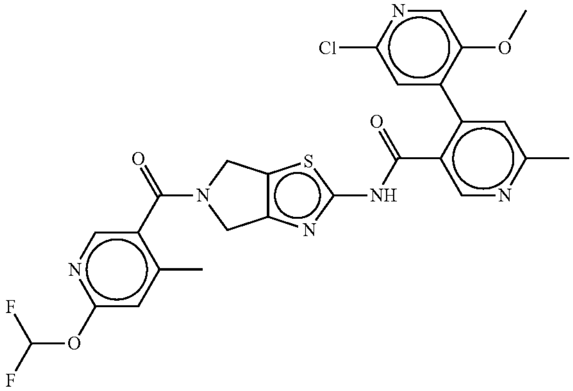 |
| 594 (840) | 2'-chloro-N-(5-(5-(difluoromethyl)-3-fluoropicolinoyl)-5,6-dihydro-4H-pyrrolo[3,4-d]thiazol-2-yl)-5'-methoxy-6-methyl-[4,4'-bipyridine]-3-carboxamide | 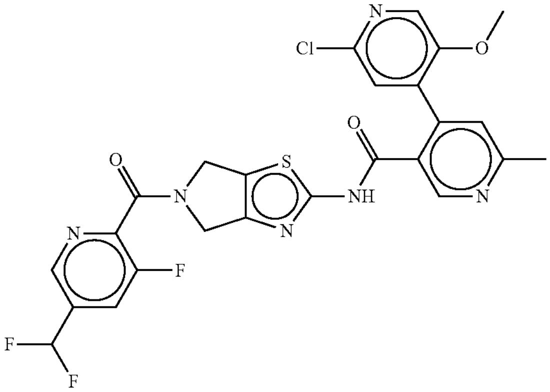 |
| 595 (839) | 2'-chloro-N-(5-(5-chloro-3-(1,1-difluoroethyl)picolinoyl)-5,6-dihydro-4H-pyrrolo[3,4-d]thiazol-2-yl)-5'-methoxy-6-methyl-[4,4'-bipyridine]-3-carboxamide | 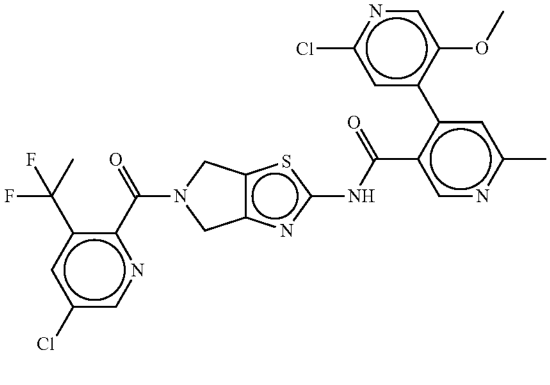 |

TABLE 1-continued

| Compound No. | Name | Structure |
|---|---|---|
| 596 (838) | 2'-chloro-N-(5-(5-(1,1-difluoroethyl)picolinoyl)-5,6-dihydro-4H-pyrrolo[3,4-d]thiazol-2-yl)-5'-methoxy-6-methyl-[4,4'-bipyridine]-3-carboxamide | 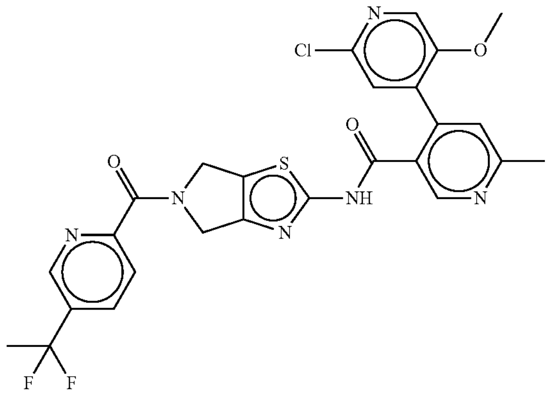 |
| 597 (837) | 2'-chloro-N-(5-(5-(difluoromethoxy)-3-methylpicolinoyl)-5,6-dihydro-4H-pyrrolo[3,4-d]thiazol-2-yl)-5'-methoxy-6-methyl-[4,4'-bipyridine]-3-carboxamide | 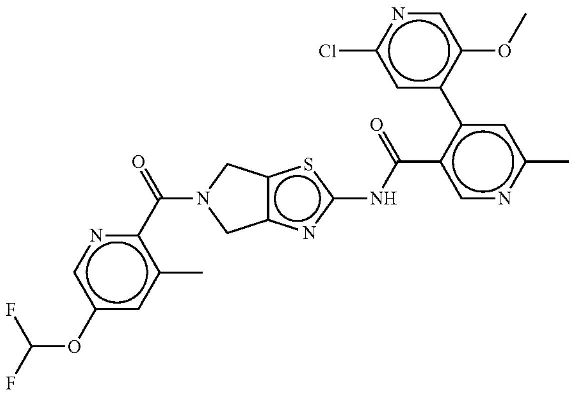 |
| 598 (836) | 2'-chloro-N-(5-(5-chloro-4-methoxypyrimidine-2-carbonyl)-5,6-dihydro-4H-pyrrolo[3,4-d]thiazol-2-yl)-5'-methoxy-6-methyl-[4,4'-bipyridine]-3-carboxamide | 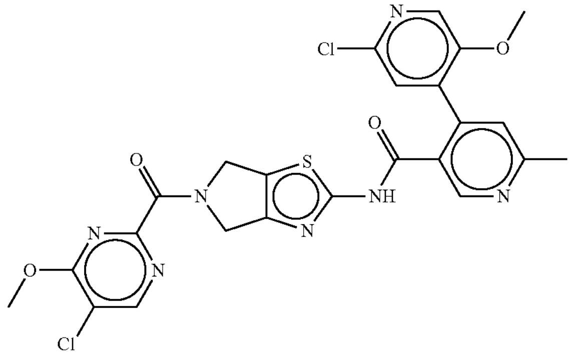 |
| 599 (899) | 2'-chloro-N-(5-(6-(difluoromethoxy)pyridazine-3-carbonyl)-5,6-dihydro-4H-pyrrolo[3,4-d]thiazol-2-yl)-5'-methoxy-6-methyl-[4,4'-bipyridine]-3-carboxamide | 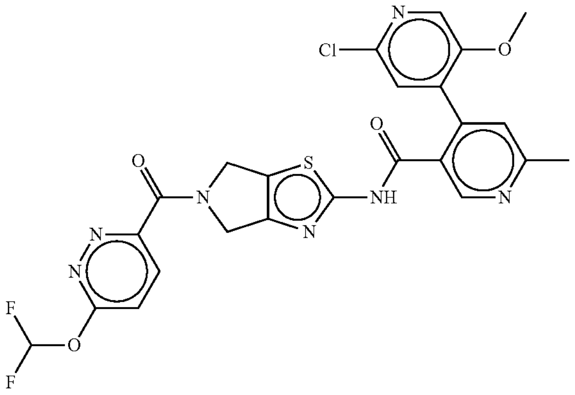 |

TABLE 1-continued

| Compound No. | Name | Structure |
|---|---|---|
| 600 (898) | 2'-chloro-N-(5-(5-chloro-4-(difluoromethyl)pyrimidine-2-carbonyl)-5,6-dihydro-4H-pyrrolo[3,4-d]thiazol-2-yl)-5'-methoxy-6-methyl-[4,4'-bipyridine]-3-carboxamide | 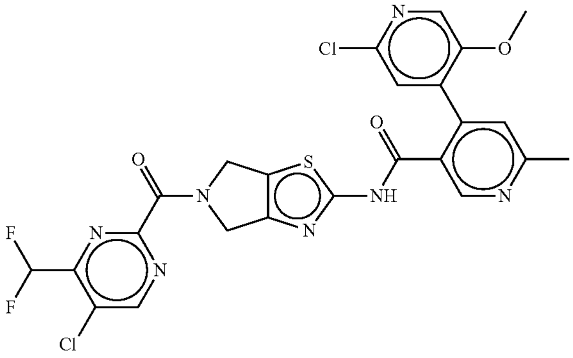 |
| 601 (897) | 2'-chloro-N-(5-(5-cyano-6-methylpicolinoyl)-5,6-dihydro-4H-pyrrolo[3,4-d]thiazol-2-yl)-5'-methoxy-6-methyl-[4,4'-bipyridine]-3-carboxamide | 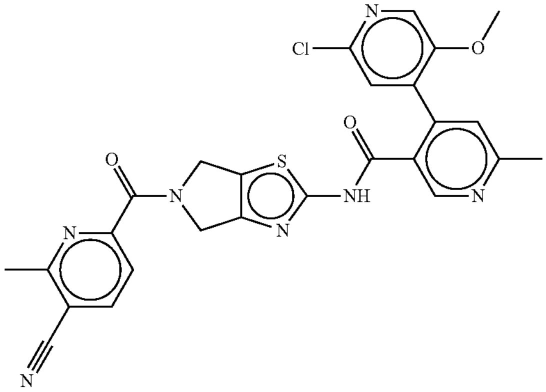 |
| 602 (896) | 2'-chloro-N-(5-(6-chloro-3-(difluoromethyl)picolinoyl)-5,6-dihydro-4H-pyrrolo[3,4-d]thiazol-2-yl)-5'-methoxy-6-methyl-[4,4'-bipyridine]-3-carboxamide | 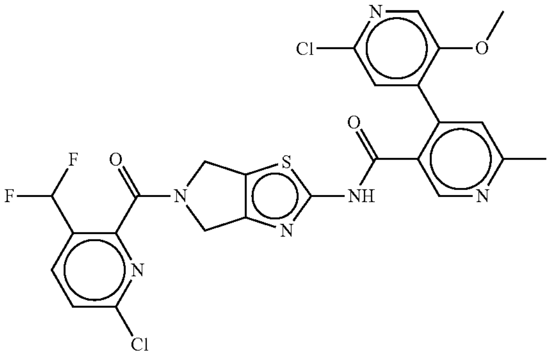 |
| 603 (895) | 2'-chloro-N-(5-(5-(difluoromethyl)-3-methylpyrazine-2-carbonyl)-5,6-dihydro-4H-pyrrolo[3,4-d]thiazol-2-yl)-5'-methoxy-6-methyl-[4,4'-bipyridine]-3-carboxamide | 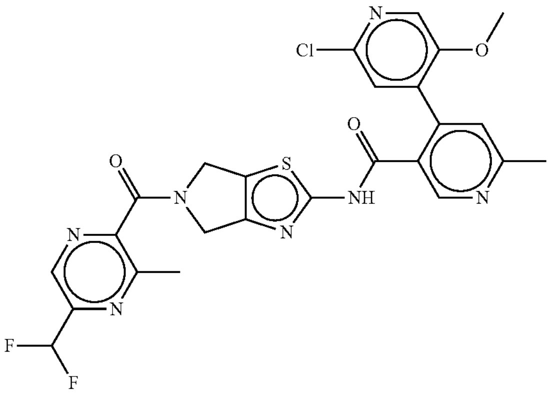 |

TABLE 1-continued

| Compound No. | Name | Structure |
|---|---|---|
| 604 (894) | 2'-chloro-N-(5-(2,5-dimethylnicotinoyl)-5,6-dihydro-4H-pyrrolo[3,4-d]thiazol-2-yl)-5'-methoxy-6-methyl-[4,4'-bipyridine]-3-carboxamide | 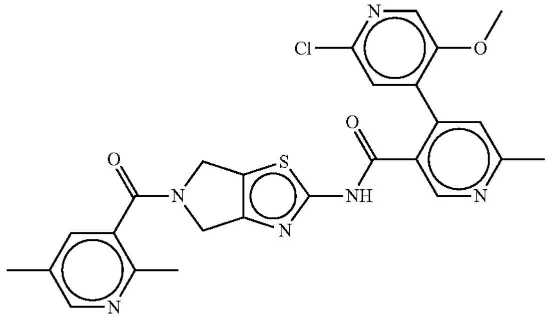 |
| 605 (893) | 2'-chloro-N-(5-(6-chloro-5-methoxy-3-methylpyrazine-2-carbonyl)-5,6-dihydro-4H-pyrrolo[3,4-d]thiazol-2-yl)-5'-methoxy-6-methyl-[4,4'-bipyridine]-3-carboxamide | 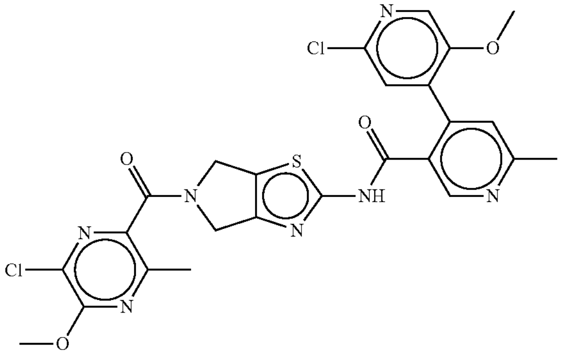 |
| 606 (892) | 2'-chloro-N-(5-(3-(difluoromethyl)-6-methoxypicolinoyl)-5,6-dihydro-4H-pyrrolo[3,4-d]thiazol-2-yl)-5'-methoxy-6-methyl-[4,4'-bipyridine]-3-carboxamide | 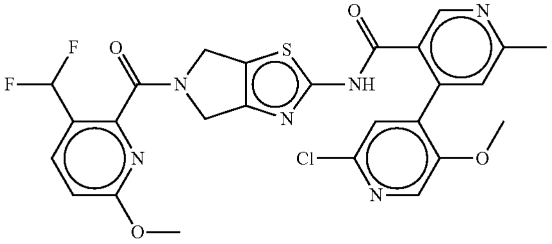 |
| 607 (891) | 2'-chloro-N-(5-(3-chloro-5-cyanopicolinoyl)-5,6-dihydro-4H-pyrrolo[3,4-d]thiazol-2-yl)-5'-methoxy-6-methyl-[4,4'-bipyridine]-3-carboxamide | 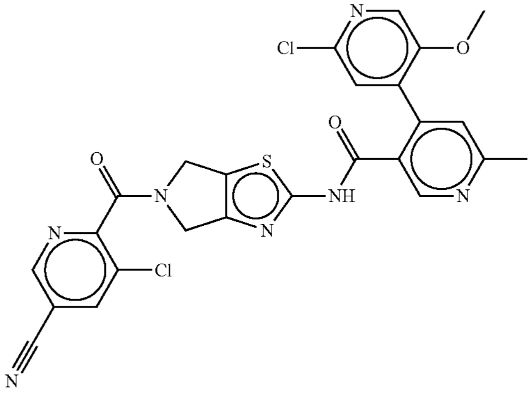 |

TABLE 1-continued

| Compound No. | Name | Structure |
|---|---|---|
| 608 (890) | 2'-chloro-N-(5-(6-(difluoromethyl)-3-methylpyrazine-2-carbonyl)-5,6-dihydro-4H-pyrrolo[3,4-d]thiazol-2-yl)-5'-methoxy-6-methyl-[4,4'-bipyridine]-3-carboxamide | 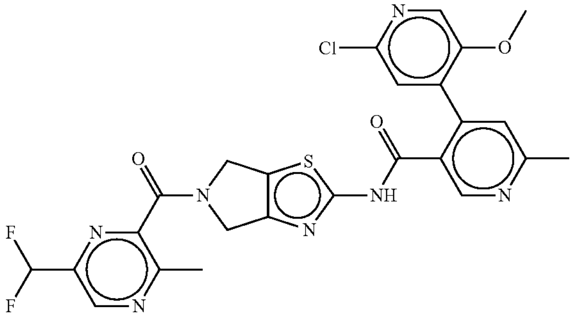 |
| 609 (889) | 2'-chloro-N-(5-(4-chloro-5-(difluoromethyl)picolinoyl)-5,6-dihydro-4H-pyrrolo[3,4-d]thiazol-2-yl)-5'-methoxy-6-methyl-[4,4'-bipyridine]-3-carboxamide | 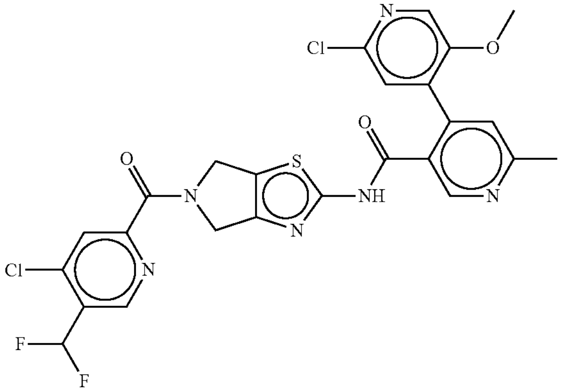 |
| 610 (888) | 2'-chloro-N-(5-(5-chloro-3-methylpyrazine-2-carbonyl)-5,6-dihydro-4H-pyrrolo[3,4-d]thiazol-2-yl)-5'-methoxy-6-methyl-[4,4'-bipyridine]-3-carboxamide | 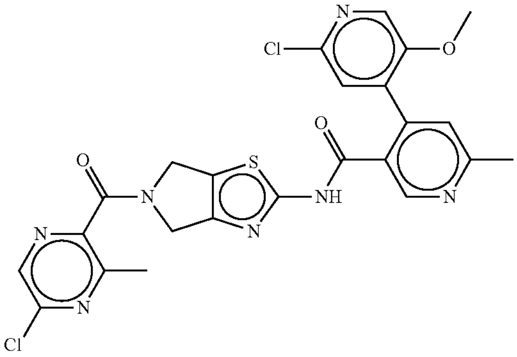 |
| 611 (887) | 2'-chloro-N-(5-(5-cyano-4-methylpicolinoyl)-5,6-dihydro-4H-pyrrolo[3,4-d]thiazol-2-yl)-5'-methoxy-6-methyl-[4,4'-bipyridine]-3-carboxamide | 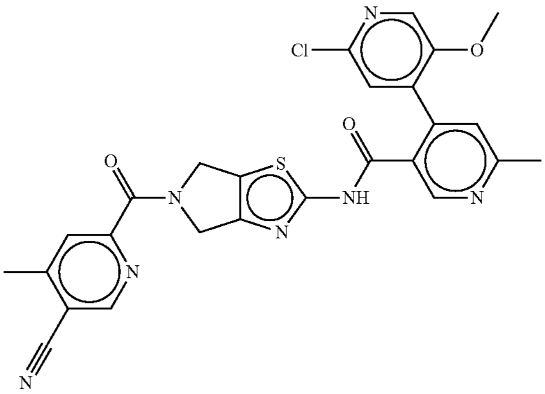 |

TABLE 2

| Compound No. | Name | Structure |
|---|---|---|
| 612 (919) | 2'-chloro-N-(5-(4-cyanopicolinoyl)-5,6-dihydro-4H-pyrrolo[3,4-d]thiazol-2-yl)-5'-methoxy-6-methyl-[4,4'-bipyridine]-3-carboxamide | 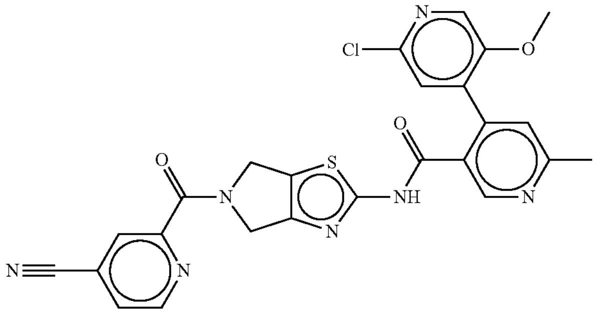 |
| 613 (902) | 2'-chloro-N-(5-((6-(difluoromethyl)pyridin-2-yl)methyl)-5,6-dihydro-4H-pyrrolo[3,4-d]thiazol-2-yl)-5'-methoxy-6-methyl-[4,4'-bipyridine]-3-carboxamide | 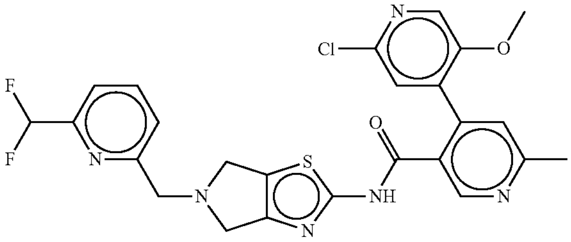 |
| 614 (948) | 2'-chloro-N-(5-(3-(difluoromethyl)-6-methylpyrazine-2-carbonyl)-5,6-dihydro-4H-pyrrolo[3,4-d]thiazol-2-yl)-5'-methoxy-6-methyl-[4,4'-bipyridine]-3-carboxamide | 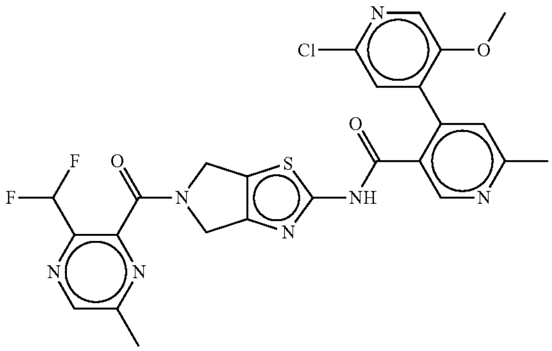 |
| 615 (904) | 2'-chloro-5'-methoxy-N-(5-(6-methoxy-3-methylpyrazine-2-carbonyl)-5,6-dihydro-4H-pyrrolo[3,4-d]thiazol-2-yl)-6-methyl-[4,4'-bipyridine]-3-carboxamide | 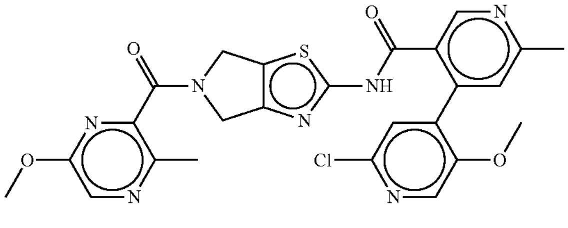 |
| 616 (967) | 2'-chloro-N-(5-(3-(difluoromethyl)-6-methoxypyrazine-2-carbonyl)-5,6-dihydro-4H-pyrrolo[3,4-d]thiazol-2-yl)-5'-methoxy-6-methyl-[4,4'-bipyridine]-3-carboxamide | 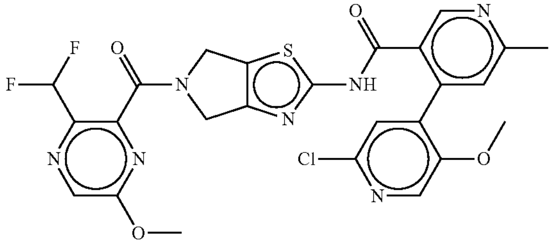 |

TABLE 2-continued

| Compound No. | Name | Structure |
|---|---|---|
| 617 (950) | 2'-chloro-N-(5-(5-(difluoromethyl)-3,6-dimethylpyrazine-2-carbonyl)-5,6-dihydro-4H-pyrrolo[3,4-d]thiazol-2-yl)-5'-methoxy-6-methyl-[4,4'-bipyridine]-3-carboxamide | 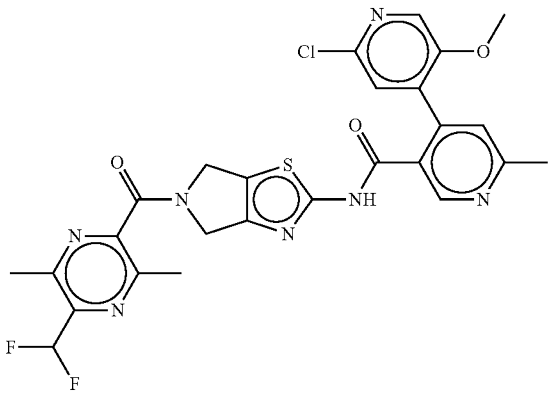 |
| 618 (939) | 2'-chloro-N-(5-(5-chloro-6-methoxy-3-methylpyrazine-2-carbonyl)-5,6-dihydro-4H-pyrrolo[3,4-d]thiazol-2-yl)-5'-methoxy-6-methyl-[4,4'-bipyridine]-3-carboxamide | 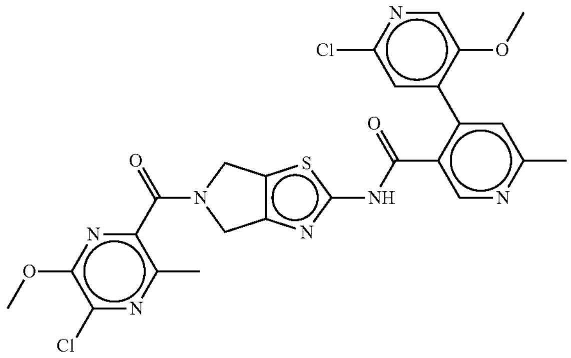 |
| 619 (953) | 2'-chloro-N-(5-(5-(difluoromethyl)-6-methoxy-3-methylpicolinoyl)-5,6-dihydro-4H-pyrrolo[3,4-d]thiazol-2-yl)-5'-methoxy-6-methyl-[4,4'-bipyridine]-3-carboxamide | 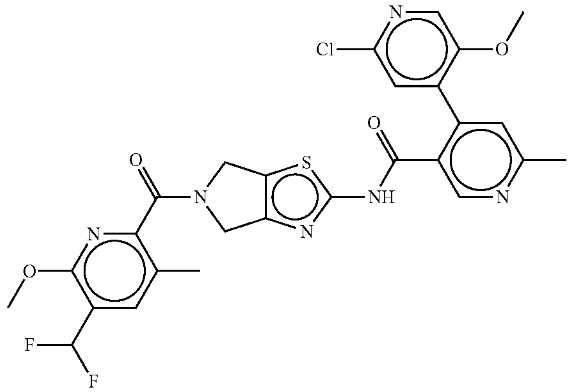 |
| 620 (977) | 2'-chloro-N-(5-(5-chloro-6-methoxy-3-methylpicolinoyl)-5,6-dihydro-4H-pyrrolo[3,4-d]thiazol-2-yl)-5'-methoxy-6-methyl-[4,4'-bipyridine]-3-carboxamide | 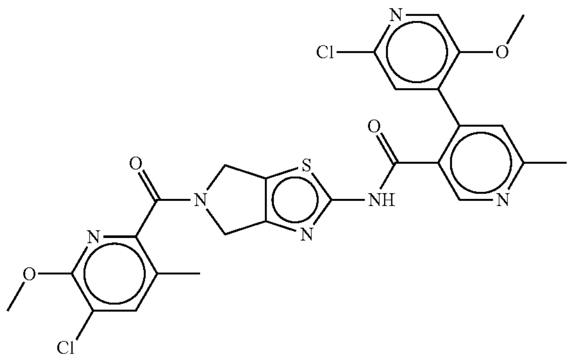 |

TABLE 2-continued

| Compound No. | Name | Structure |
|---|---|---|
| 621 (935) | 2'-chloro-N-(5-(5-(difluoromethyl)-3-fluoro-6-methylpicolinoyl)-5,6-dihydro-4H-pyrrolo[3,4-d]thiazol-2-yl)-5'-methoxy-6-methyl-[4,4'-bipyridine]-3-carboxamide | 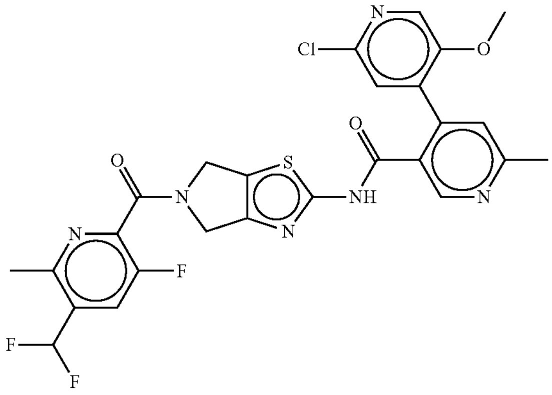 |
| 622 (915) | 2'-chloro-N-(5-(5-chloro-3,6-dimethylpyrazine-2-carbonyl)-5,6-dihydro-4H-pyrrolo[3,4-d]thiazol-2-yl)-5'-methoxy-6-methyl-[4,4'-bipyridine]-3-carboxamide | 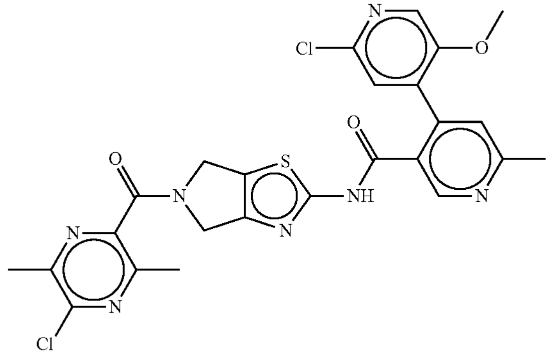 |
| 623 (1001) | 2'-chloro-N-(5-(3-chloro-5-(difluoromethyl)-6-methylpicolinoyl)-5,6-dihydro-4H-pyrrolo[3,4-d]thiazol-2-yl)-5'-methoxy-6-methyl-[4,4'-bipyridine]-3-carboxamide | 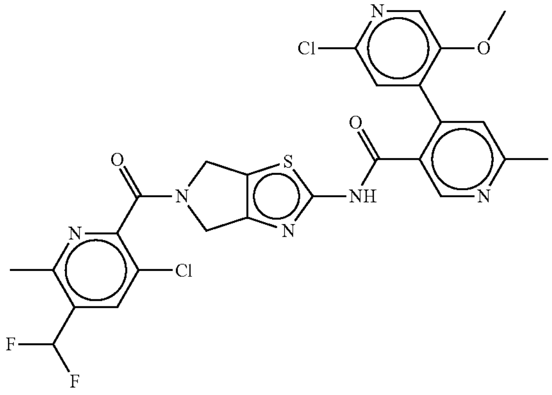 |
| 624 (928) | 2'-chloro-5'-methoxy-N-(5-(5-methoxy-3,6-dimethylpyrazine-2-carbonyl)-5,6-dihydro-4H-pyrrolo[3,4-d]thiazol-2-yl)-6-methyl-[4,4'-bipyridine]-3-carboxamide | 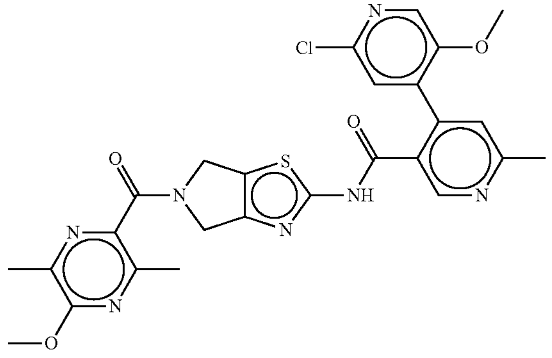 |

TABLE 2-continued

| Compound No. | Name | Structure |
|---|---|---|
| 625 (920) | 2'-chloro-5'-methoxy-6-methyl-N-(5-(3-methyl-5-(trifluoromethyl)picolinoyl)-5,6-dihydro-4H-pyrrolo[3,4-d]thiazol-2-yl)-[4,4'-bipyridine]-3-carboxamide | 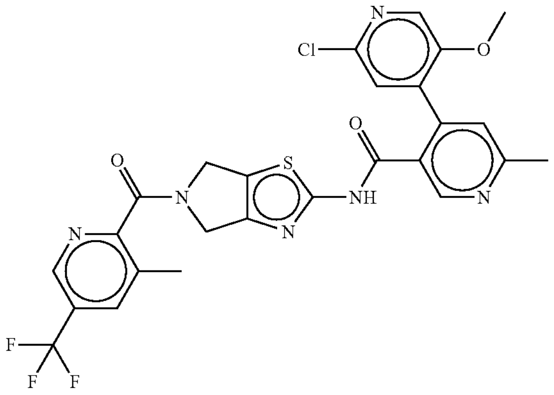 |
| 626 (933) | 2'-(difluoromethyl)-N-(5-(6-(difluoromethyl)picolinoyl)-5,6-dihydro-4H-pyrrolo[3,4-d]thiazol-2-yl)-5'-methoxy-6-methyl-[4,4'-bipyridine]-3-carboxamide | 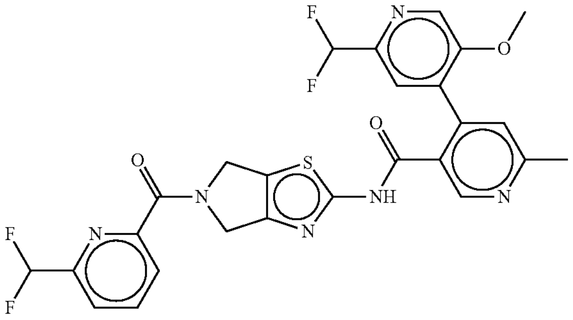 |
| 627 (932) | N-(5-(3-chloro-6-methylpicolinoyl)-5,6-dihydro-4H-pyrrolo[3,4-d]thiazol-2-yl)-2'-(difluoromethyl)-5'-methoxy-6-methyl-[4,4'-bipyridine]-3-carboxamide | 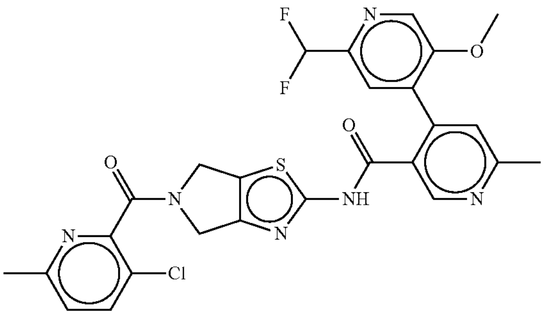 |
| 628 (931) | 2'-(difluoromethyl)-N-(5-(3,6-dimethylpyrazine-2-carbonyl)-5,6-dihydro-4H-pyrrolo[3,4-d]thiazol-2-yl)-5'-methoxy-6-methyl-[4,4'-bipyridine]-3-carboxamide | 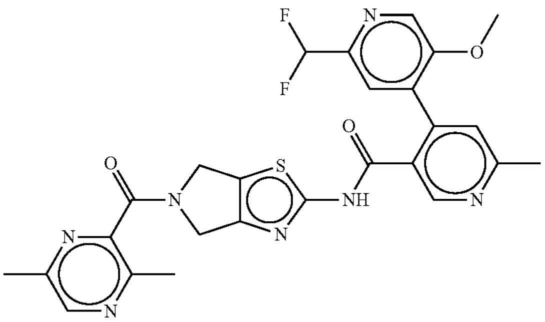 |

TABLE 2-continued

| Compound No. | Name | Structure |
|---|---|---|
| 629 (956) | 4-(6-(difluoromethyl)-3-methoxypyridazin-4-yl)-N-(5-(5-(difluoromethyl)picolinoyl)-5,6-dihydro-4H-pyrrolo[3,4-d]thiazol-2-yl)-6-methylnicotinamide | 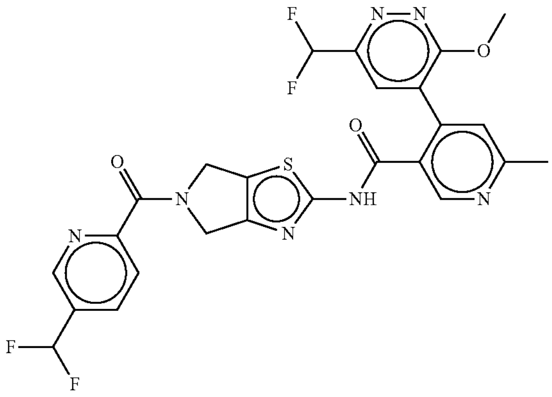 |
| 630 (958) | 4-(6-(difluoromethyl)-3-methoxypyridazin-4-yl)-N-(5-(6-(difluoromethyl)picolinoyl)-5,6-dihydro-4H-pyrrolo[3,4-d]thiazol-2-yl)-6-methylnicotinamide | 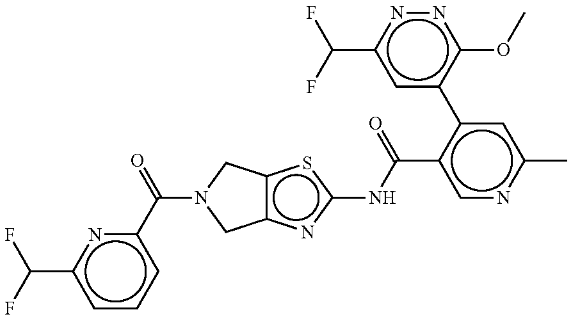 |
| 631 (930) | 2'-chloro-N-(5-(5-chloro-4-methylpyrimidine-2-carbonyl)-5,6-dihydro-4H-pyrrolo[3,4-d]thiazol-2-yl)-5'-methoxy-6-methyl-[4,4'-bipyridine]-3-carboxamide | 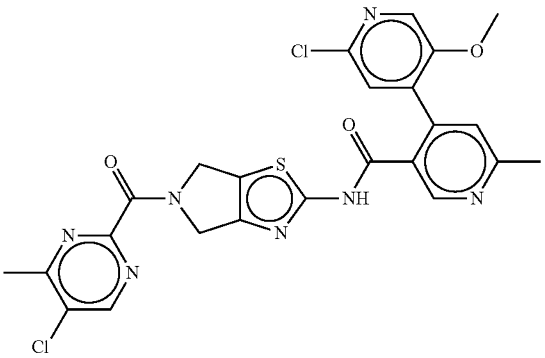 |
| 632 (914) | 2'-chloro-N-(5-(5-(difluoromethyl)-4-methylpyrimidine-2-carbonyl)-5,6-dihydro-4H-pyrrolo[3,4-d]thiazol-2-yl)-5'-methoxy-6-methyl-[4,4'-bipyridine]-3-carboxamide | 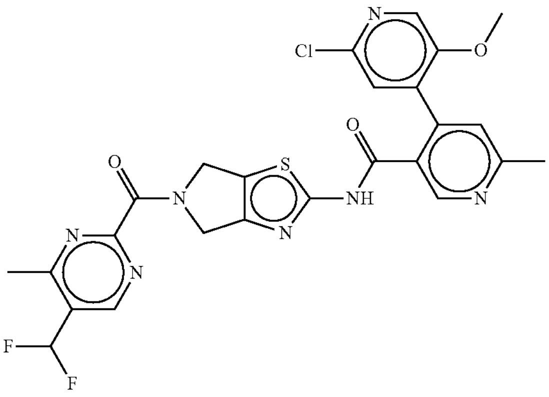 |

TABLE 2-continued

| Compound No. | Name | Structure |
|---|---|---|
| 633 (911) | 2'-chloro-5'-methoxy-6-methyl-N-(5-(2-methyl-6-(trifluoromethyl)nicotinoyl)-5,6-dihydro-4H-pyrrolo[3,4-d]thiazol-2-yl)-[4,4'-bipyridine]-3-carboxamide | 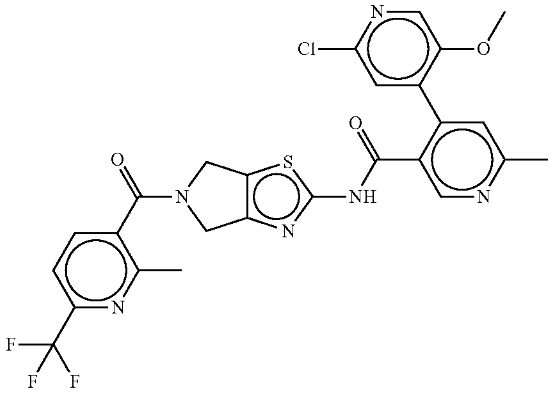 |
| 634 (957) | 2'-chloro-N-(5-(5-(difluoromethyl)-2-methylnicotinoyl)-5,6-dihydro-4H-pyrrolo[3,4-d]thiazol-2-yl)-5'-methoxy-6-methyl-[4,4'-bipyridine]-3-carboxamide | 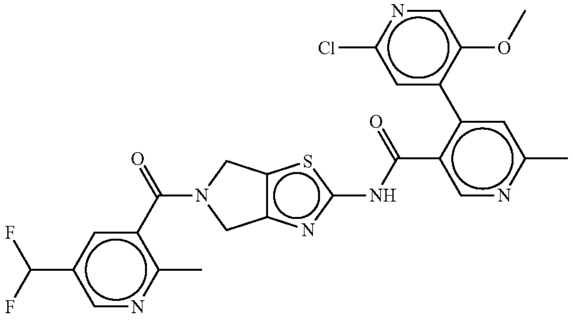 |
| 635 (934) | 2'-chloro-N-(5-(3,6-dimethylpyridazine-4-carbonyl)-5,6-dihydro-4H-pyrrolo[3,4-d]thiazol-2-yl)-5'-methoxy-6-methyl-[4,4'-bipyridine]-3-carboxamide | 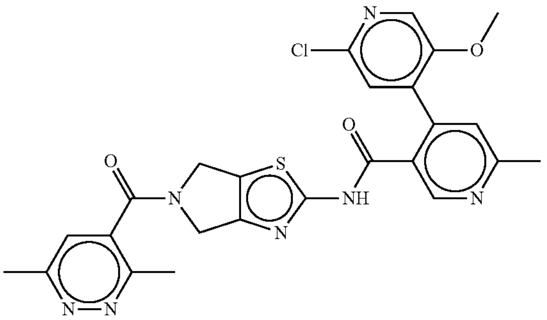 |
| 636 (944) | 2'-chloro-5'-methoxy-6-methyl-N-(5-(6-methylpyridazine-4-carbonyl)-5,6-dihydro-4H-pyrrolo[3,4-d]thiazol-2-yl)-[4,4'-bipyridine]-3-carboxamide | 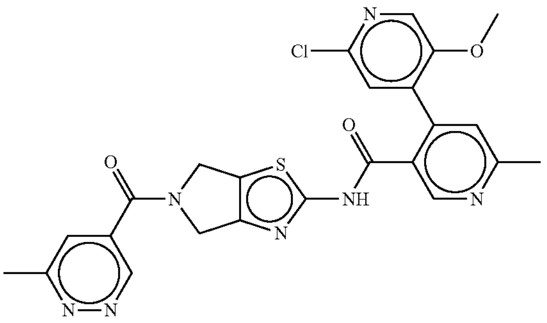 |

TABLE 2-continued

| Compound No. | Name | Structure |
|---|---|---|
| 637 (943) | 2'-chloro-5'-methoxy-6-methyl-N-(5-(3-methylpyridazine-4-carbonyl)-5,6-dihydro-4H-pyrrolo[3,4-d]thiazol-2-yl)-[4,4'-bipyridine]-3-carboxamide | 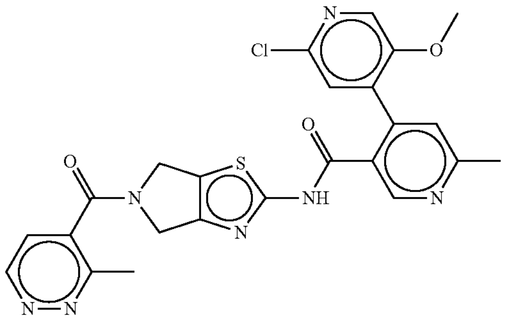 |
| 638 (942) | 2'-chloro-5'-methoxy-6-methyl-N-(5-(5-methylpyridazine-4-carbonyl)-5,6-dihydro-4H-pyrrolo[3,4-d]thiazol-2-yl)-[4,4'-bipyridine]-3-carboxamide | 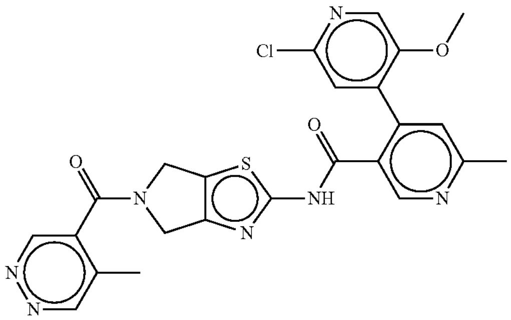 |
| 639 (941) | 2'-chloro-N-(5-(5,6-dimethylpyridazine-4-carbonyl)-5,6-dihydro-4H-pyrrolo[3,4-d]thiazol-2-yl)-5'-methoxy-6-methyl-[4,4'-bipyridine]-3-carboxamide | 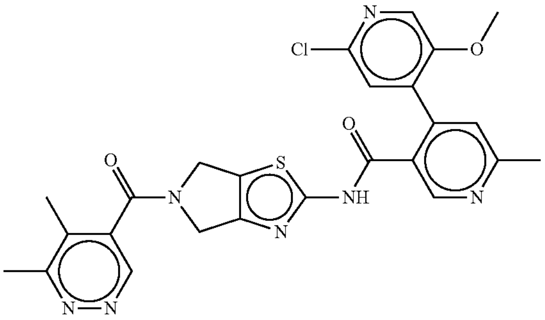 |
| 640 (929) | 2'-chloro-5'-methoxy-6-methyl-N-(5-(3-methyl-6-(trifluoromethyl)pyrazine-2-carbonyl)-5,6-dihydro-4H-pyrrolo[3,4-d]thiazol-2-yl)-[4,4'-bipyridine]-3-carboxamide | 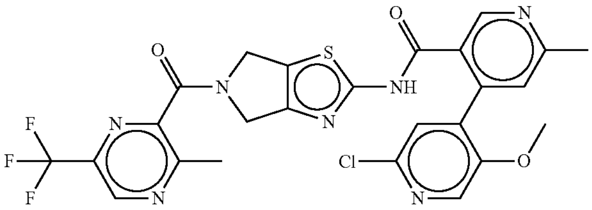 |
| 641 (991) | 2'-chloro-N-(5-(3,6-dimethyl-5-(trifluoromethyl)pyrazine-2-carbonyl)-5,6-dihydro-4H-pyrrolo[3,4-d]thiazol-2-yl)-5'-methoxy-6-methyl-[4,4'-bipyridine]-3-carboxamide | 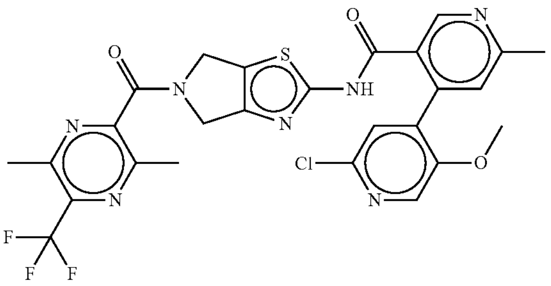 |

TABLE 2-continued

| Compound No. | Name | Structure |
|---|---|---|
| 642 (917) | 2'-chloro-5'-methoxy-6-methyl-N-(5-(6-methyl-5-(trifluoromethyl)picolinoyl)-5,6-dihydro-4H-pyrrolo[3,4-d]thiazol-2-yl)-[4,4'-bipyridine]-3-carboxamide | 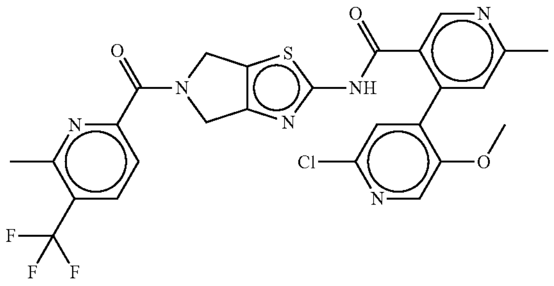 |
| 643 (954) | 2'-chloro-5'-methoxy-6-methyl-N-(5-(6-methyl-5-(trifluoromethyl)pyrazine-2-carbonyl)-5,6-dihydro-4H-pyrrolo[3,4-d]thiazol-2-yl)-[4,4'-bipyridine]-3-carboxamide | 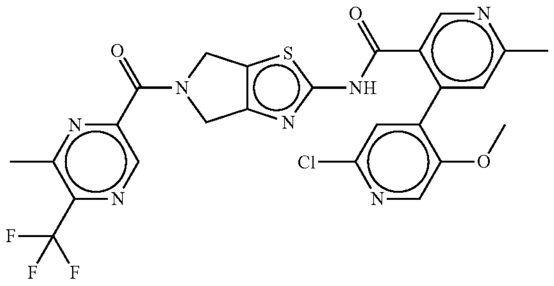 |
| 644 (912) | 2'-chloro-N-(5-(3-fluoro-5-(trifluoromethyl)picolinoyl)-5,6-dihydro-4H-pyrrolo[3,4-d]thiazol-2-yl)-5'-methoxy-6-methyl-[4,4'-bipyridine]-3-carboxamide | 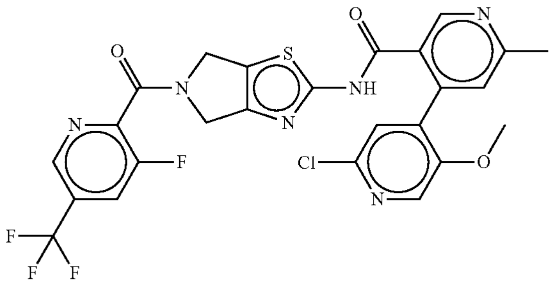 |
| 645 (980) | 2'-chloro-N-(5-(4,6-dimethyl-5-(trifluoromethyl)picolinoyl)-5,6-dihydro-4H-pyrrolo[3,4-d]thiazol-2-yl)-5'-methoxy-6-methyl-[4,4'-bipyridine]-3-carboxamide | 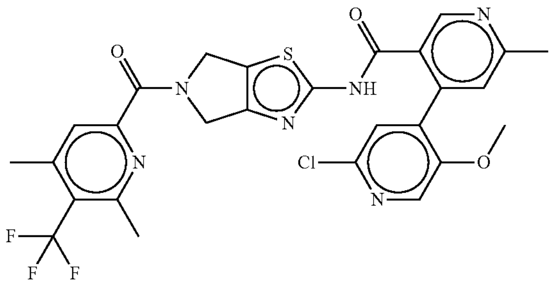 |
| 646 (992) | 2'-chloro-N-(5-(3,6-dimethyl-5-(trifluoromethyl)picolinoyl)-5,6-dihydro-4H-pyrrolo[3,4-d]thiazol-2-yl)-5'-methoxy-6-methyl-[4,4'-bipyridine]-3-carboxamide | 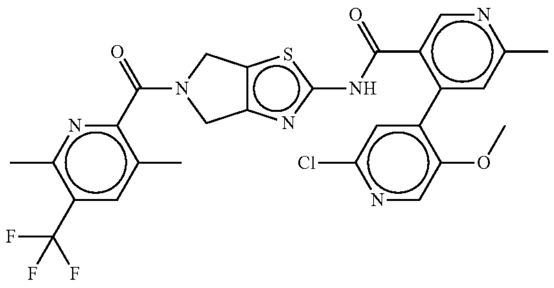 |

TABLE 2-continued

| Compound No. | Name | Structure |
|---|---|---|
| 647 (1002) | 2'-chloro-N-(5-(3,4-dimethyl-5-(trifluoromethyl)picolinoyl)-5,6-dihydro-4H-pyrrolo[3,4-d]thiazol-2-yl)-5'-methoxy-6-methyl-[4,4'-bipyridine]-3-carboxamide | 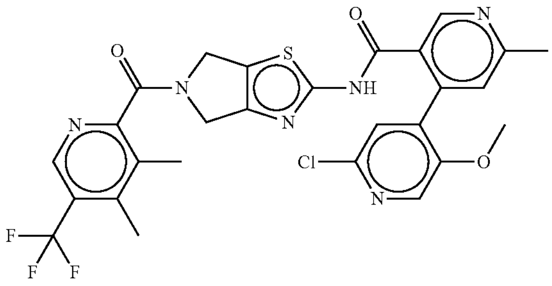 |
| 648 (918) | 2'-chloro-5'-methoxy-6-methyl-N-(5-(4-methyl-6-(trifluoromethyl)nicotinoyl)-5,6-dihydro-4H-pyrrolo[3,4-d]thiazol-2-yl)-[4,4'-bipyridine]-3-carboxamide | 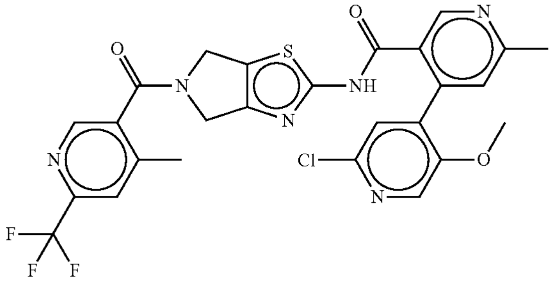 |
| 649 (988) | 2'-chloro-N-(5-(2,4-dimethyl-6-(trifluoromethyl)nicotinoyl)-5,6-dihydro-4H-pyrrolo[3,4-d]thiazol-2-yl)-5'-methoxy-6-methyl-[4,4'-bipyridine]-3-carboxamide | 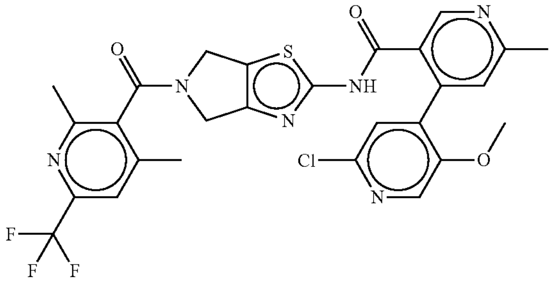 |
| 650 (971) | 2'-chloro-N-(5-(2,5-dimethyl-6-(trifluoromethyl)nicotinoyl)-5,6-dihydro-4H-pyrrolo[3,4-d]thiazol-2-yl)-5'-methoxy-6-methyl-[4,4'-bipyridine]-3-carboxamide | 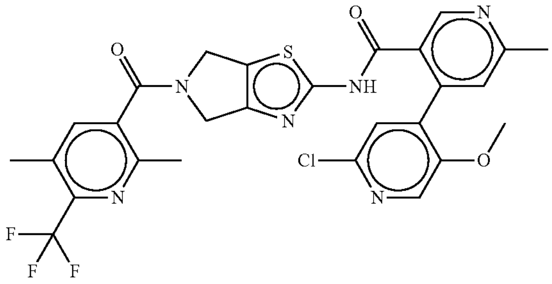 |
| 651 (1017) | 2'-chloro-N-(5-(4,5-dimethyl-6-(trifluoromethyl)nicotinoyl)-5,6-dihydro-4H-pyrrolo[3,4-d]thiazol-2-yl)-5'-methoxy-6-methyl-[4,4'-bipyridine]-3-carboxamide | 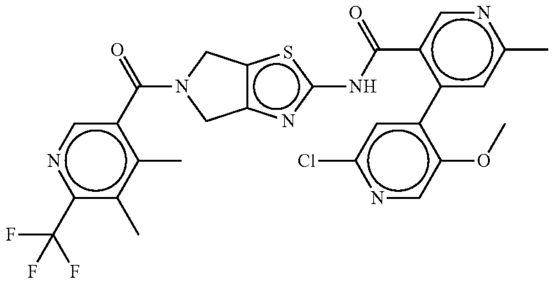 |

TABLE 3

| Compound No. | Name | Structure |
|---|---|---|
| 658 | 2'-chloro-5'-methoxy-N-(5-((1R,3S)-3-methoxycyclohexane-1-carbonyl)-5,6-dihydro-4H-pyrrolo[3,4-d]thiazol-2-yl)-6-methyl-[4,4'-bipyridine]-3-carboxamide | 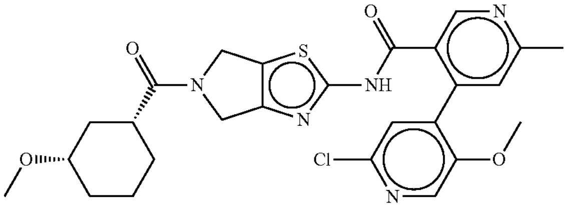 |
| 659 | 2'-chloro-5'-methoxy-N-(5-((1R,3R)-3-methoxycyclohexane-1-carbonyl)-5,6-dihydro-4H-pyrrolo[3,4-d]thiazol-2-yl)-6-methyl-[4,4'-bipyridine]-3-carboxamide | 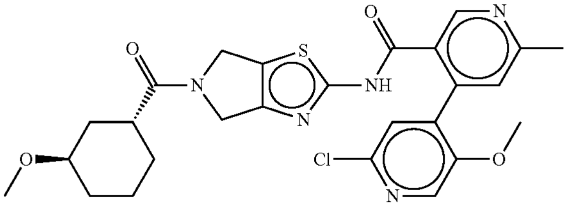 |
| 664 | (S)-2'-chloro-N-(6-(3-hydroxyazetidine-1-carbonyl)-4,5,6,7-tetrahydrobenzo[d]thiazol-2-yl)-5'-methoxy-6-methyl-[4,4'-bipyridine]-3-carboxamide | 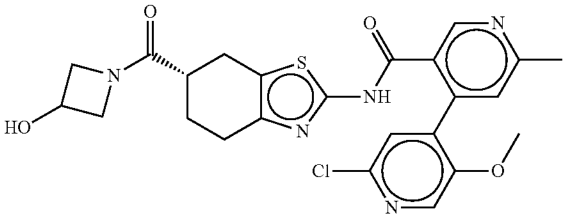 |
| 665 | (R)-2-(2'-chloro-5'-methoxy-6-methyl-[4,4'-bipyridine]-3-carboxamido)-N-((1r,3R)-3-hydroxycyclobutyl)-4,5,6,7-tetrahydrobenzo[d]thiazole-6-carboxamide | 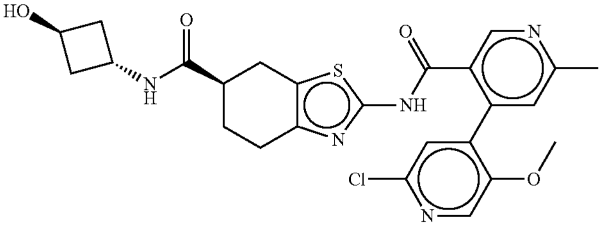 |
| 666 | 2'-chloro-N-((R)-6-((R)-3-hydroxypyrrolidine-1-carbonyl)-4,5,6,7-tetrahydrobenzo[d]thiazol-2-yl)-5'-methoxy-6-methyl-[4,4'-bipyridine]-3-carboxamide | 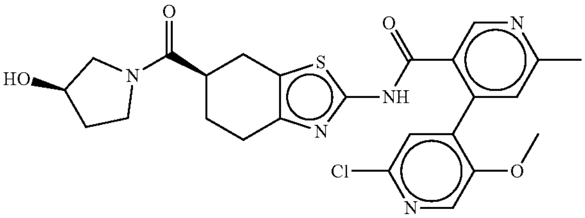 |
| 668 | (R)-2-(2'-chloro-5'-methoxy-6-methyl-[4,4'-bipyridine]-3-carboxamido)-N-((1s,3S)-3-hydroxycyclobutyl)-4,5,6,7-tetrahydrobenzo[d]thiazole-6-carboxamide | 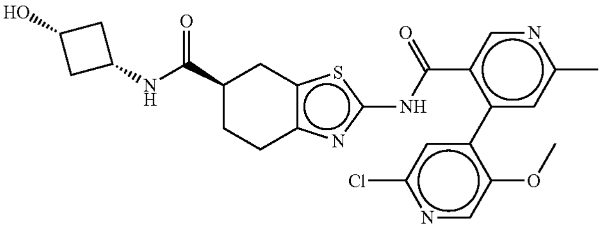 |

TABLE 3-continued

| Compound No. | Name | Structure |
|---|---|---|
| 669 | (S)-2-(2'-chloro-5'-methoxy-6-methyl-[4,4'-bipyridine]-3-carboxamido)-N-((1r,3S)-3-hydroxycyclobutyl)-4,5,6,7-tetrahydrobenzo[d]thiazole-6-carboxamide | 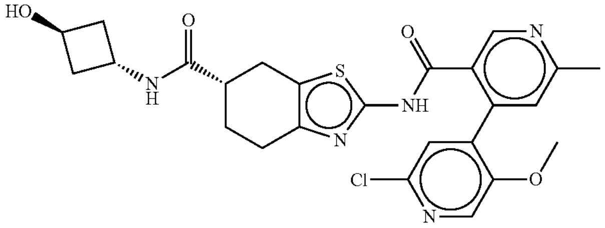 |
| 674 | (R)-2'-chloro-N-(6-(3-hydroxyazetidine-1-carbonyl)-4,5,6,7-tetrahydrobenzo[d]thiazol-2-yl)-5'-methoxy-6-methyl-[4,4'-bipyridine]-3-carboxamide | 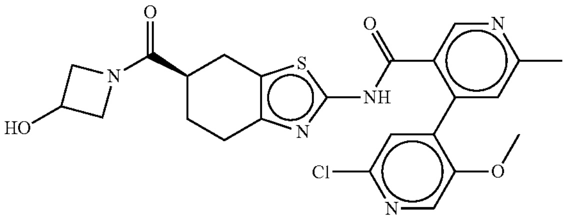 |
| 676 | 2'-chloro-N-((R)-6-((S)-3-hydroxypyrrolidine-1-carbonyl)-4,5,6,7-tetrahydrobenzo[d]thiazol-2-yl)-5'-methoxy-6-methyl-[4,4'-bipyridine]-3-carboxamide | 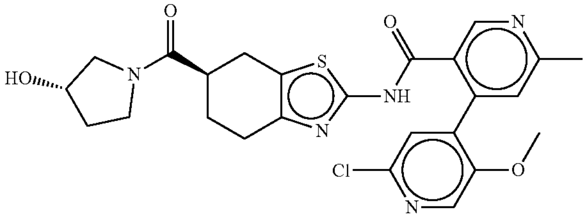 |
| 677 | (S)-2-(2'-chloro-5'-methoxy-6-methyl-[4,4'-bipyridine]-3-carboxamido)-N-((1s,3R)-3-hydroxycyclobutyl)-4,5,6,7-tetrahydrobenzo[d]thiazole-6-carboxamide | 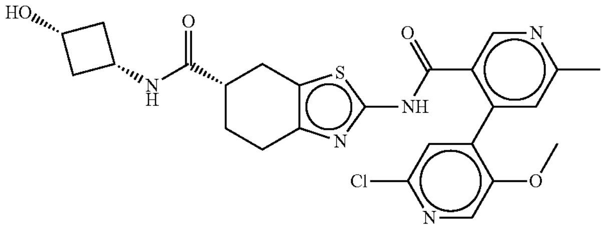 |
| 681 | 2'-chloro-N-((S)-6-((R)-3-hydroxypyrrolidine-1-carbonyl)-4,5,6,7-tetrahydrobenzo[d]thiazol-2-yl)-5'-methoxy-6-methyl-[4,4'-bipyridine]-3-carboxamide | 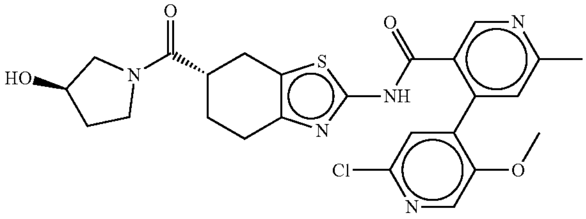 |
| 682 | (S)-2-(2'-chloro-5'-methoxy-6-methyl-[4,4'-bipyridine]-3-carboxamido)-N-((1S,2R)-2-hydroxycyclobutyl)-4,5,6,7-tetrahydrobenzo[d]thiazole-6-carboxamide | 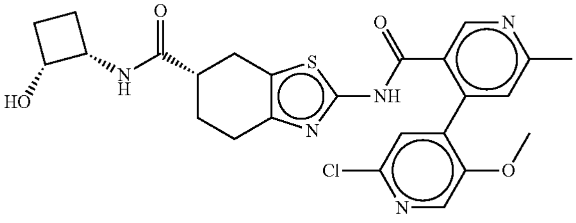 |

TABLE 3-continued

| Compound No. | Name | Structure |
|---|---|---|
| 683 | (R)-2-(2'-chloro-5'-methoxy-6-methyl-[4,4'-bipyridine]-3-carboxamido)-N-((1S,2R)-2-hydroxycyclobutyl)-4,5,6,7-tetrahydrobenzo[d]thiazole-6-carboxamide | 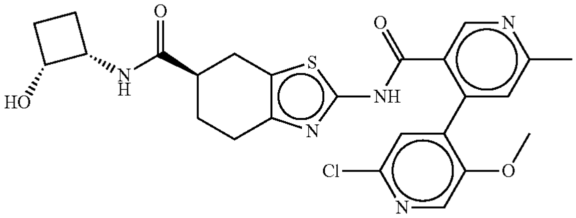 |
| 685 | (S)-2-(2'-chloro-5'-methoxy-6-methyl-(4,4'-bipyridine]-3-carboxamido)-N-((1S,2S)-2-hydroxycyclobutyl)-4,5,6,7-tetrahydrobenzo[d]thiazole-6-carboxamide | 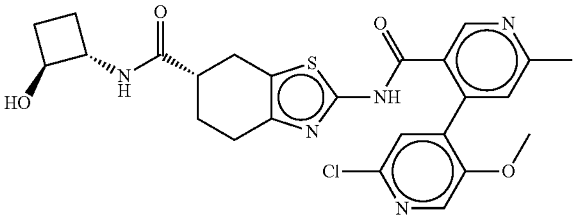 |
| 686 | 2'-chloro-N-((S)-6-((S)-3-hydroxypyrrolidine-1-carbonyl)-4,5,6,7-tetrahydrobenzo[d]thiazol-2-yl)-5'-methoxy-6-methyl-[4,4'-bipyridine]-3-carboxamide | 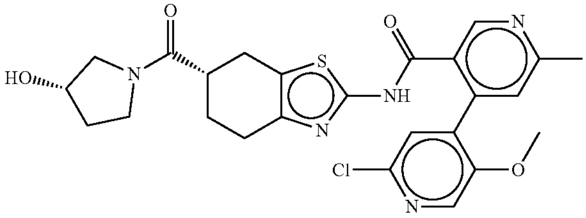 |
| 689 | (R)-2-(2'-chloro-5'-methoxy-6-methyl-[4,4'-bipyridine]-3-carboxamido)-N-((1S,2S)-2-hydroxycyclobutyl)-4,5,6,7-tetrahydrobenzo[d]thiazole-6-carboxamide | 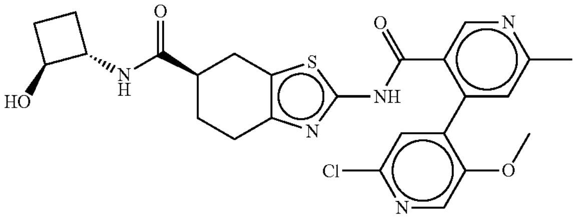 |
| 692 | (R)-2-(2'-chloro-5'-methoxy-6-methyl-[4,4'-bipyridine]-3-carboxamido)-N-((1R,2S)-2-hydroxycyclobutyl)-4,5,6,7-tetrahydrobenzo[d]thiazole-6-carboxamide | 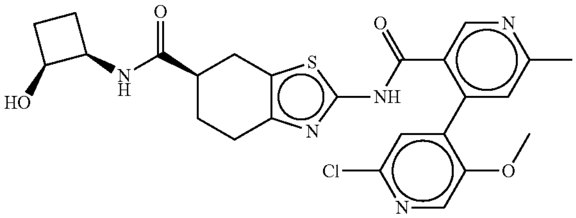 |
| 734 | 2'-chloro-N-(5-((1R,3R)-3-hydroxy-3-(trifluoromethyl)cyclopentane-1-carbonyl)-5,6-dihydro-4H-pyrrolo[3,4-d]thiazol-2-yl)-5'-methoxy-6-methyl-[4,4'-bipyridine]-3-carboxamide | 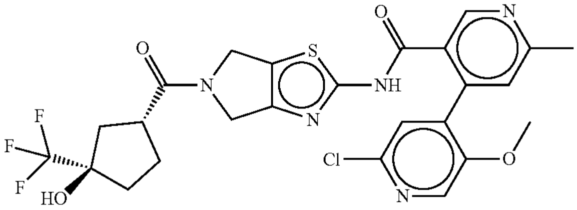 |
| 736 | 2'-chloro-N-(S-((1S,3R)-3-hydroxy-3-(trifluoromethyl)cyclopentane-1-carbonyl)-5,6-dihydro-4H-pyrrolo[3,4-d]thiazol-2-yl)-5'-methoxy-6-methyl-[4,4'-bipyridine]-3-carboxamide | 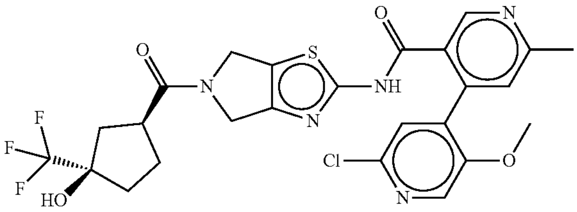 |

TABLE 3-continued

| Compound No. | Name | Structure |
|---|---|---|
| 756 | 2'-chloro-N-(5-((1S,3R)-3-hydroxy-3-(trifluoromethyl)cyclohexane-1-carbonyl)-5,6-dihydro-4H-pyrrolo[3,4-d]thiazol-2-yl)-5'-methoxy-6-methyl-[4,4'-bipyridine]-3-carboxamide | 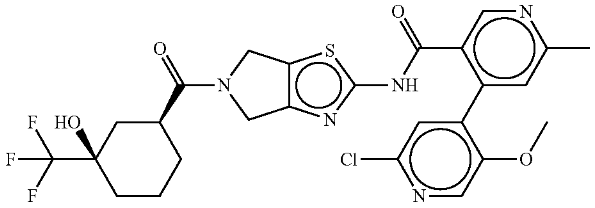 |
| 761 | 2'-chloro-N-(5-((1R,3R)-3-hydroxy-3-(trifluoromethyl)cyclohexane-1-carbonyl)-5,6-dihydro-4H-pyrrolo[3,4-d]thiazol-2-yl)-5'-methoxy-6-methyl-[4,4'-bipyridine]-3-carboxamide | 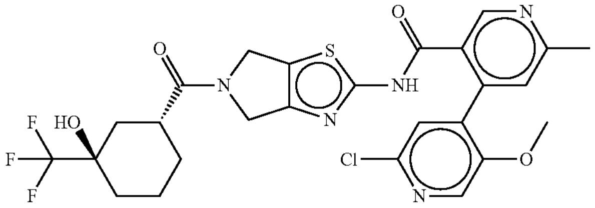 |
| 900 | 2'-chloro-N-(5-(6-(difluoromethyl)-5-methylpyrazine-2-carbonyl)-5,6-dihydro-4H-pyrrolo[3,4-d]thiazol-2-yl)-5'-methoxy-6-methyl-[4,4'-bipyridine]-3-carboxamide | 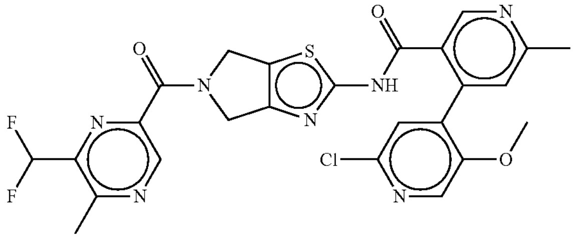 |
| 901 | 2'-chloro-N-(5-(3-(difluoromethyl)-5-methoxypicolinoyl)-5,6-dihydro-4H-pyrrolo[3,4-d]thiazol-2-yl)-5'-methoxy-6-methyl-[4,4'-bipyridine]-3-carboxamide | 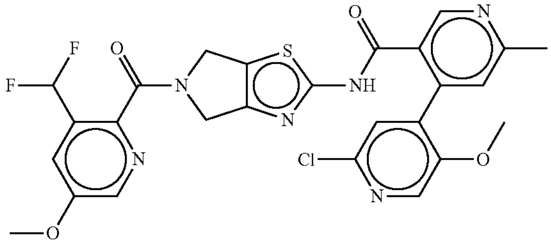 |
| 903 | 2'-chloro-N-(5-(5-(difluoromethyl)-4-methylpicolinoyl)-5,6-dihydro-4H-pyrrolo[3,4-d]thiazol-2-yl)-5'-methoxy-6-methyl-[4,4'-bipyridine]-3-carboxamide | 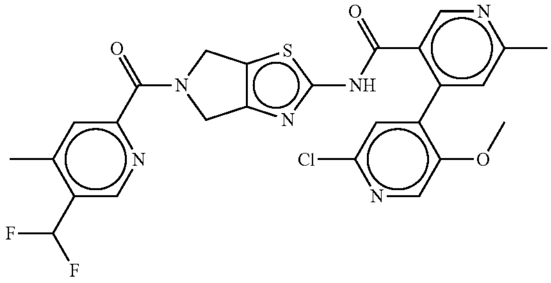 |
| 905 | 2'-chloro-5'-methoxy-N-(5-(3-methoxy-5-methylpyrazine-2-carbonyl)-5,6-dihydro-4H-pyrrolo[3,4-d]thiazol-2-yl)-6-methyl-[4,4'-bipyridine]-3-carboxamide | 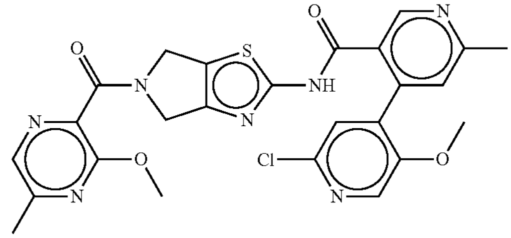 |

TABLE 3-continued

| Compound No. | Name | Structure |
|---|---|---|
| 906 | 2'-chloro-N-(5-(6-(difluoromethyl)-4-methoxypicolinoyl)-5,6-dihydro-4H-pyrrolo[3,4-d]thiazol-2-yl)-5'-methoxy-6-methyl-[4,4'-bipyridine]-3-carboxamide | 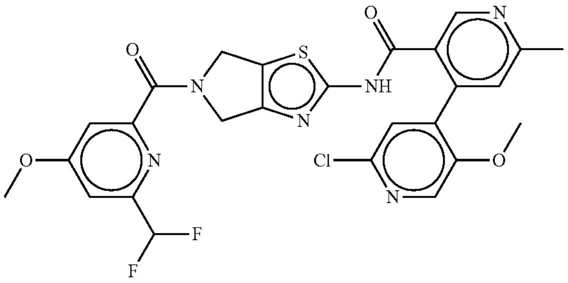 |
| 907 | 2'-chloro-N-(5-(5-(difluoromethyl)-4-methoxypyrimidine-2-carbonyl)-5,6-dihydro-4H-pyrrolo[3,4-d]thiazol-2-yl)-5'-methoxy-6-methyl-[4,4'-bipyridine]-3-carboxamide | 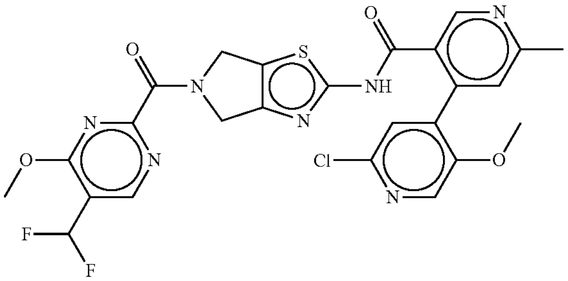 |
| 908 | 2'-chloro-N-(5-((1r,4r)-4-(difluoromethyl)cyclohexane-1-carbonyl)-5,6-dihydro-4H-pyrrolo[3,4-d]thiazol-2-yl)-5'-methoxy-6-methyl-[4,4'-bipyridine]-3-carboxamide | 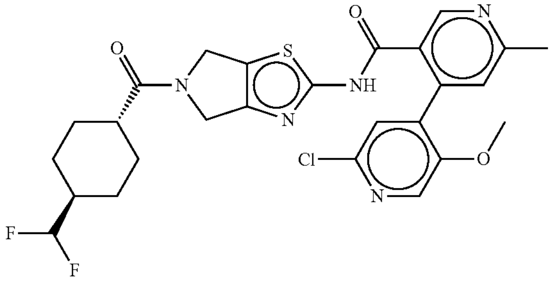 |
| 909 | 2'-chloro-N-(5-((1s,4s)-4-(difluoromethyl)cyclohexane-1-carbonyl)-5,6-dihydro-4H-pyrrolo[3,4-d]thiazol-2-yl)-5'-methoxy-6-methyl-[4,4'-bipyridine]-3-carboxamide | 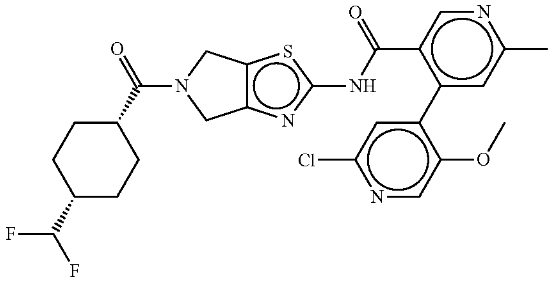 |
| 910 | 2'-chloro-N-(5-(5-chloropyrimidine-2-carbonyl)-5,6-dihydro-4H-pyrrolo[3,4-d]thiazol-2-yl)-5'-(difluoromethoxy)-6-methyl-[4,4'-bipyridine]-3-carboxamide | 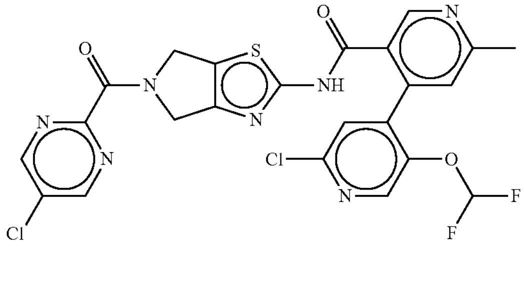 |

TABLE 3-continued

| Compound No. | Name | Structure |
|---|---|---|
| 913 | 2'-chloro-5'-(difluoromethoxy)-N-(5-(6-(difluoromethyl)picolinoyl)-5,6-dihydro-4H-pyrrolo[3,4-d]thiazol-2-yl)-6-methyl-[4,4'-bipyridine]-3-carboxamide | 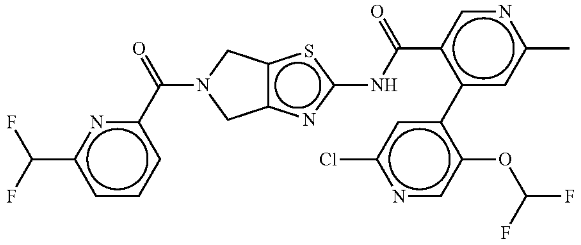 |
| 916 | 4-(5-cyano-2-(difluoromethoxy)phenyl)-N-(5-(5-(difluoromethyl)picolinoyl)-5,6-dihydro-4H-pyrrolo[3,4-d]thiazol-2-yl)-6-methylnicotinamide | 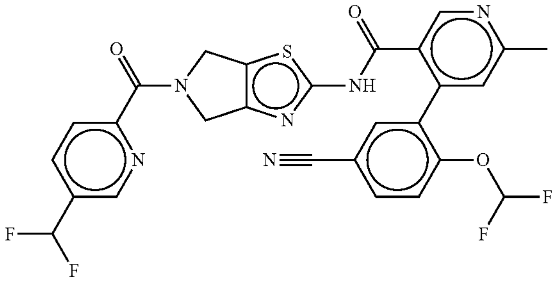 |
| 921 | 2'-chloro-N-(5-(6-chloro-4-(difluoromethyl)picolinoyl)-5,6-dihydro-4H-pyrrolo[3,4-d]thiazol-2-yl)-5'-methoxy-6-methyl-[4,4'-bipyridine]-3-carboxamide | 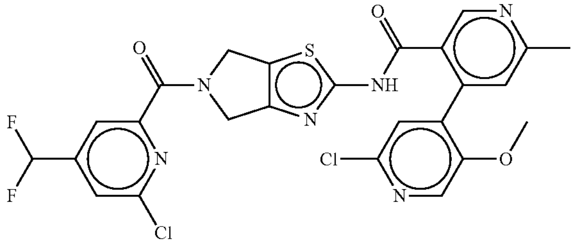 |
| 922 | 2'-chloro-N-(S-(3-chloro-6-(difluoromethyl)picolinoyl)-5,6-dihydro-4H-pyrrolo[3,4-d]thiazol-2-yl)-5'-(difluoromethoxy)-6-methyl-[4,4'-bipyridine]-3-carboxamide | 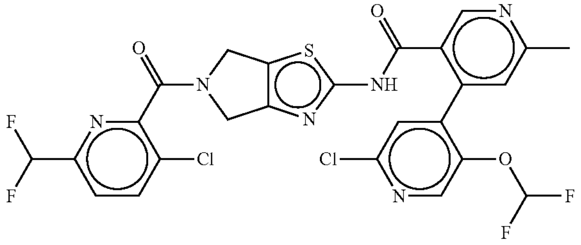 |
| 923 | 2'-chloro-N-(5-(2-chloro-6-(trifluoromethyl)nicotinoyl)-5,6-dihydro-4H-pyrrolo[3,4-d]thiazol-2-yl)-5'-methoxy-6-methyl-[4,4'-bipyridine]-3-carboxamide | 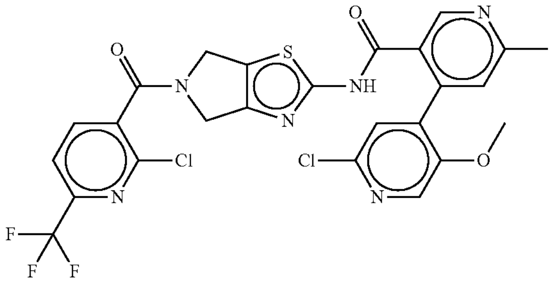 |
| 924 | 2'-chloro-N-(5-(4-(difluoromethyl)-5-methoxypyrimidine-2-carbonyl)-5,6-dihydro-4H-pyrrolo[3,4-d]thiazol-2-yl)-5'-methoxy-6-methyl-[4,4'-bipyridine]-3-carboxamide | 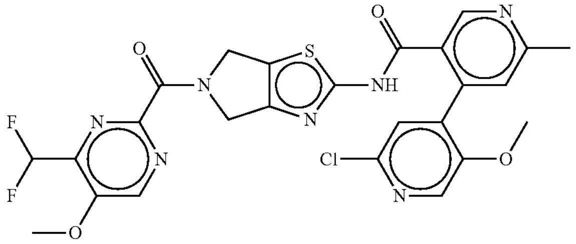 |

TABLE 3-continued

| Compound No. | Name | Structure |
|---|---|---|
| 925 | 2'-chloro-5'-methoxy-6-methyl-N-(5-((1s,4s)-4-(trifluoromethoxy)cyclohexane-1-carbonyl)-5,6-dihydro-4H-pyrrolo[3,4-d]thiazol-2-y])-[4,4'-bipyridine]-3-carboxamide | 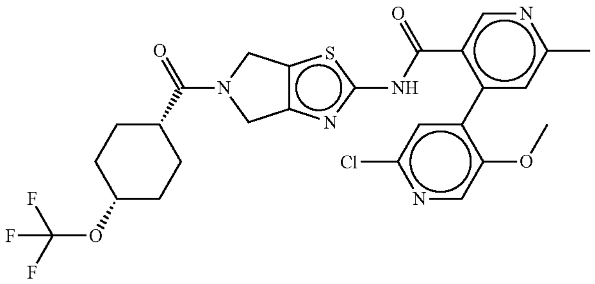 |
| 926 | 2'-chloro-N-(5-(4-chloro-3-(difluoromethyl)picolinoyl)-5,6-dihydro-4H-pyrrolo[3,4-d]thiazol-2-yl)-5'-methoxy-6-methyl-[4,4'-bipyridine]-3-carboxamide | 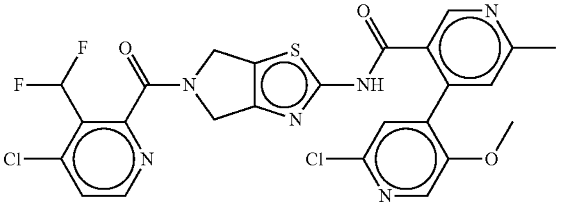 |
| 927 | 2'-chloro-N-(5-(6-chloro-5-(difluoromethyl)-3-fluoropicolinoyl)-5,6-dihydro-4H-pyrrolo[3,4-d]thiazol-2-yl)-5'-methoxy-6-methyl-[4,4'-bipyridine]-3-carboxamide | 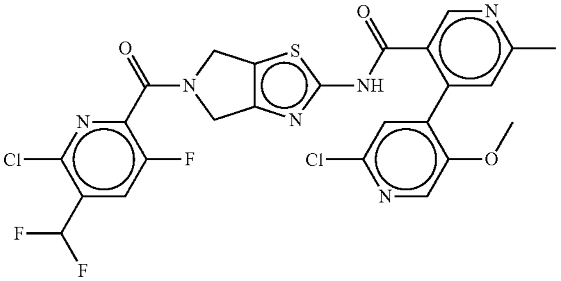 |
| 936 | 2'-chloro-N-(5-(3-fluoro-6-(trifluoromethyl)picolinoyl)-5,6-dihydro-4H-pyrrolo[3,4-d]thiazol-2-yl)-5'-methoxy-6-methyl-[4,4'-bipyridine]-3-carboxamide | 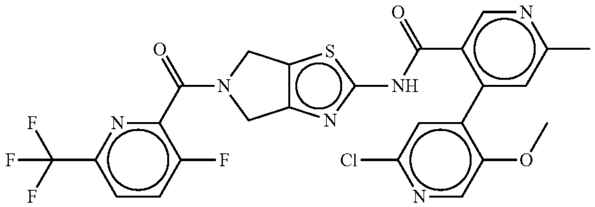 |
| 937 | 2'-chloro-5'-methoxy-N-(5-(3-methoxy-6-(trifluoromethyl)picolinoyl)-5,6-dihydro-4H-pyrrolo[3,4-d]thiazol-2-yl)-6-methyl-[4,4'-bipyridine]-3-carboxamide | 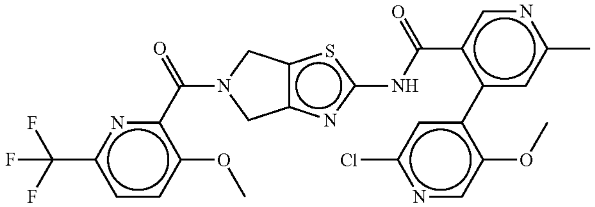 |
| 938 | 5-chloro-2-(difluoromethoxy)-N-(5-(5-(difluoromethyl)picolinoyl)-5,6-dihydro-4H-pyrrolo[3,4-d]thiazol-2-yl)-6'-methyl-[3,4'-bipyridine]-3'-carboxamide | 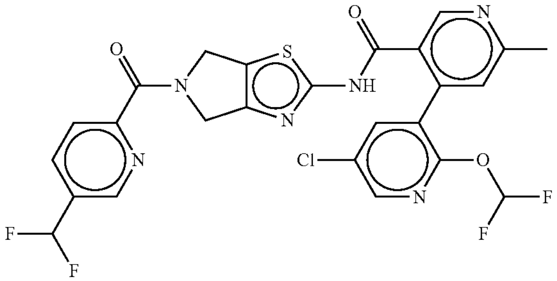 |

TABLE 3-continued

| Compound No. | Name | Structure |
|---|---|---|
| 940 | 2'-chloro-N-(5-(6-chloro-5-(difluoromethyl)-3-methylpicolinoyl)-5,6-dihydro-4H-pyrrolo[3,4-d]thiazol-2-yl)-5'-methoxy-6-methyl-[4,4'-bipyridine]-3-carboxamide | 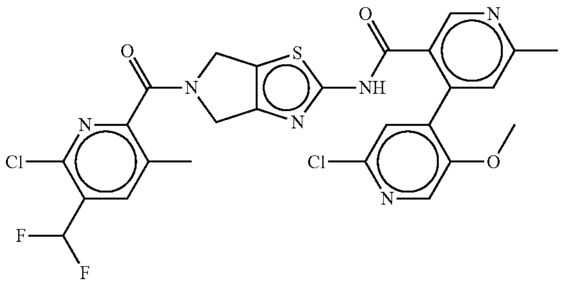 |
| 945 | 2'-chloro-5'-methoxy-N-(5-(3-methoxy-5-(trifluoromethyl)pyrazine-2-carbonyl)-5,6-dihydro-4H-pyrrolo[3,4-d]thiazol-2-yl)-6-methyl-[4,4'-bipyridine]-3-carboxamide | 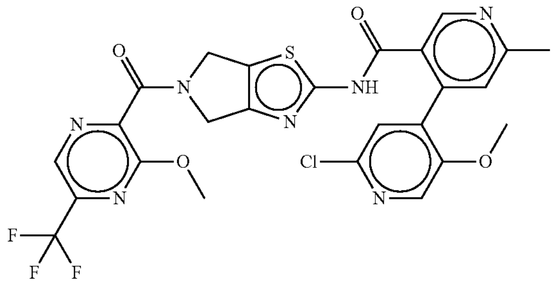 |
| 946 | 2'-chloro-6-cyclopropyl-N-(5-(6-(difluoromethyl)picolinoyl)-5,6-dihydro-4H-pyrrolo[3,4-d]thiazol-2-yl)-5'-methoxy-[4,4'-bipyridine]-3-carboxamide | 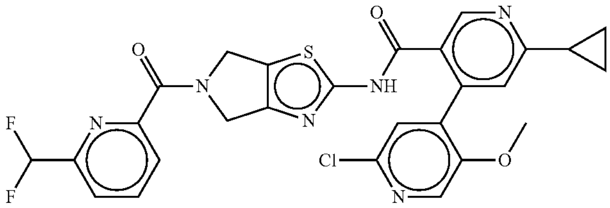 |
| 947 | 2'-chloro-N-(5-(6-(difluoromethyl)-2-methylnicotinoyl)-5,6-dihydro-4H-pyrrolo[3,4-d]thiazol-2-yl)-5'-methoxy-6-methyl-[4,4'-bipyridine]-3-carboxamide | 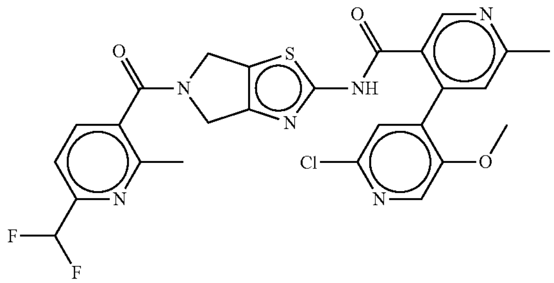 |
| 949 | 2'-chloro-N-(5-(4-(difluoromethyl)-3-fluoropicolinoyl)-5,6-dihydro-4H-pyrrolo[3,4-d]thiazol-2-yl)-5'-methoxy-6-methyl-[4,4'-bipyridine]-3-carboxamide | 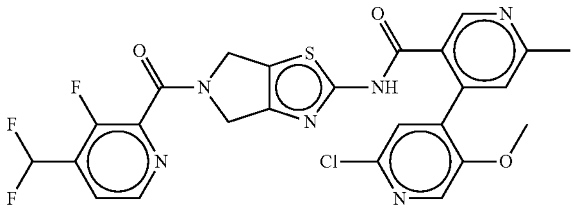 |
| 951 | 2'-chloro-5'-methoxy-6-methyl-N-(5-(3-methyl-4-(trifluoromethyl)picolinoyl)-5,6-dihydro-4H-pyrrolo[3,4-d]thiazol-2-yl)-[4,4'-bipyridine]-3-carboxamide | 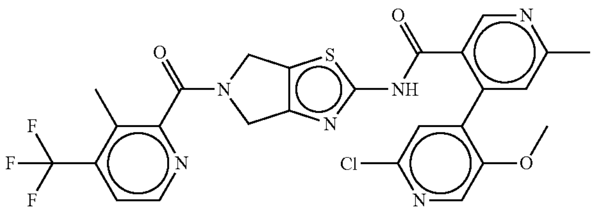 |

TABLE 3-continued

| Compound No. | Name | Structure |
|---|---|---|
| 952 | 2'-chloro-N-(5-(3-chloro-6-(trifluoromethyl)picolinoyl)-5,6-dihydro-4H-pyrrolo[3,4-d]thiazol-2-yl)-5'-methoxy-6-methyl-[4,4'-bipyridine]-3-carboxamide | 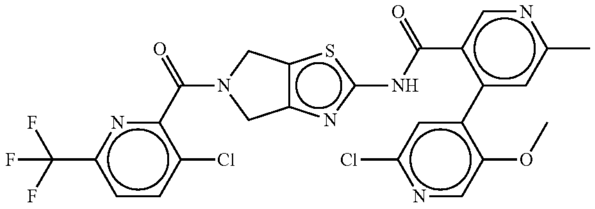 |
| 955 | 4-(6-chloro-3-(difluoromethoxy)pyridazin-4-yl)-N-(5-(5-(difluoromethyl)picolinoyl)-5,6-dihydro-4H-pyrrolo[3,4-d]thiazol-2-yl)-6-methylnicotinamide | 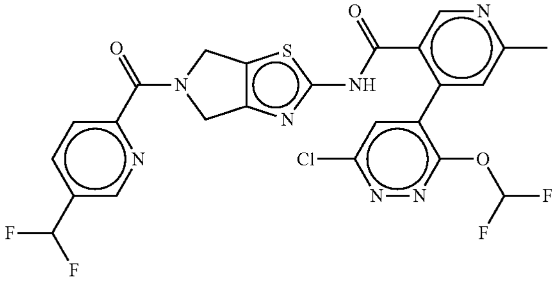 |
| 959 | 2'-chloro-5'-methoxy-6-methyl-N-(5-(1-(2,2,2-trifluoroethyl)piperidine-4-carbonyl)-5,6-dihydro-4H-pyrrolo[3,4-d]thiazol-2-yl)-[4,4'-bipyridine]-3-carboxamide | 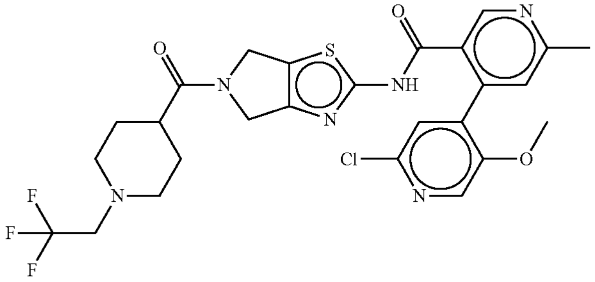 |
| 960 | 2'-chloro-5'-methoxy-6-methyl-N-(5-(1-(2,2,2-trifluoroethyl)pyrrolidine-3-carbonyl)-5,6-dihydro-4H-pyrrolo[3,4-d]thiazol-2-yl)-[4,4'-bipyridine]-3-carboxamide | 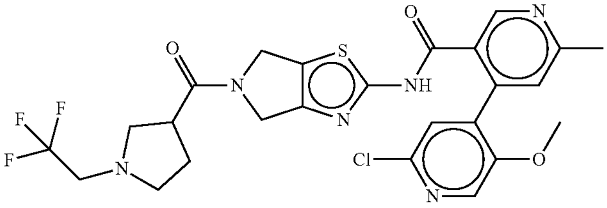 |
| 961 | 2'-chloro-N-(S-(3-fluoro-4-(trifluoromethyl)picolinoyl)-5,6-dihydro-4H-pyrrolo[3,4-d]thiazol-2-yl)-5'-methoxy-6-methyl-[4,4'-bipyridine]-3-carboxamide | 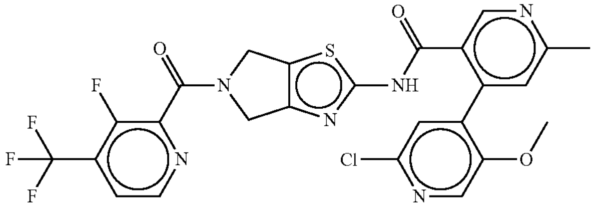 |
| 962 | 2'-chloro-5'-methoxy-N-(5-(6-methoxy-5-(trifluoromethyl)picolinoyl)-5,6-dihydro-4H-pyrrolo[3,4-d]thiazol-2-yl)-6-methyl-[4,4'-bipyridine]-3-carboxamide | 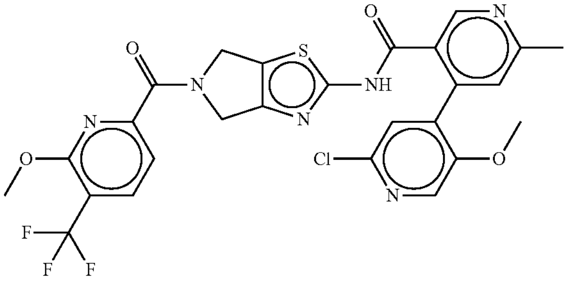 |

TABLE 3-continued

| Compound No. | Name | Structure |
|---|---|---|
| 963 | 2'-chloro-N-(5-(5-(difluoromethyl)-6-methoxypyrazine-2-carbonyl)-5,6-dihydro-4H-pyrrolo[3,4-d]thiazol-2-yl)-5'-methoxy-6-methyl-[4,4'-bipyridine]-3-carboxamide | 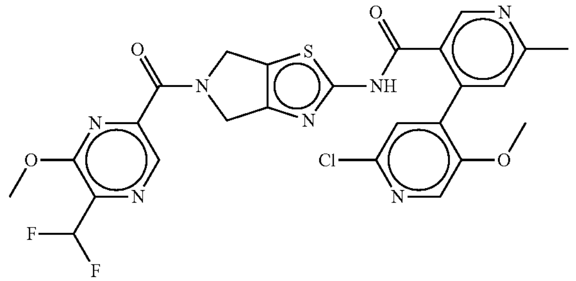 |
| 964 | 2'-chloro-N-(5-(4-(difluoromethyl)-2-fluorobenzyl)-5,6-dihydro-4H-pyrrolo[3,4-d]thiazol-2-yl)-5'-methoxy-6-methyl-[4,4'-bipyridine]-3-carboxamide | 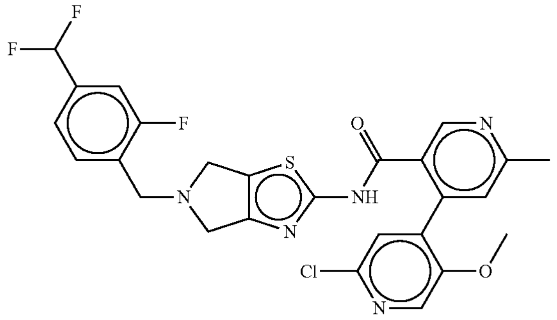 |
| 965 | 2'-chloro-5'-methoxy-6-methyl-N-(5-(3-methyl-6-(trifluoromethyl)picolinoyl)-5,6-dihydro-4H-pyrrolo[3,4-d]thiazol-2-yl)-[4,4'-bipyridine]-3-carboxamide | 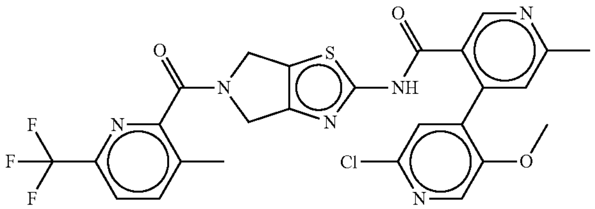 |
| 966 | 2'-chloro-N-(5-(4-(difluoromethyl)-3-methoxypicolinoyl)-5,6-dihydro-4H-pyrrolo[3,4-d]thiazol-2-yl)-5'-methoxy-6-methyl-[4,4'-bipyridine]-3-carboxamide | 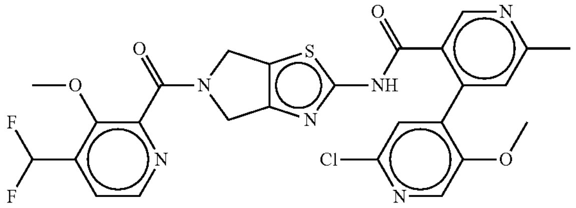 |
| 968 | 2'-chloro-5'-methoxy-N-(5-(3-methoxy-4-(trifluoromethyl)picolinoyl)-5,6-dihydro-4H-pyrrolo[3,4-d]thiazol-2-yl)-6-methyl-[4,4'-bipyridine]-3-carboxamide | 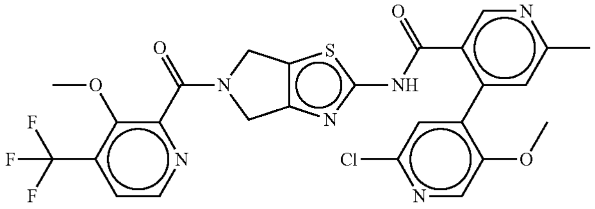 |
| 969 | 2'-chloro-N-(5-(2-ethoxy-6-(trifluoromethyl)nicotinoyl)-5,6-dihydro-4H-pyrrolo[3,4-d]thiazol-2-yl)-5'-methoxy-6-methyl-[4,4'-bipyridine]-3-carboxamide | 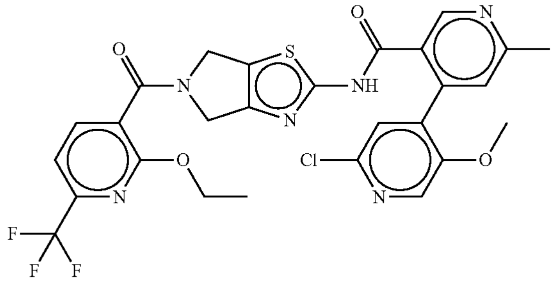 |

TABLE 3-continued

| Compound No. | Name | Structure |
|---|---|---|
| 970 | 2'-chloro-N-(5-(2-ethyl-6-(trifluoromethyl)nicotinoyl)-5,6-dihydro-4H-pyrrolo[3,4-d]thiazol-2-yl)-5'-methoxy-6-methyl-[4,4'-bipyridine]-3-carboxamide | 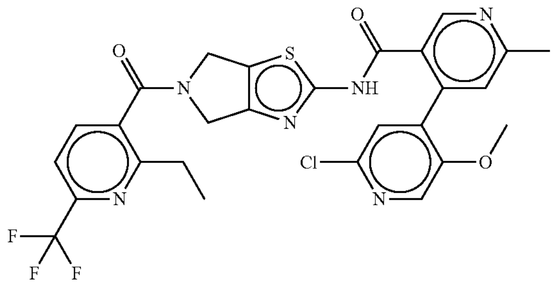 |
| 972 | 2'-chloro-N-(5-(5-(difluoromethyl)-3-methoxypyrazine-2-carbonyl)-5,6-dihydro-4H-pyrrolo[3,4-d]thiazol-2-yl)-5'-methoxy-6-methyl-[4,4'-bipyridine]-3-carboxamide | 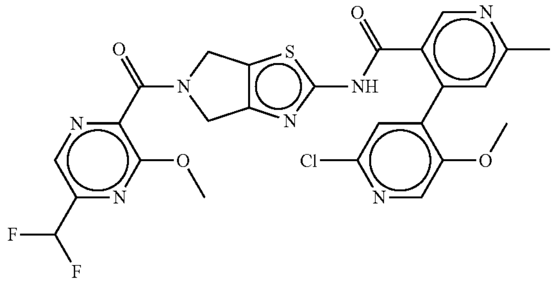 |
| 973 | 2'-chloro-N-(5-(4-chloro-6-(trifluoromethyl)nicotinoyl)-5,6-dihydro-4H-pyrrolo[3,4-d]thiazol-2-yl)-5'-methoxy-6-methyl-[4,4'-bipyridine]-3-carboxamide | 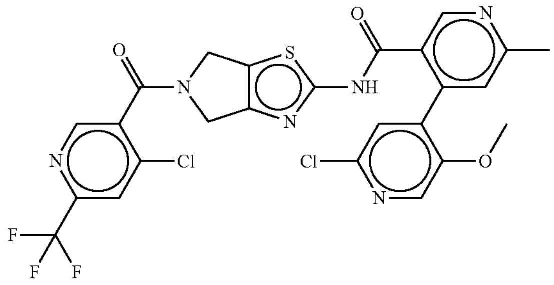 |
| 974 | 2'-chloro-5'-methoxy-N-(5-(4-methoxy-6-(trifluoromethyl)nicotinoyl)-5,6-dihydro-4H-pyrrolo[3,4-d]thiazol-2-yl)-6-methyl-[4,4'-bipyridine]-3-carboxamide | 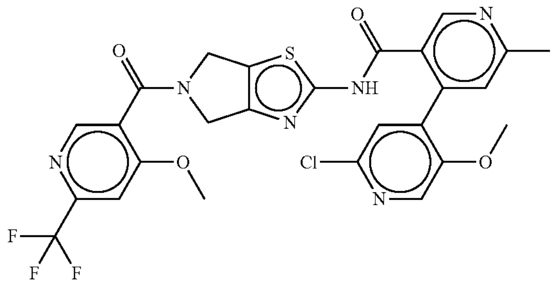 |
| 975 | 2'-chloro-N-(5-(1-(4-(difluoromethyl)-2-fluorophenyl)ethyl)-5,6-dihydro-4H-pyrrolo[3,4-d]thiazol-2-yl)-5'-methoxy-6-methyl-[4,4'-bipyridine]-3-carboxamide | 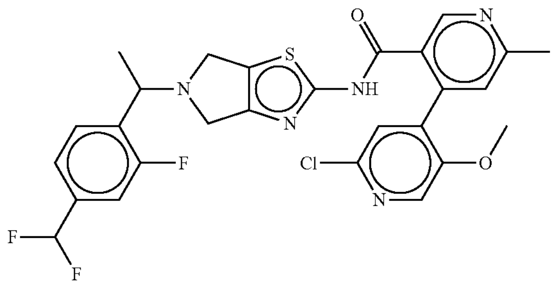 |

TABLE 3-continued

| Compound No. | Name | Structure |
|---|---|---|
| 976 | 2'-chloro-N-(5-(4-(difluoromethyl)-3-methylpicolinoyl)-5,6-dihydro-4H-pyrrolo[3,4-d]thiazol-2-yl)-5'-methoxy-6-methyl-[4,4'-bipyridine]-3-carboxamide | 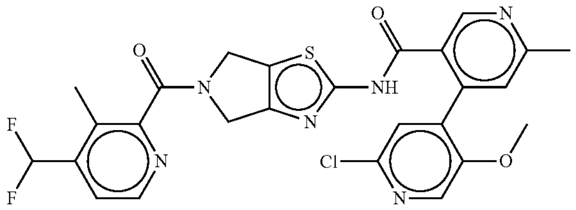 |
| 978 | 2'-chloro-N-(5-(5-cyano-3,4-dimethylpicolinoyl)-5,6-dihydro-4H-pyrrolo[3,4-d]thiazol-2-yl)-5'-methoxy-6-methyl-[4,4'-bipyridine]-3-carboxamide | 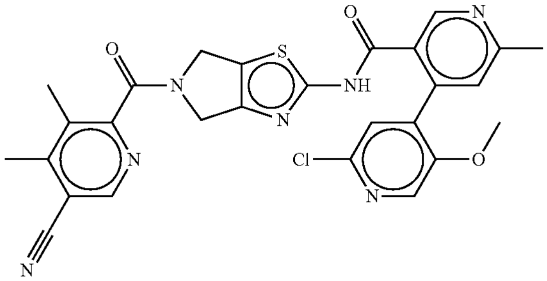 |
| 979 | 2'-chloro-N-(5-(5-cyano-3,6-dimethylpicolinoyl)-5,6-dihydro-4H-pyrrolo[3,4-d]thiazol-2-yl)-5'-methoxy-6-methyl-[4,4'-bipyridine]-3-carboxamide | 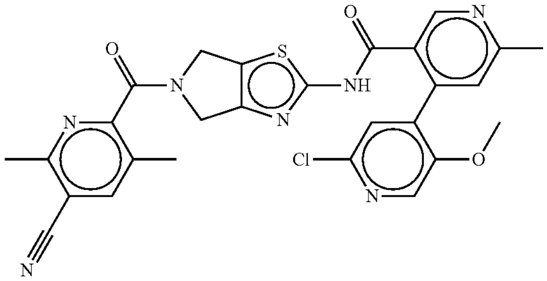 |
| 981 | 4-(6-chloro-3-methoxypyridazin-4-yl)-N-(5-(5-cyano-6-methylpicolinoyl)-5,6-dihydro-4H-pyrrolo[3,4-d]thiazol-2-yl)-6-methylnicotinamide | 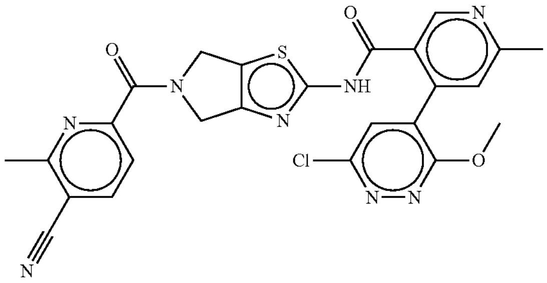 |
| 982 | 4-(6-chloro-3-oxo-2,3-dihydropyridazin-4-yl)-N-(5-(5-cyano-6-methylpicolinoyl)-5,6-dihydro-4H-pyrrolo[3,4-d]thiazol-2-yl)-6-methylnicotinamide | 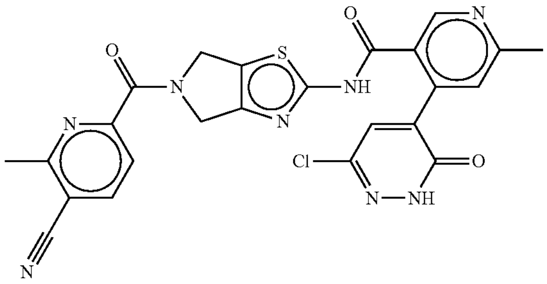 |

TABLE 3-continued

| Compound No. | Name | Structure |
|---|---|---|
| 983 | 4-(6-chloro-3-oxo-2,3-dihydropyridazin-4-yl)-6-methyl-N-(5-(5-(trifluoromethyl)pyrazine-2-carbonyl)-5,6-dihydro-4H-pyrrolo[3,4-d]thiazol-2-yl)nicotinamide | 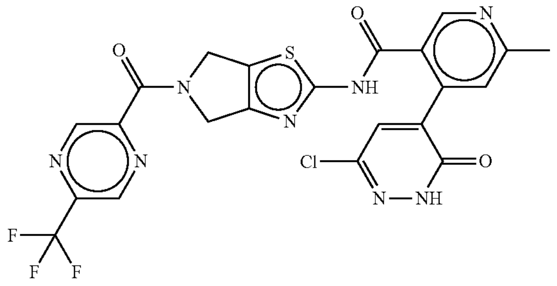 |
| 984 | 4-(6-chloro-3-methoxypyridazin-4-yl)-6-methyl-N-(5-(5-(trifluoromethyl)pyrazine-2-carbonyl)-5,6-dihydro-4H-pyrrolo[3,4-d]thiazol-2-yl)nicotinamide | 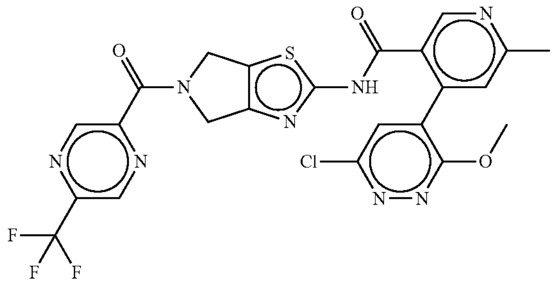 |
| 985 | 2'-chloro-N-(5-(6-(difluoromethoxy)-2-methoxynicotinoyl)-5,6-dihydro-4H-pyrrolo[3,4-d]thiazol-2-yl)-5'-methoxy-6-methyl-[4,4'-bipyridine]-3-carboxamide | 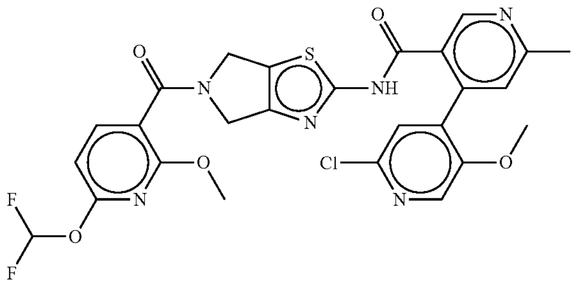 |
| 986 | 2'-chloro-5'-methoxy-N-(5-(6-methoxy-5-(trifluoromethyl)pyrazine-2-carbonyl)-5,6-dihydro-4H-pyrrolo[3,4-d]thiazol-2-yl)-6-methyl-[4,4'-bipyridine]-3-carboxamide | 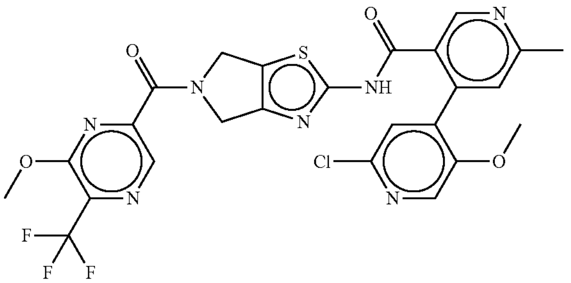 |
| 987 | 2'-chloro-5'-methoxy-N-(5-(6-methoxy-3-methyl-5-(trifluoromethyl)picolinoyl)-5,6-dihydro-4H-pyrrolo[3,4-d]thiazol-2-yl)-6-methyl-[4,4'-bipyridine]-3-carboxamide | 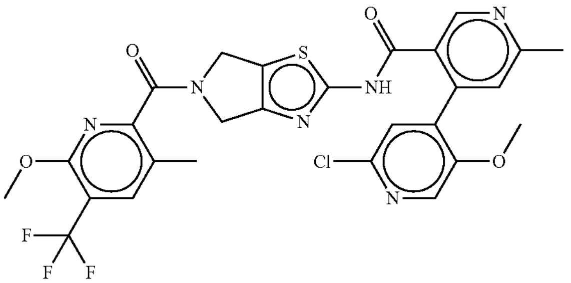 |

TABLE 3-continued

| Compound No. | Name | Structure |
|---|---|---|
| 989 | 2'-chloro-5'-methoxy-N-(5-(2-methoxy-5-methyl-6-(trifluoromethyl)nicotinoyl)-5,6-dihydro-4H-pyrrolo[3,4-d]thiazol-2-yl)-6-methyl-[4,4'-bipyridine]-3-carboxamide | 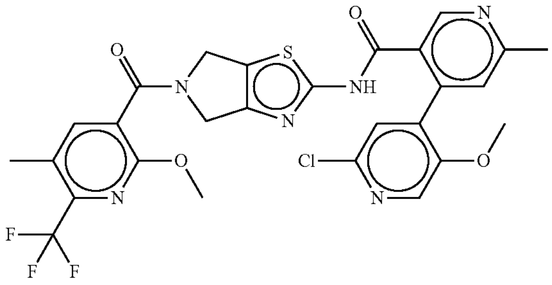 |
| 990 | 2'-chloro-N-(5-(5-(difluoromethoxy)-6-methylpyrazine-2-carbonyl)-5,6-dihydro-4H-pyrrolo[3,4-d]thiazol-2-yl)-5'-methoxy-6-methyl-[4,4'-bipyridine]-3-carboxamide | 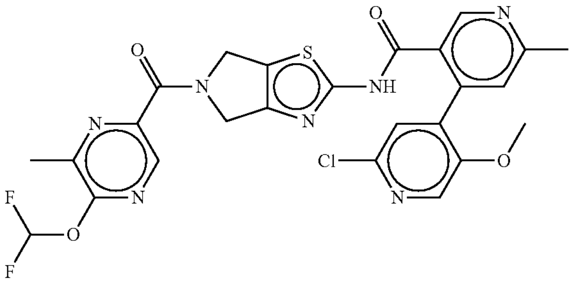 |
| 993 | 2'-chloro-5'-methoxy-N-(5-(4-methoxy-5-(trifluoromethyl)pyrimidine-2-carbonyl)-5,6-dihydro-4H-pyrrolo[3,4-d]thiazol-2-yl)-6-methyl-[4,4'-bipyridine]-3-carboxamide | 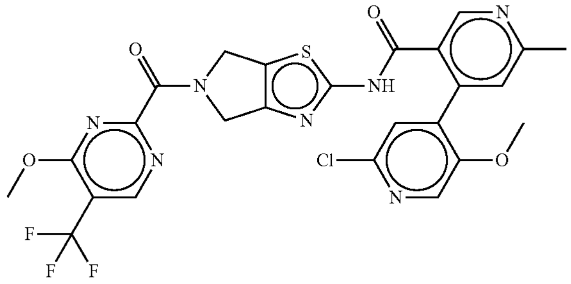 |
| 994 | 2'-chloro-5'-methoxy-N-(5-(2-methoxy-5-(trifluoromethyl)pyrimidine-4-carbonyl)-5,6-dihydro-4H-pyrrolo[3,4-d]thiazol-2-yl)-6-methyl-[4,4'-bipyridine]-3-carboxamide | 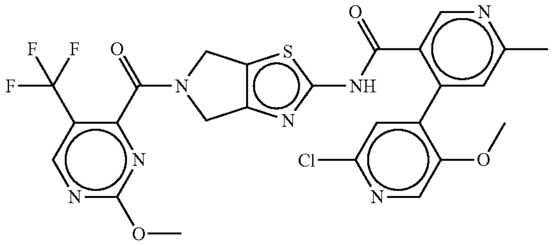 |
| 995 | 2'-chloro-5'-methoxy-6-methyl-N-(5-(6-methyl-5-(trifluoromethoxy)picolinoyl)-5,6-dihydro-4H-pyrrolo[3,4-d]thiazol-2-yl)-[4,4'-bipyridine]-3-carboxamide | 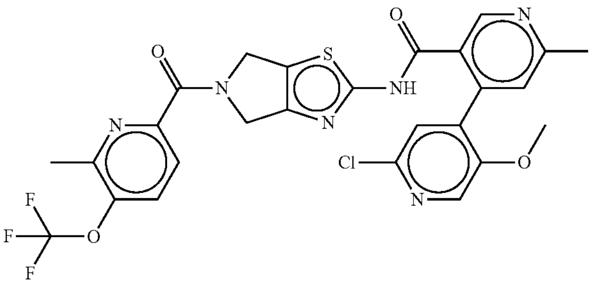 |

TABLE 3-continued

| Compound No. | Name | Structure |
|---|---|---|
| 996 | 4-(6-chloro-3-methoxypyridazin-4-yl)-N-(5-(2-methoxy-6-(trifluoromethyl)nicotinoyl)-5,6-dihydro-4H-pyrrolo[3,4-d]thiazol-2-yl)-6-methylnicotinamide | 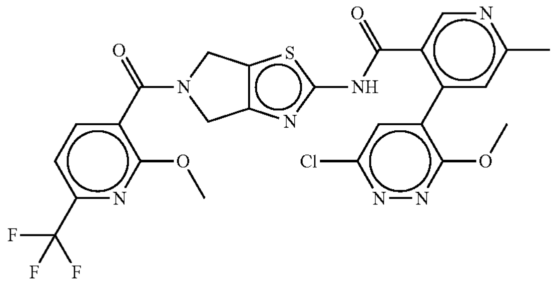 |
| 997 | 2'-chloro-N-(5-(6-chloro-5-(trifluoromethoxy)picolinoy])-5,6-dihydro-4H-pyrrolo[3,4-d]thiazol-2-yl)-5'-methoxy-6-methyl-[4,4'-bipyridine]-3-carboxamide | 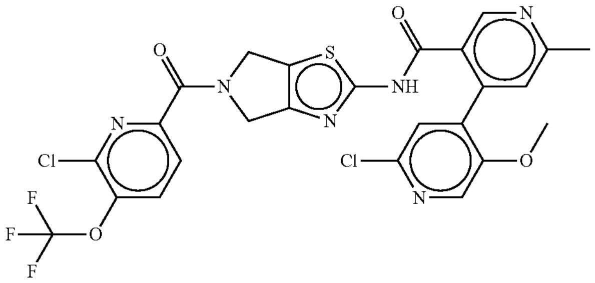 |
| 998 | 4-(6-chloro-3-oxo-2,3-dihydropyridazin-4-yl)-N-(5-(2-methoxy-6-(trifluoromethyl)nicotinoyl)-5,6-dihydro-4H-pyrrolo[3,4-d]thiazol-2-yl)-6-methylnicotinamide | 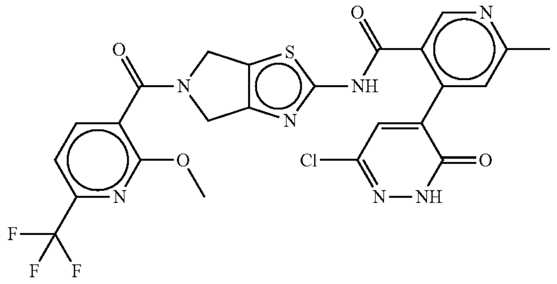 |
| 999 | 2'-chloro-N-(5-(3,6-dimethyl-4-(trifluoromethyl)picolinoyl)-5,6-dihydro-4H-pyrrolo[3,4-d]thiazol-2-yl)-5'-methoxy-6-methyl-[4,4'-bipyridine]-3-carboxamide | 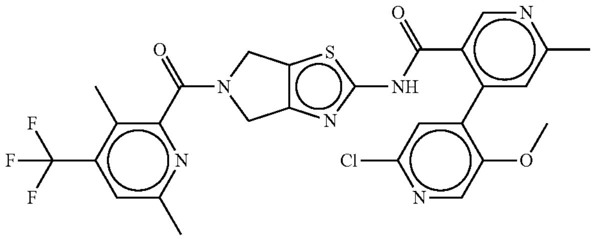 |
| 1000 | 2'-chloro-5'-methoxy-6-methyl-N-(5-(3-methyl-5-(trifluoromethyl)pyrazine-2-carbonyl)-5,6-dihydro-4H-pyrrolo[3,4-d]thiazol-2-yl)-[4,4'-bipyridine]-3-carboxamide | 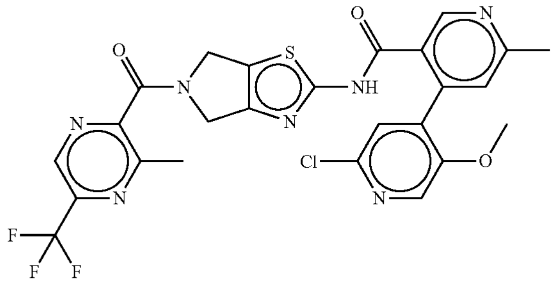 |

TABLE 3-continued

| Compound No. | Name | Structure |
|---|---|---|
| 1003 | 5-chloro-2-methoxy-N-(5-(2-methoxy-6-(trifluoromethyl)nicotinoyl)-5,6-dihydro-4H-pyrrolo[3,4-d]thiazol-2-yl)-6'-methyl-[3,4'-bipyridine]-3'-carboxamide | 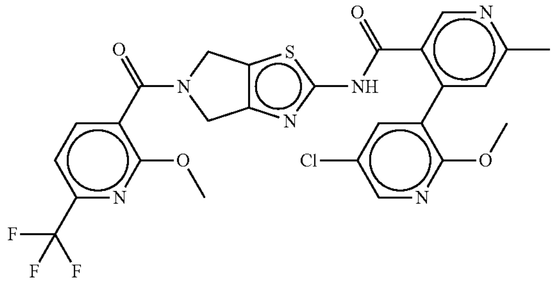 |
| 1004 | N-(5-(2-methoxy-6-(trifluoromethyl)nicotinoyl)-5,6-dihydro-4H-pyrrolo[3,4-d]thiazol-2-yl)-4-(6-methoxyimidazo[1,5-alpyridin-7-yl)-6-methylnicotinamide | 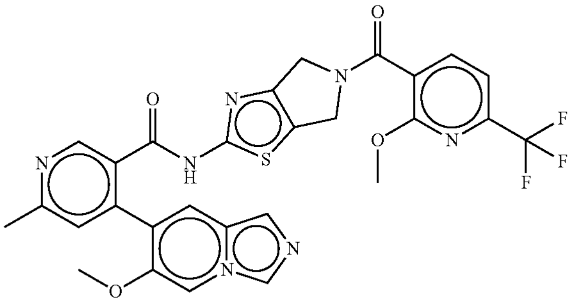 |
| 1005 | 4-(5-cyano-2-methoxyphenyl)-N-(5-(2-methoxy-6-(trifluoromethyl)nicotinoyl)-5,6-dihydro-4H-pyrrolo[3,4-d]thiazol-2-yl)-6-methylnicotinamide | 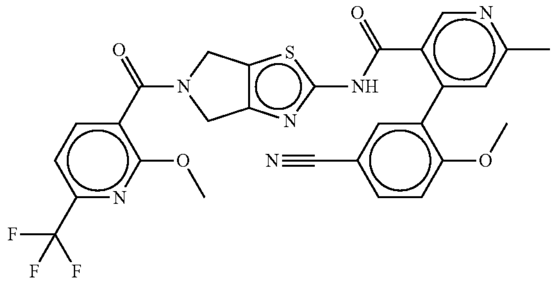 |
| 1006 | 2'-chloro-N-(5-(5-cyano-3-fluoro-6-methylpicolinoyl)-5,6-dihydro-4H-pyrrolo[3,4-d]thiazol-2-yl)-5'-methoxy-6-methyl-[4,4'-bipyridine]-3-carboxamide | 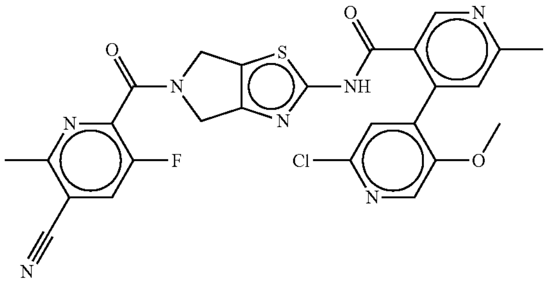 |
| 1007 | 2'-chloro-5'-methoxy-6-methyl-N-(5-(3-methyl-5-(trifluoromethoxy)picolinoyl)-5,6-dihydro-4H-pyrrolo[3,4-d]thiazol-2-yl)-[4,4'-bipyridine]-3-carboxamide | 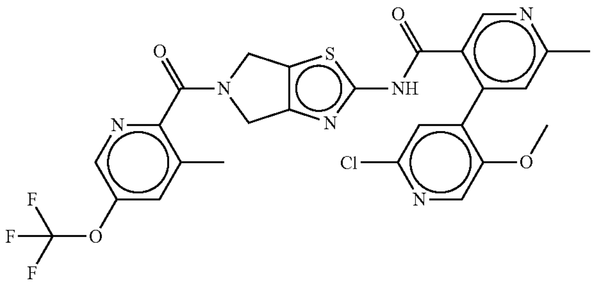 |

TABLE 3-continued

| Compound No. | Name | Structure |
|---|---|---|
| 1008 | 2'-chloro-N-(5-(5-(difluoromethoxy)-6-methylpicolinoyl)-5,6-dihydro-4H-pyrrolo[3,4-d]thiazol-2-yl)-5'-methoxy-6-methyl-[4,4'-bipyridine]-3-carboxamide | 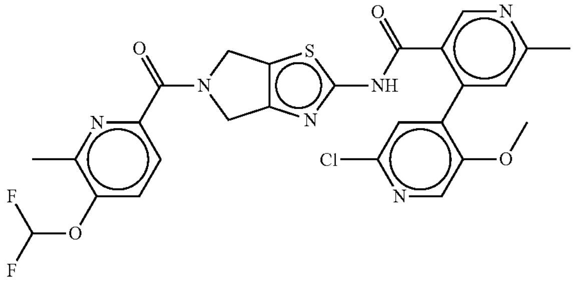 |
| 1009 | 2'-chloro-5'-methoxy-6-methyl-N-(5-(4-methyl-6-(trifluoromethoxy)nicotinoyl)-5,6-dihydro-4H-pyrrolo[3,4-d]thiazol-2-yl)-[4,4'-bipyridine]-3-carboxamide | 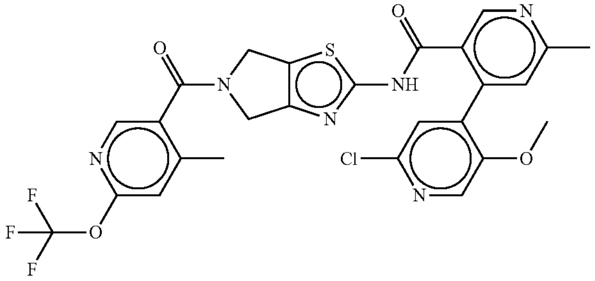 |
| 1010 | 4-(6-methoxy-1-methyl-1H-indazol-S-yl)-N-(5-(2-methoxy-6-(trifluoromethyl)nicotinoyl)-5,6-dihydro-4H-pyrrolo[3,4-d]thiazol-2-yl)-6-methylnicotinamide | 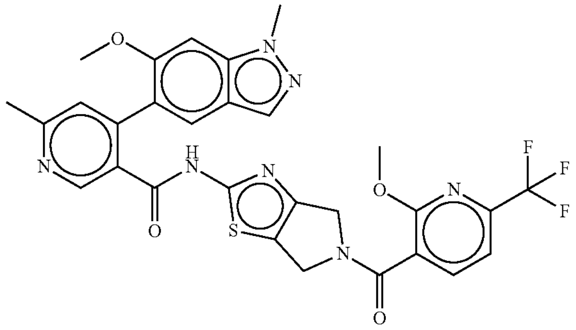 |
| 1011 | 2'-chloro-N-(5-(3,5-dimethyl-4-(trifluoromethyl)picolinoyl)-5,6-dihydro-4H-pyrrolo[3,4-d]thiazol-2-yl)-5'-methoxy-6-methyl-[4,4'-bipyridine]-3-carboxamide | 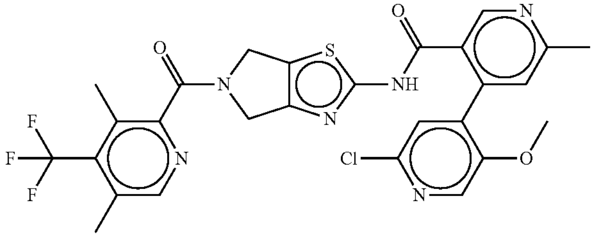 |
| 1012 | 2'-chloro-N-(5-(3,5-dimethyl-6-(trifluoromethyl)picolinoyl)-5,6-dihydro-4H-pyrrolo[3,4-d]thiazol-2-yl)-5'-methoxy-6-methyl-[4,4'-bipyridine]-3-carboxamide | 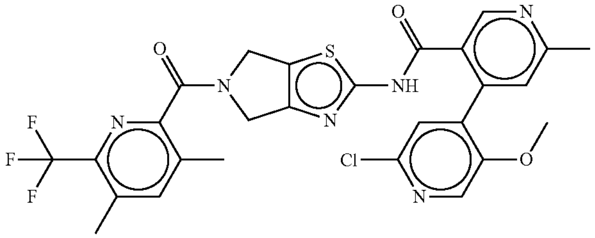 |

TABLE 3-continued

| Compound No. | Name | Structure |
|---|---|---|
| 1013 | 4-(2-fluoro-6-methoxyphenyl)-N-(5-(2-methoxy-6-(trifluoromethyl)nicotinoyl)-5,6-dihydro-4H-pyrrolo[3,4-d]thiazol-2-yl)-6-methylnicotinamide | 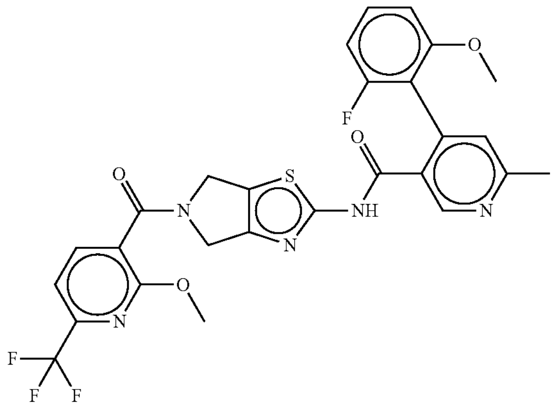 |
| 1014 | 2'-chloro-N-(5-(3-fluoro-6-methyl-5-(trifluoromethyl)picolinoyl)-5,6-dihydro-4H-pyrrolo[3,4-d]thiazol-2-yl)-5'-methoxy-6-methyl-[4,4'-bipyridine]-3-carboxamide | 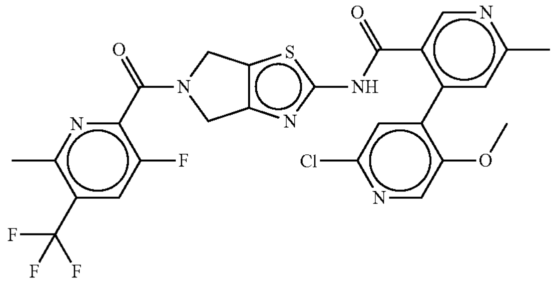 |
| 1015 | 2'-chloro-N-(5-(5-cyano-6-(difluoromethyl)picolinoyl)-5,6-dibydro-4H-pyrrolo[3,4-d]thiazol-2-yl)-5'-methoxy-6-methyl-[4,4'-bipyridine]-3-carboxamide | 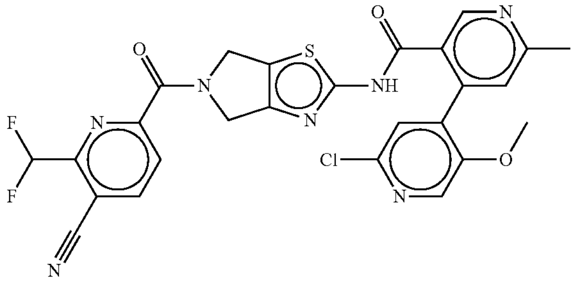 |
| 1016 | 2'-(difluoromethyl)-5'-methoxy-N-(5-(2-methoxy-6-(trifluoromethyl)nicotinoyl)-5,6-dihydro-4H-pyrrolo[3,4-d]thiazol-2-yl)-6-methyl-[4,4'-bipyridine]-3-carboxamide | 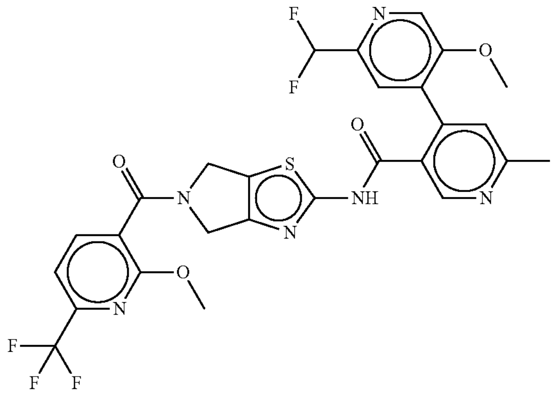 |

TABLE 3-continued

| Compound No. | Name | Structure |
|---|---|---|
| 1018 | 2'-chloro-5'-methoxy-6-methyl-N-(5-(2-methyl-6-(trifluoromethoxy)nicotinoyl)-5,6-dihydro-4H-pyrrolo[3,4-d]thiazol-2-yl)-[4,4'-bipyridine]-3-carboxamide | 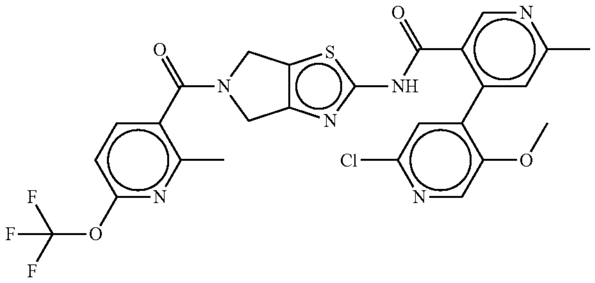 |
| 1019 | 2'-chloro-5'-methoxy-N-(5-(2-methoxy-4-methyl-6-(trifluoromethyl)nicotinoyl)-5,6-dihydro-4H-pyrrolo[3,4-d]thiazol-2-yl)-6-methyl-[4,4'-bipyridine]-3-carboxamide | 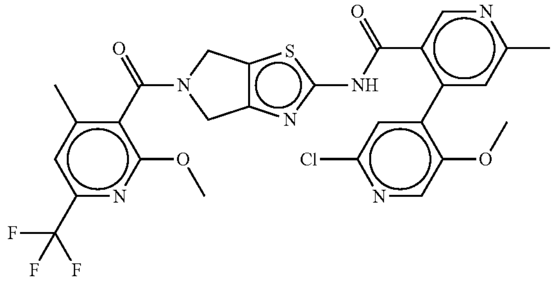 |
| 1020 | 2'-chloro-N-(5-(3-chloro-5-(difluoromethyl)-4,6-dimethylpicolinoyl)-5,6-dihydro-4H-pyrrolo[3,4-d]thiazol-2-yl)-5'-methoxy-6-methyl-[4,4'-bipyridine]-3-carboxamide | 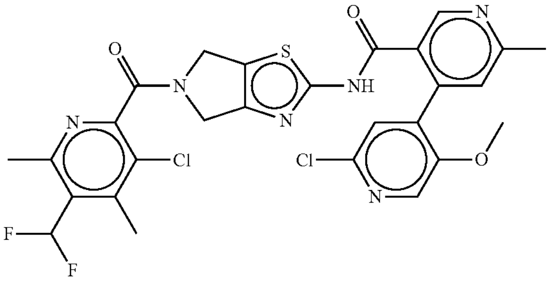 |
| 1021 | 2'-chloro-N-(S-(3-fluoro-5-methyl-6-(trifluoromethyl)picolinoyl)-5,6-dihydro-4H-pyrrolo[3,4-d]thiazol-2-yl)-5'-methoxy-6-methyl-[4,4'-bipyridine]-3-carboxamide | 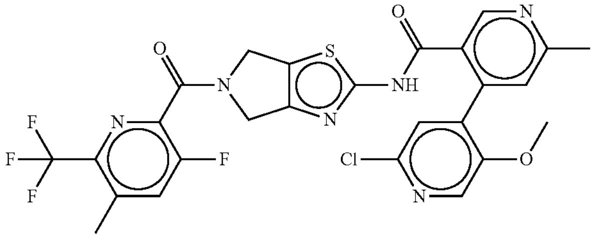 |
| 1022 | 2'-chloro-N-(5-(5-cyano-3-methyl-6-(trifluoromethyl)picolinoyl)-5,6-dihydro-4H-pyrrolo[3,4-d]thiazol-2-yl)-5'-methoxy-6-methyl-[4,4'-bipyridine]-3-carboxamide | 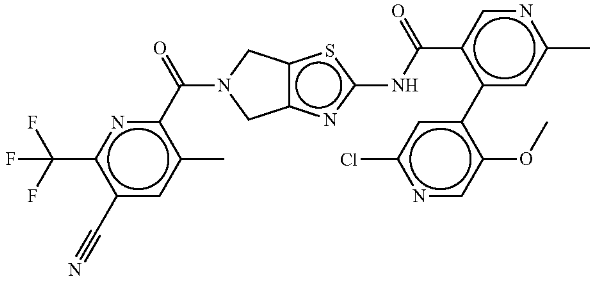 |

TABLE 3-continued

| Compound No. | Name | Structure |
|---|---|---|
| 1023 | 2'-chloro-3'-fluoro-5'-methoxy-N-(5-(2-methoxy-6-(trifluoromethyl)nicotinoyl)-5,6-dihydro-4H-pyrrolo[3,4-d]thiazol-2-yl)-6-methyl-[4,4'-bipyridine]-3-carboxamide | 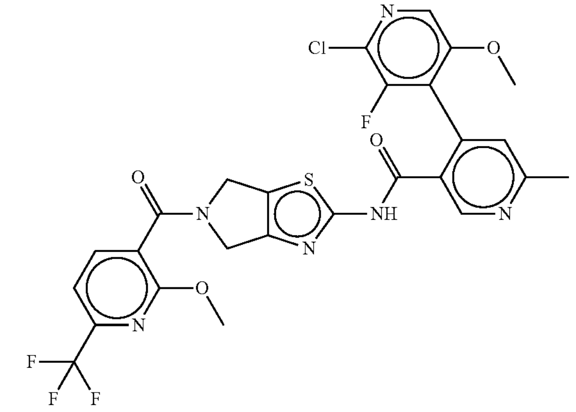 |
| 1024 | 4-(6-(difluoromethyl)-3-methoxypyridazin-4-yl)-6-methyl-N-(5-(3-methyl-4-(trifluoromethyl)picolinoyl)-5,6-dihydro-4H-pyrrolo[3,4-d]thiazol-2-yl)nicotinamide | 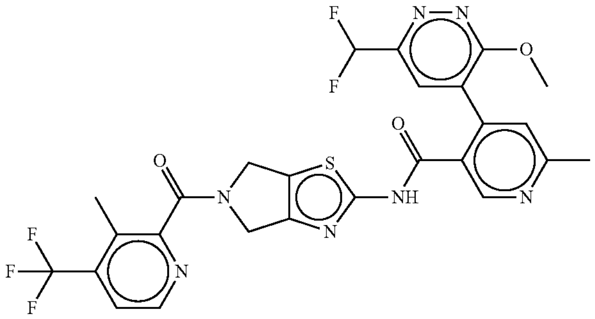 |
| 1025 | 4-(6-(difluoromethyl)-3-methoxypyridazin-4-yl)-N-(5-(2-methoxy-6-(trifluoromethyl)nicotinoyl)-5,6-dihydro-4H-pyrrolo[3,4-d]thiazol-2-yl)-6-methylnicotinamide | 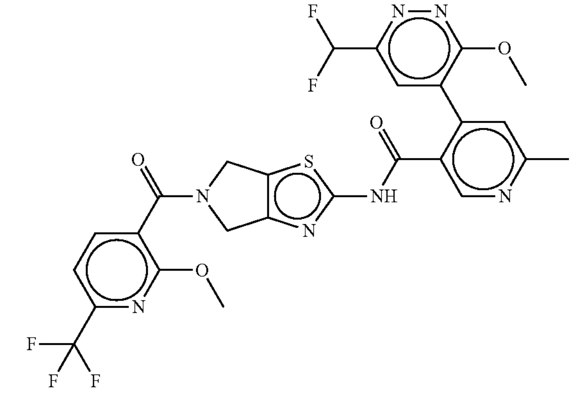 |
| 1026 | 4-(6-(difluoromethyl)-3-methoxypyridazin-4-yl)-N-(5-(3-fluoro-4-(trifluoromethyl)picolinoyl)-5,6-dihydro-4H-pyrrolo[3,4-d]thiazol-2-yl)-6-methylnicotinamide | 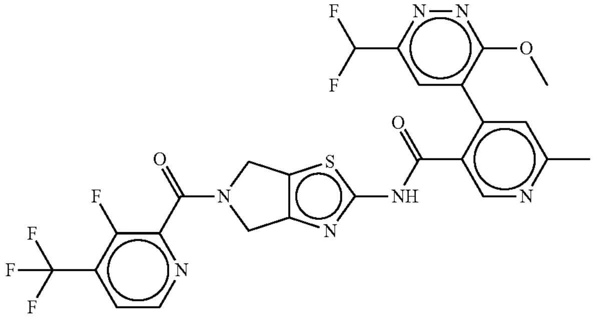 |

TABLE 3-continued

| Compound No. | Name | Structure |
|---|---|---|
| 1027 | 2'-chloro-N-(5-(5-(difluoromethoxy)-3,6-dimethylpicolinoyl)-5,6-dihydro-4H-pyrrolo[3,4-d]thiazol-2-yl)-5'-methoxy-6-methyl-[4,4'-bipyridine]-3-carboxamide | 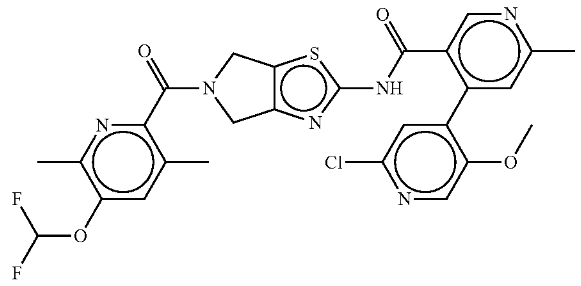 |
| 1028 | 2'-chloro-N-(5-(3,6-dimethyl-5-(trifluoromethoxy)picolinoyl)-5,6-dihydro-4H-pyrrolo[3,4-d]thiazol-2-yl)-5'-methoxy-6-methyl-[4,4'-bipyridine]-3-carboxamide | 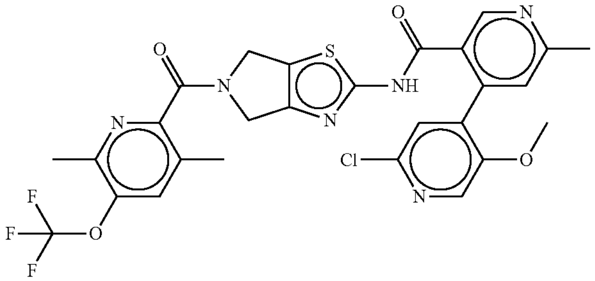 |
| 1029 | 3'-fluoro-5'-methoxy-N-(5-(2-methoxy-6-(trifluoromethyl)nicotinoyl)-5,6-dihydro-4H-pyrrolo[3,4-d]thiazol-2-yl)-2',6-dimethyl-[4,4'-bipyridine]-3-carboxamide | 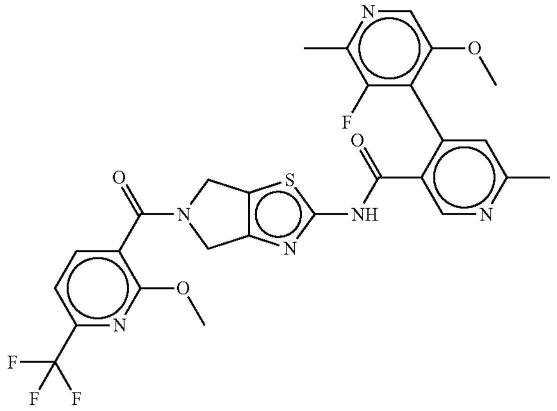 |
| 1030 | 2'-chloro-N-(5-(2-chloro-6-methoxy-4-methylnicotinoyl)-5,6-dihydro-4H-pyrrolo[3,4-d]thiazol-2-yl)-5'-methoxy-6-methyl-[4,4'-bipyridine]-3-carboxamide | 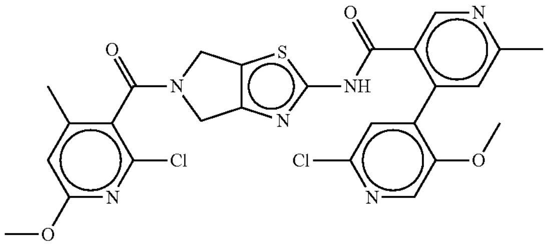 |
| 1031 | 2'-chloro-N-(5-(5-cyano-6-(trifluoromethyl)picolinoyl)-5,6-dihydro-4H-pyrrolo[3,4-d]thiazol-2-yl)-5'-methoxy-6-methyl-[4,4'-bipyridine]-3-carboxamide | 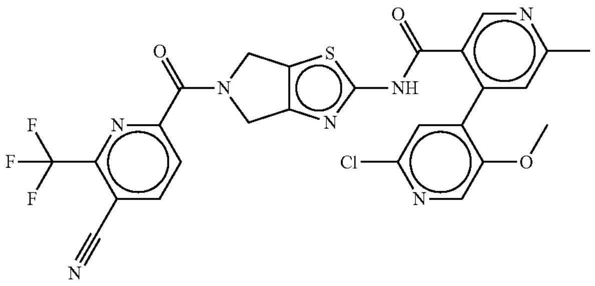 |

TABLE 3-continued

| Compound No. | Name | Structure |
|---|---|---|
| 1032 | 5-(difluoromethyl)-2-methoxy-N-(5-(2-methoxy-6-(trifluoromethyl)nicotinoyl)-5,6-dihydro-4H-pyrrolo[3,4-d]thiazol-2-yl)-6'-methyl-[3,4'-bipyridine]-3'-carboxamide | 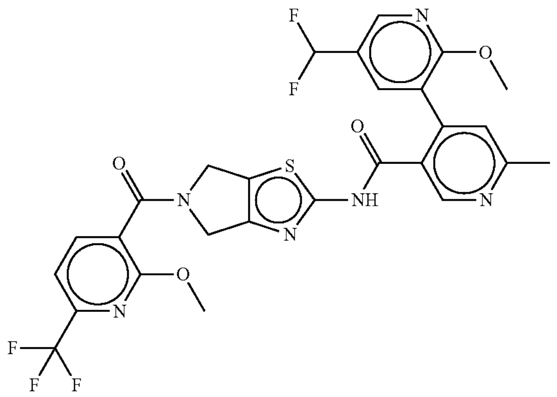 |
| 1033 | 2'-chloro-5'-methoxy-N-(5-(2-methoxy-6-(trifluoromethyl)nicotinoyl)-4-methyl-5,6-dihydro-4H-pyrrolo[3,4-d]thiazol-2-yl)-6-methyl-[4,4'-bipyridine]-3-carboxamide | 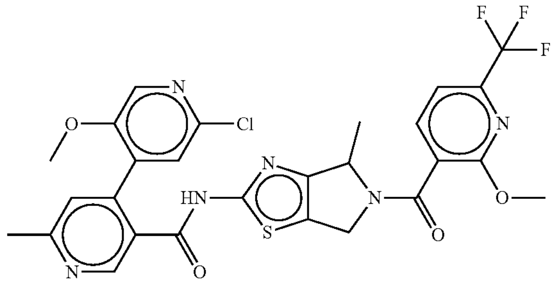 |
| 1034 | 5-chloro-2-methoxy-N-(5-(3-methoxy-4-(trifluoromethyl)picolinoyl)-5,6-dihydro-4H-pyrrolo[3,4-d]thiazol-2-yl)-6'-methyl-[3,4'-bipyridine]-3'-carboxamide | 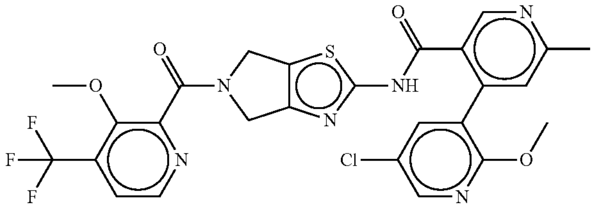 |
| 1035 | 5-chloro-2-methoxy-N-(5-(6-methoxy-5-(trifluoromethyl)picolinoyl)-5,6-dihydro-4H-pyrrolo[3,4-d]thiazol-2-yl)-6'-methyl-[3,4'-bipyridine]-3'-carboxamide | 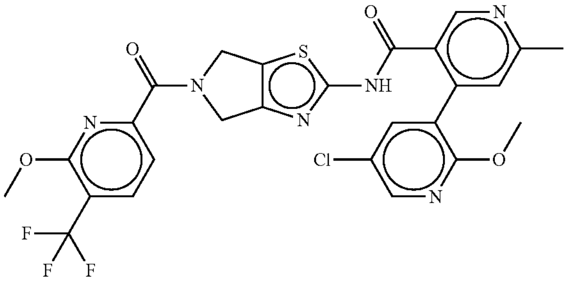 |
| 1036 | 5-chloro-2,6-dimethoxy-N-(5-(2-methoxy-6-(trifluoromethyl)nicotinoyl)-5,6-dihydro-4H-pyrrolo[3,4-d]thiazol-2-yl)-6'-methyl-[3,4'-bipyridine]-3'-carboxamide | 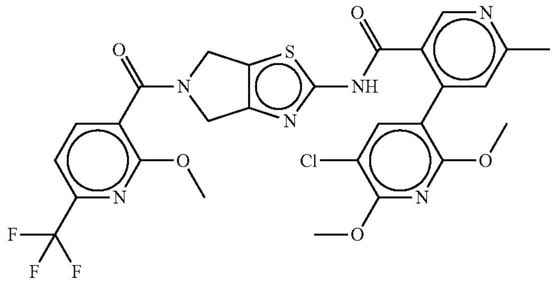 |

TABLE 3-continued

| Compound No. | Name | Structure |
|---|---|---|
| 1037 | (R or S)-2'-chloro-5'-methoxy-N-(5-(2-methoxy-6-(trifluoromethyl)nicotinoyl)-4-methyl-5,6-dihydro-4H-pyrrolo[3,4-d]thiazol-2-y])-6-methyl-[4,4'-bipyridine]-3-carboxamide | 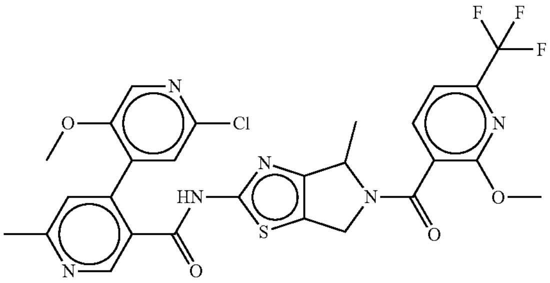 |
| 1038 | 2'-chloro-N-(5-(2-fluoro-6-methoxynicotinoyl)-5,6-dihydro-4H-pyrrolo[3,4-d]thiazol-2-yl)-5'-methoxy-6-methyl-[4,4'-bipyridine]-3-carboxamide | 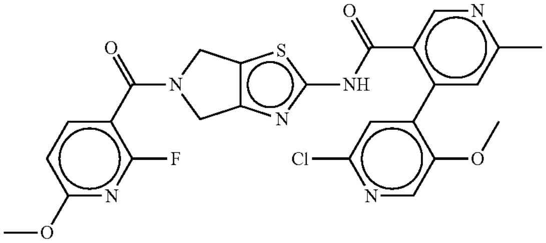 |
| 1039 | 2'-chloro-5'-methoxy-N-(5-(2-methoxy-6-(trifluoromethoxy)nicotinoyl)-5,6-dihydro-4H-pyrrolo[3,4-d]thiazol-2-yl)-6-methyl-[4,4'-bipyridine]-3-carboxamide | 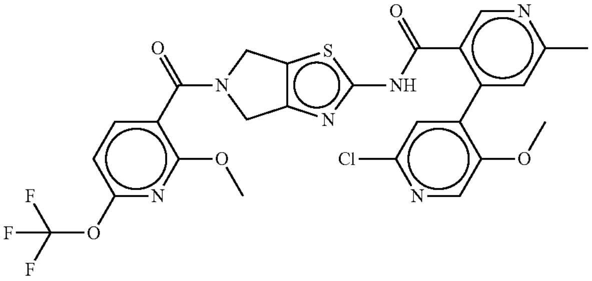 |
| 1040 | 2'-chloro-5'-methoxy-N-(S-(2-methoxy-6-(trifluoromethyl)nicotinoyl)-6-methyl-5,6-dihydro-4H-pyrrolo[3,4-d]thiazol-2-yl)-6-methyl-[4,4'-bipyridine]-3-carboxamide | 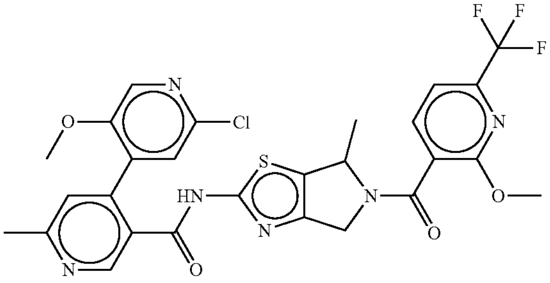 |
| 1041 | (S or R)-2'-chloro-5'-methoxy-N-(5-(2-methoxy-6-(trifluoromethyl)nicotinoyl)-4-methyl-5,6-dihydro-4H-pyrrolo[3,4-d]thiazol-2-yl)-6-methyl-[4,4'-bipyridine]-3-carboxamide | 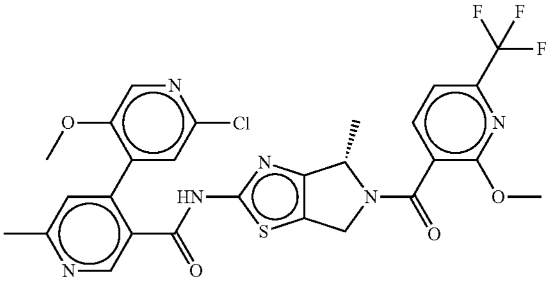 |

TABLE 3-continued

| Compound No. | Name | Structure |
|---|---|---|
| 1042 | 4-(2-(difluoromethyl)-5-methoxypyrimidin-4-yl)-N-(5-(2-methoxy-6-(trifluoromethyl)nicotinoyl)-5,6-dihydro-4H-pyrrolo[3,4-d]thiazol-2-yl)-6-methylnicotinamide | 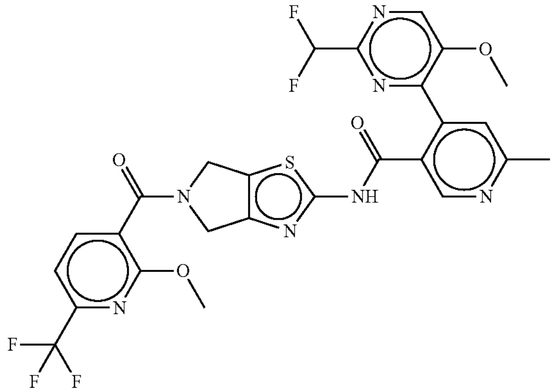 |
| 1043 | 5-chloro-2-hydroxy-N-(5-(6-methoxy-3-methyl-5-(trifluoromethyl)picolinoyl)-5,6-dihydro-4H-pyrrolo[3,4-d]thiazol-2-yl)-6'-methyl-[3,4'-bipyridine]-3'-carboxamide | 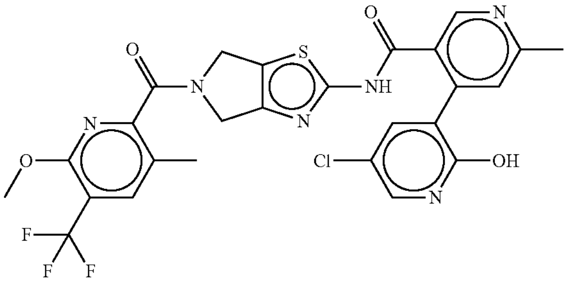 |
| 1044 | 5-chloro-2-methoxy-N-(5-(6-methoxy-3-methyl-5-(trifluoromethyl)picolinoyl)-5,6-dihydro-4H-pyrrolo[3,4-d]thiazol-2-yl)-6'-methyl-[3,4'-bipyridine]-3'-carboxamide | 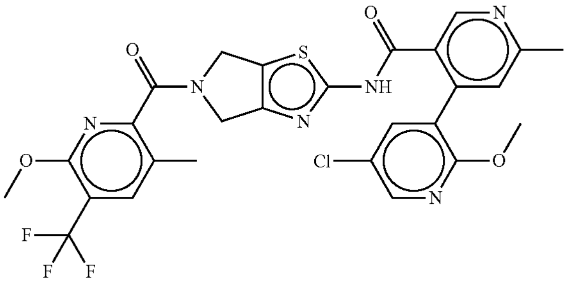 |
| 1045 | 5-chloro-N-(5-(2-methoxy-6-(trifluoromethyl)nicotinoyl)-5,6-dihydro-4H-pyrrolo[3,4-d]thiazol-2-yl)-6'-methyl-2-oxo-1,2-dihydro-[3,4'-bipyridine]-3'-carboxamide | 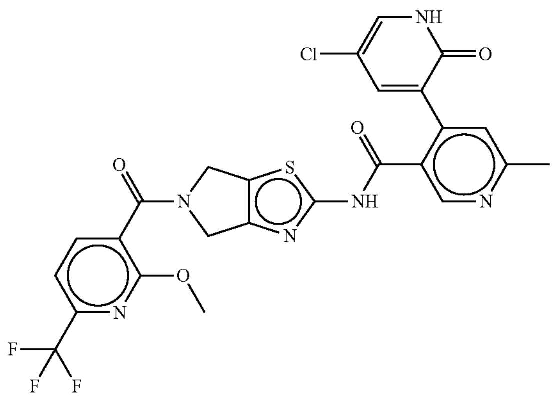 |

TABLE 3-continued

| Compound No. | Name | Structure |
|---|---|---|
| 1046 | (R or S)-2'-chloro-5'-methoxy-N-(5-(2-methoxy-6-(trifluoromethyl)nicotinoyl)-6-methyl-5,6-dihydro-4H-pyrrolo[3,4-d]thiazol-2-yl)-6-methyl-[4,4'-bipyridine]-3-carboxamide | 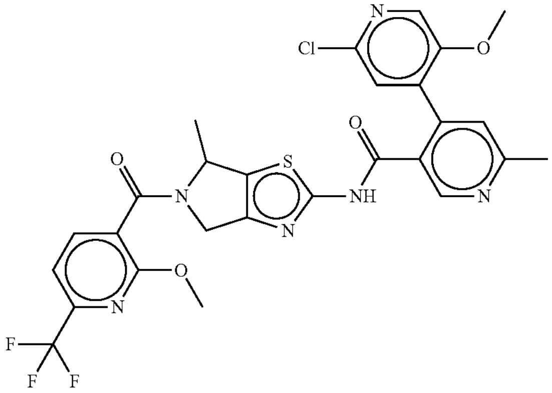 |
| 1047 | (S or R)-2'-chloro-5'-methoxy-N-(5-(2-methoxy-6-(trifluoromethyl)nicotinoyl)-6-methyl-5,6-dihydro-4H-pyrrolo[3,4-d]thiazol-2-yl)-6-methyl-[4,4'-bipyridine]-3-carboxamide | 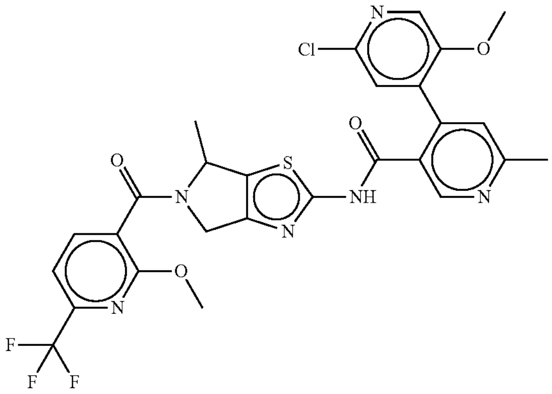 |
| 1048 | 5-cyano-2-methoxy-N-(5-(2-methoxy-6-(trifluoromethyl)nicotinoyl)-5,6-dihydro-4H-pyrrolo[3,4-d]thiazol-2-yl)-6'-methyl-[3,4'-bipyridine]-3'-carboxamide | 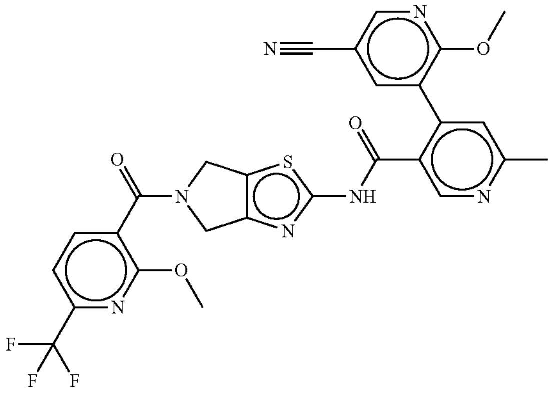 |

In some embodiments, the compound is a pharmaceutically acceptable salt of any one of the compounds described in Table 1.

In some embodiments, the compound is a pharmaceutically acceptable salt of any one of the compounds described in Table 2.

In some embodiments, the compound is a pharmaceutically acceptable salt of any one of the compounds described in Table 3.

In some aspects, the present disclosure provides a compound being an isotopic derivative (e.g., isotopically labeled compound) of any one of the compounds of the Formulae disclosed herein.

In some embodiments, the compound is an isotopic derivative of any one of the compounds described in Table 1, or a prodrug or pharmaceutically acceptable salt thereof.

In some embodiments, the compound is an isotopic derivative of any one of the compounds described in Table 1, or a pharmaceutically acceptable salt thereof.

In some embodiments, the compound is an isotopic derivative of any one of prodrugs of the compounds described in Table 1, or a pharmaceutically acceptable salt thereof.

In some embodiments, the compound is an isotopic derivative of any one of the compounds described in Table 1.

In some embodiments, the compound is an isotopic derivative of any one of the compounds described in Table 2, or a prodrug or pharmaceutically acceptable salt thereof.

In some embodiments, the compound is an isotopic derivative of any one of the compounds described in Table 2, or a pharmaceutically acceptable salt thereof.

In some embodiments, the compound is an isotopic derivative of any one of prodrugs of the compounds described in Table 2, or a pharmaceutically acceptable salt thereof.

In some embodiments, the compound is an isotopic derivative of any one of the compounds described in Table 2.

In some embodiments, the compound is an isotopic derivative of any one of the compounds described in Table 3, or a prodrug or pharmaceutically acceptable salt thereof.

In some embodiments, the compound is an isotopic derivative of any one of the compounds described in Table 3, or a pharmaceutically acceptable salt thereof.

In some embodiments, the compound is an isotopic derivative of any one of prodrugs of the compounds described in Table 3, or a pharmaceutically acceptable salt thereof.

In some embodiments, the compound is an isotopic derivative of any one of the compounds described in Table 3.

In some embodiments, the compound is selected from Compound Nos. 7, 9, 10, 15, 18, 379, 387, 389, 400, 404, 415, 425, 450, 508, 548, 584, 585, 586, 592, and 594, or a prodrug or pharmaceutically acceptable salt thereof.

In some embodiments, the compound is selected from Compound Nos. 7, 9, 10, 15, 18, 379, 387, 389, 400, 404, 415, 425, 450, 508, 548, 584, 585, 586, 592, and 594, or a pharmaceutically acceptable salt thereof.

In some embodiments, the compound is selected from Compound Nos. 7, 9, 10, 15, 18, 379, 387, 389, 400, 404, 415, 425, 450, 508, 548, 584, 585, 586, 592, and 594.

In some embodiments, the compound is selected from Compound Nos. 2, 5, 14, 49, 146, 652, 653, 655, 691, 793, 820, 828, 908, 922, 951, 952, 964, 980, 987, 990, 996, 1003, 1005, 1010, 1013, 1014, 1016, 1019, 1023, 1029, 1032, 1039, 1041, and 1046, or a prodrug or pharmaceutically acceptable salt thereof.

In some embodiments, the compound is selected from Compound Nos. 2, 5, 14, 49, 146, 652, 653, 655, 691, 793, 820, 828, 908, 922, 951, 952, 964, 980, 987, 990, 996, 1003, 1005, 1010, 1013, 1014, 1016, 1019, 1023, 1029, 1032, 1039, 1041, and 1046, or a pharmaceutically acceptable salt thereof.

In some embodiments, the compound is selected from Compound Nos. 2, 5, 14, 49, 146, 652, 653, 655, 691, 793, 820, 828, 908, 922, 951, 952, 964, 980, 987, 990, 9%, 1003, 1005, 1010, 1013, 1014, 1016, 1019, 1023, 1029, 1032, 1039, 1041, and 1046. In some embodiments, the compound is selected from Compound Nos. 7, 9, 10, 15, 18, 379, 387, 389, 400, 404, 415, 425, 450, 508, 548, 584, 585, 586, 592, 594, 2, 5, 14, 49, 146, 652, 653, 655, 691, 793, 820, 828, 908, 922, 951, 952, 964, 980, 987, 990, 9%, 1003, 1005, 1010, 1013, 1014, 1016, 1019, 1023, 1029, 1032, 1039, 1041, and 1046, or a prodrug or pharmaceutically acceptable salt thereof.

In some embodiments, the compound is selected from Compound Nos. 7, 9, 10, 15, 18, 379, 387, 389, 400, 404, 415, 425, 450, 508, 548, 584, 585, 586, 592, 594, 2, 5, 14, 49, 146, 652, 653, 655, 691, 793, 820, 828, 908, 922, 951, 952, 964, 980, 987, 990, 996, 1003, 1005, 1010, 1013, 1014, 1016, 1019, 1023, 1029, 1032, 1039, 1041, and 1046, or a pharmaceutically acceptable salt thereof.

In some embodiments, the compound is selected from Compound Nos. 7, 9, 10, 15, 18, 379, 387, 389, 400, 404, 415, 425, 450, 508, 548, 584, 585, 586, 592, 594, 2, 5, 14, 49, 146, 652, 653, 655, 691, 793, 820, 828, 908, 922, 951, 952, 964, 980, 987, 990, 996, 1003, 1005, 1010, 1013, 1014, 1016, 1019, 1023, 1029, 1032, 1039, 1041, and 1046.

In some embodiments, the compound is a compound obtainable by, or obtained by, a method described herein; optionally, the method comprises one or more steps described in Schemes 1-7.

It is understood that the isotopic derivative can be prepared using any of a variety of art-recognized techniques. For example, the isotopic derivative can generally be prepared by carrying out the procedures disclosed in the Schemes and/or in the Examples described herein, by substituting an isotopically labeled reagent for a non-isotopically labeled reagent.

In some embodiments, the isotopic derivative is a deuterium labeled compound.

In some embodiments, the isotopic derivative is a deuterium labeled compound of any one of the compounds of the Formulae disclosed herein.

The term "isotopic derivative", as used herein, refers to a derivative of a compound in which one or more atoms are isotopically enriched or labelled. For example, an isotopic derivative of a compound of Formula (I) is isotopically enriched with regard to, or labelled with, one or more isotopes as compared to the corresponding compound of Formula (I). In some embodiments, the isotopic derivative is enriched with regard to, or labelled with, one or more atoms selected from $^{2}H$, $^{13}C$, $^{14}C$, $^{15}N$, $^{18}O$, $^{29}Si$, $^{31}P$, and $^{34}S$. In some embodiments, the isotopic derivative is a deuterium labeled compound (i.e., being enriched with $^{2}H$ with regard to one or more atoms thereof). In some embodiments, the compound is a $^{18}F$ labeled compound. In some embodiments, the compound is a $^{123}I$ labeled compound, a $^{124}I$ labeled compound, a $^{125}I$ labeled compound, a $^{129}I$ labeled compound, a $^{131}I$ labeled compound, a $^{135}I$ labeled compound, or any combination thereof. In some embodiments, the compound is a $^{33}S$ labeled compound, a $^{34}S$ labeled compound, a $^{35}S$ labeled compound, a $^{36}S$ labeled compound, or any combination thereof.

It is understood that the $^{18}F$, $^{123}I$, $^{124}I$, $^{125}I$, $^{129}I$, $^{131}I$, $^{135}I$, $^{32}S$, $^{34}S$, $^{35}S$, and/or $^{36}S$ labeled compound, can be prepared using any of a variety of art-recognized techniques. For example, the deuterium labeled compound can generally be prepared by carrying out the procedures disclosed in the Schemes and/or in the Examples described herein, by substituting a $^{18}F$, $^{123}I$, $^{124}I$, $^{125}I$, $^{129}I$, $^{131}I$, $^{135}I$, $^{3}S$, $^{34}S$, $^{35}S$, and/or $^{36}S$ labeled reagent for a non-isotope labeled reagent.

A compound of the invention or a pharmaceutically acceptable salt or solvate thereof that contains one or more of the aforementioned $^{18}F$, $^{123}I$, $^{124}I$, $^{125}I$, $^{129}I$, $^{131}I$, $^{135}I$, $^{32}S$, $^{34}S$, $^{35}S$, and $^{36}S$ atom(s) is within the scope of the invention. Further, substitution with isotope (e.g., $^{18}F$, $^{123}I$, $^{124}I$, $^{125}I$, $^{129}I$, $^{131}I$, $^{135}I$, $^{3}S$, $^{34}S$, $^{35}S$, and/or $^{36}S$) may afford certain therapeutic advantages resulting from greater metabolic stability. e.g., increased in vivo half-life or reduced dosage requirements.

For the avoidance of doubt it is to be understood that, where in this specification a group is qualified by "described herein", the said group encompasses the first occurring and broadest definition as well as each and all of the particular definitions for that group.

The various functional groups and substituents making up the compounds of the Formula (I) are typically chosen such that the molecular weight of the compound does not exceed 1000 daltons. More usually, the molecular weight of the compound will be less than 900, for example less than 800, or less than 750, or less than 700, or less than 650 daltons. More conveniently, the molecular weight is less than 600 and, for example, is 550 daltons or less.

A suitable pharmaceutically acceptable salt of a compound of the disclosure is, for example, an acid-addition salt of a compound of the disclosure which is sufficiently basic, for example, an acid-addition salt with, for example, an inorganic organic acid, for example hydrochloric, hydrobromic, sulfuric, phosphoric, trifluoroacetic, formic, citric methane sulfonate or maleic acid. In addition, a suitable pharmaceutically acceptable salt of a compound of the disclosure which is sufficiently acidic is an alkali metal salt, for example a sodium or potassium salt, an alkaline earth metal salt, for example a calcium or magnesium salt, an ammonium salt or a salt with an organic base which affords a pharmaceutically acceptable cation, for example a salt with methylamine, dimethylamine, diethylamine, trimethylamine, piperidine, morpholine or tris-(2-hydroxyethyl)amine.

It will be understood that the compounds of any one of the Formulae disclosed herein and any pharmaceutically acceptable salts thereof, comprise stereoisomers, mixtures of stereoisomers, polymorphs of all isomeric forms of said compounds.

It will be understood that while compounds disclosed herein may be presented in one particular configuration. Such particular configuration is not to be construed as limiting the disclosure to one or another isomer, tautomer, regioisomer or stereoisomer, nor does it exclude mixtures of isomers, tautomers, regioisomers or stereoisomers. In some embodiments, the presentation of a compound herein in a particular configuration intends to encompass, and to refer to, each of the available isomers, tautomers, regioisomers, and stereoisomers of the compound, or any mixture thereof; while the presentation further intends to refer to the specific configuration of the compound.

It will be understood that while compounds disclosed herein may be presented without specified configuration (e.g., without specified stereochemistry). Such presentation intends to encompass all available isomers, tautomers, regioisomers, and stereoisomers of the compound. In some embodiments, the presentation of a compound herein without specified configuration intends to refer to each of the available isomers, tautomers, regioisomers, and stereoisomers of the compound, or any mixture thereof.

As used herein, the term "isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

As used herein, the term "chiral center" refers to a carbon atom bonded to four nonidentical substituents.

As used herein, the term "chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al., *Angew. Chem. Inter. Edit,* 1966, 5, 385; errata 511; Cahn et al., *Angew. Chem.* 1966, 78, 413; Calm and Ingold, *J. Chem. Soc,* 1951 (London), 612; Cahn et al., *Experientia* 1956, 12, 81; Cahn, *J. Chem. Educ,* 1964, 41, 116).

As used herein, the term "geometric isomer" means the diastereomers that owe their existence to hindered rotation about double bonds or a cycloalkyl linker (e.g., 1,3-cyclobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present disclosure may be depicted as different chiral isomers or geometric isomers. It is also to be understood that when compounds have chiral isomeric or geometric isomeric forms, all isomeric forms are intended to be included in the scope of the present disclosure, and the naming of the compounds does not exclude any isomeric forms, it being understood that not all isomers may have the same level of activity. It is to be understood that the structures and other compounds discussed in this disclosure include all atropic isomers thereof. It is also to be understood that not all atropic isomers may have the same level of activity.

As used herein, the term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

As used herein, the term "tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertible by tautomerisations is called tautomerism. Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

It is to be understood that the compounds of the present disclosure may be depicted as different tautomers. It should also be understood that when compounds have tautomeric forms, all tautomeric forms are intended to be included in the scope of the present disclosure, and the naming of the compounds does not exclude any tautomer form. It will be understood that certain tautomers may have a higher level of activity than others.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are nonsuperimposable mirror images of each other are termed "enantiomers". When a compound has an asymmetric center, for example, it is bonded to four different groups, a pair of enantiomers is possible. An enantiomer can be characterised by the absolute configuration of its asymmetric center and is described by the R and S sequencing rules of Cahn and Prelog, or by the manner in which the molecule rotates the plane of polarized light and designated as dextrorotatory or levorotatory (i.e., as (+) or (−)isomers respectively). A chiral compound can exist as either individual enantiomer or as a mixture thereof. A mixture containing equal proportions of the enantiomers is called a "racemic mixture".

The compounds of this disclosure may possess one or more asymmetric centers; such compounds can therefore be produced as individual (R) or (S) stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the disclosure may have geometric isomeric centers (E and Z isomers). It is to be understood that the present disclosure encompasses all optical, diastereoisomers and geometric isomers and mixtures thereof that possess polymerase Θ inhibitory activity.

The present disclosure also encompasses compounds of the disclosure as defined herein which comprise one or more isotopic substitutions.

It is to be understood that the compounds of any Formula described herein include the compounds themselves, as well as their salts, and their solvates, if applicable. A salt, for example, can be formed between an anion and a positively charged group (e.g., amino) on a substituted compound disclosed herein. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate).

As used herein, the term "pharmaceutically acceptable anion" refers to an anion suitable for forming a pharmaceutically acceptable salt. Likewise, a salt can also be formed between a cation and a negatively charged group (e.g., carboxylate) on a substituted compound disclosed herein. Suitable cations include sodium ion, potassium ion, magnesium ion, calcium ion, and an ammonium cation such as tetramethylammonium ion or diethylamine ion. The substituted compounds disclosed herein also include those salts containing quaternary nitrogen atoms.

It is to be understood that the compounds of the present disclosure, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

As used herein, the term "solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure origin to the reference compound.

As used herein, the term "derivative" refers to compounds that have a common core structure and are substituted with various groups as described herein.

As used herein, the term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonamides, tetrazoles, sulfonates and phosphonates. See, e.g., Patani and LaVoie, *Chem. Rev,* 96, 3147-3176, 1996.

It is also to be understood that certain compounds of any one of the Formulae disclosed herein may exist in solvated as well as unsolvated forms such as, for example, hydrated forms. A suitable pharmaceutically acceptable solvate is, for example, a hydrate such as hemi-hydrate, a mono-hydrate, a di-hydrate or a tri-hydrate. It is to be understood that the disclosure encompasses all such solvated forms that possess polymerase Θ inhibitory activity.

It is also to be understood that certain compounds of any one of the Formulae disclosed herein may exhibit polymorphism, and that the disclosure encompasses all such forms, or mixtures thereof, which possess polymerase Θ inhibitory activity. It is generally known that crystalline materials may be analysed using conventional techniques such as X-Ray Powder Diffraction analysis. Differential Scanning Calorimetry, Thermal Gravimetric Analysis, Diffuse Reflectance Infrared Fourier Transform (DRIFT) spectroscopy. Near Infrared (NIR) spectroscopy, solution and/or solid state nuclear magnetic resonance spectroscopy. The water content of such crystalline materials may be determined by Karl Fischer analysis.

Compounds of any one of the Formulae disclosed herein may exist in a number of different tautomeric forms and references to compounds of Formula (I) include all such forms. For the avoidance of doubt, where a compound can exist in one of several tautomeric forms, and only one is specifically described or shown, all others are nevertheless embraced by Formula (I). Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime thioketone/enethiol, and nitro/aci-nitro.

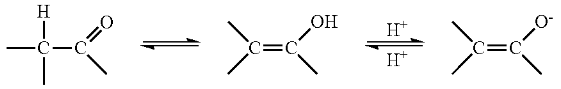

keto enol enolate

Compounds of any one of the Formulae disclosed herein containing an amine function may also form N-oxides. A reference herein to a compound of Formula (I) that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-oxides can be formed by treatment of the corresponding amine with an oxidizing agent such as hydrogen peroxide or a peracid (e.g. a peroxycarboxylic acid), see for example Advanced Organic Chemistry, by Jerry March, 4th Edition, Wiley Interscience, pages. More particularly. N-oxides can be made by the procedure of L. W. Deady (Syn. Comm, 1977, 7, 509-514) in which the amine compound is reacted with meta-chloroperoxybenzoic acid (mCPBA), for example, in an inert solvent such as dichloromethane.

The compounds of any one of the Formulae disclosed herein may be administered in the form of a prodrug which is broken down in the human or animal body to release a compound of the disclosure. A prodrug may be used to alter the physical properties and/or the pharmacokinetic properties of a compound of the disclosure. A prodrug can be formed when the compound of the disclosure contains a suitable group or substituent to which a property-modifying group can be attached. Examples of prodrugs include derivatives containing in vivo cleavable alkyl or acyl substituents at the ester or amide group in any one of the Formulae disclosed herein. In some embodiments, a prodrug of the present disclosure is compound 21a of Scheme 4. In some embodiments, a prodrug of the present disclosure is compound 21a of Scheme 4, wherein R is optionally substituted $C_1$-$C_6$ alkyl. In some embodiments, a prodrug of the present disclosure is compound 21a of Scheme 4, wherein R is $C_1$-$C_6$ alkyl optionally substituted with $C_1$-$C_6$ alkoxy, wherein the $C_1$-$C_6$ alkoxy is optionally substituted with one or more oxo or —COOH. In some embodiments, a prodrug of the present disclosure is a compound of Example 780A or 780B. In some embodiments, a prodrug of the present disclosure is a compound of Table AK. In some embodiments, a prodrug of the present disclosure is (Z)-4-((2-((2'-chloro-5'-methoxy-6-methyl-[4,4'-bipyridine]-3-carbonyl)imino)-5-(5-(difluoromethyl)picolinoyl)-5,6-dihydro-2H-pyrrolo[3,4-d]thiazol-3(4H)-yl)methoxy)-4-oxobutanoic acid. In some embodiments, a prodrug of the present disclosure is 4-((2'-chloro-N-(5-(5-(difluoromethyl)picolinoyl)-5,6-dihydro-4H-pyrrolo[3,4-d]thiazol-2-yl)-5'-methoxy-6-methyl-[4,4'-bipyridine]-3-carboxamido)methoxy)-4-oxobutanoic acid.

Accordingly, the present disclosure includes those compounds of any one of the Formulae disclosed herein as defined hereinbefore when made available by organic synthesis and when made available within the human or animal body by way of cleavage of a prodrug thereof. Accordingly, the present disclosure includes those compounds of any one of the Formulae disclosed herein that are produced by organic synthetic means and also such compounds that are produced in the human or animal body by way of metabolism of a precursor compound, that is a compound of any one of the Formulae disclosed herein may be a synthetically-produced compound or a metabolically-produced compound.

A suitable pharmaceutically acceptable prodrug of a compound of any one of the Formulae disclosed herein is one that is based on reasonable medical judgment as being suitable for administration to the human or animal body without undesirable pharmacological activities and without undue toxicity. Various forms of prodrug have been described, for example in the following documents: a) Methods in Enzymology, Vol. 42, p. 309-396, edited by K. Widder, et al. (Academic Press, 1985); b) Design of Pro-drugs, edited by H. Bundgaard, (Elsevier, 1985); c) A Textbook of Drug Design and Development, edited by Krogsgaard-Larsen and H. Bundgaard, Chapter 5 "Design and Application of Pro-drugs", by H. Bundgaard p, 113-191 (1991); d) H. Bundgaard, Advanced Drug Delivery Reviews, 8, 1-38 (1992); e) H. Bundgaard, et al., Journal of Pharmaceutical Sciences, 77, 285 (1988); f) N. Kakeya, et al., Chem. Pharm. Bull., 32, 692 (1984); g) T. Higuchi and V. Stella. "Pro-Drugs as Novel Delivery Systems", A.C.S. Symposium Series, Volume 14; and h) E. Roche (editor), "Bioreversible Carriers in Drug Design", Pergamon Press, 1987.

A suitable pharmaceutically acceptable prodrug of a compound of any one of the Formulae disclosed herein that possesses a hydroxy group is, for example, an in vivo cleavable ester or ether thereof. An in vivo cleavable ester or ether of a compound of any one of the Formulae disclosed herein containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_1$-$C_{10}$ alkanoyl groups such as acetyl, benzoyl, phenylacetyl and substituted benzoyl and phenylacetyl groups, $C_1$-$C_{10}$ alkoxycarbonyl groups such as ethoxycarbonyl, N,N—($C_1$-$C_6$ alkyl)$_2$carbamoyl, 2-dialkylaminoacetyl and 2-carboxyacetyl groups. Examples of ring substituents on the phenylacetyl and benzoyl groups include aminomethyl. N-alkylaminomethyl. N,N-dialkylaminomethyl, morpholinomethyl, piperazin-1-ylmethyl and 4-($C_1$-$C_4$ alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable prodrug of a compound of any one of the Formulae disclosed herein that possesses a carboxy group is, for example, an in vivo cleavable amide thereof, for example an amide formed with an amine such as ammonia, a $C_{1-4}$alkylamine such as methylamine, a ($C_1$-$C_4$ alkyl)$_2$amine such as dimethylamine. N-ethyl-N-methylamine or diethylamine, a $C_1$-$C_4$ alkoxy-$C_2$-$C_4$ alkylamine such as 2-methoxyethylamine, a phenyl-$C_1$-$C_4$ alkylamine such as benzylamine and amino acids such as glycine or an ester thereof. A suitable pharmaceutically acceptable prodrug of a compound of any one of the Formulae disclosed herein that possesses an amino group is, for example, an in vivo cleavable amide derivative thereof. Suitable pharmaceutically acceptable amides from an amino group include, for example an amide formed with $C_1$-$C_{10}$ alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_1$-$C_4$ alkyl)piperazin-1-ylmethyl.

The in vivo effects of a compound of any one of the Formulae disclosed herein may be exerted in part by one or more metabolites that are formed within the human or animal body after administration of a compound of any one of the Formulae disclosed herein. As stated hereinbefore, the in vivo effects of a compound of any one of the Formulae disclosed herein may also be exerted by way of metabolism of a precursor compound (a prodrug).

Suitably, the present disclosure excludes any individual compounds not possessing the biological activity defined herein.

Methods of Synthesis

In some aspects, the present disclosure provides a method of preparing a compound of the present disclosure.

In some aspects, the present disclosure provides a method of a compound, comprising one or more steps as described herein.

In some aspects, the present disclosure provides a compound obtainable by, or obtained by, or directly obtained by a method for preparing a compound as described herein.

In some aspects, the present disclosure provides an intermediate as described herein, being suitable for use in a method for preparing a compound as described herein.

The compounds of the present disclosure can be prepared by any suitable technique known in the art. Particular processes for the preparation of these compounds are described further in the accompanying examples.

In the description of the synthetic methods described herein and in any referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilized.

It will be appreciated that during the synthesis of the compounds of the disclosure in the processes defined herein, or during the synthesis of certain starting materials, it may be desirable to protect certain substituent groups to prevent their undesired reaction. The skilled chemist will appreciate when such protection is required, and how such protecting groups may be put in place, and later removed. For examples of protecting groups see one of the many general texts on the subject, for example, 'Protective Groups in Organic Synthesis' by Theodora Green (publisher; John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule. Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl, or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium on carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium on carbon.

A suitable protecting group for a carboxy group is, for example, an esterifying group, for example a methyl or an ethyl group which may be removed, for example, by hydrolysis with a base such as sodium hydroxide, or for example a tert-butyl group which may be removed, for example, by treatment with an acid, for example an organic acid such as trifluoroacetic acid, or for example a benzyl group which may be removed, for example, by hydrogenation over a catalyst such as palladium on carbon.

Once a compound of Formula (I) has been synthesized by any one of the processes defined herein, the processes may then further comprise the additional steps of: (i) removing any protecting groups present; (ii) converting the compound Formula (I) into another compound of Formula (I); (iii) forming a pharmaceutically acceptable salt, hydrate or solvate thereof; and/or (iv) forming a prodrug thereof.

The resultant compounds of Formula (I) can be isolated and purified using techniques well known in the art.

Conveniently, the reaction of the compounds is carried out in the presence of a suitable solvent, which is preferably inert under the respective reaction conditions. Examples of suitable solvents comprise but are not limited to hydrocarbons, such as hexane, petroleum ether, benzene, toluene or xylene; chlorinated hydrocarbons, such as trichlorethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF), 2-methyltetrahydrofuran, cycloheptylmethyl ether (CPME), methyl tert-butyl ether (MTBE) or dioxane; glycol ethers, such as ethylene glycol monomethyl or monoethyl ether or ethylene glycol dimethyl ether (diglyme); ketones, such as acetone, methylisobutylketone (MIBK) or butanone; amides, such as acetamide, dimethylacetamide, dimethylformamide (DMF) or N-methylpyrrolidinone (NMP); nitriles, such as acetonitrile; sulfoxides, such as dimethyl sulfoxide (DMSO); nitro compounds, such as nitromethane or nitrobenzene; esters, such as ethyl acetate or methyl acetate, or mixtures of the said solvents or mixtures with water.

The reaction temperature is suitably between about −100° C. and 300° C., depending on the reaction step and the conditions used.

Reaction times are generally in the range between a fraction of a minute and several days, depending on the reactivity of the respective compounds and the respective reaction conditions. Suitable reaction times are readily determinable by methods known in the art, for example reaction monitoring. Based on the reaction temperatures given above, suitable reaction times generally lie in the range between 10 minutes and 48 hours.

Moreover, by utilizing the procedures described herein, in conjunction with ordinary skills in the art, additional compounds of the present disclosure can be readily prepared. Those skilled in the art will readily understand that known variations of the conditions and processes of the following preparative procedures can be used to prepare these compounds.

As will be understood by the person skilled in the art of organic synthesis, compounds of the present disclosure are readily accessible by various synthetic routes, some of which are exemplified in the accompanying examples. The skilled person will easily recognise which kind of reagents and reactions conditions are to be used and how they are to be applied and adapted in any particular instance—wherever necessary or useful—in order to obtain the compounds of the present disclosure. Furthermore, some of the compounds of the present disclosure can readily be synthesized by reacting other compounds of the present disclosure under suitable conditions, for instance, by converting one particular functional group being present in a compound of the present disclosure, or a suitable precursor molecule thereof, into another one by applying standard synthetic methods, like reduction, oxidation, addition or substitution reactions; those methods are well known to the skilled person. Likewise, the skilled person will apply—whenever necessary or useful—synthetic protecting (or protective) groups; suitable protecting groups as well as methods for introducing and removing them are well-known to the person skilled in the art of chemical synthesis and are described, in more detail, in, e.g., P. G. M. Wuts, T. W. Greene, "Greene's Protective Groups in Organic Synthesis", 4th edition (2006) (John Wiley & Sons).

General routes for the preparation of a compound of the application are described in Schemes 1-7 herein.

While the present invention has been described in conjunction with the specific examples set forth below, many alternatives, modifications, and variations thereof will be apparent to those of ordinary skill in the art. In some cases, the order of carrying out the steps of the reaction schemes may be varied to facilitate the reaction or to avoid unwanted reaction products. Starting materials and intermediates are purchased from commercial sources, made from known procedures, or are otherwise illustrated.

Several methods for preparing the compounds of this invention are described in the following Schemes and Examples. Unless otherwise indicated, all variables are as previously defined.

Scheme 1

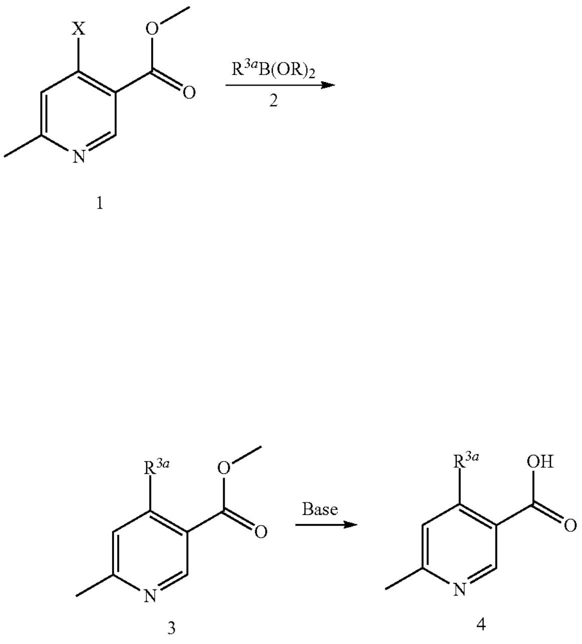

X = Cl, Br, or I

In Scheme 1, Suzuki coupling of boronic acid or boronic ester 2 with halopyridine 1 affords ester 3. The ester can be hydrolyzed under basic conditions (e.g., with NaOH) to afford carboxylic acid 4.

Scheme 2

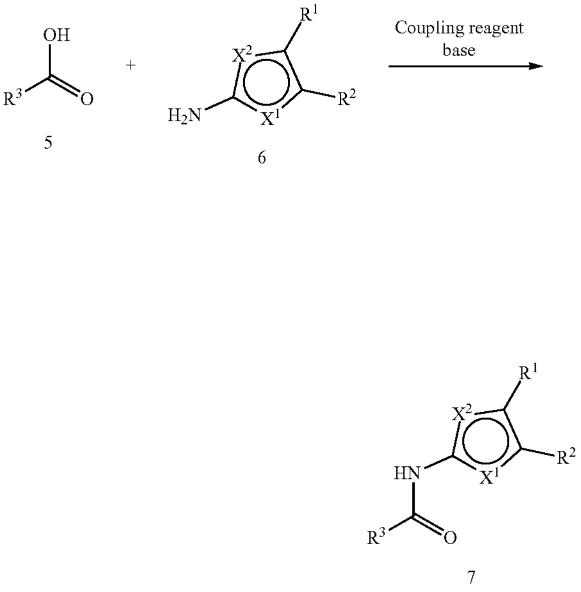

In Scheme 2, amide 7 can be formed via amide coupling between carboxylic acid 5 and amine 6 via an amide coupling using a coupling reagent (e.g., HATU, or other common amide coupling reagents) and a base (e.g., DIPEA).

Scheme 3

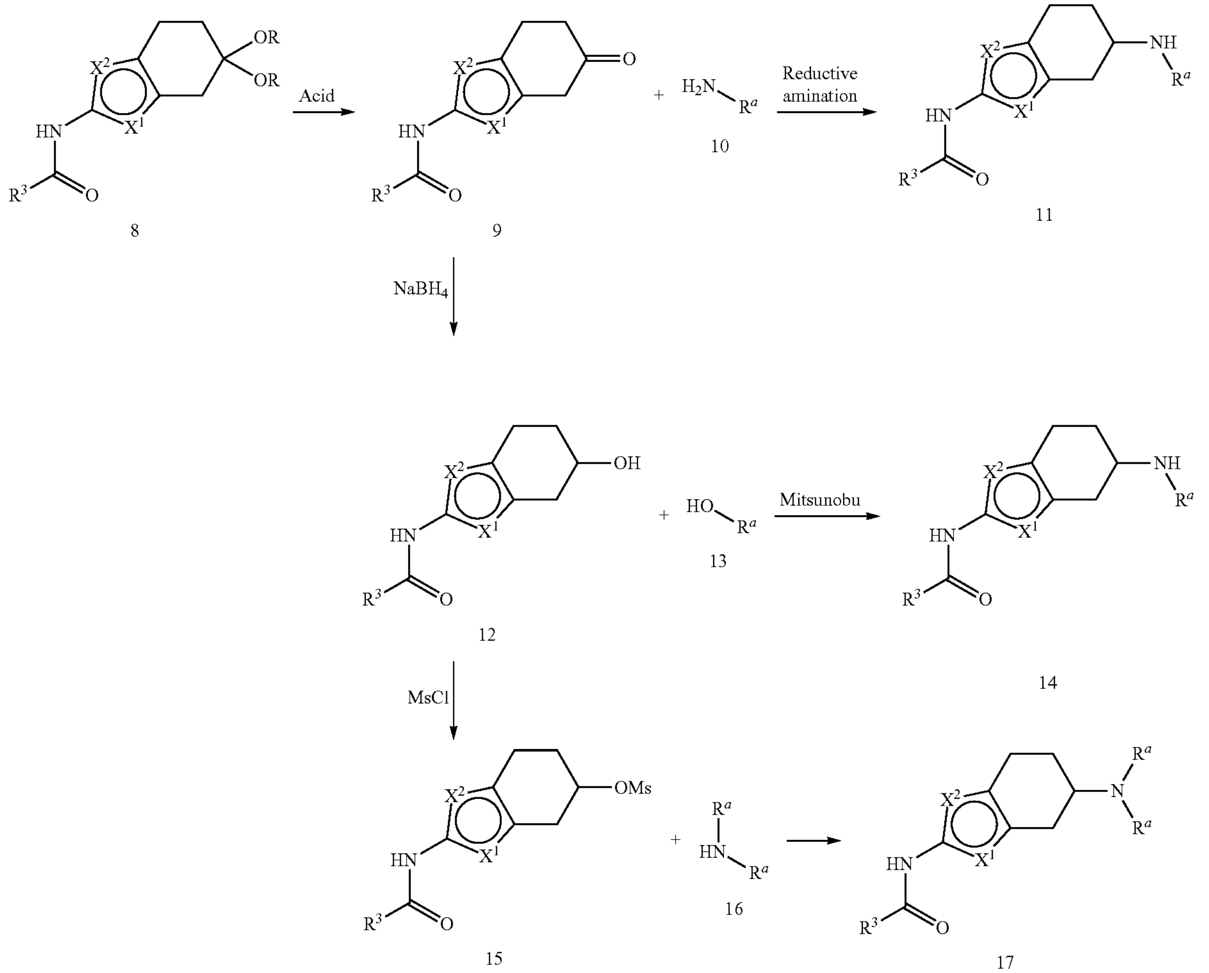

In Scheme 3, in cases where amide 7 described in Scheme 2 features a protected ketone, e.g., ketal intermediate 8, the following synthetic schemes can be employed to afford the exemplified compounds. Ketone 9 can be made via ketal 8 under acidic conditions. The ketone can be converted to amine 11 via reductive amination with an amine 10. Alternatively, ketone 9 can be reduced to alcohol 12 and converted to ether 14 via Mitsunobu reaction with alcohol 13. In another approach, alcohol 12 can be mesylated, and amines can be added via $S_N2$ reaction to form amine 17.

Scheme 4

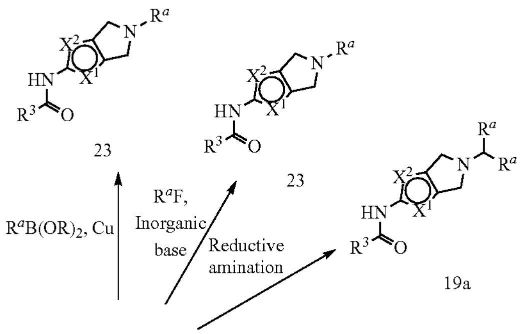

-continued

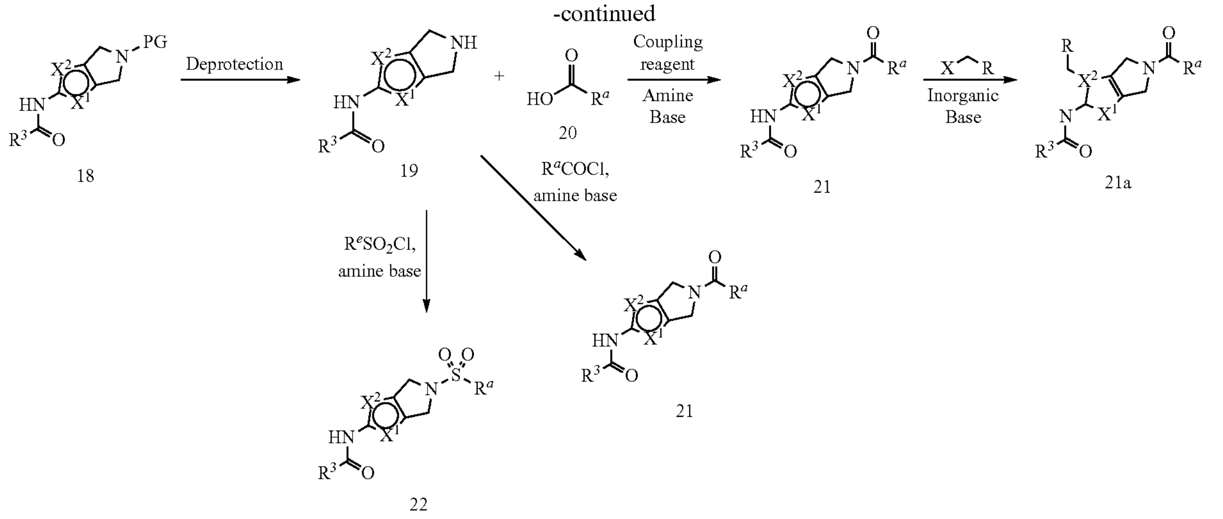

18 19 20 21 21a 21 22

In Scheme 4, in cases where amide 7 described in Scheme 2 features a protected amine intermediate 18, the following synthetic schemes can be employed to afford the exemplified compounds. Deprotection of amine 18 affords amine 19 (e.g., a Boc group would be removed through the use of an acid). Amine 19 can be used in a multitude of reactions. Reductive amination with aldehydes or ketones affords amine 19a. Amide coupling (e.g., with the use of T3P) with carboxylic acid 20 affords amide 21. Alternatively, acylation with acid chlorides also affords amide 21. Amine 19 can also be reacted with sulfonyl chlorides to afford sulfonamide or sulfamide 22. Chan-Lam coupling of amine 19 with boronic acids or esters and copper affords amine 23. In another approach, $S_NAr$ chemistry between amine 19 and aryl fluorides also affords amine 23. Compound 21 can be reacted with an alkyl halide in the presence of inorganic base to afford compound 21a, wherein R is a group that can be metabolized (e.g., compound 21a can be metabolized to release a compound of Formula (I) in vivo).

Scheme 5

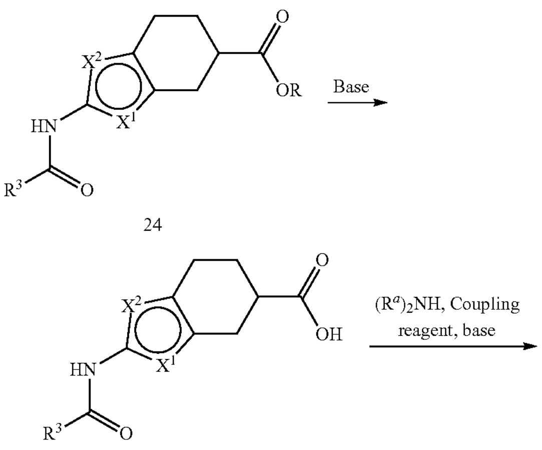

24 25

-continued

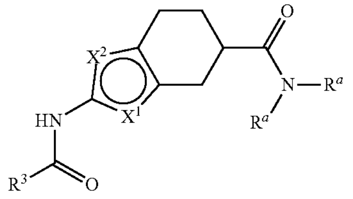

26

In Scheme 5, in cases where amide 7 described in Scheme 2 features ester intermediate 24, the following synthetic scheme can be employed to afford the exemplified compounds. Amide 26 can be formed in two steps via hydrolysis of ester 24 and amide coupling with carboxylic acid 25 (e.g., with the use of T3P).

Scheme 6

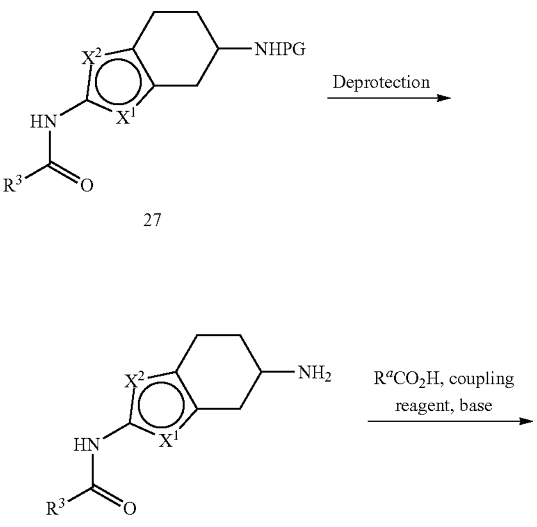

27 28

-continued

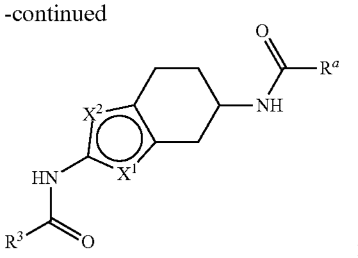

29

In Scheme 6, in cases where amide 7 described in Scheme 2 features protected amine 27, the following synthetic scheme can be employed to afford the exemplified compounds. Amide 29 can be formed in two steps via deprotection of compound 27 (e.g., a Boc group would be removed through the use of an acid). Amide coupling (e.g., with T3P) with amine 28 affords amide 29.

amine 34. Acylation of 31 with acid chlorides affords amide 35, while reaction with sulfonyl chlorides affords sulfonamide or sulfamide 36.

Biological Assays

Compounds designed, selected and/or optimized by methods described above, once produced, can be characterized using a variety of assays known to those skilled in the art to determine whether the compounds have biological activity. For example, the molecules can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) *High Throughput Sreening*, Marcel Dekker; and U.S. Pat. No. 5,763,263.

Scheme 7

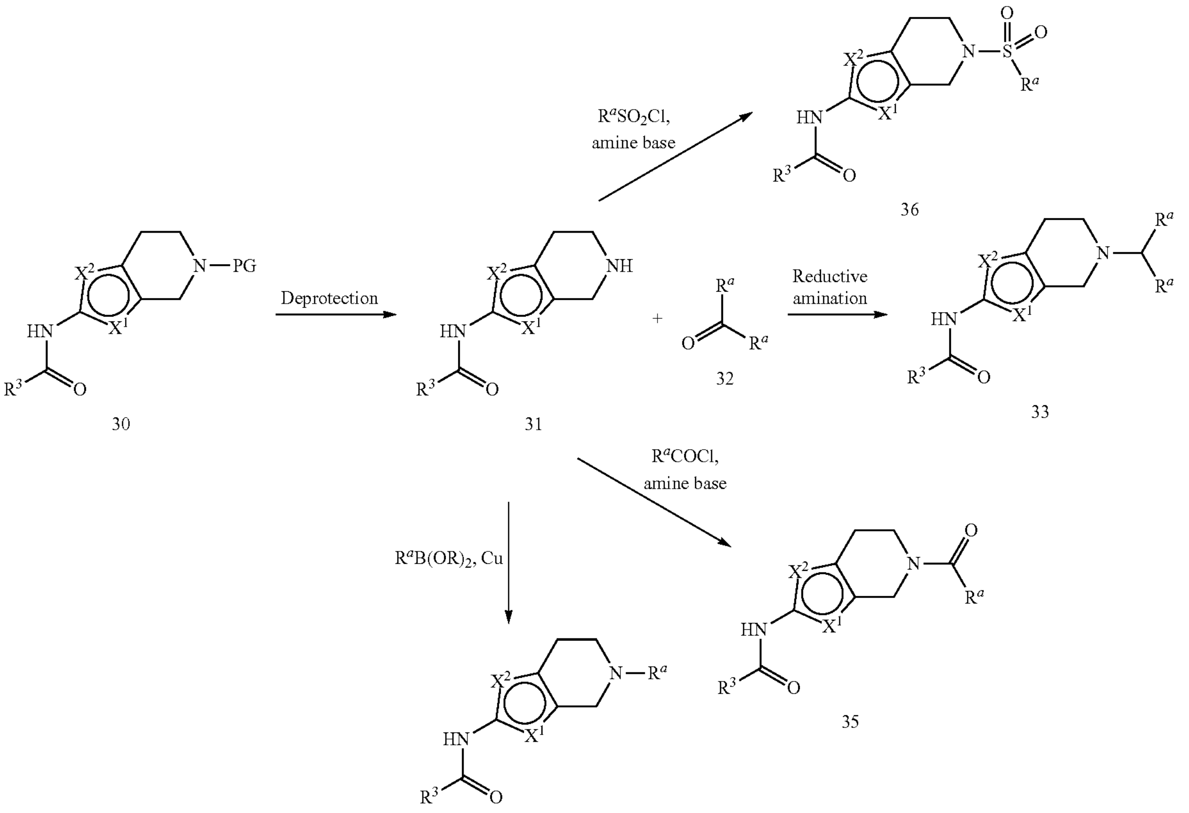

30 31 32 33 34 35 36

In Scheme 7, in cases where amide 7 described in Scheme 2 features a protected amine intermediate 30, the following synthetic schemes can be employed to afford the exemplified compounds. Deprotection of 30 affords amine 31 (e.g., a Boc group would be removed through the use of an acid). Amine 30 can be used in a variety of reactions. Reductive amination with ketone or aldehyde 32 affords amine 33. Alternatively, Chan-Lam coupling with boronic acids or esters affords High-throughput assays can use one or more different assay techniques including, but not limited to, those described below.

Various in vitro or in vivo biological assays may be suitable for detecting the effect of the compounds of the present disclosure. These in vitro or in vivo biological assays can include, but are not limited to, enzymatic activity assays, electrophoretic mobility shift assays, reporter gene assays, in vitro cell viability assays, and the assays described herein.

In some embodiments, the biological assay is described in the Examples herein.

In some embodiments, the biological assay is an ATPase assay.

In some embodiments, the ATPase assay a compound of the present disclosure is combined with biotinylated Avi-POLθ[2-894], a 50 nucleotide poly-thymine repeat single-stranded DNA, and ATP in buffer. In some embodiments, the mixture is incubated and ADP-Glo Reagent added, followed by a subsequent incubation. In some embodiments, a Kinase Detection Reagent may be added, followed by a third incubation.

In some embodiments, the activity is measured via luminescence signal (e.g., measured with the EnVision multimode plate reader).

Pharmaceutical Compositions

In some aspects, the present disclosure provides a pharmaceutical composition comprising a compound of the present disclosure as an active ingredient. In some embodiments, the present disclosure provides a pharmaceutical composition comprising at least one compound of each of the formulae described herein, or a pharmaceutically acceptable salt or solvate thereof, and one or more pharmaceutically acceptable carriers or excipients. In some embodiments, the present disclosure provides a pharmaceutical composition comprising a compound described in Table 1. In some embodiments, the present disclosure provides a pharmaceutical composition comprising at least one compound selected from Table 1. In some aspects, the present disclosure provides a pharmaceutical composition comprising the compound of any one of the preceding claims or a pharmaceutically acceptable salt thereof, and a pharmaceutically acceptable diluent or carrier.

As used herein, the term "composition" is intended to encompass a product comprising the specified ingredients in the specified amounts, as well as any product which results, directly or indirectly, from combination of the specified ingredients in the specified amounts.

The compounds of present disclosure can be formulated for oral administration in forms such as tablets, capsules (each of which includes sustained release or timed release formulations), pills, powders, granules, elixirs, tinctures, suspensions, syrups and emulsions. The compounds of present disclosure on can also be formulated for intravenous (bolus or in-fusion), intraperitoneal, topical, subcutaneous, intramuscular or transdermal (e.g., patch) administration, all using forms well known to those of ordinary skill in the pharmaceutical arts.

The formulation of the present disclosure may be in the form of an aqueous solution comprising an aqueous vehicle. The aqueous vehicle component may comprise water and at least one pharmaceutically acceptable excipient. Suitable acceptable excipients include those selected from the group consisting of a solubility enhancing agent, chelating agent, preservative, tonicity agent, viscosity/suspending agent, buffer, and pH modifying agent, and a mixture thereof.

Any suitable solubility enhancing agent can be used. Examples of a solubility enhancing agent include cyclodextrin, such as those selected from the group consisting of hydroxypropyl-β-cyclodextrin, methyl-β-cyclodextrin, randomly methylated-β-cyclodextrin, ethylated-β-cyclodextrin, triacetyl-β-cyclodextrin, peracetylated-β-cyclodextrin, carboxymethyl-β-cyclodextrin, hydroxyethyl-β-cyclodextrin, 2-hydroxy-3-(trimethylammonio)propyl-β-cyclodextrin, glucosyl-β-cyclodextrin, sulfated β-cyclodextrin (S-β-CD), maltosyl-β-cyclodextrin. β-cyclodextrin sulfobutyl ether, branched-β-cyclodextrin, hydroxypropyl-γ-cyclodextrin, randomly methylated-γ-cyclodextrin, and trimethyl-γ-cyclodextrin, and mixtures thereof.

Any suitable chelating agent can be used. Examples of a suitable chelating agent include those selected from the group consisting of ethylenediaminetetraacetic acid and metal salts thereof, disodium edetate, trisodium edetate, and tetrasodium edetate, and mixtures thereof.

Any suitable preservative can be used. Examples of a preservative include those selected from the group consisting of quaternary ammonium salts such as benzalkonium halides (preferably benzalkonium chloride), chlorhexidine gluconate, benzethonium chloride, cetyl pyridinium chloride, benzyl bromide, phenylmercury nitrate, phenylmercury acetate, phenylmercury neodecanoate, merthiolate, methylparaben, propylparaben, sorbic acid, potassium sorbate, sodium benzoate, sodium propionate, ethyl p-hydroxybenzoate, propylaminopropyl biguanide, and butyl-p-hydroxybenzoate, and sorbic acid, and mixtures thereof.

The aqueous vehicle may also include a tonicity agent to adjust the tonicity (osmotic pressure). The tonicity agent can be selected from the group consisting of a glycol (such as propylene glycol, diethylene glycol, triethylene glycol), glycerol, dextrose, glycerin, mannitol, potassium chloride, and sodium chloride, and a mixture thereof.

The aqueous vehicle may also contain a viscosity/suspending agent. Suitable viscosity/suspending agents include those selected from the group consisting of cellulose derivatives, such as methyl cellulose, ethyl cellulose, hydroxyethylcellulose, polyethylene glycols (such as polyethylene glycol 300, polyethylene glycol 400), carboxymethyl cellulose, hydroxypropylmethyl cellulose, and cross-linked acrylic acid polymers (carbomers), such as polymers of acrylic acid cross-linked with polyalkenyl ethers or divinyl glycol (Carbopols—such as Carbopol 934, Carbopol 934P, Carbopol 971, Carbopol 974 and Carbopol 974P), and a mixture thereof.

In order to adjust the formulation to an acceptable pH (typically a pH range of about 5.0 to about 9.0, more preferably about 5.5 to about 8.5, particularly about 6.0 to about 8.5, about 7.0 to about 8.5, about 7.2 to about 7.7, about 7.1 to about 7.9, or about 7.5 to about 8.0), the formulation may contain a pH modifying agent. The pH modifying agent is typically a mineral acid or metal hydroxide base, selected from the group of potassium hydroxide, sodium hydroxide, and hydrochloric acid, and mixtures thereof, and preferably sodium hydroxide and/or hydrochloric acid. These acidic and/or basic pH modifying agents are added to adjust the formulation to the target acceptable pH range. Hence it may not be necessary to use both acid and base—depending on the formulation, the addition of one of the acid or base may be sufficient to bring the mixture to the desired pH range.

The aqueous vehicle may also contain a buffering agent to stabilize the pH. When used, the buffer is selected from the group consisting of a phosphate buffer (such as sodium dihydrogen phosphate and disodium hydrogen phosphate), a borate buffer (such as boric acid, or salts thereof including disodium tetraborate), a citrate buffer (such as citric acid, or salts thereof including sodium citrate), and ε-aminocaproic acid, and mixtures thereof.

The formulation may further comprise a wetting agent. Suitable classes of wetting agents include those selected from the group consisting of polyoxypropylene-polyoxyethylene block copolymers (poloxamers), polyethoxylated ethers of castor oils, polyoxyethylenated sorbitan esters (polysorbates), polymers of oxyethylated octyl phenol (Tyloxapol), polyoxyl 40 stearate, fatty acid glycol esters, fatty acid glyceryl esters, sucrose fatty esters, and polyoxyethylene fatty esters, and mixtures thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, orange flavoring.

According to a further aspect of the disclosure there is provided a pharmaceutical composition which comprises a compound of the disclosure as defined hereinbefore, or a pharmaceutically acceptable salt, hydrate or solvate thereof, in association with a pharmaceutically acceptable diluent or carrier.

The compositions of the disclosure may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the disclosure may be obtained by conventional procedures using conventional pharmaceutical excipients, well known in the art. Thus, compositions intended for oral use may contain, for example, one or more coloring, sweetening, flavoring and/or preservative agents.

An effective amount of a compound of the present disclosure for use in therapy is an amount sufficient to treat or prevent a polymerase Θ related condition referred to herein, slow its progression and/or reduce the symptoms associated with the condition.

An effective amount of a compound of the present disclosure for use in therapy is an amount sufficient to treat a polymerase Θ related condition referred to herein, slow its progression and/or reduce the symptoms associated with the condition.

The size of the dose for therapeutic or prophylactic purposes of a compound of Formula (I) will naturally vary according to the nature and severity of the conditions, the age and sex of the animal or patient and the route of administration, according to well-known principles of medicine.

Methods of Use

In some aspects, the present disclosure provides a method of modulating DNA polymerase Θ activity, comprising contacting a cell with a compound of the present disclosure or a pharmaceutically acceptable salt thereof.

In some aspects, the present disclosure provides a method of modulating DNA polymerase Θ activity (e.g., in vitro or in vivo), comprising contacting a cell with an effective amount of a compound of the present disclosure or a pharmaceutically acceptable salt thereof.

In some aspects, the present disclosure provides a method of modulating DNA polymerase Θ activity (e.g., in vitro or in vivo), comprising contacting a cell with a compound of the present disclosure or a pharmaceutically acceptable salt thereof.

In some aspects, the present disclosure provides a method of modulating DNA polymerase Θ activity (e.g., in vitro or in vivo), comprising contacting a cell with an effective amount of a compound of the present disclosure or a pharmaceutically acceptable salt thereof.

In some aspects, the present disclosure provides a method of modulating DNA polymerase Θ activity (e.g., in vitro or in vivo), comprising contacting a cell with a compound of the present disclosure or a pharmaceutically acceptable salt thereof.

In some aspects, the present disclosure provides a method of treating or preventing a disease or disorder in a subject in need thereof, comprising administering to the subject a compound of the present disclosure or a pharmaceutically acceptable salt thereof.

In some aspects, the present disclosure provides a method of treating or preventing a disease or disorder disclosed herein in a subject in need thereof, comprising administering to the subject a therapeutically effective amount of a compound of the present disclosure or a pharmaceutically acceptable salt thereof.

In some aspects, the present disclosure provides a method of treating a disease or disorder disclosed herein in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing a disease or disorder disclosed herein in a subject in need thereof, comprising administering to the subject a compound of the present disclosure or a pharmaceutically acceptable salt thereof.

In some aspects, the present disclosure provides a method of treating a disease or disorder disclosed herein in a subject in need thereof, comprising administering to the subject a compound of the present disclosure or a pharmaceutically acceptable salt thereof, or a pharmaceutical composition of the present disclosure.

In some aspects, the present disclosure provides a method for inhibiting DNA repair by DNA polymerase Θ in a cancer cell comprising contacting the cell with an effective amount of a compound of the present disclosure or a pharmaceutically acceptable salt thereof, or a pharmaceutical composition of the present disclosure. In some embodiments, the cancer is HR deficient cancer.

In some aspects, the present disclosure provides a method for treating and/or preventing a cancer in a patient, wherein the cancer is characterized by a reduction or absence of BRCA gene expression, the absence of the BRCA gene, or reduced function of BRCA protein, comprising administering to the subject a compound of the present disclosure or a pharmaceutically acceptable salt thereof, or a pharmaceutical composition of the present disclosure.

In some embodiments, the disease or disorder is associated with an implicated DNA polymerase Θ activity. In some embodiments, the disease or disorder is a disease or disorder in which DNA polymerase Θ activity is implicated.

In some embodiments, the disease or disorder is associated with an implicated DNA polymerase Θ activity. In some embodiments, the disease or disorder is a disease or disorder in which DNA polymerase Θ activity is implicated.

In some embodiments, the disease or disorder is cancer.

In some aspects, the present disclosure provides a method of treating or preventing cancer in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating cancer in a subject in need thereof, comprising administering to the subject a therapeutically effective amount of a compound of the present disclosure or a pharmaceutically acceptable salt thereof, or a pharmaceutical composition of the present disclosure.

In some aspects, the present disclosure provides a method of treating or preventing cancer in a subject in need thereof, comprising administering to the subject a compound of the present disclosure or a pharmaceutically acceptable salt thereof, or a pharmaceutical composition of the present disclosure.

In some aspects, the present disclosure provides a method of treating cancer in a subject in need thereof, comprising administering to the subject a compound of the present disclosure or a pharmaceutically acceptable salt thereof, or a pharmaceutical composition of the present disclosure.

In some aspects, the present disclosure provides a compound of the present disclosure or a pharmaceutically acceptable salt thereof, or a pharmaceutical composition of the present disclosure for use in modulating DNA polymerase Θ activity.

In some aspects, the present disclosure provides a compound of the present disclosure or a pharmaceutically acceptable salt thereof for use in modulating DNA polymerase Θ activity (e.g., in vitro or in vivo).

In some aspects, the present disclosure provides a compound of the present disclosure or a pharmaceutically acceptable salt thereof for use in modulating DNA polymerase Θ activity (e.g., in vitro or in vivo).

In some aspects, the present disclosure provides a compound of the present disclosure or a pharmaceutically acceptable salt thereof for inhibiting DNA repair by DNA polymerase Θ in a cell. In some embodiments, the cell is HR deficient cell.

In some aspects, the present disclosure provides a compound of the present disclosure or a pharmaceutically acceptable salt thereof for use in the treatment and/or prevention of a disease in a patient, wherein the disease is characterized by overexpression of DNA polymerase Θ.

In some aspects, the present disclosure provides a compound of the present disclosure or a pharmaceutically acceptable salt thereof for use in the treatment and/or prevention of a cancer in a patient, wherein the cancer is characterized by a reduction or absence of BRCA gene expression, the absence of the BRCA gene, or reduced function of BRCA protein.

In some embodiments. BRCA is BRCA1. In some embodiments, BRCA is BRCA2.

In some aspects, the present disclosure provides a compound of the present disclosure or a pharmaceutically acceptable salt thereof for use in the treatment and/or prevention of a HR deficient cancer in a patient.

In some aspects, the present disclosure provides a compound of the present disclosure or a pharmaceutically acceptable salt thereof, or a pharmaceutical composition of the present disclosure for use in treating or preventing a disease or disorder.

In some aspects, the present disclosure provides a compound of the present disclosure or a pharmaceutically acceptable salt thereof for use in treating or preventing a disease or disorder disclosed herein.

In some aspects, the present disclosure provides a compound of the present disclosure or a pharmaceutically acceptable salt thereof for use in treating a disease or disorder disclosed herein.

In some aspects, the present disclosure provides a compound of the present disclosure or a pharmaceutically acceptable salt thereof for use in treating or preventing cancer in a subject in need thereof.

In some aspects, the present disclosure provides a compound of the present disclosure or a pharmaceutically acceptable salt thereof for use in treating cancer in a subject in need thereof.

In some aspects, the present disclosure provides use of a compound of the present disclosure or a pharmaceutically acceptable salt thereof in the manufacture of a medicament for modulating DNA polymerase Θ activity.

In some aspects, the present disclosure provides use of a compound of the present disclosure or a pharmaceutically acceptable salt thereof in the manufacture of a medicament for modulating DNA polymerase Θ activity (e.g., in vitro or in vivo).

In some aspects, the present disclosure provides use of a compound of the present disclosure or a pharmaceutically acceptable salt thereof in the manufacture of a medicament for treating or preventing a disease or disorder disclosed herein.

In some aspects, the present disclosure provides use of a compound of the present disclosure or a pharmaceutically acceptable salt thereof in the manufacture of a medicament for treating a disease or disorder disclosed herein.

In some aspects, the present disclosure provides use of a compound of the present disclosure or a pharmaceutically acceptable salt thereof in the manufacture of a medicament for treating or preventing cancer in a subject in need thereof.

In some aspects, the present disclosure provides use of a compound of the present disclosure or a pharmaceutically acceptable salt thereof in the manufacture of a medicament for treating cancer in a subject in need thereof.

The present disclosure provides compounds that function as modulators of DNA polymerase Θ activity.

In some embodiments, the compounds of the present disclosure are antagonists of the DNA polymerase Θ receptor.

In some embodiments, the modulation of the DNA polymerase Θ receptor is activation of the DNA polymerase Θ receptor.

In some embodiments, modulation is inhibition.

Effectiveness of compounds of the disclosure can be determined by industry-accepted assays/disease models according to standard practices of elucidating the same as described in the art and are found in the current general knowledge.

The present disclosure also provides a method of treating a disease or disorder in which DNA polymerase Θ activity is implicated in a patient in need of such treatment, said method comprising administering to said patient a therapeutically effective amount of a compound, or a pharmaceutically acceptable salt thereof, or a pharmaceutical composition as defined herein. In some embodiments, the cancer is lymphoma, soft tissue, rhabdoid, multiple myeloma, gastric, peripheral nervous system, rhabdomyosarcoma, bone, colorectal, mesothelioma, prostate, breast, ovarian, uterine, lung, fibroblast, central nervous system, urinary tract, upper aerodigestive, leukemia, kidney, skin, esophagus, and pancreas (data from large scale drop out screens in cancer cell lines indicate that some cell lines from the above cancers are dependent on polymerase Θ for proliferation see https://depmap.org/portal/).

In some embodiments, a HR-deficient cancer is breast cancer. Breast cancer includes, but is not limited to, lobular carcinoma in situ, a ductal carcinoma in situ, an invasive ductal carcinoma, triple negative, HER positive, estrogen receptor positive, progesterone receptor positive. HER and estrogen receptor positive, HER and estrogen and progesterone receptor, positive inflammatory breast cancer, Paget disease of nipple, Phyllodes tumor, angiosarcoma, adenoid cystic carcinoma, low-grade adenosquamous carcinoma, medullary carcinoma, mucinous carcinoma, papillary carcinoma, tubular carcinoma, metaplastic carcinoma, micropapillary carcinoma, and mixed carcinoma. In second embodiment, HR-deficient cancer is ovarian cancer. Ovarian cancer includes, but is not limited to, epithelial ovarian carcinomas, maturing teratomas, dysgerminomas, endodermal sinus tumors, granulosa-theca tumors, Sertoli-Leydig cell tumors, and primary peritoneal carcinoma. In some cases, the ovarian cancer originated form cells of the fallopian tube.

In some embodiments, the cancer is selected from ovarian, prostate, breast, pancreatic, or uterine cancer.

In some embodiments, the cancer is resistant to treatment with at least one PARP inhibitor.

In some embodiments, the cancer is resistant to treatment with one PARP inhibitor.

In some embodiments, the subject received prior treatment with PARP inhibitor and the cancer is relapsed or refractory.

In some embodiments, the PARP inhibitor is a selective PARP inhibitor.

In some embodiments, the PARP inhibitor is a non-selective PARP inhibitor.

In some embodiments, the PARP inhibitor is olaparib.

In some embodiments, the cancer has a deficiency in a DNA damage repair process.

In some embodiments, the cancer is sensitive to POLΘ inhibition.

In some embodiments, the cancer has evidence of elevated POLΘ activity.

In some embodiments, the cancer has elevated expression of POLΘ mRNA or protein.

In some embodiments, the cancer has elevated expression of POLΘ mRNA.

In some embodiments, the cancer has elevated expression of POLΘ protein.

In some embodiments, the cancer is classified by a genotype.

In some embodiments, the genotype has a modulated function.

In some embodiments, the modulated function is an inactivating mutation, deletion, or other genomic alteration.

In some embodiments, the genotype is loss of mRNA or protein expression.

In some embodiments, the cancer has modulated function of at least one gene.

In some embodiments, the gene is selected from ATM, BARD1, BRIP1, CDK12, CHEK1, CHEK2, FANCL, PALB2, RAD51B, RAD51C, RAD51D, and RAD54L.

In some embodiments, the cancer is a homologous recombination deficient (HRD) cancer.

In some embodiments, the cancer is classified as an HRD cancer because the tumor is unable to accurately repair double-strand breaks in DNA via homologous recombination.

In some embodiments, the mutation is a gene that, when lost, causes HRD.

In some embodiments, the cancer has a compromised homologous recombination (HR) or non-homologous DNA end joining (NHEJ) repair pathway.

In some embodiments, the cancer with a compromised HR is dependent on PolΘ activity.

In some embodiments, the cancer with a compromised NHEJ is dependent on PolΘ activity.

In some embodiments, the cancer is a tumor. In some embodiments, the cancer is a solid tumor.

Routes of Administration

Compounds of the present disclosure, or pharmaceutically acceptable salts thereof, may be administered alone as a sole therapy or can be administered in addition with one or more other substances and/or treatments. Such conjoint treatment may be achieved by way of the simultaneous, sequential or separate administration of the individual components of the treatment.

For example, therapeutic effectiveness may be enhanced by administration of an adjuvant (i.e. by itself the adjuvant may only have minimal therapeutic benefit, but in combination with another therapeutic agent, the overall therapeutic benefit to the individual is enhanced). Alternatively, by way of example only, the benefit experienced by an individual may be increased by administering the compound of Formula (I) with another therapeutic agent (which also includes a therapeutic regimen) that also has therapeutic benefit.

In the instances where the compound of the present disclosure is administered in combination with other therapeutic agents, the compound of the disclosure need not be administered via the same route as other therapeutic agents, and may, because of different physical and chemical characteristics, be administered by a different route. For example, the compound of the disclosure may be administered orally to generate and maintain good blood levels thereof, while the other therapeutic agent may be administered intravenously. The initial administration may be made according to established protocols known in the art, and then, based upon the observed effects, the dosage, modes of administration and times of administration can be modified by the skilled clinician.

The particular choice of other therapeutic agent will depend upon the diagnosis of the attending physicians and their judgment of the condition of the individual and the appropriate treatment protocol. According to this aspect of the disclosure there is provided a combination for use in the treatment of a disease in which DNA polymerase Θ activity is implicated comprising a compound of the disclosure as defined hereinbefore, or a pharmaceutically acceptable salt thereof, and another suitable agent.

According to a further aspect of the disclosure there is provided a pharmaceutical composition which comprises a compound of the disclosure, or a pharmaceutically acceptable salt thereof, in combination with one or more of an excipient, a carrier, a diluent, and/or a binder, (e.g., a pharmaceutically acceptable excipient, carrier, diluent, and/or binder).

In addition to its use in therapeutic medicine, compounds of Formula (I) and pharmaceutically acceptable salts thereof are also useful as pharmacological tools in the development and standardization of in vitro and in vivo test systems for the evaluation of the effects of modulators of DNA polymerase Θ activity in laboratory animals such as dogs, rabbits, monkeys, mini-pigs, rats and mice, as part of the search for new therapeutic agents.

In any of the above-mentioned pharmaceutical composition, process, method, use, medicament, and manufacturing features of the instant disclosure, any of the alternate embodiments of macromolecules of the present disclosure described herein also apply.

The compounds of the disclosure or pharmaceutical compositions comprising these compounds may be administered to a subject by any convenient route of administration, whether systemically/peripherally or topically (i.e., at the site of desired action).

Routes of administration include, but are not limited to, oral (e.g. by ingestion); buccal; sublingual; transdermal (including, e.g., by a patch, plaster, etc.); transmucosal (including, e.g., by a patch, plaster, etc.); intranasal (e.g., by nasal spray or powder); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

EXEMPLARY EMBODIMENTS

Exemplary Embodiment No. 1. A compound of Formula (I):

(I)

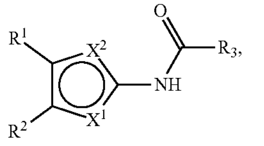

or a pharmaceutically acceptable salt, solvate, clathrate, hydrate, stereoisomer, or tautomer thereof, wherein:

$X^1$ is CH, S, or N;

$X^2$ is N, S, or O;

$R^1$ and $R^2$, together with the atoms to which they are attached, form a $C_5$-$C_{10}$ cycloalkyl or 5- to 10-membered heterocycloalkyl, wherein the $C_5$-$C_{10}$ cycloalkyl or 5- to 10-membered heterocycloalkyl is optionally substituted with one or more R;

each $R^a$ independently is oxo, halo, cyano, —$OR^{a1}$, —$N(R^{a1})_2$, —$C(O)R^{a1}$, —$C(O)N(R^{a1})_2$, —$C(O)OR^{a1}$, —$S(O)_2N(R^{a1})_2$, —$S(O)_2(R^{a1})$, $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, $C_6$-$C_{10}$ aryl, 5- to 10-membered heteroaryl, or 3- to 10-membered heterocycloalkyl, wherein the $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, $C_6$-$C_{10}$ aryl, 5- to 10-membered heteroaryl, or 3- to 10-membered heterocycloalkyl is optionally substituted with one or more RV;

each $R^{a1}$ independently is H, oxo, halo, cyano, —OH, —$NH_2$, —$C(O)(C_1$-$C_6$ alkyl), —$C(O)(C_3$-$C_{10}$ cycloalkyl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_{10}$ cycloalkyl, 3- to 10-membered heterocycloalkyl, $C_6$-$C_{10}$ aryl, or 5- to 10-membered heteroaryl, wherein the —$C(O)(C_3$-$C_{10}$ cycloalkyl), $C_1$-$C_6$ alkyl, $C_2$-$C_6$ alkenyl, $C_2$-$C_6$ alkynyl, $C_1$-$C_6$ haloalkyl, Ct-Ce alkoxy, $C_3$-$C_{10}$ cycloalkyl, 3- to 10-membered heterocycloalkyl, $C_6$-$C_{10}$ aryl, or 5- to 10-membered heteroaryl is optionally substituted with one or more $R^{a2}$;

each $R^{a2}$ independently is oxo, halo, cyano, —OH, —$NH_2$, —$NH(C_1$-$C_6$ alkyl), —$N(C_1$-$C_6$ alkyl$)_2$, $C_1$-$C_6$ alkyl optionally substituted with $C_1$-$C_6$ alkoxy or —OH, $C_3$-$C_{10}$ cycloalkyl, $C_1$-$C_6$ haloalkoxy, $C_1$-$C_6$ haloalkyl, $C_1$-$C_6$ alkoxy, 3- to 10-membered heterocycloalkyl optionally substituted with oxo, or 5- to 10-membered heteroaryl;

$R^3$ is $C_6$-$C_{10}$ aryl or 5- to 10-membered heteroaryl, wherein the $C_6$-$C_{10}$ aryl or 5- to 10-membered heteroaryl is substituted with one or more $R^{3a}$;

each $R^{3a}$ independently is halo, cyano, —OH, —$NH_2$, $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, 3- to 10-membered heterocycloalkyl, $C_6$-$C_{10}$ aryl, or 5- to 10-membered heteroaryl, wherein the $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, 3- to 10-membered heterocycloalkyl, $C_6$-$C_{10}$ aryl, or 5- to 10-membered heteroaryl is optionally substituted with one or more $R^{3a1}$; and each $R^{3a1}$ independently is oxo, halo, cyano, —OH, —$C(O)(C_1$-$C_6$ alkyl), —$C(O)(O$—$(C_1$-$C_6$ alkyl)), $C_3$-$C_{10}$ alkyl optionally substituted with $C_3$-$C_{10}$ cycloalkyl, $C_2$-$C_6$ alkenyl, $C_2$-$C_6$ alkynyl, $C_1$-$C_6$ haloalkyl, $C_1$-$C_6$ haloalkoxy, $C_1$-$C_6$ alkoxy, —$O(C_1$-$C_6$ haloalkyl), $C_3$-$C_{10}$ cycloalkyl, $C_6$-$C_{10}$ aryl, or 5- to 10-membered heteroaryl.

Exemplary Embodiment No. 2. A compound of Formula (I):

(I)

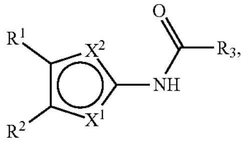

or a pharmaceutically acceptable salt, solvate, clathrate, hydrate, stereoisomer, or tautomer thereof, wherein:

$X^1$ is CH, S, or N;

$X^2$ is N, S, or O;

$R^1$ and $R^2$, together with the atoms to which they are attached, form a $C_5$-$C_{10}$ cycloalkyl or 5- to 10-membered heterocycloalkyl, wherein the $C_5$-$C_{10}$ cycloalkyl or 5- to 10-membered heterocycloalkyl is optionally substituted with one or more $R^a$;

each $R^a$ independently is oxo, halo, cyano, —$OR^{a1}$, —$N(R^{a1})_2$, —$C(O)R^{a1}$, —$C(O)N(R^{a1})_2$, —$C(O)OR^{a1}$, —$S(O)_2N(R^{a1})_2$, —$S(O)_2(R^{a1})$, $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, $C_6$-$C_{10}$ aryl, 5- to 10-membered heteroaryl, or 3- to 10-membered heterocycloalkyl, wherein the $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, $C_6$-$C_{10}$ aryl, 5- to 10-membered heteroaryl, or 3- to 10-membered heterocycloalkyl is optionally substituted with one or more $R^{a1}$;

each $R^{a1}$ independently is H, oxo, halo, cyano, —OH, —$NH_2$, —C(O)($C_1$-$C_6$ alkyl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_{10}$ cycloalkyl, 3- to 10-membered heterocycloalkyl, $C_6$-$C_{10}$ aryl, or 5- to 10-membered heteroaryl, wherein the $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_{10}$ cycloalkyl, 3- to 10-membered heterocycloalkyl, $C_6$-$C_{10}$ aryl, or 5- to 10-membered heteroaryl is optionally substituted with one or more $R^{a2}$;

each $R^{a2}$ independently is oxo, halo, cyano, —OH, —$NH_2$, $C_1$-$C_6$ alkyl optionally substituted with $C_1$-$C_6$ alkoxy, $C_1$-$C_6$ haloalkoxy, 3- to 10-membered heterocycloalkyl optionally substituted with oxo, or 5- to 10-membered heteroaryl;

$R^3$ is $C_6$-$C_{10}$ aryl or 5- to 10-membered heteroaryl, wherein the $C_6$-$C_{10}$ aryl or 5- to 10-membered heteroaryl is substituted with one or more $R^{3'}$;

each $R^{3a}$ independently is halo, cyano, —OH, —$NH_2$, $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, 3- to 10-membered heterocycloalkyl, $C_6$-$C_{10}$ aryl, or 5- to 10-membered heteroaryl, wherein the $C_1$-$C_6$ alkyl. $C_2$-$C_6$ alkenyl, $C_2$-$C_6$ alkynyl, $C_1$-$C_6$ haloalkyl, $C_3$-$C_{10}$ cycloalkyl, 3- to 10-membered heterocycloalkyl, $C_6$-$C_{10}$ aryl, or 5- to 10-membered heteroaryl is optionally substituted with one or more $R^{3a1}$; and each $R^{3a1}$ independently is oxo, halo, cyano, —OH, —C(O)($C_1$-$C_6$ alkyl), —C(O)(O—($C_1$-$C_6$ alkyl)), $C_1$-$C_6$ alkyl optionally substituted with $C_3$-$C_{10}$ cycloalkyl, $C_2$-$C_6$ alkenyl, $C_2$-$C_6$ alkynyl, $C_1$-$C_6$ haloalkyl, $C_1$-$C_6$ haloalkoxy, $C_1$-$C_6$ alkoxy, —O($C_1$-$C_6$haloalkyl), $C_3$-$C_{10}$ cycloalkyl, $C_6$-$C_{10}$ aryl, or 5- to 10-membered heteroaryl.

Exemplary Embodiment No. 3. The compound of Exemplary Embodiment No. 1 or Exemplary Embodiment No. 2, wherein:

$X^1$ is S or N;

$X^2$ is N or S;

$R^1$ and $R^2$, together with the atoms to which they are attached, form a $C_5$-$C_6$ cycloalkyl or 5- to 6-membered heterocycloalkyl, wherein the $C_5$-$C_6$ cycloalkyl or 5- to 6-membered heterocycloalkyl is optionally substituted with one or more $R^a$;

each $R^a$ independently is oxo, —$OR^{a1}$, —$N(R^{a1})_2$, —$C(O)R^{a1}$, —$C(O)N(R^{a1})_2$, —$C(O)OR^{a1}$, —$S(O)_2N(R)_2$, —$S(O)_2(R^{a1})$, $C_1$-$C_6$ alkyl, $C_3$-$C_{10}$ cycloalkyl, $C_6$-$C_{10}$ aryl, 5- to 10-membered heteroaryl, or 3- to 10-membered heterocycloalkyl, wherein the $C_1$-$C_6$ alkyl, $C_3$-$C_{10}$ cycloalkyl, $C_6$-$C_{10}$ aryl, 5- to 10-membered heteroaryl, or 3- to 10-membered heterocycloalkyl is optionally substituted with one or more $R^{a1}$;

each $R^{a1}$ independently is H, halo, cyano, —C(O)($C_1$-$C_6$ alkyl), —C(O)($C_3$-$C_{10}$ cycloalkyl), $C_1$-$C_6$ alkyl, $C_1$-$C_6$ haloalkyl, $C_3$-$C_{10}$ cycloalkyl, 3- to 10-membered heterocycloalkyl, $C_6$-$C_{10}$ aryl, or 5- to 10-membered heteroaryl, wherein the —C(O)($C_3$-$C_{10}$ cycloalkyl), $C_1$-$C_6$ alkyl, $C_1$-$C_6$ haloalkyl, $C_3$-$C_{10}$ cycloalkyl, 3- to 10-membered heterocycloalkyl. $C_6$-$C_{10}$ aryl, or 5- to 10-membered heteroaryl is optionally substituted with one or more $R^{a2}$;

each $R^{a2}$ independently is oxo, cyano, —OH, —N($C_1$-$C_6$ alkyl)$_2$, $C_1$-$C_6$ alkyl optionally substituted with $C_1$-$C_6$ alkoxy or —OH, $C_3$-$C_{10}$ cycloalkyl, $C_1$-$C_6$ haloalkoxy, $C_1$-$C_6$ haloalkyl, $C_1$-$C_6$ alkoxy, 3- to 10-membered heterocycloalkyl optionally substituted with oxo, or 5- to 10-membered heteroaryl;

$R^3$ is 5- to 10-membered heteroaryl substituted with one $R^{3a}$, $R^{3a}$ is $C_6$-$C_{10}$ aryl optionally substituted with one or more $R^{3a1}$; and each $R^{3a1}$ independently is cyano or $C_1$-$C_6$ alkoxy.

Exemplary Embodiment No. 4. The compound of Exemplary Embodiment No. 1 or Exemplary Embodiment No. 2, wherein $R^1$ and $R^2$, together with the atoms to which they are attached, form a 5-membered heterocycloalkyl or $C_6$ cycloalkyl.

Exemplary Embodiment No. 5. The compound of any one of the preceding Exemplary Embodiments, wherein each $R^a$ independently is:

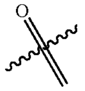,
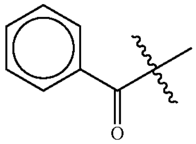,
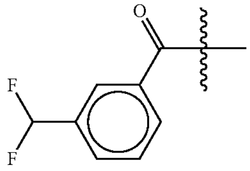,
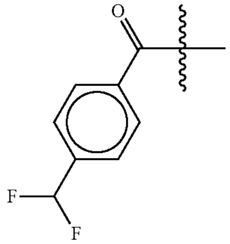,
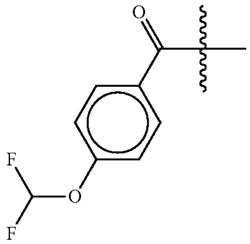,
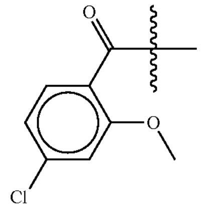,
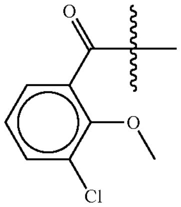,
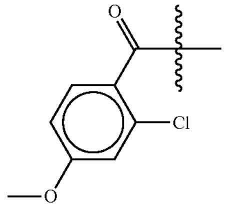,
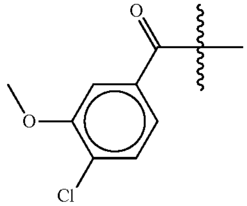,
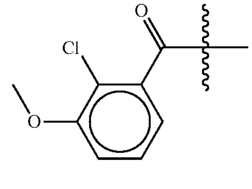,
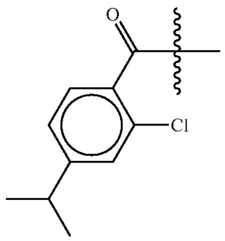,
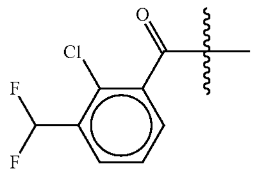, -continued
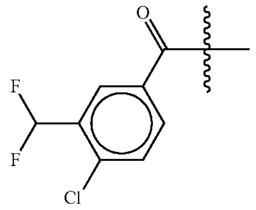
,
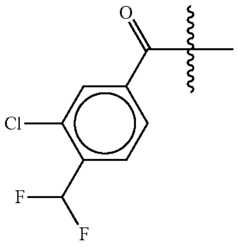
,
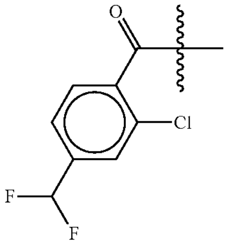
,
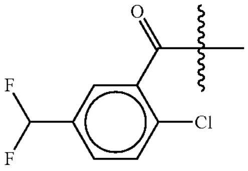
,
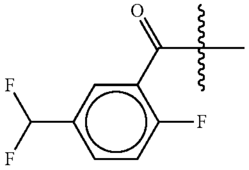
,
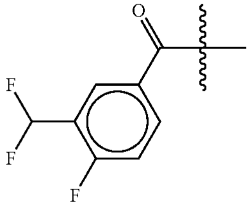
,
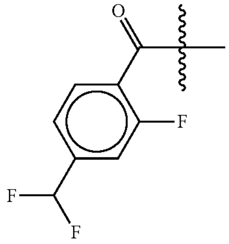
,
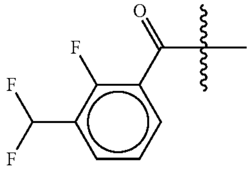
,
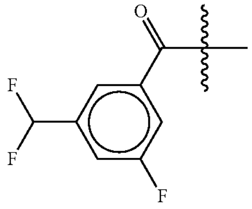
,
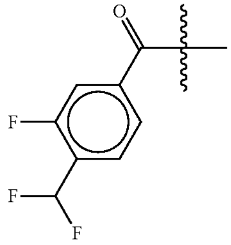
,
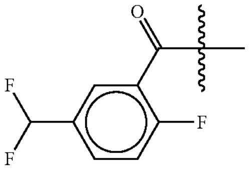
,
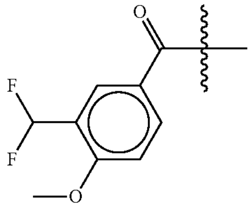
,
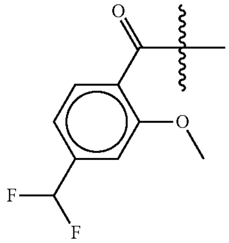
,
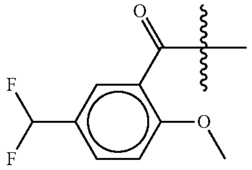
,
-continued
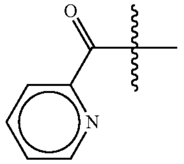
,
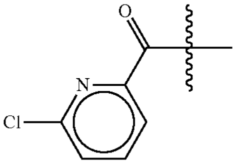
,
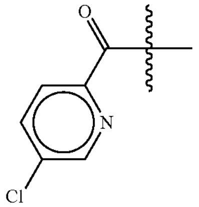
,
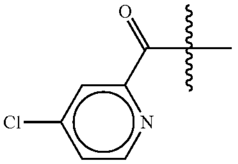
,
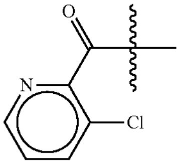
,
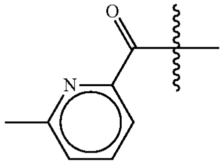
,
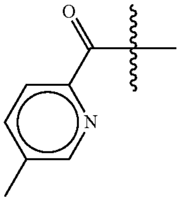
,
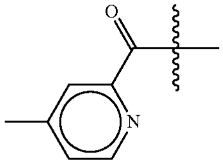
,
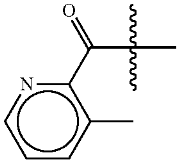
,
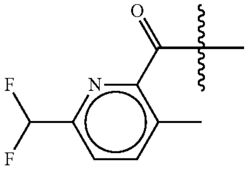
,
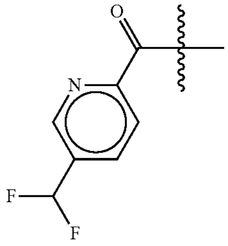
,
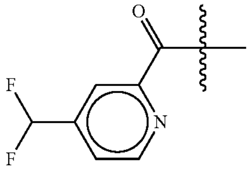
,
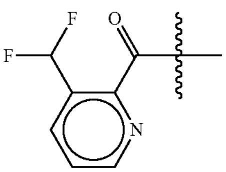
,
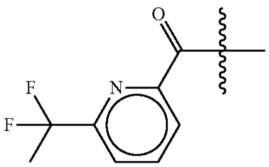
,
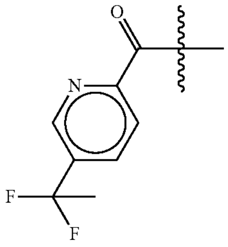
,
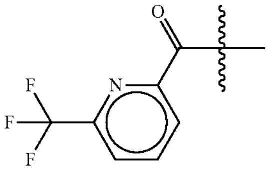
, -continued
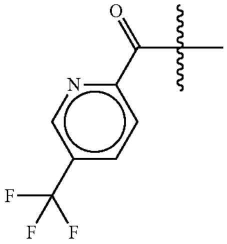,
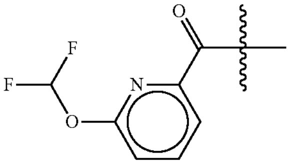,
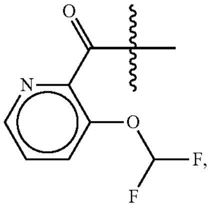
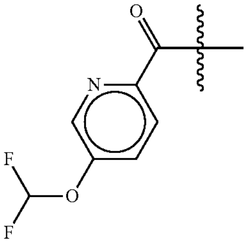,
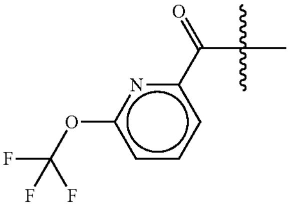,
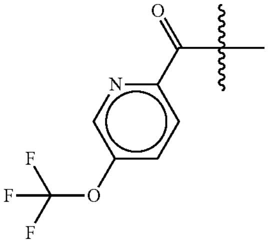,
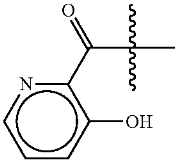,
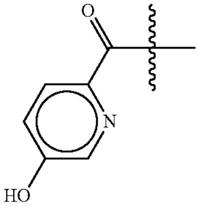,
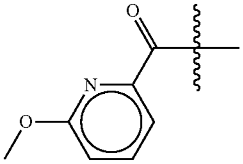,
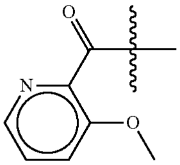,
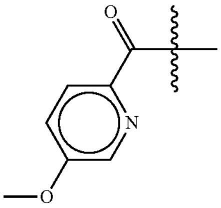,
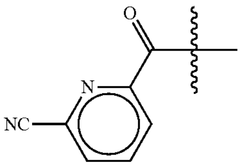,
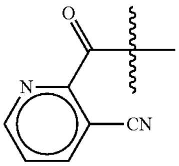,
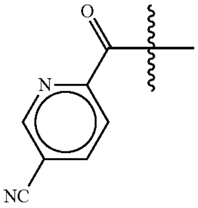,
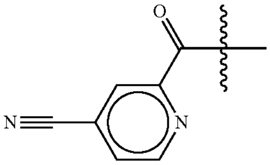,
-continued
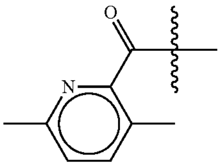,
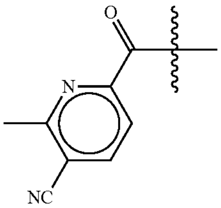,
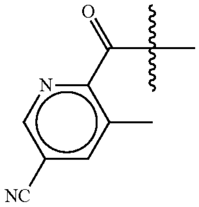,
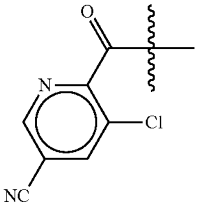,
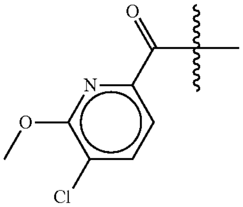,
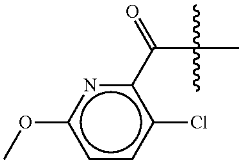,
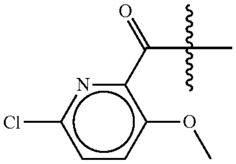,
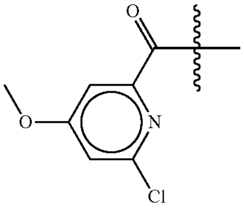,
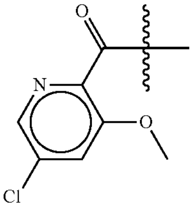,
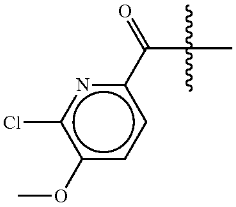,
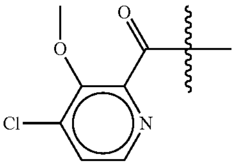,
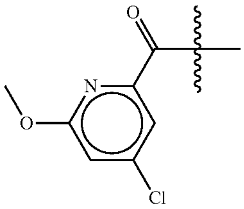,
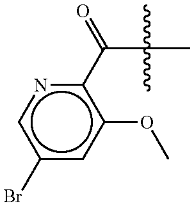,
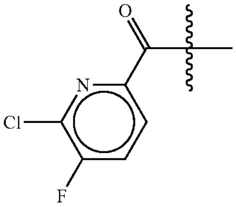,
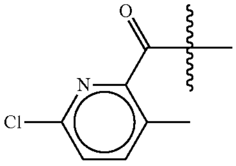,
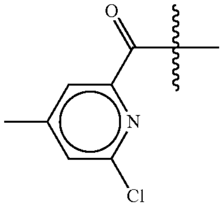, -continued
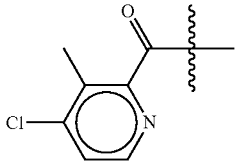,
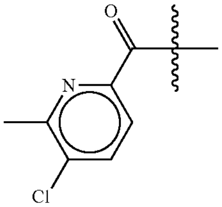,
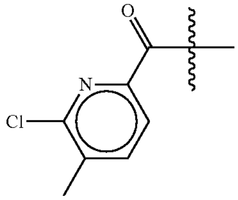,
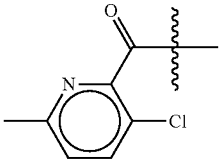,
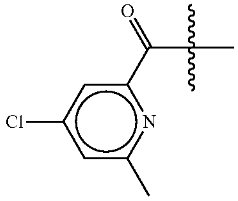,
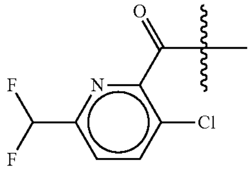,
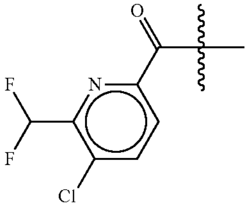,
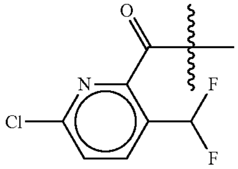,
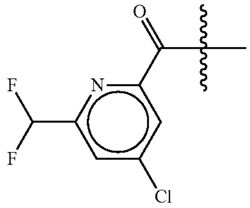,
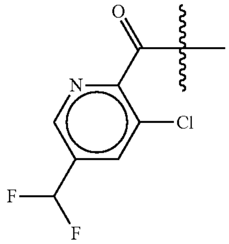,
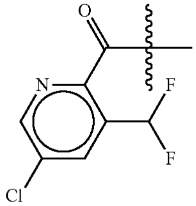,
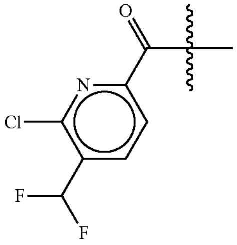,
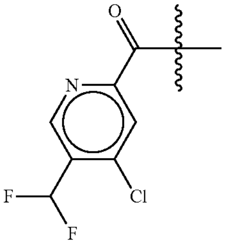,
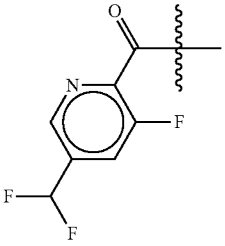,
-continued
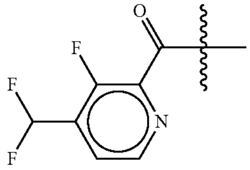,
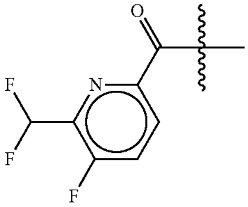,
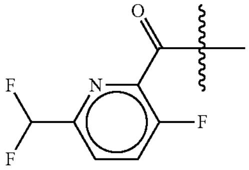,
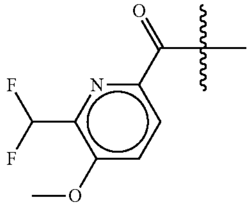,
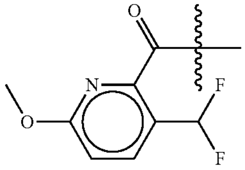,
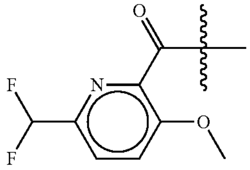,
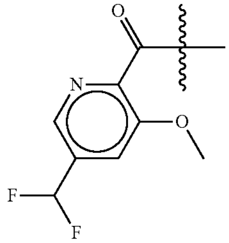,
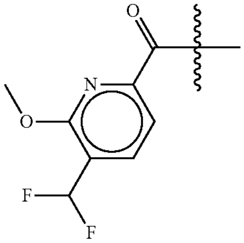,
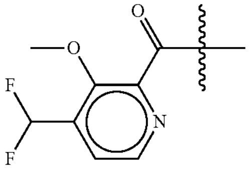,
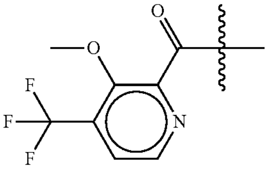,
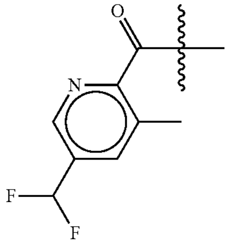,
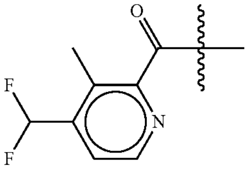,
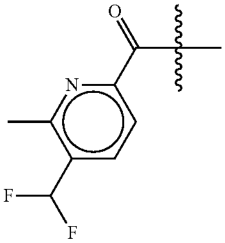,
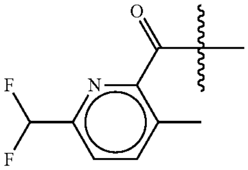,
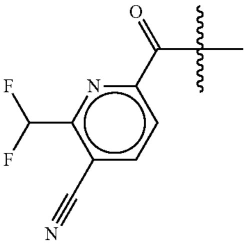,
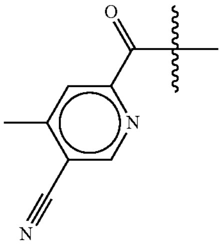, -continued
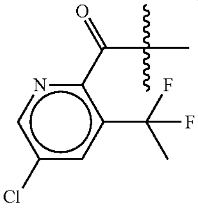
,
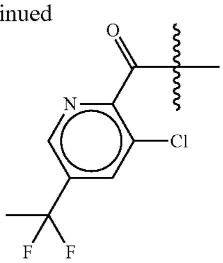
,
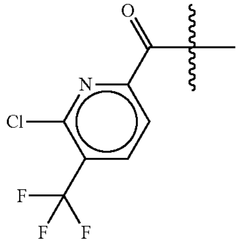
,
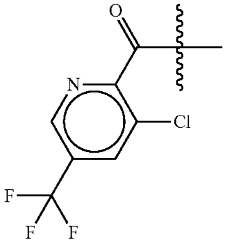
,
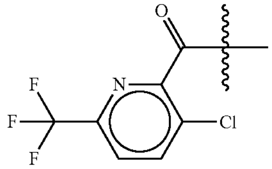
,
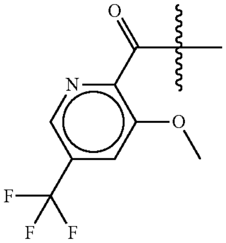
,
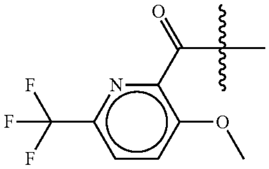
,
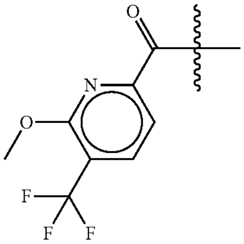
,
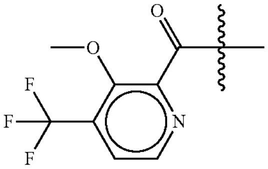
,
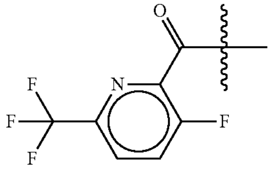
,
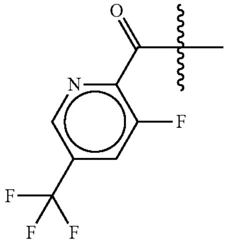
,
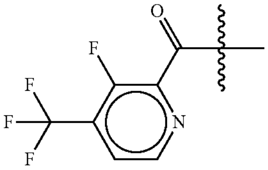
,
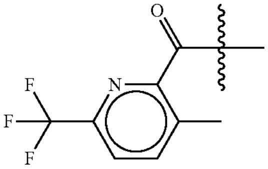
,
-continued
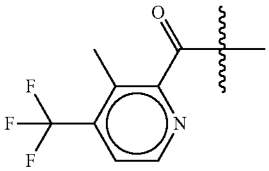
,
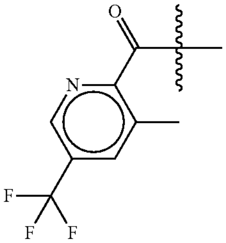
,
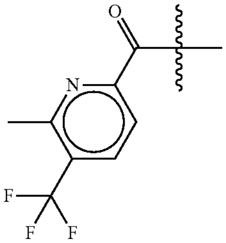
,
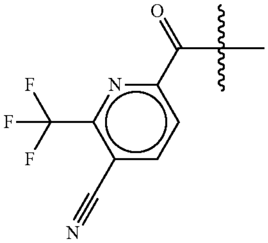
,
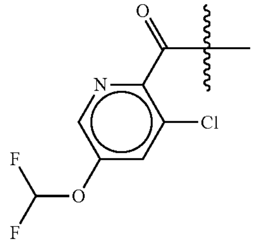
,
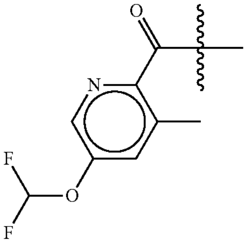
,
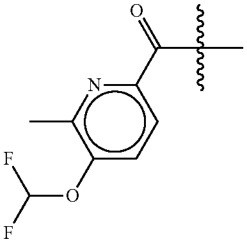
,
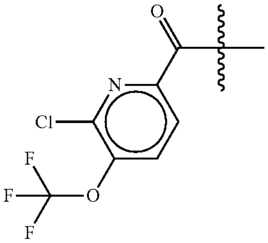
,
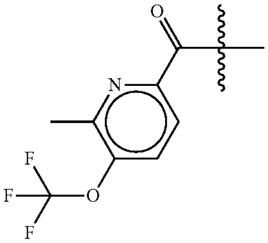
,
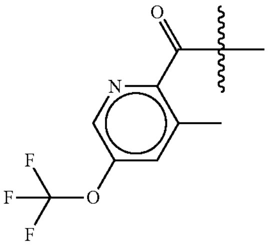
,
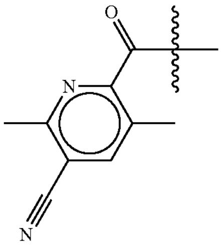
,
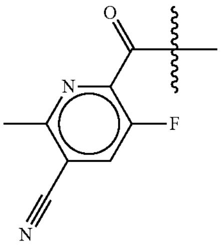
,
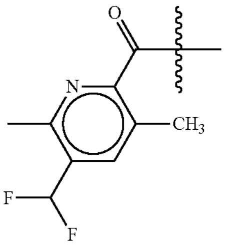
, -continued
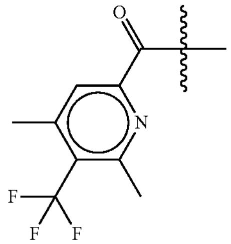,
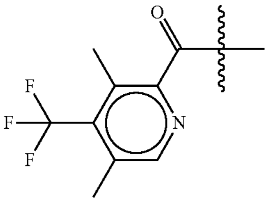,
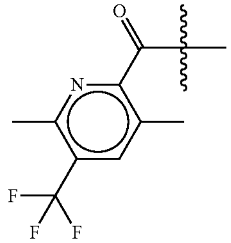,
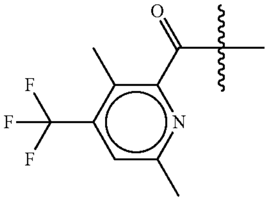,
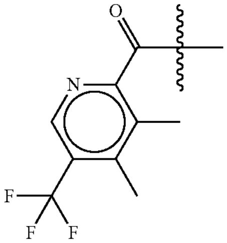,
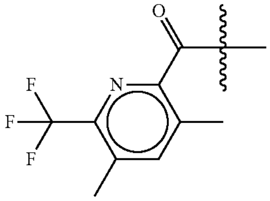,
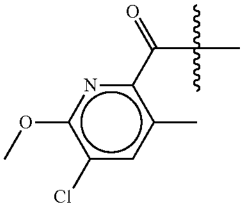,
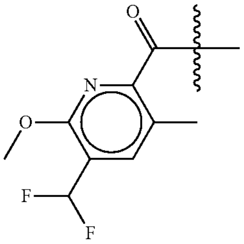,
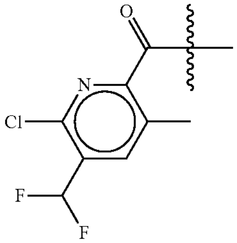,
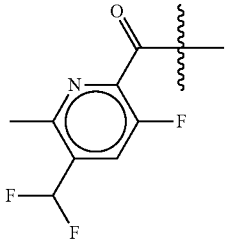,
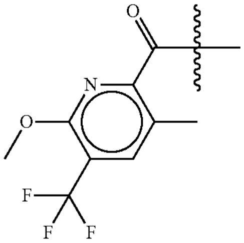,
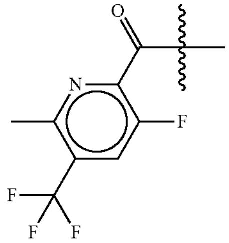,
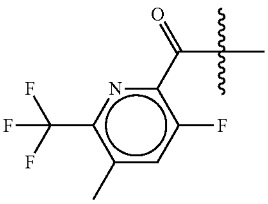,
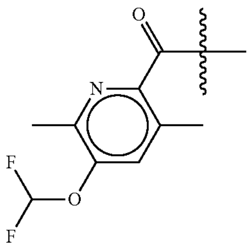,
-continued
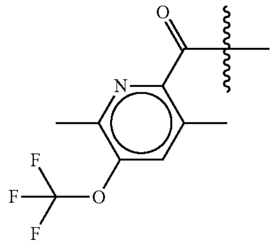,
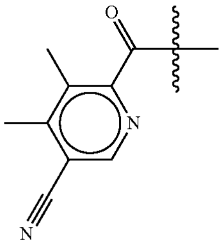,
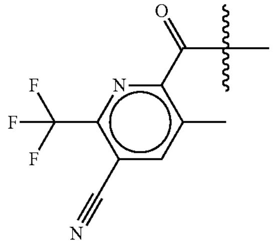,
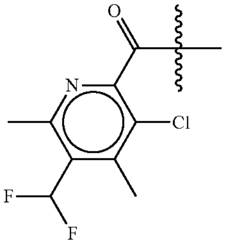,
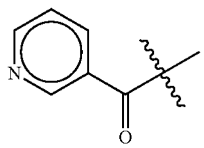,
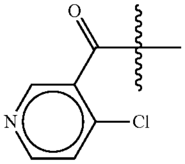,
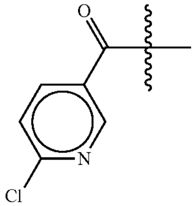,
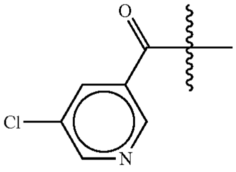,
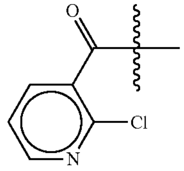,
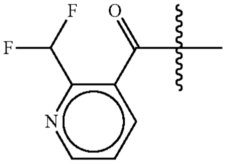,
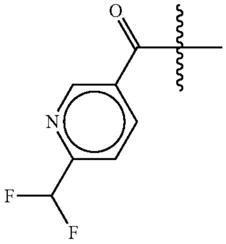,
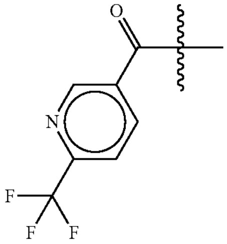,
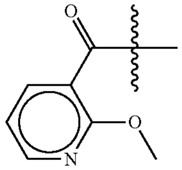,
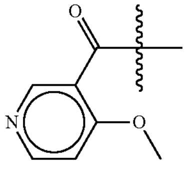,
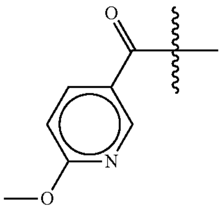,
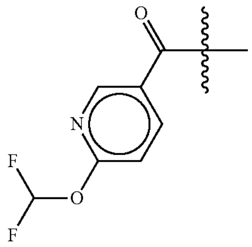,

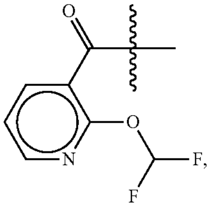,
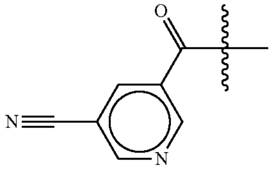,
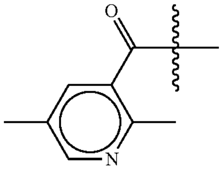,
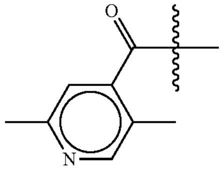,
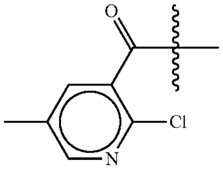,
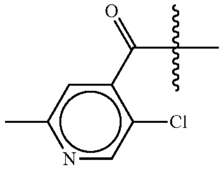,
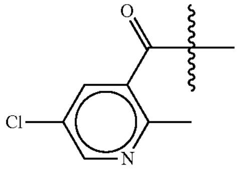,
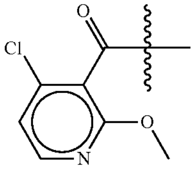,
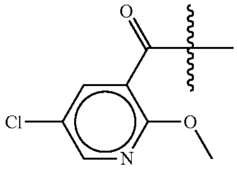,
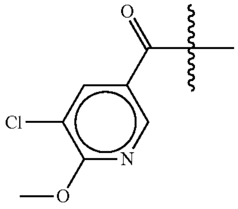,
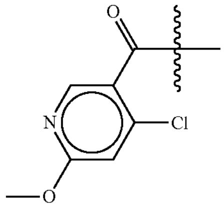,
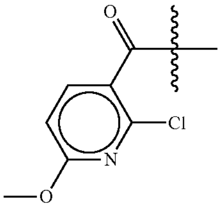,
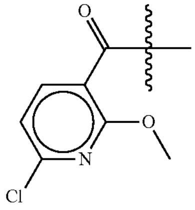,
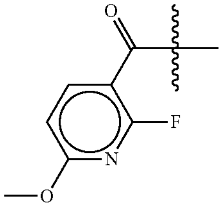,
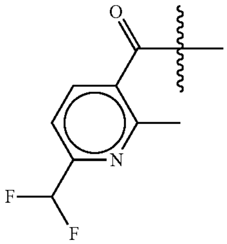,
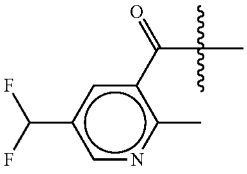,
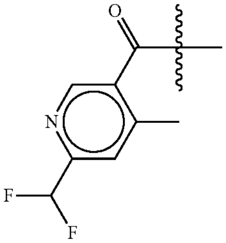,
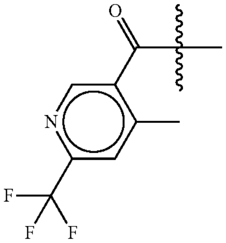,
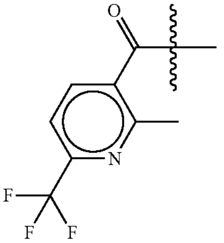,
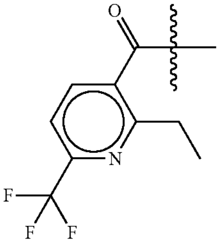,
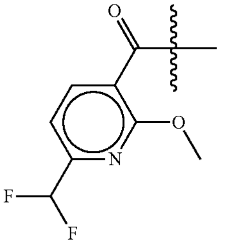,
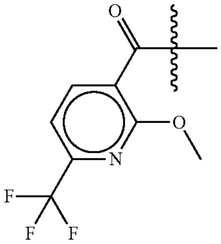,
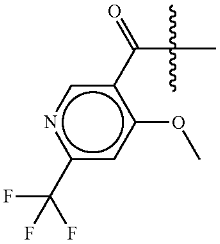,
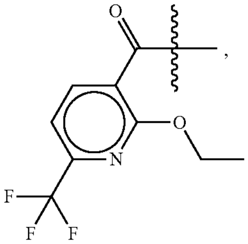,
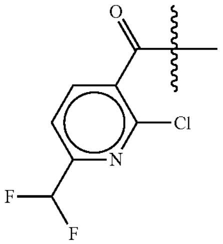,
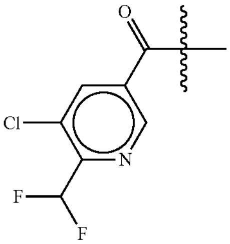,
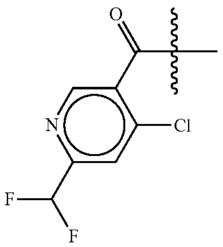,
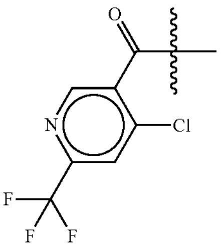, -continued
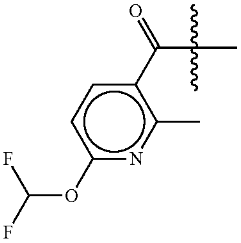,
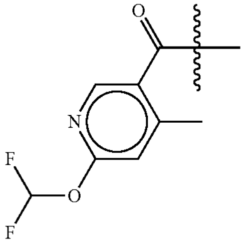,
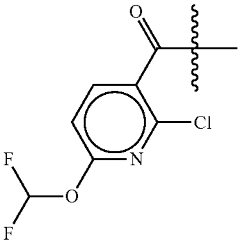,
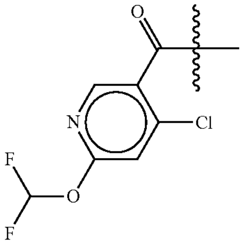,
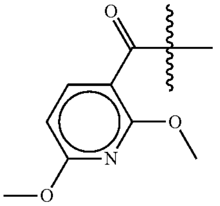,
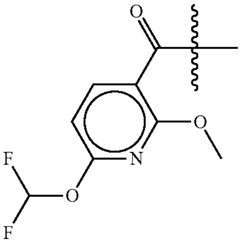,
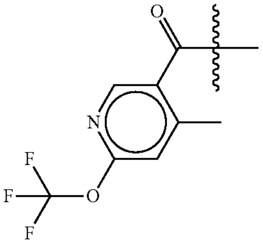,
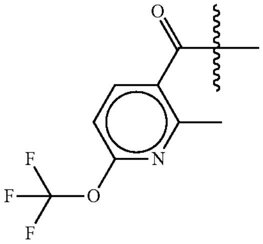,
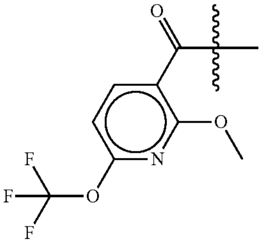,
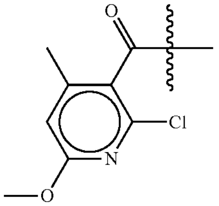,
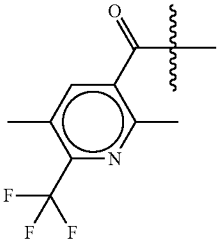,
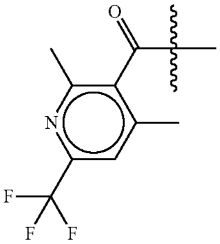,
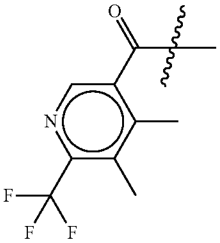,
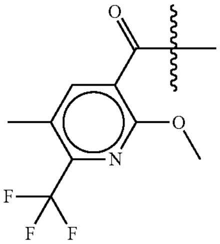,
-continued
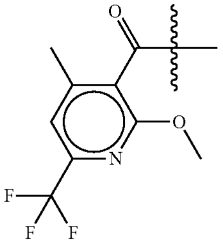,
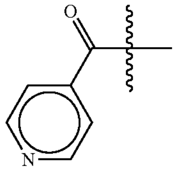,
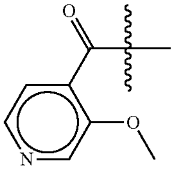,
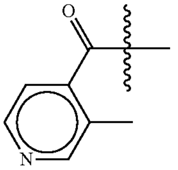,
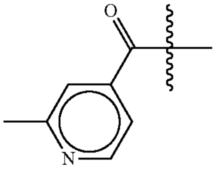,
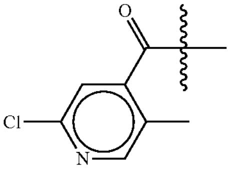,
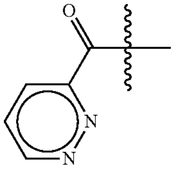,
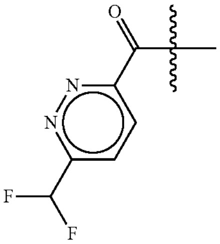,
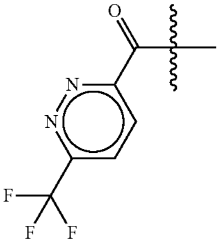,
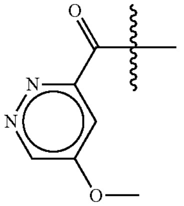,
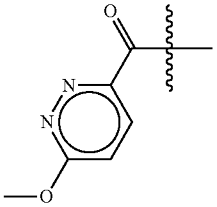,
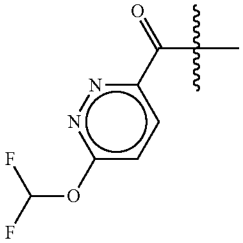,
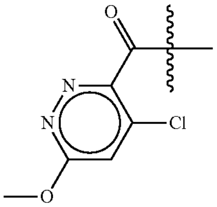,
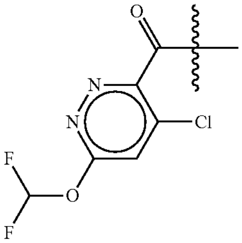,
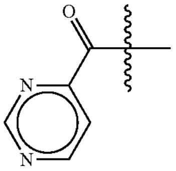,
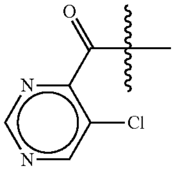, -continued
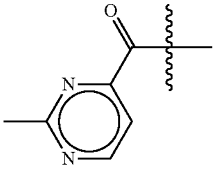,
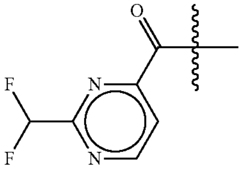,
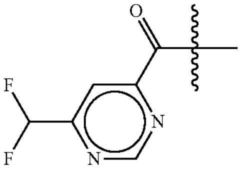,
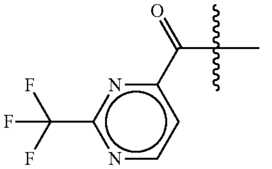,
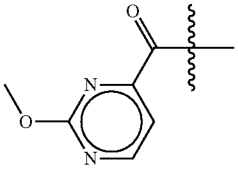,
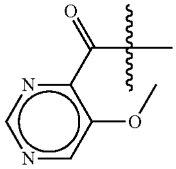,
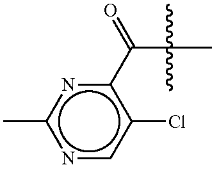,
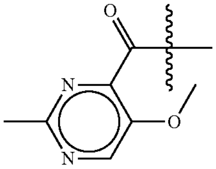,
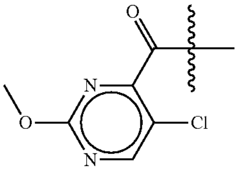,
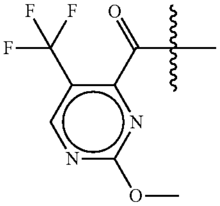,
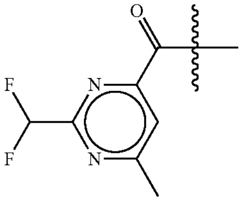,
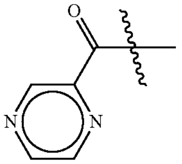,
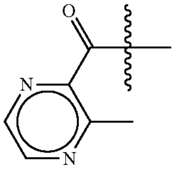,
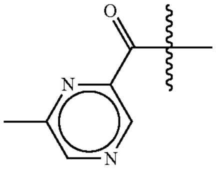,
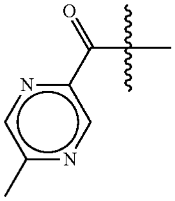,
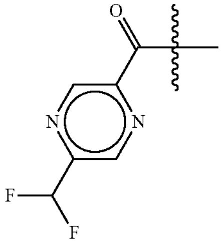,
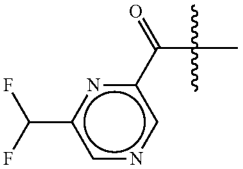,
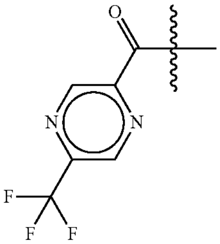,
-continued
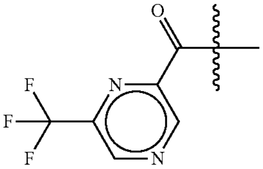,
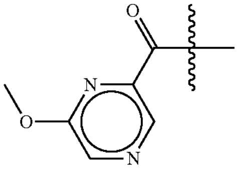,
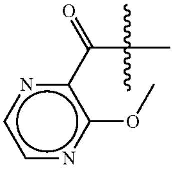,
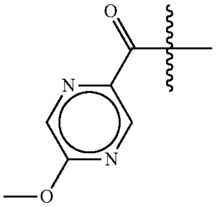,
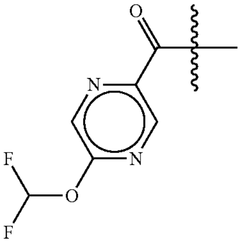,
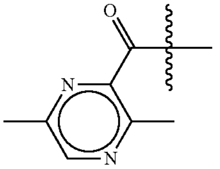,
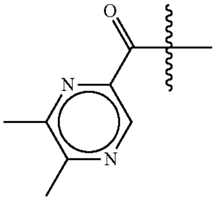,
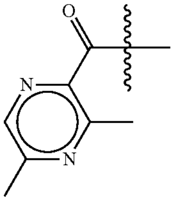,
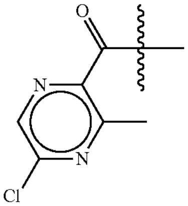,
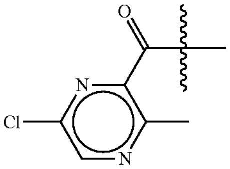,
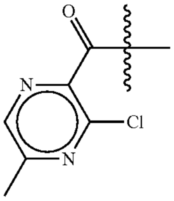,
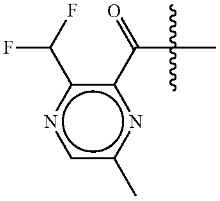,
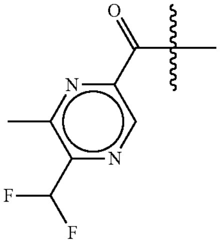,
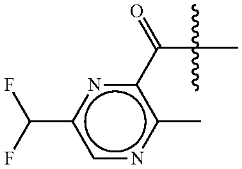,
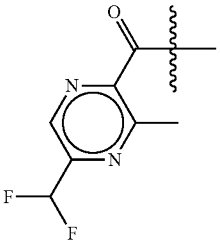,
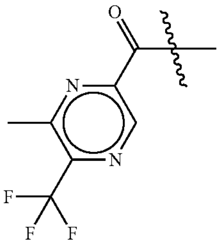, -continued
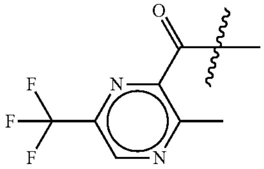,
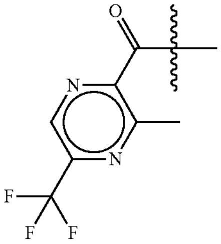,
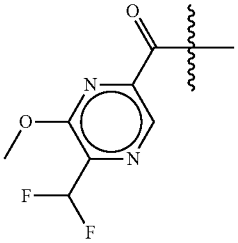,
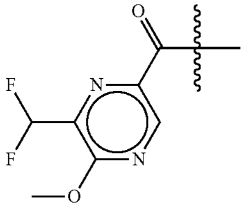,
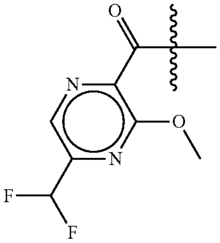,
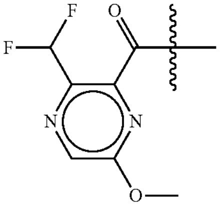,
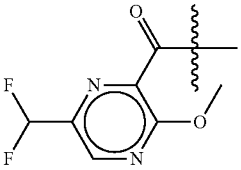,
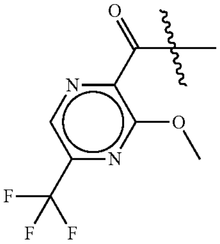,
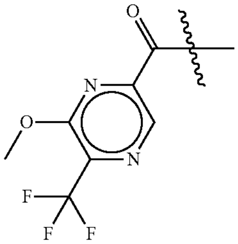,
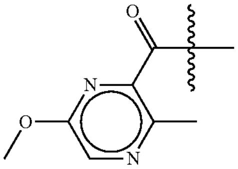,
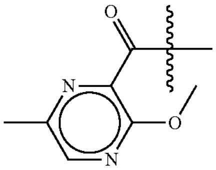,
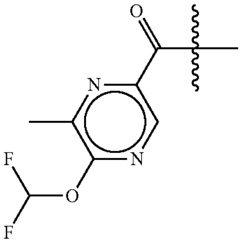,
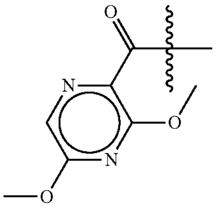,
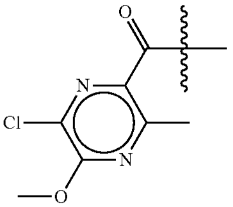,
-continued
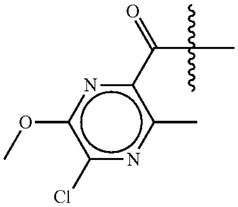,
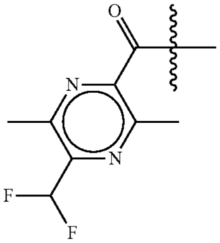,
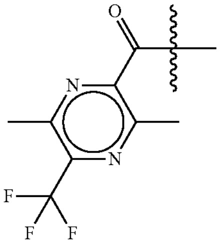,
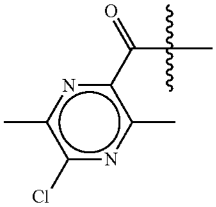,
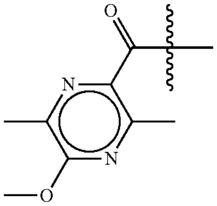,
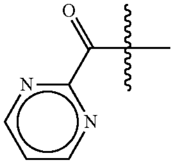,
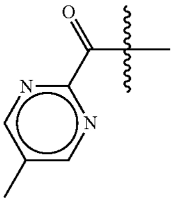,
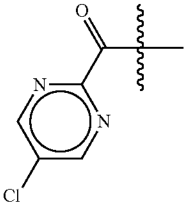,
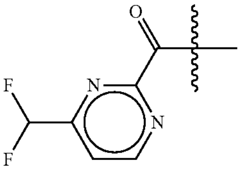,
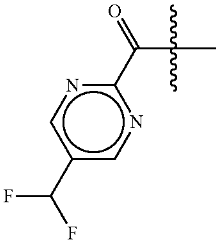,
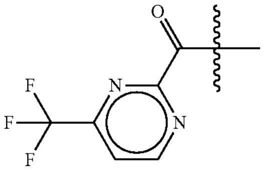,
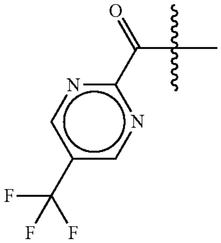,
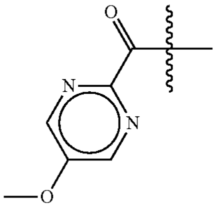,
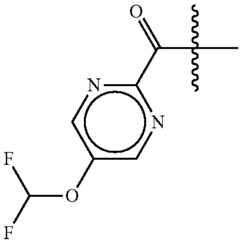, -continued
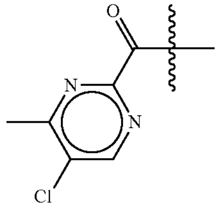,
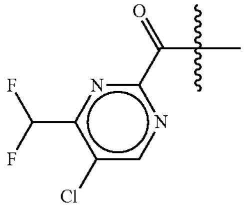,
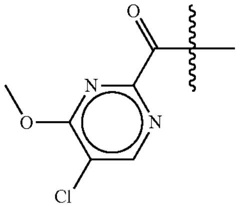,
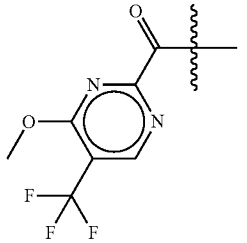,
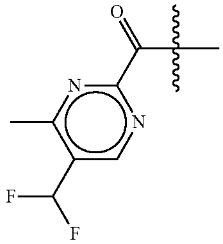,
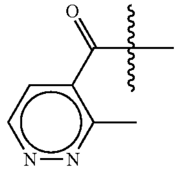,
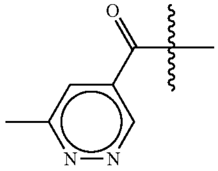,
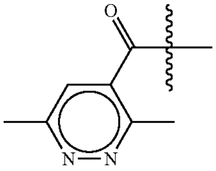,
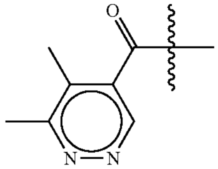,
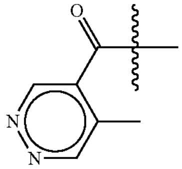,
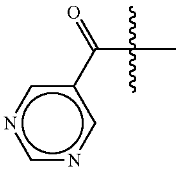,
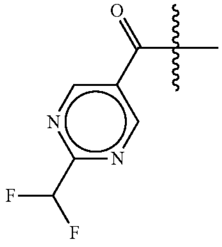,
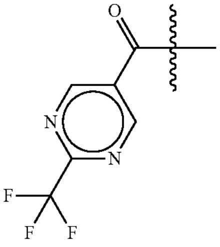,
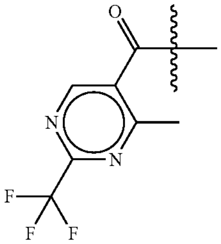,
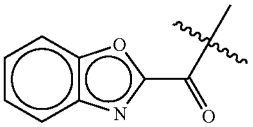,
-continued
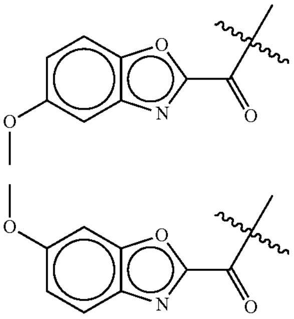,
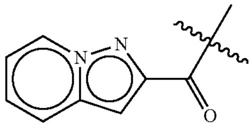,
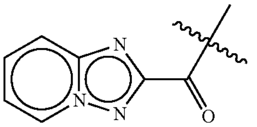,
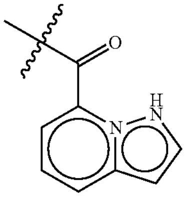,
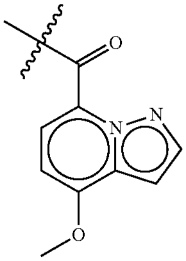,
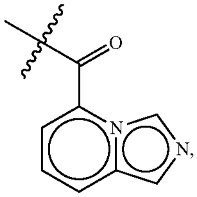,
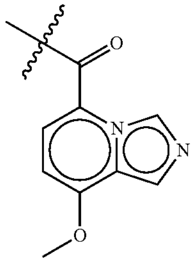,
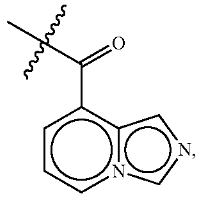,
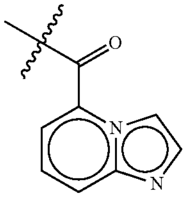,
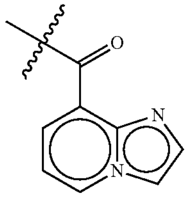,
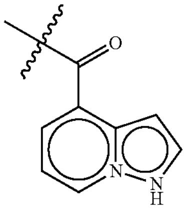,
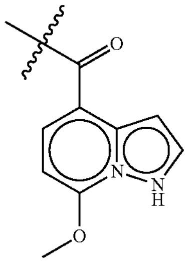, -continued
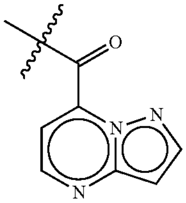,
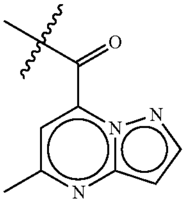,
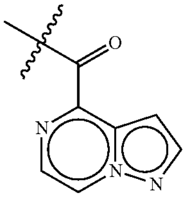,
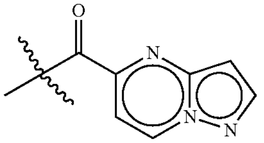,
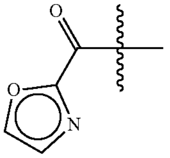,
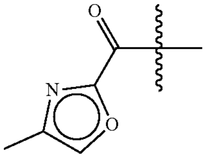,
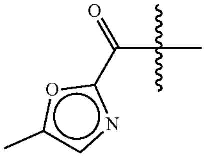,
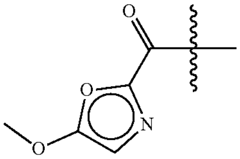,
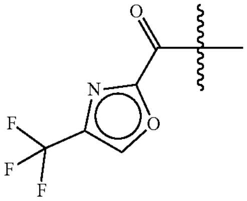,
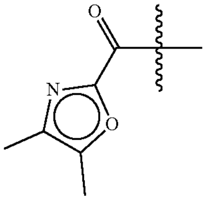,
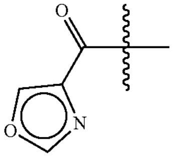,
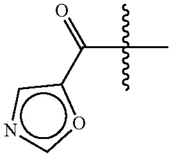,
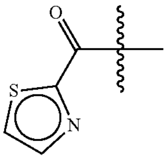,
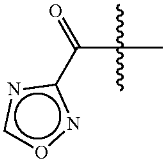,
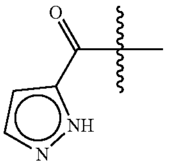,
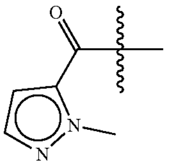,
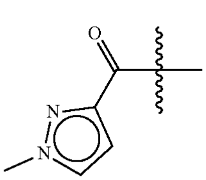,
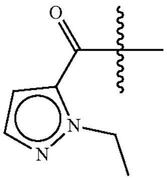,
-continued
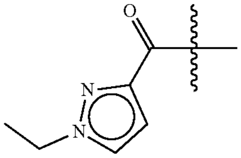,
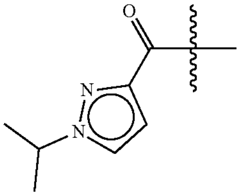,
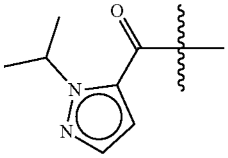,
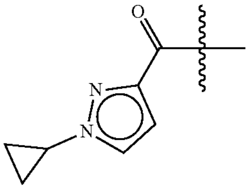,
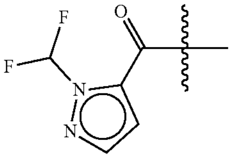,
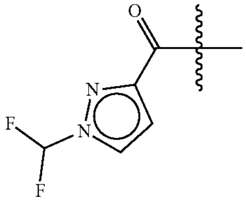,
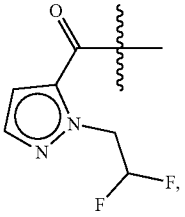
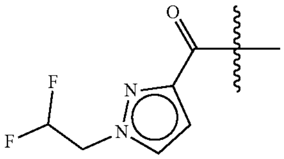,
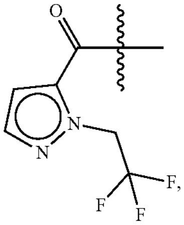
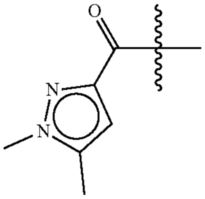,
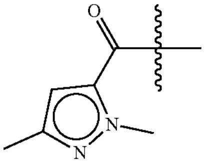,
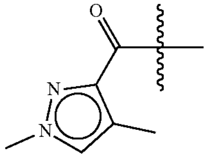,
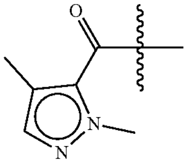,
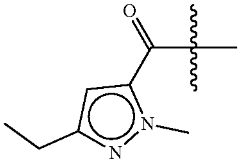,
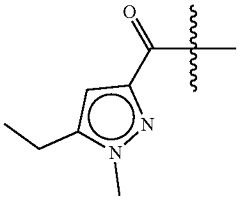,
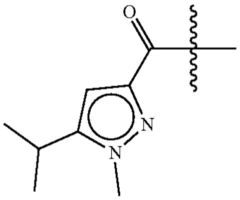, -continued
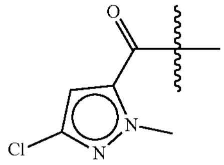, 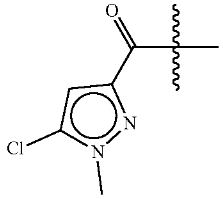,
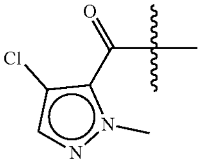, 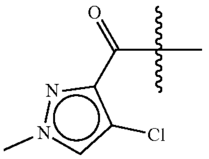,
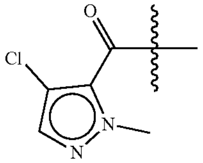, 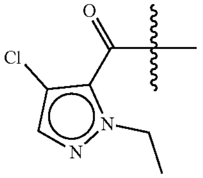,
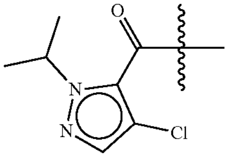, 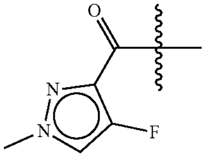,
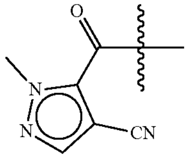, 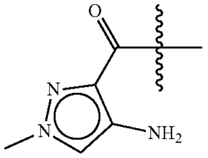,
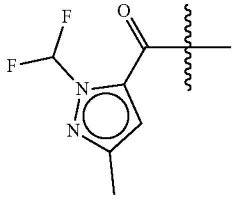, 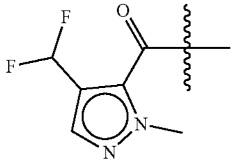,
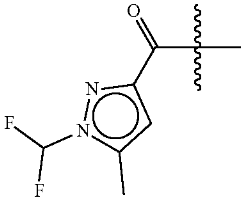, 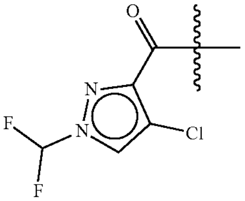,
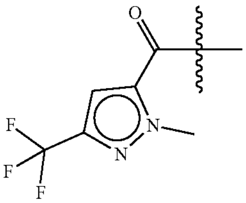, 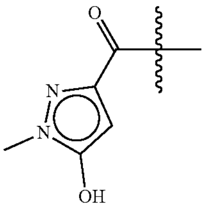,
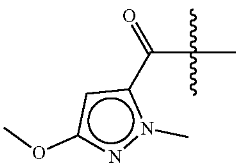, 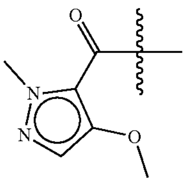,
-continued
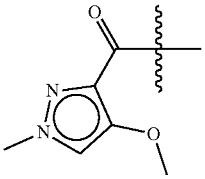, 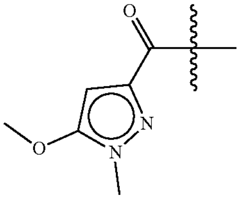,
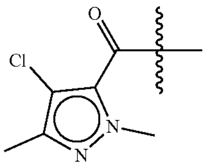, 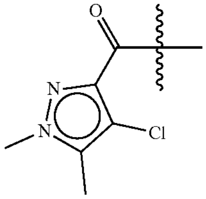,
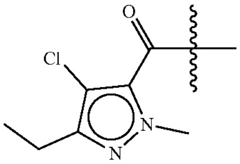, 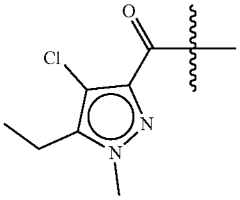,
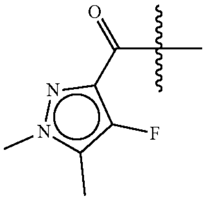, 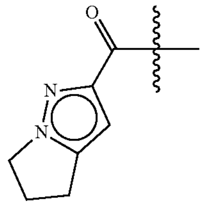,
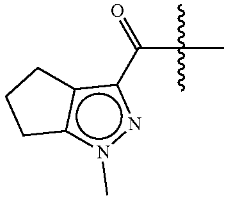, 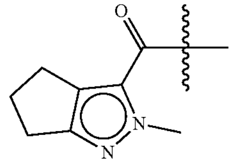,
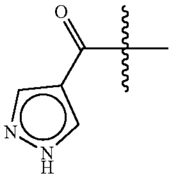, 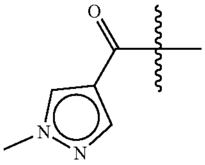,
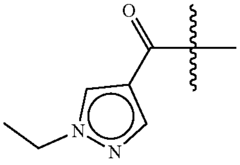, 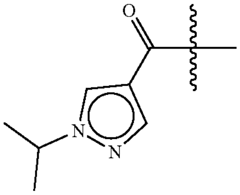,
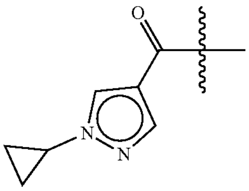, 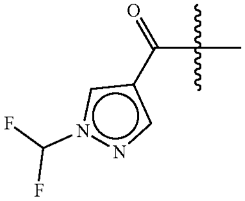, -continued
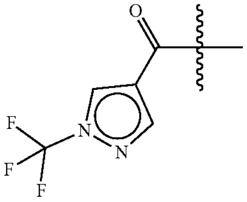,
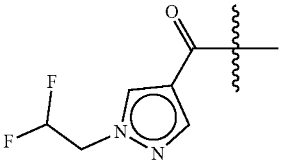,
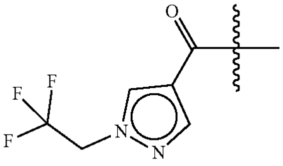,
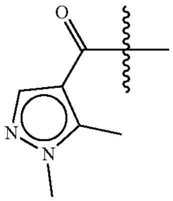,
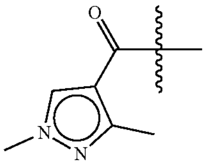,
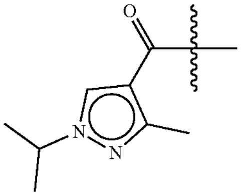,
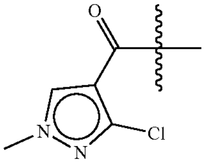,
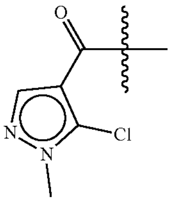,
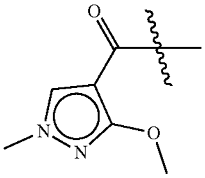,
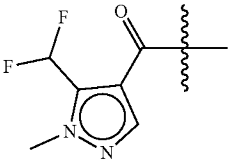,
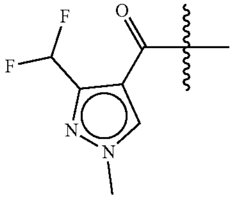,
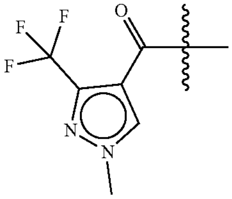,
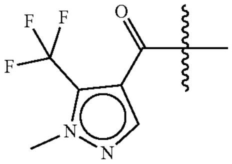,
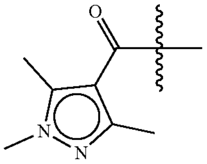,
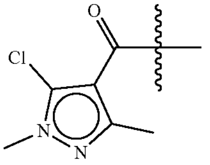,
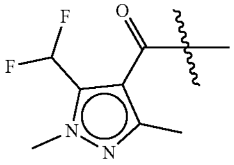,
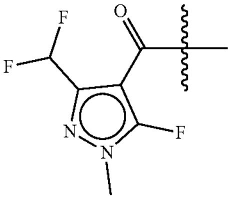,
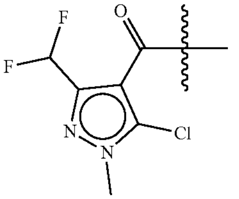,
-continued
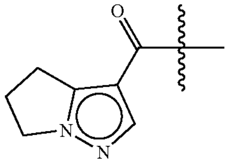,
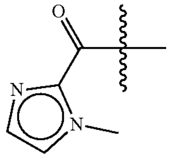,
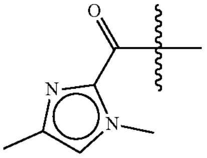,
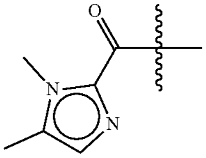,
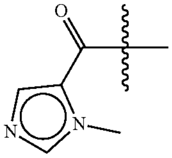,
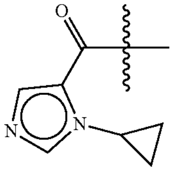,
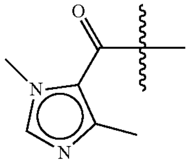,
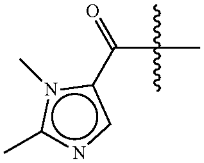,
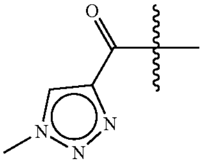,
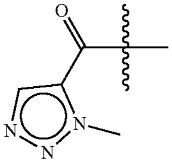,
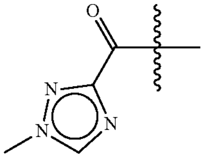,
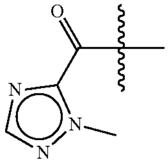,
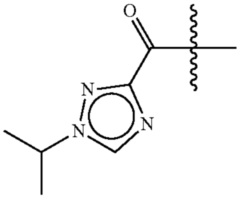,
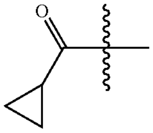,
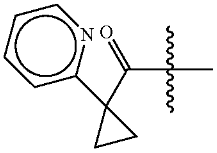,
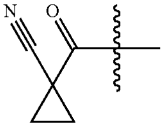,
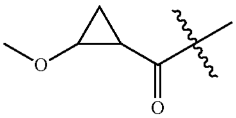,
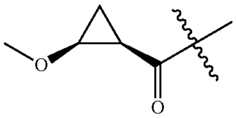,
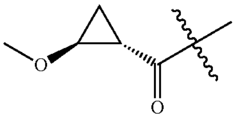, -continued
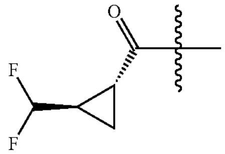, 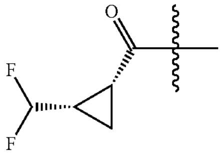,
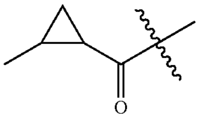, 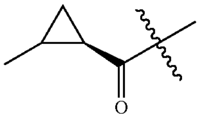,
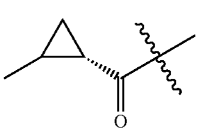, 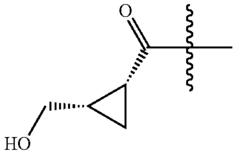,
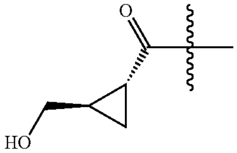, 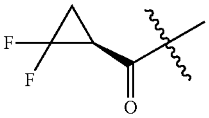,
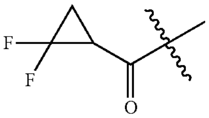, 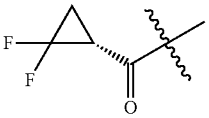,
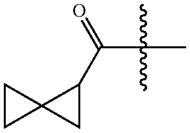, 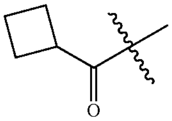,
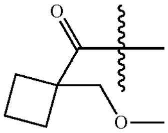, 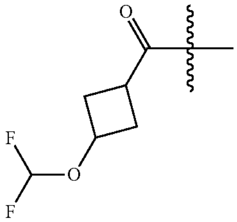,
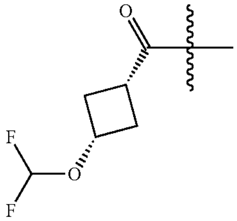, 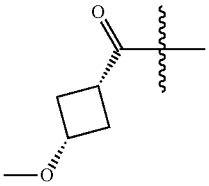,
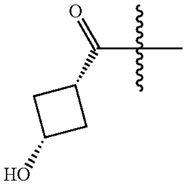, 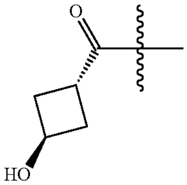,
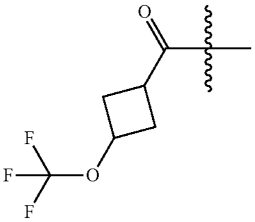, 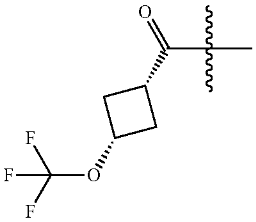,
-continued
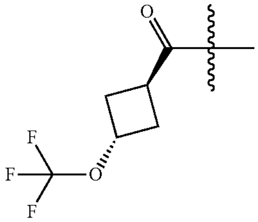, 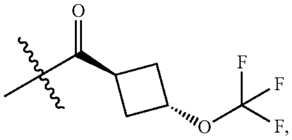
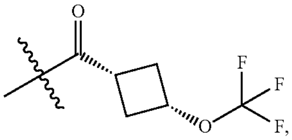 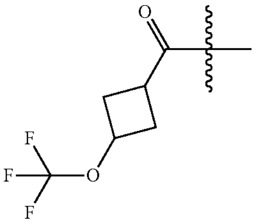,
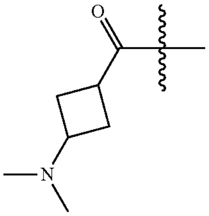, 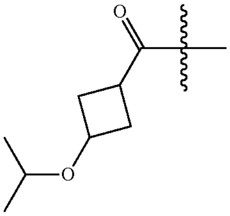,
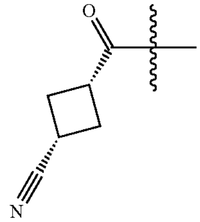, 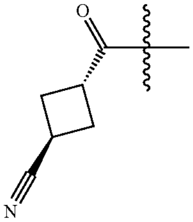,
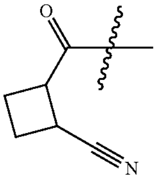, 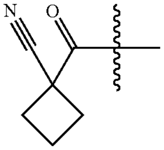, 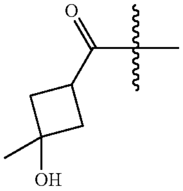,
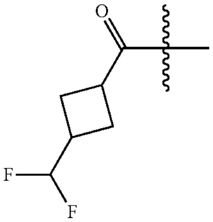, 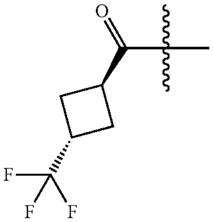,
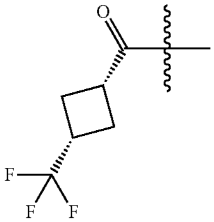, 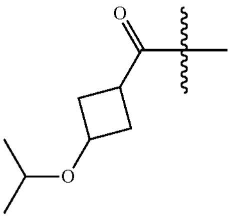,
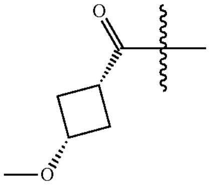, 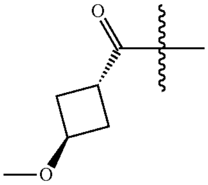, -continued
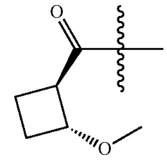,
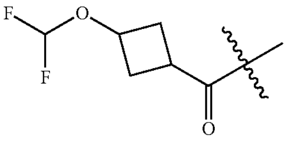,
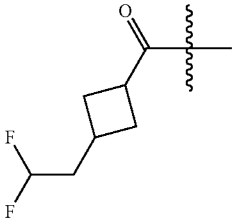,
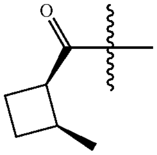,
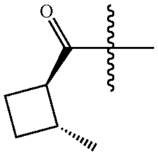,
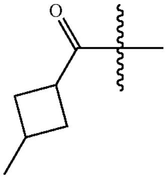,
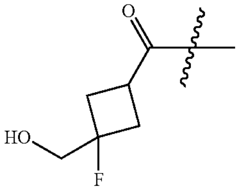,
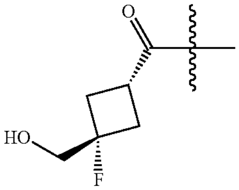,
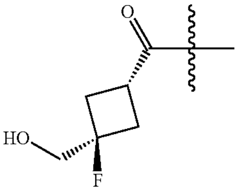,
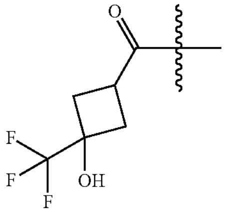,
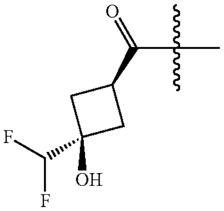,
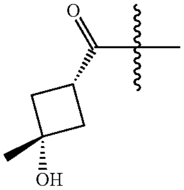,
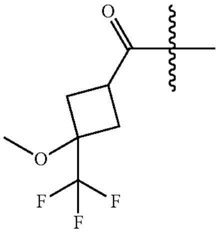,
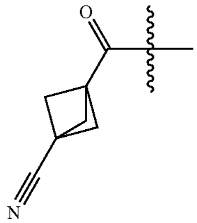,
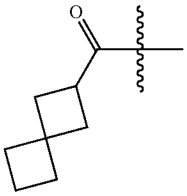,
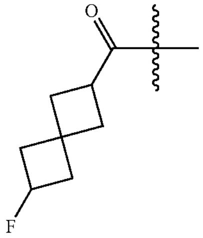,
-continued
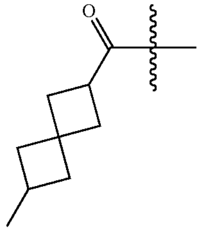,
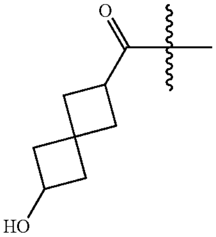,
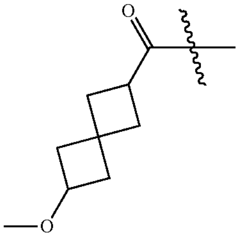,
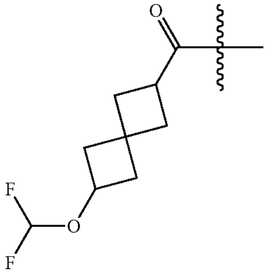,
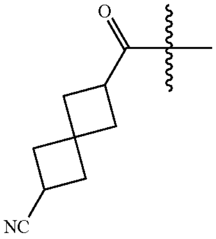,
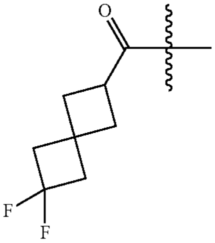,
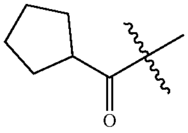,
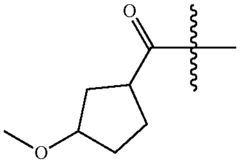,
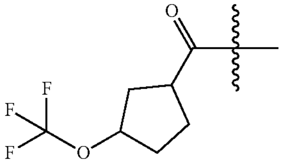,
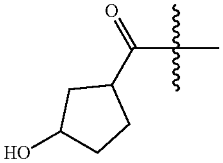,
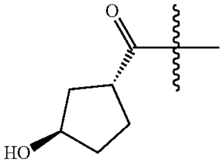,
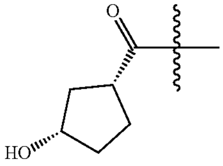,
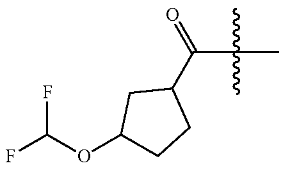,
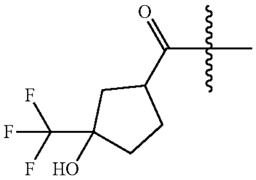,
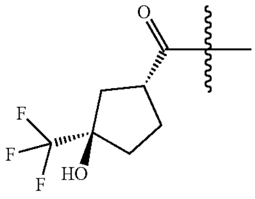,
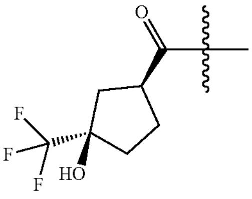, -continued
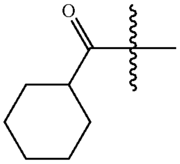,
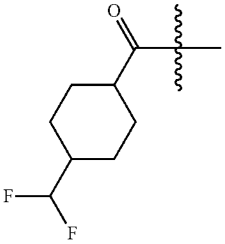,
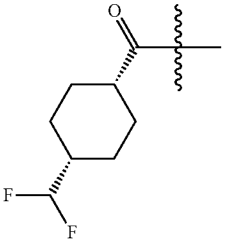,
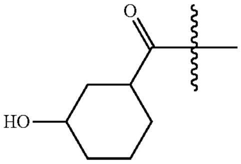,
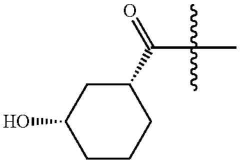,
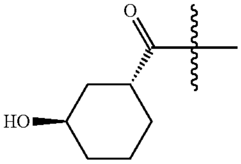,
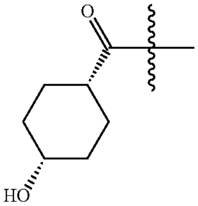,
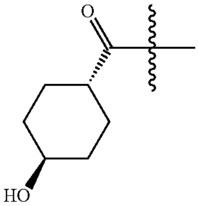,
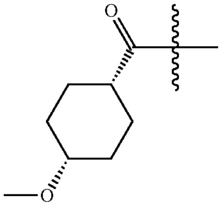,
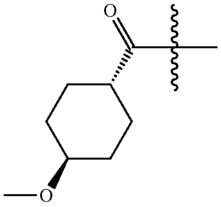,
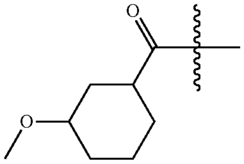,
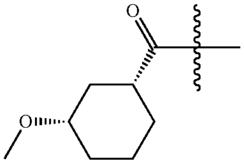,
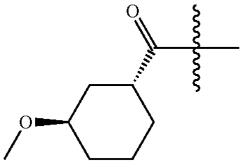,
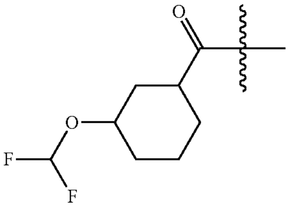,
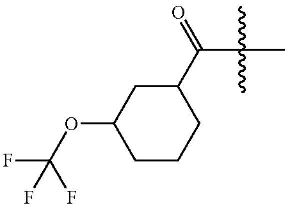,
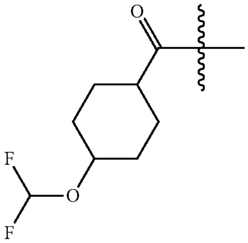,
-continued
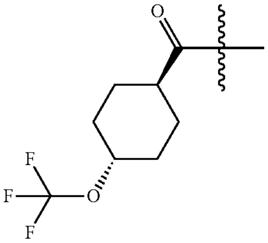.
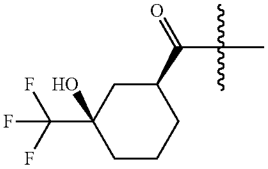,
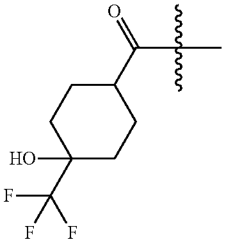,
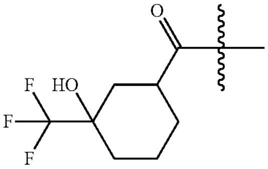,
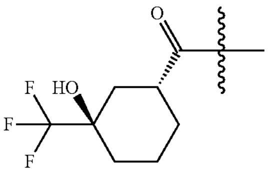,
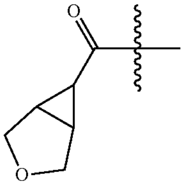,
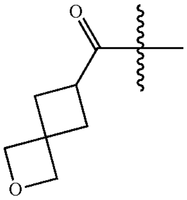,
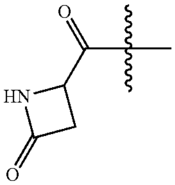,
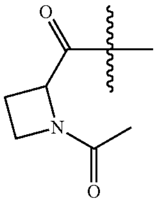,
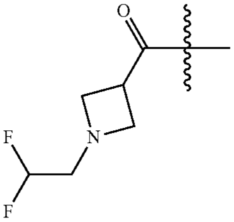,
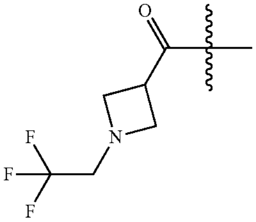,
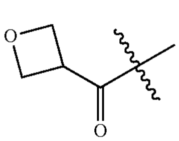,
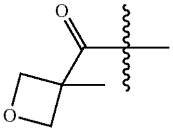,
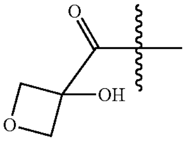,
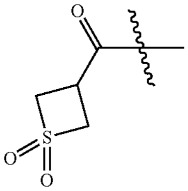,
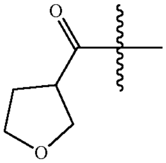,

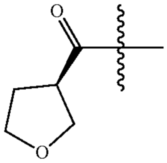 , 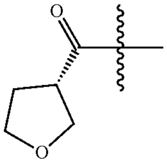 , 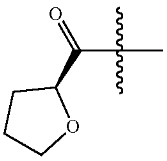 ,
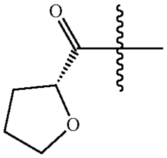 , 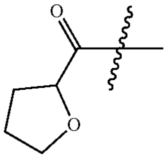 , 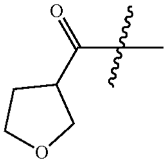 ,
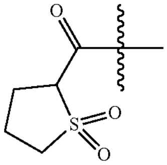 , 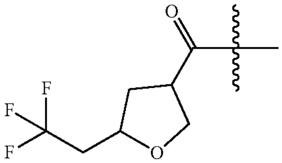 ,
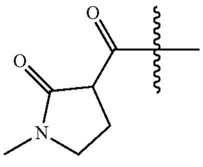 , 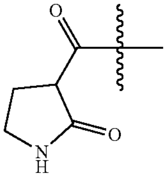 ,
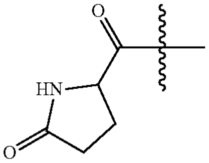 , 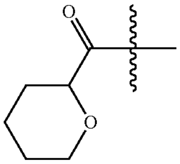 ,
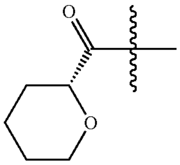 , 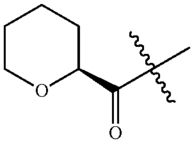 ,
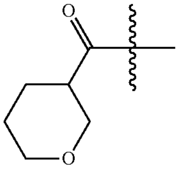 , 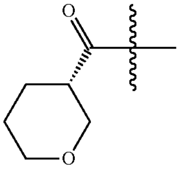 ,
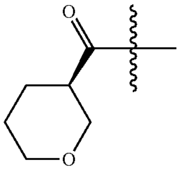 , 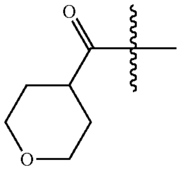 ,
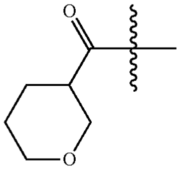 , 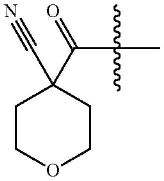 ,
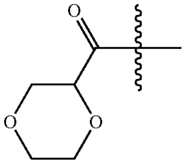 , 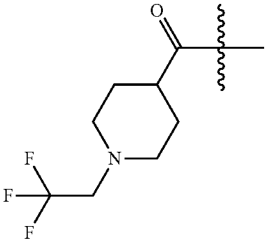 ,
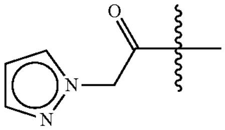 , 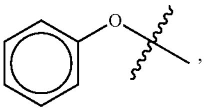 ,
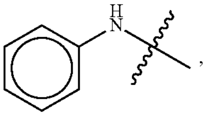 , 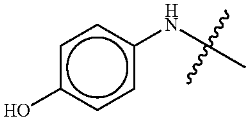 ,
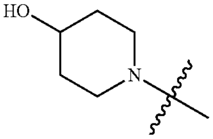 , 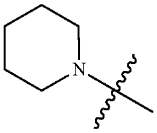 ,
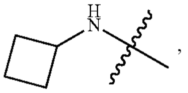 , 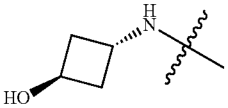 ,
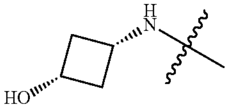 , 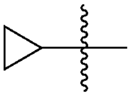 ,
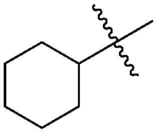 , 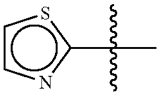 ,
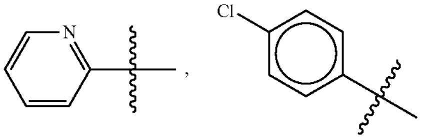 ,
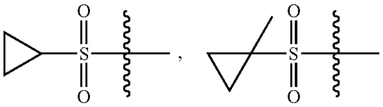 ,
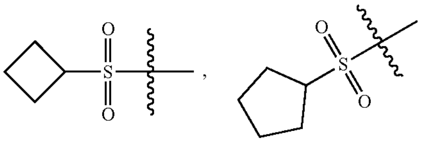 ,
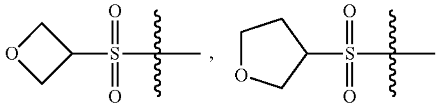 ,
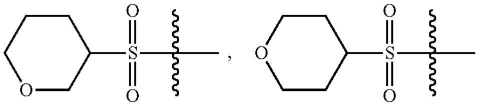 ,
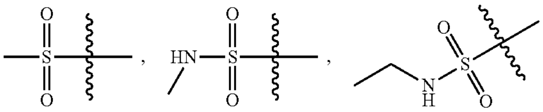 , -continued
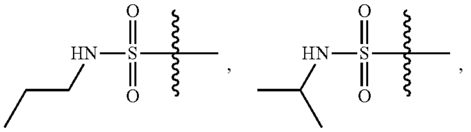
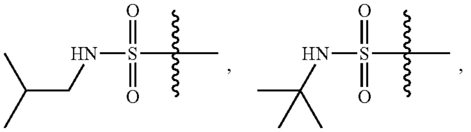
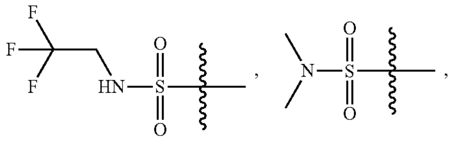
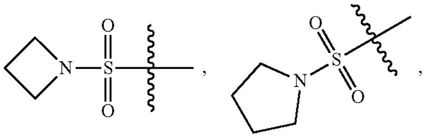
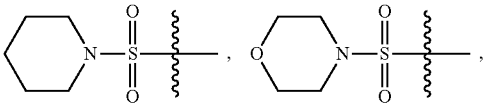
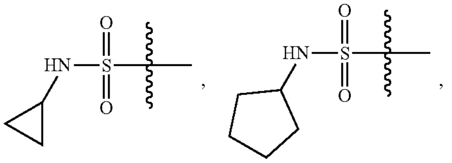
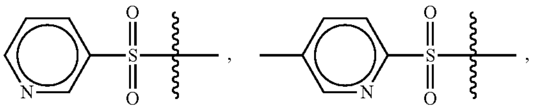
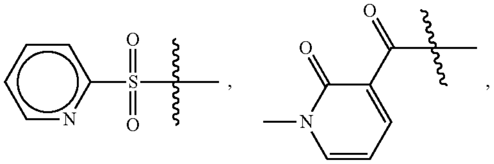
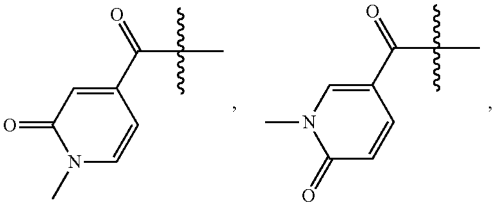
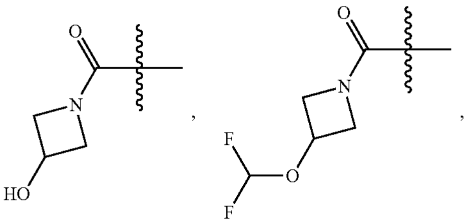
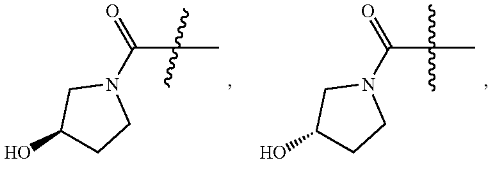
-continued
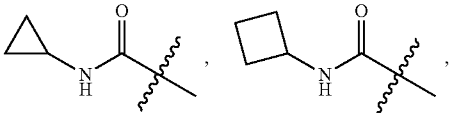
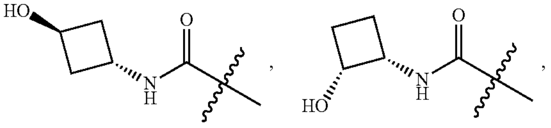
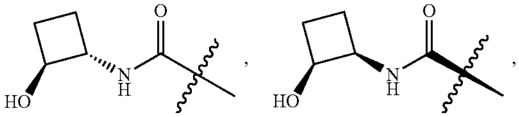
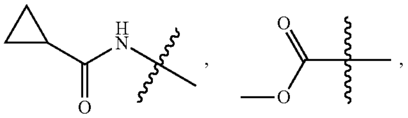
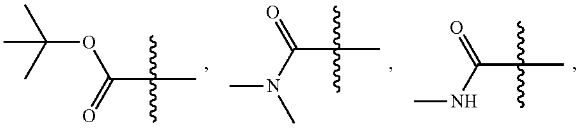
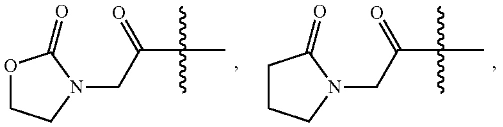
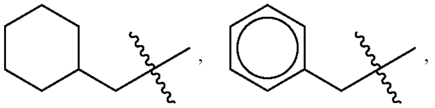
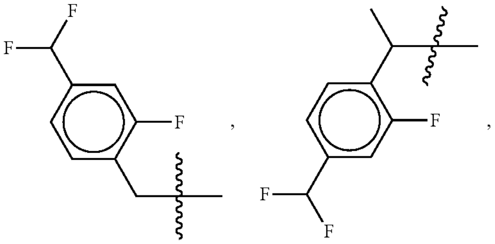
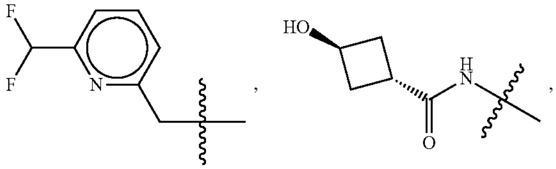
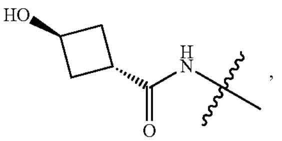
and
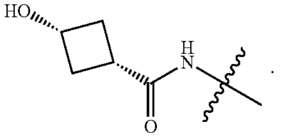
Exemplary Embodiment No. 6. The compound of any one of the preceding Exemplary Embodiments, wherein each $R^{a1}$ independently is:
H, —OH, —$CH_3$, -continued
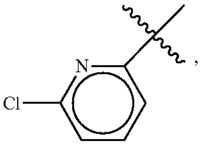
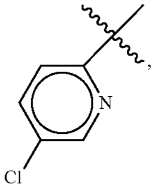
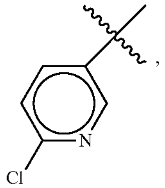
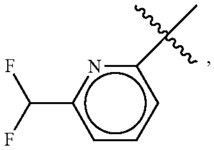
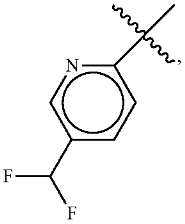
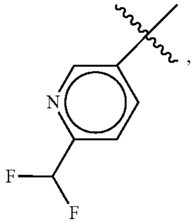
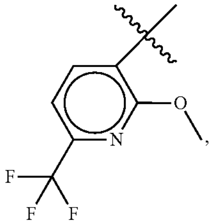
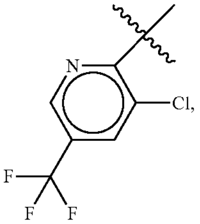
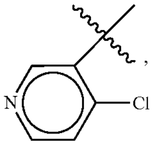
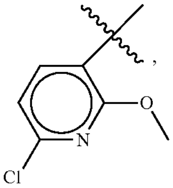
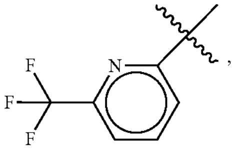
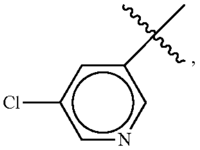
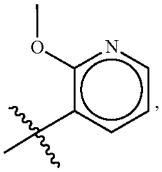
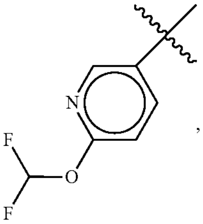
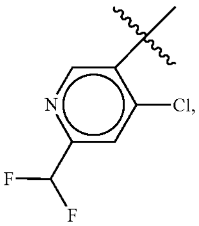
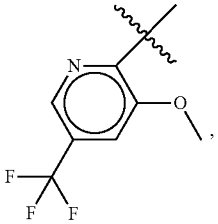
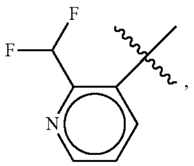
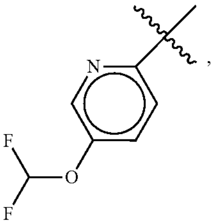
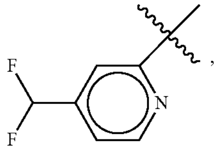
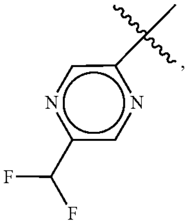
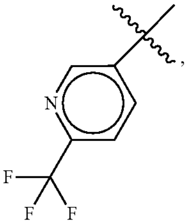
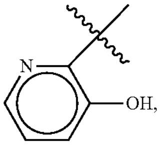
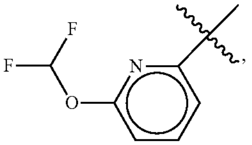
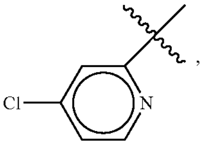
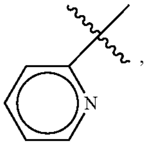
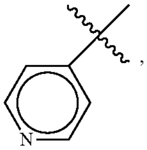
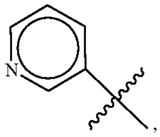
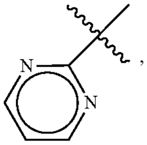
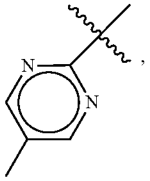
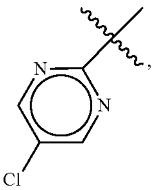
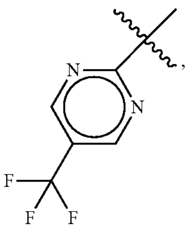

-continued
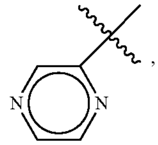
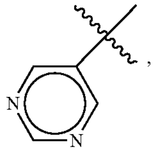
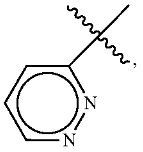
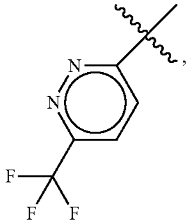
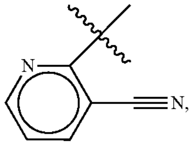
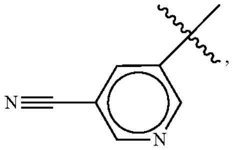
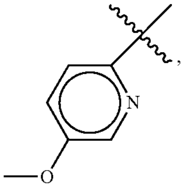
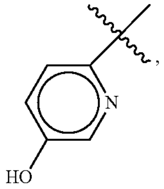
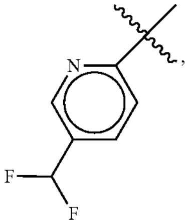
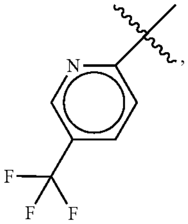
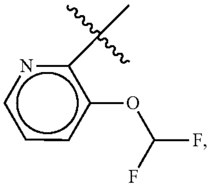
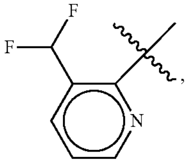
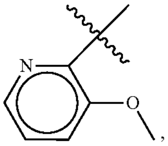
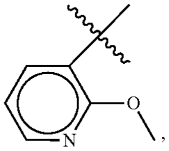
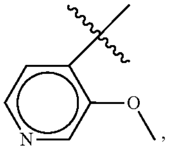
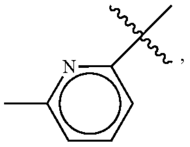
-continued
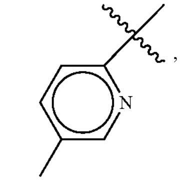
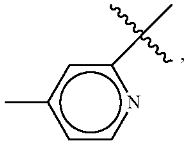
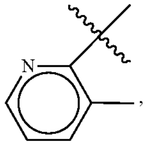
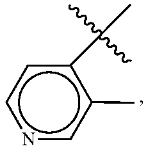
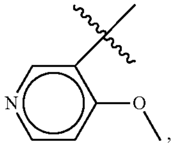
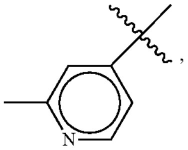
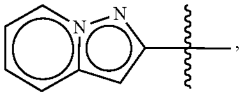
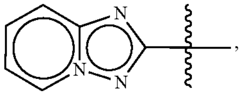
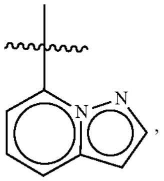
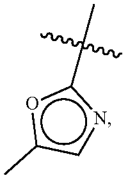
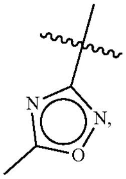
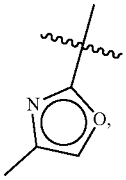
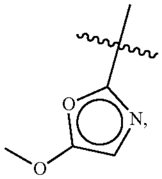
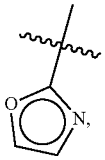
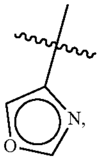
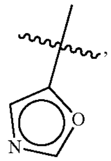
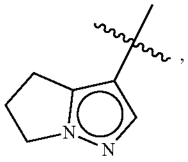

-continued
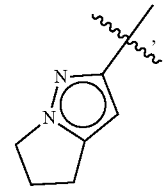
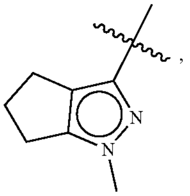
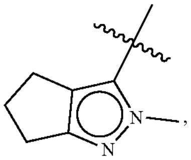
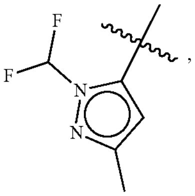
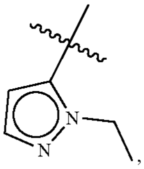
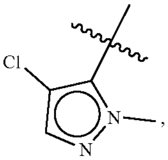
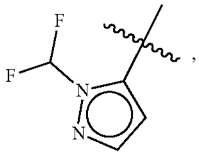
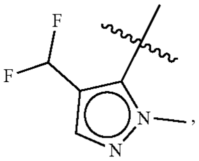
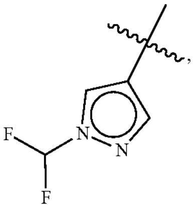
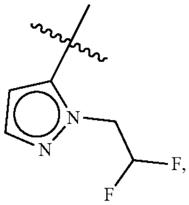
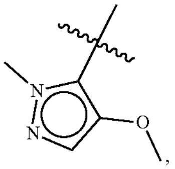
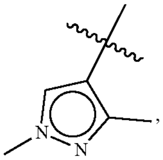
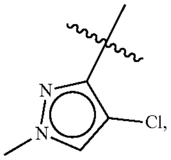
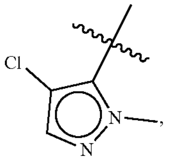
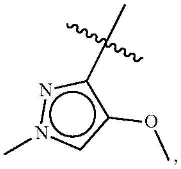
-continued
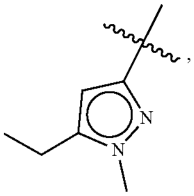
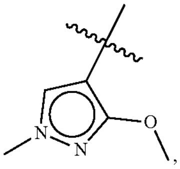
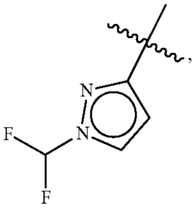
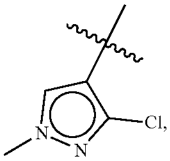
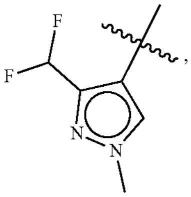
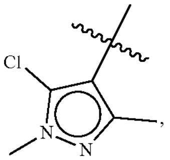
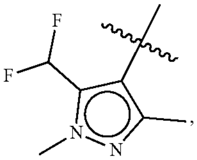
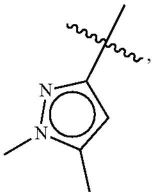
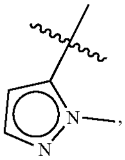
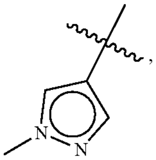
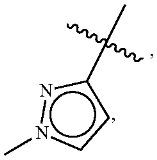
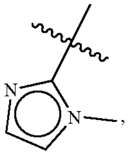

-continued
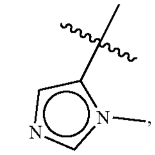
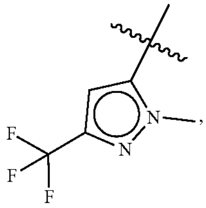
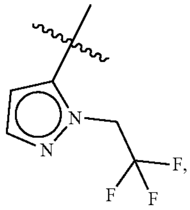
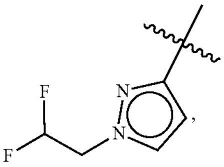
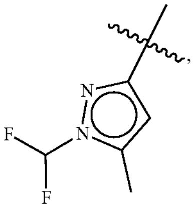
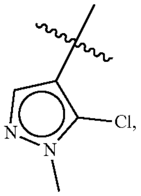
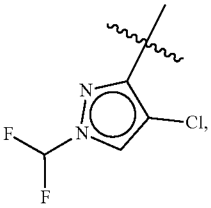
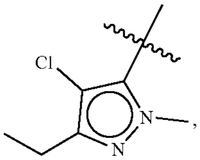
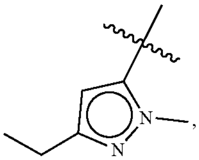
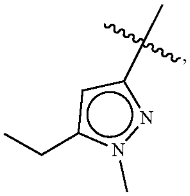
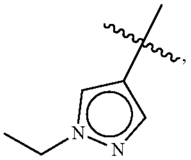
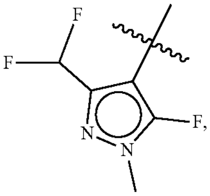
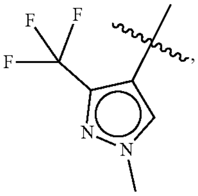
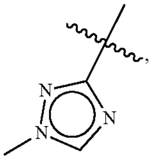
-continued
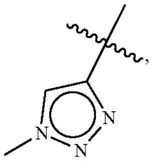
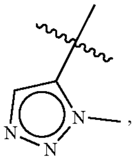
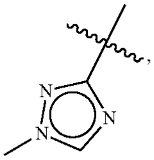
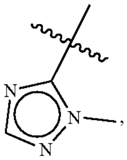
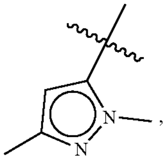
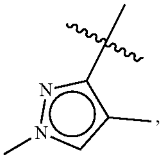
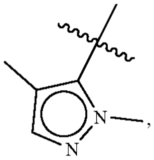
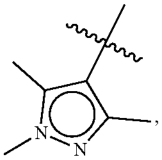
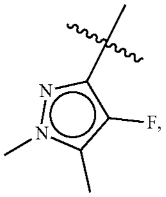
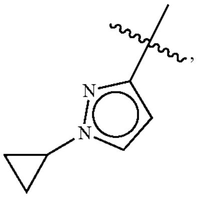
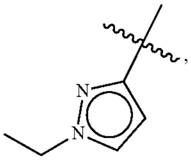
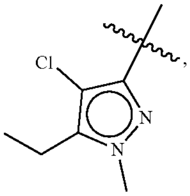
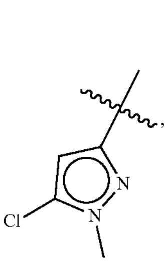
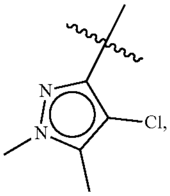

-continued
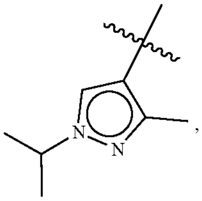
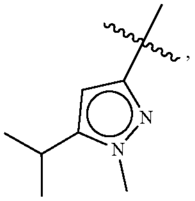
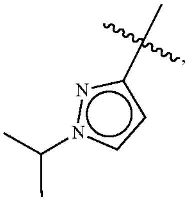
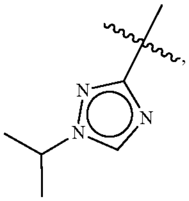
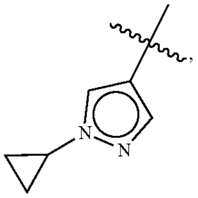
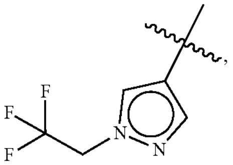
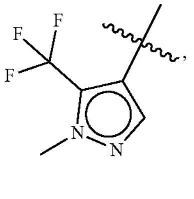
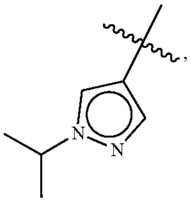
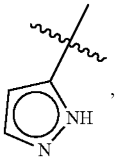
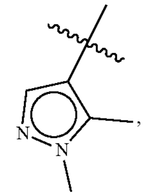
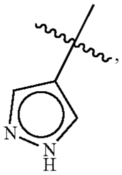
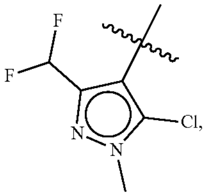
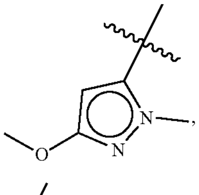
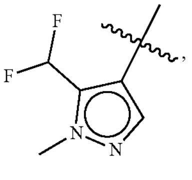
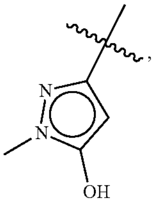
-continued
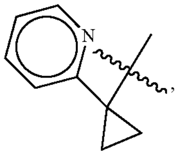
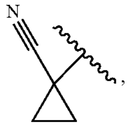
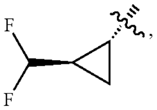
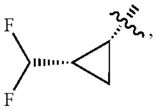
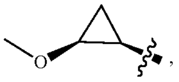
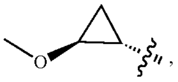
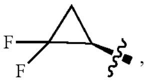
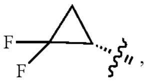
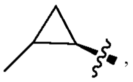
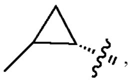
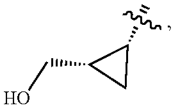
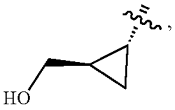
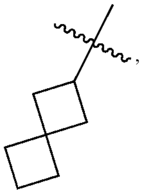
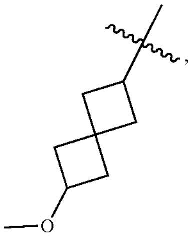
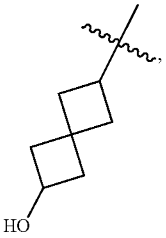
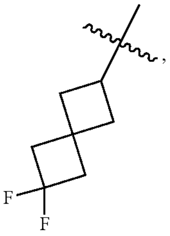
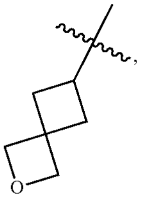
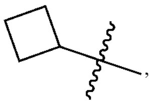
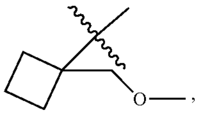
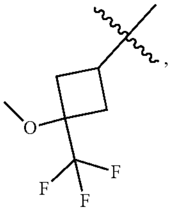

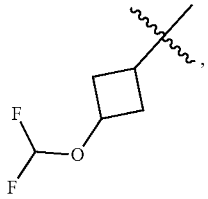,
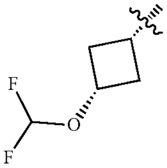,
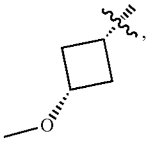,
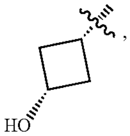,
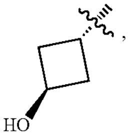,
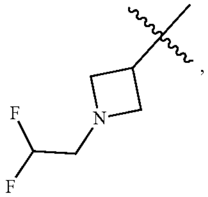,
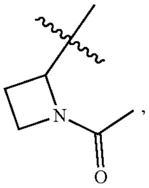,
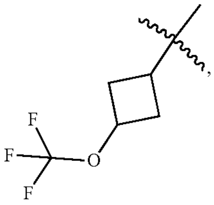,
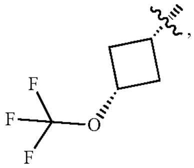,
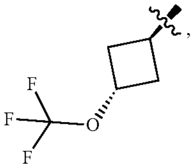,
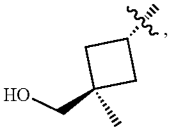,
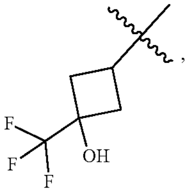,
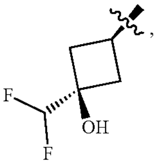,
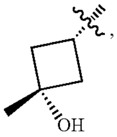,
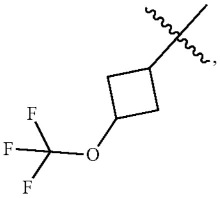,
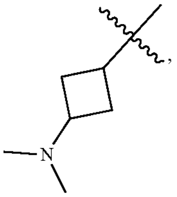,
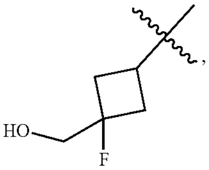,
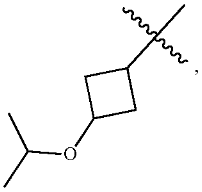,
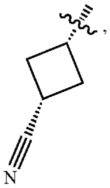,
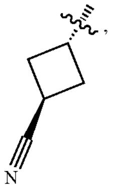,
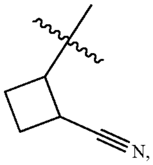,
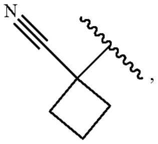,
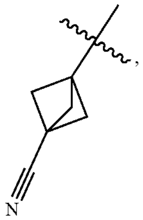,
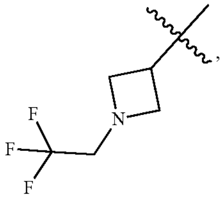,
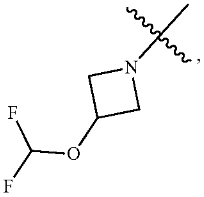,
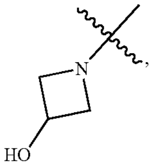,
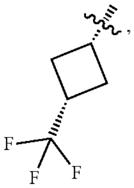,
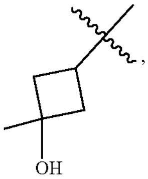,
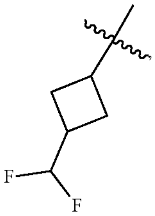,
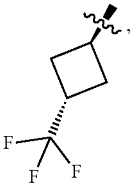,
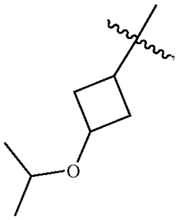,
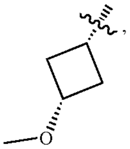,
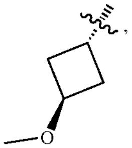,
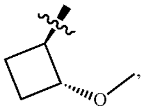, -continued
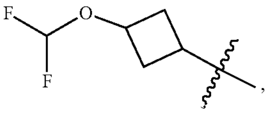
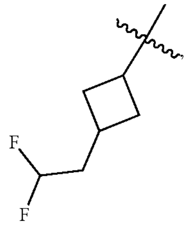
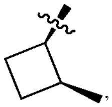
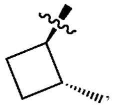
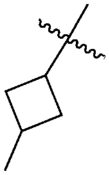
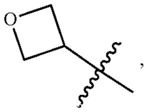
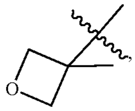
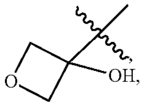
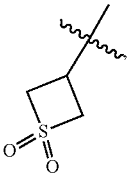
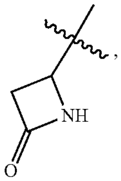
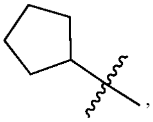
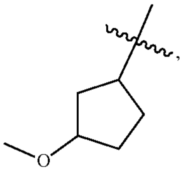
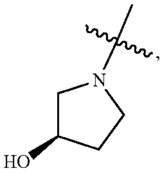
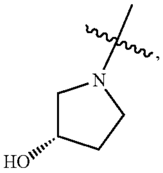
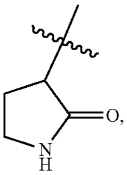
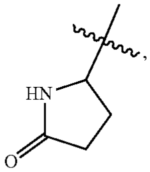
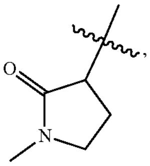
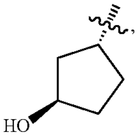
-continued
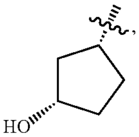
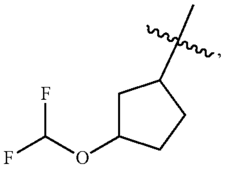
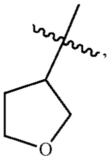
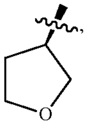
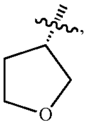
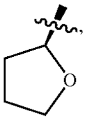
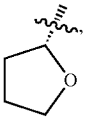
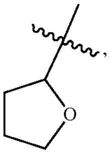
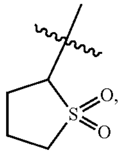
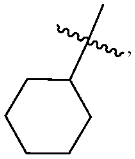
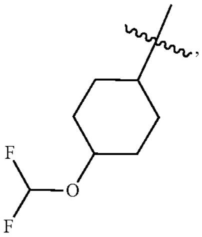
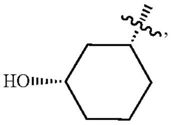
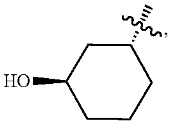
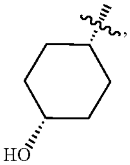
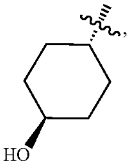
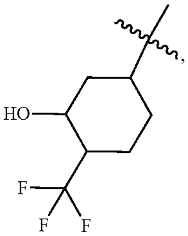
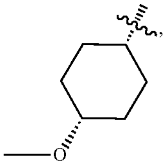
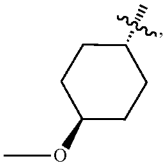
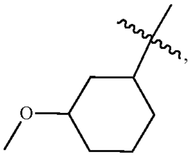

-continued
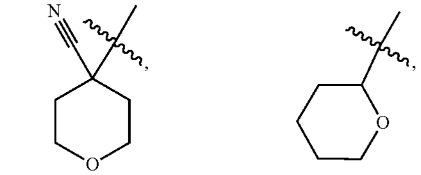
,
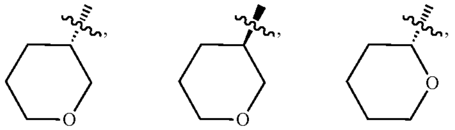
,
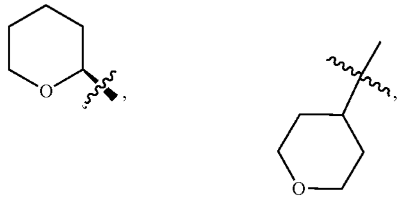
,
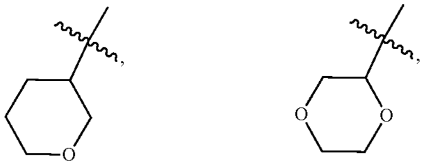
,
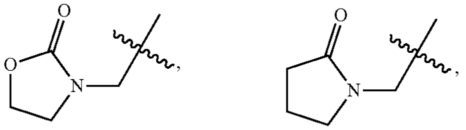
,
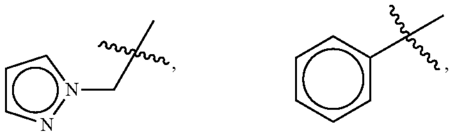
,
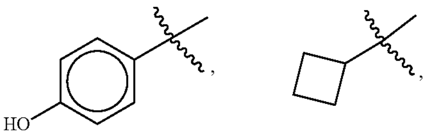
,
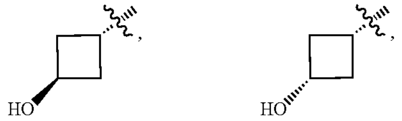
,
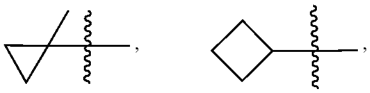
,
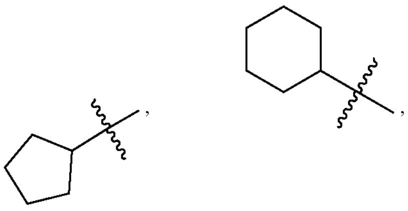
,
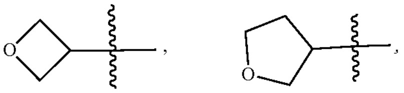
,
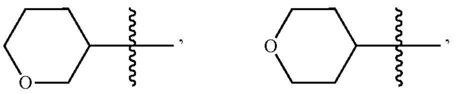
,
-continued
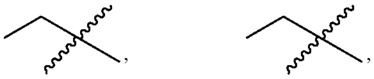
,
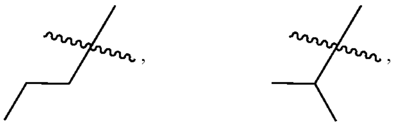
,
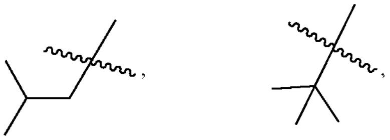
,
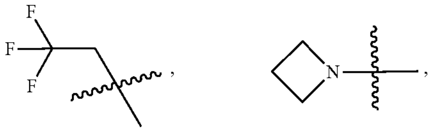
,
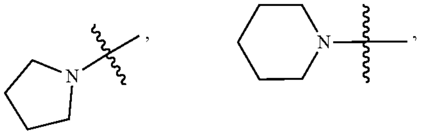
,
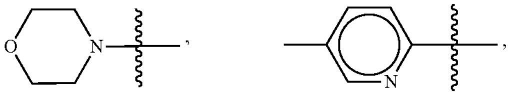
,
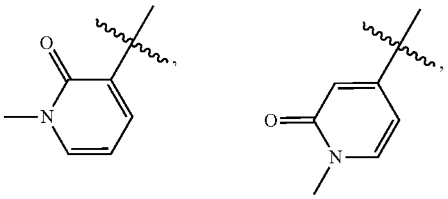
,
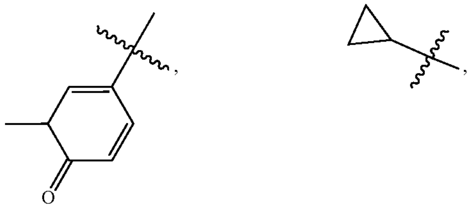
,
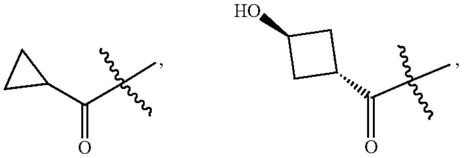
,
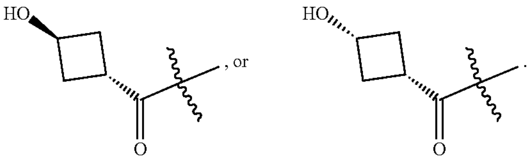
, or .
Exemplary Embodiment No. 7. The compound of any one of the preceding Exemplary Embodiments, wherein each $R^{a2}$ independently is oxo, —$CH_3$, —$CH_2CH_3$, —$CH(CH_3)_2$, —Cl, —F, —CN, —$CHF_2$, —$OCH_3$, —$CF_3$, —$OCHF_2$, —OH, —$CH_2CHF_2$, —$CH_2CF_3$, —$CH_2OH$, —$CH_2OCH_3$, —$OCF_3$, —$N(CH_3)_2$, —$OCH(CH_3)_2$,

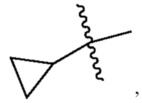
,
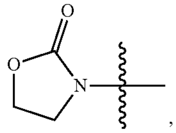
,
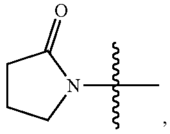
, or
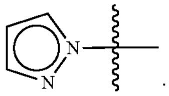
.
Exemplary Embodiment No. 8. The compound of any one of the preceding Exemplary Embodiments, wherein $R^3$ is:
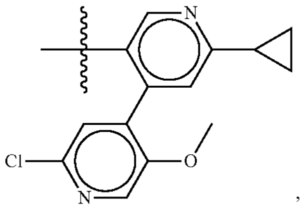
,
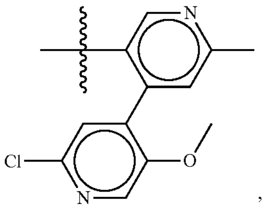
,
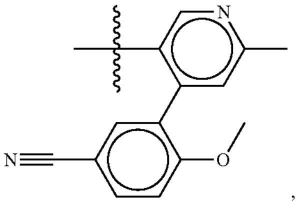
,
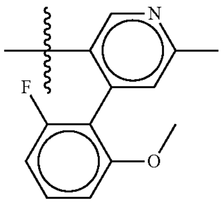
,
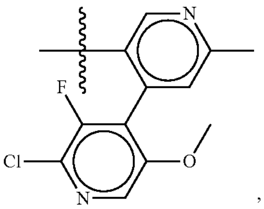
,
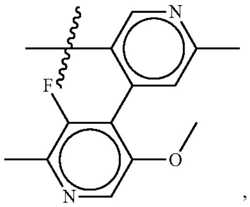
,
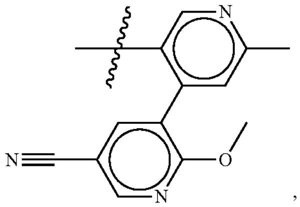
,
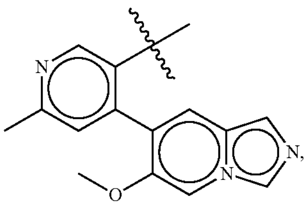
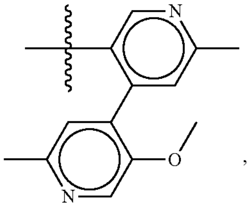
,
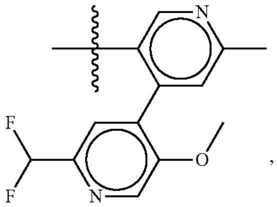
,
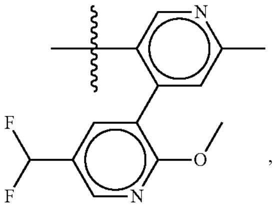
,
-continued
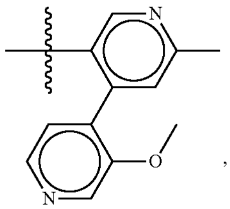
,
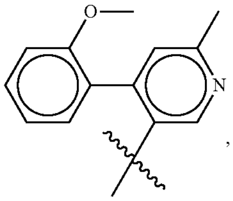
,
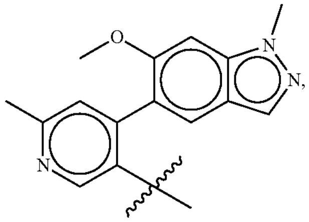
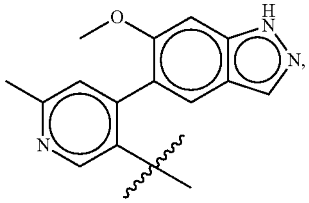
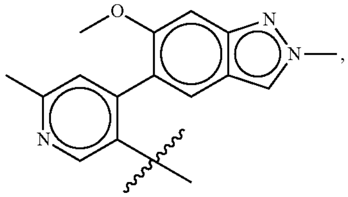
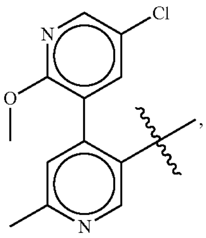
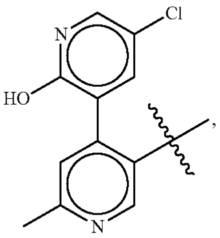
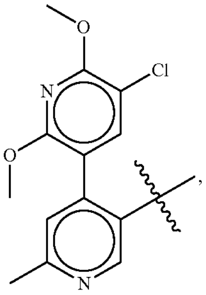
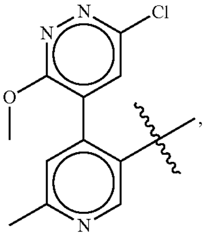
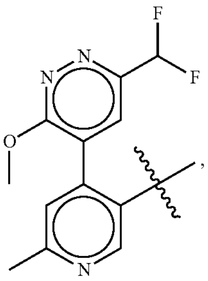
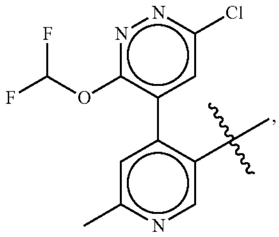

-continued
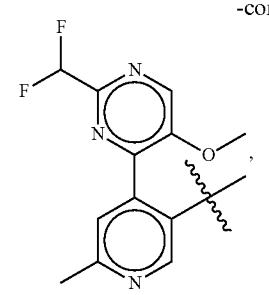
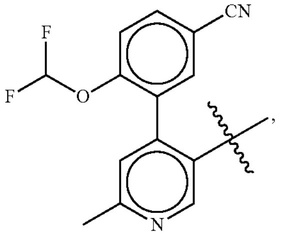
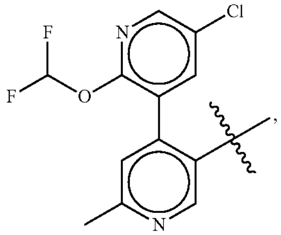
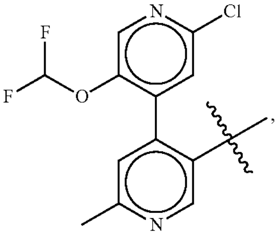
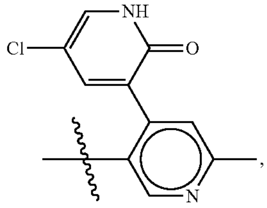
or
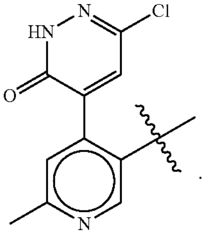
Exemplary Embodiment No. 9. The compound of any one of the preceding Exemplary Embodiments, wherein $R^{3a}$ is —$CH_3$, cyclopropyl,
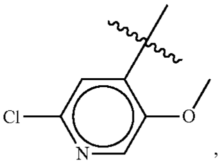
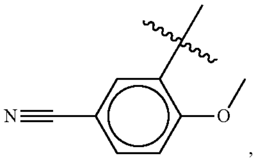
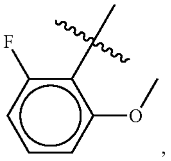
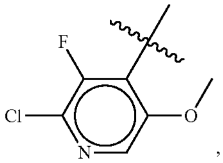
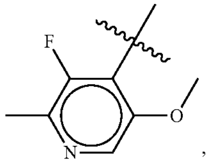
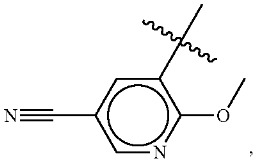
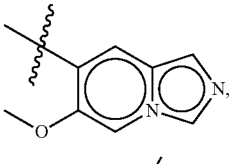
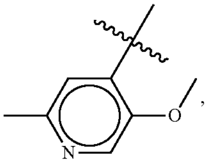
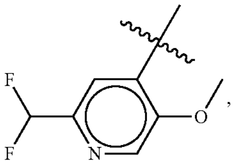
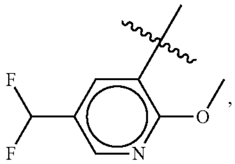
-continued
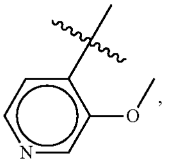
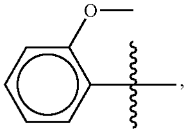
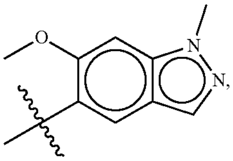
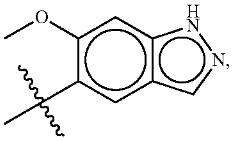
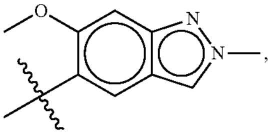
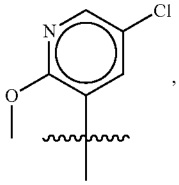
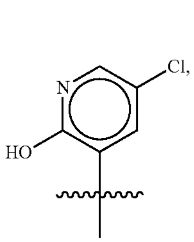
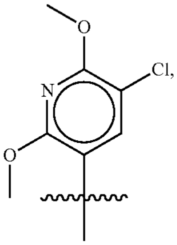
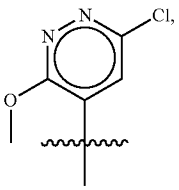
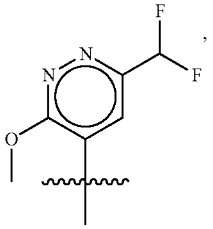
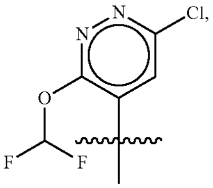
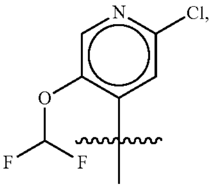
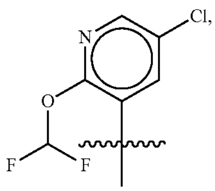
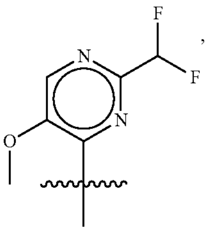
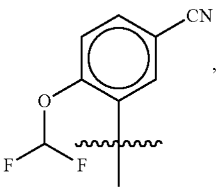
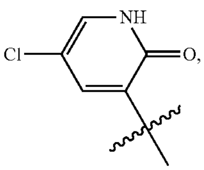
or -continued

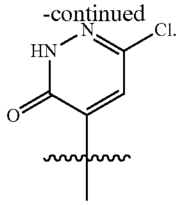

Exemplary Embodiment No. 10. The compound of any one of the preceding Exemplary Embodiments, wherein each $R^{3a1}$ independently is oxo, methyl, —$CF_2H$ cyano, —F, —Cl, —OH, —$OCF_2H$, or —$OCH_3$.

Exemplary Embodiment No. 11. The compound of any one of Exemplary Embodiment Nos. 1-4, wherein the compound is of Formula (I-A):

(I-A)

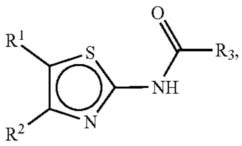

or a pharmaceutically acceptable salt, solvate, clathrate, hydrate, stereoisomer, or tautomer thereof.

Exemplary Embodiment No. 12. The compound of any one of Exemplary Embodiment Nos. 1-4, wherein the compound is of Formula (I-B), (I-C), (I-D), or (I-E):

(I-B)

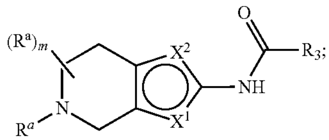

(I-C)

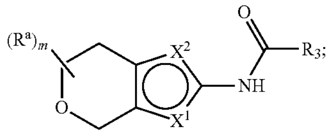

(I-D)

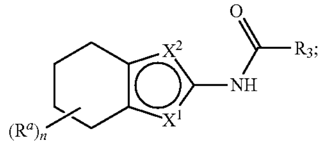

or (I-E)

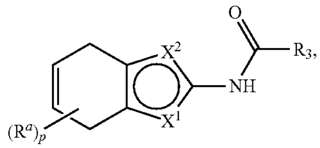

or a pharmaceutically acceptable salt, solvate, clathrate, hydrate, stereoisomer, or tautomer thereof, wherein m is 0 to 6; n is 0 to 8; and p is 0 to 6.

Exemplary Embodiment No. 13. The compound of any one of Exemplary Embodiment Nos. 1-4, wherein the compound is of Formula (I-F) or (I-Fa):

(I-F)

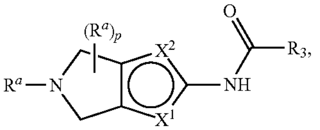

or (I-Fa)

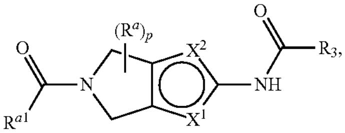

or a pharmaceutically acceptable salt, solvate, clathrate, hydrate, stereoisomer, or tautomer thereof, wherein p is 0 to 4.

Exemplary Embodiment No. 14. The compound of any one of Exemplary Embodiment Nos. 1-4, wherein the compound is of Formula (I-Fb), (I-Fb'), (I-Fc), (I-Fc'), (I-Fd), or (I-Fd'):

(I-Fb)

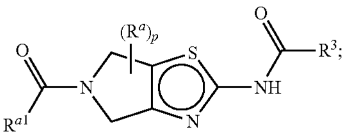

(I-Fb')

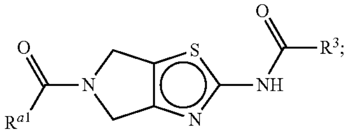

(I-Fc)

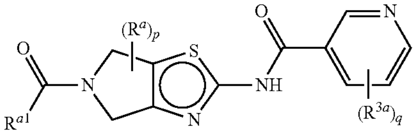

(I-Fc')

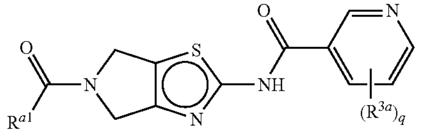

(I-Fd)

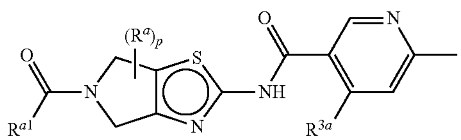

; or (I-Fd')

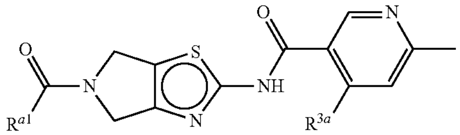

, or a pharmaceutically acceptable salt, solvate, clathrate, hydrate, stereoisomer, or tautomer thereof, wherein p is 0 to 4 and q is 0 to 4.

Exemplary Embodiment No. 15. The compound of any one of Exemplary Embodiment Nos. 1-4, wherein the compound is of Formula (I-G), (I-Ga), or (I-Ga'):

(I-G)

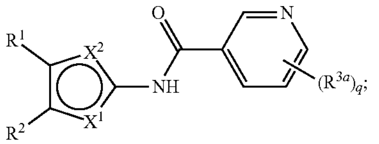

(I-Ga)

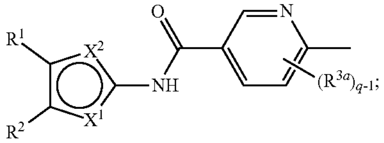

or (I-Ga')

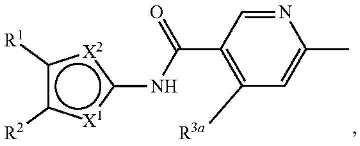

, or a pharmaceutically acceptable salt, solvate, clathrate, hydrate, stereoisomer, or tautomer thereof, wherein q is 1 to 4.

Exemplary Embodiment No. 16. The compound of any one of the preceding Exemplary Embodiments, wherein the compound is selected from Compound Nos. 7, 9, 10, 15, 18, 379, 387, 389, 400, 404, 415, 425, 450, 508, 548, 584, 585, 586, 592, 594, 2, 5, 14, 49, 146, 652, 653, 655, 691, 793, 820, 828, 908, 922, 951, 952, 964, 980, 987, 990, 996, 1003, 1005, 1010, 1013, 1014, 1016, 1019, 1023, 1029, 1032, 1039, 1041, and 1046, or a pharmaceutically acceptable salt thereof.

Exemplary Embodiment No. 17. The compound of any one of the preceding Exemplary Embodiments, wherein the compound is selected from a compound described in Table 1, Table 2, or Table 3, or a pharmaceutically acceptable salt thereof.

Exemplary Embodiment No. 18. A compound obtainable by, or obtained by, a method described herein; optionally, the method comprises one or more steps described in Schemes 1-7.

Exemplary Embodiment No. 19. A pharmaceutical composition comprising the compound of any one of the preceding Exemplary Embodiments or a pharmaceutically acceptable salt thereof, and a pharmaceutically acceptable diluent or carrier.

Exemplary Embodiment No. 20. The pharmaceutical composition of Exemplary Embodiment No. 19, wherein the compound is selected from a compound described in Table 1, Table 2, or Table 3.

Exemplary Embodiment No. 21. A method of modulating DNA polymerase Θ activity, comprising contacting a cell with a compound of any one of the preceding Exemplary Embodiments.

Exemplary Embodiment No. 22. A method of treating or preventing a disease or disorder in a subject in need thereof, comprising administering to the subject a compound of any one of Exemplary Embodiment Nos. 1-18 or pharmaceutical composition of Exemplary Embodiment No. 19 or Exemplary Embodiment No. 20.

Exemplary Embodiment No. 23. The compound of any one of Exemplary Embodiment Nos. 1-18 or pharmaceutical composition of Exemplary Embodiment No. 19 or Exemplary Embodiment No. 20 for use in modulating DNA polymerase Θ activity.

Exemplary Embodiment No. 24. The compound of any one of Exemplary Embodiment Nos. 1-18 or pharmaceutical composition of Exemplary Embodiment No. 19 or Exemplary Embodiment No. 20 for use in treating or preventing a disease or disorder.

Exemplary Embodiment No. 25. Use of the compound of any one of Exemplary Embodiment Nos. 1-18 in the manufacture of a medicament for modulating DNA polymerase Θ activity.

Exemplary Embodiment No. 26. Use of the compound of any one of Exemplary Embodiment Nos. 1-18 in the manufacture of a medicament for treating or preventing a disease or disorder.

Exemplary Embodiment No. 27. The method, compound, pharmaceutical composition, or use of any one of Exemplary Embodiment Nos. 21-26, wherein the disease or disorder is associated with an implicated DNA polymerase Θ activity.

Exemplary Embodiment No. 28. The method, compound, pharmaceutical composition, or use of any one of Exemplary Embodiment Nos. 21-27, wherein the disease or disorder is cancer.

EXAMPLES

For exemplary purpose, neutral compounds of Formula (I) are synthesized and tested in the examples. It is understood that the neutral compounds of Formula (I) may be converted to the corresponding pharmaceutically acceptable salts of the compounds using routine techniques in the art (e.g., by saponification of an ester to the carboxylic acid salt, or by hydrolyzing an amide to form a corresponding carboxylic acid and then converting the carboxylic acid to a carboxylic acid salt).

Abbreviations

ACN Acetonitrile
AcOH Acetic Acid
BAST Bis(2-methoxyethyl)aminosulfur trifluoride
Boc tert-Butoxycarbonyl
$(Boc)_2O$ Di-tert-butyl dicarbonate
DAST Diethylaminosulfur trifluoride
DCE 1,2-Dichloroethane
DCM Dichloromethane
DFMS Zinc difluoromethanesulfinate
DIAD Diisopropyl azodicarboxylate
DIPEA Diisopropylethylamine
DMAP 4-Dimethylaminopyridine
DMF Dimethylformamide
DMP Dess-Martin periodinane
DMSO Dimethyl sulfoxide
dppb 1,4-Bis(diphenylphosphino)butane
dppf 1,1'-bis(diphenylphosphino)ferrocene
dtbpf 1,1'-bis(di-tert-butylphosphino)ferrocene
EtOAc Ethyl acetate
EtOH Ethanol
g Gram
h Hours
HATU Hexafluorophosphate azabenzotriazole tetramethyl uronium
HOBt 1-Hydroxybenzotriazole hydrate
HPLC High-performance liquid chromatography
LCMS Liquid chromatography-mass spectrometry
M Molar
m/z Mass to charge ratio
MeI Iodomethane MeOH Methanol
mg Milligram
MHz Megahertz
min Minutes
mL Milliliter
mmol Millimolar
MPa Megapascal
MsCl Methanesulfonyl chloride
NaHMDS Sodium bis(trimethylsilyl)amide
NBS N-Bromosuccinimide
NMI 1-methylimidazole
NMP 1-Methyl-2-pyrrolidone
NMR Nuclear magnetic resonance
Pet ether Petroleum ether
$Pin_2B_2$ Bis(pinacolato)diboron
$PPh_3$ Triphenylphosphine
$(PPh_3)_4$ Tetrakis(triphenylphosphine)
Prep Preparative
PyBop Benzotriazol-1-yloxytripyrrolidinophosphonium hexafluorophosphate
RT Room temperature
SFC Supercritical fluid chromatography
$SOCl_2$ Thionyl chloride
T3P Propanephosphonic acid anhydride
TCFH Chloro-N,N,N',N'-tetramethylformamidinium hexafluorophosphate
TEA Triethylamine
TFA Trifiluoroacetic acid
THF Tetrahydrofuran
TLC Thin layer chromatography
TMSCl Chlorotrimethylsilane
TMSOTf Trimethylsilyl trifluoromethanesulfonate Prep-HPLC conditions (unless otherwise noted): SHIMADZU Preparative HPLC System—including a LC-20AP Pump, a SPD-20A Detector and Labsolutions (version 5.90) software. Column: Agilent 10, Prep-C18, 250×21.2 mm. Solvent/Gradient: 5-80% Acetonitrile in water containing 0.1% HCOOH. Flow Rate: 20 mL/min.

Synthesis of Intermediates

Intermediate 1: 4-(2-Methoxyphenyl)-6-methylnicotinic acid

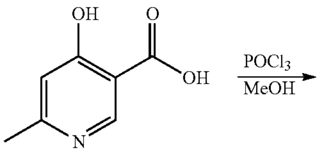

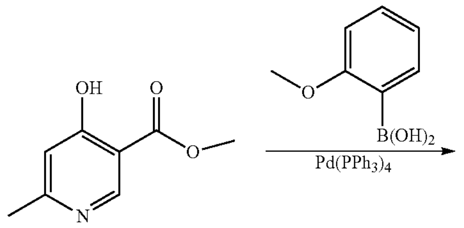

-continued

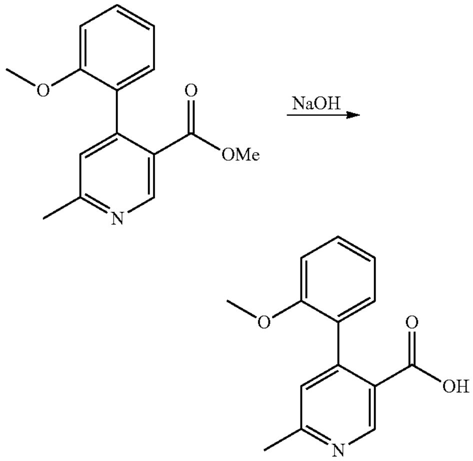

Step 1: A mixture of 4-hydroxy-6-methylnicotinic acid (10.0 g, 65.0 mmol) and $POCl_3$ (40 mL) was heated at reflux for 2 h then concentrated under reduced pressure. The residue was cooled to 0° C. and MeOH (40 mL) was added slowly dropwise. The mixture was allowed to warm to room temperature and stirred overnight. The mixture was adjusted to pH 7 with solid $Na_2CO_3$, diluted with water (500 mL) and extracted with DCM (3×300 mL). The combined organic layers were washed with water (500 mL), brine (500 mL), dried over $Na_2SO_4$, filtered and concentrated under reduced pressure. The residue was purified by silica gel chromatography (Gradient: 6.6-12.5% Petroleum ether in EtOAc) to give methyl 4-chloro-6-methylnicotinate as a colorless oil (10.4 g, 85%). LCMS: m/z=186 $[M+H]^+$, $^1H$ NMR (400 MHz, DMSO-$d_6$) δ 8.84 (s, 1H), 7.57 (s, 1H), 3.87 (s, 3H), 2.52 (s, 3H).

Step 2: To a solution of methyl 4-chloro-6-methylnicotinate (7.00 g, 37.7 mmol) in dry 1,4-dioxane (80 mL) was added (2-methoxyphenyl)boronic acid (5.73 g, 37.7 mmol), $Pd(PPh_3)_4$ (2.18 g, 1.88 mmol) and $Cs_2CO_3$ (36.9 g, 113 mmol) and the mixture was heated at 85° C. overnight. The mixture was diluted with water (100 mL), extracted with EtOAc (3×300 mL) and the combined organic layers washed with water (100 mL), brine (100 mL), dried over $Na_2SO_4$, filtered and concentrated under reduced pressure. The residue was purified by silica gel chromatography (Gradient: 6.6-25% Petroleum ether in EtOAc) to give methyl 4-(2-methoxyphenyl)-6-methylnicotinate (8.0 g, 82%) as a yellow oil. LCMS: m/z=258 $[M+H]^+$, $^1H$ NMR (400 MHz, DMSO-$d_6$) δ 8.73 (s, 1H), 7.40 (td, J=7.8, 1.8 Hz, 1H), 7.30-7.24 (m, 2H), 7.05 (t, J=8.0 Hz, 2H), 3.65 (s, 3H), 3.62 (s, 3H), 2.55 (s, 3H).

Step 3: To a solution of methyl 4-(2-methoxyphenyl)-6-methylnicotinate (8.0 g, 31.0 mmol) in water (40 mL) and MeOH (40 mL) was added NaOH (3.73 g, 93.0 mmol) and the mixture was heated at 50° C. for 2 h. The mixture was adjusted to pH 5 with 1 M aqueous HCl, extracted with a 10:1 mixture of DCM/MeOH (30 mL×10) and the combined organic layers were dried over $Na_2SO_4$, filtered and concentrated under reduced pressure to give 4-(2-methoxyphenyl)-6-methylnicotinic acid (5.5 g, 73%) as a white solid. LCMS: m/z=244 $[M+H]^+$, $^1H$ NMR (400 MHz, DMSO-$d_6$) δ 8.75 (s, 1H), 7.37 (td, J=7.8, 1.8 Hz, 1H), 7.26-7.16 (m, 2H), 7.03 (d, J=7.6 Hz, 2H), 3.67 (s, 3H), 2.53 (s, 3H).

Intermediate 13: (6-methoxyimidazo[1,5-a]pyridin-7-yl)boronic acid

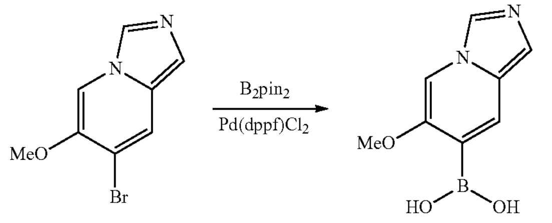 [SMILES: COc1cn2cncc2cc1Br ; COc1cn2cncc2cc1B(O)O]

A mixture of 7-bromo-6-methoxyimidazo[1,5-a]pyridine (500 mg, 2.20 mmol), KOAc (648 mg, 6.61 mmol), bis (pinacolato)diboron (1.12 g, 4.40 mmol), and $Pd(dppf)Cl_2$ (161 mg, 0.220 mmol) in 1,4-dioxane (10 mL) was heated at 100° C. overnight under $N_2$. The mixture was filtered and the filtrate concentrated under reduced pressure to afford (6-methoxyimidazo[1,5-a]pyridin-7-yl)boronic acid (1 g), which was used directly in the next step. LCMS: m/z=193 $[M+H]^+$.

Intermediate 2: 4-(5-Cyano-2-methoxyphenyl)-6-methylnicotinic acid

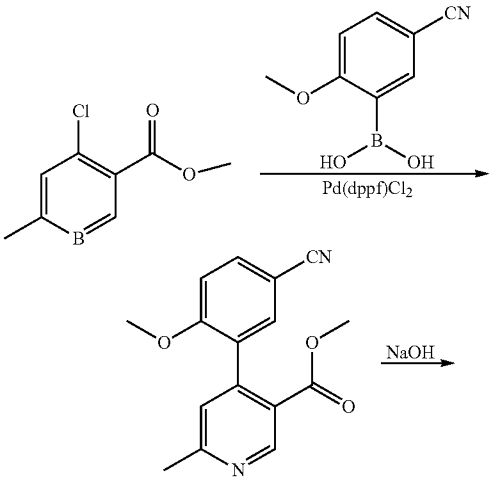

-continued

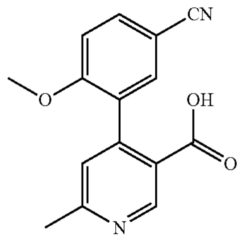

Step 1: A solution of methyl 4-chloro-6-methylnicotinate (5.2 g, 28 mmol), (5-cyano-2-methoxy phenyl)boronic acid (5.0 g 28.1 mmol), $Pd(dppf)Cl_2$ (2.0 g, 2.8 mmol) and $Na_2CO_3$ (9.0 g, 85 mmol) in 1,4-dioxane (200 mL) and water (40 mL) was heated at reflux overnight. The mixture was diluted with water (200 mL), extracted with EtOAc (2×200 mL) and the combined organic layers washed with brine (2×200 mL), dried over $Na_2SO_4$, filtered and concentrated under reduced pressure. The residue was purified by silica gel chromatography (petroleum ether/EtOAc=5/1, v/v) to give methyl 4-(5-cyano-2-methoxyphenyl)-6-methylnicotinate (5.0 g, 63%) as a yellow solid. LCMS: m/z=283 $[M+H]^+$.

Step 2: To a solution of methyl 4-(5-cyano-2-methoxyphenyl)-6-methylnicotinate (5.0 g, 18 mmol) in MeOH (200 mL) and water (400 mL) was added NaOH (2.1 g, 53 mmol) and the mixture was stirred at room temperature overnight. The mixture was diluted with water (1.0 L), extracted with EtOAc (2×1.5 L) and the combined organic layers washed with brine (2×1.0 L), dried over $Na_2SO_4$, filtered and concentrated under reduced pressure. The residue was purified by silica gel chromatography (Petroleum ether/EtOAc=1/1, v/v) to give 4-(5-cyano-2-methoxyphenyl)-6-methylnicotinic acid (3.9 g, 83%) as an off-white solid. LCMS: m/z=269 $[M+H]^+$.

TABLE U

The following intermediates were prepared using a similar procedure to that described for Intermediate 2

| Intermediate Number | Structure | Compound Name | LCMS $[M + H]^+$ | NMR |
|---|---|---|---|---|
| 14 | 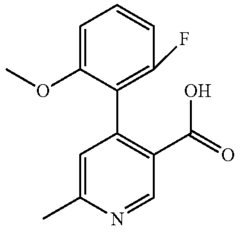 [SMILES: COc1cccc(F)c1-c1cc(C)ncc1C(=O)O] | 4-(2-Fluoro-6-methoxyphenyl)-6-methylnicotinic acid | 262 | $^1H$ NMR (400 MHZ, DMSO-$d_6$) δ 8.89 (s, 1H), 7.37 (q, J = 8.0 Hz, 1H), 7.18 (s, IH), 6.92 (d, J = 8.4 Hz, IH), 6.86 (t, J = 8.8 Hz, 1H), 3.68 (s, 3H), 2.53 (s, 3H) |

TABLE U-continued

The following intermediates were prepared using a similar procedure to that described for Intermediate 2

| Intermediate Number | Structure | Compound Name | LCMS $[M + H]^+$ | NMR |
|---|---|---|---|---|
| 15 | 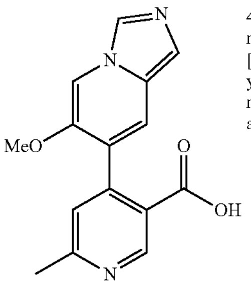 | 4-(6-methoxyimidazo[1,5-a]pyridin-7-yl)-6-methylnicotinic acid | 284 | $^1$H NMR (400 MHZ, DMSO-$d_6$) δ 8.81 (s, 1H), 8.31 (s, 1H), 8.05 (s, IH), 7.52 (s, 1H), 7.39 (s, 1H), 7.32 (s, IH), 3.64 (s, 3H), 2.55 (s, 3H) |

Intermediate 3: 2'-Chloro-5'-methoxy-6-methyl-[4,4'-bipyridine]-3-carboxylicacid

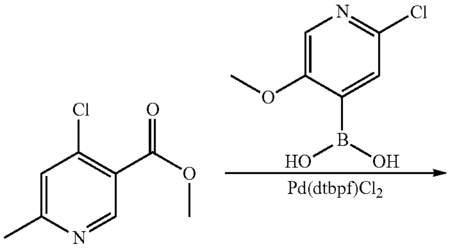

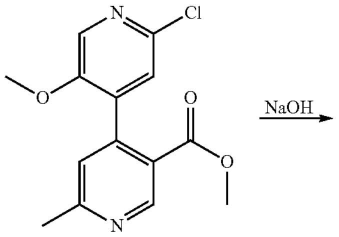

-continued

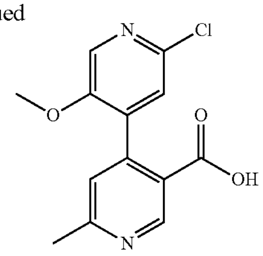

Step 1: To a solution of methyl 4-chloro-6-methylnicotinate (6.00 g, 32.1 mmol) and (2-chloro-5-methoxypyridin-4-yl)boronic acid (15.0 g, 80.2 mmol) in 1,4-dioxane (140 mL) and water (14 mL) was added Pd(dtbpf)$Cl_2$ (2.1 g, 3.2 mmol) and $K_2CO_3$ (13.3 g, 96.3 mmol) and the mixture was heated at 80° C. for 2 h. The mixture was diluted with water (200 mL), extracted with EtOAc (3×200 mL) and the combined organic layers washed with water (200 mL), brine (200 mL), dried over $Na_2SO_4$, filtered and concentrated under reduced pressure. The residue was purified by silica gel chromatography (EtOAc/petroleum ether=1/1) to give methyl 2'-chloro-5'-methoxy-6-methyl-[4,4'-bipyridine]-3-carboxylate (7.3 g, 31%) as a yellow solid. LCMS: m/z=293 $[M+H]^+$, $^1$H NMR (400 MHz, Chloroform-d) δ 9.05 (s, 1H), 8.04 (s, 1H), 7.17 (s, 1H), 7.08 (s, 1H), 3.81 (s, 3H), 3.75 (s, 3H), 2.67 (s, 3H).

Step 2: To a solution of methyl 2'-chloro-5'-methoxy-6-methyl-[4,4'-bipyridine]-3-carboxylate (14.6 g, 50.0 mmol) in MeOH (140 mL) and water (140 mL) at 0° C. was added NaOH (6.00 g, 150 mmol) and the mixture was stirred at room temperature for 2 h. The mixture was adjusted to pH 5-6 with 2 M aqueous HCl and concentrated under reduced pressure. The residue was purified on a short silica gel column (DCM/MeOH=10/1, v/v) to give 2'-chloro-5'-methoxy-6-methyl-[4,4'-bipyridine]-3-carboxylic acid (14.5 g) as a yellow solid which was used without further purification. LCMS: m/z=279 $[M+H]^+$, $^1$H NMR (400 MHz, DMSO-$d_6$) δ 8.75 (s, 1H), 8.09 (s, 6C), 7.16 (s, 1H), 6.95 (s, 1H), 3.74 (s, 3H), 2.45 (s, 3H).

TABLE A

The following intermediates were prepared using a similar procedure to that described for Intermediate 3

| Intermediate Number | Structure | Compound Name | LCMS $[M + H]^+$ | NMR |
|---|---|---|---|---|
| 4 | 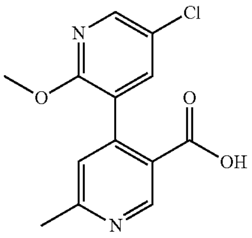 [SMILES: COc1ncc(Cl)cc1-c1cc(C)ncc1C(=O)O] | 5-Chloro-2-methoxy-6'-methyl-[3,4'-bipyridine]-3'-carboxylic acid | 279 | $^1H$ NMR (400 MHZ, DMSO-$d_6$) δ 8.88 (s, 1H), 8.26 (d, J = 2.6 Hz, 1H), 7.86 (d, J = 2.6 Hz, 1H), 7.40 (s, IH), 3.77 (s, 3H), 2.57 (s, 3H) |
| 5 | 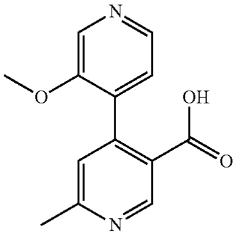 [SMILES: COc1cnccc1-c1cc(C)ncc1C(=O)O] | 3'-Methoxy-6-methyl-[4,4'-bipyridine]-3-carboxylic acid | 245 | $^1H$ NMR (400 MHZ, DMSO-$d_6$) δ 8.72 (s, 1H), 8.32 (s, 1H), 8.21 - 8.10 (m, 1H), 7.15-7.09 (m, 1H), 6.98 (s, IH), 3.76 (s, 3H), 2.46 (s, 3H) |
| 6 | 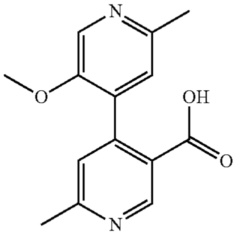 [SMILES: COc1cnc(C)cc1-c1cc(C)ncc1C(=O)O] | 5'-Methoxy-2',6-dimethyl-[4,4'-bipyridine]-3-carboxylic acid | 259 | $^1H$ NMR (400 MHZ, DMSO-$d_6$) δ 13.1 (s, IH), 8.90 (s, 1H), 8.37 (s, 1H), 7.47 (s, 1H), 7.29 (s, 1H), 3.80 (s, 3H), 2.57 (s, 3H), 2.56 (s, 3H) |
| 16 | 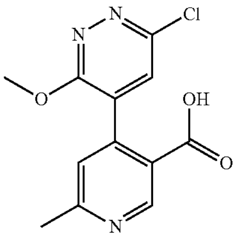 [SMILES: COc1nnc(Cl)cc1-c1cc(C)ncc1C(=O)O] | 4-(6-chloro-3-methoxypyridazin-4-yl)-6-methylnicotinic acid | 280 | $^1H$ NMR (400 MHZ, DMSO-$d_6$) δ 8.96 (s, 1H), 7.86 (s, IH), 7.40 (s, 1H), 3.93 (s, 3H), 2.57 (s, 3H) |

Intermediate 7: tert-Butyl 2-(4-(5-Cyano-2-methoxyphenyl)-6-methylnicotinamido)-4,6-dihydro-5H-pyrrolo[3,4-d]thiazole-5-carboxylate

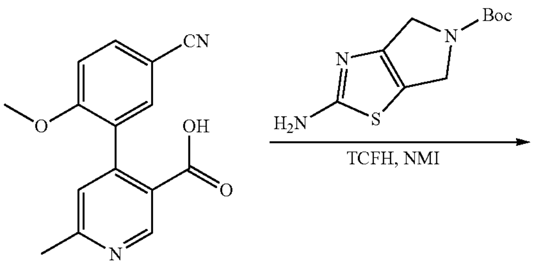

-continued

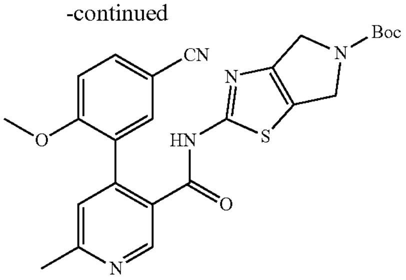

To a solution of 4-(5-cyano-2-methoxyphenyl)-6-methylnicotinic acid (1.5 g, 5.6 mmol), tert-butyl 2-amino-4,6-dihydro-5H-pyrrolo[3,4-d]thiazole-5-carboxylate (1.35 g, 5.6 mmol) and TCFH (3.2 g, 8.4 mmol) in ACN (90 mL) was added NMI (2.9 g, 22.4 mmol) and the mixture was heated at 80° C. for 20 h. The mixture was diluted with water (500 mL), extracted with EtOAc (2×500 mL) and the combined organic layers washed with brine (2×500 mL), dried over $Na_2SO_4$, filtered and concentrated under reduced pressure. The residue was purified by silica gel chromatography (Petroleum ether/EtOAc=3/1, v/v) to give tert-butyl 2-(4-(5-cyano-2-methoxyphenyl)-6-methylnicotinamido)-4,6-dihydro-5H-pyrrolo[3,4-d]thiazole-5-carboxylate as a red solid (1.18 g, 43%). LCMS: m/z=492 $[M+H]^+$, $^1H$ NMR (400 MHz, DMSO-$d_6$) δ 12.6 (s, 1H), 8.72 (s, 1H), 7.88 (dd, J=8.8, 2.2 Hz, 1H), 7.84 (d, J=2.2 Hz, 1H), 7.39 (s, 1H), 7.18 (d, J=8.8, Hz, 1H), 4.57-4.49 (m, 2H), 4.43-4.35 (m, 2H), 3.56 (s, 3H), 2.58 (s, 3H), 1.46 (s, 9H).

Intermediate 8: tert-butyl 2-(2'-Chloro-5'-methoxy-6-methyl-[4,4'-bipyridine]-3-carboxamido)-4,6-dihydro-5H-pyrrolo[3,4-d]thiazole-5-carboxylate

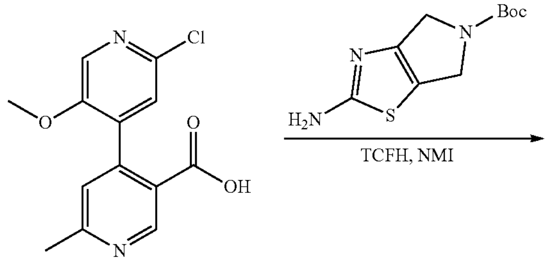

-continued

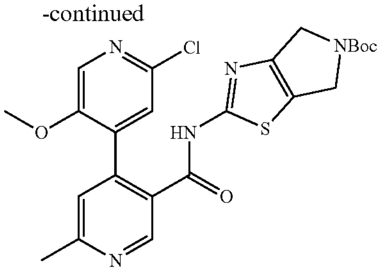

To a solution of 2'-chloro-5'-methoxy-6-methyl-[4,4'-bipyridine]-3-carboxylic acid (1.5 g, 5.4 mmol), tert-butyl 2-amino-4,6-dihydro-5H-pyrrolo[3,4-d]thiazole-5-carboxylate (1.3 g, 5.4 mmol) and TCFH (2.27 g, 8.07 mmol) in ACN (60 mL) was added NMI (1.77 g, 21.5 mmol) and the mixture was heated at 80° C. overnight. The mixture was concentrated under reduced pressure, the residue was diluted with water (50 mL) and extracted with EtOAc (2×50 mL). The combined organic layers were washed with water (50 mL), brine (50 mL), dried over $Na_2SO_4$, filtered and concentrated under reduced pressure. The residue was purified by silica gel chromatography (Pet ether/EtOAc=1/1, v/v) to give tert-butyl 2-(2'-chloro-5'-methoxy-6-methyl-[4,4'-bipyridine]-3-carboxamido)-4,6-dihydro-5H-pyrrolo[3,4-d]thiazole-5-carboxylate (2.03 g, 71%) as an off-white solid. LCMS: m/z=502 $[M+H]^+$, $^1H$ NMR (400 MHz, DMSO-$d_6$) δ 12.8 (d, J=10.6 Hz, 1H), 8.78 (s, 1H), 8.17 (d, J=2.0 Hz, 1H), 7.54 (s, 1H), 7.43 (s, 1H), 4.58-4.49 (m, 2H), 4.44-4.36 (m, 2H), 3.60 (s, 3H), 2.59 (s, 3H), 1.45 (s, 9H).

TABLE B

The following intermediates were prepared using a similar procedure to that described for Intermediate 8

| Intermediate Number | Structure | Compound Name | LCMS $[M + H]^+$ | NMR |
|---|---|---|---|---|
| 9 | 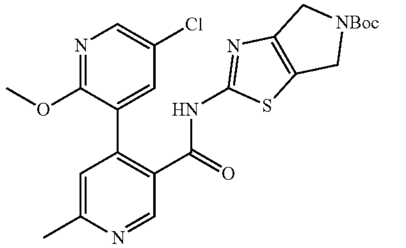 [SMILES: COc1ncc(Cl)cc1-c1cc(C)ncc1C(=O)Nc1nc2c(s1)CN(C(=O)OC(C)(C)C)C2] | tert-Butyl 2-(5-chloro-2-methoxy-6'-methyl-[3,4'-bipyridine]-3'-carboxamido)-4,6-dihydro-5H-pyrrolo[3,4-d]thiazole-5-carboxylate | 502 | $^1H$ NMR (400 MHZ, DMSO-$d_6$) δ 12.7 (s, 1H), 8.75 (s, 1H), 8.26 (d, J = 2.6 Hz, 1H), 7.96 (d, J = 2.6 Hz, 1H), 7.44 (s, 1H), 4.53 (dd, J = 12.6, 3.4 Hz, 2H), 4.41 (dd, J = 11.2, 3.6 Hz, 2H), 3.57 (s, 3H), 2.58 (s, 3H), 1.45 (s, 9H) |
| 10 | 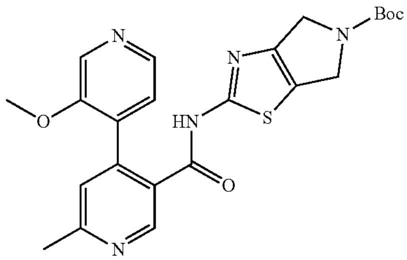 [SMILES: COc1cnccc1-c1cc(C)ncc1C(=O)Nc1nc2c(s1)CN(C(=O)OC(C)(C)C)C2] | tert-Butyl 2-(3'-methoxy-6-methyl-[4,4'-bipyridine]-3-carboxamido)-4,6-dihydro-5H-pyrrolo[3,4-d]thiazole-S-carboxylate | 468 | $^1H$ NMR (400 MHZ, DMSO-$d_6$) δ 12.7 (d, J = 10.8 Hz, 1H), 8.74 (s, IH), 8.36 (s, 1H), 8.33 (d, J = 4.8 Hz, 1H), 7.37 (d, J = 5.6 Hz, 2H), 4.53 (d, J = 12.4 Hz, 2H), 4.40 (d, J = 11.6 Hz, 2H), 3.61 (s, 3H), 2.59 (s, 3H), 1.45 (s, 9H) |

TABLE B-continued

The following intermediates were prepared using a similar procedure to that described for Intermediate 8

| Intermediate Number | Structure | Compound Name | LCMS $[M + H]^+$ | NMR |
|---|---|---|---|---|
| 11 | 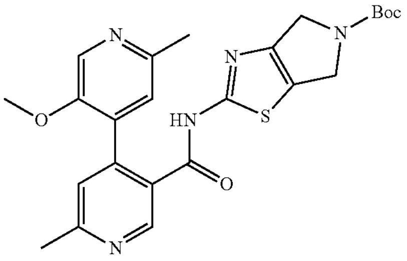 [SMILES: COc1cnc(C)cc1-c1cc(C)ncc1C(=O)Nc1nc2c(s1)CN(C(=O)OC(C)(C)C)C2] | tert-Butyl 2-(5'-methoxy-2',6-dimethyl-[4,4'-bipyridine]-3-carboxamido)-4,6-dihydro-5H-pyrrolo[3,4-d]thiazole-5-carboxylate | 482 | $^1$H NMR (400 MHZ, DMSO-$d_6$) δ 8.72 (s, 1H), 8.18 (s, 1H), 7.36 (s, 1H), 7.26 (s, 1H), 4.58-4.50 (m, 2H), 4.44-4.37 (m, 2H), 3.55 (s, 3H), 2.58 (s, 3H), 2.47 (s, 3H), 1.45 (s, 9H) |
| 12 | 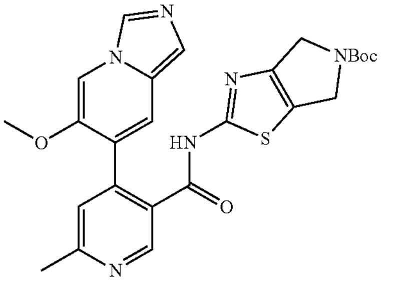 [SMILES: COc1cn2cncc2cc1-c1cc(C)ncc1C(=O)Nc1nc2c(s1)CN(C(=O)OC(C)(C)C)C2] | tert-Butyl 2-(4-(6-methoxyimidazo[1,5-a]pyridin-7-yl)-6-methylnicotinamido)-4,6-dihydro-5H-pyrrolo[3,4-d]thiazole-5-carboxylate | 507 | $^1$H NMR (400 MHZ, DMSO-$d_6$) δ 12.7 (d, J = 10.0 Hz, 1H), 8.70 (s, 1H), 8.27 (s, IH), 8.00 (s, IH), 7.64 (s, 1H), 7.43 (d, J = 3.6 Hz, 2H), 4.53 (d. J = 12.0 Hz, 2H), 4.40 (d, J = 11.0 Hz, 2H), 3.45 (s, 3H), 2.58 (s, 3H), 1.45 (s, 9H) |
| 17 | 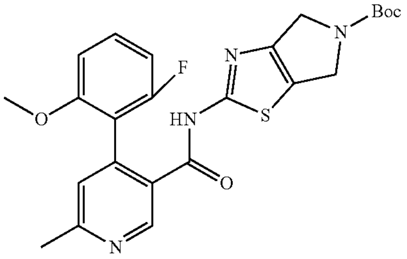 [SMILES: COc1cccc(F)c1-c1cc(C)ncc1C(=O)Nc1nc2c(s1)CN(C(=O)OC(C)(C)C)C2] | tert-Butyl 2-(4-(2-fluoro-6~methoxyphenyl)-6-methylnicotinamido)-4,6-dihydro-5H-pyrrolo[3,4-d]thiazole-5-carboxylate | 485 | $^1$H NMR (400 MHZ, DMSO-$d_6$) δ 12.7 (d, .J = 12.2 Hz, 1H), 8.77 (s, 1H), 7.42-7.35 (m, IH), 7.32 (s, 1H), 6.93-6.87 (m, 2H), 4.54-4.50 (m, 2H), 4.42-4.38 (m, 2H), 3.57 (s, 3H), 2.69 (s, 3H), 1.45 (s, 9H) |
| 8 | 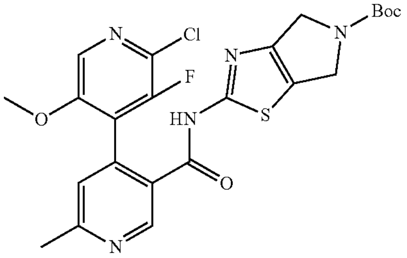 [SMILES: COc1cnc(Cl)c(F)c1-c1cc(C)ncc1C(=O)Nc1nc2c(s1)CN(C(=O)OC(C)(C)C)C2] | tert-Butyl 2-(2'-chloro-3'-fluoro-S'-methoxy-6-methyl-[4,4'-bipyridine]-3-carboxamido)-4,6-dihydro-5H-pyrrolo[3,4-d]thiazole-S-carboxylate | 520 | $^1$H NMR (400 MHZ, DMSO-$d_6$) δ 12.9 (s, IH), 8.93 (s, 1H), 8.17 (s, IH), 7.47 (s, IH), 4.53 (d, J = 12.4 Hz, 2H), 4.40 (d, J = 11.6 Hz, 2H), 3.72 (s, 3H), 2.59 (s, 3H), 1.45 (s, 9H) |
| 19 | 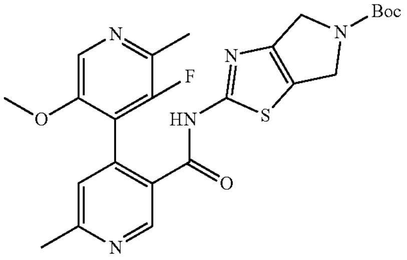 [SMILES: COc1cnc(C)c(F)c1-c1cc(C)ncc1C(=O)Nc1nc2c(s1)CN(C(=O)OC(C)(C)C)C2] | tert-Butyl 2-(3'-fluoro-5'-methoxy-2',6-dimethyl~[4,4'-bipyridine]-3-carboxamido)-4,6-dihydro-5H-pyrrolo[3,4-d]thiazole-S-carboxylate | 500 | $^1$H NMR (400 MHZ, DMSO-$d_6$) δ 12.9 (s, 1H), 8.87 (s, IH), 8.17 (s, IH), 7.39 (s, 1H), 4.52 (d, J = 12.4 Hz, 2H), 4.41 (d, J = 11.6 Hz, 2H), 3.69 (s, 3H), 2.58 (s, 3H), 2.42 (d, J = 3.0 Hz, 3H), 1.45 (s, 9H |

TABLE B-continued

The following intermediates were prepared using a similar procedure to that described for Intermediate 8

| Intermediate Number | Structure | Compound Name | LCMS $[M + H]^+$ | NMR |
|---|---|---|---|---|
| 20 | 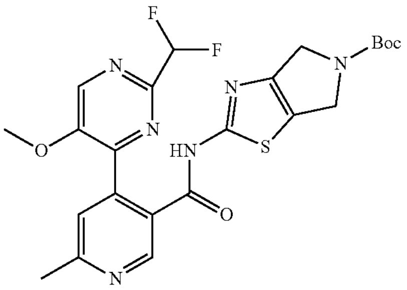 [SMILES: COc1cnc(C(F)F)nc1-c1cc(C)ncc1C(=O)Nc1nc2c(s1)CN(C(=O)OC(C)(C)C)C2] | tert-Butyl 2-(4-(2-(difluoromethyl)-5-methoxypyrimidin-4-yl)-6-methylnicotinamido)-4,6-dihydro-5H-pyrrolo[3,4-d]thiazole-5-carboxylate | 519 | $^1$H NMR (400 MHZ, Chloroform-d) δ 9.06 (s, IH), 8.51 (s, IH), 7.67 (s, 1H), 6.67 (td, J = 55.1, 5.0 Hz, 1H), 4.62 (d. J = 11.2 Hz, 2H), 4.35 (d, J = 11.8 Hz, 2H), 3.84 (s, 3H), 2.83 (s, 3H), 1.50 (s, 9H) |
| 21 | 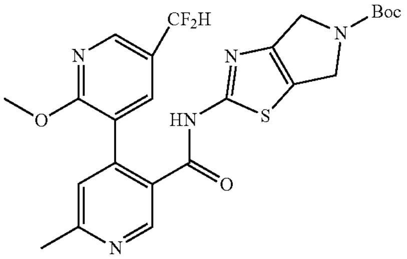 [SMILES: COc1ncc(C(F)F)cc1-c1cc(C)ncc1C(=O)Nc1nc2c(s1)CN(C(=O)OC(C)(C)C)C2] | tert-Butyl 2-(5-(difluoromethyl)-2-methoxy-6'-methyl-[3,4'-bipyridine]-3'-carboxamido)-4,6-dihydro-SH-pyrrolo[3,4~d]thiazole-5-carboxylate | 518 | $^1$H NMR (400 MHZ, DMSO-$d_6$) δ 12.8 (d, J = 10.6 Hz, 1H), 8.75 (s, IH), 8.43 (s, 1H), 8.00 (s, 1H), 7.43 (s, 1H), 7.14 (t, J = 55.4 Hz, IH), 4.61-4.49 (m, 2H), 4.46-4.34 (m, 2H), 3.63 (s, 3H), 2.59 (s, 3H), 1.45 (s, 9H) |
| 22 | 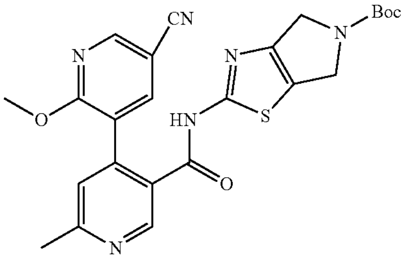 [SMILES: COc1ncc(C#N)cc1-c1cc(C)ncc1C(=O)Nc1nc2c(s1)CN(C(=O)OC(C)(C)C)C2] | tert-Butyl 2-(5-cyano-2-methoxy-6'-methyl-[3,4'-bipyridine]-3'-carboxamido)-4,6-dihydro-5H-pyrrolo[3,4-d]thiazole-5-carboxylate | 491.30 $[M - H]^-$ | $^1$H NMR (400 MHZ, DMSO-$d_6$) δ 8.78 (s, 1H), 8.73 (s, 1H), 8.31 (s, 1H), 7.46 (s, IH), 4.53 (d, J = 13.0 Hz, 2H), 4.18 (d, J = 12.4 Hz, 2H), 3.65 (s, 3H), 2.59 (s, 3H), 1.45 (s, 9H |
| 23 | 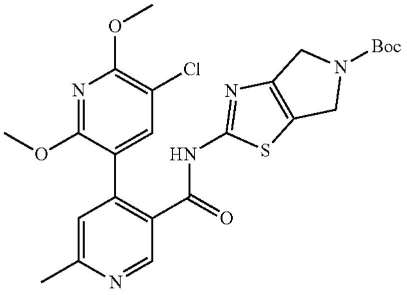 [SMILES: COc1nc(OC)c(-c2cc(C)ncc2C(=O)Nc2nc3c(s2)CN(C(=O)OC(C)(C)C)C3)cc1Cl] | tert-Butyl 2-(5-chloro-2,6-dimethoxy-6'-methyl-[3,4'-bipyridine]-3'-carboxamido)-4,6-dihydro-SH-pyrrolo[3,4~d]thiazole-5-carboxylate | 532 | $^1$H NMR (400 MHZ, DMSO-$d_6$) δ 12.7 (s, 1H), 8.66 (s, 1H), 7.92 (s, 1H), 7.38 (s, IH), 4.53 (d, J = 11.8 Hz, 2H), 4.40 (d, J = 11.4 Hz, 2H), 3.96 (s, 3H), 3.61 (s, 3H), 2.55 (s, 3H), 1.45 (s, 9H) |
| 24 | 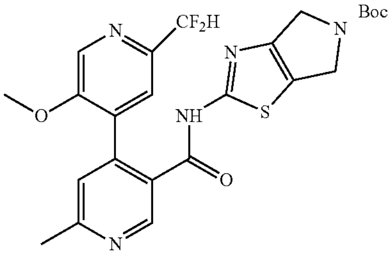 [SMILES: COc1cnc(C(F)F)cc1-c1cc(C)ncc1C(=O)Nc1nc2c(s1)CNC2 ; "Boc"] | tert-butyl 2-(2'-(difluoromethyl)-5'-methoxy-6-methyl-[4,4'-bipyridine]-3-carboxamido)-4,6-dihydro-5H-pyrrolo[3,4-d]thiazole-5-carboxylate | 518 | $^1$H NMR (400 MHZ. DMSO-$d_6$) δ 12.8 (d, J = 9.8 Hz, IH), 8.78 (s, 1H), 8.45 (s, IH), 7.69 (s, 1H), 7.43 (s, 1H), 6.98 (t. J = 55.0 Hz, 1H), 4.53 (d, J = 12.2 Hz, 2H), 4.40 (d, J = 11.8 Hz, 2H), 3.67 (s, 3H), 2.59 (s, 3H), 1.45 (s, 9H) |

TABLE B-continued

The following intermediates were prepared using a similar procedure to that described for Intermediate 8

| Intermediate Number | Structure | Compound Name | LCMS $[M + H]^+$ | NMR |
|---|---|---|---|---|
| 25 | 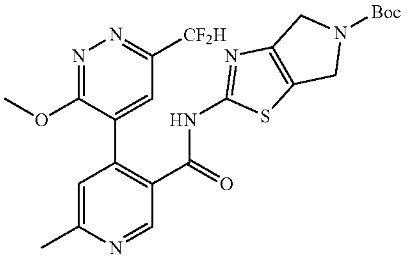 [SMILES: COc1nnc(C(F)F)cc1-c1cc(C)ncc1C(=O)Nc1nc2c(s1)CN(C(=O)OC(C)(C)C)C2] | tert-butyl 2-(4-(6-(difluoromethyl)-3-methoxypyridazin-4-vl)-6-methylnicotinamido)-4,6-dihydro-SH-pyrrolo[3,4-d]thiazole-5-carboxylate | 519 | |
| 26 | 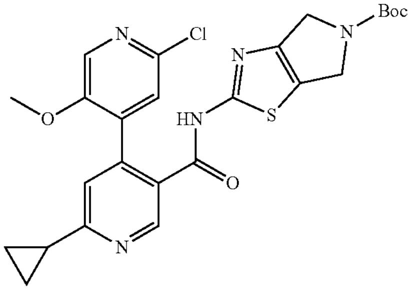 [SMILES: COc1cnc(Cl)cc1-c1cc(C2CC2)ncc1C(=O)Nc1nc2c(s1)CN(C(=O)OC(C)(C)C)C2] | tert-butyl2-(2'-chloro-6-cyclopropyl-5'-methoxy-[4,4'-bipyridine]-3-carboxamido)-4,6-dihydro-SH-pyrrolo[3,4-d]thiazole-5-carboxylate | 528 | |
| 27 | 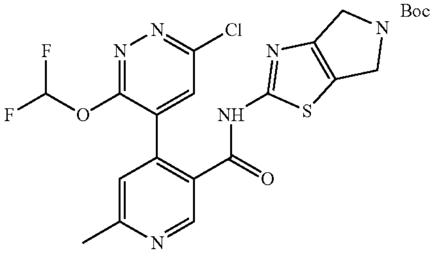 [SMILES: Cc1cc(-c2cc(Cl)nnc2OC(F)F)c(C(=O)Nc2nc3c(s2)CNC3)cn1 ; "Boc"] | tert-butyl 2-(4-(6-chloro-3-(difluoromethoxy)pyridazin~4~yl)-6-methylnicotinamido)-4,6-dihydro-5H-pyrrolo[3,4-d]thiazole-S-carboxylate | 539 | |
| 28 | 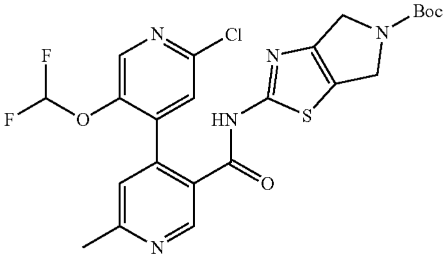 [SMILES: Cc1cc(-c2cc(Cl)ncc2OC(F)F)c(C(=O)Nc2nc3c(s2)CN(C(=O)OC(C)(C)C)C3)cn1] | tert-butyl 2-(2'-chloro-5'-(difluoromethoxy)-6-methyl-[4,4'-bipyridine]-3-carboxamido)-4,6-dihydro-5H-pyrrolo[3,4-d]thiazole-5-carboxylate | 538 | |

Intermediate 29: 3-chloro-6-(difluoromethyl)picolinic acid

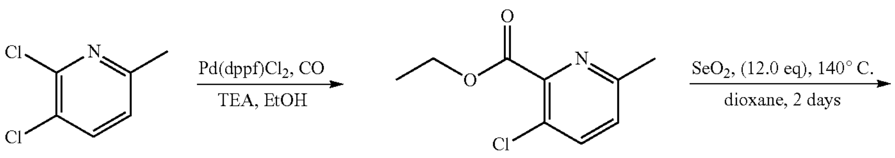

-continued

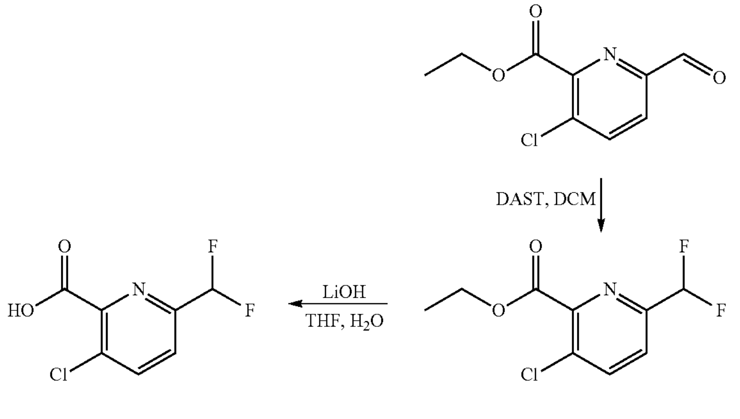

Step 1: To a stirred solution of 2,3-dichloro-6-methylpyridine (4.5 g, 28 mmol) in EtOH (100 mL) was added $Pd(dppf)Cl_2$ (2.0 g, 2.8 mmol) and TEA (14.1 g, 139 mmol) in one portion at 25° C. The reaction was charged with carbon monoxide and the mixture was stirred at 110° C. for 4 hours under 40 MPa CO. The resulting mixture was cooled to 25° C. and concentrated under reduced pressure. The residue was purified by silica gel column chromatography, eluting with PE/EA (3:1) to afford ethyl 3-chloro-6-methylpicolinate (3.2 g, 58% yield) as a yellow solid. LCMS: m/z=200 $[M+H]^+$.

Step 2: To a stirred solution of ethyl 3-chloro-6-methylpicolinate (2.0 g, 10.0 mmol) in dioxane (40 mL) was added selenium dioxide (13.3 g, 120.2 mmol) in one portion at 25° C. The reaction mixture was stirred at 140° C. for 48 h under a nitrogen atmosphere. The resulting mixture was cooled to 25° C. and diluted with water (50 mL). The mixture was extracted with ethyl acetate (3×50 mL). The combined organic layers were washed with brine, dried over $Na_2SO_4$, filtered, and concentrated under reduced pressure. The residue was purified by silica gel column chromatography, eluting with PE/EA (3/1) to afford ethyl 3-chloro-6-formylpyridine-2-carboxylate (1.1 g, 51% yield) as a yellow oil. LCMS: m/z=214 $[M+H]^+$.

Step 3: To a stirred solution of ethyl 3-chloro-6-formylpyridine-2-carboxylate (1.0 g, 4.7 mmol) in DCM (20 mL) was added DAST (1.5 g, 9.4 mmol) dropwise at 0° C. The reaction mixture was stirred at 25° C. for 2 hours under a nitrogen atmosphere. The resulting mixture was quenched with saturated $NaHCO_3$ solution. The mixture was extracted with ethyl acetate (3×20 mL). The combined organic layers were washed with brine, dried over $Na_2SO_4$, filtered, and concentrated under reduced pressure. The residue was purified by silica gel column chromatography, eluting with PE/EA (5/1) to afford ethyl 3-chloro-6-(difluoromethyl) pyridine-2-carboxylate (520 mg, 47% yield) as a yellow oil. LCMS: m/z=236 $[M+H]^+$.

Step 4: To a stirred solution of ethyl 3-chloro-6-(difluoromethyl)pyridine-2-carboxylate (500 mg, 2.1 mmol) in THF (5 mL) and $H_2O$ (1 mL) was added LiOH (178 mg, 4.2 mmol) in one portion at 25° C. The resulting mixture was stirred at 25° C. for 2 hours. The residue was acidified to pH 3 with aqueous HCl (1N), diluted with $H_2O$ (25 mL), and extracted with DCM/MeOH (5/1) (3×30 mL). The organic layer was dried over anhydrous $Na_2SO_4$. The resulting mixture was concentrated under reduced pressure to afford 3-chloro-6-(difluoromethyl)picolinic acid (300 mg, crude) as a white solid. LCMS: m/z=208 $[M+H]^+$.

Intermediate 30: 4-(difluoromethyl)-5-methoxypyrimidine-2-carboxylic acid

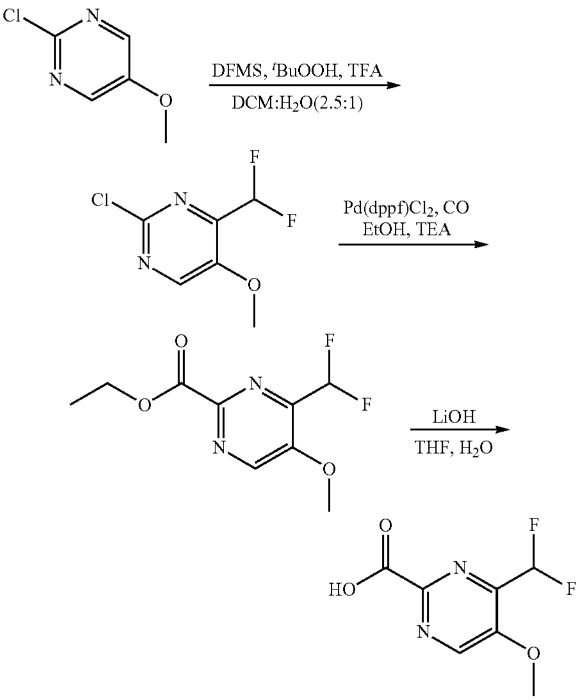

Step 1: To a stirred solution of 2-chloro-5-methoxypyrimidine (1.0 g, 7.0 mmol) and 2-hydroperoxy-2-methylpropane (2.0 g, 21.0 mmol) in DCM (10 mL) and water (4 mL) was added zinc(II) difluoromethanesulfinate (6.0 g, 21.0 mmol) and TFA (0.8 g, 7.0 mmol) in sequence. The mixture was charged with $N_2$ three times and stirred at 25° C. for 12 h under a $N_2$ atmosphere. The reaction mixture was quenched with saturated sodium thiosulfate solution and extracted with DCM (2×100 mL). The combined organic layers were washed with brine and dried over $Na_2SO_4$. After filtration, the filtrate was concentrated under reduced pressure. The resulting mixture was purified by reverse phase chromatography (10-30% ACN in water with 0.1% formic acid modifier) to afford 2-chloro-4-(difluoromethyl)-5-methoxypyrimidine (131 mg, 10% yield) as a yellow solid. LCMS: m/z=195 $[M+H]^+$.

Step 2: To a stirred solution of 2-chloro-4-(difluoromethyl)-5-methoxypyrimidine (131 mg, 0.7 mmol) and Pd(dppf)$Cl_2$ (15 mg, 21 μmol) in EtOH (5 mL) was added triethylamine (170 mg, 1.7 mmol). The mixture was charged with CO three times and stirred at 100° C. for 6 h under a CO atmosphere. The resulting mixture was cooled to 25° C. and concentrated under reduced pressure. The mixture was purified by prep-TLC (DCM/MeOH 10/1) to afford ethyl 4-(difluoromethyl)-5-methoxypyrimidine-2-carboxylate (89 mg, 57% yield) as a brown solid. LCMS: m/z=233 $[M+H]^+$.

Step 3: To a stirred solution of ethyl 4-(difluoromethyl)-5-methoxypyrimidine-2-carboxylate (79 mg, 0.3 mmol) in THF (2 mL) and water (2 mL) was added LiOH (16 mg, 0.7 mmol). The mixture was stirred at 25° C. for 2 h. The reaction mixture was acidified to pH 5 with HCl (1N) and concentrated under reduced pressure. The residue was purified by prep-TLC (MeOH) to afford 4-(difluoromethyl)-5-methoxypyrimidine-2-carboxylic acid (65 mg, 94% yield) as a brown solid. LCMS: m/z=205 $[M+H]^+$.

Intermediate 31: 2'-(difluoromethyl)-5'-methoxy-6-methyl-[4,4'-bipyridine]-3-carboxylicacid

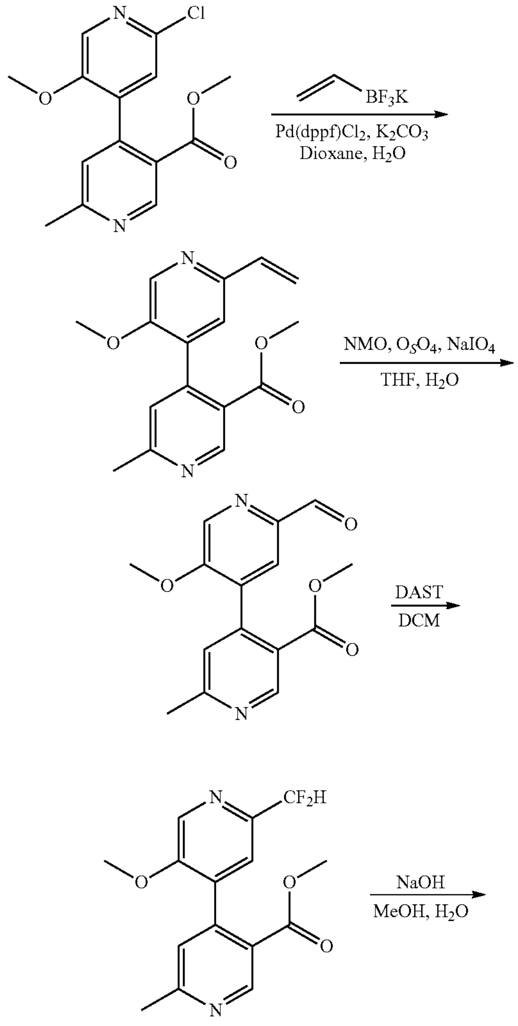

-continued

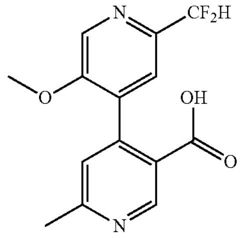

Step 1: To a solution of methyl 2'-chloro-5'-methoxy-6-methyl-[4,4'-bipyridine]-3-carboxylate (5 g, 17.1 mmol), Pd(dppf)$Cl_2$ (1.4 g, 1.7 mmol) and potassium vinyltrifluoroborate (4.6 g, 34.2 mmol) in 1,4-dioxane (10 mL) and $H_2O$ (2 mL) was added $K_2CO_3$ (4.7 g, 34.2 mmol) in one portion at 25° C. The reaction was stirred at 130° C. for 16 hours under a nitrogen atmosphere. The mixture was cooled to 25° C. and filtered. The filter cake was washed with EtOAc (3×50 mL), and the filtrate was concentrated under reduced pressure. The residue was purified by silica gel column chromatography, eluting with PE/EA (1/1) to afford methyl 5'-methoxy-6-methyl-2'-vinyl-[4,4'-bipyridine]-3-carboxylate (4.7 g, 97% yield) as a brown solid. LCMS: m/z=285 $[M+H]^+$.

Step 2: To a solution of methyl 5'-methoxy-6-methyl-2'-vinyl-[4,4'-bipyridine]-3-carboxylate (4.7 g, 16.5 mmol) and $OsO_4$ (420 mg, 1.7 mmol) in THF (40 mL) and $H_2O$ (8 mL) was added NMO (3.9 g, 33.1 mmol). The mixture was stirred at 25° C. for 1 h. $NaIO_4$ (14.1 g, 66.1 mmol) was added in portions at 25° C., and the reaction mixture was stirred at 25° C. for 16 h. The mixture was filtered and the filter cake was washed with MeOH (2×20 mL). The filtrate was concentrated under reduced pressure. The residue was purified by silica gel column chromatography, eluting with PE/EA (1/10) to afford methyl 2'-formyl-5'-methoxy-6-methyl-[4,4'-bipyridine]-3-carboxylate (600 mg, 12.7% yield) as a brown solid. LCMS: m/z=287 $[M+H]^+$.

Step 3: Completed as described in Intermediate 29: 3-chloro-6-(difluoromethyl)picolinic acid step 3 from methyl 2'-formyl-5'-methoxy-6-methyl-[4,4'-bipyridine]-3-carboxylate to afford methyl 2'-(difluoromethyl)-5'-methoxy-6-methyl-[4,4'-bipyridine]-3-carboxylate (500 mg, 84% yield) as a brown solid. LCMS: m/z=309 $[M+H]^+$.

Step 4: To a solution of methyl 2'-(difluoromethyl)-5'-methoxy-6-methyl-[4,4'-bipyridine]-3-carboxylate (450 mg, 1.5 mmol) in MeOH (6 mL) and $H_2O$ (2 mL) was added NaOH (117 mg, 2.9 mmol) at 25° C. The reaction was stirred at 50° C. for 2 h. The mixture was cooled to 25° C. and acidified to pH 2 with 1N HCl aqueous solution. The precipitated solids were collected by filtration to afford 2'-(difluoromethyl)-5'-methoxy-6-methyl-[4,4'-bipyridine]-3-carboxylic acid (400 mg, crude) as a white solid. LCMS: m/z=295 $[M+H]^+$.

TABLE V

The following intermediates were prepared using a similar procedure to that described for Intermediate 31

| Intermediate Number | Structure | Compound Name | LCMS $[M + H]^+$ |
|---|---|---|---|
| 32 | 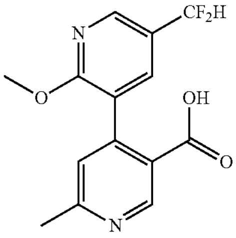 [SMILES: COc1ncc(C(F)F)cc1-c1cc(C)ncc1C(=O)O] | 5-(Difluoromethyl)-2-methoxy-6'-methyl-[3,4'-bipyridine]-3'-carboxylic acid | 295 |
| 33 | 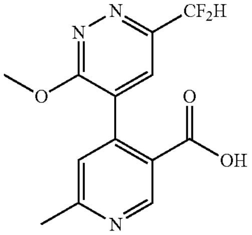 [SMILES: COc1nnc(C(F)F)cc1-c1cc(C)ncc1C(=O)O] | 4-(6-(difluoromethyl)-3-methoxypyridazin-4-yl)-6-methylnicotinic acid | 296 |

Intermediate 34: 3-methoxy-5-(trifluoromethyl)pyrazine-2-carboxylic acid

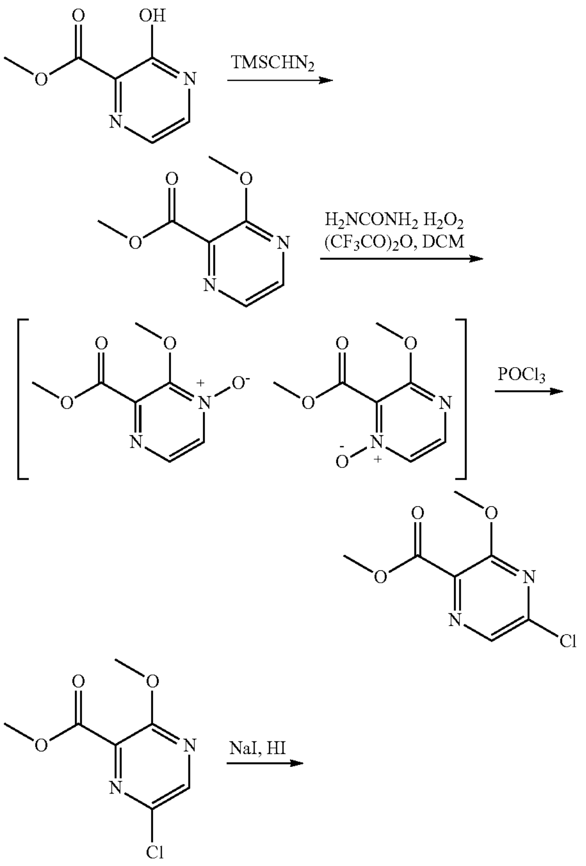

-continued

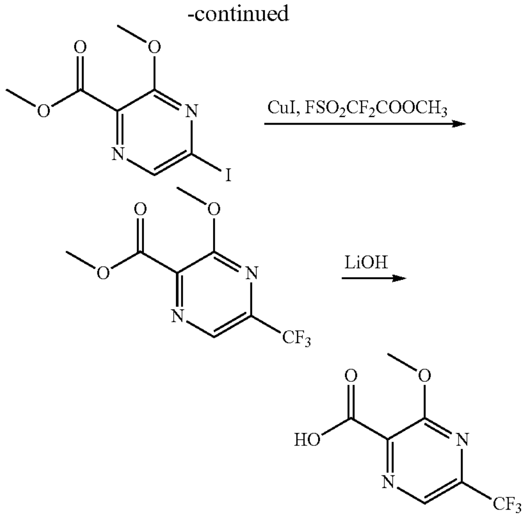

Step 1: To a solution of methyl 3-hydroxypyrazine-2-carboxylate (3.0 g, 19.5 mmol) in DCM (36 mL) and MeOH (4 mL) was added (trimethylsilyl)diazomethane solution (14.6 mL, 2 M in hexanes) dropwise at 0° C. The reaction mixture was charged with $N_2$ three times at 25° C., and the reaction mixture was stirred at 25° C. for 2 h under a nitrogen atmosphere. To the above mixture was added acetic acid (5.8 g, 96.6 mmol) in portions at 25° C., and the resulting mixture was stirred for additional 30 min at 25° C. The reaction was quenched with water (100 mL) at 0° C. The resulting mixture was extracted with DCM/MeOH (1/5, 3×100 mL), and the combined organic layers were washed with brine (3×200 mL) and dried over anhydrous $Na_2SO_4$. After filtration, the filtrate was concentrated under reduced pressure. The residue was purified by silica gel column chromatography, eluting with EA/PE (1/10) to afford methyl 3-methoxypyrazine-2-carboxylate (1.2 g, 37% yield) as a light yellow solid. LCMS: m/z=169 $[M+H]^+$.

Step 2: To a solution of methyl 3-methoxypyrazine-2-carboxylate (1.3 g, 7.4 mmol) in DCM (20 mL) was added urea-hydrogen peroxide (1/1) (1.1 g, 11.2 mmol) in one portion at 25° C. The resulting mixture was cooled to 0° C., and 2,2,2-trifluoroacetic anhydride (2.3 g, 11.2 mmol) was added dropwise under a nitrogen atmosphere. The resulting mixture was stirred for 1 h at 25° C. under a nitrogen atmosphere. The reaction was quenched with sat. $Na_2SO_3$ (aq.) (40 mL) at 25° C. The resulting mixture was extracted with DCM (3×60 mL) and the combined organic layers were dried over anhydrous $Na_2SO_4$. After filtration, the filtrate was concentrated under reduced pressure. The residue was purified by silica gel column chromatography, eluting with EA/PE (1/1) to afford a mixture of 2-methoxy-3-(methoxycarbonyl)pyrazine 1-oxide and 3-methoxy-2-(methoxycarbonyl)pyrazine 1-oxide (1.1 g, 68% yield) as a light yellow solid. LCMS: m/z=185 $[M+H]^+$.

Step 3: To a solution of 2-methoxy-3-(methoxycarbonyl) pyrazine 1-oxide and 3-methoxy-2-(methoxycarbonyl)pyrazine 1-oxide (1.3 g, 6.8 mmol) in toluene (20 mL) was added $POCl_3$ (2.1 g, 13.6 mmol) and DMF (496 mg, 6.8 mmol) in portions at 0° C. The resulting mixture was stirred at 65° C. for 3 h under a nitrogen atmosphere. The reaction was quenched with saturated $NaHCO_3$ solution (50 mL) at 0° C. The resulting mixture was extracted with EA (3×50 mL) and the combined organic layers were dried over anhydrous $Na_2SO_4$. After filtration, the filtrate was concentrated under reduced pressure. The residue was purified by silica gel column chromatography, eluting with EA/PE (1/3) to afford crude product as a light yellow solid. The crude product was purified by prep-HPLC (25-55% MeOH in water [10 mmol/L $NH_4HCO_3$ and 0.01% $NH_3 \cdot H_2O$]) to afford methyl 5-chloro-3-methoxypyrazine-2-carboxylate (130 mg, 10% yield) as a light yellow solid (LCMS: m/z=203 $[M+H]^+$) and methyl 6-chloro-3-methoxypyrazine-2-carboxylate (300 mg, 22% yield) as a light yellow solid. LCMS: m/z=203 $[M+H]^+$.

Step 4: To a solution of sodium iodide (240 mg, 1.6 mmol) in HI (2 mL, 55% wt.) was added methyl 5-chloro-3-methoxypyrazine-2-carboxylate (130 mg, 642 μmol) in portions at 0° C. The reaction was stirred for 16 h at 25° C. under a nitrogen atmosphere. The mixture was diluted with water (20 mL) and basified to pH 7 with saturated $NaHCO_3$ solution. The resulting mixture was extracted with EtOAc (3×40 mL) and the combined organic layers were dried over anhydrous $Na_2SO_4$. After filtration, the filtrate was concentrated under reduced pressure. The residue was purified by silica gel column chromatography, eluting with EA/PE (1/10) to afford methyl 5-iodo-3-methoxypyrazine-2-carboxylate (110 mg, 58% yield) as a light yellow solid. LCMS: m/z=295 $[M+H]^+$.

Step 5: To a solution of methyl 5-iodo-3-methoxypyrazine-2-carboxylate (140 mg, 476 μmol) in DMF (2 mL) were added methyl 2,2-difluoro-2-(fluorosulfonyl)acetate (274 mg, 1.4 mmol) and copper(I) iodide (18 mg, 95 μmol) in portions at 25° C. The resulting mixture was stirred at 80° C. for 16 h under a nitrogen atmosphere. The resulting mixture was cooled to 25° C. and quenched with water (20 mL). The resulting mixture was extracted with EtOAc (3×20 mL) and the combined organic layers were washed with brine and dried over anhydrous $Na_2SO_4$. After filtration, the filtrate was concentrated under reduced pressure. The residue was purified by prep-TLC (PE/EA 4/1) to afford methyl 3-methoxy-5-(trifluoromethyl)pyrazine-2-carboxylate (70 mg, 62% yield) as a light yellow solid. LCMS: m/z=237 $[M+H]^+$.

Step 6: Completed as described in Intermediate 29: 3-chloro-6-(difluoromethyl)picolinic acid step 4 from methyl 3-methoxy-5-(trifluoromethyl)pyrazine-2-carboxylate to afford 3-methoxy-5-(trifluoromethyl)pyrazine-2-carboxylic acid (60 mg, 71% yield) as a light yellow solid. LCMS: m/z=221 $[M-H]^-$.

3-methoxy-6-(trifluoromethyl)pyrazine-2-carboxylic acid can be synthesized from methyl 6-chloro-3-methoxypyrazine-2-carboxylate following steps 4-6 above.

Intermediate 35: 2'-chloro-6-cyclopropyl-5'-methoxy-[4,4'-bipyridine]-3-carboxylic acid

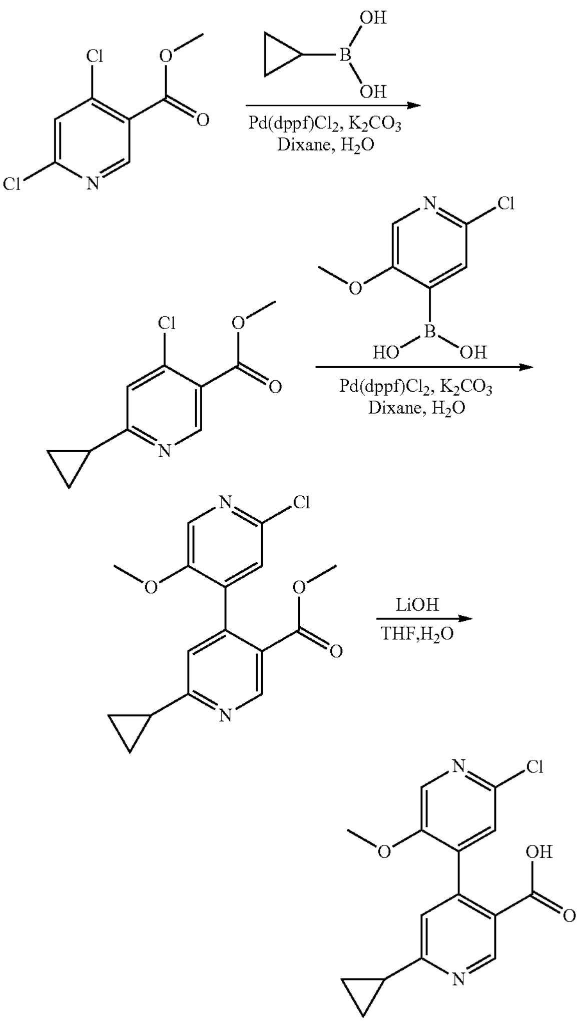

Step 1: To a solution of methyl 4,6-dichloronicotinate (15 g, 73 mmol) in 1,4-dioxane (120 mL) and water (12 mL) was added cyclopropylboronic acid (7.5 g, 87 mmol), Pd(dppf) $Cl_2$ (2.7 g, 3.6 mmol) and $K_2CO_3$ (20 g, 0.2 mmol) in one portion at 25° C. The reaction mixture was charged with $N_2$ three times and the mixture was stirred at 100° C. for 16 h under a nitrogen atmosphere. The resulting mixture was cooled 25° C. and concentrated under reduced pressure. The residue was purified by silica gel column chromatography, eluting with PE/EA (3/1) to afford methyl 4-chloro-6-cyclopropylnicotinate (5.6 g, 36% yield) as a white oil. LCMS: m/z=212 $[M+H]^+$.

Step 2: Completed as described in Intermediate 2: 4-(5-Cyano-2-methoxyphenyl)-6-methylnicotinic acid step 1 from methyl 4-chloro-6-cyclopropylnicotinate to afford methyl 2'-chloro-6-cyclopropyl-5'-methoxy-[4,4'-bipyridine]-3-carboxylate (1.6 g, 20% yield) as a white solid. LCMS: m/z=319[M+H]$^+$.

Step 3: To a solution of methyl 2'-chloro-6-cyclopropyl-5'-methoxy-[4,4'-bipyridine]-3-carboxylate (1.6 g, 5.0 mmol) in THF (12 mL) and water (4 mL) was added lithium hydroxide (360 mg, 15.0 mmol) in one portion at 25° C. The reaction mixture was stirred at 80° C. for 2 h. The resulting mixture was acidified to pH 6 with HCl (1N) and concentrated under reduced pressure. MeOH (10 mL) was added and the mixture was filtered. The filter cake was washed with MeOH (3×20 mL), and the filtrate was concentrated under reduced pressure. The residue was purified by reverse-phase flash chromatography (10-50% ACN in water with 0.1% formic acid modifier) to afford 2'-chloro-6-cyclopropyl-5'-methoxy-[4,4'-bipyridine]-3-carboxylic acid (880 mg, 58% yield) as a white solid. LCMS: m/z=305 [M+H]$^+$.

Intermediate 36: 4-(6-chloro-3-(difluoromethoxy) pyridazin-4-yl)-6-methylnicotinic acid

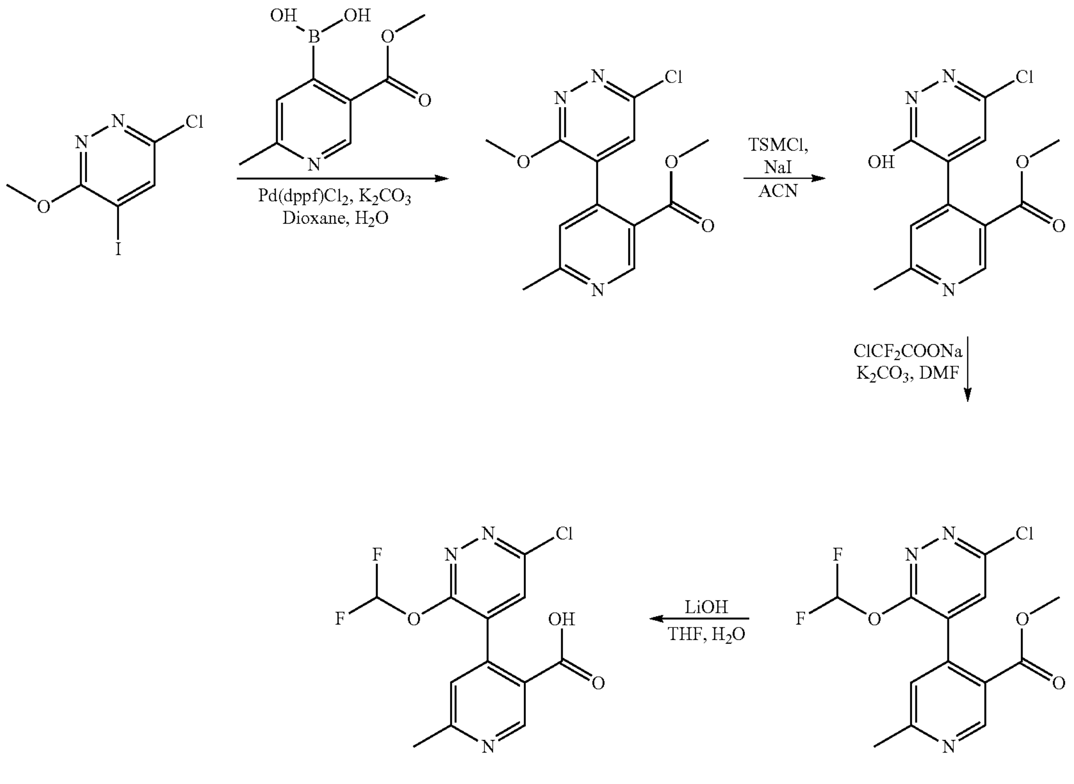

Step 1: Completed as described in Intermediate 2: 4-(5-Cyano-2-methoxyphenyl)-6-methylnicotinic acid step 1 from 6-chloro-4-iodo-3-methoxypyridazine to afford methyl 4-(6-chloro-3-methoxypyridazin-4-yl)-6-methylpyridine-3-carboxylate (800 mg, 74% yield) as a brown solid. LCMS: m/z=294 [M+H]$^+$.

Step 2: To a solution of methyl 4-(6-chloro-3-methoxypyridazin-4-yl)-6-methylpyridine-3-carboxylate (800 mg, 2.7 mmol) in ACN (10 mL) was added NaI (106 mg, 4.1 mmol) and TMSCl (444 mg, 4.1 mmol) in one portion at 25° C. The reaction was stirred at 80° C. for 3 h under a nitrogen atmosphere. The mixture was cooled to 25° C. and the resulting mixture was concentrated under reduced pressure. The residue was purified by silica gel column chromatography, eluting with PE/EA (1/1) to afford methyl 4-(6-chloro-3-hydroxypyridazin-4-yl)-6-methylpyridine-3-carboxylate (300 mg, 39% yield) as a light brown solid. LCMS: m/z=280 [M+H]$^+$.

Step 3: To a solution of methyl 4-(6-chloro-3-hydroxypyridazin-4-yl)-6-methylpyridine-3-carboxylate (300 mg, 1.1 mmol) in DMF (5 mL) was added sodium chlorodifluoroacetate (245 mg, 1.6 mmol) and $K_2CO_3$ (445 mg, 3.2 mmol) in one portion at 25° C. The reaction was stirred at 50° C. for 16 h under a nitrogen atmosphere. The mixture was cooled to 25° C., the mixture was filtered, and the filter cake was washed with MeOH (2×10 mL). The filtrate was concentrated under reduced pressure. The residue was purified by reverse-phase flash chromatography (10-70% MeCN in water with 0.1% formic acid modifier) to afford methyl 4-(6-chloro-3-(difluoromethoxy)pyridazin-4-yl)-6-methylnicotinate (200 mg, 57% yield) as a light brown solid. LCMS: m/z=330 [M+H]$^+$.

Step 4: A solution of methyl 4-(6-chloro-3-(difluoromethoxy)pyridazin-4-yl)-6-methylnicotinate (180 mg, 0.5 mmol) and LiOH (39 mg, 1.6 mmol) in THF (15 mL) and $H_2O$ (5 mL) was stirred at 25° C. for 8 h. The mixture was acidified to pH 2 with 1 N HCl aqueous solution. The resulting mixture was concentrated under reduced pressure. The residue was purified by reverse-phase flash chromatography (10-70% MeCN in water with 0.1% formic acid modifier) to afford 4-(6-chloro-3-(difluoromethoxy) pyridazin-4-yl)-6-methylnicotinic acid (50 mg, 29% yield) as an off-white solid. LCMS: m/z=316 [M+H]$^+$.

Intermediate 37: 5-(difluoromethyl)-2-methylpridine-3-carboxylic acid

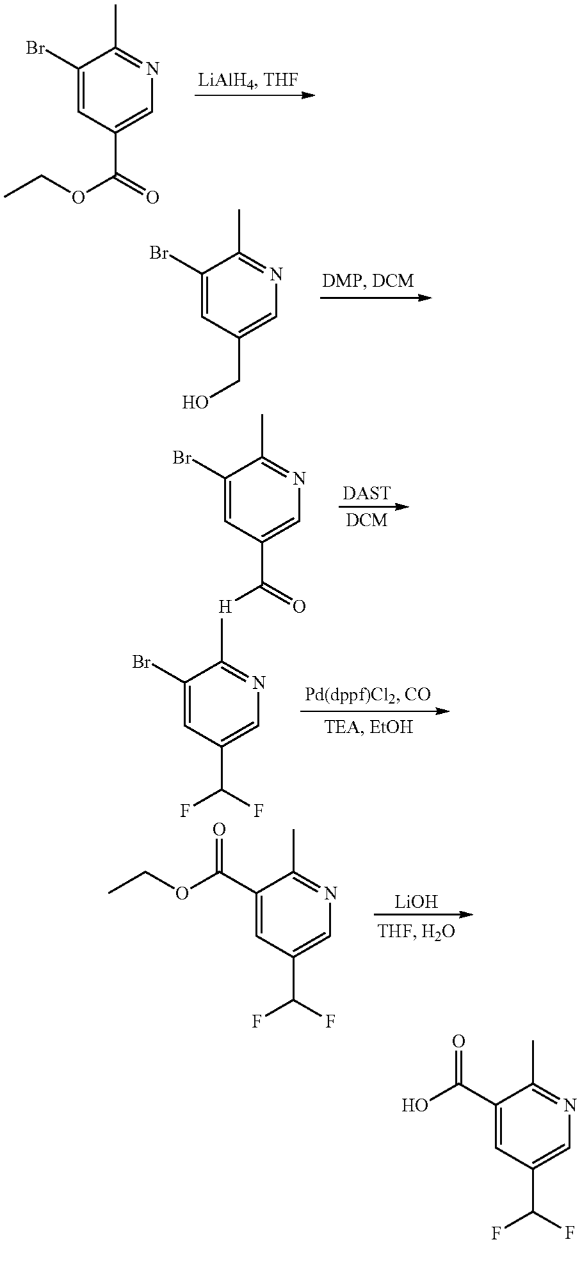

Step 1: To a stirred solution of ethyl 5-bromo-6-methylpyridine-3-carboxylate (1.0 g, 4.0 mmol) in THF (10 mL) was added $LiAlH_4$ (155 mg, 4.0 mmol) dropwise at 0° C. under a nitrogen atmosphere. The reaction mixture was stirred at 0° C. for 4 h under nitrogen atmosphere. The reaction was quenched with $Na_2SO_4 \cdot 10H_2O$ at 0° C. and the mixture was stirred at 0° C. for 10 minutes. The resulting mixture was filtered and the filter cake was washed with $Et_2O$ (3×10 mL). The filtrate was concentrated under reduced pressure and the residue was purified by reverse-phase flash chromatography (10-50% MeCN in water with 0.1% formic acid modifier) to afford (5-bromo-6-methylpyridin-3-yl)methanol (580 mg, 70% yield) as a light yellow oil. LCMS: m/z=202 $[M+H]^+$.

Step 2: To a stirred solution of (5-bromo-6-methylpyridin-3-yl)methanol (560 mg, 2.7 mmol) in DCM (6 mL) was added DMP (1410 mg, 3.3 mmol) in sequence at 0° C. under a nitrogen atmosphere. The reaction mixture was stirred at 0° C. for 4 h under a nitrogen atmosphere. After filtration, the filter cake was washed with $Et_2O$ (3×10 mL). The filtrate was concentrated under reduced pressure. The residue was purified by reverse-phase flash chromatography (10-50% MeCN in water with 0.1% formic acid modifier) to afford 5-bromo-6-methylpyridine-3-carbaldehyde (320 mg, 58% yield) as a light yellow oil. LCMS: m/z=200 $[M+H]^+$.

Step 3: Completed as described in Intermediate 29: 3-chloro-6-(difluoromethyl)picolinic acid step 3 from 5-bromo-6-methylpyridine-3-carbaldehyde to afford 3-bromo-5-(difluoromethyl)-2-methylpyridine (180 mg, 58% yield) as a light yellow oil. LCMS: m/z=222 $[M+H]^+$.

Step 4: Completed as described in Intermediate 30: 4-(difluoromethyl)-5-methoxypyrimidine-2-carboxylic acid step 2 from 3-bromo-5-(difluoromethyl)-2-methylpyridine to afford ethyl 5-(difluoromethyl)-2-methylpyridine-3-carboxylate (100 mg, 64% yield) as a white solid. LCMS: m/z=216 $[M+H]^+$.

Step 5: Completed as described in Intermediate 29: 3-chloro-6-(difluoromethyl)picolinic acid step 4 from ethyl 5-(difluoromethyl)-2-methylpyridine-3-carboxylate to afford 5-(difluoromethyl)-2-methylpyridine-3-carboxylic acid (80 mg, 92% yield) as a yellow solid. LCMS: m/z=188 $[M+H]^+$.

Intermediate 38: 2-methoxy-5-(trifluoromethyl)pyrimidine-4-carboxylicacid

Intermediate 39: 4-methoxy-5-(trifluoromethyl)pyrimidine-2-carboxylicacid

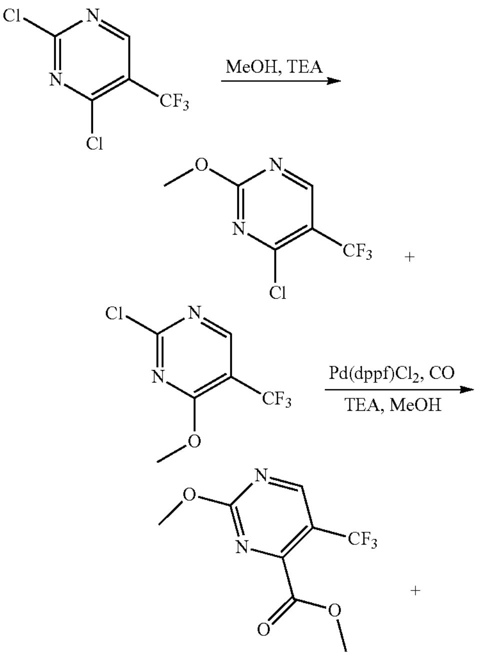

-continued

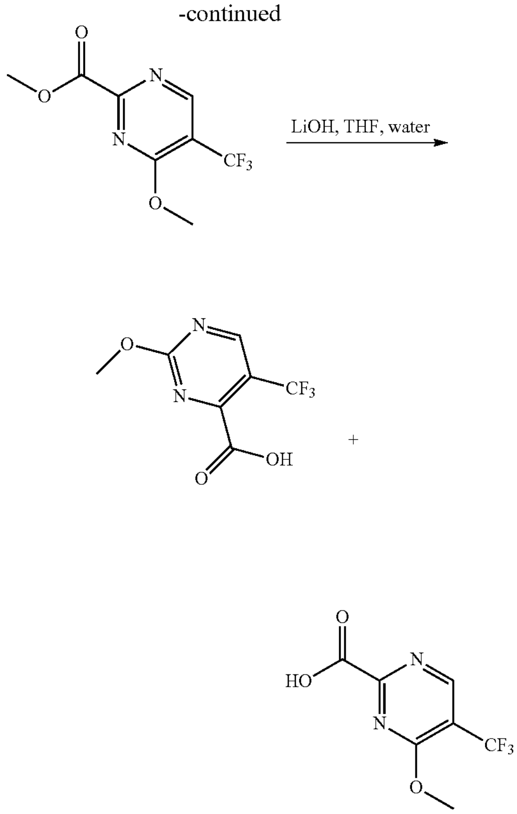

Step 1: A solution of 2,4-dichloro-5-(trifluoromethyl) pyrimidine (1.00 g, 5.00 mmol) and TEA (0.70 g, 7.00 mmol) in $CH_3OH$ (10 mL) was stirred for 3 h at 25° C. under a nitrogen atmosphere. The resulting mixture was diluted with water (50 ml) and the aqueous layer was extracted with EtOAc (3×100 ml). The combined organic layers were washed with brine (2×50 mL) and dried over anhydrous $Na_2SO_4$. After filtration, the filtrate was concentrated under reduced pressure to afford 4-chloro-2-methoxy-5-(trifluoromethyl)pyrimidine and 2-chloro-4-methoxy-5-(trifluoromethyl)pyrimidine (400 mg, mix) as an off-white solid. The crude product was used in the next step directly without further purification. $^1H$ NMR (300 MHz, DMSO-$d_6$) δ 9.04 (q, J=0.9 Hz, 1H), 8.87 (q, 0.1=1.0 Hz, 1H), 4.09 (s, 3H), 4.04 (s, 3H).

Step 2: Completed as described in Intermediate 30: 4-(difluoromethyl)-5-methoxypyrimidine-2-carboxylic acid step 2 from the mixture of 4-chloro-2-methoxy-5-(trifluoromethyl)pyrimidine and 2-chloro-4-methoxy-5-(trifluoromethyl)pyrimidine to afford methyl 4-methoxy-5-(trifluoromethyl)pyrimidine-2-carboxylate and methyl 2-methoxy-5-(trifluoromethyl)pyrimidine-4-carboxylate (300 mg, mix) as an off-white solid. The crude product was used in the next step directly without further purification. $^1H$ NMR (300 MHz, DMSO-$d_6$) δ 9.23 (s, 1H), 4.04 (s, 3H), 3.96 (s, 3H).

Step 3: Completed as described in Intermediate 29: 3-chloro-6-(difluoromethyl)picolinic acid step 4 from the mixture of methyl 4-methoxy-5-(trifluoromethyl)pyrimidine-2-carboxylate and methyl 2-methoxy-5-(trifluoromethyl)pyrimidine-4-carboxylate to afford 2-methoxy-5-(trifluoromethyl)pyrimidine-4-carboxylic acid and 4-methoxy-5-(trifluoromethyl)pyrimidine-2-carboxylic acid (40 mg, mix) as a white solid. The crude product was used in the next step directly without further purification. LCMS: m/z=223 $[M+H]^+$.

Intermediate 40: 3,6-dimethyl-4-(trifluoromethyl)picolinic acid

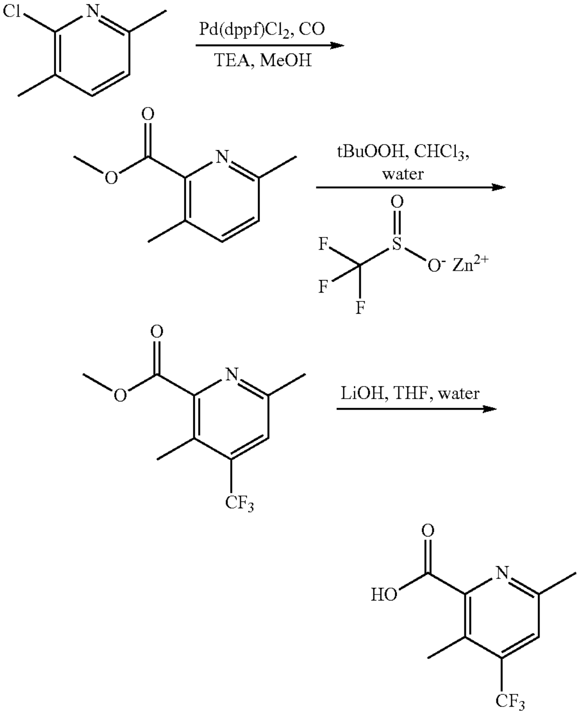

Step 1: Completed as described in Intermediate 30: 4-(difluoromethyl)-5-methoxypyrimidine-2-carboxylic acid step 2 from 2-chloro-3,6-dimethylpyridine to afford methyl 3,6-dimethylpicolinate (1 g, 40%) as yellow liquid. LCMS: m/z=166 $[M+H]^+$. $^1H$ NMR (400 MHz, DMSO-$d_6$) δ 7.65 (d, J=7.9 Hz, 1H), 7.34 (d, J=8.0 Hz, 1H), 3.86 (d, J=1.2 Hz, 3H), 2.46 (s, 3H), 2.39 (s, 3H).

Step 2: To a solution of methyl 3,6-dimethylpicolinate (1 g, 6 mmol) in $CHCl_3$ (60 mL) and water (20 mL) was added zinc trifluoromethanesulfonate (4 g, 2.00 eq) and tert-butyl hydroperoxide (2 g, 70%, 0.02 mol). The mixture was stirred at 50° C. for 16 h. The mixture was cooled to room temperature and quenched with saturated sodium bicarbonate solution and extracted with DCM (100 mL×3). The combined organic layers were washed with brine (2×100 mL) and dried over anhydrous $Na_2SO_4$. After filtration, the filtrate was concentrated under reduced pressure. The residue was purified by silica gel column chromatography, eluting with Petroleum ether/EtOAc (0-20% gradient in 30 min) to afford methyl 3,6-dimethyl-4-(trifluoromethyl)picolinate (500 mg, 40%) as yellow liquid. LCMS: m/z=234 $[M+H]^+$. $^1H$ NMR (400 MHz, DMSO-$d_6$) δ 7.77 (s, 1H), 3.91 (s, 3H), 2.56 (s, 3H), 2.40 (s, 3H), $^{19}F$ NMR (377 MHz, DMSO-$d_6$) δ -62.02.

Step 3: Completed as described in Intermediate 29: 3-chloro-6-(difluoromethyl)picolinic acid step 4 from methyl 3,6-dimethyl-4-(trifluoromethyl)picolinate to afford 3,6-dimethyl-4-(trifluoromethyl)picolinic acid (500 mg, crude) as a white solid. The crude product was used in the next step directly without further purification. LCMS: m/z=220 $[M+H]^+$.

TABLE W

| The following intermediates were prepared using a similar procedure to that described for Intermediate 40 | | | |
|---|---|---|---|
| Intermediate Number | Structure | Compound Name | LCMS |
| 41 | 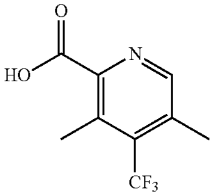 | 3,5-dimethyl-4-(trifluoromethyl)picolinic acid | 220 |
| 42 | 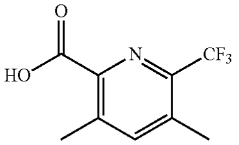 | 3,5-dimethyl-6-(trifluoromethyl)picolinic acid | 220 |
| 43 | 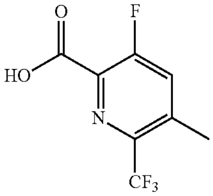 | 3-fluoro-5-methyl-6-(trifluoromethyl)picolinic acid | 224 |

Intermediate 44: 5-Cyano-3-methyl-6-(trifluoromethyl)picolinic acid

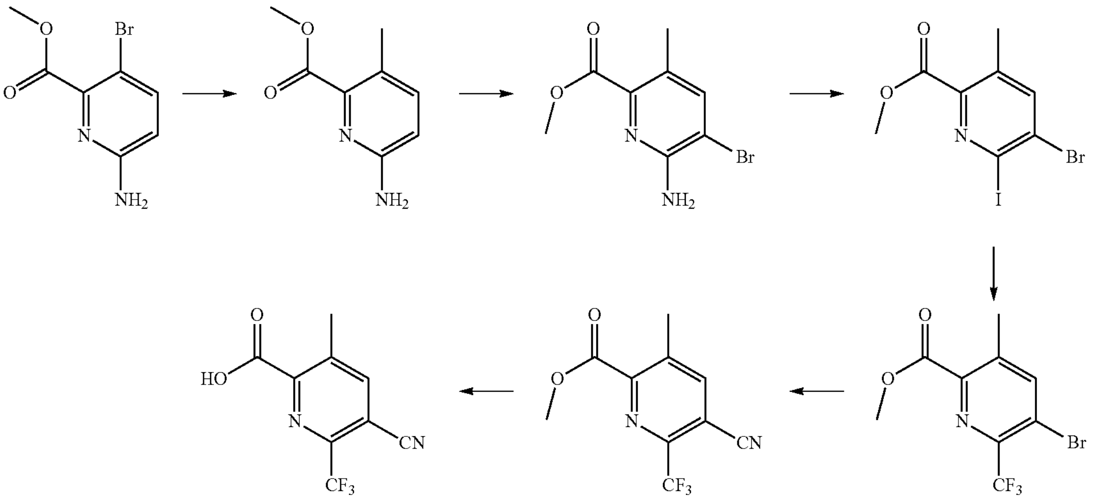

Step 1: To a solution of methyl 6-amino-3-bromopicolinate (6.4 g, 28 mmol) in 1,4-dioxane (60 mL) was added $K_2CO_3$ (11 g, 83 mmol), 2,4,6-trimethyl-1,3,5,2,4,6-trioxatriborinane (50 wt % in THF, 21 g, 83 mmol), and Pd(dppf) $Cl_2$. DCM (2.3 g, 2.8 mmol) and the mixture was heated at 115° C. under $N_2$ for 4 h in a sealed tube. The mixture was diluted with water (50 mL), extracted with EtOAc (5×50 mL), and the combined organic layers were dried over $Na_2SO_4$, filtered, and concentrated under reduced pressure. The residue was purified by silica gel chromatography (Pet. ether/EtOAc=10/1 to 5/1 to 3/1 to 1/1, v/v) to give methyl 6-amino-3-methylpicolinate (3.4 g, 70%) as a yellow oil. LCMS: m/z=167 $[M+H]^+$. $^1H$ NMR (400 MHz, DMSO-$d_6$) δ 7.32 (d, J=8.4 Hz, 1H), 6.54 (d, J=8.4 Hz, 1H), 5.98 (s, 2H), 3.77 (s, 3H), 2.21 (s, 3H).

Step 2: To a solution of methyl 6-amino-3-methylpicolinate (3.4 g, 20 mmol) in $CHCl_3$ (120 mL) was added a solution of bromine (4.9 g, 31 mmol) in $CHCl_3$ (15 mL) and the mixture was stirred at 25° C. for 16 h. The mixture was diluted with water (150 mL), extracted with DCM (5×50 mL), and the combined organic layers were dried over $Na_2SO_4$, filtered, and concentrated under reduced pressure. The residue was purified by silica gel chromatography (Pet. ether/EtOAc=10/1 to 5/1 to 3/1, v/v) to give methyl 6-amino-5-bromo-3-methylpicolinate (3.67 g, 70%) as an off-white solid. LCMS: m/z=245 $[M+H]^+$. $^1H$ NMR (400 MHz, DMSO-$d_6$) δ 7.76 (s, 1H), 6.30 (s, 2H), 3.79 (s, 3H), 2.24 (s, 3H).

Step 3: To a solution of methyl 6-amino-5-bromo-3-methylpicolinate (2.0 g, 8.2 mmol) in MeCN (80 mL) at 0° C. was added CuI (3.1 g, 16 mmol) and isopentyl nitrite (2.1 g, 18 mmol) and the mixture was stirred at 0° C. for 1 h then heated at 60° C. for 16 h. The mixture was diluted with water (50 mL), extracted with EtOAc (5×50 mL), and the combined organic layers were dried over $Na_2SO_4$, filtered, and concentrated under reduced pressure. The residue was purified by silica gel chromatography (Pet. ether/EtOAc=I/O to 10/1 to 5/1, v/v) to give methyl 5-bromo-6-iodo-3-methylpicolinate (606 mg, 20%) as a yellow solid. LCMS: m/z=356 $[M+H]^+$. $^1H$ NMR (400 MHz, DMSO-$d_6$) δ 8.15 (s, 1H), 3.86 (s, 3H), 2.39 (s, 3H).

with EtOAc (3×15 mL), and the combined organic layers were washed with water (15 mL), dried over $Na_2SO_4$, filtered, and concentrated under reduced pressure. The residue was purified by prep-TLC (Pet. ether/DCM=1/1, v/v) to give methyl 5-cyano-3-methyl-6-(trifluoromethyl)picolinate (17 mg, 41%) as a white solid. $^1H$ NMR (400 MHz, DMSO-$d_6$) δ 8.77 (s, 1H), 3.94 (s, 3H), 2.58 (s, 3H).

Step 6: Completed as described in Intermediate 29: 3-chloro-6-(difluoromethyl)picolinic acid step 4 from methyl 5-cyano-3-methyl-6-(trifluoromethyl)picolinate to afford 5-cyano-3-methyl-6-(trifluoromethyl)picolinic acid (18 mg, 84%) as a white solid, which was used directly for the next step. LCMS: m/z=229 $[M-H]^-$. $^1H$ NMR (400 MHz, DMSO-$d_6$) δ 8.29 (s, 1H), 2.33 (s, 3H).

Intermediate 45: 2'-Chloro-3'-fluoro-5'-methoxy-6-methyl-[4,4'-bipyridine]-3-carboxylic acid

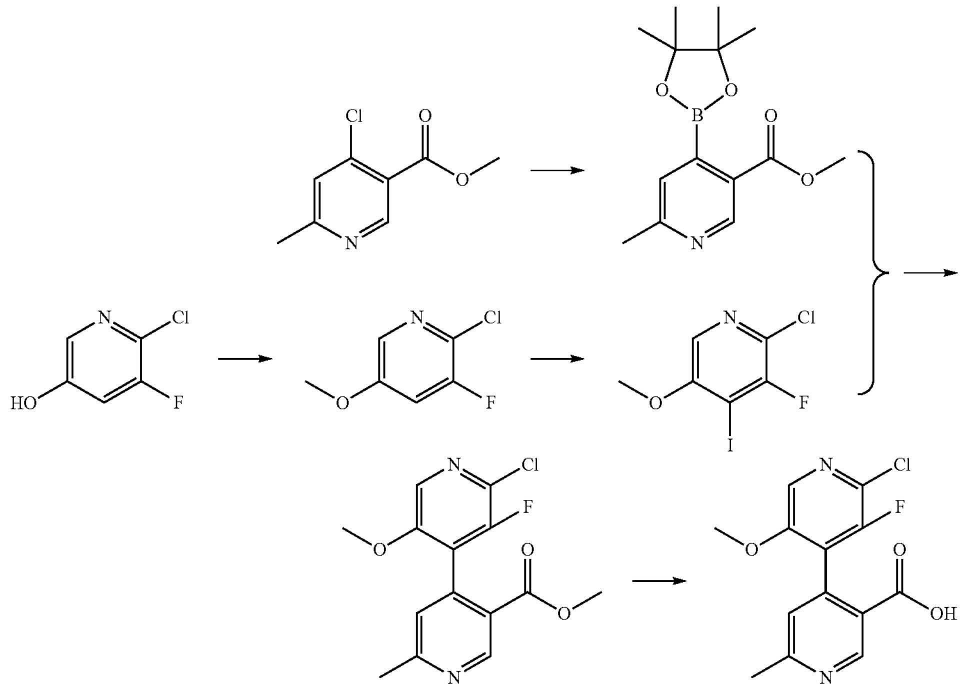

Step 4: To a solution of methyl 5-bromo-6-iodo-3-methylpicolinate (600 mg, 1.69 mmol) in NMP (8 mL) was added methyl 2,2-difluoro-2-(fluorosulfonyl)acetate (971 mg, 5.06 mmol) and CuI (64.2 mg, 0.337 mmol) and the mixture was heated at 80° C. for 16 h. The mixture was diluted with water (30 mL), extracted with EtOAc (3x30 mL), and the combined organic layers were washed with water (100 mL), dried over $Na_2SO_4$, filtered, and concentrated under reduced pressure. The residue was purified by prep-TLC (Pet. ether/DCM=1/1, v/v) to give methyl 5-bromo-3-methyl-6-(trifluoromethyl)picolinate (146 mg, 26%) as a yellow solid. LCMS: m/z=298 $[M+H]^+$. $^1H$ NMR (400 MHz, DMSO-$d_6$) δ 8.51 (s, 1H), 3.90 (s, 3H), 2.54 (s, 3H).

Step 5: To a solution of methyl 5-bromo-3-methyl-6-(trifluoromethyl)picolinate (43 mg, 0.14 mmol) in DMF (1 mL) was added zinc (2.4 mg, 0.036 mmol), $Zn(CN)_2$ (10 mg, 0.087 mmol) and $Pd(dppf)Cl_2$ (5.3 mg, 7.2 μmol) and the mixture was heated at 120° C. under $N_2$ for 16 h in a sealed tube. The mixture was diluted with water (10 mL), extracted Step 1: To a solution of methyl 4-chloro-6-methylnicotinate (5.00 g, 26.9 mmol), bis(pinacolato)diboron (20.5 g, 80.8 mmol), and KOAc (15.9 g, 162 mmol) in dioxane (100, mL) was added $Pd(dppf)Cl_2$ (2.96 g, 4.04 mmol) and the mixture was heated at 100° C. for 2 h under $N_2$. The mixture was diluted with water (25 mL), extracted with DCM (6×20 mL), and the combined organic layers were dried over $Na_2SO_4$, filtered, and concentrated under reduced pressure. The residue was purified by silica gel chromatography (DCM to DCM/MeOH=100/1, v/v) to afford methyl 6-methyl-4-(4,4,5,5-tetramethyl-1,3,2-dioxaborolan-2-yl) nicotinate (3.00 g, 38%) as a white solid. LCMS: m/z=196 $[M-C_6H_{12}+3H]^+$. $^1H$ NMR (400 MHz, DMSO-$d_6$) δ 8.93-8.88 (m, 1H), 7.36 (s, 1H), 3.87 (s, 3H), 2.54 (s, 3H), 1.33 (s, 12H).

Step 2: To a solution of 6-chloro-5-fluoropyridin-3-ol (1.00 g, 6.78 mmol) and $K_2CO_3$ (1.87 g, 13.6 mmol) in acetone (10 mL) at 0° C. was added MeI (1.15 g, 8.13 mmol) and the mixture was stirred at 25° C. for 16 h. The mixture was diluted with water (20 mL), extracted with DCM (5×20 mL), and the combined organic layers were dried over $Na_2SO_4$, filtered, and concentrated under reduced pressure. The residue was purified by silica gel chromatography (Pet. ether to Pet. ether/EtOAc=10/1, v/v) to afford 2-chloro-3-fluoro-5-methoxypyridine (900 mg, 82%) as colorless oil. LCMS: m/z=162 $[M+H]^+$. $^1H$ NMR (400 MHz, DMSO-$d_6$) δ 8.04 (d, J=2.6 Hz, 1H), 7.70 (dd, J=10.4, 2.6 Hz, 1H), 3.86 (s, 3H).

Step 3: To a solution of 2-chloro-3-fluoro-5-methoxypyridine (4.84 g, 30.0 mmol) in THF (80 mL) at −78° C. under $N_2$ was added n-butyllithium (2.5 M in hexane, 14.4 mL, 35.9 mmol) dropwise and the mixture was stirred at −78° C. for 0.5 h. Iodine (9.88 g, 38.9 mmol) was added and stirring was continued at −78° C. for 2 h, then at room temperature for 16 h. The reaction was quenched with a saturated aqueous sodium thiosulfate solution and the mixture was extracted with EtOAc (10×80 mL). The combined organic layers were washed with brine (5×100 mL), dried over $Na_2SO_4$, filtered, and concentrated under reduced pressure to afford 2-chloro-3-fluoro-4-iodo-5-methoxypyridine (8.1 g, 94%) as a brown solid. LCMS: m/z=288 $[M+H]^+$. $^1H$ NMR (400 MHz, DMSO-$d_6$) δ 7.94 (s, 1H), 3.99 (s, 3H).

Step 4: Completed as described in Intermediate 2: 4-(5-Cyano-2-methoxyphenyl)-6-methylnicotinic acid step 1 from 2-chloro-3-fluoro-4-iodo-5-methoxypyridine and methyl 6-methyl-4-(4,4,5,5-tetramethyl-1,3,2-dioxaborolan-2-yl)nicotinate to afford methyl 2'-chloro-3'-fluoro-5'-methoxy-6-methyl-[4,4'-bipyridine]-3-carboxylate (200 mg, 93%) as a yellow oil. LCMS m/z=311 $[M+H]^+$. $^1H$ NMR (400 MHz, DMSO-$d_6$) δ 9.04 (s, 1H), 8.23 (s, 1H), 7.44 (s, 1H), 3.83 (s, 3H), 3.70 (s, 3H), 2.59 (s, 3H).

Step 5: Completed as described in Intermediate 1: 4-(2-Methoxyphenyl)-6-methylnicotinic acid from methyl 2'-chloro-3'-fluoro-5'-methoxy-6-methyl-[4,4'-bipyridine]-3-carboxylate to afford 2'-chloro-3'-fluoro-5'-methoxy-6-methyl-[4,4'-bipyridine]-3-carboxylic acid (100 mg, 53%) as a white solid. LCMS: m/z=297.15 $[M+H]^+$. $^1H$ NMR (400 MHz, DMSO-$d_6$) δ 9.03 (s, 1H), 8.22 (s, 1H), 7.39 (s, 1H), 3.84 (s, 3H), 2.57 (s, 3H).

Intermediate 46: (1s,3s)-3-(Difluoromethoxy)cyclobutane-1-carboxylic acid

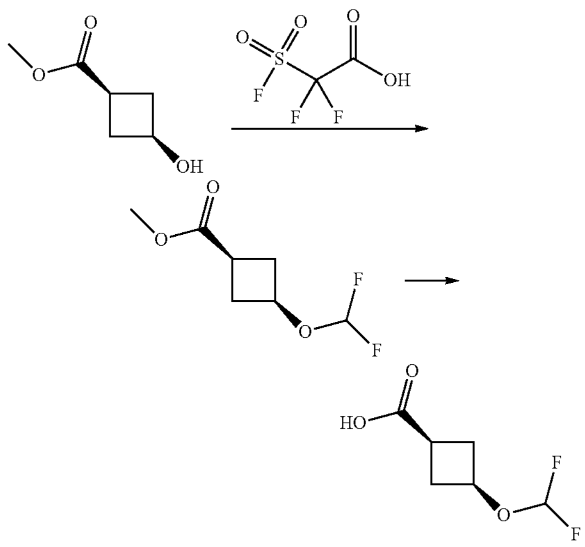

Step 1: To a solution of methyl (1s,3s)-3-hydroxycyclobutane-1-carboxylate (800 mg, 6.15 mmol) in MeCN (10 mL) was added CuI (234 mg, 1.23 mmol) and a solution of 2,2-difluoro-2-(fluorosulfonyl)acetic acid (1.31 g, 7.38 mmol) in MeCN (2 mL) and the mixture was heated at 50° C. for 3 h. The mixture was diluted with water (100 mL), extracted with EtOAc (50 mL×3) and the combined organic layers were washed with brine, dried over $Na_2SO_4$, filtered, and concentrated under reduced pressure to afford methyl (1s,3s)-3-(difluoromethoxy)cyclobutane-1-carboxylate (900 mg, 81%), which was used without further purification. $^1H$ NMR (400 MHz, DMSO-$d_6$) δ 6.81-6.41 (m, 1H), 5.27 (t, J=7.4 Hz, 1H), 3.62 (s, 3H), 2.86 (s, 1H), 2.36 (ddt, J=12.4, 7.0, 2.2 Hz, 2H), 2.19-2.16 (m, 2H).

Step 2: To a solution of methyl (1s,3s)-3-(difluoromethoxy)cyclobutane-1-carboxylate (932 mg, 5.17 mmol) in THF (10 mL) and water (2 mL) was added LiOH (285 mg, 11.9 mmol) and the mixture was stirred at room temperature for 16 h. The mixture was adjusted to pH 3 with 2 M aqueous HCl and concentrated under reduced pressure. The residue was dissolved in DCM/MeOH (15/1), filtered, and the filtrate concentrated under reduced pressure to afford (1s,3s)-3-(difluoromethoxy)cyclobutane-1-carboxylic acid (500 mg, 58%), which was used without further purification.

Intermediate 47: (1s,3s)-3-(Trifluoromethoxy)cyclobutane-1-carboxylic acid

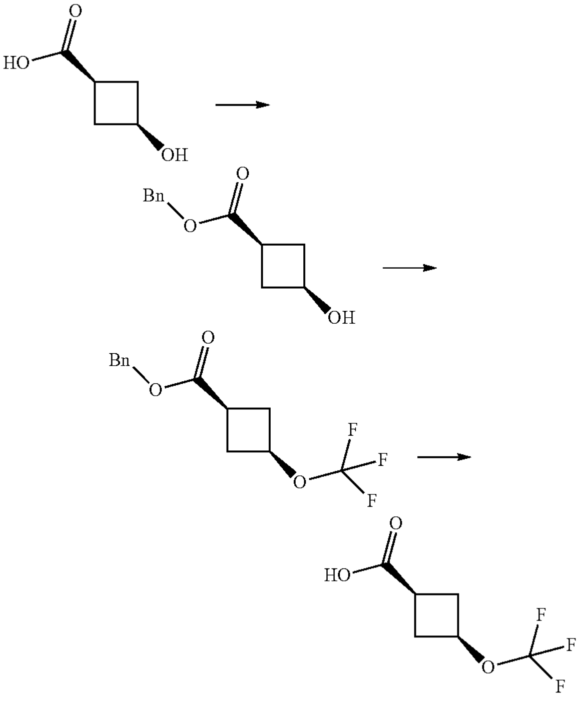

Step 1: To a solution of (1s,3s)-3-hydroxycyclobutane-1-carboxylate acid (200 mg, 1.72 mmol) in DMF (3 mL) was added $NaHCO_3$ (434 mg, 5.17 mmol) and benzyl bromide (442 mg, 2.58 mmol) and the mixture was stirred at room temperature overnight. The mixture was diluted with water (15 mL), exacted with EtOAc (30 mL×3), and the combined organic layers were washed with water (10 mL), brine (10 mL), dried over $Na_2SO_4$, filtered, and concentrated under reduced pressure to afford benzyl (1s,3s)-3-hydroxycyclobutane-1-carboxylate (308 mg, 86%) as a yellow oil. $^1$H NMR (400 MHz, DMSO-$d_6$) δ 7.35 (tdd, J=10.4, 6.4, 3.8 Hz, 5H), 5.19 (d, J=7.0 Hz, 1H), 5.08 (s, 2H), 3.97 (td, J=8.4, 6.8 Hz, 1H), 2.61 (ddd, J=10.0, 7.8, 2.2 Hz, 1H), 2.40 (tdd, J=7.6, 6.0, 2.8 Hz, 2H), 2.02-1.92 (m, 2H).

Step 2: To a solution of silver trifluoromethanesulfonate (2.24 g, 8.73 mmol), 1-chloromethyl-4-fluoro-1,4-diazoniabicyclo[2.2.2]octane bis(tetrafluoroborate) (1.16 g, 3.27 mmol), and potassium fluoride (5.08 g, 8.73 mmol) in EtOAc (10 mL) was added benzyl (1s,3s)-3-hydroxycyclobutane-1-carboxylate (450 mg, 2.18 mmol), 2-fluoropyridine (847 mg, 8.73 mmol), and (trifluoromethyl)trimethylsilane (775 mg, 5.45 mmol). The mixture was stirred at room temperature for 24 h under a $N_2$ atmosphere in the dark. The mixture was diluted with water (15 mL), extracted with EtOAc (50 mL×2), and the combined organic layers washed with water (10 mL), brine (10 mL), dried over $Na_2SO_4$, filtered, and concentrated under reduced pressure. The residue was purified by prep-TLC (Pet. ether/EtOAc=5/1, v/v) to afford benzyl (1s,3s)-3-(trifluoromethoxy)cyclobutane-1-carboxylate (320 mg, 27%) as a yellow solid. $^1$H NMR (400 MHz, Chloroform-d) δ 7.41-7.31 (m, 5H), 5.14 (s, 2H), 4.57 (p, J=7.6 Hz, 1H), 2.82-2.70 (m, 1H), 2.68-2.58 (m, 2H), 2.58-2.48 (m, 2H).

Step 3: To a solution of benzyl (1s,3s)-3-(trifluoromethoxy)cyclobutane-1-carboxylate (320 mg, 1.17 mmol) in EtOH (5 mL) was added 10% Pd/C (320 mg) and the mixture was stirred at room temperature overnight under a $H_2$ atmosphere. The mixture was filtered and the filtrate concentrated under reduced pressure to afford (1s,3s)-3-(trifluoromethoxy)cyclobutane-1-carboxylic acid (190 mg, 88%) as a brown solid. $^1$H NMR (400 MHz, DMSO-$d_6$) δ 4.73 (p, J=7.4 Hz, 1H), 2.73-2.62 (m, 1H), 2.57 (ddd, J=9.6, 7.2, 2.6 Hz, 2H), 2.26 (qd, J=9.6, 9.2, 2.6 Hz, 2H).

-continued

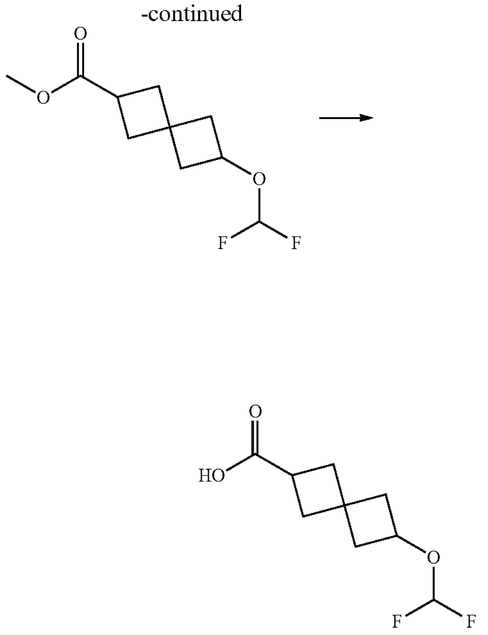

Step 1: To a solution of methyl 6-hydroxyspiro[3.3]heptane-2-carboxylate (50 mg, 0.29 mmol) and KOAc (0.17 g, 1.8 mmol) in DCM/water (1/1, 2 mL) at 0° C. was added (bromodifluoromethyl)trimethylsilane (0.24 g, 1.2 mmol) and the mixture was stirred at 25° C. for 16 h. The mixture was diluted with a saturated aqueous $NaHCO_3$ solution (10 mL), extracted with DCM (2×20 mL), and the combined organic layers were washed with brine (20 mL), dried over $Na_2SO_4$, filtered, and concentrated under reduced pressure. The residue was purified by prep-TLC (Pet. ether/EtOAc=1/1, v/v) to afford methyl 6-(difluoromethoxy)spiro[3.3]heptane-2-carboxylate (30 mg, 46%) as a yellow oil. $^1$H NMR (400 MHz, DMSO-$d_6$) δ 6.57 (t, J=76.0 Hz, 1H), 4.44 (p, J=7.4 Hz, 1H), 3.57 (s, 3H), 3.09-2.99 (m, 1H), 2.48-2.42 (m, 1H), 2.32-2.26 (m, 1H), 2.25-2.14 (m, 4H), 2.10-2.03 (m, 1H), 2.02-1.95 (m, 1H).

TABLE X

The following examples were prepared using a similar procedure to that described for Intermediate 17

| Intermediate Number | Structure | Compound Name | LCMS [M + H]$^+$ | NMR |
|---|---|---|---|---|
| 48 | 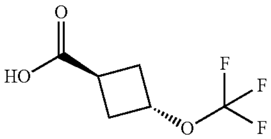 [SMILES: O=C(O)[C@H]1C[C@H](OC(F)(F)F)C1] | (1r,3r)-3-(Trifluoromethoxy)cyclobutane-1-carboxylic acid | N/A | $^1$H NMR (400 MHZ, DMSO-$d^6$) δ 4.90 (p, J = 7.2 Hz, IH), 3.01 (td, J = 9.8, 4.8 Hz, 1H), 2.56-2.50 (m, 2H), 2.47-2.40 (m, 2H) |

Intermediate 49: 6-(Difluoromethoxy)spiro[3.3]heptane-2-carboxylic acid

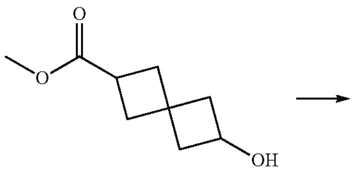

Step 2: To a solution of methyl 6-(difluoromethoxy)spiro[3.3]heptane-2-carboxylate (30 mg, 0.14 mmol) in THF/water (4/1, 2 mL) was added LiOH (9.8 mg, 0.41 mmol) and the mixture was stirred at 25° C. for 2 h then concentrated under reduced pressure to afford 6-(difluoromethoxy)spiro[3.3]heptane-2-carboxylic acid (25 mg, Li salt) as a white solid. $^1$H NMR (400 MHz, DMSO-$d_6$) δ 6.78-6.34 (m, 1H), 4.48-4.35 (m, 1H), 2.57-2.52 (M, 1H), 2.42-2.31 (m, 1H), 2.28-2.17 (m, 1H), 2.11-2.04 (m, 2H), 2.02-1.95 (m, 2H), 1.93-1.87 (m, 2H).

Intermediate 50: 5-(Difluoromethyl)-3-methoxypyrazine-2-carboxylic acid

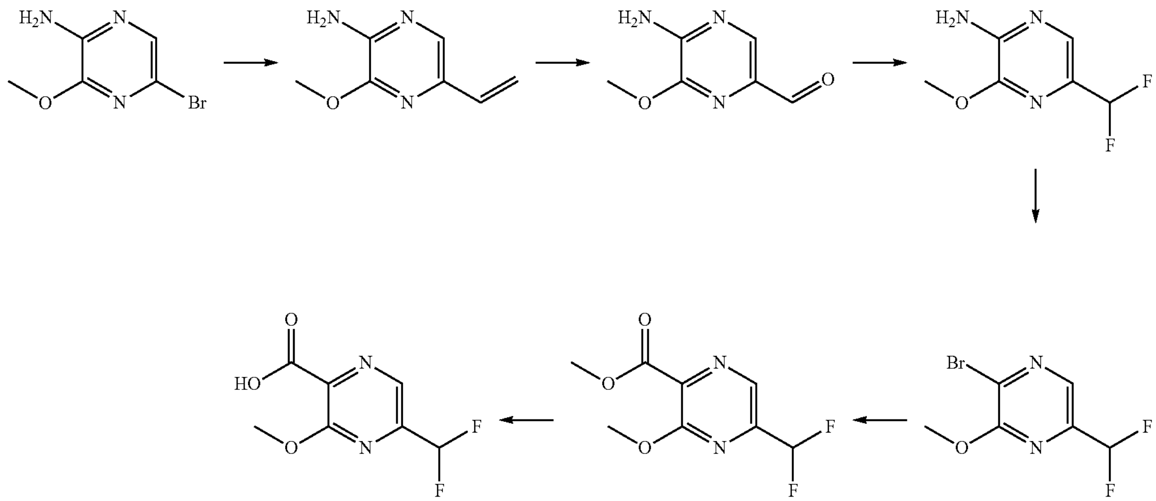

Step 1: To a solution of 5-bromo-3-methoxypyrazin-2-amine (10.0 g, 49.0 mmol) in 1,4-dioxane (100 mL) and water (25 mL) was added potassium trifluoro(vinyl)borate (6.57 g, 49.0 mmol), $K_2CO_3$ (13.6 g, 98.0 mmol), and Pd(dppf)$Cl_2$ (3.59 g, 4.90 mmol) and the mixture was heated at 80° C. for 6 h under $N_2$. The mixture was diluted with water (100 mL), extracted with EtOAc (3×100 mL), and the combined organic layers washed with brine (100 mL), dried over $Na_2SO_4$, filtered, and concentrated under reduced pressure. The residue was purified by silica gel chromatography (Pet. ether/EtOAc=10/1 to 5/1) to give 3-methoxy-5-vinylpyrazin-2-amine (2.58 g, 34%) as a yellow solid. LCMS: m/z=152 $[M+H]^+$. $^1H$ NMR (400 MHz, DMSO-$d_6$) δ 7.46 (s, 1H), 6.64-6.54 (m, 1H), 6.44 (s, 2H), 5.86 (dd, J=17.2, 2.2 Hz, 1H), 5.10 (dd, J=10.6, 2.2 Hz, 1H), 3.92 (s, 3H).

Step 2: To a solution of 3-methoxy-5-vinylpyrazin-2-amine (2.58 g, 17.1 mmol) in THF (40 mL) and water (10 mL) was added 4-methylmorpholine 4-oxide hydrate (2.31 g, 17.1 mmol) and osmium tetraoxide (434 mg, 1.71 mmol) and the mixture was stirred at 25° C. for 2 h. Sodium metaperiodate (14.6 g, 68.3 mmol) was then added and the mixture was stirred at 25° C. for a further 2 h. The mixture was diluted with water (100 mL), extracted with EtOAc (3×100 mL), and the combined organic layers were washed with brine (100 mL), dried over $Na_2SO_4$, filtered, and concentrated under reduced pressure to give 5-amino-6-methoxypyrazine-2-carbaldehyde (2.45 g, 94%) as a brown solid. LCMS: m/z=154 $[M+H]^+$. $^1H$ NMR (400 MHz, DMSO-$d_6$) δ 9.63 (s, 1H), 8.16 (s, 1H), 7.58 (s, 2H), 3.96 (s, 3H).

Step 3: To a solution of 5-amino-6-methoxypyrazine-2-carbaldehyde (2.05 g, 13.4 mmol) in DCM (40 mL) at −78° C. under $N_2$ was added DAST (8.63 g, 53.5 mmol) and the mixture was stirred at −78° C. for 3 h. The mixture was diluted with a saturated aqueous $NaHCO_3$ solution (80 mL), extracted with DCM (3×80 mL), and the combined organic layers were washed with brine (80 mL), dried over $Na_2SO_4$, filtered, and concentrated under reduced pressure. The residue was purified by silica gel chromatography (Pet. ether/EtOAc=2/1, v/v) and prep-TLC (Pet. ether/EtOAc=1/1, v/v) to give 5-(difluoromethyl)-3-methoxypyrazin-2-amine (370 mg, 16%) as a yellow solid. LCMS: m/z=176 $[M+H]^+$. $^1H$ NMR (400 MHz, DMSO-$d_6$) δ 7.73 (t, J=1.8 Hz, 1H), 6.92-6.62 (m, 3H), 3.91 (s, 3H).

Step 4: A mixture of 5-(difluoromethyl)-3-methoxypyrazin-2-amine (430 mg, 2.46 mmol), 48% HBr in water (2 mL), and AcOH (6 mL) was stirred at 5° C. for 0.5 h. Sodium nitrite (508.1 mg, 7.37 mmol) was added and the mixture was stirred at 5° C. for a further 2 h. The mixture was diluted with a saturated aqueous $NaHCO_3$ solution (40 mL), extracted with EtOAc (2×40 mL), and the combined organic layers were washed with brine (40 mL), dried over $Na_2SO_4$, filtered, and concentrated under reduced pressure. The residue was purified by prep-TLC (Pet. ether/EtOAc=15/1, v/v) to give 2-bromo-5-(difluoromethyl)-3-methoxypyrazine (174 mg, 30%) as a yellow oil. $^1H$ NMR (400 MHz, DMSO-$d_6$) δ 8.34 (d, J=1.6 Hz, 1H), 7.25-6.83 (m, 1H), 4.02 (s, 3H).

Step 5: To a solution of 2-bromo-5-(difluoromethyl)-3-methoxypyrazine (100 mg, 0.418 mmol) in MeOH (5 mL) was added $Pd(OAc)_2$ (9.39 mg, 0.042 mmol), 1,1'-ferrocendiylbis(diphenylphosphine) (23.2 mg, 0.042 mmol), and $Et_3N$ (127 mg, 1.26 mmol). The mixture was heated at 85° C. under a CO atmosphere (2 MPa) for 16 h. The mixture was filtered and the filtrate was concentrated under reduced pressure. The residue was purified by pre-TLC (Pet. ether/EtOAc=3/1, v/v) to give methyl 5-(difluoromethyl)-3-methoxypyrazine-2-carboxylate (68 mg, 75%) as a white solid. LCMS: m/z=219 $[M+H]^+$. $^1H$ NMR (400 MHz, DMSO-$d_6$) δ 8.58 (s, 1H), 7.26-6.93 (m, 1H), 4.01 (s, 3H), 3.91 (s, 3H).

Step 6: To a solution of methyl 5-(difluoromethyl)-3-methoxypyrazine-2-carboxylate (30.0 mg, 0.138 mmol) in a mixture of THF (0.5 mL) and water (0.5 mL) was added LiOH (9.88 mg, 0.413 mmol). The mixture was stirred at 25° C. for 2 h then concentrated under reduced pressure to afford 5-(difluoromethyl)-3-methoxypyrazine-2-carboxylic acid (30 mg, Li salt) as a grey solid. $^1H$ NMR (400 MHz, DMSO-$d_6$) δ 8.16 (s, 1H), 7.08-6.76 (m, 1H), 3.85 (s, 3H).

Intermediate 51: 5-(Difluoromethyl)-6-methoxypyrazine-2-carboxylic acid

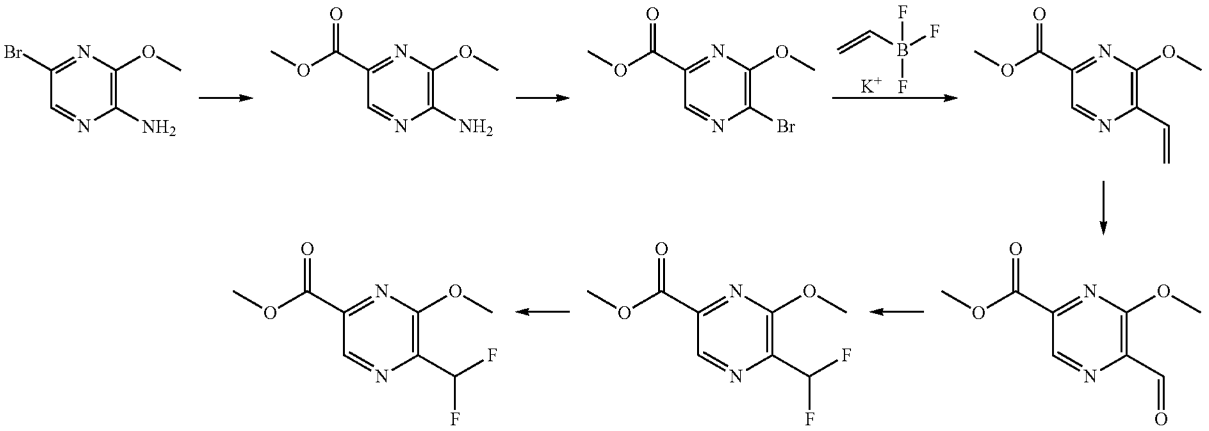

Step 1: To a solution of 5-bromo-3-methoxypyrazin-2-amine (200 mg, 0.980 mmol) in MeOH (10 mL) was added $Et_3N$ (198 mg, 1.96 mmol) and Pd(dppf)$Cl_2$ (35.9 mg, 0.049 mmol). The mixture was heated at 80° C. under a CO atmosphere (1 atm) for 16 h. The mixture was diluted with water (30 mL), extracted with EtOAc (2×30 mL), and the combined organic layers were washed with brine (30 mL), dried over $Na_2SO_4$, filtered, and concentrated under reduced pressure. The residue was purified by prep-TLC (5% MeOH in DCM) to afford methyl 5-amino-6-methoxypyrazine-2-carboxylate (65 mg, 36%) as a yellow solid. LCMS: m/z=184 $[M+H]^+$. $^1H$ NMR (400 MHz, Chloroform-d) δ 8.36 (s, 1H), 4.09 (s, 3H), 3.92 (s, 3H).

Step 2: To a solution of methyl 5-amino-6-methoxypyrazine-2-carboxylate (520 mg, 2.84 mmol) in AcOH (7 mL) at 5° C. was added 48% HBr in water (3 mL) and sodium nitrite (588 mg, 8.52 mmol). The mixture was stirred at 5° C. for 2 h. The mixture was diluted with water (50 mL), extracted with EtOAc (2×50 mL), and the combined organic layers washed with brine (50 mL), dried over $Na_2SO_4$, filtered, and concentrated under reduced pressure. The residue was purified by silica gel chromatography (0-10% EtOAc in Pet. ether) to afford methyl 5-bromo-6-methoxypyrazine-2-carboxylate (300 mg, 43%) as a yellow solid. LCMS: m/z=247 $[M+H]^+$. $^1H$ NMR (400 MHz, DMSO-$d_6$) δ 8.59 (s, 1H), 4.03 (s, 3H), 3.91 (s, 3H).

Steps 3-6 were completed as described in Intermediate 50: 5-(Difluoromethyl)-3-methoxypyrazine-2-carboxylic acid step 1-3 and 6 to afford 5-(difluoromethyl)-6-methoxypyrazine-2-carboxylic acid; LCMS: m/z=203 $[M-H]^-$.

Intermediate 52: 6-(Difluoromethyl)-3-methoxypyrazine-2-carboxylic acid

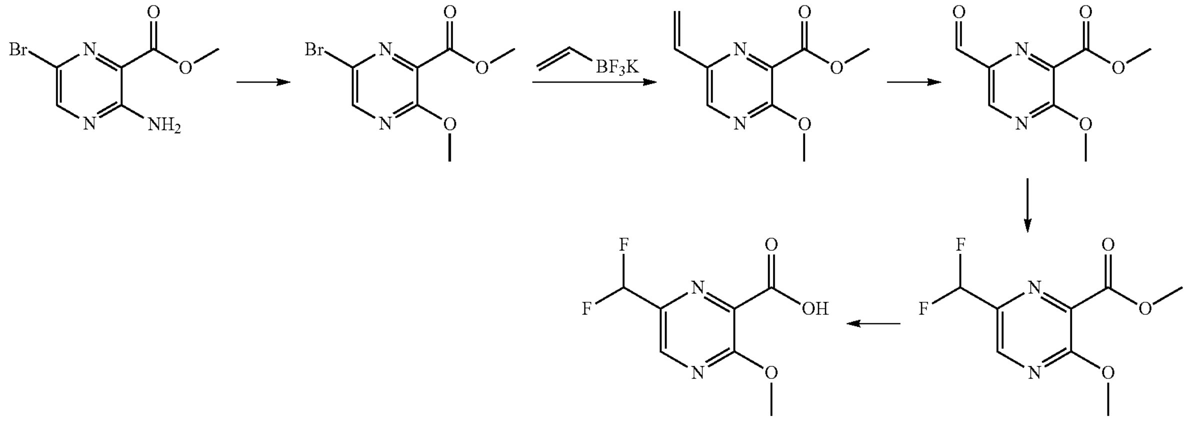

Step 1: To a solution of methyl 3-amino-6-bromopyrazine-2-carboxylate (5 g, 0.02 mol) in conc. $H_2SO_4$ (30 mL) at 0° C. was added sodium nitrite (3 g, 0.04 mol) and the mixture was stirred at 0° C. for 30 min. The mixture was poured into MeOH (270 mL) and heated at reflux for 5 h. The solvent was removed under reduced pressure and the residue diluted with water (100 mL) and extracted with EtOAc (100 mL×2). The combined organic layers were washed with a saturated aqueous $NaHCO_3$ solution (50 mL), water (50 mL), dried over $Na_2SO_4$, filtered, and concentrated under reduced pressure. The residue was purified by silica gel chromatography (Pet. ether/EtOAc=5/1, v/v) to give methyl 6-bromo-3-methoxypyrazine-2-carboxylate (1.6 g, 32%) as an off-white solid. LCMS: m/z=247 $[M+H]^+$. $^1$H NMR (400 MHz, Chloroform-d) δ 8.38 (s, 1H), 4.06 (s, 3H), 3.98 (s, 3H).

Steps 2-5 were completed starting from methyl 6-bromo-3-methoxypyrazine-2-carboxylate as described in Intermediate 50: 5-(Difluoromethyl)-3-methoxypyraine-2-carboxylic acid step 1-3 and 6 to afford 6-(Difluoromethyl)-3-methoxypyrazine-2-carboxylic acid; LCMS: m/z=205 $[M+H]^+$; $^1$H NMR (400 MHz, DMSO-$d_6$) δ 8.31 (s, 1H), 6.96 (t, J=54.6 Hz, 1H), 3.90 (s, 3H).

-continued

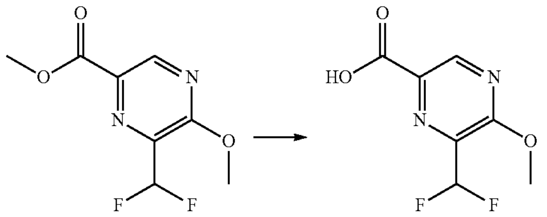

TABLE Y

The following intermediates were prepared using a similar procedure to that described for Intermediate 52 following steps 2-5.

| Intermediate Number | Structure | Compound Name | LCMS $[M + H]^+$ | NMR |
|---|---|---|---|---|
| 53 | 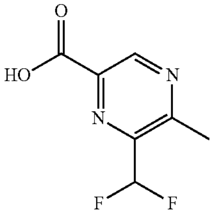 | 5-(Difluoromethyl)-6-methylpyrazine-2-carboxylic acid 6-(difluoromethyl)-5-methylpyrazine-2-carboxylic acid | 189 | $^1$H NMR (400 MHz, DMSO-$d_6$) δ 8.85 (s, IH), 7.10 (t, J = 53.6 Hz, 1H), 2.63 (s, 3H). $^1$H NMR (400 MHz, DMSO-$d_6$) δ 8.98 (s, 1H), 7.08 (t, J = 53.8 Hz, 1H), 2.62 (s, 3H). |

Intermediate 55: 6-(Difluoromethyl)-5-methoxypyrazine-2-carboxylic acid

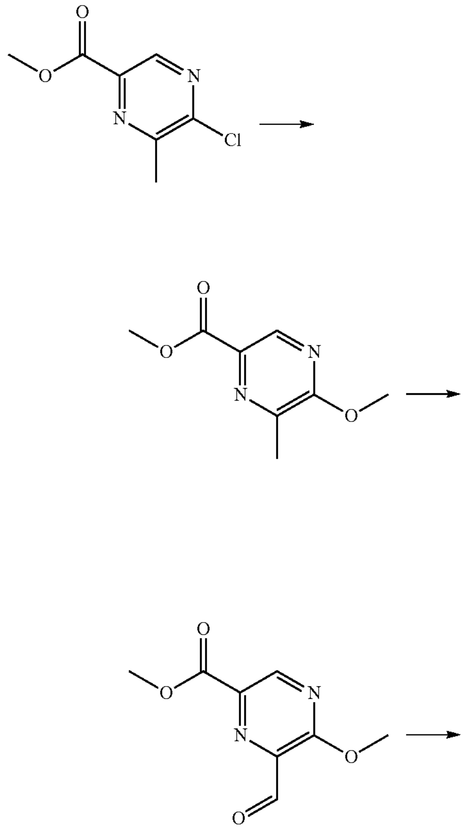

Step 1: To a solution of methyl 5-chloro-6-methylpyrazine-2-carboxylate (500 mg, 2.68 mmol) in MeOH (5 mL) at 0° C. was added NaOMe (30 wt %, 1.21 g, 6.70 mmol) dropwise over 5 min. The mixture was stirred at 25° C. for 0.5 h. The reaction was quenched with AcOH (2 mL) and the mixture was diluted with water (10 mL) and extracted with EtOAc (6×15 mL). The combined organic layers were washed with a saturated aqueous $NaHCO_3$ solution (20 mL), dried over $Na_2SO_4$, filtered, and concentrated under reduced pressure to afford methyl 5-methoxy-6-methylpyrazine-2-carboxylate (450 mg, 82%) as an off-white solid. LCMS: m/z=183 $[M+H]^+$, $^1$H NMR (400 MHz, DMSO-$d_6$) δ 8.67 (s, 1H), 4.00 (s, 3H), 3.86 (s, 3H), 2.44 (s, 3H).

Step 2: To a solution of methyl 5-methoxy-6-methylpyrazine-2-carboxylate (350 mg, 1.92 mmol) in 1,4-dioxane (7 mL) was added selenium oxide (426 mg, 3.84 mmol) and the mixture was heated at 130° C. for 16 h. The mixture was filtered and the filtrate was concentrated under reduced pressure to afford methyl 6-formyl-5-methoxypyrazine-2-carboxylate (350 mg, 93%) as a brown solid. LCMS: m/z=197 $[M+H]^+$. $^1$H NMR (400 MHz, DMSO-$d_6$) δ 10.1 (s, 1H), 9.07 (s, 1H), 4.11 (s, 3H), 3.92 (s, 3H).

Steps 3 and 4 were completed starting from methyl 6-formyl-5-methoxypyrazine-2-carboxylate as described in Intermediate 51: 5-(Difluoromethyl)-6-methoxypyrazine-2-carboxylic acid steps 5 and 6 to afford 6-(Difluoromethyl)-5-methoxypyrazine-2-carboxylic acid. LCMS: m/z=203 $[M-H]^-$. $^1$H NMR (400 MHz, DMSO-$d_6$) δ 8.80 (s, 1H), 7.04 (t, J=53.4 Hz, 1H), 4.00 (s, 3H).

Intermediate 56: 6-(Difluoromethyl)-3-methylpyrazine-2-carboxylic acid

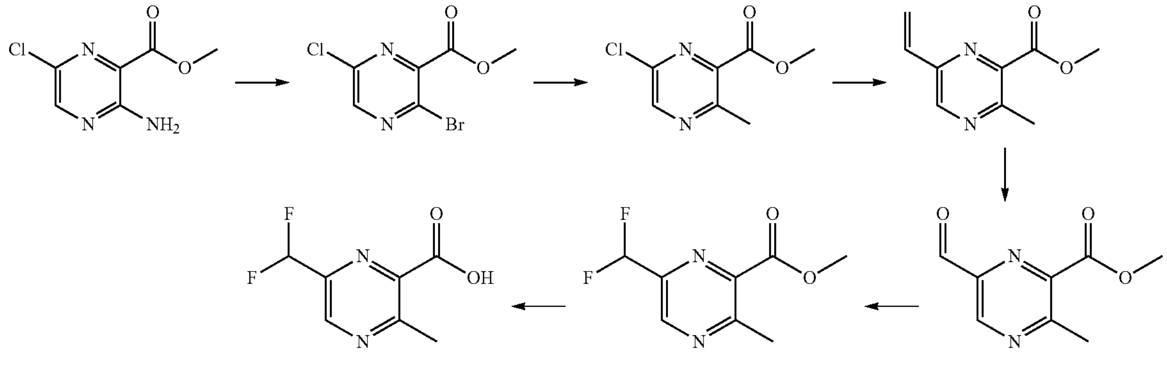

Step 1: To a solution of methyl 3-amino-6-chloropyrazine-2-carboxylate (2.00 g, 10.7 mmol) in acetic acid (15 mL) at 0° C. was added 48% HBr/water (10 mL) dropwise and the mixture was stirred for 30 min. A solution of sodium nitrite (2.21 g, 32.0 mmol) in water (5 mL) was then added dropwise and stirring was continued at 0° C. for 30 min. The reaction was quenched with a saturated aqueous sodium bisulfite solution (10 mL) and the mixture extracted with EtOAc (15 mL×3). The combined organic layers were washed with brine (20 mL), dried over $Na_2SO_4$, filtered, and concentrated under reduced pressure. The residue was purified by silica gel chromatography (Pet. ether/EtOAc=100/1, v/v) to afford methyl 3-bromo-6-chloropyrazine-2-carboxylate (1.05 g, 39%) as a colorless oil. $^1$H NMR (400 MHz, DMSO-$d_6$) δ 8.87 (s, 1H), 3.95 (s, 3H).

Step 2: To a solution of methyl 3-bromo-6-chloropyrazine-2-carboxylate (950 mg, 3.78 mmol) in DME (8 mL) was added 2,4,6-trimethyl-1,3,5,2,4,6-trioxatriborinane (1.90 g, 50 wt % in THF, 7.56 mmol), $K_2CO_3$ (1.04 g, 7.56 mmol), and Pd(dppf)$Cl_2$. DCM (309 mg, 0.378 mmol). The mixture was heated at 80° C. in a sealed tube for 16 h. The mixture was quenched with water (50 mL), extracted with EtOAc (3×20 mL), and the combined organic layers were washed with brine (30 mL), dried over $Na_2SO_4$, filtered, and concentrated under reduced pressure. The residue was purified by silica gel chromatography (Pet. ether/EtOAc=50/1, v/v) to give methyl 6-chloro-3-methylpyrazine-2-carboxylate (250 mg, 36%) as an off-white solid. LCMS: m/z=187 $[M+H]^+$. $^1$H NMR (400 MHz, DMSO-$d_6$) δ 8.89 (s, 1H), 3.91 (s, 3H), 2.72 (s, 3H).

Steps 3-6 were completed starting from methyl 6-chloro-3-methylpyrazine-2-carboxylate as described in Intermediate 50: 5-(Difluoromethyl)-3-methoxypyrazine-2-carboxylic acid step 1-3 and 6 to afford 6-(difluoromethyl)-3-methylpyrazine-2-carboxylic acid. LCMS: m/z=189 $[M+H]^+$.

Intermediate 57: 5-(Difluoromethyl)-4-methylpyrimidine-2-carboxylic acid

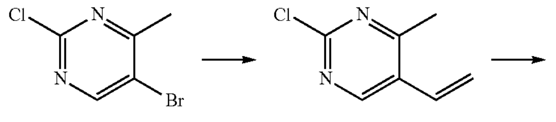

-continued

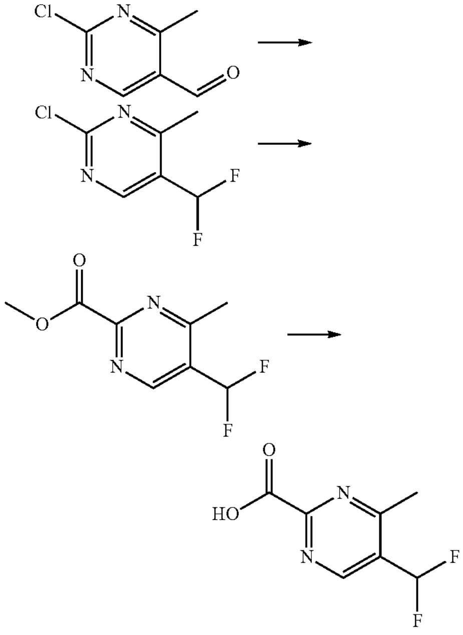

Step 1: Completed as described in Intermediate 50: 5-(Difluoromethyl)-3-methoxypyrazine-2-carboxylic acid step 1 from 5-bromo-2-chloro-4-methylpyrimidine to afford 2-chloro-4-methyl-5-vinylpyrimidine (690 mg, 47%) as a white solid. LCMS: m/z=155 $[M+H]^+$. $^1$H NMR (400 MHz, DMSO-$d_6$) δ 8.81-8.79 (m, 1H), 6.90-6.81 (m, 11H), 5.96 (dd, J=17.6, 0.8 Hz, 1H), 5.56 (dd, J=11.2, 0.8 Hz, 1H), 2.51 (s, 3H), Step 2: Completed as described in Intermediate 50: 5-(Difluoromethyl)-3-methoxypyrazine-2-carboxylic acid step 2 from 2-chloro-4-methyl-5-vinylpyrimidine to afford 2-chloro-4-methylpyrimidine-5-carbaldehyde (176 mg, 25%) as an off-white solid. $^1$H NMR (400 MHz, DMSO-$d_6$) δ 10.2 (s, 1H), 9.06 (s, 1H), 3.31 (s, 3H).

Step 3: Completed as described in Intermediate 50: 5-(Difluoromethyl)-3-methoxypyrazine-2-carboxylic acid step 3 from 2-chloro-4-methylpyrimidine-5-carbaldehyde to afford 2-chloro-5-(difluoromethyl)-4-methylpyrimidine (160 mg, 82%) as a brown oil. $^1$H NMR (400 MHz, DMSO-$d_6$) δ 8.85 (s, 1H), 7.46-7.16 (m, 1H), 2.59 (s, 3H).

Step 4: To a solution of 2-chloro-5-(difluoromethyl)-4-methylpyrimidine (100 mg, 0.560 mmol) in MeOH (8 mL) was added $Et_3N$ (68.0 mg, 0.672 mmol) and Pd(dppf)$Cl_2$ (20.5 mg, 0.028 mmol). The mixture was heated at 80° C. under a CO atmosphere (2 MPa) for 16 h. The mixture was concentrated under reduced pressure and the residue was purified by prep-TLC (Pet. ether/EtOAc=2/1, v/v) to give methyl 5-(difluoromethyl)-4-methylpyrimidine-2-carboxylate (78 mg, 69%) as a yellow oil. LCMS: m/z=203 [M+H]1; $^1$H NMR (400 MHz, DMSO-$d_6$) δ 9.04 (d, J=1.6 Hz, 1H), 7.52-7.22 (m, 1H), 3.92 (s, 3H), 2.65 (s, 3H).

Step 5: Completed as described in Intermediate 50: 5-(Difluoromethyl)-3-methoxypyrazine-2-carboxylic acid step 6 from methyl 5-(difluoromethyl)-4-methylpyrimidine-2-carboxylate to afford 5-(difluoromethyl)-4-methylpyrimidine-2-carboxylic acid (37 mg, Li salt) as a brown solid. LCMS: m/z=189 $[M+H]^+$.

Intermediate 58: 5-(Difluoromethyl)-3-methylpyrazine-2-carboxylic acid

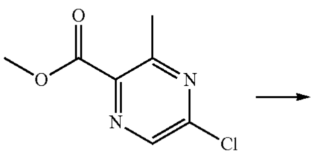

-continued

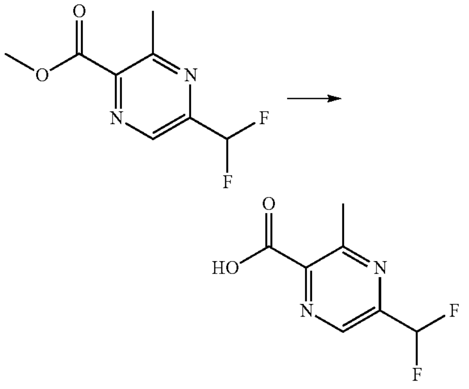

Synthesis was completed from methyl 5-chloro-3-methylpyrazine-2-carboxylate (synthesized according to WO2014/138484) as described in Intermediate 50: 5-(Difluoromethyl)-3-methoxypyrazine-2-carboxylic acid step 1-3 and 6 to afford 5-(difluoromethyl)-3-methylpyrazine-2-carboxylic acid. LCMS: m/z=189 $[M+H]^+$. $^1$H NMR (400 MHz, DMSO-$d_6$) δ 8.62 (s, 1H), 7.04 (t, J=54.2 Hz, 1H), 2.59 (s, 3H).

Intermediate 59: 3-(Difluoromethyl)-6-methylpyrazine-2-carboxylic acid

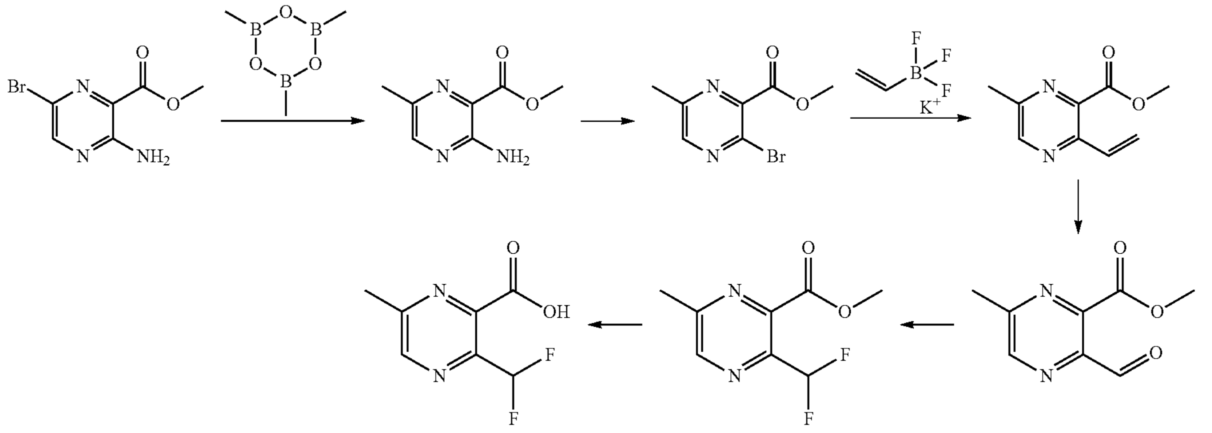

-continued

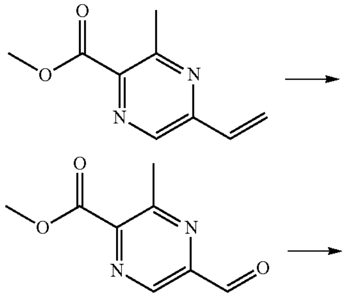

Step 1: To a solution of methyl 3-amino-6-bromopyrazine-2-carboxylate (500 mg, 2.15 mmol) in DME (5 mL) was added $K_2CO_3$ (596 mg, 4.31 mmol), 2,4,6-trimethyl-1,3,5,2,4,6-trioxatriborinane (50 wt % in THF 1.62 g, 6.46 mmol) and Pd(dppf)$Cl_2$ (158 mg, 0.215 mmol) and the mixture was heated at 80° C. in a sealed tube under $N_2$ for 16 h. The mixture was diluted with water (40 mL), extracted with EtOAc (2×40 mL) and the combined organic layers washed with brine (40 mL), dried over $Na_2SO_4$, filtered and concentrated under reduced pressure. The residue was purified by silica gel chromatography (Gradient: 0-20% EtOAc in Pet. ether) to afford methyl 3-amino-6-methylpyrazine-2-carboxylate (230 mg, 64%) as a yellow solid. LCMS: m/z=168.20 $[M+H]^+$; $^1$H NMR (400 MHz, Chloroform-d) δ 8.11 (s, 1H), 3.98 (s, 3H), 2.48 (s, 3H).

Step 2: To a solution of methyl 3-amino-6-methylpyrazine-2-carboxylate (100 mg, 0.598 mmol) in AcOH (3 mL) at 5° C. was added 48% HBr (0.5 mL) and potassium nitrite (153 mg, 1.79 mmol) and the mixture was stirred at 5° C. for 1 h. The mixture was diluted with a saturated aqueous $NaHCO_3$ solution (10 mL), extracted with EtOAc (2×20 mL) and the combined organic layers washed with a saturated $NaHCO_3$ solution (20 mL), brine (10 mL), dried over $Na_2SO_4$, filtered and concentrated under reduced pressure. The residue was purified by prep-TLC (50% EtOAc in Pet. ether) to afford methyl 3-bromo-6-methylpyrazine-2-carboxylate (30 mg, 22%) as colorless oil. LCMS: m/z=231.10 $[M+H]^+$; $^1$H NMR (400 MHz, Chloroform-d) δ 8.34 (s, 1H), 4.02 (s, 3H), 2.59 (s, 3H).

Steps 3-6 were completed starting from methyl 3-bromo-6-methylpyrazine-2-carboxylate as described in Intermediate 50: 5-(Difluoromethyl)-3-methoxypyrazine-2-carboxylic acid step 1-3 and 6 to afford 3-(difluoromethyl)-6-methylpyrazine-2-carboxylic acid. LCMS: m/z=187 $[M-H]^-$. $^1$H NMR (400 MHz, DMSO-$d_6$) δ 8.46 (s, 1H), 7.50 (t, J=54.8 Hz, 1H), 2.51 (s, 3H).

Intermediate 60: 3-(Difluoromethyl)-6-methoxypyrazine-2-carboxylic acid

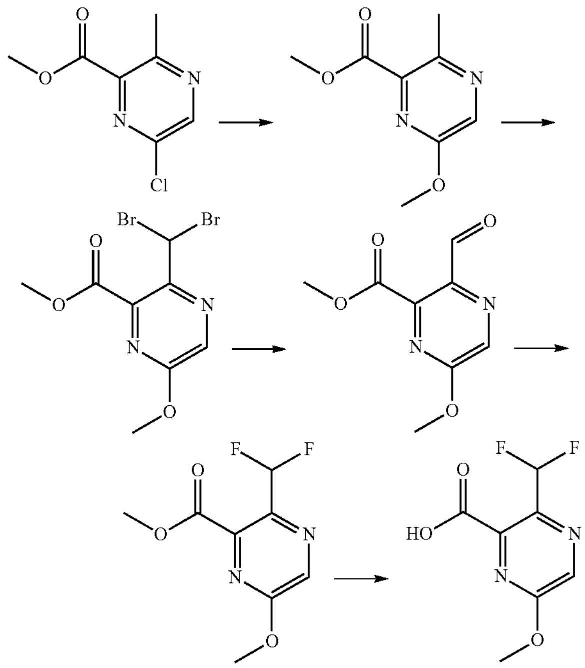

Step 1: To a solution of methyl 6-chloro-3-methylpyrazine-2-carboxylate (1.75 g, 9.38 mmol) in MeOH (40 mL) was added NaOMe (10.1 g, 30 wt % 56.3 mmol) and the mixture was heated at 70° C. for 2 h. The mixture was allowed to cool to room temperature, diluted with DCM (60 mL), washed with water (60 mL), dried over $Na_2SO_4$, filtered, and concentrated under reduced pressure to afford methyl 6-methoxy-3-methylpyrazine-2-carboxylate (1.24 g, 72%) as a yellow solid. LCMS: m/z=183 $[M+H]^+$. $^1$H NMR (400 MHz, DMSO-$d_6$) δ 8.41 (s, 1H), 3.91 (s, 3H), 3.89 (s, 3H), 2.60 (s, 3H).

Step 2: To a solution of methyl 6-methoxy-3-methylpyrazine-2-carboxylate (1.2 g, 6.6 mmol) in $CCl_4$ (20 mL) was added NBS (5.9 g, 33 mmol) and AIBN (0.11 g, 0.66 mmol) and the mixture was heated at 80° C. overnight. The mixture was diluted with a saturated aqueous sodium thiosulfate solution (50 mL) and water (50 mL), extracted with DCM (100 mL), and the organic layer was washed with water (100 mL), brine (100 mL), dried over $Na_2SO_4$, filtered, and concentrated under reduced pressure. The residue was purified by silica gel chromatography (Pet. ether/EtOAc=35/1, v/v) to afford methyl 3-(dibromomethyl)-6-methoxypyrazine-2-carboxylate (1.8 g, 80%) as an off-white solid. LCMS: m/z=339 $[M+H]^+$. $^1$H NMR (400 MHz, DMSO-$d_6$) δ 8.67 (s, 1H), 7.69 (s, 1H), 3.98 (s, 3H), 3.94 (s, 3H).

Step 3: To a solution of methyl 3-(dibromomethyl)-6-methoxypyrazine-2-carboxylate (400 mg, 1.18 mmol) in EtOH (12 mL) and water (1.2 mL) was added silver nitrate (600 mg, 3.53 mmol) and the mixture was heated at 50° C. overnight. The mixture was diluted with water (50 mL), extracted with DCM (50 mL), and the organic phase washed with water (50 mL), brine (50 mL), dried over $Na_2SO_4$, filtered, and concentrated under reduced pressure. The residue was purified by prep-TLC (Pet. ether/EtOAc=2/1, v/v) to afford methyl 3-formyl-6-methoxypyrazine-2-carboxylate (65 mg, 28%) as an off-white solid. LCMS: m/z=197 $[M+H]^+$. $^1$H NMR (400 MHz, DMSO-$d_6$) δ 10.1 (s, 1H), 8.64 (s, 1H), 4.03 (s, 3H), 3.93 (s, 3H).

Steps 4 and 5 were completed as described in Intermediate 51: 5-(Difluoromethyl)-6-methoxypyrazine-2-carboxylic acid step 5 and 6 to afford 3-(difluoromethyl)-6-methoxypyrazine-2-carboxylic acid. LCMS: m/z=205 $[M+H]^+$. $^1$H NMR (400 MHz, DMSO-$d_6$) δ 8.18 (s, 1H), 7.39 (t, J=54.8 Hz, 1H), 3.92 (s, 3H).

Intermediate 61: 5-(Difluoromethyl)-3,6-dimethylpyrazine-2-carboxylic acid

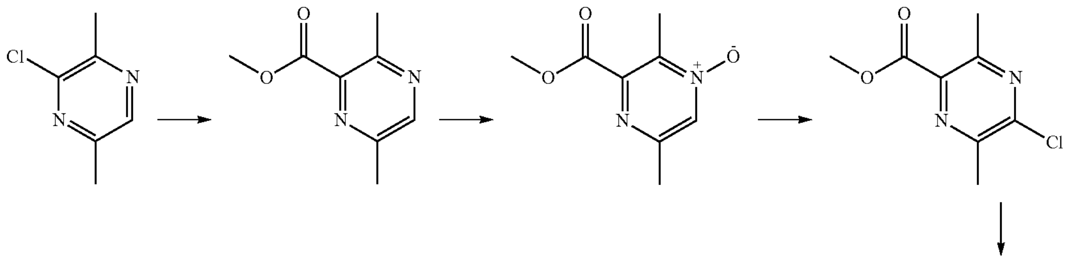

-continued

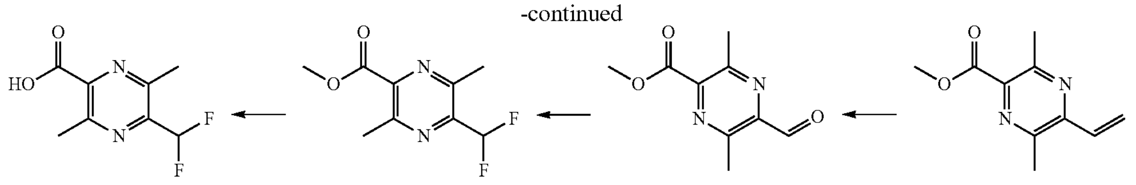

Step 1: To a solution of 3-chloro-2,5-dimethylpyrazine (7.00 g, 49.1 mmol) in MeOH (30 mL) was added Pd(dppf)$Cl_2$ (1.80 g, 2.45 mmol) and KOAc (9.64 g, 98.2 mmol) and the mixture was heated at 95° C. for 16 h under a CO atmosphere (3 MPa). The mixture was diluted with water (200 mL), extracted with DCM (3×150 mL), and the combined organic layers were washed with brine (150 mL), dried over $Na_2SO_4$, filtered, and concentrated under reduced pressure. The residue was purified by silica gel chromatography (Pet. ether/EtOAc=20/1, v/v) to afford methyl 3,6-dimethylpyrazine-2-carboxylate (6.75 g, 83%) as an off-white solid. LCMS: m/z=167 $[M+H]^+$. $^1$H NMR (400 MHz, DMSO-$d_6$) δ 8.61 (s, 1H), 3.89 (s, 3H), 2.64 (s, 3H), 2.50 (s, 3H).

Step 2: To a solution of methyl 3,6-dimethylpyrazine-2-carboxylate (3.00 g, 18.1 mmol) in DCM (20 mL) was added 3-chlorobenzoperoxoic acid (85 wt %, 7.33 g, 36.1 mmol) and the mixture was heated at 50° C. for 16 h. The mixture was diluted with water (20 mL), extracted with DCM (3×10 mL), and the combined organic layers washed with brine (30 mL), dried over $Na_2SO_4$, filtered, and concentrated under reduced pressure give 3-(methoxycarbonyl)-2,5-dimethylpyrazine 1-oxide (7.2 g, 40% Purity, 88%), which was used directly in the next step without further purification. LCMS: m/z=183 $[M+H]^+$.

Step 3: To a solution of 3-(methoxycarbonyl)-2,5-dimethylpyrazine 1-oxide (400 mg, 40% purity, 0.878 mmol) in $CCl_4$ (6 mL) was added $POCl_3$ (1.21 g, 7.90 mmol) and the mixture was heated at 90° C. for 16 h. The mixture was concentrated under reduced pressure and the residue was diluted with water (20 mL) and extracted with DCM (3×20 mL). The combined organic layers were washed with brine (20 mL), dried over $Na_2SO_4$, filtered, and concentrated under reduced pressure. The residue was purified by prep-TLC (Pet. ether/EtOAc=5/1, v/v) to afford methyl 5-chloro-3,6-dimethylpyrazine-2-carboxylate (114 mg, 64%) as an off-white solid. LCMS: m/z=201 $[M+H]^+$; $^1$H NMR (400 MHz, DMSO-$d_6$) δ 3.89 (s, 3H), 2.65 (s, 3H), 2.58 (s, 3H). Steps 4-7 were completed as described in Intermediate 50: 5-(Difluoromethyl)-3-methoxypyrazine-2-carboxylic acid step 1-3 and 6 to afford 5-(difluoromethyl)-3,6-dimethylpyrazine-2-carboxylic acid. LCMS: m/z=203 $[M+H]^+$.

Intermediate 62: 6-Chloro-5-methoxy-3-methylpyrazine-2-carboxylic acid

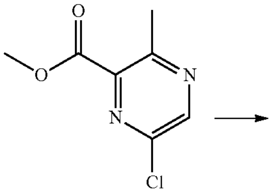

-continued

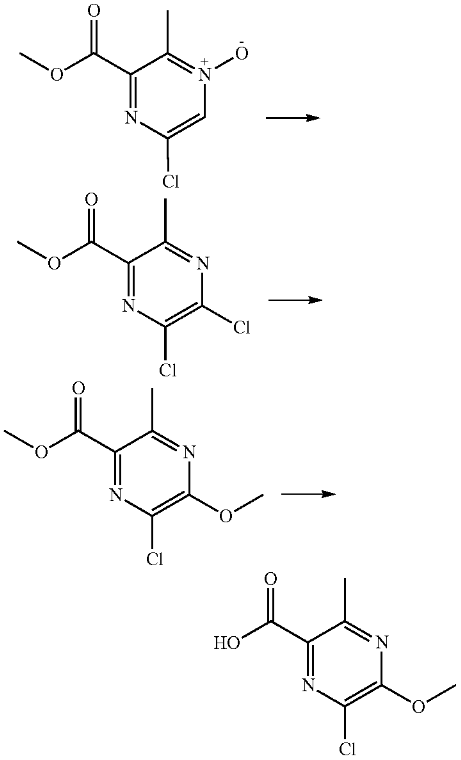

Step 1: To a solution of methyl 6-chloro-3-methylpyrazine-2-carboxylate (500 mg, 2.68 mmol) in dry DCM (5 mL) at 0° C. under a nitrogen atmosphere was added urea-hydrogen peroxide (504 mg, 5.36 mmol) followed by trifluoroacetic anhydride (1.01 g, 4.82 mmol) dropwise. The mixture was stirred at 0° C. for 1 h then at 25° C. for a further 2 h. The mixture was diluted with water (40 mL), adjusted to pH 7-8 with a saturated aqueous $NaHCO_3$ solution, and extracted with DCM (3×40 mL). The combined organic layers were washed with water (40 mL), brine (40 mL), dried over $Na_2SO_4$, filtered, and concentrated under reduced pressure. The residue was purified by silica gel chromatography (Pet. ether/EtOAc=10/1, v/v) to afford 5-chloro-3-(methoxycarbonyl)-2-methylpyrazine 1-oxide (476 mg, 87%) as an off-white solid. LCMS: m/z=203 $[M+H]^+$. $^1$H NMR (400 MHz, Chloroform-d) δ 8.30 (s, 1H), 4.02 (s, 3H), 2.64 (s, 3H).

Step 2: To a solution of 5-chloro-3-(methoxycarbonyl)-2-methylpyrazine 1-oxide (300 mg, 1.48 mmol) in toluene (5 mL) at 0° C. was added $POCl_3$ (568 mg, 3.70 mmol) dropwise followed by DMF (21.6 mg, 0.296 mmol). The mixture was stirred at 25° C. for 1 h then heated at 85° C. for 20 h. The mixture was concentrated under reduced pressure and the residue diluted with a saturated aqueous $NaHCO_3$ (30 mL) solution and extracted with EtOAc (2×30 mL). The combined organic layers were washed with water (30 mL), brine (30 mL), dried over $Na_2SO_4$, filtered, and concentrated under reduced pressure. The residue was purified by prep-TLC (Pet. ether/EtOAc=5/1, v/v) to afford methyl 5,6-dichloro-3-methylpyrazine-2-carboxylate (200 mg, 61%) as an off-white solid. LCMS: m/z=221 $[M+H]^+$. $^1H$ NMR (400 MHz, Chloroform-d) δ 4.00 (s, 3H), 2.83 (s, 3H).

Step 3: To a solution of methyl 5,6-dichloro-3-methylpyrazine-2-carboxylate (170 mg, 0.769 mmol) in MeOH (8 mL) at 0° C. under a nitrogen atmosphere was added $K_2CO_3$ (128 mg, 0.923 mmol) portionwise and the mixture was stirred at 0° C. for 0.5 h. The mixture was diluted with water (20 mL), extracted with EtOAc (2×20 mL), and the combined organic layers were washed with water (20 mL), brine (20 mL), dried over $Na_2SO_4$, filtered, and concentrated under reduced pressure to give methyl 6-chloro-5-methoxy-3-methylpyrazine-2-carboxylate (140 mg, 84%) as an off-white solid. LCMS: m/z=217 $[M+H]^+$; $^1H$ NMR (400 MHz, Chloroform-d) δ 4.10 (s, 3H), 3.96 (s, 3H), 2.78 (s, 3H).

Step 4: To a solution of methyl 6-chloro-5-methoxy-3-methylpyrazine-2-carboxylate (30 mg, 0.14 mmol) in THF (2 mL) was added a solution of NaOH (17 mg, 0.42 mmol) in water (2 mL). The mixture was stirred at 25° C. for 3 h then concentrated under reduced pressure to give 6-chloro-5-methoxy-3-methylpyrazine-2-carboxylic acid (30 mg, Na salt) as an off-white solid. LCMS: m/z=201 $[M-H]^-$. $^1H$ NMR (400 MHz, DMSO-$d_6$) δ 3.93 (s, 3H), 2.48 (s, 3H).

Intermediate 63: 5-Chloro-6-methoxy-3-methylpyrazine-2-carboxylic acid

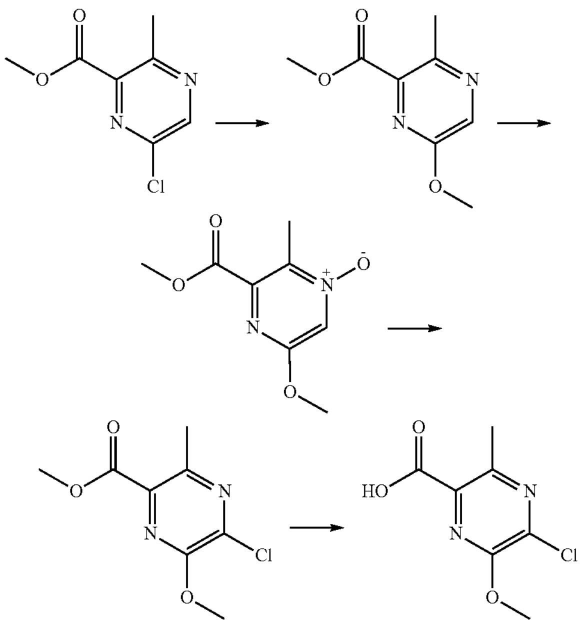

Step 1: To a solution of methyl 6-chloro-3-methylpyrazine-2-carboxylate (700 mg, 3.75 mmol) in MeOH (20 mL) was added sodium methanolate (4.05 g, 22.5 mmol) and the mixture was heated at 70° C. for 3 h. After cooling to room temperature, the mixture was diluted with water (15 mL), extracted with DCM (3×15 mL), and the combined organic layers were dried over $Na_2SO_4$, filtered, and concentrated under reduced pressure to give methyl 6-methoxy-3-methylpyrazine-2-carboxylate (461 mg, 64%) as a light pink solid. LCMS: m/z=183 $[M+H]^+$. $^1H$ NMR (400 MHz, DMSO-$d_6$) δ 8.42 (s, 1H), 3.91 (s, 3H), 3.89 (s, 3H), 2.60 (s, 3H).

Steps 2-4 were completed as described in Intermediate 62: 6-Chloro-5-methoxy-3-methylpyrazine-2-carboxylic acid step 1, 2, and 4, respectively to afford 5-chloro-6-methoxy-3-methylpyrazine-2-carboxylic acid. LCMS: m/z=203 $[M+H]^+$. $^1H$ NMR (400 MHz, DMSO-$d_6$) δ 3.89 (s, 3H), 2.35 (s, 3H).

Intermediate 64: 5-Chloro-3,6-dimethylpyrazine-2-carboxylic acid

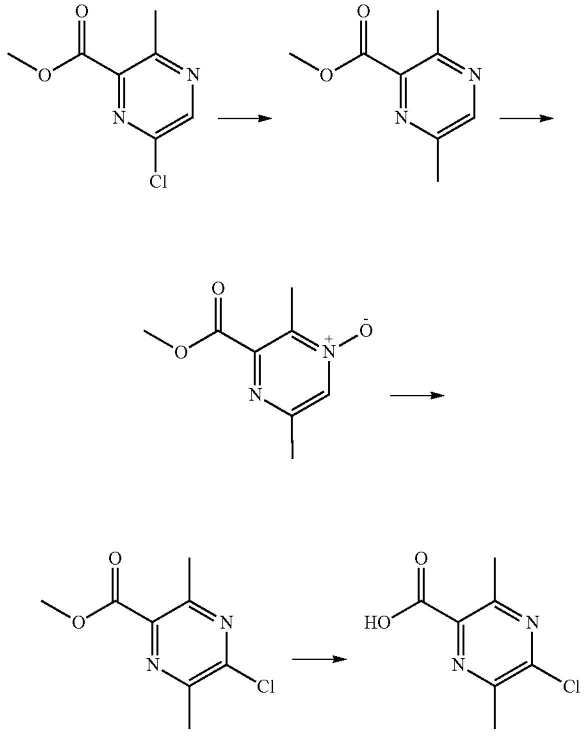

Step 1: To a solution of methyl 6-chloro-3-methylpyrazine-2-carboxylate (500 mg, 2.68 mmol) in DME (10 mL) was added $K_2CO_3$ (370 mg, 2.68 mmol), 2,4,6-trimethyl-1,3,5,2,4,6-trioxatriborinane (1.35 g, 10.7 mmol), and Pd(dppf)$Cl_2$ (196 mg, 0.268 mmol). The mixture was heated at 80° C. for 16 h in a sealed tube under $N_2$. The mixture was diluted with water (20 mL), extracted with DCM (3×30 mL), and the combined organic layers were washed with brine (20 mL), dried over $Na_2SO_4$, filtered, and concentrated under reduced pressure. The residue was purified by prep-TLC (Pet. ether/EtOAc=5/1 to 3/1, v/v) to afford methyl 3,6-dimethylpyrazine-2-carboxylate (380 mg, 86%) as a white solid. LCMS: m/z=167 $[M+H]^+$. $^1H$ NMR (400 MHz, Chloroform-d) δ 8.49 (s, 1H), 4.00 (s, 3H), 2.79 (s, 3H), 2.61 (s, 3H).

Step 2-4 were completed as described in Intermediate 62: 6-Chloro-5-methoxy-3-methylpyrazine-2-carboxylic acid step 1, 2, and 4, respectively to afford 5-chloro-3,6-dimethylpyrazine-2-carboxylic acid. LCMS: m/z=187 $[M+H]^+$. $^1H$ NMR (400 MHz, DMSO-$d_6$) δ 2.45 (s, 3H), 2.42 (s, 3H).

Intermediate 65: 3-Chloro-5-(difluoromethyl)-4,6-dimethylpicolinic acid

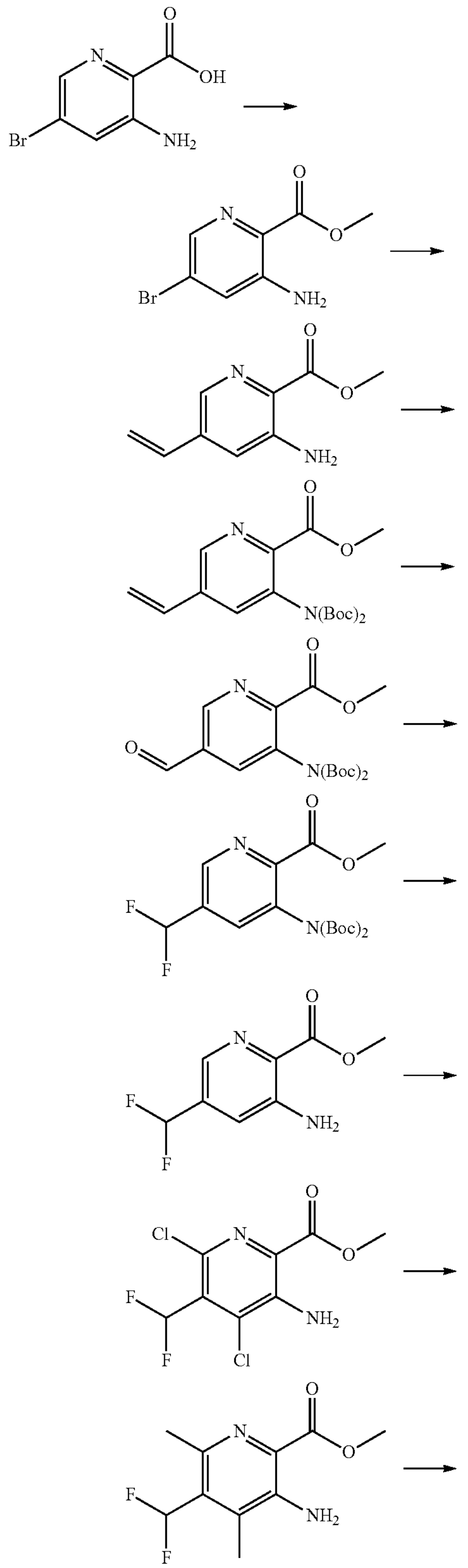

-continued

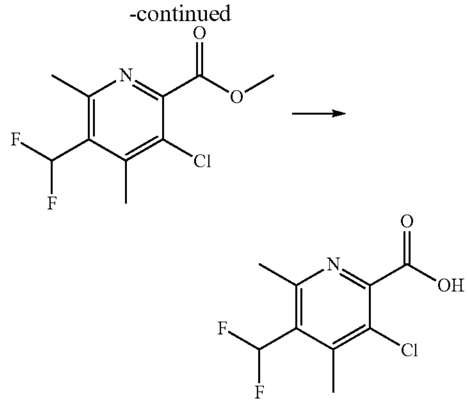

Step 1: To a solution of 3-amino-5-bromopicolinic acid (10.0 g, 46.1 mmol) and methyl iodide (13.1 g, 92.2 mmol) in DMF (100 mL) was added $K_2CO_3$ (12.7 g, 92.2 mmol) and the mixture was stirred at 25° C. for 16 h under $N_2$. The mixture was diluted with water (500 mL), extracted with EtOAc (5× 300 mL), and the combined organic layers were washed with brine (5×200 mL), dried over $Na_2SO_4$, filtered, and concentrated under reduced pressure to afford methyl 3-amino-5-bromopicolinate (10.2 g, 96%) as a yellow solid. LCMS: m/z=231 [M+H]; 1H NMR (400 MHZ, DMSO-$d_6$) δ 7.88 (d, J=2.0 Hz, 1H), 7.48 (d, J=2.0 Hz, 1H), 6.84 (s, 2H), 3.80 (s, 3H).

Step 2: To a solution of methyl 3-amino-5-bromopicolinate (10.2 g, 44.1 mmol), potassium trifluoro(vinyl)borate (11.8 g, 88.3 mmol) and $K_2CO_3$ (18.3 g, 3 Eq, 132 mmol) in toluene/EtOH (2/1, 120 mL) was added $Pd(PPh_3)_4$ (5.10 g, 4.41 mmol) and the mixture was heated at 130° C. for 0.5 h under microwave irradiation. The mixture was diluted with water (500 mL), extracted with DCM (10×20 mL), and the combined organic layers were dried over $Na_2SO_4$, filtered and concentrated under reduced pressure. The residue was purified by silica gel chromatography (Pet. ether/EtOAc=10/1 to 3/1, v/v) to afford methyl 3-amino-5-vinylpicolinate (4.00 g, 56%) as a yellow solid. LCMS: m/z=179 $[M+H]^+$. $^1H$ NMR (400 MHz, DMSO-$d_6$) δ 7.99 (d, J=1.8 Hz, 1H), 7.23 (d, J=1.8 Hz, 1H), 6.75-6.63 (m, 3H), 5.95 (d. J=17.6 Hz, 1H), 5.47 (d, J=11.0 Hz, 1H), 3.80 (s, 3H).

Step 3: To a solution of methyl 3-amino-5-vinylpicolinate (3.80 g, 21.3 mmol) and di-tert-butyl dicarbonate (18.6 g, 85.3 mmol) in DCM (40 mL) was added DMAP (261 mg, 2.13 mmol) and the mixture was stirred at 25° C. for 16 h. The mixture was diluted with water (100 mL), extracted with DCM (5×80 mL) and the combined organic layers were dried over $Na_2SO_4$, filtered, and concentrated under reduced pressure. The residue was purified by silica gel chromatography (Pet. ether/EtOAc=10/1 to 3/1, v/v) to afford methyl 3-(bis(tert-butoxycarbonyl)amino)-5-vinylpicolinate (5.79 g, 72%) as an off-white solid. LCMS: m/z=379 $[M+H]^+$. $^1H$ NMR (400 MHz, DMSO-$d_6$) δ 8.71 (d, J=1.8 Hz, 1H), 8.08 (d, J=1.8 Hz, 1H), 6.85 (dd, J=17.6, 11.0 Hz, 1H), 6.20 (d, J=17.6 Hz, 1H), 5.58 (d, J=11.0 Hz, 1H), 3.82 (s, 3H), 1.33 (s, 18H).

Step 4: To a solution of methyl 3-(bis(tert-butoxycarbonyl)amino)-5-vinylpicolinate (5.79 g, 15.3 mmol) and 4-methylmorpholine 4-oxide hydrate (2.07 g, 15.3 mmol) in THF/water (4/1, 2.5 mL) was added osmium tetraoxide (389 mg, 1.53 mmol) and the mixture was stirred at 25° C. for 2 h. Sodium periodate (13.1 g, 61.2 mmol) was added and stirring was continued at 25° C. for 1 h. The mixture was diluted with water (10 mL), extracted with DCM (5×10 mL), and the combined organic layers were dried over $Na_2SO_4$, filtered, and concentrated under reduced pressure. The residue was purified by prep-TLC (DCM/MeOH=50/1, v/v) to afford methyl 3-(bis(tert-butoxycarbonyl)amino)-5-formylpicolinate (2.3 g, 40%) as a yellow solid. LCMS: m/z=381 $[M+H]^+$. $^1H$ NMR (400 MHz, DMSO-$d_6$) δ 10.2 (s, 1H), 9.11 (d, J=1.8 Hz, 1H), 8.36 (d, J=1.8 Hz, 1H), 3.87 (s, 3H), 1.33 (s, 18H).

Step 5: To a solution of methyl 3-(bis(tert-butoxycarbonyl)amino)-5-formylpicolinate (2.31 g, 6.07 mmol) in DCM (40 mL) at −78° C. under $N_2$ was added DAST (3.92 g, 24.3 mmol) and the mixture was stirred at −78° C. for 4 h then at 25° C. for a further 16 h. The mixture was diluted with a saturated aqueous $NaHCO_3$ solution (50 mL) and water (100 mL), extracted with DCM (6×50 mL), and the combined organic layers were dried over $Na_2SO_4$, filtered, and concentrated under reduced pressure to afford methyl 3-(bis(tert-butoxycarbonyl)amino)-5-(difluoromethyl)picolinate (2.6 g) as a yellow solid, which was taken directly to the next step. $^1H$ NMR (400 MHz, DMSO-$d_6$) δ 8.85 (s, 1H), 8.21 (s, 1H), 7.25 (t, J=54.8 Hz, 1H), 3.86 (s, 3H), 1.33 (s, 18H).

Step 6: A mixture of methyl 3-(bis(tert-butoxycarbonyl)amino)-5-(difluoromethyl)picolinate (2.6 g) and 4 M HCl in MeOH solution (30 mL) was stirred at 25° C. for 1 h. The mixture was adjusted to pH 7-8 with a saturated aqueous $NaHCO_3$ saturated solution, diluted with water (100 mL), and extracted with DCM (8×60 mL). The combined organic phases were dried over $Na_2SO_4$, filtered, and concentrated under reduced pressure. The residue purified by silica gel chromatography (Pet. ether/EtOAc=10/1 to 3/1, v/v) to afford methyl 3-amino-5-(difluoromethyl)picolinate (1.00 g, 82% over two steps) as a yellow solid. LCMS: m/z=203 $[M+H]^+$. $^1H$ NMR (400 MHz, DMSO-$d_6$) δ 7.98 (s, 1H), 7.40 (s, 1H), 7.09 (t, J=55.2 Hz, 1H), 6.90 (s, 2H), 3.83 (s, 3H).

Step 7: To a solution of methyl 3-amino-5-(difluoromethyl)picolinate (700 mg, 3.46 mmol) and N-chlorosuccinimide (462 mg, 3.46 mmol) in DMF (10 mL) was added acetic acid (208 mg, 3.46 mmol) and the mixture was stirred at 25° C. for 16 h. The mixture was diluted with water (20 mL), extracted with EtOAc (6×25 mL), and the combined organic layers were washed with brine (4×20 mL), dried over $Na_2SO_4$, filtered, and concentrated under reduced pressure The residue was purified by silica gel chromatography (Pet. ether/EtOAc=20/1 to 15/1, v/v) and prep-TLC (Pet. ether/EtOAc=3/1, v/v) to afford methyl 3-amino-4,6-dichloro-5-(difluoromethyl)picolinate (200 mg, 21%) as an off-white solid. LCMS: m/z=271 $[M+H]^+$. $^1H$ NMR (400 MHz, DMSO-$d_6$) δ 7.41 (t, J=51.8 Hz, 1H), 7.21 (s, 2H), 3.88 (s, 3H).

Step 8: To a solution of methyl 3-amino-4,6-dichloro-5-(difluoromethyl)picolinate (200 mg, 0.738 mmol), 2,4,6-trimethyl-1,3,5,2,4,6-trioxatriborinane (278 mg, 2.21 mmol), and $K_2CO_3$ (306 mg, 2.21 mmol) in DME (5 mL) was added Pd(dppf)$Cl_2$ (54.0 mg, 0.074 mmol) and the mixture was heated at 90° C. for 16 h under $N_2$. The mixture was diluted with water (10 mL), extracted with EtOAc (5×15 mL), and the combined organic layers washed with brine (3×20 mL), dried over $Na_2SO_4$, filtered, and concentrated under reduced pressure. The residue was purified by prep-TLC (Pet. ether/EtOAc=3/1, v/v) to afford methyl 3-amino-5-(difluoromethyl)-4,6-dimethylpicolinate (130 mg, 77%) as a brown solid. LCMS: m/z=231 $[M+H]^+$. $^1H$ NMR (400 MHz, DMSO-$d_6$) δ 7.33 (t, J=53.0 Hz, 1H), 6.58 (s, 2H), 3.83 (s, 3H), 2.46 (s, 3H), 2.25 (s, 3H).

Step 9: To a solution of methyl 3-amino-5-(difluoromethyl)-4,6-dimethylpicolinate (50 mg, 0.22 mmol) and copper(II)chloride (35 mg, 0.26 mmol) in MeCN (3 mL) at 0° C. was added isoamyl nitrite (51 mg, 0.43 mmol) and the mixture was heated at 60° C. for 16 h. The mixture was diluted with water (15 mL), extracted with DCM (10 mL×5), and the combined organic layers were dried over $Na_2SO_4$, filtered, and concentrated under reduced pressure. The residue was purified by prep-TLC (Pet. ether/EtOAc=5/1, v/v) to afford methyl 3-chloro-5-(difluoromethyl)-4,6-dimethylpicolinate (35 mg, 64%) as a colorless oil. LCMS: m/z=250 $[M+H]^+$. $^1H$ NMR (400 MHz, DMSO-$d_6$) δ 7.43 (t, J=52.4 Hz, 1H), 3.92 (s, 3H), 2.62 (s, 3H), 2.54 (s, 3H).

Step 10: To a solution of methyl 3-chloro-5-(difluoromethyl)-4,6-dimethylpicolinate (33 mg, 0.13 mmol) in THF (2 mL) and water (1 mL) was added LiOH (9.5 mg, 0.40 mmol). The mixture was stirred at 25° C. for 1.5 h then concentrated under reduced pressure to afford 3-chloro-5-(difluoromethyl)-4,6-dimethylpicolinic acid (35 mg, Li salt) as a white solid. LCMS: m/z=236 $[M+H]^+$. $^1H$ NMR (400 MHz, DMSO-$d_6$) δ 7.29 (t, J=53.0 Hz, 1H), 2.49 (s, 3H), 2.42 (s, 3H).

Intermediate 66: 3,6-Dimethyl-5-(trifluoromethyl)pyrazine-2-carboxylic acid

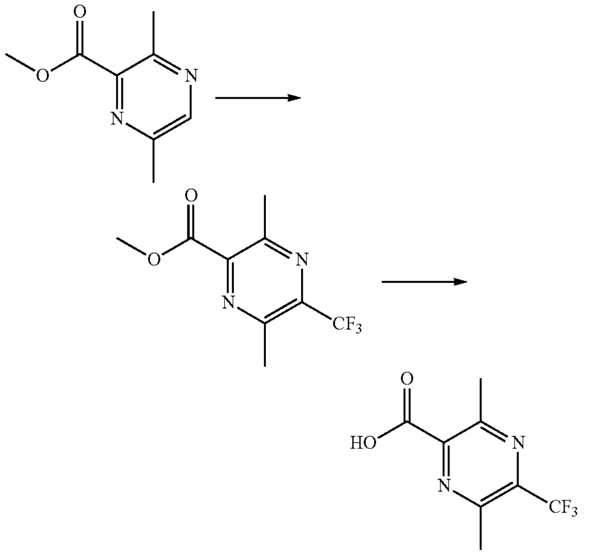

Step 1: To a solution of methyl 3,6-dimethylpyrazine-2-carboxylate (100 mg, 0.602 mmol) in MeCN (3 mL) was added bis(trifluoroacetoxy)iodo pentafluorobenzene (782 mg, 1.50 mmol) and tris(2,2'-bipyridine)ruthenium bis(hexafluorophosphate) (10.3 mg, 0.012 mmol). The mixture was stirred and irradiated under 450 nm blue LED light at 35° C. under a $N_2$ atmosphere for 12 h. The mixture was diluted with water (30 mL), extracted with EtOAc (3×20 mL), and the combined organic layers were washed with brine (20 mL), dried over $Na_2SO_4$, filtered, and concentrated under reduced pressure. The residue was purified by prep-TLC (Pet. ether/EtOAc=5/1, v/v) to afford methyl 3,6-dimethyl-5-(trifluoromethyl)pyrazine-2-carboxylate (85 mg, 60%) as an off-white solid. LCMS: m/z=235 $[M+H]^+$. $^1H$ NMR (400 MHz, DMSO-$d_6$) δ 3.94 (s, 3H), 2.71 (s, 3H), 2.67 (s, 3H).

Step 2: To a solution of methyl 3,6-dimethyl-5-(trifluoromethyl)pyrazine-2-carboxylate (40 mg, 0.17 mmol) in THF (2 mL) was added LiOH (8.2 mg, 0.34 mmol), EtOH (1 mL), and water (1 mL). The mixture was stirred at 25° C. for 2 h. The mixture was adjusted to pH 3 with 2 M aqueous HCl and concentrated under reduced pressure. The residue was washed with DCM and MeOH and the washings concentrated under reduced pressure to afford 3,6-dimethyl-5-(trifluoromethyl)pyrazine-2-carboxylic acid (40 mg) as a yellow solid, which was used without further purification. LCMS: m/z=221 $[M+H]^+$.

TABLE Z

The following intermediates were prepared using a similar procedure to that described for Intermediate 66.

| Intermediate Number | Structure | Compound Name | LCMS $[M + H]^+$ | NMR |
|---|---|---|---|---|
| 67 | 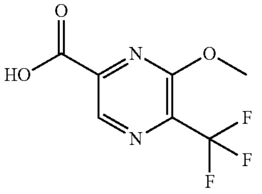 | 6-methoxy-5-(trifluoromethy 1)pyrazine-2-carboxylic acid | 223 | $^1$H NMR (400 MHZ, DMSO-$d_6$) δ 8.58 (s, IH). 4.04 (s, 3H) |

Intermediate 68: 3,4-Dimethyl-5-(trifluoromethyl)picolinic acid

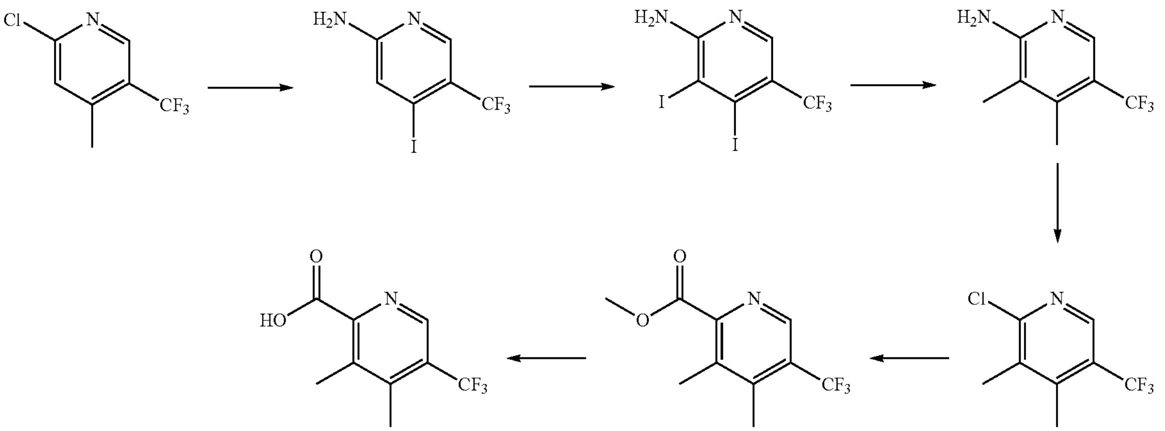

Step 1: To a solution of 2-chloro-4-iodo-5-(trifluoromethyl)pyridine (5.00 g, 16.3 mmol) in NMP (20 mL) was added ammonium acetate (18.8 g, 244 mmol) and the mixture was heated at 110° C. for 16 h. The mixture was diluted with water (20 mL), extracted with EtOAc (2×50 mL), and the combined organic layers were washed with water (20 mL), brine (10 mL), dried over $Na_2SO_4$, filtered, and concentrated under reduced pressure. The reside was purified by silica gel chromatography (Pet. ether/EtOAc=I/O to 1/1, v/v) to afford 4-iodo-5-(trifluoromethyl)pyridin-2-amine (1.7 g, 37%) as an off-white solid. LCMS: m/z=289 $[M+H]^+$. $^1$H NMR (400 MHz, DMSO-$d_6$) δ 8.12 (s, 1H), 7.13 (s, 1H), 6.85 (s, 2H).

Step 2: To a solution of 4-iodo-5-(trifluoromethyl)pyridin-2-amine (1.65 g, 5.73 mmol) in DMF (8 mL) at 0° C. under $N_2$ was added iodine chloride (2.79 g, 17.2 mmol) and the mixture was heated at 40° C. for 16 h. The mixture was diluted with a saturated aqueous $Na_2S_2O_3$ solution (20 mL) and water (20 mL), extracted with EtOAc (2×50 mL), and the combined organic layers washed with water (20 mL), brine (10 mL), dried over $Na_2SO_4$, filtered, and concentrated under reduced pressure. The residue was purified by silica gel chromatography (Pet. ether/EtOAc=I/O to 1/1, v/v) to afford 3,4-diiodo-5-(trifluoromethyl)pyridin-2-amine (1.26 g, 53%) as an off-white solid. LCMS: m/z=415 [M+H]1. $^1$H NMR (400 MHz, DMSO-$d_6$) δ 8.14 (s, 1H), 7.19 (s, 2H).

Step 3: To a solution of 3,4-diiodo-5-(trifluoromethyl)pyridin-2-amine (860 mg, 2.08 mmol), Pd(dppf)$Cl_2$ (152 mg, 0.208 mmol) and $K_2CO_3$ (861 mg, 6.23 mmol) in DME (2 mL) was added 2,4,6-trimethyl-1,3,5,2,4,6-trioxatriborinane (50 wt % in THF, 3.13 g, 12.5 mmol) and the mixture was heated at 90° C. for 16 h under $N_2$ in a sealed tube. The mixture was diluted with water (10 mL), extracted with EtOAc (2×30 mL), and the combined organic layers dried over $Na_2SO_4$, filtered, and concentrated under reduced pressure. The residue was purified by prep-TLC (Pet. ether/EtOAc=1/1, v/v) to afford 3,4-dimethyl-5-(trifluoromethyl)pyridin-2-amine (291 mg, 74%) as an off-white solid. LCMS: m/z=191 $[M+H]^+$. $^1$H NMR (400 MHz, DMSO-$d_6$) δ 8.03 (s, 1H), 6.44 (s, 2H), 2.22 (s, 3H), 2.01 (s, 3H).

Step 4: To a solution of 3,4-dimethyl-5-(trifluoromethyl)pyridin-2-amine (240 mg, 1.26 mmol) in conc. HCl (3 mL) at 0° C. was added sodium nitrite (435 mg, 6.31 mmol) and the mixture was stirred at 25° C. for 16 h. The mixture was diluted with water (10 mL), extracted with EtOAc (2×20 mL), and the combined organic layers washed with water (10 mL), brine (10 mL), dried over $Na_2SO_4$, filtered, and concentrated under reduced pressure. The residue was purified by reverse phase chromatography ($C_{18}$ silica, Gradient: 99%-100% MeCN in water with 0.2% formic acid) to afford 2-chloro-3,4-dimethyl-5-(trifluoromethyl)pyridine (61 mg, 24%) as a yellow oil. LCMS: m/z=210 $[M+H]^+$. $^1H$ NMR (400 MHz, DMSO-$d_6$) δ 8.55 (s, 1H), 2.44 (s, 3H), 2.39 (s, 3H).

Step 5: To a solution of 2-chloro-3,4-dimethyl-5-(trifluoromethyl)pyridine (61.0 mg, 0.291 mmol) in MeOH (5 mL) was added triethylamine (44.2 mg, 0.437 mmol) and Pd(dppf)$Cl_2$ (21.3 mg, 0.029 mmol) and the mixture was heated at 80° C. for 16 h under a CO atmosphere (2 MPa). The mixture was diluted with water (10 mL), extracted with EtOAc (2×20 mL), and the combined organic layers were washed with water (10 mL), brine (10 mL), dried over $Na_2SO_4$, filtered, and concentrated under reduced pressure to give methyl 3,4-dimethyl-5-(trifluoromethyl)picolinate (80 mg) as yellow oil, which was used directly in the next step. LCMS: m/z=234 $[M+H]^+$. $^1H$ NMR (400 MHz, DMSO-$d_6$) δ 8.72 (s, 1H), 3.92 (s, 3H), 2.43 (s, 3H), 2.34 (s, 3H).

Step 6: To a solution of methyl 3,4-dimethyl-5-(trifluoromethyl)picolinate (80 mg) in THF (4 mL) and water (2 mL) was added LiOH (18.7 mg, 0.782 mmol) and the mixture was stirred at 25° C. for 2 h. The mixture was adjusted to pH 5-6 with 2 M aqueous HCl, diluted with water (10 mL), and extracted with EtOAc (2×20 mL). The combined organic layers were washed with water (10 mL), brine (10 mL), dried over $Na_2SO_4$, filtered, and concentrated under reduced pressure to give 3,4-dimethyl-5-(trifluoromethyl)picolinic acid (28 mg, 44% over two steps) as a yellow solid. $^1H$ NMR (400 MHz, DMSO-$d_6$) δ 8.69 (s, 1H), 2.42 (s, 3H), 2.35 (s, 3H).

Intermediate 69:
4,6-Dimethyl-5-(trifluoromethyl)picolinic acid

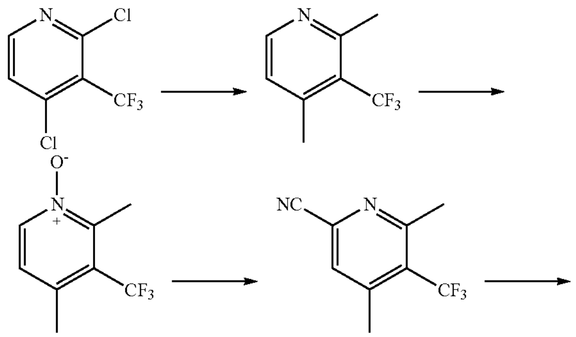

-continued

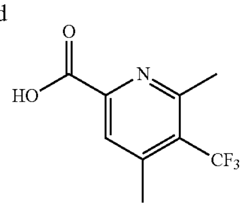

Step 1: Completed as described in Intermediate 68: 3,4-Dimethyl-5-(trifluoromethyl)picolinic acid step 3 starting from 2,4-dichloro-3-(trifluoromethyl)pyridine to afford 2,4-dimethyl-3-(trifluoromethyl)pyridine (2.1 g, 80%). LCMS: m/z=176 $[M+H]^+$. $^1H$ NMR (400 MHz, DMSO-$d_6$) δ 8.50 (d, J=5.0 Hz, 1H), 7.30 (d, J=5.0 Hz, 1H), 2.63 (q, J=3.2 Hz, 3H), 2.46 (q, J=3.2 Hz, 3H).

Step 2: A mixture of 2,4-dimethyl-3-(trifluoromethyl)pyridine (1.6 g, 9.1 mmol) and 30% $H_2O_2$ (1.0 g, 9.1 mmol) in AcOH (10 mL) was heated at 70° C. for 3 h. Additional 30% $H_2O_2$ (1.0 g, 9.1 mmol) was added and the mixture was heated at 70° C. for another 16 h. The mixture was concentrated under reduced pressure to give 2,4-dimethyl-3-(trifluoromethyl)pyridine 1-oxide (238 mg, 14%) as a yellow oil. LCMS: m/z=192 $[M+H]^+$.

Step 3: A mixture of 2,4-dimethyl-3-(trifluoromethyl)pyridine 1-oxide (420 mg, 2.20 mmol), triethylamine (889 mg, 8.79 mmol), and trimethylsilylnitrile (1.31 g, 13.2 mmol) in MeCN (10 mL) was heated at 150° C. for 4 h under microwave irradiation. The mixture was diluted with water (80 mL), extracted with DCM (3×40 mL), and the combined organic layers were washed with brine (3×50 mL), dried over $Na_2SO_4$, filtered, and concentrated under reduced pressure. The residue was purified by prep-TLC (DCM/MeOH=20/1, v/v) to give 4,6-dimethyl-5-(trifluoromethyl)picolinonitrile (87 mg, 20%) as a yellow oil. LCMS: m/z=201 $[M+H]^+$. $^1H$ NMR (400 MHz, DMSO-$d_6$) δ 8.06 (s, 1H), 2.68 (q, J=3.2 Hz, 3H), 2.53 (q, J=3.4 Hz, 3H).

Step 4: A mixture of 4,6-dimethyl-5-(trifluoromethyl)picolinonitrile (50 mg, 0.25 mmol) and NaOH (30 mg, 0.75 mmol) in EtOH (2 mL) and water (0.7 mL) was heated at 90° C. for 5 h in a sealed tube then concentrated under reduced pressure to give 4,6-dimethyl-5-(trifluoromethyl)picolinic acid (80 mg, Na salt) as a yellow solid. LCMS: m/z=220 $[M+H]^+$.

Intermediate 70:
3,6-Dimethyl-5-(trifluoromethyl)picolinic acid

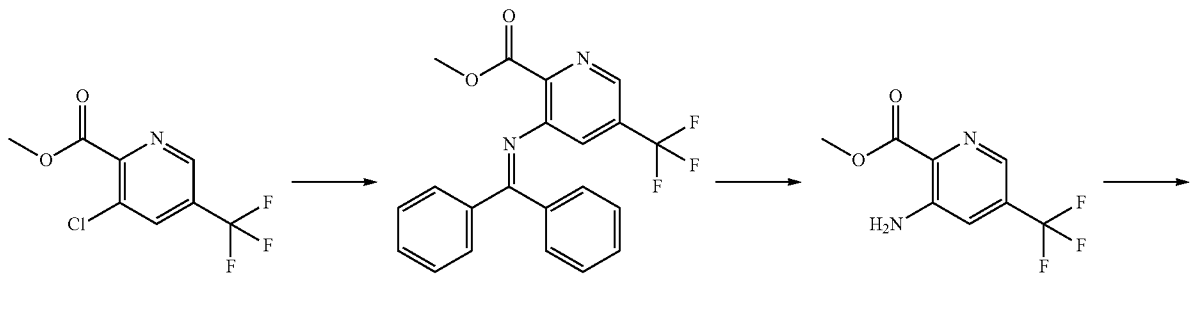

-continued

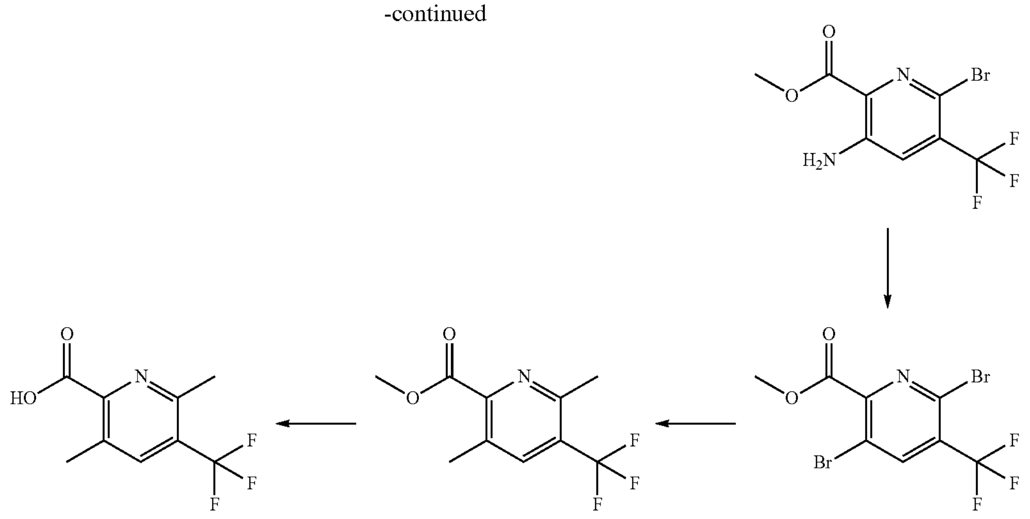

Step 1: To a solution of methyl 3-chloro-5-(trifluoromethyl)picolinate (5.00 g, 20.9 mmol) and benzophenone imine (5.67 g, 31.3 mmol) in 1,4-dioxane (30 mL) was added 4,5-bis(diphenylphosphino)-9,9-dimethyl xanthene (966 mg, 1.67 mmol), $Pd(OAc)_2$ (375 mg, 1.67 mmol), and $Cs_2CO_3$ (13.6 g, 41.7 mmol). The mixture was heated at 100° C. for 16 h under a $N_2$ atmosphere in a sealed tube. The mixture was diluted with water (10 mL), extracted with EtOAc (2×50 mL), and the combined organic layers were washed with water (10 mL), brine (10 mL), dried over $Na_2SO_4$, filtered, and concentrated under reduced pressure. The residue was purified by silica gel chromatography (Pet. ether/EtOAc=I/O to 1/1, v/v) to afford methyl 3-((diphenylmethylene)amino)-5-(trifluoromethyl)picolinate (6.3 g) as an off-white solid. LCMS: m/z=385 $[M+H]^+$.

Step 2: A mixture of methyl 3-((diphenylmethylene) amino)-5-(trifluoromethyl)picolinate (6.3 g) and a 4 M HCl in MeOH solution (15 mL) was stirred at 25° C. for 2 h. The mixture was adjusted to pH 8-9 with $Na_2CO_3$, diluted with water (10 mL), and extracted with EtOAc (2×30 mL). The combined organic layers were washed with water (10 mL), brine (10 mL), dried over $Na_2SO_4$, filtered, and concentrated under reduced pressure. The residue was purified by silica gel chromatography (Pet. ether/EtOAc=I/O to 1/1, v/v) to afford methyl 3-amino-5-(trifluoromethyl)picolinate (2.9 g, 63% over two steps) as an off-white solid. LCMS: m/z=221 $[M+H]^+$. $^1H$ NMR (400 MHz, DMS-$d_6$) δ 8.12 (d, J=2.4 Hz, 1H), 7.59 (d, J=1.2 Hz, 1H), 7.01 (s, 2H), 3.85 (s, 3H).

Step 3: To a solution of methyl 3-amino-5-(trifluoromethyl)picolinate (381 mg, 1.73 mmol) in MeCN (5 mL) at 0° C. was added NBS (400 mg, 2.25 mmol) and the mixture was stirred at 25° C. for 16 h under a $N_2$ atmosphere. The reaction was quenched with a saturated aqueous $Na_2S_2O_3$ solution (10 mL) and the mixture diluted with water (10 mL) and extracted with EtOAc (2×20 mL). The combined organic layers were washed with water (10 mL), brine (10 mL), dried over $Na_2SO_4$, filtered, and concentrated under reduced pressure. The residue was purified by silica gel chromatography (Pet. ether/EtOAc=I/O to 2/1, v/v) to afford methyl 3-amino-6-bromo-5-(trifluoromethyl)picolinate (512 mg, 98%) as a yellow solid. LCMS: m/z=299 $[M+H]^+$. $^1H$ NMR (400 MHz, DMSO-$d_6$) δ 7.76 (s, 1H), 7.16 (s, 2H), 3.85 (s, 3H).

Step 4: To a solution of methyl 3-amino-6-bromo-5-(trifluoromethyl)picolinate (562 mg, 1.88 mmol) and cupric bromide (630 mg, 2.82 mmol) in MeCN (1 mL) was added tert-butyl nitrite (291 mg, 2.82 mmol) and the mixture was stirred at 25° C. for 16 h under a $N_2$ atmosphere. The mixture was diluted with a saturated aqueous $NH_4Cl$ solution (10 mL), extracted with EtOAc (2-20 mL), and the combined organic layers washed with water (10 mL), brine (10 mL), dried over $Na_2SO_4$, filtered, and concentrated under reduced pressure. The residue was purified by prep-TLC (Pet. ether/EtOAc=10/1, v/v) to afford methyl 3,6-dibromo-5-(trifluoromethyl)picolinate (581 mg, 95%) as a yellow oil. $^1H$ NMR (400 MHz, DMSO-$d_6$) δ 8.51 (s, 1H), 3.75 (s, 3H).

Step 5: Completed as described in Intermediate 68: 3,4-Dimethyl-5-(trifluoromethyl)picolinic acid step 3 starting from methyl 3,6-dibromo-5-(trifluoromethyl)picolinate to afford methyl 3,6-dimethyl-5-(trifluoromethyl)picolinate (81 mg, 63%) as a yellow oil. LCMS: m/z=234 $[M+H]^+$. $^1H$ NMR (400 MHz, Chloroform-d) δ 7.81 (s, 1H), 4.00 (s, 3H), 2.72 (s, 3H), 2.56 (s, 3H).

Step 6: Completed as described in Intermediate 50: 5-(Difluoromethyl)-3-methoxypyrazine-2-carboxylic acid step 6 from methyl 3,6-dimethyl-5-(trifluoromethyl)picolinate to afford 3,6-dimethyl-5-(trifluoromethyl)picolinic acid (40 mg, li salt) as an off-white solid. LCMS: m/z=220 $[M+H]^+$. $^1H$ NMR (400 MHz, Methanol-$d_4$) δ 7.83 (s, 1H), 2.59 (s, 3H), 2.41 (s, 3H).

Intermediate 71: 4,5-Dimethyl-6-(trifluoromethyl)nicotinic acid

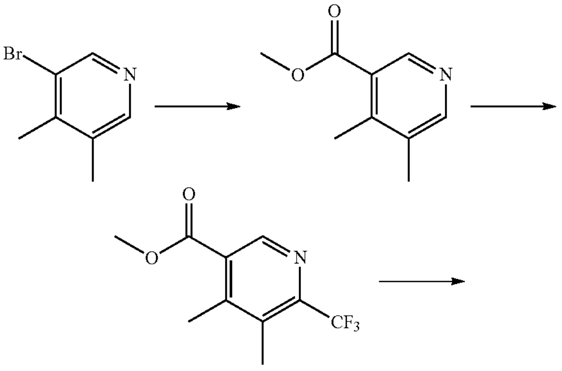

-continued

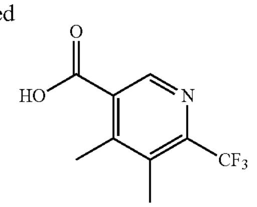

Step 1: To a solution of 3-bromo-4,5-dimethylpyridine (700 mg, 3.76 mmol) in MeOH (15 mL) was added $Pd(OAc)_2$ (84.5 mg, 0.378 mmol), dppf (209 mg, 0.378 mmol), and $Et_3N$ (1.14 g, 11.3 mmol). The mixture was heated at 85° C. under a CO atmosphere (3 MPa) for 16 h. The mixture was filtered and the filtrate concentrated under reduced pressure. The residue was purified by prep-TLC (Pet. ether/EtOAc=5/1 to 3/1, v/v) to give methyl 4,5-dimethylnicotinate (632 mg) as an off-white solid. LCMS: m/z=166 $[M+H]^+$. $^1H$ NMR (400 MHz, DMSO-$d_6$) δ 8.68 (s, 1H), 8.48 (s, 1H), 3.86 (s, 3H), 2.42 (s, 3H), 2.28 (s, 3H).

Step 2: To a solution of methyl 4,5-dimethylnicotinate (100 mg, 0.605 mmol) in $CHCl_3$ (2 mL) and water (0.57 mL) at 0° C. was added tert-butyl hydroperoxide (164 mg, 1.82 mmol), zinc trifluoromethanesulfonate (401 mg, 1.21 mmol), and trifluoroacetic acid (6.90 mg, 0.605 mmol) and the mixture was heated at 100° C. for 16 h. The mixture was diluted with water (20 mL), extracted with DCM (2×20 mL), and the combined organic layers were washed with brine (20 mL), dried over $Na_2SO_4$, filtered, and concentrated under reduced pressure. The residue was purified by prep-TLC (Pet. ether/EtOAc=5/1, v/v) to give methyl 4,5-dimethyl-6-(trifluoromethyl)nicotinate (40 mg, 29%) as a colourless oil. LCMS: m/z=234 $[M+H]^+$. $^1H$ NMR (400 MHz, Chloroform-d) δ 8.80 (s, 1H), 3.95 (s, 3H), 2.55 (s, 3H), 2.42 (s, 3H).

Step 3: Completed as described in Intermediate 50: 5-(Difluoromethyl)-3-methoxypyrazine-2-carboxylic acid step 6 from methyl 4,5-dimethyl-6-(trifluoromethyl)nicotinate to afford 4,5-dimethyl-6-(trifluoromethyl)nicotinic acid (35 mg, Li salt) as a white solid. LCMS: m/z=220 $[M+H]^+$. $^1H$ NMR (400 MHz, DMSO-$d_6$) δ 8.27 (d, J=3.6 Hz, 1H), 2.36 (s, 3H), 2.29 (s, 3H).

Intermediate 72: 5-Cyano-3-fluoro-6-methylpicolinic acid

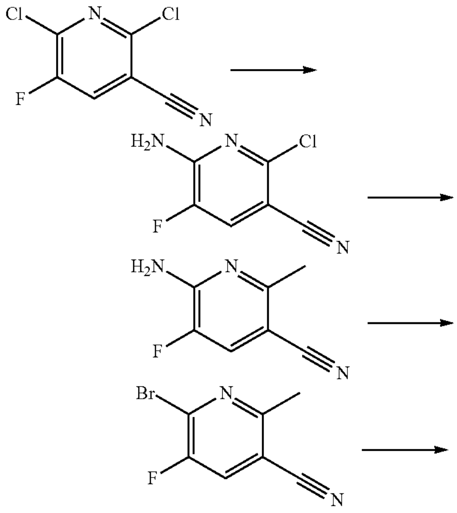

-continued

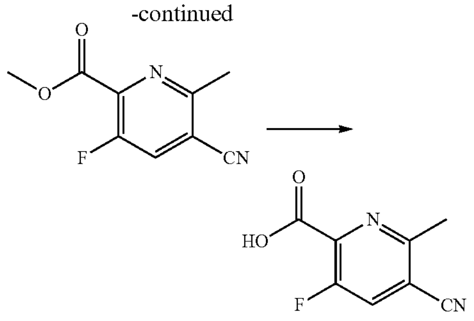

Step 1: A solution of 2,6-dichloro-5-fluoronicotinonitrile (2.00 g, 0.01 mol) in conc. $NH_{40}H$ (20 mL) was heated at 120° C. in a sealed tube for 4 h. The mixture was diluted with water (15 mL) and filtered. The collected solids were dissolved in DCM/MeOH and concentrated under reduced pressure to afford 6-amino-2-chloro-5-fluoronicotinonitrile (1.6 g, 84%) as a light-yellow solid. LCMS: m/z=172 $[M+H]^+$. $^1H$ NMR (400 MHz, DMSO-$d_6$) δ 7.98 (d, J=10.4 Hz, 1H), 7.84 (s, 2H).

Step 2: Completed as described in Intermediate 68: 3,4-Dimethyl-5-(trifluoromethyl)picolinic acid step 3 starting from 6-amino-2-chloro-5-fluoronicotinonitrile (90 mg, 0.52 mmol) to afford 6-amino-5-fluoro-2-methylnicotinonitrile (80 mg, 96%) as a white solid. LCMS: m/z=152 $[M+H]^+$. $^1H$ NMR (400 MHz, DMSO-$d_6$) δ7.72 (d, J=11.0 Hz, 1H), 7.27 (s, 2H), 2.39 (s, 3H).

Step 3: Completed as described in Intermediate 70: 3,6-Dimethyl-5-(trifluoromethyl)picolinic acid step 4 starting from 6-amino-5-fluoro-2-methylnicotinonitrile to afford 6-bromo-5-fluoro-2-methylnicotinonitrile (400 mg, 47%) as a white solid. $^1H$ NMR (400 MHz, DMSO-$d_6$) δ 8.48 (d, J=7.8 Hz, 1H), 2.65 (d, J=1.2 Hz, 3H).

Step 4: Completed as described in Intermediate 68: 3,4-Dimethyl-5-(trifluoromethyl)picolinic acid step 5 from 6-bromo-5-fluoro-2-methylnicotinonitrile to afford methyl 5-cyano-3-fluoro-6-methylpicolinate (230 mg, 63%) as a white solid. LCMS: m/z=195 $[M+H]^+$. $^1H$ NMR (400 MHz, DMSO-$d_6$) δ 8.57 (d, J=10.0 Hz, 1H), 3.92 (s, 3H), 2.68 (d, J=1.2 Hz, 3H).

Step 5: Completed as described in Intermediate 50: 5-(Difluoromethyl)-3-methoxypyrazine-2-carboxylic acid step 6 from methyl 5-cyano-3-fluoro-6-methylpicolinate to afford 5-cyano-3-fluoro-6-methylpicolinic acid (35 mg) as a white solid. LCMS: m/z=181 $[M+H]^+$. $^1H$ NMR (400 MHz, DMSO-$d_6$) δ 8.05 (d, J=8.6 Hz, 1H), 2.56 (d, J=1.0 Hz, 3H).

Intermediate 73: 5-Cyano-3,6-dimethylpicolinic acid

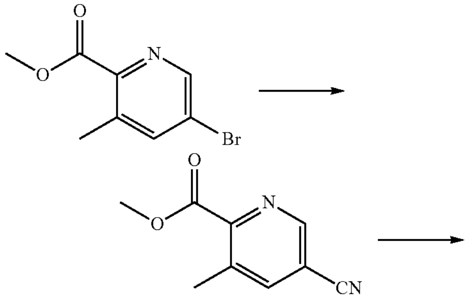

-continued

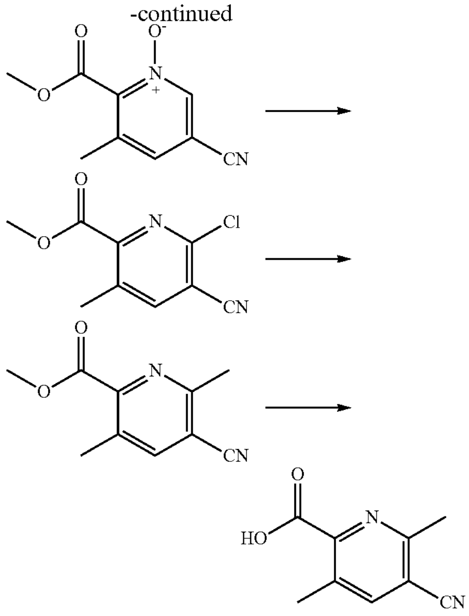

Step 1: To a solution of methyl 5-bromo-3-methylpicolinate (1.00 g, 4.35 mmol) in DMF (10 mL) was added zinc (71.0 mg, 1.09 mmol), Pd(dppf)$Cl_2$ (159 mg, 0.217 mmol), and zinc cyanide (306 mg, 2.61 mmol) and the mixture was heated at 120° C. under $N_2$ overnight. The mixture was diluted with water (50 mL), extracted with EtOAc (3×30 mL), and the combined organic layers were washed with brine (30 mL), dried over $Na_2SO_4$, filtered, and concentrated under reduced pressure. The residue was purified by silica gel chromatography (Pet. ether/EtOAc=20/1, v/v) to afford methyl 5-cyano-3-methylpicolinate (347 mg, 51%) as an off-white solid. LCMS: m/z=177 $[M+H]^+$. $^1H$ NMR (400 MHz, DMSO-$d_6$) δ 8.92 (s, 1H), 8.39 (s, 1H), 3.90 (s, 3H), 2.47 (s, 3H).

Step 2: To a solution of methyl 5-cyano-3-methylpicolinate (50 mg, 0.28 mmol) in DCM (4 mL) was added m-CPBA (98 mg, 0.57 mmol) and the mixture was heated at 50° C. for 16 h. The mixture was diluted with water (20 mL), extracted with DCM (3-10 mL), and the combined organic layers were washed with brine (30 mL), dried over $Na_2SO_4$, filtered, and concentrated under reduced pressure. The residue was purified by prep-TLC (Pet. ether/EtOAc=3/1, v/v) to afford 5-cyano-2-(methoxycarbonyl)-3-methylpyridine 1-oxide (16 mg, 30%) as an off-white solid. LCMS: m/z=193 $[M+H]^+$. $^1H$ NMR (400 MHz, DMSO-$d_6$) δ 8.88 (s, 1H), 7.89 (s, 1H), 3.93 (s, 3H), 2.24 (s, 3H).

Step 3: A solution of 5-cyano-2-(methoxycarbonyl)-3-methylpyridine 1-oxide (190 mg, 0.989 mmol) in $POCl_3$ (6 mL) was heated at 90° C. for 2 h. The mixture was concentrated under reduced pressure and the residue was diluted with water (30 mL) and extracted with DCM (3×20 mL). The combined organic layers were washed with brine (20 mL), dried over $Na_2SO_4$, filtered, and concentrated under reduced pressure. The residue was purified by prep-TLC (Pet. ether/EtOAc=3/1, v/v) to afford methyl 6-chloro-5-cyano-3-methylpicolinate (143 mg, 69%) as an off-white solid. LCMS: m/z=211 $[M+H]^+$. $^1H$ NMR (400 MHz, DMSO-$d_6$) δ 8.58 (s, 1H), 3.91 (s, 3H), 2.48 (s, 3H).

Step 4: Completed as described in Intermediate 68: 3,4-Dimethyl-5-(trifluoromethyl)picolinic acid step 3 starting from methyl 6-chloro-5-cyano-3-methylpicolinate to afford methyl 5-cyano-3,6-dimethylpicolinate (355 mg, 79%) as an off-white solid. LCMS: m/z=191 $[M+H]^+$. $^1H$ NMR (400 MHz, DMSO-d) S 8.30 (s, 1H), 3.89 (s, 3H), 2.65 (s, 3H), 2.41 (s, 3H).

Step 5: Completed as described in Intermediate 50: 5-(Difluoromethyl)-3-methoxypyrazine-2-carboxylic acid step 6 from methyl 5-cyano-3,6-dimethylpicolinate to afford 5-cyano-3,6-dimethylpicolinic acid (40 mg) as a yellow solid. LCMS: m/z=177 $[M+H]^+$.

Intermediate 74: 5-(Difluoromethoxy)-6-methylpyrazine-2-carboxylate acid

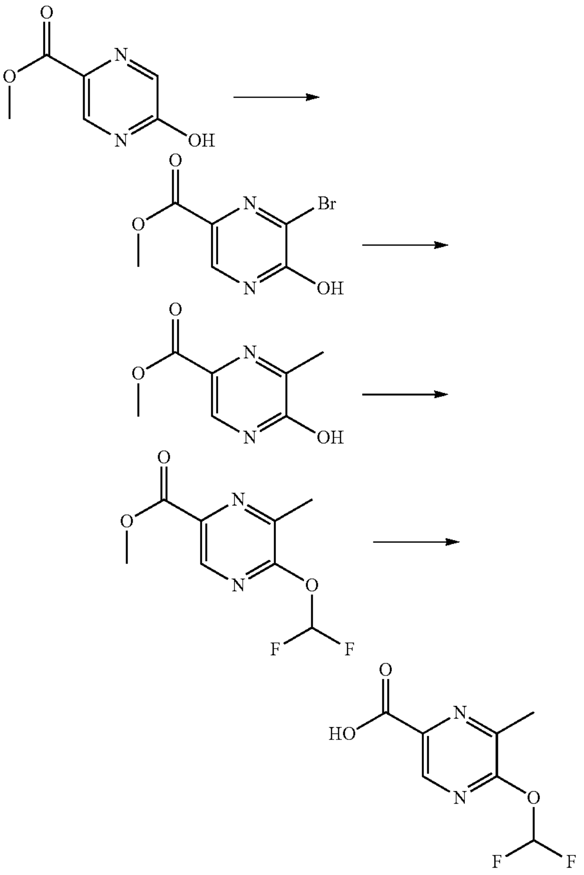

Step 1: To a solution of methyl 5-hydroxypyrazine-2-carboxylate (2.00 g, 13.0 mmol) in DMF (30 mL) at 0° C. was added NBS (2.77 g, 15.6 mmol) and the mixture was stirred at 25° C. for 5 h. The mixture was diluted with a saturated aqueous $NaHCO_3$ solution (40 mL), filtered, and the filtrate was concentrated under reduced pressure. The residue was purified directly by reverse phase chromatography (C18 column, 40 g, eluting with 20% MeCN in water with 0.1% formic acid) to give methyl 6-bromo-5-hydroxypyrazine-2-carboxylate (3.47 g) as a yellow solid. LCMS: m/z=233 $[M+H]^+$. $^1H$ NMR (40 MHz, Chloroform-d) δ 8.15 (s, 1H), 3.94 (s, 3H).

Step 2: Completed as described in Intermediate 68: 3,4-Dimethyl-5-(trifluoromethyl)picolinic acid step 3 starting from methyl 6-bromo-5-hydroxypyrazine-2-carboxylate to afford methyl 5-hydroxy-6-methylpyrazine-2-carboxylate (349 mg, 20%) as a white solid. LCMS: m/z=169 [M+H]1.

$^1$H NMR (400 MHz, Chloroform-d) δ 11.6 (s, 1H), 8.07 (s, 1H), 3.94 (s, 3H), 2.53 (s, 3H).

Step 3: To a solution of methyl 5-hydroxy-6-methylpyrazine-2-carboxylate (100 mg, 0.595 mmol) in MeCN (3 mL) was added 2-(fluorosulfonyl)difluoroacetic acid (471 mg, 2.64 mmol) and $Na_2CO_3$ (252 mg, 2.38 mmol) and the mixture was stirred at 25° C. for 48 h. The mixture was diluted with a saturated aqueous $NaHCO_3$ (10 mL) solution, extracted with EtOAc (2×20 mL), and the combined organic layers were washed with brine (20 mL), dried over $Na_2SO_4$, filtered, and concentrated under reduced pressure. The residue was purified by prep-TLC (Pet. ether/EtOAc=5/1, v/v) to give methyl 5-(difluoromethoxy)-6-methylpyrazine-2-carboxylate (20 mg, 16%) as a white solid. LCMS: m/z=219 $[M+H]^+$. $^1$H NMR (400 MHz, DMSO-$d_6$) δ 8.74 (s, 1H), 7.94-7.56 (m, 1H), 3.90 (s, 3H), 2.52 (s, 3H).

Step 4: Completed as described in Intermediate 50: 5-(Difluoromethyl)-3-methoxypyrazine-2-carboxylic acid step 6 from methyl 5-(difluoromethoxy)-6-methylpyrazine-2-carboxylate to afford 5-(difluoromethoxy)-6-methylpyrazine-2-carboxylic acid (18 mg, Li salt) as a white solid. LCMS: m/z=203 $[M-H]^-$. $^1$H NMR (400 MHz, DMSO-$d_6$) δ 8.48 (s, 1H), 7.88-7.50 (m, 1H), 2.44 (s, 3H).

Intermediate 75: 6-(Difluoromethoxy)-2-methoxynicotinic acid

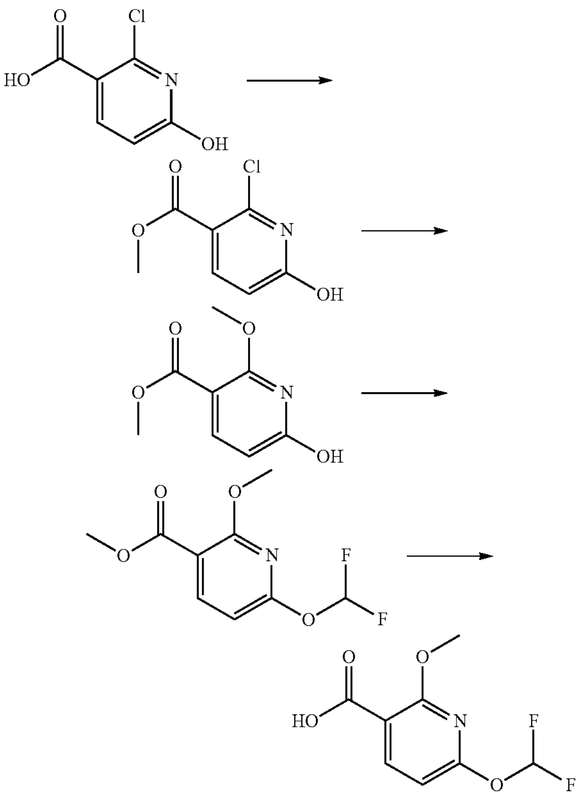

Step 1: To a solution of 2-chloro-6-hydroxynicotinic acid (2 g, 0.01 mol) in MeOH (16 mL) was added sulfuric acid (4 mL) and the mixture was heated at 70° C. overnight. The mixture was diluted with water (50 mL), extracted with EtOAc (50 mL×4), and the combined organic layers were dried over $Na_2SO_4$, filtered, and concentrated under reduced pressure to afford methyl 2-chloro-6-hydroxynicotinate (1.7 g, 82%) as a brown solid. LCMS: m/z=188 $[M+H]^+$. $^1$H NMR (400 MHz, DMSO-$d_6$) δ 12.4 (s, 1H), 8.12 (d, J=8.6 Hz, 1H), 6.69 (d, J=8.6 Hz, 1H), 3.81 (s, 3H).

Step 2: To a solution of methyl 2-chloro-6-hydroxynicotinate (200 mg, 1.07 mmol) in MeOH (5 mL) was added sodium methoxide (30 wt %, 1.15 g, 6.40 mmol) and the mixture was heated at 85° C. overnight. The mixture was diluted with water (30 mL), extracted with EtOAc (30 mL), and the organic phase was washed with brine (30 mL), dried over $Na_2SO_4$, filtered, and concentrated under reduced pressure to afford methyl 6-hydroxy-2-methoxynicotinate (70 mg, 36%) as a white solid. LCMS: m/z=184 $[M+H]^+$; $^1$H NMR (400 MHz, DMSO-$d_6$) δ 8.04 (d, J=8.2 Hz, 1H), 6.27 (d, J=8.2 Hz, 1H), 3.87 (s, 3H), 3.73 (s, 3H).

Step 3: Completed as described in Intermediate 74: 5-(Difluoromethoxy)-6-methylpyrazine-2-carboxylic acid step 3 from methyl 6-hydroxy-2-methoxynicotinate to afford methyl 6-(difluoromethoxy)-2-methoxynicotinate (30 mg, 34%) as a white solid. LCMS: m/z=234 $[M+H]^+$. $^1$H NMR (400 MHz, DMSO-$d_6$) δ 8.26 (d, J=8.2 Hz, 1H), 7.82 (t, J=72.2 Hz, 1H), 6.71 (d, J=8.2 Hz, 1H), 3.94 (s, 3H), 3.79 (s, 3H).

Step 4: Completed as described in Intermediate 50: 5-(Difluoromethyl)-3-methoxypyrazine-2-carboxylic acid step 6 from methyl 6-(difluoromethoxy)-2-methoxynicotinate to afford 6-(difluoromethoxy)-2-methoxynicotinic acid (30 mg, Li salt) as a white solid. LCMS: m/z=220 $[M+H]^+$. $^1$H NMR (400 MHz, DMSO-$d_6$) δ 7.89-7.49 (m, 2H), 6.45 (d, J=7.8 Hz, 1H), 3.79 (s, 3H).

Intermediate 76: 6-Methoxy-3-methyl-5-(trifluoromethyl)picolinic acid

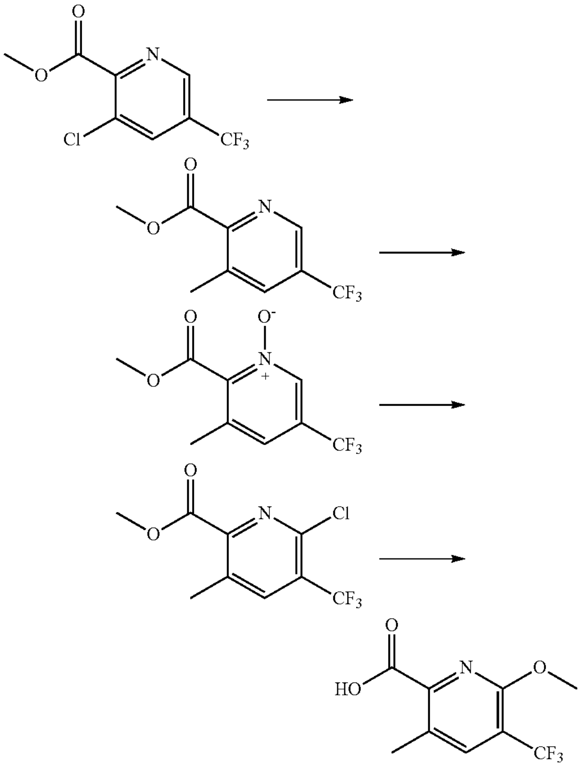

Step 1: Completed as described in Intermediate 68: 3,4-Dimethyl-5-(trifluoromethyl)picolinic acid step 3 starting from methyl 3-chloro-5-(trifluoromethyl)picolinate to afford methyl 3-methyl-5-(trifluoromethyl)picolinate (2.45 g, 67%) as a yellow oil. LCMS: m/z=220 $[M+H]^+$. $^1$H NMR (400 MHz, DMSO-$d_6$) δ 8.84 (s, 1H), 8.26 (s, 1H), 3.89 (s, 3H), 2.51 (s, 3H).

Step 2: Completed as described in Intermediate 73: 5-Cyano-3,6-dimethylpicolinic acid step 2 starting from methyl 3-methyl-5-(trifluoromethyl)picolinate to afford 2-(methoxycarbonyl)-3-methyl-5-(trifluoromethyl)pyridine 1-oxide as an off-white solid, which was used directly without further purification. LCMS: m/z=236 $[M+H]^+$.

Step 3: Completed as described in Intermediate 73: 5-Cyano-3,6-dimethylpicolinic acid step 3 starting from 2-(methoxycarbonyl)-3-methyl-5-(trifluoromethyl)pyridine 1-oxide to afford methyl 6-chloro-3-methyl-5-(trifluoromethyl)picolinate (105 mg, 45% over two steps) as a colorless oil. LCMS: m/z=254 $[M+H]^+$. $^1$H NMR (400 MHz, DMSO-$d_6$) δ 8.43 (s, 1H), 3.91 (s, 3H), 2.53 (s, 3H).

Step 4: Completed as described in Intermediate 50: 5-(Difluoromethyl)-3-methoxypyrazine-2-carboxylic acid step 6 from methyl 6-chloro-3-methyl-5-(trifluoromethyl)picolinate to afford 6-methoxy-3-methyl-5-(trifluoromethyl)picolinic acid (70 mg) as yellow oil, which was used without further purification. LCMS: m/z=236 $[M+H]^+$.

Intermediate 77: 2-Methoxy-5-methyl-6-(trifluoromethyl)nicotinic acid

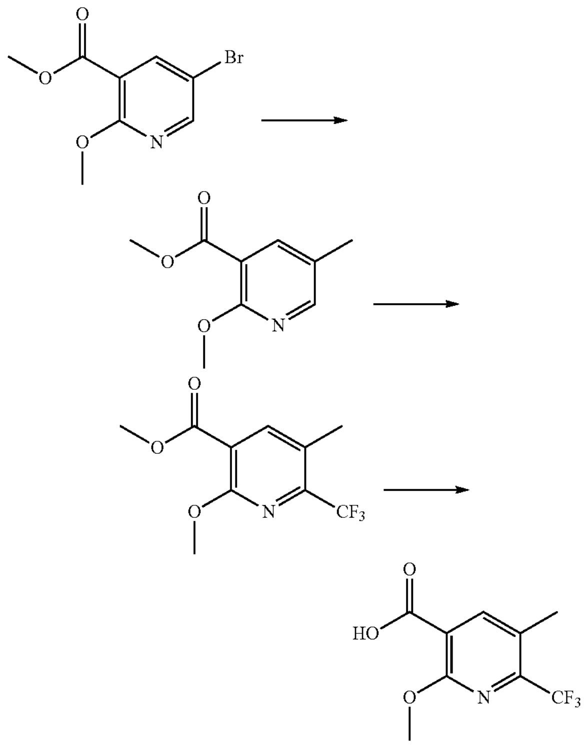

Step 1: To a solution of methyl 5-bromo-2-methoxynicotinate (2.00 g, 8.13 mmol), methyl boronic acid (730 mg, 12.2 mmol) and $K_2CO_3$ (3.37 g, 24.4 mmol) in dioxane/water (5/1, 24 mL) was added Pd(dppf)$Cl_2$ (595 mg, 0.813 mmol) and the mixture was heated at 100° C. under a $N_2$ atmosphere for 3 h. The mixture was diluted with water (50 mL), extracted with DCM (6×70 mL), and the combined organic phases dried over $Na_2SO_4$, filtered, and concentrated under reduced pressure. The residue was purified by silica gel chromatography (Pet. ether/EtOAc=10/1 to 5/1, v/v) to afford methyl 2-methoxy-5-methylnicotinate (850 mg, 58%) as a yellow oil. LCMS: m/z=182 $[M+H]^+$. $^1$H NMR (400 MHz, DMSO-$d_6$) δ 8.20-8.17 (m, 1H), 7.96-7.93 (m, 1H), 3.88 (s, 3H), 3.79 (s, 3H), 2.24 (s, 3H).

Step 2: To a solution of methyl 2-methoxy-5-methylnicotinate (200 mg, 1.10 mmol), Ru(phen)$_3C_{12}$ (70.7 mg, 0.099 mmol) and trifluoromethanesulfonyl chloride (558 mg, 3.31 mmol) in MeCN (4 mL) was added $K_2HPO_4$ (481 mg, 2.76 mmol) and the mixture was stirred and irradiated under 450 nm blue LED light at 25° C. for 16 h. The mixture was diluted with water (15 mL), extracted with DCM (7×20 mL), and the combined organic layers were dried over $Na_2SO_4$, filtered, and concentrated under reduced pressure. The residue was purified by prep-TLC (Pet. ether/EtOAc=5/1, v/v) to afford methyl 2-methoxy-5-methyl-6-(trifluoromethyl)nicotinate (100 mg, 37%) as a colorless oil. LCMS: m/z=250 $[M+H]^+$. $^1$H NMR (400 MHz, DMSO-$d_6$) δ 8.23 (s, 1H), 3.93 (s, 3H), 3.85 (s, 3H), 2.40 (q, J=2.2 Hz, 3H).

Step 3: Completed as described in Intermediate 50: 5-(Difluoromethyl)-3-methoxypyrazine-2-carboxylic acid step 6 from methyl 2-methoxy-5-methyl-6-(trifluoromethyl)nicotinate to afford 2-methoxy-5-methyl-6-(trifluoromethyl)nicotinic acid (40 mg, Li salt) as a white solid. LCMS: m/z=236 $[M+H]^+$. $^1$H NMR (400 MHz, DMSO-$d_6$) δ 7.49 (s, 1H), 3.78 (s, 3H), 2.30 (q, J=2.4 Hz, 3H).

Intermediate 78: 3-methyl-5-(trifluoromethyl)pyrazine-2-carboxylic acid

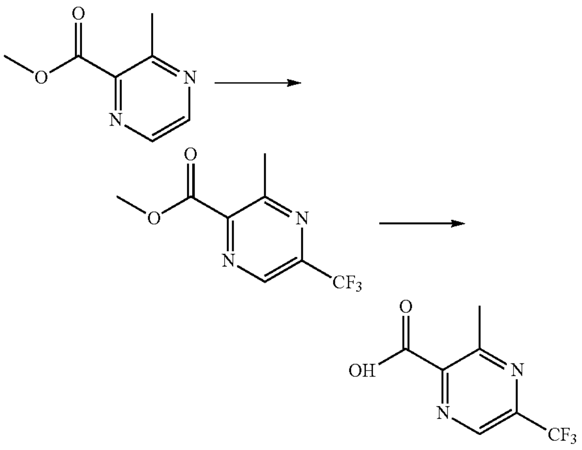

Step 1: To a solution of methyl 3-methylpyrazine-2-carboxylate (1.00 g, 6.57 mmol) in $CHCl_3$ (10 mL) and water (3 mL) was added zinc trifluoromethanesulfonate (2.62 g, 13.1 mmol) and tert-Butyl hydroperoxide (2.54 g, 70% in water, 19.7 mmol). The mixture was stirred at 50° C. for 16 h. The resulting mixture was quenched with $NaHCO_3$ (sat.). The resulting mixture was diluted with water (20 mL). The resulting mixture was extracted with EtOAc (3×20 mL). The combined organic layers were washed with brine (2×20 mL) and dried over anhydrous $Na_2SO_4$. After filtration, the filtrate was concentrated under reduced pressure. The residue was purified by silica gel column chromatography. eluting with Petroleum ether/EtOAc (0 to 50% gradient) to afford methyl 3-methyl-5-(trifluoromethyl)pyrazine-2-carboxylate (150 mg, 10.3%) as a colorless oil. LCMS: m/z=221 $[M+H]^+$, $^1H$ NMR (400 MHz, DMSO-$d_6$) δ 9.13 (s, 1H), 3.96 (s, 3H), 2.78 (s, 3H).

Step 2: Completed as described in Intermediate 50: 5-(Difluoromethyl)-3-methoxypyrazine-2-carboxylic acid step 6 from methyl methyl 3-methyl-5-(trifluoromethyl)pyrazine-2-carboxylate to afford 3-methyl-5-(trifluoromethyl)pyrazine-2-carboxylic acid (180 mg, crude) as white solid. LCMS: m/z=$[M-H]^-$=205.

Intermediate 79: 3-hydroxy-3-(trifluoromethyl)cyclohexane-1-carboxylic acid

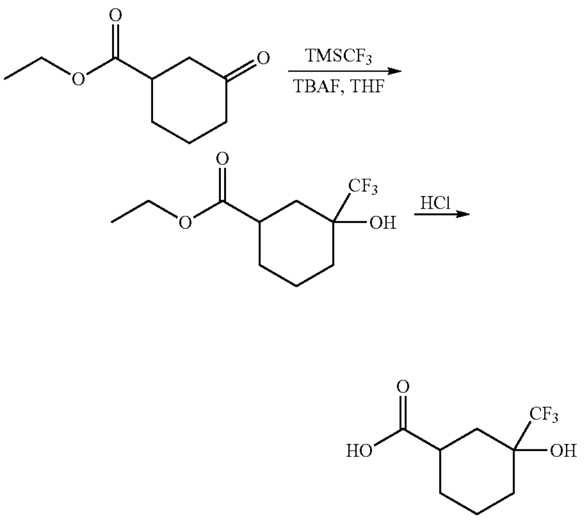

Step 1: A solution of ethyl 3-oxocyclohexane-1-carboxylate (1.0 g, 6.0 mmol) in THF (10 mL) was treated with trimethyl(trifluoromethyl)silane (3.0 g, 20.0 mmol) followed by the addition of tetrabutylammonium fluoride (11.0 g, 12.0 mmol) dropwise at 0° C. The reaction mixture was stirred at 25° C. for 2 h. The resulting mixture was quenched with water (20 mL) and extracted with EtOAc (3×50 mL). The combined organic layers were washed with brine and dried over anhydrous $Na_2SO_4$. After filtration, the filtrate was concentrated under reduced pressure. The residue was purified by silica gel column chromatography, eluting with 10/1 PE/EtOAc to afford ethyl 3-hydroxy-3-(trifluoromethyl)cyclohexane-1-carboxylate (900 mg, crude) as a light yellow oil. LCMS: m/z=241 $[M+H]^+$.

Step 2: Into a 40 mL vial were added ethyl 3-hydroxy-3-(trifluoromethyl)cyclohexane-1-carboxylate (900 mg, 3.8 mmol) in HCl (20 mL, 12 M in $H_2O$) aqueous solution at 25° C. The reaction mixture was heated to 60° C. and stirred at 60° C. for 16 h. The resulting mixture was allowed to cool to 25° C. and concentrated under reduced pressure to afford 3-hydroxy-3-(trifluoromethyl)cyclohexane-1-carboxylic acid (300 mg, crude) as a brown oil which was used in the next step directly without further purification. LCMS: m/z=213 $[M+H]^+$.

Intermediate 80: 6-(difluoromethyl)-5-methoxypicolinic acid

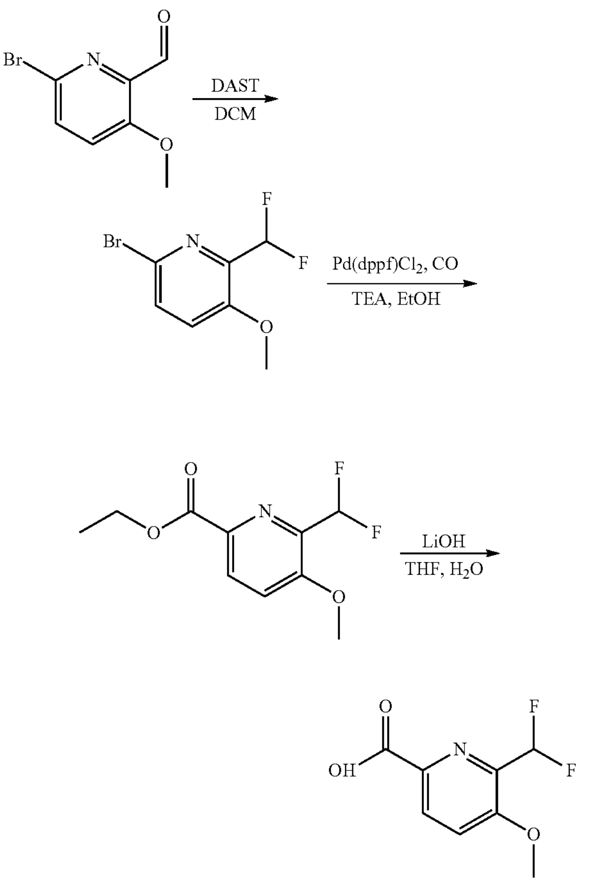

Step 1: To a stirred solution of 6-bromo-3-methoxypyridine-2-carbaldehyde (400 mg, 1.9 mmol) in DCM (6 mL) was added DAST (600 mg, 3.7 mmol) dropwise at 0° C. under a nitrogen atmosphere. The reaction mixture was stirred at 25° C. for 3 hours under a nitrogen atmosphere. The reaction was quenched with sat. $NaHCO_3$ (aq.) at 0° C. The resulting mixture was extracted with $CH_2Cl_2$ (3×30 mL). The combined organic layers were washed with brine and dried over anhydrous $Na_2SO_4$. After filtration, the filtrate was concentrated under reduced pressure. The residue was purified by prep-TLC (PE:EA 3:1) to afford 6-bromo-2-(difluoromethyl)-3-methoxypyridine (280.1 mg, 63.5% yield) as a light yellow solid. LCMS: m/z=238 $[M+H]^+$.

Step 2: Completed as described in Intermediate 68: 3,4-Dimethyl-5-(trifluoromethyl)picolinic acid step 5 from 6-bromo-2-(difluoromethyl)-3-methoxypyridine to afford ethyl 6-(difluoromethyl)-5-methoxypyridine-2-carboxylate (240.5 mg, 98.8% yield) as a light yellow solid. LCMS: m/z=232 $[M+H]^+$.

Step 3: Completed as described in Intermediate 50: 5-(Difluoromethyl)-3-methoxypyrazine-2-carboxylic acid step 6 from ethyl 6-(difluoromethyl)-5-methoxypicolinate to afford 6-(difluoromethyl)-5-methoxypicolinic acid (80.2 mg, 91.2% yield) as alight yellow solid. LCMS: m/z=204 $[M+H]^+$.

Intermediate 81: 3-chloro-5-(1,1-difluoroethyl)picolinic acid

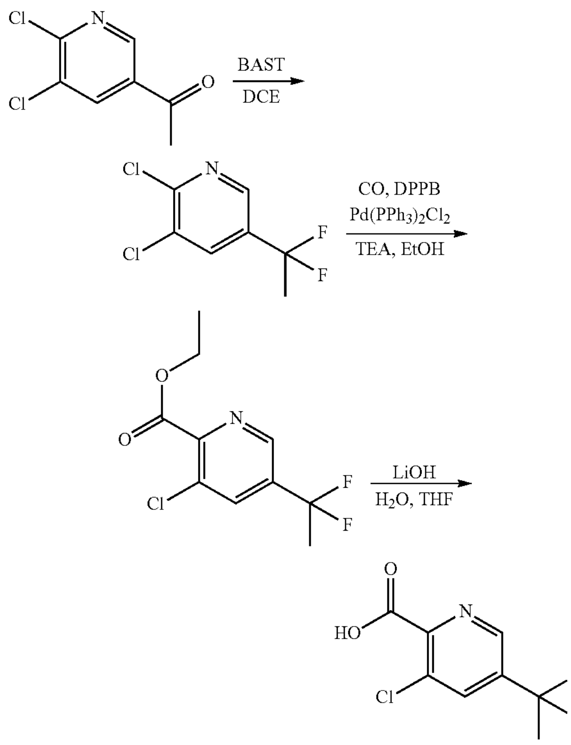

Step 1: To a stirred solution of 1-(5,6-dichloropyridin-3-yl)ethan-1-one (2.0 g, 10.0 mmol) in DCE (20 mL) was added BAST (5.0 g, 20.0 mmol) at 25° C. under a nitrogen atmosphere. The reaction mixture stirred at 80° C. for 16 hours under a nitrogen atmosphere. The resulting mixture was cooled to 25° C. The mixture was quenched with water (20 mL), basified to pH 9 with saturated $NaHCO_3$ (aq.) and extracted with EtOAc (3x50 mL). The combined organic layers were washed with brine and dried over anhydrous $Na_2SO_4$. After filtration, the filtrate was concentrated under reduced pressure. The residue was purified by silica gel column chromatography, eluting with PE/EA (10/1) to afford 2,3-dichloro-5-(1,1-difluoroethyl)pyridine (1.4 g, 60% yield) as a light yellow oil. LCMS: m/z=212 $[M+H]^+$.

Step 2: An autoclave was charged with 2,3-dichloro-5-(1,1-difluoroethyl)pyridine (1.1 g, 5.2 mmol), 4-diphenylphosphanylbutyl(diphenyl)phosphane (220 mg, 0.52 mmol), $Pd(PPh_3)_2Cl_2$ (730 mg, 1.0 mmol). TEA (1.6 g, 16.0 mmol), and EtOH (20 mL) at 25° C. The reaction mixture was stirred at 100° C. for 16 hours under carbon monoxide (40 atm). The resulting mixture was concentrated under reduced pressure. The residue was purified directly by silica gel column chromatography, eluting with PE/EA (5/1) to afford ethyl 3-chloro-5-(1,1-difluoroethyl)picolinate (1.1 g, 85% yield) as a colorless oil. LCMS: m/z=250 $[M+H]^+$.

Step 3: Completed as described in Intermediate 50: 5-(Difluoromethyl)-3-methoxypyrazine-2-carboxylic acid step 6 from ethyl 3-chloro-5-(1,1-difluoroethyl)picolinate to afford 3-chloro-5-(1,1-difluoroethyl)picolinic acid (400 mg, crude) as a white solid. LCMS: m/z=222 $[M+H]^+$.

Intermediate 82: 8-methoxyimidazo[1,5-a]pyridine-5-carboxylic acid

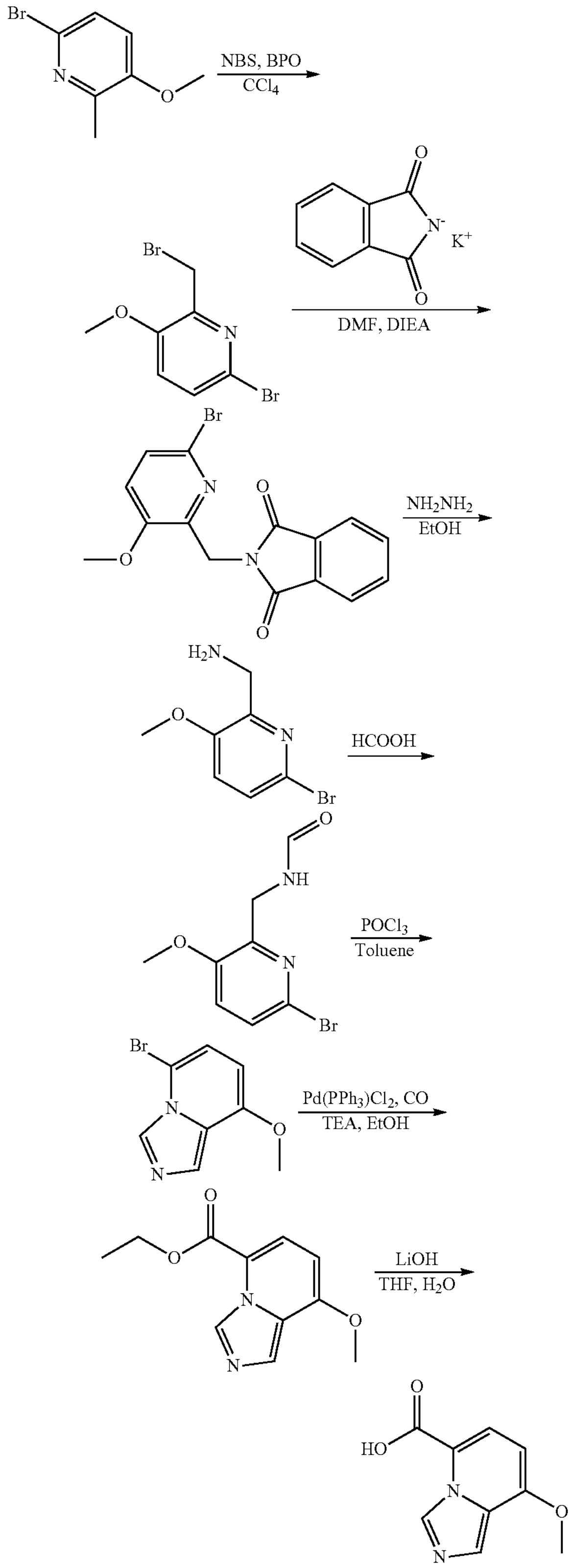

Step 2: To a solution of 6-bromo-3-methoxy-2-methylpyridine (5.0 g, 24.7 mmol) and NBS(4.8 g, mmol) in $CCl_4$ (100 mL) was added benzoic peroxyanhydride (0.6 g, 2.5 mmol) in portions at 25° C. The resulting mixture was stirred at 80° C. for 1 h under a nitrogen atmosphere. The resulting mixture was concentrated under reduced pressure. The residue was purified by silica gel column chromatography, eluting with EA/PE (1/5) to afford 6-bromo-2-(bromomethyl)-3-methoxypyridine (6.5 g, 60% yield) as a light yellow solid. LCMS: m/z=280 $[M+H]^+$.

Step 2: To a solution of 6-bromo-2-(bromomethyl)-3-methoxypyridine (6.5 g, 23.5 mmol) and DIEA (4.6 g, 35.6 mmol) in DMF (40 mL) was added potassium 1,3-dioxoisoindolin-2-ide (5.2 g, 28.1 mmol) in portions at 25° C. The reaction mixture was stirred at 50° C. for 1 h under a nitrogen atmosphere. The resulting mixture was cooled to 25° C. The reaction was quenched with water at 0° C. The resulting mixture was extracted with EtOAc (3×100 mL). The combined organic layers were extracted with brine and dried over anhydrous $Na_2SO_4$. The resulting mixture was concentrated under reduced pressure. The residue was purified by silica gel column chromatography, eluting with EA/PE (1/1) to afford 2-((6-bromo-3-methoxypyridin-2-yl)methyl)isoindoline-1,3-dione (5.0 g, 61% yield) as a light yellow solid. LCMS: m/z=347 $[M+H]^+$.

Step 3: To a solution of 2-((6-bromo-3-methoxypyridin-2-yl)methyl)isoindoline-1,3-dione (5.3 g, 15.3 mmol) in EtOH (50 mL) was added hydrazine (1.2 g, 30.0 mmol) in portions at 25° C. The resulting mixture was stirred at 25° C. for 1 hour under a nitrogen atmosphere. The resulting mixture was concentrated under reduced pressure. The residue was purified by reverse-phase flash chromatography (0-100% ACN in water with 10 mmol/L $NH_4HCO_3$ additive) to afford (6-bromo-3-methoxypyridin-2-yl)methanamine (610 mg, 18.5% yield) as a light yellow solid LCMS: m/z=217 $[M+H]^+$.

Step 4: To an 8 mL vial were added (6-bromo-3-methoxypyridin-2-yl)methanamine (600 mg, 2.8 mmol) and HCOOH (10 mL) at 25° C. The reaction mixture was stirred at 100° C. for 16 h under a nitrogen atmosphere. The resulting mixture was cooled to 25° C. The reaction was diluted with water (15 mL), and the mixture was basified to pH 7 with saturated $NaHCO_3$ (aq.) at 0° C. The resulting mixture was extracted with EtOAc (3×20 mL). The combined organic layers were dried over anhydrous $Na_2SO_4$. After filtration, the filtrate was concentrated under reduced pressure. The residue was purified by prep-TLC (MeOH/$CH_2Cl_2$ 1/20) to afford N-((6-bromo-3-methoxypyridin-2-yl)methyl)formamide (270 mg, 36% yield) as a light yellow solid. LCMS: m/z=245 $[M+H]^+$.

Step 5: To a solution of N-((6-bromo-3-methoxypyridin-2-yl)methyl)formamide (260 mg, 1.1 mmol) in toluene (5 mL) was added $POCl_3$ (488 mg, 3.2 mmol) in one portion at 25° C. The resulting mixture was stirred at 90° C. for 1 h under a nitrogen atmosphere. The resulting mixture was cooled to 25° C. The mixture was basified to pH 7 with saturated $NaHCO_3$ (aq.) at 0° C. The resulting mixture was extracted with EtOAc (3×20 mL). The combined organic layers were dried over anhydrous $Na_2SO_4$. After filtration, the filtrate was concentrated under reduced pressure. The residue was purified by prep-TLC (MeOH/$CH_2Cl_2$, 1/20) to afford 5-bromo-8-methoxyimidazole[1,5-a]pyridine (200.0 mg, 83.0% yield) as a light yellow solid. LCMS: m/z=227 $[M+H]^+$.

Step 6: Completed as described in Intermediate 81: 3-chloro-5-(1,1-difluoroethyl)picolinic acid step 2 starting from 5-bromo-8-methoxyimidazo[1,5-a]pyridine to afford ethyl 8-methoxyimidazo[1,5-a]pyridine-5-carboxylate (70 mg, 32% yield) as a light yellow solid. LCMS: m/z=221 $[M+H]^+$.

Step 7: Completed as described in Intermediate 50: 5-(Difluoromethyl)-3-methoxypyrazine-2-carboxylic acid step 6 from ethyl 8-methoxyimidazo[1,5-a]pyridine-5-carboxylate to afford 8-methoxyimidazo[1,5-a]pyridine-5-carboxylic acid (30 mg, 58% yield) as a light yellow solid. LCMS: m/z=193 $[M+H]^+$.

Intermediate 83: 4-chloro-6-methoxypyridazine-3-carboxylic acid

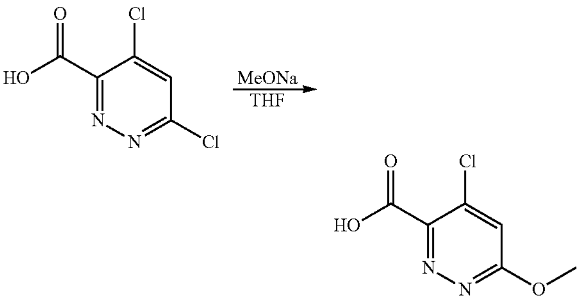

A solution of 4,6-dichloropyridazine-3-carboxylic acid (1.0 g, 5.0 mmol) and sodium methanolate (0.6 g, 10.0 mmol) in THF (10 mL) was stirred at 100° C. for 1 hour under a nitrogen atmosphere. The resulting mixture was cooled to 25° C. and concentrated under reduced pressure. The residue was purified by reverse-phase flash chromatography (10-50% MeCN in water with 0.1% formic acid additive) to afford 4-chloro-6-methoxypyridazine-3-carboxylic acid (971 mg, 99% yield) as a white solid. LCMS: m/z=$[M+H]^+$=189.

Intermediate 84: 5-chloro-4-methoxypyrimidine-2-carboxylic acid

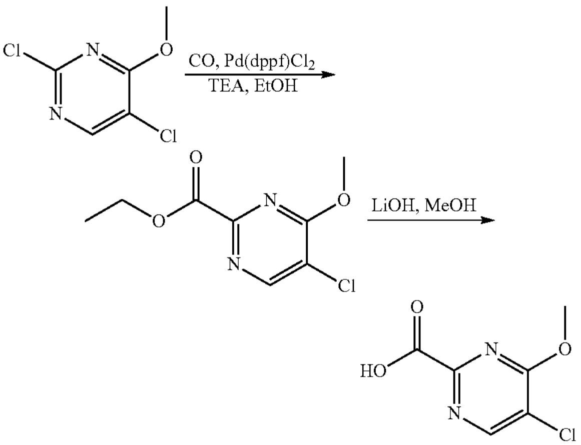

Step 1: Completed as described in Intermediate 81: 3-chloro-5-(1,1-difluoroethyl)picolinic acid step 2 starting from 2,5-dichloro-4-methoxypyrimidine to afford ethyl 5-chloro-4-methoxypyrimidine-2-carboxylate (289 mg, 48% yield) as a white solid. LCMS: m/z=217 $[M+H]^+$.

Step 2: Completed as described in Intermediate 50: 5-(Difluoromethyl)-3-methoxypyrazine-2-carboxylic acid step 6 from ethyl 5-chloro-4-methoxypyrimidine-2-carboxylate to afford 5-chloro-4-methoxypyrimidine-2-carboxylic acid (100 mg, 41% yield) as a white solid. LCMS: m/z=189 $[M+H]^+$.

TABLE AB

The following intermediate was prepared using a similar procedure to that described for Intermediate 84

| Intermediate Number | Structure | Compound Name | LCMS $[M-H]^-$ |
|---|---|---|---|
| 85 | 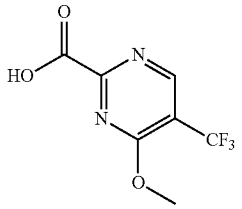 | 4-methoxy-5-(trifluoromethyl)pyrimidine-2-carboxylic acid | 221 |

Intermediate 86: 5-chloro-3-(1,1-difluoroethyl)picolinic acid

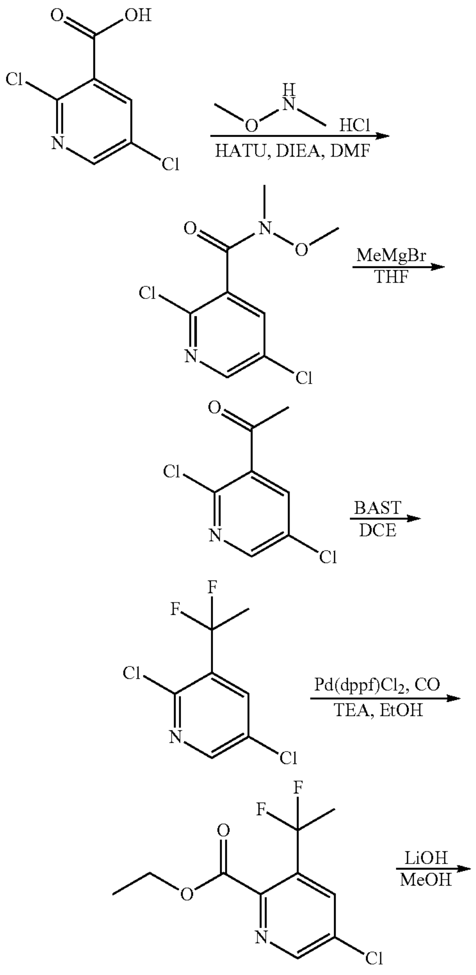

-continued

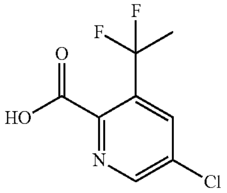

Step 1: A solution of 2,5-dichloronicotinic acid (2.0 g, 10.0 mmol) in DMF (20 mL) was treated with DIEA (4.0 g, 30.0 mmol) and HATU (5.9 g, 15.0 mmol) for 5 minutes at 25° C. followed by the addition of N,O-dimethylhydroxylamine hydrochloride (1.5 g, 15.0 mmol) in one portion at 25° C. The reaction mixture was stirred at 25° C. for 4 h. The mixture was purified directly by reverse-phase flash chromatography (0-100% ACN in water with 0.1% formic acid additive) to afford 2,5-dichloro-N-methoxy-N-methylnicotinamide (1.8 g, 74% yield) as a white solid. LCMS: m/z=235 $[M+H]^+$.

Step 2: Into a 30 mL sealed tube were added 2,5-dichloro-N-methoxy-N-methylnicotinamide (1.0 g, 4.3 mmol) and THF (10 mL) at 25° C. The resulting mixture was charged with $N_2$ three times at 25° C. and stirred at 0° C. for 5 minutes under nitrogen atmosphere. To the above mixture was added methylmagnesium bromide (0.8 g, 6.4 mmol) dropwise over 5 minutes at 0° C. under nitrogen atmosphere. The resulting mixture was warmed to 25° C. and stirred at 25° C. for 2 h. The resulting mixture was quenched with $H_2O$ (20 mL) and extracted with EtOAc (3×50 mL). The combined organic layers were washed with brine and dried over anhydrous $Na_2SO_4$. After filtration, the filtrate was concentrated under reduced pressure. The residue was purified by silica gel column chromatography, eluting with PE/EA (3/1) to afford 1-(2,5-dichloropyridin-3-yl)ethan-1-one (550 mg, 68% yield) as a light yellow liquid. LCMS: m/z=190 $[M+H]^+$.

Step 3: Into a 30 mL sealed tube were added 1-(2,5-dichloropyridin-3-yl)ethan-1-one (600 mg, 3.2 mmol) and DCE (10 mL) at 25° C. The resulting mixture was charged with $N_2$ three times at 25° C. and stirred at 0° C. for 5 minutes under a nitrogen atmosphere. To the above mixture was added BAST (3.5 g, 16.0 mmol) dropwise over 5 minutes at 0° C. The resulting mixture was stirred at 80° C. for 12 h under a nitrogen atmosphere. The resulting mixture was cooled to 25° C., quenched with $H_2O$ (80 mL), and extracted with EA (3×80 mL). The combined organic layers were washed with brine and dried over anhydrous $Na_2SO_4$. After filtration, the filtrate was concentrated under reduced pressure. The residue was purified by silica gel column chromatography, eluting with PE/EA (3/1) to afford 2,5-dichloro-3-(1,1-difluoroethyl)pyridine (474.2 mg, 70.8% yield) as a light yellow liquid. LCMS: m/z=212 $[M+H]^+$.

Step 4: Completed as described in Intermediate 81: 3-chloro-5-(1,1-difluoroethyl)picolinic acid step 2 starting from 2,5-dichloro-3-(1,1-difluoroethyl)pyridine to afford ethyl 5-chloro-3-(1,1-difluoroethyl)picolinate (41 mg, 8% yield) as a white solid. LCMS: m/z=250 $[M+H]^+$.

Step 5: Completed as described in Intermediate 50: 5-(Difluoromethyl)-3-methoxypyrazine-2-carboxylic acid step 6 from ethyl 5-chloro-3-(1,1-difluoroethyl)picolinate to afford 5-chloro-3-(1,1-difluoroethyl)picolinic acid (19.0 mg, 61.0% yield) as a white solid. LCMS: m/z=222 $[M+H]^+$.

Intermediate 87: 6-(difluoromethoxy)-4-methylnicotinic acid

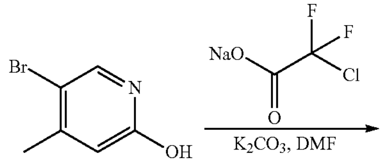

-continued

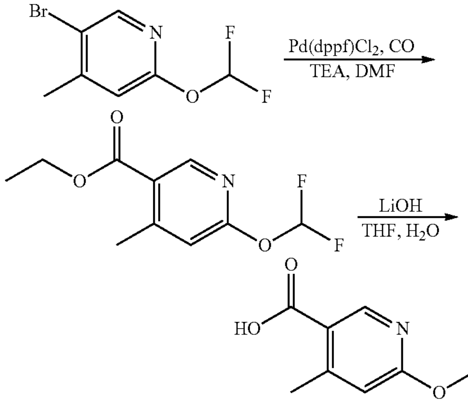

Step 1: To a stirred solution of 5-bromo-4-methylpyridin-2-ol (500 mg, 2.6 mmol) and $K_2CO_3$ (441 mg, 3.2 mmol) in DMF (10 mL) was added sodium 2-chloro-2,2-difluoroacetate (1.2 g, 8.0 mmol) in one portion at 25° C. The reaction mixture was charged with $N_2$ three times at 25° C. The resulting mixture was stirred at 100° C. for 3 h under a nitrogen atmosphere. The reaction was cooled to 25° C. The mixture was diluted with water (30 mL) and extracted with EtOAc (3×20 mL). The combined organic layers were washed with brine and dried over $Na_2SO_4$. After filtration, the filtrate was concentrated under reduced pressure. The residue was purified by Prep-TLC (PE/EA) (5/1) to afford 5-bromo-2-(difluoromethoxy)-4-methylpyridine (160.0 mg, crude) as a colorless oil. LCMS: m/z=238 $[M+H]^+$.

Step 2: Completed as described in Intermediate 81: 3-chloro-5-(1,1-difluoroethyl)picolinic acid step 2 starting from 5-bromo-2-(difluoromethoxy)-4-methylpyridine to afford ethyl 6-(difluoromethoxy)-4-methylnicotinate (40 mg, 23% yield) as a colorless oil. LCMS: m/z=232 $[M+H]^+$.

Step 3: Completed as described in Intermediate 50: 5-(Difluoromethyl)-3-methoxypyrazine-2-carboxylic acid step 6 from ethyl 6-(difluoromethoxy)-2-methylpyridine-3-carboxylate to afford 6-(difluoromethoxy)-4-methylnicotinic acid (70 mg, crude) as a white solid. LCMS: m/z=204 $[M+H]^+$.

TABLE AC

The following intermediates were prepared using a similar procedure to that described for Intermediate 87

| Intermediate Number | Structure | Compound Name | LCMS |
|---|---|---|---|
| 88 | 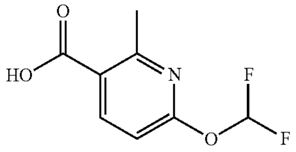 | 6-(difluoromethoxy )-2-methylpyridine-3-carboxylic acid | 204 |

Intermediate 89: 4-chloro-6-(difluoromethoxy) pyridazine-3-carboxylic acid

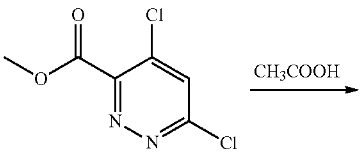

-continued

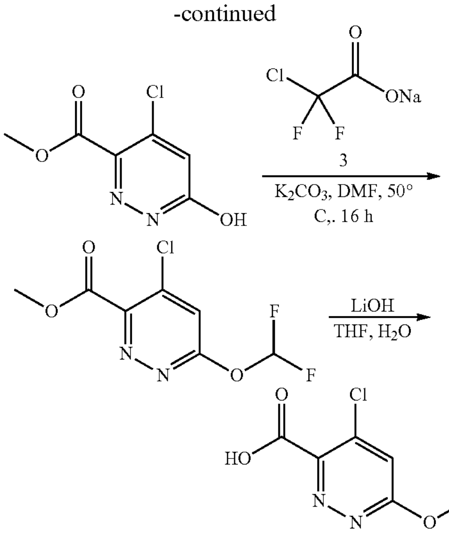

Step 1: A solution of methyl 4,6-dichloropyridazine-3-carboxylate (5.0 g, 24.1 mmol) in acetic acid (70 mL) was stirred at 110° C. for 12 hours under a nitrogen atmosphere. The reaction mixture was cooled to 25° C. and concentrated under reduced pressure. The residue was purified by silica gel column chromatography, eluting with PE/EA (1/4) to afford methyl 4-chloro-6-hydroxypyridazine-3-carboxylate (3.0 g, 66% yield) as a white solid. LCMS: m/z=189 [M+H]1.

Step 2: Completed as described in Intermediate 87: 6-(difluoromethoxy)-4-methylnicotinic acid step 1 from methyl 4-chloro-6-hydroxypyridazine-3-carboxylate to afford methyl 4-chloro-6-(difluoromethoxy) pyridazine-3-carboxylate (190 mg, 7.5% yield) as a brown solid. LCMS: m/z=239 $[M+H]^+$.

Step 3: Completed as described in Intermediate 50: 5-(difluoromethyl)-3-methoxypyrazine-2-carboxylic acid step 6 from methyl 4-chloro-6-(difluoromethoxy)pyridazine-3-carboxylate to afford 4-chloro-6-(difluoromethoxy)pyridazine-3-carboxylic acid (34 mg, 28% yield) as a yellow solid. LCMS: m/z=233 $[M-H]^-$.

Intermediate 90: 5-chloro-4-(difluoromethyl)pyrimidine-2-carboxylic acid

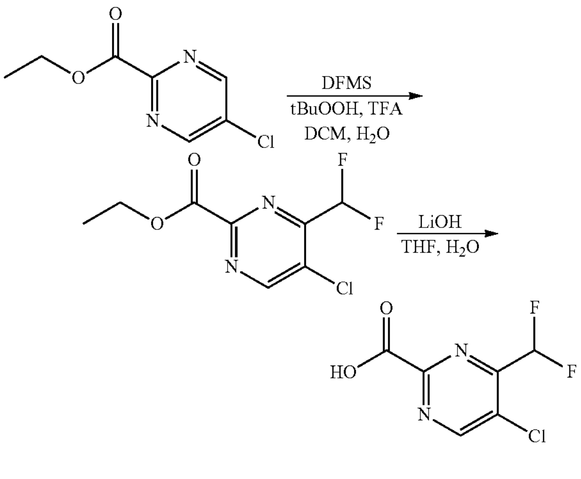

Step 1: Completed as described in Intermediate 30: 4-(difluoromethyl)-5-methoxypyrimidine-2-carboxylic acid step 1 from ethyl 5-chloropyrimidine-2-carboxylate to afford ethyl 5-chloro-4-(difluoromethyl)pyrimidine-2-carboxylate (30.0 mg, 7.9% yield) as a light yellow solid. LCMS: m/z=237 $[M+H]^+$.

Step 2: Completed as described in Intermediate 50: 5-(Difluoromethyl)-3-methoxypyrazine-2-carboxylic acid step 6 from ethyl 5-chloro-4-(difluoromethyl)pyrimidine-2-carboxylate to afford 5-chloro-4-(difluoromethyl)pyrimidine-2-carboxylic acid (30.0 mg, crude) as a light yellow solid. LCMS: m/z=207 $[M-H]^-$.

Intermediate 91: 6-(difluoromethoxy)pyridazine-3-carboxylicacid

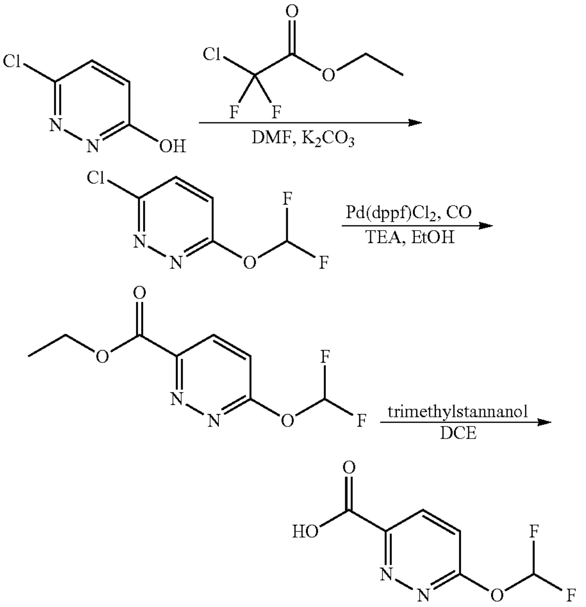

Step 1: Completed as described in Intermediate 87: 6-(difluoromethoxy)-4-methylnicotinic acid step 1 from 6-chloropyridazin-3-ol to afford 3-chloro-6-(difluoromethoxy) pyridazine (330 mg, 16% yield) as a light yellow oil. LCMS: m/z=181 $[M+H]^+$.

Step 2: Completed as described in Intermediate 81: 3-chloro-5-(1,1-difluoroethyl)picolinic acid step 2 starting from 3-chloro-6-(difluoromethoxy) pyridazine to afford ethyl 6-(difluoromethoxy) pyridazine-3-carboxylate (120 mg, 30% yield) as a brown solid. LCMS: m/z=219 $[M+H]^+$.

Step 3: A solution of ethyl 6-(difluoromethoxy) pyridazine-3-carboxylate (30 mg, 0.2 mmol) in DCE (1 mL) was treated with trimethylstannanol (124 mg, 0.7 mmol) at 25° C. The reaction mixture was stirred at 60° C. for 2 h. The resulting mixture was cooled to 25° C. and filtered. The filter cake was washed with DCM (3×3 mL). The filtrate was concentrated under reduced pressure to afford 6-(difluoromethoxy)pyridazine-3-carboxylic acid (70 mg, crude) as an off-white solid. The crude product mixture was used in the next step directly without further purification. LCMS: m/z=191 $[M+H]^+$.

Intermediate 92: 5-(difluoromethyl)-4-methoxypyrimidine-2-carboxylic acid

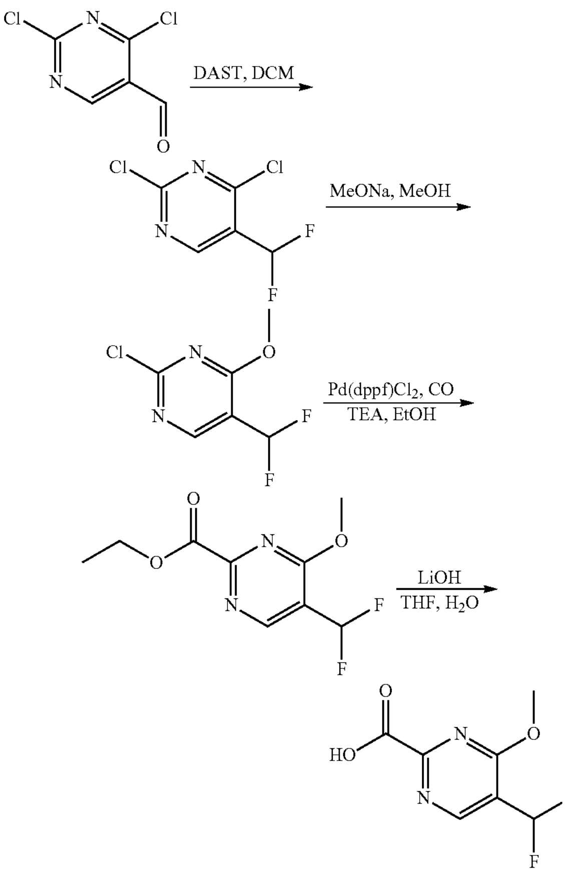

Step 1: Completed as described in Intermediate 80: 6-(difluoromethyl)-5-methoxypicolinic acid step 1 from 2,4-dichloropyrimidine-5-carbaldehyde to afford 2,4-dichloro-5-(difluoromethyl)pyrimidine (428 mg, 76% yield) as a colorless liquid. $^1$H NMR (400 MHz, DMSO-$d_6$) δ 9.06 (d, J=1.2 Hz, 1H), 7.29 (t, J=53.0 Hz, 1H).

Step 2: To a stirred solution of 2,4-dichloro-5-(difluoromethyl)pyrimidine (370 mg, 1.9 mmol,) in MeOH (10 mL) was added sodium methanolate (31 mg, 0.6 mmol) under a nitrogen atmosphere. The reaction mixture was stirred at 25° C. for 12 h. The resulting mixture was diluted with water (20 mL) and extracted with DCM (2x30 mL). The combined organic layers were washed with brine and dried over $Na_2SO_4$. After filtration, the filter cake was washed with DCM (3x20 mL) and the combined filtrates were concentrated under reduced pressure to afford 2-chloro-5-(difluoromethyl)-4-methoxypyrimidine (320 mg, crude) as a white solid. LCMS: m/z=195 $[M+H]^+$.

Step 3: Completed as described in Intermediate 68: 3,4-Dimethyl-5-(trifluoromethyl)picolinic acid step 5 from 2-chloro-5-(difluoromethyl)-4-methoxypyrimidine to afford ethyl 5-(difluoromethyl)-4-methoxypyrimidine-2-carboxylate (284 mg, 88% yield) as a colorless liquid. LCMS: m/z=233 $[M+H]^+$.

Step 4: Completed as described in Intermediate 50: 5-(Difluoromethyl)-3-methoxypyrazine-2-carboxylic acid step 6 from ethyl 5-(difluoromethyl)-4-methoxypyrimidine-2-carboxylate to afford 5-(difluoromethyl)-4-methoxypyrimidine-2-carboxylic acid (143 mg, 57% yield) as a colorless solid. LCMS: m/z=205 $[M+H]^+$.

Intermediate 93: 2-methoxy-4-methyl-6-(trifluoromethyl)nicotinic acid

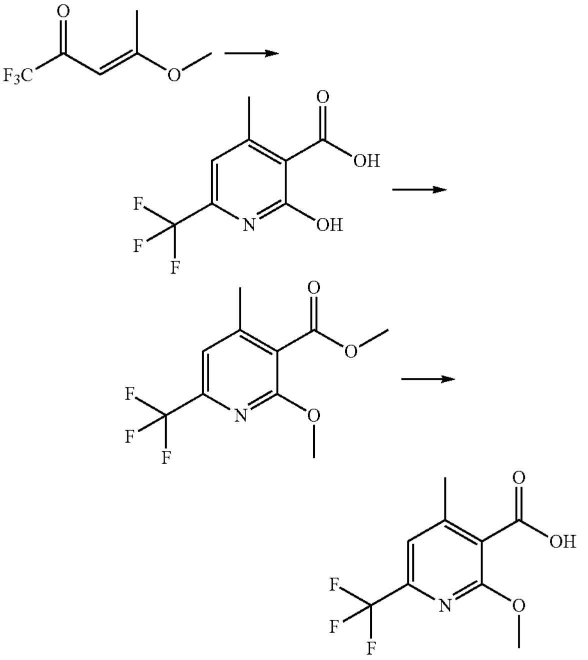

Step 1: To a solution of (E)-1,1,1-trifluoro-4-methoxypent-3-en-2-one (100 mg, 595 μmol) in EtOH (4 mL) was added sodium ethoxide (1.01 g, 1.16 mL, 20% Wt, 2.97 mmol) and ethyl 3-amino-3-oxopropanoate (78.0 mg, 595 μmol). The reaction mixture was stirred at 85° C. for 16 h. The reaction mixture was quenched with 2M HCl (5 mL) and water (30 ml) and extracted with EtOAc (3x20 mL). The combined organic layers were washed with brine (30 mL), dried over $Na_2SO_4$, filtered, and concentrated under reduced pressure to afford 2-hydroxy-4-methyl-6-(trifluoromethyl) nicotinic acid (75 mg, 51% yield) as a brown oil. LCMS: m/z=222 $[M+H]^+$. $^1$H NMR (400 MHz, DMSO-$d_6$) δ 7.27 (s, 1H), 2.34 (s, 3H).

Step 2: To a solution of 2-hydroxy-4-methyl-6-(trifluoromethyl)nicotinic acid (75 mg, 0.34 mmol) in DMF (3 mL) was added $K_2CO_3$ (0.14 g, 1.0 mmol) and MeI (0.24 g, 0.11 mL, 1.7 mmol). The reaction mixture was stirred at 70° C. for 2 h. The reaction mixture was quenched with water (30 mL) and extracted with EtOAc (3x10 mL). The combined organic lavers were washed with brine (20 mL), dried over $Na_2SO_4$, filtered, and concentrated under reduced pressure. The residue was purified by prep-TLC (Pet.ether:EtOAc 10:1) to afford methyl 2-methoxy-4-methyl-6-(trifluoromethyl)nicotinate (28 mg, 30% yield) as a yellow oil. LCMS: m/z=250 $[M+H]^+$. $^1$H NMR (400 MHz, DMSO-$d_6$) δ 7.52 (s, 1H), 3.92 (s, 3H), 3.88 (s, 3H), 2.34 (s, 3H).

Step 3: To a solution of methyl 2-methoxy-4-methyl-6-(trifluoromethyl)nicotinate (28 mg, 0.11 mmol) in THF (2 mL) was added LiOH (5.4 mg, 0.22 mmol), EtOH (I mL) and water (1 mL). The mixture was stirred at 50° C. for 2 h. Aqueous 2M HC was added to adjust pH to 3. The mixture was concentrated under reduced pressure, washed with DCM and MeOH, filtered, and concentrated under reduced pressure to afford 2-methoxy-4-methyl-6-(trifluoromethyl) nicotinic acid (30 mg, 91% yield) as a yellow solid. LCMS: m/z=236 $[M+H]^+$.

Intermediate 94: 2'-chloro-5'-(difluoromethoxy)-6-methyl-[4,4'-bipyridine]-3-carboxylic acid

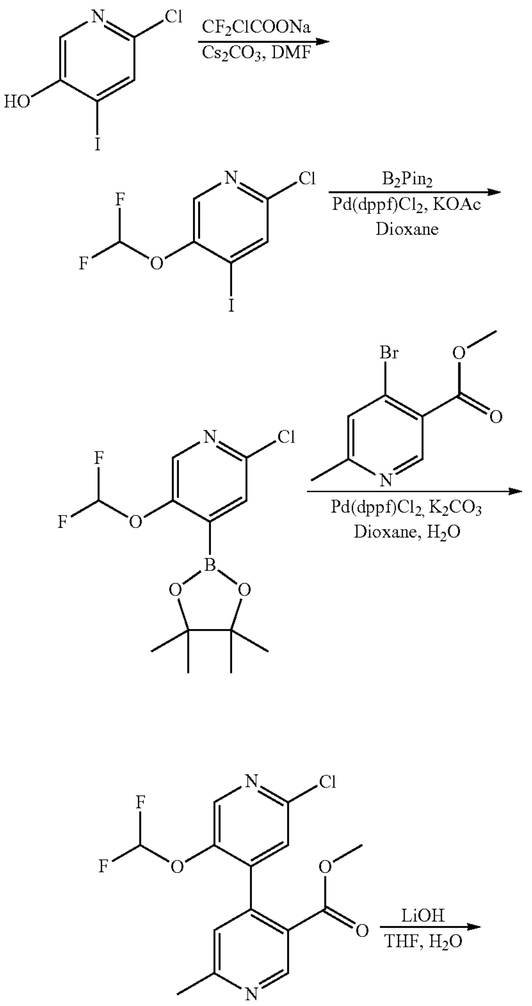

-continued

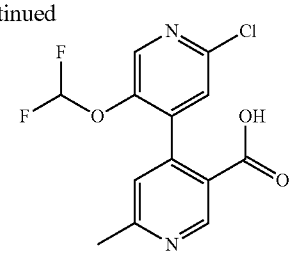

Step 1: To a stirred solution of 6-chloro-4-iodopyridin-3-ol (7.0 g, 27.4 mmol) in DMF (10 mL) were added sodium chlorodifluoroacetate (8.4 g, 55.1 mmol) and $Cs_2CO_3$ (11.5 g, 35.3 mmol) in one portion at 25° C. The reaction mixture was at 80° C. for 3 h under a nitrogen atmosphere. The resulting mixture was cooled to 25° C., diluted with $H_2O$ (50 mL), and extracted with EtOAc (3×50 mL). The combined organic layers were washed with brine (100 mL) and dried over anhydrous $Na_2SO_4$. After filtration, the filtrate was concentrated under reduced pressure, and the residue was purified by silica gel column chromatography, eluting with PE/EA (10/1) to afford 2-chloro-5-(difluoromethoxy)-4-iodopyridine (5.1 g, 61% yield) as a white solid. LCMS: m/z=306 $[M+H]^+$.

Step 2: Completed as described in Intermediate 13: (6-methoxyimidazo[1,5-a]pyridin-7-yl)boronic acid from 2-chloro-5-(difluoromethoxy)-4-iodopyridine to afford 2-chloro-5-(difluoromethoxy)-4-(4,4,5,5-tetramethyl-1,3,2-dioxaborolan-2-yl)pyridine (2.8 g, 93% yield) as a white solid. LCMS: m/z=306 $[M+H]^+$.

Step 3: Completed as described in Intermediate 2: 4-(5-Cyano-2-methoxyphenyl)-6-methylnicotinic acid step 1 from 2-chloro-5-(difluoromethoxy)-4-(4,4,5,5-tetramethyl-1,3,2-dioxaborolan-2-yl)pyridine to afford methyl 2'-chloro-5'-(difluoromethoxy)-6-methyl-[4,4'-bipyridine]-3-carboxylate (500 mg, 17% yield) as a yellow solid. LCMS: m/z=329 $[M+H]^+$.

Step 4: To a stirred solution of methyl 2'-chloro-5'-(difluoromethoxy)-6-methyl-[4,4'-bipyridine]-3-carboxylate (300 mg, 0.9 mmol) in THF (5 mL) and $H_2O$ (1 mL) was added LiOH (77 mg, 1.8 mmol) in one portion at 25° C. The resulting mixture was stirred at 25° C. for 2 h. The residue was acidified to pH 3 with HCl (1N), diluted with $H_2O$ (25 mL), extracted with DCM/MeOH (5:1) (3×30 mL), and dried over anhydrous $Na_2SO_4$. The resulting mixture was concentrated under reduced pressure to afford 2'-chloro-5'-(difluoromethoxy)-6-methyl-[4,4'-bipyridine]-3-carboxylic acid (260 mg, 91% yield) as a white solid. LCMS: m/z=315 $[M+H]^+$.

Intermediate 95: 5-(Difluoromethoxy)-3,6-dimethylpicolinic acid

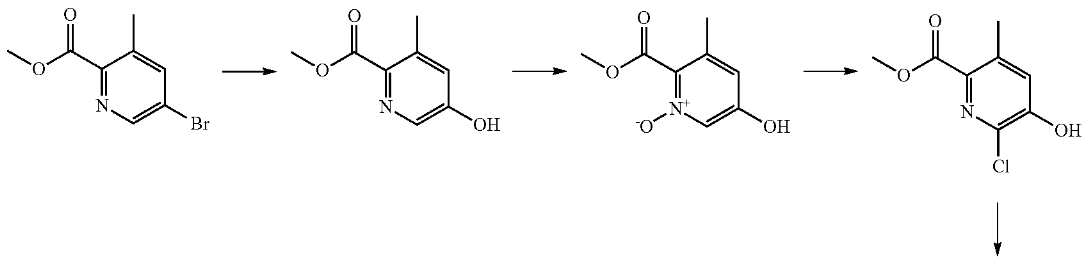

-continued

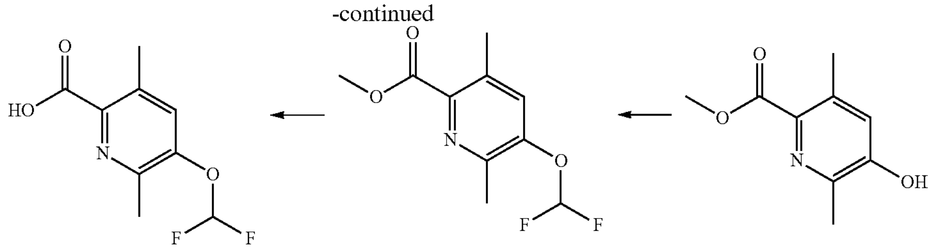

Step 1: A mixture of methyl 5-bromo-3-methylpicolinate (4.0 g, 17 mmol), acetohydroxcamic acid (7 g, 93 mmol) and $K_2CO_3$ (10.0 g, 72.5 mmol) in DMSO (80 mL) was heated at 80° C. under $N_2$ for 16 h. The mixture was diluted with water (1000 mL) and washed with EtOAc (5×200 mL). The aqueous phase was adjusted to pH 6 with 6 M aqueous HCl and extracted with EtOAc (5×300 mL). The combined organic extracts were dried over $Na_2SO_4$, filtered, and concentrated under reduced pressure to give methyl 5-hydroxy-3-methylpicolinate (4.77 g, crude) as a brown oil, which was used in the next step without further purification. LCMS: m/z=168 $[M+H]^+$. $^1H$ NMR (400 MHz, DMSO-$d_6$) δ 10.6 (s, 1H), 8.02 (d, J=2.6 Hz, 1H), 7.07 (d, J=2.6 Hz, 1H), 3.78 (s, 3H), 2.43 (s, 3H).

Step 2: To a solution of methyl 5-hydroxy-3-methylpicolinate (3.77 g, crude) in DCM (80 mL) at 0° C. was added 3-chloroperoxybenzoic acid (13.7 g, 85 wt %, 67.7 mmol) and the mixture was stirred at 25° C. for 16 h. The mixture was concentrated under reduced pressure and the residue was purified by silica gel chromatography (DCM/MeOH=100/i to 50/1 to 20/I, v/v) to give 5-hydroxy-2-(methoxycarbonyl)-3-methylpyridine 1-oxide (866 mg, 34% over two steps) as a white solid. LCMS: m/z=184 $[M+H]^+$. $^1H$ NMR (400 MHz, DMSO-$d_6$) δ 7.69 (d, J=2.0 Hz, 1H), 6.77 (d, J=1.8 Hz, 1H), 3.84 (s, 3H), 2.13 (s, 3H).

Step 3: A mixture of 5-hydroxy-2-(methoxycarbonyl)-3-methylpyridine 1-oxide (1.08 g, 5.90 mmol) and $POCl_3$ (6 mL) was heated at 105° C. for 2 h. The mixture was concentrated under reduced pressure and the residue adjusted to pH 6-7 with a saturated aqueous $Na_2CO_3$ solution and extracted with EtOAc (10×20 mL). The combined organic layers were dried over $Na_2SO_4$, filtered, and concentrated under reduced pressure. The residue was purified by prep-TLC (DCM/MeOH=20/1, v/v) to give methyl 6-chloro-5-hydroxy-3-methylpicolinate (296 mg, 25%) as an off-white solid. LCMS: m/z=202 $[M+H]^+$. $^1H$ NMR (400 MHz, DMSO-$d_6$) δ 11.5 (s, 1H), 7.22 (s, 1H), 3.80 (s, 3H), 2.45 (s, 3H).

Step 4: A mixture of methyl 6-chloro-5-hydroxy-3-methylpicolinate (310 mg, 1.54 mmol), $Pd(dppf)Cl_2$ (113 mg, 0.154 mmol), 2,4,6-trimethyl-1,3,5,2,4,6-trioxatriborinane (579 mg, 4.61 mmol) and $K_2COM$ (637 mg, 4.61 mmol) in DME (6 mL) was heated at 80° C. under $N_2$ for 16 h in a sealed tube. The mixture was concentrated under reduced pressure and the residue was purified by prep-TLC (DCM/MeOH=20/1, v/v) to give methyl 5-hydroxy-3,6-dimethylpicolinate (319 mg, >100%) as a brown solid. LCMS: m/z=182 $[M+H]^+$. $^1H$ NMR (400 MHz, DMSO-$d_6$) δ 10.5 (s, 1H), 6.98 (s, 1H), 3.77 (s, 3H), 2.39 (s, 3H), 2.29 (s, 3H).

Step 5: A mixture of methyl 5-hydroxy-3,6-dimethylpicolinate (100 mg, 0.552 mmol), sodium chloro(difluoro) acetate (168 mg, 1.10 mmol) and $K_2CO_3$ (229 mg, 1.66 mmol) in DMF (3 mL) was heated at 100° C. for 2 h. The mixture was diluted with water (40 mL), extracted with EtOAc (3×20 mL), and the combined organic layers washed with brine (3×30 mL), dried over $Na_2SO_4$, filtered, and concentrated under reduced pressure. The residue was purified by prep-TLC (DCM/MeOH=50/1, v/v) to give methyl 5-(difluoromethoxy)-3,6-dimethylpicolinate (35 mg, 28%) as a yellow oil. LCMS: m/z=232 $[M+H]^+$. $^1H$ NMR (400 MHz, DMSO-$d_6$) δ 7.58 (s, 1H), 7.33 (t, J=73.0 Hz, 1H), 3.84 (s, 3H), 2.45 (s, 3H), 2.41 (s, 3H).

Step 6: A mixture of methyl 5-(difluoromethoxy)-3,6-dimethylpicolinate (35 mg, 0.15 mmol) and LiOH (11 mg, 0.45 mmol) in THF (1.5 mL) and water (1.5 mL) was stirred at 25° C. for 2 h. The mixture was concentrated under reduced pressure to give 5-(difluoromethoxy)-3,6-dimethylpicolinic acid (33 mg, Li salt, 100%) as an off-white solid, which was used directly without purification. LCMS: m/z=218 $[M+H]^+$.

Intermediate 96: 3'-Fluoro-5'-methoxy-2' 6-dimethyl-[4,4'-bipyridine]-3-carboxylic acid

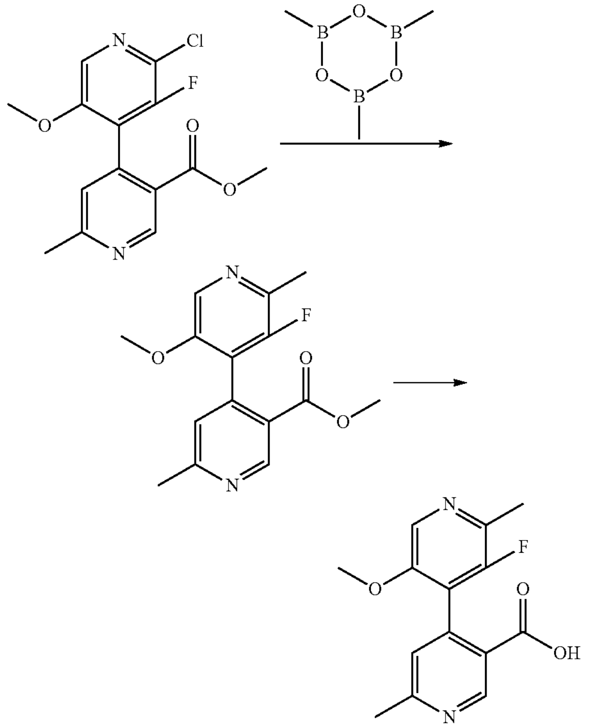

Step 1: A solution of methyl 2'-chloro-3'-fluoro-5'-methoxy-6-methyl-[4,4'-bipyridine]-3-carboxylate (240 mg, 0.772 mmol), $Cs_2CO_3$ (755 mg, 2.32 mmol), 2,4,6-trimethyl-1,3,5,2,4,6-trioxatriborinane (50 wt %, 970 mg, 3.86 mmol) and $Pd(dppf)Cl_2$—$CH_2Cl_2$ adduct (63.1 mg, 0.077 mmol) in 1,4-dioxane (6 mL) and water (0.6 mL) was heated at 100° C. under $N_2$ overnight. The mixture was poured into water (50 mL), extracted with EtOAc (50 mL×3), and the combined organic layers were washed with brine, dried over $Na_2SO_4$, filtered, and concentrated under reduced pressure. The residue was purified by prep-TLC (Pet. ether/EtOAc=2/1, v/v) to afford methyl 3'-fluoro-5'-methoxy-2',6-dimethyl-[4,4'-bipyridine]-3-carboxylate (150 mg, 67%) as a white solid. LCMS: m/z=291 $[M+H]^+$. $^1H$ NMR (400 MHz, DMSO-$d_6$) δ 8.98 (s, 1H), 8.21 (s, 1H), 7.35 (s, 1H), 3.78 (s, 3H), 3.67 (s, 3H), 2.57 (s, 3H), 2.42 (d, J=3.2 Hz, 3H).

Step 2: A mixture of methyl 3'-fluoro-5'-methoxy-2',6-dimethyl-[4,4'-bipyridine]-3-carboxylate (150 mg, 0.517 mmol) and NaOH (62.0 mg, 1.55 mmol) in MeOH (3 mL) and water (3 mL) was stirred at room temperature for 2 h. MeOH was removed under reduced pressure and the aqueous residue adjusted to pH 4-5 with 2 M aqueous HCl and concentrated under reduced pressure. The residue was purified by silica gel chromatography (DCM/MeOH=10/1, v/v) to afford 3'-fluoro-5'-methoxy-2',6-dimethyl-[4,4'-bipyridine]-3-carboxylic acid (60 mg, 42%) as a brown solid. LCMS: m/z=277 $[M+H]^+$. $^1H$ NMR (400 MHz, DMSO-$d_6$) δ 8.98 (s, 1H), 8.20 (s, 1H), 7.27 (s, 1H), 3.78 (s, 3H), 2.55 (s, 3H), 2.41 (d, J=3.0 Hz, 3H).

Intermediate 97: 5-chloro-2,6-dimethoxy-6'-methyl-[3,4'-bipyridine]-3'-carboxylic acid

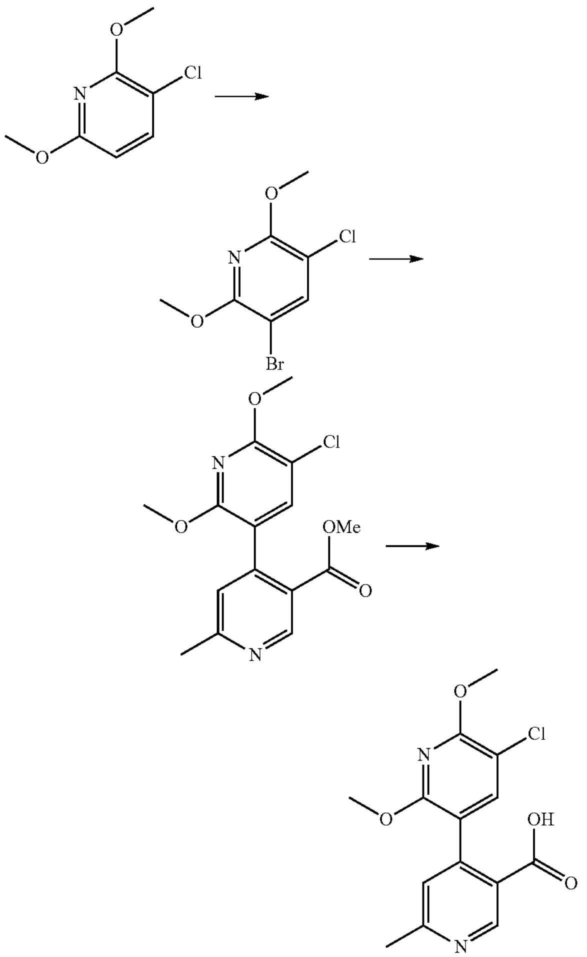

Step 1: To a solution of 3-chloro-2,6-dimethoxypyridine (1.40 g, 8.06 mmol) in DMF (8 mL) was added NBS (1.46 g, 8.1 mmol) and the mixture was stirred at 25° C. for 3.5 h. Additional NBS (0.72 g, 4.0 mmol) was added and stirring was continued at 25° C. for 2 h. The mixture was diluted with water (100 mL), extracted with EtOAc (3×40 mL), and the combined organic layers were washed with brine (3×60 mL), dried over $Na_2SO_4$, filtered, and concentrated under reduced pressure to give 3-bromo-5-chloro-2,6-dimethoxypyridine (2.0 g, 98%) as a yellow solid. $^1H$ NMR (400 MHz, DMSO-$d_6$) δ 8.10 (s, 1H), 3.95 (s, 3H), 3.94 (s, 3H).

Step 2: A mixture of 3-bromo-5-chloro-2,6-dimethoxypyridine (2.48 g, 9.82 mmol), methyl 6-methyl-4-(4,4,5,5-tetramethyl-1,3,2-dioxaborolan-2-yl)nicotinate (3.27 g, 11.8 mmol), $K_2CO_3$ (4.07 g, 29.5 mmol) and Pd(dppf)$Cl_2$ (640 mg, 0.982 mmol) in 1,4-dioxane (25 mL) and water (5.0 mL) was heated at 80° C. under $N_2$ for 2 h. The mixture was diluted with water (1000 mL), extracted with EtOAc (3×300 mL), and the combined organic layers were washed with brine (3×400 mL), dried over $Na_2SO_4$, filtered, and concentrated under reduced pressure. The residue was purified by silica gel chromatography (Pet. ether/EtOAc=20/1 to 10/1 to 5/1, v/v) to give methyl 5-chloro-2,6-dimethoxy-6'-methyl-[3,4'-bipyridine]-3'-carboxylate (1.5 g, 47%) as a yellow solid. LCMS: m/z=323 [M+H]1. $^1H$ NMR (400 MHz, DMSO-$d_6$) δ 8.77 (s, 1H), 7.88 (s, 1H), 7.33 (s, 1H), 4.01 (s, 3H), 3.80 (s, 3H), 3.69 (s, 3H), 2.54 (s, 3H).

Step 3: A mixture of methyl 5-chloro-2,6-dimethoxy-6'-methyl-[3,4'-bipyridine]-3'-carboxylate (1.57 g, 4.86 mmol) and NaOH (1.17 g, 29.2 mmol) in MeOH (51 mL) and water (17 mL) was stirred at 25° C. for 3 h. MeOH was removed under reduced pressure and the aqueous residue adjusted to pH 6 with 6 M aqueous HCl then concentrated under reduced pressure. The residue was purified by silica gel chromatography (DCM/MeOH=8/1, v/v) to give 5-chloro-2,6-dimethoxy-6'-methyl-[3,4'-bipyridine]-3'-carboxylic acid (1.35 g, 89%) as an off-white solid. LCMS: m/z=309 $[M+H]^+$. $^1H$ NMR (400 MHz, DMSO-$d_6$) δ 8.81 (s, 1H), 7.84 (s, 1H), 7.29 (s, 1H), 4.02 (s, 3H), 3.83 (s, 3H), 2.55 (s, 3H).

Intermediate 98: 4-(2-(Difluoromethyl)-5-methoxypyrimidin-4-yl)-6-methylnicotinic acid

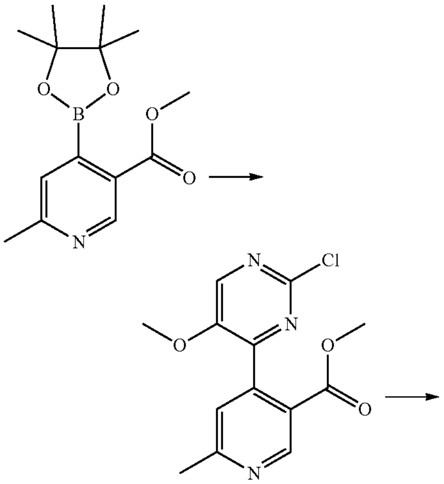

-continued

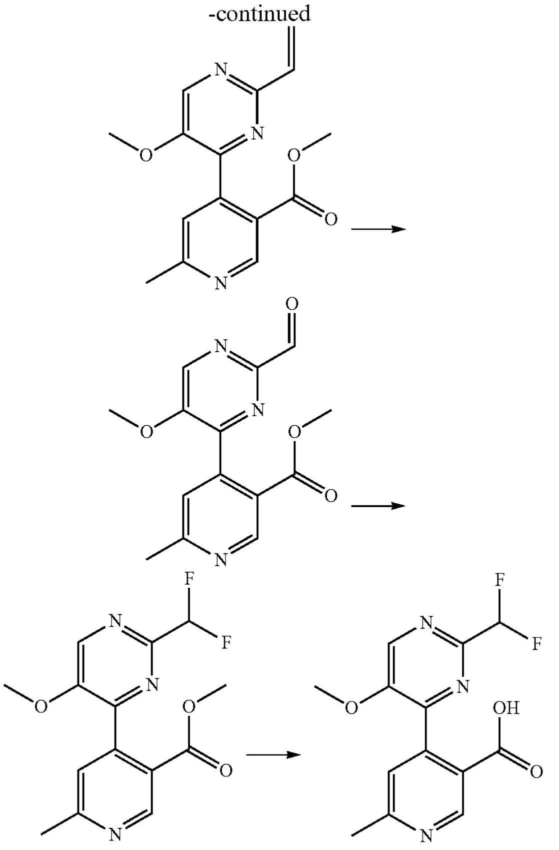

Step 1: Completed as described in Intermediate 97: 5-chloro-2,6-dimethoxy-6'-methyl-, [3,4'-bipyridine]-3'-carboxylic acid step 2 from methyl 6-methyl-4-(4,4,5,5-tetramethyl-1,3,2-dioxaborolan-2-yl)nicotinate and 2,4-dichloro-5-methoxypyrimidine to afford methyl 4-(2-chloro-5-methoxypyrimidin-4-yl)-6-methylnicotinate (1.00 g, 60%) as a yellow oil. LCMS: m/z=294 $[M+H]^+$. $^1H$ NMR (400 MHz, Chloroform-d) 9.05 (s, 1H), 8.26 (s, 1H), 7.26 (d, J=4.8 Hz, 1H), 3.84 (s, 3H), 3.77 (s, 3H), 2.66 (s, 3H).

Step 2: Completed as described in Intermediate 31: 2'-(difluoromethyl)-5'-methoxy-6-methyl-[4,4'-bipyridine]-3-carboxylic acid step 1 from methyl 4-(2-chloro-5-methoxypyrimidin-4-yl)-6-methylnicotinate to afford methyl 4-(5-methoxy-2-vinylpyrimidin-4-yl)-6-methylnicotinate (860 mg, 90%) as a yellow solid. LCMS: m/z=286 $[M+H]^+$, $^1H$ NMR (400 MHz, Chloroform-d) δ 9.04 (s, 1H), 8.38 (s, 1H), 7.34 (s, 1H), 6.88 (dd, J=17.2, 10.6 Hz, 1H), 6.49 (dd, J=17.4, 1.8 Hz, 1H), 5.64 (dd, J=10.6, 1.6 Hz, 1H), 3.86 (s, 3H), 3.74 (s, 3H), 2.69 (s, 3H).

Step 3: Completed as described in Intermediate 31: 2'-(difluoromethyl)-5'-methoxy-6-methyl-[4,4'-bipyridine]-3-carboxylic acid step 2 from methyl 4-(5-methoxy-2-vinylpyrimidin-4-yl)-6-methylnicotinate to afford methyl 4-(2-formyl-5-methoxypyrimidin-4-yl)-6-methylnicotinate (260 mg, 86%) as a white solid. LCMS: m/z=288 $[M+H]^+$, $^1H$ NMR (400 MHz, Chloroform-d) δ 10.1 (s, 1H), 9.12 (s, 1H), 8.59 (s, 1H), 7.34 (s, 1H), 3.98 (s, 3H), 3.78 (s, 3H), 2.72 (s, 3H).

Step 4: Completed as described in Intermediate 31: 2'-(difluoromethyl)-5'-methoxy-6-methyl-[4,4'-bipyridine]-3-carboxylic acid step 3 from methyl 4-(2-formyl-5-methoxypyrimidin-4-yl)-6-methylnicotinate to afford methyl 4-(2-(difluoromethyl)-5-methoxypyrimidin-4-yl)-6-methylnicotinate (66 mg, 24%) as a yellow oil. LCMS: m/z=310 $[M+H]^+$. $^1H$ NMR (400 MHz, Chloroform-d) δ 9.09 (s, 1H), 8.48 (s, 1H), 7.33 (s, 1H), 6.69 (t, J=54.6 Hz, 1H), 3.92 (s, 3H), 3.77 (s, 3H), 2.71 (s, 3H).

Step 5: Completed as described in Intermediate 31: 2'-(difluoromethyl)-5'-methoxy-6-methyl-[4,4'-bipyridine]-3-carboxylic acid step 4 from methyl 4-(2-(difluoromethyl)-5-methoxypyrimidin-4-yl)-6-methylnicotinate to afford 4-(2-(difluoromethyl)-5-methoxypyrimidin-4-yl)-6-methylnicotinic acid (60 mg, 95%) as a yellow solid. LCMS: m/z=2% $[M+H]^+$. $^1H$ NMR (400 MHz, DMSO-$d_6$) δ 8.86 (s, 1H), 8.59 (s, 1H), 7.07 (s, 1H), 6.90 (t, J=54.2 Hz, 1H), 3.83 (s, 3H), 2.51 (s, 3H).

Example 1: Synthesis of 2'-chloro-N-(5-(6-(difluoromethyl)picolinoyl)-5,6-dihydro-4H-pyrrolo[3,4-d]thiazol-2-yl)-5'-methoxy-6-methyl-[4,4'-bipyridine]-3-carboxamide

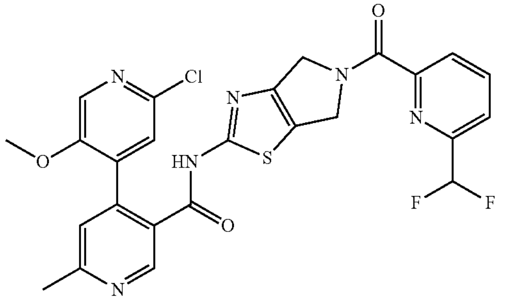 [SMILES: COc1cnc(Cl)cc1-c1cc(C)ncc1C(=O)Nc1nc2c(s1)CN(C(=O)c1cccc(C(F)F)n1)C2]

Step 1: A solution of tert-butyl 2-(2'-chloro-5'-methoxy-6-methyl-[4,4'-bipyridine]-3-carboxamido)-4,6-dihydro-5H-pyrrolo[3,4-d]thiazole-5-carboxylate (50 mg, 0.10 mmol) in 4 M HCl/MeOH (2 mL) was stirred at room temperature for 4 h. The mixture was concentrated under reduced pressure to give 2'-chloro-N-(5,6-dihydro-4H-pyrrolo[3,4-d]thiazol-2-yl)-5'-methoxy-6-methyl-[4,4'-bipyridine]-3-carboxamide hydrochloride (40 mg), which was used directly in the next step. LCMS: m/z=402 $[M+H]^+$.

Step 2: To a solution of 2'-chloro-N-(5,6-dihydro-4H-pyrrolo[3,4-d]thiazol-2-yl)-5'-methoxy-6-methyl-[4,4'-bipyridine]-3-carboxamide hydrochloride (40 mg), 6-(difluoromethyl)picolinic acid (26 mg, 0.15 mmol) and DIPEA (38 mg, 0.30 mmol) in DMF (2 mL) at 0° C. was added T3P (50% in DMF, 97 mg, 0.15 mmol) and the mixture was stirred at room temperature overnight. The mixture was diluted with water (30 mL), extracted with EtOAc (30 mL×3) and the combined organic layers dried over $Na_2SO_4$, filtered and concentrated under reduced pressure. The residue was purified by prep-TLC (DCM/MeOH=25/1, v/v) to give 2'-chloro-N-(5-(6-(difluoromethyl)picolinoyl)-5,6-dihydro-4H-pyrrolo[3,4-d]thiazol-2-yl)-5'-methoxy-6-methyl-[4,4'-bipyridine]-3-carboxamide (40 mg, 71% over two steps) as a white solid. LCMS: m/z=557 $[M+H]^+$, $^1H$ NMR (400 MHz, DMSO-d&) S 12.8 (d, J=19.2 Hz, 1H), 8.79 (d, J=3.2 Hz, 1H), 8.20 (t, J=7.8 Hz, 1H), 8.17 (d, J=2.2 Hz, 1H), 8.05-7.98 (m, 1H), 7.87 (d, J=7.8 Hz, 1H), 7.54 (d, J=1.2 Hz, 1H), 7.44 (s, 1H), 7.08 (td, J=54.8, 13.4 Hz, 1H), 5.03 (s, 1H), 4.94 (s, 1H), 4.87 (s, 1H), 4.73 (s, 1H), 3.60 (s, 3H), 2.59 (s, 3H).

TABLE C

The following examples were prepared using a similar procedure to that described for Example 1

| Ex. No. | Structure | Compound Name | LCMS [M + H]+ | NMR |
|---|---|---|---|---|
| 2 | 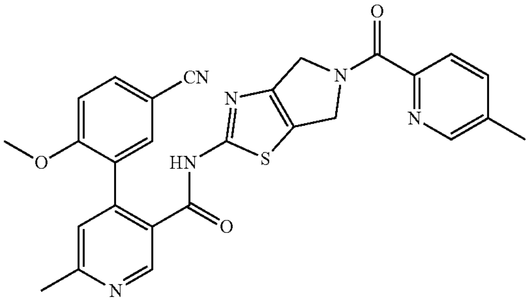 | 4-(5-Cyano-2-methoxyphenyl)-6-methyl-N-(5-(5-methyl-picolinoyl)-5,6-dihydro-4H-pyrrolo[3,4-d]thiazol-2-yl)nicotinamide | 511 | $^1$H NMR (400 MHz, DMSO-$d_6$) δ 12.7 (d, J = 6.6 Hz, 1H), 8.72 (s, 1H), 8.54-8.46 (m, 1H), 7.91-7.87 (m, 1H), 7.85 (d, J = 2.2 Hz, 1H), 7.81-7.74 (m, 2H), 7.39 (d, J = 1.4 Hz, 1H), 7.17 (d, J = 8.6 Hz, 1H), 5.06 (s, 1H), 4.94 (s, 1H), 4.83 (s, 1H), 4.70 (s, 1H), 3.57 (s, 3H), 2.57 (s, 3H), 2.38 (s, 3H) |
| 3 | 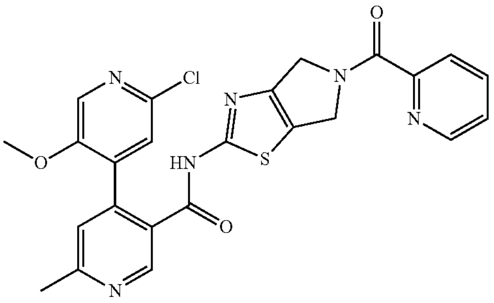 [SMILES: COc1cnc(Cl)cc1-c1cc(C)ncc1C(=O)Nc1nc2c(s1)CN(C(=O)c1ccccn1)C2] | 2'-Chloro-5'-methoxy-6-methyl-N-(5-picolinyl-5,6-dihydro-4H-pyrrolo[3,4-d]thiazol-2-yl)-[4,4'-bipyridine]-3-carboxamide | 507 | $^1$H NMR (400 MHz, DMSO-$d_6$) δ 12.8 (d, J = 7.6 Hz, 1H), 8.79 (s, 1H), 8.69-8.64 (m, 1H), 8.17 (s, 1H), 7.99 (td, J = 7.8, 1.8 Hz, 1H), 7.90-7.83 (m, 1H), 7.59-7.53 (m, 2H), 7.43 (s, 1H), 5.05 (s, 1H), 4.93 (s, 1H), 4.86 (s, 1H), 4.72 (s, 1H), 3.61 (s, 3H), 2.59 (s, 3H) |
| 4 | 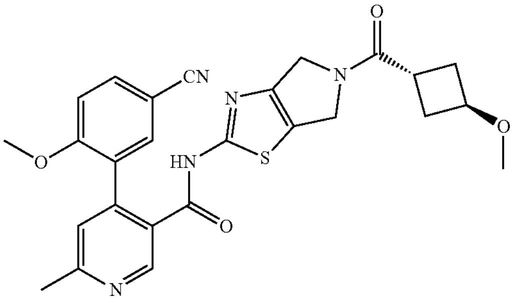 | 4-(5-Cyano-2-methoxyphenyl)-N-(5-((1r,3r)-3-methoxycyclo-butane-1-carbonyl)-5,6-dihydro-4H-pyrrolo[3,4-d]thiazol-2-yl)-6-methyl-nicotinamide | 504 | $^1$H NMR (400 MHz, DMSO-$d_6$) δ 12.6 (s, 1H), 8.71 (s, 1H), 8.03-7.80 (m, 2H), 7.38 (s, 1H), 7.20-7.10 (m, 1H), 4.67 (s, 1H), 4.60-4.52 (m, 2H), 4.44 (s, 1H), 3.97-3.88 (m, 1H), 3.56 (s, 3H), 3.28-3.19 (m, 1H), 3.14 (s, 3H), 2.58 (s, 3H), 2.45-2.38 (m, 2H), 2.18-2.07 (m, 2H) |
| 5 | 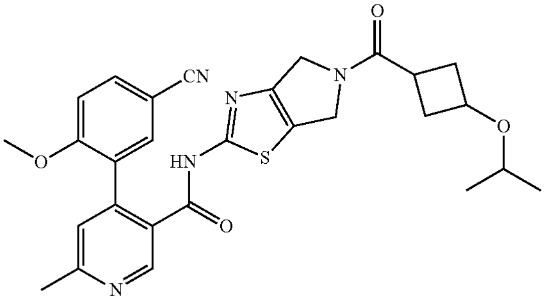 [SMILES: COc1ccc(C#N)cc1-c1cc(C)ncc1C(=O)Nc1nc2c(s1)CN(C(=O)C1CC(OC(C)C)C1)C2] | (Cis and Trans)-4-(5-Cyano-2-methoxyphenyl)-N-(5-(3-isopropoxycyclo-butane-1-carbonyl)-5,6-dihydro-4H-pyrrolo[3,4-d]thiazol-2-yl)-6-methyl-nicotinamide | 532 | $^1$H NMR (400 MHz, DMSO-$d_6$) δ 12.6 (s, 1H), 8.72 (s, 1H), 7.89 (d, J = 9.2 Hz, 1H), 7.84 (d, J = 2.2 Hz, 1H), 7.38 (s, 1H), 7.16 (d, J = 8.6 Hz, 1H), 4.74-4.64 (m, 1H), 4.61-4.52 (m, 2H), 4.46-4.39 (m, 1H), 4.13-3.88 (m, 1H), 3.60-3.52 (m, 4H), 2.89-2.74 (m, 1H), 2.57 (s, 3H), 2.48-2.38 (m, 2H), 2.17-1.94 (m, 2H), 1.06 (d, J = 6.2 Hz, 6H) |

TABLE C-continued

The following examples were prepared using a similar procedure to that described for Example 1

| Ex. No. | Structure | Compound Name | LCMS [M + H]+ | NMR |
|---|---|---|---|---|
| 6 | 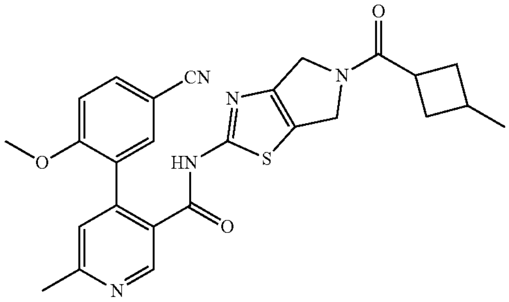 | (Cis and Trans) 4-(5-Cyano-2-methoxyphenyl)-6-methyl-N-(5-(3-methyl-cyclobutane-1-carbonyl)-5,6-dihydro-4H-pyrrolo[3,4-d]thiazol-2-yl)nicotinamide | 488 | $^1$H NMR (400 MHz, DMSO-$d_6$) δ 12.7 (d, J = 7.5 Hz, 1H), 8.71 (s, 1H), 7.92-7.87 (m, 1H), 7.85 (d, J = 2.1 Hz, 1H), 7.40 (s, 1H), 7.17 (d, J = 8.7 Hz, 1H), 4.71-4.63 (m, 1H), 4.59-4.50 (m, 2H), 4.45-4.39 (m, 1H), 3.56 (s, 3H), 3.20-3.08 (m, 1H), 2.58 (s, 3H), 2.40-2.23 (m, 3H), 1.84-1.70 (m, 2H), 1.15-0.97 (m, 3H) |
| 7* | 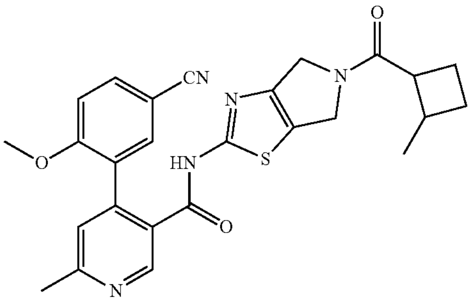 [SMILES: COc1ccc(C#N)cc1-c1cc(C)ncc1C(=O)Nc1nc2c(s1)CN(C(=O)C1CCC1C)C2] | Racemic cis-4-(5-cyano-2-methoxyphenyl)-6-methyl-N-(5-(2-methyl-cyclobutane-1-carbonyl)-5,6-dihydro-4H-pyrrolo[3,4-d]thiazol-2-yl)nicotinamide | 488 | $^1$H NMR (400 MHz, DMSO-$d_6$) δ 12.7 (s, 1H), 8.71 (s, 1H), 7.91-7.87 (m, 1H), 7.85 (s, 1H), 7.39 (s, 1H), 7.17 (d, J = 8.6 Hz, 1H), 4.72-4.65 (m, 1H), 4.61-4.56 (m, 1H), 4.51-4.43 (m, 1H), 4.37-4.30 (m, 1H), 3.57 (s, 3H), 3.46-3.40 (m, 1H), 2.85-2.74 (m, 1H), 2.58 (s, 3H), 2.20-2.07 (m, 1H), 2.06-1.75 (m, 2H), 1.49-1.37 (m, 1H), 0.94 (d, J = 7.0 Hz, 3H) |
| 8* | 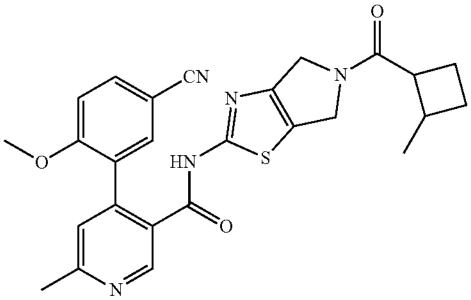 [SMILES: COc1ccc(C#N)cc1-c1cc(C)ncc1C(=O)Nc1nc2c(s1)CN(C(=O)C1CCC1C)C2] | Racemic trans-4-(5-cyano-2-methoxyphenyl)-6-methyl-N-(5-(2-methyl-cyclobutane-1-carbonyl)-5,6-dihydro-4H-pyrrolo[3,4-d]thiazol-2-yl)nicotinamide | 488 | $^1$H NMR (400 MHz, DMSO-$d_6$) δ 12.6 (s, 1H), 8.71 (s, 1H), 7.92-7.87 (m, 1H), 7.85 (d, J = 2.0 Hz, 1H), 7.40 (s, 1H), 7.17 (dd, J = 8., 1.0 Hz, 1H), 4.79-4.65 (m, 1H), 4.65-4.51 (m, 2H), 4.48-4.37 (m, 1H), 3.56 (d, J = 1.6 Hz, 3H), 2.89 (p, J = 8.4 Hz, 1H), 2.64-2.56 (m, 4H), 2.19-2.06 (m, 1H), 1.99-1.91 (m, 2H), 1.57-1.45 (m, 1H), 1.08 (d, J = 6.6 Hz, 3H) |
| 9 | 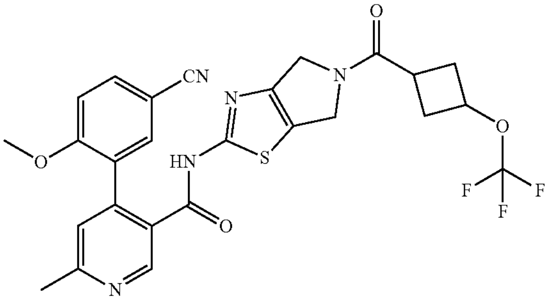 [SMILES: COc1ccc(C#N)cc1-c1cc(C)ncc1C(=O)Nc1nc2c(s1)CN(C(=O)C1CC(OC(F)(F)F)C1)C2] | (Cis and Trans)-4-(5-cyano-2-methoxyphenyl)-6-methyl-N-(5-(3-(trifluoro-methoxy) cyclobutane-1-carbonyl)-5,6-dihydro-4H-pyrrolo[3,4-d]thiazol-2-yl)nicotinamide | 558 | $^1$H NMR (400 MHz, DMSO-$d_6$) δ 12.6 (s, 1H), 8.71 (s, 1H), 7.89 (d, J = 8.8 Hz, 1H), 7.84 (d, J = 2.2 Hz, 1H), 7.39 (s, 1H), 7.17 (d, J = 8.6 Hz, 1H), 4.80 (q, J = 7.6 Hz, 1H), 4.73 (t, J = 2.8 Hz, 1H), 4.61-4.57 (m, 2H), 4.45 (t, J = 2.8 Hz, 1H), 3.56 (d, J = 1.6 Hz, 3H), 3.03-2.92 (m, 1H), 2.69-2.55 (m, 2H), 2.58 (s, 3H), 2.40-2.29 (m, 2H) |

TABLE C-continued

The following examples were prepared using a similar procedure to that described for Example 1

| Ex. No. | Structure | Compound Name | LCMS [M + H]+ | NMR |
|---|---|---|---|---|
| 10 | 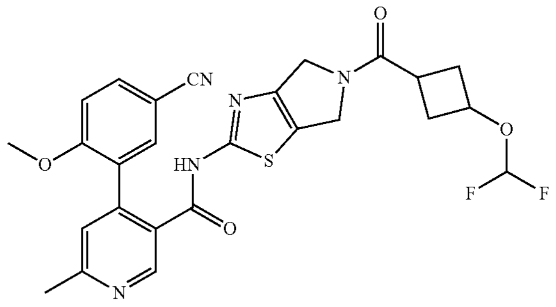 [SMILES: COc1ccc(C#N)cc1-c1cc(C)ncc1C(=O)Nc1nc2c(s1)CN(C(=O)C1CC(OC(F)F)C1)C2] | (Cis and Trans)-4-(5-Cyano-2-methoxyphenyl)-N-(5-(3-(di-fluoromethoxy) cyclobutane-1-carbonyl)-5,6-dihydro-4H-pyrrolo[3,4-d]thiazol-2-yl)-6-methyl-nicotinamide | 540 | $^1$H NMR (400 MHz, DMSO-$d_6$) δ 12.8-12.6 (m, 1H), 8.73 (s, 1H), 7.94-7.89 (m, 1H), 7.89-7.86 (m, 1H), 7.40 (s, 1H), 7.20-7.09 (m, 1H), 6.63 (t, J = 76.0 Hz, 1H), 4.77-4.72 (m, 1H), 4.65-4.56 (m, 3H), 4.50-4.44 (m, 1H), 3.56 (s, 3H), 3.02-2.91 (m, 1H), 2.63-2.54 (m, 5H), 2.32-2.21 (m, 2H) |
| 11 | 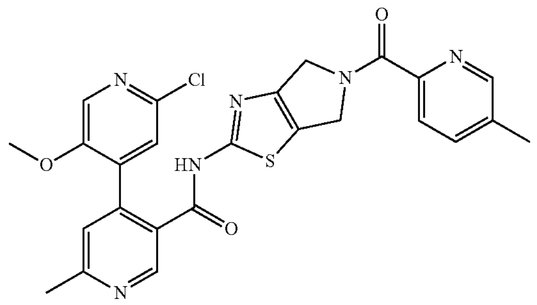 | 2'-Chloro-5'-methoxy-6-methyl-N-(5-(5-methyl-picolinyl)-5,6-dihydro-4H-pyrrolo[3,4-d]thiazol-2-yl)-[4,4'-bipyridine]-3-carboxamide | 521 | $^1$H NMR (400 MHz, DMSO-$d_6$) δ 12.8 (s, 1H), 8.79 (s, 1H), 8.50 (d, J = 8.8 Hz, 1H), 8.17 (s, 1H), 7.81-7.74 (m, 2H), 7.53 (s, 1H), 7.42 (s, 1H), 5.07 (s, 1H), 4.95 (s, 1H), 4.84 (s, 1H), 4.70 (s, 1H), 3.61 (s, 3H), 2.59 (s, 3H), 2.38 (s, 3H) |
| 12 | 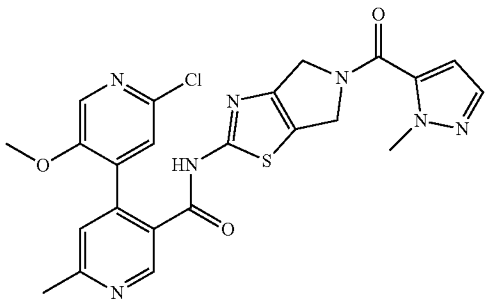 [SMILES: COc1cnc(Cl)cc1-c1cc(C)ncc1C(=O)Nc1nc2c(s1)CN(C(=O)c1ccnn1C)C2] | 2'-Chloro-5'-methoxy-6-methyl-N-(5-(1-methyl-1H-pyrazole-5-carbonyl)-5,6-dihydro-4H-pyrrolo[3,4-d]thiazol-2-yl)-[4,4'-bipyridine]-3-carboxamide | 510 | $^1$H NMR (400 MHz, DMSO-$d_6$) δ 12.8 (s, 1H), 8.80 (s, 1H), 8.16 (s, 1H), 7.54-7.50 (m, 2H), 7.41 (s, 1H), 6.85 (d, J = 20.6 Hz, 1H), 4.90 (s, 1H), 4.83-4.76 (m, 2H), 4.67 (s, 1H), 3.94 (s, 3H), 3.60 (s, 3H), 2.58 (s, 3H) |
| 13 | 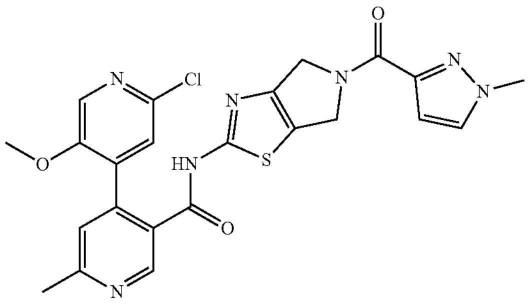 | 2'-Chloro-5'-methoxy-6-methyl-N-(5-(1-methyl-1H-pyrazole-3-carbonyl)-5,6-dihydro-4H-pyrrolo[3,4-d]thiazol-2-yl)-[4,4'-bipyridine]-3-carboxamide | 510 | $^1$H NMR (400 MHz, DMSO-$d_6$) δ 12.8 (s, 1H), 8.79 (d, J = 2.8 Hz, 1H), 8.17 (d, J = 2.0 Hz, 1H), 7.84-7.75 (m, 1H), 7.54 (d, J = 1.4 Hz, 1H), 7.43 (s, 1H), 6.73-6.70 (m, 1H), 5.19 (s, 1H), 5.04 (s, 1H), 4.78 (s, 1H), 4.65 (s, 1H), 3.94 (d, J = 6.8 Hz, 3H), 3.61 (d, J = 2.4 Hz, 3H), 2.59 (s, 3H) |

TABLE C-continued

The following examples were prepared using a similar procedure to that described for Example 1

| Ex. No. | Structure | Compound Name | LCMS [M + H]+ | NMR |
|---|---|---|---|---|
| 14 | 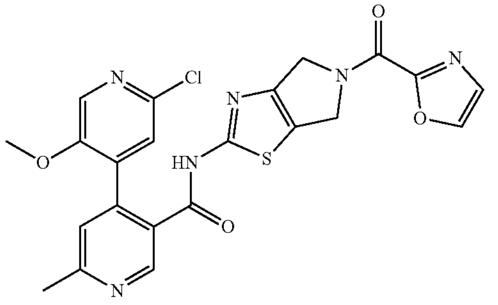 | 2'-Chloro-5'-methoxy-6-methyl-N-(5-(oxazole-2-carbonyl)-5,6-dihydro-4H-pyrrolo[3,4-d]thiazol-2-yl)-[4,4'-bipyridine]-3-carboxamide | 497 | $^1H$ NMR (400 MHz, DMSO-$d_6$) δ 12.8 (s, 1H), 8.79 (d, J = 1.8 Hz, 1H), 8.37 (s, 1H), 8.17 (d, J = 1.4 Hz, 1H), 7.56-7.52 (m, 2H), 7.43 (s, 1H), 5.26 (s, 1H), 5.13 (s, 1H), 4.83 (s, 1H), 4.70 (s, 1H), 3.61 (s, 3H), 2.59 (s, 3H) |
| 15 | 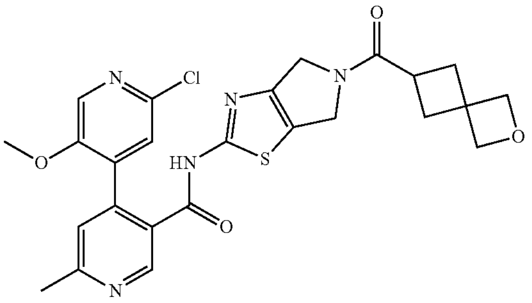 [SMILES: COc1cnc(Cl)cc1-c1cc(C)ncc1C(=O)Nc1nc2c(s1)CN(C(=O)C1CC3(COC3)C1)C2] | N-(5-(2-Oxa-spiro[3.3]hep-tane-6-carbonyl)-5,6-dihydro-4H-pyrrolo[3,4-d]thiazol-2-yl)-2'-chloro-5'-methoxy-6-methyl-[4,4'-bipyridine]-3-carboxamide | 526 | $^1H$ NMR (400 MHz, DMSO-$d_6$) δ 12.8 (s, 1H), 8.78 (s, 1H), 8.16 (s, 1H), 7.55 (s, 1H), 7.44 (s, 1H), 4.68 (s, 1H), 4.62-4.53 (m, 4H), 4.48-4.41 (m, 3H), 3.60 (s, 3H), 3.15 (s, 1H), 2.59 (s, 3H), 2.44-2.33 (m, 4H) |
| 16 | 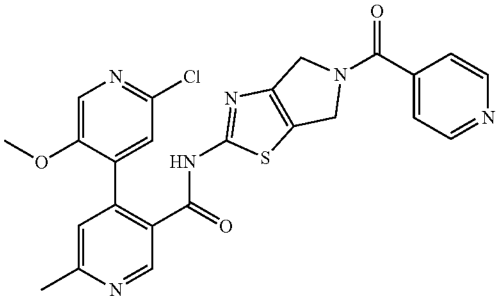 [SMILES: COc1cnc(Cl)cc1-c1cc(C)ncc1C(=O)Nc1nc2c(s1)CN(C(=O)c1ccncc1)C2] | 2'-Chloro-N-(5-isonicotinoyl-5,6-dihydro-4H-pyrrolo[3,4-d]thiazol-2-yl)-5'-methoxy-6-methyl-[4,4'-bipyridine]-3-carboxamide | 507 | $^1H$ NMR (400 MHz, DMSO-$d_6$) δ 12.8 (d, J = 6.0 Hz, 1H), 8.78 (d, J = 3.8 Hz, 1H), 8.75-8.69 (m, 2H), 8.16 (s, 1H), 7.58 (td, J = 4.6, 1.6 Hz, 2H), 7.54 (s, 1H), 7.43 (d, J = 2.0 Hz, 1H), 4.82 (s, 1H), 4.70-4.64 (m, 2H), 4.58 (s, 1H), 3.59 (s, 3H), 2.59 (d, J = 2.4 Hz, 3H) |
| 17 | 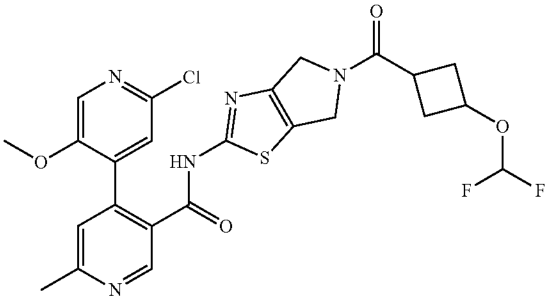 [SMILES: COc1cnc(Cl)cc1-c1cc(C)ncc1C(=O)Nc1nc2c(s1)CN(C(=O)C1CC(OC(F)F)C1)C2] | (Cis and Trans)-2'-Chloro-N-(5-(3-(difluoro-methoxy)cyclobutane-1-carbonyl)-5,6-dihydro-4H-pyrrolo[3,4-d]thiazol-2-yl)-5'-methoxy-6-methyl-[4,4'-bipyridine]-3-carboxamide | 550 | $^1H$ NMR (400 MHz, DMSO-$d_6$) δ 12.8 (s, 1H), 8.78 (s, 1H), 8.18-8.14 (m, 1H), 7.54 (s, 1H), 7.43 (s, 1H), 6.64 (t, J = 76.0 Hz, 1H), 4.77-4.41 (m, 5H), 3.59 (s, 3H), 3.02-2.91 (m, 1H), 2.59 (s, 3H), 2.57-2.52 (m, 2H), 2.30-2.19 (m, 2H) |

TABLE C-continued

The following examples were prepared using a similar procedure to that described for Example 1

| Ex. No. | Structure | Compound Name | LCMS [M + H]+ | NMR |
|---|---|---|---|---|
| 18 | 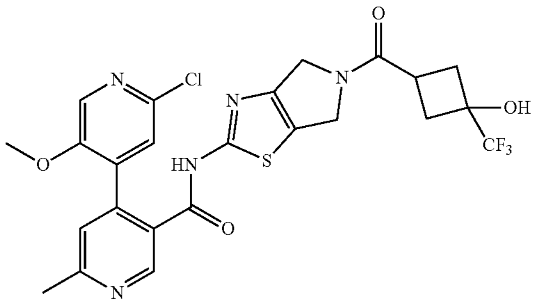 [SMILES: COc1cnc(Cl)cc1-c1cc(C)ncc1C(=O)Nc1nc2c(s1)CN(C(=O)C1CC(O)(C(F)(F)F)C1)C2] | (Cis and Trans)-2'-Chloro-N-(5-(3-hydroxy-3-(trifluoromethyl) cyclobutane-1-carbonyl)-5,6-dihydro-4H-pyrrolo[3,4-d]thiazol-2-yl)-5'-methoxy-6-methyl-[4,4'-bipyridine]-3-carboxamide | 568 | $^{1}$H NMR (400 MHz, DMSO-$d_6$) δ 12.7 (s, 1H), 8.80 (s, 1H), 8.16 (d, J = 3.2 Hz, 1H), 7.52 (s, 1H), 7.41 (s, 1H), 6.63 (d, J = 5.4 Hz, 1H), 4.73 (s, 1H), 4.59 (s, 2H), 4.45 (s, 1H), 3.59 (s, 3H), 3.06-2.97 (m, 1H), 2.68-2.55 (m, 2H), 2.58 (s, 3H), 2.49-2.41 (m, 2H) |
| 19 | 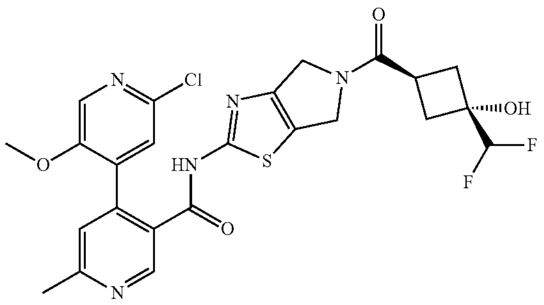 [SMILES: COc1cnc(Cl)cc1-c1cc(C)ncc1C(=O)Nc1nc2c(s1)CN(C(=O)[C@H]1C[C@@](O)(C(F)F)C1)C2] | 2'-Chloro-N-(5-((1r,3r)-3-(di-fluoromethyl)-3-hydroxy-cyclobutane-1-carbonyl)-5,6-dihydro-4H-pyrrolo[3,4-d]thiazol-2-yl)-5'-methoxy-6-methyl-[4,4'-bipyridine]-3-carboxamide | 550 | $^{1}$H NMR (400 MHz, DMSO-$d_6$) δ 12.8 (s, 1H), 8.79 (d, J = 3.2 Hz, 1H), 8.16 (s, 1H), 7.53 (d, J = 3.4 Hz, 1H), 7.42 (s, 1H), 6.13-5.79 (m, 2H), 4.71 (s, 1H), 4.60-4.56 (m, 2H), 4.45 (s, 1H), 3.59 (s, 3H), 2.98-2.87 (m, 1H), 2.58 (s, 3H), 2.50-2.42 (m, 2H), 2.34-2.22 (m, 2H) |
| 20 | 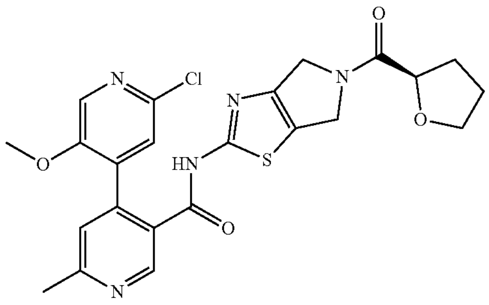 [SMILES: COc1cnc(Cl)cc1-c1cc(C)ncc1C(=O)Nc1nc2c(s1)CN(C(=O)[C@H]1CCCO1)C2] | (R)-2'-Chloro-5'-methoxy-6-methyl-N-(5-(tetrahydrofuran-2-carbonyl)-5,6-dihydro-4H-pyrrolo[3,4-d]thiazol-2-yl)-[4,4'-bipyridine]-3-carboxamide | 500 | $^{1}$H NMR (400 MHz, DMSO-$d_6$) δ 12.8 (s, 1H), 8.78 (s, 1H), 8.16 (s, 1H), 7.54 (s, 1H), 7.43 (s, 1H), 4.97-4.67 (m, 2H), 4.66-4.55 (m, 2H), 4.46 (s, 1H), 3.87-3.74 (m, 2H), 3.60 (s, 3H), 2.59 (s, 3H), 2.12-2.02 (m, 2H), 1.96-1.78 (m, 2H) |
| 21 | 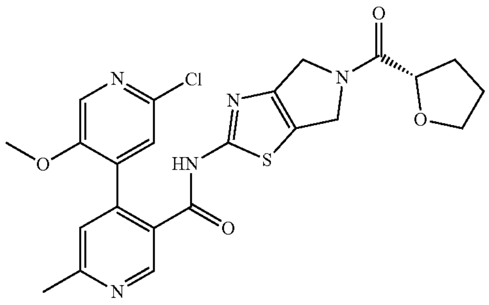 [SMILES: COc1cnc(Cl)cc1-c1cc(C)ncc1C(=O)Nc1nc2c(s1)CN(C(=O)[C@@H]1CCCO1)C2] | (S)-2'-Chloro-5'-methoxy-6-methyl-N-(5-(tetrahydrofuran-2-carbonyl)-5,6-dihydro-4H-pyrrolo[3,4-d]thiazol-2-yl)-[4,4'-bipyridine]-3-carboxamide | 500 | $^{1}$H NMR (400 MHz, DMSO-$d_6$) δ 12.8 (s, 1H), 8.78 (s, 1H), 8.16 (s, 1H), 7.54 (s, 1H), 7.44 (s, 1H), 4.97-4.67 (m, 2H), 4.66-4.55 (m, 2H), 4.46 (s, 1H), 3.88-3.72 (m, 2H), 3.60 (s, 3H), 2.59 (s, 3H), 2.13-2.02 (m, 2H), 1.96-1.77 (m, 2H) |

TABLE C-continued

The following examples were prepared using a similar procedure to that described for Example 1

| Ex. No. | Structure | Compound Name | LCMS [M + H]+ | NMR |
| --- | --- | --- | --- | --- |
| 22 | 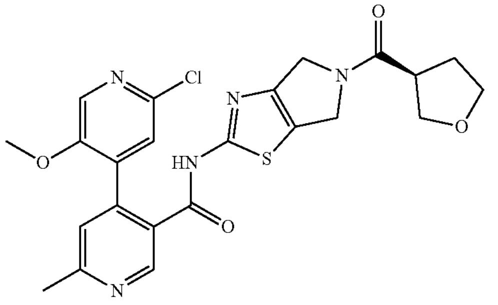 [SMILES: COc1cnc(Cl)cc1-c1cc(C)ncc1C(=O)Nc1nc2c(s1)CN(C(=O)[C@H]1CCOC1)C2] | (S)-2'-Chloro-5'-methoxy-6-methyl-N-(5-(tetrahydrofuran-3-carbonyl)-5,6-dihydro-4H-pyrrolo[3,4-d]thiazol-2-yl)-[4,4'-bipyridine]-3-carboxamide | 500 | $^1$H NMR (400 MHz, DMSO-$d_6$) δ 12.8 (s, 1H), 8.79 (s, 1H), 8.17 (d, J = 2.2 Hz, 1H), 7.54 (s, 1H), 7.43 (s, 1H), 4.90-4.82 (m, 1H), 4.77-4.70 (m, 1H), 4.59 (s, 1H), 4.46 (s, 1H), 3.99-3.91 (m, 1H), 3.81-3.69 (m, 4H), 3.60 (s, 3H), 2.59 (s, 3H), 2.06-1.98 (m, 2H) |
| 23 | 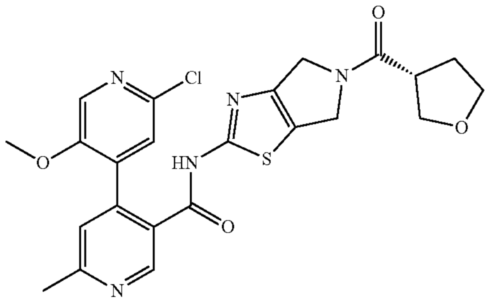 [SMILES: COc1cnc(Cl)cc1-c1cc(C)ncc1C(=O)Nc1nc2c(s1)CN(C(=O)[C@@H]1CCOC1)C2] | (R)-2'-Chloro-5'-methoxy-6-methyl-N-(5-(tetrahydrofuran-3-carbonyl)-5,6-dihydro-4H-pyrrolo[3,4-d]thiazol-2-yl)-[4,4'-bipyridine]-3-carboxamide | 500 | $^1$H NMR (400 MHz, DMSO-$d_6$) δ 8.78 (s, 1H), 8.16 (d, J = 2.4 Hz, 1H), 7.54 (s, 1H), 7.44 (s, 1H), 4.91-4.83 (m, 1H), 4.77-4.70 (m, 1H), 4.59 (s, 1H), 4.46 (s, 1H), 3.99-3.89 (m, 1H), 3.81-3.65 (m, 4H), 3.60 (s, 3H), 2.59 (s, 3H), 2.07-1.96 (m, 3H) |
| 24 | 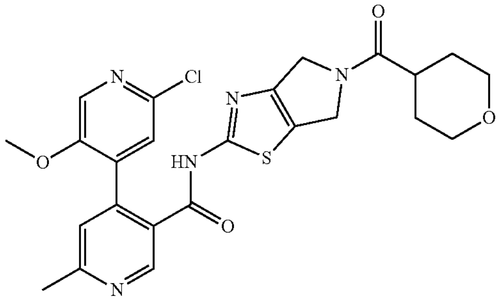 [SMILES: COc1cnc(Cl)cc1-c1cc(C)ncc1C(=O)Nc1nc2c(s1)CN(C(=O)C1CCOCC1)C2] | 2'-Chloro-5'-methoxy-6-methyl-N-(5-(tetrahydro-2H-pyran-4-carbonyl)-5,6-dihydro-4H-pyrrolo[3,4-d]thiazol-2-yl)-[4,4'-bipyridine]-3-carboxamide | 514 | $^1$H NMR (400 MHz, DMSO-$d_6$) δ 12.7 (s, 1H), 8.78 (s, 1H), 8.16 (d, J = 3.6 Hz, 1H), 7.52 (s, 1H), 7.42 (s, 1H), 4.88 (s, 1H), 4.76 (s, 1H), 4.56 (s, 1H), 4.44 (s, 1H), 3.88 (d, J = 11.2 Hz, 2H), 3.60 (s, 3H), 3.44-3.40 (m, 2H), 2.80-2.72 (m, 1H), 2.58 (s, 3H), 1.68-1.62 (m, 4H) |
| 25 | 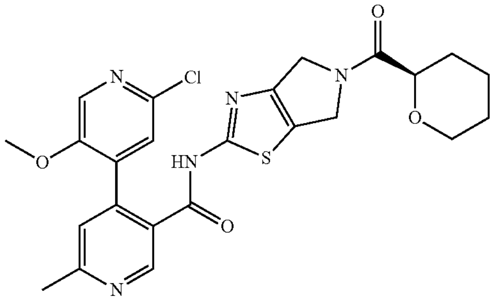 [SMILES: COc1cnc(Cl)cc1-c1cc(C)ncc1C(=O)Nc1nc2c(s1)CN(C(=O)[C@H]1CCCCO1)C2] | (R)-2'-Chloro-5'-methoxy-6-methyl-N-(5-(tetrahydro-2H-pyran-2-carobnyl)-5,6-dihydro-4H-pyrrolo[3,4-d]thiazol-2-yl)-[4,4'-bipyridine]-3-carboxamide | 514 | $^1$H NMR (400 MHz, DMSO-$d_6$) δ 12.8 (s, 1H), 8.79 (s, 1H), 8.16 (d, J = 2.6 Hz, 1H), 7.54 (s, 1H), 7.43 (s, 1H), 4.96-4.83 (m, 1H), 4.81-4.69 (m, 1H), 4.64-4.54 (m, 1H), 4.51-4.40 (m, 1H), 4.16-4.08 (m, 1H), 3.91 (d, J = 10.8 Hz, 1H), 3.60 (d, J = 2.4 Hz, 3H), 3.53-3.46 (m, 1H), 2.59 (s, 3H), 1.87-1.80 (m, 1H), 1.69-1.60 (m, 2H), 1.55-1.47 (m, 3H) |

TABLE C-continued

The following examples were prepared using a similar procedure to that described for Example 1

| Ex. No. | Structure | Compound Name | LCMS [M + H]+ | NMR |
|---|---|---|---|---|
| 26 | 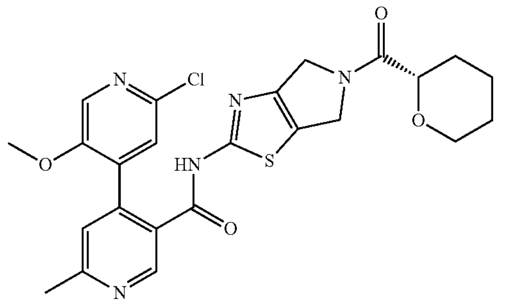 [SMILES: COc1cnc(Cl)cc1-c1cc(C)ncc1C(=O)Nc1nc2c(s1)CN(C(=O)[C@@H]1CCCCO1)C2] | (S)-2'-Chloro-5'-methoxy-6-methyl-N-(5-(tetrahydro-2H-pyran-2-carbonyl)-5,6-dihydro-4H-pyrrolo[3,4-d]thiazol-2-yl)-[4,4'-bipyridine]-3-carboxamide | 514 | $^1$H NMR (400 MHz, DMSO-$d_6$) δ 12.8 (s, 1H), 8.78 (s, 1H), 8.16 (d, J = 2.6 Hz, 1H), 7.54 (s, 1H), 7.43 (s, 1H), 4.97-4.85 (m, 1H), 4.82-4.71 (m, 1H), 4.65-4.53 (m, 1H), 4.51-4.41 (m, 1H), 4.17-4.10 (m, 1H), 3.91 (d, J = 11.4 Hz, 1H), 3.60 (d, J = 2.4 Hz, 3H), 3.53-3.46 (m, 1H), 2.59 (s, 3H), 1.88-1.80 (m, 1H), 1.69-1.60 (m, 2H), 1.58-1.47 (m, 3H) |
| 27 | 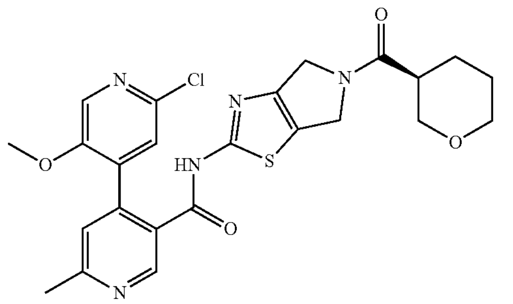 [SMILES: COc1cnc(Cl)cc1-c1cc(C)ncc1C(=O)Nc1nc2c(s1)CN(C(=O)[C@H]1CCCOC1)C2] | (S)-2'-Chloro-5'-methoxy-6-methyl-N-(5-(tetrahydro-2H-pyran-3-carbonyl)-5,6-dihydro-4H-pyrrolo[3,4-d]thiazol-2-yl)-[4,4'-bipyridine]-3-carboxamide | 514 | $^1$H NMR (400 MHz, DMSO-$d_6$) δ 12.8 (s, 1H), 8.78 (s, 1H), 8.17 (d, J = 3.8 Hz, 1H), 7.54 (s, 1H), 7.44 (s, 1H), 4.90 (s, 1H), 4.78 (s, 1H), 4.55 (s, 1H), 4.42 (s, 1H), 3.97-3.89 (m, 1H), 3.86-3.80 (m, 1H), 3.60 (s, 3H), 3.39-3.26 (m, 2H), 2.84-2.68 (m, 1H), 2.59 (s, 3H), 1.98-1.89 (m, 1H), 1.68-1.54 (m, 3H) |
| 28 | 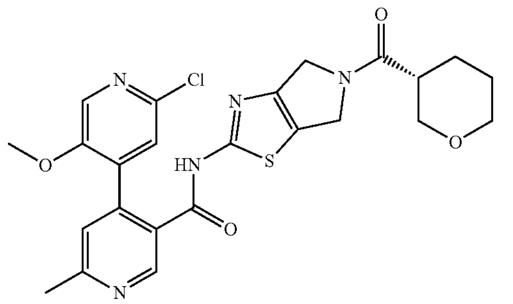 [SMILES: COc1cnc(Cl)cc1-c1cc(C)ncc1C(=O)Nc1nc2c(s1)CN(C(=O)[C@@H]1CCCOC1)C2] | (R)-2'-Chloro-5'-methoxy-6-methyl-N-(5-(tetrahydro-2H-pyran-3-carbonyl)-5,6-dihydro-4H-pyrrolo[3,4-d]thiazol-2-yl)-[4,4'-bipyridine]-3-carboxamide | 514 | $^1$H NMR (400 MHz, DMSO-$d_6$) δ 12.8 (s, 1H), 8.78 (s, 1H), 8.17 (d, J = 3.8 Hz, 1H), 7.54 (s, 1H), 7.44 (s, 1H), 4.90 (s, 1H), 4.78 (s, 1H), 4.55 (s, 1H), 4.42 (s, 1H), 3.97-3.89 (m, 1H), 3.86-3.79 (m, 1H), 3.60 (s, 3H), 3.38-3.26 (m, 2H), 2.80 2.69 (m, 1H), 2.59 (s, 3H), 1.98-1.89 (m, 1H), 1.68-1.55 (m, 3H) |
| 29 | 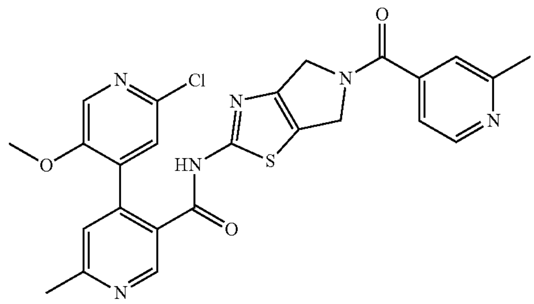 | 2'-Chloro-5'-methoxy-6-methyl-N-(5-(2-methylisonicotin-oyl)-5,6-dihydro-4H-pyrrolo[3,4-d]thiazol-2-yl)-[4,4'-bipyridine]-3-carboxamide | 521 | $^1$H NMR (400 MHz, DMSO-$d_6$) δ 12.8 (d, J = 4.2 Hz, 1H), 8.78 (d, J = 3.8 Hz, 1H), 8.56 (d, J = 5.0 Hz, 1H), 8.16 (s, 1H), 7.54 (s, 1H), 7.43 (d, J = 2.6 Hz, 2H),7.36 (t, J = 6.4 Hz, 1H), 4.81 (t, J = 2.8 Hz, 1H), 4.67 (s, 2H), 4.57 (t, J = 2.8 Hz, 1H), 3.59 (s, 3H), 2.59 (d, J = 2.4 Hz, 3H), 2.53 (d, J = 2.6 Hz, 3H) |

TABLE C-continued

The following examples were prepared using a similar procedure to that described for Example 1

| Ex. No. | Structure | Compound Name | LCMS [M + H]+ | NMR |
|---|---|---|---|---|
| 30 | 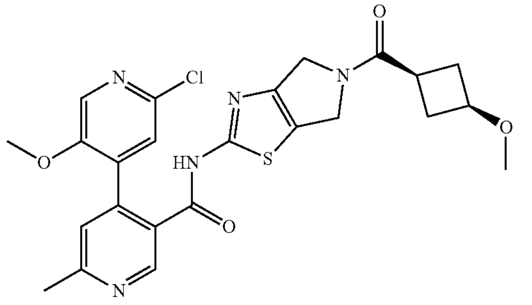 | 2'-Chloro-5'-methoxy-N-(5-((1s,3s)-3-methoxy-cyclobutane-1-carbonyl)-5,6-dihydro-4H-pyrrolo[3,4-d]thiazol-2-yl)-6-methyl-[4,4'-bipyridine]-3-carboxamide | 514 | $^{1}H$ NMR (400 MHz, DMSO-$d_6$) δ 12.8 (d, J = 9.6 Hz, 1H), 8.78 (s, 1H), 8.16 (d, J = 1.6 Hz, 1H), 7.54 (s, 1H), 7.44 (s, 1H), 4.74 (t, J = 2.8 Hz, 1H), 4.62-4.56 (m, 2H), 4.44 (t, J = 2.8 Hz, 1H), 3.84-3.75 (m, 1H), 3.59 (s, 3H), 3.13 (s, 3H), 2.85 (q, J = 8.2 Hz, 1H), 2.59 (s, 3H), 2.44 (dt, J = 7.8, 3.8 Hz, 2H), 2.01 (t, J = 10.4 Hz, 2H) |
| 31 | 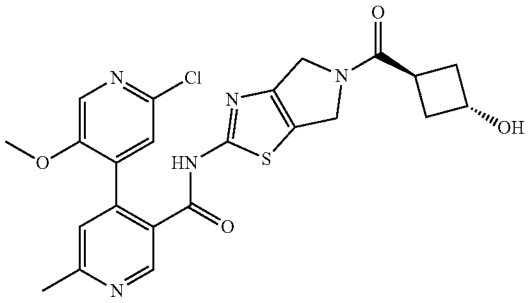 [SMILES: COc1cnc(Cl)cc1-c1cc(C)ncc1C(=O)Nc1nc2c(s1)CN(C(=O)[C@H]1C[C@H](O)C1)C2] | 2'-Chloro-N-(5-((1r,3r)-3-hydroxy-cyclobutane-1-carbonyl)-5,6-dihydro-4H-pyrrolo[3,4-d]thiazol-2-yl)-5'-methoxy-6-methyl-[4,4'-bipyridine]-3-carboxamide | 500 | $^{1}H$ NMR (400 MHz, DMSO-$d_6$) δ 12.8 (s, 1H ), 8.78 (s, 1H), 8.16 (d, J = 1.6 Hz, 1H), 7.54 (s, 1H), 7.43 (s, 1H), 5.09 (dd, J = 6.2, 1.4 Hz, 1H), 4.67 (s, 1H), 4.58 (s, 1H), 4.55 (s, 1H), 4.45 (s, 1H), 4.26-4.16 (m, 1H), 3.60 (s, 3H), 3.21-3.13 (m, 1H), 2.59 (s, 3H), 2.45-2.38 (m, 2H), 2.13-2.02 (m, 2H) |
| 32 | 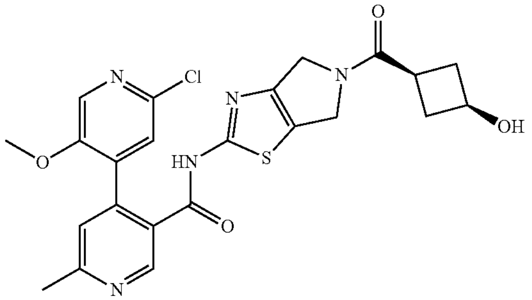 | 2'-Chloro-N-(5-((1s,3s)-3-hydroxy-cyclobutane-1-carbonyl)-5,6-dihydro-4H-pyrrolo[3,4-d]thiazol-2-yl)-5'-methoxy-6-methyl-[4,4'-bipyridine]-3-carboxamide | 500 | $^{1}H$ NMR (400 MHz, DMSO-$d_6$) δ 12.8 (s, 1H), 8.78 (s, 1H), 8.16 (d, J = 1.6 Hz, 1H), 7.54 (s, 1H), 7.43 (s, 1H), 5.11 (dd, J = 7.0, 2.4 Hz, 1H), 4.72 (s, 1H), 4.58 (s, 1H), 4.55 (s, 1H), 4.43 (s, 1H), 4.04-3.94 (m, 1H), 3.59 (s, 3H), 2.77-2.66 (m, 1H), 2.59 (s, 3H), 2.45-2.36 (m, 2H), 2.04-1.94 (m, 2H) |
| 33 | 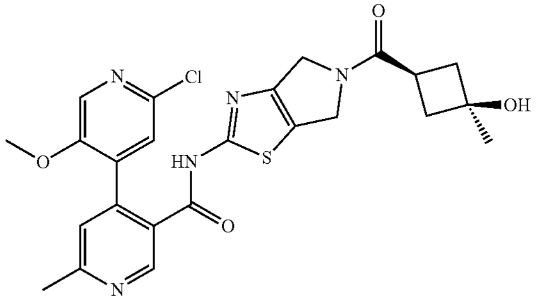 [SMILES: COc1cnc(Cl)cc1-c1cc(C)ncc1C(=O)Nc1nc2c(s1)CN(C(=O)[C@H]1C[C@@](C)(O)C1)C2] | 2'-Chloro-N-(5-((1s,3s)-3-hydroxy-3-methyl-cyclobutane-1-carbonyl)-5,6-dihydro-4H-pyrrolo[3,4-d]thiazol-2-yl)-5'-methoxy-6-methyl-[4,4'-bipyridine]-3-carboxamide | 514 | $^{1}H$ NMR (400 MHz, DMSO-$d_6$) δ 12.8 (s, 1H), 8.78 (s, 1H), 8.16 (d, J = 2.6 Hz, 1H), 7.54 (s, 1H), 7.43 (s, 1H), 5.01 (d, J = 3.8 Hz, 1H), 4.76-4.70 (m, 1H), 4.62-4.55 (m, 2H), 4.47-4.41 (m, 1H), 3.60 (s, 3H), 2.90-2.78 (m, 1H), 2.59 (s, 3H), 2.23-2.16 (m, 2H), 2.16-2.09 (m, 2H), 1.30-1.27 (m, 3H) |

TABLE C-continued

The following examples were prepared using a similar procedure to that described for Example 1

| Ex. No. | Structure | Compound Name | LCMS [M + H]+ | NMR |
|---|---|---|---|---|
| 34 | 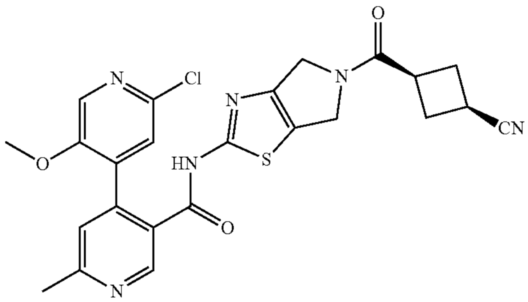 [SMILES: COc1cnc(Cl)cc1-c1cc(C)ncc1C(=O)Nc1nc2c(s1)CN(C(=O)[C@H]1C[C@@H](C#N)C1)C2] | 2'-Chloro-N-(5-((1s,3s)-3-cyano-cyclobutane-1-carbonyl)-5,6-dihydro-4H-pyrrolo[3,4-d]thiazol-2-yl)-5'-methoxy-6-methyl-[4,4'-bipyridine]-3-carboxamide | 509 | $^1$H NMR (400 MHz, DMSO-$d_6$) δ 12.8 (s, 1H), 8.78 (s, 1H), 8.16 (s, 1H), 7.54 (s, 1H), 7.43 (s, 1H), 4.69 (s, 1H), 4.57 (s, 2H), 4.45 (s, 1H), 3.59 (s, 3H), 3.44-3.34 (m, 2H), 2.59 (s, 3H), 2.58-2.53 (m, 2H), 2.48-2.41 (m, 2H) |
| 35 | 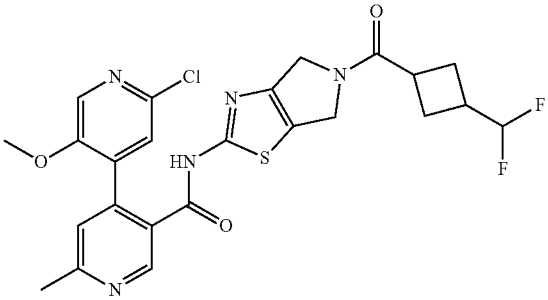 [SMILES: COc1cnc(Cl)cc1-c1cc(C)ncc1C(=O)Nc1nc2c(s1)CN(C(=O)C1CC(C(F)F)C1)C2] | (Cis and Trans)-2'-Chloro-N-(5-(3-(difluoromethyl) cyclobutane-1-carbonyl)-5,6-dihydro-4H-pyrrolo[3,4-d]thiazol-2-yl)-5'-methoxy-6-methyl-[4,4'-bipyridine]-3-carboxamide | 534 | $^1$H NMR (400 MHz, DMSO-$d_6$) δ 12.8 (s, 1H), 8.78 (s, 1H), 8.16 (d, J = 1.8 Hz, 1H), 7.54 (s, 1H), 7.43 (s, 1H), 6.36-5.84 (m, 1H), 4.75-4.65 (m, 1H), 4.63-4.53 (m, 2H), 4.49-4.41 (m, 1H), 3.60 (s, 3H), 3.44-3.32 (m, 1H), 2.77-2.63 (m, 1H), 2.59 (s, 3H), 2.41-2.33 (m, 1H), 2.27-2.15 (m, 3H) |
| 36 | 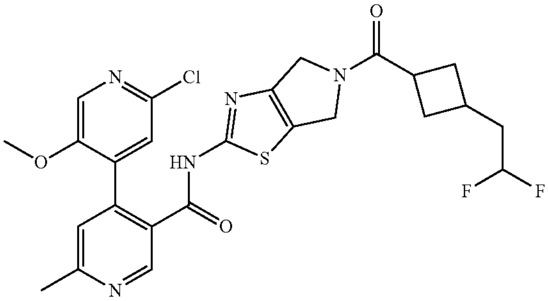 [SMILES: COc1cnc(Cl)cc1-c1cc(C)ncc1C(=O)Nc1nc2c(s1)CN(C(=O)C1CC(CC(F)F)C1)C2] | (Cis and Trans)-2'-Chloro-N-(5-(3-(2,2-difluoro-ethyl)cyclo-butane-1-carbonyl)-5,6-dihydro-4H-pyrrolo[3,4-d]thiazol-2-yl)-5'-methoxy-6-methyl-[4,4'-bipyridine]-3-carboxamide | 548 | $^1$H NMR (400 MHz, DMSO-$d_6$) δ 12.8 (s, 1H), 8.78 (s, 1H), 8.16 (d, J = 1.6 Hz, 1H), 7.54 (s, 1H), 7.44 (s, 1H), 6.20-5.83 (m, 1H), 4.75-4.64 (m, 1H), 4.62-4.50 (m, 2H), 4.44 (d, J = 10.4 Hz, 1H), 3.59 (s, 3H), 3.28-3.17 (m, 1H), 2.59 (s, 3H), 2.41-2.28 (m, 3H), 2.13-1.84 (m, 4H). |
| 37* | 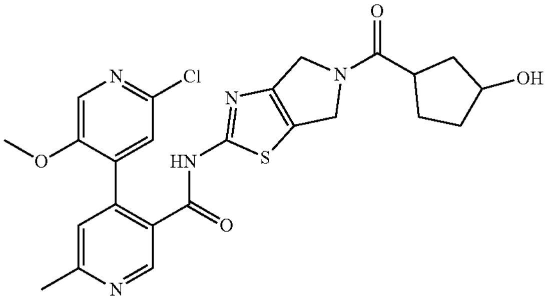 [SMILES: COc1cnc(Cl)cc1-c1cc(C)ncc1C(=O)Nc1nc2c(s1)CN(C(=O)C1CCC(O)C1)C2] | (Racemic Cis)-2'-chloro-N-(5-(3-hydroxy-cyclopen-tane-1-carbonyl)-5,6-dihydro-4H-pyrrolo[3,4-d]thiazol-2-yl)-5'-methoxy-6-methyl-[4,4'-bipyridine]-3-carboxamide | 514 | $^1$H NMR (400 MHz, DMSO-$d_6$) δ 12.8 (s, 1H), 8.78 (s, 1H), 8.17 (d, J = 1.8 Hz, 1H), 7.54 (s, 1H), 7.44 (s, 1H), 4.83 (s, 1H), 4.71 (s, 1H), 4.68-4.61 (m, 1H), 4.62-4.53 (m, 1H), 4.45 (s, 1H), 4.14-4.05 (m, 1H), 3.60 (s, 3H), 2.98-2.87 (m, 1H), 2.59 (s, 3H), 2.14-2.03 (m, 1H), 1.87-1.76 (m, 2H), 1.77-1.59 (m, 2H), 1.61-1.48 (m, 1H) |
| 38 | 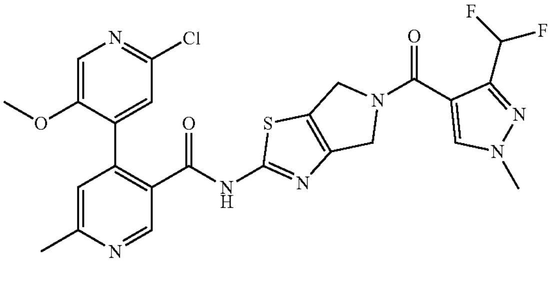 [SMILES: COc1cnc(Cl)cc1-c1cc(C)ncc1C(=O)Nc1nc2c(s1)CN(C(=O)c1cn(C)nc1C(F)F)C2] | 2'-chloro-N-(5-(3-(di-fluoromethyl)-1-methyl-1H-pyrazole-4-carbonyl)-5,6-dihydro-4H-pyrrolo[3,4-d]thiazol-2-yl)-5'-methoxy-6-methyl-[4,4'-bipyridine]-3-carboxamide | 560 | $^1$H NMR (400 MHz, DMSO-$d_6$) δ 12.8 (s, 1H), 8.80 (s, 1H), 8.51-8.39 (m, 1H), 8.17 (s, 1H), 7.54 (s, 1H), 7.45-7.08 (m, 2H), 4.94 (s 1H), 4.82 (s, 1H), 4.76 (s, 1H), 4.63 (s, 1H), 3.95 (s, 3H), 3.60 (s, 3H), 2.59 (s, 3H) |

TABLE C-continued

The following examples were prepared using a similar procedure to that described for Example 1

| Ex. No. | Structure | Compound Name | LCMS [M + H]+ | NMR |
|---|---|---|---|---|
| 39 | 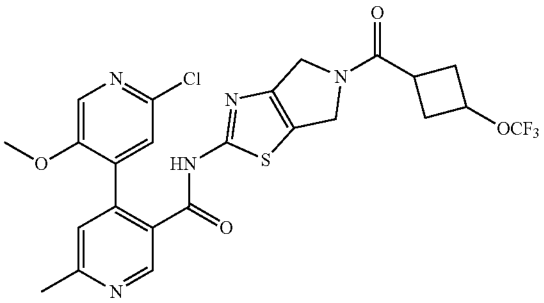 [SMILES: COc1cnc(Cl)cc1-c1cc(C)ncc1C(=O)Nc1nc2c(s1)CN(C(=O)C1CC(OC(F)(F)F)C1)C2] | (Cis and Trans)-2'-Chloro-5'-methoxy-6-methyl-N-(5-(3-(trifluoro-methoxy) cyclobutane-1-carbonyl)-5,6-dihydro-4H-pyrrolo[3,4-d]thiazol-2-yl)-[4,4'-bipyridine]-3-carboxamide | 568 | $^1$H NMR (400 MHz, DMSO-$d_6$) δ 12.8 (s, 1H),8.78 (s, 1H), 8.16 (d, J = 1.8 Hz, 1H), 7.54 (s, 1H), 7.43 (s, 1H), 4.80 (q, J = 7.6 Hz, 1H), 4.74 (s, 1H), 4.64-4.57 (m, 2H), 4.46 (s, 1H), 3.59 (s, 3H), 3.06-2.91 (m, 1H), 2.70-2.59 (m, 2H), 2.59 (s, 3H), 2.40-2.31 (m, 2H) |
| 40 | 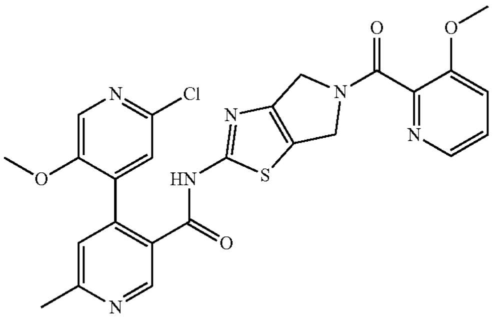 | 2'-Chloro-5'-methoxy-N-(5-(3-methoxy-picolinoyl)-5,6-dihydro-4H-pyrrolo[3,4-d]thiazol-2-yl)-6-methyl-[4,4'-bipyridine]-3-carboxamide | 537 | $^1$H NMR (400 MHz, DMSO-$d_6$) δ 12.8 (s, 1H), 8.78 (d, J = 5.6 Hz, 1H), 8.19 (d, J = 4.6 Hz, 1H), 8.16 (d, J = 4.4 Hz, 1H), 7.63 (d, J = 8.6 Hz, 1H), 7.54 (s, 1H), 7.51-7.46 (m, 1H), 7.43 (s, 1H), 4.79 (s, 1H), 4.66 (s, 1H), 4.45 (s, 1H), 4.32 (s, 1H), 3.85 (s, 3H), 3.60 (s, 3H), 2.58 (d, J = 2.8 Hz, 3H) |
| 41 | 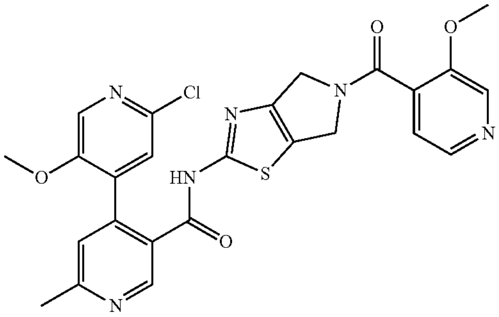 | 2'-Chloro-5'-methoxy-N-(5-(3-methoxy-isonicoti-noyl)-5,6-dihydro-4H-pyrrolo[3,4-d]thiazol-2-yl)-6-methyl-[4,4'-bipyridine]-3-carboxamide | 537 | $^1$H NMR (400 MHz, DMSO-$d_6$) δ 12.8 (s, 1H), 8.77 (d, J = 5.0 Hz, 1H), 8.54 (s, 1H), 8.32 (d, J = 4.6 Hz, 1H), 8.16 (d, J = 3.2 Hz, 1H), 7.54 (s, 1H), 7.43 (s, 1H), 7.35 (d, J = 4.6 Hz, 1H), 4.78 (s, 1H), 4.64 (s, 1H), 4.45 (s, 1H), 4.34 (s, 1H), 3.94 (d, J = 2.2 Hz, 3H), 3.59 (s, 3H), 2.58 (d, J = 2.4 Hz, 3H) |
| 42 | 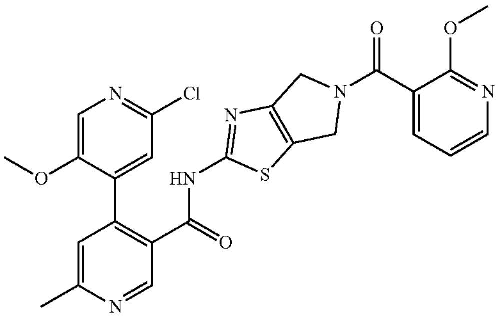 | 2'-Chloro-5'-methoxy-N-(5-(2-methoxy-nicotinoyl)-5,6-dihydro-4H-pyrrolo[3,4-d]thiazol-2-yl)-6-methyl-[4,4'-bipyridine]-3-carboxamide | 537 | $^1$H NMR (400 MHz, DMSO-$d_6$) δ 12.8 (d, J = 3.6 Hz, 1H), 8.77 (d, J = 4.8 Hz, 1H), 8.32-8.25 (m, 1H), 8.16 (d, J = 3.0 Hz, 1H), 7.79 (dd, J = 7.2, 1.8 Hz, 1H), 7.54 (s, 1H), 7.43 (d, J =1.6 Hz, 1H), 7.10 (dd, J = 7.2, 5.0 Hz, 1H), 4.78 (s, 1H), 4.67-4.61 (m, 1H), 4.52-4.46 (m, 1H), 4.41-4.34 (m, 1H), 3.92 (s, 3H), 3.60 (s, 3H), 2.59 (d, J = 2.6 Hz, 3H) |

TABLE C-continued

The following examples were prepared using a similar procedure to that described for Example 1

| Ex. No. | Structure | Compound Name | LCMS [M + H]+ | NMR |
|---|---|---|---|---|
| 43 | 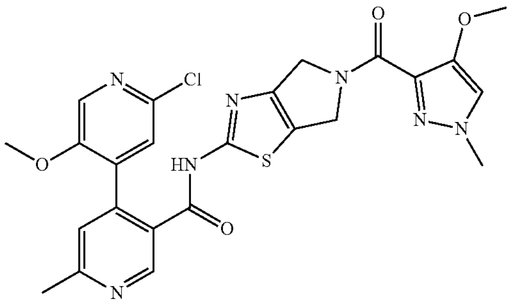 | 2'-Chloro-5'-methoxy-N-(5-(4-methoxy-1-methyl-1H-pyrazole-3-carbonyl)-5,6-dihydro-4H-pyrrolo[3,4-d]thiazol-2-yl)-6-methyl-[4,4'-bipyridine]-3-carboxamide | 540 | $^1$H NMR (400 MHz, DMSO-$d_6$) δ 12.8 (s, 1H), 8.79 (s, 1H), 8.17 (s, 1H), 7.62 (s, 1H), 7.53 (s, 1H), 7.43 (s, 1H), 4.94 (s, 1H), 4.81 (s, 1H), 4.74 (s, 1H), 4.60 (s, 1H), 3.82 (d, J = 6.0 Hz, 3H), 3.70 (d, J = 1.6 Hz, 3H), 3.61 (s, 3H), 2.59 (s, 3H) |
| 44 | 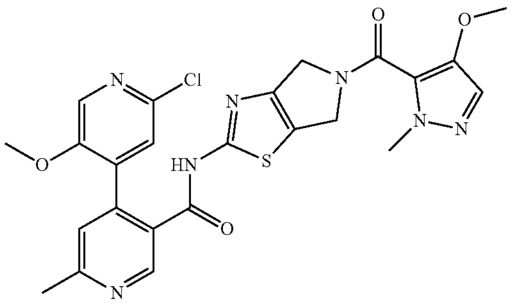 | 2'-Chloro-5'-methoxy-N-(5-(4-methoxy-1-methyl-1H-pyrazole-5-carbonyl)-5,6-dihydro-4H-pyrrolo[3,4-d]thiazol-2-yl)-6-methyl-[4,4'-bipyridine]-3-carboxamide | 540 | $^1$H NMR (400 MHz, DMSO-$d_6$) δ 12.8 (s, 1H), 8.82 (d, J = 3.0 Hz, 1H), 8.18 (s, 1H), 7.56 (s, 1H), 7.48 (s, 1H), 7.42 (d, J = 3.2 Hz, 1H), 4.84-4.78 (m, 2H), 4.72-4.64 (m, 2H), 3.80 (d, J = 5.2 Hz, 3H), 3.80 (s, 3H), 3.60 (s, 3H), 2.62 (s, 3H) |
| 45 | 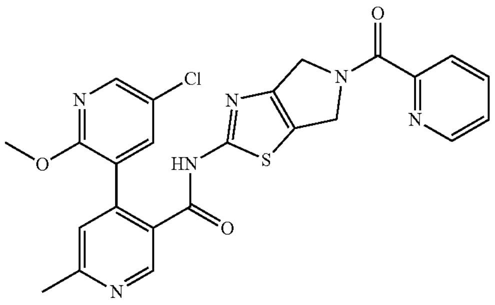 [SMILES: COc1ncc(Cl)cc1-c1cc(C)ncc1C(=O)Nc1nc2c(s1)CN(C(=O)c1ccccn1)C2] | 5-Chloro-2-methoxy-6'-methyl-N-(5-picolinyl-5,6-dihydro-4H-pyrrolo[3,4-d]thiazol-2-yl)-[3,4'-bipyridine]-3'-carboxamide | 507 | $^1$H NMR (400 MHz, DMSO-$d_6$) δ 12.8 (s, 1H), 8.76 (s, 1H), 8.69-8.64 (m, 1H), 8.28-8.24 (m, 1H), 8.02-7.95 (m, 2H), 7.86 (t, J = 7.0 Hz, 1H), 7.58-7.53 (m, 1H), 7.45 (s, 1H), 5.04 (s, 1H), 4.93 (s, 1H), 4.85 (s, 1H), 4.72 (s, 1H), 3.58 (s, 3H), 2.58 (s, 3H) |
| 46 | 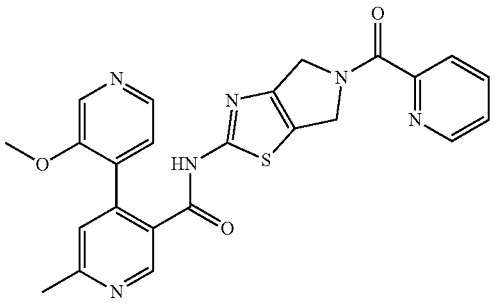 [SMILES: COc1cnccc1-c1cc(C)ncc1C(=O)Nc1nc2c(s1)CN(C(=O)c1ccccn1)C2] | 3'-Methoxy-6-methyl-N-(5-picolinyl-5,6-dihydro-4H-pyrrolo[3,4-d]thiazol-2-yl)-[4,4'-bipyridine]-3-carboxamide | 473 | $^1$H NMR (400 MHz, DMSO-$d_6$) δ 12.8-12.7 (m, 1H), 8.77 (s, 1H), 8.67 (dd, J = 9.4, 4.8 Hz, 1H), 8.40-8.35 (m, 2H), 7.99 (td, J = 7.8, 1.8 Hz, 1H), 7.86 (t, J = 6.8 Hz, 1H), 7.58-7.53 (m, 1H), 7.43 (d, J = 4.8 Hz, 1H), 7.38 (s, 1H), 5.04 (s, 1H), 4.93 (s, 1H), 4.85 (s, 1H), 4.71 (s, 1H), 3.63 (s, 3H), 2.59 (s, 3H) |

TABLE C-continued

The following examples were prepared using a similar procedure to that described for Example 1

| Ex. No. | Structure | Compound Name | LCMS [M + H]+ | NMR |
|---|---|---|---|---|
| 47 | 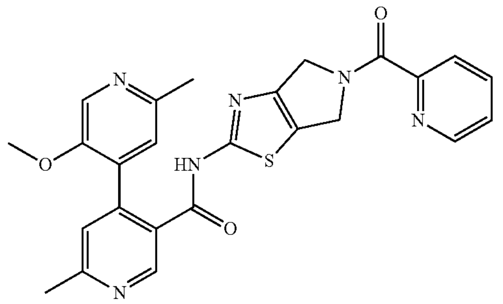 [SMILES: COc1cnc(C)cc1-c1cc(C)ncc1C(=O)Nc1nc2c(s1)CN(C(=O)c1ccccn1)C2] | 5'-Methoxy-2',6-dimethyl-N-(5-picolinoyl-5,6-dihydro-4H-pyrrolo[3,4-d]thiazol-2-yl)-[4,4'-bipyridine]-3-carboxamide | 487 | $^1$H NMR (400 MHz, DMSO-$d_6$) δ 12.8-12.7 (m, 1H), 8.73 (s, 1H), 8.69-8.63 (m, 1H), 8.18 (d, J = 1.2 Hz, 1H), 8.02-7.95 (m, 1H), 7.89-7.83 (m, 1H), 7.59-7.53 (m, 1H), 7.36 (s, 1H), 7.26 (s, 1H), 5.06-5.03 (m, 1H), 4.94-4.91 (m, 1H), 4.87-4.84 (m, 1H), 4.73-4.70 (m, 1H), 3.56 (d, J = 1.2 Hz, 3H), 2.58 (d, J = 1.8 Hz, 3H), 2.47 (d, J = 2.2 Hz, 3H) |
| 48 | 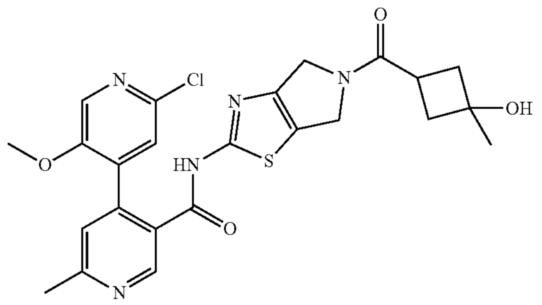 [SMILES: COc1cnc(Cl)cc1-c1cc(C)ncc1C(=O)Nc1nc2c(s1)CN(C(=O)C1CC(C)(O)C1)C2] | (Cis and Trans)-2'-Chloro-N-(5-(3-hydroxy-3-methyl-cyclobutane-1-carbonyl)-5,6-dihydro-4H-pyrrolo[3,4-d]thiazol-2-yl)-5'-methoxy-6-methyl-[4,4'-bipyridine]-3-carboxamide | 514 | $^1$H NMR (400 MHz, DMSO-$d_6$) δ 12.8 (s, 1H), 8.78 (s, 1H), 8.16 (d, J = 2.6 Hz, 1H), 7.53 (s, 1H), 7.43 (s, 1H), 5.01 (d, J = 4.2 Hz, 1H), 4.72 (s, 1H), 4.62-4.53 (m, 2H), 4.43 (s, 1H), 3.59 (s, 3H), 2.90-2.79 (m, 1H), 2.59 (s, 3H), 2.24-2.07 (m, 4H), 1.29 (d, J = 4.4 Hz, 3H) |
| 49* | 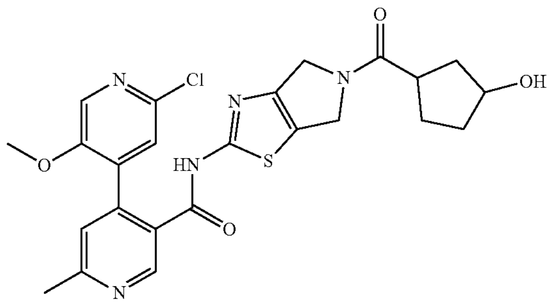 [SMILES: COc1cnc(Cl)cc1-c1cc(C)ncc1C(=O)Nc1nc2c(s1)CN(C(=O)C1CCC(O)C1)C2] | (Racemic Trans)-2'-chloro-N-(5-(3-hydroxy-cyclopen-tane-1-carbonyl)-5,6-dihydro-4H-pyrrolo[3,4-d]thiazol-2-yl)-5'-methoxy-6-methyl-[4,4'-bipyridine]-3-carboxamide | 514 | $^1$H NMR (400 MHz, DMSO-$d_6$) δ 12.9 (s, 1H), 8.78 (s, 1H), 8.17 (d, J = 1.8 Hz, 1H), 7.54 (s, 1H), 7.44 (s, 1H), 4.83 (s, 1H), 4.71 (s, 1H), 4.68-4.61 (m, 1H), 4.62-4.53 (m, 1H), 4.45 (s, 1H), 4.14-4.05 (m, 1H), 3.60 (s, 3H), 2.98-2.87 (m, 1H), 2.59 (s, 3H), 2.14-2.03 (m, 1H), 1.87-1.76 (m, 2H), 1.77-1.59 (m, 2H), 1.61-1.48 (m, 1H) |
| 50 | 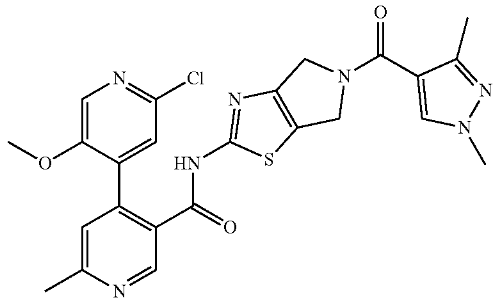 | 2'-Chloro-N-(5-(1,3-dimethyl-1H-pyrazole-4-carbonyl)-5,6-dihydro-4H-pyrrolo[3,4-d]thiazol-2-yl)-5'-methoxy-6-methyl-[4,4'-bipyridine]-3-carboxamide | 524 | $^1$H NMR (400 MHz, DMSO-$d_6$) δ 12.8 (s, 1H), 8.79 (s, 1H), 8.26-8.14 (m, 2H), 7.54 (s, 1H), 7.43 (s, 1H), 4.91 (s, 1H), 4.78 (s, 1H), 4.74 (s, 1H), 4.61 (s, 1H), 3.80 (d, J = 4.2 Hz, 3H), 3.61 (s, 3H), 2.59 (s, 3H), 2.29 (s, 3H) |

TABLE C-continued

The following examples were prepared using a similar procedure to that described for Example 1

| Ex. No. | Structure | Compound Name | LCMS [M + H]+ | NMR |
|---|---|---|---|---|
| 51 | 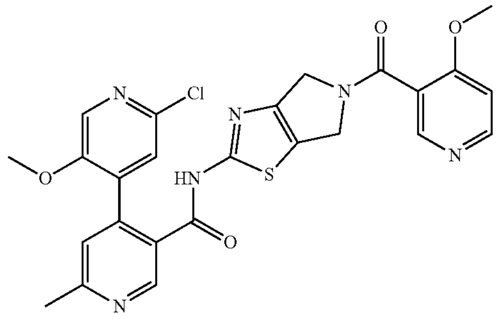 | 2'-Chloro-5'-methoxy-N-(5-(4-methoxy-nicotinoyl)-5,6-dihydro-4H-pyrrolo[3,4-d]thiazol-2-yl)-6-methyl-[4,4'-bipyridine]-3-carboxamide | 537 | $^1$H NMR (400 MHz, DMSO-$d_6$) δ 12.8 (s, 1H), 8.78 (d, J = 4.8 Hz, 1H), 8.53 (d, J = 5.4 Hz, 1H), 8.39 (s, 1H), 8.16 (d, J = 3.0 Hz, 1H), 7.53 (s, 1H), 7.42 (s, 1H), 7.21 (d, J = 5.8 Hz, 1H), 4.78 (s, 1H), 4.64 (s, 1H), 4.49 (s, 1H), 4.38 (s, 1H), 3.90 (d, J = 2.8 Hz, 3H), 3.60 (s, 3H), 2.58 (d, J = 2.4 Hz, 3H) |
| 52 | 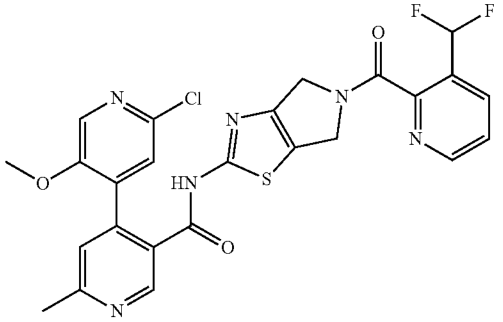 [SMILES: COc1cnc(Cl)cc1-c1cc(C)ncc1C(=O)Nc1nc2c(s1)CN(C(=O)c1ncccc1C(F)F)C2] | 2'-Chloro-N-(5-(3-(difluoromethyl) picolinyl)-5,6-dihydro-4H-pyrrolo[3,4-d]thiazol-2-yl)-5'-methoxy-6-methyl-[4,4'-bipyridine]-3-carboxamide | 557 | $^1$H NMR (400 MHz, DMSO-$d_6$) δ 12.8 (s, 1H), 8.83-8.76 (m, 2H), 8.25-8.20 (m, 1H), 8.16 (d, J = 3.4 Hz, 1H), 7.74-7.69 (m, 1H), 7.54 (s, 1H), 7.45-7.41 (m, 1H), 7.39-7.07 (m, 1H), 4.89-4.84 (m, 1H), 4.75-4.66 (m, 2H), 4.60-4.56 (m, 1H), 3.60 (s, 3H), 2.59 (d, J = 2.8 Hz, 3H) |
| 53 | 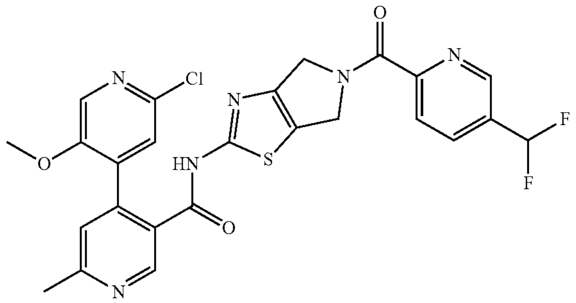 [SMILES: COc1cnc(Cl)cc1-c1cc(C)ncc1C(=O)Nc1nc2c(s1)CN(C(=O)c1ccc(C(F)F)cn1)C2] | 2'-Chloro-N-(5-(5-(difluoromethyl) picolinyl)-5,6-dihydro-4H-pyrrolo[3,4-d]thiazol-2-yl)-5'-methoxy-6-methyl-[4,4'-bipyridine]-3-carboxamide | 557 | $^1$H NMR (400 MHz, DMSO-$d_6$): δ 12.8 (d, J = 5.6 Hz, 1H), 8.87 (d, J = 7.4 Hz, 1H), 8.79 (s, 1H), 8.20 (d, J = 8.2 Hz, 1H), 8.17 (s, 1H), 7.99 (dd, J = 8.2 4.6 Hz, 1H), 7.54 (s, 1H), 7.43 (d, J = 1.4 Hz, 1H), 7.24 (t, J = 55.2 Hz, 1H), 5.02 (t, J = 2.4 Hz, 1H), 4.96-4.83 (m, 2H), 4.73 (t, J = 2.4 Hz, 1H), 3.60 (s, 3H), 2.59 (d, J = 1.8 Hz, 3H) |
| 54 | 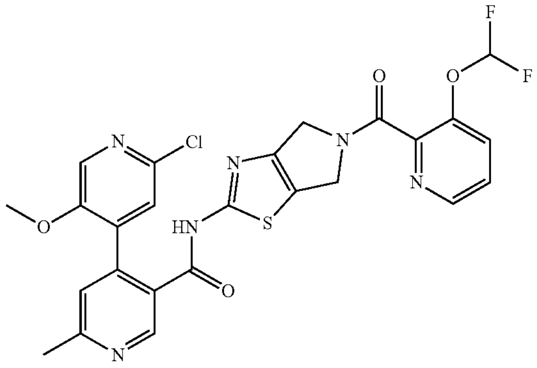 [SMILES: COc1cnc(Cl)cc1-c1cc(C)ncc1C(=O)Nc1nc2c(s1)CN(C(=O)c1ncccc1OC(F)F)C2] | 2'-Chloro-N-(5-(3-(di-fluoromethoxy) picolinoyl)-5,6-dihydro-4H-pyrrolo[3,4-d]thiazol-2-yl)-5'-methoxy-6-methyl-[4,4'-bipyridine]-3-carboxamide | 573 | $^1$H NMR (400 MHz, DMSO-$d_6$) δ 12.8 (d, J = 2.2 Hz, 1H), 8.78 (d, J = 4.8 Hz, 1H), 8.54-8.51 (m, 1H), 8.16 (d, J = 3.8 Hz, 1H), 7.89-7.85 (m, 1H), 7.65-7.60 (m, 1H), 7.54 (s, 1H), 7.50-7.12 (m, 1H), 7.43 (d, J = 1.8 Hz, 1H), 4.83 (t, J = 2.8 Hz, 1H), 4.70 (t, J = 2.6 Hz, 1H), 4.54 (t, J = 2.8 Hz, 1H), 4.43 (t, J = 2.6 Hz, 1H), 3.60 (s, 3H), 2.58 (d, J = 2.8 Hz, 3H) |

TABLE C-continued

| The following examples were prepared using a similar procedure to that described for Example 1 | | | | |
|---|---|---|---|---|
| Ex. No. | Structure | Compound Name | LCMS [M + H]+ | NMR |
| 55 | 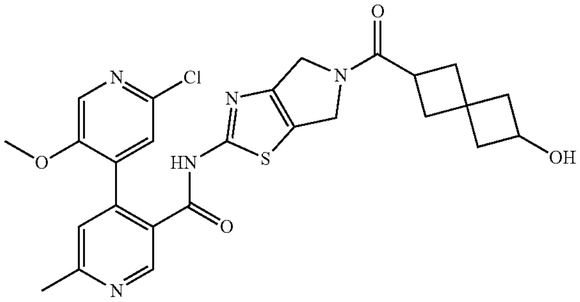 | 2'-Chloro-N-(5-(6-hydroxy-spiro[3.3]heptane-2-carbonyl)-5,6-dihydro-4H-pyrrolo[3,4-d]thiazol-2-yl)-5'-methoxy-6-methyl-[4,4'-bipyridine]-3-carboxamide | 540 | $^{1}$H NMR (400 MHz, DMSO-$d_6$) δ 12.8 (s, 1H), 8.78 (s, 1H), 8.16 (d, J = 2.6 Hz, 1H), 7.53 (s, 1H), 7.43 (s, 1H), 4.88 (d, J = 6.4 Hz, 1H), 4.67 (s, 1H), 4.54 (s, 2H), 4.41 (s, 1H), 3.98-3.88 (m, 1H), 3.61-3.58 (m, 3H), 3.24-3.17 (m, 1H), 2.59 (s, 3H), 2.44-2.35 (m, 1H), 2.21-2.06 (m, 5H), 1.88-1.80 (m, 1H), 1.77-1.70 (m, 1H) |
| 56 | 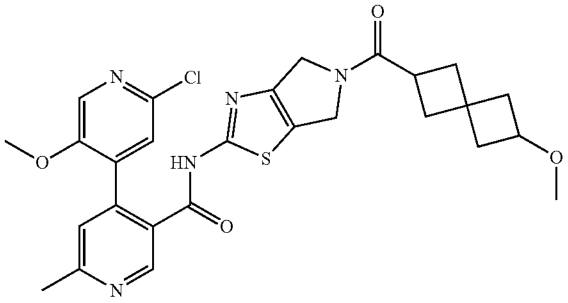 | 2'-Chloro-5'-methoxy-N-(5-(6-methoxy-spiro[3.3]heptane-2-carbonyl)-5,6-dihydro-4H-pyrrolo[3,4-d]thiazol-2-yl)-6-methyl-[4,4'-bipyridine]-3-carboxamide | 554 | $^{1}$H NMR (400 MHz, DMSO-$d_6$) δ 12.8 (s, 1H), 8.78 (s, 1H), 8.16 (d, J = 2.4 Hz, 1H), 7.54 (s, 1H), 7.43 (s, 1H), 4.68 (s, 1H), 4.55 (s, 2H), 4.42 (s, 1H), 3.76-3.67 (m, 1H), 3.59 (s, 3H), 3.27-3.17 (m, 1H), 3.09 (s, 3H), 2.59 (s, 3H), 2.46-2.36 (m, 1H), 2.26-2.08 (m, 5H), 1.90-1.83 (m, 1H), 1.77-1.71 (m, 1H) |
| 57 | 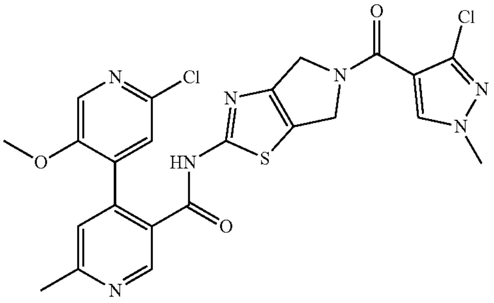 | 2'-Chloro-N-(5-(3-chloro-1-methyl-1H-pyrazole-4-carbonyl)-5,6-dihydro-4H-pyrrolo[3,4-d]thiazol-2-yl)-5'-methoxy-6-methyl-[4,4'-bipyridine]-3-carboxamide | 544 | $^{1}$H NMR (400 MHz, DMSO-$d_6$) δ 12.8 (s, 1H), 8.79 (s, 1H), 8.33 (d, J = 17.4 Hz, 1H), 8.17 (s, 1H), 7.54 (s, 1H), 7.43 (s, 1H), 4.84 (s, 1H), 4.74 (s, 2H), 4.62 (s, 1H), 3.85 (d, J = 4.4 Hz, 3H), 3.60 (s, 3H), 2.59 (s, 3H) |
| 58 | 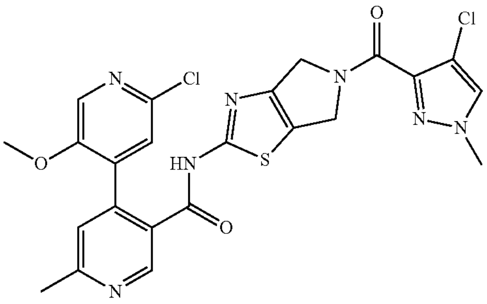 | 2'-Chloro-N-(5-(4-chloro-1-methyl-1H-pyrazole-3-carbonyl)-5,6-dihydro-4H-pyrrolo[3,4-d]thiazol-2-yl)-5'-methoxy-6-methyl-[4,4'-bipyridine]-3-carboxamide | 544 | $^{1}$H NMR (400 MHz, DMSO-$d_6$) δ 12.8 (s, 1H), 8.79 (s, 1H), 8.17 (s, 1H), 8.08 (s, 1H), 7.54 (s, 1H), 7.43 (s, 1H), 4.98 (s, 1H), 4.86 (s, 1H), 4.78 (s, 1H), 4.65 (s, 1H), 3.90 (d, J = 6.6 Hz, 3H), 3.61 (d, J = 1.6 Hz, 3H), 2.59 (s, 3H) |

TABLE C-continued

The following examples were prepared using a similar procedure to that described for Example 1

| Ex. No. | Structure | Compound Name | LCMS [M + H]+ | NMR |
|---|---|---|---|---|
| 59 | 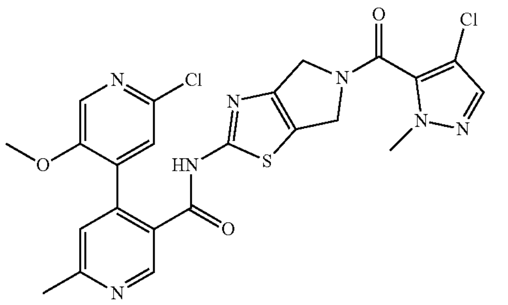 [SMILES: COc1cnc(Cl)cc1-c1cc(C)ncc1C(=O)Nc1nc2c(s1)CN(C(=O)c1c(Cl)cnn1C)C2] | 2'-Chloro-N-(5-(4-chloro-1-methyl-1H-pyrazole-5-carbonyl)-5,6-dihydro-4H-pyrrolo[3,4-d]thiazol-2-yl)-5'-methoxy-6-methyl-[4,4'-bipyridine]-3-carboxamide | 544 | $^1$H NMR (400 MHz, DMSO-$d_6$) δ 12.8 (s, 1H), 8.78 (d, J = 3.2 Hz, 1H), 8.16 (d, J = 1.4 Hz, 1H), 7.66 (s, 1H), 7.54 (s, 1H), 7.43 (s, 1H), 4.85 (s, 1H), 4.72 (s, 2H), 4.61 (s, 1H), 3.84 (s, 3H), 3.60 (s, 3H), 2.59 (d, J = 1.8 Hz, 3H) |
| 60 | 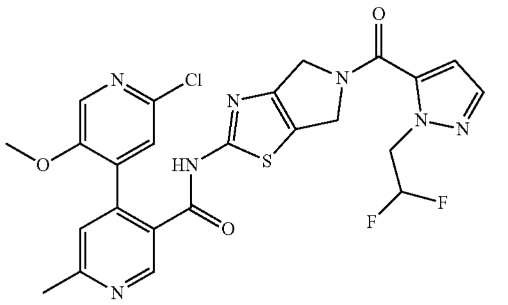 [SMILES: COc1cnc(Cl)cc1-c1cc(C)ncc1C(=O)Nc1nc2c(s1)CN(C(=O)c1ccnn1CC(F)F)C2] | 2'-Chloro-N-(5-(1-(2,2-difluoroethyl)-1H-pyrazole-5-carbonyl)-5,6-dihydro-4H-pyrrolo[3,4-d]thiazol-2-yl)-5'-methoxy-6-methyl-[4,4'-bipyridine]-3-carboxamide | 560 | $^1$H NMR (400 MHz, DMSO-$d_6$) δ 12.8 (s, 1H), 8.79 (s, 1H), 8.17 (s, 1H), 7.68-7.64 (m, 1H), 7.55 (s, 1H), 7.44 (s, 1H), 7.04-6.96 (m, 1H), 6.54-6.22 (m, 1H), 4.92 (s, 1H), 4.88-4.78 (m, 4H), 4.68 (s, 1H), 3.60 (s, 3H), 2.59 (s, 3H) |
| 61 | 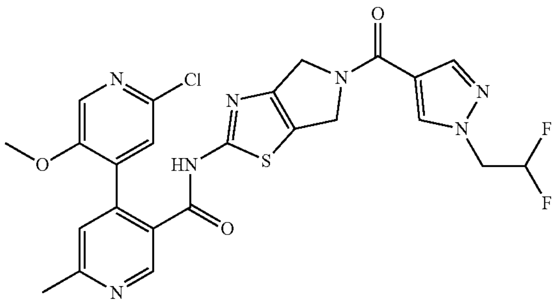 [SMILES: COc1cnc(Cl)cc1-c1cc(C)ncc1C(=O)Nc1nc2c(s1)CN(C(=O)c1cnn(CC(F)F)c1)C2] | 2'-Chloro-N-(5-(1-(2,2-difluoroethyl)-1H-pyrazole-4-carbonyl)-5,6-dihydro-4H-pyrrolo[3,4-d]thiazol-2-yl)-5'-methoxy-6-methyl-[4,4'-bipyridine]-3-carboxamide | 560 | $^1$H NMR (400 MHz, DMSO-$d_6$) δ 12.9-12.8 (m, 1H), 8.86 (s, 1H), 8.46 (d, J = 15.4 Hz, 1H), 8.24 (d, J = 2.6 Hz, 1H), 8.07 (d, J = 12.2 Hz, 1H), 7.61 (d, J = 1.8 Hz, 1H), 7.51 (s, 1H), 6.65-6.32 (m, 1H), 5.10 (s, 1H), 4.96 (s, 1H), 4.85-4.67 (m, 4H), 3.68 (s, 3H), 2.66 (s, 3H) |
| 62 | 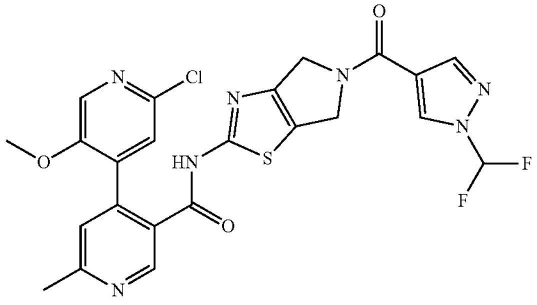 [SMILES: COc1cnc(Cl)cc1-c1cc(C)ncc1C(=O)Nc1nc2c(s1)CN(C(=O)c1cnn(C(F)F)c1)C2] | 2'-Chloro-N-(5-(1-(di-fluoromethyl)-1H-pyrazole-4-carbonyl)-5,6-dihydro-4H-pyrrolo[3,4-d]thiazol-2-yl)-5'-methoxy-6-methyl-[4,4'-bipyridine]-3-carboxamide | 546 | $^1$H NMR (400 MHz, DMSO-$d_6$) δ 12.8 (s, 1H), 8.85-8.77 (m, 2H), 8.22 (d, J = 11.4 Hz, 1H), 8.17 (d, J = 2.8 Hz, 1H), 7.88 (t, J = 58.8 Hz, 1H), 7.54 (s, 1H), 7.44 (s, 1H), 5.06 (s, 1H), 4.93 (s, 1H), 4.77 (s, 1H), 4.65 (s, 1H), 3.61 (s, 3H), 2.59 (s, 3H) |

TABLE C-continued

The following examples were prepared using a similar procedure to that described for Example 1

| Ex. No. | Structure | Compound Name | LCMS [M + H]+ | NMR |
|---|---|---|---|---|
| 63 | 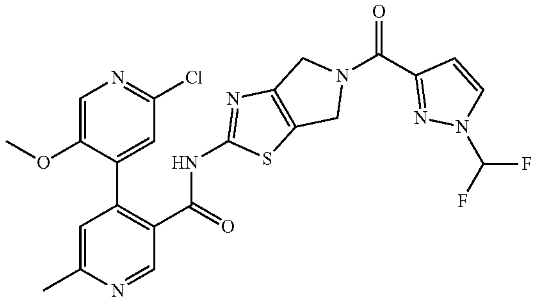 [SMILES: COc1cnc(Cl)cc1-c1cc(C)ncc1C(=O)Nc1nc2c(s1)CN(C(=O)c1ccn(C(F)F)n1)C2] | 2'Chloro-N-(5-(1-(difluoro-methyl)-1H-pyrazole-3-carbonyl)-5,6-dihydro-4H-pyrrolo[3,4-d]thiazol-2-yl)-5'-methoxy-6-methyl-[4,4'-bipyridine]-3-carboxamide | 546 | $^1$H NMR (400 MHz, DMSO-$d_6$) δ 12.8 (s, 1H), 8.79 (d, J = 2.0 Hz, 1H), 8.38 (d, J = 2.6 Hz, 1H), 8.17 (d, J = 1.4 Hz, 1H), 7.93 (td, J = 58.8, 11.2 Hz, 1H), 7.54 (s, 1H), 7.44 (s, 1H), 6.95 (dd, J = 4.8, 2.6 Hz, 1H), 5.15 (s, 1H), 5.02 (s, 1H), 4.82 (s, 1H), 4.68 (s, 1H), 3.61 (d, J = 2.2 Hz, 3H), 2.59 (s, 3H) |
| 64 | 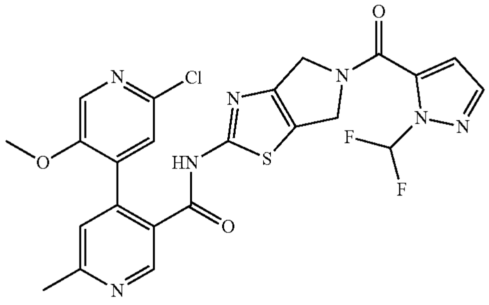 [SMILES: COc1cnc(Cl)cc1-c1cc(C)ncc1C(=O)Nc1nc2c(s1)CN(C(=O)c1ccnn1C(F)F)C2] | 2'-Chloro-N-(5-(1-(difluoro-methyl)-1H-pyrazole-5-carbonyl)-5,6-dihydro-4H-pyrrolo[3,4-d]thiazol-2-yl)-5'-methoxy-6-methyl-[4,4'-bipyridine]-3-carboxamide | 546 | $^1$H NMR (400 MHz, DMSO-$d_6$) δ 12.8 (s, 1H), 8.79 (s, 1H), 8.17 (s, 1H), 8.08-7.71 (m, 2H), 7.55 (s, 1H), 7.44 (s, 1H), 7.20-7.06 (m, 1H), 4.95 (s, 1H), 4.84 (s, 2H), 4.69 (s, 1H), 3.59 (s, 3H), 2.59 (s, 3H) |
| 65 | 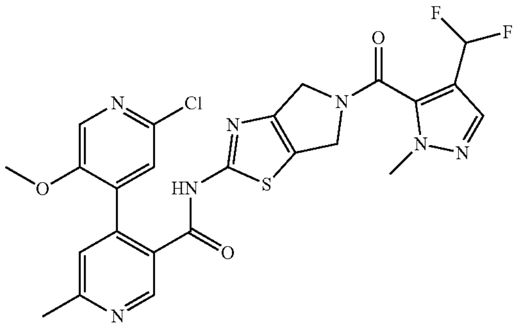 [SMILES: COc1cnc(Cl)cc1-c1cc(C)ncc1C(=O)Nc1nc2c(s1)CN(C(=O)c1c(C(F)F)cnn1C)C2] | 2'-Chloro-N-(5-(4-(difluoro-methyl)-1-methyl-1H-pyrazole-5-carbonyl)-5,6-dihydro-4H-pyrrolo[3,4-d]thiazol-2-yl)-5'-methoxy-6-methyl-[4,4'-bipyridine]-3-carboxamide | 560 | $^1$H NMR (400 MHz, DMSO-$d_6$) δ 12.8 (d, J = 3.0 Hz, 1H), 8.78 (d, J = 4.4 Hz, 1H), 8.17 (d, J = 2.2 Hz, 1H), 7.78 (s, 1H), 7.54 (s, 1H), 7.43 (s, 1H), 7.10 (td, J = 55.2, 7.8 Hz, 1H), 4.84 (s, 1H), 4.70 (s, 1H), 4.53 (s, 1H), 4.43 (s, 1H), 3.85 (s, 3H), 3.60 (s, 3H), 2.59 (d, J = 2.0 Hz, 3H) |
| 66 | 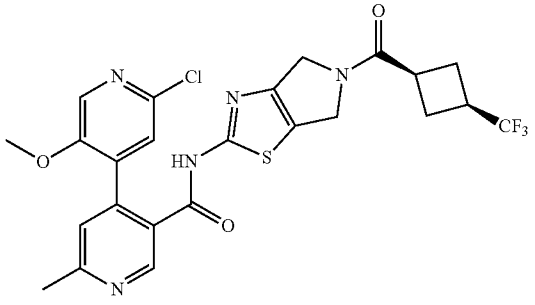 [SMILES: COc1cnc(Cl)cc1-c1cc(C)ncc1C(=O)Nc1nc2c(s1)CN(C(=O)[C@H]1C[C@@H](C(F)(F)F)C1)C2] | 2'-Chloro-5'-methoxy-6-methyl-N-(4-((1s,3s)-3-(trifluoromethyl) cyclobutane-1-carbonyl)-5,6-dihydro-4H-pyrrolo[3,4-d]thiazol-2-yl)-[4,4'-bipyridine]-3-carboxamide | 552 | $^1$H NMR (400 MHz, DMSO-$d_6$) δ 12.8 (s, 1H), 8.78 (s, 1H), 8.16 (d, J = 2.0 Hz, 1H), 7.54 (s, 1H), 7.43 (s, 1H), 4.73 (s, 1H), 4.59 (s, 2H), 4.45 (s, 1H), 3.59 (s, 3H), 3.38-3.32 (m, 1H), 3.23-3.10 (m, 1H), 2.59 (s, 3H), 2.42-2.24 (m, 4H) |

TABLE C-continued

The following examples were prepared using a similar procedure to that described for Example 1

| Ex. No. | Structure | Compound Name | LCMS [M + H]+ | NMR |
|---|---|---|---|---|
| 67 | 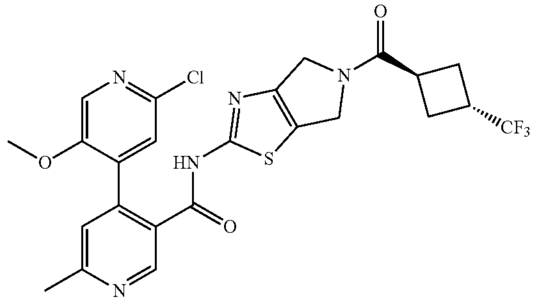 [SMILES: COc1cnc(Cl)cc1-c1cc(C)ncc1C(=O)Nc1nc2c(s1)CN(C(=O)[C@H]1C[C@H](C(F)(F)F)C1)C2] | 2'-Chloro-5'-methoxy-6-methyl-N-(5-((1r,3r)-3-(trifluoromethyl)cyclobutane-1-carbonyl)-5,6-dihydro-4H-pyrrolo[3,4-d]thiazol-2-yl)-[4,4'-bipyridine]-3-carboxamide | 552 | $^1$H NMR (400 MHz, DMSO-$d_6$) δ 12.8 (s, 1H), 8.78 (s, 1H), 8.16 (d, J = 2.8 Hz, 1H), 7.54 (s, 1H), 7.43 (s, 1H), 4.70 (s, 1H), 4.62-4.54 (m, 2H), 4.47 (s, 1H), 3.59 (s, 3H), 3.48-3.38 (m, 1H), 3.16-3.04 (m, 1H), 2.59 (s, 3H), 2.56-2.51 (m, 2H), 2.39-2.27 (m, 2H) |
| 68 | 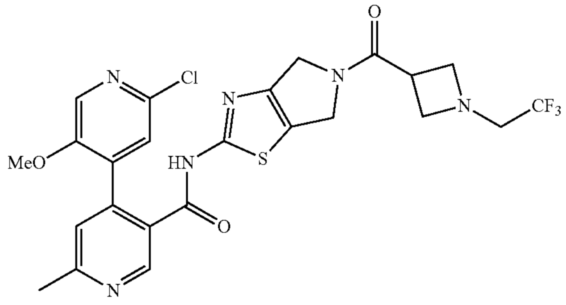 [SMILES: COc1cnc(Cl)cc1-c1cc(C)ncc1C(=O)Nc1nc2c(s1)CN(C(=O)C1CN(CC(F)(F)F)C1)C2] | 2'-Chloro-5'-methoxy-6-methyl-N-(5-(1-(2,2,2-trifluoroethyl)azetidine-3-carbonyl)-5,6-dihydro-4H-pyrrolo[3,4-d]thiazol-2-yl)-[4,4'-bipyridine]-3-carboxamide | 567 | $^1$H NMR (400 MHz, DMSO-$d_6$) δ 8.81 (d, J = 2.4 Hz, 1H), 8.15 (d, J = 2.0 Hz, 1H), 7.50 (s, 1H), 7.38 (s, 1H), 4.64 (s, 1H), 4.57 (s, 1H), 4.51 (s, 1H), 4.43 (s, 1H), 3.67-3.54 (m, 6H), 3.46-3.41 (m, 2H), 3.18 (q, J = 10.2 Hz, 2H), 2.57 (s, 3H) |
| 69 | 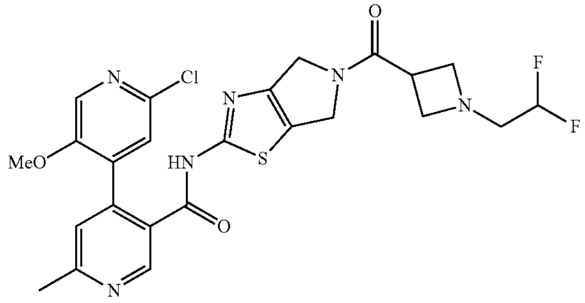 [SMILES: COc1cnc(Cl)cc1-c1cc(C)ncc1C(=O)Nc1nc2c(s1)CN(C(=O)C1CN(CC(F)F)C1)C2] | 2'-Chloro-N-(5-(1-(2,2-difluoroethyl)azetidine-3-carbonyl)-5,6-dihydro-4H-pyrrolo[3,4-d]thiazol-2-yl)-5'-methoxy-6-methyl-[4,4'-bipyridine]-3-carboxamide | 549 | $^1$H NMR (400 MHz, DMSO-$d_6$) δ 12.8-12.7 (m, 1H), 8.78 (s, 1H), 8.16 (d, J = 2.4 Hz, 1H), 7.54 (s, 1H), 7.43 (s, 1H), 6.13-5.77 (m, 1H), 4.66 (s, 1H), 4.60-4.52 (m, 2H), 4.45 (s, 1H), 3.64-3.51 (m, 6H), 3.39-3.33 (m, 2H), 2.88-2.72 (m, 2H), 2.59 (s, 3H) |
| 70 | 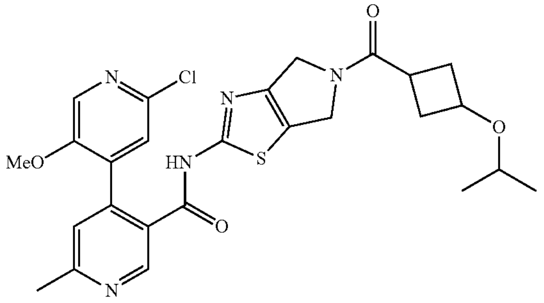 [SMILES: COc1cnc(Cl)cc1-c1cc(C)ncc1C(=O)Nc1nc2c(s1)CN(C(=O)C1CC(OC(C)C)C1)C2] | (Cis and Trans)-2'-Chloro-N-(5-(3-isopropoxycyclobutane-1-carbonyl)-5,6-dihydro-4H-pyrrolo[3,4-d]thiazol-2-yl)-5'-methoxy-6-methyl-[4,4'-bipyridine]-3-carboxamide | 542 | $^1$H NMR (400 MHz, DMSO-$d_6$) δ 12.7 (s, 1H), 8.80 (s, 1H), 8.16 (s, 1H), 7.48 (s, 1H), 7.38 (s, 1H), 4.75-4.66 (m, 1H), 4.62-4.52 (m, 2H), 4.48-4.40 (m, 1H), 3.98-3.90 (m, 1H), 3.62 (s, 3H), 3.58-3.54 (m, 1H), 2.88-2.80 (m, 1H), 2.60 (s, 3H), 2.46-2.30 (m, 2H), 2.06-1.96 (m, 2H), 1.10-1.03 (m, 6H) |

TABLE C-continued

The following examples were prepared using a similar procedure to that described for Example 1

| Ex. No. | Structure | Compound Name | LCMS [M + H]+ | NMR |
|---|---|---|---|---|
| 71 | 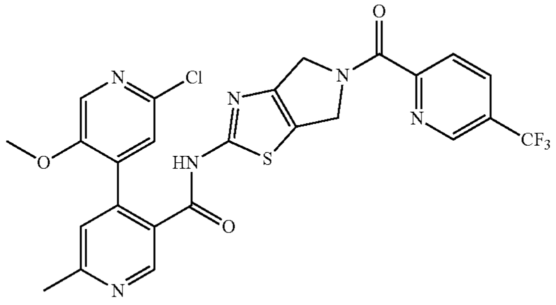 [SMILES: COc1cnc(Cl)cc1-c1cc(C)ncc1C(=O)Nc1nc2c(s1)CN(C(=O)c1ccc(C(F)(F)F)cn1)C2] | 2'-Chloro-5'-methoxy-6-methyl-N-(5-(5-(trifluoromethyl)picolinoyl)-5,6-dihydro-4H-pyrrolo[3,4-d]thiazol-2-yl)-[4,4'-bipyridine]-3-carboxamide | 575 | $^1$H NMR (400 MHz, DMSO-$d_6$) δ 12.8 (s, 1H), 9.08 (d, J = 9.8 Hz, 1H), 8.79 (d, J = 1.4 Hz, 1H), 8.42 (d, J = 8.4 Hz, 1H), 8.17 (s, 1H), 8.05 (dd, J = 8.2, 5.0 Hz, 1H), 7.54 (s, 1H), 7.43 (d, J = 1.4 Hz, 1H), 5.00 (s, 1H), 4.92-4.86 (m, 2H), 4.74 (s, 1H), 3.60 (d, J = 1.2 Hz, 3H), 2.59 (d, J = 1.6 Hz, 3H) |
| 72 | 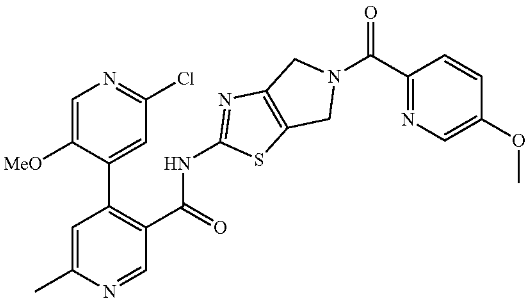 [SMILES: COc1ccc(C(=O)N2Cc3nc(NC(=O)c4cnc(C)cc4-c4cc(Cl)ncc4OC)sc3C2)nc1] | 2'-Chloro-5'-methoxy-N-(5-(5-methoxy-picolinoyl)-5,6-dihydro-4H-pyrrolo[3,4-d]thiazol-2-yl)-6-methyl-[4,4'-bipyridine]-3-carboxamide | 535 | $^1$H NMR (400 MHz, DMSO-$d_6$) δ 12.7 (s, 1H), 8.79 (s, 1H), 8.35 (dd, J = 12.6, 2.8 Hz, 1H), 8.17 (s, 1H), 7.91 (dd, J = 8.6, 4.8 Hz, 1H), 7.55 (d, J = 8.6 Hz, 2H), 7.43 (s, 1H), 5.13 (s, 1H), 5.00 (s, 1H), 4.85 (s, 1H), 4.70 (s, 1H), 3.91 (d, J = 2.4 Hz, 3H), 3.61 (s, 3H), 2.59 (s, 3H) |
| 73 | 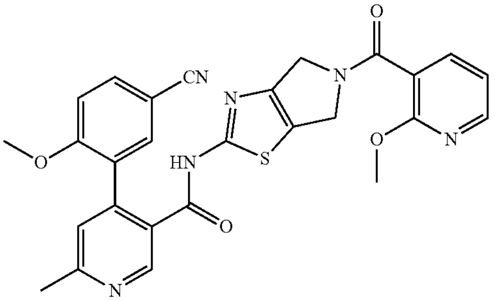 [SMILES: COc1ccc(C#N)cc1-c1cc(C)ncc1C(=O)Nc1nc2c(s1)CN(C(=O)c1cccnc1OC)C2] | 4-(5-Cyano-2-methoxyphenyl)-N-(5-(2-methoxy-nicotinoyl)-5,6-dihydro-4H-pyrrolo[3,4-d]thiazol-2-yl)-6-methyl-nicotinamide | 527 | $^1$H NMR (400 MHz, DMSO-$d_6$) δ 12.7 (s, 1H), 8.71 (d, J = 4.4 Hz, 1H), 8.30-8.27 (m, 1H), 7.89 (dt, J = 8.6, 2.6 Hz, 1H), 7.85 (d, J = 2.2 Hz, 1H), 7.79 (dd, J = 7.4, 1.8 Hz, 1H), 7.39 (d, J = 2.2 Hz, 1H), 7.17 (dd, J = 8.6, 3.0 Hz, 1H), 7.13-7.08 (m, 1H), 4.77 (t, J = 2.8 Hz, 1H), 4.63 (t, J = 2.8 Hz, 1H), 4.48 (t, J = 2.8 Hz, 1H), 4.37 (t, J = 2.8 Hz, 1H), 3.92 (d, J = 1.6 Hz, 3H), 3.56 (s, 3H), 2.57 (d, J = 2.6 Hz, 3H) |
| 74 | 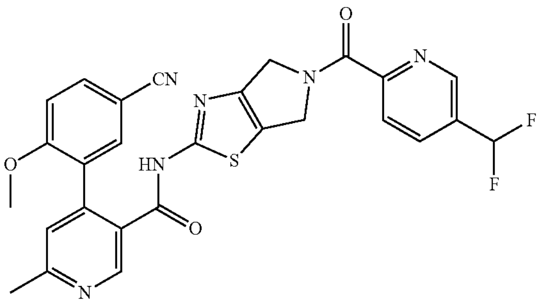 [SMILES: COc1ccc(C#N)cc1-c1cc(C)ncc1C(=O)Nc1nc2c(s1)CN(C(=O)c1ccc(C(F)F)cn1)C2] | 4-(5-Cyano-2-methoxyphenyl)-N-(5-(5-(difluoormethyl)picolinoyl)-5,6-dihydro-4H-pyrrolo[3,4-d]thiazol-2-yl)-6-methyl-nicotinamide | 547 | $^1$H NMR (400 MHz, DMSO-$d_6$) δ 12.7-12.6 (m, 1H), 8.87 (d, J = 7.4 Hz, 1H), 8.72 (s, 1H), 8.20 (d, J = 8.2 Hz, 1H), 8.01-7.97 (m, 1H), 7.89 (d, J = 8.8 Hz, 1H), 7.85 (s, 1H), 7.40 (s, 1H), 7.24 (t, J = 55.2 Hz, 1H), 7.17 (d, J = 8.6 Hz, 1H), 5.01 (s, 1H), 4.90 (s, 1H), 4.86 (s, 1H), 4.72 (s, 1H), 3.57 (s, 3H), 2.58 (s, 3H) |

TABLE C-continued

| The following examples were prepared using a similar procedure to that described for Example 1 | | | | |
|---|---|---|---|---|
| Ex. No. | Structure | Compound Name | LCMS [M + H]+ | NMR |
| 75 | 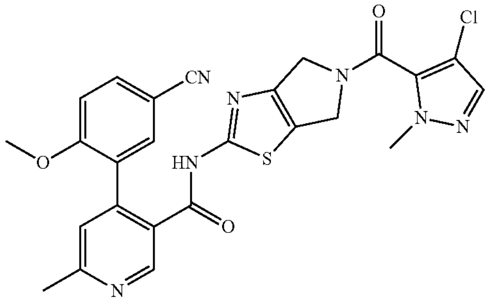 [SMILES: COc1ccc(C#N)cc1-c1cc(C)ncc1C(=O)Nc1nc2c(s1)CN(C(=O)c1c(Cl)cnn1C)C2] | N-(5-(4-Chloro-1-methyl-1H-pyrazole-5-carbonyl)-5,6-dihyrdo-4H-pyrrolo[3,4-d]thiazol-2-yl)-4-(5-cyano-2-methoxyphenyl)-6-methyl-nicotinamide | 534 | $^1$H NMR (400 MHz, DMSO-$d_6$) δ 12.7 (d, J = 10.4 Hz, 1H), 8.71 (d, J = 3.2 Hz, 1H), 7.91-7.87 (m, 1H), 7.86-7.84 (m, 1H), 7.67 (s, 1H), 7.40 (s, 1H), 7.17 (d, J = 8.8 Hz, 1H), 4.84 (s, 1H), 4.71 (s, 2H), 4.61 (s, 1H), 3.84 (s, 3H), 3.57 (s, 3H), 2.58 (d, J = 1.8 Hz, 3H) |
| 76 | 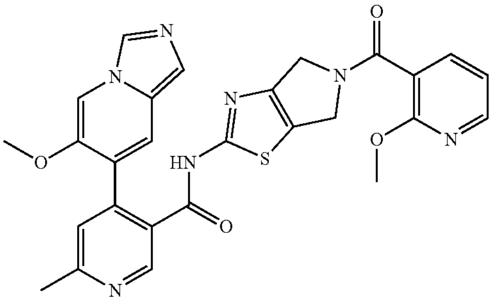 [SMILES: COc1cn2cncc2cc1-c1cc(C)ncc1C(=O)Nc1nc2c(s1)CN(C(=O)c1cccnc1OC)C2] | 4-(6-Methoxyimidazo[1,5-a]pyridin-7-yl)-N-(5-(2-methoxy-nicotinoyl)-5,6-dihydro-4H-pyrrolo[3,4-d]thiazol-2-yl)-6-methyl-nicotinamide | 542 | $^1$H NMR (400 MHz, DMSO-$d_6$) δ 12.7 (s, 1H), 8.70 (d, J = 4.6 Hz, 1H), 8.32-8.24 (m, 2H), 8.00 (d, J = 4.2 Hz, 1H), 7.79 (dd, J = 7.4, 2.0 Hz, 1H), 7.65 (s, 1H), 7.44 (dd, J = 9.2, 2.7 Hz, 2H), 7.10 (dd, J = 7.4, 5.0 Hz, 1H), 4.77 (s, 1H), 4.64 (s, 1H), 4.49 (s, 1H), 4.37 (s, 1H), 3.92 (d, J = 2.,0 Hz, 3H), 3.45 (s, 3H), 2.58 (d, J = 2.8 Hz, 3H) |
| 77 | 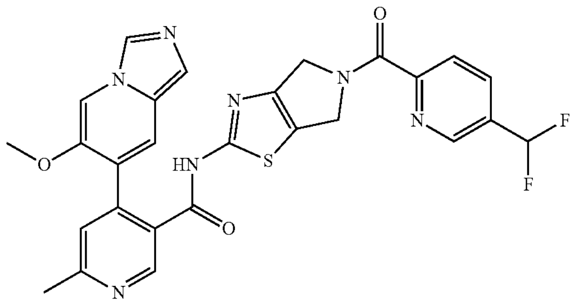 [SMILES: COc1cn2cncc2cc1-c1cc(C)ncc1C(=O)Nc1nc2c(s1)CN(C(=O)c1ccc(C(F)F)cn1)C2] | N-(5-(5-(Difluoromethyl)picolinoyl)-5,6-dihydro-4H-pyrrolo[3,4-d]thiazol-2-yl)-4-(6-methoxyimidazo[1,5-a]pyridin-7-yl)-6-methyl-nicotinamide | 562 | $^1$H NMR (400 MHz, DMSO-$d_6$) δ 12.8-12.7 (m, 1H), 8.87 (d, J = 8.8 Hz, 1H), 8.72 (s, 1H), 8.31 (s, 1H), 8.20 (d, J = 8.2 Hz, 1H), 8.02-7.96 (m, 2H), 7.65 (s, 1H), 7.46-7.41 (m, 2H), 7.24 (t, J = 55.0 Hz, 1H), 5.01 (s, 1H), 4.93-4.84 (m, 2H), 4.72 (s, 1H), 3.45 (d, J = 2.2 Hz, 3H), 2.58 (s, 3H) |
| 78 | 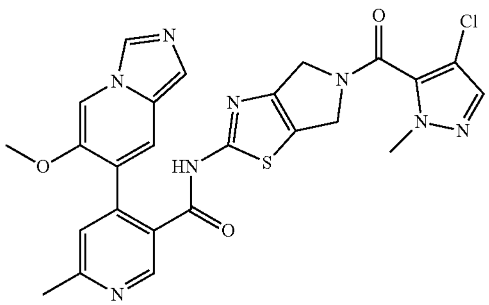 [SMILES: COc1cn2cncc2cc1-c1cc(C)ncc1C(=O)Nc1nc2c(s1)CN(C(=O)c1c(Cl)cnn1C)C2] | N-(5-(4-Chloro-1-methyl-1H-pyrazole-5-carbonyl)-5,6-dihydro-4H-pyrrolo[3,4-d]thiazol-2-yl)-4-(6-methoxyimidazo[1,5-a]pyridin-7-yl)-6-methyl-nicotinamide | 549 | $^1$H NMR (400 MHz, DMSO-$d_6$) δ 12.8-12.7 (m, 1H), 8.71 (d, J = 3.2 Hz, 1H), 8.32 (d, J = 2.4 Hz, 1H), 8.01 (d, J = 2.4 Hz, 1H), 7.67 (d, J = 1.4 Hz, 2H), 7.46 (d, J = 2.2 Hz, 1H), 7.43 (s, 1H), 4.84 (s, 1H), 4.72 (s, 2H), 4.61 (s, 1H), 3.84 (s, 3H), 3.45 (s, 3H), 2.58 (d, J = 1.8 Hz, 3H) |

TABLE C-continued

The following examples were prepared using a similar procedure to that described for Example 1

| Ex. No. | Structure | Compound Name | LCMS [M + H]+ | NMR |
|---|---|---|---|---|
| 79 | 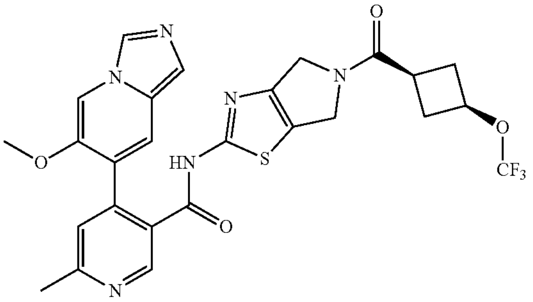 [SMILES: COc1cn2cncc2cc1-c1cc(C)ncc1C(=O)Nc1nc2c(s1)CN(C(=O)[C@H]1C[C@@H](OC(F)(F)F)C1)C2] | 4-(6-Methoxyimidazo[1,5-a]pyridin-7-yl)-6-methyl-N-(5-((1s,3s)-3-(trifluoro-methoxy)cyclobutane-1-carbonyl)-5,6-dihydro-4H-pyrrolo[3,4-d]thiazol-2-yl)nicotinamide | 573 | $^1$H NMR (400 MHz, DMSO-$d_6$) δ 12.7 (d, J = 11.6 Hz, 1H), 8.71 (s, 1H), 8.29 (s, 1H), 8.00 (s, 1H), 7.65 (s, 1H), 7.43 (d, J = 4.8 Hz, 2H), 4.86-4.76 (m, 1H), 4.73 (s, 1H), 4.64-4.56 (m, 2H), 4.45 (s, 1H), 3.44 (s, 3H), 3.05-2.92 (m, 1H), 2.68-2.57 (m, 2H), 2.59 (s, 3H), 2.42-2.29 (m, 2H) |
| 80 | 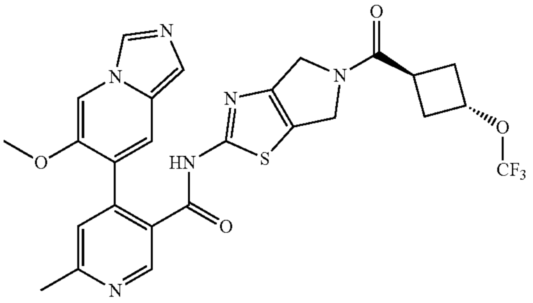 [SMILES: COc1cn2cncc2cc1-c1cc(C)ncc1C(=O)Nc1nc2c(s1)CN(C(=O)[C@H]1C[C@H](OC(F)(F)F)C1)C2] | 4-(6-Methoxyimidazo[1,5-a]pyridin-7-yl)-6-methyl-N-(5-((1r,3r)-3-(trifluoro-methoxy)cyclobutane-1-carbonyl)-5,6-dihydro-4H-pyrrolo[3,4-d]thiazol-2-yl)nicotianmide | 573 | $^1$H NMR (400 MHz, DMSO-$d_6$) δ 12.7 (s, 1H), 8.71 (s, 1H), 8.29 (s, 1H), 8.00 (s, 1H), 7.65 (s, 1H), 7.43 (d, J = 6.6 Hz, 2H), 4.93-4.84 (m, 1H), 4.71 (s, 1H), 4.62-4.55 (m, 2H), 4.47 (s, 1H), 3.44 (s, 3H), 3.42-3.35 (m, 1H), 2.65-2.56 (m, 5H), 22H obscured by solvent peak. |
| 81 | 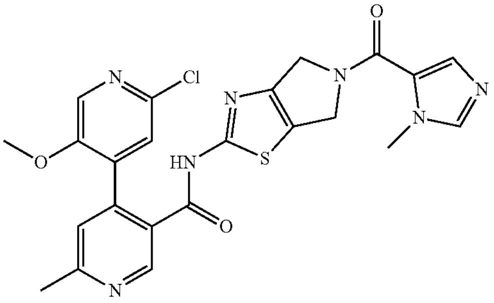 [SMILES: COc1cnc(Cl)cc1-c1cc(C)ncc1C(=O)Nc1nc2c(s1)CN(C(=O)c1cncn1C)C2] | 2'-Chloro-5'-methoxy-6-methyl-N-(5-(1-methyl-1H-imidazole-5-carbonyl)-5,6-dihydro-4H-pyrrolo[3,4-d]thiazol-2-yl)-[4,4'-bipyridine]-3-carboxamide | 510 | $^1$H NMR (400 MHz, DMSO-$d_6$) δ 12.8 (s, 1H), 8.78 (s, 1H), 8.17 (s, 1H), 7.87 (s, 1H), 7.70-7.60 (m, 1H), 7.54 (s, 1H), 7.44 (s, 1H), 5.01 (s, 1H), 4.88 (s, 1H), 4.78 (s, 1H), 4.65 (s, 1H), 3.79 (s, 3H), 3.60 (s, 3H), 2.59 (s, 3H) |
| 82 | 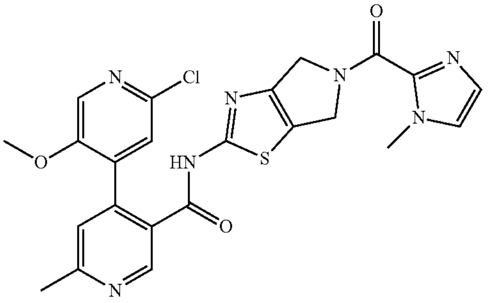 [SMILES: COc1cnc(Cl)cc1-c1cc(C)ncc1C(=O)Nc1nc2c(s1)CN(C(=O)c1nccn1C)C2] | 2'-Chloro-5'-methoxy-6-methyl-N-(5-(1-methyl-1H-imidazole-2-carbonyl)-5,6-dihydro-4H-pyrrolo[3,4-d]thiazol-2-yl)-[4,4'-bipyridine]-3-carboxamide | 510 | $^1$H NMR (400 MHz, DMSO-$d_6$) δ 12.8-12.7 (m, 1H), 8.79 (s, 1H), 8.17 (s, 1H), 7.54 (s, 1H), 7.43 (s, 1H), 7.38 (s, 1H), 7.06 (d, J = 10.4 Hz, 1H), 5.22 (s, 1H), 5.09 (s, 1H), 4.81 (s, 1H), 4.67 (s, 1H), 3.90 (s, 3H), 3.61 (s, 3H), 2.59 (s, 3H) |

TABLE C-continued

The following examples were prepared using a similar procedure to that described for Example 1

| Ex. No. | Structure | Compound Name | LCMS [M + H]+ | NMR |
|---|---|---|---|---|
| 83 | 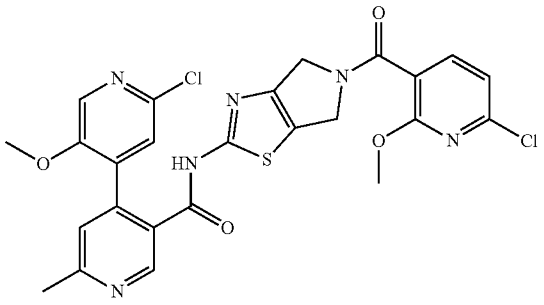 [SMILES: COc1cnc(Cl)cc1-c1cc(C)ncc1C(=O)Nc1nc2c(s1)CN(C(=O)c1ccc(Cl)nc1OC)C2] | 2'-Chloro-N-(5-(6-chloro-2-methoxy-nicotinoyl)-5,6-dihydro-4H-pyrrolo[3,4-d]thiazol-2-yl)-5'-methoxy-6-methyl-[4,4'-bipyridine]-3-carboxamide | 571 | $^1$H NMR (400 MHz, DMSO-$d_6$) δ 12.8 (s, 1H), 8.78 (d, J = 4.2 Hz, 1H), 8.16 (d, J = 1.8 Hz, 1H), 7.89-7.84 (m, 1H), 7.54 (s, 1H), 7.43 (d, J = 2.0 Hz, 1H), 7.25-7.19 (m, 1H), 4.77 (s, 1H), 4.63 (s, 1H), 4.51 (s, 1H), 4.41 (s, 1H), 3.93 (s, 3H), 3.59 (s, 3H), 2.59 (d, J = 2.2 Hz, 3H) |
| 84 | 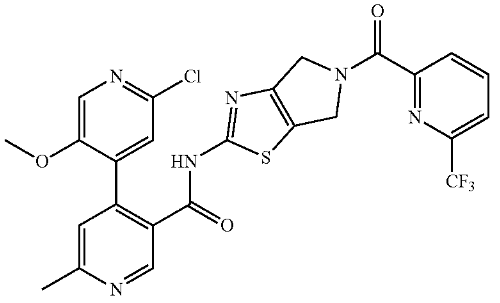 [SMILES: COc1cnc(Cl)cc1-c1cc(C)ncc1C(=O)Nc1nc2c(s1)CN(C(=O)c1cccc(C(F)(F)F)n1)C2] | 2'-Chloro-5'-methoxy-6-methyl-N-(5-(6-(trifluoromethyl)picolinoyl)-5,6-dihydro-4H-pyrrolo[3,4-d]thiazol-2-yl)-[4,4'-bipyridine]-3-carboxamide | 575 | $^1$H NMR (400 MHz, DMSO-$d_6$) δ 12.8-12.7 (m, 1H), 8.78 (d, J = 3.5 Hz, 1H), 8.30 (t, J = 7.8 Hz, 1H), 8.20-8.14 (m, 2H), 8.12-8.08 (m, 1H), 7.54 (s, 1H), 7.44 (s, 1H), 5.00 (s, 1H), 4.94 (s, 1H), 4.88 (s, 1H), 4.74 (s, 1H), 3.60 (s, 3H), 2.60 (s, 3H) |
| 85 | 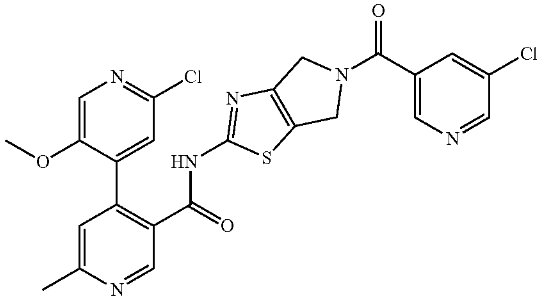 [SMILES: COc1cnc(Cl)cc1-c1cc(C)ncc1C(=O)Nc1nc2c(s1)CN(C(=O)c1cncc(Cl)c1)C2] | 2'-Chloro-N-(5-(5-chloro-nicotinoyl)-5,6-dihydro-4H-pyrrolo[3,4-d]thiazol-2-yl)-5'-methoxy-6-methyl-[4,4'-bipyridine]-3-carboxamide | 541 | $^1$H NMR (400 MHz, DMSO-$d_6$) δ 12.8-12.7 (m, 1H), 8.79-8.74 (m, 3H), 8.25-8.19 (m, 1H), 8.16 (s, 1H), 7.54 (s, 1H), 7.44 (d, J = 2.2 Hz, 1H), 4.83 (s, 1H), 4.76 (s, 1H), 4.71-4.65 (m, 2H), 3.59 (s, 3H), 2.59 (d, J = 2.2 Hz, 3H) |
| 86 | 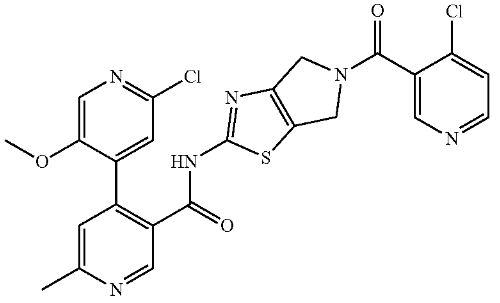 [SMILES: COc1cnc(Cl)cc1-c1cc(C)ncc1C(=O)Nc1nc2c(s1)CN(C(=O)c1cnccc1Cl)C2] | 2'-Chloro-N-(5-(4-chloronicotinoyl)-5,6-dihydro-4H-pyrrolo[3,4-d]thiazol-2-yl)-5'-methoxy-6-methyl-[4,4'-bipyridine]-3-carboxamide | 541 | $^1$H NMR (400 MHz, DMSO-$d_6$) δ 12.8-12.7 (m, 1H), 8.78 (d, J = 4.6 Hz, 1H), 8.73 (d, J = 2.2 Hz, 1H), 8.65 (d, J = 5.4 Hz, 1H), 8.16 (d, J = 2.6 Hz, 1H), 7.72 (dd, J = 5.4, 3.6 Hz, 1H), 7.54 (s, 1H), 7.43 (d, J = 2.6 Hz, 1H), 4.84 (t, J = 2.8 Hz, 1H), 4.70 (t, J = 2.7 Hz, 1H), 4.51 (t, J = 2.7 Hz, 1H), 4.41 (t, J = 2.8 Hz, 1H), 3.59 (s, 3H), 2.59 (d, J = 2.8 Hz, 3H) |
| 87 | 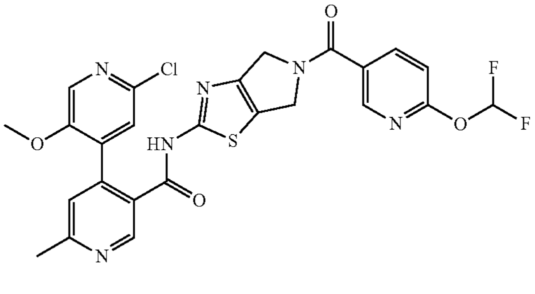 [SMILES: COc1cnc(Cl)cc1-c1cc(C)ncc1C(=O)Nc1nc2c(s1)CN(C(=O)c1ccc(OC(F)F)nc1)C2] | 2'-chloro-N-(5-(6-(difluoro-methoxy)nicotinoyl)-5,6-dihydro-4H-pyrrolo[3,4-d]thiazol-2-yl)-5'-methoxy-6-methyl-[4,4'-bipyridine]-3-carboxamide | 573 | 1H NMR (300 MHz, DMSO-d6) δ 12.80 (s, 1H), 8.79 (s, 1H), 8.56 (d, J = 7.9 Hz, 1H), 8.17 (s, 1H), 7.98 (d, J = 8.7 Hz, 1H), 7.84 (d, J = 9.2 Hz, 1H), 7.75-7.09 (m, 3H), 5.17-4.62 (m, 4H), 3.61 (d, J = 1.1 Hz, 3H), 2.59 (d, J = 1.1 Hz, 3H) |

TABLE C-continued

The following examples were prepared using a similar procedure to that described for Example 1

| Ex. No. | Structure | Compound Name | LCMS [M + H]+ | NMR |
|---|---|---|---|---|
| 88 | 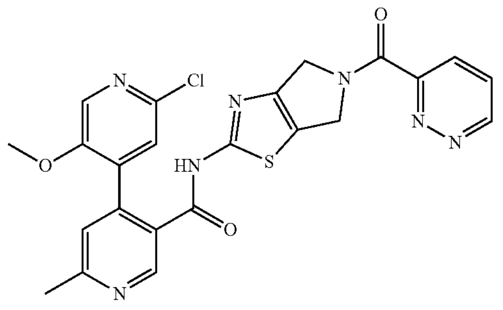 [SMILES: COc1cnc(Cl)cc1-c1cc(C)ncc1C(=O)Nc1nc2c(s1)CN(C(=O)c1cccnn1)C2] | 2'-chloro-5'-methoxy-6-methyl-N-(5-(pyridazine-3-carbonyl)-5,6-dihydro-4H-pyrrolo[3,4-d]thiazol-2-yl)-[4,4'-bipyridine]-3-carboxamide | 508 | 1H NMR (400 MHz, DMSO-d6) δ 12.84-12.80 (m, 1H), 9.51-9.23 (m, 1H), 8.79 (s, 1H), 8.17 (s, 1H), 8.06-8.07 (m, 1H), 7.90 (d, J = 8.5 Hz, 1H), 7.55 (s, 1H), 7.44 (d, J = 1.9 Hz, 1H), 5.12-4.57 (m, 4H), 3.61 (d, J = 0.9 Hz, 3H), 2.59 (d, J = 2.1 Hz, 3H) |
| 89 | 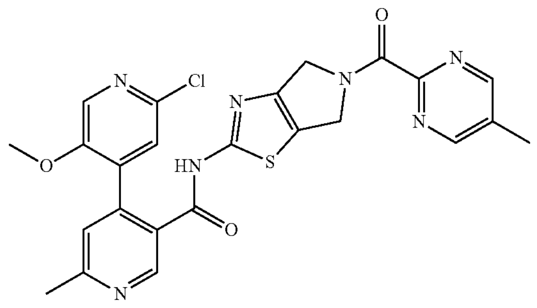 | 2'-chloro-5'-methoxy-6-methyl-N-(5-(5-methyl-pyrimidine-2-carbonyl)-5,6-dihydro-4H-pyrrolo[3,4-d]thiazol-2-yl)-[4,4'-bipyridine]-3-carboxamide | 522 | 1H NMR (300 MHz, DMSO-d6) δ 12.84 (s, 1H), 8.80 (s, 3H), 8.17 (s, 1H), 7.54 (s, 1H), 7.43 (s, 1H), 4.84-4.61 (m, 4H), 3.60 (s, 3H), 2.59 (s, 3H), 2.35 (s, 3H) |
| 90 | 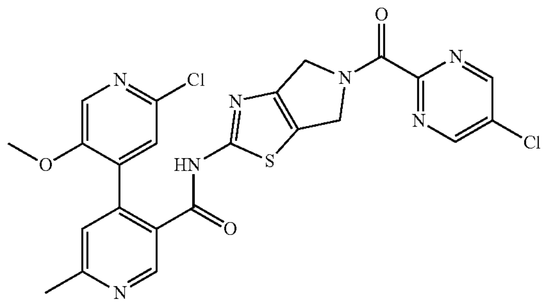 [SMILES: COc1cnc(Cl)cc1-c1cc(C)ncc1C(=O)Nc1nc2c(s1)CN(C(=O)c1ncc(Cl)cn1)C2] | 2'-chloro-N-(5-(5-chloro-pyrimidine-2-carbonyl)-5,6-dihydro-4H-pyrrolo[3,4-d]thiazol-2-yl)-5'-methoxy-6-methyl-[4,4'-bipyridine]-3-carboxamide | 542 | 1H NMR (400 MHz, DMSO-d6) δ 12.82 (s, 1H), 9.11 (d, J = 2.1 Hz, 2H), 8.79 (d, J = 3.7 Hz, 1H), 8.17 (d, J = 1.9 Hz, 1H), 7.54 (s, 1H), 7.43 (d, J = 1.7 Hz, 1H), 4.85 (t, J = 2.6 Hz, 1H), 4.80-4.69 (m, 2H), 4.66 (d, J = 2.7 Hz, 1H), 3.60 (d, J = 1.4 Hz, 3H), 2.59 (d, J = 2.2 Hz, 3H) |
| 91 | 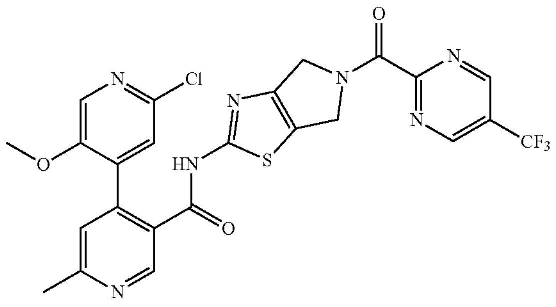 [SMILES: COc1cnc(Cl)cc1-c1cc(C)ncc1C(=O)Nc1nc2c(s1)CN(C(=O)c1ncc(C(F)(F)F)cn1)C2] | 2'-chloro-5'-methoxy-6-methyl-N-(5-(5-(trifluoromethyl)pyrimidine-2-carbonyl)-5,6-dihydro-4H-pyrrolo[3,4-d]thiazol-2-yl)-[4,4'-bipyridine]-3-carboxamide | 576 | 1H NMR (400 MHz, DMSO-d6) δ 12.83 (d, J = 7.3 Hz, 1H), 9.46 (d, J = 3.3 Hz, 2H), 8.79 (d, J = 3.7 Hz, 1H), 8.17 (d, J = 2.1 Hz, 1H), 7.54 (s, 1H), 7.43 (s, 1H), 4.88 (s, 1H), 4.75 (s, 2H), 4.65 (s, 1H), 3.60 (d, J = 1.3 Hz, 3H), 2.59 (d, J = 2.5 Hz, 3H) |

TABLE C-continued

The following examples were prepared using a similar procedure to that described for Example 1

| Ex. No. | Structure | Compound Name | LCMS [M + H]+ | NMR |
|---|---|---|---|---|
| 92 | 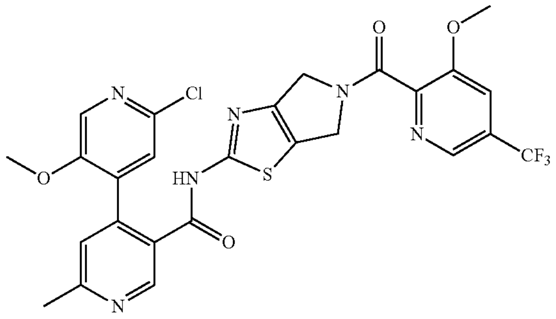 [SMILES: COc1cnc(Cl)cc1-c1cc(C)ncc1C(=O)Nc1nc2c(s1)CN(C(=O)c1ncc(C(F)(F)F)cc1OC)C2] | 2'-chloro-5'-methoxy-N-(5-(3-methoxy-5-(trifluoromethyl) picolinoyl)-5,6-dihydro-4H-pyrrolo[3,4-d]thiazol-2-yl)-6-methyl-[4,4'-bipyridine]-3-carboxamide | 605 | 1H NMR (400 MHz, DMSO-d6) δ 12.82 (d, J = 3.4 Hz, 1H), 8.78 (d, J = 4.8 Hz, 1H), 8.62-8.58 (m, 1H), 8.16 (d, J = 3.4 Hz, 1H), 7.99 (d, J = 1.7 Hz, 1H), 7.54 (s, 1H), 7.43 (d, J = 2.2 Hz, 1H), 4.75 (m, 2H), 4.42 (m, 2H), 3.96 (s, 3H), 3.60 (s, 3H), 2.58 (d, J = 2.8 Hz, 3H) |
| 93 | 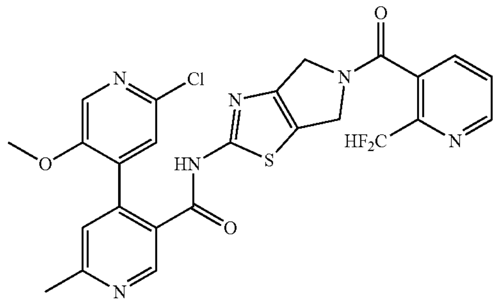 | 2'-chloro-N-(5-(2-(difluoromethyl) nicotinoyl)-5,6-dihydro-4H-pyrrolo[3,4-d]thiazol-2-yl)-5'-methoxy-6-methyl-[4,4'-bipyridine]-3-carboxamide | 557 | 1H NMR (400 MHz, DMSO-d6) δ 12.81 (s, 1H), 8.83-8.78 (m, 2H), 8.16-8.14 (m, 2H), 7.74-7.66 (m, 1H), 7.54 (d, J = 0.9 Hz, 1H), 7.43 (d, J = 2.5 Hz, 1H), 6.90-7.17 (m, 1H), 4.83 (t, J = 2.7 Hz, 1H), 4.69 (d, J = 3.0 Hz, 1H), 4.48 (d, J = 3.0 Hz, 1H), 3.59 (d, J = 0.9 Hz, 3H), 2.59 (d, J = 3.1 Hz, 3H) |
| 94 | 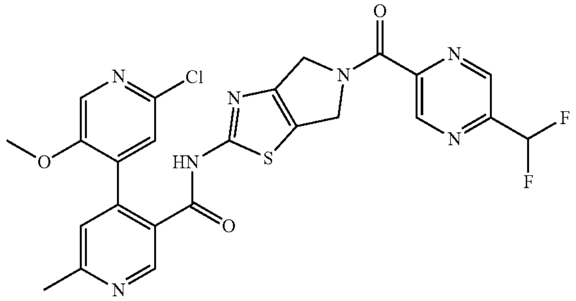 [SMILES: COc1cnc(Cl)cc1-c1cc(C)ncc1C(=O)Nc1nc2c(s1)CN(C(=O)c1cnc(C(F)F)cn1)C2] | 2'-chloro-N-(5-(5-(difluoromethyl) pyrazine-2-carbonyl)-5,6-dihydro-4H-pyrrolo[3,4-d]thiazol-2-yl)-5'-methoxy-6-methyl-[4,4'-bipyridine]-3-carboxamide | 558 | 1H NMR (300 MHz, DMSO-d6) δ 12.82 (s, 1H), 9.17 (d, J = 1.4 Hz, 1H), 9.05 (d, J = 7.1 Hz, 1H), 8.79 (d, J = 1.3 Hz, 1H), 8.17 (s, 1H), 7.55 (s, 1H), 7.42 (d, J = 11.9 Hz, 1H), 7.13 (d, J = 53.9 Hz, 1H), 5.06 (s, 1H), 4.92 (d, J = 8.8 Hz, 2H), 4.77 (d, J = 2.8 Hz, 1H), 3.60 (d, J = 1.1 Hz, 3H), 2.59 (d, J = 1.3 Hz, 3H) |
| 95 | 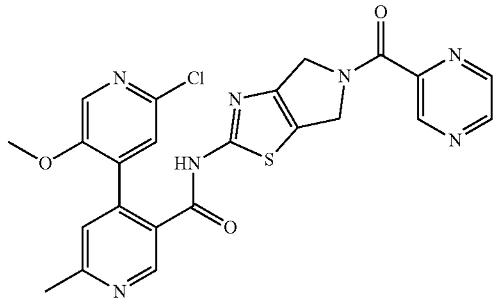 [SMILES: COc1cnc(Cl)cc1-c1cc(C)ncc1C(=O)Nc1nc2c(s1)CN(C(=O)c1cnccn1)C2] | 2'-chloro-5'-methoxy-6-methyl-N-(5-(pyrazine-2-carbonyl)-5,6-dihydro-4H-pyrrolo[3,4-d]thiazol-2-yl)-[4,4'-bipyridine]-3-carboxamide | 508 | 1H NMR (300 MHz, DMSO-d6) δ 12.82 (s, 1H), 9.07 (t, J = 1.7 Hz, 1H), 8.86-8.70 (m, 3H), 8.17 (s, 1H), 7.55 (s, 1H), 7.44 (s, 1H), 5.10-4.70 (m, 4H), 3.60 (d, J = 1.0 Hz, 3H), 2.59 (d, J = 1.3 Hz, 3H) |

TABLE C-continued

The following examples were prepared using a similar procedure to that described for Example 1

| Ex. No. | Structure | Compound Name | LCMS [M + H]+ | NMR |
|---|---|---|---|---|
| 96 | 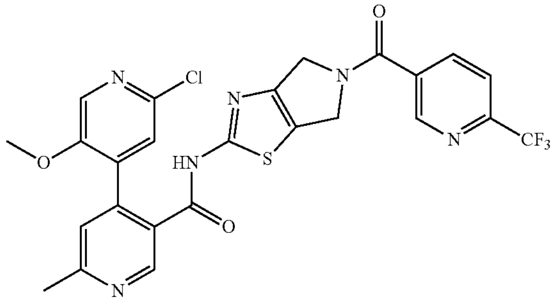 [SMILES: COc1cnc(Cl)cc1-c1cc(C)ncc1C(=O)Nc1nc2c(s1)CN(C(=O)c1ccc(C(F)(F)F)nc1)C2] | 2'-chloro-5'-methoxy-6-methyl-N-(5-(6-(trifluoromethyl) nicotinoyl)-5,6-dihydro-4H-pyrrolo[3,4-d]thiazol-2-yl)-[4,4'-bipyridine]-3-carboxamide | 575 | 1H NMR (300 MHz, DMSO-d6) δ 12.82 (s, 1H), 9.01 (s, 1H), 8.78 (d, J = 2.6 Hz, 1H), 8.34-8.36 (m, 1H), 8.17 (s, 1H), 8.09-7.99 (m, 1H), 7.55 (s, 1H), 7.44 (d, J = 2.0 Hz, 1H), 4.86 (s, 1H), 4.73 (m, 3H), 3.59 (s, 3H), 2.59 (d, J = 1.7 Hz, 3H), 2.55-2.46 (m, 3H) |
| 97 | 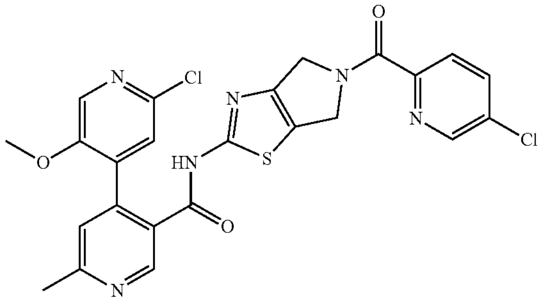 [SMILES: COc1cnc(Cl)cc1-c1cc(C)ncc1C(=O)Nc1nc2c(s1)CN(C(=O)c1ccc(Cl)cn1)C2] | 2'-chloro-N-(5-(5-chloropicolinoyl)-5,6-dihydro-4H-pyrrolo[3,4-d]thiazol-2-yl)-5'-methoxy-6-methyl-[4,4'-bipyridine]-3-carboxamide | 541 | 1H NMR (400 MHz, DMSO-d6) δ 12.81 (d, J = 5.3 Hz, 1H), 8.79 (s, 1H), 8.77-8.69 (m, 1H), 8.17 (s, 1H), 8.13 (m, 1H), 7.94-7.86 (m, 1H), 7.54 (s, 1H), 7.44 (d, J = 1.3 Hz, 1H), 5.04 (d, J = 2.7 Hz, 1H), 4.93 (t, J = 2.7 Hz, 1H), 4.85 (t, J = 2.7 Hz, 1H), 4.72 (t, J = 2.7 Hz, 1H), 3.60 (d, J = 1.6 Hz, 3H), 2.59 (d, J = 1.5 Hz, 3H) |
| 98 | 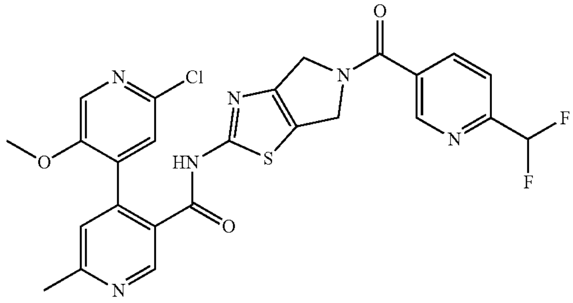 [SMILES: COc1cnc(Cl)cc1-c1cc(C)ncc1C(=O)Nc1nc2c(s1)CN(C(=O)c1ccc(C(F)F)nc1)C2] | 2'-chloro-N-(5-(6-(difluoromethyl) nicotinoyl)-5,6-dihydro-4H-pyrrolo[3,4-d]thiazol-2-yl)-5'-methoxy-6-methyl-[4,4'-bipyridine]-3-carboxamide | 557 | 1H NMR (400 MHz, DMSO-d6) δ 12.82 (s, 1H), 8.92 (d, J = 4.2 Hz, 1H), 8.78 (d, J = 3.7 Hz, 1H), 8.29-8.22 (m, 1H), 8.17 (s, 1H), 7.81 (d, J = 8.1 Hz, 1H), 7.55 (s, 1H), 7.44 (d, J = 2.3 Hz, 1H), 7.19-6.88 (m, 1H), 4.85 (s, 1H), 4.72 (d, J = 8.8 Hz, 2H), 4.66 (s, 1H), 3.59 (s, 3H), 2.59 (d, J = 2.5 Hz, 3H) |
| 99 | 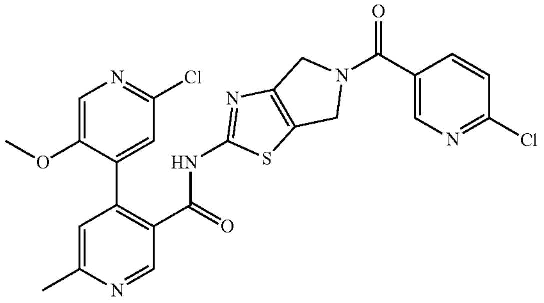 [SMILES: COc1cnc(Cl)cc1-c1cc(C)ncc1C(=O)Nc1nc2c(s1)CN(C(=O)c1ccc(Cl)nc1)C2] | 2'-chloro-N-(5-(6-chloronicotinoyl)-5,6-dihydro-4H-pyrrolo[3,4-d]thiazol-2-yl)-5'-methoxy-6-methyl-[4,4'-bipyridine]-3-carboxamide | 541 | 1H NMR (400 MHz, DMSO-d6) δ 12.81 (s, 1H), 8.79 (d, J = 3.9 Hz, 1H), 8.73-8.64 (m, 1H), 8.16-8.10 (m, 2H), 7.66-7.64 (m, 1H), 7.54 (s, 1H), 7.42 (s, 1H), 4.83 (s, 1H), 4.79-4.72 (m, 1H), 4.72-4.61 (m, 2H), 3.59 (s, 3H), 2.58 (d, J = 2.0 Hz, 3H) |

TABLE C-continued

The following examples were prepared using a similar procedure to that described for Example 1

| Ex. No. | Structure | Compound Name | LCMS [M + H]+ | NMR |
|---|---|---|---|---|
| 100 | 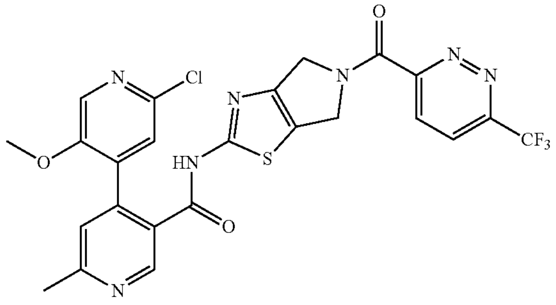 [SMILES: COc1cnc(Cl)cc1-c1cc(C)ncc1C(=O)Nc1nc2c(s1)CN(C(=O)c1ccc(C(F)(F)F)nn1)C2] | 2'-chloro-5'-methoxy-6-methyl-N-(5-(6-(trifluoromethyl)pyridazine-3-carbonyl)-5,6-dihydro-4H-pyrrolo[3,4-d]thiazol-2-yl)-[4,4'-bipyridine]-3-carboxamide | 576 | 1H NMR (300 MHz, DMSO-d6) δ 12.84 (s, 1H), 8.79 (s, 1H), 8.48 (d, J = 8.8 Hz, 1H), 8.38-8.34 (m, 1H), 8.17 (s, 1H), 7.55 (s, 1H), 7.44 (d, J = 1.8 Hz, 1H), 5.04 (s, 1H), 4.95 (s, 2H), 4.80 (s, 1H), 3.61 (s, 3H), 2.59 (d, J = 1.7 Hz, 3H) |
| 101 | 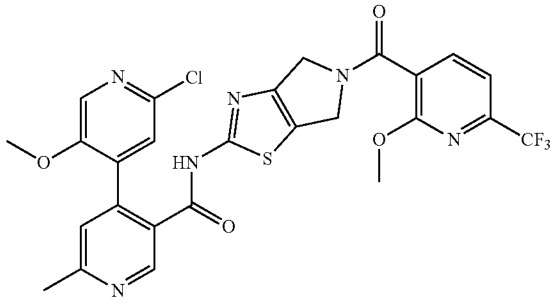 [SMILES: COc1cnc(Cl)cc1-c1cc(C)ncc1C(=O)Nc1nc2c(s1)CN(C(=O)c1ccc(C(F)(F)F)nc1OC)C2] | 2'-chloro-5'-methoxy-N-(5-(2-methoxy-6-(trifluoromethyl)nicotinoyl)-5,6-dihydro-4H-pyrrolo[3,4-d]thiazol-2-yl)-6-methyl-[4,4'-bipyridine]-3-carboxamide | 605 | 1H NMR (400 MHz, DMSO-d6) δ 12.82 (d, J = 3.2 Hz, 1H), 8.78 (d, J = 3.8 Hz, 1H), 8.16 (d, J = 1.8 Hz, 1H), 8.09 (d, J = 7.5, 2.8 Hz, 1H), 7.62 (d, J = 7.6, 3.7 Hz, 1H), 7.54 (s, 1H), 7.43 (d, J = 2.5 Hz, 1H), 4.80-4.65 (m, 2H), 4.51-4.39 (m, 2H), 3.97 (s, 3H), 3.59 (d, J = 0.8 Hz, 3H), 2.58 (d, J = 2.7 Hz, 3H) |
| 102 | 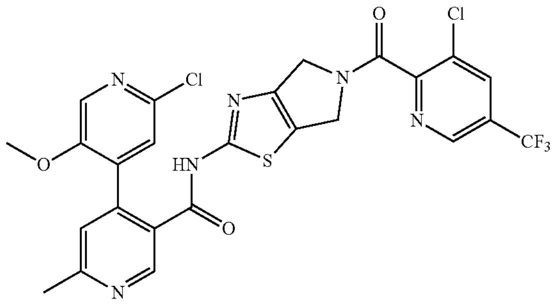 [SMILES: COc1cnc(Cl)cc1-c1cc(C)ncc1C(=O)Nc1nc2c(s1)CN(C(=O)c1ncc(C(F)(F)F)cc1Cl)C2] | 2'-chloro-N-(5-(3-chloro-5-(trifluoromethyl)picolinoyl)-5,6-dihydro-4H-pyrrolo[3,4-d]thiazol-2-yl)-5'-methoxy-6-methyl-[4,4'-bipyridine]-3-carboxamide | 609 | 1H NMR (400 MHz, DMSO-d6) δ 12.84 (s, 1H), 9.09-9.05 (m, 1H), 8.78 (d, J = 4.1 Hz, 1H), 8.75-8.70 (m, 1H), 8.17 (d, J = 3.2 Hz, 1H), 7.54 (s, 1H), 7.44 (d, J = 2.6 Hz, 1H), 4.87 (s, 1H), 4.74 (s, 1H), 4.52 (s, 1H), 4.43 (s, 1H), 3.60 (s, 3H), 2.59 (d, J = 2.9 Hz, 3H) |
| 103 | 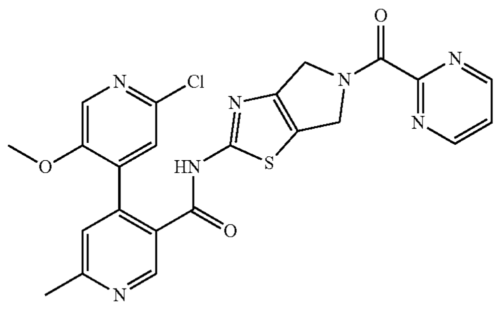 [SMILES: COc1cnc(Cl)cc1-c1cc(C)ncc1C(=O)Nc1nc2c(s1)CN(C(=O)c1ncccn1)C2] | 2'-chloro-5'-methoxy-6-methyl-N-(5-(pyrimidine-2-carbonyl)-5,6-dihydro-4H-pyrrolo[3,4-d]thiazol-2-yl)-[4,4'-bipyridine]-3-carboxamide | 508 | 1H NMR (300 MHz, DMSO-d6) δ 12.83 (s, 1H), 8.97 (d, J = 4.9 Hz, 2H), 8.80 (d, J = 2.7 Hz, 1H), 8.17 (d, J = 2.0 Hz, 1H), 7.67 (t, J = 5.0 Hz, 1H), 7.55 (s, 1H), 7.46 (s, 1H), 4.96-4.35 (m, 4H), 3.57 (s, 3H), 2.59 (d, J = 1.8 Hz, 3H) |

TABLE C-continued

The following examples were prepared using a similar procedure to that described for Example 1

| Ex. No. | Structure | Compound Name | LCMS [M + H]+ | NMR |
|---|---|---|---|---|
| 104 | 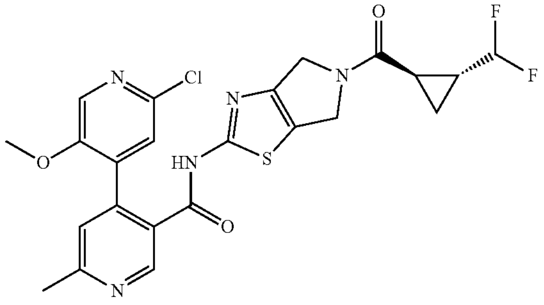 [SMILES: COc1cnc(Cl)cc1-c1cc(C)ncc1C(=O)Nc1nc2c(s1)CN(C(=O)[C@@H]1C[C@H]1C(F)F)C2] | 2'-chloro-N-(5-((1R,2R)-2-(difluoromethyl)cyclopropane-1-carbonyl)-5,6-dihydro-4H-pyrrolo[3,4-d]thiazol-2-yl)-5'-methoxy-6-methyl-[4,4'-bipyridine]-3-carboxamide | 518 [M + H]+ | 1H NMR (300 MHz, DMSO-d6) δ 8.79 (s, 1H), 8.17 (d, J = 1.3 Hz, 1H), 7.55 (s, 1H), 7.44 (s, 1H), 6.11-5.72 (m, 1H), 5.02-4.77 (m, 2H), 4.61 (s, 1H), 4.48 (s, 1H), 3.60 (d, J = 1.1 Hz, 3H), 2.59 (s, 3H), 2.17 (m, 1H), 1.86-1.77 (m, 1H), 1.13 (s, 2H) |
| 105 | 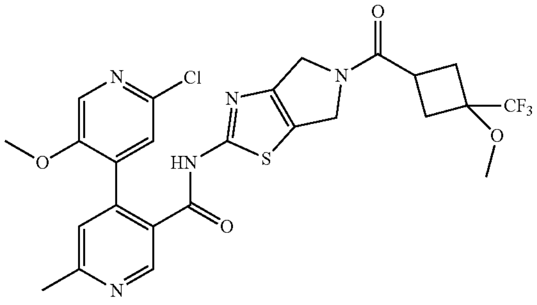 [SMILES: COc1cnc(Cl)cc1-c1cc(C)ncc1C(=O)Nc1nc2c(s1)CN(C(=O)C1CC(OC)(C(F)(F)F)C1)C2] | (Racemic)-2'-chloro-5'-methoxy-N-(5-(3-methoxy-3-(trifluoromethyl)cyclobutane-1-carbonyl)-5,6-dihydro-4H-pyrrolo[3,4-d]thiazol-2-yl)-6-methyl-[4,4'-bipyridine]-3-carboxamide | 582 | 1H NMR (400 MHz, DMSO-d6) δ 12.80 (s, 1H), 8.78 (s, 1H), 8.17 (d, J = 3.5 Hz, 1H), 7.55 (d, J = 1.1 Hz, 1H), 7.44 (s, 1H), 4.77-4.64 (m, 1H), 4.66-4.58 (m, 2H), 4.47 (d, J = 3.0 Hz, 1H), 3.59 (d, J = 1.4 Hz, 3H), 3.42 (d, J = 3.6 1.2 Hz, 1H), 3.13-3.06 (m, 1H), 2.68-2.51 (m, 9H) |
| 106 | 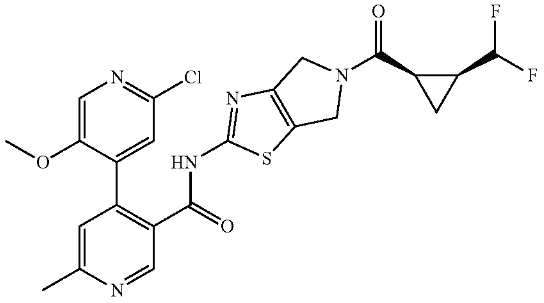 [SMILES: COc1cnc(Cl)cc1-c1cc(C)ncc1C(=O)Nc1nc2c(s1)CN(C(=O)[C@@H]1C[C@@H]1C(F)F)C2] | 2'-chloro-N-(5-((1R,2S)-2-(difluoromethyl)cyclopropane-1-carbonyl)-5,6-dihydro-4H-pyrrolo[3,4-d]thiazol-2-yl)-5'-methoxy-6-methyl-[4,4'-bipyridine]-3-carboxamide | 518 [M + H]+ | 1H NMR (400 MHz, DMSO-d6) δ 12.81 (d, J = 4.7 Hz, 1H), 8.79 (s, 1H), 8.17 (s, 1H), 7.55 (s, 1H), 7.45 (s, 1H), 6.01-5.82 (m, 1H), 5.03-4.88 (m, 2H), 4.76-4.47 (m, 2H), 3.61 (d, J = 1.2 Hz, 3H), 2.59 (s, 3H), 2.32-2.19 (m, 1H), 1.88 (d, J = 8.7 Hz, 1H), 1.29-1.20 (m, 2H) |
| 107 | 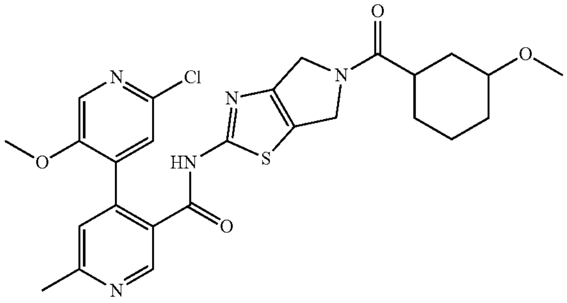 | (Racemic)-2'-chloro-5'-methoxyN-(5-(3-methoxy-cyclohexane-1-carbonyl)-5,6-dihydro-4H-pyrrolo[3,4-d]thiazol-2-yl)-6-methyl-[4,4'-bipyridine]-3-carboxamide | 542 | |

TABLE C-continued

The following examples were prepared using a similar procedure to that described for Example 1

| Ex. No. | Structure | Compound Name | LCMS [M + H]+ | NMR |
|---|---|---|---|---|
| 108[#,c] | 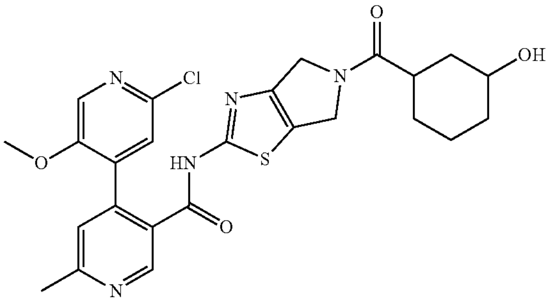 [SMILES: COc1cnc(Cl)cc1-c1cc(C)ncc1C(=O)Nc1nc2c(s1)CN(C(=O)C1CCCC(O)C1)C2] | 2'-chloro-N-(5-((1R,or S,3S and R OR 1R and S,3S or R)-3-hydroxy-cyclohex-ane-1-carbonyl)-5,6-dihydro-4H-pyrrolo[3,4-d]thiazol-2-yl)-5'-methoxy-6-methyl-[4,4'-bipyridine]-3-carboxamide | 528 | 1H NMR (400 MHz, DMSO-d6) δ 8.75 (s, 1H), 8.14 (d, J = 1.9 Hz, 1H), 7.55 (s, 1H), 7.44 (s, 1H), 4.92-4.38 (m, 4H), 3.61 (s, 3H), 3.50 (s, 1H), 2.61 (s, 3H), 2.57 (s, 1H) 1.95-1.73 (m, 2H), 1.69-1.62 (m, 2H), 1.49-1.37 (m, 2H), 1.32-1.23 (m, 2H) |
| 109[#,c] | 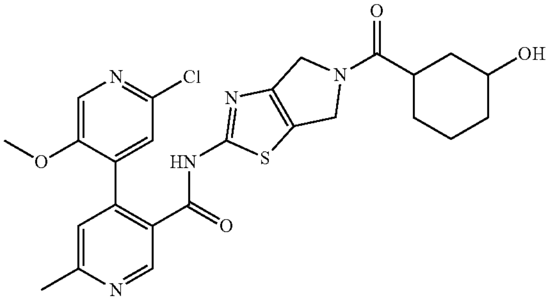 [SMILES: COc1cnc(Cl)cc1-c1cc(C)ncc1C(=O)Nc1nc2c(s1)CN(C(=O)C1CCCC(O)C1)C2] | 2'-chloro-N-(5-((1R and S,3S or R OR 1R or S,3S and R)-3-hydroxy-cyclohex-ane-1-carbonyl)-5,6-dihydro-4H-pyrrolo[3,4-d]thiazol-2-yl)-5'-methoxy-6-methyl-[4,4'-bipyridine]-3-carboxamide | 528 | 1H NMR (400 MHz, DMSO-d6) δ 12.79 (s, 1H), 8.81 (s, 1H), 8.16 (s, 1H), 7.55 (s, 1H), 7.44 (s, 1H), 4.82 (s, 1H), 4.70 (s, 1H), 4.63-4.53 (m, 2H), 4.41 (s, 1H), 3.60 (d, J = 2.1 Hz, 3H), 3.39 (s, 1H), 2.53 (m, 3H), 1.89-1.81 (m, 2H), 1.75-1.65 (m, 2H), 1.35-1.29 (m, 2H), 1.27-1.27 (m, 1H), 1.25-1.23 (m, 2H) |
| 109A | 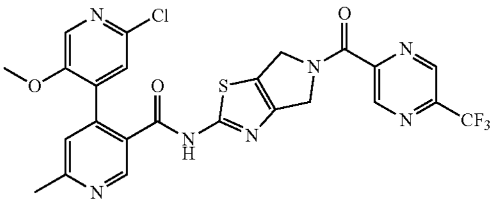 [SMILES: COc1cnc(Cl)cc1-c1cc(C)ncc1C(=O)Nc1nc2c(s1)CN(C(=O)c1cnc(C(F)(F)F)cn1)C2] | 2'-chloro-5'-methoxy-6-methyl-N-(5-(5-(trifluoromethyl) pyrazine-2-carbonyl)-5,6-dihydro-4H-pyrrolo[3,4-d]thiazol-2-yl)-[4,4'-bipyridine]-3-carboxamide | 576 | 1H NMR (400 MHz, DMSO-d6) δ 12.8 (s, 1H), 9.29 (d, J = 9.6 Hz, 1H), 9.23 (s, 1H), 8.79 (d, J = 2.0 Hz, 1H), 8.17 (s, 1H), 7.54 (s, 1H), 7.43 (s, 1H), 5.05 (s, 1H), 4.92 (s, 2H), 4.77 (s, 1H), 3.60 (s, 3H), 2.59 (s, 3H) |
| 353 | 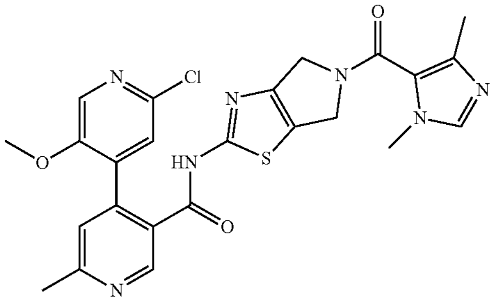 [SMILES: COc1cnc(Cl)cc1-c1cc(C)ncc1C(=O)Nc1nc2c(s1)CN(C(=O)c1c(C)ncn1C)C2] | 2'-Chloro-N-(5-(1,4-dimethyl-1H-imidazole-5-carbonyl)-5,6-dihydro-4H-pyrrolo[3,4-d]thiazol-2-yl)-5'-methoxy-6-methyl-[4,4'-bipyridine]-3-carboxamide | 524 | $^1$H NMR (400 MHz, DMSO-$d_6$) δ 12.8 (s, 1H), 8.78 (s, 1H), 8.17 (s, 1H), 7.83 (s, 1H), 7.55 (s, 1H), 7.44 (s, 1H), 4.82 (s, 1H), 4.68 (s, 2H), 4.56 (s, 1H), 3.62 (s, 3H), 3.60 (s, 3H), 2.59 (s, 3H), 2.21 (s, 3H) |
| 354 | 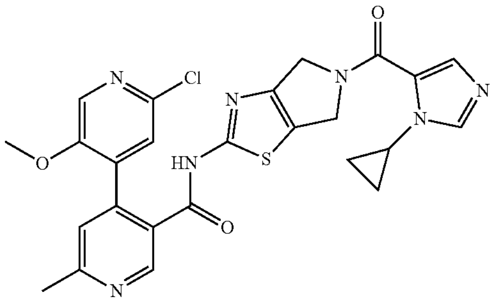 [SMILES: COc1cnc(Cl)cc1-c1cc(C)ncc1C(=O)Nc1nc2c(s1)CN(C(=O)c1cncn1C1CC1)C2] | 2'-Chloro-N-(5-(1-cyclopropyl-1H-imidazole-5-carbonyl)-5,6-dihydro-4H-pyrrolo[3,4-d]thiazol-2-yl)-5'-methoxy-6-methyl-[4,4'-bipyridine]-3-carboxamide | 536 | $^1$H NMR (400 MHz, DMSO-$d_6$) δ 12.8 (s, 1H), 8.79 (s, 1H), 8.17 (s, 1H), 7.85 (s, 1H), 7.60-7.50 (m, 2H), 7.44 (s, 1H), 4.97 (s, 1H), 4.85 (s, 1H), 4.80 (s, 1H), 4.67 (s, 1H), 3.72-3.63 (m, 1H), 3.61 (s, 3H), 2.59 (s, 3H), 0.96-0.89 (m, 4H) |

TABLE C-continued

The following examples were prepared using a similar procedure to that described for Example 1

| Ex. No. | Structure | Compound Name | LCMS [M + H]+ | NMR |
|---|---|---|---|---|
| 355 | 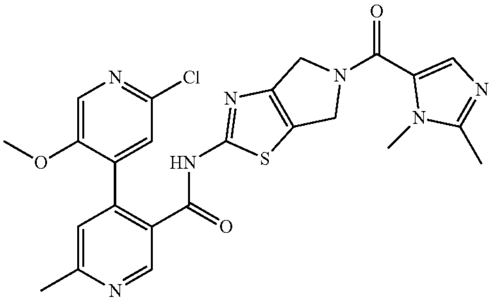 | 2'-Chloro-N-(5-(1,2-dimethyl-1H-imidazole-5-carbonyl)-5,6-dihydro-4H-pyrrolo[3,4-d]thiazol-2-yl)-5'-methoxy-6-methyl-[4,4'-bipyridine]-3-carboxamide | 524 | $^1$H NMR (400 MHz, DMSO-$d_6$) δ 12.8 (s, 1H), 8.79 (s, 1H), 8.17 (s, 1H), 7.58-7.49 (m, 2H), 7.44 (s, 1H), 4.99 (s, 1H), 4.86 (s, 1H), 4.78 (s, 1H), 4.65 (s, 1H), 3.68 (s, 3H), 3.60 (s, 3H), 2.59 (s, 3H), 2.37 (s, 3H) |
| 356 | 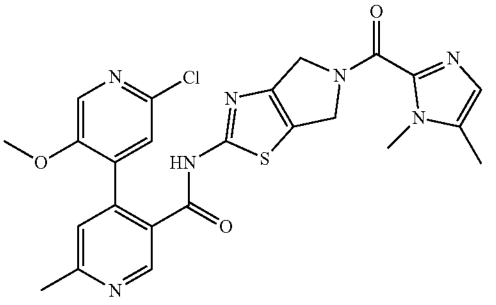 | 2'-Chloro-N-(5-(1,5-dimethyl-1H-imidazole-2-carbonyl)-5,6-dihydro-4H-pyrrolo[3,4-d]thiazol-2-yl)-5'-methoxy-6-methyl-[4,4'-bipyridine]-3-carboxamide | 524 | $^1$H NMR (400 MHz, DMSO-$d_6$) δ 8.79 (s, 1H), 8.17 (s, 1H), 7.54 (s, 1H), 7.44 (s, 1H), 6.93 (d, J = 11.4 Hz, 1H), 5.17 (s, 1H), 5.04 (s, 1H), 4.81 (s, 1H), 4.67 (s, 1H), 3.78 (s, 3H), 3.61 (s, 3H), 2.59 (s, 3H), 2.23 (s, 3H) |
| 357 | 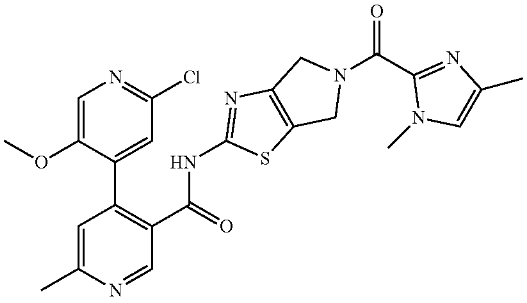 | 2'-Chloro-N-(5-(1,4-dimethyl-1H-imidazole-2-carbonyl)-5,6-dihydro-4H-pyrrolo[3,4-d]thiazol-2-yl)-5'-methoxy-6-methyl-[4,4'-bipyridine]-3-carboxamide | 524 | $^1$H NMR (400 MHz, DMSO-$d_6$) δ 12.8-12.7 (m, 1H), 8.79 (d, J = 3.4 Hz, 1H), 8.17 (d, J = 2.0 Hz, 1H), 7.54 (s, 1H), 7.43 (s, 1H), 7.07 (s, 1H), 5.21 (s, 1H), 5.08 (s, 1H), 4.79 (s, 1H), 4.65 (s, 1H), 3.83 (s, 3H), 3.61 (d, J = 2.2 Hz, 3H), 2.59 (s, 3H), 2.15 (d, J = 6.4 Hz, 3H) |
| 358 | 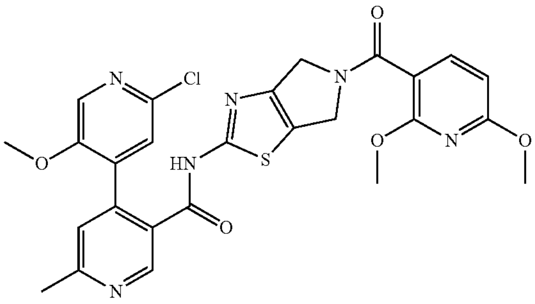 | 2'-Chloro-N-(5-(2,6-dimethoxynicotinoyl)-5,6-dihydro-4H-pyrrolo[3,4-d]thiazol-2-yl)-5'-methoxy-6-methyl-[4,4'-bipyridine]-3-carboxamide | 567 | $^1$H NMR (400 MHz, DMSO-$d_6$) δ 12.8 (s, 1H), 8.78 (d, J = 3.8 Hz, 1H), 8.16 (d, J = 2.6 Hz, 1H), 7.70 (dd, J = 8.2, 2.0 Hz, 1H), 7.54 (s, 1H), 7.43 (s, 1H), 6.47 (d, J = 8.2 Hz, 1H), 4.75 (s, 1H), 4.61 (s, 1H), 4.53 (s, 1H), 4.42 (s, 1H), 3.94 (d, J = 1.8 Hz, 3H), 3.91 (d, J = 3.0 Hz, 3H), 3.60 (s, 3H), 2.59 (d, J = 2.2 Hz, 3H) |

TABLE C-continued

The following examples were prepared using a similar procedure to that described for Example 1

| Ex. No. | Structure | Compound Name | LCMS [M + H]+ | NMR |
|---|---|---|---|---|
| 359 | 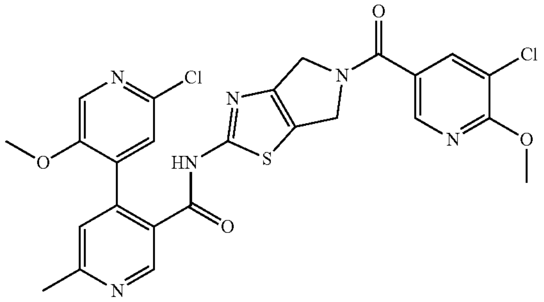 [SMILES: COc1cnc(Cl)cc1-c1cc(C)ncc1C(=O)Nc1nc2c(s1)CN(C(=O)c1cnc(OC)c(Cl)c1)C2] | 2'-Chloro-N-(5-(5-chloro-6-methoxy-nicotinoyl)-5,6-dihydro-4H-pyrrolo[3,4-d]thiazol-2-yl)-5'-methoxy-6-methyl-[4,4'-bipyridine]-3-carboxamide | 571 | $^1$H NMR (400 MHz, DMSO-$d_6$) δ 12.8 (d, J = 6.0 Hz, 1H), 8.78 (d, J = 1.8 Hz, 1H), 8.46 (dd, J = 9.6, 2.0 Hz, 1H), 8.18-8.14 (m, 2H), 7.54 (s, 1H), 7.43 (d, J = 1.8 Hz, 1H), 4.82 (s, 2H), 4.73 (s, 1H), 4.67 (s, 1H), 4.01 (d, J = 2.8 Hz, 3H), 3.59 (s, 3H), 2.59 (d, J = 1.6 Hz, 3H) |
| 360 | 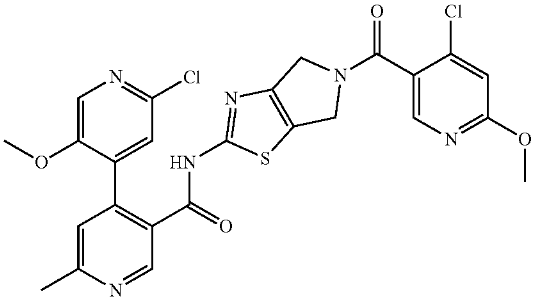 | 2'-Chloro-N-(5-(4-chloro-6-methoxy-nicotinoyl)-5,6-dihydro-4H-pyrrolo[3,4-d]thiazol-2-yl)-5'-methoxy-6-methyl-[4,4'-bipyridine]-3-carboxamide | 571 | $^1$H NMR (400 MHz, DMSO-$d_6$) δ 12.8 (d, J = 8.8 Hz, 1H), 8.78 (d, J = 3.6 Hz, 1H), 8.36 (d, J = 1.4 Hz, 1H), 8.16 (d, J = 1.6 Hz, 1H), 7.54 (s, 1H), 7.43 (d, J = 2.6 Hz, 1H), 7.16 (d, J = 4.8 Hz, 1H), 4.81 (s, 1H), 4.67 (s, 1H), 4.53 (s, 1H), 4.43 (s, 1H), 3.92 (d, J = 2.6 Hz, 3H), 3.59 (s, 3H), 2.59 (d, J = 2.6 Hz, 3H) |
| 361 | 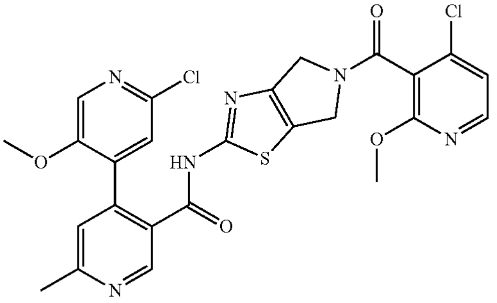 [SMILES: COc1cnc(Cl)cc1-c1cc(C)ncc1C(=O)Nc1nc2c(s1)CN(C(=O)c1c(Cl)ccnc1OC)C2] | 2'-Chloro-N-(5-(4-chloro-2-methoxy-nicotinoyl)-5,6-dihydro-4H-pyrrolo[3,4-d]thiazol-2-yl)-5'-methoxy-6-methyl-[4,4'-bipyridine]-3-carboxamide | 571 | $^1$H NMR (400 MHz, DMSO-$d_6$) δ 8.78 (d, J = 4.8 Hz, 1H), 8.26 (d, J = 5.6 Hz, 1H), 8.16 (d, J = 3.8 Hz, 1H), 7.53 (s, 1H), 7.45-7.41 (m, 1H), 7.33-7.25 (m, 1H), 4.80 (s, 1H), 4.66 (s, 1H), 4.51-4.39 (m, 1H), 4.39-4.26 (m, 1H), 3.93 (s, 3H), 3.60 (s, 3H), 2.58 (d, J = 2.6 Hz, 3H) |
| 362 | 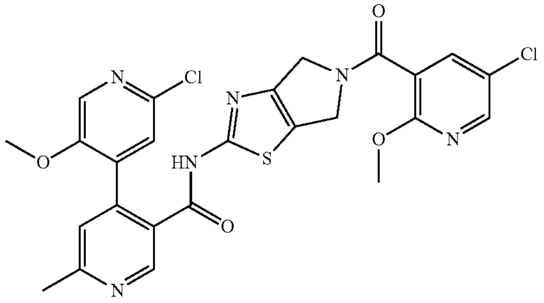 [SMILES: COc1cnc(Cl)cc1-c1cc(C)ncc1C(=O)Nc1nc2c(s1)CN(C(=O)c1cc(Cl)cnc1OC)C2] | 2'-Chloro-N-(5-(5-chloro-2-methoxy-nicotinoyl)-5,6-dihydro-4H-pyrrolo[3,4-d]thiazol-2-yl)-5'-methoxy-6-methyl-[4,4'-bipyridine]-3-carboxamide | 571 | $^1$H NMR (400 MHz, DMSO-$d_6$) δ 12.8 (s, 1H), 8.77 (d, J = 3.8 Hz, 1H), 8.34 (d, J = 2.6 Hz, 1H), 8.16 (d, J = 1.6 Hz, 1H), 7.96 (dd, J = 6.6, 2.6 Hz, 1H), 7.54 (s, 1H), 7.43 (d, J = 2.4 Hz, 1H), 4.77 (t, J = 2.6 Hz, 1H), 4.63 (t, J = 2.6 Hz, 1H), 4.53 (t, J = 2.8 Hz, 1H), 4.41 (t, J = 2.8 Hz, 1H), 3.92 (d, J = 1.8 Hz, 3H), 3.59 (s, 3H), 2.58 (d, J = 2.4 Hz, 3H) |

TABLE C-continued

The following examples were prepared using a similar procedure to that described for Example 1

| Ex. No. | Structure | Compound Name | LCMS [M + H]+ | NMR |
|---|---|---|---|---|
| 363 | 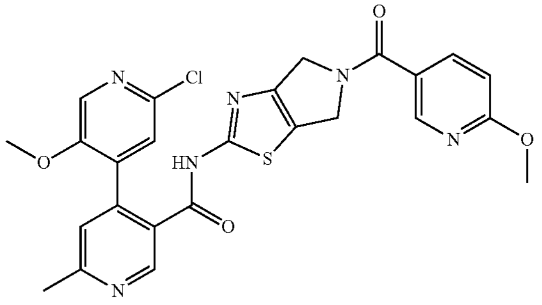 | 2'-chloro-5'-methoxy-N-(5-(6-methoxy-nicotinoyl)-5,6-dihydro-4H-pyrrolo[3,4-d]thiazol-2-yl)-6-methyl-[4,4'-bipyridine]-3-carboxamide | 537 | $^1$H NMR (400 MHz, DMSO-$d_6$) δ 12.8 (s, 1H), 8.78 (d, J = 2.4 Hz, 1H), 8.50 (dd, J = 8.8, 2.4 Hz, 1H), 8.16 (s, 1H), 8.01-7.95 (m, 1H), 7.54 (s, 1H), 7.43 (s, 1H), 6.90 (d, J = 8.6 Hz, 1H), 4.84-4.78 (m, 2H), 4.73-4.66 (m, 2H), 3.91 (d, J = 2.6 Hz, 3H), 3.59 (s, 3H), 2.59 (s, 3H) |
| 364 | 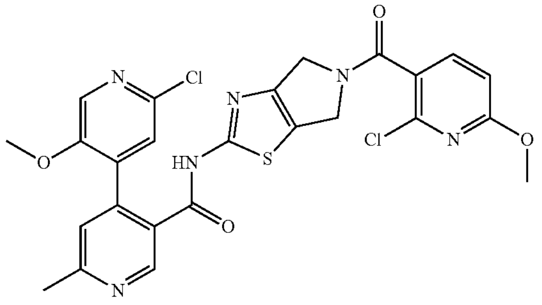 | 2'-Chloro-N-(5-(2-chloro-6-methoxy-nicotinoyl)-5,6-dihydro-4H-pyrrolo[3,4-d]thiazol-2-yl)-5'-methoxy-6-methyl-[4,4'-bipyridine]-3-carboxamide | 571 | $^1$H NMR (400 MHz, DMSO-$d_6$) δ 12.8 (d, J = 9.6 Hz, 1H), 8.78 (d, J = 3.6 Hz, 1H), 8.16 (d, J = 1.8 Hz, 1H), 7.96-7.89 (m, 1H), 7.54 (s, 1H), 7.43 (d, J = 2.8 Hz, 1H), 7.01-6.92 (m, 1H), 4.82-4.76 (m, 1H), 4.69-4.62 (m, 1H), 4.54-4.48 (m, 1H), 4.44-4.37 (m, 1H), 3.90 (d, J = 2.4 Hz, 3H), 3.59 (s, 3H), 2.59 (d, J = 2.4 Hz, 3H) |
| 365 | 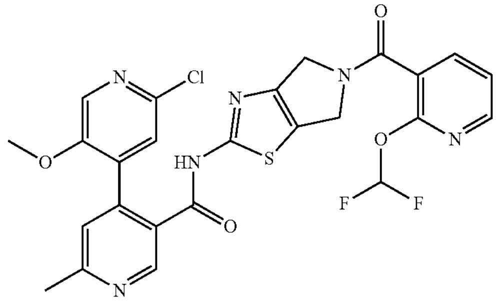 [SMILES: COc1cnc(Cl)cc1-c1cc(C)ncc1C(=O)Nc1nc2c(s1)CN(C(=O)c1cccnc1OC(F)F)C2] | 2'-Chloro-N-(5-(2-(difluoro-methoxy) nicotinoyl)-5,6-dihydro-4H-pyrrolo[3,4-d]thiazol-2-yl)-5'-methoxy-6-methyl-[4,4'-bipyridine]-3-carboxamide | 573 | $^1$H NMR (400 MHz, DMSO-$d_6$) δ 12.8 (s, 1H), 8.81-8.76 (m, 1H), 8.16 (s, 1H), 8.07-7.73 (m, 3H), 7.54 (s, 1H), 7.43 (s, 1H), 6.60-6.50 (m, 1H), 4.74 (s, 1H), 4.64 (s, 1H), 4.61 (s, 1H), 4.53 (s, 1H), 3.59- (s, 3H), 2.59 (s, 3H) |
| 366 | 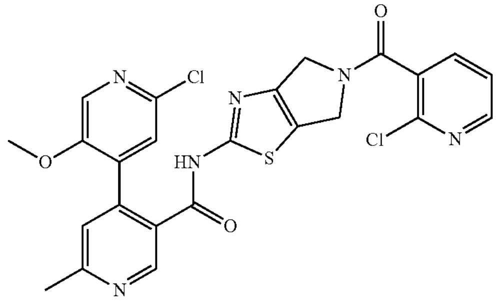 [SMILES: COc1cnc(Cl)cc1-c1cc(C)ncc1C(=O)Nc1nc2c(s1)CN(C(=O)c1cccnc1Cl)C2] | 2'-Chloro-N-(5-(2-chloro-nicotinoyl)-5,6-dihydro-4H-pyrrolo[3,4-d]thiazol-2-yl)-5'-methoxy-6-methyl-[4,4'-bipyridine]-3-carboxamide | 541 | $^1$H NMR (400 MHz, DMSO-$d_6$) δ 12.8 (s, 1H), 8.78 (s, 1H), 8.54 (s, 1H), 8.16 (s, 1H), 8.05 (d, J = 7.6 Hz, 1H), 7.62-7.51 (m, 2H), 7.43 (s, 1H), 4.82 (s, 1H), 4.68 (s, 1H), 4.49 (s, 1H), 4.39 (s, 1H), 3.60 (s, 3H), 2.58 (s, 3H) |

TABLE C-continued

The following examples were prepared using a similar procedure to that described for Example 1

| Ex. No. | Structure | Compound Name | LCMS [M + H]+ | NMR |
|---|---|---|---|---|
| 367 | 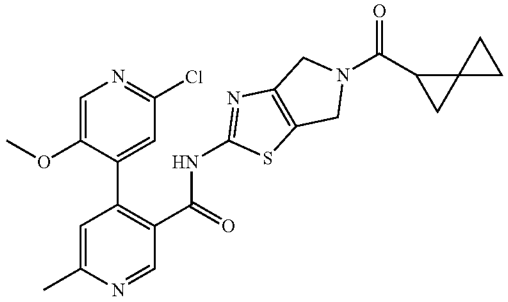 [SMILES: COc1cnc(Cl)cc1-c1cc(C)ncc1C(=O)Nc1nc2c(s1)CN(C(=O)C1CC13CC3)C2] | (Racemic)-2'-Chloro-5'-methoxy-6-methyl-N-(5-(spiro[2.2]pentane-1-carbonyl)-5,6-dihydro-4H-pyrrolo[3,4-d]thiazol-2-yl)-[4,4'-bipyridine]-3-carboxamide | 496 | $^1$H NMR (400 MHz, DMSO-$d_6$) δ 12.8 (d, J = 10.0 Hz, 1H), 8.78 (s, 1H), 8.17 (d, J = 1.8 Hz, 1H), 7.54 (s, 1H), 7.44 (s, 1H), 4.99-4.43 (m, 4H), 3.60 (s, 3H), 2.59 (s, 3H), 2.27-2.18 (m, 1H), 1.45-1.40 (m, 1H), 1.32-1.21 (m, 1H), 1.00-0.92 (m, 1H), 0.89-0.77 (m, 2H), 0.76-0.69 (m, 1H) |
| 368 | 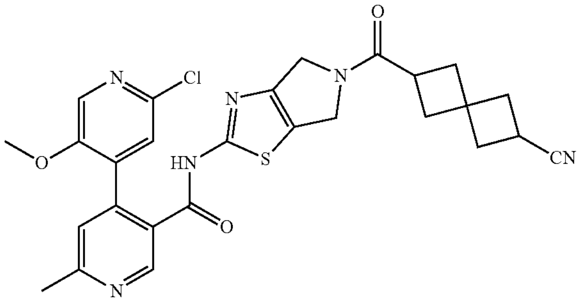 [SMILES: COc1cnc(Cl)cc1-c1cc(C)ncc1C(=O)Nc1nc2c(s1)CN(C(=O)C1CC3(CC(C#N)C3)C1)C2] | 2'-Chloro-N-(5-(6-cyanospiro[3.3]heptane-2-carbonyl)-5,6-dihydro-4H-pyrrolo[3,4-d]thiazol-2-yl)-5'-methoxy-6-methyl-[4,4'-bipyridine]-3-carboxamide | 549 | $^1$H NMR (400 MHz, DMSO-$d_6$) δ 12.8 (s, 1H), 8.78 (s, 1H), 8.16 (d, J = 2.2 Hz, 1H), 7.54 (s, 1H), 7.43 (s, 1H), 4.68 (s, 1H), 4.55 (s, 2H), 4.42 (s, 1H), 3.59 (d, J = 1.4 Hz, 3H), 3.26-3.15 (m, 2H), 2.58 (s, 3H), 2.40-2.15 (m, 8H) |
| 369 | 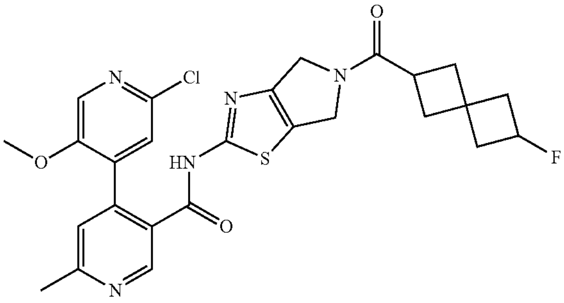 [SMILES: COc1cnc(Cl)cc1-c1cc(C)ncc1C(=O)Nc1nc2c(s1)CN(C(=O)C1CC3(CC(F)C3)C1)C2] | 2'-Chloro-N-(5-(6-fluorospiro[3.3]heptane-2-carbonyl)-5,6-dihydro-4H-pyrrolo[3,4-d]thiazol-2-yl)-5'-methoxy-6-methyl-[4,4'-bipyridine]-3-carboxamide | 542 | $^1$H NMR (400 MHz, DMSO-$d_6$) δ 12.8 (s, 1H), 8.78 (s, 1H), 8.17 (d, J = 2.4 Hz, 1H), 7.55 (s, 1H), 7.44 (s, 1H), 5.05-4.84 (m, 1H), 4.72-4.66 (m, 1H), 4.56 (s, 2H), 4.46-4.39 (m, 1H), 3.60 (d, J = 1.4 Hz, 3H), 3.27-3.23 (m, 1H), 2.59 (s, 3H), 2.38-2.00 (m, 8H) |
| 370 | 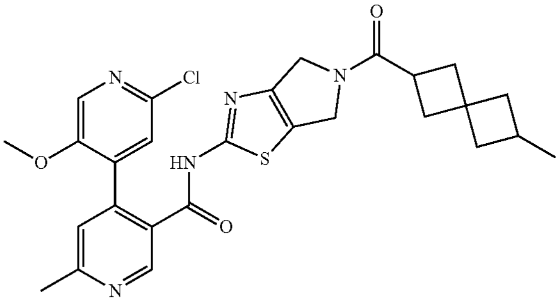 | 2'-Chloro-5'-methoxy-6-methyl-N-(5-(6-methylspiro[3.3]heptane-2-carbonyl)-5,6-dihydro-4H-pyrrolo[3,4-d]thiazol-2-yl)-[4,4'-bipyridine]-3-carboxamide | 538.25 | $^1$H NMR (400 MHz, DMSO-$d_6$) δ 12.8 (s, 1H), 8.78 (s, 1H), 8.16 (d, J = 2.6 Hz, 1H), 7.54 (s, 1H), 7.43 (s, 1H), 4.68 (s, 1H), 4.55 (s, 2H), 4.42 (s, 1H), 3.59 (s, 3H), 3.22-3.15 (m, 1H), 2.59 (s, 3H), 2.27-1.96 (m, 7H), 1.67-1.59 (m, 1H), 1.53-1.44 (m, 1H), 1.01 (d, J = 6.4 Hz, 3H) |
| 371 | 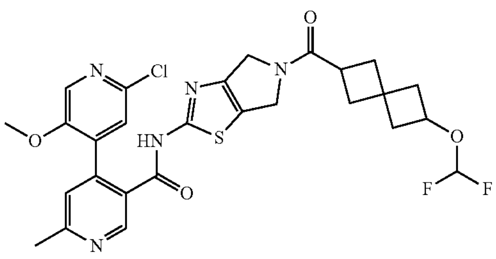 [SMILES: COc1cnc(Cl)cc1-c1cc(C)ncc1C(=O)Nc1nc2c(s1)CN(C(=O)C1CC3(CC(OC(F)F)C3)C1)C2] | 2'-Chloro-N-(5-(6-(difluoromethoxy)spiro[3.3]heptane-2-carbonyl)-5,6-dihydro-4H-pyrrolo[3,4-d]thiazol-2-yl)-5'-methoxy-6-methyl-[4,4'-bipyridine]-3-carboxamide | 590 | $^1$H NMR (400 MHz, DMSO-$d_6$) δ 12.8 (s, 1H), 8.78 (s, 1H), 8.16 (d, J = 2.4 Hz, 1H), 7.54 (s, 1H), 7.43 (s, 1H), 6.58 (t, J = 76.2 Hz, 1H), 4.68 (s, 1H), 4.55 (s, 2H), 4.49-4.44 (m, 1H), 4.42 (s, 1H), 3.59 (d, J = 1.4 Hz, 3H), 3.25-3.22 (m, 1H), 2.59 (s, 3H), 2.25-2.22 (m, 4H), 2.16-2.07 (m, 2H), 2.03-1.96 (m, 2H) |

TABLE C-continued

The following examples were prepared using a similar procedure to that described for Example 1

| Ex. No. | Structure | Compound Name | LCMS [M + H]+ | NMR |
|---|---|---|---|---|
| 372 | 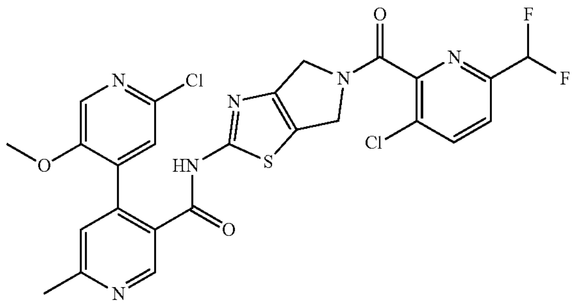 [SMILES: COc1cnc(Cl)cc1-c1cc(C)ncc1C(=O)Nc1nc2c(s1)CN(C(=O)c1nc(C(F)F)ccc1Cl)C2] | 2'-Chloro-N-(5-(3-chloro-6-(difluoromethyl)picolinoyl)-5,6-dihydro-4H-pyrrolo[3,4-d]thiazol-2-yl)-5'-methoxy-6-methyl-[4,4'-bipyridine]-3-carboxamide | 591 | $^1$H NMR (400 MHz, DMSO-$d_6$) δ 12.8 (d, J = 8.2 Hz 1H), 8.78 (d, J = 5.8 Hz, 1H), 8.38-8.32 (m, 1H), 8.16 (d, J = 4.2 Hz, 1H), 7.88 (d, J = 8.4 Hz, 1H), 7.54 (s, 1H), 7.43 (s, 1H), 7.06 (t, J = 54.6 Hz, 1H), 4.86 (s, 1H), 4.73 (s, 1H), 4.52 (s, 1H), 4.42 (s, 1H), 3.60 (s, 3H), 2.59 (d, J = 2.6 Hz, 3H) |
| 373 | 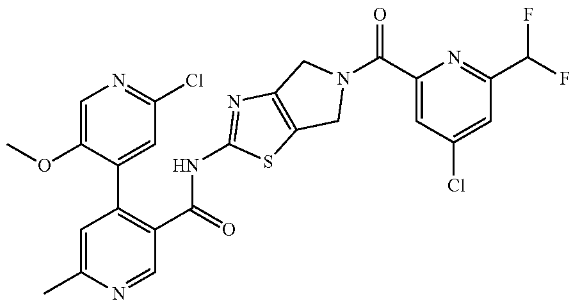 [SMILES: COc1cnc(Cl)cc1-c1cc(C)ncc1C(=O)Nc1nc2c(s1)CN(C(=O)c1cc(Cl)cc(C(F)F)n1)C2] | 2'-Chloro-N-(5-(4-chloro-6-(difluoromethyl)picolinoyl)-5,6-dihydro-4H-pyrrolo[3,4-d]thiazol-2-yl)-5'-methoxy-6-methyl-[4,4'-bipyridine]-3-carboxamide | 591 | $^1$H NMR (400 MHz, DMSO-$d_6$) δ 12.8 (d, J = 20.8 Hz, 1H), 8.82-8.76 (m, 1H), 8.19-8.15 (m, 1H), 8.12-8.07 (m, 1H), 8.07-8.03 (m, 1H), 7.55 (s, 1H), 7.44 (s, 1H), 7.26-6.91 (m, 1H), 5.01 (s, 1H), 4.94-4.90 (m, 1H), 4.88-4.85 (m, 1H), 4.73 (s, 1H), 3.60 (s, 3H), 2.59 (s, 3H) |
| 374 | 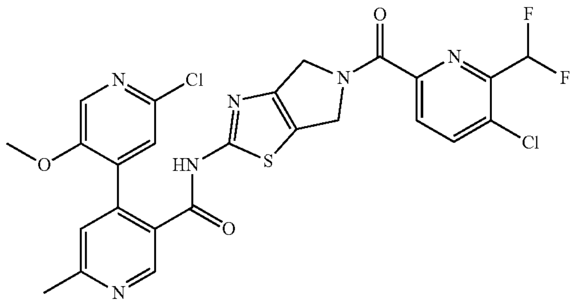 [SMILES: COc1cnc(Cl)cc1-c1cc(C)ncc1C(=O)Nc1nc2c(s1)CN(C(=O)c1ccc(Cl)c(C(F)F)n1)C2] | 2'-Chloro-N-(5-(5-chloro-6-(difluoromethyl)picolinoyl)-5,6-dihydro-4H-pyrrolo[3,4-d]thiazol-2-yl)-5'-methoxy-6-methyl-[4,4'-bipyridine]-3-carboxamide | 591 | $^1$H NMR (400 MHz, DMSO-$d_6$) δ 12.8 (d, J = 14.8 Hz, 1H), 8.79 (d, J = 2.8 Hz, 1H), 8.31 (d, J = 8.6 Hz, 1H), 8.17 (d, J = 2.2 Hz, 1H), 8.06 (dd, J = 11.0, 8.6 Hz, 1H), 7.55 (s, 1H), 7.44 (s, 1H), 7.43-7.12 (m, 1H), 5.07 (s, 1H), 4.99 (s, 1H), 4.87 (s, 1H), 4.73 (s, 1H), 3.60 (s, 3H), 2.59 (s, 3H) |
| 375 | 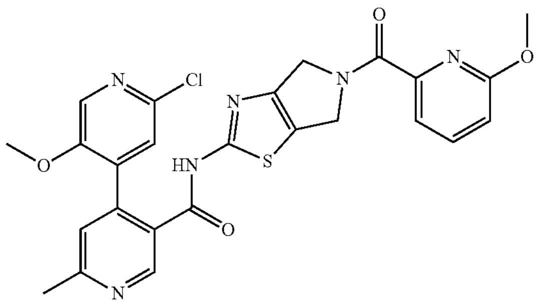 | 2'-Chloro-5'-methoxy-N-(5-(6-methoxy-picolinoyl)-5,6-dihydro-4H-pyrrolo[3,4-d]thiazol-2-yl)-6-methyl-[4,4'-bipyridine]-3-carboxamide | 537 | $^1$H NMR (400 MHz, DMSO-$d_6$) δ 12.8 (J = 13.2 Hz, 1H), 8.68 (d, J = 4.2 Hz, 1H), 8.07 (d, J = 3.6 Hz, 1H), 7.77 (dd, J = 7.8, 2.8 Hz, 1H), 7.45 (d, J = 1.4 Hz, 1H), 7.41 (dd, J = 12.6, 7.3 Hz, 1H), 7.34 (s, 1H), 6.90 (dd, J = 8.4, 5.2 Hz, 1H), 5.06 (s, 1H), 4.96 (s, 1H), 4.75 (s, 1H), 4.61 (s, 1H), 3.83 (d, J = 1.8 Hz, 3H), 3.50 (d, J = 1.2 Hz, 3H), 2.49 (s, 3H) |

TABLE C-continued

The following examples were prepared using a similar procedure to that described for Example 1

| Ex. No. | Structure | Compound Name | LCMS [M + H]+ | NMR |
|---|---|---|---|---|
| 376 | 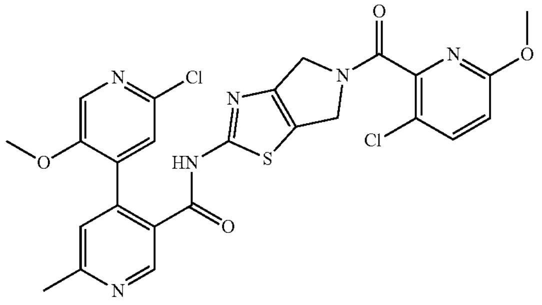 | 2'-Chloro-N-(5-(3-chloro-6-methoxy-picolinoyl)-5,6-dihydro-4H-pyrrolo[3,4-d]thiazol-2-yl)-5'-methoxy-6-methyl-[4,4'-bipyridine]-3-carboxamide | 571 | $^1$H NMR (400 MHz, DMSO-$d_6$) δ 12.8 (s, 1H), 8.78 (d, J = 4.6 Hz, 1H), 8.16 (d, J = 3.6 Hz, 1H), 8.00-7.91 (m, 1H), 7.54 (s, 1H), 7.43 (s, 1H), 7.00 (d, J = 8.8 Hz, 1H), 4.83 (s, 1H), 4.70 (s, 1H), 4.56 (s, 1H), 4.44 (s, 1H), 3.87 (s, 3H), 3.60 (s, 3H), 2.59 (s, 3H) |
| 377 | 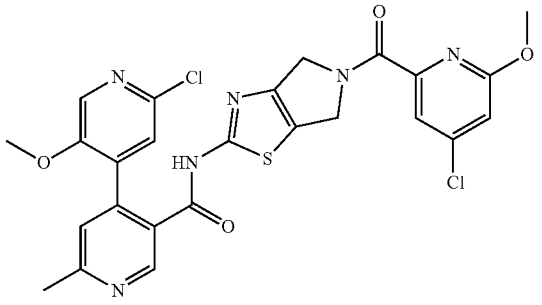 | 2'-Chloro-N-(5-(4-chloro-6-methoxy-picolinoyl)-5,6-dihydro-4H-pyrrolo[3,4-d]thiazol-2-yl)-5'-methoxy-6-methyl-[4,4'-bipyridine]-3-carboxamide | 571 | $^1$H NMR (400 MHz, DMSO-$d_6$) δ 12.8 (d, J = 14.0 Hz, 1H), 8.78 (d, J = 4.0 Hz, 1H), 8.16 (d, J = 2.8 Hz, 1H), 7.53 (d, J = 8.4 Hz, 2H), 7.44 (s, 1H), 7.20 (dd, J = 4.2, 1.6 Hz, 1H), 5.14 (s, 1H), 5.03 (s, 1H), 4.84 (s, 1H), 4.70 (s, 1H), 3.95 (s, 3H), 3.60 (s, 3H), 2.59 (s, 3H) |
| 378 | 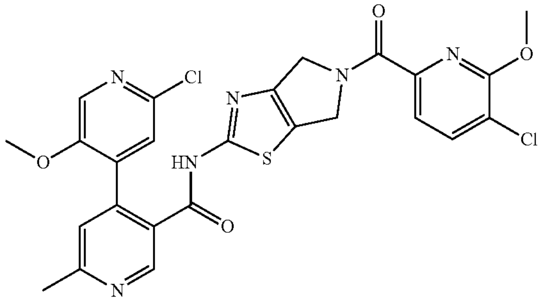 [SMILES: COc1cnc(Cl)cc1-c1cc(C)ncc1C(=O)Nc1nc2c(s1)CN(C(=O)c1ccc(Cl)c(OC)n1)C2] | 2'-chloro-N-(5-(5-chloro-6-methoxy-picolinoyl)-5,6-dihydro-4H-pyrrolo[3,4-d]thiazol-2-yl)-5'-methoxy-6-methyl-[4,4'-bipyridine]-3-carboxamide | 571 | $^1$H NMR (400 MHz, DMSO-$d_6$) δ 12.8-12.7 (m, 1H), 8.78 (d, J = 4.4 Hz, 1H), 8.17 (d, J = 3.0 Hz, 1H), 8.10-8.03 (m, 1H), 7.59-7.50 (m, 2H), 7.44 (s, 1H), 5.18 (s, 1H), 5.11-5.05 (m, 1H), 4.88-4.82 (m, 1H), 4.71 (s, 1H), 4.04 (s, 3H), 3.60 (s, 3H), 2.59 (s, 3H) |
| 379 | 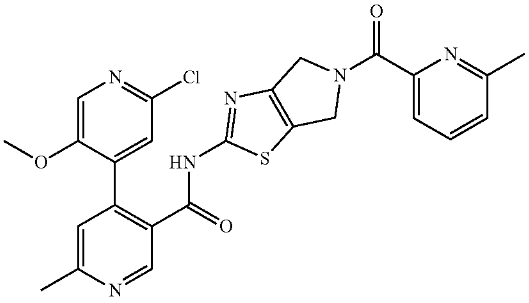 | 2'-Chloro-5'-methoxy-6-methyl-N-(5-(6-methyl-picolinoyl)-5,6-dihydro-4H-pyrrolo[3,4-d]thiazol-2-yl)-[4,4'-bipyridine]-3-carboxamide | 521 | $^1$H NMR (400 MHz, DMSO-$d_6$) δ 12.8 (d, J = 13.2 Hz, 1H), 8.98 (d, J = 2.6 Hz, 1H), 8.37 (d, J = 2.0 Hz, 1H), 8.05 (t, J = 7.8 Hz, 1H), 7.82 (dd, J = 11.4, 7.8 Hz, 1H), 7.74 (s, 1H), 7.64-7.59 (m, 1H), 5.22 (s, 1H), 5.12 (s, 1H), 5.04 (s, 1H), 4.90 (s, 1H), 3.80 (s, 3H), 2.79 (s, 3H), 2.75 (d, J = 4.8 Hz, 3H) |

TABLE C-continued

The following examples were prepared using a similar procedure to that described for Example 1

| Ex. No. | Structure | Compound Name | LCMS [M + H]$^+$ | NMR |
|---|---|---|---|---|
| 380 | 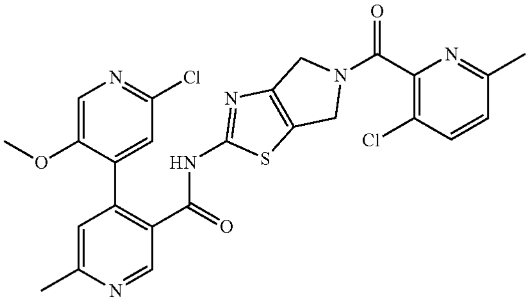 | 2'-Chloro-N-(5-(3-chloro-6-methyl-picolinoyl)-5,6-dihydro-4H-pyrrolo[3,4-d]thiazol-2-yl)-5'-methoxy-6-methyl-[4,4'-bipyridine]-3-carboxamide | 555 | $^1$H NMR (400 MHz, DMSO-$d_6$) δ 12.8 (s, 1H), 8.78 (d, J = 4.6 Hz, 1H), 8.16 (d, J = 3.2 Hz, 1H), 7.87 (d, J = 8.2 Hz, 1H), 7.58-7.52 (m, 2H), 7.44 (s, 1H), 4.83 (s 1H), 4.69 (s, 1H), 4.55 (s, 1H), 4.44 (s, 1H), 3.60 (s, 3H), 2.59 (d, J = 2.6 Hz, 3H), 2.31 (s, 3H) |
| 381 | 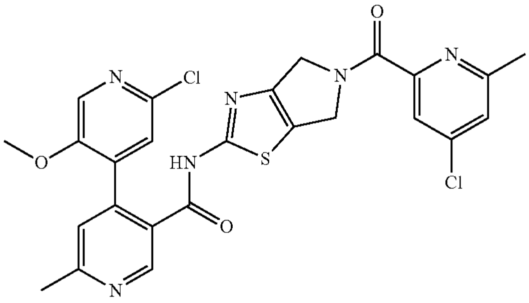 | 2'-Chloro-N-(5-(4-chloro-6-methyl-picolinoyl)-5,6-dihydro-4H-pyrrolo[3,4-d]thiazol-2-yl)-5'-methoxy-6-methyl-[4,4'-bipyridine]-3-carboxamide | 555 | $^1$H NMR (400 MHz, DMSO-$d_6$) δ 12.8 (d, J = 13.6 Hz, 1H), 8.78 (d, J = 2.4 Hz, 1H), 8.17 (s, 1H), 7.71-7.67 (m, 1H), 7.62-7.60 (m, 1H), 7.54 (s, 1H), 7.44 (s, 1H), 5.02-4.99 (m, 1H), 4.92-4.88 (m, 1H), 4.86-4.82 (m, 1H), 4.71-4.68 (m, 1H), 3.60 (s, 3H), 2.59 (s, 3H), 2.56 (d, J = 4.8 Hz, 3H) |
| 382 | 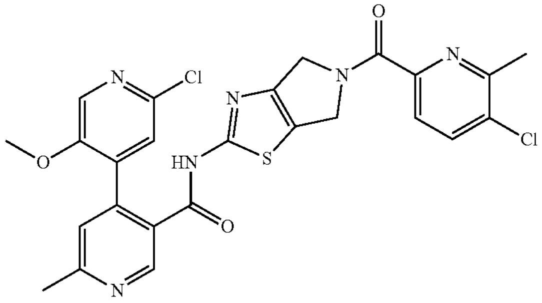 [SMILES: COc1cnc(Cl)cc1-c1cc(C)ncc1C(=O)Nc1nc2c(s1)CN(C(=O)c1ccc(Cl)c(C)n1)C2] | 2'-Chloro-N-(5-(5-chloro-6-methyl-picolinoyl)-5,6-dihydro-4H-pyrrolo[3,4-d]thiazol-2-yl)-5'-methoxy-6-methyl-[4,4'-bipyridine]-3-carboxamide | 555 | $^1$H NMR (400 MHz, DMSO-$d_6$) δ 12.8 (s, 1H), 8.79 (d, J = 4.0 Hz, 1H), 8.17 (d, J = 4.2 Hz, 1H), 8.07-8.02 (m, 1H), 7.75-7.67 (m, 1H), 7.54 (d, J = 4.2 Hz, 1H), 7.43 (s, 1H), 5.04 (s, 1H), 4.93 (s, 1H), 4.84 (s, 1H), 4.70 (s, 1H), 3.60 (d, J = 4.0 Hz, 3H), 2.63 (t, J = 4.4 Hz, 3H), 2.59 (d, J = 4.2 Hz, 3H) |
| 383 | 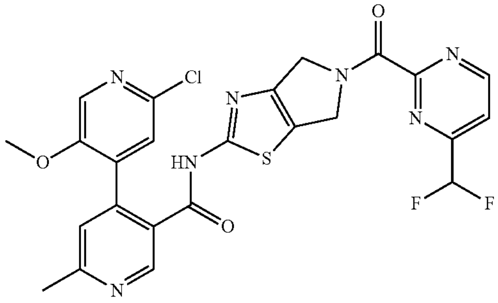 [SMILES: COc1cnc(Cl)cc1-c1cc(C)ncc1C(=O)Nc1nc2c(s1)CN(C(=O)c1nccc(C(F)F)n1)C2] | 2'-Chloro-N-(5-(4-(difluoromethyl) pyrimidine-2-carbonyl)-5,6-dihydro-4H-pyrrolo[3,4-d]thiazol-2-yl)-5'-methoxy-6-methyl-[4,4'-bipyridine]-3-carboxamide | 558 | $^1$H NMR (400 MHz, DMSO-$d_6$) δ 13.0-12.6 (m, 1H), 9.21 (d, J = 5.0 Hz, 1H), 8.78 (d, J = 4.6 Hz, 1H), 8.16 (d, J = 2.8 Hz, 1H), 7.95 (d, J = 5.0 Hz, 1H), 7.54 (s, 1H), 7.43 (s, 1H), 7.26-6.93 (m, 1H), 4.90-4.84 (m, 1H), 4.78-4.71 (m, 2H), 4.70-4.63 (m, 1H), 3.60 (s, 3H), 2.61-2.56 (m, 3H) |

TABLE C-continued

The following examples were prepared using a similar procedure to that described for Example 1

| Ex. No. | Structure | Compound Name | LCMS [M + H]+ | NMR |
|---|---|---|---|---|
| 384 | 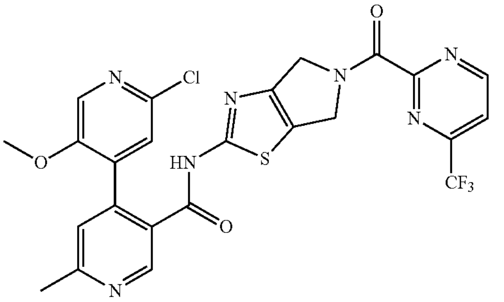 [SMILES: COc1cnc(Cl)cc1-c1cc(C)ncc1C(=O)Nc1nc2c(s1)CN(C(=O)c1nccc(C(F)(F)F)n1)C2] | 2'-Chloro-5'-methoxy-6-methyl-N-(5-(4-(trifluoromethyl) pyrimidine-2-carbonyl)-5,6-dihydro-4H-pyrrolo[3,4-d]thiazol-2-yl)-[4,4'-bipyridine]-3-carboxamide | 576 | $^1$H NMR (400 MHz, DMSO-$d_6$) δ 9.36 (d, J = 5.2 Hz, 1H), 8.79 (d, J = 4.6 Hz, 1H), 8.21 (dd, J = 5.0, 1.6 Hz, 1H), 8.17 (d, J = 3.2 Hz, 1H), 7.54 (s, 1H), 7.44 (s, 1H), 4.88 (s, 1H), 4.79 (s, 1H), 4.75 (s, 1H), 4.70 (s, 1H), 3.60 (s, 3H), 2.59 (d, J = 2.0 Hz, 3H) |
| 385 | 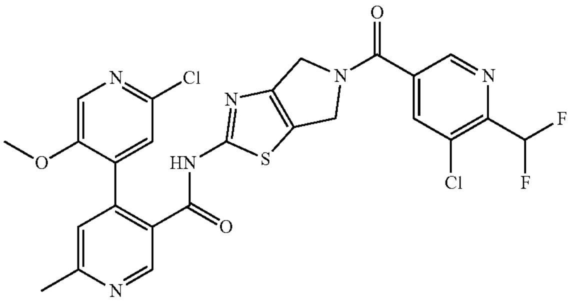 [SMILES: COc1cnc(Cl)cc1-c1cc(C)ncc1C(=O)Nc1nc2c(s1)CN(C(=O)c1cnc(C(F)F)c(Cl)c1)C2] | 2'-chloro-N-(5-(5-chloro-6-(difluoromethyl) nicotinoyl)-5,6-dihydro-4H-pyrrolo[3,4-d]thiazol-2-yl)-5'-methoxy-6-methyl-[4,4'-bipyridine]-3-carboxamide | 591 | $^1$H NMR (400 MHz, DMSO-$d_6$) δ 12.8 (d, J = 6.4 Hz, 1H), 8.87 (dd, J = 5.4, 1.6 Hz, 1H), 8.78 (d, J = 2.8 Hz, 1H), 8.40 (d, J = 7.8 Hz, 1H), 8.17 (s, 1H), 7.55 (s, 1H), 7.44 (d, J = 2.6 Hz, 1H), 7.25 (t, J = 53.2 Hz, 1H), 4.84 (s, 1H), 4.76 (s, 1H), 4.70 (s, 1H), 4.68 (s, 1H), 3.59 (s, 3H), 2.59 (d, J = 2.4 Hz, 3H) |
| 386 | 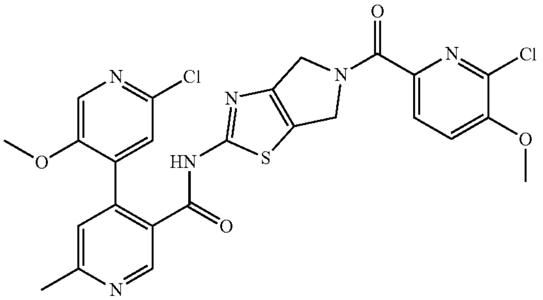 [SMILES: COc1cnc(Cl)cc1-c1cc(C)ncc1C(=O)Nc1nc2c(s1)CN(C(=O)c1ccc(OC)c(Cl)n1)C2] | 2'-Chloro-N-(5-(6-chloro-5-methoxy-picolinoyl)-5,6-dihydro-4H-pyrrolo[3,4-d]thiazol-2-yl)-5'-methoxy-6-methyl-[4,4'-bipyridine]-3-carboxamide | 571.15 | $^1$H NMR (400 MHz, DMSO-$d_6$) δ 12.8 (s, 1H), 8.79 (s, 1H), 8.17 (s, 1H), 7.99-7.91 (m, 1H), 7.77-7.72 (m, 1H), 7.54 (s, 1H), 7.44 (s, 1H), 5.11-5.07 (m, 1H), 5.01-4.97 (m, 1H), 4.86-4.82 (m, 1H), 4.72-4.66 (m, 1H), 3.98 (d, J = 1.8 Hz, 3H), 3.60 (s, 3H), 2.59 (s, 3H) |
| 387 | 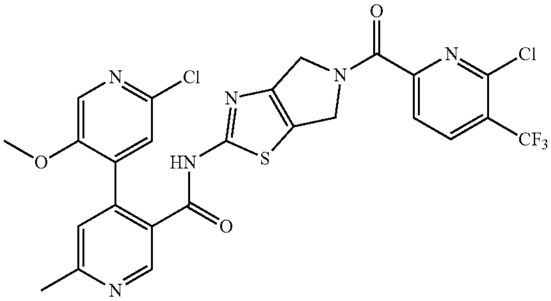 [SMILES: COc1cnc(Cl)cc1-c1cc(C)ncc1C(=O)Nc1nc2c(s1)CN(C(=O)c1ccc(C(F)(F)F)c(Cl)n1)C2] | 2'-Chloro-N-(5-(6-chloro-5-(trifluoromethyl) picolinoyl)-5,6-dihydro-4H-pyrrolo[3,4-d]thiazol-2-yl)-5'-methoxy-6-methyl-[4,4'-bipyridine]-3-carboxamide | 609 | $^1$H NMR (400 MHz, DMSO-$d_6$) δ 12.8 (s, 1H), 8.78 (s, 1H), 8.55-8.51 (m, 1H), 8.16 (s, 1H), 8.04 (t, J = 8.4 Hz, 1H), 7.54 (s, 1H), 7.43 (s, 1H), 4.99 (s, 1H), 4.90 (s, 1H), 4.87 (s, 1H), 4.73 (s, 1H), 3.60 (s, 3H), 2.59 (s, 3H) |

TABLE C-continued

| The following examples were prepared using a similar procedure to that described for Example 1 | | | | |
|---|---|---|---|---|
| Ex. No. | Structure | Compound Name | LCMS [M + H]+ | NMR |
| 388 | 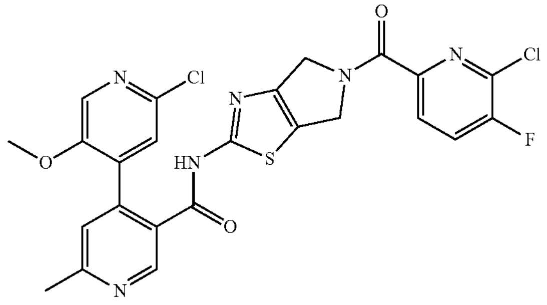 [SMILES: COc1cnc(Cl)cc1-c1cc(C)ncc1C(=O)Nc1nc2c(s1)CN(C(=O)c1ccc(F)c(Cl)n1)C2] | 2'-chloro-N-(5-(6-chloro-5-fluoropicolinoyl)-5,6-dihydro-4H-pyrrolo[3,4-d]thiazol-2-yl)-5'-methoxy-6-methyl-[4,4'-bipyridine]-3-carboxamide | 559 | $^1$H NMR (400 MHz, DMSO-$d_6$) δ 8.78 (s, 1H), 8.16 (s, 1H), 8.12 (t, J = 8.4 Hz, 1H), 7.99 (dt, J = 8.6, 4.2 Hz, 1H), 7.54 (s, 1H), 7.43 (s, 1H), 5.03 (d, 1H), 4.92 (s, 1H), 4.84 (s, 1H), 4.71 (s, 1H), 3.60 (s, 3H), 2.59 (s, 3H) |
| 389 | 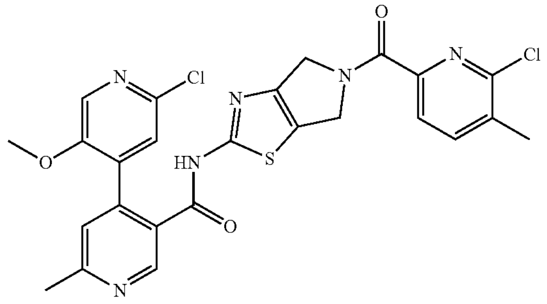 [SMILES: COc1cnc(Cl)cc1-c1cc(C)ncc1C(=O)Nc1nc2c(s1)CN(C(=O)c1ccc(C)c(Cl)n1)C2] | 2'-Chloro-N-(5-(6-chloro-5-methyl-picolinoyl)-5,6-dihydro-4H-pyrrolo[3,4-d]thiazol-2-yl)-5'-methoxy-6-methyl-[4,4'-bipyridine]-3-carboxamide | 555 | $^1$H NMR (400 MHz, DMSO-$d_6$) δ 12.8 (s, 1H), 8.79 (s, 1H), 8.17 (s, 1H), 7.99 (d, J = 7.6 Hz, 1H), 7.81 (dd, J = 12.8, 7.6 Hz, 1H), 7.54 (s, 1H), 7.44 (s, 1H), 5.03 (s, 1H), 4.94 (s, 1H), 4.84 (s, 1H), 4.70 (s, 1H), 3.60 (s, 3H), 2.59 (s, 3H), 2.42 (d, J = 2.6 Hz, 3H) |
| 390 | 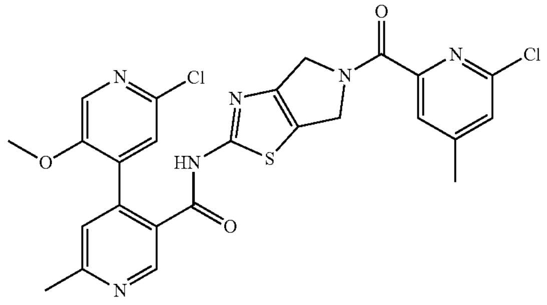 [SMILES: COc1cnc(Cl)cc1-c1cc(C)ncc1C(=O)Nc1nc2c(s1)CN(C(=O)c1cc(C)cc(Cl)n1)C2] | 2'-Chloro-N-(5-(6-chloro-4-methyl-picolinoyl)-5,6-dihydro-4H-pyrrolo[3,4-d]thiazol-2-yl)-5'-methoxy-6-methyl-[4,4'-bipyridine]-3-carboxamide | 555 | $^1$H NMR (400 MHz, DMSO-$d_6$) δ 12.8 (s, 1H), 8.81 (s, 1H), 8.19 (s, 1H), 7.72 (d, J = 11.2 Hz, 1H), 7.59 (s, 1H), 7.56 (s, 1H), 7.46 (s, 1H), 5.00 (s, 1H), 4.91 (s, 1H), 4.86 (s, 1H), 4.72 (s, 1H), 3.62 (s, 3H), 2.61 (s, 3H), 2.44 (s, 3H) |
| 391 | 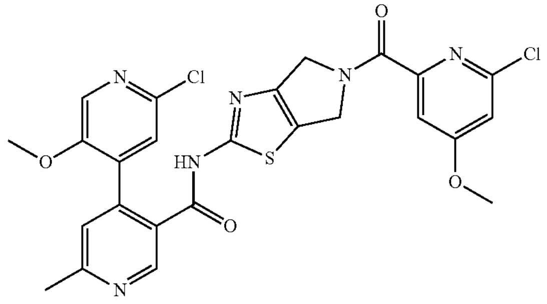 [SMILES: COc1cc(Cl)nc(C(=O)N2Cc3nc(NC(=O)c4cnc(C)cc4-c4cc(Cl)ncc4OC)sc3C2)c1] | 2'-Chloro-N-(5-(6-chloro-4-methoxy-picolinoyl)-5,6-dihydro-4H-pyrrolo[3,4-d]thiazol-2-yl)-5'-methoxy-6-methyl-[4,4'-bipyridine]-3-carboxamide | 571 | $^1$H NMR (400 MHz, DMSO-$d_6$) δ 12.8 (s, 1H), 8.79 (s, 1H), 8.17 (s, 1H), 7.54 (s, 1H), 7.44 (s, 1H), 7.39-7.35 (m, 1H), 7.31-7.28 (m, 1H), 4.95 (s, 1H), 4.86 (s, 1H), 4.83 (s, 1H), 4.69 (s, 1H), 3.93 (s, 3H), 3.60 (s, 3H), 2.59 (s, 3H) |

TABLE C-continued

The following examples were prepared using a similar procedure to that described for Example 1

| Ex. No. | Structure | Compound Name | LCMS [M + H]+ | NMR |
|---|---|---|---|---|
| 400 | 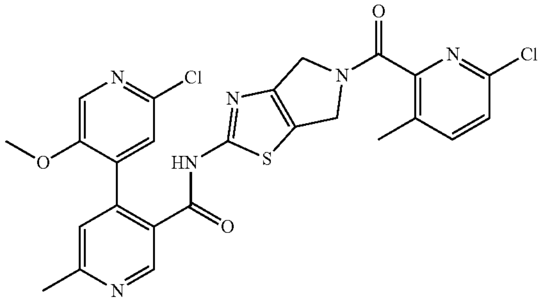 [SMILES: COc1cnc(Cl)cc1-c1cc(C)ncc1C(=O)Nc1nc2c(s1)CN(C(=O)c1nc(Cl)ccc1C)C2] | 2'-Chloro-N-(5-(6-chloro-3-methyl-picolinoyl)-5,6-dihydro-4H-pyrrolo[3,4-d]thiazol-2-yl)-5'-methoxy-6-methyl-[4,4'-bipyridine]-3-carboxamide | 555 | $^1$H NMR (400 MHz, DMSO-$d_6$) δ 12.8 (s, 1H), 8.78 (d, J = 4.6 Hz, 1H), 8.16 (d, J = 3.2 Hz, 1H), 7.87 (d, J = 8.4 Hz, 1H), 7.55 (d, J = 8.4 Hz, 1H), 7.54 (s, 1H), 7.43 (s, 1H), 4.85-4.81 (m, 1H), 4.71-4.67 (m, 1H), 4.57-4.53 (m, 1H), 4.46-4.42 (m, 1H), 3.60 (s, 3H), 2.59 (d, J = 2.4 Hz, 3H), 2.31 (s, 3H) |
| 401 | 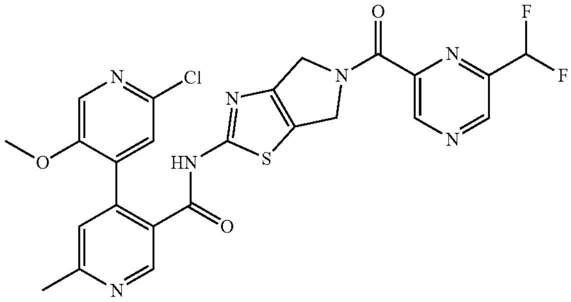 [SMILES: COc1cnc(Cl)cc1-c1cc(C)ncc1C(=O)Nc1nc2c(s1)CN(C(=O)c1cncc(C(F)F)n1)C2] | 2'-Chloro-N-(5-(6-(difluoromethyl) pyrazine-2-carbonyl)-5,6-dihydro-4H-pyrrolo[3,4-d]thiazol-2-yl)-5'-methoxy--6-methyl-[4,4'-bipyridine]-3-carboxamide | 558 | $^1$H NMR (400 MHz, DMSO-$d_6$) δ 12.8 (d, J = 20.8 Hz, 1H), 9.23 (d, J = 4.8 Hz, 1H), 9.14 (s, 1H), 8.79 (d, J = 3.2 Hz, 1H), 8.17 (d, J = 1.6 Hz, 1H), 7.55 (s, 1H), 7.44 (s, 1H), 7.23 (td, J = 54.0, 12.4 Hz, 1H), 5.05 (s, 1H), 4.94 (s, 1H), 4.89 (s, 1H), 4.76 (s, 1H), 3.60 (s, 3H), 2.59 (s, 3H) |
| 402 | 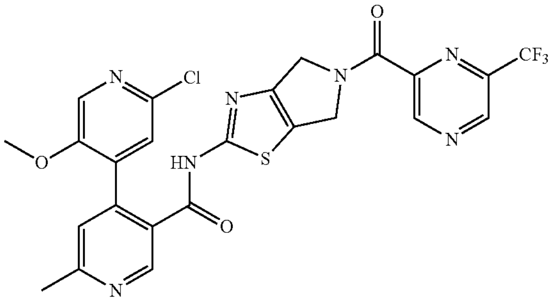 [SMILES: COc1cnc(Cl)cc1-c1cc(C)ncc1C(=O)Nc1nc2c(s1)CN(C(=O)c1cncc(C(F)(F)F)n1)C2] | 2'-Chloro-5'-methoxy-6-methyl-N-(5-(6-(trifluoromethyl) pyrazine-2-carbonyl)-5,6-dihydro-4H-pyrrolo[3,4-d]thiazol-2-yl)-[4,4'-bipyridine]-3-carboxamide | 576 | $^1$H NMR (400 MHz, DMSO-$d_6$) δ 12.8 (d, J = 13.6 Hz, 1H), 9.38 (t, J = 4.0 Hz, 2H), 8.79 (d, J = 3.8 Hz, 1H), 8.17 (d, J = 2.6 Hz, 1H), 7.55 (s, 1H), 7.44 (s, 1H), 5.04 (s, 1H), 4.93 (s, 1H), 4.91 (s, 1H), 4.77 (s, 1H), 3.60 (s, 3H), 2.59 (s, 3H) |
| 403 | 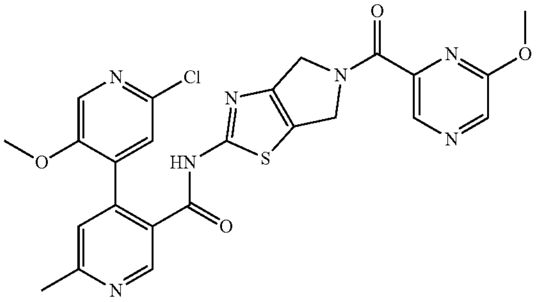 | 2'-Chloro-5'-methoxy-N-(5-(6-methoxy-pyrazine-2-carbonyl)-5,6-dihydro-4H-pyrrolo[3,4-d]thiazol-2-yl)-6-methyl-[4,4'-bipyridine]-3-carboxamide | 538 | $^1$H NMR (400 MHz, DMSO-$d_6$) δ 12.8 (d, J = 17.6 Hz, 1H), 8.78 (d, J = 4.6 Hz, 1H), 8.64 (d, J = 3.8 Hz, 1H), 8.48 (d, J = 2.6 Hz, 1H), 8.17 (d, J = 2.6 Hz, 1H), 7.54 (s, 1H), 7.44 (s, 1H), 5.15 (s, 1H), 5.03 (s, 1H), 4.87 (s, 1H), 4.73 (s, 1H), 4.00 (s, 3H), 3.60 (s, 3H), 2.59 (s, 3H) |

TABLE C-continued

| Ex. No. | Structure | Compound Name | LCMS [M + H]+ | NMR |
|---|---|---|---|---|
| The following examples were prepared using a similar procedure to that described for Example 1 | | | | |
| 404 | 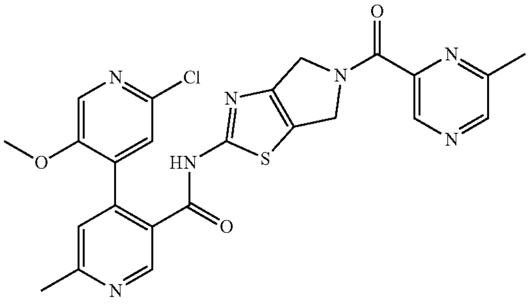 | 2'-Chloro-5'-methoxy-6-methyl-N-(5-(6-methylpyrazine-2-carbonyl)-5,6-dihydro-4H-pyrrolo[3,4-d]thiazol-2-yl)-[4,4'-bipyridine]-3-carboxamide | 522 | $^{1}H$ NMR (400 MHz, DMSO-$d_6$) δ 8.83 (d, J = 5.2 Hz, 1H), 8.79 (d, J = 2.6 Hz, 1H), 8.70 (s, 1H), 8.17 (s, 1H), 7.55 (s, 1H), 7.44 (s, 1H), 5.03 (s, 1H), 4.92 (s, 1H), 4.87 (s, 1H), 4.73 (s, 1H), 3.60 (s, 3H), 2.61-2.57 (m, 6H) |
| 405 | 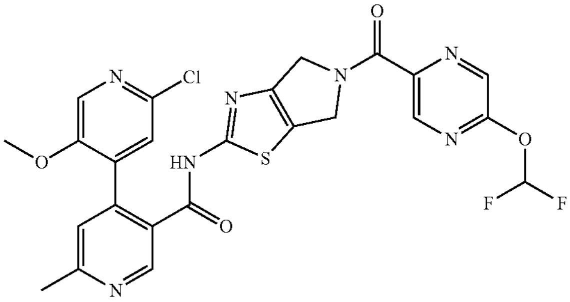 [SMILES: COc1cnc(Cl)cc1-c1cc(C)ncc1C(=O)Nc1nc2c(s1)CN(C(=O)c1cnc(OC(F)F)cn1)C2] | 2'-Chloro-N-(5-(5-(difluoro-methoxy) pyrazine-2-carbonyl)-5,6-dihydro-4H-pyrrolo[3,4-d]thiazol-2-yl)-5'-methoxy-6-methyl-[4,4'-bipyridine]-3-carboxamide | 574 | $^{1}H$ NMR (400 MHz, DMSO-$d_6$) δ 12.8 (s, 1H), 8.79 (s, 1H), 8.21 (d, J = 11.0 Hz, 1H), 8.17 (d, J = 3.8 Hz, 2H), 7.83 (t, J = 58.6 Hz, 1H), 7.54 (s, 1H), 7.43 (s, 1H), 5.11 (s, 1H), 4.96 (s, 1H), 4.83 (s, 1H), 4.69 (s, 1H), 3.61 (d, J = 2.2 Hz, 3H), 2.59 (s, 3H) |
| 407 | 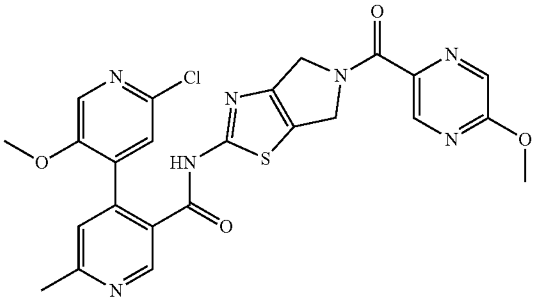 | 2'-chloro-5'-methoxy-N-(5-(5-methoxy-pyrazine-2-carbonyl)-5,6-dihydro-4H-pyrrolo[3,4-d]thiazol-2-yl)-6-methyl-1-[4,4'-bipyridine]-3-carboxamide | 538 | $^{1}H$ NMR (400 MHz, DMSO-$d_6$) δ 12.8 (d, J = 5.0 Hz, 1H), 8.79 (s, 1H), 8.72 (s, 1H), 8.37 (d, J = 11.2 Hz, 1H), 8.17 (s, 1H), 7.54 (s, 1H), 7.43 (s, 1H), 5.10 (s, 1H), 4.97 (s, 1H), 4.86 (s, 1H), 4.72 (s, 1H), 3.99 (s, 3H), 3.61 (d, J = 1.6 Hz, 3H), 2.59 (s, 3H) |
| 408 | 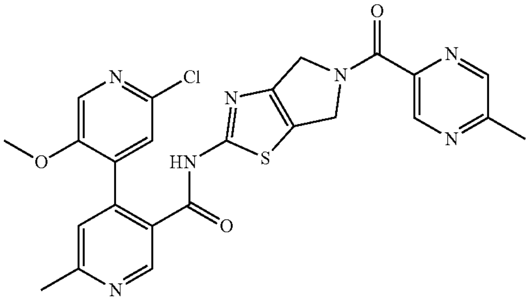 | 2'-Chloro-5'-methoxy-6-methyl-N-(5-(5-methylpyrazine-2-carbonyl)-5,6-dihydro-4H-pyrrolo[3,4-d]thiazol-2-yl)-[4,4'-bipyridine]-3-carboxamide | 522 | $^{1}H$ NMR (400 MHz, DMSO-$d_6$) δ 12.8 (s, 1H), 8.94 (s, 1H), 8.78 (s, 1H), 8.62 (d, J = 8.4 Hz, 1H), 8.16 (s, 1H), 7.54 (s, 1H), 7.43 (s, 1H), 5.07 (s, 1H), 4.94 (s, 1H), 4.86 (s, 1H), 4.73 (s, 1H), 3.60 (s, 3H), 2.58 (s, 6H) |

TABLE C-continued

| The following examples were prepared using a similar procedure to that described for Example 1 | | | | |
|---|---|---|---|---|
| Ex. No. | Structure | Compound Name | LCMS [M + H]+ | NMR |
| 409 | 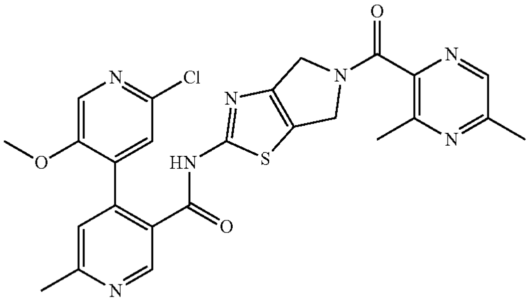 | 2'-Chloro-N-(5-(3,5-dimethyl-pyrazine-2-carbonyl)-5,6-dihydro-4H-pyrrolo[3,4-d]thiazol-2-yl)-5'-methoxy-6-methyl-[4,4'-bipyridine]-3-carboxamide | 536 | $^1$H NMR (400 MHz, DMSO-$d_6$) δ 8.77 (d, J = 4.8 Hz, 1H), 8.41 (s, 1H), 8.16 (d, J = 2.6 Hz, 1H), 7.53 (s, 1H), 7.43 (s, 1H), 4.85 (s, 1H), 4.71 (s, 1H), 4.60 (s, 1H), 4.50 (s, 1H), 3.59 (s, 3H), 3.31 (s, 3H), 2.58 (d, J = 2.6 Hz, 3H), 3H obscured by solvent peak |
| 410 | 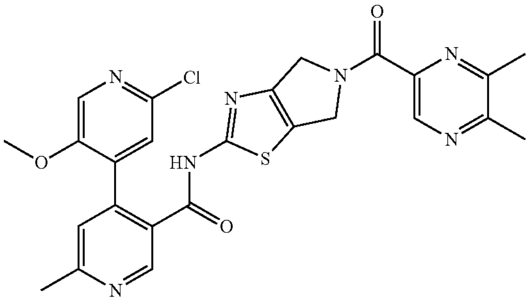 | 2'-Chloro-N-(5-(5,6-dimethyl-pyrazine-2-carbonyl)-5,6-dihydro-4H-pyrrolo[3,4-d]thiazol-2-yl)-5'-methoxy-6-methyl-[4,4'-bipyridine]-3-carboxamide | 536 | $^1$H NMR (400 MHz, DMSO-$d_6$) δ 12.8 (d, J = 13.6 Hz, 1H), 8.78 (d, J = 2.4 Hz, 1H), 8.73 (d, J = 6.2 Hz, 1H), 8.17 (s, 1H), 7.54 (s, 1H), 7.44 (s, 1H), 5.06 (s, 1H), 4.95 (s, 1H), 4.85 (s, 1H), 4.72 (s, 1H), 3.60 (s, 3H), 2.60-2.55 (m, 9H) |
| 411 | 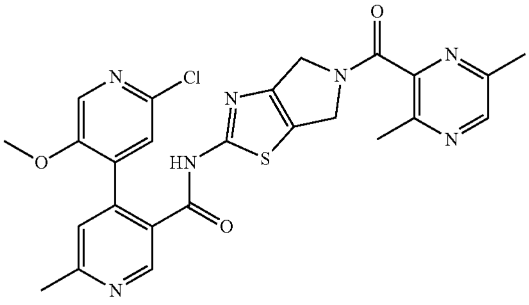 | 2'-Chloro-N-(5-(3,6-dimethyl-pyrazine-2-carbonyl)-5,6-dihydro-4H-pyrrolo[3,4-d]thiazol-2-yl)-5'-methoxy-6-methyl-[4,4'-bipyridine]-3-carboxamide | 536 | $^1$H NMR (400 MHz, DMSO-$d_6$) δ 12.8 (s, 1H), 8.78 (d, J = 5.6 Hz, 1H), 8.54 (s, 1H), 8.16 (d, J = 2.8 Hz, 1H), 7.54 (s, 1H), 7.43 (s, 1H), 4.85 (s, 1H), 4.71 (s, 1H), 4.60 (s, 1H), 4.49 (s, 1H), 3.60 (s, 3H), 2.59 (s, 3H), 6H obscured by solvent peak |
| 412 | 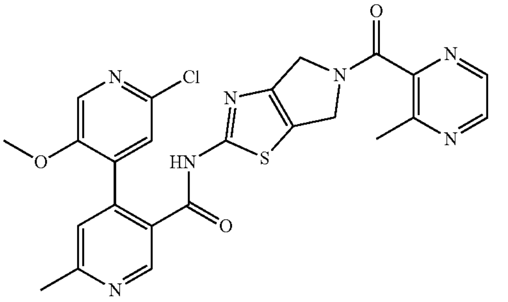 [SMILES: COc1cnc(Cl)cc1-c1cc(C)ncc1C(=O)Nc1nc2c(s1)CN(C(=O)c1nccnc1C)C2] | 2'-Chloro-5'-methoxy-6-methyl-N-(5-(3-methylpyrazine-2-carbonyl)-5,6-dihydro-4H-pyrrolo[3,4-d]thiazol-2-yl)-[4,4'-bipyridine]-3-carboxamide | 522 | $^1$H NMR (400 MHz, DMSO-$d_6$) δ 12.8 (s, 1H), 8.77 (d, J = 4.8 Hz, 1H), 8.65 (d, J = 2.6 Hz, 1H), 8.53 (d, J = 2.6 Hz, 1H), 8.16 (d, J = 2.4 Hz, 1H), 7.53 (s, 1H), 7.43 (d, J = 2.2 Hz, 1H), 4.86 (s, 1H), 4.73 (s, 1H), 4.61 (s, 1H), 4.50 (s, 1H), 3.59 (s, 3H), 2.58 (d, J = 2.8 Hz, 3H), 2.55 (s, 3H) |

TABLE C-continued

The following examples were prepared using a similar procedure to that described for Example 1

| Ex. No. | Structure | Compound Name | LCMS [M + H]+ | NMR |
| --- | --- | --- | --- | --- |
| 413 | 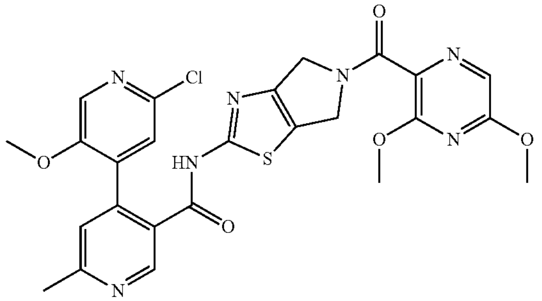 | 2'-Chloro-N-(5-(3,5-dimethoxy-pyrazine-2-carbonyl)-5,6-dihydro-4H-pyrrolo[3,4-d]thiazol-2-yl)-5'-methoxy-6-methyl-[4,4'-bipyridine]-3-carboxamide | 568 | $^1$H NMR (400 MHz, DMSO-$d_6$) δ 12.8-12.7 (m, 1H), 8.78 (d, J = 4.6 Hz, 1H), 8.20-8.13 (m, 1H), 7.90 (s, 1H), 7.54 (s, 1H), 7.43 (s, 1H), 4.79 (s, 1H), 4.66 (s, 1H), 4.59 (s, 1H), 4.48 (s, 1H), 4.01-3.95 (m, 6H), 3.60 (s, 3H), 2.61-2.56 (m, 3H) |
| 414 | 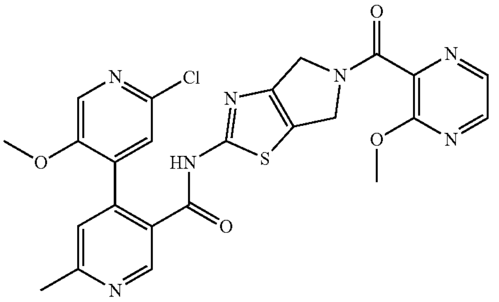 [SMILES: COc1cnc(Cl)cc1-c1cc(C)ncc1C(=O)Nc1nc2c(s1)CN(C(=O)c1nccnc1OC)C2] | 2'-Chloro-5'-methoxy-N-(5-(3-methoxy-pyrazine-2-carbonyl)-5,6-dihydro-4H-pyrrolo[3,4-d]thiazol-2-yl)-6-methyl-[4,4'-bipyridine]-3-carboxamide | 538 | $^1$H NMR (400 MHz, DMSO-$d_6$) δ 12.9-12.7 (m, 1H), 8.78 (d, J = 5.0 Hz, 1H), 8.38 (d, J = 2.8 Hz, 1H), 8.32-8.27 (m, 1H), 8.16 (d, J = 3.0 Hz, 1H), 7.54 (s, 1H), 7.43 (s, 1H), 4.85-4.79 (m, 1H), 4.72-4.66 (m, 1H), 4.59-4.53 (m, 1H), 4.48-4.42 (m, 1H), 3.96 (s, 3H), 3.60 (s, 3H), 2.61-2.56 (m, 3H) |
| 415 | 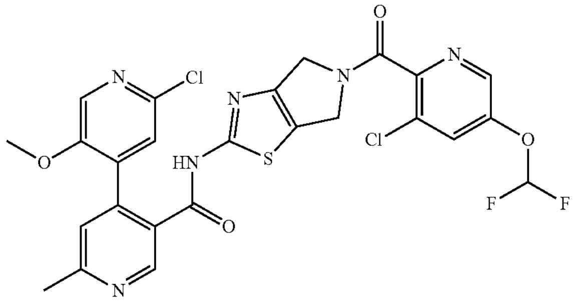 [SMILES: COc1cnc(Cl)cc1-c1cc(C)ncc1C(=O)Nc1nc2c(s1)CN(C(=O)c1ncc(OC(F)F)cc1Cl)C2] | 2'-Chloro-N-(5-(3-chloro-5-(difluoro-methoxy) picolinoyl)-5,6-dihydro-4H-pyrrolo[3,4-d]thiazol-2-yl)-5'-methoxy-6-methyl-[4,4'-bipyridine]-3-carboxamide | 607 | $^1$H NMR (400 MHz, DMSO-$d_6$) δ 12.8 (s, 1H), 8.77 (d, J = 4.4 Hz, 1H), 8.58-8.54 (m, 1H), 8.17-8.12 (m, 2H), 7.53 (s, 1H), 7.46 (t, J = 72.8 Hz, 1H), 7.43 (d, J = 2.4 Hz, 1H), 4.83 (t, J = 2.8 Hz, 1H), 4.70 (t, J = 2.8 Hz, 1H), 4.51 (t, J = 2.8 Hz, 1H), 4.40 (t, J = 2.8 Hz, 1H), 3.59 (s, 3H), 2.58 (d, J = 2.8 Hz, 3H) |
| 416 | 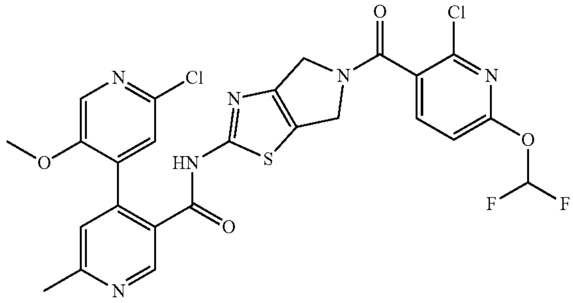 [SMILES: COc1cnc(Cl)cc1-c1cc(C)ncc1C(=O)Nc1nc2c(s1)CN(C(=O)c1ccc(OC(F)F)nc1Cl)C2] | 2'-Chloro-N-(5-(2-chloro-6-(difluoro-methoxy) nicotinoyl)-5,6-dihydro-4H-pyrrolo[3,4-d]thiazol-2-yl)-5'-methoxy-6-methyl-[4,4'-bipyridine]-3-carboxamide | 607 | $^1$H NMR (400 MHz, DMSO-$d_6$) δ 12.8 (d, J = 7.2 Hz, 1H), 8.78 (d, J = 4.0 Hz, 1H), 8.20-8.15 (m, 2H), 7.90-7.52 (m, 2H), 7.45-7.42 (m, 1H), 7.31-7.25 (m, 1H), 4.85-4.78 (m, 1H), 4.71-4.64 (m, 1H), 4.54-4.50 (m, 1H), 4.44-4.40 (m, 1H), 3.62-3.57 (m, 3H), 2.59 (s, 3H) |

TABLE C-continued

The following examples were prepared using a similar procedure to that described for Example 1

| Ex. No. | Structure | Compound Name | LCMS [M + H]+ | NMR |
|---|---|---|---|---|
| 417 | 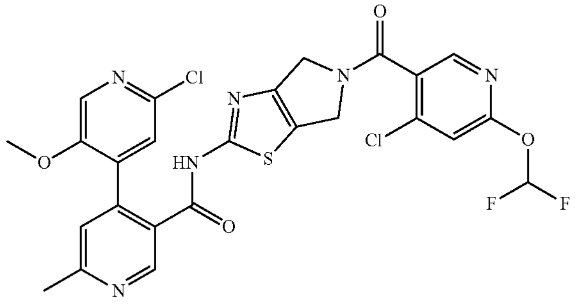 [SMILES: COc1cnc(Cl)cc1-c1cc(C)ncc1C(=O)Nc1nc2c(s1)CN(C(=O)c1cnc(OC(F)F)cc1Cl)C2] | 2'-Chloro-N-(5-(4-chloro-6-(difluoro-methoxy) nicotinyl)-5,6-dihydro-4H-pyrrolo[3,4-d]thiazol-2-yl)-5'-methoxy-6-methyl-[4,4'-bipyridine]-3-carboxamide | 607 | $^1$H NMR (400 MHz, DMSO-$d_6$) δ 12.8 (s, 1H), 8.78 (d, J = 4.4 Hz, 1H), 8.49 (d, J = 3.4 Hz, 1H), 8.16 (d, J = 1.4 Hz, 1H), 7.76 (t, J = 72.0 Hz, 1H), 7.55 (d, J = 6.8 Hz, 1H), 7.54 (s, 1H), 7.42 (s, 1H), 4.82 (s, 1H), 4.69 (s, 1H), 4.53 (s, 1H), 4.44 (s, 1H), 3.59 (s, 3H), 2.58 (d, J = 2.6 Hz, 3H) |
| 418 | 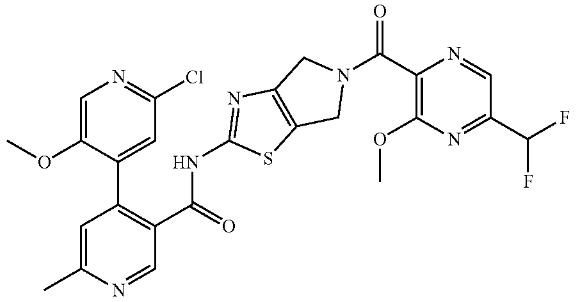 [SMILES: COc1cnc(Cl)cc1-c1cc(C)ncc1C(=O)Nc1nc2c(s1)CN(C(=O)c1ncc(C(F)F)nc1OC)C2] | 2'-Chloro-N-(5-(5-(difluoro-methyl)-3-methoxy-pyrazine-2-carbonyl)-5,6-dihydro-4H-pyrrolo[3,4-d]thiazol-2-yl)-5'-methoxy-6-methyl-[4,4'-bipyridine]-3-carboxamide | 588 | $^1$H NMR (400 MHz, DMSO-$d_6$) δ 12.8 (d, J = 5.8 Hz, 1H), 8.78 (d, J = 4.8 Hz, 1H), 8.57 (d, J = 3.2 Hz, 1H), 8.16 (d, J = 2.6 Hz, 1H), 7.54 (s, 1H), 7.43 (d, J = 2.2 Hz, 1H), 7.11 (t, J = 54.0 Hz, 1H), 4.84 (s, 1H), 4.71 (s, 1H), 4.60 (s, 1H), 4.50 (s, 1H), 4.01 (s, 3H), 3.60 (s, 3H), 2.59 (d, J = 2.6 Hz, 3H) |
| 419 | 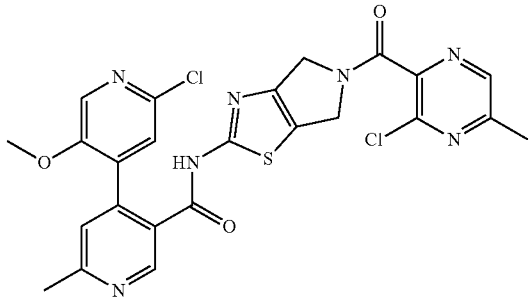 | 2'-Chloro-N-(5-(3-chloro-5-methylpyrazine-2-carbonyl)-5,6-dihydro-4H-pyrrolo[3,4-d]thiazol-2-yl)-5'-methoxy-6-methyl-[4,4'-bipyridine]-3-carboxamide | 556 | $^1$H NMR (400 MHz, DMSO-$d_6$) δ 12.8 (d, J = 4.4 Hz, 1H), 8.78 (d, J = 4.8 Hz, 1H), 8.66 (d, J = 4.4 Hz, 1H), 8.16 (d, J = 3.2 Hz, 1H), 7.54 (s, 1H), 7.43 (d, J = 2.4 Hz, 1H), 4.88-4.83 (m, 1H), 4.75-4.70 (m, 1H), 4.60-4.55 (m, 1H), 4.50-4.44 (m, 1H), 3.60 (s, 3H), 2.60-2.56 (m, 6H) |
| 420 | 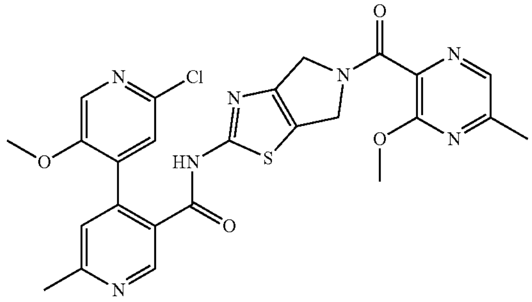 | 2'-Chloro-5'-methoxy-N-(5-(3-methoxy-5-methylpyrazine-2-carbonyl)-5,6-dihydro-4H-pyrrolo[3,4-d]thiazol-2-yl)-6-methyl-[4,4'-bipyridine]-3-carboxamide | 552 | $^1$H NMR (400 MHz, DMSO-$d_6$) δ 8.85-8.77 (m, 1H), 8.20-8.11 (m, 2H), 7.50 (s, 1H), 7.39 (s, 1H), 4.79 (s, 1H), 4.65 (s, 1H), 4.53 (s, 1H), 4.42 (s, 1H), 3.94 (s, 3H), 3.60 (s, 3H), 2.58 (s, 3H), 3H obscured by solvent peak |

TABLE C-continued

The following examples were prepared using a similar procedure to that described for Example 1

| Ex. No. | Structure | Compound Name | LCMS [M + H]+ | NMR |
|---|---|---|---|---|
| 421 | 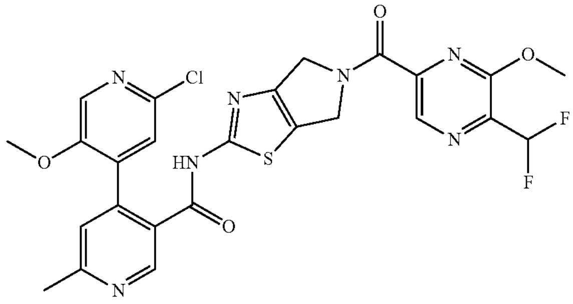 | 2'-Chloro-N-(5-(5-(difluoro-methyl)-6-methoxy-pyrazine-2-carbonyl)-5,6-dihydro-4H-pyrrolo[3,4-d]thiazol-4-yl)-5'-methoxy-6-methyl-[4,4'-bipyridine]-3-carboxamide | 588 | $^1$H NMR (400 MHz, DMSO-$d_6$) δ 12.8 (d, J = 21.2 Hz, 1H), 8.78 (d, J = 5.0 Hz, 1H), 8.73 (d, J = 1.8 Hz, 1H), 8.17 (d, J = 2.8 Hz, 1H), 7.55 (s, 1H), 7.44 (s, 1H), 7.14 (td, J = 53.2, 1.6 Hz, 1H), 5.16 (s, 1H), 5.04 (s, 1H), 4.89 (s, 1H), 4.75 (s, 1H), 4.09 (d, J = 1.2 Hz, 3H), 3.60 (s, 3H), 2.59 (s, 3H) |
| 422 | 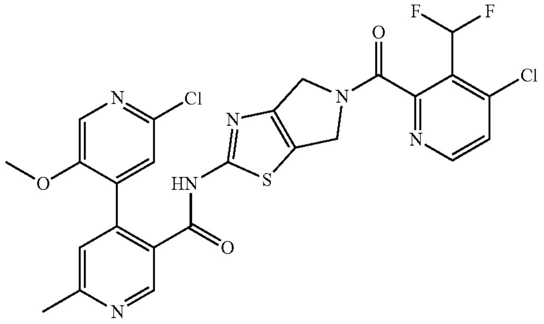 [SMILES: COc1cnc(Cl)cc1-c1cc(C)ncc1C(=O)Nc1nc2c(s1)CN(C(=O)c1nccc(Cl)c1C(F)F)C2] | 2'-chloro-N-(5-(4-chloro-3-(difluoromethyl) picolinoyl)-5,6-dihydro-4H-pyrrolo[3,4-d]thiazol-2-yl)-5'-methoxy-6-methyl-[4,4'-bipyridine]-3-carboxamide | 591 | $^1$H NMR (400 MHz, DMSO-$d_6$) δ 12.8 (s, 1H), 8.78 (d, J = 4.9 Hz, 1H), 8.75 (d, J = 5.4 Hz, 1H), 8.16 (d, J = 4.0 Hz, 1H), 7.87 (d, J = 5.4 Hz, 1H), 7.53 (s, 1H), 7.42 (s, 1H), 7.26 (td, J = 52.2, 3.4 Hz, 1H), 4.84 (s, 1H), 4.70 (s, 1H), 4.56 (s, 1H), 4.45 (s, 1H), 3.60 (s, 3H), 2.58 (d, J = 2.8 Hz, 3H) |
| 423 | 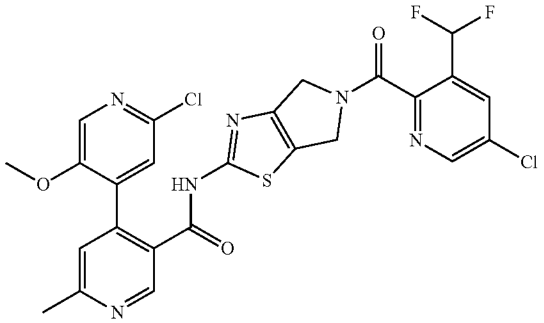 [SMILES: COc1cnc(Cl)cc1-c1cc(C)ncc1C(=O)Nc1nc2c(s1)CN(C(=O)c1ncc(Cl)cc1C(F)F)C2] | 2'-Chloro-N-(5-(5-chloro-3-(difluoromethyl) picolinoyl)-5,6-dihydro-4H-pyrrolo[3,4-d]thiazol-2-yl)-5'-methoxy-6-methyl-[4,4'-bipyridine]-3-carboxamide | 591 | $^1$H NMR (400 MHz, DMSO-$d_6$) δ 12.8 (s, 1H), 8.88 (d, J = 2.2 Hz, 1H), 8.78 (d, J = 3.8 Hz, 1H), 8.39-8.35 (m, 1H), 8.16 (d, J = 2.6 Hz, 1H), 7.54 (s, 1H), 7.43 (d, J = 2.2 Hz, 1H), 7.23 (t, J = 54.0 Hz, 1H), 4.85 (s, 1H), 4.70 (s, 2H), 4.59 (s, 1H), 3.59 (s, 3H), 2.58 (d, J = 2.4 Hz, 3H) |
| 424 | 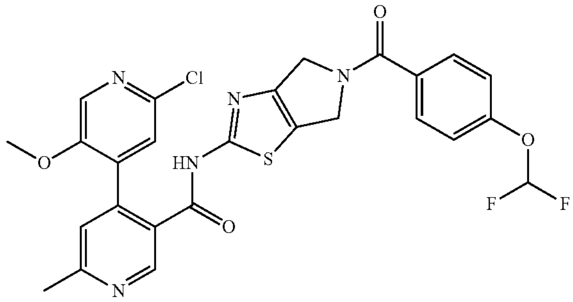 [SMILES: COc1cnc(Cl)cc1-c1cc(C)ncc1C(=O)Nc1nc2c(s1)CN(C(=O)c1ccc(OC(F)F)cc1)C2] | 2-Chloro-N-(5-(4-(difluoro-methoxy) benzoyl)-5,6-dihydro-4H-pyrrolo[3,4-d]thiazol-2-yl)-5'-methoxy-6-methyl-[4,4'-bipyridine]-3-carboxamide | 572 | $^1$H NMR (400 MHz, DMSO-$d_6$) δ 12.8 (d, J = 7.0 Hz, 1H), 8.78 (d, J = 3.2 Hz, 1H), 8.16 (s, 1H), 7.74-7.66 (m, 2H), 7.54 (s, 1H), 7.43 (s, 1H), 7.37-7.14 (m, 3H), 4.82 (s, 1H), 4.73-4.70 (m, 1H), 4.69-4.66 (m, 1H), 4.65-4.59 (m, 1H), 3.59 (s, 3H), 2.60-2.57 (m, 3H) |

TABLE C-continued

The following examples were prepared using a similar procedure to that described for Example 1

| Ex. No. | Structure | Compound Name | LCMS [M + H]+ | NMR |
|---|---|---|---|---|
| 425 | 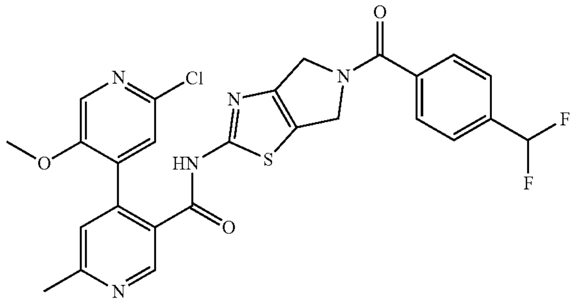 [SMILES: COc1cnc(Cl)cc1-c1cc(C)ncc1C(=O)Nc1nc2c(s1)CN(C(=O)c1ccc(C(F)F)cc1)C2] | 2'-Chloro-N-(5-(4-(difluoromethyl) benzoyl)-5,6-dihydro-4H-pyrrolo[3,4-d]thiazol-2-yl)-5'-methoxy-6-methyl-[4,4'-bipyridine]-3-carboxamide | 556 | $^1$H NMR (400 MHz, DMSO-$d_6$) δ 12.8 (d, J = 6.4 Hz, 1H), 8.78 (d, J = 3.6 Hz, 1H), 8.16 (s, 1H), 7.75 (t, J = 7.6 Hz, 2H), 7.67 (d, J = 8.0 Hz, 2H), 7.54 (s, 1H), 7.43 (d, J = 2.2 Hz, 1H), 7.08 (t, J = 55.6 Hz, 1H), 4.83 (s, 1H), 4.68 (d, J = 5.4 Hz, 2H), 4.58 (s, 1H), 3.59 (s, 3H), 2.59 (d, J = 2.6 Hz, 3H) |
| 426 | 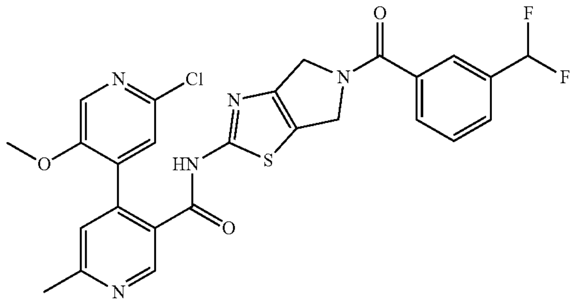 [SMILES: COc1cnc(Cl)cc1-c1cc(C)ncc1C(=O)Nc1nc2c(s1)CN(C(=O)c1cccc(C(F)F)c1)C2] | 2'-Chloro-N-(5-(3-(difluoromethyl) benzoyl)-5,6-dihydro-4H-pyrrolo[3,4-d]thiazol-2-yl)-5'-methoxy-6-methyl-[4,4'-bipyridine]-3-carboxamide | 556 | $^1$H NMR (400 MHz, DMSO-$d_6$) δ 12.8 (d, J = 5.2 Hz, 1H), 8.78 (d, J = 3.8 Hz, 1H), 8.16 (s, 1H), 7.79 (d, J = 6.8 Hz, 2H), 7.71 (d, J = 7.8 Hz, 1H), 7.64 (d, J = 7.6 Hz, 1H), 7.54 (s, 1H), 7.43 (s, 1H), 7.10 (t, J = 55.8 Hz, 1H), 4.83 (s, 1H), 4.69 (s, 2H), 4.61 (s, 1H), 3.59 (s, 3H), 2.59 (d, J = 2.4 Hz, 3H) |
| 427 | 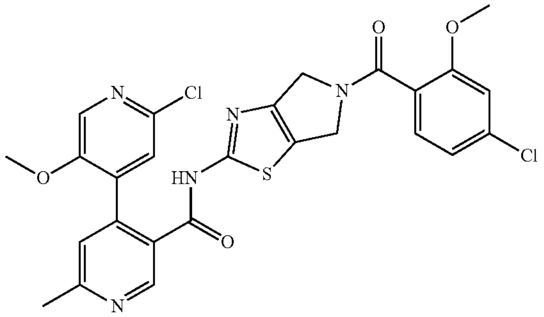 [SMILES: COc1cc(Cl)ccc1C(=O)N1Cc2nc(NC(=O)c3cnc(C)cc3-c3cc(Cl)ncc3OC)sc2C1] | 2'-Chloro-N-(5-(4-chloro-2-methoxy-benzoyl)-5,6-dihydro-4H-pyrrolo[3,4-d]thiazol-2-yl)-5'-methoxy-6-methyl-[4,4'-bipyridine]-3-carboxamide | 570 | $^1$H NMR (400 MHz, DMSO-$d_6$) δ 12.8 (d, J = 3.4 Hz, 1H), 8.77 (d, J = 4.6 Hz, 1H), 8.16 (d, J = 3.2 Hz, 1H), 7.54 (s, 1H), 7.43 (s, 1H), 7.32 (d, J = 8.2 Hz, 1H), 7.24 (s, 1H), 7.10 (d, J = 8.2 Hz, 1H), 4.75 (s, 1H), 4.61 (s, 1H), 4.44 (s, 1H), 4.32 (s, 1H), 3.85 (d, J = 2.8 Hz, 3H), 3.59 (s, 3H), 2.58 (d, J = 2.4 Hz, 3H) |
| 428 | 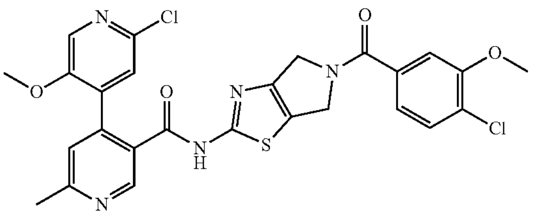 | 2'-Chloro-N-(5-(4-chloro-3-methoxy-benzoyl)-5,6-dihydro-4H-pyrrolo[3,4-d]thiazol-2-yl)-5'-methoxy-6-methyl-[4,4'-bipyridine]-3-carboxamide | 570 | $^1$H NMR (400 MHz, DMSO-$d_6$) δ 12.8 (s, 1H), 8.78 (d, J = 4.0 Hz, 1H), 8.16 (s, 1H), 7.55-7.50 (m, 2H), 7.43 (s ,1H), 7.33 (s, 1H), 7.20-7.14 (m, 1H), 4.81 (s, 1H), 4.72-4.65 (m, 2H), 4.60 (s, 2H), 3.91 (s, 3H), 3.59 (s, 3H), 2.59 (d, J = 2.0 Hz, 3H) |
| 429 | 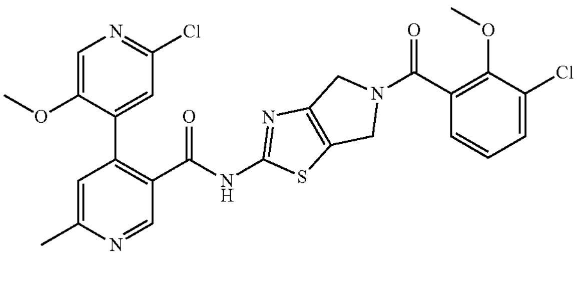 [SMILES: COc1cnc(Cl)cc1-c1cc(C)ncc1C(=O)Nc1nc2c(s1)CN(C(=O)c1cccc(Cl)c1OC)C2] | 2'-Chloro-N-(5-(3-chloro-2-methoxy-benzoyl)-5,6-dihydro-4H-pyrrolo[3,4-d]thiazol-2-yl)-5'-methoxy-6-methyl-[4,4'-bipyridine]-3-carboxamide | 570 | $^1$H NMR (400 MHz, DMSO-$d_6$) δ 12.9-12.6 (m, 1H), 8.80-8.75 (m, 1H), 8.19-8.14 (m, 1H), 7.63-7.56 (m, 1H), 7.56-7.52 (m, 1H), 7.46-7.36 (m, 2H), 7.29-7.20 (m, 1H), 4.84-4.79 (m, 1H), 4.70-4.65 (m, 1H), 4.50-4.44 (m, 1H), 4.39-4.34 (m, 1H), 3.84-3.78 (m, 3H), 3.62-3.57 (m, 3H), 2.61-2.56 (m, 3H) |

TABLE C-continued

The following examples were prepared using a similar procedure to that described for Example 1

| Ex. No. | Structure | Compound Name | LCMS [M + H]+ | NMR |
|---|---|---|---|---|
| 430 | 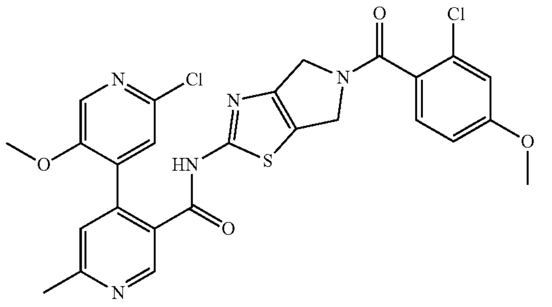 | 2'-Chloro-N-(5-(2-chloro-4-methoxy-benzoyl)-5,6-dihydro-4H-pyrrolo[3,4-d]thiazol-2-yl)-5'-methoxy-6-methyl-[4,4'-bipyridine]-3-carboxamide | 570 | $^1$H NMR (400 MHz, DMSO-$d_6$) δ 12.8 (d, J = 14.2 Hz, 1H), 8.77 (d, J = 4.0 Hz, 1H), 8.16 (d, J = 3.2 Hz, 1H), 7.54 (s, 1H), 7.47-7.41 (m, 2H), 7.15 (t, J = 2.2 Hz, 1H), 7.02 (dd, J = 8.8, 2.0 Hz, 1H), 4.78 (s, 1H), 4.65 (s, 1H), 4.44 (s, 1H), 4.33 (s, 1H), 3.82 (d, J = 2.4 Hz, 3H), 3.59 (s, 3H), 2.58 (d, J = 2.8 Hz, 3H) |
| 431 | 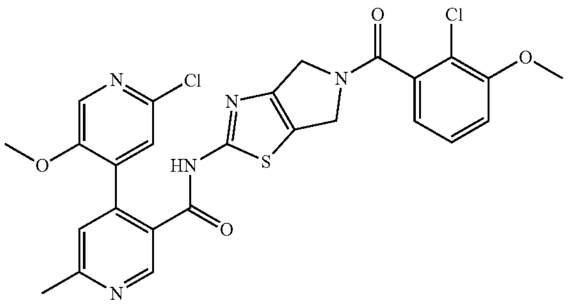 | 2'-Chloro-N-(5-(2-chloro-3-methoxy-benzoyl)-5,6-dihydro-4H-pyrrolo[3,4-d]thiazol-2-yl)-5'-methoxy-6-methyl-[4,4'-bipyridine]-3-carboxamide | 570 | $^1$H NMR (400 MHz, DMSO-$d_6$) δ 12.8 (d, J = 16.4 Hz, 1H), 8.77 (d, J = 4.0 Hz, 1H), 8.16 (d, J = 3.4 Hz, 1H), 7.53 (s, 1H), 74.7-7.39 (m, 2H), 7.23 (d, J = 8.2 Hz, 1H), 7.05 (d, J = 7.6 Hz, 1H), 4.80 (s, 1H), 4.66 (s, 1H), 4.40 (s, 1H), 4.29 (s, 1H), 3.90 (s, 3H), 3.59 (s, 3H), 2.58 (d, J = 3.0 Hz, 3H) |
| 432 | 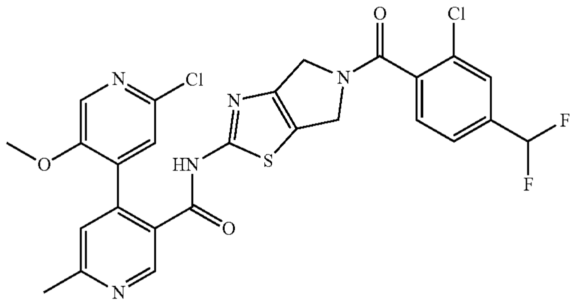 | 2'-Chloro-N-(5-(2-chloro-4-(difluoromethyl)benzoyl)-5,6-dihydro-4H-pyrrolo[3,4-d]thiazol-2-yl)-5'-methoxy-6-methyl-[4,4'-bipyridine]-3-carboxamide | 590 | $^1$H NMR (400 MHz, DMSO-$d_6$) δ 12.8 (d, J = 10.2 Hz, 1H), 8.77 (d, J = 4.4 Hz, 1H), 8.16 (d, J = 3.0 Hz, 1H), 7.81 (s, 1H), 7.73-7.65 (m, 2H), 7.54 (s, 1H), 7.43 (d, J = 2.6 Hz, 1H), 7.11 (t, J = 55.2 Hz, 1H), 4.83 (s, 1H), 4.69 (s, 1H), 4.44 (s, 1H), 4.34 (s, 1H), 3.59 (s, 3H), 2.58 (d, J = 3.0 Hz, 3H) |
| 433 | 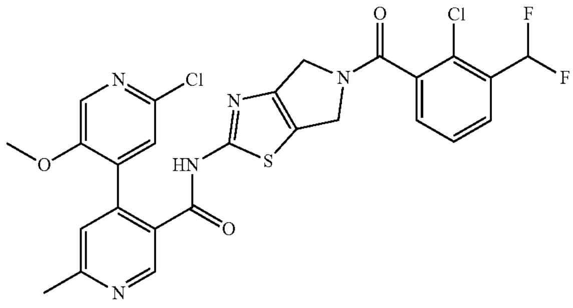 [SMILES: COc1cnc(Cl)cc1-c1cc(C)ncc1C(=O)Nc1nc2c(s1)CN(C(=O)c1cccc(C(F)F)c1Cl)C2] | 2'-Chloro-N-(5-(2-chloro-3-(difluoromethyl)benzoyl)-5,6-dihydro-4H-pyrrolo[3,4-d]thiazol-2-yl)-5'-methoxy-6-methyl-[4,4'-bipyridine]-3-carboxamide | 590 | $^1$H NMR (400 MHz, DMSO-$d_6$) δ 12.8 (d, J = 10.8 Hz, 1H), 8.77 (d, J = 5.0 Hz, 1H), 8.16 (d, J = 3.6 Hz, 1H), 7.83-7.77 (m, 1H), 7.75-7.71 (m, 1H), 7.68-7.61 (m, 1H), 7.54 (s, 1H), 7.43 (d, J = 2.4 Hz, 1H), 7.28 (td, J = 54.4, 2.8 Hz, 1H), 4.83 (s, 1H), 4.69 (s, 1H), 4.43 (s, 1H), 4.33 (s, 1H), 3.59 (s, 3H), 2.58 (d, J = 3.2 Hz, 3H) |

TABLE C-continued

The following examples were prepared using a similar procedure to that described for Example 1

| Ex. No. | Structure | Compound Name | LCMS [M + H]$^+$ | NMR |
|---|---|---|---|---|
| 434 | 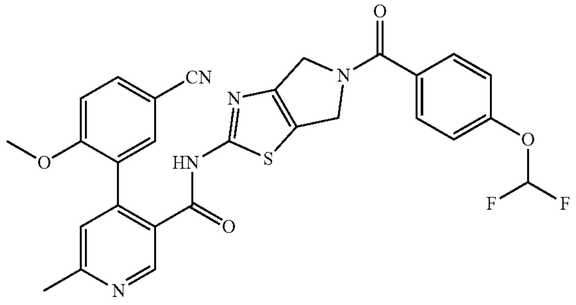 [SMILES: COc1ccc(C#N)cc1-c1cc(C)ncc1C(=O)Nc1nc2c(s1)CN(C(=O)c1ccc(OC(F)F)cc1)C2] | 4-(5-Cyano-2-methoxyphenyl)-N-(5-(4-(difluoro-methoxy) benzoyl)-5,6-dihydro-4H-pyrrolo[3,4-d]thiazol-2-yl)-6-methyl-nicotinamide | 562 | $^1$H NMR (400 MHz, DMSO-$d_6$) δ 12.7 (d, J = 6.8 Hz, 1H), 8.71 (d, J = 3.0 Hz, 1H), 7.89 (d, J = 9.0 Hz, 1H), 7.84 (s, 1H), 7.70 (t, J = 8.8 Hz, 2H), 7.55-7.34 (m, 2H), 7.26 (d, J = 8.2 Hz, 2H), 7.17 (d, J = 8.0 Hz, 1H), 4.81 (s, 1H), 4.70 (s, 1H), 4.66 (s, 1H), 4.61 (s, 1H), 3.56 (s, 3H), 2.57 (s, 3H) |
| 435 | 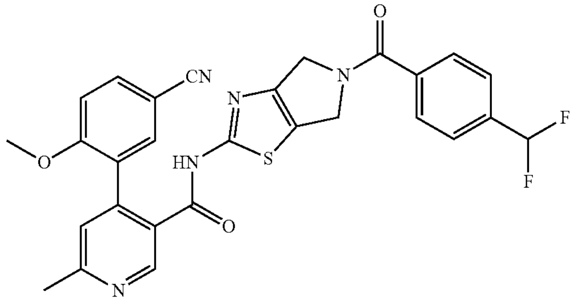 [SMILES: COc1ccc(C#N)cc1-c1cc(C)ncc1C(=O)Nc1nc2c(s1)CN(C(=O)c1ccc(C(F)F)cc1)C2] | 4-(-cyano-2-methoxyphenyl)-N-(5-(4-(difluoromethyl) benzoyl)-5,6-dihydro-4H-pyrrolo[3,4-d]thiazol-2-yl)-6-methyl-nicotinamide | 546 | $^1$H NMR (400 MHz, DMSO-$d_6$) δ 12.7 (d, J = 6.4 Hz, 1H), 8.71 (s, 1H), 7.92-7.82 (m, 2H), 7.78-7.71 (m, 2H), 7.70-7.64 (m, 2H), 7.39 (s, 1H), 7.17 (d, J = 8.8 Hz, 1H), 7.11 (t, J = 55.6 Hz, 1H), 4.82 (s, 1H), 4.71-4.63 (m, 2H), 4.57 (s, 1H), 3.56 (s, 3H), 2.57 (s, 3H) |
| 436 | 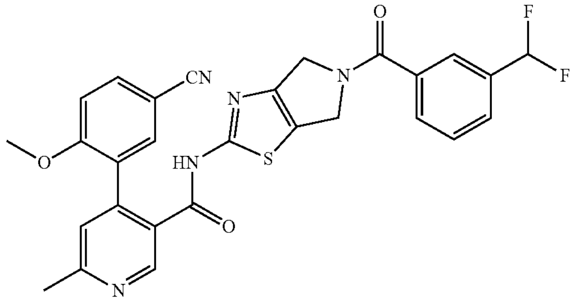 [SMILES: COc1ccc(C#N)cc1-c1cc(C)ncc1C(=O)Nc1nc2c(s1)CN(C(=O)c1cccc(C(F)F)c1)C2] | 4-(5-Cyano-2-methoxyphenyl)-N-(5-(3-(difluoromethyl) benzoyl)-5,6-dihydro-4H-pyrrolo[3,4-d]thiazol-2-yl)-6-methyl-nicotinamide | 546 | $^1$H NMR (400 MHz, DMSO-$d_6$) δ 12.7 (d, J = 4.0 Hz, 1H), 8.70 (d, J = 3.8 Hz, 1H), 7.92-7.76 (m, 4H), 7.70 (d, J = 7.8 Hz, 1H), 7.63 (t, J = 7.8 Hz, 1H), 7.39 (d, J = 2.2 Hz, 1H), 7.17 (d, J = 8.8 Hz, 1H), 7.11 (t, J = 55.6 Hz, 1H), 4.82 (s, 1H), 4.68 (s, 2H), 4.59 (s, 1H), 3.56 (s, 3H), 2.57 (d, J = 2.6 Hz, 3H) |
| 437 | 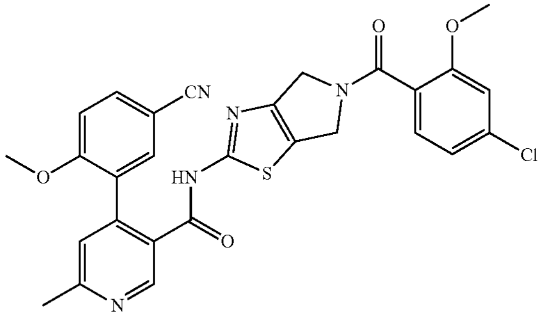 [SMILES: COc1cc(Cl)ccc1C(=O)N1Cc2nc(NC(=O)c3cnc(C)cc3-c3cc(C#N)ccc3OC)sc2C1] | N-(5-(4-Chloro-2-methoxybenzoyl)-5,6-dihydro-4H-pyrrolo[3,4-d]thiazol-2-yl)-4-(5-cyano-2-methoxyphenyl)-6-methyl-nicotinamide | 560 | $^1$H NMR (400 MHz, DMSO-$d_6$) δ 12.7 (s, 1H), 8.71 (d, J = 4.2 Hz, 1H), 7.91-7.86 (m, 1H), 7.84 (d, J = 2.2 Hz, 1H), 7.38 (s, 1H), 7.32 (d, J = 8.2 Hz, 1H), 7.24 (t, J = 1.8 Hz, 1H), 7.19-7.14 (m, 1H), 7.12-7.08 (m, 1H), 4.74 (s, 1H), 4.60 (s, 1H), 4.42 (s, 1H), 4.31 (s, 1H), 3.85 (d, J = 2.8 Hz, 3H), 3.56 (s, 3H), 2.57 (d, J = 2.6 Hz, 3H) |

TABLE C-continued

The following examples were prepared using a similar procedure to that described for Example 1

| Ex. No. | Structure | Compound Name | LCMS [M + H]+ | NMR |
|---|---|---|---|---|
| 438 | 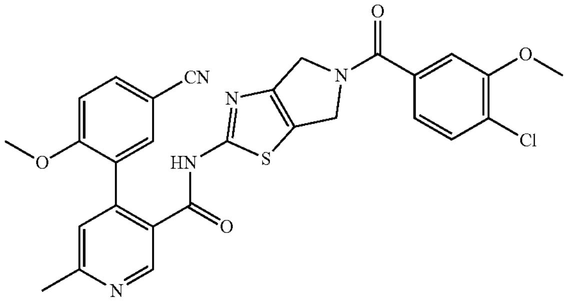 | N-(5-(4-chloro-3-methoxybenzoyl)-5,6-dihydro-4H-pyrrolo[3,4-d]thiazol-2-yl)-4-(5-cyano-2-methoxyphenyl)-6-methyl-nicotinamide | 560 | $^1$H NMR (400 MHz, DMSO-$d_6$) δ 12.7 (s, 1H), 8.71 (d, J = 3.8 Hz, 1H), 7.93-7.82 (m, 2H), 7.52 (d, J = 8.2 Hz, 1H), 7.40 (s, 1H), 7.33 (s, 1H), 7.17 (d, J = 8.2 Hz, 2H), 4.80 (s, 1H), 4.67 (d, J = 11.0 Hz, 2H), 4.59 (s, 1H), 3.90 (s, 3H), 3.56 (s, 3H), 2.58 (s, 3H) |
| 439 | 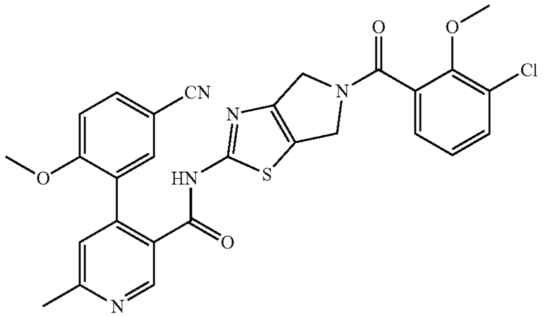 [SMILES: COc1ccc(C#N)cc1-c1cc(C)ncc1C(=O)Nc1nc2c(s1)CN(C(=O)c1cccc(Cl)c1OC)C2] | N-(5-(3-Chloro-2-methoxybenzoyl)-5,6-dihydro-4H-pyrrolo[3,4-d]thiazol-2-yl)-4-(5-cyano-2-methoxyphenyl)-6-methyl-nicotinamide | 560 | $^1$H NMR (400 MHz, DMSO-$d_6$) δ 12.7 (d, J = 14.8 Hz, 1H), 8.71 (d, J = 4.2 Hz, 1H), 7.89 (dt, J = 8.6, 2.4 Hz, 1H), 7.85 (d, J = 2.2 Hz, 1H), 7.59 (dd, J = 8.0, 1.4 Hz, 1H), 7.44-7.35 (m, 2H), 7.25 (td, J = 7.8, 2.0 Hz, 1H), 7.17 (dd, J = 8.6, 3.6 Hz, 1H), 4.81 (t, J = 2.8 Hz, 1H), 4.66 (t, J = 2.8 Hz, 1H), 4.46 (t, J = 2.8 Hz, 1H), 4.36 (t, J = 2.8 Hz, 1H), 3.81 (s, 3H), 3.56 (s, 3H), 2.57 (d, J = 3.0 Hz, 3H) |
| 440 | 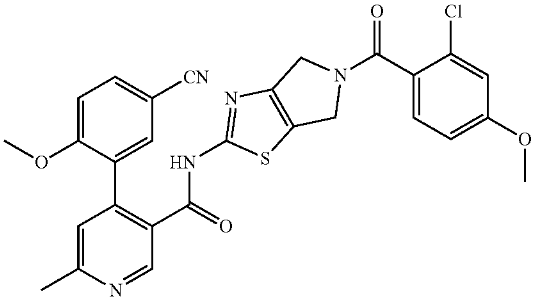 | N-(5-(2-chloro-4-methoxybenzoyl)-5,6-dihydro-4H-pyrrolo[3,4-d]thiazol-2-yl)-4-(5-cyano-2-methoxyphenyl)-6-methyl-nicotinamide | 560 | $^1$H NMR (400 MHz, DMSO-$d_6$) δ 8.70 (d, J = 4.2 Hz, 1H), 7.88 (dd, J = 8.4, 2.4 Hz, 1H), 7.84 (d, J = 2.2 Hz, 1H), 7.44 (dd, J = 8.4, 1.4 Hz, 1H), 7.39 (d, J = 2.8 Hz, 1H), 7.19-7.14 (m, 2H), 7.05-6.99 (m, 1H), 4.78 (s, 1H), 4.63 (s, 1H), 4.43 (s, 1H), 4.32 (s, 1H), 3.82 (d, J = 2.8 Hz, 3H), 3.56 (s, 3H), 2.57 (d, J = 2.8 Hz, 3H) |
| 441 | 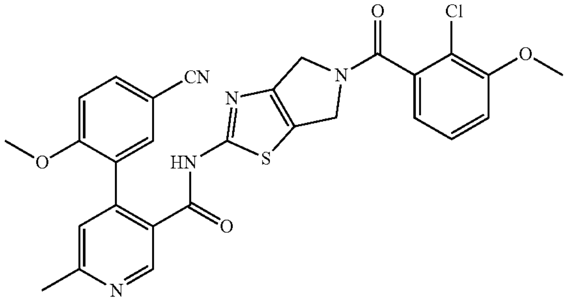 | N-(5-(2-Chloro-3-methoxybenzoyl)-5,6-dihydro-4H-pyrrolo[3,4-d]thiazol-2-yl)-4-(5-cyano-2-methoxyphenyl)-6-methyl-nicotinamide | 560 | $^1$H NMR (400 MHz, DMSO-$d_6$) δ 12.7 (d, J = 15.6 Hz, 1H), 8.73 (d, J = 3.8 Hz, 1H), 7.91-7.87 (m, 1H), 7.85 (d, J = 2.4 Hz, 1H), 7.47-7.39 (m, 2H), 7.23 (d, J = 8.2 Hz, 1H), 7.20-7.14 (m, 1H), 7.05 (d, J = 7.6 Hz, 1H), 4.79 (s, 1H), 4.65 (s, 1H), 4.39 (s, 1H), 4.28 (s, 1H), 3.90 (s, 3H), 3.56 (s, 3H), 2.59 (d, J = 3.2 Hz, 3H) |

TABLE C-continued

The following examples were prepared using a similar procedure to that described for Example 1

| Ex. No. | Structure | Compound Name | LCMS [M + H]+ | NMR |
|---|---|---|---|---|
| 442 | 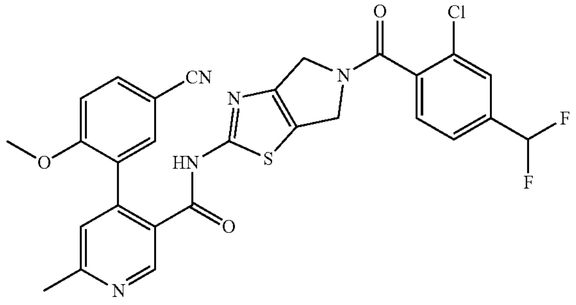 [SMILES: COc1ccc(C#N)cc1-c1cc(C)ncc1C(=O)Nc1nc2c(s1)CN(C(=O)c1ccc(C(F)F)cc1Cl)C2] | N-(5-(2-Chloro-4-(difluoromethyl) benzoyl)-5,6-dihydro-4H-pyrrolo[3,4-d]thiazol-2-yl)-4-(5-cyano-2-methoxyphenyl)-6-methyl-nicotinamide | 580 | $^1$H NMR (400 MHz, DMSO-$d_6$) δ 12.7 (s, 1H), 8.71 (s, 1H), 7.94-7.80 (m, 3H), 7.69 (s, 2H), 7.38 (s, 1H), 7.29-7.09 (m, 2H), 4.80 (s, 1H), 4.67 (s, 1H), 4.42 (s, 1H), 4.32 (s, 1H), 3.56 (s, 3H), 2.56 (s, 3H) |
| 443 | 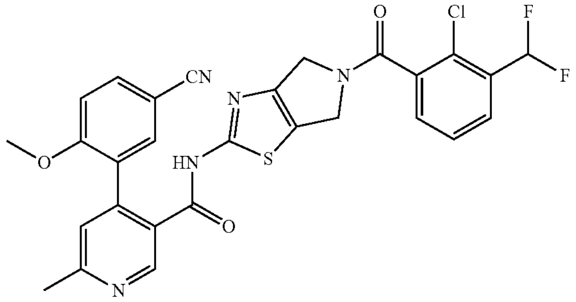 [SMILES: COc1ccc(C#N)cc1-c1cc(C)ncc1C(=O)Nc1nc2c(s1)CN(C(=O)c1cccc(C(F)F)c1Cl)C2] | N-(5-(2-Chloro-3-(difluoromethyl) benzoyl)-5,6-dihydro-4H-pyrrolo[3,4-d]thiazol-2-yl)-4-(5-cyano-2-methoxyphenyl)-6-methyl-nicotinamide | 580 | $^1$H NMR (400 MHz, DMSO-$d_6$) δ 12.7 (d, J = 9.2 Hz, 1H), 8.70 (d, J = 4.8 Hz, 1H), 7.88 (dt, J = 8.8, 2.6 Hz, 1H), 7.84 (d, J = 2.2 Hz, 1H), 7.79 (d, J = 7.6 Hz, 1H), 7.72 (d, J = 7.6 Hz, 1H), 7.63 (dt, J = 8.8, 4.6 Hz, 1H), 7.42-7.12 (m, 3H), 4.82 (s, 1H), 4.68 (s, 1H), 4.42 (s, 1H), 4.31 (s, 1H), 3.56 (s, 3H), 2.57 (d, J = 3.2 Hz, 3H) |
| 444 | 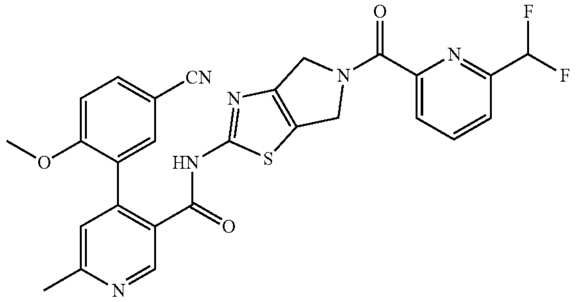 [SMILES: COc1ccc(C#N)cc1-c1cc(C)ncc1C(=O)Nc1nc2c(s1)CN(C(=O)c1cccc(C(F)F)n1)C2] | 4-(5-Cyano-2-methoxyphenyl)-N-(5-(6-(difluoromethyl) picolinoyl)-5,6-dihydro-4H-pyrrolo[3,4-d]thiazol-2-yl)-6-methyl-nicotinamide | 547 | $^1$H NMR (400 MHz, DMSO-$d_6$) δ 12.7 (s, 1H), 8.71 (d, J = 2.6 Hz, 1H), 8.19 (t, J = 7.8 Hz, 1H), 8.00 (dd, J = 10.4, 8.0 Hz, 1H), 7.92-7.83 (m, 3H), 7.40 (s, 1H), 7.22-6.91 (m, 2H), 5.02 (s, 1H), 4.93 (s, 1H), 4.86 (s, 1H), 4.72 (s, 1H), 3.57 (s, 3H), 2.58 (s, 3H) |
| 445 | 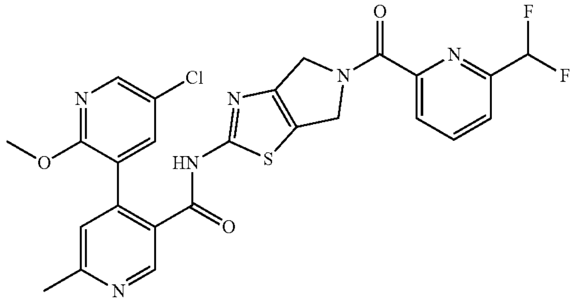 [SMILES: COc1ncc(Cl)cc1-c1cc(C)ncc1C(=O)Nc1nc2c(s1)CN(C(=O)c1cccc(C(F)F)n1)C2] | 5-Chloro-N-(5-(6-(difluoromethyl) picolinoyl)-5,6-dihydro-4H-pyrrolo[3,4-d]thiazol-2-yl)-2-methoxy-6'-methyl-[3,4'-bipyridine]-3'-carboxamide | 557 | $^1$H NMR (400 MHz, DMSO-$d_6$) δ 12.8 (d, J = 19.2 Hz, 1H), 8.75 (d, J = 3.0 Hz, 1H), 8.26 (s, 1H), 8.20 (t, J = 7.8 Hz, 1H), 8.02 (d, J = 9.2 Hz, 1H), 7.99-7.94 (m, 1H), 7.87 (d, J = 7.8 Hz, 1H), 7.45 (s, 1H), 7.07 (td, J = 54.8, 13.4 Hz, 1H), 5.03 (s, 1H), 4.94 (s, 1H), 4.86 (s, 1H), 4.73 (s, 1H), 3.57 (s, 3H), 2.58 (s, 3H) |

TABLE C-continued

The following examples were prepared using a similar procedure to that described for Example 1

| Ex. No. | Structure | Compound Name | LCMS [M + H]+ | NMR |
|---|---|---|---|---|
| 446 | 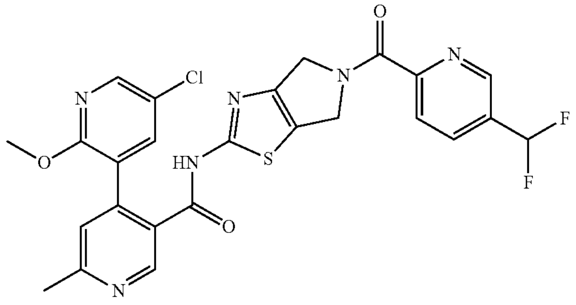 [SMILES: COc1ncc(Cl)cc1-c1cc(C)ncc1C(=O)Nc1nc2c(s1)CN(C(=O)c1ccc(C(F)F)cn1)C2] | 5-Chloro-N-(5-(5-(difluoromethyl)picolinoyl)-5,6-dihydro-4H-pyrrolo[3,4-d]thiazol-2-yl)-2-methoxy-6'-methyl-[3,4'-bipyridine]-3'-carboxamide | 557 | $^1$H NMR (400 MHz, DMSO-$d_6$) δ 12.8 (d, J = 5.6 Hz, 1H), 8.87 (d, J = 7.4 Hz, 1H), 8.75 (s, 1H), 8.26 (d, J = 2.2 Hz, 1H), 8.20 (d, J = 8.2 Hz, 1H), 8.03-7.94 (m, 2H), 7.45 (d, J = 1.8 Hz, 1H), 7.25 (t, J = 55.0 Hz, 1H), 5.01 (s, 1H), 4.91 (s, 1H), 4.87 (s, 1H), 4.73 (s, 1H), 3.57 (s, 3H), 2.58 (d, J = 1.8 Hz, 3H) |
| 447 | 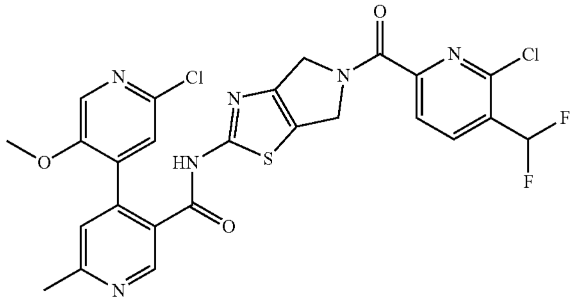 [SMILES: COc1cnc(Cl)cc1-c1cc(C)ncc1C(=O)Nc1nc2c(s1)CN(C(=O)c1ccc(C(F)F)c(Cl)n1)C2] | 2'-Chloro-N-(5-(6-chloro-5-(difluoromethyl)picolinoyl)-5,6-dihydro-4H-pyrrolo[3,4-d]thiazol-2-yl)-5'-methoxy-6-methyl-[4,4'-bipyridine]-3-carboxamide | 591 | $^1$H NMR (400 MHz, DMSO-$d_6$) δ 12.8 (s, 1H), 8.79 (s, 1H), 8.34 (d, J = 8.0 Hz, 1H), 8.17 (s, 1H), 8.04-7.97 (m, 1H), 7.54 (s, 1H), 7.46-7.16 (m, 2H), 5.00 (s, 1H), 4.91 (s, 1H), 4.86 (s, 1H), 4.72 (s, 1H), 3.60 (s, 3H), 2.59 (s, 3H) |
| 448 | 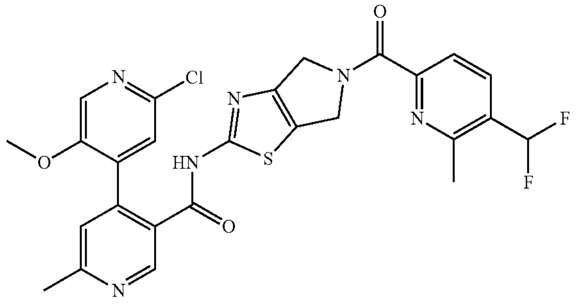 [SMILES: COc1cnc(Cl)cc1-c1cc(C)ncc1C(=O)Nc1nc2c(s1)CN(C(=O)c1ccc(C(F)F)c(C)n1)C2] | 2'-Chloro-N-(5-(5-(difluoromethyl)-6-methylpicolinyl)-5,6-dihydro-4H-pyrrolo[3,4-d]thiazol-2-yl)-5'-methoxy-6-methyl-[4,4'-bipyridine]-3-carboxamide | 571 | $^1$H NMR (400 MHz, DMSO-$d_6$) δ 12.8 (d, J = 11.8 Hz, 1H), 8.78 (d, J = 2.6 Hz, 1H), 8.17 (d, J = 1.6 Hz, 1H), 8.10 (d, J = 8.2 Hz, 1H), 7.78 (t, J = 8.8 Hz, 1H), 7.56 (s, 1H), 7.44 (s, 1H), 7.32 (td, J = 54.8, 2.4 Hz, 1H), 5.01 (s, 1H), 4.92 (s, 1H), 4.85 (s, 1H), 4.72 (s, 1H), 3.60 (s, 3H), 2.66 (d, J = 4.0 Hz, 3H), 2.58 (s, 3H) |
| 449 | 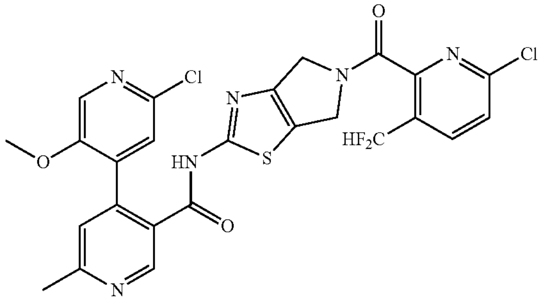 | 2'-Chloro-N-(5-(6-chloro-3-(difluoromethyl)picolinyl)-5,6-dihydro-4H-pyrrolo[3,4-d]thiazol-2-yl)-5'-methoxy-6-methyl-[4,4'-bipyridine]-3-carboxamide | 591 | $^1$H NMR (400 MHz, DMSO-$d_6$) δ 12.8 (s, 1H), 8.78 (d, J = 3.6 Hz, 1H), 8.28 (dd, J = 8.6, 3.6 Hz, 1H), 8.16 (d, J = 3.6 Hz, 1H), 7.86 (d, J = 8.4 Hz, 1H), 7.54 (s, 1H), 7.44 (d, J = 1.6 Hz, 1H), 7.23 (td, J = 54.2, 3.8 Hz, 1H), 4.85 (s, 1H), 4.71 (s, 2H), 4.60 (s, 1H), 3.59 (s, 3H), 2.59 (d, J = 2.2 Hz, 3H) |

TABLE C-continued

The following examples were prepared using a similar procedure to that described for Example 1

| Ex. No. | Structure | Compound Name | LCMS [M + H]+ | NMR |
|---|---|---|---|---|
| 450 | 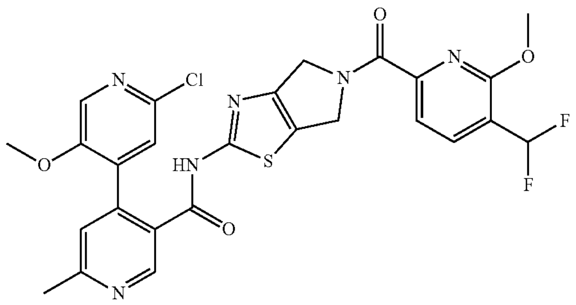 [SMILES: COc1cnc(Cl)cc1-c1cc(C)ncc1C(=O)Nc1nc2c(s1)CN(C(=O)c1ccc(C(F)F)c(OC)n1)C2] | 2'-Chloro-N-(5-(5-(difluoromethyl)-6-methoxy-picolinoyl)-5,6-dihydro-4H-pyrrolo[3,4-d]thiazol-2-yl)-5'-methoxy-6-methyl-[4,4'-bipyridine]-3-carboxamide | 587 | $^1$H NMR (400 MHz, DMSO-$d_6$) δ 12.8 (d, J = 12.8 Hz, 1H), 8.78 (d, J = 4.4 Hz, 1H), 8.17 (d, J = 3.2 Hz, 1H), 8.12 (d, J = 7.8 Hz, 1H), 7.65-7.59 (m, 1H), 7.55 (d, J = 1.2 Hz, 1H), 7.44 (s, 1H), 7.13 (td, J = 54.4, 2.4 Hz, 1H), 5.15 (s, 1H), 5.05 (s, 1H), 4.86 (s, 1H), 4.72 (s, 1H), 4.03 (s, 3H), 3.60 (s, 3H), 2.59 (s, 3H) |
| 451 | 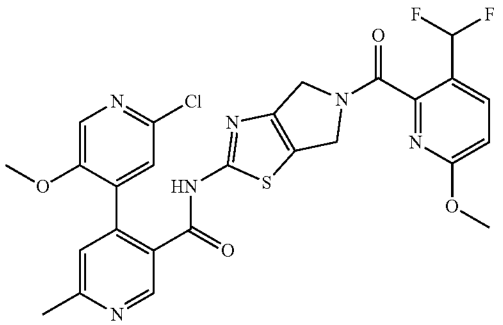 | 2'-Chloro-N-(5-(3-(difluoromethyl)-6-methoxy-picolinoyl)-5,6-dihydro-4H-pyrrolo[3,4-d]thiazol-2-yl)-5'-methoxy-6-methyl-[4,4'-bipyridine]-3-carboxamide | 587 | $^1$H NMR (400 MHz, DMSO-$d_6$) δ 12.8 (d, J = 7.0 Hz, 1H), 8.78 (d, J = 5.0 Hz, 1H), 8.16 (d, J = 4.5 Hz, 1H), 8.09 (d, J = 9.6 Hz, 1H), 7.54 (s, 1H), 7.44 (s, 1H), 7.14 (t, J = 54.8 Hz, 1H), 7.10 (d, J = 8.4 Hz, 1H), 4.85 (s, 1H), 4.76 (s, 1H), 4.71 (s, 1H), 4.65 (s, 1H), 3.95 (s, 3H), 3.60 (s, 3H), 2.59 (s, 3H) |
| 452 | 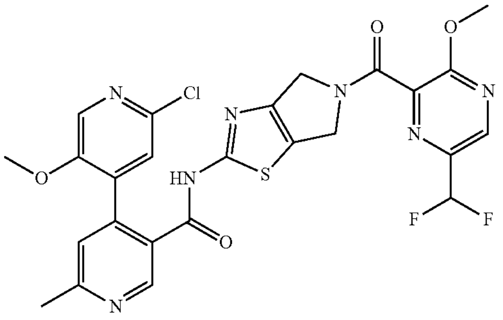 [SMILES: COc1cnc(Cl)cc1-c1cc(C)ncc1C(=O)Nc1nc2c(s1)CN(C(=O)c1nc(C(F)F)cnc1OC)C2] | 2'-Chloro-N-(5-(6-(difluoromethyl)-3-methoxypyrazine-2-carbonyl)-5,6-dihydro-4H-pyrrolo[3,4-d]thiazol-2-yl)-5'-methoxy-6-methyl-[4,4'-bipyridine]-3-carboxamide | 588 | $^1$H NMR (400 MHz, DMSO-$d_6$) δ 12.8 (s, 1H), 8.78 (d, J = 6.0 Hz, 1H), 8.70 (d, J = 1.2 Hz, 1H), 8.16 (d, J = 3.4 Hz, 1H), 7.54 (s, 1H), 7.43 (s, 1H), 7.11 (td, J = 54.2, 1.6 Hz, 1H), 4.84 (s, 1H), 4.71 (s, 1H), 4.60 (s, 1H), 4.50 (s, 1H), 4.03 (s, 3H), 3.60 (s, 3H), 2.59 (d, J = 2.4 Hz, 3H) |
| 453 | 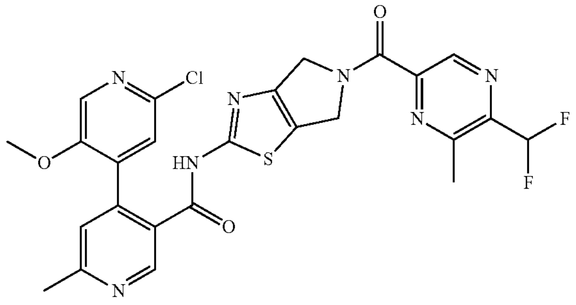 [SMILES: COc1cnc(Cl)cc1-c1cc(C)ncc1C(=O)Nc1nc2c(s1)CN(C(=O)c1cnc(C(F)F)c(C)n1)C2] | 2'-chloro-N-(5-(5-(difluoromethyl)-6-methylpyrazine-2-carbonyl)-5,6-dihydro-4H-pyrrolo[3,4-d]thiazol-2-yl)-5'-methoxy-6-methyl-[4,4'-bipyridine]-3-carboxamide | 572 | $^1$H NMR (400 MHz, DMSO-$d_6$) δ 12.8 (d, J = 14.4 Hz, 1H), 8.94 (d, J = 3.8 Hz, 1H), 8.79 (d, J = 2.4 Hz, 1H), 8.17 (s, 1H), 7.54 (s, 1H), 7.44 (s, 1H), 7.26 (t, J = 52.8 Hz, 1H), 5.04 (s, 1H), 4.92 (s, 1H), 4.88 (s, 1H), 4.75 (s, 1H), 3.60 (s, 3H), 2.76-2.70 (m, 3H), 2.59 (s, 3H) |

TABLE C-continued

The following examples were prepared using a similar procedure to that described for Example 1

| Ex. No. | Structure | Compound Name | LCMS [M + H]+ | NMR |
|---|---|---|---|---|
| 454 | 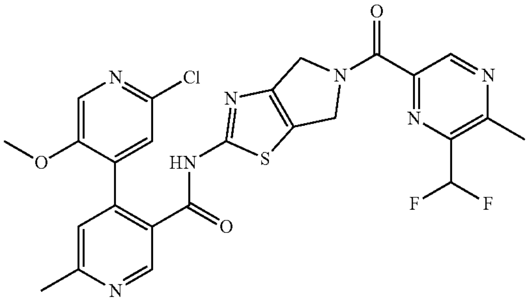 | 2'-chloro-N-(5-(6-(difluoromethyl)-5-methylpyrazine-2-carbonyl)-5,6-dihydro-4H-pyrrolo[3,4-d]thiazol-2-yl)-5'-methoxy-6-methyl-[4,4'-bipyridine]-3-carboxamide | 572 | $^1$H NMR (400 MHz, DMSO-$d_6$) δ 12.8 (d, J = 19.4 Hz, 1H), 9.11 (d, J = 6.6 Hz, 1H), 8.79 (d, J = 2.8 Hz, 1H), 8.17 (d, J = 1.6 Hz, 1H), 7.55 (s, 1H), 7.44 (s, 1H), 7.22 (dd, J = 53.4, 16.4 Hz, 1H), 5.10 (s, 1H), 4.99 (s, 1H), 4.88 (s, 1H), 4.75 (s, 1H), 3.60 (s, 3H), 2.73 (s, 3H), 2.59 (s, 3H) |
| 455 | 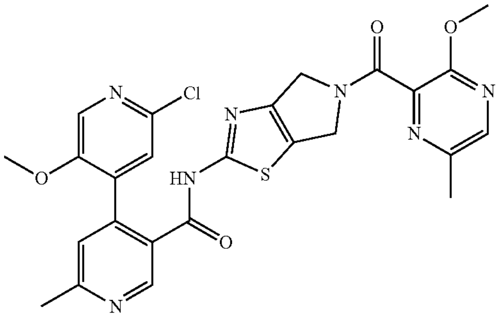 | 2'-Chloro-5'-methoxy-N-(5-(3-methoxy-6-methylpyrazine-2-carbonyl)-5,6-dihydro-4H-pyrrolo[3,4-d]thiazol-2-yl)-6-methyl-[4,4'-bipyridine]-3-carboxamide | 552 | $^1$H NMR (400 MHz, DMSO-$d_6$) δ 12.8 (s, 1H), 8.78 (d, J = 5.6 Hz, 1H), 8.24 (s, 1H), 8.16 (d, J = 3.2 Hz, 1H), 7.54 (s, 1H), 7.43 (d, J = 1.4 Hz, 1H), 4.81 (s, 1H), 4.67 (s, 1H), 4.55 (s, 1H), 4.44 (s, 1H), 3.93 (s, 3H), 3.60 (s, 3H), 2.59 (d, J = 2.4 Hz, 3H), 2.45 (d, J = 1.8 Hz, 3H) |
| 456 | 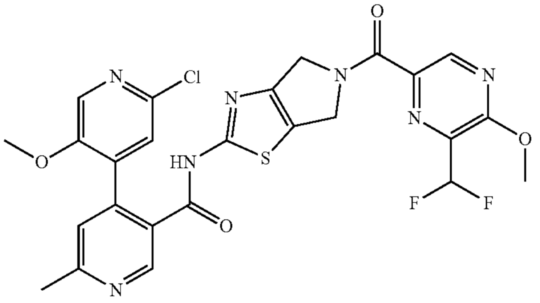 | 2'-Chloro-N-(5-(6-(difluoromethyl)-5-methoxypyrazine-2-carbonyl)-5,6-dihydro-4H-pyrrolo[3,4-d]thiazol-2-yl)-5'-methoxy-6-methyl-[4,4'-bipyridine]-3-carboxamide | 588 | $^1$H NMR (400 MHz, DMSO-$d_6$) δ 12.8 (d, J = 14.4 Hz, 1H), 8.92-8.88 (m, 1H), 8.79 (d, J = 2.6 Hz, 1H), 8.17 (d, J = 1.8 Hz, 1H), 7.55 (s, 1H), 7.44 (s, 1H), 7.16 (td, J = 53.2, 12.7 Hz, 1H), 5.11 (s, 1H), 5.00 (s, 1H), 4.87 (s, 1H), 4.73 (s, 1H), 4.08 (s, 3H), 3.60 (s, 3H), 2.59 (s, 3H) |
| 457 | 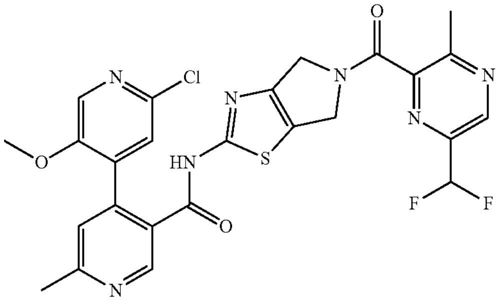 [SMILES: COc1cnc(Cl)cc1-c1cc(C)ncc1C(=O)Nc1nc2c(s1)CN(C(=O)c1nc(C(F)F)cnc1C)C2] | 2'-Chloro-N-(5-(6-(difluoromethyl)-3-methylpyrazine-2-carbonyl)-5,6-dihydro-4H-pyrrolo[3,4-d]thiazol-2-yl)-5'-methoxy-6-methyl-[4,4'-bipyridine]-3-carboxamide | 572 | $^1$H NMR (400 MHz, DMSO-$d_6$) δ 12.8 (s, 1H), 8.97 (s, 1H), 8.78 (d, J = 6.2 Hz, 1H), 8.16 (d, J = 3.0 Hz, 1H), 7.54 (s, 1H), 7.43 (s, 1H), 7.16 (td, J = 54.2, 3.9 Hz, 1H), 4.88 (s, 1H), 4.75 (s, 1H), 4.65 (s, 1H), 4.55 (s, 1H), 3.59 (s, 3H), 2.65 (s, 3H), 2.59 (d, J = 2.2 Hz, 3H) |

TABLE C-continued

The following examples were prepared using a similar procedure to that described for Example 1

| Ex. No. | Structure | Compound Name | LCMS [M + H]+ | NMR |
|---|---|---|---|---|
| 458 | 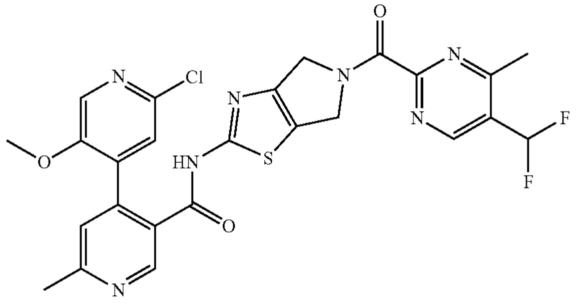 [SMILES: COc1cnc(Cl)cc1-c1cc(C)ncc1C(=O)Nc1nc2c(s1)CN(C(=O)c1ncc(C(F)F)c(C)n1)C2] | 2'-Chloro-N-(5-(5-(difluoromethyl)-4-methylpyrimidine-2-carbonyl)-5,6-dihydro-4H-pyrrolo[3,4-d]thiazol-2-yl)-5'-methoxy-6-methyl-[4,4'-bipyridine]-3-carboxamide | 572 | $^1$H NMR (400 MHz, DMSO-$d_6$) δ 12.8 (d, J = 11.2 Hz, 1H), 9.02 (s, 1H), 8.78 (d, J = 4.2 Hz, 1H), 8.17 (d, J = 2.6 Hz, 1H), 7.54 (s, 1H), 7.52-7.23 (m, 2H), 4.85 (s, 1H), 4.72 (s, 2H), 4.63 (s, 1H), 3.60 (s, 3H), 2.66 (s, 3H), 2.59 (d, J = 2.2 Hz, 3H) |
| 459 | 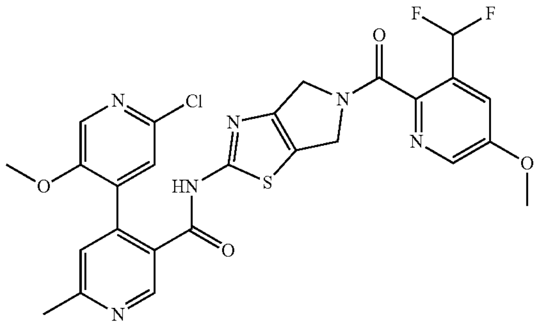 | 2'-Chloro-N-(5-(3-(difluoromethyl)-5-methoxy-picolinoyl)-5,6-dihydro-4H-pyrrolo[3,4-d]thiazol-2-yl)-5'-methoxy-6-methyl-[4,4'-bipyridine]-3-carboxamide | 587 | $^1$H NMR (400 MHz, DMSO-$d_6$) δ 12.8 (s, 1H), 8.78 (d, J = 3.8 Hz, 1H), 8.49 (t, J = 3.8 Hz, 1H), 8.16 (d, J = 2.8 Hz, 1H), 7.69 (t, J = 2.8 Hz, 1H), 7.54 (s, 1H), 7.43 (s, 1H), 7.25 (td, J = 54.8, 3.2 Hz, 1H), 4.83 (s, 1H), 4.73 (s, 1H), 4.70 (s, 1H), 4.63 (s, 1H), 3.97 (d, J = 2.4 Hz, 3H), 3.60 (s, 3H), 2.59 (d, J = 2.4 Hz, 3H) |
| 460 | 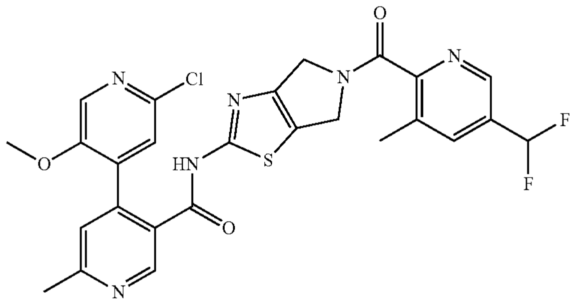 [SMILES: COc1cnc(Cl)cc1-c1cc(C)ncc1C(=O)Nc1nc2c(s1)CN(C(=O)c1ncc(C(F)F)cc1C)C2] | 2'-Chloro-N-(5-(5-(difluoromethyl)-3-methylpicolinoyl)-5,6-dihydro-4H-pyrrolo[3,4-d]thiazol-2-yl)-5'-methoxy-6-methyl-[4,4'-bipyridine]-3-carboxamide | 571 | $^1$H NMR (400 MHz, DMSO-$d_6$) δ 12.8 (d, J = 4.2 Hz, 1H), 8.78 (d, J = 4.6 Hz, 1H), 8.66 (s, 1H), 8.16 (d, J = 2.8 Hz, 1H), 8.03 (s, 1H), 7.54 (s, 1H), 7.43 (d, J = 2.4 Hz, 1H), 7.19 (dt, J = 55.2, 1.6 Hz, 1H), 4.85 (s, 1H), 4.72 (s, 1H), 4.52 (s, 1H), 4.42 (s, 1H), 3.60 (s, 3H), 2.58 (d, J = 3.2 Hz, 3H), 2.38 (s, 3H) |
| 461 | 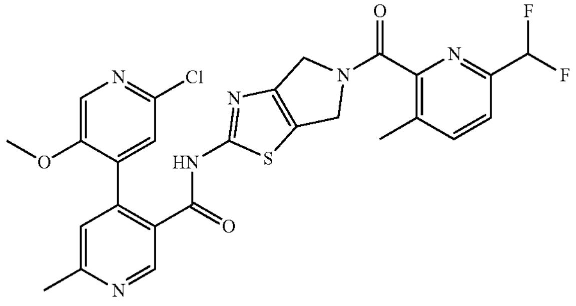 [SMILES: COc1cnc(Cl)cc1-c1cc(C)ncc1C(=O)Nc1nc2c(s1)CN(C(=O)c1nc(C(F)F)ccc1C)C2] | 2'-Chloro-N-(5-(6-(difluoromethyl)-3-methylpicolinoyl)-5,6-dihydro-4H-pyrrolo[3,4-d]thiazol-2-yl)-5'-methoxy-6-methyl-[4,4'-bipyridine]-3-carboxamide | 571 | $^1$H NMR (400 MHz, DMSO-$d_6$) δ 12.8 (s, 1H), 8.78 (d, J = 6.4 Hz, 1H), 8.16 (d, J = 3.4 Hz, 1H), 8.03-7.96 (m, 1H), 7.72 (d, J = 8.0 Hz, 1H), 7.54 (d, J = 1.6 Hz, 1H), 7.43 (s, 1H), 6.99 (td, J = 54.8, 4.4 Hz, 1H), 4.88-4.83 (m, 1H), 4.74-4.69 (m, 1H), 4.57-4.52 (m, 1H), 4.47-4.42 (m, 1H), 3.59 (s, 3H), 2.59 (d, J = 2.4 Hz, 3H), 2.39 (s, 3H) |

TABLE C-continued

The following examples were prepared using a similar procedure to that described for Example 1

| Ex. No. | Structure | Compound Name | LCMS [M + H]+ | NMR |
|---|---|---|---|---|
| 462 | 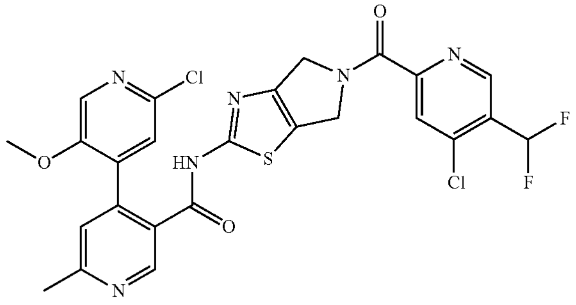 [SMILES: COc1cnc(Cl)cc1-c1cc(C)ncc1C(=O)Nc1nc2c(s1)CN(C(=O)c1cc(Cl)c(C(F)F)cn1)C2] | 2'-Chloro-N-(5-(4-chloro-5-(difluoromethyl) picolinoyl)-5,6-dihydro-4H-pyrrolo[3,4-d]thiazol-2-yl)-5'-methoxy-6-methyl-[4,4'-bipyridine]-3-carboxamide | 591 | $^1$H NMR (400 MHz, DMSO-$d_6$) δ 12.8 (d, J = 3.6 Hz, 1H), 8.91 (d, J = 9.2 Hz, 1H), 8.79 (s, 1H), 8.17 (s, 1H), 8.07 (s, 1H), 7.54 (s, 1H), 7.44 (s, 1H), 7.38 (t, J = 53.6 Hz, 1H), 5.01 (s, 1H), 4.90 (s, 1H), 4.87 (s, 1H), 4.73 (s, 1H), 3.60 (s, 3H), 2.59 (s, 3H) |
| 463 | 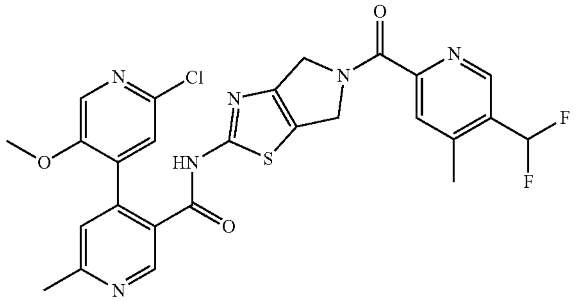 [SMILES: COc1cnc(Cl)cc1-c1cc(C)ncc1C(=O)Nc1nc2c(s1)CN(C(=O)c1cc(C)c(C(F)F)cn1)C2] | 2'-Chloro-N-(5-(5-(difluoromethyl)-4-methylpicolinoyl)-5,6-dihydro-4H-pyrrolo[3,4-d]thiazol-2-yl)-5'-methoxy-6-methyl-[4,4'-bipyridine]-3-carboxamide | 571 | $^1$H NMR (400 MHz, DMSO-$d_6$) δ 12.8 (s, 1H), 8.79 (s, 1H), 8.73 (d, J = 8.4 Hz, 1H), 8.17 (s, 1H), 7.97-7.81 (m, 1H), 7.54 (s, 1H), 7.43 (s, 1H), 7.33 (t, J = 54.0 Hz, 1H), 5.00 (s, 1H), 4.90 (s, 1H), 4.86 (s, 1H), 4.72 (s, 1H), 3.60 (s, 3H), 2.59 (s, 3H), 3H obscured by solvent peak |
| 464 | 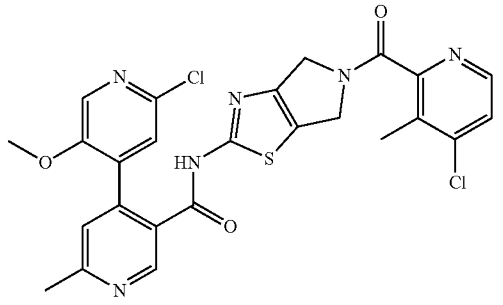 [SMILES: COc1cnc(Cl)cc1-c1cc(C)ncc1C(=O)Nc1nc2c(s1)CN(C(=O)c1nccc(Cl)c1C)C2] | 2'-chloro-N-(5-(4-chloro-3-methylpicolinoyl)-5,6-dihydro-4H-pyrrolo[3,4-d]thiazol-2-yl)-5'-methoxy-6-methyl-[4,4'-bipyridine]-3-carboxamide | 555 | $^1$H NMR (400 MHz, DMSO-$d_6$) δ 12.8 (s, 1H), 8.78 (d, J = 4.8 Hz, 1H), 8.43 (d, J = 5.4 Hz, 1H), 8.16 (s, 1H), 7.65 (d, J = 5.4 Hz, 1H), 7.54 (s, 1H), 7.43 (s, 1H), 4.85 (s, 1H), 4.71 (s, 1H), 4.51 (s, 1H), 4.41 (s, 1H), 3.60 (s, 3H), 2.59 (s, 3H), 2.34 (s, 3H) |
| 465 | 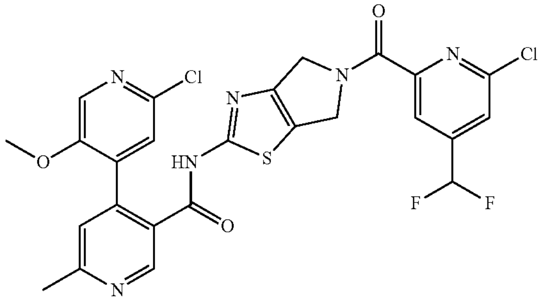 [SMILES: COc1cnc(Cl)cc1-c1cc(C)ncc1C(=O)Nc1nc2c(s1)CN(C(=O)c1cc(C(F)F)cc(Cl)n1)C2] | 2'-Chloro-N-(5-(6-chloro-4-(difluoromethyl) picolinoyl)-5,6-dihydro-4H-pyrrolo[3,4-d]thiazol-2-yl)-5'-methoxy-6-methyl-[4,4'-bipyridine]-5-carboxamide | 591 | $^1$H NMR (400 MHz, DMSO-$d_6$) δ 12.8 (s, 1H), 8.79 (s, 1H), 8.17 (s, 1H), 8.03 (d, J = 9.2 Hz, 1H), 7.95 (s, 1H), 7.55 (s, 1H), 7.44 (s, 1H), 7.20 (t, J = 54.8 Hz, 1H), 5.03 (s, 1H), 4.94 (s, 1H), 4.87 (s, 1H), 4.73 (s, 1H), 3.60 (s, 3H), 2.59 (s, 3H) |

TABLE C-continued

The following examples were prepared using a similar procedure to that described for Example 1

| Ex. No. | Structure | Compound Name | LCMS [M + H]+ | NMR |
|---|---|---|---|---|
| 466 | 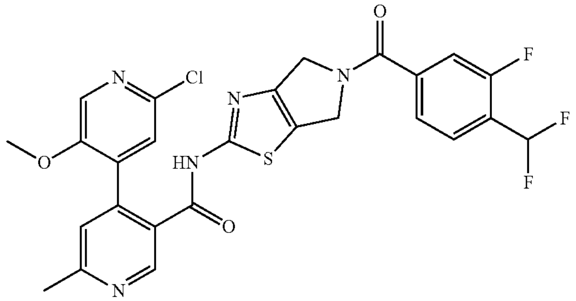 [SMILES: COc1cnc(Cl)cc1-c1cc(C)ncc1C(=O)Nc1nc2c(s1)CN(C(=O)c1ccc(C(F)F)c(F)c1)C2] | 2'-Chloro-N-(5-(4-(difluoromethyl)-3-fluorobenzoyl)-5,6-dihydro-4H-pyrrolo[3,4-d]thiazol-2-yl)-5'-methoxy-6-methyl-[4,4'-bipyridine]-3-carboxamide | 574 | $^1$H NMR (400 MHz, DMSO-$d_6$) δ 12.8 (d, J = 6.8 Hz, 1H), 8.78 (d, J = 3.0 Hz, 1H), 8.16 (s, 1H), 7.75 (t, J = 7.6 Hz, 1H), 7.65 (d, J = 10.6 Hz, 1H), 7.60-7.53 (m, 2H), 7.43 (d, J = 2.4 Hz, 1H), 7.27 (t, J = 54.2 Hz, 1H), 4.82 (s, 1H), 4.68 (s, 2H), 4.60 (s, 1H), 3.59 (s, 3H), 2.59 (d, J = 2.4 Hz, 3H) |
| 467 | 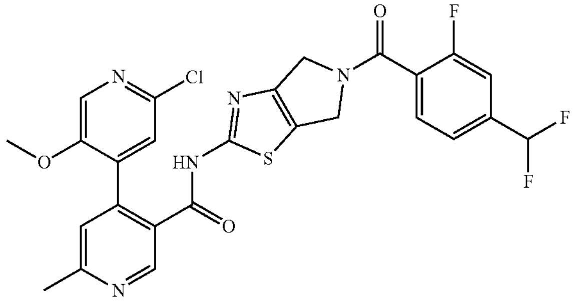 [SMILES: COc1cnc(Cl)cc1-c1cc(C)ncc1C(=O)Nc1nc2c(s1)CN(C(=O)c1ccc(C(F)F)cc1F)C2] | 2'-Chloro-N-(5-(4-(difluoromethyl)-2-fluorobenzoyl)-5,6-dihydro-4H-pyrrolo[3,4-d]thiazol-2-yl)-5'-methoxy-6-methyl-[4,4'-bipyridine]-3-carboxamide | 574 | $^1$H NMR (400 MHz, DMSO-$d_6$) δ 12.8 (d, J = 9.0 Hz, 1H), 8.78 (d, J = 4.0 Hz, 1H), 8.16 (d, J = 2.0 Hz, 1H), 7.72 (t, J = 7.2 Hz, 1H), 7.61 (dd, J = 9.8, 3.6 Hz, 1H), 7.55 (d, J = 7.2 Hz, 2H), 7.43 (d, J = 2.8 Hz, 1H), 7.11 (t, J = 55.4 Hz, 1H), 4.83 (s, 1H), 4.69 (s, 1H), 4.55 (s, 1H), 4.45 (s, 1H), 3.59 (s, 3H), 2.58 (d, J = 2.8 Hz, 3H) |
| 468 | 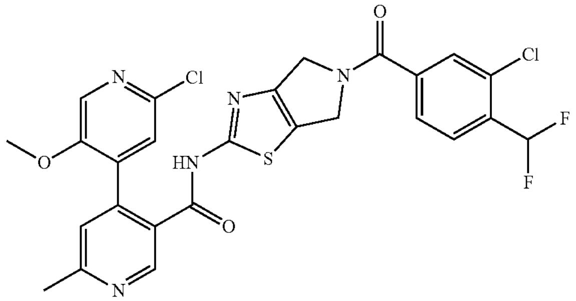 [SMILES: COc1cnc(Cl)cc1-c1cc(C)ncc1C(=O)Nc1nc2c(s1)CN(C(=O)c1ccc(C(F)F)c(Cl)c1)C2] | 2'-chloro-N-(5-(3-chloro-4-(difluoromethyl)benzoyl)-5,6-dihydro-4H-pyrrolo[3,4-d]thiazol-2-yl)-5'-methoxy-6-methyl-[4,4'-bipyridine]-3-carboxamide | 590 | $^1$H NMR (400 MHz, DMSO-$d_6$) δ 12.8 (s, 1H), 8.78 (d, J = 3.0 Hz, 1H), 8.16 (s, 1H), 7.84 (s, 1H), 7.80 (d, J = 8.0 Hz, 1H), 7.72 (t, J = 8.4 Hz, 1H), 7.54 (s, 1H), 7.43 (s, 1H), 7.27 (t, J = 54.2 Hz, 1H), 4.82 (s, 1H), 4.68 (s, 2H), 4.60 (s, 1H), 3.59 (s, 3H), 2.58 (d, J = 2.2 Hz, 3H) |
| 469 | 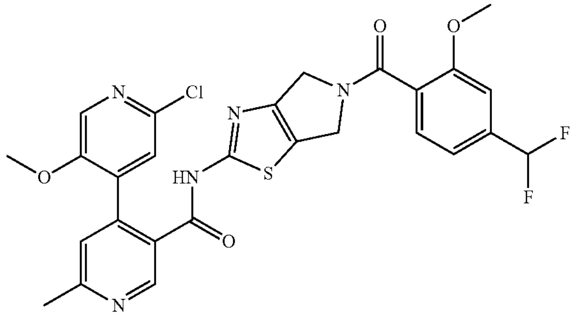 [SMILES: COc1cc(C(F)F)ccc1C(=O)N1Cc2nc(NC(=O)c3cnc(C)cc3-c3cc(Cl)ncc3OC)sc2C1] | 2'-Chloro-N-(5-(4-(difluoromethyl)-2-methoxybenzoyl)-5,6-dihydro-4H-pyrrolo[3,4-d]thiazol-2-yl)-5'-methoxy-6-methyl-[4,4'-bipyridine]-3-carboxamide | 586 | $^1$H NMR (400 MHz, Chloroform-d) δ 8.83 (d, J = 11.8 Hz, 1H), 8.04 (d, J = 4.8 Hz, 1H), 7.37-7.28 (m, 1H), 7.23 (d, J = 4.6 Hz, 1H), 7.16-7.04 (m, 2H), 7.03-6.86 (m, 1H), 6.63 (td, J = 56.2, 11.0 Hz, 1H), 4.88 (s, 1H), 4.51 (s, 1H), 4.26 (s, 1H), 3.90-3.79 (m, 4H), 3.69 (d, J = 2.2 Hz, 3H), 2.68 (d, J = 5.0 Hz, 3H) |

TABLE C-continued

The following examples were prepared using a similar procedure to that described for Example 1

| Ex. No. | Structure | Compound Name | LCMS [M + H]+ | NMR |
| --- | --- | --- | --- | --- |
| 470 | 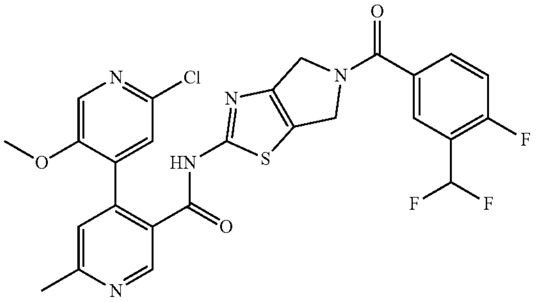 | 2'-Chloro-N-(5-(3-(difluoromethyl)-4-fluorobenzoyl)-5,6-dihydro-4H-pyrrolo[3,4-d]thiazol-2-yl)-5'-methoxy-6-methyl-[4,4'-bipyridine]-3-carboxamide | 574 | $^1$H NMR (400 MHz, DMSO-$d_6$) δ 12.8 (s, 1H), 8.78 (s, J = 3.4 Hz, 1H), 8.16 (s, 1H), 7.96-7.86 (m, 2H), 7.54 (s, 1H), 7.49 (t, J = 9.4 Hz, 1H), 7.43 (s, 1H), 7.25 (t, J = 54.0 Hz, 1H), 4.82 (s, 1H), 4.72 (s, 1H), 4.68 (s, 1H), 4.64 (s, 1H), 3.59 (s, 3H), 2.58 (s, 3H) |
| 471 | 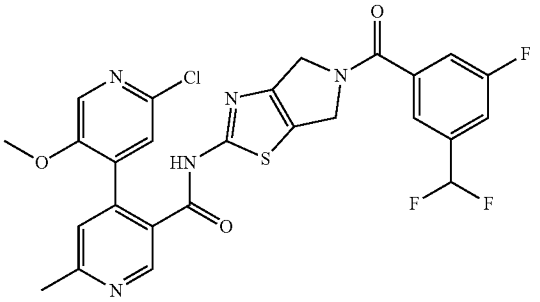 [SMILES: COc1cnc(Cl)cc1-c1cc(C)ncc1C(=O)Nc1nc2c(s1)CN(C(=O)c1cc(F)cc(C(F)F)c1)C2] | 2'-Chloro-N-(5-(3-(difluoromethyl)-5-fluorobenzoyl)-5,6-dihydro-4H-pyrrolo[3,4-d]thiazol-2-yl)-5'-methoxy-6-methyl-[4,4'-bipyridine]-3-carboxamide | 574 | $^1$H NMR (400 MHz, Chloroform-d) δ 10.4 (s, 1H), 8.84 (s, 1H), 8.05 (s, 1H), 7.53-7.43 (m, 1H), 7.38-2.26 (m, 2H), 7.21 (s, 1H), 7.12 (s, 1H), 6.64 (t, J = 56.0 Hz, 1H), 4.94 (s, 1H), 4.70 (s, 1H), 4.46 (s, 1H), 4.18 (s, 1H), 3.72 (s, 3H), 2.68 (s, 3H) |
| 472 | 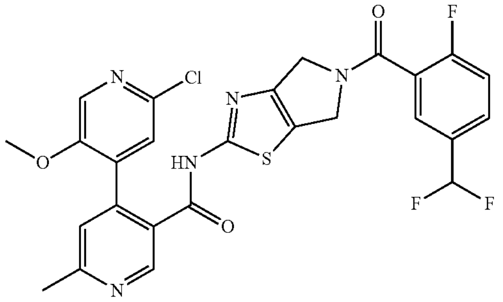 [SMILES: COc1cnc(Cl)cc1-c1cc(C)ncc1C(=O)Nc1nc2c(s1)CN(C(=O)c1cc(C(F)F)ccc1F)C2] | 2'-Chloro-N-(5-(5-(difluoromethyl)-2-fluorobenzoyl)-5,6-dihydro-4H-pyrrolo[3,4-d]thiazol-2-yl)-5'-methoxy-6-methyl-[4,4'-bipyridine]-3-carboxamide | 574 | $^1$H NMR (400 MHz, DMSO-$d_6$) δ 12.8 (d, J = 8.2 Hz, 1H), 8.78 (d, J = 4.8 Hz, 1H), 8.16 (d, J = 2.8 Hz, 1H), 7.82-7.74 (m, 2H), 7.53 (d, J = 6.2 Hz, 2H), 7.43 (d, J = 2.4 Hz, 1H), 7.08 (t, J = 55.6 Hz, 1H), 4.83 (t, J = 2.8 Hz, 1H), 4.69 (t, J = 2.6 Hz, 1H), 4.56 (t, J = 2.8 Hz, 1H), 4.46 (t, J = 2.8 Hz, 1H), 3.59 (s, 3H), 2.59 (d, J = 2.8 Hz, 3H) |
| 473 | 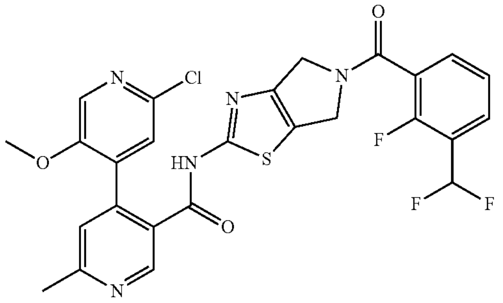 [SMILES: COc1cnc(Cl)cc1-c1cc(C)ncc1C(=O)Nc1nc2c(s1)CN(C(=O)c1cccc(C(F)F)c1F)C2] | 2'-Chloro-N-(5-(3-(difluoromethyl)-2-fluorobenzoyl)-5,6-dihydro-4H-pyrrolo[3,4-d]thiazol-2-yl)-5'-methoxy-6-methyl-[4,4'-bipyridine]-3-carboxamide | 574 | $^1$H NMR (400 MHz, DMSO-$d_6$) δ 12.8 (d, J = 4.8 Hz, 1H), 8.78 (d, J = 4.8 Hz, 1H), 8.16 (d, J = 2.6 Hz, 1H), 7.77 (t, J = 7.2 Hz, 2H), 7.54 (s, 1H), 7.50-7.42 (m, 2H), 7.27 (t, J = 54.2 Hz, 1H), 4.83 (s, 1H), 4.69 (s, 1H), 4.56 (s, 1H), 4.45 (s, 1H), 3.59 (s, 3H), 2.58 (d, J = 2.6 Hz, 3H) |

TABLE C-continued

The following examples were prepared using a similar procedure to that described for Example 1

| Ex. No. | Structure | Compound Name | LCMS [M + H]+ | NMR |
|---|---|---|---|---|
| 474 | 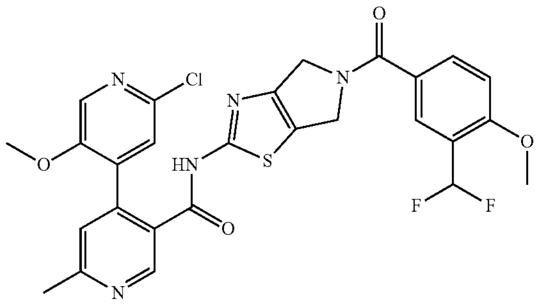 | 2'-chloro-N-(5-(3-(difluoromethyl)-4-methoxybenzoyl)-5,6-dihydro-4H-pyrrolo[3,4-d]thiazol-2-yl)-5'-methoxy-6-methyl-[4,4'-bipyridine]-3-carboxamide | 586 | $^1$H NMR (400 MHz, DMSO-$d_6$) δ 12.8 (d, J = 6.4 Hz, 1H), 8.78 (d, J = 3.2 Hz, 1H), 8.17 (s, 1H), 7.91-7.81 (m, 1H), 7.78-7.73 (m, 1H), 7.54 (s, 1H), 7.43 (s, 1H), 7.25 (s, 1H), 7.11 (t, J = 54.8 Hz, 1H), 4.82 (s, 1H), 4.76 (s, 1H), 4.67 (s, 2H), 3.92 (d, J = 2.2 Hz, 3H), 3.59 (s, 3H), 2.59 (s, 3H) |
| 475 | 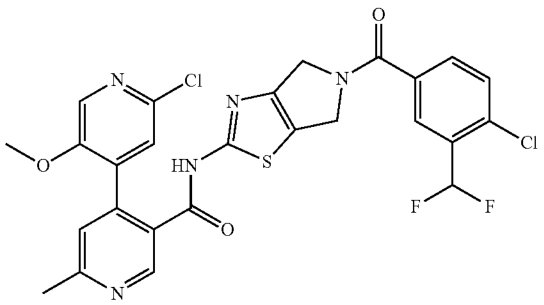 [SMILES: COc1cnc(Cl)cc1-c1cc(C)ncc1C(=O)Nc1nc2c(s1)CN(C(=O)c1ccc(Cl)c(C(F)F)c1)C2] | 2'-Chloro-N-(5-(4-chloro-3-(difluoromethyl)benzoyl)-5,6-dihydro-4H-pyrrolo[3,4-d]thiazol-2-yl)-5'-methoxy-6-methyl-[4,4'-bipyridine]-3-carboxamide | 590 | $^1$H NMR (400 MHz, DMSO-$d_6$) δ 12.8 (s, 1H), 8.78 (d, J = 3.6 Hz, 1H), 8.16 (s, 1H), 7.90 (s, 1H), 7.84 (t, J = 9.8 Hz, 1H), 7.72 (d, J = 8.2 Hz, 1H), 7.54 (s, 1H), 7.43 (s, 1H), 7.26 (t, J = 54.0 Hz, 1H), 4.82 (s, 1H), 4.70 (s, 1H), 4.68 (s, 1H), 4.62 (s, 1H), 3.59 (s, 3H), 2.58 (s, 3H) |
| 476 | 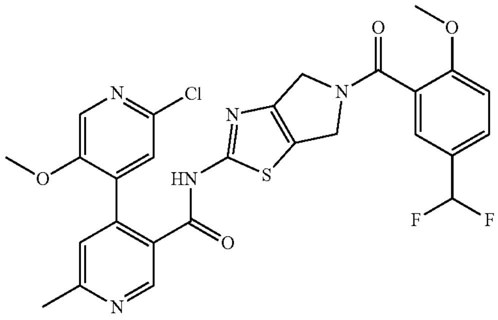 [SMILES: COc1ccc(C(F)F)cc1C(=O)N1Cc2nc(NC(=O)c3cnc(C)cc3-c3cc(Cl)ncc3OC)sc2C1] | 2'-Chloro-N-(5-(5-(difluoromethyl)-2-methoxybenzoyl)-5,6-dihydro-4H-pyrrolo[3,4-d]thiazol-2-yl)-5'-methoxy-6-methyl-[4,4'-bipyridine]-3-carboxamide | 586 | $^1$H NMR (400 MHz, DMSO-$d_6$) δ 12.8 (s, 1H), 8.77 (d, J = 5.2 Hz, 1H), 8.16 (d, J = 4.6 Hz, 1H), 7.65 (d, J = 8.8 Hz, 1H), 7.53 (s, 1H), 7.51 (d, J = 2.2 Hz, 1H), 7.43 (d, J = 1.6 Hz, 1H), 7.27 (d, J = 8.6 Hz, 1H), 6.99 (t, J = 56.0 Hz, 1H), 4.77 (s, 1H), 4.63 (s, 1H), 4.44 (s, 1H), 4.33 (s, 1H), 3.87 (d, J = 3.2 Hz, 3H), 3.59 (s, 3H), 2.58 (d, J = 2.6 Hz, 3H) |
| 477 | 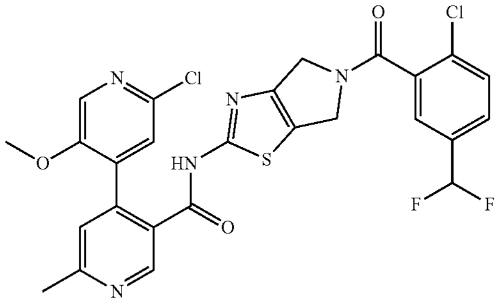 | 2'-chloro-N-(5-(2-chloro-5-(difluoromethyl)benzoyl)-5,6-dihydro-4H-pyrrolo[3,4-d]thiazol-2-yl)-5'-methoxy-6-methyl-[4,4'-bipyridine]-3-carboxamide | 590 | $^1$H NMR (400 MHz, DMSO-$d_6$) δ 12.8 (s, 1H), 8.78 (d, J = 5.0 Hz, 1H), 8.16 (d, J = 3.8 Hz, 1H), 7.80-7.73 (m, 2H), 7.70 (d, J = 8.4 Hz, 1H), 7.54 (s, 1H), 7.43 (d, J = 2.4 Hz, 1H), 7.09 (t, J = 55.4 Hz, 1H), 4.83 (s, 1H), 4.68 (s, 1H), 4.45 (s, 1H), 4.34 (s, 1H), 3.59 (s, 3H), 2.58 (d, J = 3.0 Hz, 3H) |

TABLE C-continued

The following examples were prepared using a similar procedure to that described for Example 1

| Ex. No. | Structure | Compound Name | LCMS [M + H]+ | NMR |
|---|---|---|---|---|
| 478 | 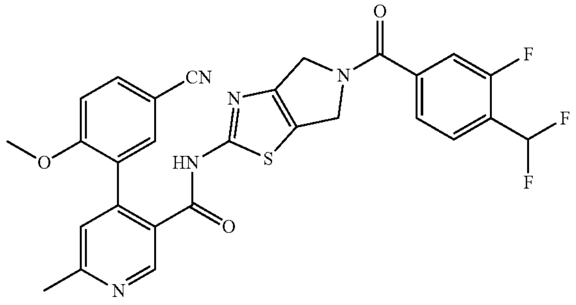 [SMILES: COc1ccc(C#N)cc1-c1cc(C)ncc1C(=O)Nc1nc2c(s1)CN(C(=O)c1ccc(C(F)F)c(F)c1)C2] | 4-(5-Cyano-2-methoxyphenyl)-N-(5-(4-(difluoromethyl)-3-fluorobenzoyl)-5,6-dihydro-4H-pyrrolo[3,4-d]thiazol-2-yl)-6-methyl-nicotinamide | 564 | $^{1}H$ NMR (400 MHz, DMSO-$d_6$) δ 12.7 (d, J = 6.8 Hz, 1H), 8.71 (d, J = 3.0 Hz, 1H), 7.92-7.87 (m, 1H), 7.86-7.83 (m, 1H), 7.78-7.71 (m, 1H), 7.65 (d, J = 10.6 Hz, 1H), 7.60-7.54 (m, 1H), 7.41-7.38 (m, 1H), 7.29-7.11 (m, 2H), 4.81 (s, 1H), 4.67 (s, 1H), 4.59 (s, 1H), 3.56 (s, 3H), 2.58 (d, J = 2.4 Hz, 3H) |
| 479 | 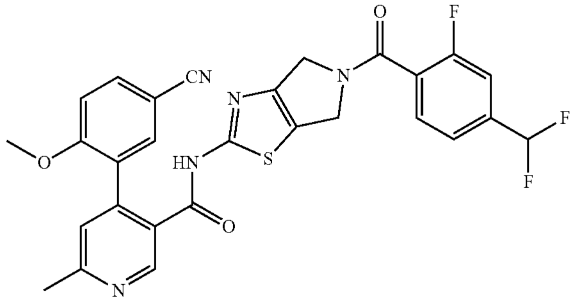 [SMILES: COc1ccc(C#N)cc1-c1cc(C)ncc1C(=O)Nc1nc2c(s1)CN(C(=O)c1ccc(C(F)F)cc1F)C2] | 4-(5-Cyano-2-methoxyphenyl)-N-(5-(4-(difluoromethyl)-2-fluorobenzoyl)-5,6-dihydro-4H-pyrrolo[3,4-d]thiazol-2-yl)-6-methyl-nicotinamide | 564 | $^{1}H$ NMR (400 MHz, DMSO-$d_6$) δ 12.7 (s, 1H), 8.71 (d, J = 4.0 Hz, 1H), 7.93-7.86 (m, 1H), 7.84 (d, J = 2.0 Hz, 1H), 7.72 (t, J = 7.2 Hz, 1H), 7.60 (dd, J = 10.0, 4.4 Hz, 1H), 7.54 (d, J = 8.0 Hz, 1H), 7.39 (d, J = 3.2 Hz, 1H), 7.27-6.95 (m, 2H), 4.82 (s, 1H), 4.68 (s, 1H), 4.54 (s, 1H), 4.44 (s, 1H), 3.56 (s, 3H), 2.57 (d, J = 3.0 Hz, 3H) |
| 480 | 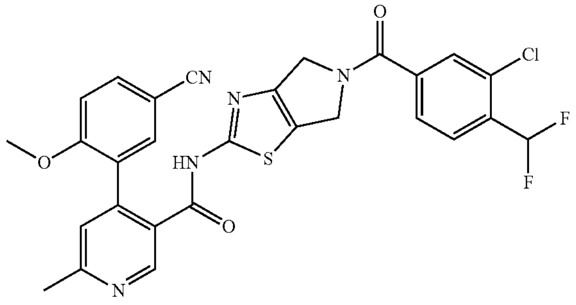 [SMILES: COc1ccc(C#N)cc1-c1cc(C)ncc1C(=O)Nc1nc2c(s1)CN(C(=O)c1ccc(C(F)F)c(Cl)c1)C2] | N-(5-(3-Chloro-4-(difluoromethyl)benzoyl)-5,6-dihydro-4H-pyrrolo[3,4-d]thiazol-2-yl)-4-(5-cyano-2-methoxyphenyl)-6-methyl-nicotinamide | 580 | $^{1}H$ NMR (400 MHz, DMSO-$d_6$) δ 12.7 (s, 1H), 8.71 (d, J = 3.0 Hz, 1H), 7.89 (dd, J = 8.4, 2.2 Hz, 1H), 7.84 (d, J = 2.4 Hz, 2H), 7.79 (d, J = 8.2 Hz, 1H), 7.76-7.69 (m, 1H), 7.39 (d, J = 3.0 Hz, 1H), 7.29-7.10 (m, 2H), 4.81 (s, 1H), 4.67 (s, 2H), 4.59 (s, 1H), 3.56 (s, 3H), 2.57 (d, J = 2.4 Hz, 3H) |
| 481 | 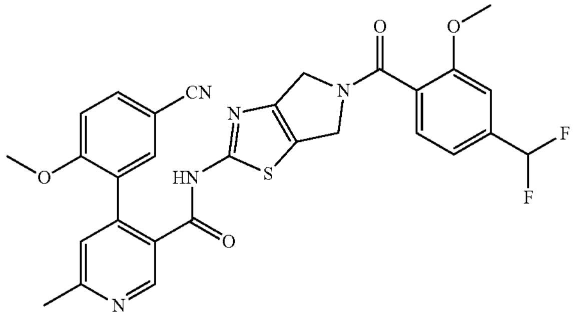 [SMILES: COc1cc(C(F)F)ccc1C(=O)N1Cc2nc(NC(=O)c3cnc(C)cc3-c3cc(C#N)ccc3OC)sc2C1] | 4-(5-Cyano-2-methoxyphenyl)-N-(5-(4-(difluoromethyl)-2-methoxybenzoyl)-5,6-dihydro-4H-pyrrolo[3,4-d]thiazol-2-yl)-6-methyl-nicotinamide | 576 | $^{1}H$ NMR (400 MHz, DMSO-$d_6$) δ 12.7 (d, J = 6.6 Hz, 1H), 8.70 (d, J = 4.2 Hz, 1H), 7.94-7.79 (m, 2H), 7.44 (d, J = 7.6 Hz, 1H), 7.39 (d, J = 2.8 Hz, 1H), 7.32 (s, 1H), 7.24 (d, J = 7.8 Hz, 1H), 7.17 (dd, J = 8.7, 3.7 Hz, 1H), 7.06 (td, J = 56.0, 3.2 Hz, 1H), 4.77 (s, 1H), 4.63 (s, 1H), 4.42 (s, 1H), 4.31 (s, 1H), 3.87 (d, J = 2.2 Hz, 3H), 3.56 (s, 3H), 2.57 (d, J = 3.0 Hz, 3H) |

TABLE C-continued

The following examples were prepared using a similar procedure to that described for Example 1

| Ex. No. | Structure | Compound Name | LCMS [M + H]+ | NMR |
|---|---|---|---|---|
| 482 | 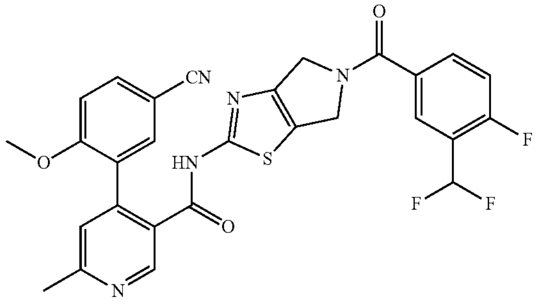 [SMILES: COc1ccc(C#N)cc1-c1cc(C)ncc1C(=O)Nc1nc2c(s1)CN(C(=O)c1ccc(F)c(C(F)F)c1)C2] | 4-(5-Cyano-2-methoxyphenyl)-N-(5-(3-(difluoromethyl)-4-fluorobenzoyl)-5,6-dihydro-4H-pyrrolo[3,4-d]thiazol-2-yl)-6-methyl-nicotinamide | 564 | $^1$H NMR (400 MHz, DMSO-$d_6$) δ 12.7 (d, J = 3.4 Hz, 1H), 8.71 (d, J = 3.2 Hz, 1H), 7.94-7.82 (m, 4H), 7.55-7.43 (m, 1H), 7.39 (s, 1H), 7.27-7.09 (m, 2H), 4.82 (s, 1H), 4.71 (s, 1H), 4.67 (s, 1H), 4.62 (s, 1H), 3.56 (s, 3H), 2.58 (s, 3H) |
| 483 | 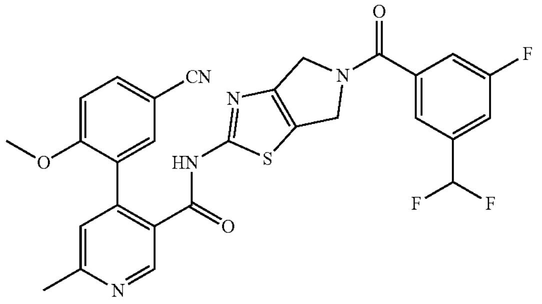 [SMILES: COc1ccc(C#N)cc1-c1cc(C)ncc1C(=O)Nc1nc2c(s1)CN(C(=O)c1cc(F)cc(C(F)F)c1)C2] | 4-(5-Cyano-2-methoxyphenyl)-N-(5-(3-(difluoromethyl)-5-fluorobenzoyl)-5,6-dihydro-4H-pyrrolo[3,4-d]thiazol-2-yl)-6-methyl-nicotinamide | 564 | $^1$H NMR (400 MHz, Chloroform-d) δ 10.1 (s, 1H), 8.89 (s, 1H), 7.83-7.73 (m, 1H), 7.62 (d, J = 2.0 Hz, 1H), 7.51 (s, 1H), 7.44-7.32 (m, 2H), 7.17 (s, 1H), 7.03 (d, J = 8.8 Hz, 1H), 6.68 (t, J = 56.2 Hz, 1H), 4.98 (s, 1H), 4.73 (s, 1H), 4.57 (s, 1H), 4.29 (s, 1H), 3.76 (s, 3H), 2.72 (s, 3H) |
| 484 | 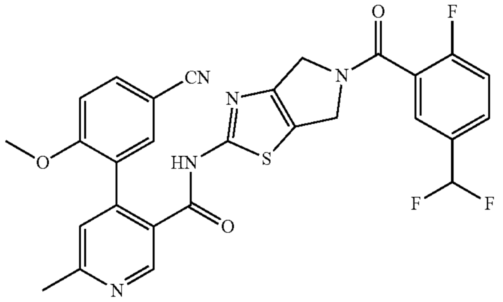 [SMILES: COc1ccc(C#N)cc1-c1cc(C)ncc1C(=O)Nc1nc2c(s1)CN(C(=O)c1cc(C(F)F)ccc1F)C2] | 4-(5-Cyano-2-methoxyphenyl)-N-(5-(5-(difluoromethyl)-2-fluorobenzoyl)-5,6-dihydro-4H-pyrrolo[3,4-d]thiazol-2-yl)-6-methyl-nicotinamide | 564 | $^1$H NMR (400 MHz, DMSO-$d_6$) δ 12.7 (s, 1H), 8.71 (d, J = 4.6 Hz, 1H), 7.91-7.86 (m, 1H), 7.84 (d, J = 2.0 Hz, 1H), 7.82-7.75 (m, 2H), 7.56-7.49 (m, 1H), 7.39 (d, J = 2.6 Hz, 1H), 7.19-7.14 (m, 1H), 7.08 (t, J = 55.6 Hz, 1H), 4.82 (s, 1H), 4.68 (s, 1H), 4.55 (s, 1H), 4.45 (s, 1H), 3.57 (d, J = 3.6 Hz, 3H), 2.57 (d, J = 2.8 Hz, 3H) |
| 485 | 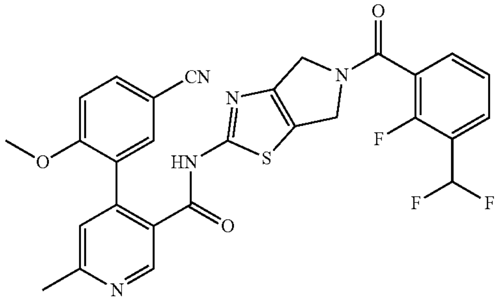 [SMILES: COc1ccc(C#N)cc1-c1cc(C)ncc1C(=O)Nc1nc2c(s1)CN(C(=O)c1cccc(C(F)F)c1F)C2] | 4-(5-Cyano-2-methoxyphenyl)-N-(5-(3-(difluoromethyl)-2-fluorobenzoyl)-5,6-dihydro-4H-pyrrolo[3,4-d]thiazol-2-yl)-6-methyl-nicotinamide | 564 | $^1$H NMR (400 MHz, DMSO-$d_6$) δ 12.7 (s, 1H), 8.71 (d, J = 4.6 Hz, 1H), 7.89 (dt, J = 8.6, 2.2 Hz, 1H), 7.85 (d, J = 2.2 Hz, 1H), 7.76 (t, J = 7.0 Hz, 2H), 7.47 (td, J = 7.6, 2.2 Hz, 1H), 7.39 (d, J = 2.8 Hz, 1H), 7.27 (t, J = 54.4 Hz, 1H), 7.17 (dd, J = 8.7, 2.8 Hz, 1H), 4.82 (s, 1H), 4.68 (s, 1H), 4.55 (s, 1H), 4.44 (s, 1H), 3.56 (s, 3H), 2.57 (d, J = 2.8 Hz, 3H) |

TABLE C-continued

The following examples were prepared using a similar procedure to that described for Example 1

| Ex. No. | Structure | Compound Name | LCMS [M + H]+ | NMR |
|---|---|---|---|---|
| 486 | 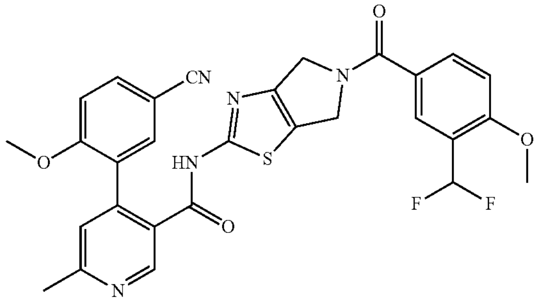 | 4-(5-Cyano-2-methoxyphenyl)-N-(5-(3-(difluoromethyl)-4-methoxybenzoyl)-5,6-dihydro-4H-pyrrolo[3,4-d]thiazol-2-yl)-6-methyl-nicotinamide | 576 | $^1$H NMR (400 MHz, DMSO-$d_6$) δ 12.7 (s, 1H), 8.71 (d, J = 2.8 Hz, 1H), 7.93-7.79 (m, 3H), 7.75 (d, J = 6.6 Hz, 1H), 7.39 (s, 1H), 7.27-6.96 (m, 3H), 4.80 (s, 1H), 4.75 (s, 1H), 4.66 (s, 2H), 3.91 (d, J = 2.2 Hz, 3H), 3.56 (s, 3H), 2.57 (s, 3H) |
| 487 | 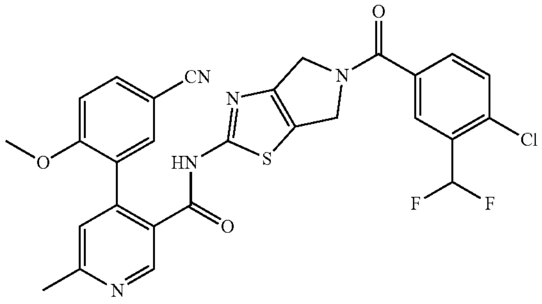 [SMILES: COc1ccc(C#N)cc1-c1cc(C)ncc1C(=O)Nc1nc2c(s1)CN(C(=O)c1ccc(Cl)c(C(F)F)c1)C2] | N-(5-(4-Chloro-3-(difluoromethyl)benzoyl)-5,6-dihydro-4H-pyrrolo[3,4-d]thiazol-2-yl)-4-(5-cyano-2-methoxyphenyl)-6-methyl-nicotinamide | 580 | $^1$H NMR (400 MHz, DMSO-$d_6$) δ 12.7 (d, J = 4.4 Hz, 1H), 8.71 (d, J = 3.2 Hz, 1H), 7.93-7.87 (m, 2H), 7.87-7.80 (m, 2H), 7.72 (d, J = 8.4 Hz, 1H), 7.43-7.09 (m, 3H), 4.82 (s, 1H), 4.73-4.65 (m, 2H), 4.64-4.58 (m, 1H), 3.56 (s, 3H), 2.58 (s, 3H) |
| 488 | 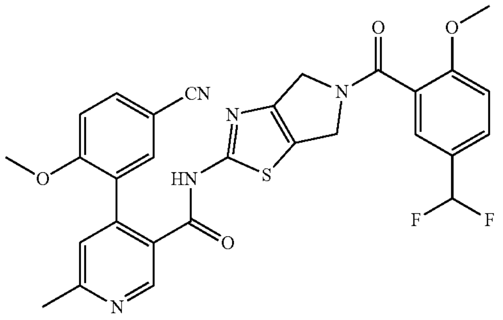 | 4-(5-Cyano-2-methoxyphenyl)-N-(5-(5-(difluoromethyl)-2-methoxybenzoyl)-5,6-dihydro-4H-pyrrolo[3,4-d]thiazol-2-yl)-6-methyl-nicotinamide | 576 | $^1$H NMR (400 MHz, DMSO-$d_6$) δ 12.7 (s, 1H), 8.70 (d, J = 4.8 Hz, 1H), 7.88 (d, J = 9.6 Hz, 1H), 7.84 (d, J = 2.2 Hz, 1H), 7.65 (d, J = 8.4 Hz, 1H), 7.51 (s, 1H), 7.39 (d, J = 2.0 Hz, 1H), 7.27 (d, J = 8.8 Hz, 1H), 7.16 (dd, J = 8.6, 4.6 Hz, 1H), 6.99 (t, J = 56.0 Hz, 1H), 4.76 (s, 1H), 4.62 (s, 1H), 4.43 (s, 1H), 4.31 (s, 1H), 3.87 (d, J = 3.0 Hz, 3H), 3.56 (s, 3H), 2.57 (d, J = 2.8 Hz, 3H) |
| 489 | 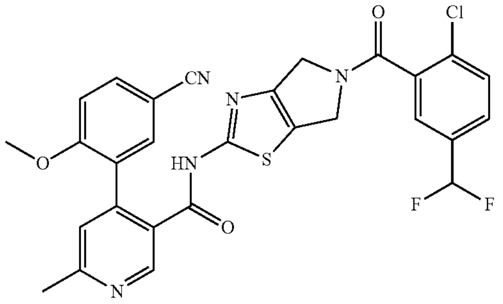 | N-(5-(2-Chloro-5-(difluoromethyl)benzoyl)-5,6-dihydro-4H-pyrrolo[3,4-d]thiazol-2-yl)-4-(5-cyano-2-methoxyphenyl)-6-methyl-nicotinamide | 580 | $^1$H NMR (400 MHz, DMSO-$d_6$) δ 12.7 (br s, 1H), 8.71 (d, J = 4.8 Hz, 1H), 7.89 (dt, J = 8.6, 2.4 Hz, 1H), 7.84 (d, J = 2.0 Hz, 1H), 7.79-7.73 (m, 2H), 7.70 (d, J = 8.6 Hz, 1H), 7.38 (d, J = 3.0 Hz, 1H), 7.16 (dd, J = 8.7, 3.8 Hz, 1H), 7.09 (t, J = 55.6 Hz, 1H), 4.81 (s, 1H), 4.67 (s, 1H), 4.44 (s, 1H), 4.33 (s, 1H), 3.56 (s, 3H), 2.57 (d, J = 3.0 Hz, 3H) |

TABLE C-continued

The following examples were prepared using a similar procedure to that described for Example 1

| Ex. No. | Structure | Compound Name | LCMS [M + H]+ | NMR |
|---|---|---|---|---|
| 490 | 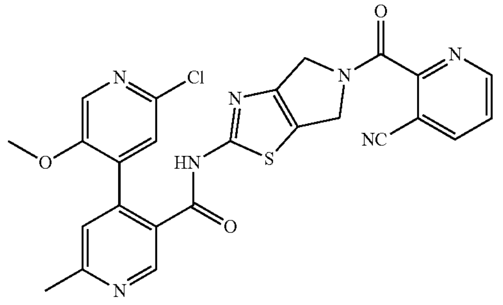 [SMILES: COc1cnc(Cl)cc1-c1cc(C)ncc1C(=O)Nc1nc2c(s1)CN(C(=O)c1ncccc1C#N)C2] | 2'-Chloro-N-(5-(3-cyanopicolinoyl)-5,6-dihydro-4H-pyrrolo[3,4-d]thiazol-2-yl)-5'-methoxy-6-methyl-[4,4'-bipyridine]-3-carboxamide | 532 | $^1$H NMR (400 MHz, DMSO-$d_6$) δ 12.8 (s, 1H), 8.91-8.87 (m, 1H), 8.78 (d, J = 4.2 Hz, 1H), 8.53-8.46 (m, 1H), 8.16 (s, 1H), 7.79-7.73 (m, 1H), 7.54 (s, 1H), 7.43 (d, J = 1.6 Hz, 1H), 4.91-4.86 (m, 2H), 4.76 (s, 2H), 3.60 (d, J = 1.4 Hz, 3H), 2.58 (d, J = 2.4 Hz, 3H) |
| 491 | 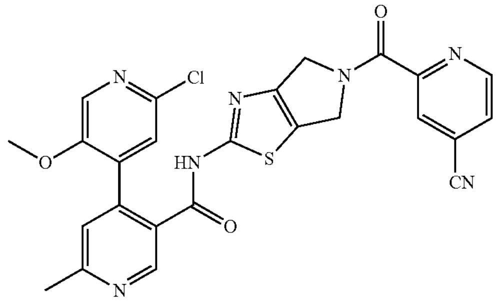 [SMILES: COc1cnc(Cl)cc1-c1cc(C)ncc1C(=O)Nc1nc2c(s1)CN(C(=O)c1cc(C#N)ccn1)C2] | 2'-Chloro-N-(5-(4-cyanopicolinoyl)-5,6-dihydro-4H-pyrrolo[3,4-d]thiazol-2-yl)-5'-methoxy-6-methyl-[4,4'-bipyridine]-3-carboxamide | 532 | $^1$H NMR (400 MHz, DMSO-$d_6$) δ 12.8 (s, 1H), 8.95-8.89 (m, 1H), 8.79 (s, 1H), 8.26 (s, 1H), 8.17 (s, 1H), 8.07-8.02 (m, 1H), 7.54 (s, 1H), 7.43 (s, 1H), 5.02 (s, 1H), 4.90 (s, 1H), 4.89 (s, 1H), 4.74 (s, 1H), 3.60 (s, 3H), 2.59 (s, 3H) |
| 492 | 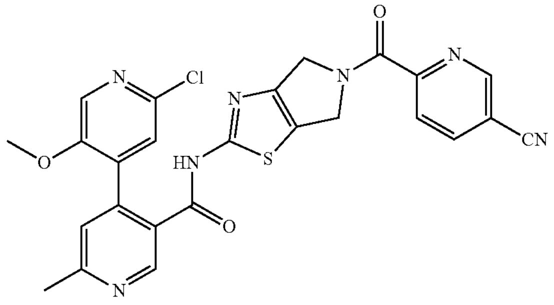 [SMILES: COc1cnc(Cl)cc1-c1cc(C)ncc1C(=O)Nc1nc2c(s1)CN(C(=O)c1ccc(C#N)cn1)C2] | 2'-chloro-N-(5-(5-cyanopicolinoyl)-5,6-dihydro-4H-pyrrolo[3,4-d]thiazol-2-yl)-5'-methoxy-6-methyl-[4,4'-bipyridine]-3-carboxamide | 532 | $^1$H NMR (400 MHz, DMSO-$d_6$) δ 12.8 (s, 1H), 9.13 (d, J = 6.2 Hz, 1H), 8.79 (s, 1H), 8.51 (d, J = 8.4 Hz, 1H), 8.17 (s, 1H), 8.01 (d, J = 8.2 Hz, 1H), 7.54 (s, 1H), 7.43 (s, 1H), 4.99 (s, 1H), 4.87 (s, 2H), 4.73 (s, 1H), 3.60 (d, J = 1.6 Hz, 3H), 2.59 (s, 3H). |
| 493 | 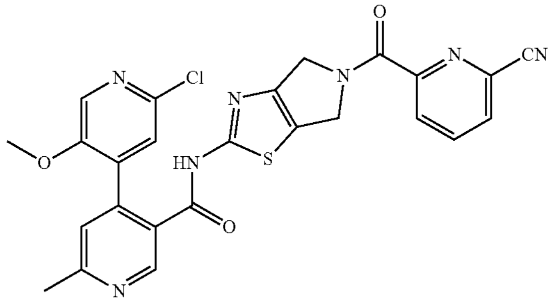 [SMILES: COc1cnc(Cl)cc1-c1cc(C)ncc1C(=O)Nc1nc2c(s1)CN(C(=O)c1cccc(C#N)n1)C2] | 2'-chloro-N-(5-(6-cyanopicolinoyl)-5,6-dihydro-4H-pyrrolo[3,4-d]thiazol-2-yl)-5'-methoxy-6-methyl-[4,4'-bipyridine]-3-carboxamide | 532 | $^1$H NMR (400 MHz, DMSO-$d_6$) δ 12.8 (s, 1H), 8.79 (s, 1H), 8.28-8.20 (m, 2H), 8.17 (d, J = 2.2 Hz, 1H), 8.16-8.11 (m, 1H), 7.54 (s, 1H), 7.44 (s, 1H), 5.01 (s, 1H), 4.93-4.84 (m, 2H), 4.73 (s, 1H), 3.60 (s, 3H), 2.59 (s, 3H) |

TABLE C-continued

| The following examples were prepared using a similar procedure to that described for Example 1 | | | | |
|---|---|---|---|---|
| Ex. No. | Structure | Compound Name | LCMS [M + H]+ | NMR |
| 494 | 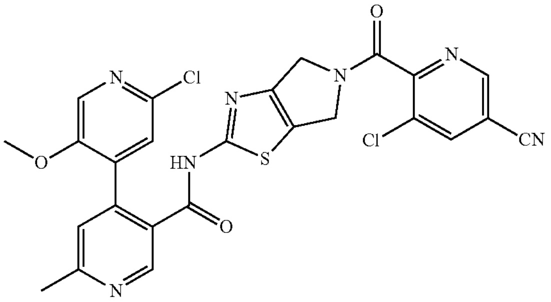 [SMILES: COc1cnc(Cl)cc1-c1cc(C)ncc1C(=O)Nc1nc2c(s1)CN(C(=O)c1ncc(C#N)cc1Cl)C2] | 2'-Chloro-N-(5-(3-chloro-5-cyanopicolinoyl)-5,6-dihydro-4H-pyrrolo[3,4-d]thiazol-2-yl)-5'-methoxy-6-methyl-[4,4'-bipyridine]-3-carboxamide | 566 | $^1$H NMR (400 MHz, DMSO-$d_6$) δ 12.8 (s, 1H), 9.10 (dd, J = 4.4, 1.6 Hz, 1H), 8.83 (dd, J = 4.6, 1.6 Hz, 1H), 8.79 (d, J = 5.4 Hz, 1H), 8.16 (d, J = 3.0 Hz, 1H), 7.52 (s, 1H), 7.41 (s, 1H), 4.85 (s, 1H), 4.72 (s, 1H), 4.51 (s, 1H), 4.39 (s, 1H), 3.60 (s, 3H), 2.58 (d, J = 2.4 Hz, 3H) |
| 495 | 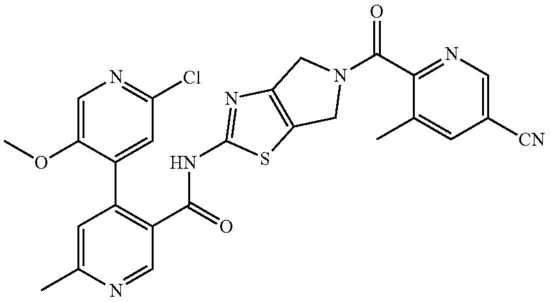 [SMILES: COc1cnc(Cl)cc1-c1cc(C)ncc1C(=O)Nc1nc2c(s1)CN(C(=O)c1ncc(C#N)cc1C)C2] | 2'-Chloro-N-(5-(5-cyano-3-methyl-picolinoyl)-5,6-dihydro-4H-pyrrolo[3,4-d]thiazol-2-yl)-5'-methoxy-6-methyl-[4,4'-bipyridine]-3-carboxamide | 546 | $^1$H NMR (400 MHz, DMSO-$d_6$) δ 12.8 (s, 1H), 8.92 (s, 1H), 8.78 (d, J = 5.2 Hz, 1H), 8.37 (s, 1H), 8.16 (d, J = 2.4 Hz, 1H), 7.54 (s, 1H), 7.43 (d, J = 2.4 Hz, 1H), 4.85 (s, 1H), 4.72 (s, 1H), 4.52 (s, 1H), 4.41 (s, 1H), 3.59 (s, 3H), 2.58 (d, J = 2.8 Hz, 3H), 2.36 (s, 3H) |
| 496 | 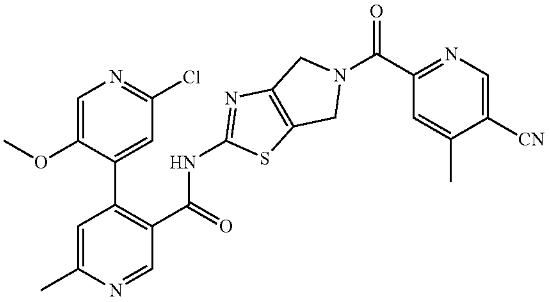 [SMILES: COc1cnc(Cl)cc1-c1cc(C)ncc1C(=O)Nc1nc2c(s1)CN(C(=O)c1cc(C)c(C#N)cn1)C2] | 2'-Chloro-N-(5-(5-cyano-4-methyl-picolinoyl)-5,6-dihydro-4H-pyrrolo[3,4-d]thiazol-2-yl)-5'-methoxy-6-methyl-[4,4'-bipyridine]-3-carboxamide | 546 | $^1$H NMR (400 MHz, DMSO-$d_6$) δ 12.8 (s, 1H), 9.02 (d, J = 6.3 Hz, 1H), 8.78 (s, 1H), 8.17 (s, 1H), 7.95 (s, 1H), 7.54 (s, 1H), 7.43 (s, 1H), 4.99 (s, 1H), 4.86 (s, 2H), 4.72 (s, 1H), 3.60 (s, 3H), 2.59 (s, 6H) |
| 497 | 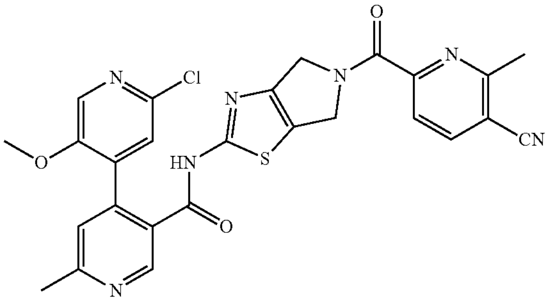 [SMILES: COc1cnc(Cl)cc1-c1cc(C)ncc1C(=O)Nc1nc2c(s1)CN(C(=O)c1ccc(C#N)c(C)n1)C2] | 2'-Chloro-N-(5-(5-cyano-6-methyl-picolinoyl)-5,6-dihydro-4H-pyrrolo[3,4-d]thiazol-2-yl)-5'-methoxy-6-methyl-[4,4'-bipyridine]-3-carboxamide | 546 | $^1$H NMR (400 MHz, DMSO-$d_6$) δ 12.8 (s, 1H), 8.78 (s, 1H), 8.42 (d, J = 8.2 Hz, 1H), 8.17 (s, 1H), 7.81 (d, J = 7.0 Hz, 1H), 7.54 (s, 1H), 7.44 (s, 1H), 4.98 (s, 1H), 4.86 (s, 2H), 4.71 (s, 1H), 3.60 (s, 3H), 2.76 (s, 3H), 2.59 (s, 3H) |

TABLE C-continued

| The following examples were prepared using a similar procedure to that described for Example 1 | | | | |
|---|---|---|---|---|
| Ex. No. | Structure | Compound Name | LCMS [M + H]+ | NMR |
| 498 | 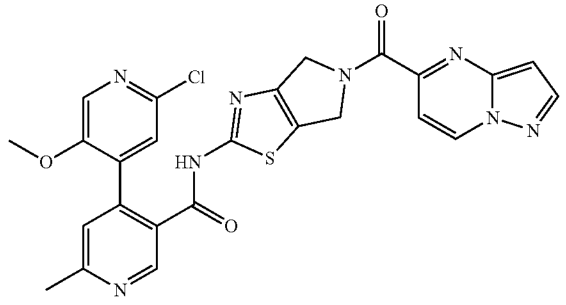 [SMILES: COc1cnc(Cl)cc1-c1cc(C)ncc1C(=O)Nc1nc2c(s1)CN(C(=O)c1ccn3nccc3n1)C2] | 2'-Chloro-5'-methoxy-6-methyl-N-(5-(pyrazolo[1,5-a]pyrimidine-5-carbonyl)-5,6-dihydro-4H-pyrrolo[3,4-d]thiazol-2-yl)-[4,4'-bipyridine]-3-carboxamide | 547 | $^1$H NMR (400 MHz, DMSO-$d_6$) δ 12.8 (s, 1H), 9.29-9.24 (m, 1H), 8.79 (s, 1H), 8.36 (t, J = 2.2 Hz, 1H), 8.17 (s, 1H), 7.54 (s, 1H), 7.44 (s, 1H), 7.41-7.28 (m, 1H), 6.93-6.89 (m, 1H), 5.17 (s, 1H), 5.04 (s, 1H), 4.88 (s, 1H), 4.74 (s, 1H), 3.61 (d, J = 1.6 Hz, 3H), 2.59 (d, J = 1.4 Hz, 3H) |
| 499 | 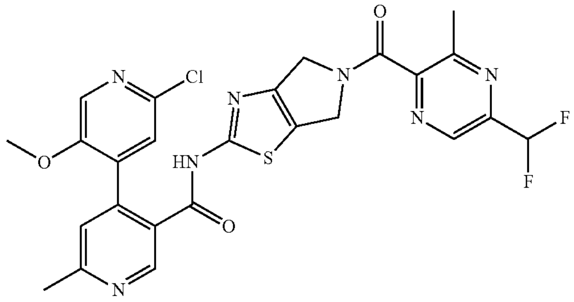 [SMILES: COc1cnc(Cl)cc1-c1cc(C)ncc1C(=O)Nc1nc2c(s1)CN(C(=O)c1ncc(C(F)F)nc1C)C2] | 2'-Chloro-N-(5-(5-(difluoromethyl)-3-methylpyrazine-2-carbonyl)-5,6-dihydro-4H-pyrrolo[3,4-d]thiazol-2-yl)-5'-methoxy-6-methyl-[4,4'-bipyridine]-3-carboxamide | 572 | $^1$H NMR (400 MHz, DMSO-$d_6$) δ 12.8 (s, 1H), 8.84 (s, 1H), 8.78 (d, J = 5.0 Hz, 1H), 8.16 (d, J = 2.2 Hz, 1H), 7.53 (s, 1H), 7.43 (d, J = 2.2 Hz, 1H), 7.15 (t, J = 54.0 Hz, 1H), 4.88 (s, 1H), 4.75 (s, 1H), 4.64 (s, 1H), 4.54 (s, 1H), 3.60 (s, 3H), 2.62 (s, 3H), 2.58 (d, J = 2.8 Hz, 3H) |
| 500 | 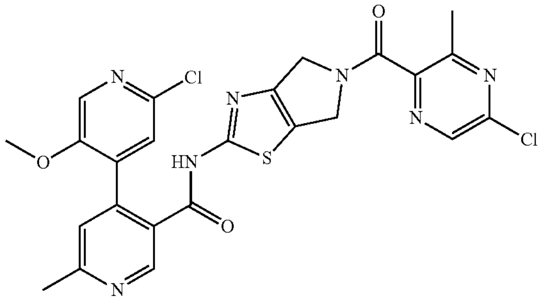 [SMILES: COc1cnc(Cl)cc1-c1cc(C)ncc1C(=O)Nc1nc2c(s1)CN(C(=O)c1ncc(Cl)nc1C)C2] | 2'-Chloro-N-(5-(5-chloro-3-methylpyrazine-2-carbonyl)-5,6-dihydro-4H-pyrrolo[3,4-d]thiazol-2-yl)-5'-methoxy-6-methyl-[4,4'-bipyridine]-3-carboxamide | 556 | $^1$H NMR (400 MHz, DMSO-$d_6$) δ 12.8 (s, 1H), 8.78 (d, J = 4.6 Hz, 1H), 8.69 (d, J = 1.6 Hz, 1H), 8.16 (d, J = 1.6 Hz, 1H), 7.54 (s, 1H), 7.43 (d, J = 2.2 Hz, 1H), 4.86 (s, 1H), 4.73 (s, 1H), 4.65 (s, 1H), 4.53 (s, 1H), 3.60 (s, 3H), 2.59 (d, J = 2.4 Hz, 3H), 2.56 (d, J = 1.4 Hz, 3H) |
| 501 | 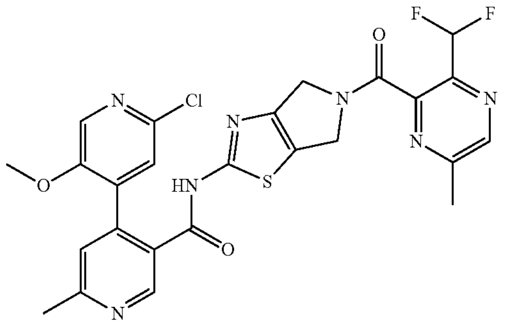 [SMILES: COc1cnc(Cl)cc1-c1cc(C)ncc1C(=O)Nc1nc2c(s1)CN(C(=O)c1nc(C)cnc1C(F)F)C2] | 2'-Chloro-N-(5-(3-(difluoromethyl)-6-methylpyrazine-2-carbonyl)-5,6-dihydro-4H-pyrrolo[3,4-d]thiazol-2-yl)-5'-methoxy-6-methyl-[4,4'-bipyridine]-3-carboxamide | 572 | $^1$H NMR (400 MHz, DMSO-$d_6$) δ 12.8 (s, 1H), 8.82 (s, 1H), 8.79 (d, J = 5.4 Hz, 1H), 8.16 (d, J = 3.4 Hz, 1H), 7.53 (s, 1H), 7.43 (s, 1H), 7.16 (t, J = 53.4 Hz, 1H), 4.85 (s, 1H), 4.71 (s, 2H), 4.59 (s, 1H), 3.59 (s, 3H), 2.64 (d, J = 2.6 Hz, 3H), 2.59 (d, J = 2.2 Hz, 3H) |

TABLE C-continued

The following examples were prepared using a similar procedure to that described for Example 1

| Ex. No. | Structure | Compound Name | LCMS [M + H]+ | NMR |
|---|---|---|---|---|
| 502 | 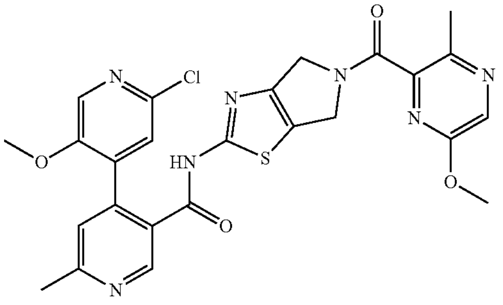 | 2'-Chloro-5'-methoxy-N-(5-(6-methoxy-3-methylpyrazine-2-carbonyl)-5,6-dihydro-4H-pyrrolo[3,4-d]thiazol-2-yl)-6-methyl-[4,4'-bipyridine]-3-carboxamide | 552 | $^1$H NMR (400 MHz, DMSO-$d_6$) δ 12.8 (d, J = 10.2 Hz, 1H), 8.77 (d, J = 5.6 Hz, 1H), 8.33 (s, 1H), 8.16 (d, J = 3.0 Hz, 1H), 7.54 (s, 1H), 7.43 (s, 1H), 4.85 (s, 1H), 4.72 (s, 1H), 4.68 (s, 1H), 4.55 (s, 1H), 3.91 (d, J = 1.6 Hz, 3H), 3.59 (d, 3H), 2.58 (d, J = 2.2 Hz, 3H), 2.45 (s, 3H) |
| 503 | 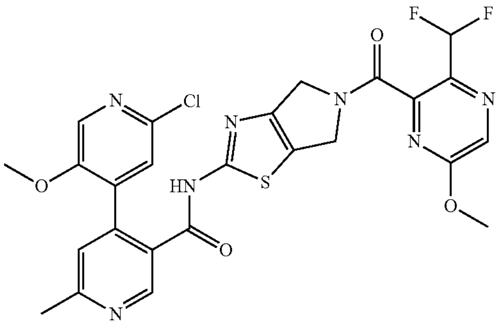 [SMILES: COc1cnc(C(F)F)c(C(=O)N2Cc3nc(NC(=O)c4cnc(C)cc4-c4cc(Cl)ncc4OC)sc3C2)n1] | 2'-Chloro-N-(5-(3-(difluoromethyl)-6-methoxy-pyrazine-2-carbonyl)-5,6-dihydro-4H-pyrrolo[3,4-d]thiazol-2-yl)-5'-methoxy-6-methyl-[4,4'-bipyridine]-3-carboxamdie | 588 | $^1$H NMR (400 MHz, DMSO-$d_6$) δ 12.8 (d, J = 14.8 Hz, 1H), 8.78 (d, J = 5.6 Hz, 1H), 8.56 (d, J = 1.8 Hz, 1H), 8.16 (d, J = 3.8 Hz, 1H), 7.54 (s, 1H), 7.43 (s, 1H), 7.13 (td, J = 53.2, 0.8 Hz, 1H), 4.86 (s, 1H), 4.79 (s, 1H), 4.72 (s, 1H), 4.66 (s, 1H), 4.02 (d, J = 2.2 Hz, 3H), 3.59 (s, 3H), 2.59 (d, J = 2.0 Hz, 3H) |
| 504 | 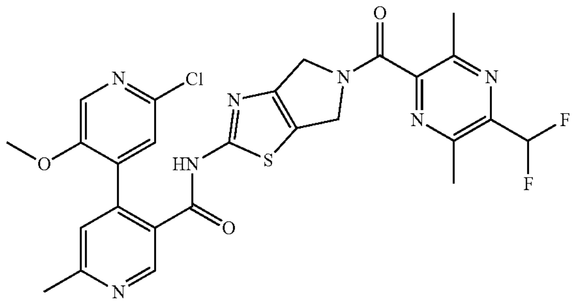 [SMILES: COc1cnc(Cl)cc1-c1cc(C)ncc1C(=O)Nc1nc2c(s1)CN(C(=O)c1nc(C)c(C(F)F)nc1C)C2] | 2'-Chloro-N-(5-(5-(difluoromethyl)-3,6-dimethylpyrazine-2-carbonyl)-5,6-dihydro-4H-pyrrolo[3,4-d]thiazol-2-yl)-5'-methoxy-6-methyl-[4,4'-bipyridine]-3-carboxamide | 586 | $^1$H NMR (400 MHz, DMSO-$d_6$) δ 12.8 (d, J = 9.8 Hz, 1H), 8.78 (d, J = 5.0 Hz, 1H), 8.17 (d, J = 2.2 Hz, 1H), 7.54 (s, 1H), 7.44 (s, 1H), 7.19 (t, J = 53.6 Hz, 1H), 4.87 (s, 1H), 4.74 (s, 1H), 4.64 (s, 1H), 4.54 (s, 1H), 3.60 (s, 3H), 2.64 (s, 3H), 2.59 (d, J = 2.4 Hz, 3H), 2.56 (s, 3H) |
| 505 | 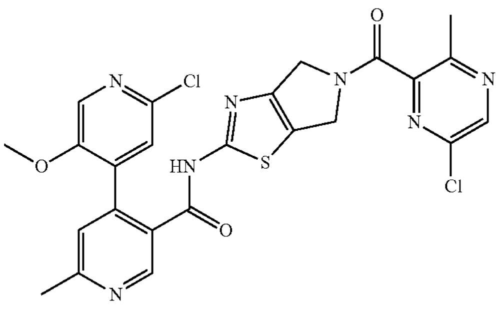 [SMILES: COc1cnc(Cl)cc1-c1cc(C)ncc1C(=O)Nc1nc2c(s1)CN(C(=O)c1nc(Cl)cnc1C)C2] | 2'-Chloro-N-(5-(6-chloro-3-methylpyrazine-2-carbonyl)-5,6-dihydro-4H-pyrrolo[3,4-d]thiazol-2-yl)-5'-methoxy-6-methyl-[4,4'-bipyridine]-3-carboxamide | 556 | $^1$H NMR (400 MHz, DMSO-$d_6$) δ 12.8 (s, 1H), 8.83 (d, J = 1.6 Hz, 1H), 8.78 (d, J = 4.4 Hz, 1H), 8.16 (d, J = 2.4 Hz, 1H), 7.54 (s, 1H), 7.43 (d, J = 2.0 Hz, 1H), 4.86 (t, J = 2.6 Hz, 1H), 4.73 (t, J = 2.8 Hz, 1H), 4.66 (t, J = 3.0 Hz, 1H), 4.55 (t, J = 2.4 Hz, 1H), 3.60 (s, 3H), 2.59 (d, J = 2.4 Hz, 3H), 2.56 (d, J = 1.2 Hz, 3H) |

TABLE C-continued

The following examples were prepared using a similar procedure to that described for Example 1

| Ex. No. | Structure | Compound Name | LCMS [M + H]+ | NMR |
|---|---|---|---|---|
| 506 | 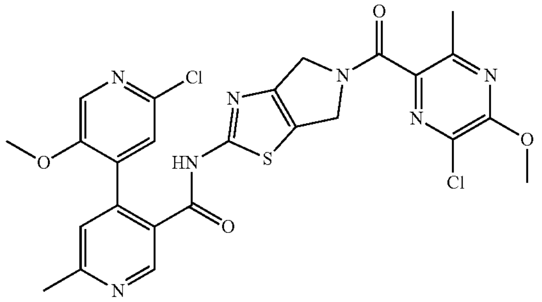 | 2'-Chloro-N-(5-(6-chloro-5-methoxy-3-methylpyrazine-2-carbonyl)-5,6-dihydro-4H-pyrrolo[3,4-d]thiazol-2-yl)-5'-methoxy-6-methyl-[4,4'-bipyridine]-3-carboxamide | 586 | $^1$H NMR (400 MHz, DMSO-$d_6$) δ 12.8 (s, 1H), 8.78 (d, J = 4.2 Hz, 1H), 8.16 (d, J = 2.2 Hz, 1H), 7.54 (s, 1H), 7.43 (d, J = 1.6 Hz, 1H), 4.83 (t, J = 2.6 Hz, 1H), 4.71-4.66 (m, 2H), 4.56 (t, J = 2.6 Hz, 1H), 4.04 (d, J = 1.4 Hz, 3H), 3.60 (s, 3H), 2.59 (d, J = 2.0 Hz, 3H), 2.50 (s, 3H) |
| 507 | 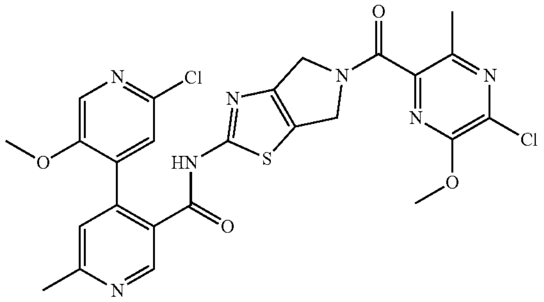 [SMILES: COc1cnc(Cl)cc1-c1cc(C)ncc1C(=O)Nc1nc2c(s1)CN(C(=O)c1nc(OC)c(Cl)nc1C)C2] | 2'-chloro-N-(5-(5-chloro-6-methoxy-3-methylpyrazine-2-carbonyl)-5,6-dihydro-4H-pyrrolo[3,4-d]thiazol-2-yl)-5'-methoxy-6-methyl-[4,4'-bipyridine]-3-carboxamide | 586 | $^1$HNMR (400 MHz, DMSO-$d_6$) δ 12.8 (br s, 1H), 8.80 (d, J = 6.2 Hz, 1H), 8.16 (s, 1H), 7.51 (s, 1H), 7.40 (s, 1H), 4.84 (s, 1H), 4.70 (s, 2H), 4.58 (s, 1H), 4.04-3.96 (m, 3H), 3.60 (s, 3H), 2.58 (s, 3H), 2.44 (s, 3H) |
| 508 | 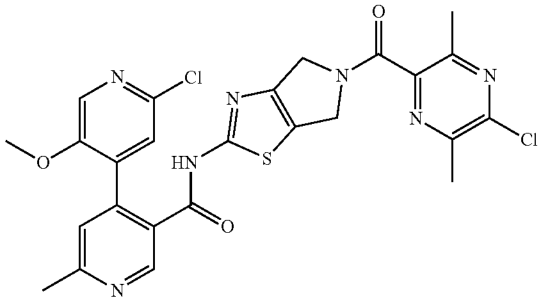 [SMILES: COc1cnc(Cl)cc1-c1cc(C)ncc1C(=O)Nc1nc2c(s1)CN(C(=O)c1nc(C)c(Cl)nc1C)C2] | 2'-Chloro-N-(5-(5-chloro-3,6-dimethyl-pyrazine-2-carbonyl)-5,6-dihydro-4H-pyrrolo[3,4-d]thiazol-2-yl)-5'-methoxy-6-methyl-[4,4'-bipyridine]-3-carboxamide | 570 | $^1$H NMR (400 MHz, DMSO-$d_6$) δ 12.8 (d, J = 12.8 Hz, 1H), 8.78 (d, J = 5.2 Hz, 1H), 8.16 (d, J = 1.8 Hz, 1H), 7.54 (s, 1H), 7.44 (d, J = 1.8 Hz, 1H), 4.84 (s, 1H), 4.71 (s, 1H), 4.64 (s, 1H), 4.53 (s, 1H), 3.59 (s, 3H), 2.59 (s, 3H), 2.58 (s, 3H), 2.49 (s, 3H) |
| 509 | 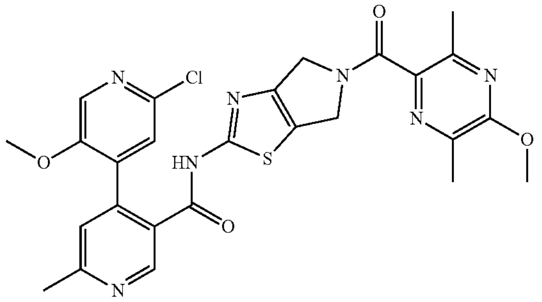 | 2'-Chloro-5'-methoxy-N-(5-(5-methoxy-3,6-dimethyl-pyrazine-2-carbonyl)-5,6-dihydro-4H-pyrrolo[3,4-d]thiazol-2-yl)-6-methyl-[4,4'-bipyridine]-3-carboxamide | 566 | $^1$H NMR (400 MHz, DMSO-$d_6$) δ 12.8 (s, 1H), 8.78 (d, J = 5.2 Hz, 1H), 8.16 (d, J = 2.4 Hz, 1H), 7.54 (s, 1H), 7.43 (s, 1H), 4.82 (s, 1H), 4.68 (s, 1H), 4.63 (s, 1H), 4.52 (s, 1H), 3.96 (d, J = 2.1 Hz, 3H), 3.59 (s, 3H), 2.58 (d, J = 2.0 Hz, 3H), 2.44 (s, 3H), 2.39 (d, J = 2.8 Hz, 3H) |

TABLE C-continued

| Ex. No. | Structure | Compound Name | LCMS [M + H]+ | NMR |
|---|---|---|---|---|
| | The following examples were prepared using a similar procedure to that described for Example 1 | | | |
| 510 | 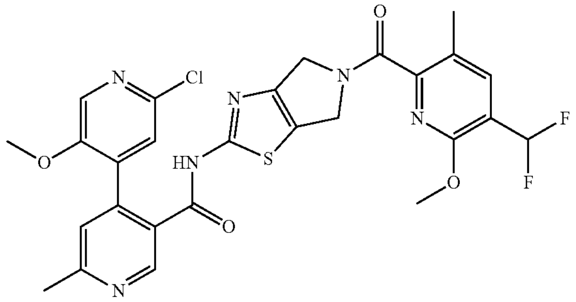 [SMILES: COc1cnc(Cl)cc1-c1cc(C)ncc1C(=O)Nc1nc2c(s1)CN(C(=O)c1nc(OC)c(C(F)F)cc1C)C2] | 2'-chloro-N-(5-(5-(difluoro-methyl)-6-methoxy-3-methyl-picolinoyl)-5,6-dihydro-4H-pyrrolo[3,4-d]thiazol-2-yl)-5'-methoxy-6-methyl-[4,4'-bipyridine]-3-carboxamide | 601 | $^{1}$H NMR (400 MHz, DMSO-$d_6$) δ 12.8 (s, 1H), 8.78 (d, J = 5.0 Hz, 1H), 8.17 (d, J = 3.0 Hz, 1H), 7.95 (s, 1H), 7.54 (s, 1H), 7.43 (d, J = 1.8 Hz, 1H), 7.09 (td, J = 54.6, 2.2 Hz, 1H), 4.84 (s, 1H), 4.70 (s, 1H), 4.61 (s, 1H), 4.49 (s, 1H), 3.93 (s, 3H), 3.60 (s, 3H), 2.59 (d, J = 2.6 Hz, 3H), 2.28 (s, 3H) |
| 511 | 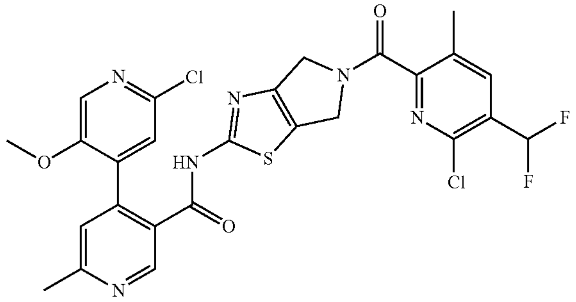 [SMILES: COc1cnc(Cl)cc1-c1cc(C)ncc1C(=O)Nc1nc2c(s1)CN(C(=O)c1nc(Cl)c(C(F)F)cc1C)C2] | 2'-chloro-N-(5-(6-chloro-5-(difluoro-methyl)-3-methyl-picolinoyl)-5,6-dihydro-4H-pyrrolo[3,4-d]thiazol-2-yl)-5'-methoxy-6-methyl-[4,4'-bipyridine]-3-carboxamide | 605 | $^{1}$H NMR (400 MHz, DMSO-$d_6$) δ 12.8 (d, J = 4.2 Hz, 1H), 8.78 (d, J = 4.6 Hz, 1H), 8.21 (d, J = 3.4 Hz, 1H), 8.17 (d, J = 3.0 Hz, 1H), 7.54 (s, 1H), 7.44 (d, J = 2.2 Hz, 1H), 7.26 (t, J = 53.6 Hz, 1H), 4.85 (s, 1H), 4.72 (s, 1H), 4.57 (s, 1H), 4.47 (s, 1H), 3.60 (s, 3H), 2.59 (d, J = 2.6 Hz, 3H), 2.39 (s, 3H) |
| 512 | 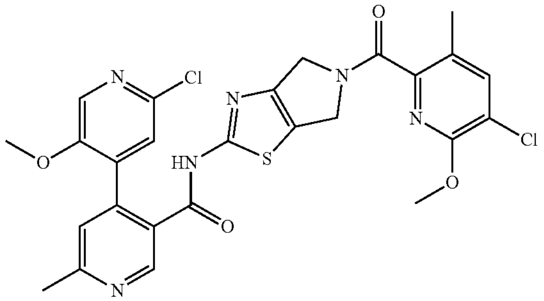 [SMILES: COc1cnc(Cl)cc1-c1cc(C)ncc1C(=O)Nc1nc2c(s1)CN(C(=O)c1nc(OC)c(Cl)cc1C)C2] | 2'-Chloro-N-(5-(5-chloro-6-methoxy-3-methyl-picolinoyl)-5,6-dihydro-4H-pyrrolo[3,4-d]thiazol-2-yl)-5'-methoxy-6-methyl-[4,4'-bipyridine]-3-carboxamide | 585 | $^{1}$H NMR (400 MHz, DMSO-$d_6$) δ 12.8 (s, 1H), 8.78 (d, J = 4.8 Hz, 1H), 8.16 (d, J = 2.8 Hz, 1H), 7.93 (d, J = 2.2 Hz, 1H), 7.54 (s, 1H), 7.43 (d, J = 1.6 Hz, 1H), 4.82 (s, 1H), 4.68 (s, 1H), 4.62 (s, 1H), 4.50 (s, 1H), 3.93 (d, J = 1.8 Hz, 3H), 3.60 (s, 3H), 2.59 (d, J = 2.2 Hz, 3H), 2.24 (s, 3H) |
| 513 | 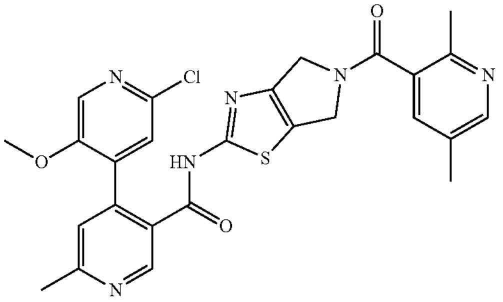 [SMILES: COc1cnc(Cl)cc1-c1cc(C)ncc1C(=O)Nc1nc2c(s1)CN(C(=O)c1cc(C)cnc1C)C2] | 2'-Chloro-N-(5-(2,5-dimethyl-nicotinoyl)-5,6-dihydro-4H-pyrrolo[3,4-d]thiazol-2-yl)-5'-methoxy-6-methyl-[4,4'-bipyridine]-3-carboxamide | 535 | $^{1}$H NMR (400 MHz, DMSO-$d_6$) δ 12.8 (s, 1H), 8.77 (d, J = 5.8 Hz, 1H), 8.36 (s, 1H), 8.16 (d, J = 1.6 Hz, 1H), 7.62 (s, 1H), 7.53 (s, 1H), 7.43 (s, 1H), 4.81 (s, 1H), 4.67 (s, 1H), 4.45 (s, 1H), 4.35 (s, 1H), 3.59 (s, 3H), 2.58 (d, J = 3.0 Hz, 3H), 2.41 (s, 3H), 2.30-2.28 (m, 3H) |

TABLE C-continued

The following examples were prepared using a similar procedure to that described for Example 1

| Ex. No. | Structure | Compound Name | LCMS [M + H]+ | NMR |
|---|---|---|---|---|
| 514 | 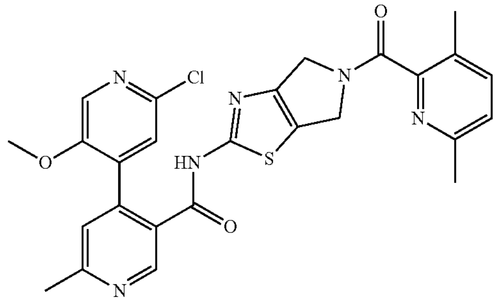 [SMILES: COc1cnc(Cl)cc1-c1cc(C)ncc1C(=O)Nc1nc2c(s1)CN(C(=O)c1nc(C)ccc1C)C2] | 2'-chloro-N-(5-(3,6-dimethyl-picolinoyl)-5,6-dihydro-4H-pyrrolo[3,4-d]thiazol-2-yl)-5'-methoxy-6-methyl-[4,4'-bipyridine]-3-carboxamide | 535 | $^1$H NMR (400 MHz, DMSO-$d_6$) δ 12.8 (d, J = 2.8 Hz, 1H), 8.78 (d, J = 5.8 Hz, 1H), 8.16 (d, J = 3.6 Hz, 1H), 7.65 (d, J = 8.0 Hz, 1H), 7.54 (s, 1H), 7.43 (s, 1H), 7.26 (dd, J = 7.8, 2.6 Hz, 1H), 4.82 (s, 1H), 4.68 (s, 1H), 4.51 (s, 1H), 4.40 (s, 1H), 3.60 (s, 3H), 2.59 (d, J = 2.6 Hz, 3H), 2.46 (d, J = 2.6 Hz, 3H), 2.26 (s, 3H) |
| 515 | 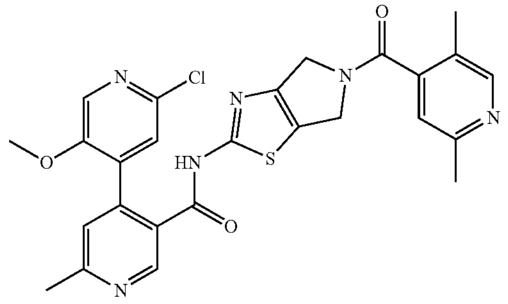 [SMILES: COc1cnc(Cl)cc1-c1cc(C)ncc1C(=O)Nc1nc2c(s1)CN(C(=O)c1cc(C)ncc1C)C2] | 2'-Chloro-N-(5-(2,5-dimethyl-isonicotin-oyl)-5,6-dihydro-4H-pyrrolo[3,4-d]thiazol-2-yl)-5'-methoxy-6-methyl-[4,4'-bipyridine]-3-carboxamide | 535 | $^1$H NMR (400 MHz, DMSO-$d_6$) δ 12.8 (s, 1H), 8.77 (d, J = 5.4 Hz, 1H), 8.40 (s, 1H), 8.16 (d, J = 1.6 Hz, 1H), 7.53 (s, 1H), 7.43 (d, J = 2.4 Hz, 1H), 7.25 (d, J = 4.0 Hz, 1H), 4.81 (s, 1H), 4.67 (s, 1H), 4.43 (s, 1H), 4.33 (s, 1H), 3.59 (s, 3H), 2.58 (d, J = 2.8 Hz, 3H), 2.46 (d, J = 2.2 Hz, 3H), 2.21 (s, 3H) |
| 516 | 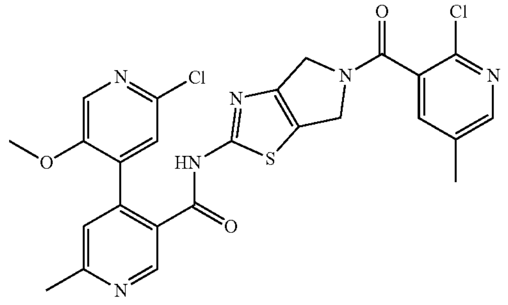 | 2'-Chloro-N-(5-(2-chloro-5-methyl-nicotinoyl)-5,6-dihydro-4H-pyrrolo[3,4-d]thiazol-2-yl)-5'-methoxy-6-methyl-[4,4'-bipyridine]-3-carboxamide | 555 | $^1$H NMR (400 MHz, DMSO-$d_6$) δ 12.8 (d, J = 7.8 Hz, 1H), 8.78 (d, J = 4.4 Hz, 1H), 8.38-8.35 (m, 1H), 8.17-8.15 (m, 1H), 7.90-7.84 (m, 1H), 7.54 (s, 1H), 7.46-7.41 (m, 1H), 4.81 (s, 1H), 4.67 (s, 1H), 4.50 (s, 1H), 4.39 (s, 1H), 3.59 (s, 3H), 2.58 (d, J = 2.8 Hz, 3H), 2.33 (s, 3H) |
| 517 | 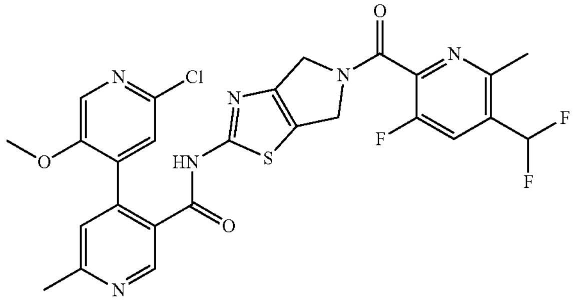 [SMILES: COc1cnc(Cl)cc1-c1cc(C)ncc1C(=O)Nc1nc2c(s1)CN(C(=O)c1nc(C)c(C(F)F)cc1F)C2] | 2'-chloro-N-(5-(5-(difluoromethyl)-3-fluoro-6-methyl-picolinoyl)-5,6-dihydro-4H-pyrrolo[3,4-d]thiazol-2-yl)-5'-methoxy-6-methyl-[4,4'-bipyridine]-3-carboxamide | 589 | $^1$H NMR (400 MHz, DMSO-$d_6$) δ 12.8 (s, 1H), 8.78 (d, J = 4.6 Hz, 1H), 8.16 (d, J = 2.4 Hz, 1H), 8.11-8.05 (m, 1H), 7.54 (s, 1H), 7.43 (s, 1H), 7.30 (t, J = 54.0 Hz, 1H), 4.88-4.82 (m, 1H), 4.73-4.67 (m, 2H), 4.61-4.57 (m, 1H), 3.60 (s, 3H), 2.62-2.56 (m, 6H) |

TABLE C-continued

| The following examples were prepared using a similar procedure to that described for Example 1 | | | | |
|---|---|---|---|---|
| Ex. No. | Structure | Compound Name | LCMS [M + H]+ | NMR |
| 518 | 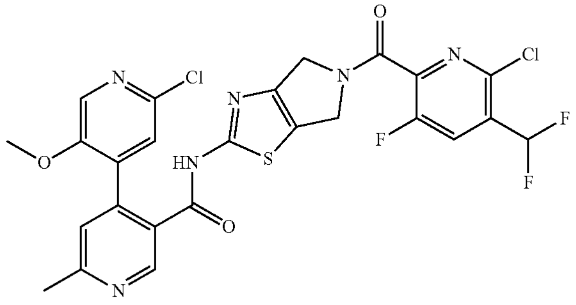 [SMILES: COc1cnc(Cl)cc1-c1cc(C)ncc1C(=O)Nc1nc2c(s1)CN(C(=O)c1nc(Cl)c(C(F)F)cc1F)C2] | 2'-chloro-N-(5-(6-chloro-5-(difluoromethyl)-3-fluoropicolinoyl)-5,6-dihydro-4H-pyrrolo[3,4-d]thiazol-2-yl)-5'-methoxy-6-methyl-[4,4'-bipyridine]-3-carboxamide | 609 | $^1$H NMR (400 MHz, DMSO-$d_6$) δ 12.8 (s, 1H), 8.79 (d, J = 3.8 Hz, 1H), 8.45-8.38 (m, 1H), 8.16 (d, J = 2.0 Hz, 1H), 7.54 (s, 1H), 7.43 (s, 1H), 7.28 (t, J = 53.2 Hz, 1H), 4.86 (s, 1H), 4.74 (s,1H), 4.73 (s, 1H), 4.64 (s, 1H), 3.60 (s, 3H), 2.59 (d, J = 2.2 Hz, 3H) |
| 519 | 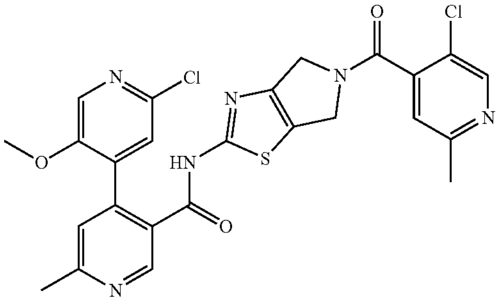 | 2'-chloro-N-(5-(5-chloro-2-methylisonicotinoyl)-5,6-dihydro-4H-pyrrolo[3,4-d]thiazol-2-yl)-5'-methoxy-6-methyl-[4,4'-bipyridine]-3-carboxamide | 555 | $^1$H NMR (400 MHz, DMSO-$d_6$) δ 12.8 (d, J = 8.4 Hz, 1H), 8.78 (d, J = 4.0 Hz, 1H), 8.40 (d, J = 2.6 Hz, 1H), 8.16 (s, 1H), 7.63 (d, J = 9.2 Hz, 1H), 7.54 (s, 1H), 7.43 (d, J = 3.0 Hz, 1H), 4.81 (s, 1H), 4.67 (s, 1H), 4.48 (s, 1H), 4.38 (s, 1H), 3.59 (s, 3H), 2.59 (d, J = 2.6 Hz, 3H), 2.25 (s, 3H) |
| 520 | 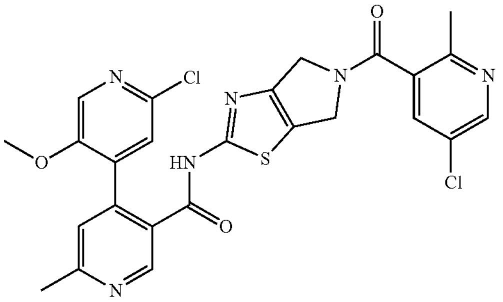 [SMILES: COc1cnc(Cl)cc1-c1cc(C)ncc1C(=O)Nc1nc2c(s1)CN(C(=O)c1cc(Cl)cnc1C)C2] | 2'-Chloro-N-(5-(5-chloro-2-methyl-nicotinoyl)-5,6-dihydro-4H-pyrrolo[3,4-d]thiazol-2-yl)-5'-methoxy-6-methyl-[4,4'-bipyridine]-3-carboxamide | 555 | $^1$H NMR (400 MHz, DMSO-$d_6$) δ 12.8 (d, J = 8.4 Hz, 1H), 8.78 (d, J = 4.4 Hz, 1H), 8.59 (d, J = 2.4 Hz, 1H), 8.16 (s, 1H), 8.05 (dd, J = 8.8, 2.4 Hz, 1H), 7.54 (s, 1H), 7.43 (d, J = 2.8 Hz, 1H), 4.82 (s, 1H), 4.68 (s, 1H), 4.50 (s, 1H), 4.40 (s, 1H), 3.59 (s, 3H), 2.59 (d, J = 2.8 Hz, 3H), 2.46 (s, 3H) |
| 521 | 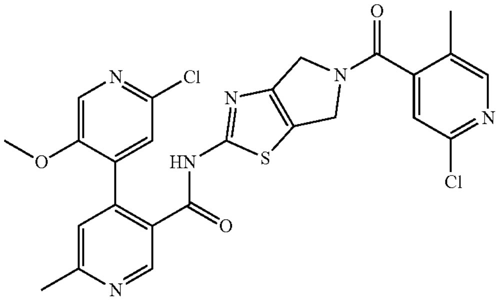 [SMILES: COc1cnc(Cl)cc1-c1cc(C)ncc1C(=O)Nc1nc2c(s1)CN(C(=O)c1cc(Cl)ncc1C)C2] | 2'-Chloro-N-(5-(2-chloro-5-methylisonicotinoyl)-5,6-dihydro-4H-pyrrolo[3,4-d]thiazol-2-yl)-5'-methoxy-6-methyl-[4,4'-bipyridine]-3-carboxamide | 555 | $^1$H NMR (400 MHz, DMSO-$d_6$) δ 12.8 (d, J = 8.8 Hz, 1H), 8.77 (d, J = 4.0 Hz, 1H), 8.40 (d, J = 2.6 Hz, 1H), 8.16 (s, 1H), 7.63 (d, J = 9.2 Hz, 1H), 7.54 (s, 1H), 7.43 (d, J = .30 Hz, 1H), 4.81 (t, J = 2.8 Hz, 1H), 4.67 (t, J = 2.6 Hz, 1H), 4.48 (t, J = 2.6 Hz, 1H), 4.38 (t, J = 2.8 Hz, 1H), 3.59 (s, 3H), 2.58 (d, J = 2.6 Hz, 3H), 2.25 (s, 3H) |

TABLE C-continued

The following examples were prepared using a similar procedure to that described for Example 1

| Ex. No. | Structure | Compound Name | LCMS [M + H]+ | NMR |
|---|---|---|---|---|
| 522 | 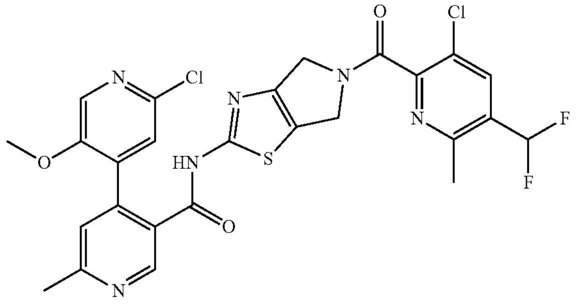 [SMILES: COc1cnc(Cl)cc1-c1cc(C)ncc1C(=O)Nc1nc2c(s1)CN(C(=O)c1nc(C)c(C(F)F)cc1Cl)C2] | 2'-Chloro-N-(5-(3-chloro-5-(difluoromethyl)-6-methyl-picolinoyl)-5,6-dihydro-4H-pyrrolo[3,4-d]thiazol-2-yl)-5'-methoxy-6-methyl-[4,4'-bipyridine]-3-carboxamide | 605 | $^1$H NMR (400 MHz, DMSO-$d_6$) δ 12.8 (s, 1H), 8.78 (d, J = 4.8 Hz, 1H), 8.23 (d, J = 6.0 Hz, 1H), 8.16 (d, J = 3.4 Hz, 1H), 7.54 (s, 1H), 7.43 (d, J = 2.4 Hz, 1H), 7.29 (t, J = 54.0 Hz, 1H), 4.85 (s, 1H), 4.71 (s, 1H), 4.51 (s, 1H), 4.41 (s, 1H), 3.60 (s, 3H), 2.61 (s, 3H), 2.59 (d, J = 2.6 Hz, 3H) |
| 523 | 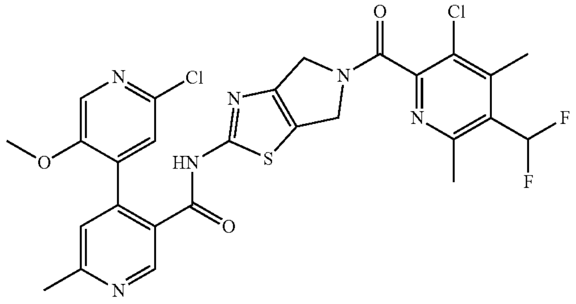 [SMILES: COc1cnc(Cl)cc1-c1cc(C)ncc1C(=O)Nc1nc2c(s1)CN(C(=O)c1nc(C)c(C(F)F)c(C)c1Cl)C2] | 2'-chloro-N-(5-(3-chloro-5-(difluoromethyl)-4,6-dimethyl-picolinoyl)-5,6-dihydro-4H-pyrrolo[3,4-d]thiazol-2-yl)-5'-methoxy-6-methyl-[4,4'-bipyridine]-3-carboxamide | 619 | $^1$H NMR (400 MHz, DMSO-$d_6$) δ 12.8 (s, 1H), 8.78 (d, J = 4.8 Hz, 1H), 8.16 (d, J = 3.2 Hz, 1H), 7.54 (s, 1H), 7.45 (t, J = 52.4 Hz, 1H), 7.43 (d, J = 2.0 Hz, 1H), 4.86-4.81 (m, 1H), 4.73-4.68 (m, 1H), 4.50-4.46 (m, 1H), 4.40-4.36 (m, 1H), 3.60 (s, 3H), 2.65 (s, 3H), 2.58 (d, J = 2.6 Hz, 3H), 2.56 (s, 3H) |
| 524 | 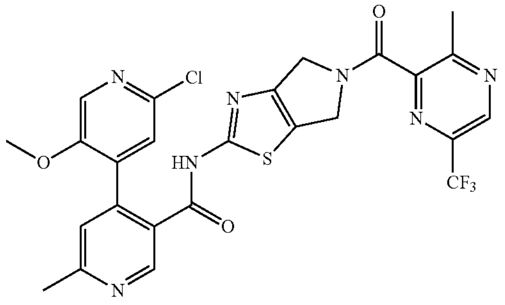 [SMILES: COc1cnc(Cl)cc1-c1cc(C)ncc1C(=O)Nc1nc2c(s1)CN(C(=O)c1nc(C(F)(F)F)cnc1C)C2] | 2'-Chloro-5'-methoxy-6-methyl-N-(5-(3-methyl-6-(trifluoromethyl) pyrazine-2-carbonyl)-5,6-dihydro-4H-pyrrolo[3,4-d]thiazol-2-yl)-[4,4'-bipyridine]-3-carboxamide | 590 | $^1$H NMR (400 MHz, DMSO-$d_6$) δ 12.8 (s, 1H), 9.21 (d, J = 2.2 Hz, 1H), 8.78 (d, J = 6.4 Hz, 1H), 8.16 (d, J = 4.2 Hz, 1H), 7.54 (s, 1H), 7.43 (s, 1H), 4.89 (s, 1H), 4.76 (s, 1H), 4.66 (s, 1H), 4.56 (s, 1H), 3.60 (s, 3H), 2.70 (s, 3H), 2.59 (d, J = 2.2 Hz, 3H) |
| 525 | 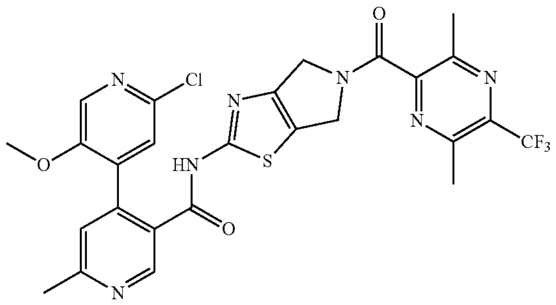 [SMILES: COc1cnc(Cl)cc1-c1cc(C)ncc1C(=O)Nc1nc2c(s1)CN(C(=O)c1nc(C)c(C(F)(F)F)nc1C)C2] | 2'-Chloro-N-(5-(3,6-dimethyl-5-(trifluoromethyl) pyrazine-2-carbonyl)-5,6-dihydro-4H-pyrrolo[3,4-d]thiazol-2-yl)-5'-methoxy-6-methyl-[4,4'-bipyridine]-3-carboxamide | 604 | $^1$H NMR (400 MHz, DMSO-$d_6$) δ 12.8 (d, J = 12.2 Hz, 1H), 8.78 (d, J = 4.8 Hz, 1H), 8.17 (d, J = 1.8 Hz, 1H), 7.54 (s, 1H), 7.43 (d, J = 1.8 Hz, 1H), 4.88 (s, 1H), 4.75 (s, 1H), 4.66 (s, 1H), 4.55 (s, 1H), 3.60 (s, 3H), 2.68 (s, 3H), 2.59 (s, 6H) |

TABLE C-continued

The following examples were prepared using a similar procedure to that described for Example 1

| Ex. No. | Structure | Compound Name | LCMS [M + H]$^+$ | NMR |
|---|---|---|---|---|
| 526 | 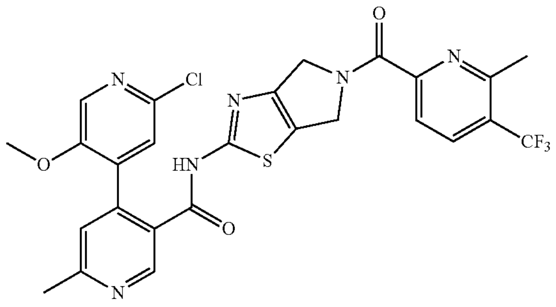 [SMILES: COc1cnc(Cl)cc1-c1cc(C)ncc1C(=O)Nc1nc2c(s1)CN(C(=O)c1ccc(C(F)(F)F)c(C)n1)C2] | 2'-Chloro-5'-methoxy-6-methyl-N-(5-(6-methyl-5-(trifluoromethyl)picolinoyl)-5,6-dihydro-4H-pyrrolo[3,4-d]thiazol-2-yl)-[4,4'-bipyridine]-3-carboxamide | 589 | $^1$H NMR (400 MHz, DMSO-$d_6$) δ 12.8 (d, J = 12.0 Hz, 1H), 8.81-8.76 (m, 1H), 8.29 (d, J = 8.4 Hz, 1H), 8.20-8.15 (m, 1H), 7.88-7.81 (m, 1H), 7.54 (s, 1H), 7.44 (s, 1H), 5.00 (s, 1H), 4.90 (s, 1H), 4.86 (s, 1H), 4.73 (s, 1H), 3.60 (s, 3H), 2.72 (s, 3H), 2.59 (s, 3H) |
| 527 | 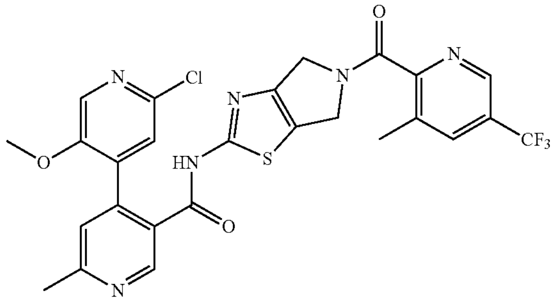 [SMILES: COc1cnc(Cl)cc1-c1cc(C)ncc1C(=O)Nc1nc2c(s1)CN(C(=O)c1ncc(C(F)(F)F)cc1C)C2] | 2'-Chloro-5'-methoxy-6-methyl-N-(5-(3-methyl-5-(trifluoromethyl)picolinoyl)-5,6-dihydro-4H-pyrrolo[3,4-d]thiazol-2-yl)-[4,4'-bipyridine]-3-carboxamide | 589 | $^1$H NMR (400 MHz, DMSO-$d_6$) δ 12.8 (s, 1H), 8.85 (s, 1H), 8.78 (d, J = 4.4 Hz, 1H), 8.27 (s, 1H), 8.16 (d, J = 2.4 Hz, 1H), 7.53 (s, 1H), 7.43 (d, J = 2.4 Hz, 1H), 4.86 (t, J = 2.6 Hz, 1H), 4.73 (t, J = 2.6 Hz, 1H), 4.53 (t, J = 2.6 Hz, 1H), 4.43 (t, J = 2.6 Hz, 1H), 3.60 (s, 3H), 2.59 (d, J = 2.8 Hz, 3H), 2.42 (s, 3H) |
| 528 | 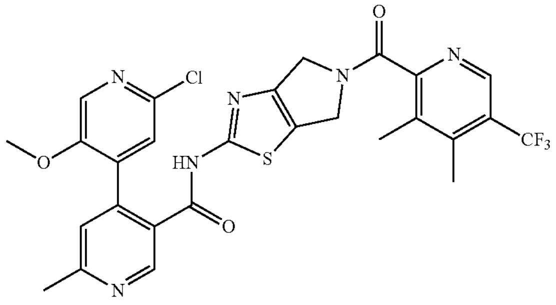 [SMILES: COc1cnc(Cl)cc1-c1cc(C)ncc1C(=O)Nc1nc2c(s1)CN(C(=O)c1ncc(C(F)(F)F)c(C)c1C)C2] | 2'-Chloro-N-(5-(3,4-dimethyl-5-(trifluoromethyl)picolinoy)-5,6-dihydro-4H-pyrrolo[3,4-d]thiazol-2-yl)-5'-methoxy-6-methyl-[4,4'-bipyridine]-3-carboxamide | 603 | $^1$H NMR (400 MHz, DMSO-$d_6$) δ 12.8 (s, 1H), 8.77 (s, 1H), 8.73 (s, 1H), 8.16 (s, 1H), 7.53 (s, 1H), 7.43 (s, 1H), 4.85 (s, 1H), 4.72 (s, 1H), 4.45 (s, 1H), 4.35 (s, 1H), 3.59 (s, 3H), 2.58 (s, 3H), 2.43 (s, 3H), 2.31 (s, 3H) |
| 529 | 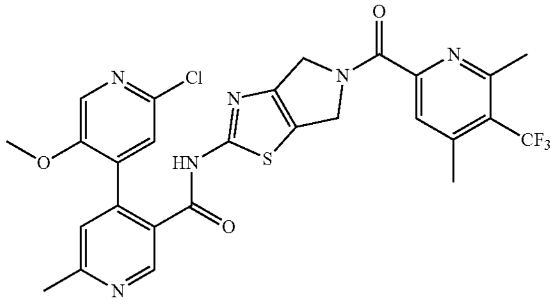 [SMILES: COc1cnc(Cl)cc1-c1cc(C)ncc1C(=O)Nc1nc2c(s1)CN(C(=O)c1cc(C)c(C(F)(F)F)c(C)n1)C2] | 2'-Chloro-N-(5-(4,6-dimethyl-5-(trifluoromethyl)picolinoyl)-5,6-dihydro-4H-pyrrolo[3,4-d]thiazol-2-yl)-5'-methoxy-6-methyl-[4,4'-bipyridine]-3-carboxamide | 603 | $^1$H NMR (400 MHz, DMSO-$d_6$) δ 12.8 (d, J = 11.2 Hz, 1H), 8.78 (d, J = 2.2 Hz, 1H), 8.17 (s, 1H), 7.72 (d, J = 7.0 Hz, 1H), 7.54 (s, 1H), 7.44 (s, 1H), 4.99 (s, 1H), 4.90 (s, 1H), 4.85 (s, 1H), 4.71 (s, 1H), 3.60 (s, 3H), 2.74-2.69 (m, 3H), 2.59 (s, 3H), 2.57-2.52 (m, 3H) |

TABLE C-continued

| The following examples were prepared using a similar procedure to that described for Example 1 | | | | |
|---|---|---|---|---|
| Ex. No. | Structure | Compound Name | LCMS $[M + H]^+$ | NMR |
| 530 | 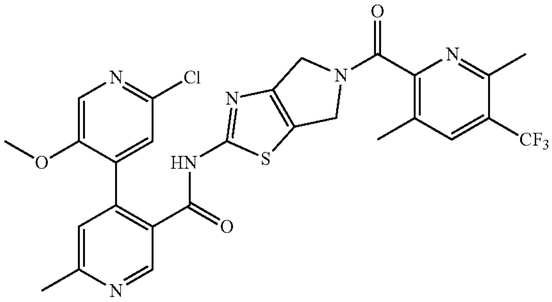 [SMILES: COc1cnc(Cl)cc1-c1cc(C)ncc1C(=O)Nc1nc2c(s1)CN(C(=O)c1nc(C)c(C(F)(F)F)cc1C)C2] | 2'-Chloro-N-(5-(3,6-dimethyl-5-(trifluoromethyl)picolinoyl)-5,6-dihydro-4H-pyrrolo[3,4-d]thiazol-2-yl)-5'-methoxy-6-methyl-[4,4'-bipyridine]-3-carboxamide | 603 | $^1H$ NMR (400 MHz, DMSO-$d_6$) δ 12.8 (d, J = 4.6 Hz, 1H), 8.77 (d, J = 4.8 Hz, 1H), 8.16 (d, J = 2.6 Hz, 1H), 8.13 (d, J = 3.4 Hz, 1H), 7.53 (s, 1H), 7.43 (d, J = 1.6 Hz, 1H), 4.84 (s, 1H), 4.71 (s, 1H), 4.53 (s, 1H), 4.43 (s, 1H), 3.59 (s, 3H), 2.62 (s, 3H), 2.58 (d, J = 2.4 Hz, 3H), 2.35 (s, 3H) |
| 531 | 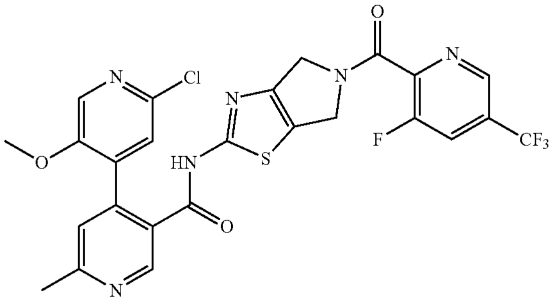 [SMILES: COc1cnc(Cl)cc1-c1cc(C)ncc1C(=O)Nc1nc2c(s1)CN(C(=O)c1ncc(C(F)(F)F)cc1F)C2] | 2'-Chloro-N-(5-(3-fluoro-5-(trifluoromethyl)picolinoyl)-5,6-dihydro-4H-pyrrolo[3,4-d]thiazol-2-yl)-5'-methoxy-6-methyl-[4,4'-bipyridine]-3-carboxamide | 593 | $^1H$ NMR (400 MHz, DMSO-$d_6$) δ 12.8 (d, J = 2.6 Hz, 1H), 8.96 (s, 1H), 8.78 (d, J = 3.8 Hz, 1H), 8.59-8.54 (m, 1H), 8.16 (d, J = 1.8 Hz, 1H), 7.54 (s, 1H), 7.43 (d, J = 2.4 Hz, 1H), 4.87 (s, 1H), 4.74 (s, 1H), 4.70 (s, 1H), 4.60 (s, 1H), 3.60 (d, J = 1.0 Hz, 3H), 2.59 (d, J = 2.8 Hz, 3H) |
| 532 | 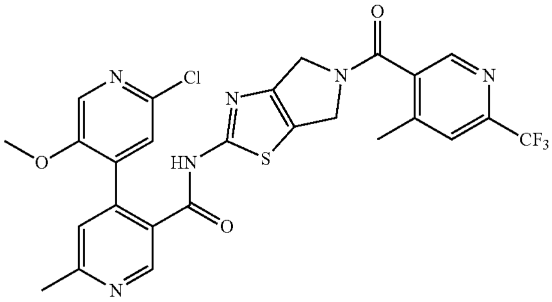 [SMILES: COc1cnc(Cl)cc1-c1cc(C)ncc1C(=O)Nc1nc2c(s1)CN(C(=O)c1cnc(C(F)(F)F)cc1C)C2] | 2'-Chloro-5'-methoxy-6-methyl-N-(5-(4-methyl-6-(trifluoromethyl)nicotinoyl)-5,6-dihydro-4H-pyrrolo[3,4-d]thiazol-2-yl)-[4,4'-bipyridine]-3-carboxamide | 589 | $^1H$ NMR (400 MHz, DMSO-$d_6$) δ 12.8 (s, 1H), 8.78 (t, J = 3.8 Hz, 2H), 8.17 (s, 1H), 7.95 (d, J = 3.6 Hz, 1H), 7.54 (s, 1H), 7.43 (d, J = 2.8 Hz, 1H), 4.86 (s, 1H), 4.72 (s, 1Hz), 4.50 (s, 1H), 4.42 (s, 1H), 3.59 (d, J = 1.2 Hz, 3H), 2.58 (d, J = 3.0 Hz, 3H), 2.43 (s, 3H) |
| 533 | 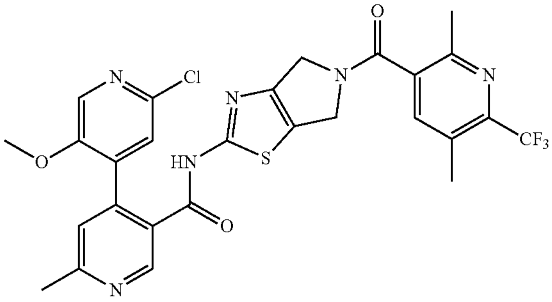 [SMILES: COc1cnc(Cl)cc1-c1cc(C)ncc1C(=O)Nc1nc2c(s1)CN(C(=O)c1cc(C)c(C(F)(F)F)nc1C)C2] | 2'-Chloro-N-(5-(2,5-dimethyl-6-(trifluoromethyl)nicotinoyl)-5,6-dihydro-4H-pyrrolo[3,4-d]thiazol-2-yl)-5'-methoxy-6-methyl-[4,4'-bipyridine]-3-carboxamide | 603 | $^1H$ NMR (400 MHz, DMSO-$d_6$) δ 12.8 (s, 1H), 8.78 (d, J = 4.8 Hz, 1H), 8.16 (s, 1H), 7.99 (d, J = 8.4 Hz, 1H), 7.54 (s, 1H), 7.43 (d, J = 3.0 Hz, 1H), 4.84 (s, 1H), 4.71 (s, 1H), 4.50 (s, 1H), 4.42 (s, 1H), 3.59 (s, 3H), 2.59 (d, J = 2.8 Hz, 3H), 2.49 (s, 3H), 2.45 (s, 3H) |

TABLE C-continued

The following examples were prepared using a similar procedure to that described for Example 1

| Ex. No. | Structure | Compound Name | LCMS [M + H]+ | NMR |
|---|---|---|---|---|
| 534 | 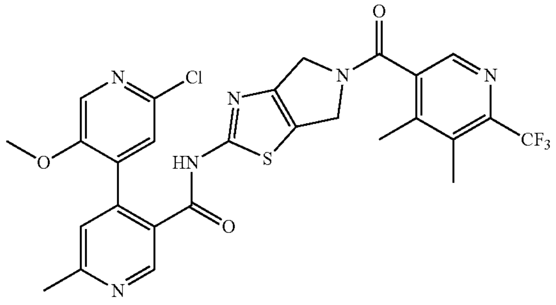 [SMILES: COc1cnc(Cl)cc1-c1cc(C)ncc1C(=O)Nc1nc2c(s1)CN(C(=O)c1cnc(C(F)(F)F)c(C)c1C)C2] | 2'-Chloro-N-(5-(4,5-dimethyl-6-(trifluoromethyl) nicotinoyl)-5,6-dihydro-4H-pyrrolo[3,4-d]thiazol-2-yl)-5'-methoxy-6-methyl-[4,4'-bipyridine]-3-carboxamide | 603 | $^1$H NMR (400 MHz, DMSO-$d_6$) δ 12.8 (s, 1H), 8.77 (d, J = 4.6 Hz, 1H), 8.54 (d, J = 2.8 Hz, 1H), 8.16 (d, J = 1.6 Hz, 1H), 7.54 (s, 1H), 7.43 (d, J = 3.6 Hz, 1H), 4.86 (s, 1H), 4.73 (s, 1H), 4.45 (s, 1H), 4.37 (s, 1H), 3.59 (s, 3H), 2.58 (d, J = 3.2 Hz, 3H), 2.41 (s, 3H), 2.34 (d, J = 2.0 Hz, 3H) |
| 535 | 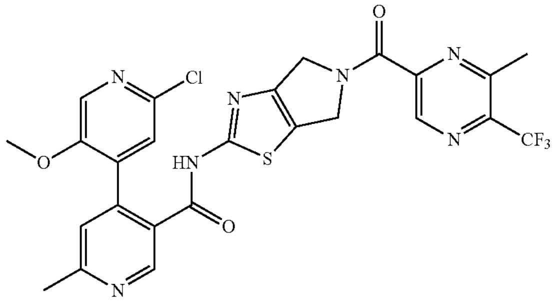 [SMILES: COc1cnc(Cl)cc1-c1cc(C)ncc1C(=O)Nc1nc2c(s1)CN(C(=O)c1cnc(C(F)(F)F)c(C)n1)C2] | 2'-Chloro-5'-methoxy-6-methyl-N-(5-(6-methyl-5-(trifluoromethyl) pyrazine-2-carbonyl)-5,6-dihydro-4H-pyrrolo[3,4-d]thiazol-2-yl)-[4,4'-bipyridine]-3-carboxamide | 590 | $^1$H NMR (400 MHz, DMSO-$d_6$) δ 12.8 (s, 1H), 9.00 (s, 1H), 8.79 (d, J = 2.6 Hz, 1H), 8.17 (s, 1H), 7.54 (s, 1H), 7.43 (s, 1H), 5.04 (s, 1H), 4.92 (s, 1H), 4.89 (s, 1H), 4.76 (s, 1H), 3.60 (s, 3H), 2.77 (d, J = 3.0 Hz, 3H), 2.59 (s, 3H) |
| 536 | 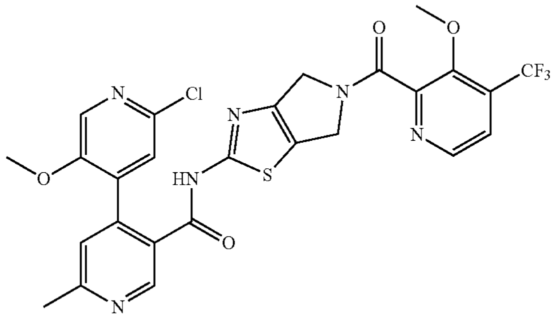 [SMILES: COc1cnc(Cl)cc1-c1cc(C)ncc1C(=O)Nc1nc2c(s1)CN(C(=O)c1nccc(C(F)(F)F)c1OC)C2] | 2'-Chloro-5'-methoxy-N-(5-(3-methoxy-4-(trifluoromethyl) picolinoyl)-5,6-dihydro-4H-pyrrolo[3,4-d]thiazol-2-yl)-6-methyl-[4,4'-bipyridine]-3-carboxamide | 605 | $^1$H NMR (400 MHz, DMSO-$d_6$) δ 12.8 (s, 1H), 8.78 (d, J = 4.4 Hz, 1H), 8.61-8.57 (m, 1H), 8.16 (d, J = 3.8 Hz, 1H), 7.85 (d, J = 4.8 Hz, 1H), 7.54 (s, 1H), 7.44-7.42 (m, 1H), 4.88 (s, 1H), 4.75 (s, 1H), 4.66 (s, 1H), 4.57 (s, 1H), 3.93 (s, 3H), 3.60 (s, 3H), 2.59 (d, J = 2.6 Hz, 3H) |
| 537 | 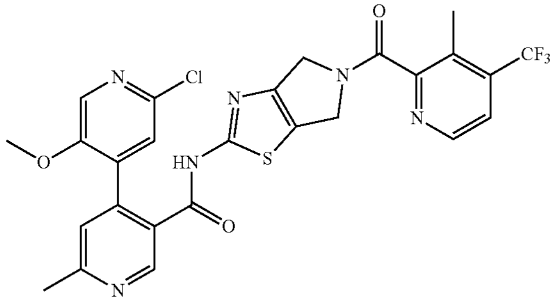 [SMILES: COc1cnc(Cl)cc1-c1cc(C)ncc1C(=O)Nc1nc2c(s1)CN(C(=O)c1nccc(C(F)(F)F)c1C)C2] | 2'-Chloro-5'-methoxy-6-methyl-N-(5-(3-methyl-4-(trifluoromethyl) picolinoyl)-5,6-dihydro-4H-pyrrolo[3,4-d]thiazol-2-yl)-[4,4'-bipyridine]-3-carboxamide | 589 | $^1$H NMR (400 MHz, DMSO-$d_6$) δ 12.8 (s, 1H), 8.78 (d, J = 5.8 Hz, 1H), 8.75-8.71 (m, 1H), 8.16 (d, J = 2.8 Hz, 1H), 7.82 (d, J = 5.2 Hz, 1H), 7.54 (s, 1H), 7.43 (d, J = 2.4 Hz, 1H), 4.87 (s, 1H), 4.74 (s, 1H), 4.51 (s, 1H), 4.42 (s, 1H), 3.59 (s, 3H), 2.58 (d, J = 3.2 Hz, 3H), 2.45-2.42 (m, 3H) |

TABLE C-continued

The following examples were prepared using a similar procedure to that described for Example 1

| Ex. No. | Structure | Compound Name | LCMS [M + H]+ | NMR |
|---|---|---|---|---|
| 538 | 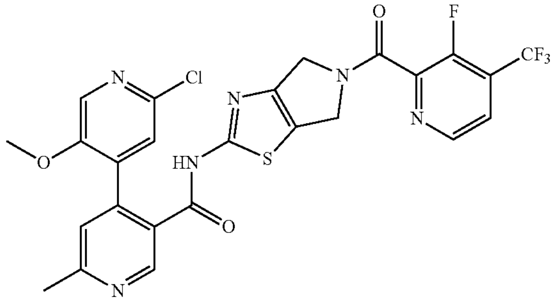 [SMILES: COc1cnc(Cl)cc1-c1cc(C)ncc1C(=O)Nc1nc2c(s1)CN(C(=O)c1nccc(C(F)(F)F)c1F)C2] | 2'-Chloro-N-(5-(3-fluoro-4-(trifluoromethyl)picolinoyl)-5,6-dihydro-4H-pyrrolo[3,4-d]thiazol-2-yl)-5'-methoxy-6-methyl-[4,4'-bipyridine]-3-carboxamide | 593 | $^1$H NMR (400 MHz, DMSO-$d_6$) δ 12.8 (s, 1H), 8.81-8.74 (m, 2H), 8.16 (s, 1H), 8.07-8.02 (m, 1H), 7.54 (s, 1H), 7.43 (s, 1H), 4.88 (s, 1H), 4.75 (s, 2H), 4.65 (s, 1H), 3.60 (s, 3H), 2.59 (d, J = 2.6 Hz, 3H) |
| 539 | 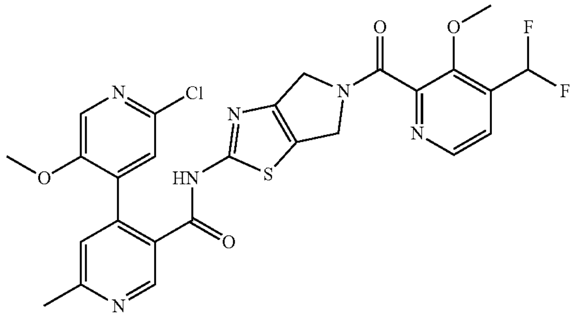 [SMILES: COc1cnc(Cl)cc1-c1cc(C)ncc1C(=O)Nc1nc2c(s1)CN(C(=O)c1nccc(C(F)F)c1OC)C2] | 2'-Chloro-N-(5-(4-(difluoromethyl)-3-methoxy-picolinoyl)-5,6-dihydro-4H-pyrrolo[3,4-d]thiazol-2-yl)-5'-methoxy-6-methyl-[4,4'-bipyridine]-3-carboxamide | 587 | $^1$H NMR (400 MHz, DMSO-$d_6$) δ 12.8 (s, 1H), 8.78 (d, J = 4.4 Hz, 1H), 8.53 (d, J = 5.0 Hz, 1H), 8.16 (d, J = 3.8 Hz, 1H), 7.69 (d, J = 4.8 Hz, 1H), 7.54 (s, 1H), 7.43 (d, J = 1.8 Hz, 1H), 7.26 (t, J = 54.4 Hz, 1H), 4.86 (t, J = 2.6 Hz, 1H), 4.73 (t, J = 2.8 Hz, 1H), 4.62 (t, J = 2.8 Hz, 1H), 4.53 (t, J = 2.8 Hz, 1H), 3.90 (s, 3H), 3.60 (s, 3H), 2.59 (d, J = 2.8 Hz, 3H) |
| 540 | 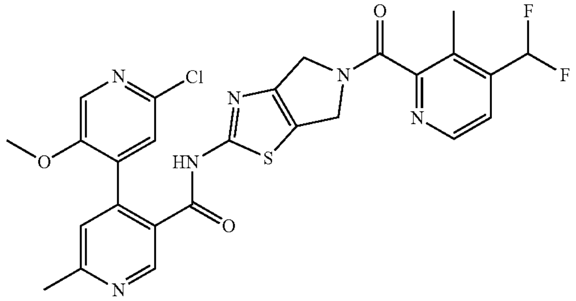 [SMILES: COc1cnc(Cl)cc1-c1cc(C)ncc1C(=O)Nc1nc2c(s1)CN(C(=O)c1nccc(C(F)F)c1C)C2] | 2'-Chloro-N-(5-(4-(difluoromethyl)-3-methyl-picolinoyl)-5,6-dihydro-4H-pyrrolo[3,4-d]thiazol-2-yl)-5'-methoxy-6-methyl-[4,4'-bipyridine]-3-carboxamide | 571 | $^1$H NMR (400 MHz, DMSO-$d_6$) δ 12.8 (s, 1H), 8.78 (d, J = 5.4 Hz, 1H), 8.64 (d, J = 5.0 Hz, 1H), 8.16 (d, J = 3.4 Hz, 1H), 7.63 (d, J = 5.0 Hz, 1H), 7.53 (s, 1H), 7.43 (d, J = 1.6 Hz, 1H), 7.31 (t, J = 53.6 Hz, 1H), 4.86 (s, 1H), 4.72 (s, 1H), 4.49 (s, 1H), 4.38 (s, 1H), 3.60 (s, 3H), 2.58 (d, J = 3.0 Hz, 3H), 2.37 (s, 3H) |
| 541 | 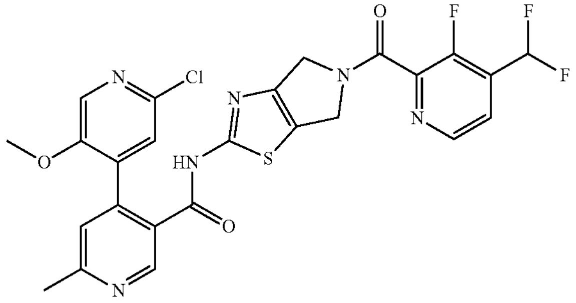 [SMILES: COc1cnc(Cl)cc1-c1cc(C)ncc1C(=O)Nc1nc2c(s1)CN(C(=O)c1nccc(C(F)F)c1F)C2] | 2'-Chloro-N-(5-(4-(difluoro-methyl)-3-fluoro-picolinoyl)-5,6-dihydro-4H-pyrrolo[3,4-d]thiazol-2-yl)-5'-methoxy-6-methyl-[4,4'-bipyridine]-3-carboxamide | 575 | $^1$H NMR (400 MHz, DMSO-$d_6$) δ 12.8 (s, 1H), 8.78 (d, J = 4.6 Hz, 1H), 8.68 (d, J = 4.8 Hz, 1H), 8.16 (d, J = 2.4 Hz, 1H), 7.87-7.83 (m, 1H), 7.54 (s, 1H), 7.43 (s, 1H), 7.38 (t, J = 53.6 Hz, 1H), 4.87 (s, 1H), 4.76-4.69 (m, 2H), 4.61 (s, 1H), 3.60 (s, 3H), 2.59 (d, J = 2.6 Hz, 3H) |

TABLE C-continued

The following examples were prepared using a similar procedure to that described for Example 1

| Ex. No. | Structure | Compound Name | LCMS [M + H]+ | NMR |
|---|---|---|---|---|
| 542 | 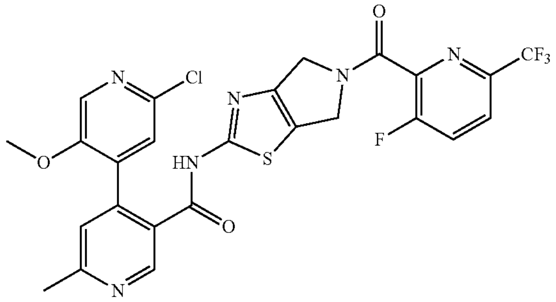 [SMILES: COc1cnc(Cl)cc1-c1cc(C)ncc1C(=O)Nc1nc2c(s1)CN(C(=O)c1nc(C(F)(F)F)ccc1F)C2] | 2'-Chloro-N-(5-(3-fluoro-6-(trifluoromethyl)picolinoyl)-5,6-dihydro-4H-pyrrolo[3,4-d]thiazol-2-yl)-5'-methoxy-6-methyl-[4,4'-bipyridine]-3-carboxamide | 593 | $^1$H NMR (400 MHz, DMSO-$d_6$) δ 12.8 (d, J = 11.2 Hz, 1H), 8.78 (d, J = 5.6 Hz, 1H), 8.29-8.20 (m, 2H), 8.16 (d, J = 4.2 Hz, 1H), 7.54 (s ,1H), 7.44 (s, 1H), 4.88 (s, 1H), 4.75 (s, 1H), 4.72 (s, 1H), 4.62 (s, 1H), 3.60 (s, 3H), 2.59 (s, 3H) |
| 543 | 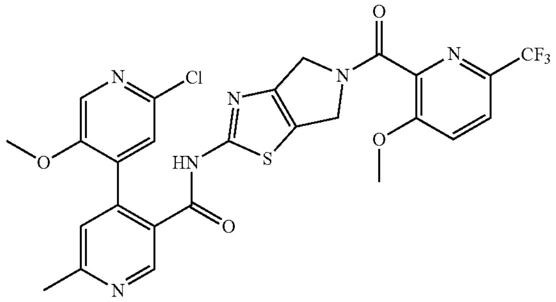 [SMILES: COc1cnc(Cl)cc1-c1cc(C)ncc1C(=O)Nc1nc2c(s1)CN(C(=O)c1nc(C(F)(F)F)ccc1OC)C2] | 2'-Chloro-5'-methoxy-N-(5-(3-methoxy-6-(trifluoromethyl)picolinoyl)-5,6-dihydro-4H-pyrrolo[3,4-d]thiazol-2-yl)-6-methyl-[4,4'-bipyridine]-3-carboxamide | 605 | $^1$H NMR (400 MHz, DMSO-$d_6$) δ 12.8 (d, J = 8.4 Hz, 1H), 8.78 (d, J = 6.2 Hz, 1H), 8.16 (d, J = 5.2 Hz, 1H), 8.03 (d, J = 8.8 Hz, 1H), 7.88-7.82 (m, 1H), 7.54 (s, 1H), 7.43 (s, 1H), 4.84-4.80 (m, 1H), 4.71-4.67 (m, 1H), 4.50-4.45 (m, 1H), 4.39-4.34 (m, 1H), 3.95 (s, 3H), 3.59 (s, 3H), 2.58 (d, J = 2.6 Hz, 3H) |
| 544 | 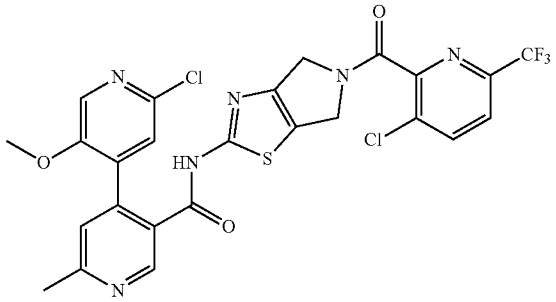 [SMILES: COc1cnc(Cl)cc1-c1cc(C)ncc1C(=O)Nc1nc2c(s1)CN(C(=O)c1nc(C(F)(F)F)ccc1Cl)C2] | 2'-Chloro-N-(5-(3-chloro-6-(trifluoromethyl)picolinoyl)-5,6-dihydro-4H-pyrrolo[3,4-d]thiazol-2-yl)-5'-methoxy-6-methyl-[4,4'-bipyridine]-3-carboxamide | 609 | $^1$H NMR (400 MHz, DMSO-$d_6$) δ 12.8 (s, 1H), 8.78 (d, J = 5.8 Hz, 1H), 8.50-8.44 (m, 1H), 8.16 (d, J = 5.0 Hz, 1H), 8.12 (dd, J = 8.4, 2.8 Hz, 1H), 7.54 (s, 1H), 7.43 (s, 1H), 4.87 (s, 1H), 4.74 (s, 1H), 4.52 (s, 1H), 4.42 (s, 1H), 3.59 (s, 3H), 2.58 (d, J = 2.2 Hz, 3H) |
| 545 | 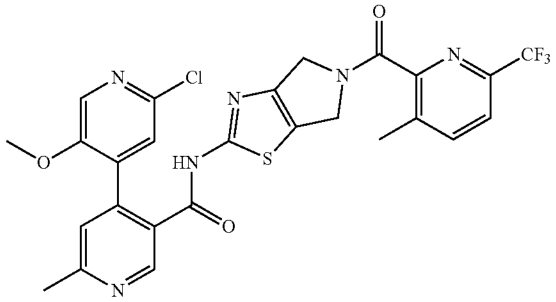 [SMILES: COc1cnc(Cl)cc1-c1cc(C)ncc1C(=O)Nc1nc2c(s1)CN(C(=O)c1nc(C(F)(F)F)ccc1C)C2] | 2'-Chloro-5'-methoxy-6-methyl-N-(5-(3-methyl-6-(trifluoromethyl)picolinoyl)-5,6-dihydro-4H-pyrrolo[3,4-d]thiazol-2-yl)-[4,4'-bipyridine]-3-carboxamide | 589 | $^1$H NMR (400 MHz, DMSO-$d_6$) δ 12.8 (d, J = 6.4 Hz, 1H), 8.78 (d, J = 6.4 Hz, 1H), 8.16 (d, J = 4.8 Hz, 1H), 8.10 (d, J = 8.2 Hz, 1H), 7.94 (d, J = 8.0 Hz, 1H), 7.56-7.52 (m, 1H), 7.43 (s, 1H), 4.89-4.84 (m, 1H), 4.76-4.71 (m, 1H), 4.55-4.51 (m, 1H), 4.47-4.41 (m, 1H), 3.60 (s, 3H), 2.59 (d, J = 2.4 Hz, 3H), 2.43 (s, 3H) |

TABLE C-continued

| The following examples were prepared using a similar procedure to that described for Example 1 | | | | |
|---|---|---|---|---|
| Ex. No. | Structure | Compound Name | LCMS [M + H]+ | NMR |
| 546 | 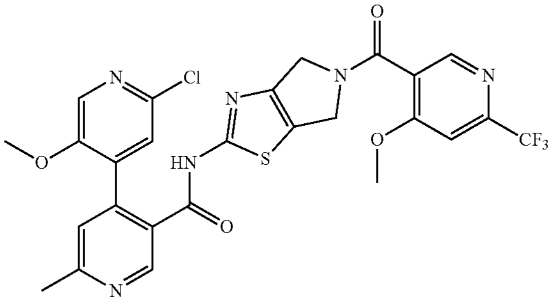 [SMILES: COc1cc(C(F)(F)F)ncc1C(=O)N1Cc2nc(NC(=O)c3cnc(C)cc3-c3cc(Cl)ncc3OC)sc2C1] | 2'-Chloro-5'-methoxy-N-(5-(4-methoxy-6-(trifluoromethyl)nicotinoyl)-5,6-dihydro-4H-pyrrolo[3,4-d]thiazol-2-yl)-6-methyl-[4,4'-bipyridine]-3-carboxamide | 605 | $^1$H NMR (400 MHz, DMSO-$d_6$) δ 12.8 (s, 1H), 8.78 (d, J = 4.2 Hz, 1H), 8.60 (d, J = 4.2 Hz, 1H), 8.16 (d, J = 2.2 Hz, 1H), 7.68 (d, J = 4.6 Hz, 1H), 7.54 (s, 1H), 7.43 (d, J = 2.4 Hz, 1H), 4.82-4.78 (m, 1H), 4.69-4.65 (m, 1H), 4.54-4.50 (m, 1H), 4.43-4.40 (m, 1H), 4.03 (d, J = 1.6 Hz, 3H), 3.59 (s, 3H), 2.59 (d, J = 2.6 Hz, 3H) |
| 547 | 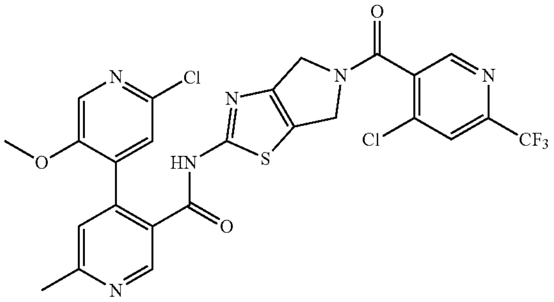 [SMILES: COc1cnc(Cl)cc1-c1cc(C)ncc1C(=O)Nc1nc2c(s1)CN(C(=O)c1cnc(C(F)(F)F)cc1Cl)C2] | 2'-Chloro-N-(5-(4-chloro-6-(trifluoromethyl)nicotinoyl)-5,6-dihydro-4H-pyrrolo[3,4-d]thiazol-2-yl)-5'-methoxy-6-methyl-[4,4'-bipyridine]-3-carboxamide | 609 | $^1$H NMR (400 MHz, DMSO-$d_6$) δ 12.8 (s, 1H), 8.96 (d, J = 6.8 Hz, 1H), 8.78 (d, J = 3.8 Hz, 1H), 8.34 (d, J = 9.8 Hz, 1H), 8.19-8.14 (m, 1H), 7.54 (s, 1H), 7.46-7.40 (m, 1H), 4.86 (s, 1H), 4.73 (s, 1H), 4.54 (s, 1H), 4.46 (s, 1H), 3.60 (s, 3H), 2.59 (d, J = 3.0 Hz, 3H) |
| 548 | 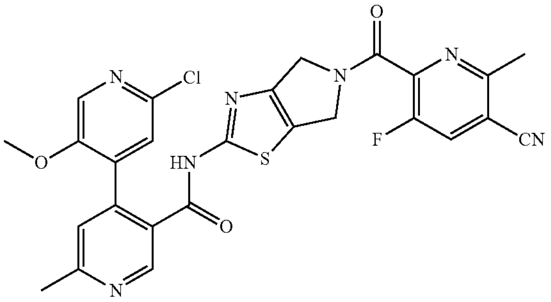 [SMILES: COc1cnc(Cl)cc1-c1cc(C)ncc1C(=O)Nc1nc2c(s1)CN(C(=O)c1nc(C)c(C#N)cc1F)C2] | 2'-Chloro-N-(5-(5-cyano-3-fluoro-6-methyl-picolinoyl)-5,6-dihydro-4H-pyrrolo[3,4-d]thiazol-2-yl)-5'-methoxy-6-methyl-[4,4'-bipyridine]-3-carboxamide | 564 | $^1$H NMR (400 MHz, DMSO-$d_6$) δ 12.8 (d, J = 12.6 Hz, 1H), 8.78 (d, J = 5.0 Hz, 1H), 8.57 (dd, J = 9.0, 3.8 Hz, 1H), 8.16 (d, J = 1.6 Hz, 1H), 7.54 (s, 1H), 7.43 (s, 1H), 4.85 (s, 1H), 4.73-4.68 (m, 2H), 4.57 (s, 1H), 3.59 (s, 3H), 2.70 (d, J = 1.6 Hz, 3H), 2.59 (d, J = 2.0 Hz, 3H) |
| 549 | 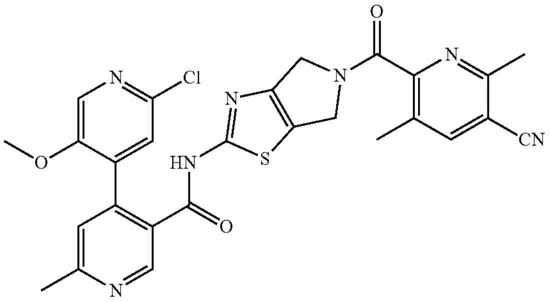 [SMILES: COc1cnc(Cl)cc1-c1cc(C)ncc1C(=O)Nc1nc2c(s1)CN(C(=O)c1nc(C)c(C#N)cc1C)C2] | 2'-chloro-N-(5-(5-cyano-3,6-dimethyl-picolinoyl)-5,6-dihydro-4H-pyrrolo[3,4-d]thiazol-2-yl)-5'-methoxy-6-methyl-[4,4'-bipyridine]-3-carboxamide | 560 | $^1$H NMR (400 MHz, DMSO-$d_6$) δ 12.8 (d, J = 8.4 Hz, 1H), 8.78 (d, J = 5.5 Hz, 1H), 8.32-8.25 (m, 1H), 8.16 (s, 1H), 7.54 (s, 1H), 7.43 (s, 1H), 4.84 (s, 1H), 4.70 (s, 1H), 4.53 (s, 1H), 4.41 (s, 1H), 3.59 (s, 3H), 2.67 (s, 3H), 2.59 (s, 3H), 2.31 (s, 3H) |

TABLE C-continued

The following examples were prepared using a similar procedure to that described for Example 1

| Ex. No. | Structure | Compound Name | LCMS [M + H]+ | NMR |
|---|---|---|---|---|
| 550 | 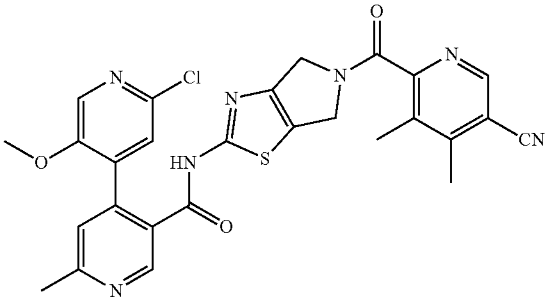 [SMILES: COc1cnc(Cl)cc1-c1cc(C)ncc1C(=O)Nc1nc2c(s1)CN(C(=O)c1ncc(C#N)c(C)c1C)C2] | 2'-chloro-N-(5-(5-cyano-3,4-dimethyl-picolinoyl)-5,6-dihydro-4H-pyrrolo[3,4-d]thiazol-2-yl)-5'-methoxy-6-methyl-[4,4'-bipyridine]-3-carboxamide | 560 | $^1$H NMR (400 MHz, DMSO-$d_6$) δ 12.8 (s, 1H), 8.84 (s, 1H), 8.77 (d, J = 5.6 Hz, 1H), 8.16 (d, J = 2.8 Hz, 1H), 7.53 (s, 1H), 7.43 (d, J = 2.6 Hz, 1H), 4.85 (s, 1H), 4.72 (s, 1H), 4.45 (s, 1H), 4.34 (s, 1H), 3.59 (s, 3H), 2.58 (d, J = 2.8 Hz, 3H), 2.51 (s, 3H), 2.28 (s, 3H) |
| 551 | 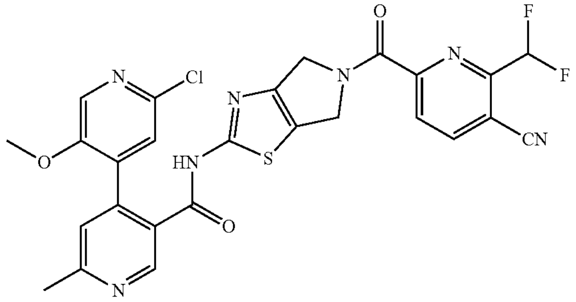 [SMILES: COc1cnc(Cl)cc1-c1cc(C)ncc1C(=O)Nc1nc2c(s1)CN(C(=O)c1ccc(C#N)c(C(F)F)n1)C2] | 2'-chloro-N-(5-(5-cyano-6-(difluoromethyl) picolinoyl)-5,6-dihydro-4H-pyrrolo[3,4-d]thiazol-2-yl)-5'-methoxy-6-methyl-[4,4'-bipyridine]-3-carboxamide | 582 | $^1$H NMR (400 MHz, DMSO-$d_6$) δ 12.8 (d, J = 19.4 Hz, 1H), 8.79 (d, J = 3.2 Hz, 1H), 8.73 (dd, J = 8.2, 2.8 Hz, 1H), 8.22-8.15 (m, 2H), 7.54 (s, 1H), 7.44 (s, 1H), 7.28 (td, J = 53.2, 14.0 Hz, 1H), 5.02 (s, 1H), 4.92 (s, 1H), 4.88 (s, 1H), 4.74 (s, 1H), 3.60 (s, 3H), 2.59 (s, 3H) |
| 552 | 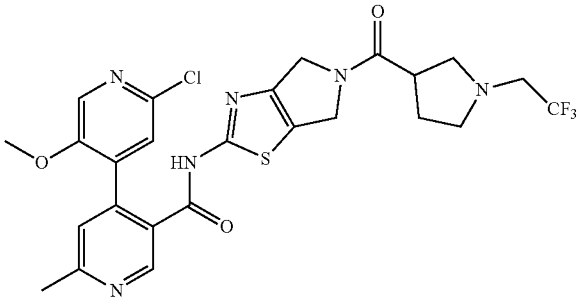 [SMILES: COc1cnc(Cl)cc1-c1cc(C)ncc1C(=O)Nc1nc2c(s1)CN(C(=O)C1CCN(CC(F)(F)F)C1)C2] | 2'-Choro-5'-methoxy-6-methyl-N-(5-(1-(2,2,2-tri-fluoroethyl)pyr-rolidine-3-carbonyl)-5,6-dihydro-4H-pyrrolo[3,4-d]thiazol-2-yl)-[4,4'-bipyridine]-3-carobxamide | 581 | $^1$H NMR (400 MHz, DMSO-$d_6$) δ 12.8 (s, 1H), 8.79 (s, 1H), 8.16 (d, J = 2.1 Hz, 1H), 7.54 (s, 1H), 7.43 (s, 1H), 4.84 (s, 1H), 4.72 (s, 1H), 4.58 (s, 1H), 4.45 (s, 1H), 3.59 (s, 3H), 3.30-3.17 (m, 3H), 3.09-3.03 (m, 1H), 2.89-2.77 (m, 2H), 2.68-2.63 (m, 1H), 2.59 (s, 3H), 2.09-1.91 (m, 2H) |
| 553 | 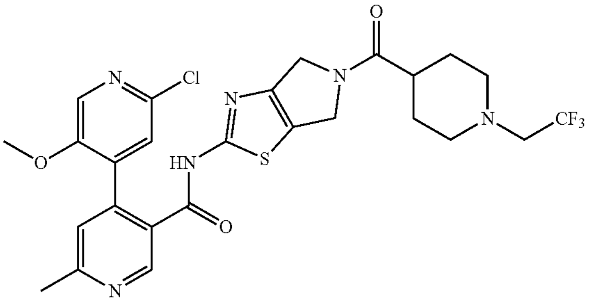 [SMILES: COc1cnc(Cl)cc1-c1cc(C)ncc1C(=O)Nc1nc2c(s1)CN(C(=O)C1CCN(CC(F)(F)F)CC1)C2] | 2'-Choro-5'-methoxy-6-methyl-N-(5-(1-(2,2,2-trifluoroethyl)pi-peridine-4-carbonyl)-5,6-dihydro-4H-pyrrolo[3,4-d]thiazol-2-yl)-[4,4'-bipyridine]-3-carboxamide | 595 | $^1$H NMR (400 MHz, DMSO-$d_6$) δ 12.8 (s, 1H), 8.78 (s, 1H), 8.17 (d, J = 4.1 Hz, 1H), 7.54 (d, J = 1.4 Hz, 1H), 7.44 (s, 1H), 4.88 (s, 1H), 4.75 (s, 1H), 4.57 (s, 1H), 4.44 (s, 1H), 3.59 (d, J = 1.8 Hz, 3H), 3.21-3.11 (m, 2H), 2.95 (d, J = 11.2 Hz, 2H), 2.59 (s, 3H), 2.48-2.34 (m, 3H), 1.75-1.54 (m, 4H) |

TABLE C-continued

The following examples were prepared using a similar procedure to that described for Example 1

| Ex. No. | Structure | Compound Name | LCMS [M + H]+ | NMR |
|---|---|---|---|---|
| 554 | 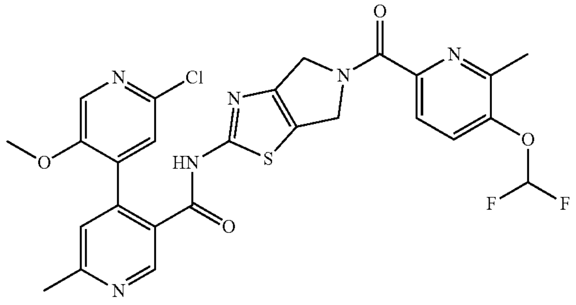 [SMILES: COc1cnc(Cl)cc1-c1cc(C)ncc1C(=O)Nc1nc2c(s1)CN(C(=O)c1ccc(OC(F)F)c(C)n1)C2] | 2'-Chloro-N-(5-(5-(difluoro-methoxy)-6-methyl-picolinoyl)-5,6-dihydro-4H-pyrrolo[3,4-d]thiazol-2-yl)-5'-methoxy-6-methyl-[4,4'-bipyridine]-3-carboxamide | 587 | $^1$H NMR (400 MHz, DMSO-$d_6$) δ 12.8 (s, 1H), 8.79 (d, J = 2.0 Hz, 1H), 8.17 (d, J = 1.2 Hz, 1H), 7.82-7.71 (m, 2H), 7.54 (s, 1H), 7.43 (s, 1H), 7.37 (td, J = 73.2, 1.6 Hz, 1H), 5.06 (s, 1H), 4.96 (s, 1H), 4.84 (s, 1H), 4.70 (s, 1H), 3.61 (s, 3H), 2.59 (s, 3H), 2.52 (s, 3H) |
| 555 | 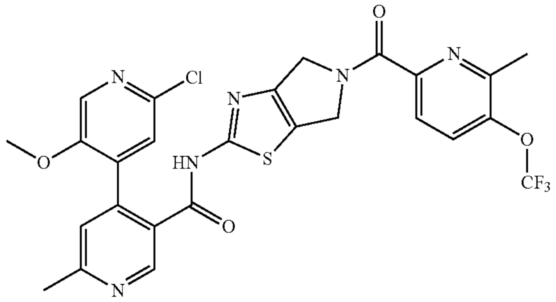 [SMILES: COc1cnc(Cl)cc1-c1cc(C)ncc1C(=O)Nc1nc2c(s1)CN(C(=O)c1ccc(OC(F)(F)F)c(C)n1)C2] | 2'-Chloro-5'-methoxy-6-methyl-N-(5-(6-methyl-5-(trifluoro-methoxy) picolinoyl)-5,6-dihydro-4H-pyrrolo[3,4-d]thiazol-2-yl)-[4,4'-bipyridine]-3-carboxamide | 605 | $^1$H NMR (400 MHz, DMSO-$d_6$) δ 12.8 (s, 1H), 8.79 (s, 1H), 8.17 (s, 1H), 8.01-7.95 (m, 1H), 7.86-7.79 (m, 1H), 7.54 (s, 1H), 7.43 (s, 1H), 5.03 (s, 1H), 4.94 (s, 1H), 4.85 (s, 1H), 4.71 (s, 1H), 3.60 (s, 3H), 2.61-2.55 (m, 6H) |
| 556 | 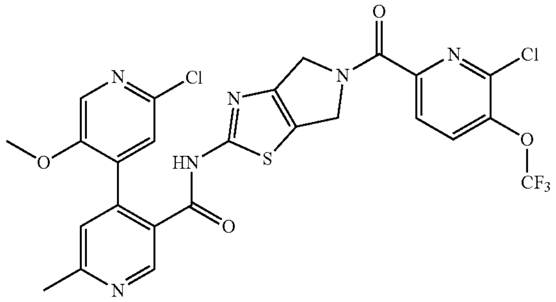 [SMILES: COc1cnc(Cl)cc1-c1cc(C)ncc1C(=O)Nc1nc2c(s1)CN(C(=O)c1ccc(OC(F)(F)F)c(Cl)n1)C2] | 2'-Chloro-N-(5-(6-chloro-5-(trifluoro-methoxy) picolinoyl)-5,6-dihydro-4H-pyrrolo[3,4-d]thiazol-2-yl)-5'-methoxy-6-methyl-[4,4'-bipyridine]-3-carboxamide | 625 | $^1$H NMR (400 MHz, DMSO-$d_6$) δ 12.8 (s, 1H), 8.79 (s, 1H), 8.28 (d, J = 8.4 Hz, 1H), 8.17 (s, 1H), 8.07-7.99 (m, 1H), 7.54 (s, 1H), 7.43 (s, 1H), 5.02 (s, 1H), 4.93 (s, 1H), 4.86 (s, 1H), 4.72 (s, 1H), 3.60 (s, 3H), 2.59 (s, 3H) |
| 557 | 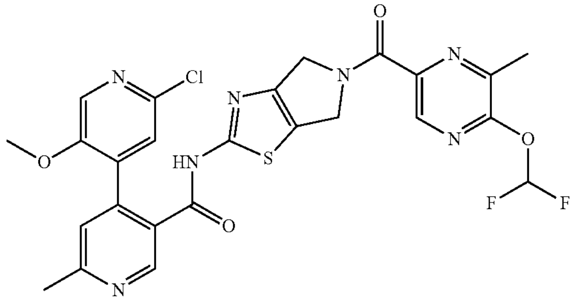 [SMILES: COc1cnc(Cl)cc1-c1cc(C)ncc1C(=O)Nc1nc2c(s1)CN(C(=O)c1cnc(OC(F)F)c(C)n1)C2] | 2'-Chloro-N-(5-(5-(difluoro-methoxy)-6-methylpyrazine-2-carbonyl)-5,6-dihydro-4H-pyrrolo[3,4-d]thiazol-2-yl)-5'-methoxy-6-methyl-[4,4'-bipyridine]-3-carboxamide | 588 | $^1$H NMR (400 MHz, DMSO-$d_6$) δ 12.8 (d, J = 15.8 Hz, 1H), 8.78 (d, J = 2.2 Hz, 1H), 8.58 (d, J = 2.6 Hz, 1H), 8.17 (s, 1H), 7.76 (td, J = 71.6, 1.2 Hz, 1H), 7.55 (s, 1H), 7.44 (s, 1H), 5.07 (s, 1H), 4.94 (s, 1H), 4.86 (s, 1H), 4.72 (s, 1H), 3.60 (s, 3H), 2.59 (s, 3H), 2.54 (d, J = 4.2 Hz, 3H) |

TABLE C-continued

The following examples were prepared using a similar procedure to that described for Example 1

| Ex. No. | Structure | Compound Name | LCMS [M + H]+ | NMR |
|---|---|---|---|---|
| 558 | 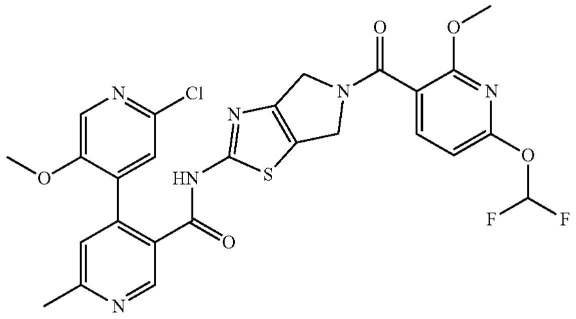 [SMILES: COc1cnc(Cl)cc1-c1cc(C)ncc1C(=O)Nc1nc2c(s1)CN(C(=O)c1ccc(OC(F)F)nc1OC)C2] | 2'-Chloro-N-(5-(6-(difluoro methoxy)-2-methoxy-nicotinoyl)-5,6-dihydro-4H-pyrrolo[3,4-d]thiazol-2-yl)-5'-methoxy-6-methyl-[4,4'-bipyridine]-3-carboxamide | 603 | $^1$H NMR (400 MHz, DMSO-$d_6$) δ 12.8 (s, 1H), 8.78 (d, J = 4.2 Hz, 1H), 8.16 (d, J = 1.8 Hz, 1H), 7.92 (d, J = 8.0 Hz, 1H), 7.81 (t, J = 72.4 Hz, 1H), 7.53 (s, 1H), 7.43 (s, 1H), 6.74 (dd, J = 8.0, 1.8 Hz, 1H), 4.77 (s, 1H), 4.63 (s, 1H), 4.52 (s, 1H), 4.42 (s, 1H), 3.94 (d, J = 1.6 Hz, 3H), 3.59 (s, 3H), 2.58 (d, J = 2.2 Hz, 3H) |
| 559 | 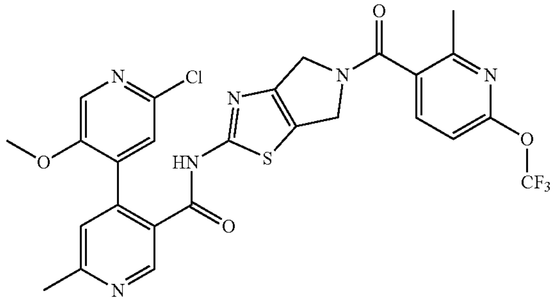 [SMILES: COc1cnc(Cl)cc1-c1cc(C)ncc1C(=O)Nc1nc2c(s1)CN(C(=O)c1ccc(OC(F)(F)F)nc1C)C2] | 2'-Chloro-5'-methoxy-6-methyl-N-(5-(2-methyl-6-(trifluoro-methoxy) nicotinoyl)-5,6-dihydro-4H-pyrrolo[3,4-d]thiazol-2-yl)-[4,4'-bipyridine]-3-carboxamide | 605 | $^1$H NMR (400 MHz, DMSO-$d_6$) δ 12.8 (s, 1H), 8.77 (d, J = 4.2 Hz, 1H), 8.16 (s, 1H), 8.08 (d, J = 8.4 Hz, 1H), 7.53 (s, 1H), 7.43 (d, J = 2.8 Hz, 1H), 7.21 (dd, J = 8.2, 4.4 Hz, 1H), 4.83 (s, 1H), 4.69 (s, 1H), 4.48 (s, 1H), 4.40 (s, 1H), 3.59 (s, 3H), 2.58 (d, J = 2.6 Hz, 3H), 2.46 (s, 3H) |
| 560 | 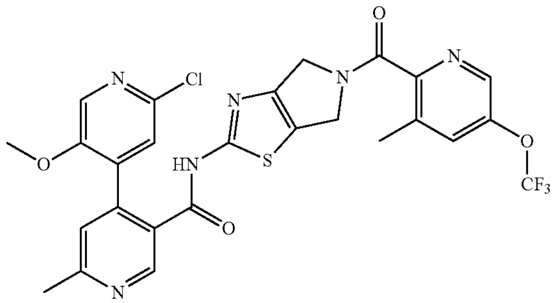 [SMILES: COc1cnc(Cl)cc1-c1cc(C)ncc1C(=O)Nc1nc2c(s1)CN(C(=O)c1ncc(OC(F)(F)F)cc1C)C2] | 2'-Chloro-5'-methoxy-6-methyl-N-(5-(3-methyl-5-(trifluoro-methoxy) picolinoyl)-5,6-dihydro-4H-pyrrolo[3,4-d]thiazol-2-yl)-[4,4'-bipyridine]-3-carboxamide | 605 | $^1$H NMR (400 MHz, DMSO-$d_6$) δ 12.8 (d, J = 3.6 Hz, 1H), 8.78 (d, J = 3.8 Hz, 1H), 8.54 (s, 1H), 8.16 (d, J = 1.8 Hz, 1H), 7.96 (s, 1H), 7.54 (s, 1H), 7.43 (d, J = 2.0 Hz, 1H), 4.85 (s, 1H), 4.71 (s, 1H), 4.55 (s, 1H), 4.44 (s, 1H), 3.60 (s, 3H), 2.59 (d, J = 2.6 Hz, 3H), 2.39 (s, 3H) |
| 561 | 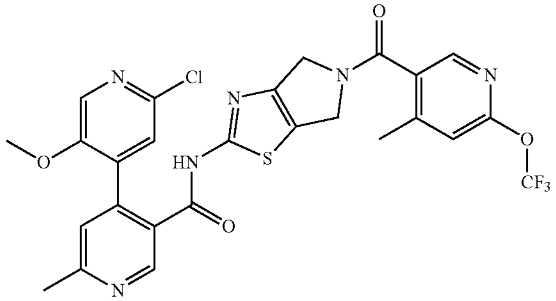 [SMILES: COc1cnc(Cl)cc1-c1cc(C)ncc1C(=O)Nc1nc2c(s1)CN(C(=O)c1cnc(OC(F)(F)F)cc1C)C2] | 2'-Chloro-5'-methoxy-6-methyl-N-(5-(4-methyl-6-(trifluoro-methoxy) nicotinoyl)-5,6-dihydro-4H-pyrrolo[3,4-d]thiazol-2-yl)-[4,4'-bipyridine]-3-carboxamide | 605 | $^1$H NMR (400 MHz, DMSO-$d_6$) δ 12.8 (d, J = 8.2 Hz, 1H), 8.77 (d, J = 3.6 Hz, 1H), 8.42 (d, J = 2.8 Hz, 1H), 8.17 (s, 1H), 7.54 (s, 1H), 7.43 (d, J = 2.8 Hz, 1H), 7.31 (d, J = 4.2 Hz, 1H), 4.83 (s, 1H), 4.70 (s, 1H), 4.53 (s, 1H), 4.44 (s, 1H), 3.59 (s, 3H), 2.59 (d, J = 2.8 Hz, 3H), 2.37 (s, 3H) |

TABLE C-continued

The following examples were prepared using a similar procedure to that described for Example 1

| Ex. No. | Structure | Compound Name | LCMS [M + H]+ | NMR |
|---|---|---|---|---|
| 562 | 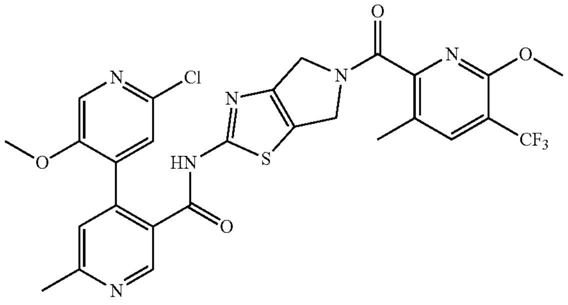 | 2'-chloro-5'-methoxy-N-(5-(6-methoxy-3-methyl-5-(trifluoromethyl)picolinoyl)-5,6-dihydro-4H-pyrrolo[3,4-d]thiazol-2-yl)-6-methyl-[4,4'-bipyridine]-3-carboxamide | 619 | $^1$H NMR (400 MHz, DMSO-$d_6$) δ 12.7 (s, 1H), 8.79 (d, J = 4.6 Hz, 1H), 8.40-8.07 (m, 2H), 7.49 (s, 1H), 7.40 (s, 1H), 4.85 (s, 1H), 4.71 (s, 1H), 4.64-4.57 (m, 1H), 4.52-4.46 (m, 1H), 4.05-3.96 (m, 3H), 3.62 (s, 3H), 2.59 (d, J = 2.2 Hz, 3H), 2.42-2.28 (m, 3H) |
| 563 | 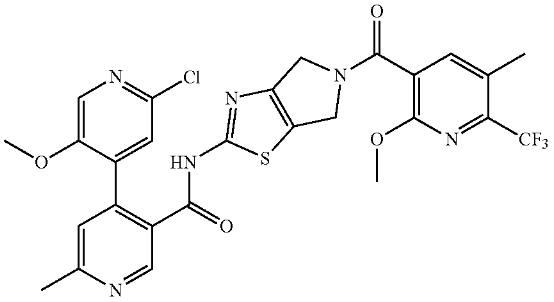 [SMILES: COc1cnc(Cl)cc1-c1cc(C)ncc1C(=O)Nc1nc2c(s1)CN(C(=O)c1cc(C)c(C(F)(F)F)nc1OC)C2] | 2'-Chloro-5'-methoxy-N-(5-(2-methoxy-5-methyl-6-(trifluoromethyl)nicotinoyl)-5,6-dihydro-4H-pyrrolo[3,4-d]thiazol-2-yl)-6-methyl-[4,4'-bipyridine]-3-carboxamide | 619 | $^1$H NMR (400 MHz, DMSO-$d_6$) δ 12.8 (s, 1H), 8.78 (d, J = 3.8 Hz, 1H), 8.16 (d, J = 1.4 Hz, 1H), 7.95 (d, J = 5.0 Hz, 1H), 7.54 (s, 1H), 7.43 (d, J = 2.2 Hz, 1H), 4.81-4.77 (m, 1H), 4.65 (s, 1H), 4.54-4.50 (m, 1H), 4.42 (s, 1H), 3.94 (d, J = 1.0 Hz, 3H), 3.59 (d, J = 1.0 Hz, 3H), 2.58 (d, J = 2.4 Hz, 3H), 2.40 (d, J = 2.4 Hz, 3H) |
| 564 | 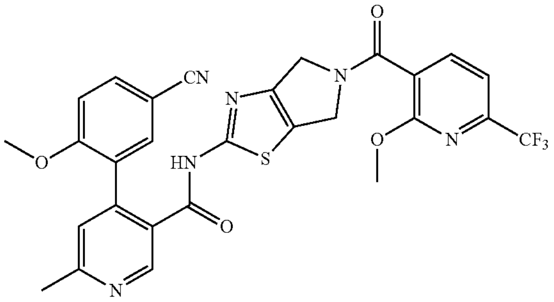 [SMILES: COc1ccc(C#N)cc1-c1cc(C)ncc1C(=O)Nc1nc2c(s1)CN(C(=O)c1ccc(C(F)(F)F)nc1OC)C2] | 4-(5-cyano-2-methoxyphenyl)-N-(5-(2-methoxy-6-(trifluoromethyl)nicotinoyl)-5,6-dihydro-4H-pyrrolo[3,4-d]thiazol-2-yl)-6-methyl-nicotinamide | 595 | $^1$H NMR (400 MHz, DMSO-$d_6$) δ 12.7 (d, J = 3.2 Hz, 1H), 8.71 (d, J = 3.8 Hz, 1H), 8.08 (dd, J = 7.4, 3.0 Hz, 1H), 7.89 (dt, J = 8.6, 2.3 Hz, 1H), 7.85 (d, J = 2.2 Hz, 1H), 7.61 (dd, J = 7.6, 4.2 Hz, 1H), 7.39 (d, J = 3.0 Hz, 1H), 7.17 (dd, J = 8.8, 1.9 Hz, 1H), 4.79 (s, 1H), 4.65 (s, 1H), 4.50 (s, 1H), 4.41 (s, 1H), 3.97 (s, 3H), 3.56 (s, 3H), 2.57 (d, J = 2.8 Hz, 3H) |
| 565 | 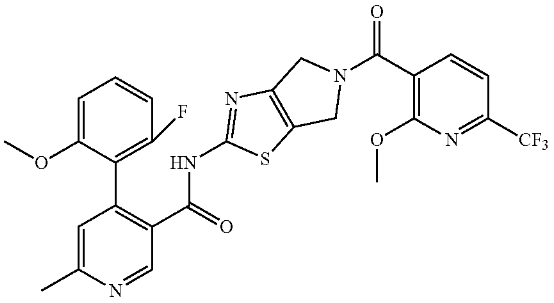 [SMILES: COc1cccc(F)c1-c1cc(C)ncc1C(=O)Nc1nc2c(s1)CN(C(=O)c1ccc(C(F)(F)F)nc1OC)C2] | 4-(2-Fluoro-6-methoxyphenyl)-N-(5-(2-methoxy-6-(trifluoromethyl)nicotinoyl)-5,6-dihydro-4H-pyrrolo[3,4-d]thiazol-2-yl)-6-methyl-nicotinamide | 588 | $^1$H NMR (400 MHz, DMSO-$d_6$) δ 12.8 (d, J = 7.6 Hz, 1H), 8.77 (d, J = 4.2 Hz, 1H), 8.08 (d, J = 7.6 Hz, 1H), 7.61 (dd, J = 7.6, 2.6 Hz, 1H), 7.43-7.35 (m, 1H), 7.33 (s, 1H), 6.95-6.85 (m, 2H), 4.79 (s, 1H), 4.66 (s, 1H), 4.50 (s, 1H), 4.41 (s, 1H), 3.97 (d, J = 1.6 Hz, 3H), 3.56 (s, 3H), 2.56 (d, J = 2.8 Hz, 3H) |

TABLE C-continued

The following examples were prepared using a similar procedure to that described for Example 1

| Ex. No. | Structure | Compound Name | LCMS [M + H]+ | NMR |
|---|---|---|---|---|
| 566 | 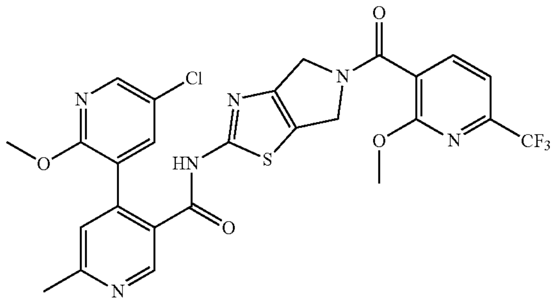 [SMILES: COc1nc(C(F)(F)F)ccc1C(=O)N1Cc2nc(NC(=O)c3cnc(C)cc3-c3cc(Cl)cnc3OC)sc2C1] | 5-Chloro-2-methoxy-N-(5-(2-methoxy-6-(trifluoromethyl) nicotinoyl)-5,6-dihydro-4H-pyrrolo[3,4-d]thiazol-2-yl) 6'-methyl-[3,4'-bipyridine]-3'-carboxamide | 605 | $^1H$ NMR (400 MHz, DMSO-$d_6$) δ 12.8 (s, 1Hz), 8.74 (d, J = 4.0 Hz, 1H), 8.25 (t, J = 2.8 Hz, 1H), 8.08 (dd, J = 7.4, 2.2 Hz, 1H), 7.96 (d, J = 2.6 Hz, 1H), 7.61 (dd, J = 7.4, 4.2 Hz, 1H, 7.45 (d, J = 2.6 Hz, 1H), 4.80 (s, 1H), 4.66 (s, 1H), 4.51 (s, 1H), 4.42 (s, 1H), 3.98 (s, 3H), 3.57 (s, 3H), 2.58 (d, J = 2.6 Hz, 3H) |
| 567 | 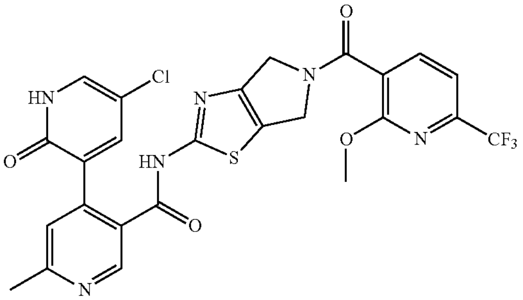 [SMILES: COc1nc(C(F)(F)F)ccc1C(=O)N1Cc2nc(NC(=O)c3cnc(C)cc3-c3cc(Cl)c[nH]c3=O)sc2C1] | 5-chloro-N-(5-(2-methoxy-6-(trifluoromethyl) nicotinoyl)-5,6-dihydro-4H-pyrrolo[3,4-d]thiazol-2-yl)-6'-methyl-2-oxo-1,2-dihydro-[3,4'-bipyridine]-3'-carboxamide | 591 | $^1H$ NMR (400 MHz, DMSO-$d_6$) δ 12.70 (d, J = 4.8 Hz, 1H), 12.08 (s, 1H), 8.66 (d, J = 3.0 Hz, 1H), 8.09 (dd, J = 7.4, 5.0 Hz, 1H), 7.72 (d, J = 2.8 Hz, 1H), 7.68 (s, 1H), 7.62 (dd, J = 7.4, 5.0 Hz, 1H), 7.38 (d, J = 2.6 Hz, 1H), 4.81 (s, 1H), 4.65 (s, 1H), 4.52 (s, 1H), 4.40 (s, 1H), 3.98 (s, 3H), 2.56 (d, J = 2.4 Hz, 3H) |
| 568 | 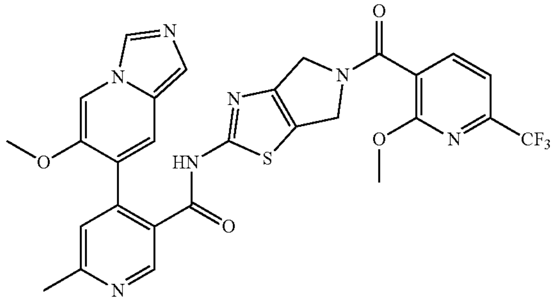 [SMILES: COc1cn2cncc2cc1-c1cc(C)ncc1C(=O)Nc1nc2c(s1)CN(C(=O)c1ccc(C(F)(F)F)nc1OC)C2] | N-(5-(2-Methoxy-6-(trifluoromethyl) nicotinoyl)-5,6-dihydro-4H-pyrrolo[3,4-d]thiazol-2-yl)-4-(6-methoxyimidazo [1,5-a]pyridin-7-yl)-6-methyl-nicotinamide | 610 | $^1H$ NMR (400 MHz, DMSO-$d_6$) δ 12.7 (d, J = 3.6 Hz, 1H), 8.70 (d, J = 3.8 Hz, 1H), 8.28 (d, J = 3.8 Hz, 1H), 8.08 (dd, J = 7.4, 2.6 Hz, 1H), 8.00 (d, J = 3.0 Hz, 1H), 7.67-7.59 (m, 2H), 7.46-7.40 (m, 2H), 4.79 (s, 1H), 4.66 (s, 1H), 4.51 (s, 1H), 4.41 (s, 1H), 3.97 (s, 3H), 3.44 (s, 3H), 2.58 (d, J = 2.6 Hz, 3H) |
| 569 | 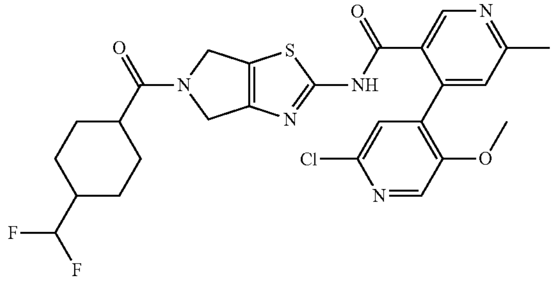 [SMILES: COc1cnc(Cl)cc1-c1cc(C)ncc1C(=O)Nc1nc2c(s1)CN(C(=O)C1CCC(C(F)F)CC1)C2] | (Cis and Trans)-2'-chloro-N-(5-(4-(difluoromethyl) cyclohexane-1-carbonyl)-5,6-dihydro-4H-pyrrolo[3,4-d]thiazol-2-yl)-5'-methoxy-6-methyl-[4,4'-bipyridine]-3-carboxamide | 562 | $^1H$ NMR (400 MHz, DMSO-d6) δ 12.79 (s, 1H), 8.79 (s, 1H), 8.17 (d, J = 3.9 Hz, 1H), 7.55 (d, J = 1.0 Hz, 1H), 7.44 (s, 1H), 6.00-5.86 (m, 1H), 4.92-4.39 (m, 4H), 3.60 (d, J = 1.5 Hz, 3H), 2.49 (s, 3H), 2.47-2.40 (m, 1H), 1.87-1.78 (m, 5H), 1.51-1.34 (m, 2H), 1.28-1.15 (m, 2H) |
| 570 | 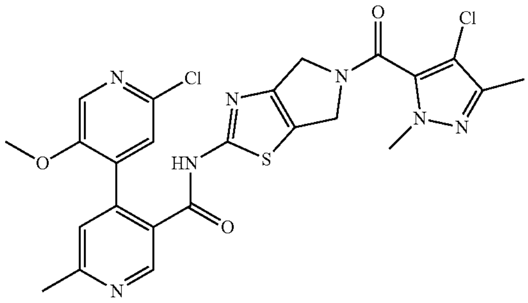 | 2'-chloro-N-(5-(4-chloro-1,3-dimethyl-1H-pyrazole-5-carbonyl)-5,6-dihydro-4H-pyrrolo[3,4-d]thiazol-2-yl)-5'-methoxy-6-methyl-[4,4'-bipyridine]-3-carboxamide | 558 | $^1H$ NMR (400 MHz, DMSO-$d_6$) δ 12.28 (s, 1H), 8.79 (d, J = 2.8 Hz, 1H), 8.17 (s, 1H), 7.55 (s, 1H), 7.44 (s, 1H), 4.85 (s, 1H), 4.72 (s, 2H), 4.62 (s, 1H), 3.77 (s, 3H), 3.60 (s, 3H), 2.59 (s, 3H), 2.17 (d, J = 4.1 Hz, 3H) |

TABLE C-continued

The following examples were prepared using a similar procedure to that described for Example 1

| Ex. No. | Structure | Compound Name | LCMS [M + H]+ | NMR |
| --- | --- | --- | --- | --- |
| 571 | 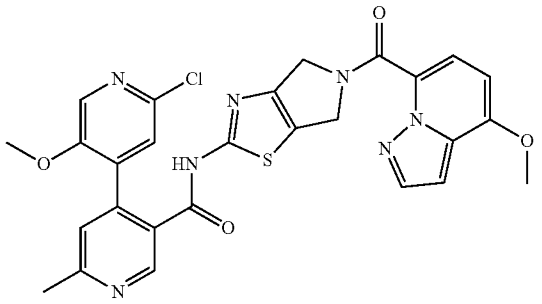 | 2'-chloro-5'-methoxy-N-(5-(4-methoxypyrazolo[1,5-a]pyridine-7-carbonyl)-5,6-dihydro-4H-pyrrolo[3,4-d]thiazol-2-yl)-6-methyl-[4,4'-bipyridine]-3-carboxamide | 576 | $^1$H NMR (400 MHz, DMSO-$d_6$) δ 8.75 (d, J = 7.7 Hz, 1H), 8.20-8.09 (m, 1H), 8.02 (d, J = 2.3 Hz, 1H), 7.53 (d, J = 1.9 Hz, 1H), 7.42 (d, J = 5.5 Hz, 1H), 7.07-7.05 (m, J = 7.8, 2.0 Hz, 1H), 6.86-6.68 (m, 2H), 4.89 (s, 1H), 4.74 (s, 1H), 4.48 (s, 1H), 4.34 (s, 1H), 4.04-3.96 (m, 3H), 3.60 (s, 3H), 2.60 (d, J = 4.0 Hz, 3H) |
| 572 | 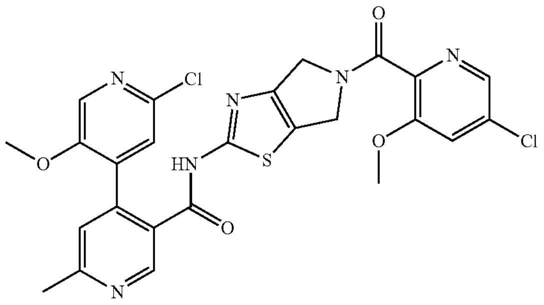 [SMILES: COc1cnc(Cl)cc1-c1cc(C)ncc1C(=O)Nc1nc2c(s1)CN(C(=O)c1ncc(Cl)cc1OC)C2] | 2'-chloro-N-(5-(5-chloro-3-methoxy-picolinoyl)-5,6-dihydro-4H-pyrrolo[3,4-d]thiazol-2-yl)-5'-methoxy-6-methyl-[4,4'-bipyridine]-3-carboxamide | 571 | $^1$H NMR (400 MHz, DMSO-$d_6$) δ 12.80 (s, 1H), 8.78 (d, J = 3.8 Hz, 1H), 8.25 (dd, J = 3.2 Hz, 1H), 8.16 (d, J = 4.0 Hz, 1H), 7.84 (dd, J = 4.9 Hz, 1H), 7.53 (s, 1H), 7.42 (d, J = 3.8 Hz, 1H), 4.79 (d, J = 2.8 Hz, 1H), 4.65 (d, J = 2.8 Hz, 1H), 4.47 (s, 1H), 4.33 (d, J = 2.9 Hz, 1H), 3.89 (s, 3H), 3.60 (s, 3H), 2.58 (d, J = 2.6 Hz, 3H) |
| 573 | 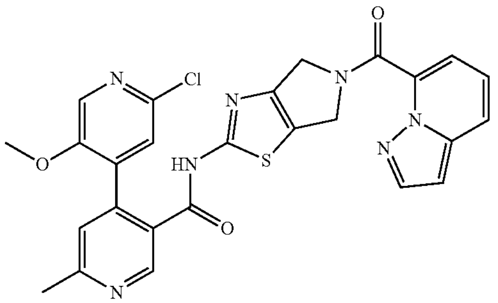 [SMILES: COc1cnc(Cl)cc1-c1cc(C)ncc1C(=O)Nc1nc2c(s1)CN(C(=O)c1cccc3ccnn13)C2] | 2'-chloro-5'-methoxy-6-methyl-N-(5-(pyrazolo[1,5-a]pyridine-7-carbonyl)-5,6-dihydro-4H-pyrrolo[3,4-d]thiazol-2-yl)-[4,4'-bipyridine]-3-carboxamide | 546 | $^1$H NMR (400 MHz, DMSO-$d_6$) δ 12.81 (s, 1H), 8.78 (d, J = 8.6 Hz, 1H), 8.16 (d, J = 6.8 Hz, 1H), 8.09 (d, J = 2.1 Hz, 1H), 7.85 (d, J = 8.5 Hz, 1H), 7.53 (s, 1H), 7.42 (d, J = 3.0 Hz, 1H), 7.33 (t, J = 7.9 Hz, 1H), 7.09 (d, J = 6.8 Hz, 1H), 6.77 (d, J = 2.1 Hz, 1H), 4.83 (d, J = 56.7 Hz, 2H), 4.40 (d, J = 46.9 Hz, 2H), 3.60 (d, J = 2.0 Hz, 3H), 2.58 (d, J = 4.3 Hz, 3H) |
| 574 | 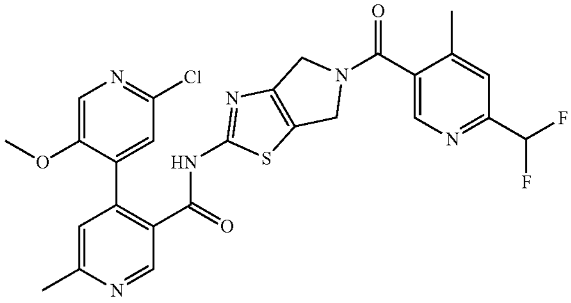 [SMILES: COc1cnc(Cl)cc1-c1cc(C)ncc1C(=O)Nc1nc2c(s1)CN(C(=O)c1cnc(C(F)F)cc1C)C2] | 2'-chloro-N-(5-(6-(difluoroemthyl)-4-methyl-nicotinoyl)-5,6-dihydro-4H-pyrrolo[3,4-d]thiazol-2-yl)-5'-methoxy-6-methyl-[4,4'-bipyridine]-3-carboxamide | 571 | $^1$H NMR (400 MHz, DMSO-$d_6$) δ 12.82 (d, J = 5.7 Hz, 1H), 8.78 (d, J = 4.9 Hz, 1H), 8.69 (s, 1H), 8.17 (d, J = 1.5 Hz, 1H), 7.70 (d, J = 2.9 Hz, 1H), 7.54 (s, 1H), 7.43 (d, J = 3.0 Hz, 1H), 6.98 (m, 1H), 4.85 (s, 1H), 4.71 (s, 1H), 4.49 (s, 1H), 4.40 (s, 1H), 3.59 (d, J = 1.2 Hz, 3H), 2.59 (d, J = 3.2 Hz, 3H), 2.40 (s, 3H) |

TABLE C-continued

The following examples were prepared using a similar procedure to that described for Example 1

| Ex. No. | Structure | Compound Name | LCMS [M + H]+ | NMR |
|---|---|---|---|---|
| 575 | 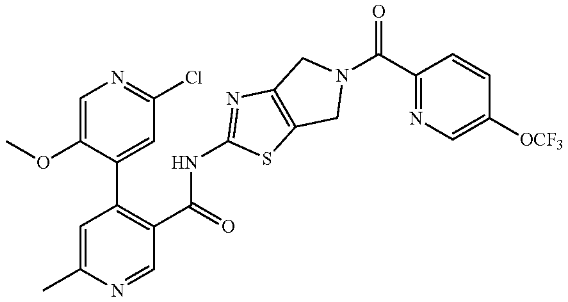 [SMILES: COc1cnc(Cl)cc1-c1cc(C)ncc1C(=O)Nc1nc2c(s1)CN(C(=O)c1ccc(OC(F)(F)F)cn1)C2] | 2'-chloro-5'-methoxy-6-methyl-N-(5-(5-(trifluoro-methoxy) picolinoyl)-5,6-dihydro-4H-pyrrolo[3,4-d]thiazol-2-yl)-[4,4'-bipyridine]-3-carboxamide | 591 | $^1$H NMR (300 MHz, DMSO-$d_6$) δ 12.81 (d, J = 6.4 Hz, 1H), 8.82-8.72 (m, 2H), 8.17 (s, 1H), 8.12-7.98 (m, 2H), 7.55 (s, 1H), 7.44 (s, 1H), 4.90 (m, 4H), 3.60 (d, J = 1.1 Hz, 3H), 2.59 (d, J = 1.1 Hz, 3H) |
| 576[&,a] | 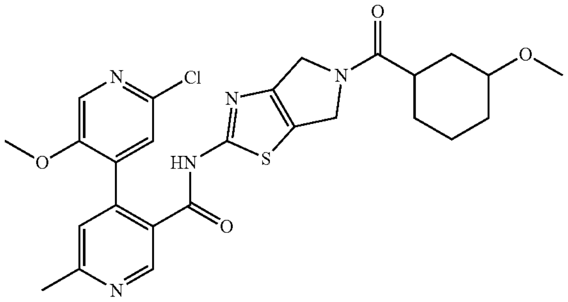 | 2'-chloro-5'-methoxy-N-(5-((1R,or S,3S and R OR 1R and S,3S or R)-3-methoxycyclo-hexane-1-carbonyl)-5,6-dihydro-4H-pyrrolo[3,4-d]thiazol-2-yl)-6-methyl-[4,4'-bipyridine]-3-carboxamide | 542 | $^1$H NMR (400 MHz, DMSO-$d_6$) δ 12.80 (s, 1H), 8.79 (s, 1H), 8.17 (d, J = 3.8 Hz, 1H), 7.55 (d, J = 1.5 Hz, 1H), 7.44 (s, 1H), 4.87 (d, J = 7.6 Hz, 1H), 4.75 (d, J = 8.6 Hz, 1H), 4.57 (s, 1H), 4.44 (s, 1H), 3.60 (d, J = 1.9 Hz, 3H), 3.24 (d, J = 1.2 Hz, 4H), 2.59 (s, 3H), 2.11-1.98 (m, 3H), 1.73 (d, J = 30.4 Hz, 2H), 1.37-1.13 (m, 4H) |
| 577[&,a] | 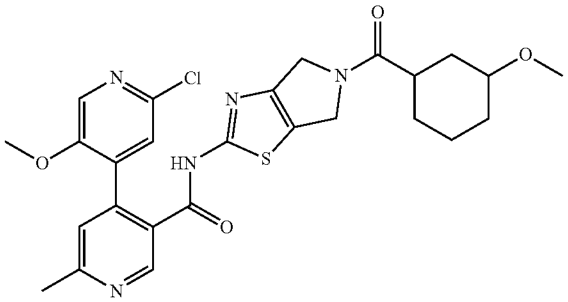 | 2'-chloro-5'-methoxy-N-(5-((1R or S,3R and S OR 1R and S,3R or S)-3-methoxycyclo-hexane-1-carbonyl)-5,6-dihydro-4H-pyrrolo[3,4-d]thiazol-2-yl)-6-methyl-[4,4'-bipyridine]-3-carboxamide | 542 | $^1$H NMR (400 MHz, DMSO-$d_6$) δ 9.15 (s, 1H), 8.28 (d, J = 2.0 Hz, 1H), 8.17 (s, 1H), 7.73 (s, 1H), 4.94-4.66 (m, 2H), 4.61 (s, 1H), 4.47 (s, 1H), 3.65 (s, 3H), 3.59 (s, 1H), 3.26 (d, J = 4.1 Hz, 3H), 2.91 (s, 3H), 2.82-2.74 (m, 1H), 1.95-1.79 (m, 2H), 1.73 (d, J = 11.8 Hz, 1H), 1.60-1.48 (m, 3H), 1.456-1.32 (m, 2H) |
| 578 | 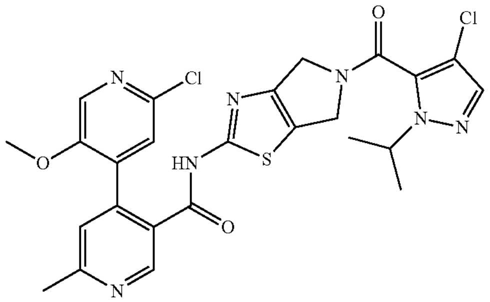 [SMILES: COc1cnc(Cl)cc1-c1cc(C)ncc1C(=O)Nc1nc2c(s1)CN(C(=O)c1c(Cl)cnn1C(C)C)C2] | 2'-chloro-N-(5-(4-chloro-1-isopropyl-1H-pyrazole-5-carbonyl)-5,6-dihydro-4H-pyrrolo[3,4-d]thiazol-2-yl)-5'-methoxy-6-methyl-[4,4'-bipyridine]-3-carboxamide | 570 | $^1$H NMR (400 MHz, DMSO-$d_6$) δ 12.82 (s, 1H), 8.75 (d, J = 7.7 Hz, 1H), 8.20-8.09 (m, 1H), 7.53 (d, J = 1.9 Hz, 1H), 7.42 (d, J = 5.5 Hz, 1H), 7.07-7.05 (m, J = 7.8, 2.0 Hz, 1H), 4.89-4.66 (m, 3H), 4.57-4.54 (m, 2H), 3.60 (s, 3H), 2.60 (s, 3H), 1.40-1.38 (m, 6H) |

TABLE C-continued

| The following examples were prepared using a similar procedure to that described for Example 1 | | | | |
|---|---|---|---|---|
| Ex. No. | Structure | Compound Name | LCMS [M + H]+ | NMR |
| 579 | 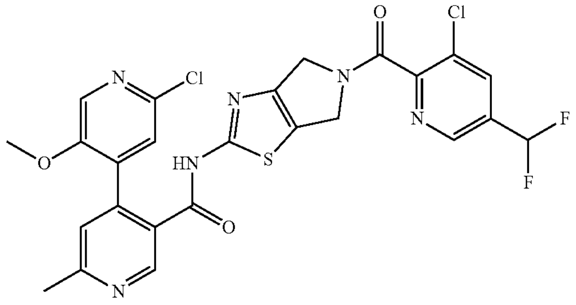 [SMILES: COc1cnc(Cl)cc1-c1cc(C)ncc1C(=O)Nc1nc2c(s1)CN(C(=O)c1ncc(C(F)F)cc1Cl)C2] | 2'-chloro-N-(5-(3-chloro-5-(difluoromethyl) picolinoyl)-5,6-dihydro-4H-pyrrolo[3,4-d]thiazol-2-yl)-5'-methoxy-6-methyl-[4,4'-bipyridine]-3-carboxamide | 591 | $^1$H NMR (300 MHz, DMSO-$d_6$) δ 12.84 (s, 1H), 8.87-8.82 (m, 1H), 8.78 (d, J = 3.4 Hz, 1H), 8.41 (d, J = 5.0 Hz, 1H), 8.16 (d, J = 2.7 Hz, 1H), 7.54 (s, 1H), 7.43 (s, 1H), 7.23 (t, J = 54.8 Hz, 1H), 4.86 (s, 1H), 4.73 (s, 1H), 4.51 (s, 1H), 4.41 (s, 1H), 3.60 (s, 3H), 2.58 (d, J = 2.2 Hz, 3H) |
| 580 | 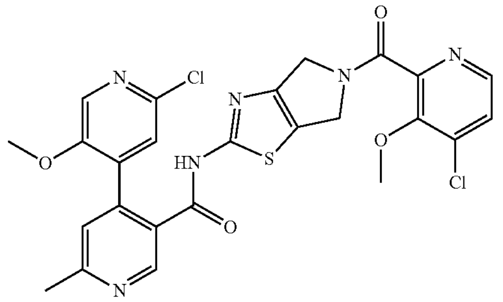 [SMILES: COc1cnc(Cl)cc1-c1cc(C)ncc1C(=O)Nc1nc2c(s1)CN(C(=O)c1nccc(Cl)c1OC)C2] | 2'-chloro-N-(5-(4-chloro-3-methoxy-picolinoyl)-5,6-dihydro-4H-pyrrolo[3,4-d]thiazol-2-yl)-5'-methoxy-6-methyl-[4,4'-bipyridine]-3-carboxamide | 571 | $^1$H NMR (300 MHz, DMSO-$d_6$) δ 12.83 (s, 1H), 8.79 (d, J = 3.3 Hz, 1H), 8.37 (d, J = 5.1, 1.3 Hz, 1H), 8.17 (d, J = 2.8 Hz, 1H), 7.76 (d, J = 5.2, 0.7 Hz, 1H), 7.55 (s, 1H), 7.44 (d, J = 1.7 Hz, 1H), 4.85 (s, 1H), 4.72 (s, 1H), 4.57 (s, 1H), 4.47 (s, 1H), 3.90 (d, J = 0.6 Hz, 3H), 3.60 (s, 3H), 2.59 (d, J = 2.1 Hz, 3H) |
| 581 | 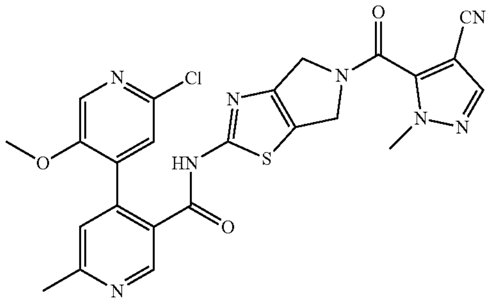 [SMILES: COc1cnc(Cl)cc1-c1cc(C)ncc1C(=O)Nc1nc2c(s1)CN(C(=O)c1c(C#N)cnn1C)C2] | 2'-chloro-N-(5-(4-cyano-1-methyl-1H-pyrazole-5-carbonyl)-5,6-dihydro-4H-pyrrolo[3,4-d]thiazol-2-yl)-5'-methoxy-6-methyl-[4,4'-bipyridine]-3-carboxamide | 535 | $^1$H NMR (400 MHz, DMSO-$d_6$) δ 8.80 (s, 1H), 8.21 (d, J = 2.5 Hz, 1H), 8.16 (d, J = 1.8 Hz, 1H), 7.54 (s, 1H), 7.43 (s, 1H), 4.90-4.67 (m, 5H), 3.94 (s, 3H), 3.61 (s, 3H), 2.59 (d, J = 1.7 Hz, 3H) |
| 582 | 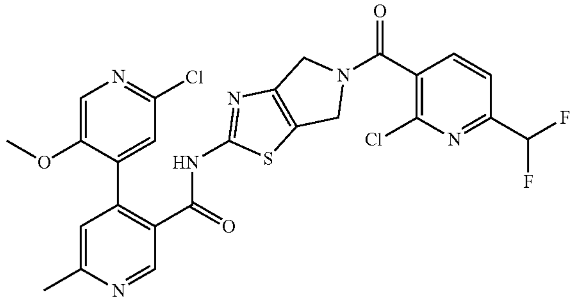 [SMILES: COc1cnc(Cl)cc1-c1cc(C)ncc1C(=O)Nc1nc2c(s1)CN(C(=O)c1ccc(C(F)F)nc1Cl)C2] | 2'-chloro-N-(5-(2-chloro-6-(difluoromethyl) nicotinoyl)-5,6-dihydro-4H-pyrrolo[3,4-d]thiazol-2-yl)-5'-methoxy-6-methyl-[4,4'-bipyridine]-3-carboxamide | 591 | $^1$H NMR (400 MHz, DMSO-$d_6$) δ 12.83 (s, 1H), 8.82-8.80 (m, 1H), 8.30-8.26 (m, 1H), 8.16-8.15 (m, 1H), 7.89-7.86 (m, 1H), 7.52-7.41 (m, 2H), 7.19-6.92 (m, 1H), 4.76 (d, J = 56.0 Hz, 2H), 4.51-4.42 (m, 2H), 3.60 (s, 3H), 2.58 (s, 3H) |

TABLE C-continued

| The following examples were prepared using a similar procedure to that described for Example 1 | | | | |
|---|---|---|---|---|
| Ex. No. | Structure | Compound Name | LCMS [M + H]+ | NMR |
| 583 | 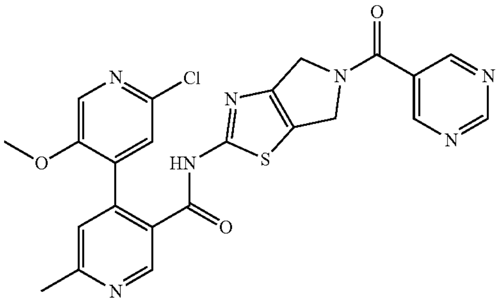 [SMILES: COc1cnc(Cl)cc1-c1cc(C)ncc1C(=O)Nc1nc2c(s1)CN(C(=O)c1cncnc1)C2] | 2'-chloro-5'-methoxy-6-methyl-N-(5-(pyrimidine-5-carbonyl)-5,6-dihydro-4H-pyrrolo[3,4-d]thiazol-2-yl)-[4,4'-bipyridine]-3-carboxamide | 508 | $^1$H NMR (400 MHz, DMSO-$d_6$) δ 12.80 (s, 1H), 9.31 (d, J = 0.9 Hz, 1H), 9.08 (d, J = 2.5 Hz, 2H), 8.79 (d, J = 3.5 Hz, 1H), 8.17 (s, 1H), 7.54 (s, 1H), 7.43 (d, J = 2.0 Hz, 1H), 4.85-4.82 (m, 2H), 4.73-4.71 (m, 2H), 3.59 (s, 3H), 2.59 (d, J = 2.1 Hz, 3H) |
| 584 | 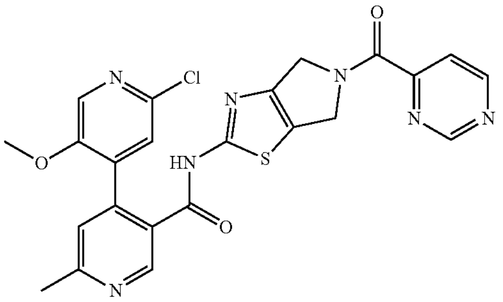 [SMILES: COc1cnc(Cl)cc1-c1cc(C)ncc1C(=O)Nc1nc2c(s1)CN(C(=O)c1ccncn1)C2] | 2'-chloro-5'-methoxy-6-methyl-N-(5-(pyrimidine-4-carbonyl)-5,6-dihydro-4H-pyrrolo[3,4-d]thiazol-2-yl)-[4,4'-bipyridine]-3-carboxamide | 508 | $^1$H NMR (400 MHz, DMSO-$d_6$) δ 12.81 (s, 1H), 9.34-9.33 (m, 1H), 9.05 (d, J = 5.1 Hz, 1H), 8.79 (s, 1H), 8.17 (s, 1H), 7.90-7.88 (m, 1H), 7.54 (s, 1H), 7.43 (s, 1H), 5.02 (s, 1H), 4.94-4.83 (m, 2H), 4.73 (s, 1H), 3.60 (d, J = 1.3 Hz, 3H), 2.59 (d, J = 1.7 Hz, 3H) |
| 585 | 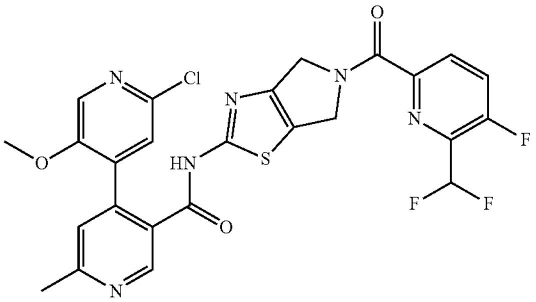 | 2'-chloro-N-(5-(6-(difluoromethyl)-5-fluoropicolinoyl)-5,6-dihydro-4H-pyrrolo[3,4-d]thiazol-2-yl)-5'-methoxy-6-methyl-[4,4'-bipyridine]-3-carboxamide | 575 | $^1$H NMR (400 MHz, DMSO-$d_6$) δ 12.80 (d, J = 17.9 Hz, 1H), 8.81 (d, J = 2.4 Hz, 1H), 8.21-8.09 (m, 3H), 7.59-7.35 (m, 2H), 7.24-7.11 (m, 1H), 5.11-5.05 (m, 1H), 5.01-4.96 (m, 1H), 4.87 (t, J = 2.5 Hz, 1H), 4.73 (s, 1H), 3.61 (s, 3H), 2.60 (s, 3H) |
| 586 | 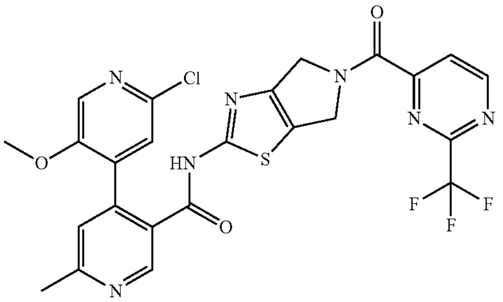 [SMILES: COc1cnc(Cl)cc1-c1cc(C)ncc1C(=O)Nc1nc2c(s1)CN(C(=O)c1ccnc(C(F)(F)F)n1)C2] | 2'-chloro-5'-methoxy-6-methyl-N-(5-(2-(trifluoromethyl)pyrimidine-4-carbonyl)-5,6-dihydro-4H-pyrrolo[3,4-d]thiazol-2-yl)-[4,4'-bipyridine]-3-carboxamide | 576 | $^1$H NMR (400 MHz, DMSO-$d_6$) δ 12.79 (s, 1H), 9.30 (d, J = 5.1 Hz, 1H), 8.79 (d, J = 3.2 Hz, 1H), 8.22-8.16 (m, 2H), 7.54 (d, J = 1.4 Hz, 1H), 7.43 (s, 1H), 4.99 (s, 1H), 4.90 (d, J = 11.6 Hz, 2H), 4.75 (s, 1H), 3.60 (s, 3H), 2.59 (s, 3H) |

TABLE C-continued

| The following examples were prepared using a similar procedure to that described for Example 1 | | | | |
|---|---|---|---|---|
| Ex. No. | Structure | Compound Name | LCMS [M + H]+ | NMR |
| 587 | 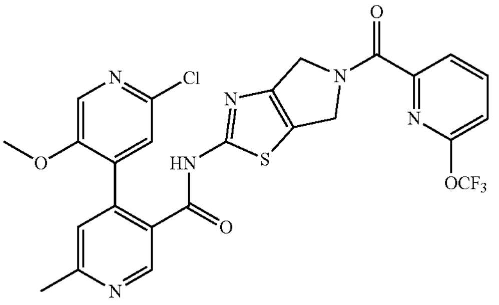 [SMILES: COc1cnc(Cl)cc1-c1cc(C)ncc1C(=O)Nc1nc2c(s1)CN(C(=O)c1cccc(OC(F)(F)F)n1)C2] | 2'-chloro-5'-methoxy-6-methyl-N-(5-(6-(trifluoro-methoxy) picolinoyl)-5,6-dihydro-4H-pyrrolo[3,4-d]thiazol-2-yl)-[4,4'-bipyridine]-3-carboxamide | 591 | $^1$H NMR (400 MHz, DMSO-$d_6$) δ 12.80 (d, J = 11.9 Hz, 1H), 8.79 (s, 1H), 8.22 (t, J = 7.9 Hz, 1H), 8.17 (d, J = 3.9 Hz, 1H), 7.93 (dd, J = 25.5, 7.6 Hz, 1H), 7.55 (s, 1H), 7.49 (d, J = 8.3 Hz, 1H), 7.44 (s, 1H), 4.99 (d, J = 16.3 Hz, 2H), 4.87 (s, 1H), 4.73 (s, 1H), 3.61 (s, 3H), 2.59 (s, 3H) |
| 588 | 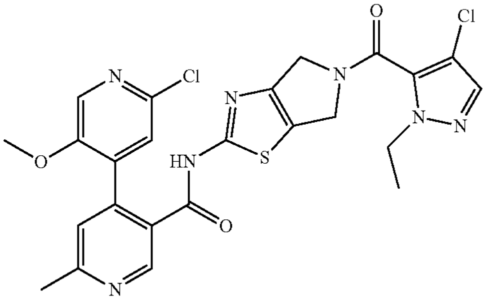 [SMILES: CCn1ncc(Cl)c1C(=O)N1Cc2nc(NC(=O)c3cnc(C)cc3-c3cc(Cl)ncc3OC)sc2C1] | 2'-chloro-N-(5-(4-chloro-1-ethyl-1H-pyrazole-5-carbonyl)-5,6-dihydro-4H-pyrrolo[3,4-d]thiazol-2-yl)-5'-methoxy-6-methyl-[4,4'-bipyridine]-3-carboxamide | 558 | $^1$H NMR (400 MHz, DMSO-$d_6$) δ 8.80 (s, 1H), 8.17 (d, J = 2.5 Hz, 1H), 7.70 (s, 1H), 7.54-7.46 (m, 2H), 4.85 (s, 1H), 4.73-7.68 (m, 2H), 4.58 (s, 1H), 4.20-4.08 (m, 2H), 3.81 (s, 1H), 3.61 (s, 3H), 2.59 (s, 3H), 1.35-1.32 (m, 3H) |
| 589 | 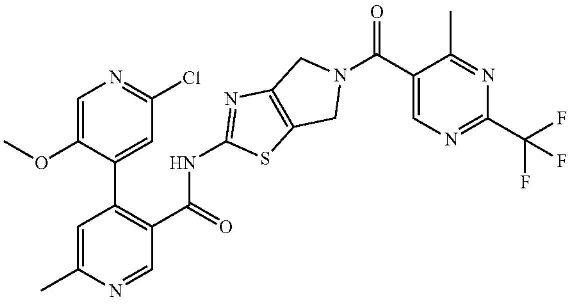 [SMILES: COc1cnc(Cl)cc1-c1cc(C)ncc1C(=O)Nc1nc2c(s1)CN(C(=O)c1cnc(C(F)(F)F)nc1C)C2] | 2'-chloro-5'-methoxy-6-methyl-N-(5-(4-methyl-2-(trifluoromethyl) pyrimidine-5-carbonyl)-5,6-dihydro-4H-pyrrolo[3,4-d]thiazol-2-yl)-[4,4'-bipyridine]-3-carboxamide | 590 | $^1$H NMR (400 MHz, DMSO-$d_6$) δ 12.82 (s, 1H), 9.14 (d, J = 8.3 Hz, 1H), 8.78 (d, J = 4.6 Hz, 1H), 8.17 (s, 1H), 7.54 (s, 1H), 7.43 (d, J = 3.3 Hz, 1H), 4.87 (t, J = 2.7 Hz, 1H), 4.74 (t, J = 2.6 Hz, 1H), 4.61 (t, J = 2.7 Hz, 1H), 4.53 (t, J = 2.6 Hz, 1H), 3.59 (s, 3H), 2.62 (d, J = 2.3 Hz, 3H), 2.59 (d, J = 3.0 Hz, 3H) |
| 590 | 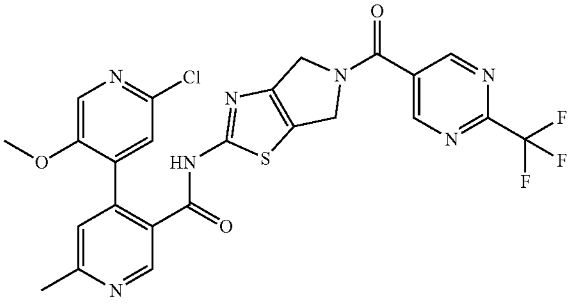 [SMILES: COc1cnc(Cl)cc1-c1cc(C)ncc1C(=O)Nc1nc2c(s1)CN(C(=O)c1cnc(C(F)(F)F)nc1)C2] | 2'-chloro-5'-methoxy-6-methyl-N-(5-(2-(trifluoromethyl) pyrimidine-5-carbonyl)-5,6-dihydro-4H-pyrrolo[3,4-d]thiazol-2-yl)-[4,4'-bipyridine]-3-carboxamide | 576 | $^1$H NMR (300 MHz, DMSO-$d_6$) δ 12.84 (s, 1H), 9.34 (s, 2H), 8.79 (d, J = 2.6 Hz, 1H), 8.17 (d, J = 1.2 Hz, 1H), 7.55 (s, 1H), 7.44 (d, J = 2.1 Hz, 1H), 4.92-4.79 (m, 2H), 4.75 (d, J = 6.7 Hz, 2H), 3.59 (s, 3H), 2.59 (d, J = 1.8 Hz, 3H) |

TABLE C-continued

The following examples were prepared using a similar procedure to that described for Example 1

| Ex. No. | Structure | Compound Name | LCMS [M + H]+ | NMR |
|---|---|---|---|---|
| 591 | 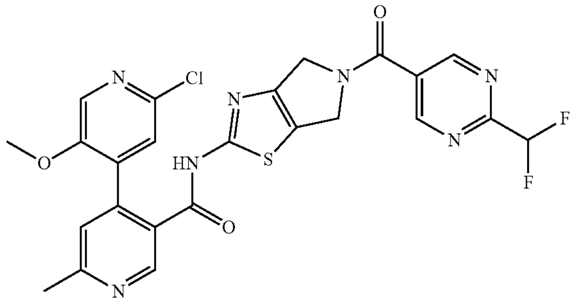 [SMILES: COc1cnc(Cl)cc1-c1cc(C)ncc1C(=O)Nc1nc2c(s1)CN(C(=O)c1cnc(C(F)F)nc1)C2] | 2'-chloro-N-(5-(2-(difluromethyl) pyrimidine-5-carbonyl)-5,6-dihydro-4H-pyrrolo[3,4-d]thiazol-2-yl)-5'-methoxy-6-methyl-[4,4'-bipyridine]-3-carboxamide | 558 | $^1$H NMR (400 MHz, DMSO-$d_6$) δ 12.82 (s, 1H), 9.25 (s, 2H), 8.78 (s, 1H), 8.17 (d, J = 1.6 Hz, 1H), 7.54 (s, 1H), 7.44 (s, 1H), 7.06 (t, J = 53.7 Hz, 1H), 4.85 (d, J = 14.1 Hz, 2H), 4.74 (d, J = 11.3 Hz, 2H), 3.62 (s, 3H), 2.59 (s, 3H) |
| 592 | 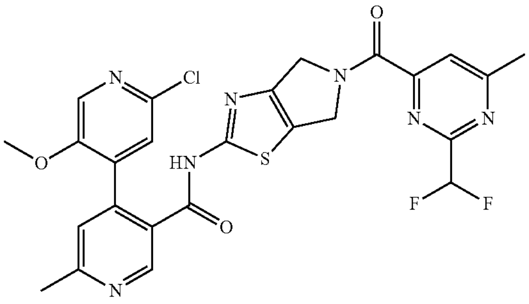 | 2'-chloro-N-(5-(2-(difluoromethyl)-6-methyl-pyrimidine-4-carbonyl)-5,6-dihydro-4H-pyrrolo[3,4-d]thiazol-2-yl)-5'-methoxy-6-methyl-[4,4'-bipyridine]-3-carboxamide | 572 | $^1$H NMR (400 MHz, DMSO-$d_6$) δ 12.79 (d, J = 14.6 Hz, 1H), 8.79 (d, J = 2.8 Hz, 1H), 8.17 (d, J = 1.7 Hz, 1H), 7.93 (d, J = 6.3 Hz, 1H), 7.55 (d, J = 1.0 Hz, 1H), 7.44 (s, 1H), 7.03-6.88 (m, 1H), 4.98-4.70 (m, 4H), 3.60 (s, 3H), 2.65 (d, J = 1.1 Hz, 3H), 2.59 (s, 3H) |
| 593 | 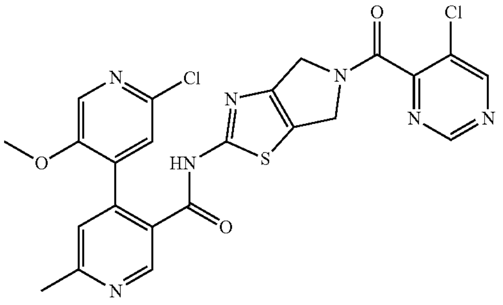 | 2'-chloro-N-(5-(5-chloro-pyrimidine-4-carbonyl)-5,6-dihydro-4H-pyrrolo[3,4-d]thiazol-2-yl)-5'-methoxy-6-methyl-[4,4'-bipyridine]-3-carboxamide | 542 | $^1$H NMR (400 MHz, DMSO-$d_6$) δ 9.27 (d, J = 2.9 Hz, 1H), 9.14-9.20 (m, 1H), 8.79 (d, J = 5.0 Hz, 1H), 8.16 (d, J = 3.0 Hz, 1H), 7.53 (s, 1H), 7.42 (s, 1H), 4.86 (s, 1H), 4.73 (s, 1H), 4.58 (s, 1H), 4.47 (s, 1H), 3.60 (s, 3H), 2.58 (d, J = 2.5 Hz, 3H) |
| 594 | 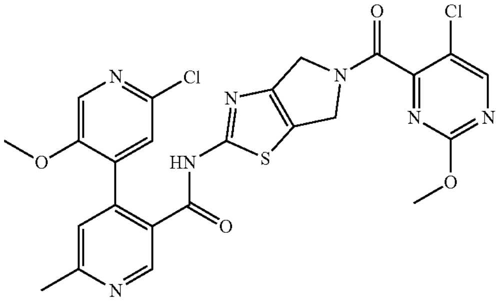 [SMILES: COc1ncc(Cl)c(C(=O)N2Cc3nc(NC(=O)c4cnc(C)cc4-c4cc(Cl)ncc4OC)sc3C2)n1] | 2'-chloro-N-(5-(5-chloro-2-methoxy-pyrimidine-4-carbonyl)-5,6-dihydro-4H-pyrrolo[3,4-d]thiazol-2-yl)-5'-methoxy-6-methyl-[4,4'-bipyridine]-3-carboxamide | 572 | $^1$H NMR (300 MHz, DMSO-$d_6$) δ 12.86 (s, 1H), 8.93 (s, 1H), 8.78 (s, 1H), 8.18 (s, 1H), 7.56 (s, 1H), 7.44 (s, 1H), 4.85 (s, 1H), 4.73 (s, 1H), 4.64 (s, 1H), 4.51 (s, 1H), 3.97 (s, 3H), 3.60 (s, 3H), 2.59 (d, J = 1.6 Hz, 3H) |

TABLE C-continued

| The following examples were prepared using a similar procedure to that described for Example 1 | | | | |
|---|---|---|---|---|
| Ex. No. | Structure | Compound Name | LCMS [M + H]+ | NMR |
| 595 | 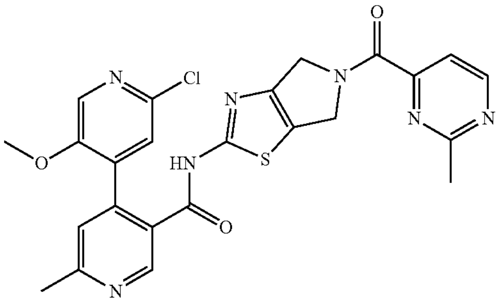 [SMILES: COc1cnc(Cl)cc1-c1cc(C)ncc1C(=O)Nc1nc2c(s1)CN(C(=O)c1ccnc(C)n1)C2] | 2'-chloro-5'-methoxy-6-methyl-N-(5-(2-methyl-pyrimidine-4-carbonyl)-5,6-dihydro-4H-pyrrolo[3,4-d]thiazol-2-yl)-[4,4'-bipyridine]-3-carboxamide | 522 | $^1$H NMR (400 MHz, DMSO-$d_6$) δ 12.80 (s, 1H), 8.92-8.90 (m, 1H), 8.79 (d, J = 2.7 Hz, 1H), 8.17 (d, J = 2.5 Hz, 1H), 7.64 (d, J = 7.4 Hz, 1H), 7.55 (d, J = 2.5 Hz, 1H), 7.44 (d, J = 2.4 Hz, 1H), 4.98 (s, 1H), 4.86 (d, J = 10.1 Hz, 2H), 4.71 (s, 1H), 3.61 (d, J = 2.6 Hz, 3H), 2.71 (t, J = 3.5 Hz, 3H), 2.60 (d, J = 2.5 Hz, 3H) |
| 596 | 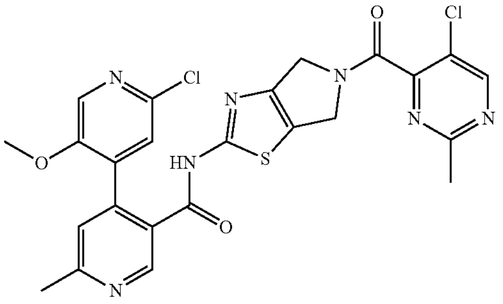 | 2'-chloro-N-(5-(5-chloro-2-methyl-pyrimidine-4-carbonyl)-5,6-dihydro-4H-pyrrolo[3,4-d]thiazol-2-yl)-5'-methoxy-6-methyl-[4,4'-bipyridine]-3-carboxamide | 556 | $^1$H NMR (400 MHz, DMSO-$d_6$) δ 12.83 (s, 1H), 9.01 (d, J = 5.9 Hz, 1H), 8.78 (d, J = 4.6 Hz, 1H), 8.16 (d, J = 2.7 Hz, 1H), 7.54 (d, J = 2.2 Hz, 1H), 7.44 (d, J = 2.2 Hz, 1H), 4.85 (s, 1H), 4.72 (s, 1H), 4.58 (d, J = 3.1 Hz, 1H), 4.47 (d, J = 3.0 Hz, 1H), 3.60 (s, 3H), 2.68 (s, 3H), 2.59 (d, J = 2.5 Hz, 3H) |
| 597 | 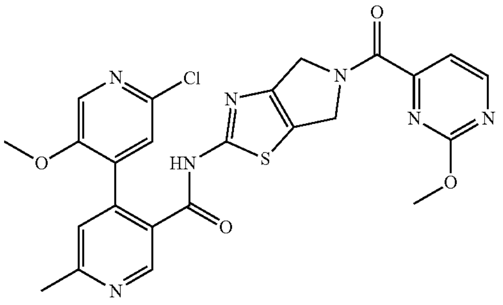 [SMILES: COc1nccc(C(=O)N2Cc3nc(NC(=O)c4cnc(C)cc4-c4cc(Cl)ncc4OC)sc3C2)n1] | 2'-chloro-5'-methoxy-N-(5-(2-methoxy-pyrimidine-4-carbonyl)-5,6-dihydro-4H-pyrrolo[3,4-d]thiazol-2-yl)-6-methyl-[4,4'-bipyridine]-3-carboxamide | 538 | $^1$H NMR (400 MHz, DMSO-$d_6$) δ 12.79 (s, 1H), 8.82 (d, J = 4.9 Hz, 1H), 8.79 (s, 1H), 8.17 (d, J = 1.4 Hz, 1H), 7.54 (s, 1H), 7.48 (t, J = 5.1 Hz, 1H), 7.44 (s, 1H), 5.05 (d, J = 2.9 Hz, 1H), 4.94 (d, J = 2.5 Hz, 1H), 4.85 (d, J = 2.8 Hz, 1H), 4.71 (d, J = 2.9 Hz, 1H), 3.99 (d, J = 1.5 Hz, 3H), 3.60 (s, 3H), 2.59 (d, J = 1.2 Hz, 3H) |
| 598 | 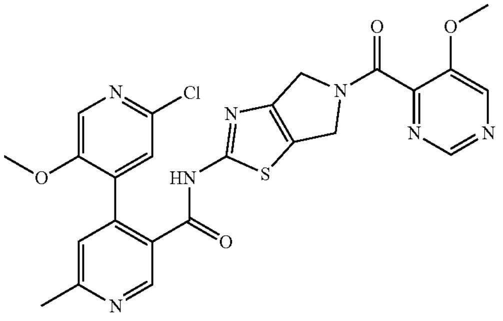 | 2'-chloro-5'-methoxy-N-(5-(5-methoxy-pyrimidine-4-carbonyl)-5,6-dihydro-4H-pyrrolo[3,4-d]thiazol-2-yl)-6-methyl-[4,4'-bipyridine]-3-carboxamide | 538 | $^1$H NMR (300 MHz, DMSO-$d_6$) δ 12.82 (s, 1H), 8.97-8.67 (m, 3H), 8.16 (d, J = 2.6 Hz, 1H), 7.54 (s, 1H), 7.43 (s, 1H), 4.81-4.40 (m, 4H), 3.98 (s, 3H), 3.60 (s, 3H), 2.59 (d, J = 2.0 Hz, 3H) |

TABLE C-continued

The following examples were prepared using a similar procedure to that described for Example 1

| Ex. No. | Structure | Compound Name | LCMS [M + H]+ | NMR |
|---|---|---|---|---|
| 599 | 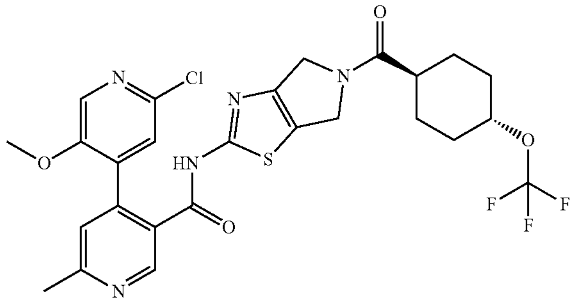 [SMILES: COc1cnc(Cl)cc1-c1cc(C)ncc1C(=O)Nc1nc2c(s1)CN(C(=O)[C@H]1CC[C@H](OC(F)(F)F)CC1)C2] | 2'-chloro-5'-methoxy-6-methyl-N-(5-((1r,4r)-4-(trifluoro-methoxy) cyclohexane-1-carbonyl)-5,6-dihydro-4H-pyrrolo[3,4-d]thiazol-2-yl)-[4,4'-bipyridine]-3-carboxamide | 596 | $^1$H NMR (400 MHz, DMSO-$d_6$) δ 12.79 (s, 1H), 8.79 (s, 1H), 8.17 (d, J = 4.5 Hz, 1H), 7.55 (d, J = 1.5 Hz, 1H), 7.44 (s, 1H), 5.30-4.12 (m, 5H), 3.60 (d, J = 2.0 Hz, 3H), 2.59 (s, 3H), 2.51 (s, 1H), 2.15-1.99 (m, 2H), 1.86 (d, J = 9.2 Hz, 2H), 1.54 (t, J = 9.0 Hz, 4H) |
| 600 | 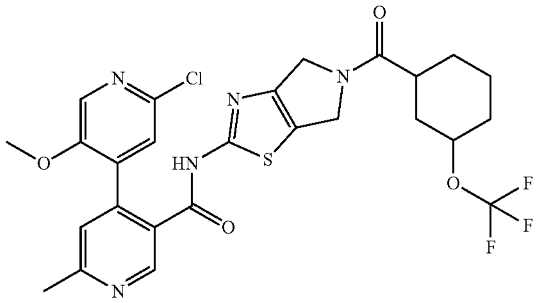 [SMILES: COc1cnc(Cl)cc1-c1cc(C)ncc1C(=O)Nc1nc2c(s1)CN(C(=O)C1CCCC(OC(F)(F)F)C1)C2] | (Racemic) 2'-chloro-5'-methoxy-6-methyl-N-(5-(3-(trifluoro-methoxy) cyclohexane-1-carbonyl)-5,6-dihydro-4H-pyrrolo[3,4-d]thiazol-2-yl)-[4,4'-bipyridine]-3-carboxamide | 596 | $^1$H NMR (400 MHz, DMSO-$d_6$) δ 12.79 (s, 1H), 8.79 (s, 1H), 8.17 (d, J = 3.3 Hz, 1H), 7.54 (d, J = 1.5 Hz, 1H), 7.44 (s, 1H), 5.05-4.65 (m, 2H), 4.57 (s, 1H), 4.49-4.36 (m, 2H), 3.60 (d, J = 2.1 Hz, 3H), 2.72 (q, J = 13.7, 12.5 Hz, 1H), 2.59 (s, 3H), 2.12-1.99 (m, 2H), 1.80 (q, J = 17.3, 12.8 Hz, 2H), 1.59 (q, J = 11.7 Hz, 1H), 1.44 (q, J = 10.9, 10.2 Hz, 2H), 1.23 (q, J = 11.5, 10.1 Hz, 1H) |
| 601 | 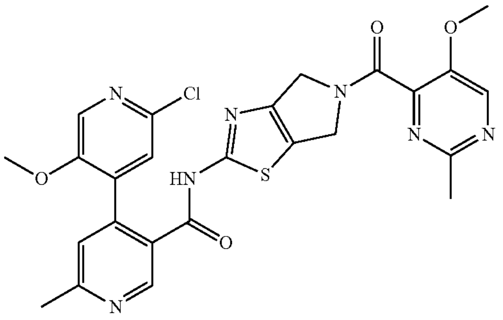 | 2'-chloro-5'-methoxy-N-(5-(5-methoxy-2-methyl-pyrimidine-4-carbonyl)-5,6-dihydro-4H-pyrrolo[3,4-d]thiazol-2-yl)-6-methyl-[4,4'-bipyridine]-3-carboxamide | 552 | $^1$H NMR (300 MHz, DMSO-$d_6$) δ 12.81 (d, J = 5.8 Hz, 1H), 8.74 (dd, J = 24.5, 3.0 Hz, 2H), 8.16 (d, J = 2.5 Hz, 1H), 7.49 (d, J = 31.8 Hz, 2H), 4.79-4.39 (m, 4H), 3.93 (s, 3H), 3.59 (s, 3H), 2.59 (d, J = 1.6 Hz, 6H) |
| 602 | 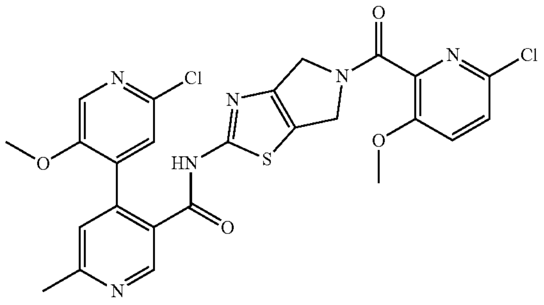 [SMILES: COc1cnc(Cl)cc1-c1cc(C)ncc1C(=O)Nc1nc2c(s1)CN(C(=O)c1nc(Cl)ccc1OC)C2] | 2'-chloro-N-(5-(6-chloro-3-methoxy-picolinoyl)-5,6-dihydro-4H-pyrrolo[3,4-d]thiazol-2-yl)-5'-methoxy-6-methyl-[4,4'-bipyridine]-3-carboxamide | 571 | $^1$H NMR (300 MHz, DMSO-$d_6$) δ 12.70 (s, 1H), 8.79 (d, J = 3.5 Hz, 1H), 8.17 (d, J = 2.9 Hz, 1H), 7.64-7.61 (m, 1H), 7.63 (d, J = 8.8 Hz, 1H), 7.55 (s, 1H), 7.44 (s, 1H), 4.79 (s, 1H), 4.66 (s, 1H), 4.50 (s, 1H), 4.39 (s, 1H), 3.88 (d, J = 1.1 Hz, 3H), 3.60 (s, 3H), 2.59 (d, J = 1.6 Hz, 3H) |

TABLE C-continued

The following examples were prepared using a similar procedure to that described for Example 1

| Ex. No. | Structure | Compound Name | LCMS [M + H]+ | NMR |
|---|---|---|---|---|
| 603 | 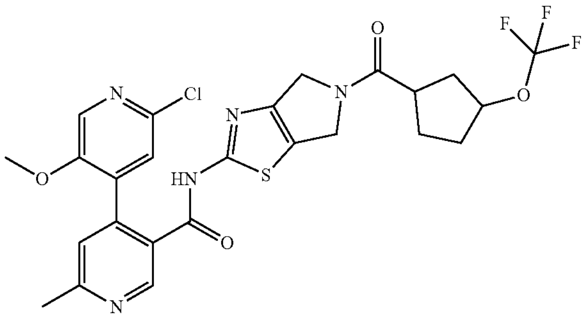 [SMILES: COc1cnc(Cl)cc1-c1cc(C)ncc1C(=O)Nc1nc2c(s1)CN(C(=O)C1CCC(OC(F)(F)F)C1)C2] | (Racemic)-2'-chloro-5'-methoxy-6-methyl-N-(5-(3-(trifluoro-methoxy) cyclopentane-1-carbonyl)-5,6-dihydro-4H-pyrrolo[3,4-d]thiazol-2-yl)-[4,4'-bipyridine]-3-carboxamide | 582 | $^1$H NMR (400 MHz, DMSO-$d_6$) δ 12.78 (s, 1H), 8.79 (s, 1H), 8.17 (d, J = 1.9 Hz, 1H), 7.54 (s, 1H), 7.44 (s, 1H), 4.85 (s, 1H), 4.72 (s, 1H), 4.60-4.46 (m, 2H), 3.60 (d, J = 1.3 Hz, 3H), 3.01 (q, J = 7.8 Hz, 1H), 2.59 (s, 3H), 2.38 (m, 1H), 2.13-1.78 (m, 6H) |
| 604[&,b] | 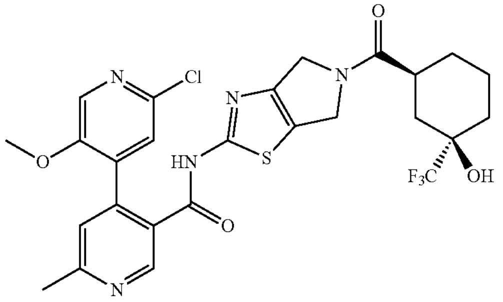 [SMILES: COc1cnc(Cl)cc1-c1cc(C)ncc1C(=O)Nc1nc2c(s1)CN(C(=O)[C@H]1CCC[C@](O)(C(F)(F)F)C1)C2] | 2'-chloro-N-(5-((1S or R,3R and S OR 1S and R,3R or S)-3-hydroxy-3-(trifluoromethyl) cyclohexane-2-carbonyl)-5,6-dihydro-4H-pyrrolo[3,4-d]thiazol-2-yl)-5'-methoxy-6-methyl-[4,4'-bipyridine]-3-carboxamide | 596 | $^1$H NMR (400 MHz, DMSO-$d_6$) δ 12.82 (s, 1H), 8.80 (s, 1H), 8.17 (d, J = 3.1 Hz, 1H), 7.54 (s, 1H), 7.42 (s, 1H), 5.84 (s, 1H), 4.88-4.44 (m, 4H), 3.60 (d, J = 2.5 Hz, 3H), 2.87-2.81 (m, 1H), 2.59 (s, 3H), 1.83-1.54 (m, 6H), 1.50-1.38 (m, 1H), 1.34-1.31 (m, 1H) |
| 605[&,b] | 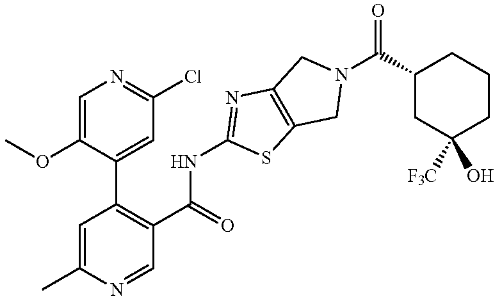 [SMILES: COc1cnc(Cl)cc1-c1cc(C)ncc1C(=O)Nc1nc2c(s1)CN(C(=O)[C@@H]1CCC[C@](O)(C(F)(F)F)C1)C2] | 2'-chloro-N-(5-((1R or S,3R and S OR 1R and S, 3R or S)-3-hydroxy-3-(trifluoromethyl) cyclohexane-1-carbonyl)-5,6-dihydro-4H-pyrrolo[3,4-d]thiazol-2-yl)-5'-methoxy-6-methyl-[4,4'-bipyridine]-3-carboxamide | 596 | $^1$H NMR (400 MHz, DMSO-$d_6$) δ 12.79 (s, 1H), 8.80 (s, 1H), 8.16 (d, J = 3.0 Hz, 1H), 7.53 (s, 1H), 7.41 (s, 1H), 5.83 (s, 1H), 4.87 (d, J = 3.2 Hz, 1H), 4.75 (d, J = 3.4 Hz, 1H), 4.57 (d, J = 3.1 Hz, 1H), 4.43 (d, J = 3.2 Hz, 1H), 3.60 (d, J = 2.5 Hz, 3H), 2.87-2.81 (m, 1H), 2.58 (s, 3H), 1.92-1.54 (m, 6H), 1.51-1.40 (m, 1H), 1.39-1.25 (m, 1H) |
| 606 | 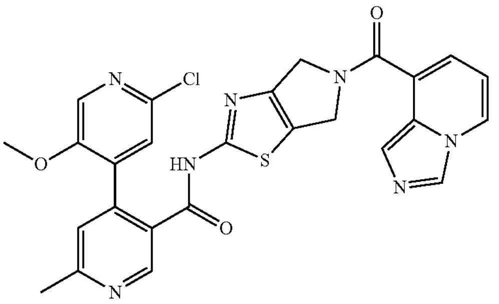 [SMILES: COc1cnc(Cl)cc1-c1cc(C)ncc1C(=O)Nc1nc2c(s1)CN(C(=O)c1cccn3cncc13)C2] | 2'-chloro-N-(5-(imidazo[1,5-a]pyridine-8-carbonyl)-5,6-dihydro-4H-pyrrolo[3,4-d]thiazol-2-yl)-5'-methoxy-6-methyl-[4,4'-bipyridine]-3-carboxamide | 546 | $^1$H NMR (400 MHz, DMSO-$d_6$) δ 12.78 (s, 1H), 8.78 (d, J = 5.3 Hz, 1H), 8.49-8.41 (m, 2H), 8.16 (d, J = 4.3 Hz, 1H), 7.53 (d, J = 1.9 Hz, 1H), 7.42 (d, J = 2.1 Hz, 1H), 7.39-7.34 (m, 1H), 7.13-7.01 (m, 1H), 6.74 (d, J = 7.8, 5.9 Hz, 1H), 5.13-4.27 (m, 4H), 3.59 (d, J = 1.7 Hz, 3H, 2.58 (d, J = 3.0 Hz, 3H) |

TABLE C-continued

The following examples were prepared using a similar procedure to that described for Example 1

| Ex. No. | Structure | Compound Name | LCMS [M + H]+ | NMR |
|---|---|---|---|---|
| 607 | 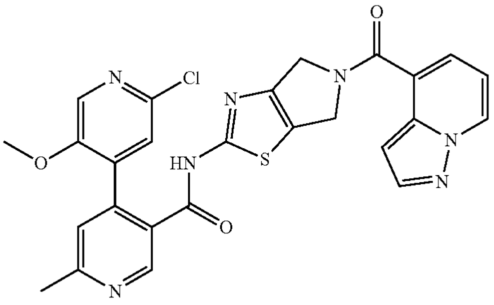 [SMILES: COc1cnc(Cl)cc1-c1cc(C)ncc1C(=O)Nc1nc2c(s1)CN(C(=O)c1cccn3nccc13)C2] | 2'-chloro-5'-methoxy-6-methyl-N-(5-(pyrazolo[1,5-a]pyridine-4-carbonyl)-5,6-dihydro-4H-pyrrolo[3,4-d]thiazol-2-yl)-[4,4'-bipyridine]-3-carboxamide | 544 | $^1$H NMR (400 MHz, DMSO-$d_6$) δ 12.79 (s, 1H), 8.84-8.75 (m, 2H), 8.19-8.12 (m, 1H), 8.08 (d,J = 2.7 Hz, 1H), 7.53 (s, 1H), 7.52-7.43 (m, 1H), 7.43 (s, 1H), 6.98 (t, J = 6.9 Hz, 1H), 6.66 (d, J = 2.3 Hz, 1H), 4.89 (s, 1H), 4.75 (s, 1H), 4.65 (s, 1H), 4.57 (s, 1H), 3.59 (s, 3H), 2.58 (d, J = 3.1 Hz, 3H) |
| 608 | 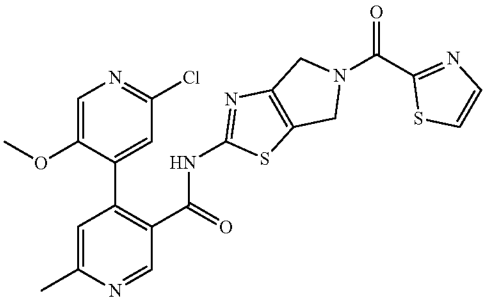 | 2'-chloro-5'-methoxy-6-methyl-N-(5-(thiazole-2-carbonyl)-5,6-dihydro-4H-pyrrolo[3,4-d]thiazol-2-yl)-[4,4'-bipyridine]-3-carboxamide | 513 | $^1$H NMR (400 MHz, DMSO-$d_6$) δ 12.83 (d, J = 19.9 Hz, 1H), 8.80 (d, J = 2.5 Hz, 1H), 8.18 (d, J = 1.6 Hz, 1H), 8.15-8.07 (m, 2H), 7.55 (s, 1H), 7.44 (s, 1H), 5.35 (d, J = 2.7 Hz, 1H), 5.21 (d, J = 2.6 Hz, 1H), 4.86 (d, J = 2.8 Hz, 1H), 4.73 (s, 1H), 3.61 (d, J = 1.4 Hz, 3H), 2.59 (s, 3H) |
| 609 | 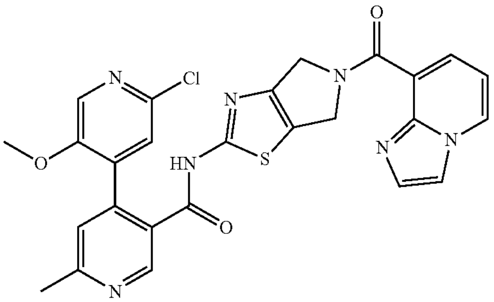 [SMILES: COc1cnc(Cl)cc1-c1cc(C)ncc1C(=O)Nc1nc2c(s1)CN(C(=O)c1cccn3ccnc13)C2] | 2'-chloro-N-(5-(imidazo[1,2-a]pyridine-8-carbonyl)-5,6-dihydro-4H-pyrrolo[3,4-d]thiazol-2-yl)-5'-methoxy-6-methyl-[4,4'-bipyridine]-3-carboxamide | 546 | $^1$H NMR (400 MHz, DMSO-$d_6$) δ 12.79 (s, 1H), 8.78 (d, J = 9.0 Hz, 1H), 8.73-8.64 (m, 1H), 8.16 (d, J = 7.3 Hz, 1H), 8.07 (t, J = 1.5 Hz, 1H), 7.64 (s, 1H), 7.54 (d, J = 2.6 Hz, 1H), 7.43 (d, J = 2.2 Hz, 1H), 7.40-7.34 (m, 1H), 7.01 (t, J = 6.9 Hz, 1H), 4.86 (s, 1H), 4.72 (s, 1H), 4.60 (s, 1H), 4.50 (s, 1H), 3.59 (d, J = 2.0 Hz, 3H), 2.58 (d, J = 4.0 Hz, 3H) |
| 610 | 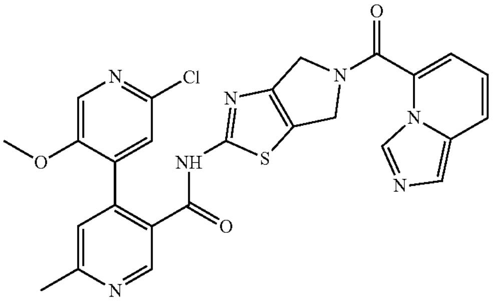 [SMILES: COc1cnc(Cl)cc1-c1cc(C)ncc1C(=O)Nc1nc2c(s1)CN(C(=O)c1cccc3cncn13)C2] | 2'-chloro-N-(5-(imidazo[1,5-a]pyridine-5-carbonyl)-5,6-dihydro-4H-pyrrolo[3,4-d]thiazol-2-yl)-5'-methoxy-6-methyl-[4,4'-bipyridine]-3-carboxamide | 546 | $^1$H NMR (040 MHz, DMSO-$d_6$) δ 12.81 (s, 1H), 8.78 (s, 1H), 8.41 (s, 1H), 8.17 (s, 1H), 7.72 (d, J = 9.1 Hz, 1H), 7.54 (s, 1H), 7.50 (s, 1H), 7.43 (s, 1H), 7.16-7.15 (m, 1H), 6.87 (t, J = 7.9 Hz, 1H), 4.91 (d, J = 23.4 Hz, 2H), 4.80 (s, 2H), 3.59 (s, 3H), 2.59 (s, 3H) |

TABLE C-continued

The following examples were prepared using a similar procedure to that described for Example 1

| Ex. No. | Structure | Compound Name | LCMS [M + H]+ | NMR |
|---|---|---|---|---|
| 611 | 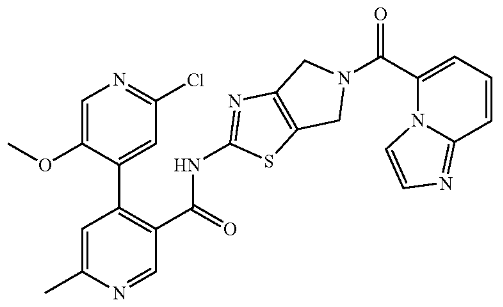 [SMILES: COc1cnc(Cl)cc1-c1cc(C)ncc1C(=O)Nc1nc2c(s1)CN(C(=O)c1cccc3nccn13)C2] | 2'-chloro-N-(5-(imidazo[1,2-a]pyridine-5-carbonyl)-5,6-dihydro-4H-pyrrolo[3,4-d]thiazol-2-yl)-5'-methoxy-6-methyl-[4,4'-bipyridine]-3-carboxamide | 546 | $^1$H NMR (400 MHz, DMSO-$d_6$) δ 12.81 (s, 1H), 8.78 (d, J = 4.4 Hz, 1H), 8.16 (s, 1H), 8.01 (s, 1H), 7.74 (d, J = 14.5 Hz, 2H), 7.54 (s, 1H), 7.41 (d, J = 19.0 Hz, 3H), 4.95 (s, 1H), 4.80 (s, 2H), 4.73 (s, 1H), 3.59 (s, 3H), 2.59 (d, J = 3.0 Hz, 3H) |
| 612 | 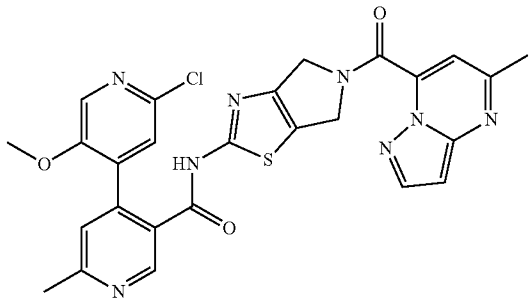 | 2'-chloro-5'-methoxy-6-methyl-N-(5-(5-methyl-pyrazolo[1,5-a]pyrimidine-7-carbonyl)-5,6-dihydro-4H-pyrrolo[3,4-d]thiazol-2-yl)-[4,4'-bi-pyridine]-3-carboxamide | 561 | $^1$H NMR (400 MHz, DMSO-$d_6$) δ 12.80 (d, J = 3.4 Hz, 1H), 8.79 (s, 1H), 8.36 (t, J = 2.3 Hz, 1H), 8.17 (s, 1H), 7.55 (s, 1H), 7.44 (s, 1H) 7.41 (s, 1H), 6.92 (dd, J = 11.3 Hz, 1H), 5.16-5.04 (s, 2H), 4.88-4.74 (m, 1H), 3.61 (d, J = 1.4 Hz, 3H), 2.81 (s, 3H), 2.59 (d, J = 1.3 Hz, 3H) |
| 613 | 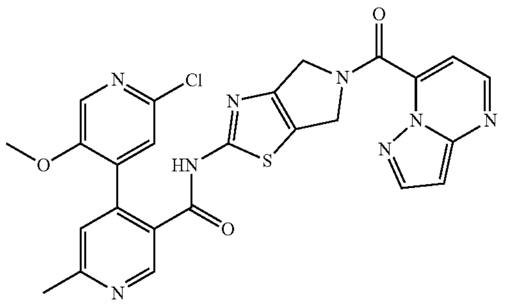 [SMILES: COc1cnc(Cl)cc1-c1cc(C)ncc1C(=O)Nc1nc2c(s1)CN(C(=O)c1ccnc3ccnn13)C2] | 2'-chloro-5'-methoxy-6-methyl-N-(5-(pyrazolo[1,5-a]pyrimidine-7-carbonyl)-5,6-dihydro-4H-pyrrolo[3,4-d]thiazol-2-yl)-[4,4'-bi-pyridine]-3-carboxamide | 547 | $^1$H NMR (400 MHz, DMSO-$d_6$) δ 12.81 (s, 1H), 8.83-8.65 (m, 2H), 8.31 (dd, J = 5.6 Hz, 1H), 8.15 (d, J = 5.9 Hz, 1H), 7.53 (d, J = 1.9 Hz, 1H), 7.41 (d, J = 3.4 Hz, 1H), 7.27 (dd, J = 4.1 Hz, 1H), 6.89 (t, J = 2.2 Hz, 1H), 4.91 (s, 1H), 4.78 (s, 1H), 4.52 (s, 1H), 4.42 (s, 1H), 3.59 (s, 3H), 2.58 (d, J = 4.0 Hz, 3H) |
| 614 | 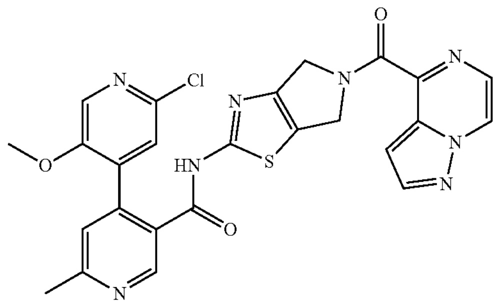 [SMILES: COc1cnc(Cl)cc1-c1cc(C)ncc1C(=O)Nc1nc2c(s1)CN(C(=O)c1nccn3nccc13)C2] | 2'-chloro-5'-methoxy-6-methyl-N-(5-(pyrazolo[1,5-a]pyrazine-4-carbonyl)-5,6-dihydro-4H-pyrrolo[3,4-d]thiazol-2-yl)-[4,4'-bipyridine]-3-carboxamide | 547 | $^1$H NMR (400 MHz, DMSO-$d_6$) δ 12.80 (s, 1H), 8.95 (d, J = 4.7 Hz, 1H), 8.79 (d, J = 1.9 Hz, 1H), 8.26 (t, J = 2.2 Hz, 1H), 8.17 (d, J = 1.5 Hz, 1H), 8.02 (m, 1H), 7.54 (s, 1H), 7.43 (s, 1H), 7.14 (s, 1H), 5.09 (s, 1H), 4.95 (d, J = 13.9 Hz, 2H), 4.80 (s, 1H), 3.61 (d, J = 1.4 Hz, 3H), 2.59 (d, J = 2.1 Hz, 3H) |

TABLE C-continued

| Ex. No. | Structure | Compound Name | LCMS [M + H]+ | NMR |
|---|---|---|---|---|
| The following examples were prepared using a similar procedure to that described for Example 1 | | | | |
| 615 | 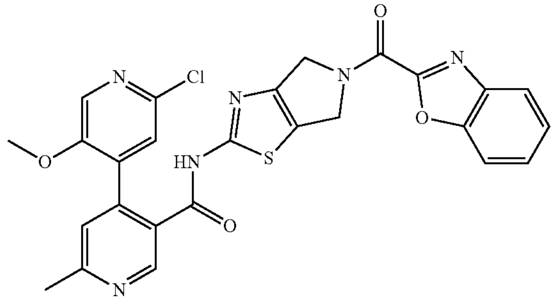 [SMILES: COc1cnc(Cl)cc1-c1cc(C)ncc1C(=O)Nc1nc2c(s1)CN(C(=O)c1nc3ccccc3o1)C2] | N-(5-(benzo [d]oxazole-2-carbonyl)-5,6-dihydro-4H-pyrrolo[3,4-d]thiazol-2-yl)-2'-chloro-5'-methoxy-6-methyl-[4,4'-bipyridine]-3-carboxamide | 547 | $^1$H NMR (400 MHz, DMSO-$d_6$) δ 12.83 (s, 1H), 8.81 (d, J = 3.1 Hz, 1H), 8.18 (d, J = 2.4 Hz, 1H), 8.04-7.84 (m, 2H), 7.60 (t, J = 7.8 Hz, 1H), 7.53 (d, J = 8.9 Hz, 2H), 7.44 (s, 1H), 5.40 (s, 1H), 5.25 (s, 1H), 4.90 (s, 1H), 4.77 (s, 1H), 3.62 (s, 3H), 2.59 (s, 3H) |
| 616 | 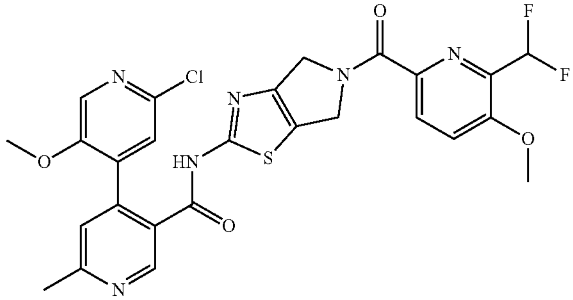 [SMILES: COc1cnc(Cl)cc1-c1cc(C)ncc1C(=O)Nc1nc2c(s1)CN(C(=O)c1ccc(OC)c(C(F)F)n1)C2] | 2'-chloro-N-(5-(6-(difluoromethyl)-5-methoxy-picolinoyl)-5,6-dihydro-4H-pyrrolo[3,4-d]thiazol-2-yl)-5'-methoxy-6-methyl-[4,4'-bipyridine]-3-carboxamide | 587 | 1H NMR (400 MHz, DMSO-$d_6$) δ 12.78 (d, J = 14.5 Hz, 1H), 8.79 (d, J = 2.7 Hz, 1H), 8.17 (d, J = 2.7 Hz, 1H), 8.13-8.08 (m, 1H), 7.83 (d, J = 8.9 Hz, 1H), 7.55 (d, J = 1.2 Hz, 1H), 7.44 (s, 1H), 7.29-6.99 (m, 1H), 5.14 (s, 1H), 5.04 (s, 1H), 4.85 (s, 1H), 4.71 (s, 1H), 3.98 (d, J = 1.6 Hz, 3H), 3.61 (s, 3H), 2.59 (s, 3H) |
| 617 | 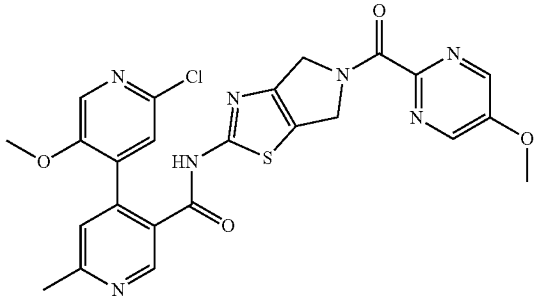 | 2'-chloro-5'-methoxy-N-(5-(5-methoxy-pyrimidine-2-carbonyl)-5,6-dihydro-4H-pyrrolo[3,4-d]thiazol-2-yl)-6-methyl-[4,4'-bipyridine]-3-carboxamide | 538 | $^1$H NMR (300 MHz, DMSO-$d_6$) δ 12.81 (s, 1H), 8.78 (d, J = 2.7 Hz, 1H), 8.68 (d, J = 1.0 Hz, 2H), 8.17 (d, J = 1.7 Hz, 1H), 7.54 (s, 1H), 7.43 (s, 1H), 4.81 (d, J = 14.1 Hz, 2H), 4.69 (s, 2H), 3.99 (d, J = 1.7 Hz, 3H), 3.60 (s, 3H), 2.59 (d, J = 1.6 Hz, 3H) |
| 618 | 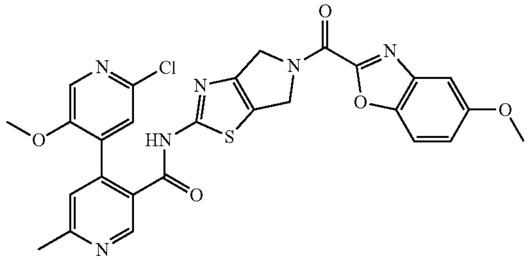 | 2'-chloro-5'-methoxy-N-(5-(5-methoxy-benzo[d] oxazole-2-carbonyl)-5,6-dihydro-4H-pyrrolo[3,4-d]thiazol-2-yl)-6-methyl-[4,4'-bipyridine]-3-carboxamide | 577 | $^1$H NMR (400 MHz, DMSO-$d_6$) δ 12.86 (s, 1H), 8.81 (d, J = 2.3 Hz, 1H), 8.18 (d, J = 2.4 Hz, 1H), 7.80 (d, J = 9.0 Hz, 1H), 7.57-7.49 (m, 3H), 7.18-7.16 (m, 1H), 5.37 (s, 1H), 5.23 (s, 1H), 4.89 (s, 1H), 4.76 (s, 1H), 3.85 (d, J = 2.3 Hz, 3H), 3.62 (d, J = 2.0 Hz, 3H), 2.59 (s, 3H) |
| 619 | 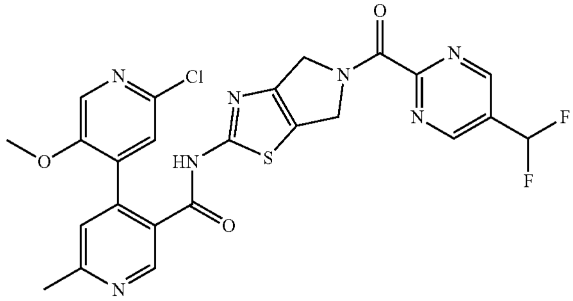 [SMILES: COc1cnc(Cl)cc1-c1cc(C)ncc1C(=O)Nc1nc2c(s1)CN(C(=O)c1ncc(C(F)F)cn1)C2] | 2'-chloro-N-(5-(5-(difluoromethyl) pyrimidine-2-carbonyl)-5,6-dihydro-4H-pyrrolo[3,4-d]thiazol-2-yl)-5'-methoxy-6-methyl-[4,4'-bipyridine]-3-carboxamide | 558 | $^1$H NMR (400 MHz, DMSO-$d_6$) δ 12.84 (d, J = 4.7 Hz, 1H), 9.22 (d, J = 2.0 Hz, 2H), 8.79 (d, J = 3.7 Hz, 1H), 8.17 (d, J = 2.4 Hz, 1H), 7.55 (s, 1H), 7.50-7.11 (m, 2H), 4.87 (t, J = 2.6 Hz, 1H), 4.74 (s, 2H), 4.65 (t, J = 2.7 Hz, 1H), 3.60 (s, 3H), 2.59 (d, J = 2.5 Hz, 3H) |

TABLE C-continued

The following examples were prepared using a similar procedure to that described for Example 1

| Ex. No. | Structure | Compound Name | LCMS [M + H]+ | NMR |
|---|---|---|---|---|
| 620 | 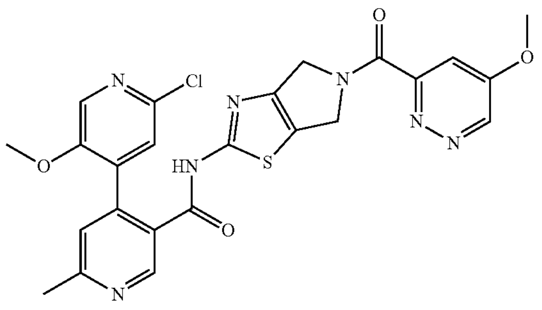 | 2'-chloro-5'-methoxy-N-(5-(5-methoxy-pyridazine-3-carbonyl)-5,6-dihydro-4H-pyrrolo[3,4-d]thiazol-2-yl)-6-methyl-[4,4'-bipyridine]-3-carboxamide | 538 | $^1$H NMR (400 MHz, DMSO-$d_6$) δ 12.82 (s, 1H), 8.12 (dd, J = 3.0, 1.6 Hz, 1H), 8.81 (s, 1H), 8.17 (s, 1H), 7.58-7.56 (m, 2H), 7.53 (s, 1H), 7.42 (s, 1H), 4.99-4.75 (m, 4H), 3.99 (s, 3H), 3.61 (s, 3H), 2.59 (d, J = 1.9 Hz, 3H) |
| 621 | 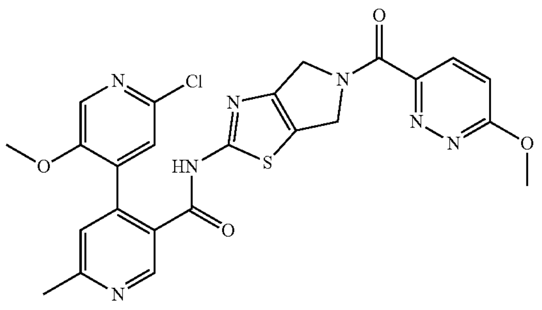 | 2'-chloro-5'-methoxy-N-(5-(6-methoxy-pyridazine-3-carbonyl)-5,6-dihydro-4H-pyrrolo[3,4-d]thiazol-2-yl)-6-methyl-[4,4'-bipyridine]-3-carboxamide | 536 | $^1$H NMR (400 MHz, DMSO-$d_6$) δ 12.82 (d, J = 22.1 Hz, 1H), 8.79 (s, 1H), 8.17 (s, 1H), 8.02-7.98 (m, 1H), 7.54 (s, 1H), 7.44 (d, J = 2.0 Hz, 1H), 7.41-7.36 (m, 1H), 5.12 (t, J = 2.6 Hz, 1H), 5.02 (t, J = 2.6 Hz, 1H), 4.89 (t, J = 2.5 Hz, 1H), 4.75 (d, J = 3.2 Hz, 1H), 4.12 (d, J = 4.5 Hz, 3H), 3.61 (s, 3H), 2.59 (d, J = 1.8 Hz, 3H) |
| 622 | 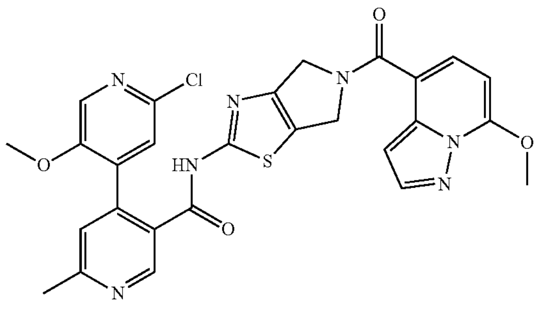 | 2'-chloro-5'-methoxy-N-(4-(7-methoxypyrazolo[1,5-a]pyridine-4-carbonyl)-5,6-dihydro-4H-pyrrolo[3,4-d]thiazol-2-yl)-6-methyl-[4,4'-bipyridine]-3-carboxamide | 576 | $^1$H NMR (400 MHz, Methanol-$d_4$) δ 8.75 (s, 1H), 8.06 (d, J = 6.2 Hz, 2H), 7.56 (d, J = 7.7 Hz, 1H), 7.48 (s, 1H), 7.41 (s, 1H), 6.71 (s, 1H), 6.46 (d, J = 7.8 Hz, 1H), 4.99 (s, 1H), 4.80 (d, J = 15.6 Hz, 2H), 4.57 (s, 1H), 4.24 (s, 3H), 3.67 (s, 3H), 2.65 (d, J = 3.5 Hz, 3H) |
| 623 | 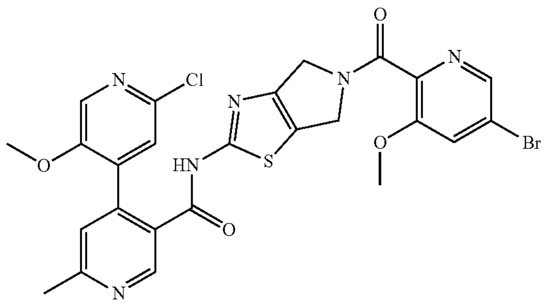 [SMILES: COc1cnc(Cl)cc1-c1cc(C)ncc1C(=O)Nc1nc2c(s1)CN(C(=O)c1ncc(Br)cc1OC)C2] | N-(5-(5-bromo-3-methoxy-picolinoyl)-5,6-dihydro-4H-pyrrolo[3,4-d]thiazol-2-yl)-2'-chloro-5'-methoxy-6-methyl-[4,4'-bipyridine]-3-carboxamide | 615, 617 | $^1$H NMR (400 MHz, DMSO-$d_6$) δ 12.81 (s, 1H), 8.78 (d, J = 4.6 Hz, 1H), 8.33 (t, J = 1.8 Hz, 1H), 8.16 (d, J = 3.3 Hz, 1H), 7.96-7.95 (m, 1H), 7.54 (s, 1H), 7.43 (d, J = 2.4 Hz, 1H), 4.79 (t, J = 2.8 Hz, 1H), 4.68-4.63 (m, 1H), 1H), 4.47 (t, J = 2.5 Hz, 1H), 4.35 (d, J = 2.9 Hz, 1H), 3.89 (s, 3H), 3.60 (s, 3H), 2.59 (d, J = 2.5 Hz, 3H) |

TABLE C-continued

The following examples were prepared using a similar procedure to that described for Example 1

| Ex. No. | Structure | Compound Name | LCMS [M + H]+ | NMR |
|---|---|---|---|---|
| 624 | 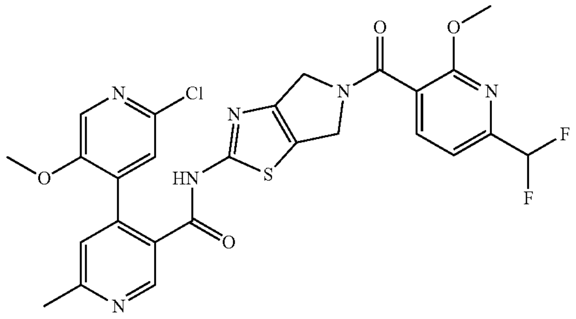 [SMILES: COc1cnc(Cl)cc1-c1cc(C)ncc1C(=O)Nc1nc2c(s1)CN(C(=O)c1ccc(C(F)F)nc1OC)C2] | 2'-chloro-N-(5-(6-(difluoromethyl)-2-methoxy-nicotinoyl)-5,6-dihydro-4H-pyrrolo[3,4-d]thiazol-2-yl)-5'-methoxy-6-methyl-[4,4'-bipyridine]-3-carboxamide | 587 | $^1$H NMR (400 MHz, DMSO-$d_6$) δ 12.81 (d, J = 5.0 Hz, 1H), 8.78 (d, J = 4.4 Hz, 1H) ,8.17 (d, J = 2.4 Hz, 1H), 7.99 (d, J = 7.5 Hz, 1H), 7.54 (s, 1H), 7.46-7.36 (m, 2H), 6.94 (d, J = 1.8 Hz, 1H), 4.80 (d, J = 3.2 Hz, 1H), 4.66 (s, 1H), 4.50 (s, 1H), 4.40 (d, J = 3.0 Hz, 1H), 3.96 (s, 3H), 3.60 (s, 3H), 2.59 (d, J = 2.7 Hz, 3H) |
| 625 | 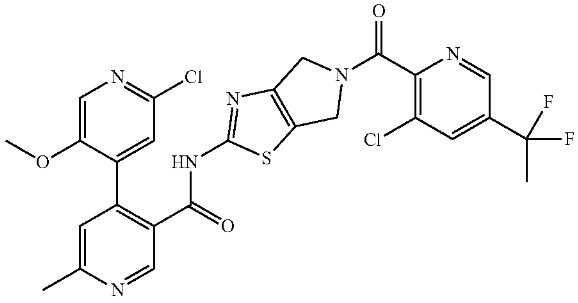 [SMILES: COc1cnc(Cl)cc1-c1cc(C)ncc1C(=O)Nc1nc2c(s1)CN(C(=O)c1ncc(C(C)(F)F)cc1Cl)C2] | 2'-chloro-N-(5-(3-chloro-5-(1,1-difluoro-ethyl)pico-linoyl)-5,6-dihydro-4H-pyrrolo[3,4-d]thiazol-2-yl)-5'-methoxy-6-methyl-[4,4'-bipyridine]-3-carboxamide | 605 | $^1$H NMR (400 MHz, DMSO-$d_6$) δ 12.82 (s, 1H), 8.85-8.79 (m, 1H), 8.79 (d, J = 4.1 Hz, 1H), 8.45-8.35 (m, 1H), 8.16 (d, J = 3.1 Hz, 1H), 7.53 (s, 1H), 7.42 (d, J = 2.5 Hz, 1H), 4.86-4.73 (m, 2H), 4.51-4.41 (m, 2H), 3.60 (s, 3H), 2.58 (d, J = 2.9 Hz, 3H), 2.13-2.03 (m, 3H) |
| 626 | 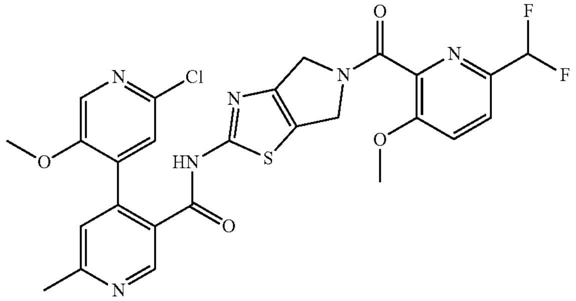 [SMILES: COc1cnc(Cl)cc1-c1cc(C)ncc1C(=O)Nc1nc2c(s1)CN(C(=O)c1nc(C(F)F)ccc1OC)C2] | 2'-chloro-N-(5-(6-(difluoromethyl)-3-methoxy-picolinoyl)-5,6-dihydro-4H-pyrrolo[3,4-d]thiazol-2-yl)-5'-methoxy-6-methyl-[4,4'-bipyridine]-3-carboxamide | 587 | $^1$H NMR (400 MHz, DMSO-$d_6$) δ 12.80 (d, J = 7.5 Hz, 1H), 8.78 (d, J = 6.3 Hz, 1H), 8.16 (d, J = 4.4 Hz, 1H), 7.80 (d, J = 2.3 Hz, 2H), 7.54 (s, 1H), 7.43 (s, 1H), 7.11-6.80 (m, 1H), 4.81 (s, 1H), 4.67 (s, 1H), 4.46 (s, 1H), 4.35 (s, 1H), 3.92 (s, 3H), 3.60 (s, 3H), 2.59 (d, J = 2.6 Hz, 3H) |
| 627 | 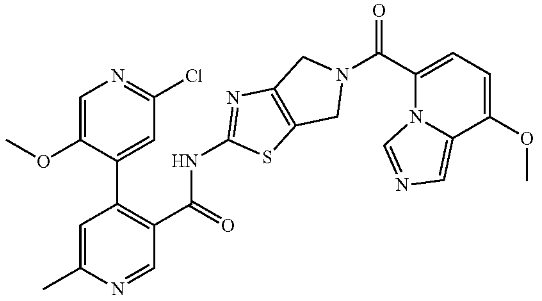 | 2'-chloro-5'-methoxy-N-(5-(8-methoxyimidazo[1,5-a]pyridine-5-carbonyl)-5,6-dihydro-4H-pyrrolo[3,4-d]thiazol-2-yl)-6-methyl-[4,4'-bipyridine]-3-carboxamide | 576 | $^1$H NMR (400 MHz, DMSO-$d_6$) δ 8.76 (s, 1H), 8.43 (s, 1H), 8.13 (s, 1H), 7.49 (d, J = 16.1 Hz, 2H), 7.39 (s, 1H), 7.21 (d, J = 7.3 Hz, 1H), 6.29 (d, J = 7.7 Hz, 1H), 4.90 (d, J = 3.0 Hz, 2H), 4.77 (d, J = 9.3 Hz, 2H), 3.96 (s, 3H), 3.58 (s, 3H), 2.57 (s, 3H |

TABLE C-continued

The following examples were prepared using a similar procedure to that described for Example 1

| Ex. No. | Structure | Compound Name | LCMS [M + H]+ | NMR |
|---|---|---|---|---|
| 628 | 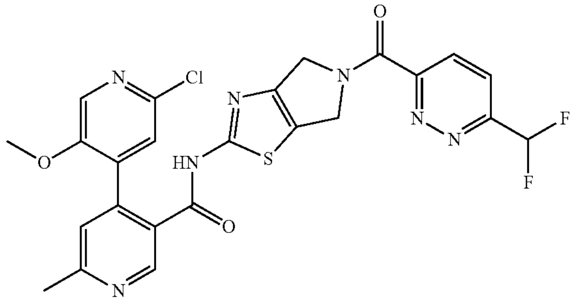 [SMILES: COc1cnc(Cl)cc1-c1cc(C)ncc1C(=O)Nc1nc2c(s1)CN(C(=O)c1ccc(C(F)F)nn1)C2] | 2'-chloro-N-(5-(6-(difluoromethyl)pyridazine-3-carbonyl)-5,6-dihydro-4H-pyrrolo[3,4-d]thiazol-2-yl)-5'-methoxy-6-methyl-[4,4'-bipyridine]-3-carboxamide | 558 | $^1$H NMR (400 MHz, DMSO-$d_6$) δ 12.83 (d, J = 14.6 Hz, 1H), 8.79 (s, 1H), 8.32-8.21 (m, 2H), 8.17 (s, 1H), 7.55 (s, 1H), 7.53-7.21 (m, 2H), 5.04 (s, 1H), 4.94 (d, J = 5.4 Hz, 2H), 4.79 (s, 1H), 3.61 (s, 3H), 2.59 (d, J = 2.3 Hz, 3H) |
| 629 | 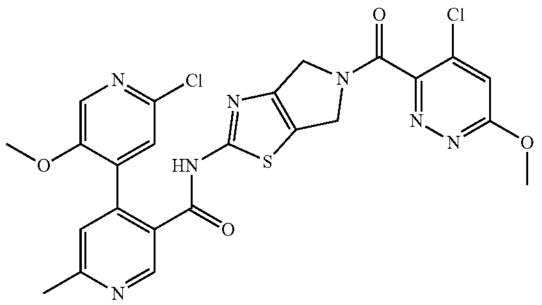 | 2'-chloro-N-(5-(4-chloro-6-methoxy-pyridazine-3-carbonyl)-5,6-dihydro-4H-pyrrolo[3,4-d]thiazol-2-yl)-5'-methoxy-6-methyl-[4,4'-bipyridine]-3-carboxamide | 572 | 1H NMR (400 MHz, DMSO-$d_6$) δ 12.82 (s, 1H), 8.78 (d, J = 4.8 Hz, 1H), 8.16 (d, J = 2.8 Hz, 1H), 7.79 (d, J = 3.4 Hz, 1H), 7.54 (s, 1H), 7.43 (d, J = 2.4 Hz, 1H), 4.85 (s, 1H), 4.72 (s, 1H), 4.55 (d, J = 3.3 Hz, 1H), 4.44 (d, J = 3.2 Hz, 1H), 3.99 (s, 3H), 3.60 (s, 3H), 2.59 (d, J = 2.7 Hz, 3H) |
| 630 | 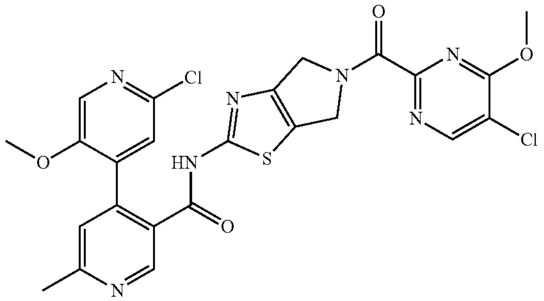 | 2'-chloro-N-(5-(5-chloro-4-methoxy-pyrimidine-2-carbonyl)-5,6-dihydro-4H-pyrrolo[3,4-d]thiazol-2-yl)-5'-methoxy-6-methyl-[4,4'-bipyridine]-3-carboxamide | 572 | $^1$H NMR (300 MHz, DMSO-$d_6$) δ 12.81 (s, 1H), 8.81 (d, J = 11.4, 2.2 Hz, 2H), 8.17 (d, J = 1.5 Hz, 1H), 7.54 (s, 1H), 7.43 (s, 1H), 4.82 (s, 2H), 4.69 (s, 2H), 4.08 (d, J = 1.6 Hz, 3H), 3.60 (s, 3H), 2.59 (d, J = 1.5 Hz, 3H) |
| 631 | 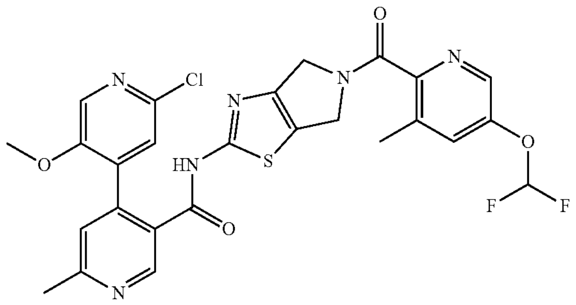 [SMILES: COc1cnc(Cl)cc1-c1cc(C)ncc1C(=O)Nc1nc2c(s1)CN(C(=O)c1ncc(OC(F)F)cc1C)C2] | 2'-chloro-N-(5-(5-(difluoro methoxy)-3-methyl-picolinoyl)-5,6-dihydro-4H-pyrrolo[3,4-d]thiazol-2-yl)-5'-methoxy-6-methyl-[4,4'-bipyridine]-3-carboxamide | 587 | $^1$H NMR (400 MHz, DMSO-$d_6$) δ 12.79 (s, 1H), 8.79 (d, J = 4.5 Hz, 1H), 8.37 (d, J = 2.6 Hz, 1H), 8.17 (d, J = 2.3 Hz, 1H), 7.71 (t, J = 3.0 Hz, 1H), 7.54 (s, 1H), 7.43 (d, J = 2.3 Hz, 1H), 7.39 (d, J = 2.6 Hz, 1H), 4.85-4.70 (m, 2H), 4.60-4.40 (m, 2H), 3.61 (s, 3H), 2.59 (d, J = 2.8 Hz, 3H), 2.37 (s, 3H) |

TABLE C-continued

| The following examples were prepared using a similar procedure to that described for Example 1 | | | | |
|---|---|---|---|---|
| Ex. No. | Structure | Compound Name | LCMS [M + H]+ | NMR |
| 632 | 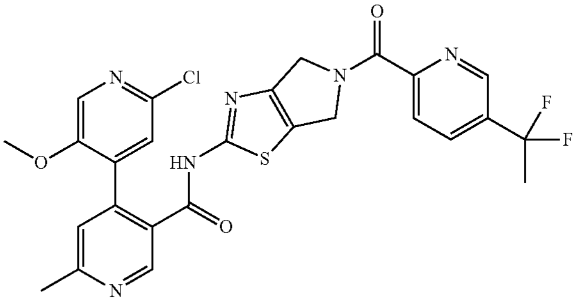 [SMILES: COc1cnc(Cl)cc1-c1cc(C)ncc1C(=O)Nc1nc2c(s1)CN(C(=O)c1ccc(C(C)(F)F)cn1)C2] | 2'-chloro-N-(5-(5-(1,1-di-fluoroethyl)pico-linoyl)-5,6-dihydro-4H-pyrrolo[3,4-d]thiazol-2-yl)-5'-methoxy-6-methyl-[4,4'-bipyridine]-3-carboxamide | 571 | $^1$H NMR (400 MHz, DMSO-$d_6$) δ 12.80 (s, 1H), 8.92-8.85 (m, 1H), 8.80 (s, 1H), 8.22-8.14 (m, 2H), 7.97 (t, J = 7.9 Hz, 1H), 7.53 (s, 1H), 7.42 (s, 1H), 5.02 (s, 1H), 4.92 (s, 1H), 4.87 (s, 1H), 4.72 (s, 1H), 3.61 (s, 3H), 2.58 (s, 3H), 2.13-2.03 (m, 3H) |
| 633 | 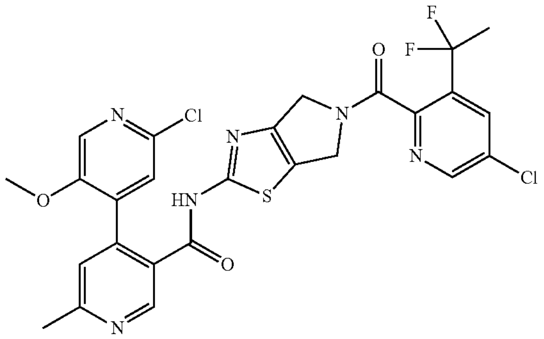 [SMILES: COc1cnc(Cl)cc1-c1cc(C)ncc1C(=O)Nc1nc2c(s1)CN(C(=O)c1ncc(Cl)cc1C(C)(F)F)C2] | 2'-chloro-N-(5-(5-chloro-3-(1,1-difluoro-ethyl)pico-linoyl)-5,6-dihydro-4H-pyrrolo[3,4-d]thiazol-2-yl)-5'-methoxy-6-methyl-[4,4'-bipyridine]-3-carboxamide | 605 | $^1$H NMR (400 MHz, DMSO-$d_6$) δ 12.56 (s, 1H), 8.84 (d, J = 3.3, 2.3 Hz, 1H), 8.80 (d, J = 5.5 Hz, 1H), 8.27 (d, J = 3.8, 2.2 Hz, 1H), 8.15 (d, J = 4.2 Hz, 1H), 7.50 (d, J = 1.1 Hz, 1H), 7.39 (d, J = 1.8 Hz, 1H), 4.79 (t, J = 2.6 Hz, 1H), 4.65 (t, J = 2.6 Hz, 1H), 4.46 (t, J = 2.7 Hz, 1H), 4.34 (t, J = 2.7 Hz, 1H), 3.60 (s, 3H), 2.58 (d, J = 2.7 Hz, 3H), 2.07 (t, J = 19.2 Hz, 3H) |
| 634 | 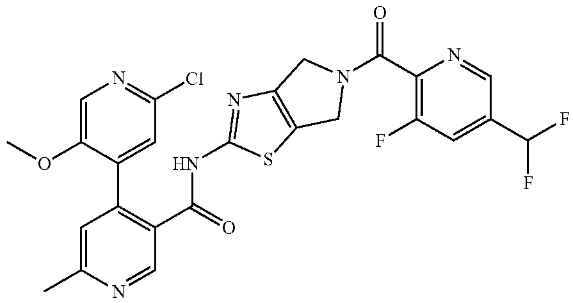 [SMILES: COc1cnc(Cl)cc1-c1cc(C)ncc1C(=O)Nc1nc2c(s1)CN(C(=O)c1ncc(C(F)F)cc1F)C2] | 2'-chloro-N-(5-(5-(difluoromethyl)-3-fluoropicolinyl)-5,6-dihydro-4H-pyrrolo[3,4-d]thiazol-2-yl)-5'-methoxy-6-methyl-[4,4'-bipyridine]-3-carboxamide | 575 | $^1$H NMR (400 MHz, DMSO-$d_6$) δ 12.83 (s, 1H), 8.79 (d, J = 4.0 Hz, 1H), 8.77-8.71 (m, 1H), 8.24-8.21 (m, 1H), 8.17 (d, J = 2.2 Hz, 1H), 7.54 (s, 1H), 7.44 (d, J = 2.3 Hz, 1H), 7.19 (d, J = 54.7 Hz, 1H), 4.87 (s, 1H), 4.77-4.66 (m, 2H), 4.59 (s, 1H), 3.60 (s, 3H), 2.59 (d, J = 2.6 Hz, 3H) |
| 635 | 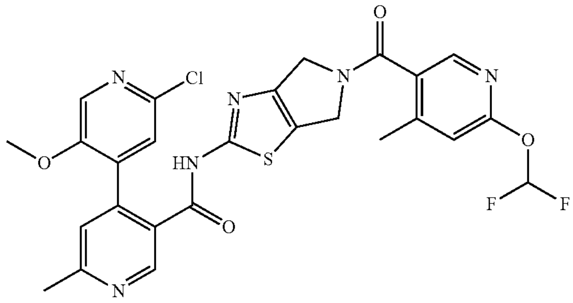 [SMILES: COc1cnc(Cl)cc1-c1cc(C)ncc1C(=O)Nc1nc2c(s1)CN(C(=O)c1cnc(OC(F)F)cc1C)C2] | 2'-chloro-N-(5-(6-(difluoro-methoxy)-4-methyl-nicotinoyl)-5,6-dihydro-4H-pyrrolo[3,4-d]thiazol-2-yl)-5'-methoxy-6-methyl-[4,4'-bipyridine]-3-carboxamide | 587 | $^1$H NMR (400 MHz, DMSO-$d_6$) δ 11.47 (s, 1H), 8.85 (d, J = 8.2 Hz, 1H), 8.32 (d, J = 2.6 Hz, 1H), 8.15 (d, J = 1.6 Hz, 1H), 7.92-7.54 (m, 1H), 7.45 (d, J = 4.0 Hz, 1H), 7.33 (s, 1H), 7.09 (s, 1H), 4.65-4.8 (m, 2H), 4.48-4.38 (m, 2H), 3.61 (s, 3H), 2.57 (d, J = 1.9 Hz, 3H), 2.34 (s, 3H) |

TABLE C-continued

The following examples were prepared using a similar procedure to that described for Example 1

| Ex. No. | Structure | Compound Name | LCMS [M + H]+ | NMR |
|---|---|---|---|---|
| 636 | 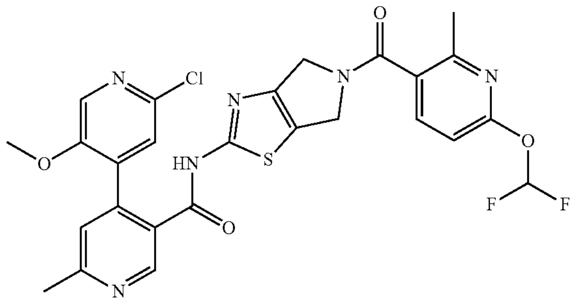 [SMILES: COc1cnc(Cl)cc1-c1cc(C)ncc1C(=O)Nc1nc2c(s1)CN(C(=O)c1ccc(OC(F)F)nc1C)C2] | 2'-chloro-N-(5-(6-(difluoro-methoxy)-2-methyl-nicotinoyl)-5,6-dihydro-4H-pyrrolo[3,4-d]thiazol-2-yl)-5'-methoxy-6-methyl-[4,4'-bipyridine]-3-carboxamide | 587 | $^1$H NMR (400 MHz, DMSO-d6) δ 12.80 (s, 1H), 8.79 (d, J = 5.0 Hz, 1H), 8.17 (s, 1H), 7.98 (d, J = 8.3 Hz, 1H), 7.74-7.56 (m, 1H), 7.54 (s, 1H), 7.43 (d, J = 2.5 Hz, 1H), 7.01-6.99 (m, 1H), 4.82-4.68 (m, 2H), 4.48-4.39 (m, 2H), 3.60 (s, 3H), 2.59 (d, J = 2.8 Hz, 3H), 2.44 (s, 3H) |
| 637 | 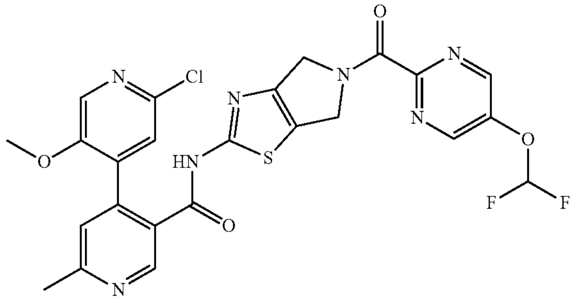 [SMILES: COc1cnc(Cl)cc1-c1cc(C)ncc1C(=O)Nc1nc2c(s1)CN(C(=O)c1ncc(OC(F)F)cn1)C2] | 2'-chloro-N-(5-(5-(difluoro-methoxy) pyrimidine-2-carbonyl)-5,6-dihydro-4H-pyrrolo[3,4-d]thiazol-2-yl)-5'-methoxy-6-methyl-[4,4'-bipyridine]-3-carboxamide | 574 | $^1$H NMR (400 MHz, DMSO-$d_6$) δ 12.80 (s, 1H), 8.94 (d, J = 1.7 Hz, 2H), 8.79 (d, J = 3.8 Hz, 1H), 8.17 (d, J = 2.0 Hz, 1H), 7.73-7.17 (m, 3H), 4.85 (t, J = 2.6 Hz, 1H), 4.79-4.70 (m, 2H), 4.68-4.62 (m, 1H), 3.60 (d, J = 1.3 Hz, 3H), 2.58 (d, J = 2.2 Hz, 3H) |
| 638 | 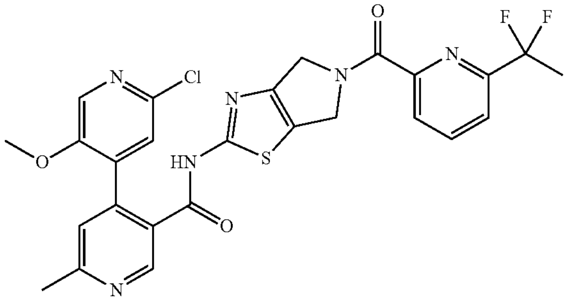 [SMILES: COc1cnc(Cl)cc1-c1cc(C)ncc1C(=O)Nc1nc2c(s1)CN(C(=O)c1cccc(C(C)(F)F)n1)C2] | 2'-chloro-N-(5-(6-(1,1-difluoro-ethyl)pico-linoyl)-5,6-dihydro-4H-pyrrolo[3,4-d]thiazol-2-yl)-5'-methoxy-6-methyl-[4,4'-bipyridine]-3-carboxamide | 571 | $^1$H NMR (300 MHz, DMSO-$d_6$) δ 12.78 (s, 1H), 8.79 (d, J = 3.3 Hz, 1H), 8.29-8.14 (m, 2H), 8.02 (t, J = 7.9 Hz, 1H), 7.90-7.87 (m, 1H), 7.56 (d, J = 1.2 Hz, 1H), 7.45 (s, 1H), 5.07 (s, 1H), 4.98 (s, 1H), 4.88 (s, 1H), 4.74 (s, 1H), 3.61 (s, 3H), 2.60 (s, 3H), 2.15-2.02 (m, 3H) |
| 639 | 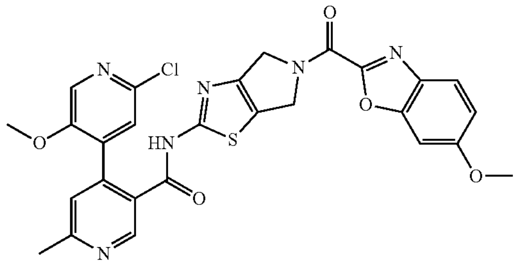 | 2'-chloro-5'-methoxy-N-(5-(6-methoxy-benzo[d] oxazole-2-carbonyl)-5,6-dihydro-4H-pyrrolo[3,4-d]thiazol-2-yl)-6-methyl-[4,4'-bipyridine]-3-carboxamide | 577 | $^1$H NMR (400 MHz, DMSO-$d_6$) δ 12.83 (s, 1H), 8.80 (d, J = 3.7 Hz, 1H), 8.18 (d, J = 2.6 Hz, 1H), 7.82 (d, J = 15.1, 8.9 Hz, 1H), 7.60-7.40 (m, 3H), 7.10 (d, J = 8.9, 2.9 Hz, 1H), 5.36 (s, 1H), 5.21 (t, J = 2.2 Hz, 1H), 4.88 (d, J = 2.8 Hz, 1H), 4.74 (d, J = 3.0 Hz, 1H), 3.87 (s, 3H), 3.62 (d, J = 1.8 Hz, 3H), 2.60 (s, 3H) |
| 640 | 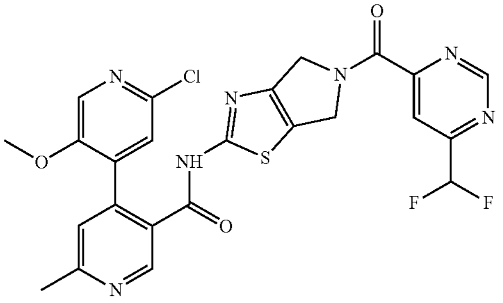 [SMILES: COc1cnc(Cl)cc1-c1cc(C)ncc1C(=O)Nc1nc2c(s1)CN(C(=O)c1cc(C(F)F)ncn1)C2] | 2'-chloro-N-(5-(6-(difluoromethyl) pyrimidine-4-carbonyl)-5,6-dihydro-4H-pyrrolo[3,4-d]thiazol-2-yl)-5'-methoxy-6-methyl-[4,4'-bipyridine]-3-carboxamide | 558 | $^1$H NMR (400 MHz, DMSO-$d_6$) δ 12.82 (s, 1H), 9.50 (d, J = 6.9, 1.3 Hz, 1H), 8.80 (d, J = 1.5 Hz, 1H), 8.17 (s, 1H), 8.12 (d, J = 1.3 Hz, 1H), 7.54 (s, 1H), 7.43 (s, 1H), 7.12 (t, J = 54.0 Hz, 1H), 5.11-4.64 (m, 4H), 3.60 (d, J = 1.5 Hz, 3H), 2.59 (d, J = 1.6 Hz, 3H) |

TABLE C-continued

| The following examples were prepared using a similar procedure to that described for Example 1 | | | | |
|---|---|---|---|---|
| Ex. No. | Structure | Compound Name | LCMS [M + H]+ | NMR |
| 641 | 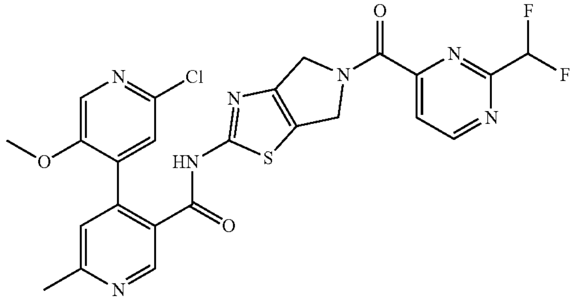 [SMILES: COc1cnc(Cl)cc1-c1cc(C)ncc1C(=O)Nc1nc2c(s1)CN(C(=O)c1ccnc(C(F)F)n1)C2] | 2'-chloro-N-(5-(2-(difluoromethyl) pyrimidine-4-carbonyl)-5,6-dihydro-4H-pyrrolo[3,4-d]thiazol-2-yl)-5'-methoxy-6-methyl-[4,4'-bipyridine]-3-carboxamide | 558 | $^1$H NMR (400 MHz, DMSO-$d_6$) δ 12.80 (d, J = 14.4 Hz, 1H), 9.22 (d, J = 5.1 Hz, 1H), 8.79 (d, J = 2.7 Hz, 1H), 8.17 (d, J = 1.8 Hz, 1H), 8.04 (t, J = 5.7 Hz, 1H), 7.55 (d, J = 2.9 Hz, 1H), 7.45 (s, 1H), 7.23 (s, 1H), 5.00 (s, 1H), 4.90 (d, J = 16.5 Hz, 2H), 4.74 (s, 1H), 3.45 (s, 3H), 2.48 (s, 3H) |
| 642 | 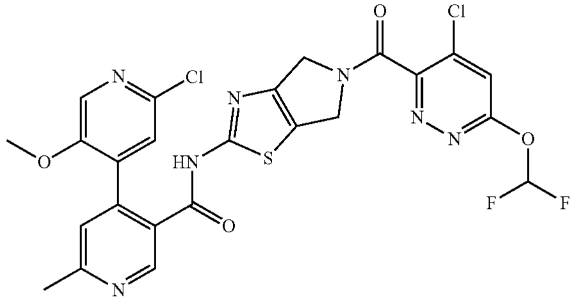 [SMILES: COc1cnc(Cl)cc1-c1cc(C)ncc1C(=O)Nc1nc2c(s1)CN(C(=O)c1nnc(OC(F)F)cc1Cl)C2] | 2'-chloro-N-(5-(4-chloro-6-(difluoro-methoxy) pyridazine-3-carbonyl)-5,6-dihydro-4H-pyrrolo[3,4-d]thiazol-2-yl)-5'-methoxy-6-methyl-[4,4'-bipyridine]-3-carboxamide | 608 | $^1$H NMR (400 MHz, DMSO-$d_6$) δ 12.85 (s, 1H), 8.79 (d, J = 4.2 Hz, 1H), 8.21-8.17 (m, 2H), 8.15-7.78 (m, 1H), 7.55 (s, 1H), 7.44 (d, J = 2.9 Hz, 1H), 4.91 (s, 1H), 4.78 (s, 1H), 4.64 (s, 1H), 4.53 (s, 1H), 3.61 (s, 3H), 2.60 (d, J = 3.0 Hz, 3H) |
| 643 | 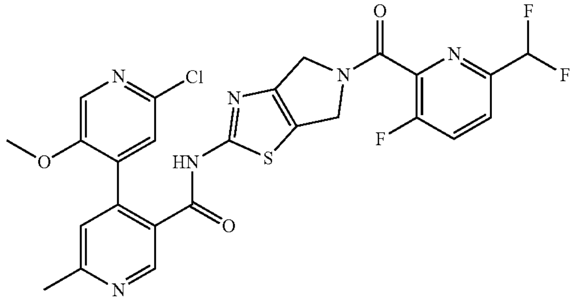 [SMILES: COc1cnc(Cl)cc1-c1cc(C)ncc1C(=O)Nc1nc2c(s1)CN(C(=O)c1nc(C(F)F)ccc1F)C2] | 2'-chloro-N-(5-(6-(difluoromethyl)-3-fluoropicolinoyl)-5,6-dihydro-4H-pyrrolo[3,4-d]thiazol-2-yl)-5'-methoxy-6-methyl-[4,4'-bipyridine]-3-carboxamide | 575 | $^1$H NMR (400 MHz, DMSO-$d_6$) δ 12.81 (s, 1H), 8.79 (d, J = 5.5 Hz, 1H), 8.20-8.09 (m, 2H), 7.97-7.95 (m, 1H), 7.54 (d, J = 1.1 Hz, 1H), 7.44 (s, 1H), 7.06-6.92 (m, 1H), 4.8 (s, 1H), 4.72 (d, J = 7.6 Hz, 2H), 4.61 (d, J = 3.0 Hz, 1H), 3.60 (s, 3H), 2.59 (d, J = 2.1 Hz, 3H) |
| 644 | 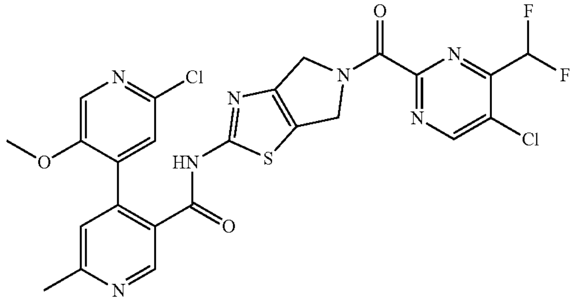 [SMILES: COc1cnc(Cl)cc1-c1cc(C)ncc1C(=O)Nc1nc2c(s1)CN(C(=O)c1ncc(Cl)c(C(F)F)n1)C2] | 2'-chloro-N-(5-(5-chloro-4-(difluoromethyl) pyrimidine-2-carbonyl)-5,6-dihydro-4H-pyrrolo[3,4-d]thiazol-2-yl)-5'-methoxy-6-methyl-[4,4'-bipyridine]-3-carboxamide | 592 | $^1$H NMR (400 MHz, DMSO-$d_6$) δ 9.29 (s, 1H), 9.16 (d, J = 4.7 Hz, 1H), 8.28 (d, J = 3.3 Hz, 1H), 8.18 (s, 1H), 7.73 (d, J = 1.4 Hz, 1H), 7.44-7.17 (m, 1H), 4.91-4.87 (m, 2H), 4.77 (s, 2H), 3.65 (s, 3H), 2.90 (d, J = 1.5 Hz, 3H) |

TABLE C-continued

The following examples were prepared using a similar procedure to that described for Example 1

| Ex. No. | Structure | Compound Name | LCMS [M + H]+ | NMR |
|---|---|---|---|---|
| 645 | 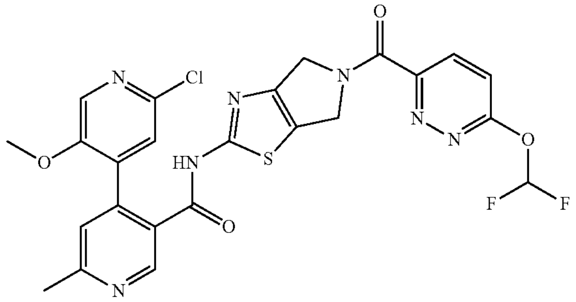 [SMILES: COc1cnc(Cl)cc1-c1cc(C)ncc1C(=O)Nc1nc2c(s1)CN(C(=O)c1ccc(OC(F)F)nn1)C2] | 2'-chloro-N-(5-(6-(difluoro-methoxy) pyridazine-3-carbonyl)-5,6-dihydro-4H-pyrrolo[3,4-d]thiazol-2-yl)-5'-methoxy-6-methyl-[4,4'-bipyridine]-3-carboxamide | 574 | $^1$H NMR (400 MHz, DMSO-$d_6$) δ 12.84 (d, J = 19.7 Hz, 1H), 8.80 (s, 1H), 8.23-8.17 (m, 2H), 8.02-8.00 (m, 1H), 7.71 (d, J = 9.1 Hz, 1H), 7.55 (s, 1H), 7.44 (d, J = 2.0 Hz, 1H), 5.09 (s, 1H), 4.98 (d, J = 2.9 Hz, 1H), 4.91 (d, J = 2.9 Hz, 1H), 4.77 (s, 1H), 3.61 (s, 3H), 2.60 (d, J = 2.0 Hz, 3H) |
| 646 | 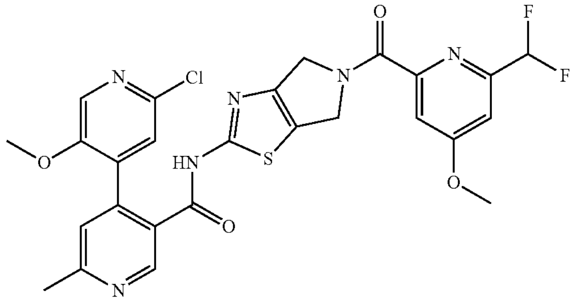 [SMILES: COc1cc(C(=O)N2Cc3nc(NC(=O)c4cnc(C)cc4-c4cc(Cl)ncc4OC)sc3C2)nc(C(F)F)c1] | 2'-chloro-N-(5-(6-(difluoromethyl)-4-methoxy-picolinoyl)-yl)-5,6-dihydro-4H-pyrrolo[3,4-d]thiazol-2-yl)-5'-methoxy-6-methyl-[4,4'-bipyridine]-3-carboxamide | 587 | $^1$H NMR (400 MHz, DMSO-$d_6$) δ 12.78 (d, J = 18.3 Hz, 1H), 8.79 (d, J = 3.1 Hz, 1H), 8.17 (d, J = 2.1 Hz, 1H), 7.55-7.48 (m, 2H), 7.44 (s, 1H), 7.39 (t, J = 2.4 Hz, 1H), 7.00 (d, J = 54.8, 12.4 Hz, 1H), 4.99 (s, 1H), 4.95-4.82 (m, 2H), 4.72 (d, J = 3.1 Hz, 1H), 3.97 (s, 3H), 3.60 (s, 3H), 2.59 (s, 3H) |
| 647 | 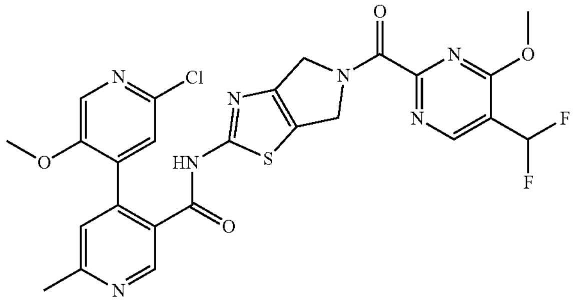 [SMILES: COc1cnc(Cl)cc1-c1cc(C)ncc1C(=O)Nc1nc2c(s1)CN(C(=O)c1ncc(C(F)F)c(OC)n1)C2] | 2'-chloro-N-(5-(5-(difluoromethyl)-4-methoxy-pyrimidine-2-carbonyl)-5,6-dihydro-4H-pyrrolo[3,4-d]thiazol-2-yl)-5'-methoxy-6-methyl-[4,4'-bipyridine]-3-carboxamide | 588 | $^1$H NMR (400 MHz, DMSO-$d_6$) δ 12.80 (d, J = 9.4 Hz, 1H), 8.87 (s, 1H), 8.78 (d, J = 4.0 Hz, 1H), 8.17 (d, J = 2.1 Hz, 1H), 7.54 (s, 1H), 7.43 (s, 1H), 7.30-7.03 (m, 1H), 4.82 (d, J = 21.6 Hz, 2H), 4.70 (d, J = 13.0 Hz, 2H), 4.08 (d, J = 1.7 Hz, 3H), 3.60 (s, 3H), 2.59 (d, J = 2.2 Hz, 3H) |
| 648 | 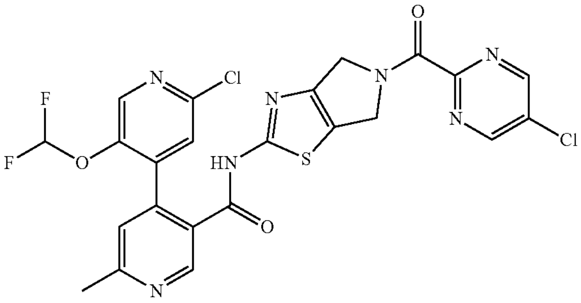 [SMILES: Cc1cc(-c2cc(Cl)ncc2OC(F)F)c(C(=O)Nc2nc3c(s2)CN(C(=O)c2ncc(Cl)cn2)C3)cn1] | 2'-chloro-N-(5-(5-chloro-pyrimidine-2-carbonyl)-5,6-dihydro-4H-pyrrolo[3,4-d]thiazol-2-yl)-5'-(difluoro-methoxy)-6-methyl-[4,4'-bi-pyridine]-3-carboxamide | 578 | $^1$H NMR (400 MHz, DMSO-$d_6$) δ 12.93 (s, 1H), 9.11 (s, 2H), 8.94 (d, J = 4.2 Hz, 1H), 8.34 (s, 1H), 7.72 (s, 1H), 7.45 (s, 1H), 7.10 (t, J = 72.5 Hz, 1H), 4.85 (d, J = 3.5 Hz, 1H), 4.78-4.69 (m, 2H), 4.66 (d, J = 2.7 Hz, 1H), 2.61 (d, J = 2.1 Hz, 3H) |

TABLE C-continued

The following examples were prepared using a similar procedure to that described for Example 1

| Ex. No. | Structure | Compound Name | LCMS [M + H]+ | NMR |
|---|---|---|---|---|
| 649 | 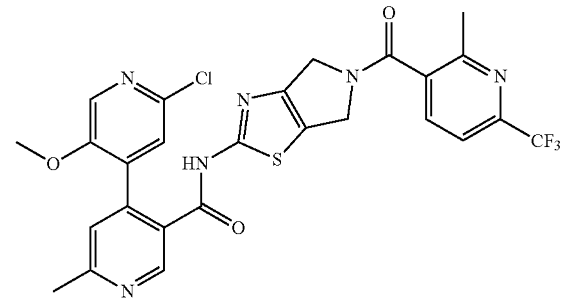 [SMILES: COc1cnc(Cl)cc1-c1cc(C)ncc1C(=O)Nc1nc2c(s1)CN(C(=O)c1ccc(C(F)(F)F)nc1C)C2] | 2'-chloro-5'-methoxy-6-methyl-N-(5-(2-methyl-6-(trifluoromethyl)nicotinoyl)-5,6-dihydro-4H-pyrrolo[3,4-d]thiazol-2-yl)-[4,4'-bipyridine]-3-carboxamide | 589 | $^1$H NMR (400 MHz, DMSO-$d_6$) δ 12.81 (s, 1H), 8.78 (d, J = 4.8 Hz, 1H), 8.19-8.11 (m, 2H), 7.84 (d, J = 7.9, 3.7 Hz, 1H), 7.54 (s, 1H), 7.43 (d, J = 2.9 Hz, 1H), 4.85 (s, 1H), 4.71 (s, 1H), 4.48 (s, 1H), 4.40 (s, 1H), 3.59 (d, J = 1.0 Hz, 3H), 2.59-2.56 (m, 6H) |
| 650 | 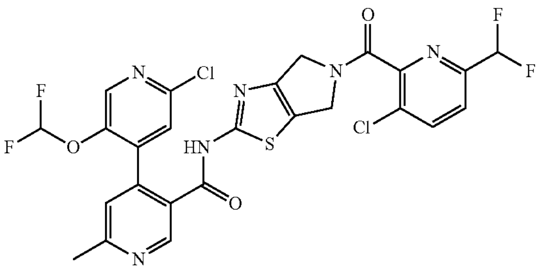 [SMILES: Cc1cc(-c2cc(Cl)ncc2OC(F)F)c(C(=O)Nc2nc3c(s2)CN(C(=O)c2nc(C(F)F)ccc2Cl)C3)cn1] | 2'-chloro-N-(5-(3-chloro-6-(difluoromethyl)picolinoyl)-5,6-dihydro-4H-pyrrolo[3,4-d]thiazol-2-yl)-5'-(difluoro-methoxy)-6-methyl-[4,4'-bipyridine]-3-carboxamide | 627 | $^1$H NMR (400 MHz, DMSO-$d_6$) δ 12.96 (s, 1H), 8.93 (d, J = 6.8 Hz, 1H), 8.39-8.30 (m, 2H), 7.88 (d, J = 8.5 Hz, 1H), 7.72 (d, J = 1.8 Hz, 1H), 7.45 (s, 1H), 7.30-6.91 (m, 2H), 4.86 (t, J = 2.6 Hz, 1H), 4.73 (s, 1H), 4.51 (t, J = 2.7 Hz, 1H), 4.42 (d, J = 3.0 Hz, 1H), 2.60 (d, J = 2.7 Hz, 3H) |
| 651 | 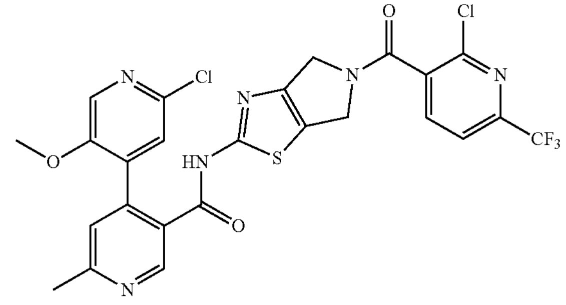 [SMILES: COc1cnc(Cl)cc1-c1cc(C)ncc1C(=O)Nc1nc2c(s1)CN(C(=O)c1ccc(C(F)(F)F)nc1Cl)C2] | 2'-chloro-N-(5-(2-chloro-6-(trifluoromethyl)nicotinoyl)-5,6-dihydro-4H-pyrrolo[3,4-d]thiazol-2-yl)-5'-methoxy-6-methyl-[4,4'-bipyridine]-3-carboxamide | 609 | $^1$H NMR (400 MHz, DMSO-$d_6$) δ 12.85 (d, J = 2.9 Hz, 1H), 8.79 (d, J = 3.7 Hz, 1H), 8.42-8.37 (m, 1H), 8.19-8.11 (m, 2H), 7.55 (s, 1H), 7.44 (d, J = 3.3 Hz, 1H), 4.88 (s, 1H), 4.72 (s, 1H), 4.58 (s, 1H), 4.44 (s, 1H), 3.60 (s, 3H), 2.59 (d, J = 2.9 Hz, 3H) |
| 652 | 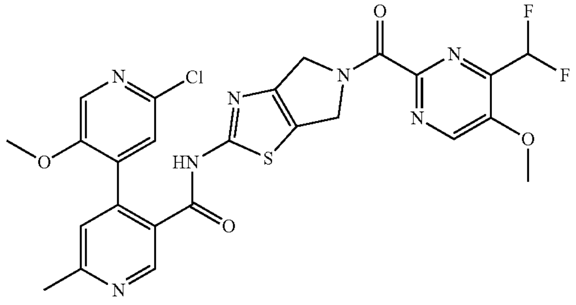 [SMILES: COc1cnc(Cl)cc1-c1cc(C)ncc1C(=O)Nc1nc2c(s1)CN(C(=O)c1ncc(OC)c(C(F)F)n1)C2] | 2'-chloro-N-(5-(4-(difluoromethyl)-5-methoxy-pyrimidine-2-carbonyl)-5,6-dihydro-4H-pyrrolo[3,4-d]thiazol-2-yl)-5'-methoxy-6-methyl-[4,4'-bipyridine]-3-carboxamide | 588 | $^1$H NMR (400 MHz, DMSO-$d_6$) δ 12.8 (s, 1H), 9.00 (d, J = 2.0 Hz, 1H), 8.79 (d, J = 4.7 Hz, 1H), 8.17 (d, J = 3.2 Hz, 1H), 7.54 (s, 1H), 7.43 (s, 1H), 7.17-7.03 (m, 1H), 4.83 (d, J = 14.5 Hz, 2H), 4.72 (s, 2H), 4.10 (d, J = 2.2 Hz, 3H), 3.60 (s, 3H), 2.59 (d, J = 1.8 Hz, 3H) |
| 653 | 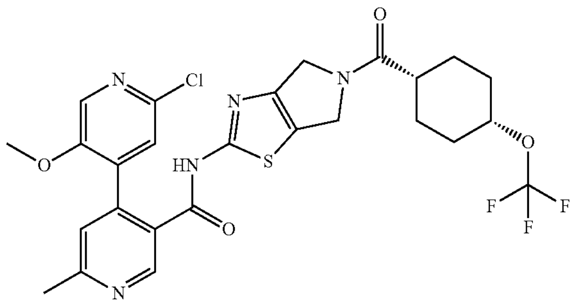 [SMILES: COc1cnc(Cl)cc1-c1cc(C)ncc1C(=O)Nc1nc2c(s1)CN(C(=O)[C@H]1CC[C@@H](OC(F)(F)F)CC1)C2] | 2'-chloro-5'-methoxy-6-methyl-N-(5-((1s,4s)-4-(trifluoro-methoxy)cyclohexane-1-carbonyl)-5,6-dihydro-4H-pyrrolo[3,4-d]thiazol-2-yl)-[4,4'-bipyridine]-3-carboxamide | 596 | $^1$H NMR (400 MHz, DMSO-$d_6$) δ 12.79 (s, 1H), 8.79 (s, 1H), 8.17 (d, J = 3.5 Hz, 1H), 7.54 (d, J = 1.4 Hz, 1H), 7.43 (s, 1H), 4.88 (d, J = 3.5 Hz, 1H), 4.75 (s, 1H), 4.68 (s, 1H), 4.58 (d, J = 3.5 Hz, 1H), 4.44 (s, 1H), 3.60 (d, J = 1.9 Hz, 3H), 2.66-2.58 (m, 4H), 1.94 (s, 2H), 1.71-1.65 (m, 6H) |

TABLE C-continued

The following examples were prepared using a similar procedure to that described for Example 1

| Ex. No. | Structure | Compound Name | LCMS [M + H]+ | NMR |
|---|---|---|---|---|
| 654 | 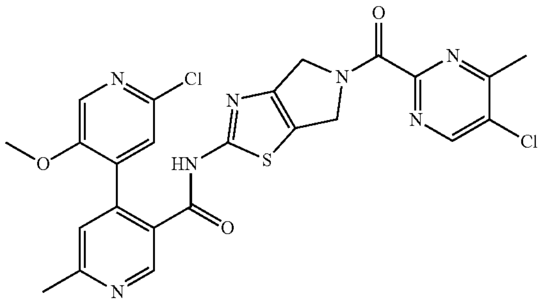 | 2'-chloro-N-(5-(5-chloro-4-methyl-pyrimidine-2-carbonyl)-5,6-dihydro-4H-pyrrolo[3,4-d]thiazol-2-yl)-5'-methoxy-6-methyl-[4,4'-bipyridine]-3-carboxamide | 556 | $^1$H NMR (400 MHz, DMSO-$d_6$) δ 12.80 (d, J = 12.5 Hz, 1H), 8.96 (d, J = 2.2 Hz, 1H), 8.78 (d, J = 4.1 Hz, 1H), 8.17 (d, J = 2.1 Hz, 1H), 7.54 (s, 1H), 7.43 (s, 1H), 4.84 (t, J = 2.6 Hz, 1H), 4.78-4.69 (m, 2H), 4.64 (t, J = 2.7 Hz, 1H), 3.60 (d, J = 1.2 Hz, 3H), 2.63 (s, 3H), 2.59 (d, J = 2.1 Hz, 3H) |
| 655 | 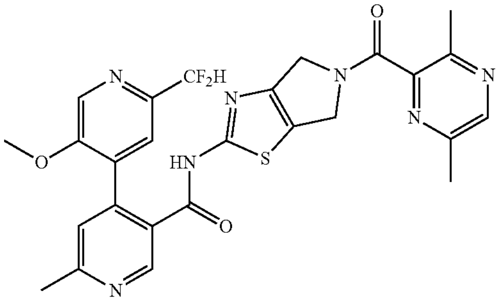 [SMILES: COc1cnc(C(F)F)cc1-c1cc(C)ncc1C(=O)Nc1nc2c(s1)CN(C(=O)c1nc(C)cnc1C)C2] | 2'-(difluoro-methyl)-N-(5-(3,6-dimethyl-pyrazine-2-carbonyl)-5,6-dihydro-4H-pyrrolo[3,4-d]thiazol-2-yl)-5'-methoxy-6-methyl-[4,4'-bipyridine]-3-carboxamide | 552 | $^1$H NMR (400 MHz, Chloroform-d) δ 9.07 (s, 1H), 8.42 (d, J = 12.6 Hz, 1H), 8.34 (s, 1H), 7.61 (s, 1H), 7.36 (s, 1H), 6.68 (s, 1H), 4.97 (s, 1H), 4.72 (s, 1H), 4.56 (s, 1H), 4.33 (s, 1H), 3.79 (s, 3H), 2.84 (s, 3H), 2.62 (s, 3H), 2.56 (s, 2H), 2.47 (s, 2H) |
| 656 | 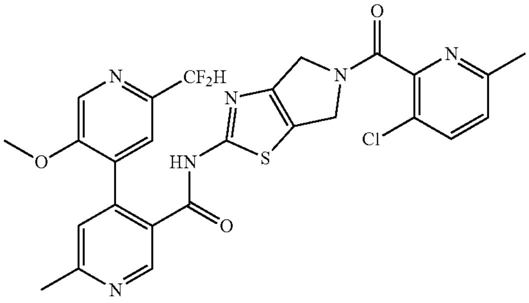 | N-(5-(3-chloro-6-methyl-picolinoyl)-5,6-dihydro-4H-pyrrolo[3,4-d]thiazol-2-yl)-2'-(difluoromethyl)-5'-methoxy-6-methyl-[4,4'-bipyridine]-3-carboxamide | 571 | $^1$H NMR (400 MHz, DMSO-$d_6$) δ 12.82 (s, 1H), 8.78 (d, J = 4.8 Hz, 1H), 8.45 (d, J = 3.5 Hz, 1H), 7.87 (d, J = 8.2 Hz, 1H), 7.69 (d, J = 1.4 Hz, 1H), 7.55 (dd, J = 8.2, 1.8 Hz, 1H), 7.43 (d, J = 2.2 Hz, 1H), 7.11-6.83 (m, 1H), 4.83 (t, J = 2.7 Hz, 1H), 4.70 (t, J = 2.6 Hz, 1H), 4.55 (t, J = 2.7 Hz, 1H), 4.44 (t, J = 2.7 Hz, 1H), 3.67 (s, 3H), 2.60 (d, J = 2.5 Hz, 3H), 2.31 (s, 3H) |
| 657 | 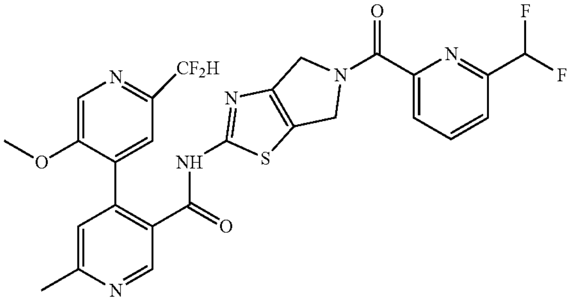 [SMILES: COc1cnc(C(F)F)cc1-c1cc(C)ncc1C(=O)Nc1nc2c(s1)CN(C(=O)c1cccc(C(F)F)n1)C2] | 2'-(difluoro-methyl)-N-(5-(6-(difluoromethyl)picolinoyl)-5,6-dihydro-4H-pyrrolo[3,4-d]thiazol-2-yl)-5'-methoxy-6-methyl-[4,4'-bipyridine]-3-carboxamide | 573 | 1H NMR (300 MHz, DMSO-$d_6$) δ 12.81 (s, 1H), 8.80 (d, J = 2.3 Hz, 1H), 8.47 (d, J = 1.7 Hz, 1H), 8.21 (t, J = 7.8 Hz, 1H), 8.09-7.96 (m, 1H), 7.88 (d, J = 7.8 Hz, 1H), 7.71 (s, 1H), 7.45 (s, 1H), 7.32-6.76 (m, 2H), 5.03 (s, 1H), 4.95 (s, 1H), 4.87 (s, 1H), 4.74 (s, 1H), 3.68 (s, 3H), 2.61 (s, 3H) |

TABLE C-continued

| The following examples were prepared using a similar procedure to that described for Example 1 | | | | |
|---|---|---|---|---|
| Ex. No. | Structure | Compound Name | LCMS [M + H]+ | NMR |
| 658 | 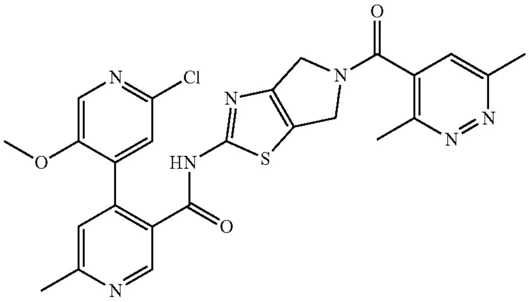 | 2'-chloro-N-(5-(3,6-dimethyl-pyridazine-4-carbonyl)-5,6-dihydro-4H-pyrrolo[3,4-d]thiazol-2-y)-5'-methoxy-6-methyl-[4,4'-bipyridine]-3-carboxamide | 536 | $^1$H NMR (400 MHz, DMSO-$d_6$) δ 12.81 (s, 1H), 8.78 (d, J = 5.4 Hz, 1H), 8.17 (s, 1H), 7.63 (d, J = 9.5 Hz, 1H), 7.54 (d, J = 1.0 Hz, 1H), 7.43 (d, J = 2.9 Hz, 1H), 4.83 (t, J = 2.8 Hz, 1H), 4.70 (t, J = 2.6 Hz, 1H), 4.52 (t, J = 2.7 Hz, 1H), 4.43 (t, J = 2.8 Hz, 1H), 3.59 (s, 3H), 2.62 (d, J = 2.2 Hz, 3H), 2.60-2.56 (m, 6H) |
| 659 | 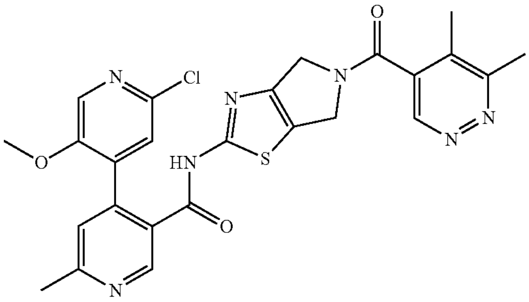 | 2'-chloro-N-(5-(5,6-dimethyl-pyridazine-4-carbonyl)-5,6-dihydro-4H-pyrrolo[3,4-d]thiazol-2-yl)-5'-methoxy-6-methyl-[4,4'-bipyridine]-3-carboxamide | 536 | $^1$H NMR (400 MHz, DMSO-$d_6$) δ 12.81 (s, 1H), 9.06 (d, J = 4.2 Hz, 1H), 8.78 (d, J = 5.4 Hz, 1H), 8.17 (d, J = 1.9 Hz, 1H), 7.54 (s, 1H), 7.43 (d, J = 3.3 Hz, 1H), 4.85 (t, J = 2.8 Hz, 1H), 4.71 (t, J = 2.7 Hz, 1H), 4.46 (t, J = 2.8 Hz, 1H), 4.36 (t, J = 2.8 Hz, 1H), 3.59 (s, 3H), 2.65 (s, 3H), 2.59 (d, J = 3.2 Hz, 3H), 2.27 (s, 3H) |
| 660 | 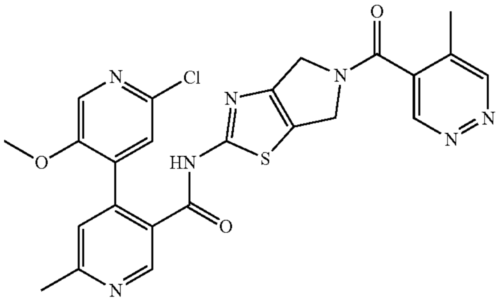 [SMILES: COc1cnc(Cl)cc1-c1cc(C)ncc1C(=O)Nc1nc2c(s1)CN(C(=O)c1cnncc1C)C2] | 2'-chloro-5'-methoxy-6-methyl-N-(5-(5-methyl-pyridazine-4-carbonyl)-5,6-dihydro-4H-pyrrolo[3,4-d]thiazol-2-yl)-[4,4'-bipyridine]-3-carboxamide | 522 | $^1$H NMR (400 MHz, DMSO-$d_6$) δ 12.81 (s, 1H), 9.30-9.21 (m, 2H), 8.78 (d, J = 5.4 Hz, 1H), 8.16 (d, J = 1.2 Hz, 1H), 7.54 (s, 1H), 7.43 (d, J = 2.8 Hz, 1H), 4.84 (d, J = 2.9 Hz, 1H), 4.71 (s, 1H), 4.51 (s, 1H), 4.41 (t, J = 2.8 Hz, 1H), 3.59 (s, 3H), 2.59 (d, J = 3.0 Hz, 3H), 2.33 (s, 3H) |
| 661 | 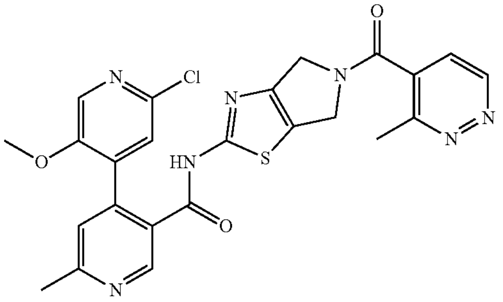 [SMILES: COc1cnc(Cl)cc1-c1cc(C)ncc1C(=O)Nc1nc2c(s1)CN(C(=O)c1ccnnc1C)C2] | 2'-chloro-5'-methoxy-6-methyl-N-(5-(3-methyl-pyridazine-4-carbonyl)-5,6-dihydro-4H-pyrrolo[3,4-d]thiazol-2-yl)-[4,4'-bipyridine]-3-carboxamide | 522 | $^1$H NMR (400 MHz, DMSO-$d_6$) δ 12.81 (s, 1H), 9.26-9.20 (m, 1H), 8.78 (d, J = 5.4 Hz, 1H), 8.17 (s, 1H), 7.77 (t, J = 4.9 Hz, 1H), 7.54 (s, 1H), 7.43 (d, J = 2.9 Hz, 1H), 4.84 (t, J = 2.7 Hz, 1H), 4.71 (t, J = 2.7 Hz, 1H), 4.51 (t, J = 2.7 Hz, 1H), 4.43 (d, J = 2.7 Hz, 1H), 3.59 (s, 3H), 2.64 (s, 3H), 2.59 (d, J = 3.0 Hz, 3H) |

TABLE C-continued

The following examples were prepared using a similar procedure to that described for Example 1

| Ex. No. | Structure | Compound Name | LCMS [M + H]+ | NMR |
|---|---|---|---|---|
| 662 | 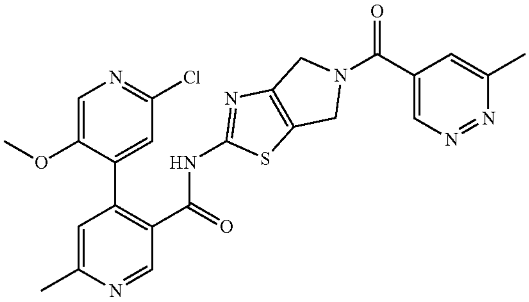 | 2'-chloro-5'-methoxy-6-methyl-N-(5-(6-methyl-pyridazine-4-carbonyl)-5,6-dihydro-4H-pyrrolo[3,4-d]thiazol-2-yl)-[4,4'-bipyridine]-3-carboxamide | 522 | $^1$H NMR (400 MHz, DMSO-$d_6$) δ 12.81 (s, 1H), 9.25 (t, J = 2.1 Hz, 1H), 8.78 (d, J = 3.6 Hz, 1H), 8.17 (s, 1H), 7.81 (d, J = 3.5, 2.1 Hz, 1H), 7.54 (s, 1H), 7.44 (d, J = 2.1 Hz, 1H), 4.83 (t, J = 2.6 Hz, 1H), 4.78-4.68 (m, 3H), 3.59 (s, 3H), 2.70 (d, J = 3.3 Hz, 3H), 2.59 (d, J = 2.2 Hz, 3H) |
| 663 | 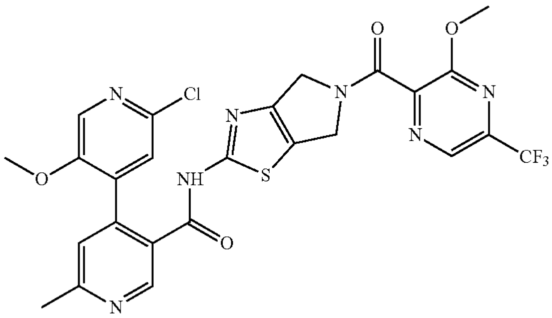 [SMILES: COc1cnc(Cl)cc1-c1cc(C)ncc1C(=O)Nc1nc2c(s1)CN(C(=O)c1ncc(C(F)(F)F)nc1OC)C2] | 2'-chloro-5'-methoxy-N-(5-(3-methoxy-5-(trifluoromethyl) pyrazine-2-carbonyl)-5,6-dihydro-4H-pyrrolo[3,4-d]thiazol-2-yl)-6-methyl-[4,4'-bipyridine]-3-carboxamide | 606 | $^1$H NMR (400 MHz, DMSO-$d_6$) δ 12.84 (d, J = 8.8 Hz, 1H), 8.82-8.78 (m, 2H), 8.17 (d, J = 2.2 Hz, 1H), 7.54 (s, 1H), 7.43 (d, J = 2.5 Hz, 1H), 4.85 (s, 1H), 4.72 (s, 1H), 4.63 (d, J = 2.9 Hz, 1H), 4.52 (s, 1H), 4.03 (s, 3H), 3.60 (s, 3H), 2.59 (d, J = 2.8 Hz, 3H) |
| 664 | 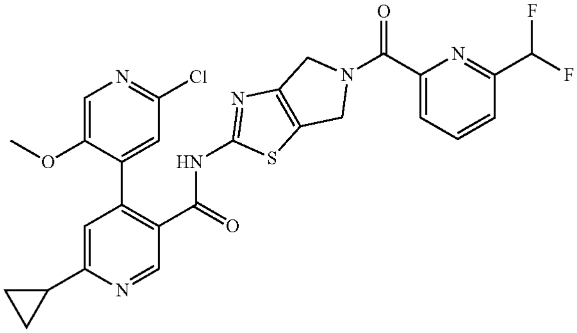 [SMILES: COc1cnc(Cl)cc1-c1cc(C2CC2)ncc1C(=O)Nc1nc2c(s1)CN(C(=O)c1cccc(C(F)F)n1)C2] | 2'-chloro-6-cyclopropyl-N-(5-(6-(difluoromethyl) picolinoyl)-5,6-dihydro-4H-pyrrolo[3,4-d]thiazol-2-yl)-5'-methoxy-[4,4'-bipyridine]-3-carboxamide | 583 | $^1$H NMR (400 MHz, DMSO-$d_6$) δ 12.70 (d, J = 19.3 Hz, 1H), 8.72 (d, J = 3.2 Hz, 1H), 8.24-8.10 (m, 2H), 8.01 (dd, J = 11.4, 7.8 Hz, 1H), 7.8 7(d, J = 7.8 Hz, 1H), 7.58 (d, J = 1.0 Hz, 1H), 7.46 (s, 1H), 7.08 (dd, J = 54.8, 13.5 Hz, 1H), 5.03 (d, J = 3.2 Hz, 1H), 4.94 (s, 1H), 4.87 (s, 1H), 4.73 (d, J = 3.1 Hz, 1H), 3.60 (s, 3H), 2.26 (p, J = 7.4 Hz, 1H), 1.27-0.87 (m, 4H) |
| 665 | 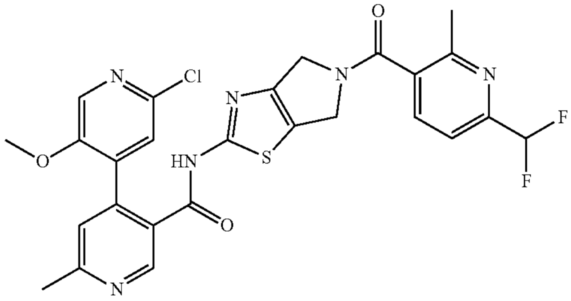 [SMILES: COc1cnc(Cl)cc1-c1cc(C)ncc1C(=O)Nc1nc2c(s1)CN(C(=O)c1ccc(C(F)F)nc1C)C2] | 2'-chloro-N-(5-(6-(difluoromethyl)-2-methyl-nicotinoyl)-5,6-dihydro-4H-pyrrolo[3,4-d]thiazol-2-yl)-5'-methoxy-6-methyl-[4,4'-bipyridine]-3-carboxamide | 571 | $^1$H NMR (400 MHz, DMSO-$d_6$) δ 12.74 (s, 1H), 8.82 (d, J = 6.7 Hz, 1H), 8.16 (d, J = 2.0 Hz, 1H), 8.05 (d, J = 7.8 Hz, 1H), 7.62 (d, J = 7.9 Hz, 1H), 7.50 (d, J = 2.2 Hz, 1H), 7.39 (s, 1H), 7.10-6.82 (m, 1H), 4.83-4.70 (m, 2H), 4.48-4.37 (m, 2H), 3.61 (d, J = 1.2 Hz, 3H), 2.58 (d, J = 2.6 Hz, 3H), 2.53 (s, 3H) |

TABLE C-continued

The following examples were prepared using a similar procedure to that described for Example 1

| Ex. No. | Structure | Compound Name | LCMS [M + H]+ | NMR |
|---|---|---|---|---|
| 666 | 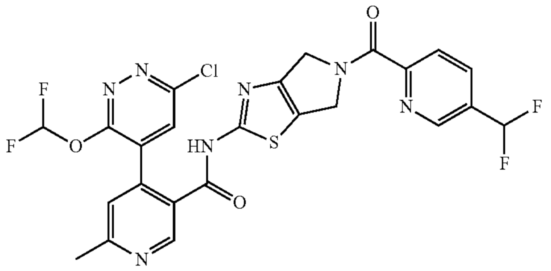 [SMILES: Cc1cc(-c2cc(Cl)nnc2OC(F)F)c(C(=O)Nc2nc3c(s2)CN(C(=O)c2ccc(C(F)F)cn2)C3)cn1] | 4-(6-chloro-3-(difluoro-methoxy) pyridazin-4-yl)-N-(5-(5-(difluoromethyl) picolinoyl)-5,6-dihydro-4H-pyrrolo[3,4-d]thiazol-2-yl)-6-methyl-nicotinamide | 594 | $^1$H NMR (300 MHz, DMSO-$d_6$) δ 13.03 (d, J = 3.6 Hz, 1H), 9.03-8.72 (m, 2H), 8.33-8.13 (m, 1H), 8.09-7.93 (m, 2H), 7.87-7.67 (m, 1H), 7.49 (s, 1H), 7.25 (t, J = 55.1 Hz, 1H), 5.03 (s, 1H), 4.93 (s, 1H), 4.88 (s, 1H), 4.74 (s, 1H), 2.61 (s, 3H) |
| 667 | 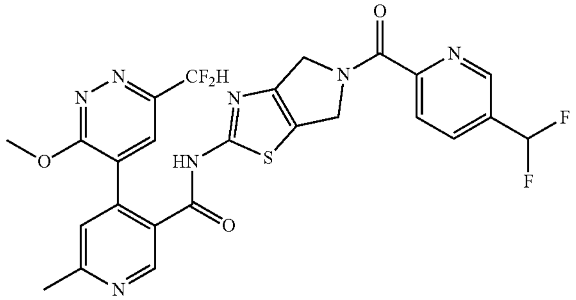 [SMILES: COc1nnc(C(F)F)cc1-c1cc(C)ncc1C(=O)Nc1nc2c(s1)CN(C(=O)c1ccc(C(F)F)cn1)C2] | 4-(6-(difluoromethyl)-3-methoxy-pyridazin-4-yl)-N-(5-(5-(difluoromethyl) picolinoyl)-5,6-dihydro-4H-pyrrolo[3,4-d]thiazol-2-yl)-6-methyl-nicotinamide | 574 | $^1$H NMR (400 MHz, DMSO-$d_6$) δ 12.99 (s, 1H), 8.88 (d, J = 13.4 Hz, 2H), 8.20 (d, J = 8.2 Hz, 1H), 8.07 (s, 1H), 8.02-7.96 (m, 1H), 7.55 (s, 1H), 7.41-7.11 (m, 2H), 5.02 (s, 1H), 4.93 (s, 1H), 4.87 (s, 1H), 4.75 (s, 1H), 3.83 (s, 3H), 2.61 (d, J = 1.7 Hz, 3H) |
| 668 | 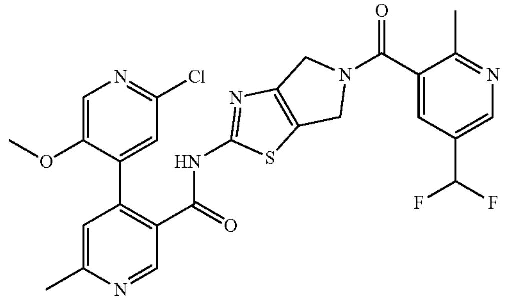 [SMILES: COc1cnc(Cl)cc1-c1cc(C)ncc1C(=O)Nc1nc2c(s1)CN(C(=O)c1cc(C(F)F)cnc1C)C2] | 2'-chloro-N-(5-(5-(difluoro-methyl)-2-methyl-nicotinoyl)-5,6-dihydro-4H-pyrrolo[3,4-d]thiazol-2-yl)-5'-methoxy-6-methyl-[4,4'-bipyridine]-3-carboxamide | 571 | $^1$H NMR (400 MHz, DMSO-$d_6$) δ 12.80 (d, J = 5.1 Hz, 1H), 8.81-8.72 (m, 2H), 8.16 (d, J = 2.3 Hz, 1H), 8.08 (s, 1H), 7.54 (s, 1H), 7.43 (d, J = 2.6 Hz, 1H), 7.14 (s, 1H), 4.84 (s, 1H), 4.70 (s, 1H), 4.47 (s, 1H), 4.38 (s, 1H), 3.59 (s, 3H), 2.65 (s, 3H), 2.50 (s, 3H) |
| 669 | 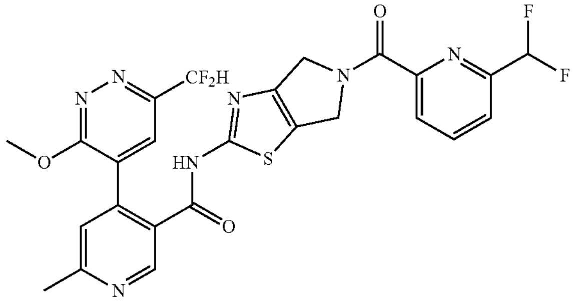 [SMILES: COc1nnc(C(F)F)cc1-c1cc(C)ncc1C(=O)Nc1nc2c(s1)CN(C(=O)c1cccc(C(F)F)n1)C2] | 4-(6-(difluoromethyl)-3-methoxy-pyridazin-4-yl)-N-(5-(6-(difluoromethyl) picolinoyl)-5,6-dihydro-4H-pyrrolo[3,4-d]thiazol-2-yl)-6-methyl-nicotinamide | 574 | $^1$H NMR (400 MHz, DMSO-$d_6$) δ 12.97 (s, 1H), 8.90 (d, J = 3.8 Hz, 1H), 8.20 (t, J = 7.8 Hz, 1H), 8.09-7.98 (m, 2H), 7.91-7.85 (m, 1H), 7.55 (s, 1H), 7.41-6.92 (m, 2H), 5.07-4.71 (m, 4H), 3.83 (d, J = 2.0 Hz, 3H), 2.61 (s, 3H) |
| 670 | 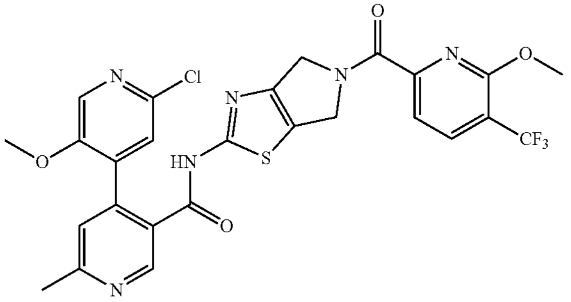 | 2'-choro-5'-methoxy-N-(5-(6-methoxy-5-(trifluoromethyl) picolinoyl)-5,6-dihydro-4H-pyrrolo[3,4-d]thiazol-2-yl)-6-methyl-[4,4'-bipyridine]-3-carboxmaide | 605 | $^1$H NMR (300 MHz, DMSO-d6) δ 12.79 (d, 1H), 8.79 (d, 1H), 8.29 (d, 1H), 8.17 (d, 1H), 7.68-7.60 (m, 1H), 7.56 (d, 1H), 7.45 (s, 1H), 5.19-5.00 (m, 2H), 4.80 (m, 2H), 4.08 (s, 3H), 3.60 (d, 3H), 2.59 (s, 3H) |

TABLE C-continued

| The following examples were prepared using a similar procedure to that described for Example 1 | | | | |
|---|---|---|---|---|
| Ex. No. | Structure | Compound Name | LCMS [M + H]+ | NMR |
| 671 | 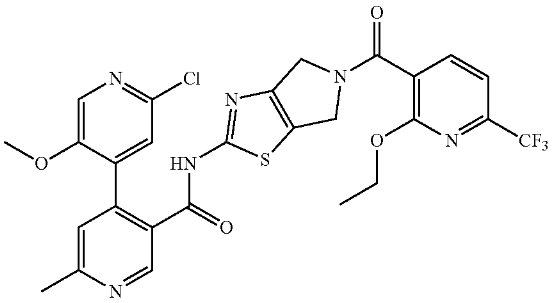 [SMILES: CCOc1nc(C(F)(F)F)ccc1C(=O)N1Cc2nc(NC(=O)c3cnc(C)cc3-c3cc(Cl)ncc3OC)sc2C1] | 2'-chloro-N-(5-(2-ethoxy-6-(trifluoromethyl)nicotinoyl)-5,6-dihydro-4H-pyrrolo[3,4-d]thiazol-2-yl)-5'-methoxy-6-methyl-[4,4'-bipyridine]-3-carboxamide | 619 | $^1$H NMR (400 MHz, DMSO-$d_6$): δ 12.82 (s ,1H), 8.78 (d, J = 3.0 Hz, 1H), 8.17 (d, J = 1.8 Hz, 1H), 8.07 (dd, J = 7.5, 2.1 Hz, 1H), 7.59 (dd, J = 7.6, 3.5 Hz, 1H), 7.55 (s, 1H), 7.44 (d, J = 2.4 Hz, 1H), 4.81 (t, J = 2.8 Hz, 1H), 4.67 (d, J = 2.7 Hz, 1H), 4.52 (t, J = 2.6 Hz, 1H), 4.49-4.39 (m, 3H), 3.60 (s, 3H), 2.59 (d, J = 2.6 Hz, 3H), 1.35-1.29 (m, 3H) |
| 672 | 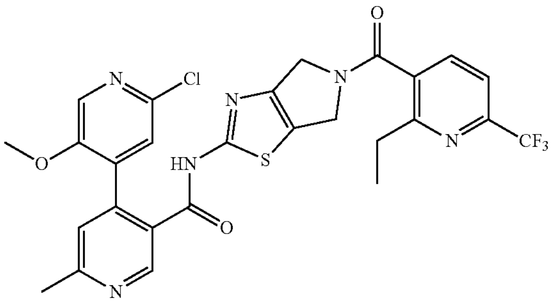 [SMILES: CCc1nc(C(F)(F)F)ccc1C(=O)N1Cc2nc(NC(=O)c3cnc(C)cc3-c3cc(Cl)ncc3OC)sc2C1] | 2'-chloro-N-(5-(2-ethyl-6-(trifluoromethyl)nicotinoyl)-5,6-dihydro-4H-pyrrolo[3,4-d]thiazol-2-yl)-5'-methoxy-6-methyl-[4,4'-b]pyridine]-3-carboxamide | 603 | $^1$H NMR (400 MHz, DMSO-$d_6$) δ 12.64 (s, 1H), 8.78 (d, J = 5.0 Hz, 1H), 8.20-8.10 (m, 2H), 7.85 (dd, J = 7.9, 4.3 Hz, 1H), 7.54 (d, J = 0.9 Hz, 1H), 7.43 (d, J = 2.9 Hz, 1H), 4.86 (t, J = 2.7 Hz, 1H), 4.72 (t, J = 2.8 Hz, 1H), 4.47 (t, J = 2.6 Hz, 1H), 4.39 (t, J = 2.7 Hz, 1H), 3.60 (d, J = 1.0 Hz, 3H), 2.85 (q, J = 7.5 Hz, 2H), 2.59 (d, J = 3.1 Hz, 3H), 1.24 (t, J = 7.5 Hz, 3H) |
| 673 | 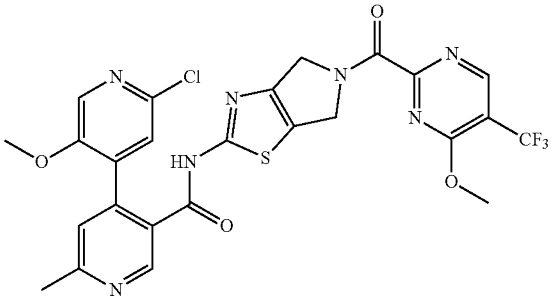 [SMILES: COc1cnc(Cl)cc1-c1cc(C)ncc1C(=O)Nc1nc2c(s1)CN(C(=O)c1ncc(C(F)(F)F)c(OC)n1)C2] | 2'-chloro-5'-methoxy-N-(5-(4-methoxy-5-(trifluoromethyl)pyrimidine-2-carbonyl)-5,6-dihydro-4H-pyrrolo[3,4-d]thiazol-2-yl)-6-methyl-[4,4'-bipyridine]-3-carboxamide | 606 | $^1$H NMR (400 MHz, DMSO-d6) δ 12.85 (s, 1H), 9.22 (d, J = 5.1 Hz, 1H), 8.79 (d, J = 5.1 Hz, 1H), 8.17 (d, J = 3.4 Hz, 1H), 7.54 (d, J = 1.7 Hz, 1H), 7.43 (d, J = 1.8 Hz, 1H), 4.84 (d, J = 2.6 Hz, 1H), 4.70-40.65 (m, 2H), 4.53 (t, J = 2.6 Hz, 1H), 4.06 (d, J = 1.8 Hz, 3H), 3.60 (d, J = 1.7 Hz, 3H), 2.59 (d, J = 2.2 Hz, 3H) |
| 674 | 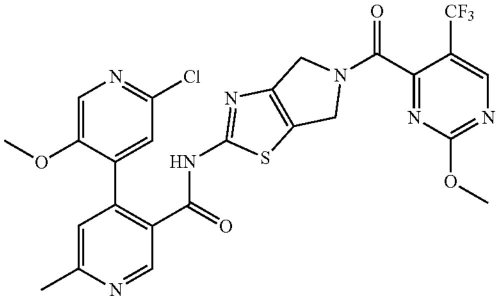 | 2'-chloro-5'-methoxy-N-(5-(2-methoxy-5-(trifluoromethyl)pyrimidine-4-carbonyl)-5,6-dihydro-4H-pyrrolo[3,4-d]thiazol-2-yl)-6-methyl-[4,4'-bipyridine]-3-carboxamide | 606 | $^1$H NMR (400 MHz, DMSO-d6) δ 9.05 (s, 1H), 8.87 (d, J = 6.8 Hz, 1H), 8.14 (d, J = 1.7 Hz, 1H), 7.44 (s, 1H), 7.31 (s, 1H), 4.71 (dd, J = 52.1, 21.3 Hz, 4H), 4.12 (s, 3H), 3.61 (s, 3H), 2.56 (s, 3H) |

TABLE C-continued

The following examples were prepared using a similar procedure to that described for Example 1

| Ex. No. | Structure | Compound Name | LCMS [M + H]+ | NMR |
|---|---|---|---|---|
| 675 | 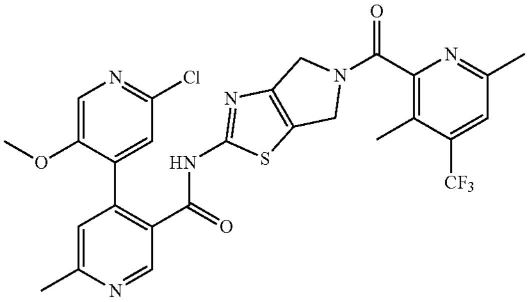 | 2'-chloro-N-(5-(3,6-dimethyl-4-(trifluoromethyl) picolinoyl)-5,6-dihydro-4H-pyrrolo[3,4-d]thiazol-2-yl)-5'-methoxy-6-methyl-[4,4'-bipyridine]-3-carboxamide | 603 | $^1$H NMR (400 MHz, DMSO-$d_6$) δ 12.74 (s, 1H), 8.79 (d, J = 6.5 Hz, 1H), 8.16 (d, J = 2.9 Hz, 1H), 7.71 (s, 1H), 7.54 (s, 1H), 7.42 (d, J = 1.8 Hz, 1H), 4.78 (d, J = 53.8, 2.8 Hz, 2H), 4.45 (d, J = 40.7, 2.8 Hz, 2H), 3.59 (s, 3H), 2.58 (t, J = 2.4 Hz, 6H), 2.37 (s, 3H) |
| 676 | 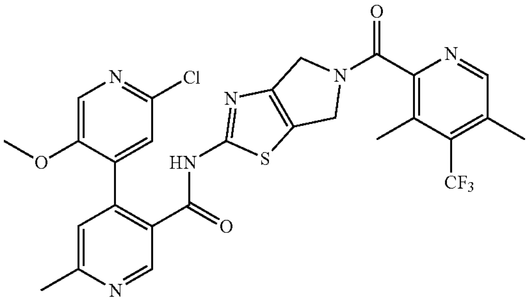 | 2'-chloro-N-(5-(3,5-dimethyl-4-(trifluoromethyl) picolinoyl)-5,6-dihydro-4H-pyrrolo[3,4-d]thiazol-2-yl)-5'-methoxy-6-methyl-[4,4'-bipyridine]-3-carboxamide | 603 | $^1$H NMR (300 MHz, DMSO-d6) δ 12.84 (s, 1H), 8.79 (d, J = 3.9 Hz, 1H), 8.59 (d, J = 2.9 Hz, 1H), 8.17 (d, J = 2.1 Hz, 1H), 7.55 (s, 1H), 7.45 (d, J = 2.1 Hz, 1H), 4.91-4.68 (m, 2H), 4.44 (dt, J = 28.1, 2.6 Hz, 2H), 3.60 (s, 3H), 2.59 (d, J = 2.2 Hz, 3H), 2.48 (s, 3H), 2.41 (q, J = 3.0 Hz, 3H) |
| 677 | 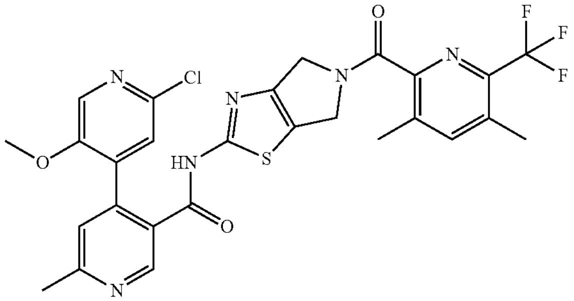 [SMILES: COc1cnc(Cl)cc1-c1cc(C)ncc1C(=O)Nc1nc2c(s1)CN(C(=O)c1nc(C(F)(F)F)c(C)cc1C)C2] | 2'-chloro-N-(5-(3,5-dimethyl-6-(trifluoromethyl) picolinoyl)-5,6-dihydro-4H-pyrrolo[3,4-d]thiazol-2-yl)-5'-methoxy-6-methyl-[4,4'-bipyridine]-3-carboxamide | 603 | $^1$H NMR (300 MHz, DMSO-d6) δ 12.81 (s, 1H), 8.79 (d, J = 4.3 Hz, 1H), 8.17 (d, J = 3.5 Hz, 1H), 7.95 (s, 1H), 7.55 (d, J = 0.9 Hz, 1H), 7.44 (s, 1H), 4.90-4.68 (m, 2H), 4.52 (d, J = 24.1 Hz, 2H), 3.60 (s, 3H), 2.59 (d, J = 1.6 Hz, 3H), 2.48 (d, J = 2.2 Hz, 3H), 2.40 (d, J = 2.0 Hz, 3H) |
| 678 | 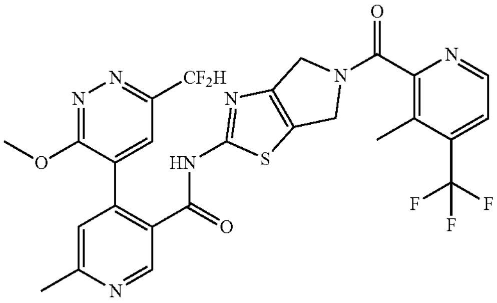 [SMILES: COc1nnc(C(F)F)cc1-c1cc(C)ncc1C(=O)Nc1nc2c(s1)CN(C(=O)c1nccc(C(F)(F)F)c1C)C2] | 4-(6-(di-fluoromethyl)-3-methoxy-pyridazin-4-yl)-6-methyl-N-(5-(3-methyl-4-(trifluoromethyl) picolinoyl)-5,6-dihdyro-4H-pyrrolo[3,4-d]thiazol-2-yl)nicotinamide | 606 | $^1$H NMR (400 MHz, DMSO-$d_6$) δ 8.97 (d, J = 7.3 Hz, 1H), 8.73 (d, J = 5.1 Hz, 1H), 8.34 (s, 1H), 7.95 (d, J = 8.9 Hz, 1H), 7.81 (t, J = 4.5 Hz, 1H), 7.46-7.34 (m, 1H), 7.23 (d, J = 4.4 Hz, 1H), 4.82 (s, 1H), 4.69 (s, 1H), 4.46 (s, 1H), 4.36 (s, 1H), 3.82 (s, 3H), 2.58 (s, 3H), 2.43 (s, 3H) |

TABLE C-continued

The following examples were prepared using a similar procedure to that described for Example 1

| Ex. No. | Structure | Compound Name | LCMS [M + H]+ | NMR |
|---|---|---|---|---|
| 679 | 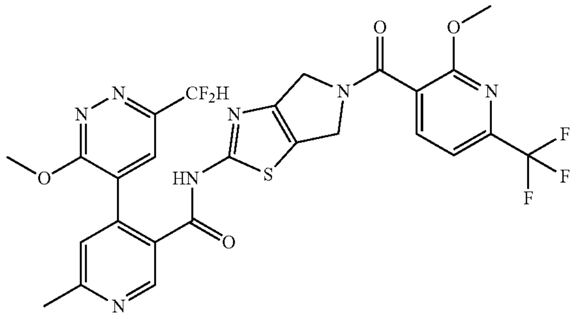 [SMILES: COc1nc(C(F)(F)F)ccc1C(=O)N1Cc2nc(NC(=O)c3cnc(C)cc3-c3cc(C(F)F)nnc3OC)sc2C1] | 4-(6-(di-fluoromethyl)-3-methoxy-pyridazin-4-yl)-N-(5-(2-methoxy-6-(trifluoro-methyl) nicotinoyl)-5,6-dihydro-4H-pyrrolo[3,4-d]thiazol-2-yl)-6-methyl-nicotinamide | 622 | $^1$H NMR (400 MHz, DMSO-$d_6$): δ 13.00 (s, 1H), 8.88 (d, J = 4.6 Hz, 1H), 8.09 (d, J = 8.8 Hz, 2H), 7.62 (dd, J = 7.4, 2.4 Hz, 1H), 7.55 (d, J = 2.2 Hz, 1H), 7.26 (m, 1H), 4.74 (d, J = 48.5 Hz, 2H), 4.47 (d, J = 34.2 Hz, 2H), 3.97 (d, J = 1.7 Hz, 3H), 3.82 (d, J = 1.8 Hz, 3H), 2.61 (d, J = 2.6 Hz, 3H) |
| 680 | 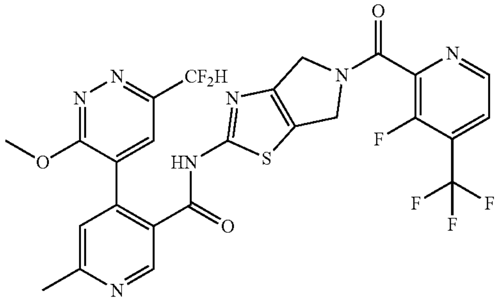 [SMILES: COc1nnc(C(F)F)cc1-c1cc(C)ncc1C(=O)Nc1nc2c(s1)CN(C(=O)c1nccc(C(F)(F)F)c1F)C2] | 4-(6-(difluoro-methyl)-3-methoxy-pyridazin-4-yl)-N-(5-(3-fluoro-4-(trifluoromethyl) picolinoyl)-5,6-dihydro-4H-pyrrolo[3,4-d]thiazol-2-yl)-6-methyl-nicotinamide | 610 | $^1$H NMR (400 MHz, DMSO-$d_6$) δ 13.00 (s, 1H), 8.93 (d, J = 6.3 Hz, 1H), 8.77 (s, 1H), 8.09-7.93 (m, 2H), 7.50 (s, 1H), 7.40-7.08 (m, 1H), 4.86 (s, 1H), 4.73 (s, 2H), 4.64 (s, 1H), 3.82 (s, 3H), 2.60 (d, J = 2.3 Hz, 3H) |
| 681 | 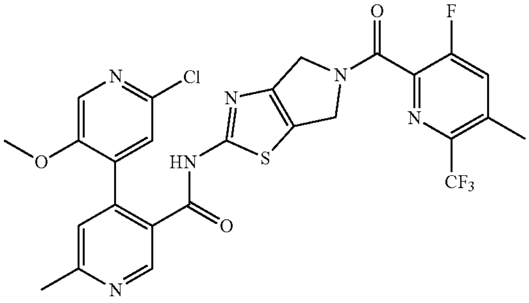 | 2'-Chloro-N-(5-(3-fluoro-5-methyl-6-(trifluoromethyl) picolinoyl)-5,6-dihydro-4H-pyrrolo[3,4-d]thiazol-2-yl)-5'-methoxy-6-methyl-[4,4'-bipyridine]-3-carboxamide | 607 | $^1$H NMR (400 MHz, DMSO-$d_6$) 12.8 (br s, 1H), 8.79 (d, J = 4.8 Hz, 1H), 8.19-8.12 (m, 2H), 7.53 (s, 1H), 7.42 (s, 1H), 4.85 (s, 1H), 4.72 (s, 2H), 4.64 (s, 1H), 3.60 (s, 3H), 2.58 (s, 3H), 2.55 (s, 3H). |
| 682 | 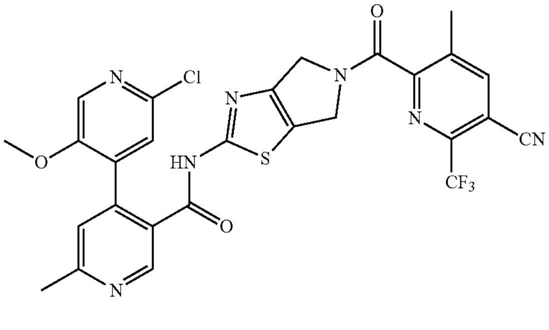 [SMILES: COc1cnc(Cl)cc1-c1cc(C)ncc1C(=O)Nc1nc2c(s1)CN(C(=O)c1nc(C(F)(F)F)c(C#N)cc1C)C2] | 2'-Chloro-N-(5-(5-cyano-3-methyl-6-(trifluoromethyl) picolinoyl)-5,6-dihydro-4H-pyrrolo[3,4-d]thiazol-2-yl)-5'-methoxy-6-methyl-[4,4'-bipyridine]-3-carboxamide | 614 | $^1$H NMR (400 MHz, DMSO-$d_6$) δ 12.8 (s, 1H), 8.80-8.73 (m, 2H), 8.16 (d, J = 3.8 Hz, 1H), 7.54 (s, 1H), 7.43 (s, 1H), 4.87 (s, 1H), 4.74 (s, 1H), 4.56 (s, 1H), 4.46 (s, 1H), 3.59 (s, 3H), 2.58 (s, 3H), 2.47 (s, 3H). |

TABLE C-continued

The following examples were prepared using a similar procedure to that described for Example 1

| Ex. No. | Structure | Compound Name | LCMS [M + H]+ | NMR |
|---|---|---|---|---|
| 683 | 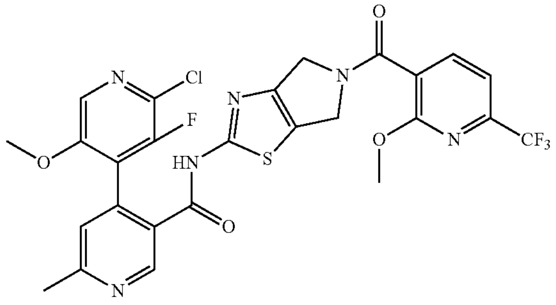 [SMILES: COc1cnc(Cl)c(F)c1-c1cc(C)ncc1C(=O)Nc1nc2c(s1)CN(C(=O)c1ccc(C(F)(F)F)nc1OC)C2] | 2'-Chloro-3'-fluoro-5'-methoxy-N-(5-(2-methoxy-6-(trifluoromethyl) nicotinoyl)-5,6-dihydro-4H-pyrrolo[3,4-d]thiazol-2-yl)-6-methyl-[4,4'-bipyridine]-3-carboxamide | 623 | $^1$H NMR (400 MHz, DMSO-$d_6$) δ 13.0 (s, 1H), 8.93 (d, J = 4.2 Hz, 1H), 8.18 (d, J = 3.0 Hz, 1H), 8.10-8.06 (m, 1H), 7.65-7.59 (m, 1H), 7.49 (s, 1H), 4.82-4.77 (m, 1H), 4.69-4.65 (m, 1H), 4.53-4.49 (m, 1H), 4.45-4.40 (m, 1H), 3.97 (s, 3H), 3.71 (s, 3H), 2.59 (d, J = 2.8 Hz, 3H) |
| 684 | 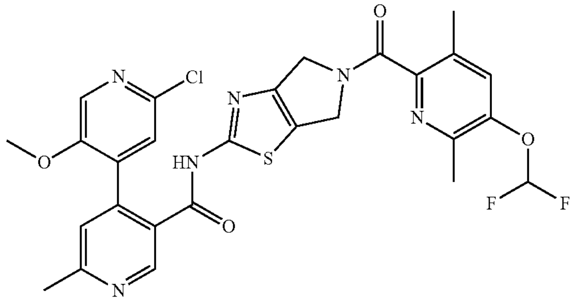 [SMILES: COc1cnc(Cl)cc1-c1cc(C)ncc1C(=O)Nc1nc2c(s1)CN(C(=O)c1nc(C)c(OC(F)F)cc1C)C2] | 2'-Chloro-N-(5-(5-(difluoro-methoxy)-3,6-dimethyl picolinoyl)-5,6-dihydro-4H-pyrrolo[3,4-d]thiazol-2-yl)-5'-methoxy-6-methyl-[4,4'-bipyridine]-3-carboxamide | 601 | $^1$H NMR (400 MHz, DMSO-$d_6$) δ 12.8 (s, 1H), 8.78 (d, J = 5.2 Hz, 1H), 8.16 (d, J = 2.6 Hz, 1H), 7.59 (d, J = 4.0 Hz, 1H), 7.54 (s, 1H), 7.43 (s, 1H), 7.31 (t, J = 51.2 Hz, 1H), 4.82 (s, 1H), 4.69 (s, 1H), 4.55 (s, 1H), 4.44 (s, 1H), 3.59 (s, 3H), 2.59 (d, J = 2.2 Hz, 3H), 2.43 (d, J = 2.2 Hz, 3H), 2.31 (s, 3H). |
| 685 | 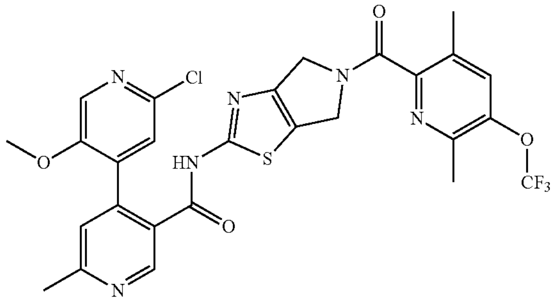 [SMILES: COc1cnc(Cl)cc1-c1cc(C)ncc1C(=O)Nc1nc2c(s1)CN(C(=O)c1nc(C)c(OC(F)(F)F)cc1C)C2] | 2'-Chloro-N-(5-(3,6-dimethyl-5-(trifluoro-methoxy) picolinoyl)-5,6-dihydro-4H-pyrrolo[3,4-d]thiazol-2-yl)-5'-methoxy-6-methyl-[4,4'-bipyridine]-3-carboxamide | 619 | $^1$H NMR (400 MHz, Chloroform-d) δ 8.99 (d, J = 10.8 Hz, 1H), 8.05 (s, 1H), 7.43 (s, 1H), 7.29 (s, 1H), 7.27 (s, 1H), 4.95 (s, 1H), 4.69 (s, 1H), 4.55 (s, 1H), 4.40 (s, 1H), 3.72 (d, J = 2.8 Hz, 3H), 2.78 (d, J = 6.6 Hz, 3H), 2.55-2.45 (m, 3H), 2.41 (s, 3H). |
| 686 | 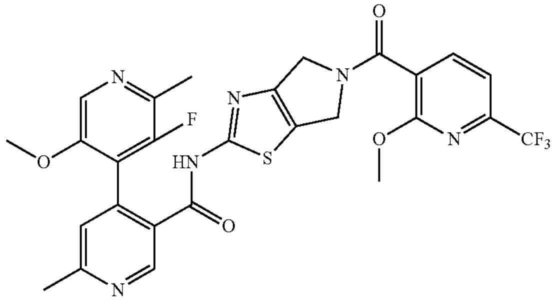 [SMILES: COc1cnc(C)c(F)c1-c1cc(C)ncc1C(=O)Nc1nc2c(s1)CN(C(=O)c1ccc(C(F)(F)F)nc1OC)C2] | 3'-Fluoro-5'-methoxy-N-(5-(2-methoxy-6-(trifluoromethyl) nicotinoyl)-5,6-dihydro-4H-pyrrolo[3,4-d]thiazol-2-yl)-2',6-dimethyl-[4,4'-bipyridine]-3-carboxamide | 603 | $^1$H NMR (400 MHz, DMSO-$d_6$) δ 12.9 (d, J = 6.4 Hz, 1H), 8.87 (d, J = 4.4 Hz, 1H), 8.16 (d, J = 3.8 Hz, 1H), 8.08 (d, J = 7.6, 1.6 Hz, 1H), 7.61 (dd, J = 7.4, 2.2 Hz, 1H), 7.43-7.38 (m, 1H), 4.82-4.77 (m, 1H), 4.69-4.64 (m, 1H), 4.53-4.48 (m, 1H), 4.45-4.39 (m, 1H), 3.97 (d, J = 1.6 Hz, 3H), 3.65 (s, 3H), 2.58 (d, J = 2.8 Hz, 3H), 2.44-2.39 (m, 3H). |

TABLE C-continued

The following examples were prepared using a similar procedure to that described for Example 1

| Ex. No. | Structure | Compound Name | LCMS [M + H]$^+$ | NMR |
|---|---|---|---|---|
| 687 | 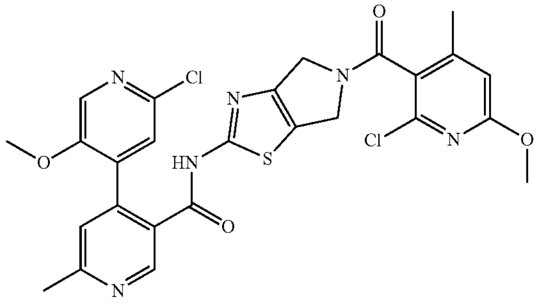 | 2'-Chloro-N-(5-(2-chloro-6-methoxy-4-methyl-nicotinoyl)-5,6-dihydro-4H-pyrrolo[3,4-d]thiazol-2-yl)-5'-methoxy-6-methyl-[4,4'-bipyridine]-3-carboxamide | 585 | $^1$H NMR (400 MHz, DMSO-$d_6$) δ 12.8 (s, 1H), 8.77 (d, J = 3.8 Hz, 1H), 8.16 (d, J = 2.6 Hz, 1H), 7.53 (s, 1H), 7.42 (s, 1H) 6.86 (d, J = 3.4 Hz, 1H), 4.81 (s, 1H), 4.67 (s, 1H), 4.52-4.37 (m, 1H), 4.34 (s, 1H), 3.87 (s, 3H), 3.60 (s, 3H), 2.58 (s, 3H), 2.26 (s, 3H). |
| 688 | 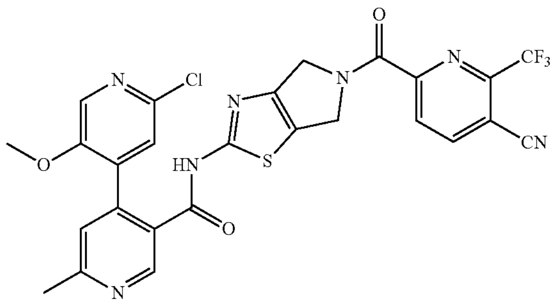 [SMILES: COc1cnc(Cl)cc1-c1cc(C)ncc1C(=O)Nc1nc2c(s1)CN(C(=O)c1ccc(C#N)c(C(F)(F)F)n1)C2] | 2'-Chloro-N-(5-(5-cyano-6-(trifluoromethyl)picolinoyl)-5,6-dihydro-4H-pyrrolo[3,4-d]thiazol-2-yl)-5'-methoxy-6-methyl-[4,4'-bipyridine]-3-carboxamide | 600 | $^1$H NMR (400 MHz, DMSO-$d_6$) δ 12.8 (d, J = 10.8 Hz, 1H), 9.39 (dd, J = 5.2, 1.6 Hz, 1H), 9.13-9.02 (m, 1H), 8.78 (d, J = 5.8 Hz, 1H), 8.16 (d, J = 3.8 Hz, 1H), 7.54 (s, 1H), 7.43 (d, J = 2.4 Hz, 1H), 4.85 (s, 1H), 4.72 (s, 1H), 4.54 (s, 1H), 4.42 (s, 1H), 3.60 (s, 3H), 2.58 (d, J = 2.8 Hz, 3H). |
| 689 | 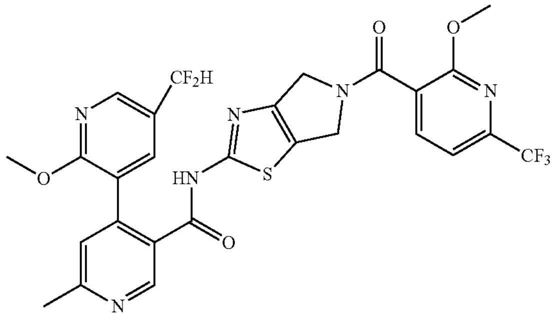 [SMILES: COc1nc(C(F)(F)F)ccc1C(=O)N1Cc2nc(NC(=O)c3cnc(C)cc3-c3cc(C(F)F)cnc3OC)sc2C1] | 5-(Difluoro-methyl)-2-methoxy-N-(5-(2-methoxy-6-(trifluoromethyl)nicotinoyl)-5,6-dihydro-4H-pyrrolo[3,4-d]thiazol-2-yl)-6'-methyl-[3,4'-bipyridine]-3'-carboxamide | 621 | $^1$H NMR (400 MHz, DMSO-$d_6$) δ 12.8 (d, J = 3.8 Hz, 1H), 8.75 (d, J = 4.4 Hz, 1H), 8.43 (s, 1H), 8.11-8.06 (m, 1H), 8.01 (s, 1H), 7.61 (dd, J = 7.4, 3.5 Hz, 1H), 7.44 (d, J = 2.8 Hz, 1H), 7.14 (td, J = 55.3, 3.9 Hz, 1H), 4.83-4.78 (m, 1H), 4.70-4.65 (m, 1H), 4.53-4.49 (m, 1H), 4.44-4.39 (m, 1H), 3.98 (s, 3H), 3.62 (s, 3H), 2.59 (d, J = 2.6 Hz, 3H). |
| 690 | 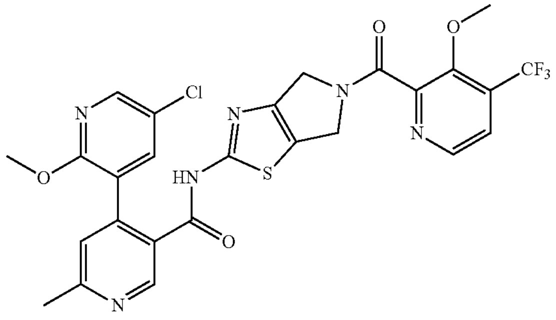 [SMILES: COc1ncc(Cl)cc1-c1cc(C)ncc1C(=O)Nc1nc2c(s1)CN(C(=O)c1nccc(C(F)(F)F)c1OC)C2] | 5-Chloro-2-methoxy-N-(5-(3-methoxy-4-(trifluoromethyl)picolinoyl)-5,6-dihydro-4H-pyrrolo[3,4-d]thiazol-2-yl)-6'-methyl-[3,4'-bipyridine]-3'-carboxamide | 605 | $^1$H NMR (400 MHz, DMSO-$d_6$) δ 12.8 (s, 1H), 8.75 (d, J = 4.2 Hz, 1H), 8.59 (t, J = 3.8 Hz, 1H), 8.25 (t, J = 2.8 Hz, 1H), 7.96 (d, J = 2.6 Hz, 1H), 7.85 (d, J = 4.8 Hz, 1H), 7.45 (d, J = 2.4 Hz, 1H), 4.87 (s, 1H), 4.74 (s, 1H), 4.65 (s, 1H), 4.57 (s, 1H), 3.93 (s, 3H), 3.57 (s, 3H), 2.58 (d, J = 2.6 Hz, 3H). |

TABLE C-continued

The following examples were prepared using a similar procedure to that described for Example 1

| Ex. No. | Structure | Compound Name | LCMS [M + H]+ | NMR |
|---|---|---|---|---|
| 691 | 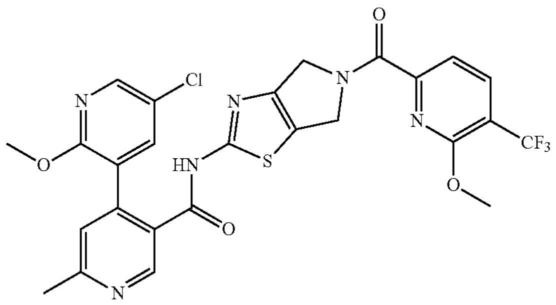 [SMILES: COc1ncc(Cl)cc1-c1cc(C)ncc1C(=O)Nc1nc2c(s1)CN(C(=O)c1ccc(C(F)(F)F)c(OC)n1)C2] | 5-Chloro-2-methoxy-N-(5-(6-methoxy-5-(trifluoromethyl) picolinoyl)-5,6-dihydro-4H-pyrrolo[3,4-d]thiazol-2-yl)-6'-methyl-[3,4'-bipyridine]-3'-carboxamide | 605 | $^1$H NMR (400 MHz, DMSO-$d_6$) δ 12.7 (d, J = 12.4 Hz, 1H), 8.75 (d, J = 4.0 Hz, 1H), 8.31-8.23 (m, 2H), 7.99-7.95 (m, 1H), 7.63 (t, J = 8.0 Hz, 1H), 7.45 (s, 1H), 5.13 (s, 1H), 5.04 (s, 1H), 4.87 (s, 1H), 4.73 (s, 1H), 4.08 (s, 3H), 3.58 (s, 3H), 2.58 (s, 3H). |
| 692 | 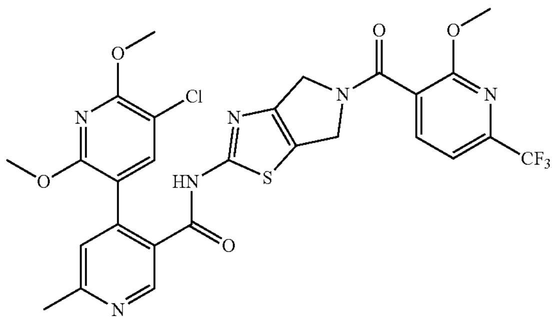 [SMILES: COc1nc(OC)c(-c2cc(C)ncc2C(=O)Nc2nc3c(s2)CN(C(=O)c2ccc(C(F)(F)F)nc2OC)C3)cc1Cl] | 5-Chloro-2,6-dimethoxy-N-(5-(2-methoxy-6-(trifluoromethyl) nicotinoyl)-5,6-dihydro-4H-pyrrolo[3,4-d]thiazol-2-yl)-6'-methyl-[3,4'-bipyridine]-3'-carboxamide | 635 | $^1$H NMR (400 MHz, DMSO-$d_6$) δ 12.7 (d, J = 2.6 Hz, 1H), 8.67 (d, J = 2.6 Hz, 1H), 8.09 (dd, J = 7.4, 3.2 Hz, 1H), 7.94 (s, 1H), 7.62 (dd, J = 7.6, 4.2 Hz, 1H), 7.39 (d, J = 3.2 Hz, 1H), 4.81 (s, 1H), 4.66 (s, 1H), 4.52 (s, 1H), 4.42 (s, 1H), 4.00-3.94 (m, 6H), 3.61 (d, J = 1.4 Hz, 3H), 2.56 (d, J = 2.6 Hz, 3H). |
| 693 | 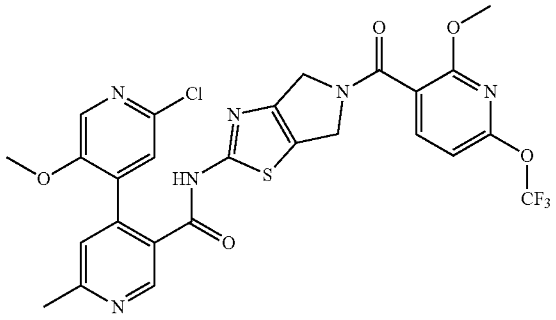 [SMILES: COc1cnc(Cl)cc1-c1cc(C)ncc1C(=O)Nc1nc2c(s1)CN(C(=O)c1ccc(OC(F)(F)F)nc1OC)C2] | 2'-Chloro-5'-methoxy-N-(5-(2-methoxy-6-(trifluoro-methoxy) nicotinoyl)-5,6-dihydro-4H-pyrrolo[3,4-d]thiazol-2-yl)-6-methyl-[4,4'-bipyridine]-3-carboxamide | 621 | H NMR (400 MHz, DMSO-$d_6$) δ 12.8 (d, J = 3.0 Hz, 1H), 8.78 (d, J = 3.4 Hz, 1H), 8.16 (s, 1H), 8.03 (dd, J = 7.8, 1.4 Hz, 1H), 7.54 (s, 1H), 7.43 (s, 1H), 6.96 (dd, J = 7.8, 4.0 Hz, 1H), 4.78 (s, 1H), 4.64 (s, 1H), 4.53 (s, 1H), 4.43 (s, 1H), 3.92 (s, 3H), 3.60 (s, 3H), 2.59 (d, J = 2.2 Hz, 3H). |
| 694 | 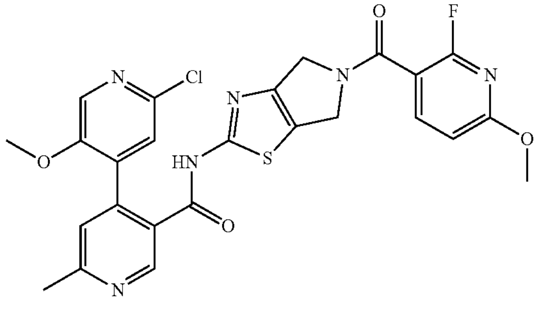 | 2'-Chloro-N-(5-(2-fluoro-6-methoxy-nicotinoyl)-5,6-dihydro-4H-pyrrolo[3,4-d]thiazol-2-yl)-5'-methoxy-6-methyl-[4,4'-bipyridine]-3-carboxamide | 555 | $^1$H NMR (400 MHz, DMSO-$d_6$) δ 12.8 (s, 1H), 8.81 (d, J = 3.8 Hz, 1H), 8.19 (d, J = 3.0 Hz, 1H), 8.11-8.02 (m, 1H), 7.56 (s, 1H), 7.44 (s, 1H), 6.91 (d, J = 8.2 Hz, 1H), 4.82 (s, 1H), 4.68 (s, 1H), 4.64 (s 1H), 4.54 (s, 1H), 3.92 (d, J = 2.4 Hz, 3H), 3.61 (s, 3H), 2.61 (d, J = 2.2 Hz, 3H). |

TABLE C-continued

| The following examples were prepared using a similar procedure to that described for Example 1 | | | | |
|---|---|---|---|---|
| Ex. No. | Structure | Compound Name | LCMS [M + H]+ | NMR |
| 695 | 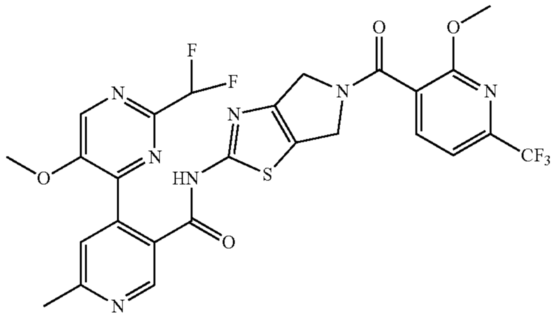 [SMILES: COc1cnc(C(F)F)nc1-c1cc(C)ncc1C(=O)Nc1nc2c(s1)CN(C(=O)c1ccc(C(F)(F)F)nc1OC)C2] | 4-(2-(Di-fluoromethyl)-5-methoxy-pyrimidin-4-yl)-N-(5-(2-methoxy-6-(trifluoromethyl) nicotinoyl)-5,6-dihydro-4H-pyrrolo[3,4-d]thiazol-2-yl)-6-methyl-nicotinamide | 622 | $^1$H NMR (400 MHz, DMSO-$d_6$) δ 13.0 (d, J = 6.6 Hz, 1H), 8.87 (d, J = 4.2 Hz, 1H), 8.79 (d, J = 3.2 Hz, 1H), 8.09 (d, J = 7.6 Hz, 1H), 7.62 (d, J = 7.4 Hz, 1H), 7.54 (s, 1H), 6.95 (td, J = 54.2, 4.4 Hz, 1H), 4.80 (s, 1H), 4.68 (s, 1H), 4.51 (s, 1H), 4.43 (s, 1H), 3.98 (d, J = 1.8 Hz, 3H), 3.78 (d, J = 1.8 Hz, 3H), 2.63 (d, J = 2.6 Hz, 3H). |
| 696 | 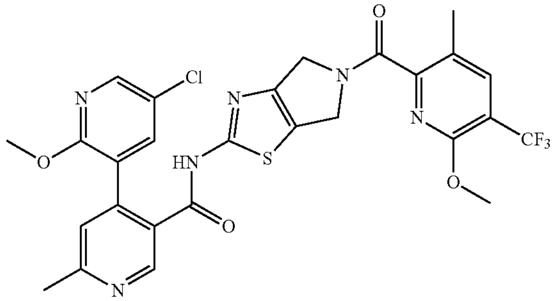 [SMILES: COc1ncc(Cl)cc1-c1cc(C)ncc1C(=O)Nc1nc2c(s1)CN(C(=O)c1nc(OC)c(C(F)(F)F)cc1C)C2] | 5-Chloro-2-methoxy-N-(5-(6-methoxy-3-methyl-5-(trifluoromethyl) picolinoyl)-5,6-dihydro-4H-pyrrolo[3,4-d]thiazol-2-yl)-6'-methyl-[3,4'-bipyridine]-3'-carboxamide | 619 | H NRM (400 MHz, DMSO-$d_6$) δ 12.8 (s, 1H), 8.74 (d, J = 4 .2 Hz, 1H), 8.27-8.24 (m, 1H), 8.13 (d, J = 3.2 Hz, 1H), 7.97 (d, J = 2.6 Hz, 1H), 7.45 (d, J = 2.0 Hz, 1H), 4.84 (s, 1H), 4.71 (s, 1H), 4.61 (s, 1H), 4.50 (s, 1H), 3.97 (d, J = 1.8 Hz, 3H), 3.57 (s, 3H), 2.58 (d, J = 2.2 Hz, 3H), 2.29 (s, 3H). |
| 698 | 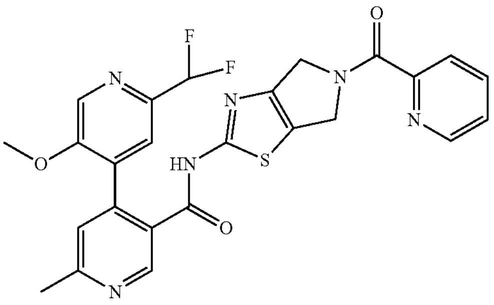 [SMILES: COc1cnc(C(F)F)cc1-c1cc(C)ncc1C(=O)Nc1nc2c(s1)CN(C(=O)c1ccccn1)C2] | 2'-(difluoro-methyl)-5'-methoxy-6-methyl-N-(5-picolinoyl-5,6-dihydro-4H-pyrrolo[3,4-d]thiazol-2-yl)-[4,4'-bipyridine]-3-carboxamide | 523 | $^1$H NMR (400 MHz, DMSO-$d_6$) δ 12.8 (s, 1H), 8.79 (s, 1H), 8.69-8.64 (m, 1H), 8.45 (s, 1H), 8.01-7.95 (m, 1H), 7.88-7.82 (m, 1H), 7.69 (s, 1H), 7.59-7.53 (m, 1H), 7.43 (s, 1H), 6.98 (td, J = 54.8, 2.0 Hz, 1H), 5.04 (s, 1H), 4.93 (s, 1H), 4.85 (s, 1H), 4.71 s, 1H), 3.68 (s, 3H), 2.59 (d, J = 1.8 Hz, 3H). |
| 699 | 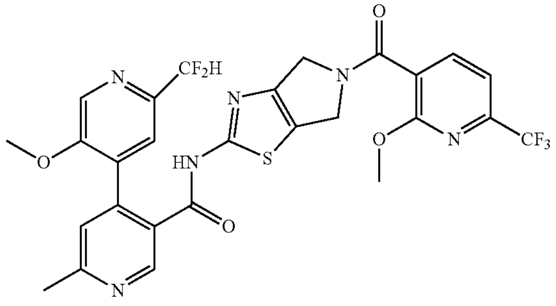 [SMILES: COc1cnc(C(F)F)cc1-c1cc(C)ncc1C(=O)Nc1nc2c(s1)CN(C(=O)c1ccc(C(F)(F)F)nc1OC)C2] | 2'-(Difluoro-methyl)-5'-methoxy-N-(5-(2-methoxy-6-(trifluoromethyl) nicotinoyl)-5,6-dihdyro-4H-pyrrolo[3,4-d]thiazol-2-yl)-6-methyl-[4,4'-bipyridine]-3-carboxamide | 621 | $^1$H NMR (400 MHz, DMSO-$d_6$) δ 12.8 (d, J = 3.6 Hz, 1H), 8.78 (d, J = 4.2 Hz, 1H), 8.45 (d, J = 2.2 Hz, 1H), 8.08 (dd, J = 7.6, 2.6 Hz, 1H), 7.69 (d, J = 1.6 Hz, 1H), 7.61 (dd, J = 7.6, 2.8 Hz, 1H), 7.43 (d, J = 2.8 Hz, 1H), 6.97 (td, J = 55.2, 3.6 Hz, 1H), 4.80 (s, 1H), 4.67 (s, 1H), 4.51 (s, 1H), 4.42 (s, 1H), 3.97 (s, 3H), 3.67 (s, 3H), 2.60 (d, J = 2.8 Hz, 3H) |

TABLE C-continued

| The following examples were prepared using a similar procedure to that described for Example 1 | | | | |
|---|---|---|---|---|
| Ex. No. | Structure | Compound Name | LCMS [M + H]+ | NMR |
| 700 | 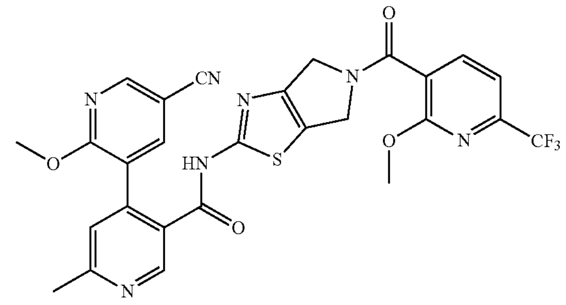 [SMILES: COc1nc(C(F)(F)F)ccc1C(=O)N1Cc2nc(NC(=O)c3cnc(C)cc3-c3cc(C#N)cnc3OC)sc2C1] | 5-cyano-2-methoxy-N-(5-(2-methoxy-6-(trifluoromethyl) nicotinoyl)-5,6-dihydro-4H-pyrrolo[3,4-d]thiazol-2-yl)-6'-methyl-[3,4'-bipyridine]-3'-carboxamide | 596 | $^1$H NMR (400 MHz, DMSO-$d_6$) δ 12.84 (s, 1H), 8.78 (d, J 4 .2 Hz, 1H), 8.76-8.72 (m, 1H), 8.33 (d, J = 2.2 Hz, 1H), 8.09 (d, J = 7.4, 2.0 Hz, 1H), 7.62 (dd, J = 7.6, 4.0 Hz, 1H), 7.47 (d, J = 2.4 Hz, 1H), 4.80 (s, 1H), 4.66 (s, 1H), 4.51 (s, 1H), 4.42 (s, 1H), 3.97 (s, 3H), 3.65 (s, 3H), 2.59 (d, J = 2.6 Hz, 3H) |

*Racemic diastereomer with known relative stereochemistry

#Single unknown enantiomer

&Mixture of cis or trans isomers

[a]Reverse phase chromatography conditions to separate Example 576 and 577: prep-HPLC with the following conditions (Column: Sunfire prep C18 column, 30*150 mm, 5 μm; Mobile Phase A: water (0.05% TFA), Mobile Phase B: MeOH--HPLC; Flow rate: 60 mL/min; Gradient isocratic 45% B to 60% B in 10 min; Wave Length: 254 nm/220 nm; RT1 (min): 12.28/14.00).

[b]Conditions to separate Example 604 and 605: The racemic product (20 mg) was separated by prep-CHIRAL-HPLC with the following conditions (Column: CHIRALPAK IA, 2*25 cm, 5 μm: Mobile Phase A: MTBE: Hex = 1:1 (0.1% FA), Mobile Phase B: MeOH--HPLC:; Flow rate: 20 mL/min: Gradient: isocratic 15; Wave Length: 212/302 nm; RT1 (min): 9.4; RT2 (min): 12.155; Sample Solvent: MeOH--HPLC; Injection Volumne: 2\0.5 mL; Number Of Runs: 3).

[c]Chiral separation conditions for Example 108 and 109: prep-SFC with the following conditions CHIRAL ART Cellulose-SB column, 4.6 x 100 mm, 3 μm; Mobile Phase 10-50% MeOH with 20 mM $NH_3$ modifier in $CO_2$ for 2 min, then 50%/50% MeOH with 20 mM NH3 modifier/CO2 for 1 min; flow rate 2 mL/min, Prak 1: 2.68 min (Example 108); Peak 2: 2.85 min (Example 109).

Example 110: Synthesis of tert-Butyl 2-(4-(2-methoxyphenyl)-6-methylnicotinamido)-6,7-dihydrothiazolo[5,4-c]pyridine-5(4H)-carboxylate

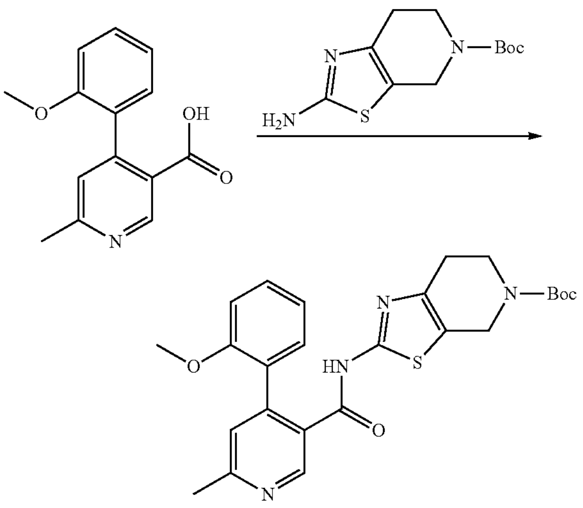

A solution of 4-(2-methoxyphenyl)-3-methylnicotinic acid (80 mg, 0.33 mmol), tert-butyl 2-amino-6,7-dihydrothiazolo[5,4-c]pyridine-5(4H)-carboxylate (92.4 mg, 0.36 mmol), HATU (163 mg, 0.43 mmol) and DIPEA (127 mg, 0.99 mmol) in DMF (3 mL) was heated at 80° C. overnight. The mixture was diluted with water (30 mL), extracted with EtOAc (3x30 mL) and the combined organic layers washed with brine, dried over $Na_2SO_4$, filtered and concentrated under reduced pressure. The residue was purified by prep-HPLC to give tert-butyl 2-(4-(2-methoxyphenyl)-6-methylnicotinamido)-6,7-dihydrothiazolo[5,4-c]pyridine-5(4H)-carboxylate (50 mg, 32%) as a white solid. LCMS: m/z=481 $[M+H]^+$, $^1$H NMR (400 MHz, DMSO-$d_6$): δ 12.4 (s, 1H), 8.62 (s, 1H), 7.42-7.30 (m, 2H), 7.28 (s, 1H), 7.06 (t, J=7.6 Hz, 1H), 6.97 (d, J=8.2 Hz, 1H), 4.48 (s, 2H), 3.64 (t, J=5.8 Hz, 2H), 3.50 (s, 3H), 2.65 (t, J=6.0 Hz, 2H), 2.56 (s, 3H), 1.42 (s, 9H).

Example 111: Synthesis of 4-(2-Methoxyphenyl)-6-methyl-N-(4,5,6,7-tetrahydrothiazolo[5,4-c]pyridin-2-yl)nicotinamide

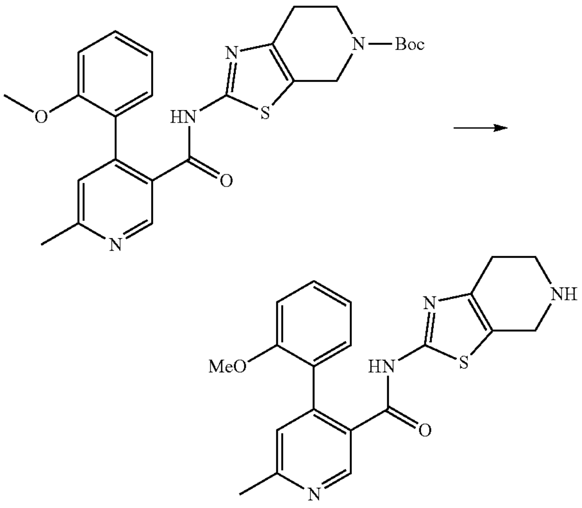

To a solution of tert-butyl 2-(4-(2-methoxyphenyl)-6-methylnicotinamido)-6,7-dihydrothiazolo[5,4-c]pyridine-5 (4H)-carboxylate (40 mg, 0.08 mmol) in MeOH (4 mL) was added 4 M HCl/MeOH (1 mL) and the mixture was stirred at room temperature overnight. The reaction was quenched with a saturated aqueous $NaHCO_3$ solution and the mixture extracted with 10/1 DCM/MeOH (4×20 mL). The combined organic layers were washed with brine, dried over $Na_2SO_4$, filtered and concentrated under reduced pressure. The residue was purified by prep-HPLC to give 4-(2-methoxyphenyl)-6-methyl-N-(4,5,6,7-tetrahydrothiazolo[5,4-c]pyridin-2-yl)nicotinamide (12 mg, 38%) as a white solid. LCMS: m/z=381 $[M+H]^+$, $^1H$ NMR (400 MHz, DMSO-$d_6$): δ 8.62 (s, 1H), 8.22 (s, 1H), 7.43-7.30 (m, 2H), 7.28 (s, 1H), 7.06 (t, J=7.4 Hz, 1H), 6.98 (d, J=8.2 Hz, 1H), 3.89 (s, 2H), 3.50 (s, 3H), 3.07 (t, J=5.3 Hz, 2H), 2.62 (d, J=5.6 Hz, 2H), 2.56 (s, 3H).

Example 112: Synthesis of N-(5-Cyclohexyl-4,5,6,7-tetrahydrothiazolo[5,4-c]pyridin-2-yl)-4-(2-methoxyphenyl)-6-methylnicotinamide

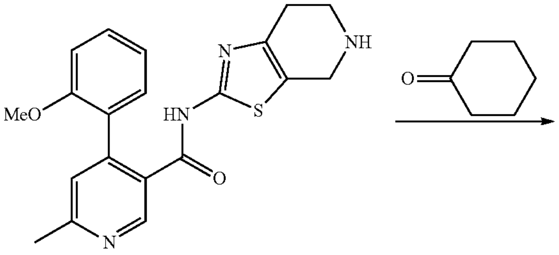

-continued

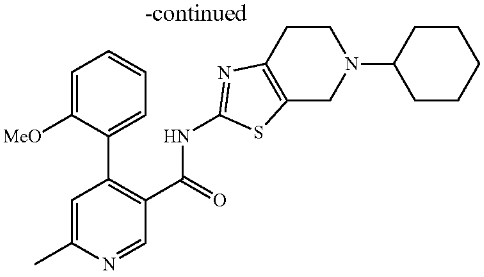

To a solution of 4-(2-methoxyphenyl)-6-methyl-N-(4,5,6,7-tetrahydrothiazolo[5,4-c]pyridin-2-yl)nicotinamide (30 mg, 0.08 mmol) and cyclohexanone (16 mg, 0.16 mmol) in DCE (2 mL) at 0° C. was added $NaBH(OAc)_3$ (34 mg, 0.26 mmol) and the mixture was stirred at room temperature overnight. The mixture was diluted with water (10 mL), extracted with DCM (10 mL×4) and the combined organic layers washed with brine, dried over $Na_2SO_4$, filtered and concentrated. The residue was purified by prep-TLC (DCM/MeOH=20/1, v/v) to give N-(5-cyclohexyl-4,5,6,7-tetrahydrothiazolo[5,4-c]pyridin-2-yl)-4-(2-methoxyphenyl)-6-methylnicotinamide (25.9 mg, 70%) as a yellow solid. LCMS: m/z=463 $[M+H]^+$, $^1H$ NMR (400 MHz, DMSO-$d_6$): δ 12.3 (s, 1H), 8.62 (s, 1H), 7.44-7.23 (m, 3H), 7.06 (t, J=7.6 Hz, 1H), 6.97 (d, J=8.4 Hz, 1H), 3.85-3.64 (m, 1H), 3.49 (s, 3H), 3.12-2.79 (m, 6H), 2.56 (s, 3H), 2.03-1.54 (m, 5H), 1.41-1.03 (m, 5H).

TABLE D

The following examples were prepared using a similar procedure to that described for Example 112.

| Ex. No. | Structure | Compound Name | LCMS $[M + H]^+$ | NMR |
|---|---|---|---|---|
| 113 | 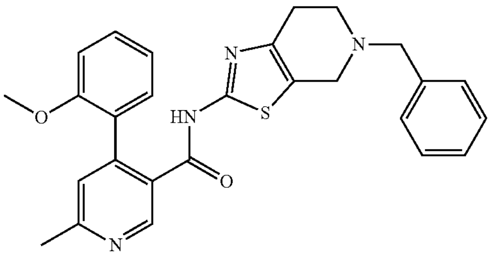 [SMILES: COc1ccccc1-c1cc(C)ncc1C(=O)Nc1nc2c(s1)CN(Cc1ccccc1)CC2] | N-(5-Benzyl-4,5,6,7-tetrahydrothiazolo [5,4-c] pyridin-2-yl)-4-(2-methoxyphenyl)-6-methylnicotinamide | 471 | $^1H$ NMR (400 MHZ, DMSO-$d_6$) δ 12.3 (s, 1H), 8.61 (s, 1H), 7.41-7.23 (m, 8H), 7.12-6.91 (m, 2H), 3.68 (s, 2H), 3.54 (s, 2H), 3.49 (s, 3H), 2.81-2.73 (m, 2H), 2.70-2.61 (m, 2H), 2.55 (s, 3H) |
| 114 | 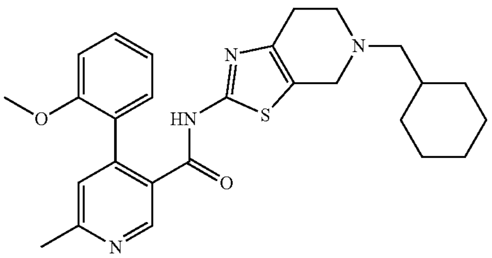 [SMILES: COc1ccccc1-c1cc(C)ncc1C(=O)Nc1nc2c(s1)CN(CC1CCCCC1)CC2] | N-(5-(Cyclohexylmethyl)-4,5,6,7-tetrahydrothiazolo [5,4-c] pyridin-2-yl)-4-(2-methoxyphenyl)-6-methylnicotinamide | 477 | $^1H$ NMR (400 MHZ, DMSO-$d_6$) δ 12.3 (s, 1H), 8.61 (s, 1H), 7.37 (t, J = 7.8 Hz, 1H), 7.32 (d, J = 7.5 Hz, 1H), 7.27 (s, 1H), 7.05 (t, J = 7.6 Hz, 1H), 6.97 (d, J = 8.2 Hz, 1H), 3.50 (s, SH), 2.74-2.58 (m, 4H), 2.55 (s, 3H), 2.34-2.24 (m, 2H), 1.79-1.70 (m, 2H), 1.70-1.59 (m, 3H), 1.58-1.48 (m, 1H), 1.27-1.12 (m, 3H), 0.910.78 (m, 2H) |

TABLE D-continued

The following examples were prepared using a similar procedure to that described for Example 112.

| Ex. No. | Structure | Compound Name | LCMS [M + H]+ | NMR |
|---|---|---|---|---|
| 701 | 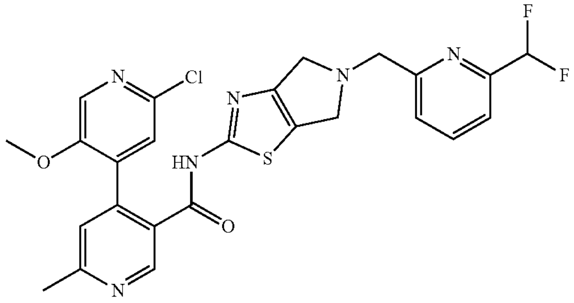 [SMILES: COc1cnc(Cl)cc1-c1cc(C)ncc1C(=O)Nc1nc2c(s1)CN(Cc1cccc(C(F)F)n1)C2] | 2'-Chloro-N-(5-((6-(difluoromethyl) pyridin-2-yl)methyl)-5,6-dihydro-4H-pyrrolo[3,4-d]thiazol-2-yl)-5'-methoxy-6-methyl-[4,4'-bipyridine]-3-carboxamide | 543 | $^1$H NMR (400 MHZ, DMSO-$d_6$) δ 12.7 (s, 1H), 8.77 (s, 1H), 8.16 (s, 1H), 8.01 (t, J = 7.8 Hz, 1H), 7.69 (d, J = 7.8 Hz, 1H), 7.61 (s, 1H), 7.53 (s, 1H), 7.42 (s, 1H), 6.94 (t, J = 55.0 Hz, 1H), 4.15 (s, 2H), 4.04 (s, 2H), 3.90 (s, 2H), 3.60 (s, 3H), 2.58 (s, 3H) |
| 702 | 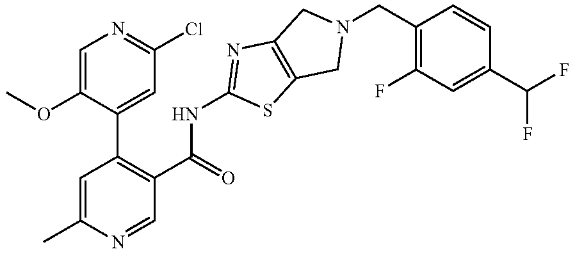 [SMILES: COc1cnc(Cl)cc1-c1cc(C)ncc1C(=O)Nc1nc2c(s1)CN(Cc1ccc(C(F)F)cc1F)C2] | 2'-chloro-N-(5-(4-(difluoromethyl)-2-fluorobenzyl)-5,6-dihydro-4H-pyrrolo[3,4-d] thiazol-2-yl)-5'-methoxy-6-methyl-[4,4'-bipyridine]-3-carboxamide | 560 | $^1$H NMR (400 MHZ, DMSO-$d_6$) δ 12.7 (s, 1H), 8.77 (s, 1H), 8.16 (s, 1H), 7.68 (t, J = 7.6 Hz, 1H), 7.52 (s. 1H), 7.46-7.39 (m, 3H), 7.05 (t, J = 55.8 Hz, 1H), 4.05 (s, 2H), 3.98 (s, 2H), 3.84 (s, 2H), 3.59 (s, 3H), 2.58 (s, 3H |
| 703 | 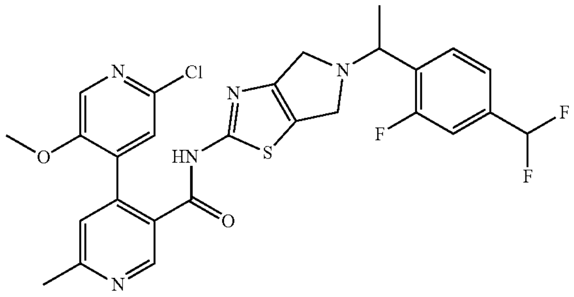 [SMILES: COc1cnc(Cl)cc1-c1cc(C)ncc1C(=O)Nc1nc2c(s1)CN(C(C)c1ccc(C(F)F)cc1F)C2] | 2'-Chloro-N-(5-(1-(4-(difluoromethyl)-2-fluorophenyl)ethyl)-5,6-dihydro-4H-pyrrolo[3,4-d] thiazol-2-yl)-5'-methoxy-6-methyl-[4,4'-bipyridine]-3-carboxamide | 574 | $^1$H NMR (400 MHZ, DMSO-$d_6$) δ 12.7 (s, 1H), 8.76 (s, 1H), 8.16 (s, 1H), 7.76-7.68 (m, 1H), 7.52 (s, 1H), 7.47-7.38 (m, 3H), 7.04 (t, J = 55.6 Hz, 1H), 4.31-4.20 (m, 1H), 3.90-3.85 (m, 2H), 3.81-3.71 (m, 2H), 3.59 (s, 3H), 2.58 (s, 3H), 1.40 (d, J = 6.4 Hz, 3H) |

Example 115: Synthesis of N-(5-(4-Chlorophenyl)-4,5,6,7-tetrahydrothiazolo[5,4-c]pyrindin-2-yl)-4-(2-methoxyphenyl)-6-methylnicotinamide

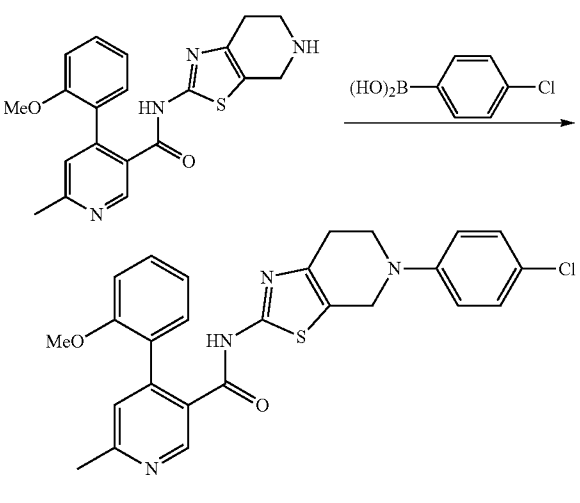

To a solution of 4-(2-methoxyphenyl)-6-methyl-N-(4,5,6,7-tetrahydrothiazolo[5,4-c]pyridin-2-yl)nicotinamide (40 mg, 0.1 mmol) in DCM (5 mL) was added pyridine (33 mg, 0.42 mmol) and the mixture was stirred at room temperature for 3 min. (4-Chlorophenyl)boronic acid (33 mg, 0.21 mmol) and $Cu(OAc)_2$ (19 mg, 0.1 mmol) were then added and the mixture was stirred at room temperature under air for 24 h. The mixture was diluted with water, adjusted to pH 6 with 50% aqueous NaOH and extracted with DCM (3×20 mL). The combined organic layers were dried over $Na_2SO_4$, filtered and concentrated under reduced pressure. The residue was purified by prep-TLC (DCM/MeOH=15/1, v/v) to give N-(5-(4-chlorophenyl)-4,5,6,7-tetrahydrothiazolo[5,4-c]pyridin-2-yl)-4-(2-methoxyphenyl)-6-methylnicotinamide (5.9 mg, 11%) as a yellow solid. LCMS: m/z=491 $[M+H]^+$, $^1$H NMR (400 MHz, DMSO-$d_6$): δ 8.62 (s, 1H), 7.41-7.20 (m, 5H), 7.09-6.95 (m, 4H), 4.38 (s, 2H), 3.65 (t, J=5.8 Hz, 2H), 3.50 (s, 3H), 2.69 (t, J=5.4 Hz, 2H), 2.56 (s, 3H).

Example 116: Synthesis of N-(5-benzoyl-4,5,6,7-tetrahydrothiazolo[5,4-c]pyridin-2-yl)-4-(2-methoxyphenyl)-6-methylnicotinamide

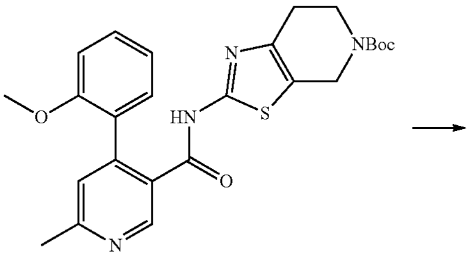

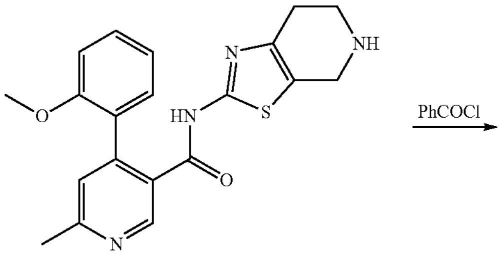

-continued

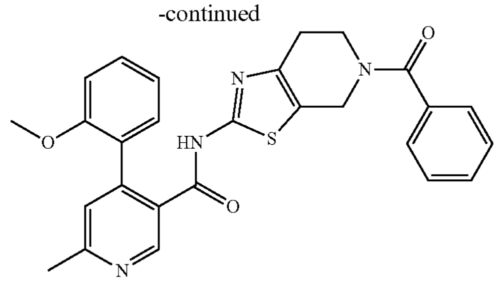

A mixture of tert-butyl 2-(4-(2-methoxyphenyl)-6-methylnicotinamido)-6,7-dihydrothiazolo[5,4-c]pyridine-5(4H)-carboxylate (70 mg, 0.14 mmol) and TFA (0.2 mL) in DCM (3 mL) was stirred at room temperature for 3 h then concentrated under reduced pressure. The residue was dissolved in DCM (3 mL), TEA (20 mg, 0.19 mmol) was added followed by benzoyl chloride (22 mg, 0.15 mmol) and the mixture was stirred at room temperature for 3 h. The mixture was diluted with water (20 mL), extracted with EtOAc (2×20 mL) and the combined organic extracts washed with water (20 mL), brine (20 mL), dried over $Na_2SO_4$, filtered and concentrated under reduced pressure. The residue was purified by prep-TLC (DCM/MeOH=25/1, v/v) to give N-(5-benzoyl-4,5,6,7-tetrahydrothiazolo[5,4-c]pyridin-2-yl)-4-(2-methoxyphenyl)-6-methylnicotinamide (38 mg, 60%) as a white solid. LCMS: m/z=485 $[M+H]^+$, $^1H$ NMR (400 MHz, DMSO-4): 12.3 (s, 1H), 8.65 (s, 1H), 7.53-7.45 (m, 5H), 7.42-7.34 (m, 2H), 7.31 (s, 1H)) 7.08 (t, J=7.2 Hz, 1H), 6.99 (d, J=8.2 Hz, 8H), 4.84-4.51 (m, 2H) 4.03-3.58 (m, 2H), 3.52 (s, 3H), 2.80-2.72 (m, 2H), 2.58 (s, 3H).

TABLE E

The following examples were prepared using a similar procedure to that described for Example 116 using an appropriately substituted acyl-, sulfonyl-, or sulfamyl chloride reagent.

| Ex. No. | Structure | Compound Name | LCMS $[M + H]^+$ | NMR |
|---|---|---|---|---|
| 117 | 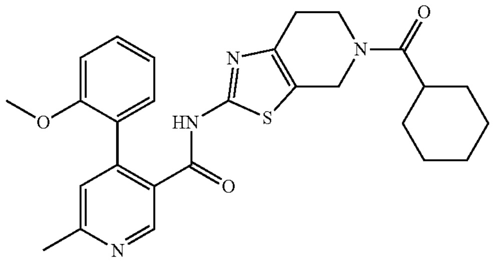 [SMILES: COc1ccccc1-c1cc(C)ncc1C(=O)Nc1nc2c(s1)CN(C(=O)C1CCCCC1)CC2] | N-(5-(Cyclohexanecarbonyl)-4,5,6,7-tetrahydrothiazolo [5,4-c]pyridin-2-yl)-4-(2-methoxyphenyl)-6-methylnicotinamide | 491 | $^1H$ NMR (400 MHZ, DMSO-$d_6$) δ 12.4 (s, 1H), 8.63 (s, 1H), 7.41-7.30 (m, 2H), 7.28 (s, 1H), 7.06 (t, J = 7.5 Hz, 1H), 6.97 (d, J = 8.4 Hz, 1H), 4.73-4.53 (m, 2H), 3.83-3.70 (m, 2H), 3.50 (s, 3H), 2.78-2.57 (m, 3H), 2.56 (s, 3H), 1.76-1.54 (m, 5H), 1.42-1.08 (m, 5H) |
| 118 | 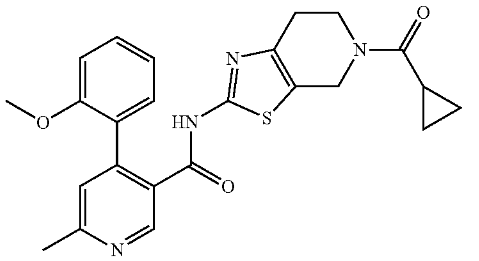 [SMILES: COc1ccccc1-c1cc(C)ncc1C(=O)Nc1nc2c(s1)CN(C(=O)C1CC1)CC2] | N-(5-(Cyclopropanecarbonyl)-4,5,6,7-tetrahydrothiazolo [5,4-c]pyridin-2-yl)-4-(2-methoxyphenyl)-6-methylnicotinamide | 449 | $^1H$ NMR (400 MHZ, DMSO-$d_6$) δ 12.3 (s, 1H), 8.62 (s, 1H), 7.38 (t, J = 7.8 Hz, 1H), 7.33 (d, J = 7.5 Hz, 1H), 7.29 (s, 1H), 7.06 (t, J = 7.6 Hz, 1H), 6.97 (d, J = 8.4 Hz, 1H), 4.93-4.54 (m, 2H), 4.04-3.71 (m, 2H), 3.49 (s, 3H), 2.81-2.60 (m, 2H), 2.56 (s, 3H), 2.16-1.94 (m, 1H), 0.80-0.67 (m, 4H) |

TABLE E-continued

The following examples were prepared using a similar procedure to that described for Example 116 using an appropriately substituted acyl-, sulfonyl-, or sulfamyl chloride reagent.

| Ex. No. | Structure | Compound Name | LCMS $[M + H]^+$ | NMR |
|---|---|---|---|---|
| 119 | 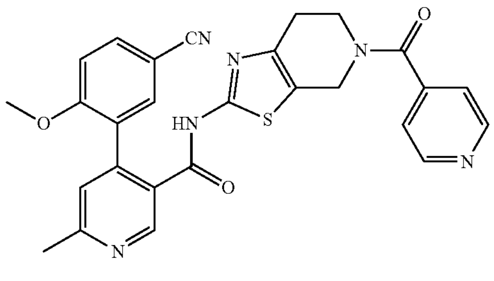 [SMILES: COc1ccc(C#N)cc1-c1cc(C)ncc1C(=O)Nc1nc2c(s1)CN(C(=O)c1ccncc1)CC2] | 4-(5-cyano-2-methoxyphenyl)-N-(5-isonicotinoyl-4,5,6,7-tetrahydrothiazolo [5,4-c]pyridin-2-yl)-6-methylnicotinamide | 511 | $^1H$ NMR (400 MHZ, Chloroform-d)) δ 8.77-8.73 (m, 3H), 8.09 (d, J = 7.8 Hz, 1H), 7.75-7.72 (m, 1H), 7.59-7.52 (m, 2H), 7.32-7.18 (m, 1H), 6.99-6.97 (m, 1H), 4.88 (s, 1H), 4.50 (s, 1H), 3.96 (s, 1H), 3.71 (s, 3H), 3.58 (s, 1H), 2.69 (s, 3H), 2.51 (s, 2H). |
| 120 | 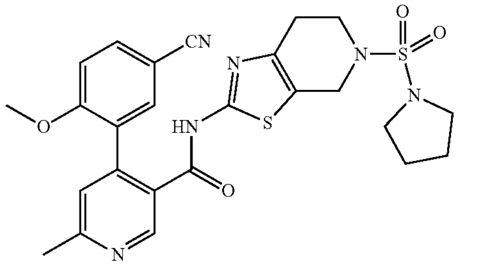 [SMILES: COc1ccc(C#N)cc1-c1cc(C)ncc1C(=O)Nc1nc2c(s1)CN(S(=O)(=O)N1CCCC1)CC2] | 4-(5-cyano-2-methoxyphenyl)-6-methyl-N-(5-(pyrrolidin-1-ylsulfonyl)-4,5,6,7-tetrahydrothiazolo [5,4-c]pyridin-2-yl)nicotinamide | 538 | $^1H$ NMR (400 MHZ, DMSO-$d_6$) δ 12.50 (s, 1H), 8.70 (s, 1H), 7.90-7.83 (m, 2H), 7.38 (s, 1H), 7.17 (d, J = 8.7 Hz, 1H), 4.37 (s, 2H), 3.56 (d. J = 8.5 Hz, 5H), 3.24-3.16 (m, 4H), 2.73 (t, J = 5.8 Hz, 2H), 2.57 (s, 3H), 1.87-1.76 (m, 4H). |
| 121 | 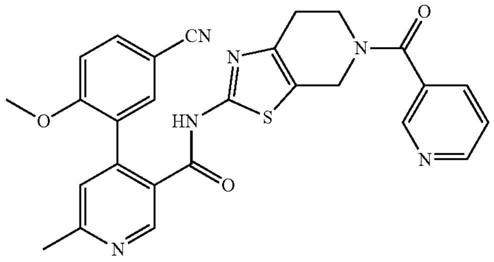 [SMILES: COc1ccc(C#N)cc1-c1cc(C)ncc1C(=O)Nc1nc2c(s1)CN(C(=O)c1cccnc1)CC2] | 4-(5-cyano-2-methoxyphenyl)-6-methyl-N-(5-nicotinoyl-4,5,6,7-tetrahydrothiazolo [5,4-c]pyridin-2-yl)nicotinamide | 511 | $^1H$ NMR (400 MHZ, DMSO-$d_6$) δ 12.52 (s, 1H), 8.86-8.48 (m, 3H), 8.07-7.70 (m, 3H), 7.51 (m, 1H), 7.38 (s, 1H), 7.17 (d. J = 8.8 Hz, 1H), 4.77 (s, 1H), 4.59 (s, 1H), 3.97 (s, 1H), 3.60 (m, 4H), 2.82-2.65 (m, 2H), 2.57 (s, 3H). |
| 122 | 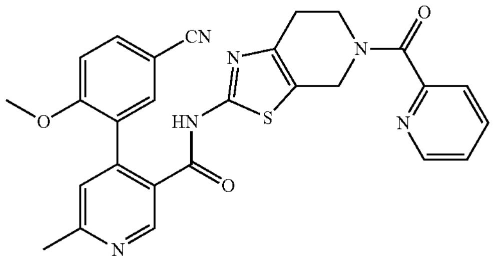 [SMILES: COc1ccc(C#N)cc1-c1cc(C)ncc1C(=O)Nc1nc2c(s1)CN(C(=O)c1ccccn1)CC2] | 4-(5-cyano-2-methoxyphenyl)-6-methyl-N-(5-picolinoyl-4,5,6,7-tetrahydrothiazolo [5,4-c]pyridin-2-yl)nicotinamide | 511 | $^1H$ NMR (400 MHZ, DMSO-$d_6$) δ 12.51 (s, 1H), 8.72-8.68 (m, 1H), 8.63-8.60 (m, 1H), 8.01-7.80 (m, 3H), 7.67-7.58 (m, 1H), 7.56-7.47 (m, 1H), 7.38 (d, J = 7.6 Hz, 1H), 7.18-7.14 (m, 1H), 4.80 (s, 1H), 4.63 (s, 1H), 3.98-3.67 (m, 2H), 3.59-3.56 (m, 3H), 2.75 (m, 2H), 2.57 (d, J = 4.2 Hz, 3H) |
| 123 | 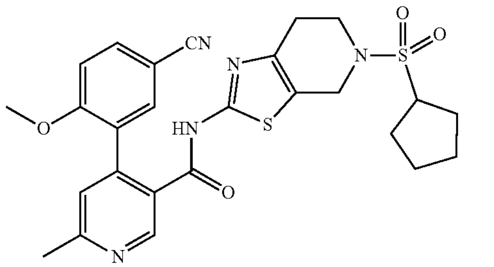 [SMILES: COc1ccc(C#N)cc1-c1cc(C)ncc1C(=O)Nc1nc2c(s1)CN(S(=O)(=O)C1CCCC1)CC2] | 4-(5-cyano-2-methoxyphenyl)-N-(5-(cyclopentylsulfonyl)-4,5,6,7-tetrahydrothiazolo [5,4-c]pyridin-2-yl)-6-methylnicotinamide | 538 | $^1H$ NMR (400 MHZ, DMSO-$d_6$) δ 12.52 (s, 1H), 8.70 (s, 1H), 7.89 (d, J = 8.6, 1H), 7.84 (d, J = 2.1 Hz, 1H), 7.38 (s, 1H), 7.17 (d, J = 8.7 Hz, 1H), 4.45 (s, 2H), 3.72-3.68 (m, 1H), 3.61-3.57 (m, 5H), 2.80-2.63 (m, 2H), 2.57 (s, 3H), 1.98-1.82 (m, 4H), 1.78-1.58 (m, 4H) |

TABLE E-continued

The following examples were prepared using a similar procedure to that described for Example 116 using an appropriately substituted acyl-, sulfonyl-, or sulfamyl chloride reagent.

| Ex. No. | Structure | Compound Name | LCMS $[M + H]^+$ | NMR |
|---|---|---|---|---|
| 124 | 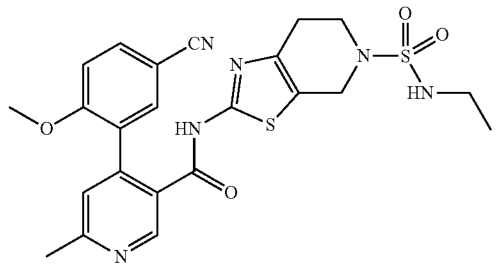 [SMILES: CCNS(=O)(=O)N1CCc2nc(NC(=O)c3cnc(C)cc3-c3cc(C#N)ccc3OC)sc2C1] | 4-(5-cyano-2-methoxyphenyl)-N-(5-(N-ethylsulfamoyl)-4,5,6,7-tetrahydrothiazolo[5,4-c]pyridin-2-yl)-6-methylnicotinamide | 513 | $^1H$ NMR (400 MHZ, DMSO-$d_6$) δ 12.51 (s, 1H), 8.71 (s, 1H), 7.95-7.87 (m, 1H), 7.87-7.80 (m, 1H), 7.40 (d, J = 6.4 Hz, 1H), 7.35-7.32 (m, 1H), 7.17 (d, J = 8.7 Hz, 1H), 4.29 (s, 2H), 3.57 (s, 3H), 3.48-3.36 (m, 2H), 2.93-2.84 (m, 2H), 2.78-2.65 (m, 2H), 2.58 (d, J = 1.6 Hz, 3H), 1.05-1.01 (m, 3H). |

Example 125: Synthesis of 4-(2-Methoxyphenyl)-6-methyl-N-(6-oxo-4,5,6,7-tetrahydrobenzo[d]thiazol-2-yl)nicotinamide

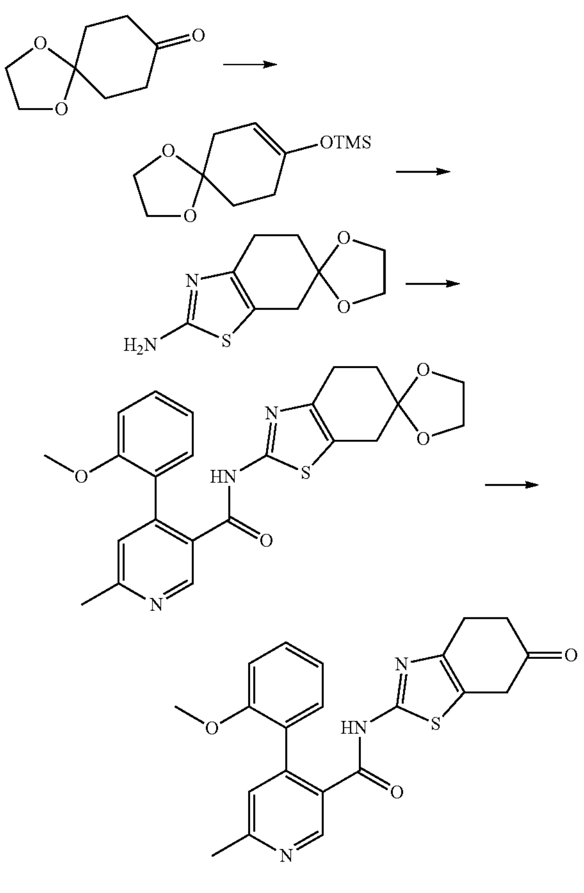

Step 1: To a solution of 1,4-dioxaspiro[4.5]decan-8-one (5.0 g, 32 mmol) and TEA (9.72 g, 96.0 mmol) in DCM (300 mL) at 0° C. was added a solution of TMSOTf (8.68 g, 39.1 mmol) in DCM (100 mL) and the mixture was stirred at 0° C. for 2 h. The mixture was washed with a saturated aqueous $NaHCO_3$ solution (30 mL) and water (200 mL). The organic phase was dried over $Na_2SO_4$, filtered, and concentrated under reduced pressure to afford ((1,4-dioxaspiro[4.5]dec-7-en-8-yl)oxy)trimethylsilane (6 g, 82%) as a yellow oil. $^1H$ NMR (400 MHz, DMSO-$d_6$) δ 4.67-4.63 (m, 1H), 3.86 (s, 4H), 2.17-2.12 (m, 2H), 2.12-2.04 (m, 2H), 1.69 (t, J=6.6 Hz, 2H), 0.15 (s, 9H).

Step 2: A mixture of ((1,4-dioxaspiro[4.5]dec-7-en-8-yl)oxy)trimethylsilane (2.0 g, 8.8 mmol), NBS (1.87 g, 10.5 mmol) and sodium acetate (107 mg, 1.31 mmol) in THF (40 mL) and $H_2O$ (40 mL) was stirred at room temperature for 2 h. Thiourea (733 mg, 9.63 mmol) was added and the mixture was heated at 80° C. for 6 h then allowed to cool to room temperature and stirred overnight. Most of THF was removed under reduced pressure and the aqueous residue was adjusted to pH 9 with 2 M NaOH and extracted with DCM (3×60 mL). The combined organic layers were washed with brine (50 mL), dried over $Na_2SO_4$, filtered, and concentrated under reduced pressure to afford 4,7-dihydro-5H-spiro[benzo[d]thiazole-6,2'-[1,3]dioxolan]-2-amine (1.8 g, 96%) as a yellow solid. LCMS: m/z=213 $[M+H]^+$, $^1H$ NMR (400 MHz, DMSO-$d_6$): δ 6.65 (s, 2H), 3.91 (s, 4H), 2.67-2.64 (m, 2H), 2.56 (s, 1H), 2.49-2.46 (m, 1H), 1.81 (t, J=6.5 Hz, 2H).

Step 3: A mixture of 4-(2-methoxyphenyl)-6-methylnicotinic acid (1.1 g, 4.5 mmol), DIPEA (2.92 g, 22.6 mmol,) and HATU (2.06 g, 5.43 mmol) in NMP (10 mL) was stirred at room temperature for 2 h, 4,7-Dihydro-5H-spiro[benzo[d]thiazole-6,2'-[1,3]dioxolan]-2-amine (1.15 mg, 5.43 mmol) was added and the mixture was heated at 80° C. overnight. The mixture was poured into water (100 mL), extracted with EtOAc (3×60 mL) and the combined organic layers washed with brine (50 mL), dried over $Na_2SO_4$, filtered, and concentrated under reduced pressure. The residue was purified by silica gel chromatography (0-2% MeOH/DCM) to afford N-(4,7-dihydro-5H-spiro[benzo[d]thiazole-6,2'-[1,3]dioxolan]-2-yl)-4-(2-methoxyphenyl)-6-methylnicotinamide (1.7 g, 85%) as a yellow oil. LCMS: m/z=438 $[M+H]^+$.

Step 4: A mixture of N-(4,7-dihydro-5H-spiro[benzo[d]thiazole-6,2'-[1,3]dioxolan]-2-yl)-4-(2-methoxyphenyl)-6-methylnicotinamide (1.7 g, 3.89 mmol) and conc. HCl (1.5 mL) in water (20 mL) was heated at 70° C. for 1.5 h. The mixture was adjusted to pH 9 with 2 M NaOH, extracted with DCM (3×50 mL) and the combined organic layers washed with brine (30 mL), dried over $Na_2SO_4$, filtered, and concentrated under reduced pressure to afford 4-(2-methoxyphenyl)-6-methyl-N-(6-oxo-4,5,6,7-tetrahydrobenzo[d]thiazol-2-yl)nicotinamide (1.0 g, 65%) as a yellow oil. LCMS: m/z=394 $[M+H]^+$, $^1H$ NMR (400 MHz, DMSO-$d_6$) δ 12.4 (s, 1H), 8.62 (s, 1H), 7.40-7.32 (m, 2H), 7.29 (s, 1H), 7.09-7.03 (m, 1H), 6.98 (d, J=8.2 Hz, 1H), 3.53 (s, 2H), 3.50 (s, 3H), 2.97 (t, J=7.0 Hz, 2H), 2.66 (t, J=6.8 Hz, 2H), 2.56 (s, 3H).

TABLE F

The following example was prepared using a similar procedure to that described for Example 125

| Ex. No. | Structure | Compound Name | LCMS [M + H]+ | NMR |
|---|---|---|---|---|
| 126 | 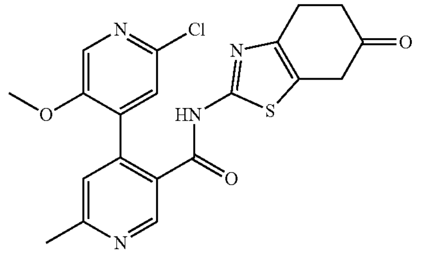 [SMILES: COc1cnc(Cl)cc1-c1cc(C)ncc1C(=O)Nc1nc2c(s1)CC(=O)CC2] | 2'-Chloro-5'-methoxy-6-methyl-N-(6-oxo-4,5,6,7-tetrahydrobenzo[d]thiazol-2-yl)-[4,4'-bipyridine]-3-carboxamide | 429 | $^1$H NMR (400 MHz, DMSO-$d_6$) δ 12.6 (s, 1H), 8.77 (s, 1H), 8.16 (s, 1H), 7.52 (s, 1H), 7.42 (s, 1H), 3.61 (s, 3H), 3.54 (s, 2H), 2.99 (t, J = 6.8 Hz, 2H), 2.67 (t, J = 6.8 Hz, 2H), 2.58 (s, 3H) |

Example 127: Synthesis of (Racemic)-N-(6-(4-Chlorophenyl)-4,5,6,7-tetrahydrobenzo[d]thiazol-2-yl)-4-(2-methoxyphenyl)-6-methylnicotinamide

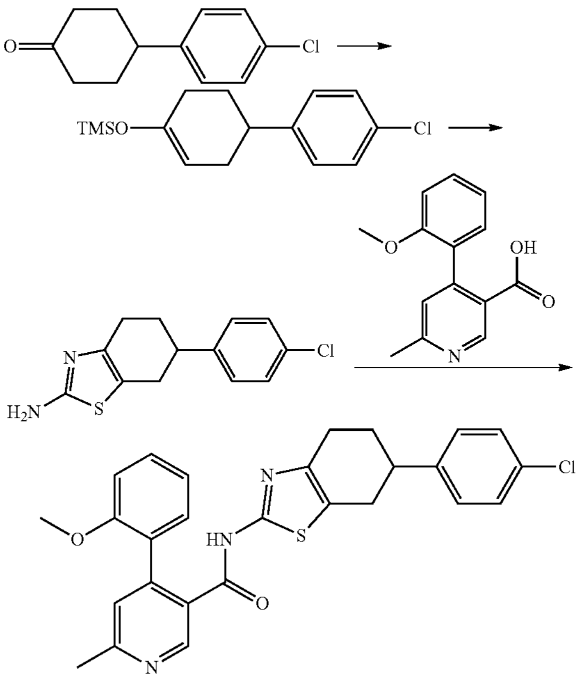

Step 1: To a solution of 4-(4-chlorophenyl)cyclohexan-1-one (800 mg, 3.83 mmol) and TEA (1.16 g, 11.5 mmol) in DCM (10 mL) at 0° C. was added a solution of TMSOTf (1.28 g, 5.75 mmol) in DCM (10 mL) and the mixture was stirred at 0° C. for 2 h. The mixture was diluted with water (60 mL), extracted with DCM (2×50 mL) and the combined organic layers washed with brine (30 mL), dried over $Na_2SO_4$, filtered, and concentrated under reduced pressure. The residue was purified by silica gel chromatography (0-2% EtOAc/heptane) to afford ((4'-chloro-1,2,3,6-tetrahydro-[1,1'-biphenyl]-4-yl)oxy)trimethylsilane (600 mg, 55%) as a yellow oil. $^1$H NMR (400 MHz, DMSO-$d_6$): δ 7.36-7.26 (m, 4H), 4.91-4.82 (m, 1H), 2.78-2.68 (m, 1H), 2.25-2.06 (m, 3H), 2.00-1.89 (m, 1H), 1.87-1.72 (m, 2H), 0.17 (s, 9H).

Step 2: A mixture of ((4'-chloro-1,2,3,6-tetrahydro-[1,1'-biphenyl]-4-yl)oxy)trimethylsilane (600 mg, 2.14 mmol), NBS (456 mg, 2.56 mmol) and sodium acetate (26 mg, 0.32 mmol) in THF (10 mL) and water (10 mL) was stirred at room temperature for 2 h. Thiourea (178 mg, 2.35 mmol) was added and the mixture was heated at 80° C. for 6 h, then allowed to cool to room temperature and stirred overnight. The mixture was adjusted to pH 8-9 with 50% aqueous NaOH, extracted with EtOAc (3×50 mL) and the combined organic layers washed with brine (50 mL), dried over $Na_2SO_4$, filtered, and concentrated under reduced pressure. The residue was purified by silica gel chromatography (0-3.3% MeOH/DCM) to afford 6-(4-chlorophenyl)-4,5,6,7-tetrahydrobenzo[d]thiazol-2-amine (500 mg, 88%) as a yellow solid. LCMS: m/z=265 [M+H]$^+$, $^1$H NMR (400 MHz, DMSO-$d_6$): δ 7.38-7.30 (m, 4H), 6.63 (s, 2H), 3.04-2.94 (m, 1H), 2.76-2.68 (m, 1H), 2.63-2.51 (m, 2H), 2.48-2.43 (m, 1H), 1.96-1.86 (m, 2H).

Step 3: A mixture of 4-(2-methoxyphenyl)-6-methylnicotinic acid (100 mg, 0.411 mmol), DIPEA (159 mg, 1.23 mmol) and HATU (172 mg, 0.452 mmol) in NMP (3 mL) was stirred at RT for 2 h, 6-(4-Chlorophenyl)-4,5,6,7-tetrahydrobenzo[d]thiazol-2-amine (108 mg, 0.411 mmol) was added and the mixture was heated at 80° C. overnight. The mixture was poured into water (30 mL), extracted with EtOAc (3×40 mL) and the combined organic layers washed with brine (50 mL), dried over $Na_2SO_4$, filtered, and concentrated under reduced pressure. The residue was purified by prep-TLC (DCM/MeOH=50/1, v/v) to afford (R and S)—N-(6-(4-chlorophenyl)-4,5,6,7-tetrahydrobenzo[d]thiazol-2-yl)-4-(2-methoxyphenyl)-6-methylnicotinamide (70 mg, 35%) as a white solid. LCMS: m/z=490 [M+H]$^+$, $^1$H NMR (400 MHz, DMSO-$d_6$): δ 12.3 (s, 1H), 8.62 (s, 1H), 7.41-7.35 (m, 5H), 7.33 (dd, J=7.6, 1.7 Hz, 1H) 7.28 (s, 1H), 7.06 (t, J=7.2 Hz, 1H), 6.98 (d, J=8.2 Hz, 1H), 3.51 (s, 3H), 3.09-3.00 (m, 1H), 2.96-2.87 (m, 1H), 2.74-2.67 (m, 3H), 2.56 (s, 3H), 2.04-1.97 (m, 2H).

Example 128A & 128B: Synthesis of (R or S)—N-(6-(4-chlorophenyl)-4,5,6,7-tetrahydrobenzo[d]thiazol-2-yl)-4-(2-methoxyphenyl)-6-methylnicotinamide (128A) & (S or R)—N-(6-(4-chlorophenyl)-4,5,6,7-tetrahydrobenzo[d]thiazol-2-yl)-4-(2-methoxyphenyl)-6-methylnicotinamide (128B) with arbitrarily assigned stereochemistry

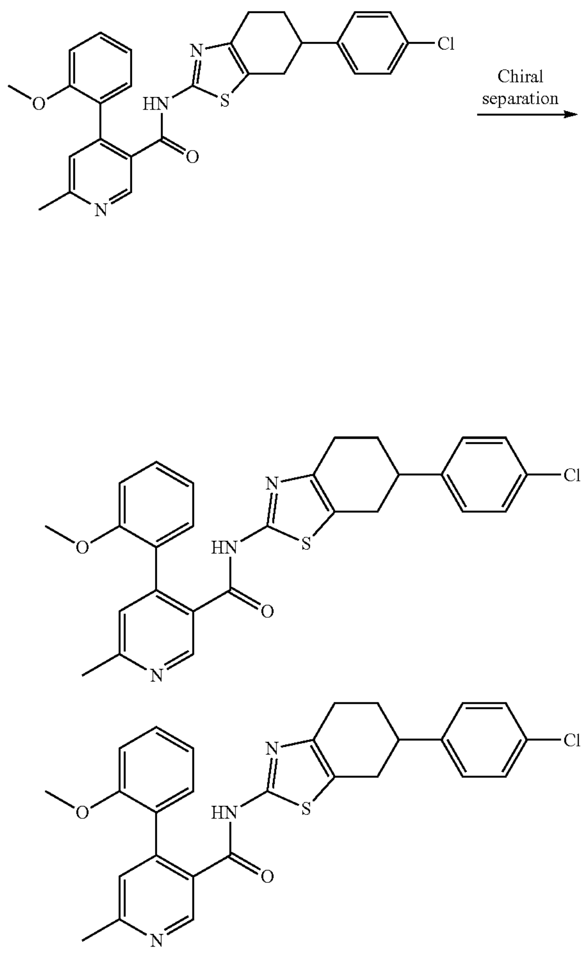

N-(6-(4-Chlorophenyl)-4,5,6,7-tetrahydrobenzo[d]thiazol-2-yl)-4-(2-methoxyphenyl)-6-methylnicotinamide (Example 127) was purified by chiral SFC (Column: Daicel Chiralpak, AD-H, 30×250 mm; Mobile Phase: 10% Ethanol/hexane, 90% carbon dioxide; Flow rate: 60 mL/min) to afford two peaks:

Example 128A: Peak 1, retention time 17.9 min. LCMS: m/z=490 $[M+H]^+$, $^1$H NMR (400 MHz, DMSO-$d_6$) δ 12.3 (s, 1H), 8.62 (s, 1H), 7.42-7.35 (m, 5H), 7.33 (dd, J=7.5, 1.8 Hz, 1H), 7.28 (s, 1H), 7.06 (t, J=7.4 Hz, 1H), 6.98 (d, J=8.2 Hz, 1H), 3.51 (s, 3H), 3.10-3.00 (m, 1H), 3.09-3.00 (m, 1H), 2.75-2.66 (m, 3H), 2.56 (s, 3H), 2.04-1.96 (m, 2H).

Example 128B: Peak 2, retention time 20.0 min. LCMS: m/z=490 $[M+H]^+$, $^1$H NMR (400 MHz, DMSO-$d_6$) δ 12.2 (br s, 1H), 8.62 (s, 1H), 7.40-7.35 (m, 5H), 7.33 (dd, J=7.6, 1.7 Hz, 1H), 7.28 (s, 1H), 7.06 (J=7.4 Hz, 1H), 6.98 (d, J=8.2 Hz, 1H), 3.51 (s, 3H), 3.10-2.99 (m, 1H), 2.93-2.85 (m, 1H), 2.75-2.66 (m, 3H), 2.56 (s, 3H), 2.03-1.95 (m, 2H).

Example 129: Synthesis of N-(6-(4-Chlorophenyl)-4,7-dihydrobenzo[d]thiazol-2-yl)-4-(2-methoxy phenyl)-6-methylnicotinamide

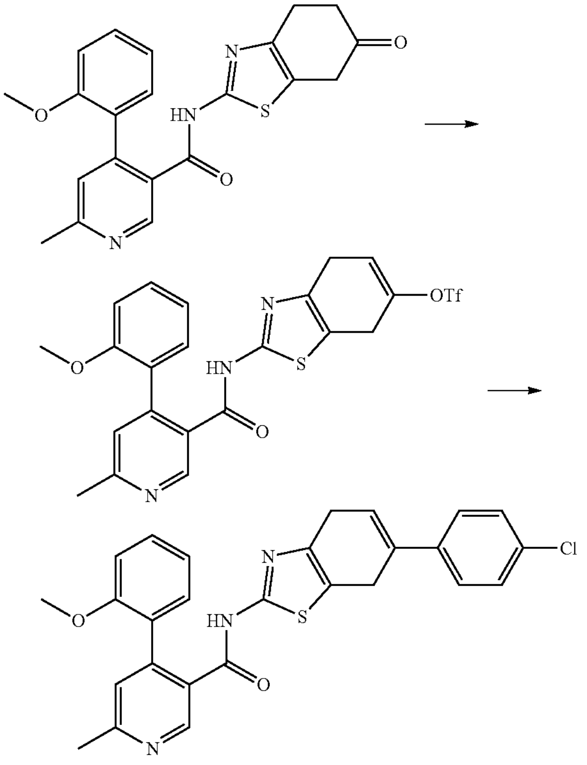

Step 1: To a solution of 4-(2-methoxyphenyl)-6-methyl-N-(6-oxo-4,5,6,7-tetrahydrobenzo[d]thiazol-2-yl)nicotinamide (500 mg, 1.27 mmol) in THF (10 mL) at −78° C. was added NaHMDS (350 mg, 1.91 mmol) and the mixture was stirred at −78° C. for 1 h. A solution of 1,1,1-trifluoro-N-phenyl-N-((trifluoromethyl)sulfonvl)methanesulfonamide (590 mg, 1.65 mmol) in THF (5 mL) was added and the mixture was allowed to warm to room temperature and stirred overnight. The mixture was poured into water (50 mL), extracted with DCM (3×40 mL) and the combined organic layers washed with brine (40 mL), dried over $Na_2SO_4$, filtered, and concentrated under reduced pressure. The residue was purified by silica gel chromatography (0-2% MeOH/DCM) to afford 2-(4-(2-methoxyphenyl)-6-methylnicotinamido)-4,7-dihydrobenzo[d]thiazol-6-yl trifluoromethanesulfonate (210 mg, 22%) as a yellow oil. LCMS: m/z=526 $[M+H]^+$.

Step 2: A mixture of 2-(4(2-methoxyphenyl)-6-methylnicotinamido)-4,7-dihydrobenzo[d]thiazol-6-yl trifluoromethanesulfonate (200 mg, 0.380 mmol), (4-chlorophenyl)boronic acid (119 mg, 0.761 mmol), $Pd(PPh_3)_4$ (44 mg, 0.038 mmol) and $K_2CO_3$ (157 mg, 1.14 mmol) in 1,4-dioxane (4 mL) and water (1 mL) was heated at 100° C. for 1 h under microwave irradiation. The mixture was poured into water (50 mL), extracted with DCM (3×50 mL) and the combined organic layers washed with brine (30 mL), dried over $Na_2SO_4$, filtered, and concentrated under reduced pressure. The residue was purified by prep-TLC (DCM/MeOH=40/1, v/v) to afford N-(6-(4-chlorophenyl)-4,7-dihydrobenzo[d]thiazol-2-yl)-4-(2-methoxyphenyl)-6-methylnicotinamide (55 mg, 30%) as a yellow solid. LCMS: m/z=488 $[M+H]^+$,

$^1$H NMR (400 MHz, Chloroform-d): δ 8.70 (s, 1H), 7.44-7.28 (m, 5H), 7.18 (s, 1H), 7.14-7.08 (m, 1H), 7.06-6.98 (m, 1H), 6.95-6.89 (m, 1H), 6.71 (s, 1H), 3.64 (s, 3H), 2.71-2.58 (m, 5H), 2.41-2.15 (m, 2H).

Example 130: Synthesis of 4-(2-Methoxyphenyl)-6-methyl-N-(4-oxo-4,5,6,7-tetrahydrothiazolo[5,4-c]pyridin-2-yl)nicotinamide

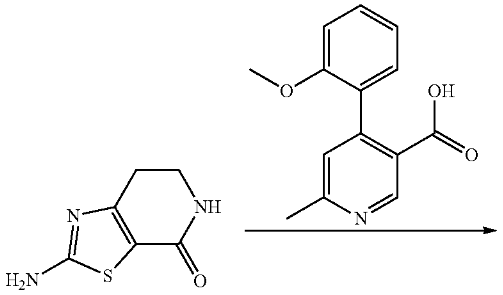

-continued

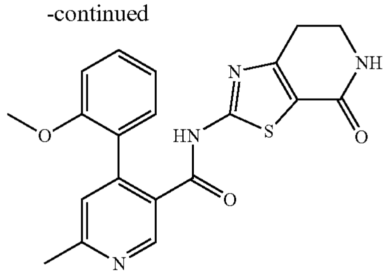

To a solution of 4-(2-methoxyphenyl)-6-methylnicotinic acid (143 mg, 0.59 mmol) in DMF (4 mL) at room temperature was added HATU (337 mg, 0.88 mmol) and DIPEA (229 mg, 1.77 mmol) and the mixture was stirred for 30 min. 2-Amino-6,7-dihydrothiazolo[5,4-c]pyridin-4(5H)-one (100 mg, 0.59 mmol) was added and the mixture was heated at 80° C. overnight. After cooling to RT, the mixture was diluted with water (40 mL), extracted with EtOAc (3×30 mL) and the combined organic layers washed with water (40 mL), brine (40 mL), dried over $Na_2SO_4$, filtered, and concentrated under reduced pressure. The residue was purified by perp-TLC (DCM/MeOH=10/1, v/v) to give 4-(2-methoxyphenyl)-6-methyl-N-(4-oxo-4,5,6,7-tetrahydrothiazolo[5,4-c]pyridin-2-yl)nicotinamide (99 mg, 42%) as a white solid. LCMS: m/z=395 $[M+H]^+$; $^1$H NMR (400 MHz, DMSO-$d_6$): δ 8.66 (s, 1H), 7.61 (s, 1H), 7.42-7.35 (m, 2H), 7.32 (s, 1H), 7.08 (t, J=7.4 Hz, 1H), 6.98 (d, J=8.2 Hz, 1H), 3.48 (s, 3H), 3.44 (dd, J=7.2, 2.4 Hz, 2H), 2.85 (t, J=7.0 Hz, 2H), 2.57 (s, 3H).

TABLE G

The following examples were prepared using a similar procedure to that described for Example 130

| Ex. No. | Structure | Compound Name | LCMS $[M + H]^+$ | NMR |
|---|---|---|---|---|
| 131 | 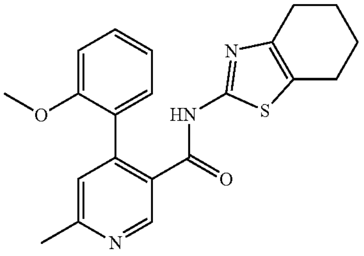 [SMILES: COc1ccccc1-c1cc(C)ncc1C(=O)Nc1nc2c(s1)CCCC2] | 4-(2-Methoxyphenyl)-6-methyl-N-(4,5,6,7-tetrahydrobenzo[d]thiazol-2-yl)nicotinamide | 380 | $^1$H NMR (400 MHz, DMSO-$d_6$) δ 12.2 (s, 1H), 8.60 (s, 1H), 7.37 (t. J = 7.8 Hz, 1H), 7.32 (d, J = 6.6 Hz, 1H), 7.27 (s, 1H), 7.05 (t, J = 7.4 Hz, 1H), 6.97 (d, J = 8.2 Hz, 1H), 3.50 (s, 3H), 2.65-2.59 (m, 2H), 2.58-2.53 (m, 5H), 1.82-1.72 (m, 4H) |
| 132 | 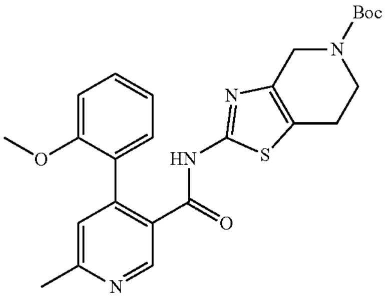 [SMILES: COc1ccccc1-c1cc(C)ncc1C(=O)Nc1nc2c(s1)CCN(C(=O)OC(C)(C)C)C2] | tert-Butyl2-(4-(2-methoxyphenyl)-6-methylnicotinamido)-6,7-dihydrothiazolo[4,5-c]pyridine-5(4H)-carboxylate | 481 | $^1$H NMR (400 MHz, DMSO-$d_6$) δ 12.4 (s, 1H), 8.63 (s, 1H), 7.42-7.29 (m, 3H), 7.06 (t, J = 7.4 Hz, 1H), 6.98 (d, J = 8.6 Hz, 1H), 4.38 (s, 2H), 3.66-3.60 (m, 2H), 3.50 (s, 3H), 2.74-2.68 (m, 2H), 2.56 (s, 3H), 1.43 (s, 9H) |

TABLE G-continued

The following examples were prepared using a similar procedure to that described for Example 130

| Ex. No. | Structure | Compound Name | LCMS $[M + H]^+$ | NMR |
|---|---|---|---|---|
| 133 | 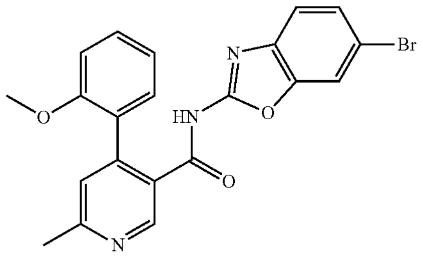 [SMILES: COc1ccccc1-c1cc(C)ncc1C(=O)Nc1nc2ccc(Br)cc2o1] | N-(6-Bromobenzo[d]oxazol-2-yl)-4-(2-methoxyphenyl)-6-methylnicotinamide | 438 | $^1H$ NMR (400 MHz, DMSO-$d_6$) δ 12.1 (s, 1H), 8.70 (s, 1H), 7.95 (s, 1H), 7.58-7.48 (m, 2H), 7.39 (s, 1H), 7.33 (d, J = 6.6 Hz, 2H), 7.08-6.97 (m, 2H), 3.61 (s, 3H), 2.59 (s, 3H) |

Example 134: Synthesis of 4-(2-Methoxyphenyl)-6-methyl-N-(5-(pyridin-2-yl)-5,6-dihydro-4H-pyrrolo[3,4-d]thiazol-2-yl)nicotinamide

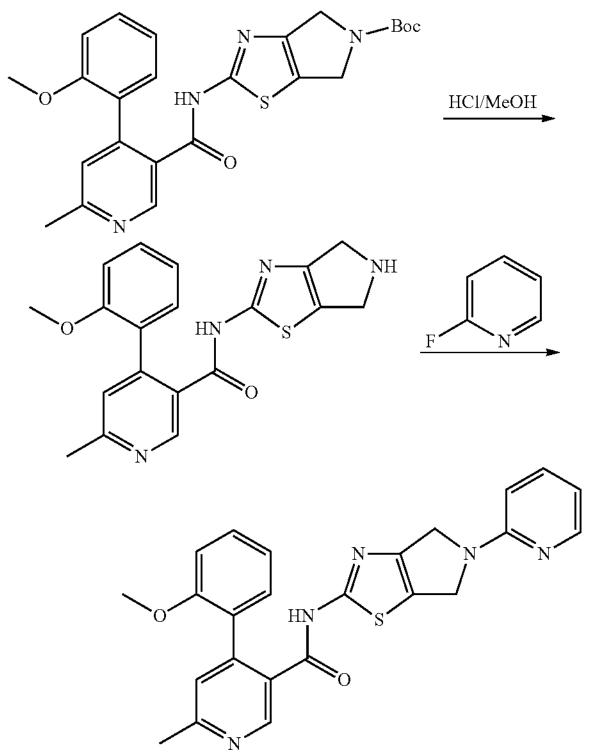

A solution of tert-butyl 2-(4-(2-methoxyphenyl)-6-methylnicotinamido)-4,6-dihydro-5H-pyrrolo[3,4-d]thiazole-5-carboxylate (200 mg, 0.43 mmol) in 4 M HCl/MeOH (3 mL) was stirred at room temperature for 2 h. The mixture was concentrated under reduced pressure and the residue was dissolved in DMSO (3 mL). $Cs_2CO_3$ (280 mg, 0.885 mmol) and 2-fluoropyridine (416 mg, 4.29 mmol) were added and the mixture was heated at 130° C. overnight. After cooling to room temperature, the mixture was diluted with water (30 mL), extracted with EtOAc (3×40 mL) and the combined organic layers washed with water (20 mL), brine (20 mL), dried over $Na_2SO_4$, filtered and concentrated under reduced pressure. The residue was purified by prep-TLC (DCM/MeOH=25/1, v/v) to give 4-(2-methoxyphenyl)-6-methyl-N-(5-(pyridin-2-yl)-5,6-dihydro-4H-pyrrolo[3,4-d]thiazol-2-yl)nicotinamide (33 mg, 17%) as a yellow solid. LCMS: m/z=444 $[M+H]^+$, $^1H$ NMR (400 MHz, DMSO-$d_6$): δ 12.6 (s, 1H), 8.66 (s, 1H), 8.13 (dd, J=5.0, 1.8 Hz, 1H), 7.57 (ddd, J=8.8, 7.2, 1.8 Hz 1H), 7.41-7.34 (m, 2H), 7.30 (s, 1H), 7.07 (t, J=7.6 Hz, 1H), 6.99 (d, J=8.4 Hz, 1H), 6.64 (dd, J=7.2, 5.0 Hz, 1H), 6.56 (d, J=8.6 Hz, 1H), 4.69 (dd, J=4.8, 2.6 Hz, 2H), 4.55 (t, J=3.6 Hz, 2H), 3.51 (s, 3H), 2.57 (s, 3H).

Example 135: Synthesis of N-(5-Cyclopropyl-6-oxo-5,6-dihydro-4H-pyrrolo[3,4-d]thiazol-2-yl)-4-(2-methoxyphenyl)-6-methylnicotinamide

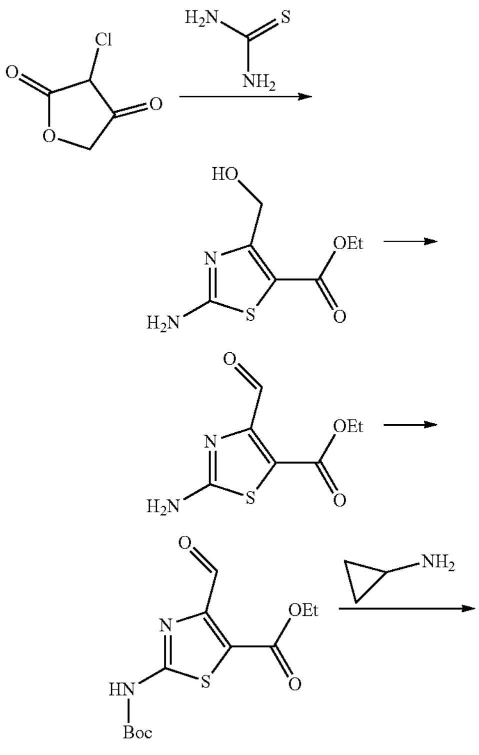

-continued

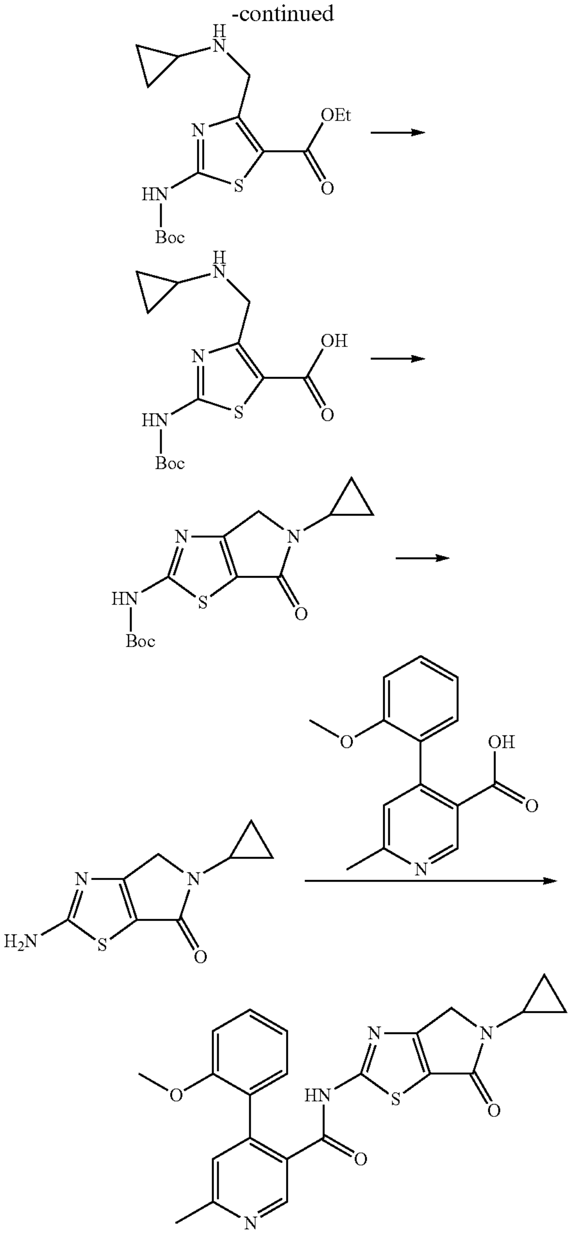

Step 7: To a solution or 3-chlorofuran-2,4(3H,5H)-dione (2 g, 15 mmol) in EtOH (12 mL) at room temperature was added thiourea (1.3 g, 17 mmol) and the mixture was heated at reflux for 4 h. The mixture was concentrated under reduced pressure and the residue poured into 1 M HCl, then basified with a saturated aqueous $Na_2CO_3$ solution. The resulting solid was collected by filtration and dried in vacuo to give ethyl 2-amino-4-(hydroxymethyl)thiazole-5-carboxylate (2.2 g, 73%). LCMS: m/z=203 $[M+H]^+$ Step 2: To a solution of ethyl 2-amino-4-(hydroxymethyl) thiazole-5-carboxylate (1.45 g, 7.17 mmol) in THF (20 mL) at room temperature was added $MnO_2$ (3.1 g, 35.9 mmol) and the mixture was stirred overnight. After filtration, the filtrate was concentrated under reduced pressure and the residue purified by silica gel chromatography (0-2% MeOH/DCM) to give ethyl 2-amino-4-formylthiazole-5-carboxylate (675 mg, 48%) as a yellow solid. LCMS: m/z=201 $[M+H]^+$.

Step 3: To a solution of ethyl 2-amino-4-formylthiazole-5-carboxylate (670 mg, 3.34 mmol) and $(Boc)_2O$ (730 mg, 3.34 mmol) in DCM (6 mL) was added DMAP (81 mg, 0.66 mmol) and TEA (372 mg, 3.68 mmol) and the mixture was heated at 85° C. overnight. The mixture was diluted with water (50 mL), extracted with DCM (3×20 mL) and the combined organic layers washed with water (50 mL), brine (50 mL), dried over $Na_2SO_4$, filtered and concentrated under reduced pressure. The residue was purified by prep-TLC (DCM/MeOH=20/1, v/v) to give ethyl 2-((tert-butoxycarbonyl)amino)-4-formylthiazole-5-carboxylate (173 mg, 17%) as a yellow solid. LCMS: m/z=301 $[M+H]^+$, $^1H$ NMR (400 MHz, DMSO-$d_6$) δ 10.4 (s, 1H), 4.34 (d, J=7.0 Hz, 2H), 1.49 (d, J=3.0 Hz, 9H), 1.32 (t, J=7.0 Hz, 3H).

Step 4: To a mixture of ethyl 2-((tert-butoxycarbonyl) amino)-4-formylthiazole-5-carboxylate (170 mg, 0.56 mmol) and cyclopropanamine (48 mg, 0.84 mmol) in DCE (2 mL) was added acetic acid (catalytic) and the mixture was heated at 50° C. overnight in a sealed tube. After cooling to 0° C., $NaBH_4$ (21 mg, 0.56 mmol) was added and the mixture was stirred at room temperature for 2 h. The mixture was diluted with water (30 mL), extracted with EtOAc (3×30 mL) and the combined organic layers washed with water (30 mL), brine (30 mL), dried over $Na_2SO_4$, filtered and concentrated under reduced pressure. The residue was purified by prep-TLC (DCM/MeOH=10/1, v/v) to give ethyl 2-((tert-butoxycarbonyl)amino)-4-((cyclopropylamino) methyl)thiazole-5-carboxylate (141 mg, 73%) as a yellow solid. LCMS: m/z=342 $[M+H]^+$, $^1H$ NMR (400 MHz, DMSO-$d_6$): δ 4.24 (q, J=7.0 Hz, 2H), 4.04 (s, 2H), 3.17 (s, 2H), 1.49 (s, 9H), 1.28 (t, J=7.0 Hz, 3H), 0.40-0.35 (m, 2H), 0.28 (t, J=2.8 Hz, 2H).

Step 5: To a solution of ethyl 2-((tert-butoxycarbonyl) amino)-4-((cyclopropylamino)methyl)thiazole-5-carboxylate (140 mg, 0.41 mmol) in THF (2 mL) and water (2 mL) at room temperature was added LiOH (29 mg, 1.2 mmol) and the mixture was stirred overnight. The mixture was concentrated under reduced pressure to afford 2-((tert-butoxycarbonyl)amino)-4-((cyclopropylamino)methyl)thiazole-5-carboxylic acid (128 mg), which was directly in the next step without further purification. LCMS: m/z=314 $[M+H]^+$.

Step 6: To a solution of 2-((tert-butoxycarbonyl)amino)-4-((cyclopropylamino)methyl)thiazole-5-carboxylic acid (128 mg) in DMF (2 mL) at 0° C. was added T3P (50% in DMF, 779 mg, 2.4 mmol) and the mixture was stirred at room temperature for 2 h. The mixture was diluted with water (20 mL), extracted with EtOAc (3×20 mL) and the combined organic layers washed with water (20 mL), brine (20 mL), dried over $Na_2SO_4$, filtered and concentrated under reduced pressure to give tert-butyl (5-cyclopropyl-6-oxo-5,6-dihydro-4H-pyrrolo[3,4-d]thiazol-2-yl)carbamate (178 mg) which was used directly in the next step without further purification. LCMS: m/z=296 $[M+H]^+$. $^1H$ NMR (400 MHz, DMSO-$d_6$): δ 12.0 (s, 1H), 4.31 (s, 2H), 2.80 (tt, J=7.2, 4.0 Hz, 1H), 1.50 (s, 9H), 0.80-0.76 (m, 2H), 0.76-0.72 (m, 2H).

Step 7: To a solution of tert-butyl (5-cyclopropyl-6-oxo-5,6-dihydro-4H-pyrrolo[3,4-d]thiazol-2-yl)carbamate (100 mg, 0.31 mmol) in 1,4-dioxane (3 mL) was added 4 M HCl/1,4-dioxane (3 mL) and the mixture was stirred at room temperature overnight. The solvent was removed under reduced pressure to give 2-amino-5-cyclopropyl-4,5-dihydro-6H-pyrrolo[3,4-d]thiazol-6-one (60 mg), which was used directly in the next step without further purification. LCMS: m/z=196 $[M+H]^+$.

Step 8: To a solution of 4-(2-methoxyphenyl)-6-methylnicotinic acid (66 mg, 0.33 mmol) in NMP (3 mL) was added HATU (154 mg, 0.4 mmol) and DIPEA (218 mg, 1.69 mmol) and the mixture was stirred at room temperature for 30 min. 2-Amino-5-cyclopropyl-4,5-dihydro-6H-pyrrolo[3,4-d]thiazol-6-one (98 mg, 0.4 mmol) was added and stirring was continued at room temperature overnight. The mixture was diluted with water (40 mL), extracted with EtOAc (3×20 mL) and the combined organic layers washed with water (40 mL), brine (40 mL), dried over $Na_2SO_4$, filtered and concentrated under reduced pressure. The residue was purified by prep-TLC (DCM/MeOH=20/1, v/v) to give N-(5-cyclopropyl-6-oxo-5,6-dihydro-4H-pyrrolo[3,4-d]thiazol-2-yl)-4-(2-methoxyphenyl)-6-methylnicotinamide (6.8 mg, 4%) as a yellow solid. LCMS: m/z=421 $[M+H]^+$, $^1H$ NMR (400 MHz, DMSO-$d_6$) δ 13.0 (s, 1H), 8.67 (s, 1H), 7.42-7.36 (m, 2H), 7.32 (s, 1H), 7.08 (t, J=7.2 Hz, 1H), 6.96 (d, J=8.0 Hz, 1H), 4.38 (s, 2H), 3.45 (s, 3H), 2.57 (s, 3H), 2.01-1.94 (m, 1H), 0.81-0.73 (m, 4H).

Example 136: Synthesis of N-(5-Cyclopropyl-4-oxo-5,6-dihydro-4H-pyrrolo[3,4-d]thiazol-2-yl)-4-(2-methoxyphenyl)-6-methylnicotinamide

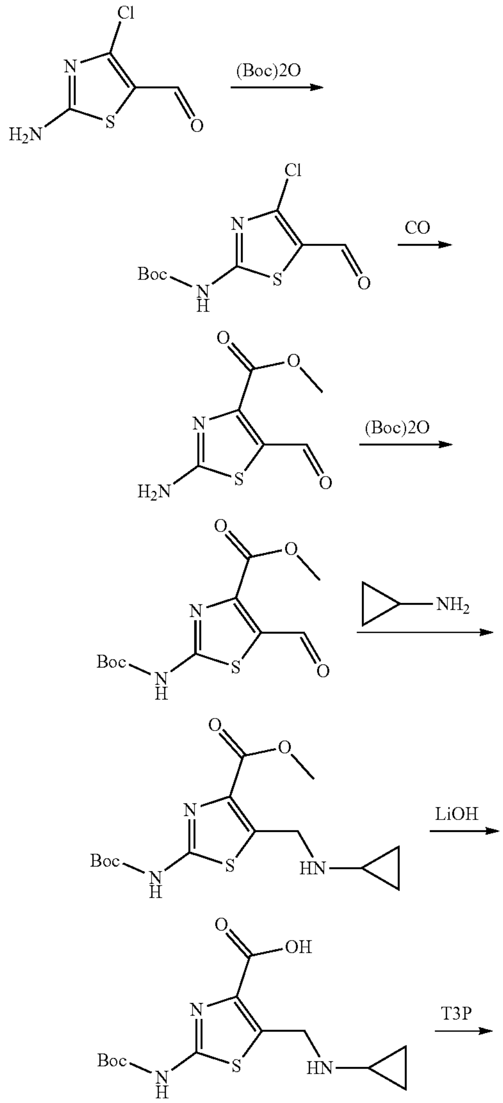

-continued

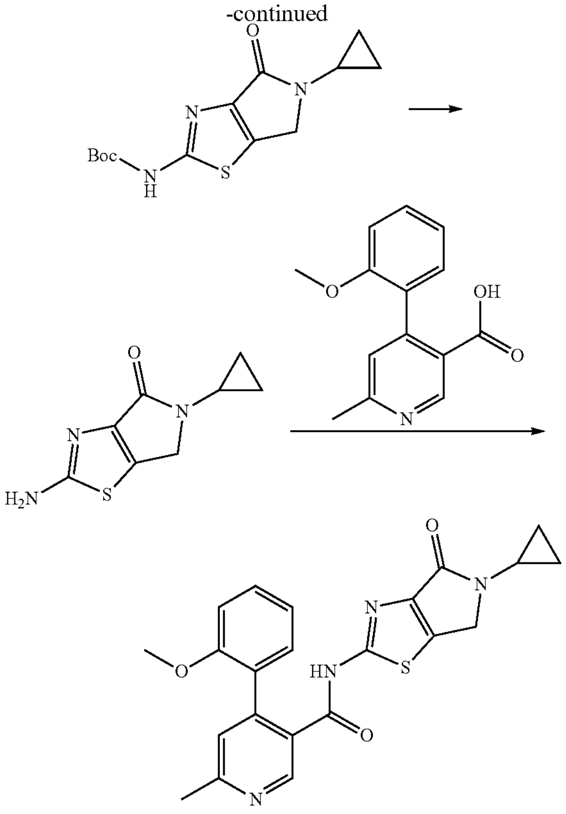

Step 1: A mixture of 2-amino-4-chlorothiazole-5-carbaldehyde (1 g, 6 mmol), $(Boc)_2O$ (2 g, 9.2 mmol), DMAP (75 mg, 0.6 mmol) and TEA (1.24 g, 12.3 mmol) in DMF (20 mL) was stirred at room temperature for 2 h. The mixture was diluted with water (200 mL), extracted with EtOAc (2×200 mL) and the combined organic layers washed with brine (50 mL), dried over $Na_2SO_4$, filtered and concentrated under reduced pressure. The residue was purified by silica gel chromatography (5-10% EtOAc/Petroleum ether) to give tert-butyl (4-chloro-5-formylthiazole-2-yl)carbamate (1.34 g, 84%) as a yellow solid. LCMS: m/z=261 $[M-H]^-$, $^1H$ NMR (400 MHz, DMSO-$d_6$) δ 12.5 (s, 1H), 9.87 (s, 1H), 1.51 (s, 9H)

Step 2: A mixture of tert-butyl (4-chloro-5-formylthiazole-2-yl)carbamate (500 mg, 1.9 mmol), Pd(dppf)$Cl_2$ (69 mg, 0.1 mmol) and TEA (385.2 mg, 3.8 mmol) in MeOH (10 mL) was heated at 100° C. in a sealed vessel under a CO atmosphere (1 MPa) overnight. The mixture was concentrated under reduced pressure and the residue was diluted with water (30 mL) and extracted with EtOAc (3×40 mL). The combined organic layers were washed with brine (30 mL), dried over $Na_2SO_4$, filtered and concentrated under reduced pressure. The residue was purified by prep-TLC (DCM/MeOH=20/1, v/v) to give methyl 2-amino-5-formylthiazole-4-carboxylate (30 mg, 9%) as a brown solid. LCMS: m/z=185 $[M-H]^-$, $^1H$ NMR (400 MHz_, DMSO-$d_6$) δ 10.1 (s, 1H), 8.40 (s, 2H), 3.85 (s, 3H).

Step 3: A mixture of methyl 2-amino-5-formylthiazole-4-carboxylate (30 mg, 0.16 mmol), $(Boc)_{20}$ (52.7 mg, 0.24 mmol), DMAP (2.0 mg, 0.02 mmol) and TEA (32.6 mg, 0.32 mmol) in DMF (1 mL) was stirred at room temperature for 2 h. The mixture was diluted with water (10 mL), extracted with EtOAc (3×10 mL) and the combined organic layers washed with brine (10 mL), dried over $Na_2SO_4$, filtered and concentrated under reduced pressure. The residue was purified by prep-TLC (DCM/MeOH=20/1, v/v) to give methyl 2-((tert-butoxycarbonyl)amino)-5-formylthiazole-4-carboxylate (20 mg, 43%) as a white solid. LCMS: m/z=285 $[M-H]^-$.

Step 4: A mixture of methyl 2-((tert-butoxycarbonyl) amino)-5-formylthiazole-4-carboxylate (50 mg, 0.17 mmol), cyclopropanamine (50 mg, 0.87 mmol) and one drop of AcOH in MeOH (0 mL) was heated at 50° C. in a sealed-tube overnight. After cooling to 0° C., $NaBH_4$ (13.2 mg, 0.35 mmol) was added and the mixture was stirred at room temperature for 2 h. The mixture was diluted with water (20 mL), extracted with DCM (3×20 mL) and the combined organic layers washed with brine (10 mL), dried over $Na_2SO_4$, filtered and concentrated under reduced pressure. The residue was purified by prep-TLC (DCM/MeOH=20/1, v/v) to give methyl 2-((tert-butoxycarbonyl) amino)-5-((cyclopropylamino)methyl)thiazole-4-carboxylate (65 mg, 81%) as a white solid. LCMS: m/z=328 $[M+H]^+$, $^1H$ NMR (400 MHz, DMSO-$d_6$): δ 11.6 (s, 1H), 4.24 (s, 2H), 3.78 (s, 3H), 3.51 (s, 1H), 2.25 (s, 1H), 1.47 (s, 9H), 0.49-0.35 (m, 4H).

In Step 5: To a solution of methyl 2-((tert-butoxycarbonyl)amino)-5-((cyclopropylamino)methyl)thiazole-4-carboxylate (65 mg, 0.2 mmol) in THF (0.5 mL) and MeOH (0.5 mL) was added LiOH (14.3 mg, 0.6 mmol) and water (1 mL) and the mixture was stirred at room temperature overnight. The mixture was concentrated under reduced pressure to give 2-((tert-butoxycarbonyl)amino)-5-((cyclopropylamino)methyl)thiazole-4-carboxylic acid (62 mg), which was used directly in the next step. LCMS: m/z=314 $[M+H]^+$ Step 6: A mixture of 2-((tert-butoxycarbonyl)amino)-5-((cyclopropylamino)methyl)thiazole-4-carboxylic acid (62 mg, 0.2 mmol) and DIPEA (77 mg, 0.6 mmol) in DMF (2 mL) was stirred at room temperature for 2 min, then cooled to 0° C. and T3P (189 mg, 0.3 mmol) was added. The mixture was allowed to warm to room temperature and stirred for 2 h. The mixture was diluted with water (20 mL), extracted with EtOAc (3×20 mL) and the combined organic layers washed with brine (10 mL), dried over $Na_2SO_4$, filtered and concentrated under reduced pressure. The residue was purified by prep-TLC (DCM/MeOH=20/1, v/v) to give tert-butyl (5-cyclopropyl-4-oxo-5,6-dihydro-4H-pyrrolo[3,4-d-]dithiazol-2-yl)carbamate (40 mg, 69%) as a white solid. LCMS: m/z=294 $[M-H]^-$, $^1H$ NMR (400 MHz, DMSO-$d_6$) δ 11.7 (s, 1H), 4.39 (s, 2H), 2.79 (tt, J=7.2, 4.2 Hz, 1H), 1.49 (s, 9H), 0.76 (tt, J=7.2, 2.4 Hz, 4H).

Step 7: To a solution of tert-butyl (5-cyclopropyl-4-oxo-5,6-dihydro-4H-pyrrolo[3,4-d]thiazol-2-yl)carbamate (130 mg, 0.44 mmol) in MeOH (1 mL) was added 4 M HCl/MeOH (4 mL) and the mixture was stirred at room temperature overnight. The mixture was concentrated under reduced pressure to give 2-amino-5-cyclopropyl-5,6-dihydro-4H-pyrrolo[3,4-d]thiazol-4-one, which was used directly in the next step. LCMS: m/z=196 $[M+H]^+$.

Step 8: A mixture of 4-(2-methoxyphenyl)-6-methylnicotinic acid (53.6 mg, 0.22 mmol), 2-amino-5-cyclopropyl-5,6-dihydro-4H-pyrrolo[3,4-d]thiazol-4-one (43 mg, 0.22 mmol), HATU (100 mg, 0.26 mmol) and DIPEA (142 mg, 1.1 mmol) in NMP (2 mL) was stirred at room temperature overnight then heated at 50° C. overnight. The mixture was diluted with water (20 mL), extracted with EtOAc (3×20 mL) and the combined organic layers washed with brine (10 mL), dried over $Na_2SO_4$, filtered, and concentrated under reduced pressure. The residue was purified by prep-TLC (DCM/MeOH=20/1, v/v) to give N-(5-cyclopropyl-4-oxo-5,6-dihydro-4H-pyrrolo[3,4-d]thiazol-2-yl)-4-(2-methoxyphenyl)-6-methylnicotinamide (8 mg, 9%) as a white solid. LCMS: m/z=421 $[M+H]^+$, $^1H$ NMR (400 MHz, DMSO-$d_6$) δ 12.7 (s, 1H), 8.66 (s, 1H), 7.41-7.34 (m, 2H), 7.31 (s, 1H), 7.07 (t, J=7.4 Hz, 1H), 6.96 (d, J=8.2 Hz, 1H), 4.42 (s, 2H), 3.46 (s, 3H), 2.57 (s, 3H), 2.04-1.93 (m, 1H), 0.86-0.74 (m, 4H).

Example 137: Synthesis of (Racemic)-4-(2-Methoxyphenyl)-6-methyl-N-(6-(phenylamino)-4,5,6,7-tetrahydrobenzo[d]thiazol-2-yl)nicotinamide

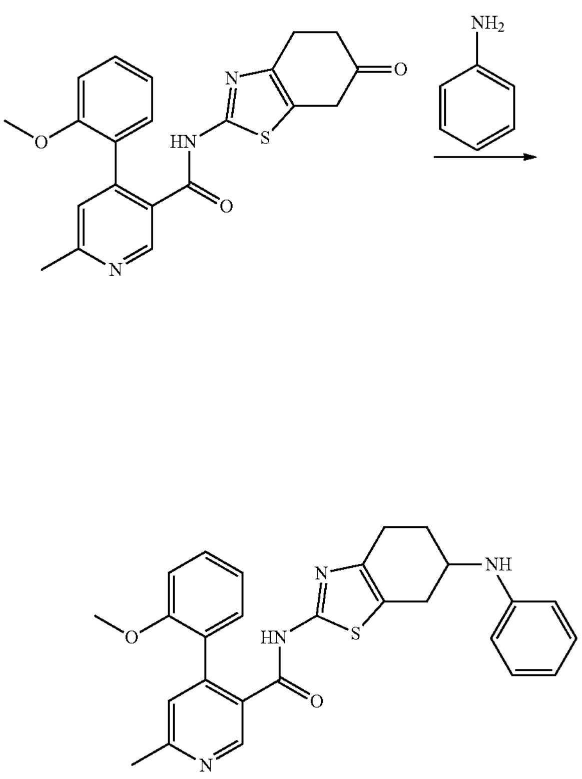

A mixture of 4-(2-methoxyphenyl)-6-methyl-N-(6-oxo-4,5,6,7-tetrahydrobenzo[d]thiazol-2-yl)nicotinamide (300 mg, 0.762 mmol), aniline (142 mg, 1.52 mmol), acetic acid (catalytic) and $NaBH(OAc)_3$ (323 mg, 1.52 mmol) in DCE (5 mL) was stirred at RT overnight. The mixture was poured into water (30 mL), extracted with EtOAc (3×20 mL) and the combined organic layers washed with brine (10 mL), dried over $Na_2SO_4$, filtered and concentrated under reduced pressure. The residue was purified by silica gel chromatography (0-2% MeOH/DCM) then prep-TLC (DCM/MeOH=50/1, v/v) to afford (Racemic)-4-(2-methoxyphenyl)-6-methyl-N-(6-(phenylamino)-4,5,6,7-tetrahydrobenzo[d]thiazol-2-yl)nicotinamide (85 mg, 23%) as a yellow solid. LCMS: m/z=471 $[M+H]^+$, $^1H$ NMR (400 MHz, DMSO-$d_6$) δ 12.3 (s, 1H), 8.61 (s, 1H), 7.41-7.29 (m, 2H), 7.28 (s, 1H), 7.10-7.02 (m, 3H), 6.98 (d, J=8.2 Hz, 1H), 6.64 (d, J=8.0 Hz, 2H), 6.52 (t., J=7.2 Hz, 1H), 5.58 (d, J=8.1 Hz, 1H), 3.81-3.69 (m, 1H), 3.51 (s, 3H), 3.02 (dd, J=15.9, 5.0 Hz, 1H), 2.79-2.68 (m, 2H), 2.58-2.52 (m, 4H), 2.15-2.03 (m, 1H), 1.79-1.67 (m, 1H).

TABLE H

The following examples were prepared from 2'-chloro-5'-methoxy-6-methyl-N-(6-oxo-4,5,6,7-tetrahydrobenzo[d]thiazol-2-yl)-[4,4'-bipyridine]-3-carboxamide using a similar procedure to that described for Example 137

| Ex. No. | Structure | Compound Name | LCMS $[M + H]^+$ | NMR |
|---|---|---|---|---|
| 138 | 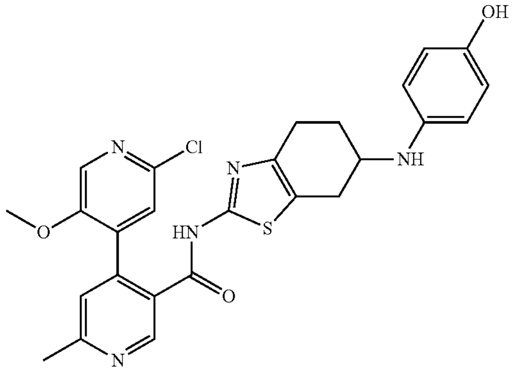 [SMILES: COc1cnc(Cl)cc1-c1cc(C)ncc1C(=O)Nc1nc2c(s1)CC(Nc1ccc(O)cc1)CC2] | (Racemic)-2'-Chloro-N-(6-((4-hydroxyphenyl) amino)-4,5,6,7-tetrahydrobenzo[d] thiazol-2-yl)-5'-methoxy-6-methyl-[4,4'-bipyridine]-3-carboxamide | 522 | $^1$H NMR (400 MHz, DMSO-$d_6$) δ 12.5 (s, 1H), 8.76 (s, 1H), 8.40 (s, 1H), 8.16 (s, 1H), 7.50 (s, 1H), 7.40 (s, 1H), 6.57-6.48 (m, 4H), 4.95-4.81 (m, 1H), 3.68-3.56 (m, 4H), 3.03-2.93 (m, 1H), 2.77-2.68 (m, 2H), 2.58 (s, 3H), 2.11-2.02 (m, 1H), 1.75-1.62 (m, 1H) |
| 139 | 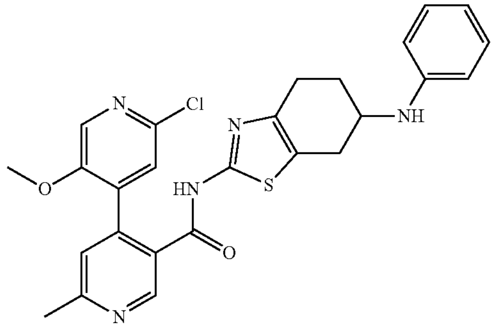 [SMILES: COc1cnc(Cl)cc1-c1cc(C)ncc1C(=O)Nc1nc2c(s1)CC(Nc1ccccc1)CC2] | (Racemic)-2'-Chloro-5'-methoxy-6-methyl-N-(6-(phenylamino)-4,5,6,7-tetrahydrobenzo[d] thiazol-2-yl)-[4,4'-bipyridine]-3-carboxamide | 506 | $^1$H NMR (400 MHz, DMSO-$d_6$) δ 12.5 (s, 1H), 8.78 (s, 1H), 8.16 (s, 1H), 7.52 (s, 1H), 7.46 (s, 1H), 7.20-7.14 (m, 2H), 6.82 (d, J = 7.8 Hz, 2H), 6.74 (s, 1H), 6.26 (s, 1H), 3.85-3.77 (m, 1H), 3.62 (s, 3H), 3.02 (dd. J = 16.0, 5.0 Hz, 1H), 2.78-2.68 (m, 2H), 2.65-2.55 (m, 4H), 2.14-2.06 (m, 1H), 1.84-1.74 (m, 1H) |
| 140 | 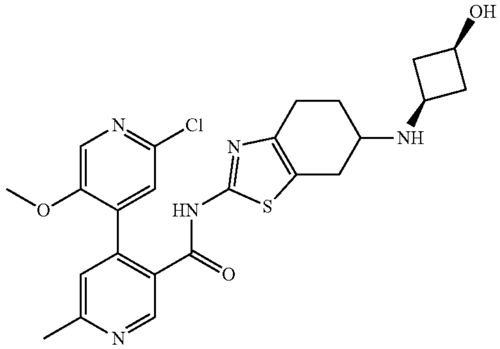 [SMILES: COc1cnc(Cl)cc1-c1cc(C)ncc1C(=O)Nc1nc2c(s1)CC(N[C@H]1C[C@@H](O)C1)CC2] | 2'-Chloro-N-(6-(((1s,3s)-3-hydroxycyclobutyl) amino)-4,5,6,7-tetrahydrobenzo[d] thiazol-2-yl)-5'-methoxy-6-methyl-[4,4'-bipyridine]-3-carboxamide | 500 | $^1$H NMR (400 MHz, DMSO-$d_6$) δ 12.5 (s, 1H), 8.76 (s, 1H), 8.16 (s, 1H), 7.52 (s, 1H), 7.42 (s, 1H), 3.93-3.87 (m, 1H), 3.60 (s, 3H), 3.47-3.38 (m, 1H), 3.12-3.04 (m, 1H), 2.78-2.64 (m, 4H), 2.58 (s, 3H), 2.57-2.54 (m, 2H), 2.22-2.11 (m, 1H), 2.05-1.76 (m, 3H) |
| 141 | 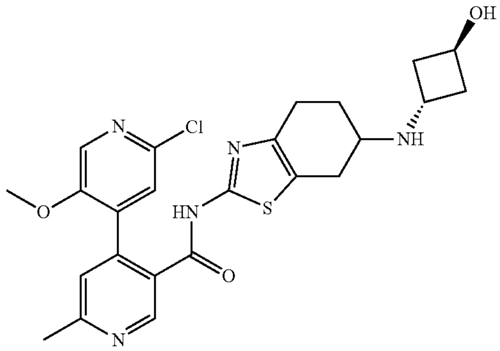 [SMILES: COc1cnc(Cl)cc1-c1cc(C)ncc1C(=O)Nc1nc2c(s1)CC(N[C@H]1C[C@H](O)C1)CC2] | 2'-Chloro-N-(6-(((1r,3r)-3-hydroxycyclobutyl) amino)-4,5,6,7-tetrahydrobenzo[d] thiazol-2-yl)-5'-methoxy-6-methyl-[4.4'-bipyridine]-3-carboxamide | 500 | $^1$H NMR (400 MHz, DMSO-$d_6$) δ 12.5 (s, 1H), 8.76 (s, 1H), 8.16 (s, 1H), 7.52 (s, 1H), 7.41 (s, 1H), 4.41-4.32 (m, 1H), 3.96-3.84 (m, 1H), 3.61 (s, 3H), 3.49-3.36 (m, 1H), 3.12-3.02 (m, 1H), 2.81-2.65 (m, 3H), 2.58 (s, 3H), 2.47-2.38 (m, 2H), 2.25-2.08 (m, 3H), 1.95-1.81 (m, 1H) |

TABLE H-continued

The following examples were prepared from 2'-chloro-5'-methoxy-6-methyl-N-(6-oxo-4,5,6,7-tetrahydrobenzo[d]thiazol-2-yl)-[4,4'-bipyridine]-3-carboxamide using a similar procedure to that described for Example 137

| Ex. No. | Structure | Compound Name | LCMS [M + H]+ | NMR |
| --- | --- | --- | --- | --- |
| 142 | 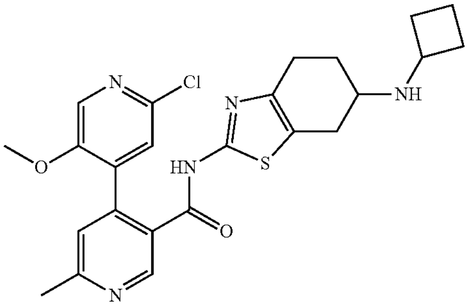 [SMILES: COc1cnc(Cl)cc1-c1cc(C)ncc1C(=O)Nc1nc2c(s1)CC(NC1CCC1)CC2] | (Racemic)-2'-Chloro-N-(6-(cyclobutylamino)-4,5,6,7-tetrahydrobenzo[d]thiazol-2-yl)-5'-methoxy-6-methyl-[4,4'-bipyridine]-3-carboxamide | 484 | $^1$H NMR (400 MHz, DMSO-$d_6$) δ 12.5 (s, 1H), 9.13 (s, 1H), 8.76 (s, 1H), 8.16 (s, 1H), 7.51 (s, 1H), 7.41 (s, 1H), 3.88-3.76 (m, 1H), 3.60 (s, 3H), 3.45-3.36 (m, 1H), 3.13-3.02 (m, 1H), 2.78-2.64 (m, 3H), 2.58 (s, 3H), 2.27-2.11 (m, 5H), 1.90-1.70 (m, 3H) |

Example 143A & 143B: Synthesis of (R or S)-4-(2-Methoxyphenyl)-6-methyl-N-(6-(phenylamino)-4,5,6,7-tetrahydrobenzo[d]thiazol-2-yl)nicotinamide (143A) & (S or R)-4-(2-Methoxyphenyl)-6-methyl-N-(6-(phenylamino)-4,5,6,7-tetrahydrobenzo[d]thiazol-2-yl)nicotinamide (143B) with arbitrarily assigned stereochemistry

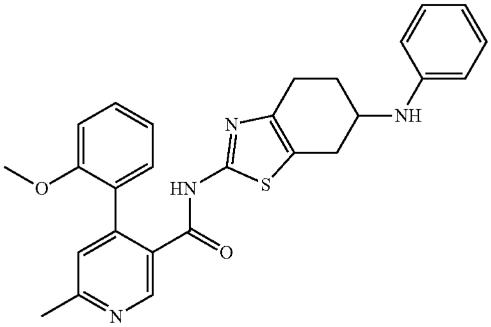

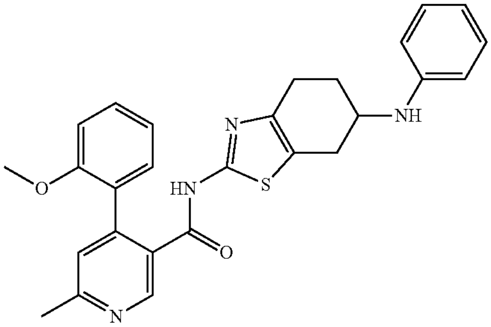

4-(2-methoxyphenyl)-6-methyl-N-(6-(phenylamino)-4,5,6,7-tetrahydrobenzo[d]thiazol-2-yl)nicotinamide (Example 137) was purified by chiral SFC (Column: Daicel Chiralpak, AS 20*250 mm, 10 um; Mobile Phase: 30% MeOH (0.2% $NH_3$ modifier), 70% carbon dioxide; Flow rate: 100 mL/min) to afford two peaks:

Example 143A: Peak 1, retention time 2.49 min. LCMS: m/z=471 [M+H]$^+$, $^1$H NMR (MeOD, 400 MHz) S 8.50 (s, 1H), 7.32-7.25 (m, 3H), 7.03-6.95 (m, 3H), 6.86 (d, J=8.4 Hz, 1H), 6.59 (d, J=8.0 Hz, 2H), 6.53 (t, J=7.2 Hz, 1H), 3.75-3.66 (m, 1H), 3.49 (s, 3H), 3.03-2.98 (m, 1H), 2.56-2.44 (m, 6H), 2.09-2.04 (m, 1H), 1.74-1.62 (m, 1H).

Example 143B: Peak 2, retention time 3.18 min. LCMS: m/z=471 [M+H]$^+$, $^1$H NMR (MeOD, 400 MHz) δ 8.50 (s, 1H), 7.32-7.25 (m, 3H), 7.03-6.95 (m, 3H), 6.86 (d, J=8.4 Hz, 1H), 6.59 (d, J=8.0 Hz, 2H), 6.53 (t, J=7.2 Hz, 1H), 3.75-3.66 (m, 1H), 3.49 (s, 3H), 3.03-2.98 (m, 1H), 2.56-2.44 (m, 6H), 2.09-2.04 (m, 1H), 1.74-1.62 (m, 1H).

Example 144: Synthesis of (Racemic)-4-(2-Methoxyphenyl)-6-methyl-N-(6-phenoxy-4,5,6,7-tetrahydrobenzo[d]thiazol-2-yl)nicotinamide

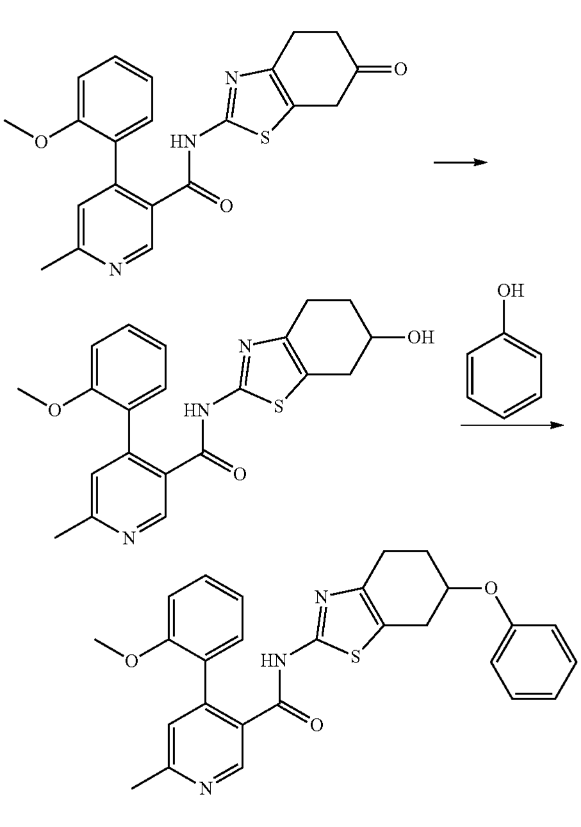

Step 1: To a solution of 4-(2-methoxyphenyl)-6-methyl-N-(6-oxo-4,5,6,7-tetrahydrobenzo[d]thiazol-2-yl)nicotinamide (30 mg, 0.076 mmol) in MeOH (2 mL) was added $NaBH_4$ (6 mg, 0.152 mmol) and the mixture was stirred at room temperature for 0.5 h. The mixture was diluted with water (10 mL), extracted with DCM (3×10 mL) and the combined organic layers washed with brine (10 mL), dried over $Na_2SO_4$, filtered and concentrated under reduced pressure. The residue was purified by prep-TLC (DCM/MeOH=20/1, v/v) to afford N-(6-hydroxy-4,5,6,7-tetrahydrobenzo[d]thiazol-2-yl)-4-(2-methoxyphenyl)-6-methylnicotinamide (20 mg, 66%) as a white solid. LCMS: m/z=396[M+H]$^+$. $^1$H NMR (400 MHz, DMSO-$d_6$): δ 12.2 (s, 1H), 8.60 (s, 1H), 7.40-7.34 (m, 1H), 7.34-7.30 (m, 1H), 7.27 (s, 1H), 7.08-7.02 (m, 1H), 6.97 (d, J=8.2 Hz, 1H), 4.92-4.85 (m, 1H), 4.03-3.94 (m, 1H), 3.50 (s, 3H), 2.91-2.81 (m, 1H), 2.72-2.53 (m, 5H), 2.49-2.44 (m, 1H), 1.94-1.84 (m, 1H), 1.80-1.68 (m, 1H).

Step 2: To a solution of N-(6-hydroxy-4,5,6,7-tetrahydrobenzo[d]thiazol-2-yl)-4-(2-methoxyphenyl)-6-methylnicotinamide (250 mg, 0.632 mmol), phenol (89 mg, 0.95 mmol) and $PPh_3$ (331 mg, 1.26 mmol) in DCM (6 mL) was added DIAD (255 mg, 1.26 mmol) and the mixture was stirred at room temperature overnight. The mixture was poured into water (50 mL), extracted with EtOAc (3×30 mL) and the combined organic layers washed with brine (30 mL), dried over $Na_2SO_4$, filtered and concentrated under reduced pressure. The residue was purified by prep HPLC and prep-TLC (DCM/MeOH=40/1, v/v) to afford (Racemic)-4-(2-methoxyphenyl)-6-methyl-N-(6-phenoxy-4,5,6,7-tetrahydrobenzo[d]thiazol-2-yl)nicotinamide (36 mg, 12%) as a white solid. LCMS: m/z=472 [M+H]$^+$, $^1$H NMR (400 MHz, DMSO-$d_6$): δ 12.3 (s, 1H), 8.62 (s, 1H), 7.41-7.35 (m, 1H), 7.34-7.25 (m, 4H), 7.09-7.03 (m, 1H), 7.02-6.96 (m, 3H), 6.96-6.90 (m, 1H), 4.88 (s, 1H), 3.51 (s, 3H), 3.15-3.07 (m, 1H), 2.83-2.68 (m, 3H), 2.56 (s, 3H), 2.13-1.98 (m, 2H).

Example 145: Synthesis of N-(6,7-Dihydro-4H-pyrano[4,3-d]thiazol-2-yl)-4-(2-methoxyphenyl)-6-methylnicotinamide

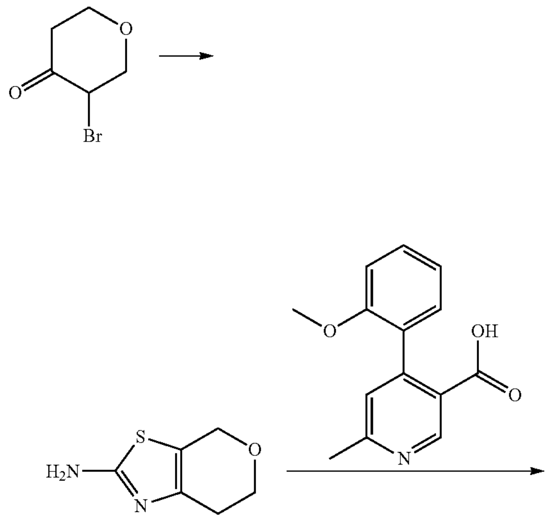

-continued

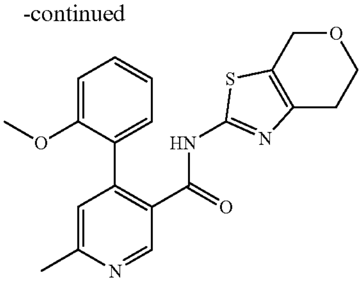

Step 1: A solution of 3-bromotetrahydro-4H-pyran-4-one (200 mg, 1.12 mmol), thiourea (85 mg, 1.12 mmol) and $NaHCO_3$ (93 mg, 1.12 mmol) in EtOH (8 mL) was heated at reflux for 4 h. The mixture was concentrated under reduced pressure and the residue purified by prep-TLC (DCM/MeOH=20/1, v/v) to give 6,7-dihydro-4H-pyrano[4,3-d]thiazol-2-amine (160 mg, 93%) as a yellow solid. LCMS: m/z=157 [M+H]$^+$, $^1$H NMR (400 MHz, DMSO-$d_6$): δ 6.79 (s, 2H), 4.49 (t., =2.2 Hz, 2H), 3.83 (t., =5.6 Hz, 2H), 2.47 (q., =3.4, 2.8 Hz, 2H).

Step 2: A mixture of 4-(2-methoxyphenyl)-6-methylnicotinic acid (50 mg, 0.20 mmol), HATU (120 mg, 0.30 mmol) and DIPEA (79 mg, 0.061 mmol) in NMP (4 mL) was stirred at room temperature for 2 h, 6,7-Dihydro-4H-pyrano[4,3-d]thiazol-2-amine (35 mg, 0.22 mmol) was then added and the mixture heated at 80° C. overnight. The mixture was diluted with water (10 mL), extracted with EtOAc (30 mL×3) and the combined organic layers were washed with brine (20 mL), dried over $Na_2SO_4$, filtered and concentrated under reduced pressure. The residue was purified by prep-TLC (DCM/MeOH=20/1, v/v) to give N-(6,7-dihydro-4H-pyrano[4,3-d]thiazol-2-yl)-4-(2-methoxyphenyl)-6-methylnicotinamide (41 mg, 52%) as a yellow solid. LCMS: m/z=382 [M+H]$^+$, $^1$H NMR (400 MHz, DMSO-$d_6$): δ 12.4 (s, 1H), 8.62 (s, 1H), 7.40-7.31 (m, 2H), 7.28 (s, 1H), 7.06 (t, J=7.6 Hz, 1H), 6.97 (d, J=8.2 Hz, 1H), 4.67 (s, 2H), 3.91 (t, J=5.6 Hz, 2H), 3.50 (s, 3H), 2.68 (d, J=5.8 Hz, 2H), 2.56 (s, 3H).

Example 146: Synthesis of tert-Butyl 2-(4-(2-methoxyphenyl)-6-methylnicotinamido)-4,6-dihydro-5H-pyrrolo[3,4-d]thiazole-5-carboxylate

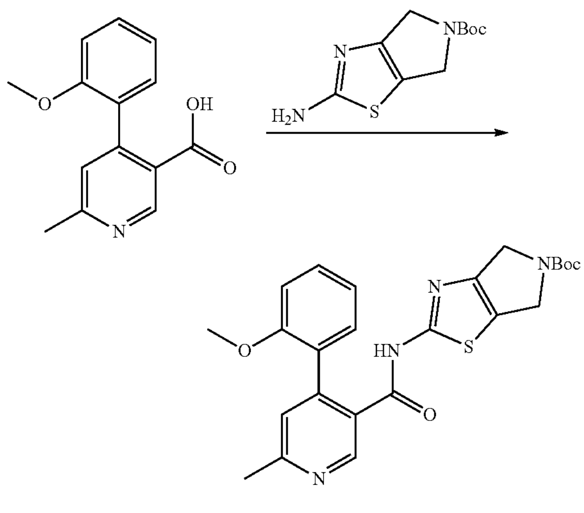

A mixture of 4-(2-methoxyphenyl)-6-methylnicotinic acid (300 mg, 1.23 mmol), HATU (563 mg, 1.48 mmol) and DIPEA (477 mg, 3.69 mmol) in NMP (6 mL) was stirred at room temperature for 3 h. tert-Butyl 2-amino-4,6-dihydro-5H-pyrrolo[3,4-d]thiazole-5-carboxylate (386 mg, 1.59 mmol) was added and stirring was continued at room temperature overnight. The mixture was diluted with water (10 mL), extracted with EtOAc (3x20 mL) and the combined organic phases washed with water (30 mL), brine (20 mL), dried over $Na_2SO_4$, filtered and concentrated under reduced pressure. The residue was purified by prep-TLC (DCM/MeOH=40/1, v/v) to give tert-butyl 2-(4-(2-methoxyphenyl)-6-methylnicotinamido)-4,6-dihydro-5H-pyrrolo[3,4-d]thiazole-5-carboxylate (36 mg, 8%) as a yellow solid. LCMS: m/z=467 $[M+H]^+$, $^1H$ NMR (400 MHz, DMSO-$d_6$): δ 7.82 (s, 1H), 6.58 (d, J=7.6 Hz, 2H), 6.55 (s, 1H), 6.30-6.25 (m, 1H), 6.14 (d, J=8.4 Hz, 1H), 3.83-3.76 (m, 2H), 3.59 (d, J=3.6 Hz, 2H), 2.77 (s, 3H), 1.83 (s, 3H), 0.71 (s, 9H).

Example 147: Synthesis of N-(5,6-Dihydro-4H-pyrrolo[3,4-d]thiazol-2-yl)-4-(2-methoxyphenyl)-6-methylnicotinamide

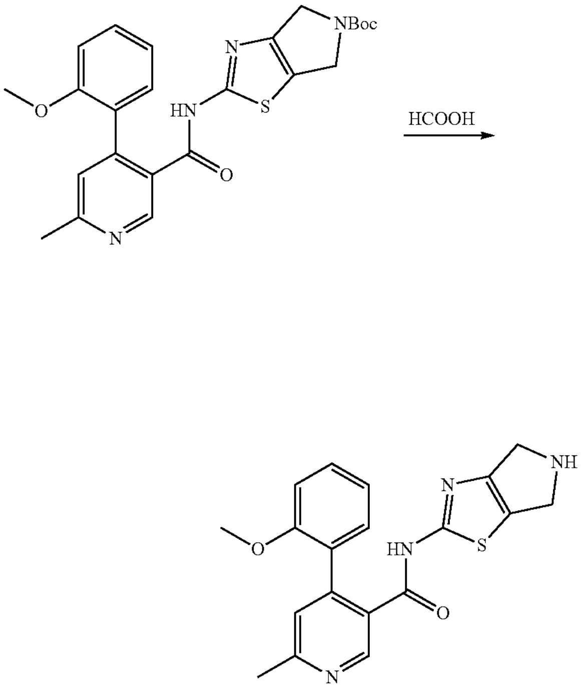

A mixture of tert-butyl 2-(4-(2-methoxyphenyl)-6-methylnicotinamido)-4,6-dihydro-5H-pyrrolo[3,4-d]thiazole-5-carboxylate (62 mg, 0.13 mmol) and formic acid (2 mL) was stirred at room temperature for 4 h. The mixture was concentrated under reduced pressure to give N-(5,6-dihydro-4H-pyrrolo[3,4-d]thiazol-2-yl)-4-(2-methoxyphenyl)-6-methylnicotinamide as a black oil, which was used directly in the next step. LCMS: m/z=367 $[M+H]^+$, $^1H$ NMR (400 MHz, DMSO-$d_6$) δ 8.63 (s, 1H), 8.24 (s, 1H), 7.41-7.32 (m, 2H), 7.29 (s, 1H), 7.06 (t, J=7.6 Hz, 1H), 6.97 (d, J=8.2 Hz, 1H), 4.12 (s, 2H), 3.95 (s, 2H), 3.49 (s, 3H), 2.56 (s, 3H).

Example 148: Synthesis of N-(5-(1-Cyanocyclopropane-1-carbonyl)-5,6-dihydro-4H-pyrrolo[3,4-d]thiazol-2-yl)-4-(2-methoxyphenyl)-6-methylnicotinamide

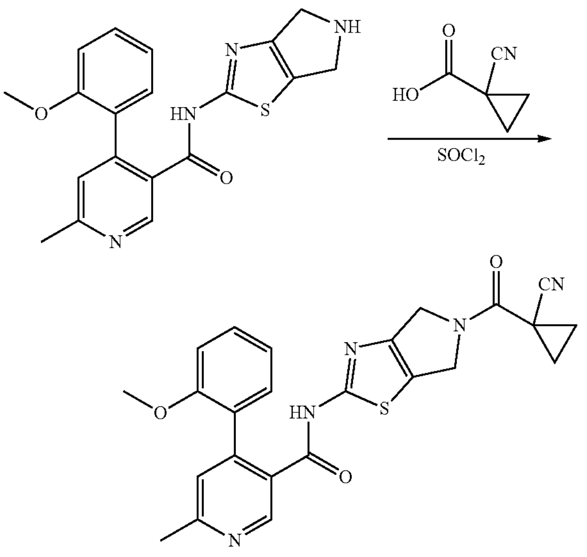

A mixture of 1-cyanocyclopropane-1-carboxylic acid (20 mg, 0.18 mmol) and thionyl chloride (1 mL) was heated at 80° C. for 2 h then concentrated under reduced pressure. The residue was dissolved in DCM (1 mL) and added to a solution of N-(5,6-dihydro-4H-pyrrolo[3,4-d]thiazol-2-yl)-4-(2-methoxyphenyl)-6-methylnicotinamide (25 mg, 0.068 mmol) and TEA (41 mg, 0.408 mmol) in DCM (1 mL) and the mixture was stirred at room temperature overnight. The mixture was diluted with water (10 mL), extracted with DCM (3x20 mL) and the combined organic phases dried over $Na_2SO_4$, filtered and concentrated under reduced pressure. The residue was purified by prep-TLC (DCM/MeOH=40/1, v/v) to give N-(5-(1-cyanocyclopropane-1-carbonyl)-5,6-dihydro-4H-pyrrolo[3,4-d]thiazol-2-yl)-4-(2-methoxyphenyl)-6-methylnicotinamide (5.3 mg, 17%) as a yellow solid. LCMS: m/z=460 $[M+H]^+$, $^1H$ NMR (400 MHz, DMSO-$d_6$): δ 12.6 (d, J=22.8 Hz, 1H), 8.65 (d, J=2.0 Hz, 1H), 7.41-7.33 (m, 2H), 7.30 (s, 1H), 7.07 (t, J=7.6 Hz, 1H), 6.98 (d, J=8.4 Hz, 1H), 5.10 (d, J=3.4 Hz, 1H), 4.96 (d, J=3.2 Hz, 1H), 4.66 (d, J=2.8 Hz, 1H), 4.52 (s, 1H), 3.49 (d, J=1.6 Hz, 3H), 2.57 (s, 3H), 1.62-1.60 (m, 4H).

Example 149: Synthesis of 4-(2-Methoxyphenyl)-6-methyl-N-(5-picolinoyl-5,6-dihydro-4H-pyrrolo[3,4-d]thiazol-2-yl) nicotinamide

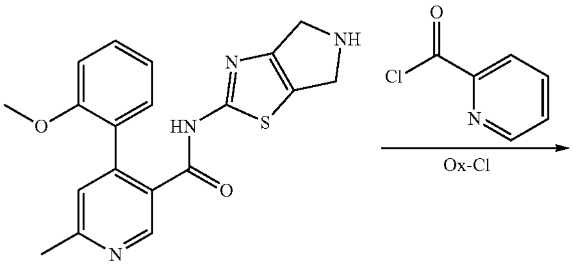

-continued

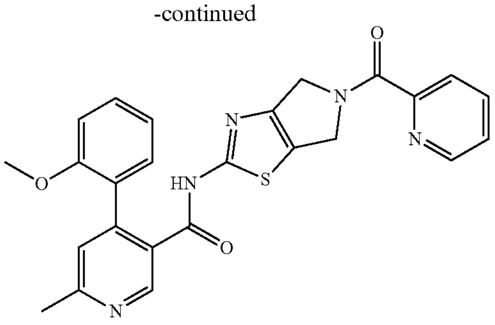

To a solution of picolinic acid (_mg, 0.28 mmol) in DCM (2 mL) was a F (0.01 mL) and oxalyl chloride (108 mg, 0.85 mmol) and the mixture was stirred at room temperature for 1 h. The mixture was concentrated under reduced pressure and the residue added to a solution of N-(5,6-dihydro-4H-pyrrolo[3,4-d]thiazol-2-yl)-4-(2-methoxyphenyl)-6-methyl-nicotinamide (40 mg, 0.11 mmol) and TEA (33 mg, 0.33 mmol) in DCM (2 mL). The mixture was stirred at room temperature for 2 h then diluted with DCM and washed with water. The organic laver was dried over $Na_2SO_4$, filtered and concentrated under reduced pressure. The residue was purified by prep-TLC (DCM/MeOH=10/1, v/v) to give 4-(2-methoxyphenyl)-6-methyl-N-(5-picolinoyl-5,6-dihydro-4H-pyrrolo[3,4-d]thiazol-2-yl)nicotinamide (9 mg, 17%) as yellow solid. LCMS m/z=472 $[M+H]^+$; $^1H$ NMR (400 MHz, DMSO-$d_6$) δ 12.6 (d, J=9.4 Hz, 1H), 8.64 (s, 1H), 7.97 (t, J=7.8 Hz, 1H), 7.86 (t, J=6.4 Hz, 1H), 7.55 (t, J=6.2 Hz, 1H), 7.42-7.13 (t, 4H), 7.06 (t, J=7.6 Hz, H), 6.99 (t, J=7.6 Hz, 1H), 5.03 (s, 1H), 4.92 (s, 1H), 4.85 (s, 1H), 4.70 (s, 1H), 3.49 (s, 3H), 2.56 (s, 3H).

TABLE I

The following examples were prepared using a similar procedure to that described for Example 149

| Ex. No. | Structure | Compound Name | LCMS $[M + H]^+$ | NMR |
|---|---|---|---|---|
| 150 | 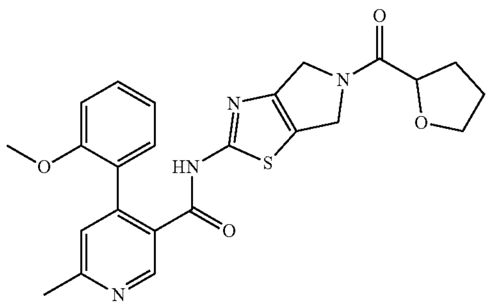 [SMILES: COc1ccccc1-c1cc(C)ncc1C(=O)Nc1nc2c(s1)CN(C(=O)C1CCCO1)C2] | (Racemic)-4-(2-Methoxyphenyl)-6-methyl-N-(5-(tetrahydrofuran-2-carbonyl)-5,6-dihydro-4H-pyrrolo[3,4-d]thiazol-2-yl)nicotinamide | 465 | $^1H$ NMR (400 MHz, DMSO-$d_6$) δ 12.6 (s, 1H), 8.64 (s, 1H), 7.43-7.33 (m, 2H), 7.30 (s, 1H), 7.06 (t, J = 7.4 Hz, 1H), 6.97 (d, J = 8.2 Hz, 1H), 4.98-4.65 (m, 2H), 4.65-4.56 (m, 2H), 4.45 (s, 1H), 3.87-3.73 (m, 2H), 3.49 (d, J = 1.6 Hz, 3H), 2.57 (s, 3H), 2.14-2.02 (m, 2H), 1.94-1.77 (m, 2H) |
| 151 | 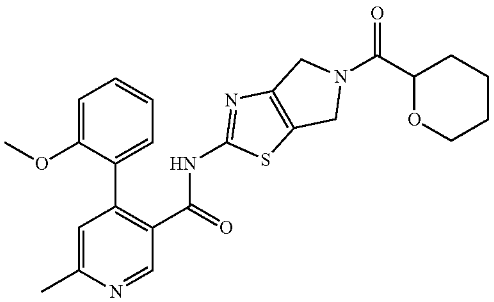 [SMILES: COc1ccccc1-c1cc(C)ncc1C(=O)Nc1nc2c(s1)CN(C(=O)C1CCCCO1)C2] | (Racemic)-4-(2-Methoxyphenyl)-6-methyl-N-(5-(tetrahydro-2H-pyran-2-carbonyl)-5,6-dihydro-4H-pyrrolo[3,4-d]thiazol-2-yl)nicotinamide | 479 | $^1H$ NMR (400 MHz, DMSO-$d_6$) δ 8.64 (s, 1H), 7.43-7.23 (m, 3H), 7.11-6.94 (m, 2H), 4.96-4.82 (m, 1H), 4.80-4.37 (m, 4H), 4.17-4.06 (m, 2H), 3.90 (d, J = 11.4 Hz, 3H), 2.56 (s, 3H), 2.06-1.74 (m, 1H), 1.72-1.40 (m, 5H) |
| 704 | 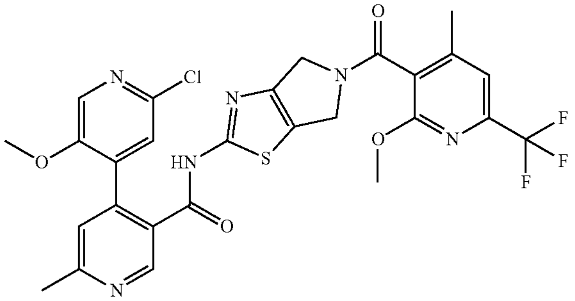 [SMILES: COc1cnc(Cl)cc1-c1cc(C)ncc1C(=O)Nc1nc2c(s1)CN(C(=O)c1c(C)cc(C(F)(F)F)nc1OC)C2] | 2'-chloro-5'-methoxy-N-(5-(2-methoxy-4-methyl-6-(trifluoromethyl)nicotinoyl)-5,6-dihydro-4H-pyrrolo[3,4-d]thiazol-2-yl)-6-methyl-[4,4'-bipyridine]-3-carboxamide | 619 | $^1H$ NMR (400 MHz, DMSO-$d_6$) δ 12.81 (s, 1H), 8.77 (d, J = 4.6 Hz, 1H), 8.17 (d, J = 2.6 Hz, 1H), 7.54 (d, J = 3.2 Hz, 2H), 7.43 (d, J = 2.2 Hz, 1H), 4.82 (s, 1H), 4.68 (s, 1H), 4.43 (q, J = 13.8 Hz, 1H), 4.32 (s, 1H), 3.94 (s, 3H), 3.60 (d, J = 1.4 Hz, 3H), 2.59 (d, J = 2.6 Hz, 3H), 2.35 (s, 3H) |

Example 152: Synthesis of (Racemic)-4-(5-Cyano-2-methoxyphenyl)-6-methyl-N-(6-(phenylamino)-4,5,6,7-tetrahydrobenzo[d]thizaol-2- yl)nicotinamide

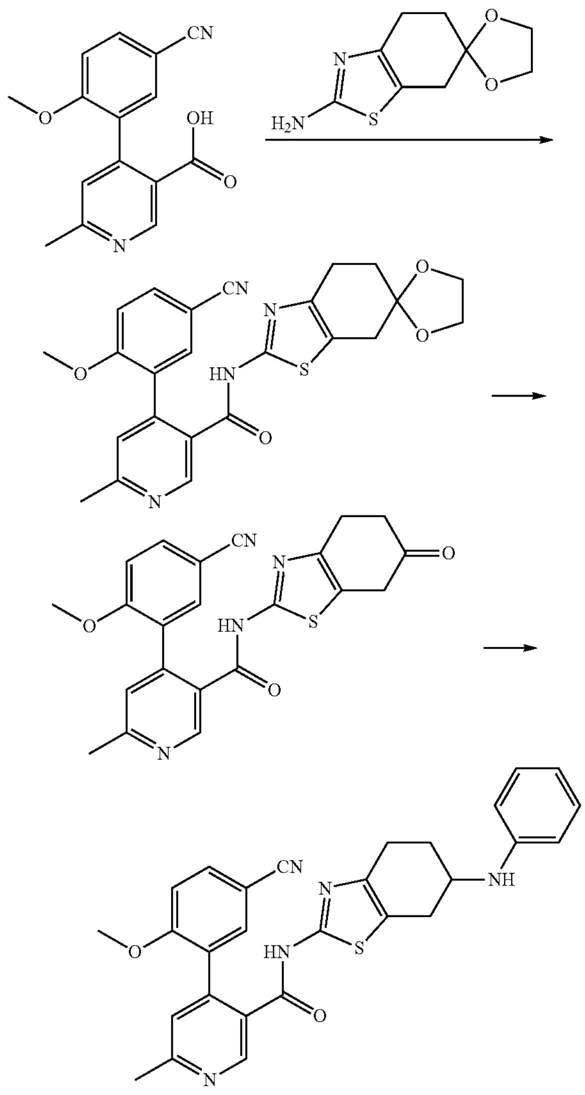

Step 1: A mixture of 4-(5-cyano-2-methoxyphenyl)-6-methylnicotinic acid (50 mg, 0.186 mmol), DIPEA (72 mg, 0.56 mmol) and HATU (106 mg, 0.279 mmol) in NMP (2 mL) was stirred at room temperature for 2 h. 4,7-Dihydro-5H-spiro[benzo[d]thiazole-6,2'-[1,3]dioxolan]-2-amine (47 mg, 0.22 mmol) was added and the mixture was heated at 80° C. overnight. After cooling to RT, the mixture was poured into water (30 mL), extracted with EtOAc (3x30 mL) and the combined organic layers washed with brine (30 mL), dried over $Na_2SO_4$, filtered, and concentrated under reduced pressure. The residue was purified by prep-TLC (DCM/MeOH=20/1, v/v) to afford 4-(5-cyano-2-methoxyphenyl)-N-(4,7-dihydro-5H-spiro[benzo[d]thiazole-6,2'-[1,3]dioxolan]-2-yl)-6-methylnicotinamide (60 mg, 69%) as a brown solid. LCMS: m/z=463 $[M+H]^+$.

Step 2: A mixture of 4-(5-cyano-2-methoxyphenyl)-N-(4,7-dihydro-5H-spiro[benzo[d]thiazole-6,2'-[1,3]dioxolan]-2-yl)-6-methylnicotinamide (40 mg, 0.086 mmol) and 1 M aqueous HCl (2 mL) was heated at 50° C. for 2 h. The mixture was adjusted to pH 8 with 2 M aqueous NaOH, extracted with DCM (3x20 mL) and the combined organic layers washed with brine (10 mL), dried over $Na_2SO_4$, filtered, and concentrated under reduced pressure. The residue was purified by prep-TLC (DCM/MeOH=30/1, v/v) to afford 4-(5-cyano-2-methoxyphenyl)-6-methyl-N-(6-oxo-4,5,6,7-tetrahydrobenzo[d]thiazol-2-yl)nicotinamide (40 mg, 74%) as a yellow oil. LCMS: m/z=419 $[M+H]^+$, $^1$H NMR (400 MHz, DMSO-$d_6$): δ 12.5 (s, 1H), 8.70 (s, 1H), 7.91-7.86 (m, 1H), 7.85-7.81 (m, 1H), 7.38 (s, 1H), 7.17 (d, J=8.7 Hz, 1H), 3.58 (s, 3H), 3.53 (s, 2H), 2.97 (t, J=6.9 Hz, 2H), 2.66 (t, J=6.9 Hz, 2H), 2.57 (s, 3H).

Step 3: A mixture of 4-(5-cyano-2-methoxyphenyl)-6-methyl-N-(6-oxo-4,5,6,7-tetrahydrobenzo[d]thiazol-2-yl) nicotinamide (200 mg, 0.478 mmol), aniline (89 mg, 0.96 mmol), acetic acid (2 drops) and $NaBH(OAc)_3$ (202 mg, 0.955 mmol) in DCE (6 mL) was stirred at room temperature overnight. The mixture was poured into water (30 mL), extracted with DCM (3x20 mL) and the combined organic layers washed with brine (10 mL), dried over $Na_2SO_4$, filtered and concentrated under reduced pressure. The residue was purified by prep-HPLC to afford (Racemic)-4-(5-cyano-2-methoxyphenyl)-6-methyl-N-(6-(phenylamino)-4,5,6,7-tetrahydrobenzo[d]thiazol-2-yl)nicotinamide (75 mg, 31%) as a white solid. LCMS: m/z=496 $[M+H]^+$, $^1$H NMR (400 MHz, DMSO-$d_6$): δ 12.3 (s, 1H), 8.69 (s, 1H), 7.92-7.86 (m, 1H), 7.84-7.79 (m, 1H), 7.37 (s, 1H), 7.17 (d, J=8.8 Hz, 1H), 7.11-7.03 (m, 2H), 6.64 (d. J=8.0 Hz, 2H), 6.56-6.49 (m, 1H), 5.58 (s, 1H), 3.81-3.70 (m, 1H), 3.59 (s, 3H), 3.07-2.99 (m, 1H), 2.78-2.69 (m, 2H), 2.60-2.52 (m, 4H), 2.16-2.03 (m, 1H), 1.81-1.65 (m, 1H).

Example 153: Synthesis of 4-(2-methoxyphenyl)-6-methyl-N-(5-(thiazol-2-yl)-5,6-dihydro-4H-pyrrolo[3,4-d]thiazol-2-yl)nicotinamide

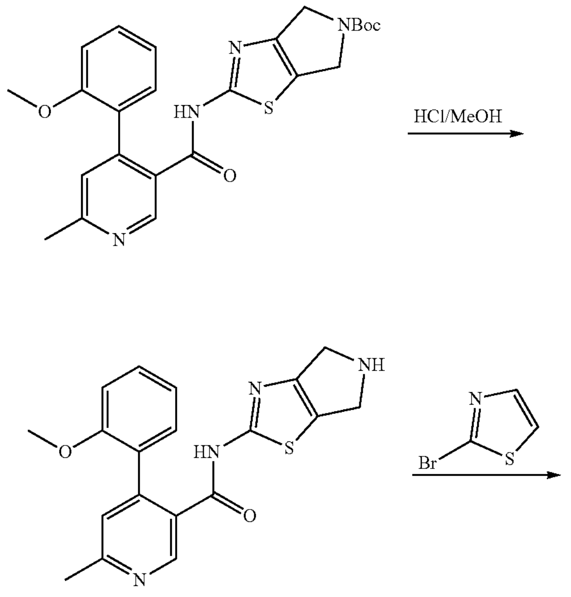

-continued

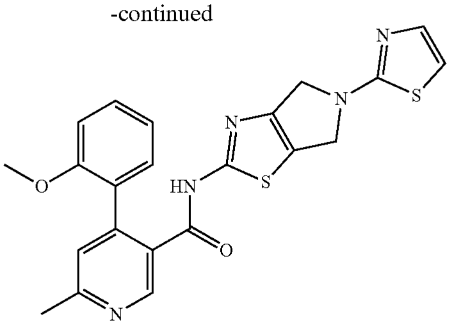

A mixture of tert-butyl 2-(4-(2-methoxyphenyl)-6-methylnicotinamido)-4,6-dihydro-5H-pyrrolo[3,4-d]thiazole-5-carboxylate (200 mg, 0.43 mmol) and 4 M HCl/MeOH (3 mL) was stirred at room temperature for 2 h then concentrated under reduced pressure. The residue was dissolved in DMSO (2 mL), then $Cs_2CO_3$ (419 mg, 1.28 mmol), CsF (195 mg, 1.28 mmol) and 2-bromothiazole (422 mg, 2.57 mmol) were added and the mixture was heated at 130° C. overnight. The mixture was diluted with water (30 mL), extracted with EtOAc (3×40 mL) and the combined organic phases washed with water (20 mL), brine (20 mL), dried over $Na_2SO_4$, filtered and concentrated under reduced pressure. The residue was purified by prep-TLC (DCM/MeOH=35/1, v/v) to give 4-(2-methoxyphenyl)-6-methyl-N-(5-(thiazol-2-yl)-5,6-dihydro-4H-pyrrolo[3,4-d]thiazol-2-yl)nicotinamide (50 mg, 26%) as a white solid. LCMS: m/z=450 $[M+H]^+$, $^1$H NMR (400 MHz, DMSO-$d_6$): δ 12.6 (s, 1H), 8.65 (s, 1H), 7.41-7.33 (m, 2H), 7.31 (s, 1H), 7.20 (d, J=3.6 Hz, 1H), 7.07 (td, J=7.6, 1.0 Hz, 1H), 6.98 (d, J=8.2 Hz, 1H), 6.82 (d, J=3.6 Hz, 1H), 4.73-4.66 (m, 2H), 4.56 (t, J=3.4 Hz, 2H), 3.50 (s, 3H), 2.57 (s, 3H).

Example 154: Synthesis of Methyl 2-(4-(2-methoxyphenyl)-6-methylnicotinamido)-4,6-dihydro-5H-pyrrolo[3,4-d]thiazole-5-carboxylate

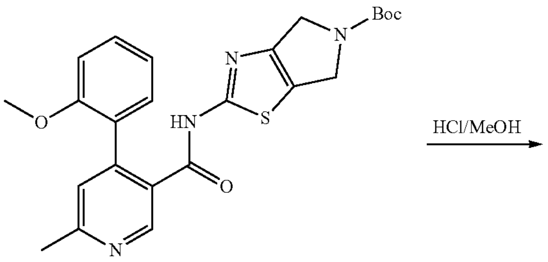

-continued

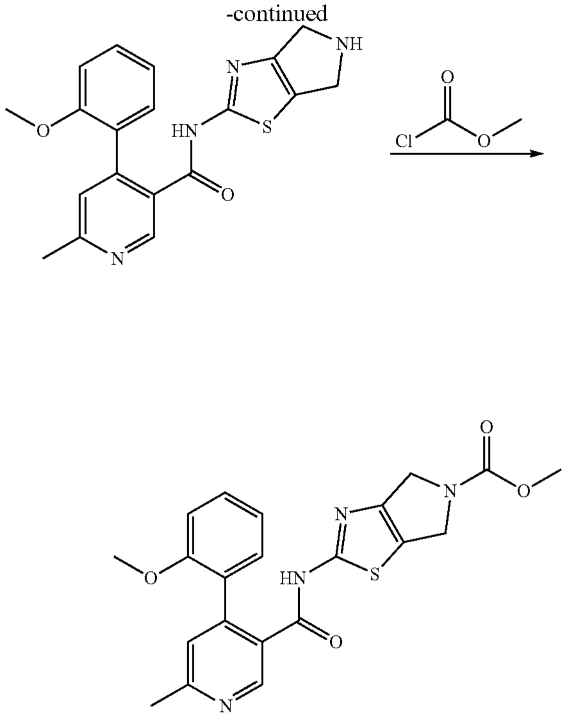

A mixture of tert-butyl 2-(4-(2-methoxyphenyl)-6-methylnicotinamido)-4,6-dihydro-5H-pyrrolo[3,4-d]thiazole-5-carboxylate (40 mg, 0.10 mmol) and 4 M HC/MeOH (3 mL) was stirred at room temperature for 2 h then concentrated under reduced pressure. The residue was dissolved in DCM (3 mL), cooled to 0° C., TEA (61 mg, 0.6 mmol) and methyl carbonochloridate (16 mg, 0.17 mmol) were added and the mixture was stirred at room temperature overnight. The mixture was diluted with water, extracted with EtOAc (3×20 mL), dried over $Na_2SO_4$, filtered and concentrated under reduced pressure. The residue was purified by prep-TLC (DCM/MeOH=10/1, v/v) and prep-HPLC to give methyl 2-(4-(2-methoxyphenyl)-6-methylnicotinamido)-4,6-dihydro-5H-pyrrolo[3,4-d]thiazole-5-carboxylate (12.7 mg, 31%) as a yellow solid. LCMS: m/z=425 $[M+H]^{30}$, $^1$H NMR (400 MHz, DMSO-$d_6$) δ 12.6 (s, 1H), 8.64 (s, 1H), 7.37 (d, J=1.8 Hz, 1H), 7.33 (dd, J=7.6, 1.8 Hz, 1H), 7.28 (s, 1H), 7.05 (t, J=7.4 Hz, 1H), 6.97 (d, J=8.2 Hz, 1H), 4.57 (dt, J=12.0, 3.2 Hz, 2H), 4.44 (dt, J=12.8, 3.2 Hz, 2H), 3.66 (s, 3H), 3.49 (s, 3H), 2.56 (s, 3H).

TABLE J

The following examples were prepared using a similar procedure to that described for Example 154 using an appropriately substituted acyl-, sulfonyl-, or sulfamyl chloride reagent.

| Ex. No. | Structure | Compound Name | LCMS $[M + H]^+$ | NMR |
|---|---|---|---|---|
| 155 | 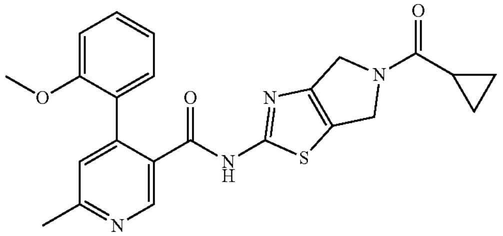 [SMILES: COc1ccccc1-c1cc(C)ncc1C(=O)Nc1nc2c(s1)CN(C(=O)C1CC1)C2] | N-(5-(Cyclopropane-carbonyl)-5,6-dihydro-4H-pyrrolo[3,4-d]thiazol-2-yl)-4-(2-methoxyphenyl)-6-methylnicotinamide | 435 | $^1$H NMR (400 MHz, DMSO-$d_6$) δ 12.6 (d, J = 6.8 Hz, 1H), 8.65 (s, 1H), 7.42-7.32 (m, 2H), 7.30 (s, 1H), 7.07 (t, J = 7.6 Hz, 1H), 6.98 (d, J = 8.4 Hz, 1H), 4.96 (t, J = 3.2 Hz, 1H), 4.83 (t, J = 3.0 Hz, 1H), 4.58 (t, J = 3.0 Hz, 1H), 4.44 (t, J = 2.8 Hz, 1H), 3.50 (s. 3H), 2.57 (s, 3H), 1.93-1.74 m, 1H), 0.84-0.75 (m, 4H) |

TABLE J-continued

The following examples were prepared using a similar procedure to that described for Example 154 using an appropriately substituted acyl-, sulfonyl-, or sulfamyl chloride reagent.

| Ex. No. | Structure | Compound Name | LCMS [M + H]$^+$ | NMR |
|---|---|---|---|---|
| 156 | 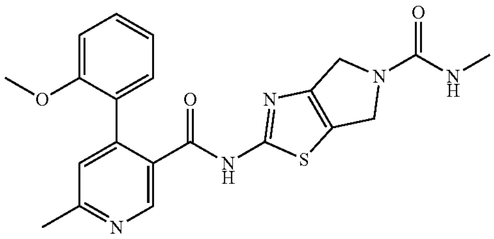 | 2-(4-(2-Methoxyphenyl)-6-methylnicotinamido)-N-methyl-4,6-dihydro-5H-pyrrolo[3,4-d]thiazole-5-carboxamide | 424 | $^1$H NMR (400 MHz, DMSO-$d_6$) δ 12.5 (s, 1H), 8.64 (s, 1H), 7.41-7.32 (m, 2H), 7.29 (s, 1H), 7.06 (t, J = 7.6 Hz, 1H), 6.98 (d, J = 8.4 Hz, 1H), 6.27 (d, J = 5.2 Hz, 1H), 4.50 (s, 2H), 4.37 (s, 2H), 3.50 (s, 3H), 2.63 (d, J = 4.2 Hz, 3H), 2.56 (s, 3H) |
| 157 | 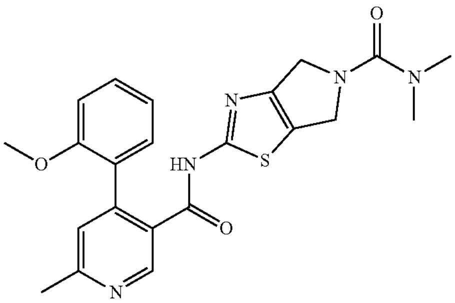 | 2-(4-(2-Methoxyphenyl)-6-methylnicotinamido)-N,N-dimethyl-4,6-dihydro-5H-pyrrolo[3,4-d]thiazole-5-carboxamide | 438 | $^1$H NMR (400 MHz, DMSO-$d_6$) δ 12.5 (s, 1H), 8.64 (s, 1H), 7.40-7.33 (m, 2H), 7.29 (s, 1H), 7.06 (t, J = 7.4 Hz, 1H), 6.97 (d, J = 8.2 Hz, 1H), 4.64 (t. J = 3.4 Hz, 2H), 4.50 (t, J = 3.4 Hz, 2H), 3.49 (s, 3H), 2.82 (s, 6H), 2.56 (s, 3H) |
| 158 | 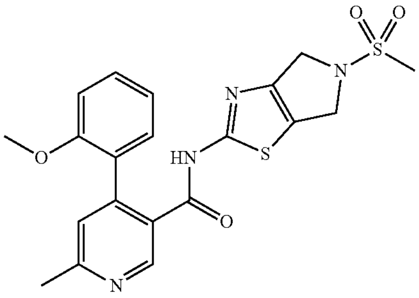 | 4-(2-Methoxyphenyl)-6-methyl-N-(5-(methylsulfonyl)-5,6-dihydro-4H-pyrrolo[3,4-d]thiazol-2-yl)nicotinamide | 445 | $^1$H NMR (400 MHz, DMSO-$d_6$) δ 12.6 (s, 1H), 8.62 (s, 1H), 7.41-7.31 (m, 2H), 7.29 (s, 1H), 7.06 (t, J = 7.4 Hz, 1H), 6.97 (d, J = 8.2 Hz, 1H), 4.58 (s, 2H), 4.46 (s, 2H), 3.48 (s, 3H), 3.00 (s, 3H), 2.56 (s, 3H) |
| 159 | 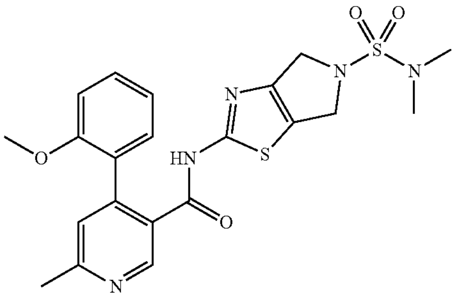 | N-(5-(N,N-Dimethylsulfamoyl)-5,6-dihydro-4H-pyrrolo[3,4-d]thiazol-2-yl)-4-(2-methoxyphenyl)-6-methylnicotinamide | 474 | $^1$H NMR (400 MHz, DMSO-$d_6$) δ 12.6 (s, 1H), 8.64 (s, 1H), 7.42-7.28 (m, 3H), 7.07 (t, J = 7.6 Hz, 1H), 6.98 (d, J = 8.2 Hz, 1H), 4.60-4.54 (m, 2H), 4.44-4.41 (m, 2H), 3.49 (s, 3H), 2.80 (s, 6H), 2.57 (s, 3H) |
| 160 | 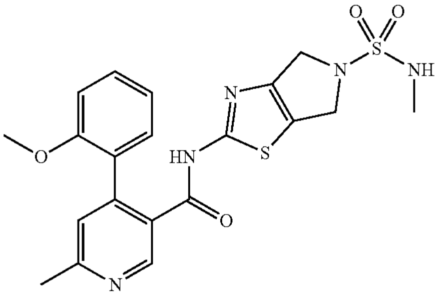 | 4-(2-Methoxyphenyl)-6-methyl-N-(5-(N-methylsulfamoyl)-5,6-dihydro-4H-pyrrolo[3,4-d]thiazol-2-yl)nicotinamide | 460 | $^1$H NMR (400 MHz, DMSO-$d_6$) δ 12.6 (s, 1H), 8.64 (s, 1H), 7.40-7.32 (m, 2H), 7.30 (s, 1H), 7.27-7.22 (m, 1H), 7.06 (t. J = 7.4 Hz, 1H), 6.97 (d, J = 8.2 Hz, 1H), 4.580-4.48 (m, 2H), 4.41-4.31 (m, 2H), 3.49 (s, 3H), 2.59-2.54 (m, 6H) |

TABLE J-continued

The following examples were prepared using a similar procedure to that described for Example 154 using an appropriately substituted acyl-, sulfonyl-, or sulfamyl chloride reagent.

| Ex. No. | Structure | Compound Name | LCMS [M + H]+ | NMR |
|---|---|---|---|---|
| 161 | 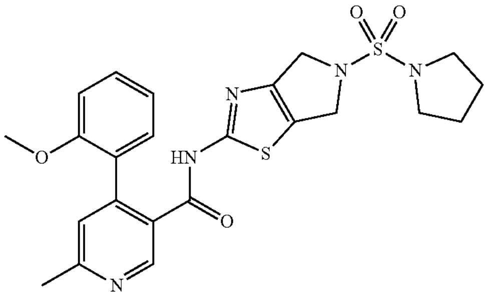 [SMILES: COc1ccccc1-c1cc(C)ncc1C(=O)Nc1nc2c(s1)CN(S(=O)(=O)N1CCCC1)C2] | 4-(2-Methoxyphenyl)-6-methyl-N-(5-(pyrrolidin-1-ylsulfonyl)-5,6-dihydro-4H-pyrrolo[3,4-d]thiazol-2-yl)nicotinamide | 500 | $^1$H NMR (400 MHz, DMSO-$d_6$) δ 12.6 (s, 1H), 8.64 (s, 1H), 7.41-7.28 (m, 3H), 7.07 (t, J = 7.4 Hz, 1H), 6.98 (d, J = 8.2 Hz, 1H), 4.58-4.53 (m, 2H), 4.43-4.39 (m, 2H), 3.50 (s, 3H), 3.28-3.23 (m, 4H), 2.57 (s, 3H), 1.89-1.81 (m, 4H) |
| 162 | 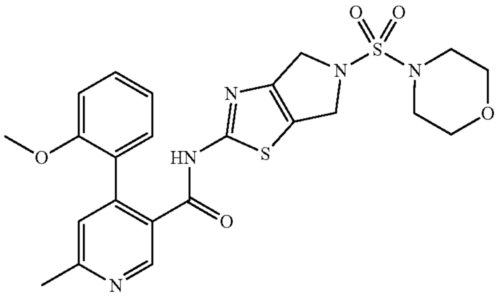 [SMILES: COc1ccccc1-c1cc(C)ncc1C(=O)Nc1nc2c(s1)CN(S(=O)(=O)N1CCOCC1)C2] | 4-(2-Methoxyphenyl)-6-methyl-N-(5-(morpholinosulfonyl)-5,6-dihydro-4H-pyrrolo[3,4-d]thiazol-2-yl)nicotinamide | 516 | $^1$H NMR (400 MHz, DMSO-$d_6$) δ 12.6 (s, 1H), 8.64 (s, 1H), 7.41-7.33 (m, 2H), 7.30 (s, 1H), 7.07 (t, J = 7.4 Hz, 1H), 6.98 (d. J = 8.2 Hz, 1H), 4.65-4.55 (m, 2H), 4.51-4.43 (m, 2H), 3.65-3.61 (m, 4H), 3.50 (s, 3H), 3.19-3.14 (m, 4H), 2.57 (s, 3H) |
| 163 | 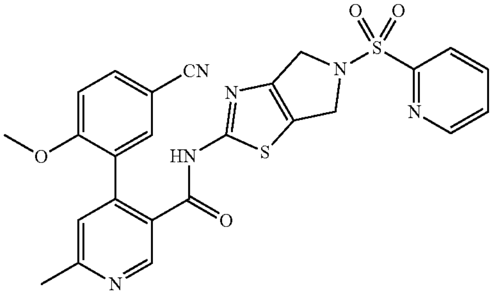 [SMILES: COc1ccc(C#N)cc1-c1cc(C)ncc1C(=O)Nc1nc2c(s1)CN(S(=O)(=O)c1ccccn1)C2] | 4-(5-Cyano-2-methoxyphenyl)-6-methyl-N-(5-(pyridin-2-ylsulfonyl)-5,6-dihydro-4H-pyrrolo[3,4-d]thiazol-2-yl)nicotinamide | 533 | $^1$H NMR (400 MHz, DMSO-$d_6$) δ 12.6 (s, 1H), 8.68 (d, J = 4.4 Hz, 2H), 8.10 (dd, J = 7.8, 1.7 Hz, 1H), 8.00 (d, J = 7.8 Hz, 1H), 7.88 (dd, J = 8.6, 2.2 Hz, 1H), 7.82 (d, J = 2.2 Hz, 1H), 7.71-7.65 (m, 1H), 7.38 (s, 1H), 7.15 (d, J = 8.8 Hz, 1H), 4.73 (t, J = 3.4 Hz, 2H), 4.59 (t, J = 3.4 Hz, 2H), 3.53 (s, 3H), 2.57 (s, 3H) |
| 164 | 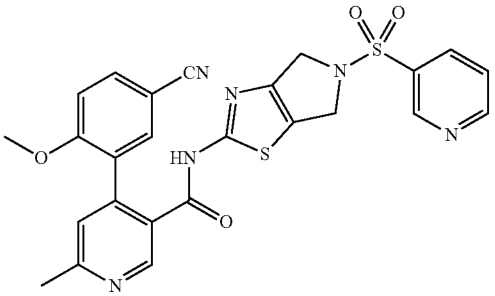 [SMILES: COc1ccc(C#N)cc1-c1cc(C)ncc1C(=O)Nc1nc2c(s1)CN(S(=O)(=O)c1cccnc1)C2] | 4-(5-Cyano-2-methoxyphenyl)-6-methyl-N-(5-(pyridin-3-ylsulfonyl)-5,6-dibydro-4H-pyrrolo[3,4-d]thiazol-2-yl)nicotinamide | 533 | $^1$H NMR (400 MHz, DMSO-$d_6$) δ 12.6 (s, 1H), 9.06 (d, J = 2.4 Hz, 1H), 8.86 (d, J = 4.8 Hz, 1H), 8.68 (s, 1H), 8.30 (d, J = 8.0 Hz, 1H), 7.90-7.80 (m, 2H), 7.66 (dd, J = 8.0, 4.8 Hz, 1H), 7.36 (s, 1H), 7.14 (d, J = 8.6 Hz, 1H), 4.62 (s, 2H), 4.50 (s, 2H), 3.52 (s, 3H), 2.56 (s, 3H) |
| 165 | 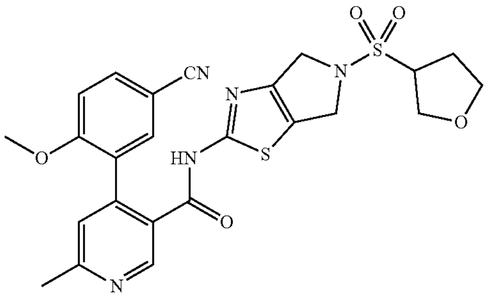 [SMILES: COc1ccc(C#N)cc1-c1cc(C)ncc1C(=O)Nc1nc2c(s1)CN(S(=O)(=O)C1CCOC1)C2] | (Racemic)-4-(5-Cyano-2-methoxyphenyl)-6-methyl-N-(5-((tetrahydrofuran-3-yl)sulfonyl)-5,6-dihydro-4H-pyrrolo[3,4-d]thiazol-2-yl)nicotinamide | 526 | $^1$H NMR (400 MHz, DMSO-$d_6$) δ 12.7 (s, 1H), 8.71 (s, 1H), 7.89 (dd, J = 8.6, 2.2 Hz, 1H), 7.85 (d, J = 2.2 Hz, 1H), 7.40 (s, 1H), 7.17 (d, J = 8.8 Hz, 1H), 4.66 (t, J = 3.4 Hz, 2H), 4.53 (t, J = 3.6 Hz, 2H), 4.29-4.19 (m, 1H), 3.98-3.91 (m, 2H), 3.87-3.80 (m, 1H), 3.71-3.64 (m, 1H), 3.57 (s, 3H), 2.58 (s, 3H), 2.25-2.16 (m, 2H) |

TABLE J-continued

| The following examples were prepared using a similar procedure to that described for Example 154 using an appropriately substituted acyl-, sulfonyl-, or sulfamyl chloride reagent. | | | | |
|---|---|---|---|---|
| Ex. No. | Structure | Compound Name | LCMS [M + H]+ | NMR |
| 166 | 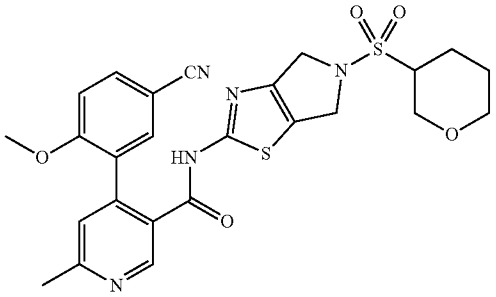 [SMILES: COc1ccc(C#N)cc1-c1cc(C)ncc1C(=O)Nc1nc2c(s1)CN(S(=O)(=O)C1CCCOC1)C2] | (Racemic)-4-(5-Cyano-2-methoxyphenyl)-6-methyl-N-(5-((tetrahydro-2H-pyran-3-yl)sulfonyl)-5,6-dihydro-4H-pyrrolo[3,4-d]thiazol-2-yl)nicotinamide | 540 | $^1$H NMR (400 MHz, DMSO-$d_6$) δ 12.7 (s, 1H), 8.71 (s, 1H), 7.89 (dd, J = 8.6, 2.0 Hz, 1H), 7.85 (d, J = 2.0 Hz, 1H), 7.40 (s, 1H), 7.17 (d, J = 8.6 Hz, 1H), 4.66 (s, 2H), 4.53 (s, 2H), 4.07-4.01 (m, 1H), 3.80-3.74 (m, 1H), 3.70-3.60 (m, 1H), 3.57 (s, 3H), 3.51 (t, J = 10.6 Hz, 1H), 3.36-3.28 (m, 1H), 2.58 (s, 3H), 2.13-2.04 (m, 1H), 1.86-1.74 (m, 1H), 1.72-1.64 (m, 1H), 1.63-1.53 (m, 1H) |
| 167 | 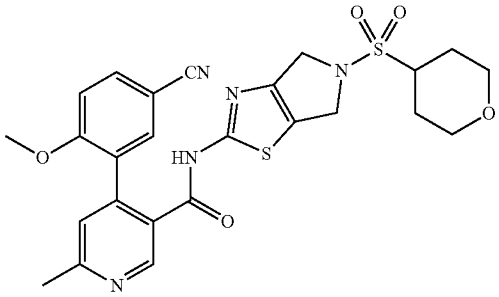 [SMILES: COc1ccc(C#N)cc1-c1cc(C)ncc1C(=O)Nc1nc2c(s1)CN(S(=O)(=O)C1CCOCC1)C2] | 4-(5-Cyano-2-methoxyphenyl)-6-methyl-N-(5-((tetrahydro-2H-pyran-4-yl)sulfonyl)-5,6-dihydro-4H-pyrrolo[3,4-d]thiazol-2-yl)nicotinamide | 540 | $^1$H NMR (400 MHz, DMSO-$d_6$) δ 12.7 (s, 1H), 8.71 (s, 1H), 7.89 (dd, J = 8.6, 2.2 Hz, 1H), 7.85 (d, J = 2.2 Hz, 1H), 7.40 (s, 1H), 7.17 (d, J = 8.8 Hz, 1H), 4.68-4.65 (m, 2H), 4.55-4.51 (m, 2H), 3.94-3.89 (m, 2H), 3.75-3.67 (m, 1H), 3.57 (s, 3H), 3.37-3.27 (m, 2H), 2.58 (s, 3H), 1.89-1.81 (m, 2H), 1.78-1.65 (m, 2H) |
| 168 | 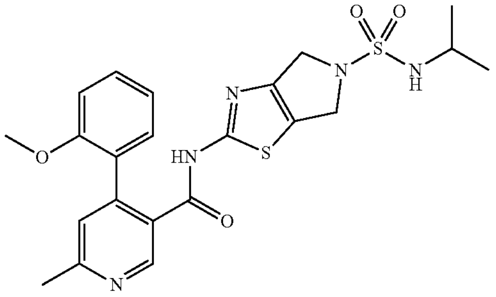 [SMILES: COc1ccccc1-c1cc(C)ncc1C(=O)Nc1nc2c(s1)CN(S(=O)(=O)NC(C)C)C2] | N-(5-(N-Isopropylsulfamoyl)-5,6-dihydro-4H-pyrrolo[3,4-d]thiazol-2-yl)-4-(2-methoxyphenyl)-6-methylnicotinamide | 488 | $^1$H NMR (400 MHz, DMSO-$d_6$) δ 12.4 (s, 1H), 8.65 (s, 1H), 7.41-7.30 (m, 2H), 7.28 (s, 1H), 7.15 (d, J = 7.6 Hz, 1H), 7.06 (t, J = 7.4 Hz, 1H), 6.98 (d, J = 8.2 Hz, 1H), 4.53-4.49 (m, 2H), 4.37-4.33 (m, 2H), 3.52 (s, 3H), 3.50-3.41 (m, 1H), 2.57 (s, 3H), 1.10 (d, J = 6.4 Hz, 6H) |
| 169 | 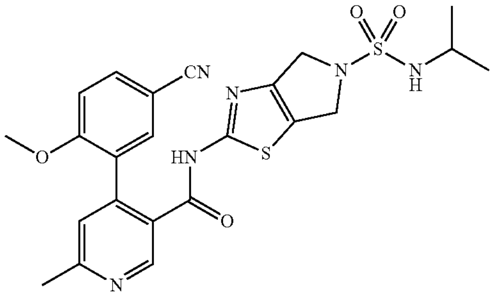 [SMILES: COc1ccc(C#N)cc1-c1cc(C)ncc1C(=O)Nc1nc2c(s1)CN(S(=O)(=O)NC(C)C)C2] | 4-(5-Cyano-2-methoxyphenyl)-N-(5-(N-isopropylsulfamoyl)-5,6-dihydro-4H-pyrrolo[3,4-d]thiazol-2-yl)-6-methylnicotinamide | 513 | $^1$H NMR (400 MHz, DMSO-$d_6$) δ 12.6 (s, 1H), 8.71 (s, 1H), 7.89 (dd, J = 8.6, 2.1 Hz, 1H), 7.85 (d, J = 2.0 Hz, 1H), 7.40 (s, 1H), 7.28 (d, J = 7.8 Hz, 1H), 7.17 (d, J = 8.8 Hz, 1H), 4.56-4.47 (m, 2H), 4.37-4.33 (m, 2H), 3.57 (s, 3H), 3.47-3.41 (m, 1H), 2.58 (s, 3H), 1.08 (d, J = 6.6 Hz, 6H) |
| 170 | 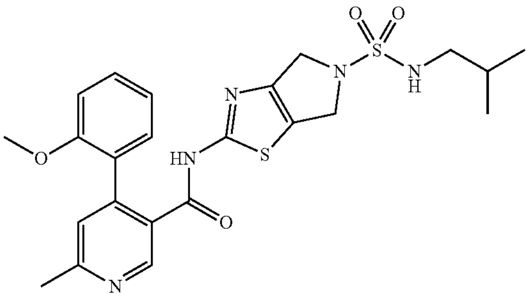 [SMILES: COc1ccccc1-c1cc(C)ncc1C(=O)Nc1nc2c(s1)CN(S(=O)(=O)NCC(C)C)C2] | N-(5-(N-Isobutylsulfamoyl)-5,6-dihydro-4H-pyrrolo[3,4-d]thiazol-2-yl)-4-(2-methoxyphenyl)-6-methylnicotinamide | 502 | $^1$H NMR (400 MHz, DMSO-$d_6$) δ 12.6 (s, 1H), 8.64 (s, 1H), 7.42-7.32 (m, 3H), 7.30 (s, 1H), 7.06 (t, J = 7.4 Hz, 1H), 6.97 (d, J = 8.4 Hz, 1H), 4.53-4.49 (m, 2H), 4.38-4.34 (m, 2H), 3.49 (s, 3H), 2.76 (t, J = 6.4 Hz, 2H), 2.57 (s, 3H), 1.71-1.60 (m, 1H), 0.85 (d, J = 6.6 Hz, 6H) |

TABLE J-continued

The following examples were prepared using a similar procedure to that described for Example 154 using an appropriately substituted acyl-, sulfonyl-, or sulfamyl chloride reagent.

| Ex. No. | Structure | Compound Name | LCMS [M + H]+ | NMR |
|---|---|---|---|---|
| 171 | 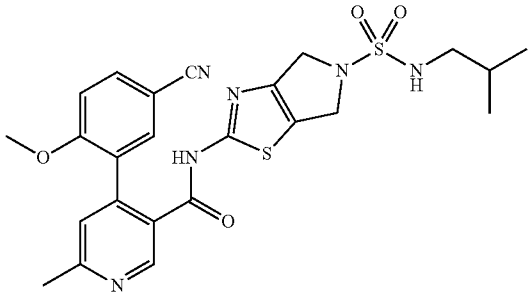 [SMILES: COc1ccc(C#N)cc1-c1cc(C)ncc1C(=O)Nc1nc2c(s1)CN(S(=O)(=O)NCC(C)C)C2] | 4-(5-Cyano-2-methoxyphenyl)-N-(5-(N-isobutylsulfamoyl)-5,6-dihydro-4H-pyrrolo[3,4-d]thiazol-2-yl)-6-methylnicotinamide | 526 | $^1H$ NMR (400 MHz, DMSO-$d_6$) δ 12.6 (s, 1H), 8.72 (s, 1H), 7.89 (d, J = 2.2 Hz, 1H), 7.83 (d, J = 2.2 Hz, 1H), 7.41-7.31 (m, 2H), 7.17 (d, J = 8.8 Hz, 1H), 4.50 (t, J = 3.6 Hz, 2H), 4.36 (t, J = 3.6 Hz, 2H), 3.57 (s, 3H), 2.76 (t, J = 6.4 Hz, 2H), 2.57 (s, 3H), 1.72-1.60 (m, 1H), 0.85 (d, J = 6.8 Hz, 6H) |
| 172 | 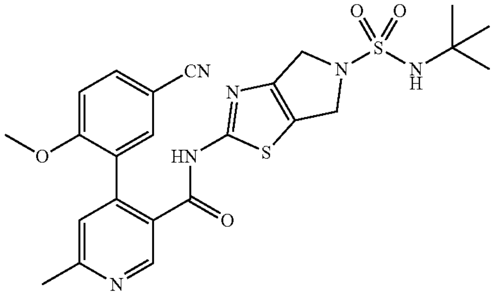 [SMILES: COc1ccc(C#N)cc1-c1cc(C)ncc1C(=O)Nc1nc2c(s1)CN(S(=O)(=O)NC(C)(C)C)C2] | N-(5-(N-(tert-Butyl)sulfamoyl)-5,6-dihydro-4H-pyrrolo[3,4-d]thiazol-2-yl)-4-(5-cyano-2-methoxyphenyl)-6-methylnicotinamide | 527 | $^1H$ NMR (400 MHz, DMSO-$d_6$) δ 12.6 (s, 1H), 8.71 (s, 1H), 7.94-7.82 (m, 2H), 7.39 (s, 1H), 7.17 (d, J = 8.6 Hz, 1H), 7.00 (s, 1H), 4.51-4.47 (m, 2H), 4.37-4.33 (m, 2H), 3.57 (s, 3H), 2.58 (s, 3H), 1.25 (s, 9H) |
| 173 | 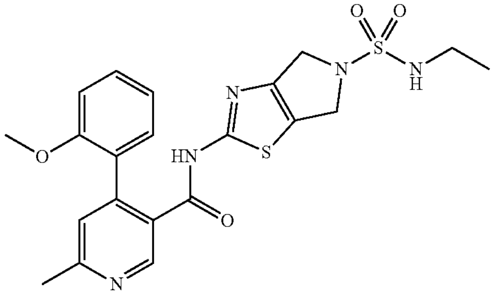 [SMILES: CCNS(=O)(=O)N1Cc2nc(NC(=O)c3cnc(C)cc3-c3ccccc3OC)sc2C1] | N-(5-(N-Ethylsulfamoyl)-5,6-dihydro-4H-pyrrolo[3,4-d]thiazol-2-yl)-4-(2-methoxyphenyl)-6-methylnicotinamide | 474 | $^1H$ NMR (400 MHz, DMSO-$d_6$) δ 12.6 (s, 1H), 8.64 (s, 1H), 7.41-7.29 (m, 4H), 7.06 (t, J = 7.4 Hz, 1H), 6.97 (d, J = 8.2 Hz, 1H), 4.53-4.49 (m, 2H), 4.38-4.34 (m, 2H), 3.49 (s, 3H), 3.02-2.94 (m, 2H), 2.57 (s, 3H), 1.05 (t, J = 7.2 Hz, 3H) |
| 174 | 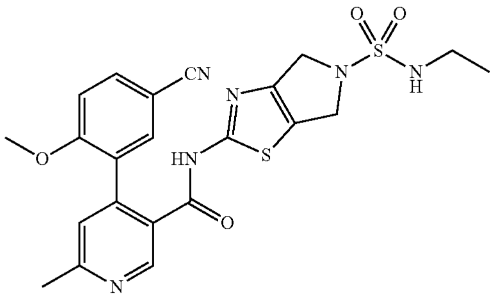 [SMILES: CCNS(=O)(=O)N1Cc2nc(NC(=O)c3cnc(C)cc3-c3cc(C#N)ccc3OC)sc2C1] | 4-(5-Cyano-2-methoxyphenyl)-N-(5-(N-ethylsulfamoyl)-5,6-dihydro-4H-pyrrolo[3,4-d]thiazol-2-yl)-6-methylnicotinamide | 499 | $^1H$ NMR (400 MHz, DMSO-$d_6$) δ 12.6 (s, 1H), 8.71 (s, 1H), 7.91-7.87 (m, 1H), 7.85 (d, J = 2.0 Hz, 1H), 7.40 (s, 1H), 7.32 (t, J = 5.6 Hz, 1H), 7.17 (d, J = 8.8 Hz, 1H), 4.51 (s, 2H), 4.37 (s, 2H), 3.57 (s, 3H), 3.01-2.95 (m, 2H), 2.58 (s, 3H), 1.05 (t, J = 7.2 Hz, 3H) |
| 175 | 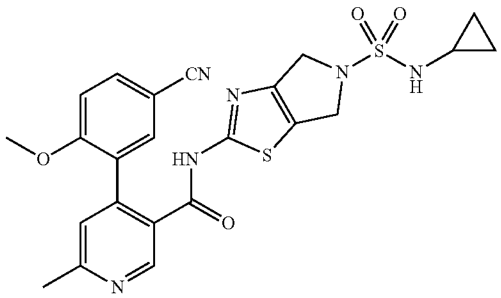 [SMILES: COc1ccc(C#N)cc1-c1cc(C)ncc1C(=O)Nc1nc2c(s1)CN(S(=O)(=O)NC1CC1)C2] | 4-(5-Cyano-2-methoxyphenyl)-N-(5-(N-cyclopropylsulfamoyl)-5,6-dihydro-4H-pyrrolo[3,4-d]thiazol-2-yl)-6-methylnicotinamide | 511 | $^1H$ NMR (400 MHz, DMSO-$d_6$) δ 12.7 (s, 1H), 8.71 (s, 1H), 7.89 (dd, J = 8.6, 2.2 Hz, 1H), 7.84 (d, J = 2.2 Hz, 1H), 7.69 (d, J = 2.6 Hz, 1H), 7.40 (s, 1H), 7.17 (d, J = 8.8 Hz, 1H), 4.60-4.56 (m, 2H), 4.46-4.41 (m, 2H), 3.57 (s, 3H), 2.58 (s, 3H), 2.41-2.34 (m, 1H), 0.56-0.50 (m, 2H), 0.45-0.39 (m, 2H) |

TABLE J-continued

The following examples were prepared using a similar procedure to that described for Example 154 using an appropriately substituted acyl-, sulfonyl-, or sulfamyl chloride reagent.

| Ex. No. | Structure | Compound Name | LCMS [M + H]+ | NMR |
|---|---|---|---|---|
| 176 | 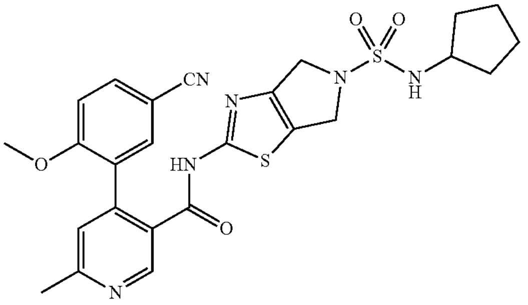 [SMILES: COc1ccc(C#N)cc1-c1cc(C)ncc1C(=O)Nc1nc2c(s1)CN(S(=O)(=O)NC1CCCC1)C2] | 4-(5-Cyano-2-methoxyphenyl)-N-(5-(N-cyclopentylsulfamoyl)-5,6-dihydro-4H-pyrrolo[3,4-d]thiazol-2-yl)-6-methylnicotinamide | 539 | $^1$H NMR (400 MHz, DMSO-$d_6$) δ 12.6 (s, 1H), 8.71 (s, 1H), 7.89 (dd, J = 8.6, 2.1 Hz, 1H), 7.85 (d, J = 2.2 Hz, 1H), 7.41-7.36 (m, 2H), 7.17 (d, J = 8.7 Hz, 1H), 4.52-4.49 (m, 2H), 4.38-4.34 (m, 2H), 3.65-3.59 (m, 1H), 3.57 (s, 3H), 2.58 (s, 3H), 1.81-1.71 (m, 2H), 1.65-1.54 (m, 2H), 1.50-1.32 (m, 4H) |
| 177 | 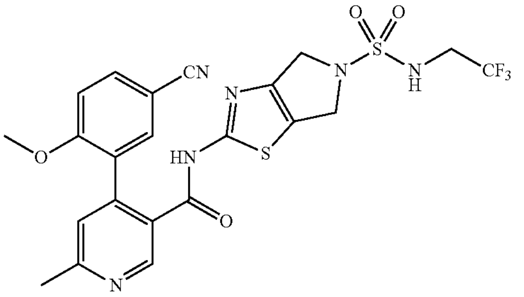 [SMILES: COc1ccc(C#N)cc1-c1cc(C)ncc1C(=O)Nc1nc2c(s1)CN(S(=O)(=O)NCC(F)(F)F)C2] | 4-(5-Cyano-2-methoxyphenyl)-6-methyl-N-(5-(N-(2,2,2-trifluoroethyl) sulfamoyl)-5,6-dihydro-4H-pyrrolo[3,4-d]thiazol-2-yl)nicotinamide | 553 | $^1$H NMR (400 MHz, DMSO-$d_6$) δ 12.7 (s, 1H), 8.71 (s, 1H), 8.30-8.22 (m, 1H), 7.92-7.87 (m, 1H), 7.86-7.83 (m, 1H), 7.40 (s, 1H), 7.17 (d, J = 8.8 Hz, 1H), 4.57-4.51 (m, 2H), 4.44-4.37 (m, 2H), 3.89-3.79 (m, 2H), 3.57 (s, 3H), 2.58 (s, 3H) |
| 178 | 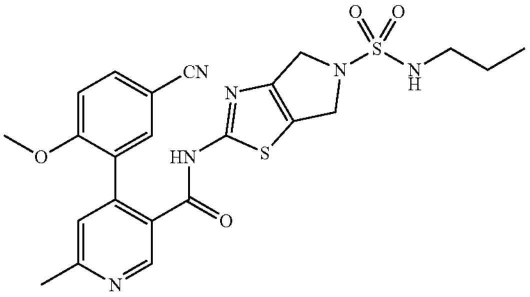 [SMILES: CCCNS(=O)(=O)N1Cc2nc(NC(=O)c3cnc(C)cc3-c3cc(C#N)ccc3OC)sc2C1] | 4-(5-Cyano-2-methoxyphenyl)-6-methyl-N-(5-(N-propylsulfamoyl)-5,6-dihydro-4H-pyrrolo[3,4-d]thiazol-2-yl)nicotinamide | 513 | $^1$H NMR (400 MHz, DMSO-$d_6$) δ 12.7 (s, 1H), 8.69 (s, 1H), 7.88 (dd, J = 8.6, 2.2 Hz, 1H), 7.84 (d, J = 2.2 Hz, 1H), 7.39 (s, 1H), 7.35 (t, J = 5.8 Hz, 1H), 7.16 (d, J = 8.6 Hz, 1H), 4.51 (t, J = 3.6 Hz, 2H), 4.36 (t, J = 3.6 Hz, 2H), 3.57 (S, 3H), 2.93-2.86 (m, 2H), 2.58 (s, 3H), 1.48-1.38 (m, 2H), 0.83 (t, J = 7.4 Hz, 3H) |
| 179 | 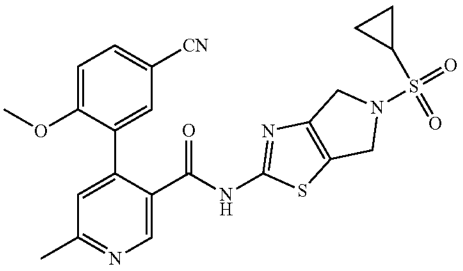 [SMILES: COc1ccc(C#N)cc1-c1cc(C)ncc1C(=O)Nc1nc2c(s1)CN(S(=O)(=O)C1CC1)C2] | 4-(5-Cyano-2-methoxyphenyl)-N-(5-(cyclopropylsulfonyl)-5,6-dihydro-4H-pyrrolo[3,4-d]thiazol-2-yl)-6-methylnicotinamide | 496 | $^1$H NMR (400 MHz, DMSO-$d_6$) δ 12.7 (s, 1H), 8.70 (s, 1H), 7.88 (dd, J = 8.6, 2.2 Hz, 1H), 7.84 (d, J = 2.0 Hz, 1H), 7.39 (s, 1H), 7.17 (d, J = 8.8 Hz, 1H), 4.65-4.61 (m. 2H), 4.53-4.48 (m, 2H), 3.57 (s, 3H), 2.86-2.77 (m, 1H), 2.57 (s, 3H), 1.03-0.96 (m, 4H) |
| 180 | 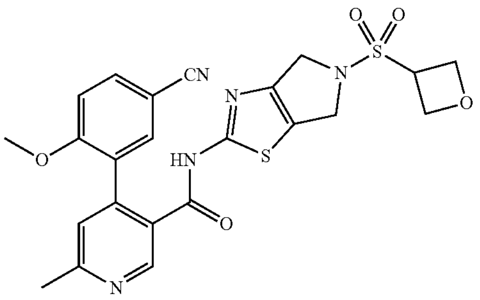 [SMILES: COc1ccc(C#N)cc1-c1cc(C)ncc1C(=O)Nc1nc2c(s1)CN(S(=O)(=O)C1COC1)C2] | 4-(5-cyano-2-methoxyphenyl)-6-methyl-N-(5-(oxetan-3-ylsulfonyl)-5,6-dihydro-4H-pyrrolo[3,4-d]thiazol-2-yl)nicotinamide | 512 | $^1$H NMR (400 MHz, DMSO-$d_6$) δ 8.72 (s, 1H), 7.87 (d, J = 8.8 Hz, 1H), 7.80 (d, J = 2.2 Hz, 1H), 7.37 (s, 1H), 7.17 (d, J = 8.6 Hz, 1H), 5.00-4.90 (m, 1H), 4.87-4.76 (m, 4H), 4.61 (s, 2H), 4.47 (s, 2H), 3.60 (s, 3H), 2.59 (s, 3H) |

TABLE J-continued

The following examples were prepared using a similar procedure to that described for Example 154 using an appropriately substituted acyl-, sulfonyl-, or sulfamyl chloride reagent.

| Ex. No. | Structure | Compound Name | LCMS [M + H]+ | NMR |
|---|---|---|---|---|
| 181 | 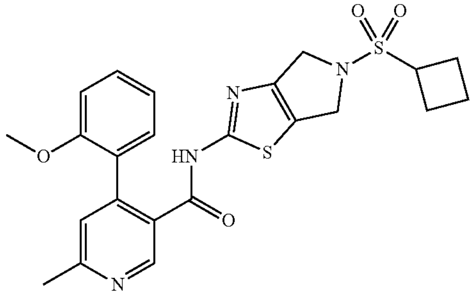 [SMILES: COc1ccccc1-c1cc(C)ncc1C(=O)Nc1nc2c(s1)CN(S(=O)(=O)C1CCC1)C2] | N-(5-(Cyclobutylsulfonyl)-5,6-dihydro-4H-pyrrolo[3,4-d]thiazol-2-yl)-4-(2-methoxyphenyl)-6-methylnicotinamide | 485 | $^1$H NMR (400 MHz, DMSO-$d_6$) δ 12.6 (s, 1H), 8.62 (s, 1H), 7.40-7.31 (m, 2H), 7.29 (s, 1H), 7.06 (t, J = 7.4 Hz, 1H), 6.97 (d, J = 8.2 Hz, 1H), 4.58 (t, J = 3.6 Hz, 2H), 4.43 (t, J = 3.6 Hz, 2H), 4.27-4.17 (m, 1H), 3.49 (s, 3H), 2.56 (s, 3H), 2.45-2.31 (m, 2H), 2.24-2.16 (m, 2H), 1.99-1.90 (m, 2H) |
| 182 | 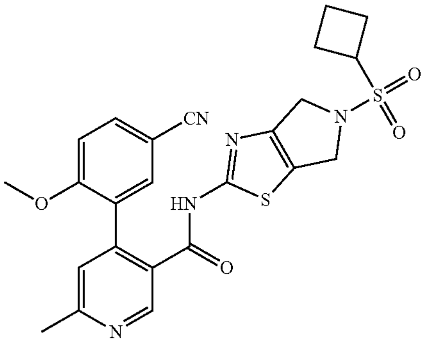 [SMILES: COc1ccc(C#N)cc1-c1cc(C)ncc1C(=O)Nc1nc2c(s1)CN(S(=O)(=O)C1CCC1)C2] | 4-(5-Cyano-2-methoxyphenyl)-N-(5-(cyclobutylsulfonyl)-5,6-dihydro-4H-pyrrolo[3,4-d]thiazol-2-yl)-6-methylnicotinamide | 510 | $^1$H NMR (400 MHz, DMSO-$d_6$) δ 12.7 (s, 1H), 8.69 (s, 1H), 7.87 (dd, J = 8.6, 2.2 Hz, 1H), 7.82 (d, J = 2.1 Hz, 1H), 7.38 (s, 1H), 7.16 (d, J = 8.8 Hz, 1H), 4.57 (s, 2H), 4.43 (s, 2H), 4.27-4.15 (m, 1H), 3.56 (s, 3H), 2.57 (s, 3H), 2.44-2.35 (m, 2H), 2.25-2.14 (m, 2H), 2.03-1.91 (m, 2H) |
| 183 | 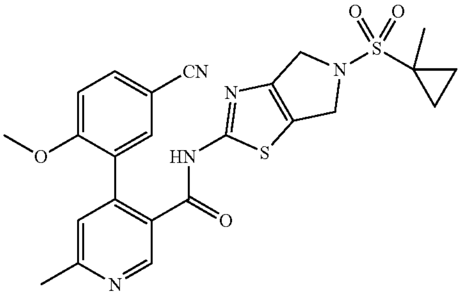 [SMILES: COc1ccc(C#N)cc1-c1cc(C)ncc1C(=O)Nc1nc2c(s1)CN(S(=O)(=O)C1(C)CC1)C2] | 4-(5-Cyano-2-methoxyphenyl)-6-methyl-N-(5-((1-methylcyclopropyl) sulfonyl)-5,6-dihydro-4H-pyrrolo[3,4-d]thiazol-2-yl)nicotinamide | 510 | $^1$H NMR (400 MHz, DMSO-$d_6$) δ 12.7 (s, 1H), 8.71 (s, 1H), 7.89 (dd, J = 8.6, 2.2 Hz, 1H), 7.85 (d, J = 2.2 Hz, 1H), 7.40 (s, 1H), 7.17 (d, J = 8.6 Hz, 1H), 4.69-4.62 (m, 2H), 4.55-4.49 (m, 2H), 3.57 (s, 3H), 2.58 (s, 3H), 1.43 (s, 3H), 1.24-1.22 (m, 2H), 0.92-0.88 (m, 2H) |
| 184 | 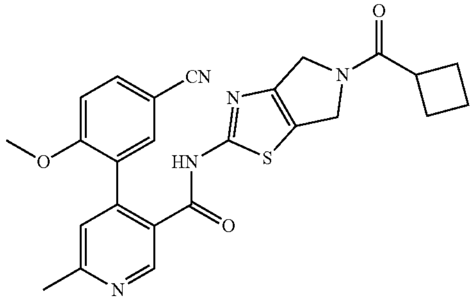 [SMILES: COc1ccc(C#N)cc1-c1cc(C)ncc1C(=O)Nc1nc2c(s1)CN(C(=O)C1CCC1)C2] | 4-(5-Cyano-2-methoxyphenyl)-N-(5-(cyclobutane-carbonyl)-5,6-dihydro-4H-pyrrolo[3,4-d]thiazol-2-yl)-6-methylnicotinamide | 474 | $^1$H NMR (400 MHz, DMSO-$d_6$) δ 12.6 (s, 1H), 8.71 (s, 1H), 7.91-7.87 (m, 1H), 7.84 (d, J = 2.2 Hz, 1H), 7.39 (s, 1H), 7.19-7.15 (m, 1H), 4.68 (s, 1H), 4.55 (s, 2H), 4.42 (s, 1H), 3.56 (d, J = 1.6 Hz, 3H), 3.40-3.32 (m, 1H), 2.58 (s, 3H), 2.21-2.11 (m, 4H), 1.96-1.87 (m, 1H), 1.82-1.74 (m, 1H) |

TABLE J-continued

The following examples were prepared using a similar procedure to that described for Example 154 using an appropriately substituted acyl-, sulfonyl-, or sulfamyl chloride reagent.

| Ex. No. | Structure | Compound Name | LCMS [M + H]+ | NMR |
|---|---|---|---|---|
| 185 | 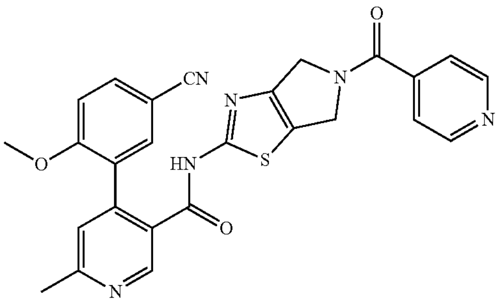 [SMILES: COc1ccc(C#N)cc1-c1cc(C)ncc1C(=O)Nc1nc2c(s1)CN(C(=O)c1ccncc1)C2] | 4-(5-Cyano-2-methoxyphenyl)-N-(5-isonicotinoyl-5,6-dihydro-4H-pyrrolo[3,4-d]thiazol-2-yl)-6-methylnicotinamide | 497 | $^1$H NMR (400 MHz, DMSO-$d_6$) δ 12.5 (s, 1H), 8.75-8.62 (m, 3H), 7.86 (dt, J = 8.6, 2.0 Hz, 1H), 7.80 (d, J = 2.0 Hz, 1H), 7.58-7.54 (m, 2H), 7.36 (d, J = 1.8 Hz, 1H), 7.16 (d, J = 8.6 Hz, 1H), 4.82 (s, 1H), 4.66 (s, 2H), 4.56 (s, 1H), 3.59 (s, 3H), 2.58 (s, 3H) |
| 186 | 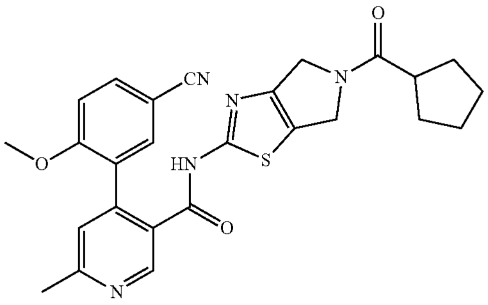 [SMILES: COc1ccc(C#N)cc1-c1cc(C)ncc1C(=O)Nc1nc2c(s1)CN(C(=O)C1CCCC1)C2] | 4-(5-Cyano-2-methoxyphenyl)-N-(5-(cyclopentane-carbonyl)-5,6-dihydro-4H-pyrrolo[3,4-d]thiazol-2-yl)-6-methylnicotinamide | 488 | $^1$H NMR (400 MHz, DMSO-$d_6$) δ 12.7 (s, 1H), 8.72 (s, 1H), 7.89 (dd, J = 8.7, 2.0 Hz, 1H), 7.84 (d, J = 2.0 Hz, 1H), 7.39 (s, 1H), 7.17 (dd, J = 8.8, 1.5 Hz, 1H), 4.84 (t, J = 2.8 Hz, 1H), 4.71 (t, J = 3.0 Hz, 1H), 4.56 (t, J = 3.0 Hz, 1H), 4.43 (t, J = 2.8 Hz, 1H), 3.57 (d, J = 1.4 Hz, 3H), 2.96-2.84 (m, 1H), 2.58 (s, 3H), 1.91-1.78 (m, 2H), 1.74-1.60 (m, 4H), 1.59-1.48 (m, 2H) |
| 187 | 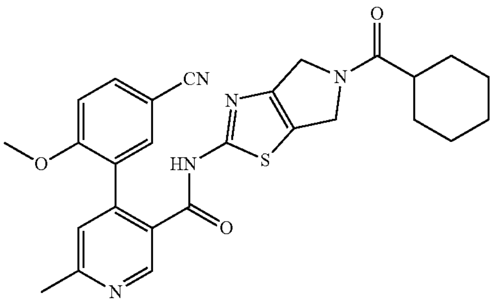 [SMILES: COc1ccc(C#N)cc1-c1cc(C)ncc1C(=O)Nc1nc2c(s1)CN(C(=O)C1CCCCC1)C2] | 4-(5-Cyano-2-methoxyphenyl)-N-(5-(cyclohexane-carbonyl)-5,6-dihydro-4H-pyrrolo[3,4-d]thiazol-2-yl)-6-methylnicotinamide | 502 | $^1$H NMR (400 MHz, DMSO-$d_6$) δ 12.7 (d, J = 2.8 Hz, 1H), 8.71 (s, 1H), 7.91-7.87 (m, 1H), 7.86-7.84 (m, 1H), 7.39 (s, 1H), 7.19-7.15 (m, 1H), 4.85 (t, J = 3.0 Hz, 1H), 4.72 (t, J = 3.0 Hz, 1H), 4.55 (t, J = 3.0 Hz, 1H), 4.41 (t, J = 2.8 Hz, 1H), 3.57 (d, J = 1.8 Hz, 3H), 2.58 (s, 3H), 2.49-2.40 (m, 1H), 1.80-1.60 (m, 6H), 1.41-1.30 (m, 4H) |
| 188 | 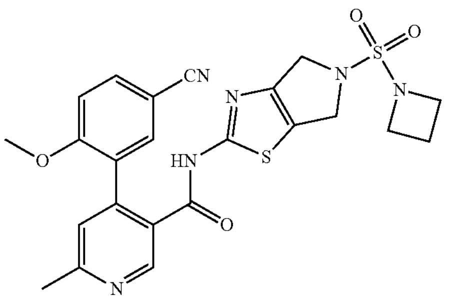 [SMILES: COc1ccc(C#N)cc1-c1cc(C)ncc1C(=O)Nc1nc2c(s1)CN(S(=O)(=O)N1CCC1)C2] | N-(5-(azetidin-1-ylsulfonyl)-5,6-dihydro-4H-pyrrolo[3,4-d]thiazol-2-yl)-4-(5-cyano-2-methoxyphenyl)-6-methylnicotinamide | 511 | $^1$H NMR (400 MHz, DMSO-$d_6$) δ 12.7 (s, 1H), 8.71 (s, 1H), 7.89 (dd, J = 8.6, 2.2 Hz, 1H), 7.85 (d. J = 2.2 Hz, 1H), 7.40 (s, 1H), 7.17 (d, J = 8.8 Hz, 1H), 4.59-4.55 (m, 2H), 4.45-4.41 (m, 2H), 3.88-3.82 (m, 4H), 3.57 (s, 3H), 2.58 (s, 3H), 2.22-2.13 (m, 2H) |

TABLE J-continued

The following examples were prepared using a similar procedure to that described for Example 154 using an appropriately substituted acyl-, sulfonyl-, or sulfamyl chloride reagent.

| Ex. No. | Structure | Compound Name | LCMS $[M + H]^+$ | NMR |
|---|---|---|---|---|
| 189 | 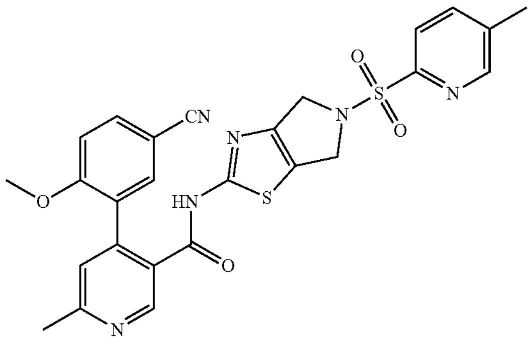 | 4-(5-Cyano-2-methoxyphenyl)-6-methyl-N-(5-((5-methylpyridin-2-yl)sulfonyl)-5,6-dihydro-4H-pyrrolo[3,4-d]thiazol-2-yl)nicotinamide | 547 | $^1H$ NMR (400 MHz, DMSO-$d_6$) δ 12.6 (s, 1H), 8.68 (s, 1H), 8.52 (s, 1H), 7.91-7.86 (m, 3H), 7.82 (d, J = 2.2 Hz, 1H), 7.38 (s, 1H), 7.15 (d, J = 8.8 Hz, 1H), 4.71 (t, J = 3.4 Hz, 2H), 4.57 (t, J = 3.4 Hz, 2H), 3.54 (s, 3H), 2.57 (s, 3H), 2.36 (s, 3H) |
| 190 | 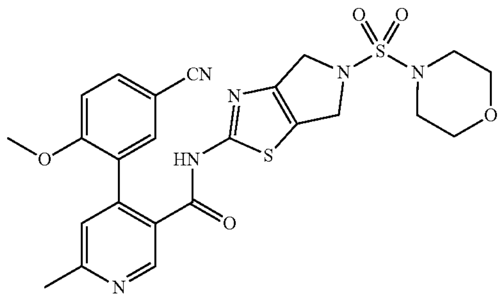 [SMILES: COc1ccc(C#N)cc1-c1cc(C)ncc1C(=O)Nc1nc2c(s1)CN(S(=O)(=O)N1CCOCC1)C2] | 4-(5-Cyano-2-methoxyphenyl)-6-methyl-N-(5-(morpholinosulfonyl)-5,6-dihydro-4H-pyrrolo[3,4-d]thiazol-2-yl)nicotinamide | 541 | $^1H$ NMR (400 MHz, DMSO-$d_6$) δ 12.7 (s, 1H), 8.71 (s, 1H), 7.89 (d, J = 8.6 Hz, 1H), 7.84 (d, J = 2.0 Hz, 1H), 7.39 (s, 1H), 7.17 (d, J = 8.6 Hz, 1H), 4.63-4.58 (m, 2H), 4.49-4.45 (m, 2H), 3.63 (t, J = 4.8 Hz, 4H), 3.57 (s, 3H), 3.17 (t, J = 4.6 Hz, 4H), 2.58 (s, 3H) |
| 191 | 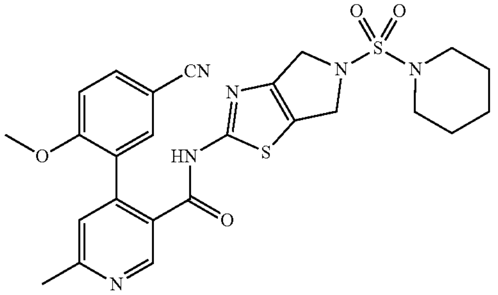 | 4-(5-Cyano-2-methoxyphenyl)-6-methyl-N-(5-(piperidin-1-ylsulfonyl)-5,6-dihydro-4H-pyrrolo[3,4-d]thiazol-2-yl)nicotinamide | 539 | $^1H$ NMR (400 MHz, DMSO-$d_6$) δ 12.5 (s, 1H), 8.72 (s, 1H), 7.87 (dd, J = 8.6, 2.2 Hz, 1H), 7.80 (d, J = 2.0 Hz, 1H), 7.38 (s, 1H), 7.17 (d, J = 8.6 Hz, 1H), 4.57 (t, J = 3.4 Hz, 2H), 4.42 (t, J = 3.6 Hz, 2H), 3.60 (s, 3H), 3.20-3.17 (m, 4H, partly obscured by water peak), 2.59 (s, 3H), 1.59-1.47 (m, 6H) |
| 192 | 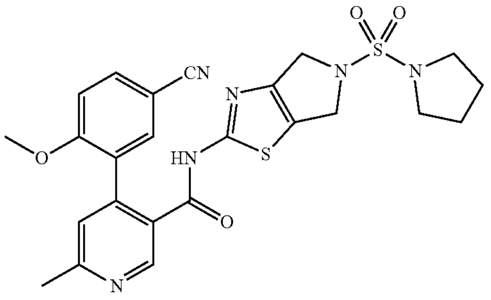 | 4-(5-Cyano-2-methoxyphenyl)-6-methyl-N-(5-(pyrrolidin-1-ylsulfonyl)-5,6-dihydro-4H-pyrrolo[3,4-d]thiazol-2-yl)nicotinamide | 525 | $^1H$ NMR (400 MHz, DMSO-$d_6$) δ 12.5 (s, 1H), 8.72 (s, 1H), 7.89-7.85 (m, 1H), 7.80 (d, J = 2.0 Hz, 1H), 7.37 (s, 1H), 7.17 (d, J = 8.6 Hz, 1H), 4.59-4.55 (m, 2H), 4.44-4.40 (m, 2H), 3.60 (s, 3H), 3.30-3.25 (m, 4H), 2.59 (s, 3H), 1.90-1.83 (m, 4H) |

TABLE J-continued

The following examples were prepared using a similar procedure to that described for Example 154 using an appropriately substituted acyl-, sulfonyl-, or sulfamyl chloride reagent.

| Ex. No. | Structure | Compound Name | LCMS [M + H]$^+$ | NMR |
|---|---|---|---|---|
| 193 | 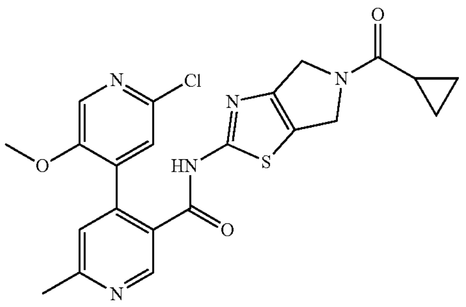 [SMILES: COc1cnc(Cl)cc1-c1cc(C)ncc1C(=O)Nc1nc2c(s1)CN(C(=O)C1CC1)C2] | 2'-Chloro-N-(5-(cyclopropane-carbonyl)-5,6-dihydro-4H-pyrrolo[3,4-d]thiazol-2-yl)-5'-methoxy-6-methyl-[4,4'-bipyridine]-3-carboxamide | 470 | $^1$H NMR (400 MHz, DMSO-$d_6$) δ 12.6 (s, 1H), 8.81 (s, 1H), 8.16 (s, 1H), 7.49 (s, 1H), 7.40 (s, 1H), 4.97 (s, 1H), 4.83 (s, 1H), 4.59 (s, 1H), 4.45 (s, 1H), 3.63 (s, 3H), 2.59 (s, 3H), 1.88-1.78 (m, 1H), 0.84-0.75 (m, 4H) |
| 194 | 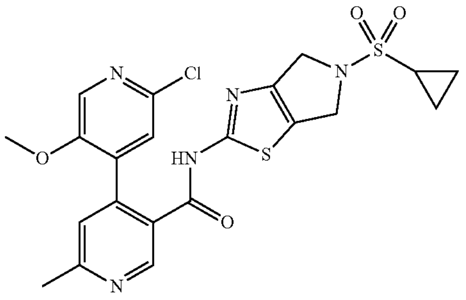 [SMILES: COc1cnc(Cl)cc1-c1cc(C)ncc1C(=O)Nc1nc2c(s1)CN(S(=O)(=O)C1CC1)C2] | 2'-Chloro-N-(5-(cyclopropylsulfonyl)-5,6-dihydro-4H-pyrrolo[3,4-d]thiazol-2-yl)-5'-methoxy-6-methyl-[4,4'-bipyridine]-3-carboxamide | 506 | $^1$H NMR (400 MHz, DMSO-$d_6$) δ 12.8 (s, 1H), 8.78 (s, 1H), 8.17 (s, 1H), 7.54 (s, 1H), 7.43 (s, 1H), 4.65 (t, J = 3.6 Hz, 2H), 4.52 (t, J = 3.6 Hz, 2H), 3.61 (s, 3H), 2.88-2.80 (m, 1H), 2.59 (s, 3H), 1.04-0.96 (m, 4H) |
| 705 | 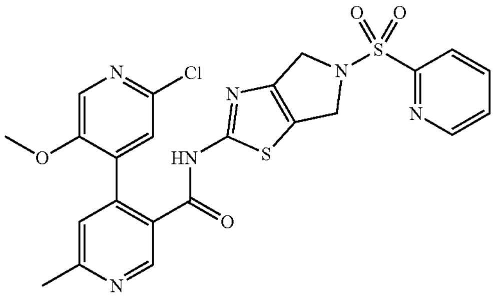 [SMILES: COc1cnc(Cl)cc1-c1cc(C)ncc1C(=O)Nc1nc2c(s1)CN(S(=O)(=O)c1ccccn1)C2] | 2'-chloro-5'-methoxy-6-methyl-N-(5-(pyridin-2-ylsulfonyl)-5,6-dihydro-4H-pyrrolo[3,4-d]thiazol-2-yl)-[4,4'-bipyridine]-3-carboxamide | 543 | $^1$H NMR (400 MHz, DMSO-$d_6$) δ 12.75 (s, 1H), 8.76 (s, 1H), 8.72-8.59 (m, 1H), 8.14-8.09 (m, 2H), 8.01 (d, J = 7.8 Hz, 1H), 7.70-7.67 (m, 1H), 7.52 (s, 1H), 7.42 (s, 1H), 4.74 (t, J = 3.4 Hz, 2H), 4.61 (t, J = 3.4 Hz, 2H), 3.57 (s, 3H), 2.58 (s, 3H) |

Example 195: Synthesis of (S)-4-(5-Cyano-2-methoxyphenyl)-6-methyl-N-(5-(tetrahydrofuran-2-carbonyl)-5,6-dihydro-4H-pyrrolo[3,4-]thiazol-2-yl) nicotinamide

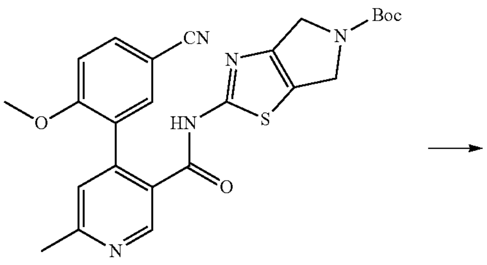

-continued

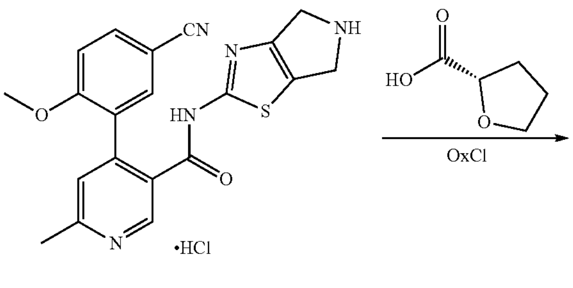

-continued

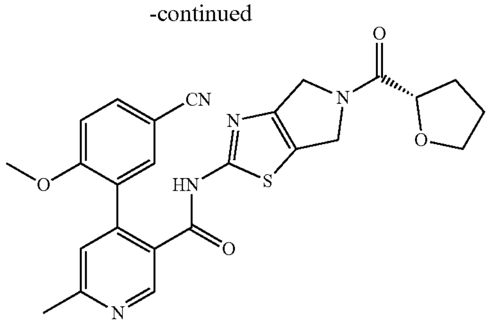

Step 1: A mixture of tert-butyl 2-(4-(5-cyano-2-methoxyphenyl)-6-methylnicotinamido)-4,6-dihydro-5H-pyrrolo[3,4-d]thiazole-5-carboxylate (50 mg, 0.10 mmol) and 4 M HCl/MeOH (5 mL) was stirred at room temperature for 2 h. The mixture was concentrated under reduced pressure to give 4-(5-cyano-2-methoxyphenyl)-N-(5,6-dihydro-4H-pyrrolo[3,4-d]thiazol-2-yl)-6-methylnicotinamide hydrochloride (40 mg), which was used directly in the next step. LCMS: m/z=392 $[M+H]^+$.

Step 2: To a solution of (S-tetrahydrofuran-2-carboxylic acid (50 mg, 0.43 mmol) and DMF (catalytic) in DCM (5 mL) at 0° C. was added oxalyl chloride (163 mg, 1.29 mmol) and the mixture was stirred at room temperature for 1 h. The mixture was concentrated under reduced pressure and the residue dissolved in DCM (1 mL)M and added to a solution of 4-(5-cyano-2-methoxyphenyl)-N-(5,6-dihydro-4H-pyrrolo[3,4-d]thiazol-2-yl)-6-methylnicotinamide hydrochloride (40 mg, 0.10 mmol) and TEA (62 mg 0.61 mmol) in DCM (5 mL). The mixture was stirred at room temperature for 2 h, then diluted with water (10 mL) and extracted with DCM (30 mL×3). The combined organic layers were washed with brine, dried over $Na_2SO_4$, filtered and concentrated under reduced pressure. The residue was purified by prep-TLC (DCM/MeOH=20/1, v/v) to give(S)-4-(5-cyano-2-methoyphenyl)-6-methyl-N-(5-(tetrahydrofuran-2-carbonyl)-5,6-dihydro-4H-pyrrolo[3,4-d]thiazol-2-yl)nicotinamide (30 mg, 60%) as a white solid. LCMS: m/z=490 $[M+H]^+$, $^1H$ NMR (400 MHz, DMSO-$d_6$): δ 12.7 (s, 1H), 8.71 (s, 1H), 7.91-7.87 (n, 14H), 7.86-7.84 (92, 1H), 7.40 (s, 1H), 7.19-7.15 (m, 1H) 4.96-4.66 (m, 2H), 4.61 (dd, J=13.8, 7.2 Hz, 2H), 4.45 (s, 1H), 3.85-3.76 (2H), 3.57 (d, J=1.8 Hz, 3H), 2.58 (s, 3H), 2.07 (d, J=7.2 Hz, 2H), 1.87 (tt, J=12.6, 5.8 Hz, 2H).

TABLE K

The following examples were prepared using a similar procedure to that described for Example 195

| Ex. No. | Structure | Compound Name | LCMS $[M+H]^+$ | NMR |
|---|---|---|---|---|
| 196 | 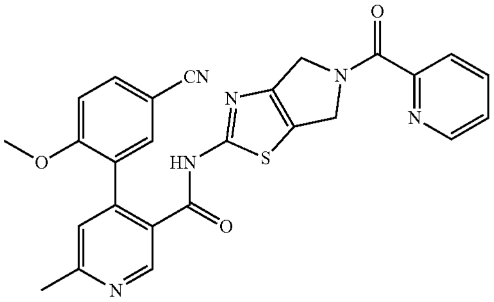 | 4-(5-Cyano-2-methoxyphenyl)-6-methyl-N-(5-picolinoyl-5,6-dihydro-4H-pyrrolo[3,4-d]thiazol-2-yl)nicotinamide | 497 | $^1H$ NMR (400 MHz, DMSO-$d_6$) δ 12.7 (d, J = 7.2 Hz, 1H), 8.72 (s, 1H), 8.66 (t, J = 6.4 Hz, 1H), 8.02-7.96 (m, 1H), 7.92-7.84 (m, 3H), 7.56 (t, J = 6.2 Hz, 1H), 7.38 (s, 1H), 7.18 (d, J = 8.6 Hz, 1H), 5.04 (s, 1H), 4.92 (s, 1H), 4.86 (s, 1H), 4.72 (s, 1H), 3.56 (d, J = 1.8 Hz, 3H), 2.58 (d, J = 1.6 Hz, 3H) |
| 197 | 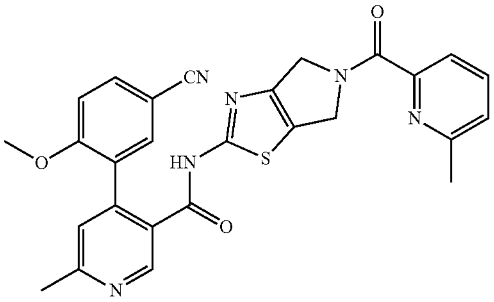 [SMILES: COc1ccc(C#N)cc1-c1cc(C)ncc1C(=O)Nc1nc2c(s1)CN(C(=O)c1cccc(C)n1)C2] | 4-(5-Cyano-2-methoxyphenyl)-6-methyl-N-(5-(6-methylpicolinoyl)-5,6-dihydro-4H-pyrrolo[3,4-d]thiazol-2-yl)nicotinamide | 511 | $^1H$ NMR (400 MHz, DMSO-$d_6$) δ 12.7 (d, J = 13.8 Hz, 1H), 8.71 (d, J = 2.0 Hz, 1H), 7.91-7.82 (m, 3H), 7.61 (dd, J = 11.6, 7.8 Hz, 1H), 7.40 (d, J = 6.8 Hz, 2H), 7.17 (dd, J = 8.8, 2.2 Hz, 1H), 5.00 (s, 1H), 4.91 (s, 1H), 4.83 (s, 1H), 4.69 (s, 1H), 3.57 (s, 3H), 2.58 (s, 3H), 2.55 (d, J = 4.6 Hz, 3H) |
| 198 | 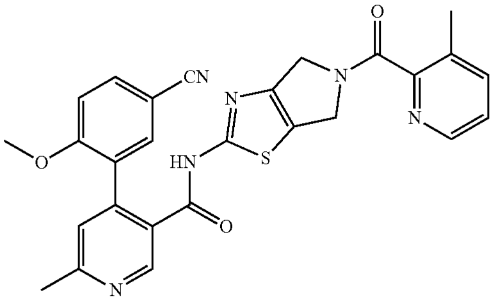 [SMILES: COc1ccc(C#N)cc1-c1cc(C)ncc1C(=O)Nc1nc2c(s1)CN(C(=O)c1ncccc1C)C2] | 4-(5-Cyano-2-methoxyphenyl)-6-methyl-N-(5-(3-methylpicolinoyl)-5,6-dihydro-4H-pyrrolo[3,4-d]thiazol-2-yl)nicotinamide | 511 | $^1H$ NMR (400 MHz, DMSO-$d_6$) δ 12.7 (s, 1H), 8.72 (d, J = 4.8 Hz, 1H), 8.44 (d, J = 4.8 Hz, 1H), 7.88 (dt, J = 8.6, 2.6 Hz, 1H), 7.83 (d, J = 2.2 Hz, 1H), 7.78 (d, J = 7.8 Hz, 1H), 7.43-7.35 (m, 2H), 7.17 (dd, J = 8.8, 3.4 Hz, 1H), 4.82 (s, 1H), 4.68 (s, 1H), 4.50 (s, 1H), 4.38 (s, 1H), 3.56 (s, 3H), 2.57 (d, J = 3.2 Hz, 3H), 2.31 (s, 3H) |

TABLE K-continued

| The following examples were prepared using a similar procedure to that described for Example 195 | | | | |
|---|---|---|---|---|
| Ex. No. | Structure | Compound Name | LCMS [M + H]+ | NMR |
| 199 | 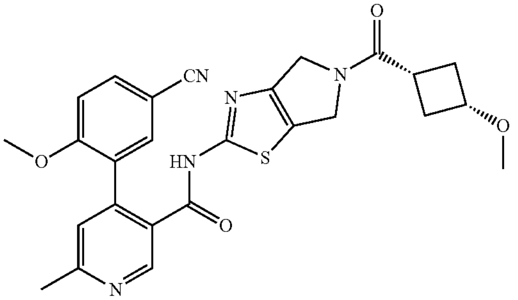 | 4-(5-Cyano-2-methoxyphenyl)-N-(5-((1s,3s)-3-methoxy-cyclobutane-1-carbonyl)-5,6-dihydro-4H-pyrrolo[3,4-d]thiazol-2-yl)-6-methylnicotinamide | 504 | $^1$H NMR (400 MHz, DMSO-$d_6$) δ 12.6 (s, 1H), 8.72 (s, 1H), 7.88 (dt, J = 8.6, 1.6 Hz, 1H), 7.85 (d. J = 2.2 Hz, 1H), 7.38 (s, 1H), 7.18 (dd, J = 8.8, 1.3 Hz, 1H), 4.72 (s, 1H), 4.62-4.56 (m, 2H), 4.42 (s, 1H), 3.82-3.76 (m, 1H), 3.56 (d, J = 1.6 Hz, 3H), 3.14 (s, 3H), 2.90-2.78 (m, 1H), 2.58 (s, 3H), 2.46-2.38 (m, 2H), 2.02-1.96 (m, 2H) |
| 200 | 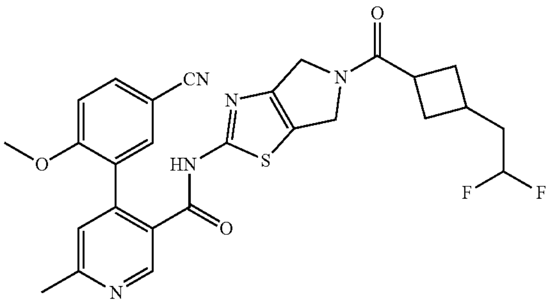 | (Cis and Trans)-4-(5-Cyano-2-methoxyphenyl)-N-(5-(3-(2,2-difluoroethyl) cyclobutane-1-carbonyl)-5,6-dihydro-4H-pyrrolo[3,4-d]thiazol-2-yl)-6-methylnicotinamide | 538 | $^1$H NMR (400 MHz, DMSO-$d_6$) δ 12.6 (s, 1H), 8.71 (s, 1H), 7.89 (dt, J = 8.6, 1.8 Hz, 1H), 7.85 (d, J = 2.2 Hz, 1H), 7.39 (s, 1H), 7.17 (d, J = 8.6 Hz, 1H), 6.19-5.85 (m, 1H), 4.71-4.63 (m, 1H), 4.60-4.50 (m, 2H), 4.46-4.39 (m, 1H), 3.56 (s, 3H), 3.28-3.15 (m, 1H), 2.58 (s, 3H), 2.43-2.26 (m, 2H), 2.06-1.83 (m, 5H) |
| 201* | 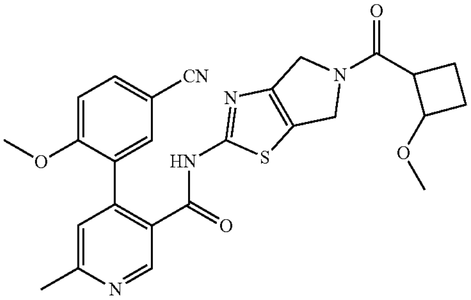 [SMILES: COc1ccc(C#N)cc1-c1cc(C)ncc1C(=O)Nc1nc2c(s1)CN(C(=O)C1CCC1OC)C2] | (Racemic Trans)-4-(5-cyano-2-methoxyphenyl)-N-(5-(2-methoxy-cyclobutane-1-carbonyl)-5,6-dihydro-4H-pyrrolo[3,4-d]thiazol-2-yl)-6-methylnicotinamide | 504 | $^1$H NMR (400 MHz, DMSO-$d_6$) δ 8.71 (s, 1H), 7.89 (dd, J = 8.8, 1.8 Hz, 1H), 7.84 (d, J = 2.2 Hz, 1H), 7.39 (s, 1H), 7.17 (d, J = 8.8 Hz, 1H), 4.88-4.68 (m, 2H), 4.61-4.52 (m, 2H), 4.46-4.40 (m, 1H), 4.06-3.98 (m, 1H), 3.56 (s, 3H), 3.23-3.12 (m, 1H), 3.15 (s, 3H), 2.58 (s, 3H), 2.14-1.95 (m, 2H), 1.81-1.71 (m, 1H), 1.63-1.54 (m, 1H) |
| 202 | 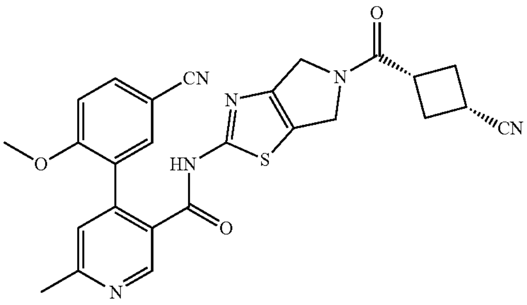 [SMILES: COc1ccc(C#N)cc1-c1cc(C)ncc1C(=O)Nc1nc2c(s1)CN(C(=O)[C@H]1C[C@@H](C#N)C1)C2] | 4-(5-Cyano-2-methoxyphenyl)-N-(5-((1s,3s)-3-cyanocyclobutane-1-carbonyl)-5,6-dihydro-4H-pyrrolo[3,4-d]thiazol-2-yl)-6-methylnicotinamide | 499 | $^1$H NMR (400 MHz, Methanol-$d_4$) δ 8.72-8.67 (m, 1H), 7.82-7.75 (m, 2H), 7.40 (d, J = 6.2 Hz, 1H), 7.12 (t, J = 7.4 Hz, 1H), 4.79-4.67 (m, 2H), 4.62-4.50 (m, 3H), 3.65 (d, J = 6.2 Hz, 3H), 3.54-3.42 (m, 1H), 2.70-2.57 (m, 7H) |

TABLE K-continued

The following examples were prepared using a similar procedure to that described for Example 195

| Ex. No. | Structure | Compound Name | LCMS [M + H]+ | NMR |
|---|---|---|---|---|
| 203 | 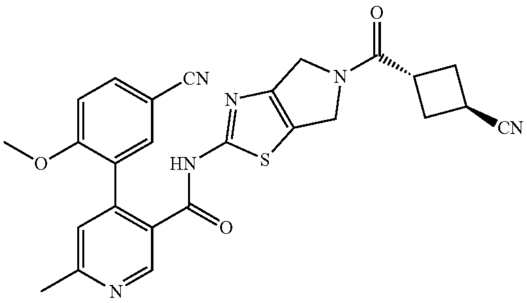 [SMILES: COc1ccc(C#N)cc1-c1cc(C)ncc1C(=O)Nc1nc2c(s1)CN(C(=O)[C@H]1C[C@H](C#N)C1)C2] | 4-(5-Cyano-2-methoxyphenyl)-N-(5-((1r,3r)-3-cyanocyclobutane-1-carbonyl)-5,6-dihydro-4H-pyrrolo[3,4-d]thiazol-2-yl)-6-methylnicotinamide | 499 | $^1H$ NMR (400 MHz, DMSO-$d_6$) δ 12.7 (d, J = 3.2 Hz, 1H), 8.71 (s, 1H), 7.93-7.80 (m, 2H), 7.40 (s, 1H), 7.17 (dd, J = 8.6, 2.4 Hz, 1H), 4.69 (s, 1H), 4.61-4.52 (m, 2H), 4.44 (s, 1H), 3.62-3.53 (m, 1H), 3.56 (s, 3H), 2.69-2.60 (m, 2H), 2.58 (s, 3H), 2.55-2.51 (m, 3H, partly obscured by solvent peak) |
| 204 | 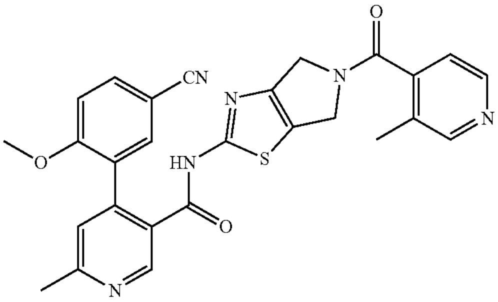 [SMILES: COc1ccc(C#N)cc1-c1cc(C)ncc1C(=O)Nc1nc2c(s1)CN(C(=O)c1ccncc1C)C2] | 4-(5-Cyano-2-methoxyphenyl)-6-methyl-N-(5-(3-methyliso-nicotinoyl)-5,6-dihydro-4H-pyrrolo[3,4-d]thiazol-2-yl)nicotinamide | 511 | $^1H$ NMR (400 MHz, DMSO-$d_6$) δ 12.7 (d, J = 7.0 Hz, 1H), 8.70 (d, J = 5.2 Hz, 1H), 8.56 (s, 1H), 8.50 (d, J = 4.8 Hz, 1H), 7.89 (dt, J = 8.6, 2.8 Hz, 1H), 7.84 (d, J = 2.2 Hz, 1H), 7.40 (t, J = 3.8 Hz, 2H), 7.19-7.15 (m, 1H), 4.84-4.79 (m, 1H), 4.67 (t, J = 2.8 Hz, 1H), 4.42 (t, J = 2.8 Hz, 1H), 4.32 (t, J = 2.8 Hz, 1H), 3.56 (s, 3H), 2.57 (d, J = 3.2 Hz, 3H), 2.27 (s, 3H) |
| 205 | 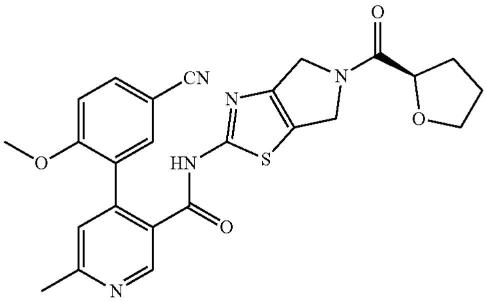 [SMILES: COc1ccc(C#N)cc1-c1cc(C)ncc1C(=O)Nc1nc2c(s1)CN(C(=O)[C@H]1CCCO1)C2] | (R)-4-(5-Cyano-2-methoxyphenyl)-6-methyl-N-(5-(tetrahydrofuran-2-carbonyl)-5,6-dihydro-4H-pyrrolo[3,4-d]thiazol-2-yl)nicotinamide | 490 | $^1H$ NMR (400 MHz, DMSO-$d_6$) δ 12.7 (s, 1H), 8.71 (s, 1H), 7.89 (dd, J = 8.4, 1.8 Hz, 1H), 7.85 (d, J = 2.0 Hz, 1H), 7.39 (s, 1H), 7.17 (d, J = 8.6 Hz, 1H), 4.98-4.66 (m, 2H), 4.66-4.56 (m, 2H), 4.45 (s, 1H), 3.86 3.75 (m, 2H), 3.57 (d, J = 1.6 Hz, 3H), 2.58 (s, 3H), 2.12-2.02 (m, 2H), 1.95-1.79 (m, 2H) |
| 206 | 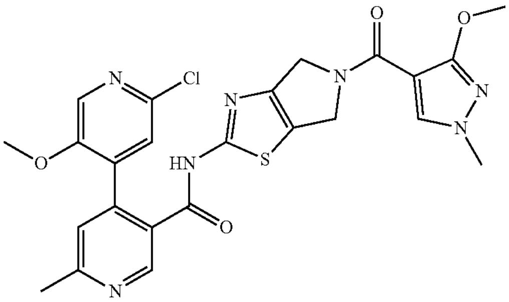 | 2'-Chloro-5'-methoxy-N-(5-(3-methoxy-1-methyl-1H-pyrazole-4-carbonyl)-5,6-dihydro-4H-pyrrolo[3,4-d]thiazol-2-yl)-6-methyl-[4,4'-bipyridine]-3-carboxamide | 540 | $^1H$ NMR (400 MHz, DMSO-$d_6$) δ 12.8 (s, 1H), 8.79 (s, 1H), 8.17 (s, 1H), 7.99 (d, J = 13.6 Hz, 1H), 7.54 (s, 1H), 7.43 (s, 1H), 4.83 (s, 1H), 4.70 (s, 2H), 4.57 (s, 1H), 3.85 (s, 3H), 3.72 (s, 3H), 3.60 (s, 3H), 2.59 (s, 3H) |

*Racemic diastereomer with known relative stereochemistry

Example 207: Synthesis of (Cis and Trans)-4-(5-Cyano-2-methoxyphenyl)-N-(5-(3-(difluoromethyl) cyclobutane-1-carbonyl)-5,6-dihydro-4H-pyrrolo[3,4-d]thiazol-2-yl)-6-methylnicotinamide

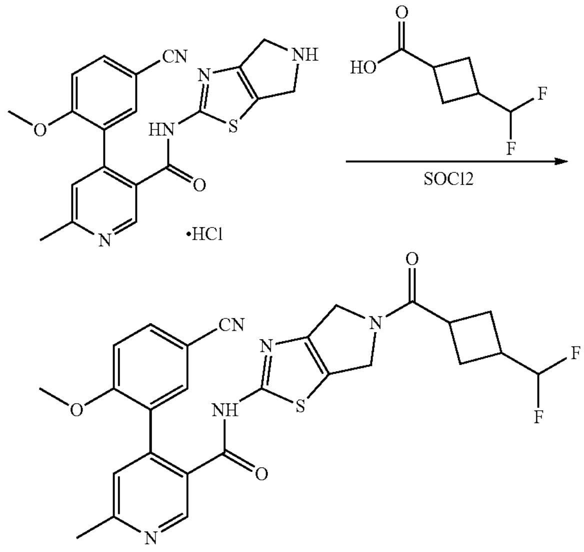

A mixture of 3-(difluoromethyl)cyclobutane-1-carboxylic acid (50 mg, 0.3 mmol) and $SOCl_2$ (2 mL) was heated at 65° C. for 2 h then concentrated under reduced pressure. The residue was dissolved in DCM (1 mL) and slowly added to a solution of 4-(5-cyano-2-methoxyphenyl)-N-(5,6-dihydro-4H-pyrrolo[3,4-d]thiazol-2-yl)-6-methylnicotinamide hydrochloride (80 mg) and TEA (101 mg, 1.0 mmol) in DCM (2 mL). The mixture was stirred at room temperature for 2 h then diluted with water (20 mL) and extracted with DCM (3×20 mL). The combined organic layers were washed with water (20 mL), brine (20 mL), dried over $Na_2SO_4$, filtered and concentrated under reduced pressure. The residue was purified by prep-TLC (DCM/MeOH=20/1, v/v) to give (Cis and Trans)-4-(5-cyano-2-methoxyphenyl)-N-(5-(3-(difluoromethyl)cyclobutane-1-carbonyl)-5,6-dihydro-4H-pyrrolo[3,4-d]thiazol-2-yl)-6-methylnicotinamide (80 mg, 75%) as a white solid. LCMS: m/z=524 $[M+H]^+$, $^1H$ NMR (400 MHz, DMSO-$d_6$) δ 12.7 (d, J=8.8 Hz, 1H), 8.71 (s, 1H), 7.89 (dd, J=9.0, 1.6 Hz, 1H), 7.85 (d, J=2.0 Hz, 1H), 7.40 (s, 1H), 7.20-7.14 (m, 1H), 6.36-5.84 (m, 1H), 4.73-4.64 (m, 1H), 4.61-4.51 (nm, 2H), 4.47-4.40 (m, 11H), 3.56 (s, 3H), 3.42-3.24 (m, 11H), 2.77-2.61 (m, 1H), 2.58 (s, 3H), 2.32-2.11 (m, 4H).

TABLE L

The following examples were prepared using a similar procedure to that described for Example 207

| Ex. No. | Structure | Compound Name | LCMS $[M + H]^+$ | NMR |
|---|---|---|---|---|
| 208 | 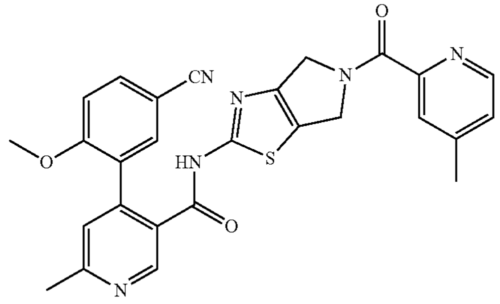 [SMILES: COc1ccc(C#N)cc1-c1cc(C)ncc1C(=O)Nc1nc2c(s1)CN(C(=O)c1cc(C)ccn1)C2] | 4-(5-cyano-2-methoxyphenyl)-6-methyl-N-(5-(4-methylpicolinoyl)-5,6-dihydro-4H-pyrrolo[3,4-d]thiazol-2-yl)nicotinamide | 511 | $^1H$ NMR (400 MHz, DMSO-$d_6$) δ 12.7 (s, 1H), 8.72 (s, 1H), 8.51 (dd, J = 7.8, 5.0 Hz, 1H), 7.88 (d, J = 8.6 Hz, 1H), 7.85-7.82 (m, 1H), 7.69 (d, J = 4.8 Hz, 1H), 7.38 (s, 2H), 7.17 (d, J = 8.6 Hz, 1H), 5.02 (s, 1H), 4.90 (s, 1H), 4.83 (s, 1H), 4.69 (s, 1H), 3.58 (s, 3H), 2.58 (s, 3H), 2.40 (s, 3H) |
| 209 | 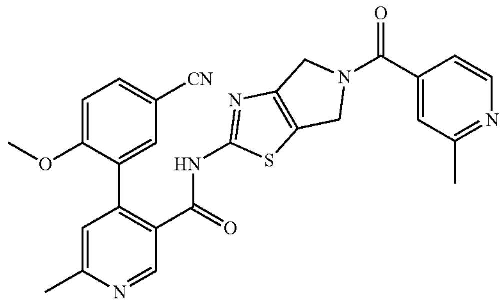 [SMILES: COc1ccc(C#N)cc1-c1cc(C)ncc1C(=O)Nc1nc2c(s1)CN(C(=O)c1ccnc(C)c1)C2] | 4-(5-Cyano-2-methoxyphenyl)-6-methyl-N-(5-(2-methylisonicotinoyl)-5,6-dihydro-4H-pyrrolo[3,4-d]thiazol-2-yl)nicotinamide | 511 | $^1H$ NMR (400 MHz, DMSO-$d_6$) δ 12.5 (s, 1H), 8.72 (d, J = 3.6 Hz, 1H), 8.56 (d, J = 5.0 Hz, 1H), 7.86 (dt, J = 8.6, 1.8 Hz, 1H), 7.80 (d, J = 2.2 Hz, 1H), 7.42 (s, 1H), 7.37 (s, 1H), 7.34 (d, J = 5.4 Hz, 1H), 7.17 (d, J = 8.6 Hz, 1H), 4.81 (s, 1H), 4.66 (s, 2H), 4.55 (s, 1H), 3.59 (s, 3H), 2.58 (s, 3H), 2.53 (s, 3H) |

TABLE L-continued

The following examples were prepared using a similar procedure to that described for Example 207

| Ex. No. | Structure | Compound Name | LCMS $[M + H]^+$ | NMR |
|---|---|---|---|---|
| 706 | 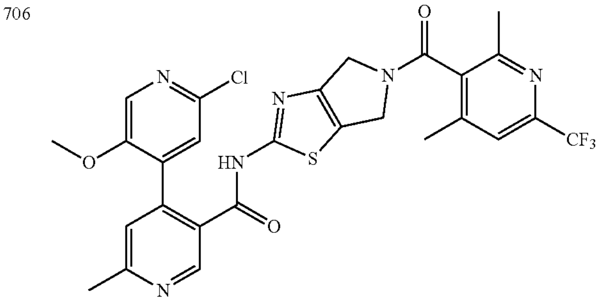 | 2'-Chloro-N-(5-(2,4-dimethyl-6-(trifluoromethyl) nicotinoyl)-5,6-dihydro-4H-pyrrolo[3,4-d]thiazol-2-yl)-5'-methoxy-6-methyl-[4,4'-bipyridine]-3-carboxamide | 603 | $^1$H NMR (400 MHz, DMSO-$d_6$) δ 12.8 (s, 1H), 8.77 (d, J = 4.8 Hz, 1H), 8.17 (d, J = 2.6 Hz, 1H), 7.76 (d, J = 5.0 Hz, 1H), 7.54 (s, 1H), 7.43 (d, J = 3.0 Hz, 1H), 4.88 (s, 1H), 4.75 (s, 1H), 4.45-4.22 (m, 2H), 3.60 (s, 3H), 2.59 (d, J = 3.2 Hz, 3H), 2.51 (d, J = 2.0 Hz, 3H), 2.37 (s, 3H) |

Example 210: Synthesis of 4-(5-Cyano-2-methoyphenyl)-N-(5-cyclopropyl-5,6-dihydro-4H-pyrrolo[3,4-d]thiazol-2-yl)-6-methylnicotinamide

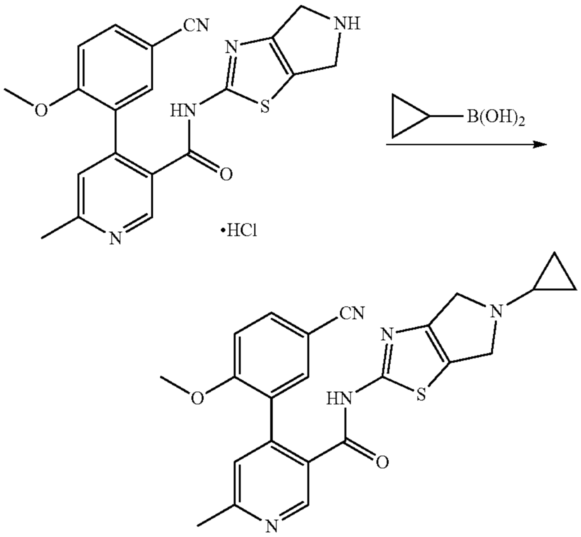

A mixture of 4-(5-cyano-2-methoxyphenyl)-N-(5,6-dihydro-4H-pyrrolo[3,4-d]thiazol-2-yl)-6-methylnicotinamide hydrochloride (125 mg, 0.29 mmol), cyclopropylboronic acid (55 mg, 0.64 mmol), $Cu(OAc)_2$ (64 mg, 0.32 mmol), 2,2'-bipyridine (49 mg, 0.32 mmol) and $Na_2CO_3$ (67 mg, 0.67 mmol) in DCE (8 mL) was heated at 70° C. for 4 h. The mixture was diluted with water (30 mL), extracted with EtOAc (3×30 mL) and the combined organic layers washed with water (30 mL), dried over $Na_2SO_4$, filtered and concentrated under reduced pressure. The residue was purified by prep-TLC (DCM/MeOH=30/1, v/v) to give 4-(5-cyano-2-methoxyphenyl)-N-(5-cyclopropyl-5,6-dihydro-4H-pyrrolo[3,4-d]thiazol-2-yl)-6-methylnicotinamide (10 mg, 7%) as yellow oil. LCMS: m/z=432 $[M+H]^+$, $^1$H NMR (400 MHz, DMSO-$d_6$): δ 12.8 (s, 1H), 8.72 (s, 1H), 7.91 (dd, J=8.6, 2.2 Hz, 1H), 7.86 (d, J=2.2 Hz, 1H), 7.42 (s, 1H), 7.18 (d, J=8.8 Hz, 1H), 4.81-4.52 (m, 4H), 3.56 (s, 3H), 2.59 (s, 3H), 2.04-1.94 (n, 1H), 1.01-0.82 (m, 4H).

Example 211: Synthesis of (S)-2'-Chloro-N-(6-(cyclopropanecarboxamido)-4,5,6,7-tetrahydrobenzo[d]thiazol-2-yl)-5'-methoxy-6-methyl-[4,4'-bipyridine]-3-carboxamide

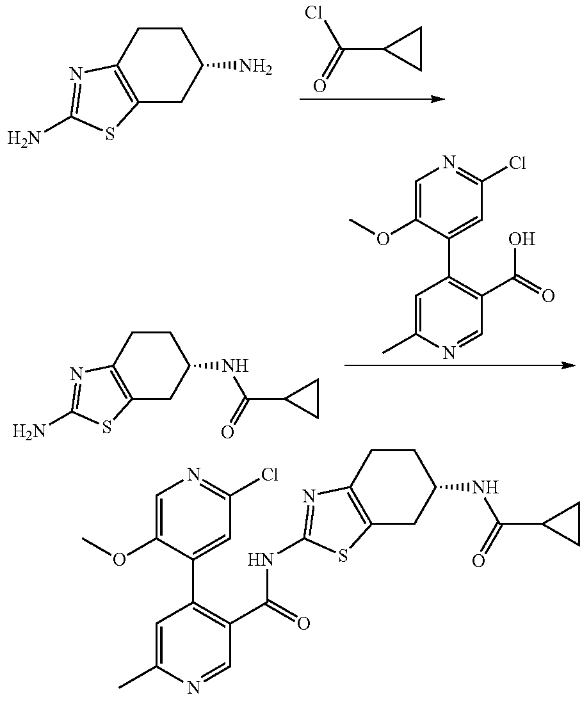

Step 1: To a solution of (S)-4,5,6,7-tetrahydrobenzo[d]thiazole-2,6-diamine (100 mg, 0.59 mmol) and DIPEA (229 mg, 1.77 mmol) in DMF (3 mL) at 0° C. was added cyclopropanecarbonyl chloride (55 mg, 0.53 mmol) and the mixture was stirred at room temperature for 10 min. The mixture was diluted with water (20 mL), extracted with EtOAc (40 mL×3) and the combined organic layers washed with brine (20 mL), dried over $Na_2SO_4$, filtered and concentrated under reduced pressure. The residue was purified by prep-TLC (DCM/MeOH=10/1, v/v) to give (S)—N-(2-amino-4,5,6,7-tetrahydrobenzo[d]thiazol-6-yl)cyclopropanecarboxamide (100 mg, 71%) as a white solid. LCMS:

m/z=238 [M+H]$^+$, $^1$H NMR (400 MHz, DMSO-$d_6$) δ 8.12 (d, J=7.8 Hz, 1H), 6.64 (s, 2H), 4.03-3.92 (m, 1H), 2.77-2.65 (m, 1H), 2.53 (d, J=6.2 Hz, 1H), 2.48-2.31 (m, 2H), 1.90-1.79 (m, 1H), 1.74-1.63 (m, 1H), 1.57 (td, J=7.6, 3.8 Hz, 1H), 0.70-0.57 (m, 4H).

Step 2: To a solution of (S)—N-(2-amino-4,5,6,7-tetrahydrobenzo[d]thiazol-6-yl)cyclopropanecarboxamide (80 mg, 0.33 mmol), 2'-chloro-5'-methoxy-6-methyl-[4,4'-bipyridine]-3-carboxylic acid (112 mg, 0.40 mmol) and TCFH (141 mg, 0.50 mmol) in ACN (8 mL) was added NMI (110 mg, 1.35 mmol) and the mixture was stirred at room temperature overnight. The mixture was diluted with water (20 mL), extracted with EtOAc (40 mL×3) and the combined organic layers washed with brine (20 mL), dried over $Na_2SO_4$, filtered and concentrated under reduced pressure. The residue was purified by prep-TLC (DCM/MeOH=20/1, v/v) to give (S)-2'-chloro-N-(6-(cyclopropanecarboxamido)-4,5,6,7-tetrahydrobenzo[d]thiazol-2-yl)-5'-methoxy-6-methyl-[4,4'-bipyridine]-3-carboxamide (140 mg, 83%) as a white solid. LCMS: m/z=498 [M+H]$^+$, H NMR (400 MHz, DMSO-$d_6$) δ 12.5 (s, 1H), 8.76 (s, 1H), 8.18 (d, J=7.6 Hz, 1H), 8.16 (s, 1H), 7.50 (s, 1H), 7.40 (s, 1H), 4.10-3.98 (m, 1H), 3.62 (s, 3H), 2.92 (dd, J=16.2, 5.4 Hz, 1H), 2.77-2.60 (m, 3H), 2.58 (s, 3H), 1.98-1.88 (m, 1H), 1.83-1.71 (m, 1H), 1.57 (td, J=7.8, 3.8 Hz, 1H), 0.70-0.60 (m, 4H).

-continued

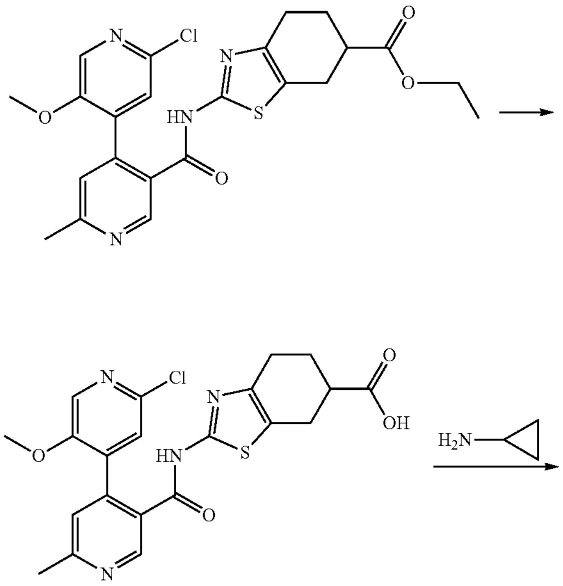

TABLE M

The following examples were prepared using a similar procedure to that described for Example 211

| Ex. No. | Structure | Compound Name | LCMS [M + H]$^+$ | NMR |
|---|---|---|---|---|
| 212 | 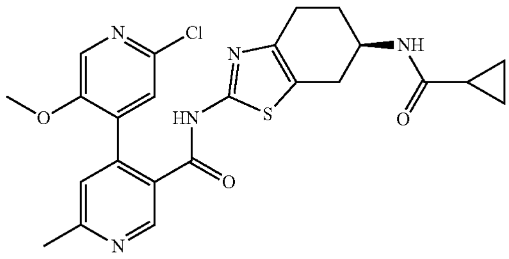 [SMILES: COc1cnc(Cl)cc1-c1cc(C)ncc1C(=O)Nc1nc2c(s1)C[C@H](NC(=O)C1CC1)CC2] | (R)-2'-Chloro-N-(6-(cyclopropanecarboxamido)-4,5,6,7-tetrahydrobenzo[d]thiazol-2-yl)-5'-methoxy-6-methyl-[4,4'-bipyridine]-3-carboxamide | 498 | $^1$H NMR (400 MHz, DMSO-$d_6$) δ 12.5 (s, IH), 8.76 (s, 1H), 8.21-8.13 (m, 2H), 7.50 (s, 1H), 7.40 (s, 1H), 4.09-3.99 (m, 1H), 3.62 (s, 3H), 2.96-2.87 (m, 1H), 2.76-2.64 (m, 2H), 2.58 (s, 3H), 2.55-2.51 (m, 1H), 1.99-1.89 (m, 1H), 1.84-1.72 (m, 1H), 1.62-1.53 (m, 1H), 0.69-0.60 (m. 4H) |

Example 213: Synthesis of (Racemic)-2-(2'-chloro-5'-methoxy-6-methyl-[4,4'-bipyridine]-3-carboxamido)-N-cyclopropyl-4,5,6,7-tetrahydrobenzo[d]thiazole-6-carboxamide

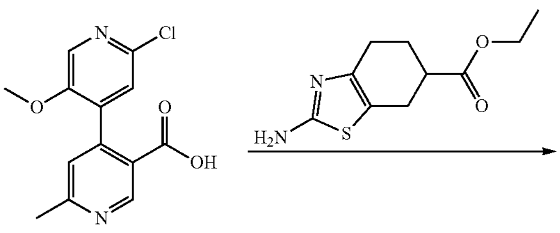

-continued

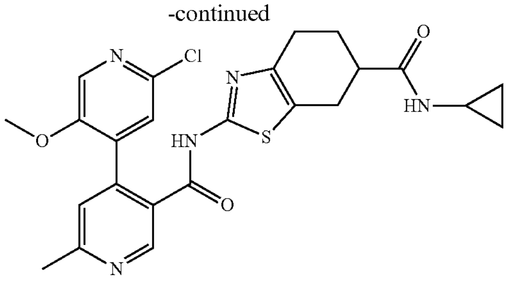

Step 1: A mixture of 2'-chloro-5'-methoxy-6-methyl-[4,4'-bipyridine]-3-carboxylic acid (200 mg, 0.72 mmol), ethyl 2-amino-4,5,6,7-tetrahydrobenzo[d]thiazole-6-carboxylate (160 mg, 0.72 mmol), TCFH (300 mg, 1.08 mmol) and NMI (240 mg, 2.88 mmol) in ACN (6 mL) was heated at 80° C. for 16 h. After cooling to room temperature, the mixture was diluted with water (6 mL), extracted with EtOAc (6×10 mL), dried over $Na_2SO_4$, filtered and concentrated under reduced pressure. The residue was purified by prep-TLC (DCM/MeOH=15/1, v/v) to give ethyl 2-(2'-chloro-5'-methoxy-6-methyl-[4,4'-bipyridine]-3-carboxamido)-4,5,6,7-tetrahydrobenzo[d]thiazole-6-carboxylate (209 mg, 60%) as a gray solid. LCMS: m/z=487 $[M+H]^+$.

Step 2: To a solution of ethyl 2-(2'-chloro-5'-methoxy-6-methyl-[4,4'-bipyridine]-3-carboxamido)-4,5,6,7-tetrahydrobenzo[d]thiazole-6-carboxylate (209 mg, 0.43 mmol) in THF (2 mL) and water (2 mL) was added LiOH (29 mg, 1.2 mmol) and the mixture was stirred at room temperature for 2 h. The mixture was concentrated under reduced pressure and the residue was dissolved in DMF (3 mL). Cyclopropanamine (28 mg, 0.50 mmol), DIPEA (128 mg, 0.99 mmol) and T3P (50% in DMF, 157 mg, 0.25 mmol) were added and the mixture was stirred at room temperature overnight. The mixture was diluted with water (40 mL), extracted with EtOAc (2×30 mL) and the combined organic layers were washed with water (20 mL), brine (20 mL), dried over $Na_2SO_4$, filtered and concentrated under reduced pressure. The residue was purified by prep-TLC (DCM/MeOH=20/1, v/v) to give (Racemic)-2-(2'-chloro-5'-methoxy-6-methyl-[4,4'-bipyridine]-3-carboxamido)-N-cyclopropyl-4,5,6,7-tetrahydrobenzo[d]thiazole-6-carboxamide (87 mg, 41%) as an off-white solid. LCMS: m/z=498 $[M+H]^+$, $^1$H NMR (400 MHz, DMSO-$d_6$): δ 12.4 (s, 1H), 8.75 (s, 1H), 8.16 (s, 1H), 8.01 (d, J=4.2 Hz, 1H), 7.50 (s, 1H), 7.40 (s, 1H), 3.61 (s, 3H), 2.76-2.60 (m, 4H), 2.57 (s, 3H), 2.50-2.43 (m, 1H), 2.03-1.90 (m, 2H), 1.80-1.70 (m, 1H), 0.64-0.54 (m, 2H), 0.43-0.32 (m, 2H).

Example 214A & 214B: Synthesis of (R or S)-2-(2'-Chloro-5'-methoxy-6-methyl-[4,4'-bipyridine]-3-carboxamido)-N-cyclopropyl-4,5,6,7-tetrahydrobenzo[d]thiazole-6-carboxamide (214A) & (S or R)-2-(2'-Chloro-5'-methoxy-6-methyl-[4,4'-bipyridine]-3-carboxamido)-N-cyclopropyl-4,5,6,7-tetrahydrobenzo[d]thiazole-6-carboxamide (214B) with arbitrarily assigned stereochemistry

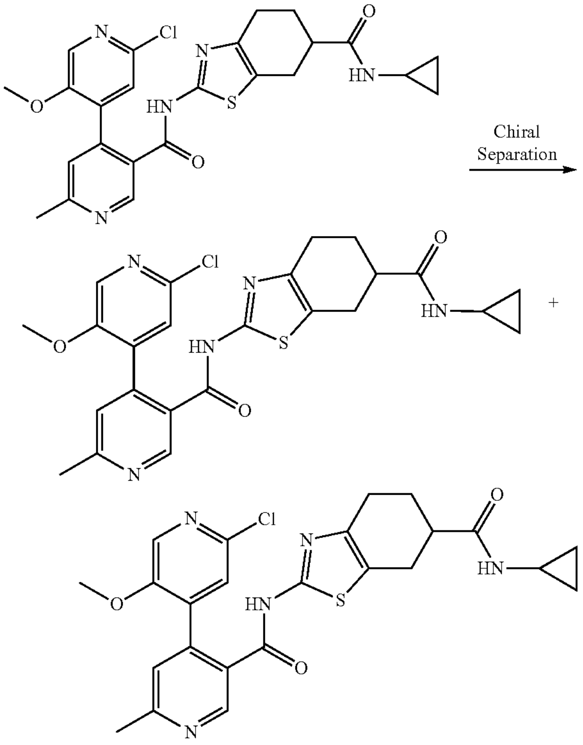

2-(2'-Chloro-5'-methoxy-6-methyl-[4,4'-bipyridine]-3-carboxamido)-N-cyclopropyl-4,5,6,7-tetrahydrobenzo[d]thiazole-6-carboxamide was purified by chiral prep HPLC (Column: Chiralcel, OZ-H, 4.6 mm I.D.×25 cm L, 5 μm; Mobile Phase: 100% MeOH; Flow rate: 1.0 mL/min) to afford two peaks:

Example 214A: Peak 1, retention time 5.17 min. (R or S)-2-(2'-Chloro-5'-methoxy-6-methyl-[4,4'-bipyridine]-3-carboxamido)-N-cyclopropyl-4,5,6,7-tetrahydrobenzo[d]thiazole-6-carboxamide: LCMS: m/z=498 $[M+H]^+$, $^1$H NMR (400 MHz, DMSO-$d_6$) δ 12.5 (s, 1H), 8.75 (s, 1H), 8.16 (s, 1H), 7.96 (d, J=4.2 Hz, 1H), 7.50 (s, 1H), 7.40 (s, 1H), 3.61 (s, 3H), 2.78-2.70 (m, 2H), 2.67-2.60 (m, 2H), 2.57 (s, 3H), 2.50-2.43 (m, 1H), 2.04-1.91 (m, 2H), 1.81-1.68 (m, 1H), 0.64-0.58 (m, 2H), 0.41-0.36 (m, 2H).

Example 214B: Peak 2, retention time 10.7 min (S or R)-2-(2'-Chloro-5'-methoxy-6-methyl-[4,4'-bipyridine]-3-carboxamido)-N-cyclopropyl-4,5,6,7-tetrahydrobenzo[d]thiazole-6-carboxamide: LCMS: m/z=498 $[M+H]^+$, $^1$H NMR (400 MHz, DMSO-$d_6$) δ 12.5 (s, 1H), 8.78 (s, 1H), 8.17 (s, 1H), 7.97 (d, J=4.2 Hz, 1H), 7.51 (s, 1H), 7.44 (s, 1H), 3.61 (s, 3H), 2.76-2.70 (m, 2H), 2.68-2.60 (m, 2H), 2.59 (s, 3H), 2.50-2.43 (m, 1H), 2.04-1.90 (m, 2H), 1.81-1.69 (m, 1H), 0.64-0.58 (m, 2H), 0.41-0.36 (m, 2H).

Example 215: Synthesis of (Racemic)-2'-Chloro-N-(6-(4-hydroxypiperidin-1-yl)-4,5,6,7-tetrahydrobenzo[d]thiazol-2-yl)-5'-methoxy-6-methyl-[4,4'-bipyridine]-3-carboxamide

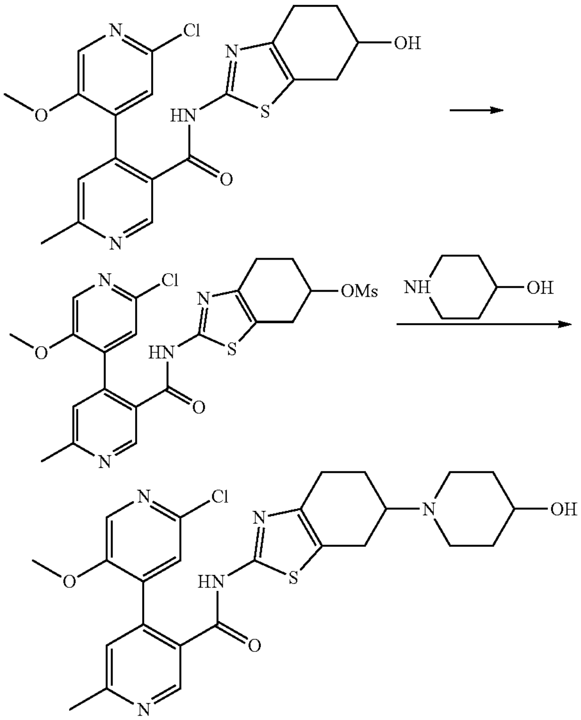

Step 1: To a solution of 2'-chloro-N-(6-hydroxy-4,5,6,7-tetrahydrobenzo[d]thiazol-2-yl)-5'-methoxy-6-methyl-[4,4'-bipyridine]-3-carboxamide (70 mg, 0.16 mmol; See, e.g., Example 144) in DCM (2 mL) was added MsCl (48.4 mg, 0.422 mmol) and TEA (49.3 mg, 0.487 mmol) and the mixture was stirred at room temperature for 4 h. The mixture was diluted with water (20 mL), extracted with EtOAc (20 mL×2) and the combined organic layers washed with brine, dried over $Na_2SO_4$, filtered and concentrated under reduced pressure. The residue was purified by prep-TLC (DCM/MeOH=15/1, v/v) to afford 2-(2'-chloro-5'-methoxy-6-methyl-[4,4'-bipyridine]-3-carboxamido)-4,5,6,7-tetrahydrobenzo[d]thiazol-6-yl methanesulfonate (70 mg, 84%) as a yellow solid. LCMS: m/z=508 $[M+H]^+$, $^1H$ NMR (400 MHz, DMSO-$d_6$) δ 8.76 (s, 1H), 8.16 (s, 1H), 7.51 (s, 1H), 7.41 (s, 1H), 5.19-5.13 (m, 1H), 3.61 (s, 3H), 3.24 (s, 3H), 3.14 (d, J=14.4 Hz, 1H), 2.97-2.88 (m, 1H), 2.72 (t, J=6.6 Hz, 2H), 2.58 (s, 3H), 2.21-2.05 (m, 2H).

Step 2: To a solution of 2-(2'-chloro-5'-methyl-6-methyl-[4,4'-bipyridine]-3-carboxamido)-4,5,6,7-tetrahydrobenzo[d]thiazol-6-yl methanesulfonate (60 mg, 0.118 mmol) in ACN (2 mL) was added piperidin-4-ol (358 mg, 3.54 mmol) and the mixture was heated at 80° C. overnight. The mixture was diluted with water (10 mL), extracted with EtOAc (20 mL×3) and the combined organic layers washed with brine, dried over $Na_2SO_4$, filtered and concentrated under reduced pressure. The residue was purified by prep-TLC (DCM/MeOH=15/1, v/v) to afford (Racemic)-2'-chloro-N-(6-(4-hydroxypiperidin-1-yl)-4,5,6,7-tetrahydrobenzo[d]thiazol-2-yl)-5'-methoxy-6-methyl-[4,4'-bipyridine]-3-carboxamide (25 mg, 47%) as a yellow solid. LCMS: m/z=514 [M+H]1, $^1H$ NMR (400 MHz, Chloroform-d) δ 8.79 (s, 1H), 7.98 (s, 1H), 7.28 (s, 1H), 7.19 (s, 1H), 4.16 (s, 1H), 3.67 (s, 3H), 3.40-3.21 (m, 4H), 3.08-2.98 (m, 1H), 2.93-2.83 (m, 1H), 2.81-2.73 (m, 1H), 2.67 (s, 3H), 2.63-2.45 (m, 3H), 2.06-1.97 (m, 3H), 1.97-1.83 (m, 3H).

TABLE N

The following examples were prepared using a similar procedure to that described for Example 215

| Ex. No. | Structure | Compound Name | LCMS $[M + H]^+$ | NMR |
|---|---|---|---|---|
| 216 | 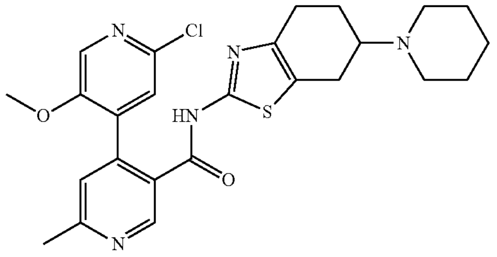 [SMILES: COc1cnc(Cl)cc1-c1cc(C)ncc1C(=O)Nc1nc2c(s1)CC(N1CCCCC1)CC2] | (Racemic)-2'-Chloro-5'-methoxy-6-methyl-N-(6-(piperidin-1-yl)-4,5,6,7-tetrahydrobenzo[d]thiazol-2-yl)-[4,4'-bipyridine]-3-carboxamide | 498 | $^1H$ NMR (400 MHz, DMSO-$d_6$) δ 8.78 (s, 1H), 8.19 (s, 1H), 7.55 (s, 1H), 7.44 (s, 1H), 3.67-3.55 (m, 1H), 3.60 (s, 3H), 3.53-3.36 (m, 2H), 3.25-3.13 (m, 1H), 3.11-2.91 (m, 3H), 2.86-2.75 (m, 1H), 2.74-2.63 (m, 1H), 2.58 (s, 3H), 2.44-2.37 (m, 1H), 2.00-1.63 (m, 1H), 1.49-1.33 (m, 1H) |

Example 217: Synthesis of 2'-Chloro-N-(5-(3-hydroxyazetidine-1-carbonyl)-5,6-dihydro-4H-pyrrolo[3,4-d]thiazol-2-yl)-5'-methoxy-6-methyl-[4,4'-bipyridine]-3-carboxamide

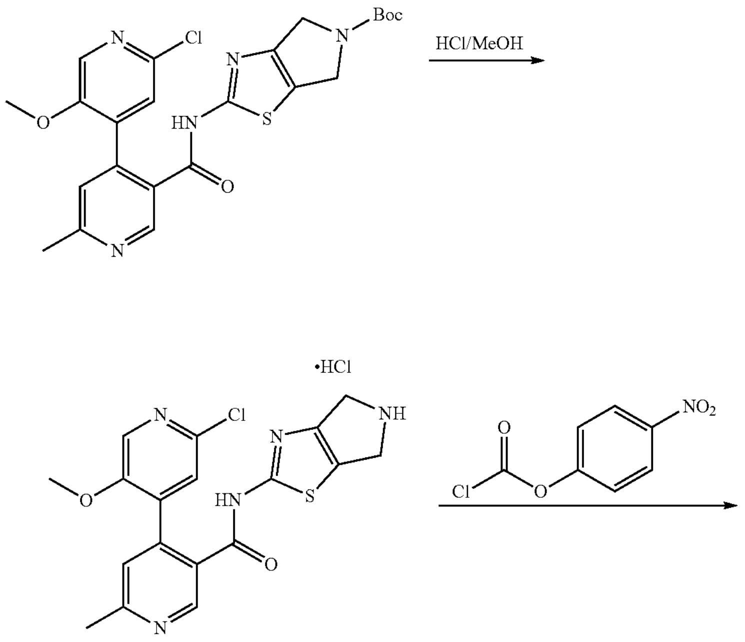

-continued

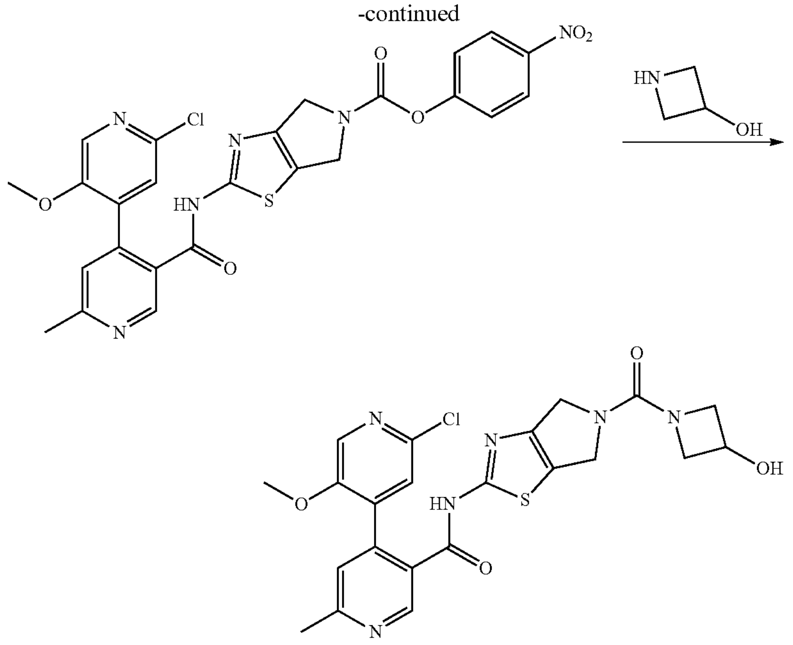

Step 1: A solution of tert-butyl 2-(2'-chloro-5'-methoxy-6-methyl-[4,4'-bipyridine]-3-carboxamido)-4,6-dihydro-5H-pyrrolo[3,4-d]thiazole-5-carboxylate (50 mg, 0.099 mmol) in 4 M HCl/MeOH (3 mL) was stirred at room temperature for 4 h then concentrated under reduced pressure. The residue was dissolved in DCM (3 mL), cooled to 0° C., TEA (30 mg, 0.298 mmol) and 4-nitrophenyl carbonochloridate (22 mg, 0.109 mmol) were added and the mixture was stirred at 0° C. for 2 h. The mixture was diluted with water (10 mL), exacted with EtOAc (10 mL×3) and the combined organic layers washed with brine (10 mL), dried over $Na_2SO_4$, filtered and concentrated under reduced pressure. The residue was purified by prep-TLC (DCM/MeOH=20/1, v/v) to give 4-nitrophenyl 2-(2'-chloro-5'-methoxy-6-methyl-[4,4'-bipyridine]-3-carboxamido)-4,6-dihydro-5H-pyrrolo[3,4-d]thiazole-5-carboxylate (50 mg, 89%) as a white solid. LCMS: m/z=565 $[M-H]^-$. $^1H$ NMR (400 MHz, DMSO-$d_6$) δ 12.8 (s, 1H), 8.79 (s, 1H), 8.31 (d, J=9.2 Hz, 2H), 8.17 (s, 1H), 7.55 (s, 1H), 7.51 (dd, J=9.0, 1.8 Hz, 2H), 7.44 (s, 1H), 4.89 (s, 1H), 4.77 (s, 1H), 4.70 (s, 1H), 4.57 (s, 1H), 3.61 (s, 3H), 2.59 (s, 3H).

Step 2: To a solution of 4-nitrophenyl 2-(2'-chloro-5'-methoxy-6-methyl-[4,4'-bipyridine]-3-carboxamido)-4,6-dihydro-5H-pyrrolo[3,4-d]thiazole-5-carboxylate (45 mg, 0.079 mmol) in DMF (2 mL) was added TEA (16 mg, 0.16 mmol) and azetidin-3-ol (7 mg, 0.95 mmol) and the mixture was stirred at room temperature for 4 h. Additional TEA (30 mg, 0.30 mmol) was added and stirring was continued at room temperature for a further 4 h. The mixture was concentrated under reduced pressure and the residue purified by prep-TLC (DCM/MeOH=20/1, v/v) to give 2'-chloro-N-(5-(3-hydroxyazetidine-1-carbonyl)-5,6-dihydro-4H-pyrrolo[3,4-d]thiazol-2-yl)-5'-methoxy-6-methyl-[4,4'-bipyridine]-3-carboxamide (10 mg, 25%) as a white solid. LCMS: m/z=501 $[M+H]^+$. $^1H$ NMR (400 MHz, DMSO-$d_6$) δ 12.7 (s, 1H), 8.78 (s, 1H), 8.16 (s, 1H), 7.54 (s, 1H), 7.43 (s, 1H), 5.60 (d, J=6.2 Hz, 1H), 4.56 (s, 2H), 4.46-4.39 (m, 3H), 4.13 (t, J=7.8, Hz, 2H), 3.73 (dd, J=8.8, 4.8 Hz, 2H), 3.60 (s, 3H), 2.59 (s, 3H).

TABLE O

The following examples were prepared using a similar procedure to that described for Example 217

| Ex. No. | Structure | Compound Name | LCMS $[M + H]^+$ | NMR |
|---|---|---|---|---|
| 218 | 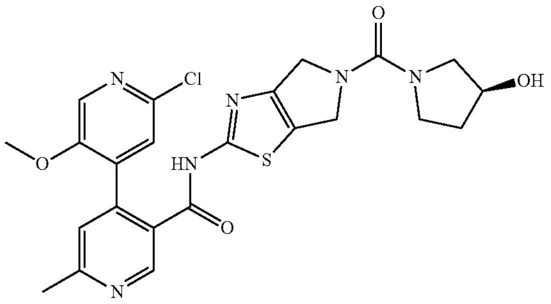 [SMILES: COc1cnc(Cl)cc1-c1cc(C)ncc1C(=O)Nc1nc2c(s1)CN(C(=O)N1CC[C@H](O)C1)C2] | (S)-2'-Chloro-N-(5-(3-hydroxypyrrolidine-1-carbonyl)-5,6-dihydro-4H-pyrrolo[3,4-d]thiazol-2-yl)-5'-methoxy-6-methyl-[4,4'-bipyridine]-3-carboxamide | 515 | $^1H$ NMR (400 MHz, DMSO-$d_6$) δ 12.7 (s, 1H), 8.78 (s, 1H), 8.16 (s, 1H), 7.54 (s, 1H), 7.43 (s, 1H), 4.90 (d, J = 3.6 Hz, 1H), 4.78-4.71 (m, 1H), 4.65-4.51 (m, 2H), 4.46-4.38 (m, 1H), 4.26 (s, 1H), 3.60 (s, 3H), 3.54-3.47 (m, 2H), 3.41-3.34 (m, 1H), 3.23-3.17 (m, 1H), 2.59 (s, 3H), 1.92-1.69 (m, 2H) |

TABLE O-continued

| The following examples were prepared using a similar procedure to that described for Example 217 | | | | |
|---|---|---|---|---|
| Ex. No. | Structure | Compound Name | LCMS [M + H]$^+$ | NMR |
| 219 | 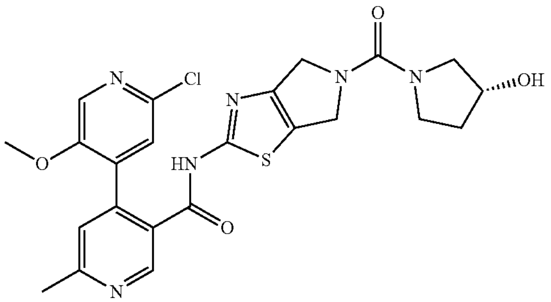 [SMILES: COc1cnc(Cl)cc1-c1cc(C)ncc1C(=O)Nc1nc2c(s1)CN(C(=O)N1CC[C@@H](O)C1)C2] | (R)-2'-Chloro-N-(5-(3-hydroxypyrrolidine-1-carbonyl)-5,6-dihydro-4H-pyrrolo[3,4-d]thiazol-2-yl)-5'-methoxy-6-methyl-[4,4'-bipyridine]-3-carboxamide | 515 | $^1$H NMR (400 MHz, DMSO-$d_6$) δ 12.7 (s, 1H), 8.78 (s, 1H), 8.16 (s, 1H), 7.54 (s, 1H), 7.43 (s, 1H), 4.90 (d, J = 3.4 Hz, 1H), 4.79-4.71 (m, 1H), 4.65-4.52 (m, 2H), 4.46-4.38 (m, 1H), 4.26 (s, 1H), 3.60 (s, 3H), 3.54-3.46 (m, 2H), 3.41-3.33 (m, 1H), 3.23-3.16 (m, 1H), 2.59 (s, 3H), 1.91-1.71 (m, 2H) |
| 220 | 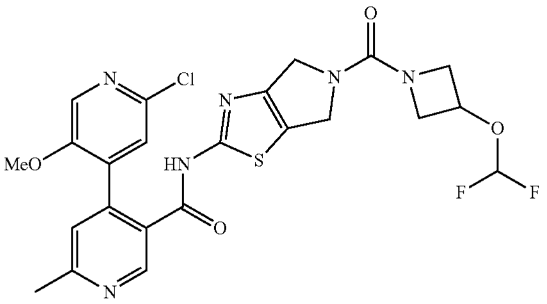 [SMILES: COc1cnc(Cl)cc1-c1cc(C)ncc1C(=O)Nc1nc2c(s1)CN(C(=O)N1CC(OC(F)F)C1)C2] | 2'-Chloro-N-(5-(3-(difluoromethoxy) azetidine-1-carbonyl)-5,6-dihydro-4H-pyrrolo[3,4-d]thiazol-2-yl)-5'-methoxy-6-methyl-[4,4'-bipyridine]-3-carboxamide | 551 | $^1$H NMR (400 MHz, DMSO-$d_6$) 12.8 (s, 1H), δ 8.78 (s, 1H), 8.16 (s, 1H), 7.54 (s, 1H), 7.44 (s, 1H), 6.76 (t, J = 74.8 Hz, 1H), 4.98-4.91 (m, 1H), 4.58 (t, J = 3.2 Hz, 2H), 4.44 (t, J = 3.4 Hz, 2H), 4.29 (dd, J = 9.4, 6.8 Hz, 2H), 3.95 (dd, J = 9.6, 4.2 Hz, 2H), 3.60 (s, 3H), 2.59 (s, 3H) |

Example 221: Synthesis of 2'-Chloro-N—((S)-6-((1s,3R)-3-hydroxycyclobutane-1-carboxamido)-4,5,6,7-tetrahydrobenzo[d]thiazol-2-yl)-5'-methoxy-6-methyl-[4,4'-bipyridine]-3-carboxamide

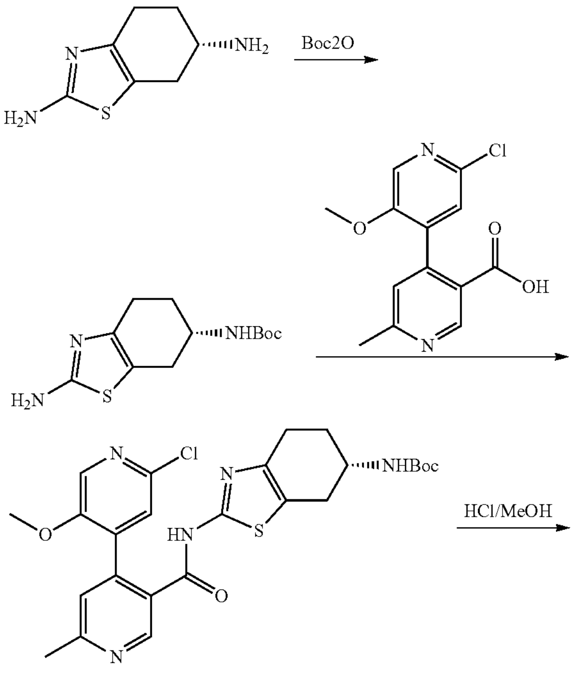

-continued

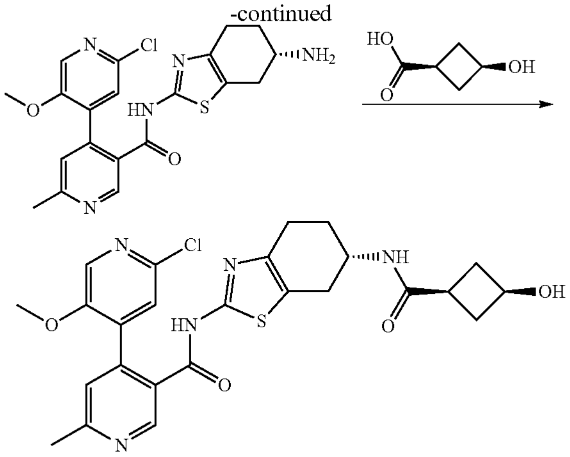

Step 1: To a solution of (S)-4,5,6,7-tetrahydrobenzo[d]thiazole-2,6-diamine (500 mg, 2.95 mmol) in THF (10 mL) was added di-tert-butyl dicarbonate (645 mg, 2.95 mmol) and $K_2CO_3$ (817 mg, 5.91 mmol) and the mixture was stirred at room temperature for 6 h. The mixture was diluted with water (45 mL), exacted with EtOAc (45 mL×2) and the combined organic layers washed with water (40 mL), brine (40 mL), dried over $Na_2SO_4$, filtered and concentrated under reduced pressure. The residue was purified by silica gel chromatography (DCM/MeOH=50/1, v/v) to give tert-butyl (S)-(2-amino-4,5,6,7-tetrahydrobenzo[d]thiazol-6-yl)carbamate (680 mg, 85%) as a white solid. LCMS: m/z=270 [M+H]$^+$. $^1$H NMR (400 MHz, DMSO-$d_6$) δ 6.91 (d, J=7.8 Hz, 1H), 6.61 (s, 2H), 3.63 (s, 1H), 2.68 (dd, J=15.4, 5.2 Hz, 1H), 2.41 (d, J=27.4 Hz, 2H), 2.37-2.30 (m, 1H), 1.85 (d, J=12.8 Hz, 1H), 1.67-1.54 (m, 1H), 1.39 (s, 9H).

Step 2: To a solution of tert-butyl (S)-(2-amino-4,5,6,7-tetrahydrobenzo[d]thiazol-6-yl) carbamate (680 mg, 2.52 mmol) in ACN (15 mL) was added 2'-chloro-5'-methoxy-6-methyl-[4,4'-bipyridine]-3-carboxylic acid (844 mg, 3.03 mmol), TCFH (1.42 g, 5.05 mmol) and 1-methylimidazole (830 mg, 10.1 mmol) and the mixture was heated at 80° C. overnight. The mixture was diluted with EtOAc (40 mL), washed with water (40 mL) and brine (40 mL), dried over $Na_2SO_4$, filtered and concentrated under reduced pressure. The residue was purified by silica gel chromatography (DCM/MeOH=100/1-60/1, v/v) to give tert-butyl (S)-(2-(2'-chloro-5'-methoxy-6-methyl-[4,4'-bipyridine]-3-carboxamido)-4,5,6,7-tetrahydrobenzo[d]thiazol-6-yl)carbamate (340 mg, 25%) as a white solid. LCMS: m/z=530 $[M+H]^+$. $^1H$ NMR (400 MHz, DMSO-$d_6$) δ 12.5 (s, 1H), 8.76 (s, 1H), 8.16 (s, 1H), 7.50 (s, 1H), 7.40 (s, 1H), 7.00 (d, J=7.8 Hz, 1H), 3.67 (s, 1H), 3.61 (s, 3H), 2.91-2.82 (m, 2H), 2.74-2.61 (m, 2H), 2.58 (s, 3H), 1.91 (s, 1H), 1.72 (dd, J=16.8, 10.2 Hz, 1H), 1.39 (s, 9H).

Step 3: A solution of tert-butyl (S)-(2-(2'-chloro-5'-methoxy-6-methyl-[4,4'-bipyridine]-3-carboxamido)-4,5,6,7-tetrahydrobenzo[d]thiazol-6-yl)carbamate (100 mg, 0.188 mmol) in 4 M HCl/MeOH (10 mL) was stirred at room temperature for 2.5 h. The mixture was concentrated under reduced pressure to give (S)—N-(6-amino-4,5,6,7-tetrahydrobenzo[d]thiazol-2-yl)-2'-chloro-5'-methoxy-6-methyl-[4,4'-bipyridine]-3-carboxamide hydrochloride, which was used directly in the next step. LCMS: m/z=430 $[M+H]^+$.

Step 4: To a solution of (S)—N-(6-amino-4,5,6,7-tetrahydrobenzo[d]thiazol-2-yl)-2'-chloro-5'-methoxy-6-methyl-[4,4'-bipyridine]-3-carboxamide hydrochloride (40 mg, 0.086 mmol), DIPEA (60 mg, 0.465 mmol) and (1s,3s)-3-hydroxycyclobutane-1-carboxylic acid (33 mg, 0.279 mmol) in DMF (2 mL) at 0° C. was added T3P (50% in DMF, 45 mg, 0.071 mmol) and the mixture was stirred at room temperature overnight. The mixture was diluted with water (20 mL), exacted with EtOAc (20 mL×3) and the combined organic layers were dried over $Na_2SO_4$, filtered and concentrated under reduced pressure. The residue was purified by prep-TLC (DCM/MeOH=20/1, v/v) to give 2'-chloro-N—((S)-6-((1s,3R)-3-hydroxycyclobutane-1-carboxamido)-4,5,6,7-tetrahydrobenzo[d]thiazol-2-yl)-5'-methoxy-6-methyl-[4,4'-bipyridine]-3-carboxamide (25 mg, 55%) as a white solid. LCMS: m/z=528 $[M+H]^+$. $^1H$ NMR (400 MHz, DMSO-$d_6$) δ 12.5 (s, 1H), 8.77 (s, 1H), 8.17 (s, 1H), 7.88 (d, J=7.6 Hz, 1H), 7.52 (s, 1H), 7.42 (s, 1H), 5.08 (s, 1H), 4.06-3.85 (m, 2H), 3.63 (s, 3H), 2.95-2.85 (m, 1H), 2.76-2.64 (m, 2H), 2.59 (s, 3H), 2.47-2.32 (m, 2H), 2.29-2.20 (m, 2H), 2.01-1.88 (m, 3H), 1.82-1.69 (m, 1H).

TABLE P

The following examples were prepared using a similar procedure to that described for Example 221

| Ex. No. | Structure | Compound Name | LCMS $[M + H]^+$ | NMR |
|---|---|---|---|---|
| 222 | 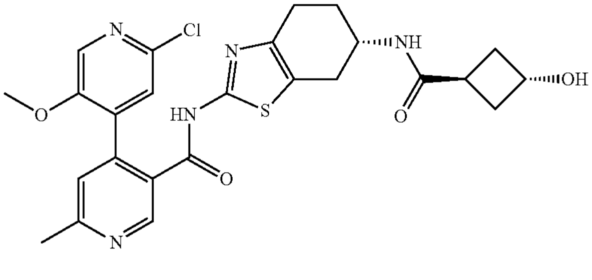 [SMILES: COc1cnc(Cl)cc1-c1cc(C)ncc1C(=O)Nc1nc2c(s1)C[C@@H](NC(=O)[C@H]1C[C@H](O)C1)CC2] | 2'-Chloro-N-((S)-6-((1r,3S)-3-hydroxycyclobutane-1-carboxamido)-4,5,6,7-tetrahydrobenzo[d]thiazol-2-yl)-5'-methoxy-6-methyl-[4,4'-bipyridine]-3-carboxamide | 528 | $^1H$ NMR (400 MHz, DMSO-$d_6$) δ 12.5 (s, 1H), 8.78 (s, 1H), 8.18 (s, 1H), 7.84 (d, J = 7.6 Hz, 1H), 7.52 (s, 1H), 7.42 (s, 1H), 5.01 (d, J = 6.0 Hz, 1H), 4.32-4.22 (m, 1H), 4.08-3.97 (m, 1H), 3.64 (s, 3H), 2.97-2.79 (m, 2H), 2.73-2.65 (m, 2H), 2.60 (s, 3H), 2.33-2.24 (m, 2H), 2.04-1.88 (m, 4H), 1.82-1.69 (m, 1H) |
| 223 | 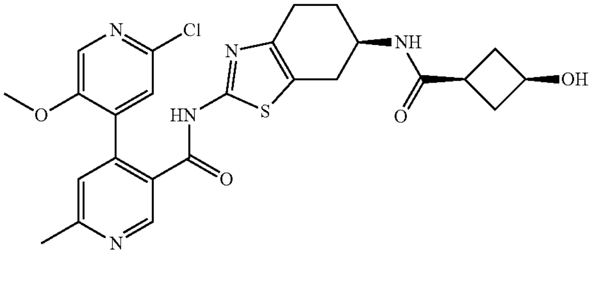 [SMILES: COc1cnc(Cl)cc1-c1cc(C)ncc1C(=O)Nc1nc2c(s1)C[C@H](NC(=O)[C@H]1C[C@@H](O)C1)CC2] | 2'-Chloro-N-((R)-6-((1s,3s)-3-hydroxycyclobutane-1-carboxamido)-4,5,6,7-tetrahydrobenzo[d]thiazol-2-yl)-5'-methoxy-6-methyl-[4,4'-bipyridine]-3-carboxamide | 528 | $^1H$ NMR (400 MHz, DMSO-$d_6$) δ 12.5 (s, 1H), 8.76 (s, 1H), 8.16 (s, 1H), 7.83 (d, J = 7.6 Hz, 1H), 7.50 (s, 1H), 7.40 (s, 1H), 5.06 (d, J = 7.0 Hz, 1H), 4.05-3.94 (m, 1H), 3.94-3.84 (m, 1H), 3.61 (s, 3H), 2.94-2.84 (m, 1H), 2.73-2.62 (m, 2H), 2.58 (s, 3H), 2.42-2.30 (m, 1H), 2.27-2.18 (m, 2H), 2.04-1.84 (m, 4H), 1.80-1.67 (m, 1H) |
| 224 | 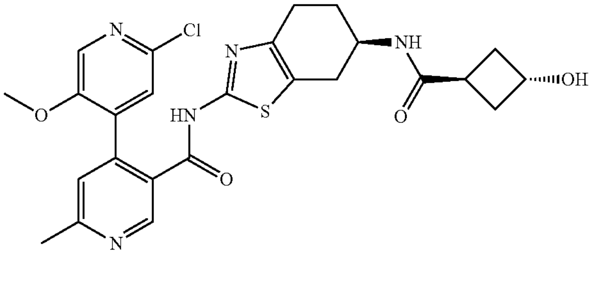 [SMILES: COc1cnc(Cl)cc1-c1cc(C)ncc1C(=O)Nc1nc2c(s1)C[C@H](NC(=O)[C@H]1C[C@H](O)C1)CC2] | 2'-Chloro-N-((R)-6-((1r,3R)-3-hydroxycyclobutane-1-carboxamido)-4,5,6,7-tetrahydrobenzo[d]thiazol-2-yl)-5'-methoxy-6-methyl-[4,4'-bipyridine]-3-carboxamide | 528 | $^1H$ NMR (400 MHz, DMSO-$d_6$) δ 12.5 (s, 1H), 8.75 (s, 1H), 8.16 (s, 1H), 7.82 (d, J = 7.6 Hz, 1H), 7.51 (s, 1H), 7.40 (s, 1H), 4.99 (d, J = 6.2 Hz, 1H), 4.30-4.20 (m, 1H), 4.07-3.95 (m, 1H), 3.61 (s, 3H), 2.95-2.76 (m, 2H), 2.71-2.62 (m, 2H), 2.58 (s, 3H), 2.30-2.21 (m, 2H), 2.02-1.83 (m, 4H), 1.79-1.66 (m, 1H) |

Example 225: Synthesis of 2'-Chloro-N-(5-(1s,3s)-3-(difluoromethoxy)cyclobutane-1-carbonyl)-5,6-dihydro-4H-pyrrolo[3,4-d]thiazol-2-yl)-5'-methoxy-6-methyl-[4,4'-bipyridine]-3-carboxamide

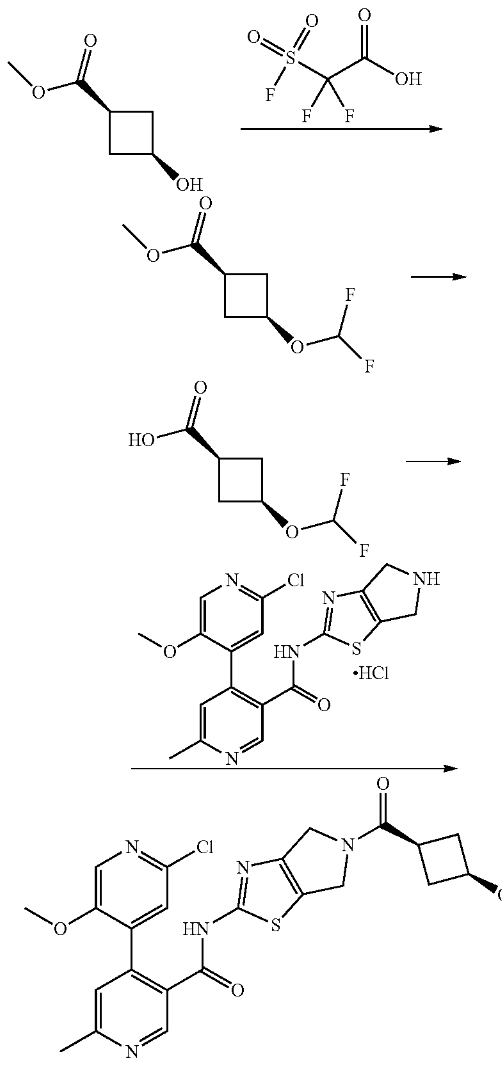

Step 1: To a solution of methyl (1s,3s)-3-hydroxycyclobutane-1-carboxylate (800 mg, 6.15 mmol) in ACN (10 mL) was added CuI (234 mg, 1.23 mmol) and a solution of 2,2-difluoro-2-(fluorosulfonyl)acetic acid (1.31 g, 7.38 mmol) in ACN (2 mL) and the mixture was heated at 50° C. for 3 h. The mixture was diluted with water (100 mL), extracted with EtOAc (50 mL×3) and the combined organic phases washed with brine, dried over $Na_2SO_4$, filtered and concentrated under reduced pressure to afford methyl (1s,3s)-3-(difluoromethoxy)cyclobutane-1-carboxylate (900 mg, 81%), which was used without further purification. $^1H$ NMR (400 MHz, DMSO-$d_6$) δ 6.81-6.41 (m, 1H), 5.27 (t, J=7.4 Hz, 1H), 3.62 (s, 3H), 2.86 (s, 1H), 2.36 (ddt, J=12.4, 7.0, 2.2 Hz, 2H), 2.19-2.16 (m, 2H).

Step 2: To a solution of methyl (1s,3s)-3-(difluoromethoxy)cyclobutane-1-carboxylate (932 mg, 5.17 mmol) in THF (10 mL) and water (2 mL) was added LiOH (285 mg, 11.9 mmol) and the mixture was stirred at room temperature for 16 h. The mixture was adjusted to pH 3 with 2 M aqueous HCl and concentrated under reduced pressure. The residue was dissolved in DCM/MeOH (15/1), filtered and the filtrate concentrated under reduced pressure to afford (1s,3s)-3-(difluoromethoxy)cyclobutane-1-carboxylic acid (500 mg, 58%), which was used without further purification.

Step 3: To a solution of 2'-chloro-N-(5,6-dihydro-4H-pyrrolo[3,4-d]thiazol-2-yl)-5'-methoxy-6-methyl-[4,4'-bipyridine]-3-carboxamide hydrochloride (806 mg, 1.84 mmol) in DMF (10 mL) at 0° C. was added (1s,3s)-3-(difluoromethoxy)cyclobutane-1-carboxylic acid (500 mg, 3.01 mmol), DIPEA (779 mg, 6.03 mmol) and T3P (50% in DMF, 1.28 g, 2.01 mmol) and the mixture was stirred at RT overnight. The mixture was diluted with water (100 mL), extracted with DCM (3×50 mL) and the combined organic phases were dried over $Na_2SO_4$, filtered and concentrated under reduced pressure. The residue was purified by silica chromatography (DCM/MeOH=100/1 to 25/1) and prep-HPLC to afford 2'-Chloro-N-(5-((1s,3s)-3-(difluoromethoxy)cyclobutane-1-carbonyl)-5,6-dihydro-4H-pyrrolo[3,4-d]thiazol-2-yl)-5'-methoxy-6-methyl-[4,4'-bipyridine]-3-carboxamide (50 mg, 5%) as a yellow solid. LCMS: m/z=550 $[M+H]^+$, $^1H$ NMR (400 MHz, DMSO-$d_6$) δ 12.8 (s, 1H), 8.80 (s, 1H), 8.17 (d, J=1.6 Hz, 1H), 7.55 (s, 1H), 7.46 (s, 1H), 6.63 (t, J=75.7 Hz, 1H), 4.74 (t, J=2.8 Hz, 1H), 4.63-4.52 (m, 3H), 4.45 (t, J=2.8 Hz, 1H), 3.58 (s, 3H), 3.00-2.91 (m, 1H), 2.60 (s, 3H), 2.57-2.54 (m, 2H), 2.29-2.19 (m, 2H).

Example 226: Synthesis of 2'-Chloro-5'-methoxy-6-methyl-N-(5-((1s,3s)-3-(trifluoromethoxy)cyclobutane-1-carbonyl)-5,6-dihydro-4H-pyrrolo[3,4-d]thiazol-2-yl)-[4,4'-bipyridine]-3-carboxamide

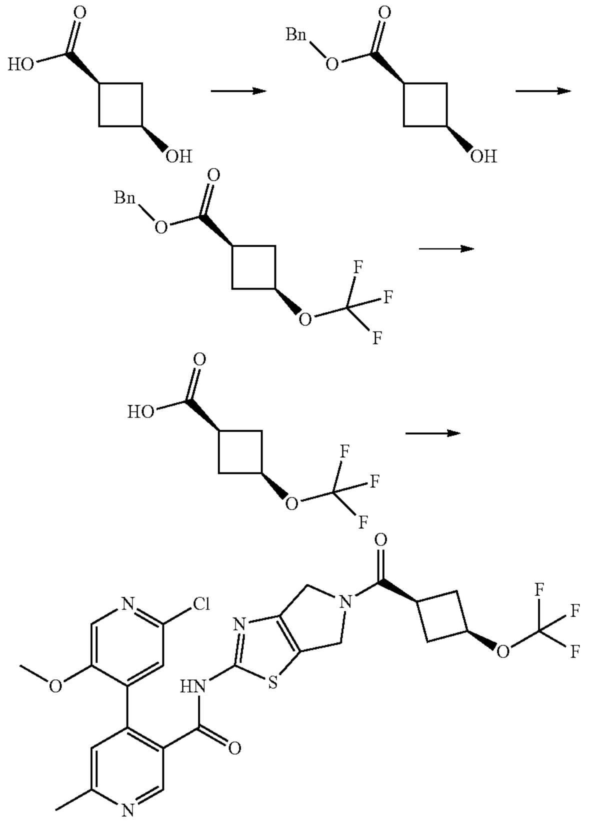

Step 1: To a solution of (1s,3s)-3-hydroxycyclobutane-1-carboxylic acid (200 mg, 1.72 mmol) in DMF (3 mL) was added $NaHCO_3$ (434 mg, 5.17 mmol) and benzyl bromide (441.9 mg, 2.58 mmol) and the mixture was stirred at room temperature overnight. The mixture was diluted with water (15 mL), extracted with EtOAc (30 mL×3) and the combined organic layers were washed with water (10 mL), brine (10 mL), dried over $Na_2SO_4$, filtered and concentrated under reduced pressure to afford benzyl (1s,3s)-3-hydroxycyclobutane-1-carboxylate (308 mg, 86%) as a yellow oil. $^1H$ NMR (400 MHz, DMSO-$d_6$) δ 7.35 (tdd, J=10.4, 6.4, 3.8 Hz, 5H), 5.19 (d, J=7.0 Hz, 1H), 5.08 (s, 2H), 3.97 (td, J=8.4, 6.8 Hz, 1H), 2.61 (ddd, J=10.0, 7.8, 2.2 Hz, 1H), 2.40 (tdd, J=7.6, 6.0, 2.8 Hz, 2H), 2.02-1.92 (m, 2H).

Step 2: To a solution of silver trifluoromethanesulfonate (2.24 g, 8.73 mmol), 1-chloromethyl-4-fluoro-1,4-diazoniabicyclo[2.2.2]octane bis(tetrafluoroborate) (1.16 g, 3.27 mmol) and potassium fluoride (5.08 g, 8.73 mmol) in EtOAc (10 mL) was added benzyl (1s,3s)-3-hydroxycyclobutane-1-carboxylate (450 mg, 2.18 mmol), 2-fluoropyridine (847 mg, 8.73 mmol) and (trifluoromethyl)trimethylsilane (775 mg, 5.45 mmol) and the mixture was stirred at room temperature for 24 h under a $N_2$ atmosphere in the dark. The mixture was diluted with water (15 mL), extracted with EtOAc (50 mL×2) and the combined organic layers washed with water (10 mL), brine (10 mL), dried over $Na_2SO_4$, filtered and concentrated under reduced pressure. The residue was purified by prep-TLC (Petroleum ether/EtOAc=5/1, v/v) to afford benzyl (1s,3s)-3-(trifluoromethoxy)cyclobutane-1-carboxylate (320 mg, 27%) as a yellow solid. $^1H$ NMR (400 MHz, Chloroform-t) S 7.41-7.31 (m, 5H), 5.14 (s, 2H), 4.57 (p, J=7.6 Hz, 1H), 2.82-2.70 (m, 1H), 2.68-2.58 (m, 2H), 2.58-2.48 (m, 2H).

Step 3: To a solution of benzyl (1s,3s)-3-(trifluoromethoxy)cyclobutane-1-carboxylate (320 mg, 1.17 mmol) in EtOH (5 mL) was added 10% Pd/C (320 mg) and the mixture was stirred at room temperature overnight under a $H_2$ atmosphere. The mixture was filtered and the filtrate concentrated under reduced pressure to afford (1s,3s)-3-(trifluoromethoxy)cyclobutane-1-carboxylic acid (190 mg, 88%) as a brown solid. $^1H$ NMR (400 MHz, DMSO-$d_6$) δ 4.73 (p, J=7.4 Hz, 1H), 2.73-2.62 (m, 1H), 2.57 (ddd, J=9.6, 7.2, 2.6 Hz, 2H), 2.26 (qd, J=9.6, 9.2, 2.6 Hz, 2H).

Step 4: To a solution of 2'-chloro-N-(5,6-dihydro-4H-pyrrolo[3,4-d]thiazol-2-yl)-5'-methoxy-6-methyl-[4,4'-bipyridine]-3-carboxamide hydrochloride (80.1 mg, 0.182 mmol), DIPEA (128.7 mg, 0.996 mmol) and (1s,3s)-3-(trifluoromethoxy)cyclobutane-1-carboxylic acid (44 mg, 0.239 mmol) in DMF (2 mL) at 0° C. was added T3P (50% in DMF, 128.7 mg, 0.202 mmol) and the mixture was stirred at room temperature overnight. The mixture was diluted with water (10 mL), extracted with EtOAc (20 mL×2) and the combined organic layers washed with water (20 mL), brine (10 mL), dried over $Na_2SO_4$, filtered and concentrated under reduced pressure. The residue was purified by prep-TLC (DCM/MeOH=10/1, v/v) to afford 2'-chloro-5'-methoxy-6-methyl-N-(5-((1s,3s)-3-(trifluoromethoxy)cyclobutane-1-carbonyl)-5,6-dihydro-4H-pyrrolo[3,4-d]thiazol-2-yl)-[4,4'-bipyridine]-3-carboxamide (70 mg, 53%) as a white solid. LCMS: m/z=568 $[M+H]^+$, $^1H$ NMR (400 MHz, DMSO-d) S 12.6 (s, 1H), 8.79 (s, 1H), 8.16 (s, 1H), 7.49 (s, 1H), 7.41 (s, 1H), 4.84-4.76 (m, 1H), 4.74 (s, 1H), 4.60 (s, 2H), 4.46 (s, 1H), 3.62 (s, 3H), 3.05-2.93 (m, 1H), 2.70-2.59 (m, 2H), 2.60 (s, 3H), 2.43-2.32 (m, 2H).

TABLE Q

The following examples were prepared using a similar procedure to that described for Example 226

| Ex. No. | Structure | Compound Name | LCMS $[M + H]^+$ | NMR |
|---|---|---|---|---|
| 227 | 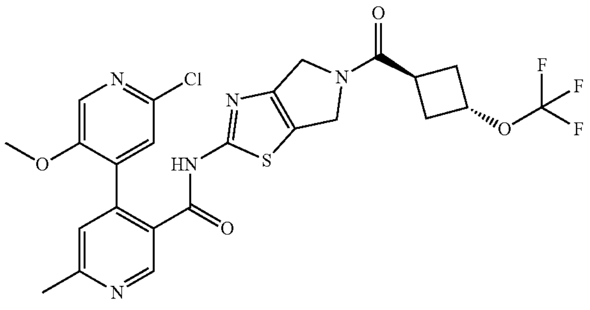 [SMILES: COc1cnc(Cl)cc1-c1cc(C)ncc1C(=O)Nc1nc2c(s1)CN(C(=O)[C@H]1C[C@H](OC(F)(F)F)C1)C2] | 2'-chloro-5'-methoxy-6-methyl-N-(5-((1r,3r)-3-(trifluoromethoxy)cyclobutane-1-carbonyl)-5,6-dihydro-4H-pyrrolo[3,4-d]thiazol-2-yl)-[4,4'-bipyridine]-3-carboxamide | 568 | $^1H$ NMR (400 MHz, DMSO-$d_6$) δ 12.8 (s, 1H), 8.78 (s, 1H), 8.16 (d, J = 2.0 Hz, 1H), 7.54 (s, 1H), 7.44 (s, 1H), 4.94-4.84 (m, 1H), 4.71 (s, 1H), 4.63-4.56 (m, 2H), 4.47 (s, 1H), 3.59 (s, 3H), 3.44-3.33 (m, 2H), 2.65-2.57 (m, 2H), 2.59 (s, 3H), 2.47-2.41 (m, 1H, partly obscured by solvent peak) |

Example 228: Synthesis of (R or S)-2-(2'-Chloro-5'-methoxy-6-methyl-[4,4'-bipyridine]-3-carboxamido)-N-cyclobutyl-4,5,6,7-tetrahydrobenzo[d]thiazole-6-carboxamide with arbitrary enantiomer assignment

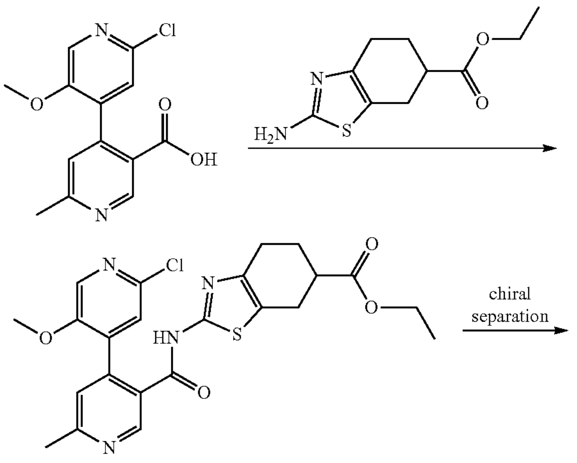

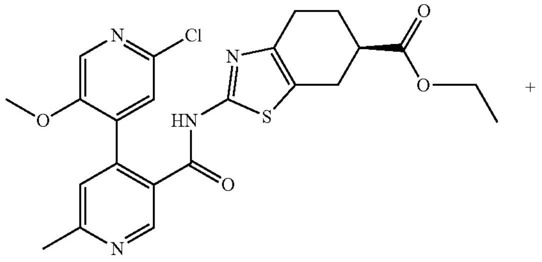

P1 assumed

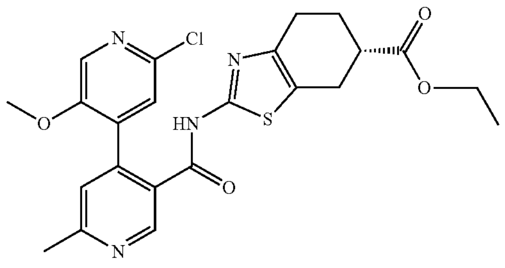

P2 assumed

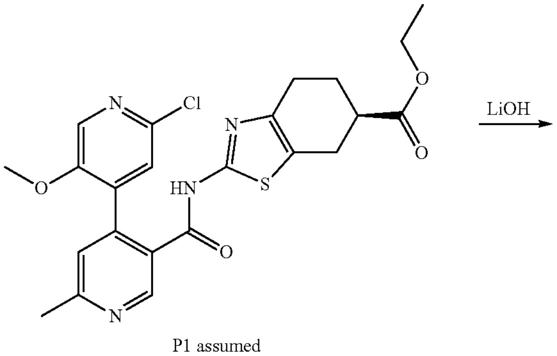

P1 assumed

-continued

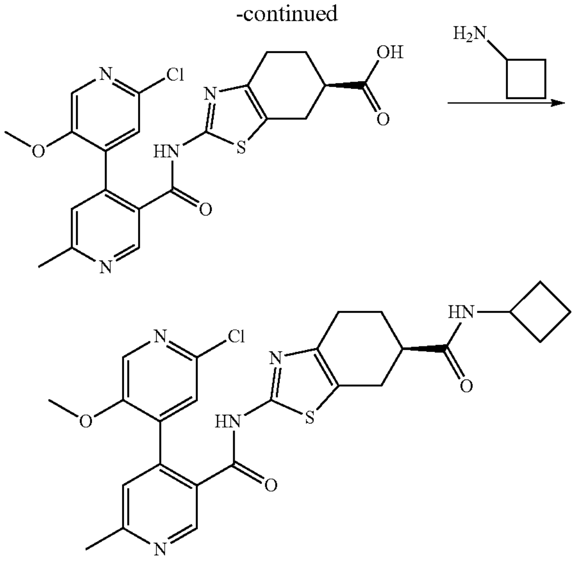

Step 1: To a solution of 2'-chloro-5'-methoxy-6-methyl-[4,4'-bipyridine]-3-carboxylic acid (1.00 g, 3.59 mmol) in ACN (20 mL) was added ethyl 2-amino-4,5,6,7-tetrahydrobenzo[d]thiazole-6-carboxylate (812 mg, 3.59 mmol), TCFH (1.51 g, 5.38 mmol), 1-methyl-1H-imidazole (1.18 g, 14.4 mmol) and NMP (2 mL) and the mixture was heated at 80° C. overnight. The mixture was diluted with water (200 mL), exacted with EtOAc (200 mL) and the organic layer washed with water (200 mL), brine (200 mL), dried over $Na_2SO_4$, filtered and concentrated under reduced pressure. The mixture was purified by silica gel chromatography (Petroleum Ether/EtOAc=2/1, v/v) to give ethyl 2-(2'-chloro-5'-methoxy-6-methyl-[4,4'-bipyridine]-3-carboxamido)-4,5,6,7-tetrahydrobenzo[d]thiazole-6-carboxylate (1.00 g, 57%) as a white solid. LCMS: m/z=487 $[M+H]^+$. $^1H$ NMR (400 MHz, DMSO-$d_6$) δ 8.78 (s, 11H), 8.19 (s, 1H), 7.53 (s, 1H), 7.43 (s, 1H), 4.12 (dd, J=7.2, 2.0 Hz, 2H), 3.63 (s, 3H), 2.93 (t, J=10.4 Hz, 1H), 2.89-2.80 (m, 2H), 2.67 (t, J=6.4 Hz, 2H), 2.60 (s, 3H), 2.24-2.10 (m, 1H), 1.92-1.81 (m, 1H), 1.22 (t, J=7.2 Hz, 3H).

Step 2: Ethyl 2-(2'-chloro-5'-methoxy-6-methyl-[4,4'-bipyridine]-3-carboxamido)-4,5,6,7-tetrahydrobenzo[d]thiazole-6-carboxylate (2.3 g) was purified by chiral prep HPLC (UniChiral CNZ-5H, 30 mm I.D.×250 mm L. Mobile Phase: n-Hexane/Ethanol=50/50, Flow rate: 50 mL/min) to afford two peaks:

Peak 1 11.4 mm, ethyl (R or S)-2-(2'-chloro-5'-methoxy-6-methyl-[4,4'-bipyridine]-3-carboxamido)-4,5,6,7-tetrahydrobenzo[d]thiazole-6-carboxylate (990 mg, 39%) as a yellow solid.

Peak 2 14.8 min. ethyl (S or R)-2-(2'-chloro-5'-methoxy-6-methyl-[4,4'-bipyridine]-3-carboxamido)-4,5,6,7-tetrahydrobenzo[d]thiazole-6-carboxylate (900 mg, 39%) as a yellow solid. R and S stereochemistry were arbitrarily assigned.

Step 3: To a solution of ethyl (R or S)-2-(2'-chloro-5'-methoxy-6-methyl-[4,4'-bipyridine]-3-carboxamido)-4,5,6,7-tetrahydrobenzo[d]thiazole-6-carboxylate (Peak 1, 50 mg, 0.102 mmol) in THF (1 mL) and water (1 mL) was added LiOH (8 mg, 0.308 mmol) and the mixture was stirred at room temperature for 2 h. The solvent was removed under reduced pressure and the residue dissolved in DMF (2 mL), cooled to 0° C., DIPEA (53 mg, 0.41 mmol), cyclobutanamine (11 mg, 0.153 mmol) and T3P (50% in DMF, 98 mg, 0.154 mmol) were added and the mixture was stirred at room temperature overnight. The mixture was diluted with water (20 mL), extracted with EtOAc (20 mL) and the organic layer washed with water (20 mL), brine (20 mL), dried over $Na_2SO_4$, filtered and concentrated under reduced pressure. The residue was purified by prep-TLC (DCM/MeOH=10/1, v/v) to give (R or S)-2-(2'-chloro-5'-methoxy-6-methyl-[4,4'-bipyridine]-3-carboxamido)-N-cyclobutyl-4,5,6,7-tetrahydrobenzo[d]thiazole-6-carboxamide (30 mg, 57%) as a white solid. LCMS: m/z=512 $[M+H]^+$. $^1H$ NMR (400 MHz, DMSO-$d_6$) δ 12.5 (s, 1H), 8.76 (s, 1H), 8.19-8.13 (m, 2H), 7.50 (s, 1H), 7.40 (s, 1H), 4.25-4.14 (m, 1H), 3.61 (s, 3H), 2.79-2.61 (m, 4H), 2.62-2.54 (m, 4H), 2.20-2.10 (m, 2H), 2.02-1.94 (m, 1H), 1.92-1.82 (m, 2H), 1.80-1.68 (M, 1H), 1.67-1.56 (m, 2H).

TABLE R

The following examples were prepared using a similar procedure to the described for Example 228 using either Peak 1 or Peak 2 from step 2

| Ex. No. | Structure | Compound Name | LCMS $[M + H]^+$ | NMR |
|---|---|---|---|---|
| 229 | 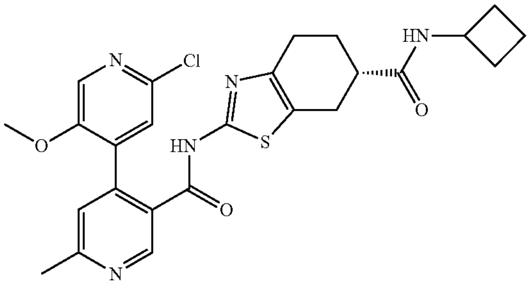 [SMILES: COc1cnc(Cl)cc1-c1cc(C)ncc1C(=O)Nc1nc2c(s1)C[C@@H](C(=O)NC1CCC1)CC2] | (S or R)-2-(2'-Chloro-5'-methoxy-6-methyl-[4,4'-bipyridine]-3-carboxamido)-N-cyclobutyl-4,5,6,7-tetrahydrobenzo[d]thiazole-6-carboxamide | 512 | $^1H$ NMR (400 MHz, DMSO-$d_6$) δ 12.5 (s, 1H), 8.76 (s, 1H), 8.18-8.13 (m, 2H), 7.50 (s, 1H), 7.40 (s, 1H), 4.25-4.14 (m, 1H), 3.61 (s, 3H), 2.80-2.62 (m, 4H), 2.62-2.54 (m, 4H), 2.20-2.11 (m, 2H), 2.02-1.95 (m, 1H), 1.92-1.82 (m, 2H), 1.81-1.70 (m, 1H), 1.67-1.57 (m, 2H) |
| 707 | 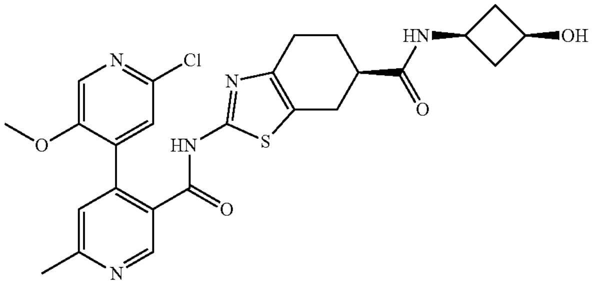 [SMILES: COc1cnc(Cl)cc1-c1cc(C)ncc1C(=O)Nc1nc2c(s1)C[C@H](C(=O)N[C@H]1C[C@@H](O)C1)CC2] | (R)-2-(2'-Chloro-5'-methoxy-6-methyl-[4,4'-bipyridine]-3-carboxamido)-N-((1s,3S)-3-hydroxycyclobutyl)-4,5,6,7-tetrahydrobenzo[d]thiazole-6-carboxamide | 528 | $^1H$ NMR (40 0MHz, DMSO-$d_6$) δ 8.76 (s, 1H), 8.16 (s, 1H), 7.50 (s, 1H), 7.40 (s, 1H), 3.81-3.74 (m, 1H), 3.71-3.65 (m, 1H), 3.61 (s, 3H), 2.74-2.64 (m, 4H), 2.62-2.55 (m, 4H), 2.50-2.44 (m, 2H), 1.98-1.95 (m, 1H), 1.79-1.67 (m, 3H) |
| 708 | 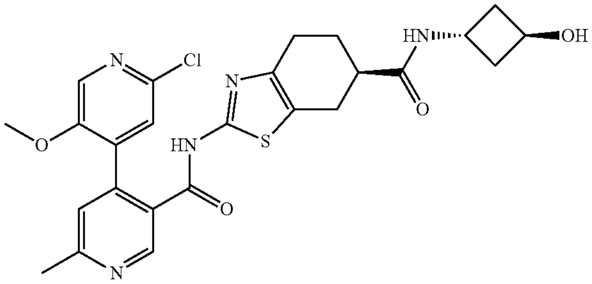 [SMILES: COc1cnc(Cl)cc1-c1cc(C)ncc1C(=O)Nc1nc2c(s1)C[C@H](C(=O)N[C@H]1C[C@H](O)C1)CC2] | (R)-2-(2'-Chloro-5'-methoxy-6-methyl-[4,4'-bipyridine]-3-carboxamido)-N-((1r,3R)-3-hydroxycyclobutyl)-4,5,6,7-tetrahydrobenzo[d]thiazole-6-carboxamide | 528 | $^1H$ NMR (400 MHz, DMSO-$d_6$) δ 8.76 (s, 1H), 8.16 (s, 1H), 7.50 (s, 1H), 7.40 (s, 1H), 4.29-4.13 (m, 2H), 3.61 (s, 3H), 2.75-2.63 (m, 3H), 2.60-2.55 (m, 5H), 2.13-2.05 (m, 4H), 2.03-1.93 (m, 1H), 1.81-1.68 (m, 1H) |
| 709 | 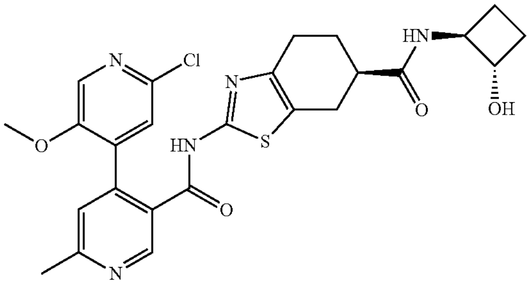 [SMILES: COc1cnc(Cl)cc1-c1cc(C)ncc1C(=O)Nc1nc2c(s1)C[C@H](C(=O)N[C@H]1CC[C@@H]1O)CC2] | (R)-2-(2'-Chloro-5'-methoxy-6-methyl-[4,4'-bipyridine]-3-carboxamido)-N-((1S,2S)-2-hydroxycyclobutyl)-4,5,6,7-tetrahydrobenzo[d]thiazole-6-carboxamide | 528 | $^1H$ NMR (400 MHz, DMSO-$d_6$) δ 8.75 (s, 1H), 8.16 (s, 1H), 7.50 (s, 1H), 7.40 (s, 1H), 3.98-3.91 (m, 1H), 3.85-3.79 (m, 1H), 3.61 (s, 3H), 2.82-2.69 (m, 2H), 2.57 (s, 3H), 2.51 (s, 1H), 2.04-1.70 (m, 4H), 1.42-1.32 (m, 1H), 1.28-1.23 (m, 2H), 1.21-1.12 (m, 1H) |

TABLE R-continued

The following examples were prepared using a similar procedure to the described for Example 228 using either Peak 1 or Peak 2 from step 2

| Ex. No. | Structure | Compound Name | LCMS [M + H]+ | NMR |
|---|---|---|---|---|
| 710 | 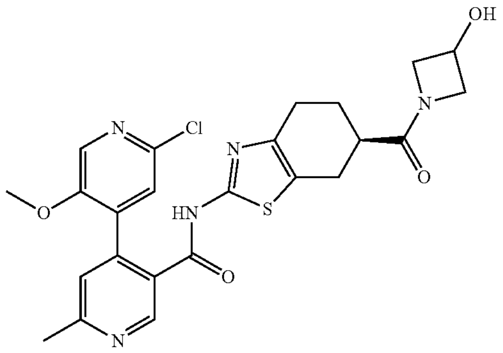 [SMILES: COc1cnc(Cl)cc1-c1cc(C)ncc1C(=O)Nc1nc2c(s1)C[C@H](C(=O)N1CC(O)C1)CC2] | (R)-2'-Chloro-N-(6-(3-hydroxyazetidine-1-carbonyl)-4,5,6,7-tetrahydrobenzo[d]thiazol-2-yl)-5'-methoxy-6-methyl-[4,4'-bipyridine]-3-carboxamide | 514 | $^1$H NMR (400 MHz, DMSO-$d_6$) δ 8.76 (s, 1H), 8.16 (s, 1H), 7.51 (s, 1H), 7.40 (s, 1H), 4.51-4.33 (m, 2H), 4.09-4.00 (m, 1H), 3.97-3.88 (m, 1H), 3.64-3.56 (m, 4H), 2.74-2.63 (m, 5H), 2.58 (s, 3H), 1.98-1.90 (m, 1H), 1.76-1.64 (m, 1H) |
| 711 | 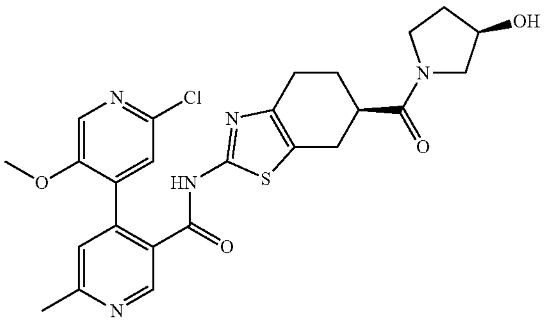 [SMILES: COc1cnc(Cl)cc1-c1cc(C)ncc1C(=O)Nc1nc2c(s1)C[C@H](C(=O)N1CC[C@@H](O)C1)CC2] | 2'-Chloro-N-((R)-6-((R)-3-hydroxypyrrolidine-1-carbonyl)-4,5,6,7-tetrahydrobenzo[d]thiazol-2-yl)-5'-methoxy-6-methyl-[4,4'-bipyridine]-3-carboxamide | 528 | $^1$H NMR (400 MHz, DMSO-$d_6$) δ 8.76 (s, 1H), 8.16 (s, 1H), 7.51 (s, 1H), 7.41 (s, 1H), 4.35-4.21 (m, 1H), 3.65-3.57 (m, 4H), 3.47-3.35 (m, 2H), 3.30-3.25 (m, 1H), 2.94-2.80 (m, 1H), 2.80-2.72 (m, 2H), 2.72-2.66 (m, 2H), 2.58 (s, 3H), 2.06-1.67 (m, 4H) |
| 712 | 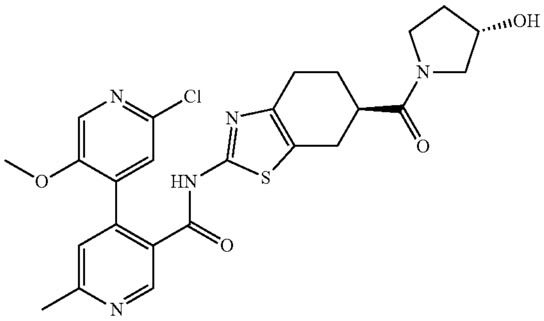 [SMILES: COc1cnc(Cl)cc1-c1cc(C)ncc1C(=O)Nc1nc2c(s1)C[C@H](C(=O)N1CC[C@H](O)C1)CC2] | 2'-Chloro-N-((R)-6-((S)-3-hydroxypyrrolidine-1-carbonyl)-4,5,6,7-tetrahydrobenzo[d]thiazol-2-yl)-5'-methoxy-6-methyl-[4,4'-bipyridine]-3-carboxamide | 528 | $^1$H NMR (400 MHz, DMSO-$d_6$) δ 8.76 (s, 1H), 8.16 (s, 1H), 7.51 (s, 1H), 7.40 (s, 1H), 4.34-4.22 (m, 1H), 3.64-3.58 (m, 4H), 3.42-3.35 (m, 1H), 3.30-3.25 (m, 1H), 2.94-2.80 (m, 1H), 2.79-2.73 (m, 2H), 2.70-2.64 (m, 2H), 2.58 (s, 3H), 2.54-2.51 (m, 1H, partly obscured by solvent), 2.03-1.89 (m, 2H), 1.89-1.81 (m, 1H), 1.77-1.71 (m, 1H) |
| 713 | 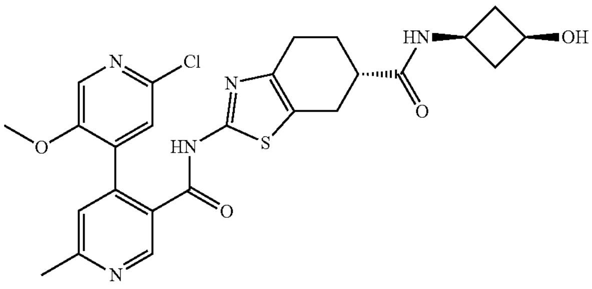 [SMILES: COc1cnc(Cl)cc1-c1cc(C)ncc1C(=O)Nc1nc2c(s1)C[C@@H](C(=O)N[C@H]1C[C@@H](O)C1)CC2] | (S)-2-(2'-Chloro-5'-methoxy-6-methyl-[4,4'-bipyridine]-3-carboxamido)-N-((1s,3R)-3-hydroxycyclobutyl)-4,5,6,7-tetrahydrobenzo[d]thiazole-6-carboxmaide | 528 | $^1$H NMR (400 MHz, DMSO-$d_6$) δ 8.76 (s, 1H), 8.16 (s, 1H), 7.50 (s, 1H), 7.40 (s, 1H), 3.83-3.74 (m, 1H), 3.72-3.64 (m, 1H), 3.61 (s, 3H), 2.79-2.64 (m, 4H), 2.60-2.53 (m, 4H), 2.47-2.45 (m, 2H), 2.00-1.93 (m, 1H), 1.80-1.68 (m, 3H) |

TABLE R-continued

The following examples were prepared using a similar procedure to the described for Example 228 using either Peak 1 or Peak 2 from step 2

| Ex. No. | Structure | Compound Name | LCMS [M + H]+ | NMR |
|---|---|---|---|---|
| 714 | 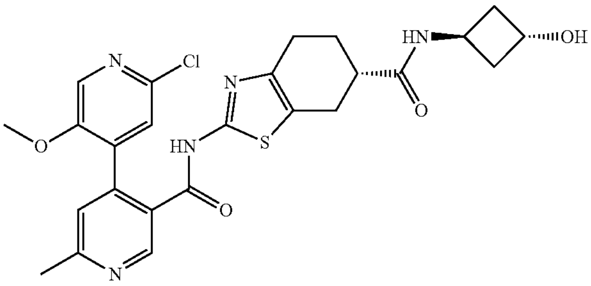 [SMILES: COc1cnc(Cl)cc1-c1cc(C)ncc1C(=O)Nc1nc2c(s1)C[C@@H](C(=O)N[C@H]1C[C@H](O)C1)CC2] | (S)-2-(2'-Chloro-5'-methoxy-6-methyl-[4,4'-bipyridine]-3-carboxamido)-N-((1r,3S)-3-hydroxycyclobutyl)-4,5,6,7-tetrahydrobenzo[d]thiazole-6-carboxamide | 528 | $^1$H NMR (400 MHz, DMSO-$d_6$) δ 12.5 (s, 1H), 8.76 (s, 1H), 8.16 (s, 1H), 8.15 (d, J = 6.8 Hz, 1H), 7.50 (s, 1H), 7.40 (s, 1H), 4.29-4.13 (m, 2H), 3.61 (s, 3H), 2.77-2.64 (m, 3H), 2.58 (s, 5H), 2.13-2.04 (m, 4H), 2.03-1.93 (m, 1H), 1.81-1.68 (m, 1H) |
| 715 | 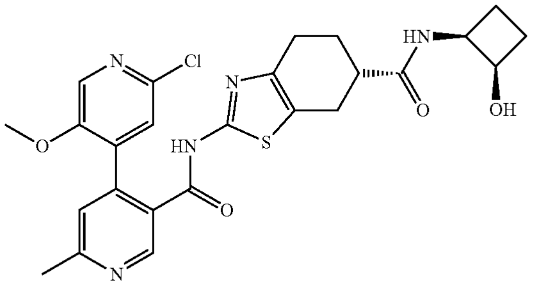 | (S)-2-(2'-Chloro-5'-methoxy-6-methyl-[4,4'-bipyridine]-3-carboxamido)-N-((1S,2R)-2-hydroxycyclobutyl)-4,5,6,7-tetrahydrobenzo[d]thiazole-6-carboxamide | 528 | $^1$H NMR (400 MHz, DMSO-$d_6$) δ 8.76 (s, 1H), 8.16 (s, 1H), 7.86-7.79 (m, 1H), 7.51 (s, 1H), 7.41 (s, 1H), 4.25-4.17 (m, 2H), 3.61 (s, 3H), 2.81-2.72 (m, 2H), 2.68-2.63 (m, 2H), 2.58 (s, 3H), 2.08-1.90 (m, 4H), 1.91-1.68 (m, 3H) |
| 716 | 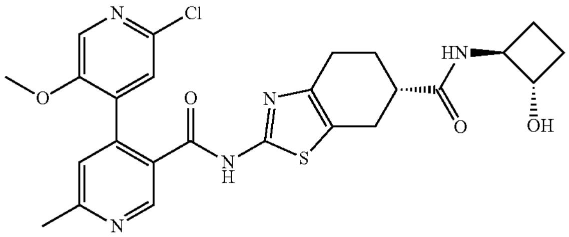 [SMILES: COc1cnc(Cl)cc1-c1cc(C)ncc1C(=O)Nc1nc2c(s1)C[C@@H](C(=O)N[C@H]1CC[C@@H]1O)CC2] | (S)-2-(2'-Chloro-5'-methoxy-6-methyl-[4,4'-bipyridine]-3-carboxamido)-N-((1S,2S)-2-hydroxycyclobutyl)-4,5,6,7-tetrahydrobenzo[d]thiazole-6-carboxamide | 528 | $^1$H NMR (400 MHz, DMSO-$d_6$) δ 12.5 (s, 1H), 8.76 (s, 1H), 8.22-8.18 (m, 1H), 8.16 (s, 1H), 7.50 (s, 1H), 7.40 (s, 1H), 3.99-3.92 (m, 1H), 3.89-3.78 (m, 1H), 3.61 (s, 3H), 2.80-2.63 (m, 5H), 2.57 (s, 3H), 2.04-1.68 (m, 4H), 1.43-1.30 (m, 1H), 1.21-1.13 (m, 1H) |
| 717 | 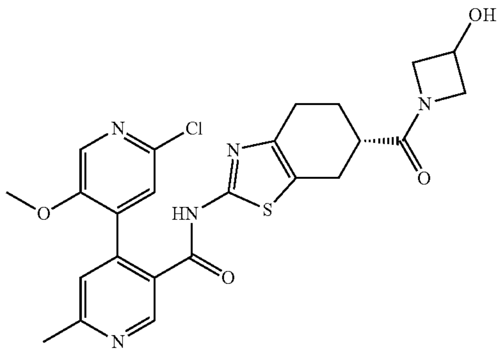 [SMILES: COc1cnc(Cl)cc1-c1cc(C)ncc1C(=O)Nc1nc2c(s1)C[C@@H](C(=O)N1CC(O)C1)CC2] | (S)-2'-Chloro-N-(6-(3-hydroxyazetidine-1-carbonyl)-4,5,6,7-tetrahydrobenzo[d]thiazol-2-yl)-5'-methoxy-6-methyl-[4,4'-bipyridine]-3-carboxamide | 514 | $^1$H NMR (400 MHz, DMSO-$d_6$) δ 12.5 (s, 1H), 8.76 (s, 1H), 8.16 (s, 1H), 7.51 (s, 1H), 7.41 (s, 1H), 4.49-4.32 (m, 2H), 4.08-4.00 (m, 1H), 3.97-3.88 (m, 1H), 3.61 (s, 4H), 2.76-2.62 (m, 5H), 2.58 (s, 3H), 1.99-1.90 (m, 1H), 1.70 (br s, 1H) |
| 718 | 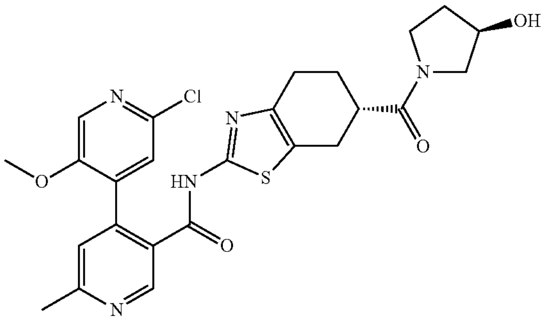 [SMILES: COc1cnc(Cl)cc1-c1cc(C)ncc1C(=O)Nc1nc2c(s1)C[C@@H](C(=O)N1CC[C@@H](O)C1)CC2] | 2'-Chloro-N-((S)-6-((R)-3-hydroxypyrrolidine-1-carbonyl)-4,5,6,7-tetrahydrobenzo[d]thiazol-2-yl)-5'-methoxy-6-methyl-[4,4'-bipyridine]-3-carboxamide | 528 | $^1$H NMR (400 MHz, DMSO-$d_6$) δ 8.76 (s, 1H), 8.16 (s, 1H), 7.51 (s, 1H), 7.41 (s, 1H), 4.33-4.21 (m, 1H), 3.67-3.55 (m, 1H), 3.61 (s, 3H), 3.46-3.27 (m, 3H, partly obscured by water), 2.80-2.72 (m, 2H), 2.71-2.62 (m, 3H), 2.58 (s, 3H), 2.03-1.66 (m, 4H) |

TABLE R-continued

The following examples were prepared using a similar procedure to the described for Example 228 using either Peak 1 or Peak 2 from step 2

| Ex. No. | Structure | Compound Name | LCMS $[M + H]^+$ | NMR |
|---|---|---|---|---|
| 719 | 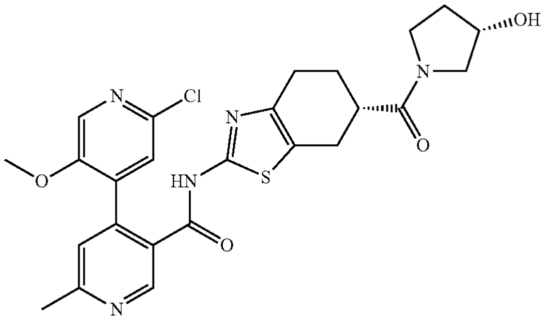 [SMILES: COc1cnc(Cl)cc1-c1cc(C)ncc1C(=O)Nc1nc2c(s1)C[C@@H](C(=O)N1CC[C@H](O)C1)CC2] | 2'-Chloro-N-((S)-6-((S)-3-hydroxypyrrolidine-1-carbonyl)-4,5,6,7-tetrahydrobenzo[d]thiazol-2-yl)-5'-methoxy-6-methyl-[4,4'-bipyridine]-3-carboxamide | 528 | $^1H$ NMR (400 MHz, DMSO-$d_6$) δ 8.76 (s, 1H), 8.16 (s, 1H), 7.51 (s, 1H), 7.40 (s, 1H), 4.33-4.22 (m, 1H), 3.64-3.57 (m, 1H), 3.61 (s, 3H), 3.44-3.24 (m, 3H, partly obscured by water), 2.92-2.80 (m, 1H), 2.79-2.73 (m, 2H), 2.69-2.65 (m, 2H), 2.58 (s, 3H), 2.03-1.91 (m, 2H), 1.90-1.80 (m, 1H), 1.76-1.69 (m, 1H) |

Example 720A & 720B: Synthesis of (R)-2-(2'-Chloro-5'-methoxy-6-methyl-[4,4'-bipyridine]-3-carboxamido)-N-((1 S,2R)-2-hydroxycyclobutyl)-4,5,6,7-tetrahydrobenzo[d]thiazole-6-carboxamide (720A) & (R)-2-(2'-Chloro-5'-methoxy-6-methyl-[4,4'-bipyridine]-3-carboxamido)-N-((1R,2S)-2-hydroxycyclobutyl)-4,5,6,7-tetrahydrobenzo[d]thiazole-6-carboxamide (720B) with Arbitrarily Assigned Stereochemistry

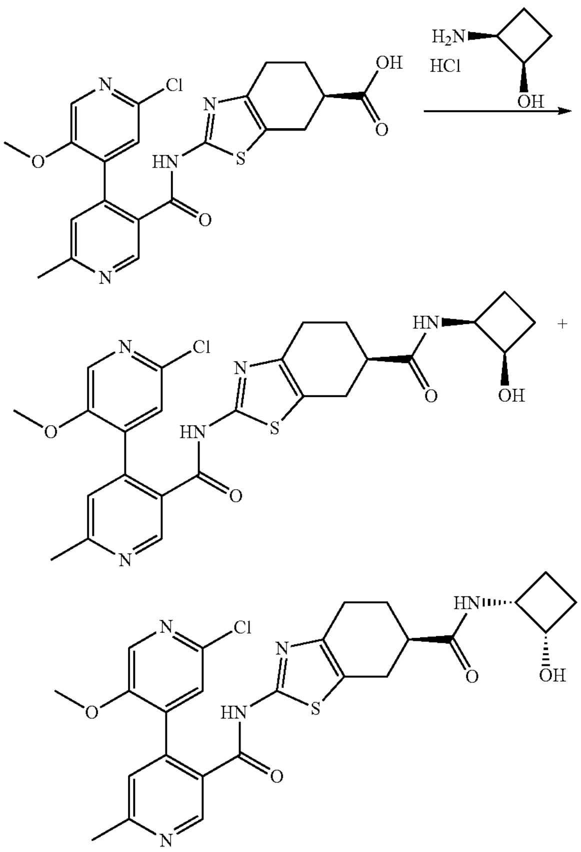

To a solution of (R)-2-(2'-chloro-5'-methoxy-6-methyl-[4,4'-bipyridine]-3-carboxamido)-4,5,6,7-tetrahydrobenzo[d]thiazole-6-carboxylic acid (45 mg, 0.098 mmol), cis-2-aminocyclobutane-1-ol hydrochloride (18 mg, 0.15 mmol) and DIPEA (63 mg, 0.49 mmol) in DMF (5 mL) at 0° C. was added T3P (50% in DMF, 190 mg, 0.29 mmol) and the mixture was stirred at room temperature for 16 h. The mixture was diluted with water (10 mL), extracted with EtOAc (2×10 mL), and the combined organic layers were washed with brine (10 mL), dried over $Na_2SO_4$, filtered, and concentrated under reduced pressure. The residue was purified by prep-TLC (DCM/MeOH=10/1, v/v) to afford two diastereoisomers which were arbitrarily assigned:

Example 720A: Higher polarity fraction (R)-2-(2'-chloro-5'-methoxy-6-methyl-[4,4'-bipyridine]-3-carboxamido)-N-((1S,2R)-2-hydroxycyclobutyl)-4,5,6,7-tetrahydrobenzo[d]thiazole-6-carboxamide (15.7 mg, 30%) obtained as a white solid. LCMS: m/z=528 $[M+H]^+$; $^1H$ NMR (400 MHz, DMSO-$d_6$) δ 12.4 (s, 1H), 8.76 (s, 1H), 8.16 (s, 1H), 7.83 (d, J=7.2 Hz, 1H), 7.51 (s, 1H), 7.40 (s, 1H), 5.05 (d, J=4.4 Hz, 1H), 4.24-4.18 (m, 2H), 3.61 (s, 3H), 2.78-2.71 (m, 2H), 2.70-2.63 (m, 2H), 2.58 (s, 3H), 2.07-1.95 (m, 4H), 1.87-1.80 (m, 1H), 1.79-1.70 (m, 2H).

Example 720B: Lower polarity fraction (R)-2-(2'-chloro-5'-methoxy-6-methyl-[4,4'-bipyridine]-3-carboxamido)-N-((1R,2S)-2-hydroxycyclobutyl)-4,5,6,7-tetrahydrobenzo[d]thiazole-6-carboxamide (17.2 mg, 33%) obtained as a white solid. LCMS: m/z=528 $[M+H]^+$, $^1H$ NMR (400 MHz, DMSO-$d_6$) δ 12.4 (s, 1H), 8.77 (s, 1H), 8.16 (s, 1H), 7.81 (d, J=7.2 Hz, 1H), 7.50 (s, 1H), 7.40 (s, 1H), 5.03 (d, J=4.4 Hz, 1H), 4.24-4.18 (m, 2H), 3.61 (s, 3H), 2.82-2.71 (m, 2H), 2.70-2.64 (m, 2H), 2.58 (s, 3H), 2.05-1.94 (m, 4H), 1.88-1.80 (m, 1H), 1.79-1.70 (m, 2H).

Example 230: Synthesis of 4-(6-Methoxy-1-methyl-1H-indazol-5-yl)-N-(5-(2-methoxynicotinoyl)-5,6-dihydro-4H-pyrrolo[3,4-d]thiazol-2-yl)-6-methylnicotinamide

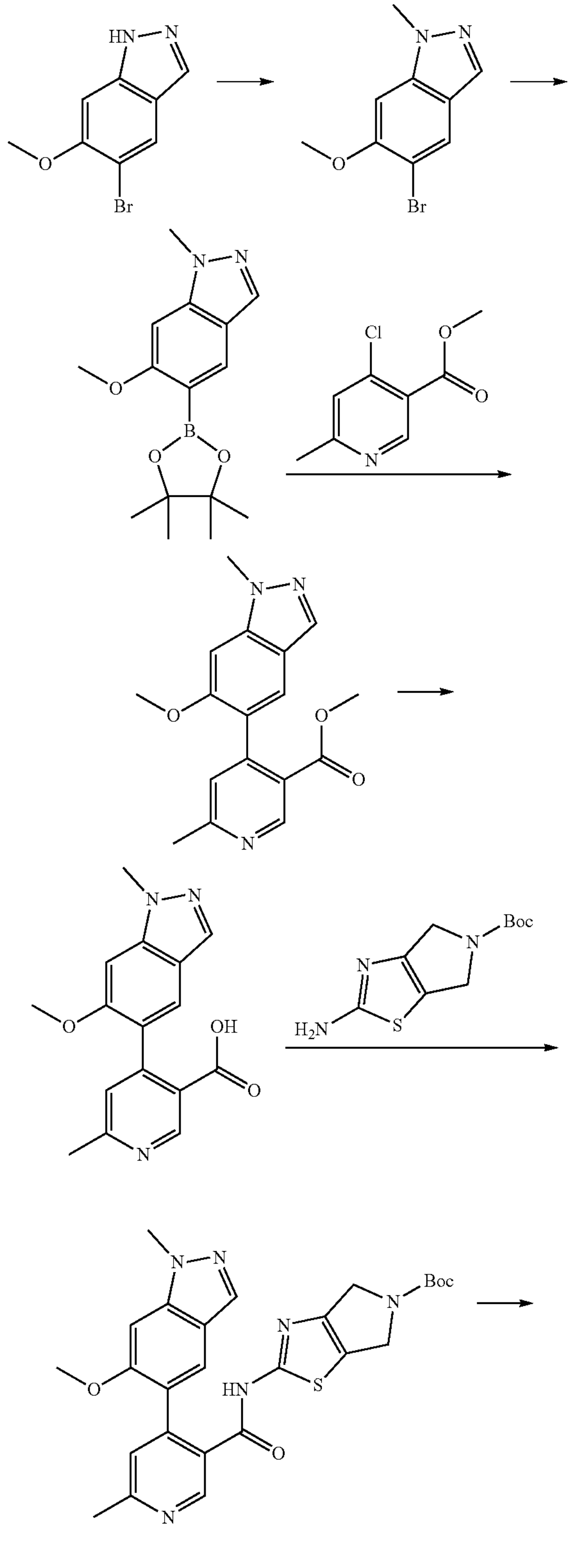

-continued

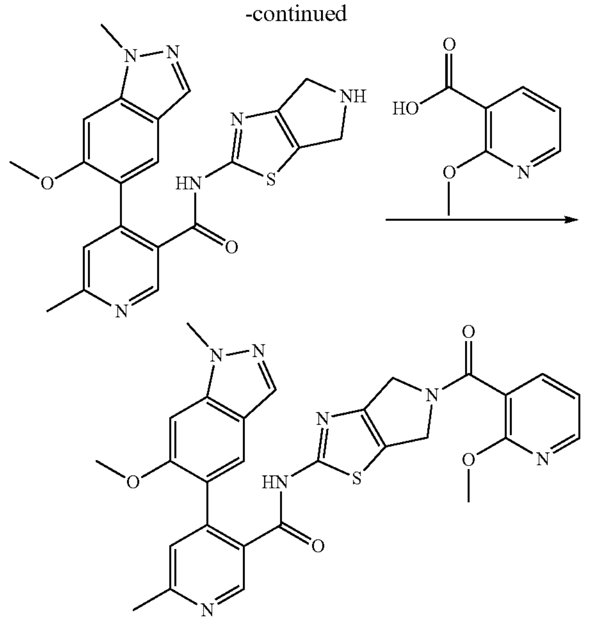

Step 1: To a solution of 5-bromo-6-methoxy-1H-indazole (2.00 g, 8.85 mmol) in DMF (20 mL) at 0° C. was added NaH (60% w/w in oil, 708 mg, 17.7 mmol) and MeI (1.9 g 13 mmol) and the mixture was stirred at room temperature for 2 h. The mixture was diluted with water (50 mL), extracted with EtOAc (2×50 mL) and the combined organic layers washed with brine (50 mL), dried over $Na_2SO_4$, filtered and concentrated under reduced pressure. The residue was purified by silica gel chromatography (Petroleum Ether/EtOAc=5/1, v/v) to afford 5-bromo-6-methoxy-1-methyl-1H-indazole (1.2 g, 57%) as a white solid. $^1H$ NMR (400 MHz, Chloroform-$d_6$) δ 7.89 (s, 1H), 7.83 (s, 1H), 6.74 (s, 1H), 4.03 (s, 3H), 3.98 (s, 3H).

Step 2: To a solution of 5-bromo-6-methoxy-1-methyl-1H-indazole (500 mg, 2.1 mmol) in 1-4 dioxane (8 mL) was added $Pin_2B_2$ (1.33 g, 5.25 mmol), Pd(dppf)$Cl_2$ (152.3 mg, 0.21 mmol) and KOAc (617.4 mg, 6.3 mmol) and the mixture was heated at 100° C. overnight under $N_2$. The mixture was filtered and the filtrate concentrated under reduced pressure to afford 6-methoxy-1-methyl-5-(4,4,5,5-tetramethyl-1,3,2-dioxaborolan-2-yl)-1H-indazole (600 mg, 99%), which was used directly in the next step. LCMS m/z=289 $[M+H]^+$.

Step 3: To a solution of 6-methoxy-1-methyl-5-(4,4,5,5-tetramethyl-1,3,2-dioxaborolan-2-yl)-1H-indazole (600 mg, 2.08 mmol) in 1,4-dioxane (8 mL) and water (2 mL) was added methyl 4-chloro-6-methylnicotinate (772 mg, 4.17 mmol), Pd(dtbpf)$Cl_2$ (134 mg, 0.208 mmol) and $K_2CO_3$ (861 mg, 6.24 mmol) and the mixture was heated at 100° C. overnight under $N_2$. The mixture was diluted with water (50 mL), extracted with EtOAc (2×50 mL) and the combined organic layers washed with brine (50 mL), dried over $Na_2SO_4$, filtered and concentrated under reduced pressure. The residue was purified by silica gel chromatography (Petroleum Ether/EtOAc=1/1) to afford methyl 4-(6-methoxy-1-methyl-1H-indazol-5-yl)-6-methylnicotinate (450 mg, 69%) as a yellow solid. LCMS: m/z=312 $[M+H]^+$.

Step 4: To a solution of methyl 4-(6-methoxy-1-methyl-1H-indazol-5-yl)-6-methylnicotinate (50 mg, 0.16 mmol) in MeOH (2 mL) and water (2 mL) was added NaOH (20 mg, 0.48 mmol) and the mixture was heated at 50° C. for 3 h. the mixture was adjusted to pH 5-6 with 2 M aqueous HCl and the resulting precipitate was collected by filtration to afford 4-(6-methoxy-1-methyl-1H-indazol-5-yl)-6-methylnicotinic acid (40 mg, 84%) as a yellow solid. LCMS m/z=298 $[M+H]^+$.

Step 5: To a solution of 4-(6-methoxy-1-methyl-1H-indazol-5-yl)-6-methylnicotinic acid (40 mg, 0.13 mmol) in ACN (4 mL) was added tert-butyl 2-amino-4,6-dihydro-5H-pyrrolo[3,4-d]thiazole-5-carboxylate (33 mg, 0.13 mmol), TCFH (57 mg, 0.2 mmol) and 1-methyl-1H-imidazole (44 mg 0.54 mmol) and the mixture was heated at 80° C. overnight. The mixture was diluted with water (10 mL), extracted with EtOAc (2×10 mL) and the combined organic layers washed with brine (10 mL), dried over $Na_2SO_4$, filtered and concentrated under reduced pressure. The residue was purified by prep-TLC (DCM/MeOH=15/1) to afford tert-butyl 2-(4-(6-methoxy-1-methyl-1H-indazol-5-yl)-6-methylnicotinamido)-4,6-dihydro-5H-pyrrolo[3,4-d]thiazole-5-carboxylate (60 mg, 86%) as a yellow solid. LCMS: m/z=521 $[M+H]^+$. $^1$H NMR (400 MHz, DMSO-$d_6$) δ 12.6 (d, J=10.2 Hz, 1H), 8.64 (s, 1H), 7.99 (s, 1H), 7.71 (s, 1H), 7.35 (s, 1H), 7.08 (s, 1H), 4.52 (d, J=11.8 Hz, 2H), 4.38 (s, 2H), 4.01 (s, 3H), 3.57 (d, J=2.2 Hz, 3H), 2.57 (s, 3H), 1.45 (s, 9H).

Step 6: A solution of tert-butyl 2-(4-(6-methoxy-1-methyl-1H-indazol-5-yl)-6-methylnicotinamido)-4,6-dihydro-5H-pyrrolo[3,4-d]thiazole-5-carboxylate (60 mg, 0.12 mmol) in 4 M HCl/MeOH (4 mL) was stirred at room temperature for 2 h then concentrated under reduced pressure. The residue was dissolved in DMF (3 mL), cooled to 0° C. 2-methoxynicotinic acid (26.2 mg, 0.17 mmol), DIPEA (73.7 mg, 0.57 mmol) and T3P (50% in DMF, 109 mg, 0.171 mmol) were added and the mixture was stirred at room temperature overnight. The mixture was diluted with water (10 mL), extracted with EtOAc (2×10 mL) and the combined organic layers washed with brine (10 mL), dried over $Na_2SO_4$, filtered and concentrated under reduced pressure. The residue was purified by prep-TLC (DCM/MeOH=15/1) to afford 4-(6-methoxy-1-methyl-1H-indazol-5-yl)-N-(5-(2-methoxynicotinoyl)-5,6-dihydro-4H-pyrrolo[3,4-d]thiazol-2-yl)-6-methylnicotinamide (27.0 mg, 43%) as a white solid. LCMS: m/z=556 $[M+H]^+$. $^1$H NMR (400 MHz, DMSO-$d_6$) δ 12.6 (s, 1H), 8.64 (d, J=3.8 Hz, 1H), 8.30-8.26 (m, 1H), 7.9 (d, J=2.4 Hz, 1H), 7.78 (dd, J=7.4, 1.8 Hz, 1), 7.71 (d, J=1.6 Hz, 1H), 7.35 (d, J=2.4 Hz, 1H), 7.12-7.07 (m, 2H), 4.76 (s, 1H), 4.62 (s, 1H), 4.47 (s, 1H), 4.36 (s, 1H), 4.01 (d, J=4.2 Hz, 3H), 3.92 (d, J=2.4 Hz, 3H), 3.57 (s, 3H), 2.57 (d, J=2.6 Hz, 3H).

TABLE AD

The following examples were prepared using a similar procedure to that described for Example 228

| Ex No. | Structure | Compound Name | LCMS $[M + H]^+$ | NMR |
|---|---|---|---|---|
| 721 | 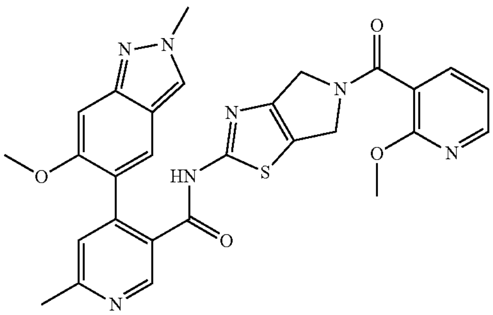 [SMILES: COc1cc2nn(C)cc2cc1-c1cc(C)ncc1C(=O)Nc1nc2c(s1)CN(C(=O)c1cccnc1OC)C2] | 4-(6-Methoxy-2-methyl-2H-indazol-5-yl)-N-(5-(2-methoxynicotinoyl)-5,6-dihydro-4H-pyrrolo[3,4-d]thiazol-2-yl)-6-methylnicotinamide | 556 | $^1$H NMR (400 MHZ, DMSO-$d_6$) δ 12.5 (s, 1H), 8.63 (d, J = 3.8 Hz, 1H), 8.32-8.26 (m, 2H), 7.81-7.76 (m, 1H), 7.67 (s, 1H), 7.35 (d, J = 2.8 Hz, 1H), 7.12-7.07 (m, 1H), 6.88 (d, J = 3.2 Hz, 1H), 4.76 (s, 1H), 4.61 (s, 1H), 4.47 (s, 1H), 4.35 (s, 1H), 4.11 (d, J = 2.8 Hz, 3H), 3.91 (d, J = 2.0 Hz, 3H), 3.49 (s, 3H), 2.57 (d, J = 2.4 Hz, 3H) |
| 722 | 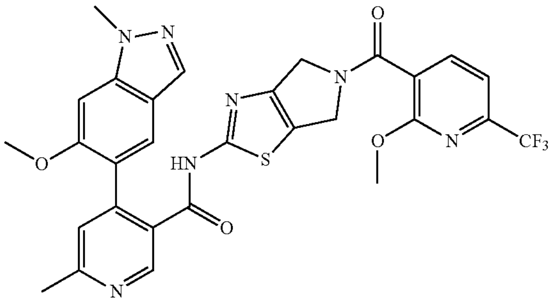 [SMILES: COc1cc2c(cnn2C)cc1-c1cc(C)ncc1C(=O)Nc1nc2c(s1)CN(C(=O)c1ccc(C(F)(F)F)nc1OC)C2] | 4-(6-Methoxy-1-methyl-1H-indazol-5-yl)-N-(5-(2-methoxy-6-(trifluoromethyl)nicotinoyl)-5,6-dihydro-4H-pyrrolo[3,4-d]thiazol-2-yl)-6-methylnicotinamide | 624 | $^1$H NMR (400 MHZ, DMSO-$d_6$) δ 12.6 (s, 1H), 8.64 (d, J = 3.0 Hz, 1H), 8.08 (dd, J = 7.4, 2.6 Hz, 1H), 7.99 (d, J = 2.4 Hz, 1H), 7.71 (d, J = 1.8 Hz, 1H), 7.61 (dd, J = 7.4, 2.8 Hz, 1H), 7.35 (d, J = 3.0 Hz, 1H), 7.08 (d, J = 2.8 Hz, 1H), 4.78 (s, 1H), 4.65 (s, 1H), 4.49 (s, 1H), 4.40 (s, 1H), 4.01 (d, J = 3.8 Hz, 3H), 3.97 (s, 3H), 3.57 (s, 3H), 2.57 (d, J = 2.8 Hz, 3H) |

Example 231: Synthesis of 2'-chloro-N-(5-(4-chloro-6-(difluoromethyl)nicotinoyl)-5,6-dihydro-4H-pyrrolo[3,4-d]thiazol-2-yl)-5'-methoxy-6-methyl-[4,4'-bipyridine]-3-carboxamide

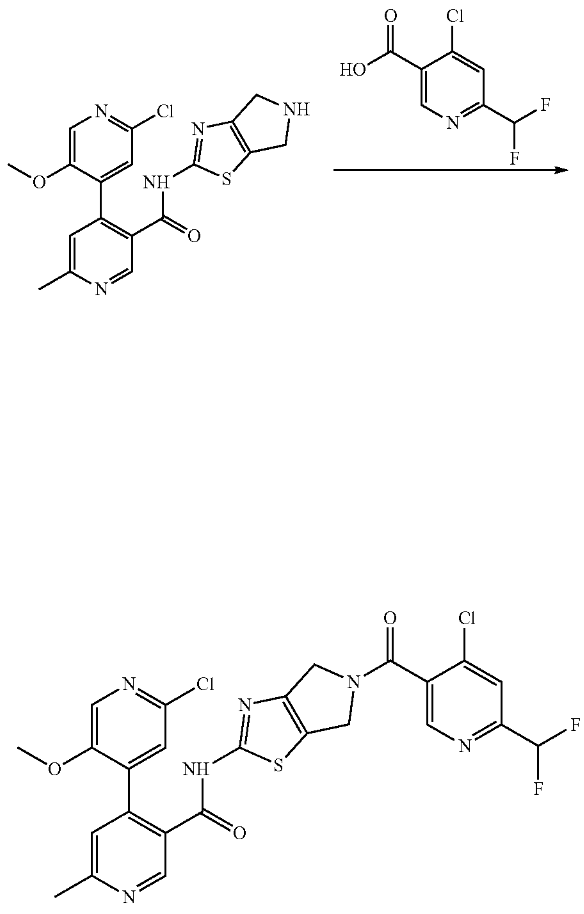

A solution of 4-chloro-6-(difluoromethyl)pyridine-3-carboxylic acid (62 mg, 0.3 mmol) and HOBt (45 mg, 0.3 mmol) in DMF (2 mL) was stirred for 5 minutes at 25° C. To the above mixture was added a solution of TEA (91 mg, 0.9 mmol) and 2'-chloro-5'-methoxy-6-methyl-N-{4H,5H,6H-pyrrolo[3,4-d][1,3]thiazol-2-yl}-[4,4'-bipyridine]-3-carboxamide (120 mg, 0.3 mmol) in DMF (1 mL) dropwise at 25° C. The reaction mixture was stirred at 25° C. for 16 h. The resulting mixture was purified directly by reverse phase flash chromatography (ACN-water with 0.1% formic acid modifier) to afford crude product. The crude product (70 mg) was purified by prep-HPLC (40-60% ACN (1% $NH_3$)-water (0.1% formic acid) to afford 2'-chloro-N-{5-[4-chloro-6-(difluoromethyl)pyridine-3-carbonyl]-4H,6H-pyrrolo[3,4-d][1,3]thiazol-2-yl}-5'-methoxy-6-methyl-[4,4'-bipyridine]-3-carboxamide (35.1 mg, 19.1% yield) as a white solid. LCMS: m/z=591 $[M+H]^+$. $^1H$ NMR (400 MHz, DMSO-$d_6$) δ 12.84 (d, J=6.0 Hz, 1H), 8.88 (d, J=4.6 Hz, 1H), 8.78 (d, J=4.2 Hz, 1H), 8.17 (d, J=2.0 Hz, 1H), 8.04 (d, J=7.1 Hz, 1H), 7.55 (s, 1H), 7.44 (d, J=3.1 Hz, 1H), 7.05 (d, J=0.9 Hz, 1H), 4.86 (t. J=2.7 Hz, 1H), 4.72 (t, J=2.7 Hz, 1H), 4.53 (t, J=2.6 Hz, 1H), 4.44 (d, J=2.8 Hz, 1H), 3.59 (s, 3H), 2.59 (d, J=3.0 Hz, 3H).

Example 232: Synthesis of N-(5-(1,2,4-oxadiazole-3-carbonyl)-5,6-dihydro-4H-pyrrolo[3,4-d]thiazol-2-yl)-2'-chloro-5'-methoxy-6-methyl-[4,4'-bipyridine]-3-carboxamide

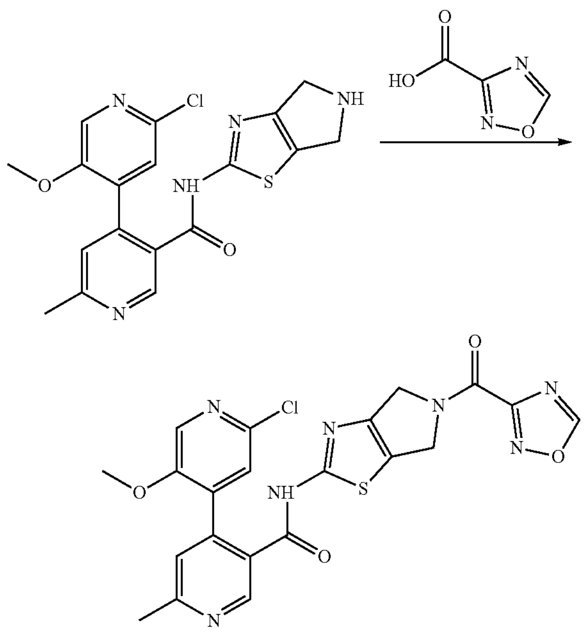

To a mixture of 1,2,4-oxadiazole-3-carboxylic acid (17 mg, 0.15 mmol) in THF (1 mL) was added TEA (30 mg, 0.30 mmol) and PyBOP (78 mg, 0.15 mmol). The reaction mixture was stirred for 15 min at 30° C., and then 2'-chloro-N-(5,6-dihydro-4H-pyrrolo[3,4-d]thiazol-2-yl)-5'-methoxy-6-methyl-[4,4'-bipyridine]-3-carboxamide hydrochloride (43 mg, 0.10 mmol) was added. The reaction mixture was stirred for 16 h at 30° C., and the crude product was purified directly by prep-HPLC (40-60% ACN (1% $NH_3$)-water (0.1% formic acid) to afford N-(5-(1,2,4-oxadiazole-3-carbonyl)-5,6-dihydro-4H-pyrrolo[3,4-d]thiazol-2-yl)-2'-chloro-5'-methoxy-6-methyl-[4,4'-bipyridine]-3-carboxamide as an off-white solid. LCMS: m/z=498 $[M+H]^+$.

Example 233: Synthesis of 2'-chloro-5'-methoxy-6-methyl-N-(5-(4-methyloxazole-2-carbonyl)-5,6-dihydro-4H-pyrrolo[3,4-d]thiazol-2-yl)-[4,4'-bipyridine]-3-carboxamide

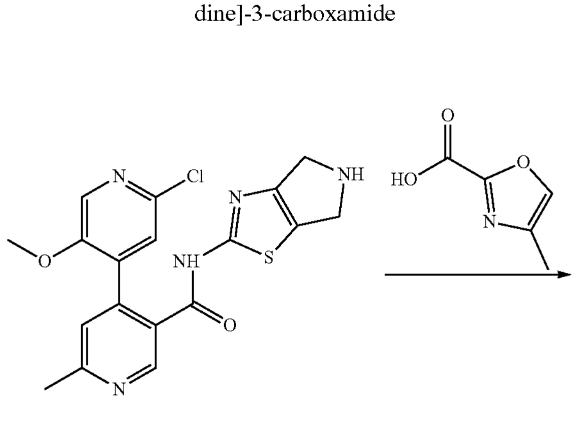

-continued

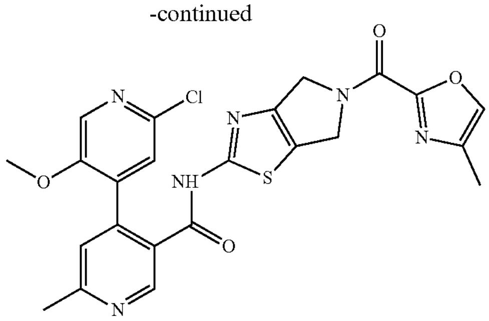

To a mixture of 4-methyloxazole-2-carboxylic acid (19 mg, 0.15 mmol) in DMF (1 mL) was added DIPEA (39 mg, 0.30 mmol) and HATU (46 mg, 0.12 mmol). After the reaction mixture was stirred for 30 min at 30° C. 2'-chloro-N-(5,6-dihydro-4H-pyrrolo[3,4-d]thiazol-2-yl)-5'-methoxy-6-methyl-[4,4'-bipyridine]-3-carboxamide hydrochloride (43 mg, 0.10 mmol) was added, and the reaction mixture was stirred for 1 h. The crude product was purified directly by prep-HPLC (40-60% ACN (1% $NH_3$)-water (0.1% formic acid) to afford 2'-chloro-5'-methoxy-6-methyl-N-(5-(4-methyloxazole-2-carbonyl)-5,6-dihydro-4H-pyrrolo[3,4-d]thiazol-2-yl)-[4,4'-bipyridine]-3-carboxamide as a tan solid. LCMS: m/z=511 $[M+H]^+$. $^1H$ NMR (400 MHz, DMSO-$d_6$) δ 12.87-12.82 (m, 1H), 8.82-8.80 (m, 1H), 8.19 (s, 1H), 8.07 (s, 1H), 7.56 (s, 1H), 7.47-7.46 (m, 1H), 5.26 (s, 1H), 5.11 (s, 1H), 4.82 (s, 1H), 4.69 (s, 1H), 3.62 (s, 3H), 2.61-2.60 (m, 3H), 2.22-2.21 (m, 3H).

TABLE S

The following examples were prepared using a similar procedure to that described for Example 233

| Ex. No. | Structure | Compound Name | LCMS $[M + H]^+$ | NMR |
|---|---|---|---|---|
| 234 | 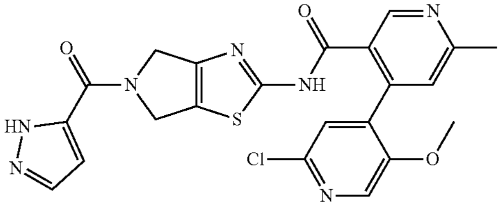 [SMILES: COc1cnc(Cl)cc1-c1cc(C)ncc1C(=O)Nc1nc2c(s1)CN(C(=O)c1ccn[nH]1)C2] | 2'-chloro-5'-methoxy-6-methyl-N-[5-(1H-pyrazole-5-carbonyl)-4H,5H,6H-pyrrolo[3,4-d][1,3]thiazol-2-yl]-[4,4'-bipyridine]-3-carboxamide | 496 | |
| 235 | 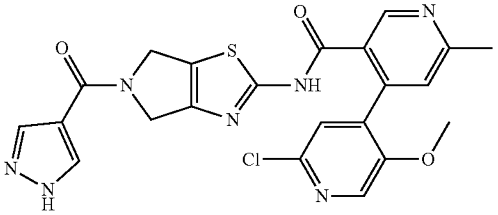 [SMILES: COc1cnc(Cl)cc1-c1cc(C)ncc1C(=O)Nc1nc2c(s1)CN(C(=O)c1cn[nH]c1)C2] | 2'-chloro-5'-methoxy-6-methyl-N-[5-(1H-pyrazole-4-carbonyl)-4H,5H,6H-pyrrolo[3,4-d][1,3]thiazol-2-yl]-[4,4'-bipyridine]-3-carboxamide | 496 | |
| 236 | 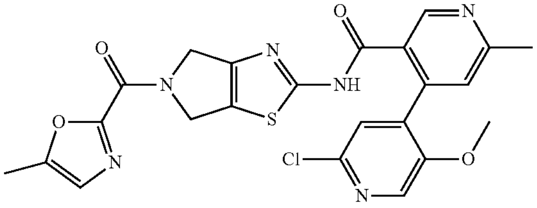 | 2'-chloro-5'-methoxy-6-methyl-N-[5-(5-methyl-1,3-oxazole-2-carbonyl)-4H,5H,6H-pyrrolo[3,4-d][1,3]thiazol-2-yl]-[4,4'-bipyridine]-3-carboxamide | 511 | |
| 237 | 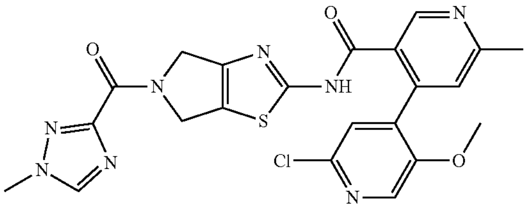 | 2'-chloro-5'-methoxy-6-methyl-N-[5-(1-methyl-1H-1,2,4-triazole-3-carbonyl)-4H,5H,6H-pyrrolo[3,4-d][1,3]thiazol-2-yl]-[4,4'-bipyridine]-3-carboxamide | 511 | |
| 238 | 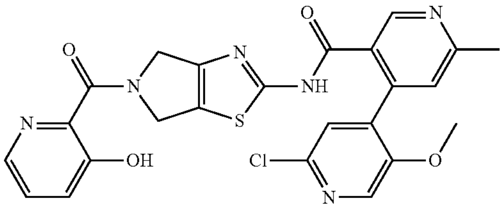 [SMILES: COc1cnc(Cl)cc1-c1cc(C)ncc1C(=O)Nc1nc2c(s1)CN(C(=O)c1ncccc1O)C2] | 2'-chloro-N-[5-(3-hydroxypyridine-2-carbonyl)-4H,5H,6H-pyrrolo[3,4-d][1,3]thiazol-2-yl]-5'-methoxy-6-methyl-[4,4'-bipyridine]-3-carboxamide | 523 | |

TABLE S-continued

| The following examples were prepared using a similar procedure to that described for Example 233 | | | | |
|---|---|---|---|---|
| Ex. No. | Structure | Compound Name | LCMS $[M + H]^+$ | NMR |
| 239 | 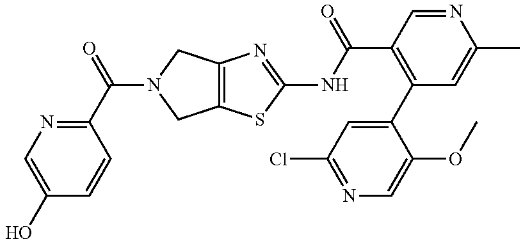 [SMILES: COc1cnc(Cl)cc1-c1cc(C)ncc1C(=O)Nc1nc2c(s1)CN(C(=O)c1ccc(O)cn1)C2] | 2'-chloro-N-[5-(5-hydroxypyridine-2-carbonyl)-4H,5H,6H-pyrrolo[3,4-d][1,3]thiazol-2-yl]-5' methoxy-6-methyl-[4,4'-bipyridine]-3-carboxamide | 523 | |
| 240 | 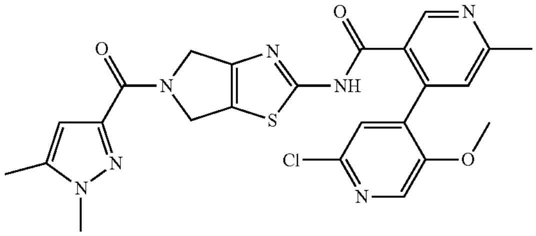 | 2'-chloro-N-[5-(1,5-dimethyl-1H-pyrazole-3-carbonyl)-4H,5H,6H-pyrrolo[3,4-d][1,3]thiazol-2-yl]-5'-methoxy-6-methyl-[4,4'-bipyridine]-3-carboxamide | 524 | |
| 241 | 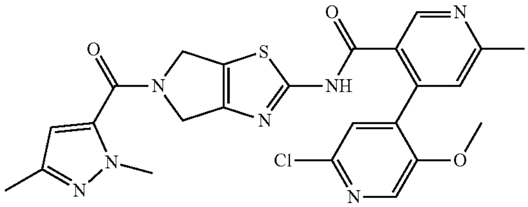 | 2'-chloro-N-[5-(1,3-dimethyl-1H-pyrazole-5-carbonyl)-4H,5H,6H-pyrrolo[3,4-d][1,3]thiazol-2-yl]-5'-methoxy-6-methyl-[4,4'-bipyridine]-3-carboxamide | 524 | |
| 242 | 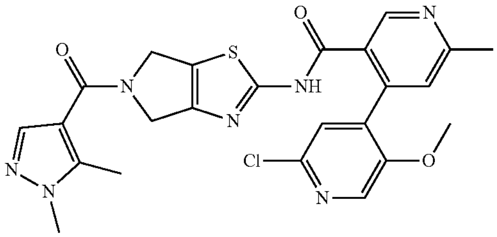 [SMILES: COc1cnc(Cl)cc1-c1cc(C)ncc1C(=O)Nc1nc2c(s1)CN(C(=O)c1cnn(C)c1C)C2] | 2'-chloro-N-[5-(1,5-dimethyl-1H-pyrazole-4-carbonyl)-4H,5H,6H-pyrrolo[3,4-d][1,3]thiazol-2-yl]-5'-methoxy-6-methyl-[4,4'-bipyridine]-3-carboxamide | 524 | |
| 243 | 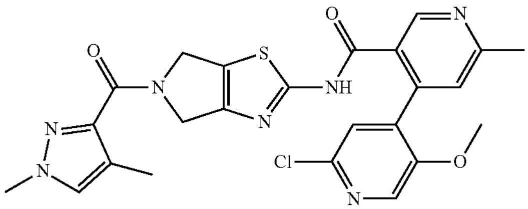 | 2'-chloro-N-[5-(1,4-dimethyl-1H-pyrazole-3-carbonyl)-4H,5H,6H-pyrrolo[3,4-d][1,3]thiazol-2-yl]-5'-methoxy-6-methyl-[4,4'-bipyridine]-3-carboxamide | 524 | |
| 244 | 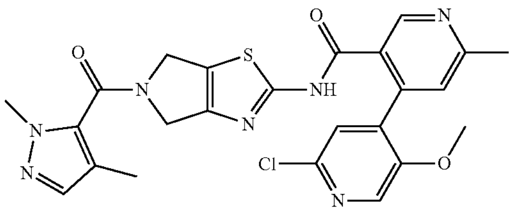 | 2'-chloro-N-[5-(1,4-dimethyl-1H-pyrazole-5-carbonyl)-4H,5H,6H-pyrrolo[3,4-d][1,3]thiazol-2-yl]-5'-methoxy-6-methyl-[4,4'-bipyridine]-3-carboxamide | 524 | |

TABLE S-continued

The following examples were prepared using a similar procedure to that described for Example 233

| Ex. No. | Structure | Compound Name | LCMS $[M + H]^+$ | NMR |
|---|---|---|---|---|
| 245 | 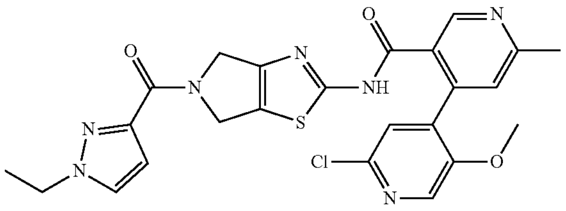 [SMILES: CCn1ccc(C(=O)N2Cc3nc(NC(=O)c4cnc(C)cc4-c4cc(Cl)ncc4OC)sc3C2)n1] | 2'-chloro-N-[5-(1-ethyl-1H-pyrazole-3-carbonyl)-4H,5H,6H-pyrrolo[3,4-d][1,3]thiazol-2-yl]-5'-methoxy-6-methyl-[4,4'-bipyridine]-3-carboxamide | 524 | |
| 246 | 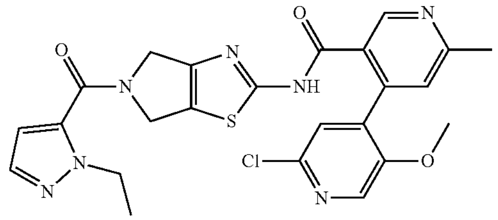 [SMILES: CCn1nccc1C(=O)N1Cc2nc(NC(=O)c3cnc(C)cc3-c3cc(Cl)ncc3OC)sc2C1] | 2'-chloro-N-[5-(1-ethyl-1H-pyrazole-5-carbonyl)-4H,5H,6H-pyrrolo[3,4-d][1,3]thiazol-2-yl]-5'-methoxy-6-methyl-[4,4'-bipyridine]-3-carboxamide | 524 | |
| 247 | 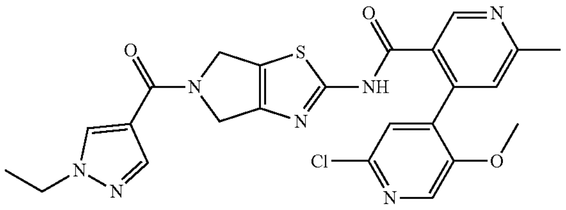 [SMILES: CCn1cc(C(=O)N2Cc3nc(NC(=O)c4cnc(C)cc4-c4cc(Cl)ncc4OC)sc3C2)cn1] | 2'-chloro-N-[5-(1-ethyl-1H-pyrazole-4-carbonyl)-4H,5H,6H-pyrrolo[3,4-d][1,3]thiazol-2-yl]-5'-methoxy-6-methyl-[4,4'-bipyridine]-3-carboxamide | 524 | |
| 248 | 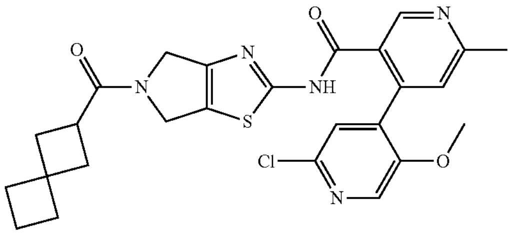 [SMILES: COc1cnc(Cl)cc1-c1cc(C)ncc1C(=O)Nc1nc2c(s1)CN(C(=O)C1CC3(CCC3)C1)C2] | 2'-chloro-5'-methoxy-6-methyl-N-(5-{spiro[3.3]heptane-2-carbonyl}-4H,5H,6H-pyrrolo[3,4-d][1,3]thiazol-2-yl)-[4,4'-bipyridine]-3-carboxamide | 524 | |
| 249 | 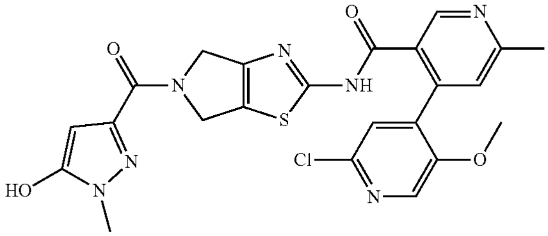 [SMILES: COc1cnc(Cl)cc1-c1cc(C)ncc1C(=O)Nc1nc2c(s1)CN(C(=O)c1cc(O)n(C)n1)C2] | 2'-chloro-N-[5-(5-hydroxy-1-methyl-1H-pyrazole-3-carbonyl)-4H,5H,6H-pyrrolo[3,4-d][1,3]thiazol-2-yl]-5'-methoxy-6-methyl-[4,4'-bipyridine]-3-carboxamide | 526 | |
| 250 | 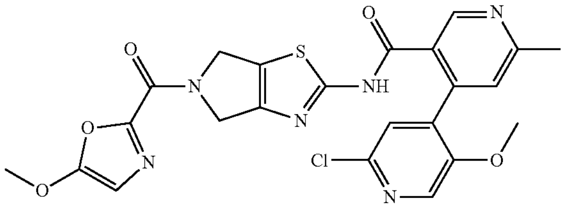 | 2'-chloro-5'-methoxy-N-[5-(5-methoxy-1,3-oxazole-2-carbonyl)-4H,5H,6H-pyrrolo[3,4-d][1,3]thiazol-2-yl]-6-methyl-[4,4'-bipyridine]-3-carboxamide | 527 | |

TABLE S-continued

| The following examples were prepared using a similar procedure to that described for Example 233 | | | | |
|---|---|---|---|---|
| Ex. No. | Structure | Compound Name | LCMS [M + H]+ | NMR |
| 251 | 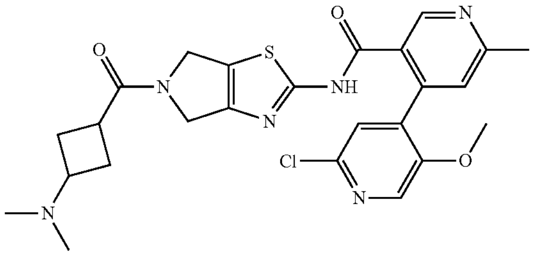 | 2'-chloro-N-{5-[3-(dimethylamino)cyclobutanecarbonyl]-4H,5H,6H-pyrrolo[3,4-d][1,3]thiazol-2-yl}-5'-methoxy-6-methyl-[4,4'-bipyridine]-3-carboxamide | 527 | |
| 252 | 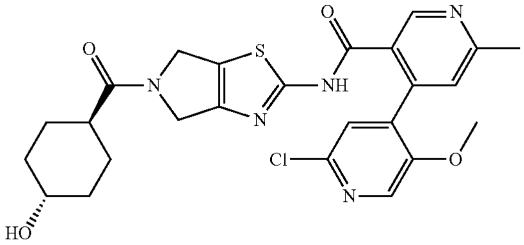 [SMILES: COc1cnc(Cl)cc1-c1cc(C)ncc1C(=O)Nc1nc2c(s1)CN(C(=O)[C@H]1CC[C@H](O)CC1)C2] | 2'-chloro-5'-methoxy-6-methyl-N-{5-[(1r,4r)-4-hydroxycyclohexanecarbonyl]-4H,5H,6H-pyrrolo[3,4-d][1,3]thiazol-2-yl}-[4,4'-bipyridine]-3-carboxamide | 528 | |
| 253 | 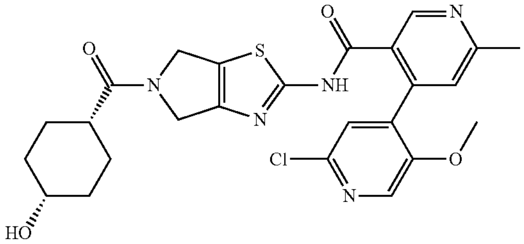 [SMILES: COc1cnc(Cl)cc1-c1cc(C)ncc1C(=O)Nc1nc2c(s1)CN(C(=O)[C@H]1CC[C@@H](O)CC1)C2] | 2'-chloro-5'-methoxy-6-methyl-N-{5-[(1s,4s)-4-hydroxycyclohexanecarbonyl]-4H,5H,6H-pyrrolo[3,4-d][1,3]thiazol-2-yl}-[4,4'-bipyridine]-3-carboxamide | 528 | |
| 254 | 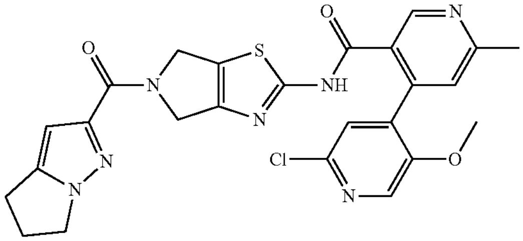 [SMILES: COc1cnc(Cl)cc1-c1cc(C)ncc1C(=O)Nc1nc2c(s1)CN(C(=O)c1cc3n(n1)CCC3)C2] | 2'-chloro-5'-methoxy-6-methyl-N-(5-{4H,5H,6H-pyrrolo[1,2-b]pyrazole-2-carbonyl}-4H,5H,6H-pyrrolo[3,4-d][1,3]thiazol-2-yl)-[4,4'-bipyridine]-3-carboxamide | 536 | |
| 255 | 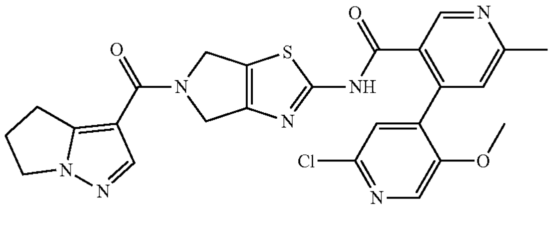 [SMILES: COc1cnc(Cl)cc1-c1cc(C)ncc1C(=O)Nc1nc2c(s1)CN(C(=O)c1cnn3c1CCC3)C2] | 2'-chloro-5'-methoxy-6-methyl-N-(5-{4H,5H,6H-pyrrolo[1,2-b]pyrazole-3-carbonyl}-4H,5H,6H-pyrrolo[3,4-d][1,3]thiazol-2-yl)-[4,4'-bipyridine]-3-carboxamide | 536 | |
| 256 | 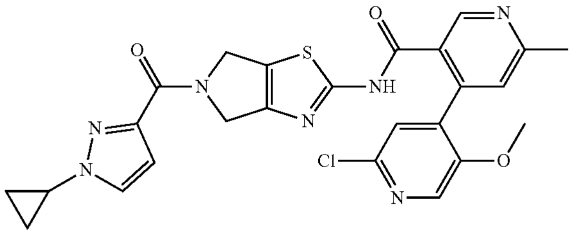 [SMILES: COc1cnc(Cl)cc1-c1cc(C)ncc1C(=O)Nc1nc2c(s1)CN(C(=O)c1ccn(C3CC3)n1)C2] | 2'-chloro-N-[5-(1-cyclopropyl-1H-pyrazole-3-carbonyl)-4H,5H,6H-pyrrolo[3,4-d][1,3]thiazol-2-yl]-5'-methoxy-6-methyl-[4,4'-bipyridine]-3-carboxamide | 536 | |

TABLE S-continued

The following examples were prepared using a similar procedure to that described for Example 233

| Ex. No. | Structure | Compound Name | LCMS $[M + H]^+$ | NMR |
|---|---|---|---|---|
| 257 | 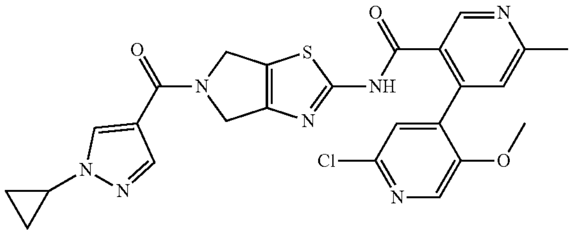 [SMILES: COc1cnc(Cl)cc1-c1cc(C)ncc1C(=O)Nc1nc2c(s1)CN(C(=O)c1cnn(C3CC3)c1)C2] | 2'-chloro-N-[5-(1-cyclopropyl-1H-pyrazole-4-carbonyl)-4H,5H,6H-pyrrolo[3,4-d][1,3]thiazol-2-yl]-5'-methoxy-6-methyl-[4,4'-bipyridine]-3-carboxamide | 536 | |
| 258 | 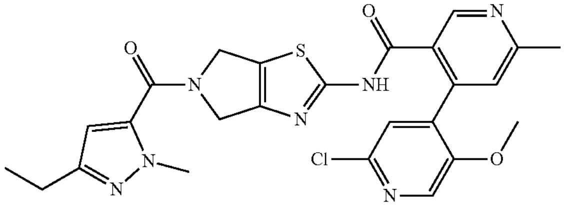 | 2'-chloro-N-[5-(3-ethyl-1-methyl-1H-pyrazole-5-carbonyl)-4H,5H,6H-pyrrolo[3,4-d][1,3]thiazol-2-yl]-5'-methoxy-6-methyl-[4,4'-bipyridine]-3-carboxamide | 538 | |
| 259 | 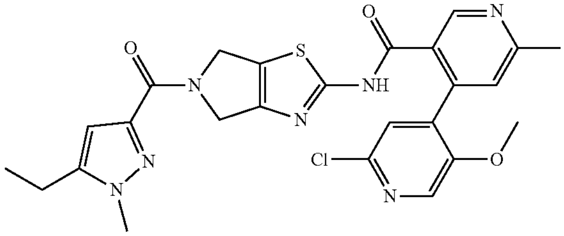 [SMILES: CCc1cc(C(=O)N2Cc3nc(NC(=O)c4cnc(C)cc4-c4cc(Cl)ncc4OC)sc3C2)nn1C] | 2'-chloro-N-[5-(5-ethyl-1-methyl-1H-pyrazole-3-carbonyl)-4H,5H,6H-pyrrolo[3,4-d][1,3]thiazol-2-yl]-5'-methoxy-6-methyl-[4,4'-bipyridine]-3-carboxamide | 538 | |
| 260 | 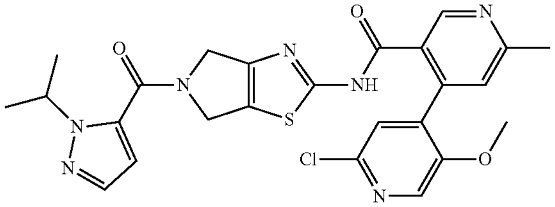 [SMILES: COc1cnc(Cl)cc1-c1cc(C)ncc1C(=O)Nc1nc2c(s1)CN(C(=O)c1ccnn1C(C)C)C2] | 2'-chloro-5'-methoxy-6-methyl-N-{5-[1-(propan-2-yl)-1H-pyrazole-5-carbonyl]-4H,5H,6H-pyrrolo[3,4-d][1,3]thiazol-2-yl}-[4,4'-bipyridine]-3-carboxamide | 538 | |
| 261 | 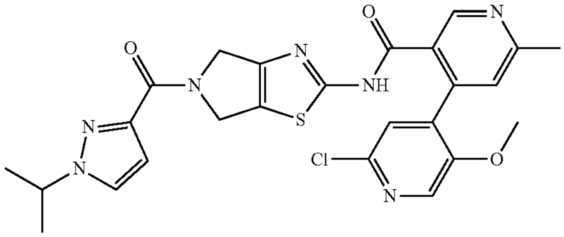 | 2'-chloro-5'-methoxy-6-methyl-N-{5-[1-(propan-2-yl)-1H-pyrazole-3-carbonyl]-4H,5H,6H-pyrrolo[3,4-d][1,3]thiazol-2-yl}-[4,4'-bipyridine]-3-carboxamide | 538 | |
| 262 | 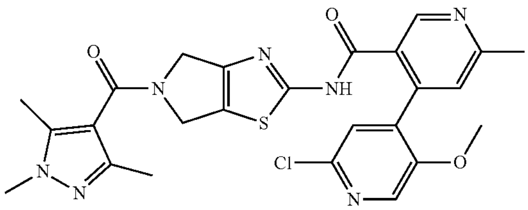 | 2'-chloro-5'-methoxy-6-methyl-N-[5-(1,3,5-trimethyl-1H-pyrazole-4-carbonyl)-4H,5H,6H-pyrrolo[3,4-d][1,3]thiazol-2-yl]-[4,4'-bipyridine]-3-carboxamide | 538 | |

TABLE S-continued

| Ex. No. | Structure | Compound Name | LCMS [M + H]+ | NMR |
|---|---|---|---|---|
| The following examples were prepared using a similar procedure to that described for Example 233 | | | | |
| 263 | 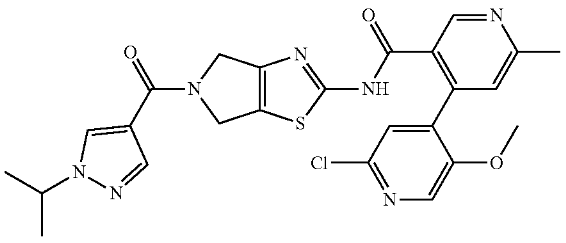 [SMILES: COc1cnc(Cl)cc1-c1cc(C)ncc1C(=O)Nc1nc2c(s1)CN(C(=O)c1cnn(C(C)C)c1)C2] | 2'-chloro-5'-methoxy-6-methyl-N-{5-[1-(propan-2-yl)-1H-pyrazole-4-carbonyl]-4H,5H,6H-pyrrolo[3,4-d][1,3]thiazol-2-yl}-[4,4'-bipyridine]-3-carboxamide | 538 | |
| 264 | 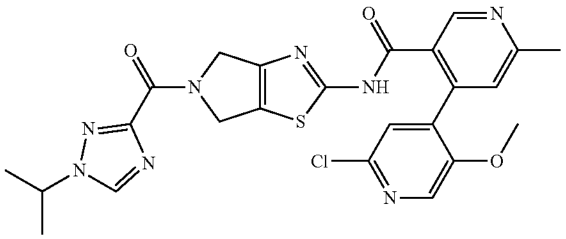 [SMILES: COc1cnc(Cl)cc1-c1cc(C)ncc1C(=O)Nc1nc2c(s1)CN(C(=O)c1ncn(C(C)C)n1)C2] | 2'-chloro-5'-methoxy-6-methyl-N-{5-[1-(propan-2-yl)-1H-1,2,4-triazole-3-carbonyl]-4H,5H,6H-pyrrolo[3,4-d][1,3]thiazol-2-yl}-[4,4'-bipyridine]-3-carboxamide | 539 | |
| 265 | 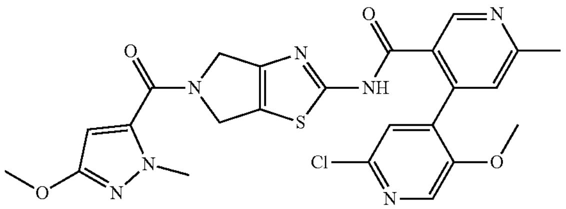 | 2'-chloro-5'-methoxy-N-[5-(3-methoxy-1-methyl-1H-pyrazole-5-carbonyl)-4H,5H,6H-pyrrolo[3,4-d][1,3]thiazol-2-yl]-6-methyl-[4,4'-bipyridine]-3-carboxamide | 540 | |
| 266 | 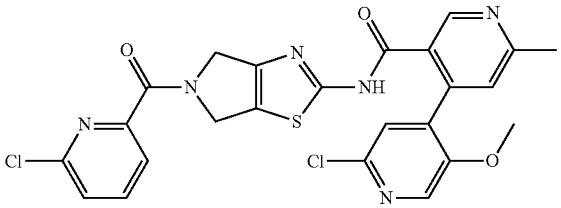 [SMILES: COc1cnc(Cl)cc1-c1cc(C)ncc1C(=O)Nc1nc2c(s1)CN(C(=O)c1cccc(Cl)n1)C2] | 2'-chloro-N-[5-(6-chloropyridine-2-carbonyl)-4H,5H,6H-pyrrolo[3,4-d][1,3]thiazol-2-yl]-5'-methoxy-6-methyl-[4,4'-bipyridine]-3-carboxamide | 541 | |
| 267 | 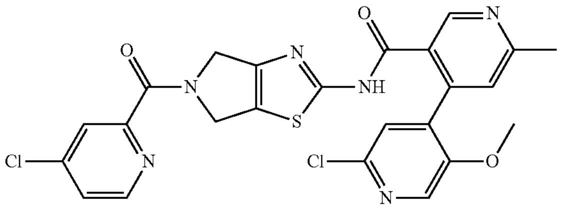 [SMILES: COc1cnc(Cl)cc1-c1cc(C)ncc1C(=O)Nc1nc2c(s1)CN(C(=O)c1cc(Cl)ccn1)C2] | 2'-chloro-N-[5-(4-chloropyridine-2-carbonyl)-4H,5H,6H-pyrrolo[3,4-d][1,3]thiazol-2-yl]-5'-methoxy-6-methyl-[4,4'-bipyridine]-3-carboxamide | 541 | |
| 268 | 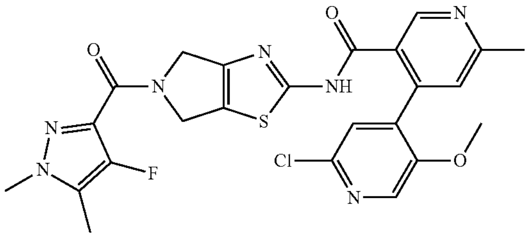 | 2'-chloro-N-[5-(4-fluoro-1,5-dimethyl-1H-pyrazole-3-carbonyl)-4H,5H,6H-pyrrolo[3,4-d][1,3]thiazol-2-yl]-5'-methoxy-6-methyl-[4,4'-bipyridine]-3-carboxamide | 542 | |

TABLE S-continued

The following examples were prepared using a similar procedure to that described for Example 233

| Ex. No. | Structure | Compound Name | LCMS [M + H]$^+$ | NMR |
|---|---|---|---|---|
| 269 | 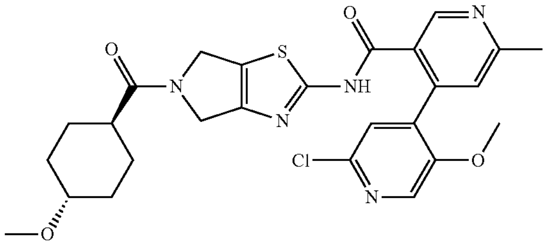 | 2'-chloro-5'-methoxy-6-methyl-N-{5-[(1r,4r)-4-methoxycyclohexane-carbonyl]-4H,5H,6H-pyrrolo[3,4-d][1,3]thiazol-2-yl}-[4,4'-bipyridine]-3-carboxamide | 542 | |
| 270 | 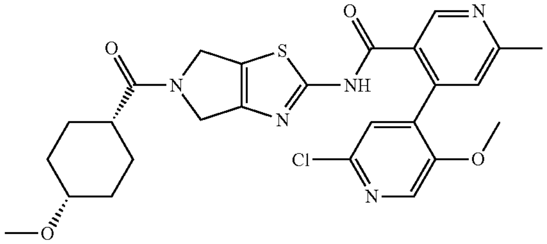 | 2'-chloro-5'-methoxy-6-methyl-N-{5-[(1s,4s)-4-methoxycyclohexane-carbonyl]-4H,5H,6H-pyrrolo[3,4-d][1,3]thiazol-2-yl}-[4,4'-bipyridine]-3-carboxamide | 542 | |
| 271 | 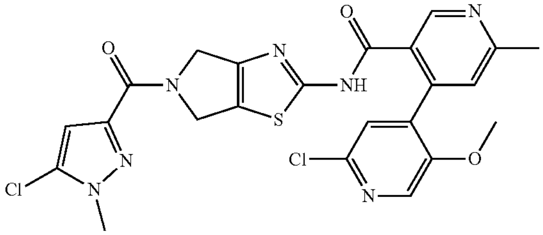 [SMILES: COc1cnc(Cl)cc1-c1cc(C)ncc1C(=O)Nc1nc2c(s1)CN(C(=O)c1cc(Cl)n(C)n1)C2] | 2'-chloro-N-[5-(5-chloro-1-methyl-1H-pyrazole-3-carbonyl)-4H,5H,6H-pyrrolo[3,4-d][1,3]thiazol-2-yl]-5'-methoxy-6-methyl-[4,4'-bipyridine]-3-carboxamide | 544 | |
| 272 | 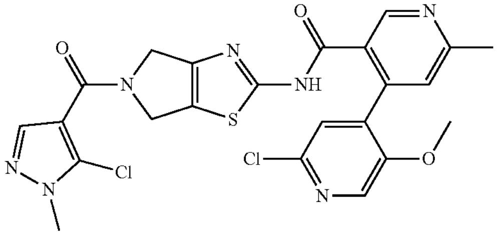 [SMILES: COc1cnc(Cl)cc1-c1cc(C)ncc1C(=O)Nc1nc2c(s1)CN(C(=O)c1cnn(C)c1Cl)C2] | 2'-chloro-N-[5-(5-chloro-1-methyl-1H-pyrazole-4-carbonyl)-4H,5H,6H-pyrrolo[3,4-d][1,3]thiazol-2-yl]-5'-methoxy-6-methyl-[4,4'-bipyridine]-3-carboxamide | 544 | |
| 273 | 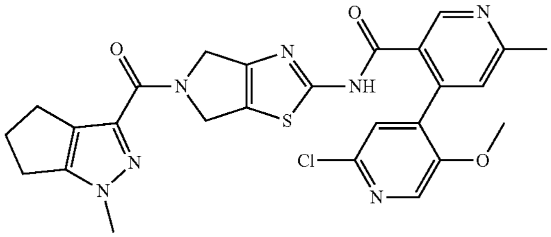 [SMILES: COc1cnc(Cl)cc1-c1cc(C)ncc1C(=O)Nc1nc2c(s1)CN(C(=O)c1nn(C)c3c1CCC3)C2] | 2'-chloro-5'-methoxy-6-methyl-N-(5-{1-methyl-1H,4H,5H,6H-cyclopenta[c]pyrazole-3-carbonyl}-4H,5H,6H-pyrrolo[3,4-d][1,3]thiazol-2-yl)-[4,4'-bipyridine]-3-carboxamide | 550 | |
| 274 | 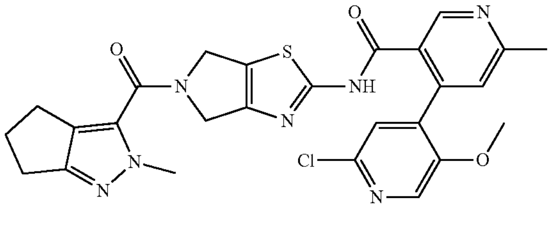 [SMILES: COc1cnc(Cl)cc1-c1cc(C)ncc1C(=O)Nc1nc2c(s1)CN(C(=O)c1c3c(nn1C)CCC3)C2] | 2'-chloro-5'-methoxy-6-methyl-N-(5-{2-methyl-2H,4H,5H,6H-cyclopenta[c]pyrazole-3-carbonyl}-4H,5H,6H-pyrrolo[3,4-d][1,3]thiazol-2-yl)-[4,4'-bipyridine]-3-carboxamide | 550 | |

TABLE S-continued

The following examples were prepared using a similar procedure to that described for Example 233

| Ex. No. | Structure | Compound Name | LCMS [M + H]+ | NMR |
|---|---|---|---|---|
| 275 | 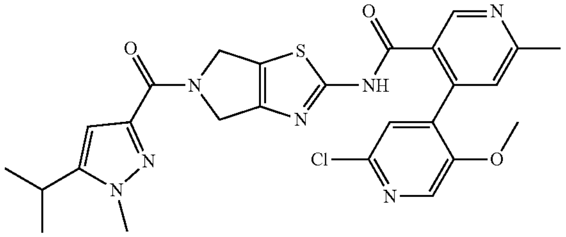 [SMILES: COc1cnc(Cl)cc1-c1cc(C)ncc1C(=O)Nc1nc2c(s1)CN(C(=O)c1cc(C(C)C)n(C)n1)C2] | 2'-chloro-5'-methoxy-6-methyl-N-{5-[1-methyl-5-(propan-2-yl)-1H-pyrazole-3-carbonyl]-4H,5H,6H-pyrrolo[3,4-d][1,3]thiazol-2-yl}-[4,4'-bipyridine]-3-carboxamide | 552 | |
| 276 | 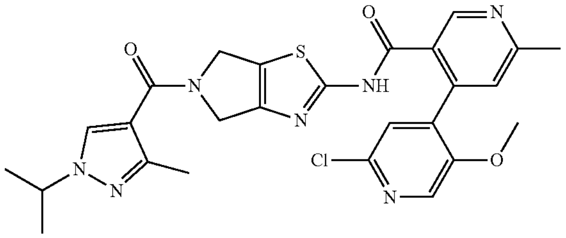 [SMILES: COc1cnc(Cl)cc1-c1cc(C)ncc1C(=O)Nc1nc2c(s1)CN(C(=O)c1cn(C(C)C)nc1C)C2] | 2'-chloro-5'-methoxy-6-methyl-N-{5-[3-methyl-1-(propan-2-yl)-1H-pyrazole-4-carbonyl]-4H,5H,6H-pyrrolo[3,4-d][1,3]thiazol-2-yl}-[4,4'-bipyridine]-3-carboxamide | 552 | |
| 277 | 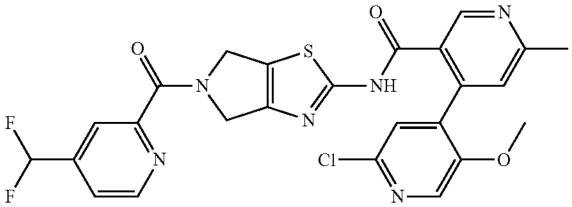 [SMILES: COc1cnc(Cl)cc1-c1cc(C)ncc1C(=O)Nc1nc2c(s1)CN(C(=O)c1cc(C(F)F)ccn1)C2] | 2'-chloro-N-{5-[4-(difluoromethyl)pyridine-2-carbonyl]-4H,5H,6H-pyrrolo[3,4-d][1,3]thiazol-2-yl}-5'-methoxy-6-methyl-[4,4'-bipyridine]-3-carboxamide | 557 | |
| 278 | 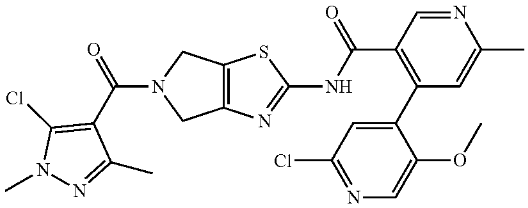 | 2'-chloro-N-[5-(5-chloro-1,3-dimethyl-1H-pyrazole-4-carbonyl)-4H,5H,6H-pyrrolo[3,4-d][1,3]thiazol-2-yl]-5'-methoxy-6-methyl-[4,4'-bipyridine]-3-carboxamide | 558 | |
| 279 | 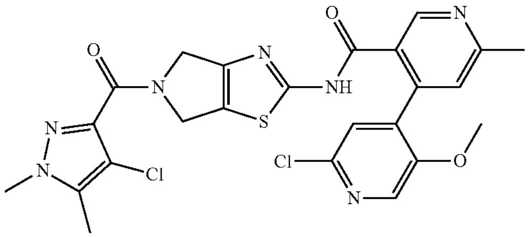 | 2'-chloro-N-[5-(4-chloro-1,5-dimethyl-1H-pyrazole-3-carbonyl)-4H,5H,6H-pyrrolo[3,4-d][1,3]thiazol-2-yl]-5'-methoxy-6-methyl-[4,4'-bipyridine]-3-carboxamide | 558 | |
| 280 | 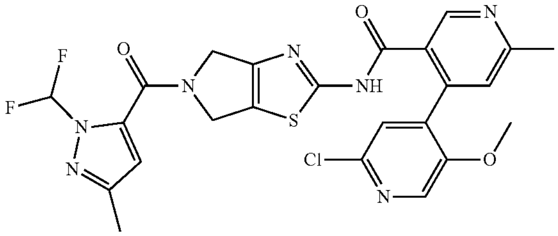 [SMILES: COc1cnc(Cl)cc1-c1cc(C)ncc1C(=O)Nc1nc2c(s1)CN(C(=O)c1cc(C)nn1C(F)F)C2] | 2'-chloro-N-{5-[1-(difluoromethyl)-3-methyl-1H-pyrazole-5-carbony1]-4H,5H,6H-pyrrolo[3,4-d][1,3]thiazol-2-yl}-5'-methoxy-6-methyl-[4,4'-bipyridine]-3-carboxamide | 560 | |

TABLE S-continued

| The following examples were prepared using a similar procedure to that described for Example 233 | | | | |
|---|---|---|---|---|
| Ex. No. | Structure | Compound Name | LCMS [M + H]+ | NMR |
| 281 | 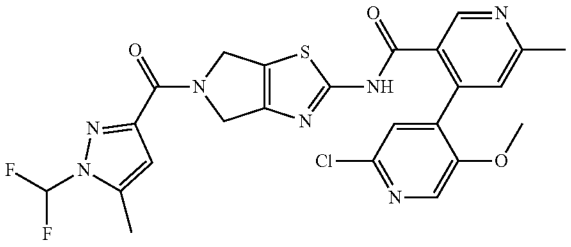 [SMILES: COc1cnc(Cl)cc1-c1cc(C)ncc1C(=O)Nc1nc2c(s1)CN(C(=O)c1cc(C)n(C(F)F)n1)C2] | 2'-chloro-N-{5-[1-(difluoromethyl)-5-methyl-1H-pyrazole-3-carbonyl]-4H,5H,6H-pyrrolo[3,4-d][1,3]thiazol-2-yl}-5'-methoxy-6-methyl-[4,4'-bipyridine]-3-carboxamide | 560 | |
| 282 | 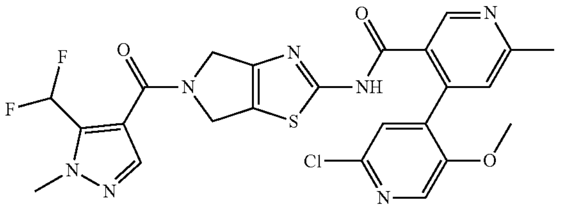 [SMILES: COc1cnc(Cl)cc1-c1cc(C)ncc1C(=O)Nc1nc2c(s1)CN(C(=O)c1cnn(C)c1C(F)F)C2] | 2'-chloro-N-{5-[5-(difluoromethyl)-1-methyl-1H-pyrazole-4-carbonyl]-4H,5H,6H-pyrrolo[3,4-d][1,3]thiazol-2-yl}-5'-methoxy-6-methyl-[4,4'-bipyridine]-3-carboxamide | 560 | |
| 283 | 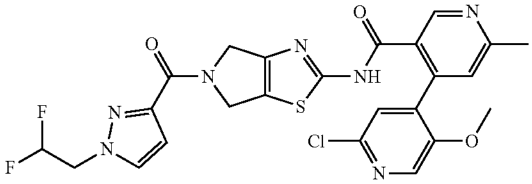 [SMILES: COc1cnc(Cl)cc1-c1cc(C)ncc1C(=O)Nc1nc2c(s1)CN(C(=O)c1ccn(CC(F)F)n1)C2] | 2'-chloro-N-{5-[1-(2,2-difluoroethyl)-1H-pyrazole-3-carbonyl]-4H,5H,6H-pyrrolo[3,4-d][1,3]thiazol-2-yl}-5'-methoxy-6-methyl-[4,4'-bipyridine]-3-carboxamide | 560 | |
| 284 | 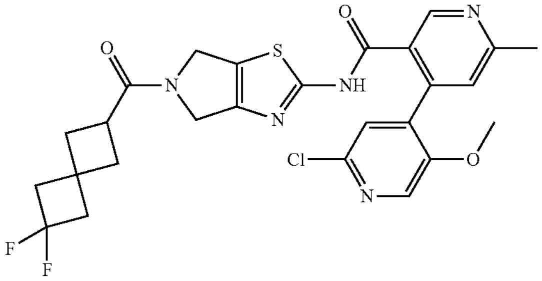 [SMILES: COc1cnc(Cl)cc1-c1cc(C)ncc1C(=O)Nc1nc2c(s1)CN(C(=O)C1CC3(C1)CC(F)(F)C3)C2] | 2'-chloro-N-(5-{6,6-difluorospiro[3.3]heptane-2-carbonyl}-4H,5H,6H-pyrrolo[3,4-d][1,3]thiazol-2-yl)-5'-methoxy-6-methyl-[4,4'-bipyridine]-3-carboxamide | 560 | |
| 285 | 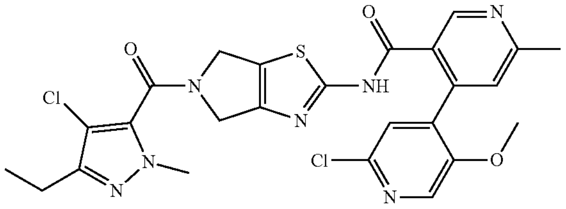 [SMILES: CCc1nn(C)c(C(=O)N2Cc3nc(NC(=O)c4cnc(C)cc4-c4cc(Cl)ncc4OC)sc3C2)c1Cl] | 2'-chloro-N-[5-(4-chloro-3-ethyl-1-methyl-1H-pyrazole-5-carbonyl)-4H,5H,6H-pyrrolo[3,4-d][1,3]thiazol-2-yl]-5'-methoxy-6-methyl-[4,4'-bipyridine]-3-carboxamide | 572 | |
| 286 | 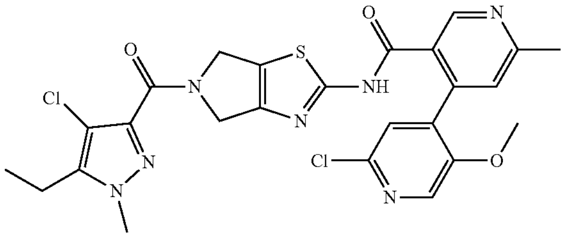 [SMILES: CCc1c(Cl)c(C(=O)N2Cc3nc(NC(=O)c4cnc(C)cc4-c4cc(Cl)ncc4OC)sc3C2)nn1C] | 2'-chloro-N-[5-(4-chloro-5-ethyl-1-methyl-1H-pyrazole-3-carbonyl)-4H,5H,6H-pyrrolo[3,4-d][1,3]thiazol-2-yl]-5'-methoxy-6-methyl-[4,4'-bipyridine]-3-carboxamide | 572 | |

TABLE S-continued

The following examples were prepared using a similar procedure to that described for Example 233

| Ex. No. | Structure | Compound Name | LCMS [M + H]+ | NMR |
|---|---|---|---|---|
| 287 | 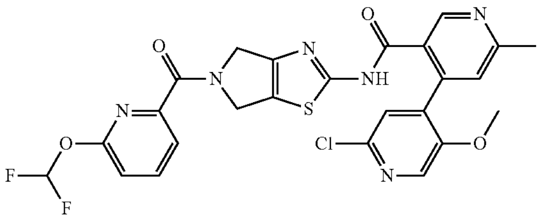 [SMILES: COc1cnc(Cl)cc1-c1cc(C)ncc1C(=O)Nc1nc2c(s1)CN(C(=O)c1cccc(OC(F)F)n1)C2] | 2'-chloro-N-{5-[6-(difluoromethoxy) pyridine-2-carbonyl]-4H,5H,6H-pyrrolo[3,4-d][1,3]thiazol-2-yl}-5'-methoxy-6-methyl-[4,4'-bipyridine]-3-carboxamide | 573 | |
| 288 | 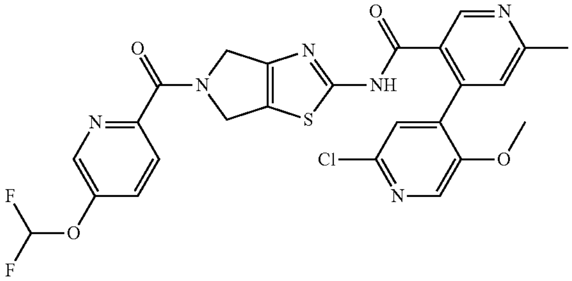 [SMILES: COc1cnc(Cl)cc1-c1cc(C)ncc1C(=O)Nc1nc2c(s1)CN(C(=O)c1ccc(OC(F)F)cn1)C2] | 2'-chloro-N-(5-(5-(difluoromethoxy) picolinoyl)-5,6-dihydro-4H-pyrrolo[3,4-d] thiazol-2-yl)-5'-methoxy-6-methyl-[4,4'-bipyridine]-3-carboxamide | 573 | |
| 289 | 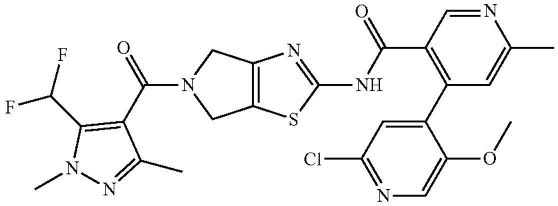 [SMILES: COc1cnc(Cl)cc1-c1cc(C)ncc1C(=O)Nc1nc2c(s1)CN(C(=O)c1c(C)nn(C)c1C(F)F)C2] | 2'-chloro-N-{5-[5-(difluoromethyl)-1,3-dimethyl-1H-pyrazole-4-carbonyl]-4H,5H,6H-pyrrolo[3,4-d][1,3]thiazol-2-yl}-5'-methoxy-6-methyl-[4,4'-bipyridine]-3-carboxamide | 574 | |
| 290 | 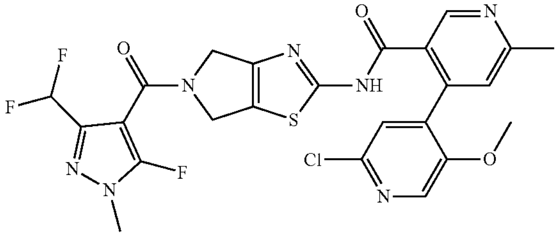 [SMILES: COc1cnc(Cl)cc1-c1cc(C)ncc1C(=O)Nc1nc2c(s1)CN(C(=O)c1c(C(F)F)nn(C)c1F)C2] | 2'-chloro-N-{5-[3-(difluoromethyl)-5-fluoro-1-methyl-1H-pyrazole-4-carbonyl]-4H,5H,6H-pyrrolo[3,4-d][1,3]thiazol-2-yl}-5'-methoxy-6-methyl-[4,4'-bipyridine]-3-carboxamide | 578 | |
| 291 | 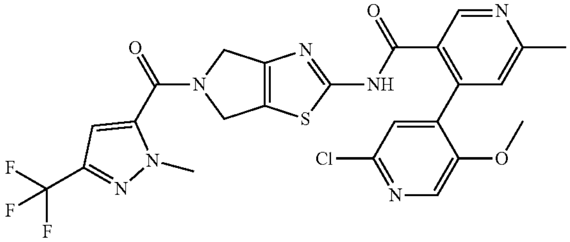 [SMILES: COc1cnc(Cl)cc1-c1cc(C)ncc1C(=O)Nc1nc2c(s1)CN(C(=O)c1cc(C(F)(F)F)nn1C)C2] | 2'-chloro-5'-methoxy-6-methyl-N-{5-[1-methyl-3-(trifluoromethyl)-1H-pyrazole-5-carbonyl]-4H,5H,6H-pyrrolo[3,4-d][1,3]thiazol-2-yl}-[4,4'-bipyridine]-3-carboxamide | 578 | |
| 292 | 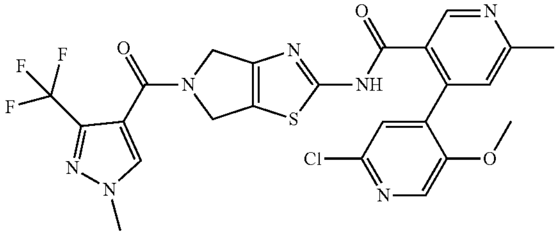 [SMILES: COc1cnc(Cl)cc1-c1cc(C)ncc1C(=O)Nc1nc2c(s1)CN(C(=O)c1cn(C)nc1C(F)(F)F)C2] | 2'-chloro-5'-methoxy-6-methyl-N-{5-[1-methyl-3-(trifluoromethyl)-1H-pyrazole-4-carbonyl]-4H,5H,6H-pyrrolo[3,4-d][1,3]thiazol-2-yl}-[4,4'-bipyridine]-3-carboxamide | 578 | |

TABLE S-continued

The following examples were prepared using a similar procedure to that described for Example 233

| Ex. No. | Structure | Compound Name | LCMS [M + H]+ | NMR |
|---|---|---|---|---|
| 293 | 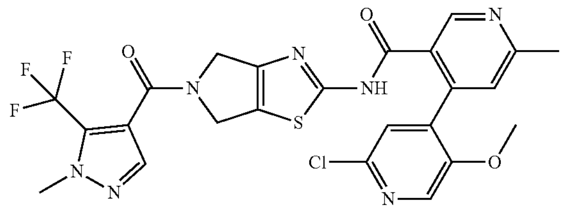 [SMILES: COc1cnc(Cl)cc1-c1cc(C)ncc1C(=O)Nc1nc2c(s1)CN(C(=O)c1cnn(C)c1C(F)(F)F)C2] | 2'-chloro-5'-methoxy-6-methyl-N-{5-[1-methyl-5-(trifluoromethyl)-1H-pyrazole-4-carbonyl]-4H,5H,6H-pyrrolo[3,4-d][1,3]thiazol-2-yl}-[4,4'-bipyridine]-3-carboxamide | 578 | |
| 294 | 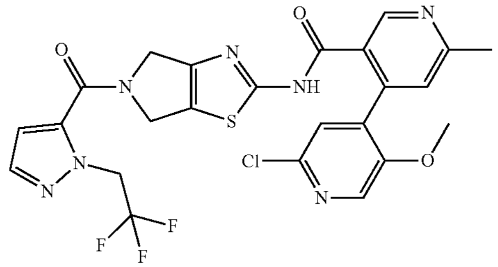 [SMILES: COc1cnc(Cl)cc1-c1cc(C)ncc1C(=O)Nc1nc2c(s1)CN(C(=O)c1ccnn1CC(F)(F)F)C2] | 2'-chloro-5'-methoxy-6-methyl-N-{5-[1-(2,2,2-trifluoroethyl)-1H-pyrazole-5-carbonyl]-4H,5H,6H-pyrrolo[3,4-d][1,3]thiazol-2-yl}-[4,4'-bipyridine]-3-carboxamide | 578 | |
| 295 | 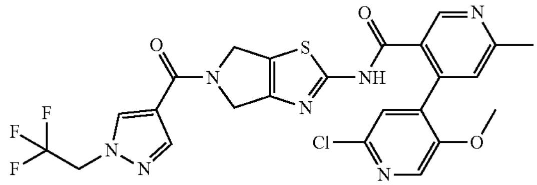 [SMILES: COc1cnc(Cl)cc1-c1cc(C)ncc1C(=O)Nc1nc2c(s1)CN(C(=O)c1cnn(CC(F)(F)F)c1)C2] | 2'-chloro-5'-methoxy-6-methyl-N-{5-[1-(2,2,2-trifluoroethyl)-1H-pyrazole-4-carbonyl]-4H,5H,6H-pyrrolo[3,4-d][1,3]thiazol-2-yl}-[4,4'-bipyridine]-3-carboxamide | 578 | |
| 296 | 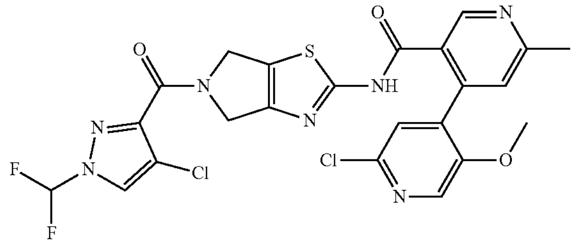 [SMILES: COc1cnc(Cl)cc1-c1cc(C)ncc1C(=O)Nc1nc2c(s1)CN(C(=O)c1nn(C(F)F)cc1Cl)C2] | 2'-chloro-N-{5-[4-chloro-1-(difluoromethyl)-1H-pyrazole-3-carbonyl]-4H,5H,6H-pyrrolo[3,4-d][1,3]thiazol-2-yl}-5'-methoxy-6-methyl-[4,4'-bipyridine]-3-carboxamide | 580 | |
| 297 | 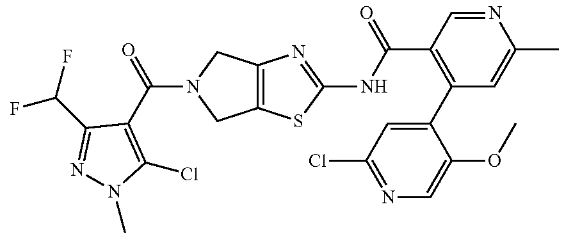 | 2'-chloro-N-{5-[5-chloro-3-(difluoromethyl)-1-methyl-1H-pyrazole-4-carbonyl]-4H,5H,6H-pyrrolo[3,4-d][1,3]thiazol-2-yl}-5'-methoxy-6-methyl-[4,4'-bipyridine]-3-carboxamide | 594 | |
| 298 | 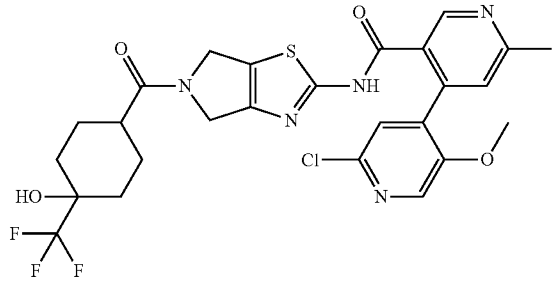 [SMILES: COc1cnc(Cl)cc1-c1cc(C)ncc1C(=O)Nc1nc2c(s1)CN(C(=O)C1CCC(O)(C(F)(F)F)CC1)C2] | 2'-chloro-N-{5-[4-hydroxy-4-(trifluoromethyl)cyclohexanecarbonyl]-4H,5H,6H-pyrrolo[3,4-d][1,3]thiazol-2-yl}-5'-methoxy-6-methyl-[4,4'-bipyridine]-3-carboxamide | 596 | |

TABLE S-continued

The following examples were prepared using a similar procedure to that described for Example 233

| Ex. No. | Structure | Compound Name | LCMS [M + H]+ | NMR |
|---|---|---|---|---|
| 723 | 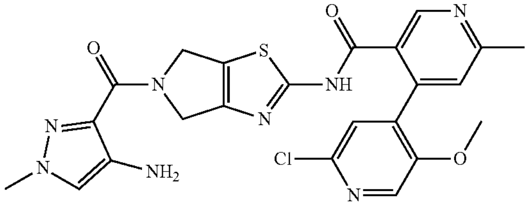 | N-(5-(4-amino-1-methyl-1H-pyrazole-3-carbonyl)-5,6-dihydro-4H-pyrrolo[3,4-d] thiazol-2-yl)2'-chloro-5'-methoxy-6-methyl-[4,4'-bipyridine]-3-carboxamide | 525 | |
| 724 | 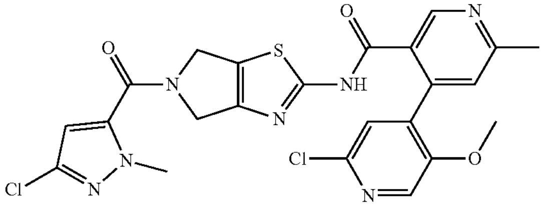 [SMILES: COc1cnc(Cl)cc1-c1cc(C)ncc1C(=O)Nc1nc2c(s1)CN(C(=O)c1cc(Cl)nn1C)C2] | 2'-chloro-N-(5-(3-chloro-1-methyl-1H-pyrazole-5-carbonyl)-5,6-dihydro-4H-pyrrolo[3,4-d]thiazol-2-yl)-5'-methoxy-6-methyl-[4,4'-bipyridine]-3-carboxamide | 544 | |
| 725 | 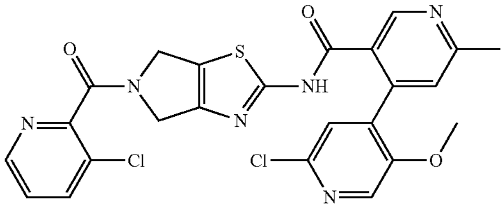 [SMILES: COc1cnc(Cl)cc1-c1cc(C)ncc1C(=O)Nc1nc2c(s1)CN(C(=O)c1ncccc1Cl)C2] | 2'-chloro-N-(5-(3-chloropicolinoyl)-5,6-dihydro-4H-pyrrolo[3,4-d]thiazol-2-yl)-5'-methoxy-6-methyl-[4,4'-bipyridine]-3-carboxamide | 541 | |
| 726 | 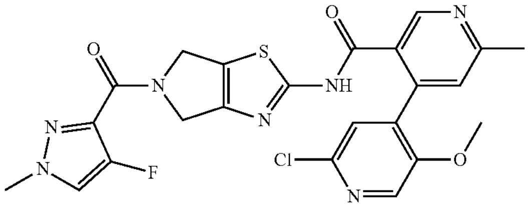 | 2'-chloro-N-(5-(4-fluoro-1-methyl-1H-pyrazole-3-carbonyl)-5,6-dihydro-4H-pyrrolo[3,4-d]thiazol-2-yl)-5'-methoxy-6-methyl-[4,4'-bipyridine]-3-carboxamide | 528 | |
| 727 | 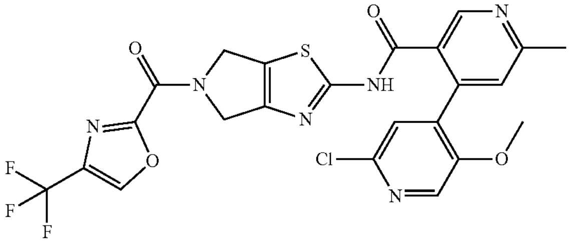 [SMILES: COc1cnc(Cl)cc1-c1cc(C)ncc1C(=O)Nc1nc2c(s1)CN(C(=O)c1nc(C(F)(F)F)co1)C2] | 2'-chloro-5'-methoxy-6-methyl-N-(5-(4-(trifluoromethyl) oxazole-2-carbonyl)-5,6-dihydro-4H-pyrrolo[3,4-d]thiazol-2-yl)-[4,4'-bipyridine]-3-carboxamide | 565 | |
| 728 | 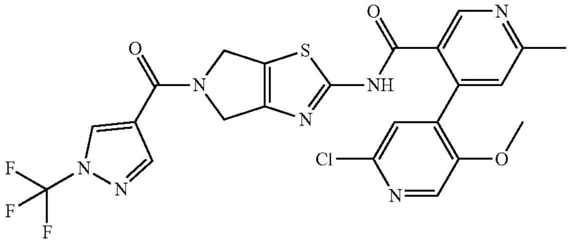 [SMILES: COc1cnc(Cl)cc1-c1cc(C)ncc1C(=O)Nc1nc2c(s1)CN(C(=O)c1cnn(C(F)(F)F)c1)C2] | 2'-chloro-5'-methoxy-6-methyl-N-(5-(1-(trifluoromethyl)-1H-pyrazole-4-carbonyl)-5,6-dihydro-4H-pyrrolo[3,4-d]thiazol-2-yl)-[4,4'-bipyridine]-3-carboxamide | 564 | |

TABLE S-continued

The following examples were prepared using a similar procedure to that described for Example 233

| Ex. No. | Structure | Compound Name | LCMS $[M + H]^+$ | NMR |
|---|---|---|---|---|
| 729 | 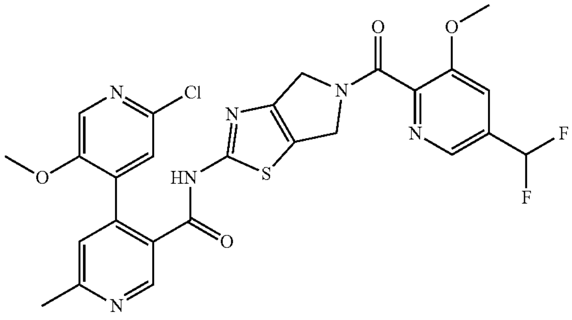 [SMILES: COc1cnc(Cl)cc1-c1cc(C)ncc1C(=O)Nc1nc2c(s1)CN(C(=O)c1ncc(C(F)F)cc1OC)C2] | 2'-chloro-N-(5-(5-(difluoromethyl)-3-methoxypicolinoyl)-5,6-dihydro-4H-pyrrolo[3,4-d]thiazol-2-yl)-5'-methoxy-6-methyl-[4,4'-bipyridine]-3-carboxamide | 587 | $^1$H NMR (300 MHZ, DMSO-$d_6$) δ 12.81 (s, 1H), 8.80 (d, J = 4.0 Hz, 1H), 8.42 (s, 1H), 8.16 (d, J = 2.8 Hz, 1H), 7.82 (s, 1H), 7.52 (s, 1H), 7.45-6.97 (m, 2H), 4.80 (s, 1H), 4.66 (s, 1H), 4.45 (s, 1H), 4.34 (s, 1H), 3.92 (s, 3H), 3.60 (s, 3H), 2.58 (d, J = 2.2 Hz, 3H) |
| 730[#,c] | 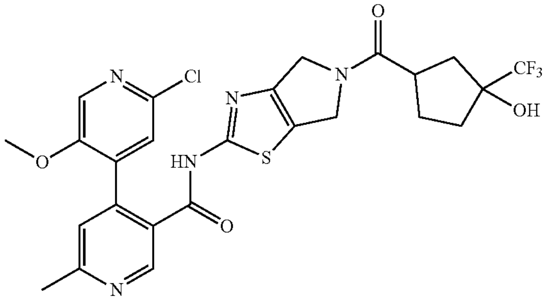 [SMILES: COc1cnc(Cl)cc1-c1cc(C)ncc1C(=O)Nc1nc2c(s1)CN(C(=O)C1CCC(O)(C(F)(F)F)C1)C2] | 2'-chloro-N-(5-((1S or R,3R and S OR 1S and R,3R or S)-3-hydroxy-3-(trifluoromethyl) cyclopentane-1-carbonyl)-5,6-dihydro-4H-pyrrolo[3,4-d]thiazol-2-yl)-5'-methoxy-6-methyl-[4,4'-bipyridine]-3-carboxamide | 582 | $^1$H NMR (300 MHZ, DMSO-$d_6$) δ13.03 (s, 1H), 8.79 (s, 1H), 8.17 (d, J = 1.6 Hz, 1H), 7.55 (s, 1H), 7.44 (s, 1H), 5.96 (d, J = 2.9 Hz, 1H), 4.87 (s, 1H), 4.75 (s, 1H), 4.59 (s, 1H), 4.46 (s, 1H), 3.60 (s, 3H), 3.09-3.01 (m, 1H), 2.59 (s, 3H), 1.98 (d, J = 9.0 Hz, 2H), 1.81 (d, J = 5.3 Hz, 2H), 1.78 (s, 2H) |
| 731[#,c] | 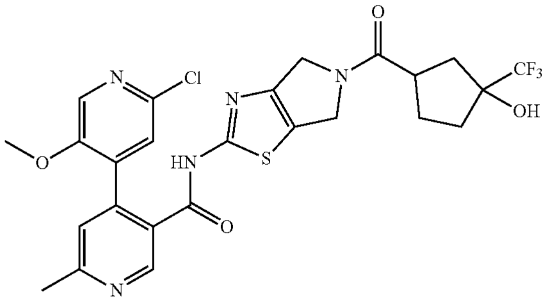 [SMILES: COc1cnc(Cl)cc1-c1cc(C)ncc1C(=O)Nc1nc2c(s1)CN(C(=O)C1CCC(O)(C(F)(F)F)C1)C2] | 2'-chloro-N-(5-((1R or S,3R and S OR 1R and S,3R or S)-3-hydroxy-3-(trifluoromethyl) cyclopentane-1-carbonyl)-5,6-dihydro-4H-pyrrolo[3,4-d]thiazol-2-yl)-5'-methoxy-6-methyl-[4,4'-bipyridine]-3-carboxamide | 582 | $^1$H NMR (300 MHZ, DMSO-$d_6$) δ12.88 (s, 1H), 8.79 (s, 1H), 8.17 (d, J = 2.1 Hz, 1H), 7.54 (s, 1H), 7.43 (s, 1H), 6.05 (d, J = 5.0 Hz, 1H), 4.86 (s, 1H), 4.74 (s, 1H), 4.60 (s. 1H), 4.47 (s, 1H), 3.60 (s, 3H), 3.09 (d. J = 8.4 Hz, 1H), 2.59 (s, 3H), 2.28 (dd, J = 14.2, 9.5 Hz, 1H), 2.02 (t, J = 9.4 Hz, 3H), 1.87 (d. J = 5.2 Hz, 2H) |
| 754 | 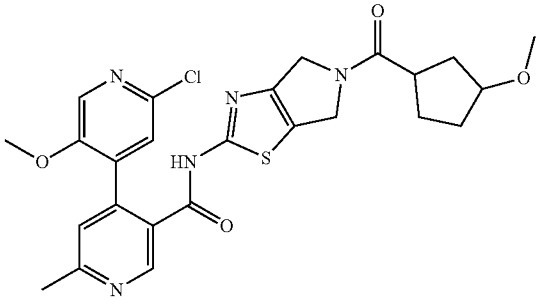 | (Racemic)-2'-chloro-5'-methoxy-N-(5-(3-methoxycyclopentane-1-carbonyl)-5,6-dihydro-4H-pyrrolo[3,4-d]thiazol-2-yl)-6-methyl-[4,4'-bipyridine]-3-carboxamide | 528 | $^1$H NMR (400 MHZ, DMSO-$d_6$) δ 12.78 (s, 1H), 8.79 (s, 1H), 8.16 (s, 1H), 7.53 (s, 1H), 7.42 (s, 1H), 4.91-4.79 (m. 1H), 4.71 (m, 1H), 4.57 (t, J = 2.8 Hz, 1H), 4.62-4.44 (m, 1H), 3.90-3.74 (m, 1H), 3.57-3.63 (m, 3H), 3.22-3.13 (m, 3H), 3.10-2.82 (m, 1H), 2.58 (s, 3H), 2.26-2.14 (m, 1H), 2.00-1.88 (m, 1H), 1.90-1,72 (m, 2H), 1.76-1.61 (m, 2H) |

TABLE S-continued

The following examples were prepared using a similar procedure to that described for Example 233

| Ex. No. | Structure | Compound Name | LCMS $[M + H]^+$ | NMR |
|---|---|---|---|---|
| 755 | 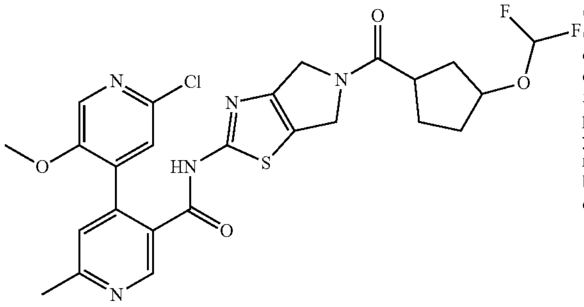 [SMILES: COc1cnc(Cl)cc1-c1cc(C)ncc1C(=O)Nc1nc2c(s1)CN(C(=O)C1CCC(OC(F)F)C1)C2] | (Racemic)-2'-chloro-N-(5-(3-(difluoromethoxy) cyclopentane-1-carbonyl)-5,6-dihydro-4H-pyrrolo[3,4-d]thiazol-2-yl)-5'-methoxy-6-methyl-[4,4'-bipyridine]-3-carboxamide | 564 | $^1H$ NMR (400 MHZ, DMSO-$d_6$) δ 12.97-12.64 (m, 1H), 8.79 (s, 1H), 8.17 (d, J = 2.0 Hz, 1H), 7.56 (s, 1H), 7.45 (s, 1H), 6,95-6.14 (m, 1H), 5.01-4.33 (m, 5H), 3.60 (d, J = 1.2 Hz, 3H), 2.99-2.96 (m, 1H), 2.59 (s, 3H), 2.32-2.29 (m, 1H), 2.09-1.51 (m, 5H) |
| 756 | 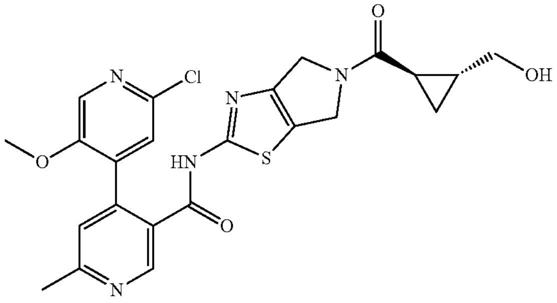 [SMILES: COc1cnc(Cl)cc1-c1cc(C)ncc1C(=O)Nc1nc2c(s1)CN(C(=O)[C@@H]1C[C@H]1CO)C2] | 2'-chloro-N-(5-((1R,2R)-2-(hydroxymethyl) cyclopropane-1-carbonyl)-5,6-dihydro-4H-pyrrolo[3,4-d]thiazol-2-yl)-5'-methoxy-6-methyl-[4,4'-bipyridine]-3-carboxamide | 500 | $^1H$ NMR (300 MHZ, DMSO-$d_6$) δ 12.80 (s, 1H). 8.82 (s, 1H), 8.16 (s, 1H), 7.52 (s, 1H), 7.40 (s, 1H), 4.96 (s, 1H), 4.84 (s, 1H), 4.64 (t, J = 5.8 Hz, 1H), 4.57 (s, 1H), 4,43 (s, 1H), 3.60 (s, 3H), 3.56-3.50 (m, 1H), 3.28-3.20 (m, 1H), 2.58 (s, 3H), 1.80-1.64 (m, 1H), 1,40 (s, 1H), 1.01-0.97 (m, 1H), 0.76 (s, 1H) |
| 757 | 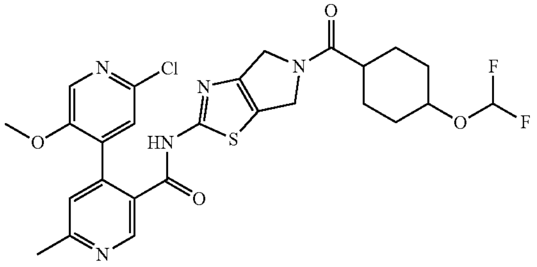 [SMILES: COc1cnc(Cl)cc1-c1cc(C)ncc1C(=O)Nc1nc2c(s1)CN(C(=O)C1CCC(OC(F)F)CC1)C2] | (Cis and Trans)-2'-chloro-N-(5-(4-(difluoromethoxy) cyclohexane-1-carbonyl)-5,6-dihydro-4H-pyrrolo[3,4-d]thiazol-2-yl)-5'-methoxy-6-methyl-[4,4'-bipyridine]-3-carboxamide | 576 $(M - H)^-$ | $^1H$ NMR (400 MHZ, DMSO-$d_6$) δ 12.81 (s, 1H), 8.79 (s. 1H), 8.17 (d, J = 4.1 Hz, 1H), 7.54 (s, 1H), 7.43 (s, 1H), 6.79-6.67 (m, 1H), 4.87-4.40 (m, 4H), 4.04 (s, 1H), 3.60 (d, J = 1.8 Hz, 3H), 2.59 (s, 3H), 2.02 (s, 2H), 1.84 (s, 2H), 1.76-1.12 (m, 5H |
| 758 | 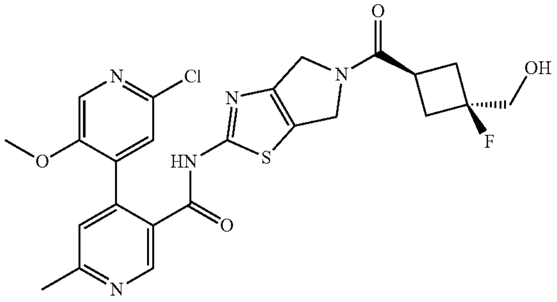 [SMILES: COc1cnc(Cl)cc1-c1cc(C)ncc1C(=O)Nc1nc2c(s1)CN(C(=O)[C@H]1C[C@](F)(CO)C1)C2] | 2'-chloro-N-(5-((1s,3s)-3-fluoro-3-(hydroxymethyl) cyclobutane-1-carbonyl)-5,6-dihydro-4H-pyrrolo[3,4-d]thiazol-2-yl)-5'-methoxy-6-methyl-[4,4'-bipyridine]-3-carboxamide | 532 | $^1H$ NMR (300 MHZ, DMSO-$d_6$) δ 8.80 (s, 1H), 8.16 (s, 1H), 7.52 (s, 1H), 7.41 (s, 1H), 4.97 (s, 1H), 4.70 (t, J = 2.9 Hz, 1H), 4.57 (s, 2H), 4.44 (t, J = 2.9 Hz, 1H), 3.60 (s, 3H), 3.54 (s, 1H), 3.45 (s, 1H), 2.58 (s, 3H), 2.48-2.25 (m, 5H) |
| 759 | 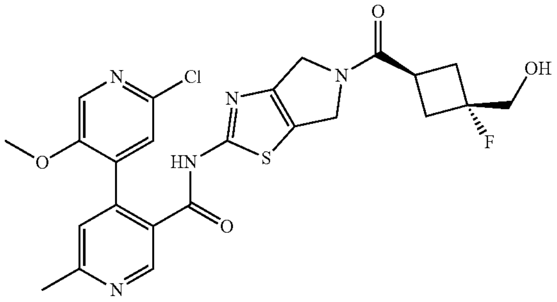 [SMILES: COc1cnc(Cl)cc1-c1cc(C)ncc1C(=O)Nc1nc2c(s1)CN(C(=O)[C@H]1C[C@@](F)(CO)C1)C2] | 2'-chloro-N-(5-((1r,3r)-3-fluoro-3-(hydroxymethyl) cyclobutane-1-carbonyl)-5,6-dihydro-4H-pyrrolo[3,4-d]thiazol-2-yl)-5'-methoxy-6-methyl-[4,4'-bipyridine]-3-carboxamide | 532 | $^1H$ NMR (300 MHZ, DMSO-$d_6$) δ 12.81 (s, 1H), 8.79 (s, 1H), 8.17 (d, J = 1.5 Hz, 1H), 7.56 (s, 1H), 7.45 (s, 1H), 5.13 (s, 1H), 4.74 (s, 1H), 4.61 (s, 2H), 4.47 (s, 1H), 3.60 (s, 3H), 3.57-3.51 (m, 2H), 2.87-2.84 (m, 1H), 2.60 (s, 3H), 2.46-2.25 (m, 4H) |

TABLE S-continued

The following examples were prepared using a similar procedure to that described for Example 233

| Ex. No. | Structure | Compound Name | LCMS [M + H]+ | NMR |
|---|---|---|---|---|
| 760 | 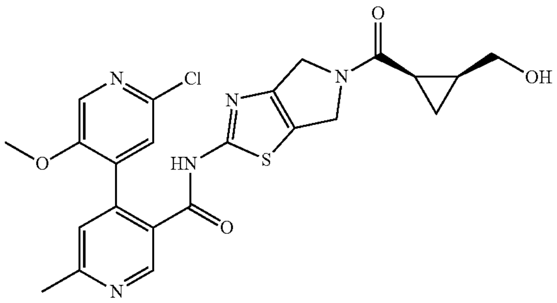 [SMILES: COc1cnc(Cl)cc1-c1cc(C)ncc1C(=O)Nc1nc2c(s1)CN(C(=O)[C@@H]1C[C@@H]1CO)C2] | 2'-chloro-N-(5-((1R,2S)-2-(hydroxymethyl)cyclopropane-1-carbonyl)-5,6-dihydro-4H-pyrrolo[3,4-d]thiazol-2-yl)-5'-methoxy-6-methyl-[4,4'-bipyridine]-3-carboxamide | 500 | $^1$H NMR (300 MHZ, DMSO-d$_6$) δ 12.77 (s, 1H), 8.82 (s, 1H), 8.15 (s, 1H), 7.50 (s, 1H), 7.38 (s, 1H), 4.89-3.83 (m, 2H), 4.62-4.29 (m. 3H), 3.61-3.54 (m, 4H), 3.23-3.17 (m, 1H), 2.58 (s, 3H), 2.03-1.85 (m, 1H), 1.49 (s, 1H), 0.98-0.78 (m, 2H) |
| 761‡ | 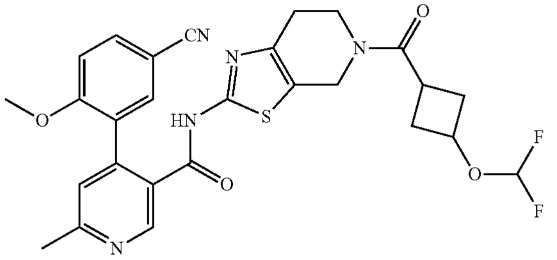 [SMILES: COc1ccc(C#N)cc1-c1cc(C)ncc1C(=O)Nc1nc2c(s1)CN(C(=O)C1CC(OC(F)F)C1)CC2] | (Cis and Trans) 4-(5-cyano-2-methoxyphenyl)-N-(5-(3-(difluoromethoxy)cyclobutane-1-carbonyl)-4,5,6,7-tetrahydrothiazolo[5,4-c]pyridin-2-yl)-6-methylnicotinamide | 554 | $^1$H NMR (300 MHZ, DMSO-d$_6$) δ 12.43 (s, 1H), 8.70 (s, 1H), 7.91-7.83 (m, 2H), 7.38 (s, 1H), 7.17 (d, J = 8,7 Hz, 1H), 6.88-6.38 (m, 1H), 4.50 (d, J = 7.1 Hz, 3H), 3.79 (s, 1H), 3.68 (s, 1H), 3.59-3.53 (m, 3H), 3.11-3.06 (m, 2H), 2.76-2.69 (m,3H), 2.74-2.68 (m, 3H), 2.21 (s, 2H) |
| 762‡ ,#,d | 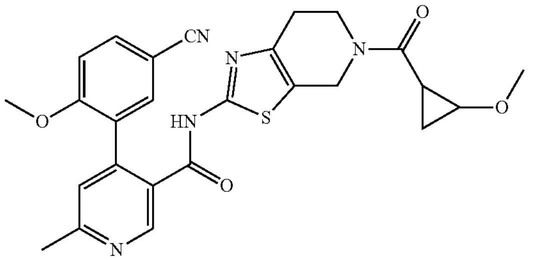 | 4-(5-cyano-2-methoxyphenyl)-N-(5-(2-methoxycyclopropane-1-carbonyl)-4,5,6,7-tetrahydrothiazolo[5,4-c]pyridin-2-yl)-6-methylnicotinamide Mixture of isomers | 504 | $^1$H NMR (400 MHZ, DMSO-d$_6$) δ 12.49 (s, 1H), 8.70 (s, 1H), 7.90-7.87 (m, 1H), 7.83 (s, 1H), 7.38 (s, 1H), 7.17-7.15 (m, 1H), 4,95-4.88 (m, 1H), 4.65-4.53 (m, 1H), 4.04-3.98 (m, 1H), 3.83-3.73 (m, 1H), 3.57 (s, 3H), 3.40 (d, J = 6.4 Hz, (H), 3.30 (s, 3H), 2.77 (s, 1H), 2.62 (s, 1H), 2.57 (s, 3H), 2.30-2.20 (m, 7.6 Hz, 1H), 1.10 (t, J = 6.0 Hz, 2H) |
| 763‡ ,#,e | 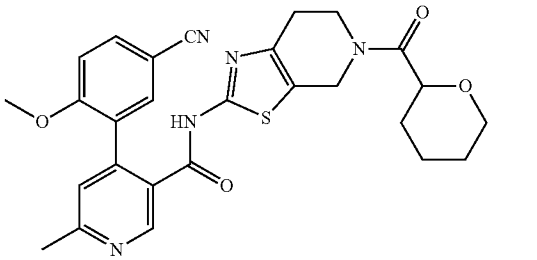 [SMILES: COc1ccc(C#N)cc1-c1cc(C)ncc1C(=O)Nc1nc2c(s1)CN(C(=O)C1CCCCO1)CC2] | (R or S)-4-(5-cyano-2-methoxyphenyl)-6-methyl-N-(5-(tetrahydro-2H-pyran-2-carbonyl)-4,5,6,7-tetrahydrothiazolo[5,4-c]pyridin-2-yl)nicotinamide | 518 | $^1$H NMR (400 MHZ, DMSO-d$_6$) δ 12.48 (s, 1H), 8.70 (s, 1H), 7.92 7.81 (m, 2H), 7.38 (s, 1H), 7.207.12 (m, J = 8.8, 4.5 Hz, 1H), 4.73-4.47 (m, 2H), 4.26-4.16 (m, 1H), 3.93-3.72 (m, 3H), 3.60-3.48 (m, 4H), 2.74 (s,1H), 2.63 (s, 1H), 2.57-2.50 (m, 4H), 1,81 (s, 1H), 1.65-1.47 (m, 5H) |
| 764‡ ,#,f | 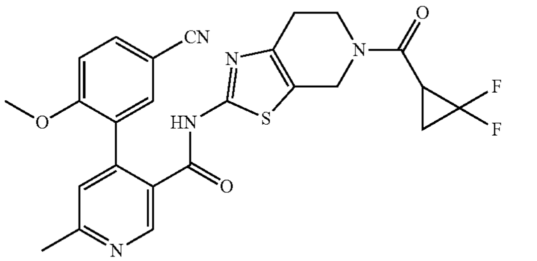 [SMILES: COc1ccc(C#N)cc1-c1cc(C)ncc1C(=O)Nc1nc2c(s1)CN(C(=O)C1CC1(F)F)CC2] | (R or S)-4-(5-cyano-2-methoxyphenyl)-N-(5-(2,2-difluorocyclopropane-1-carbonyl)-4,5,6,7-tetrahydrothiazolo[5,4-c]pyridin-2-yl)-6-methylnicotinamide | 510 | $^1$H NMR (400 MHZ, DMSO-d$_6$) δ 12.51 (s, 1H), 8.70 (s, 1H), 7.92-7.87 (m, 1H), 7.84 (s, 1H), 7.38 (s, 1H), 7.21-7.15 (m, 1H), 4.97-4.48 (m, 2H), 4.17-3.72 (m, 2H), 3.57 (d, J = 4.4 Hz, 3H), 2.90-2.83 (m, 1H), 2.74-2.69 (m, 2H), 2.57 (s, 3H), 2.02-1.79 (m, 2H) |

TABLE S-continued

The following examples were prepared using a similar procedure to that described for Example 233

| Ex. No. | Structure | Compound Name | LCMS $[M + H]^+$ | NMR |
|---|---|---|---|---|
| 765[‡,#,f] | 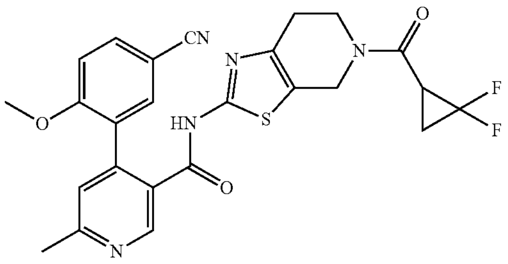 [SMILES: COc1ccc(C#N)cc1-c1cc(C)ncc1C(=O)Nc1nc2c(s1)CN(C(=O)C1CC1(F)F)CC2] | (S or R)-4-(5-cyano-2-methoxyphenyl)-N-(5-(2,2-difluorocyclopropane-1-carbonyl)-4,5,6,7-tetrahydrothiazolo[5,4-c]pyridin-2-yl)-6-methylnicotinamide | 510 | $^1$H NMR (400 MHZ, DMSO-$d_6$) δ 12.50 (s, 1H), 8.70 (s, 1H), 7.92-7.87 (m, 1H), 7.84 (s, 1H), 7.38 (s, 1H), 7.21-7.15 (m, 1H), 4.97-4.48 (m, 2H), 4.17-3.72 (m, 2H), 3.57 (d, J = 4.3 Hz, 3H), 2.90-2.83 (m, 1H), 2.74-2.69 (m, 2H), 2.57 (s, 3H), 2.05-1.78 (m, 2H) |
| 766[‡,g] | 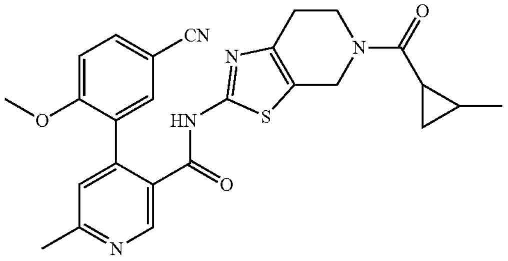 | 4-(5-cyano-2-methoxyphenyl)-6-methyl-N-(5-(2-methylcyclopropane-1-carbonyl)-4,5,6,7-tetrahydrothiazolo[5,4-c]pyridin-2-yl)nicotinamide Mixture of isomers | 488 | $^1$H NMR (400 MHZ, DMSO-$d_6$) δ 12.49 (s, 1H), 8.70 (s, 1H), 7.89-7.83 (m, 2H), 7.36 (s, 1H), 7.17 (s, 2H), 4.94-4.46 (m, 2H), 4.11-4.03 (m, 1H), 3.86-3.78 (m, 1H), 3.57 (s, 3H), 2.68 (m, 1H), 2.57 (s, 4H), 2.04-1.91 (m, 1H), 1.31-1.21 (m, 2H), 0.93 (d, J = 6.1 Hz, 1H), 0.86-0.71 (m, 3H) |
| 767[‡,g] | 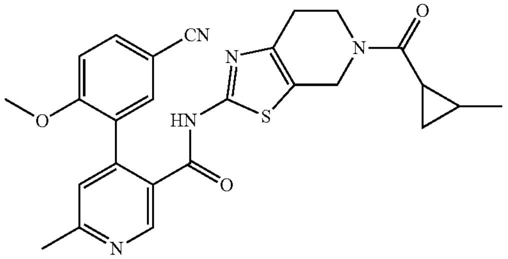 | 4-(5-cyano-2-methoxyphenyl)-6-methyl-N-(5-(2-methylcyclopropane-1-carbonyl)-4,5,6,7-tetrahydrothiazolo[5,4-c]pyridin-2-yl)nicotinamide Mixture of isomers | 488 | $^1$H NMR (400 MHZ, DMSO-$d_6$) δ 12.49 (s, 1H), 8.70 (s, 1H), 7.89-7.83 (m, 2H), 7.38 (s, 1H), 7.17 (d, J = 8.7 Hz, 1H), 4.85 (s, 1H), 4.58 (s, 1H), 3.96 (s, 1H), 3.78 (s, 1H), 3.57 (s, 3H), 2.76 (s, 1H), 2.57 (s, 4H), 1.81 (m, 1H), 1.17-1.06 (m, 5H), 0.96 (s, 1H) |
| 768[‡,d] | 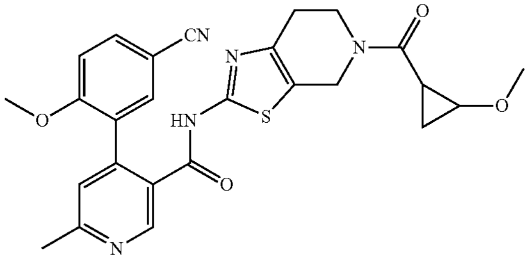 | 4-(5-cyano-2-methoxyphenyl)-N-(5-(2-methoxycyclopropane-1-carbonyl)-4,5,6,7-tetrahydrothiazolo[5,4-c]pyridin-2-yl)-6-methylnicotinamide Mixture of isomers | 504 | $^1$H NMR (400 MHZ, DMSO-$d_6$) δ 12.49 (s, 1H), 8.70 (s, 1H), 7.90-7.83 (m, 1H), 7.83 (s, 1H), 7.38 (s, 1H), 7.17-7.15 (m, 1H), 4.97-4.83 (m, 1H), 4.58-4.53 (m, 1H), 4.06-4.01 (m, 1H), 3.89-3.67 (m, 1H), 3.57 (s, 3H), 3.40 (d, J = 6.4 Hz, 1H), 3.30 (s, 3H), 2.77 (s, 1H), 2.62 (s, 1H), 2.57 (s, 3H), 2.30-2.20(m, 7.6 Hz, 1H), 1.10 (t, J = 6.0 Hz, 2H) |
| 769[‡,#,e] | 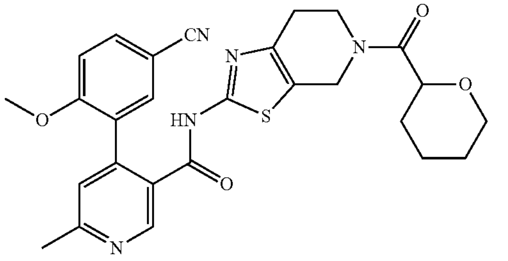 [SMILES: COc1ccc(C#N)cc1-c1cc(C)ncc1C(=O)Nc1nc2c(s1)CN(C(=O)C1CCCCO1)CC2] | (S or R)-4-(5-cyano-2-methoxyphenyl)-6-methyl-N-(5-(tetrahydro-2H-pyran-2-carbonyl)-4,5,6,7-tetrahydrothiazolo[5,4-c]pyridin-2-yl)nicotinamide | 518 | $^1$H NMR (400 MHZ, DMSO-$d_6$) δ 12.47 (s, 1H), 8.69 (s, 1H), 7.92 7.81 (m, 2H), 7.38 (s, 1H), 7.17 (m, 1H), 4.69-4.58 (m, 2H), 4.27-4.16 (m, 1H), 3.89-3.73 (m, 3H), 3.57 (d, J = 6.7 Hz, 4H), 2.74 (s, 1H), 2.57-2.50 (m, 4H), 1.81 (s, 1H), 1.66-1.41 (m, 5H) |

TABLE S-continued

The following examples were prepared using a similar procedure to that described for Example 233

| Ex. No. | Structure | Compound Name | LCMS [M + H]+ | NMR |
|---|---|---|---|---|
| 770#,h | 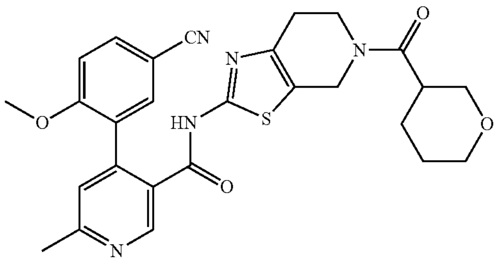 [SMILES: COc1ccc(C#N)cc1-c1cc(C)ncc1C(=O)Nc1nc2c(s1)CN(C(=O)C1CCCOC1)CC2] | (R or S)-4-(5-cyano-2-methoxyphenyl)-6-methyl-N-(S-(tetrahydro-2H-pyran-3-carbonyl)-4,5,6,7-tetrahydrothiazolo[5,4-c]pyridin-2-yl)nicotinamide | 518 | $^1$H NMR (400 MHZ, DMSO-$d_6$) δ 12.48 (s, 1H), 8.69 (s, 1H), 7.95-7.89 (m, 1H), 7.83 (d, J = 2.1 Hz, 1H), 7.38 (s, 1H), 7.23-7.07 (m, 1H), 4.64 (m, 2H), 3.81 (s, 4H), 3.57 (d, J = 2.9 Hz, 3H), 3.38 (m, 1H), 3.28 (d, J = 7.7 Hz, 1H), 3.01-2.84 (m, 1H), 2.75 (s, 1H), 2.57 (s, 4H), 1.98-1.61 (m, 1H), 1.58 (m, 3H) |
| 771#,h | 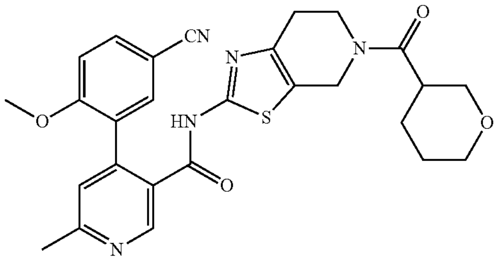 [SMILES: COc1ccc(C#N)cc1-c1cc(C)ncc1C(=O)Nc1nc2c(s1)CN(C(=O)C1CCCOC1)CC2] | (S or R)-4-(5-cyano-2-methoxyphenyl)-6-methyl-N-(5-(tetrahydro-2H-pyran-3-carbonyl)-4,5,6,7-tetrahydrothiazolo[5,4-c]pyridin-2-yl)nicotinamide | 518 | $^1$H NMR (400 MHZ, DMSO-$d_6$) δ 12.48 (s, 1H), 8.69 (s, 1H), 7.95-7.89 (m, 1H), 7.83 (d, J = 2.2 Hz, 1H), 7.38 (s, 1H), 7.16 (d, J = 8.7 Hz, 1H), 4.64 (m, 2H), 3.81 (s, 4H), 3.57 (d, J = 2.8 Hz, 3H), 3.38 (m, 1H), 3.28 (m, 1H), 2.75 (s, 1H), 2.64 (m, 1H), 2.57 (s, 4H), 1.83 (m, 1H), 1.60 (s, 3H). |
| 772‡ | 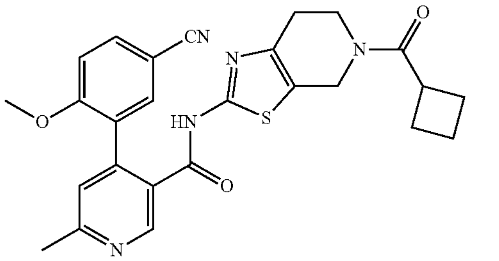 [SMILES: COc1ccc(C#N)cc1-c1cc(C)ncc1C(=O)Nc1nc2c(s1)CN(C(=O)C1CCC1)CC2] | 4-(5-cyano-2-methoxyphenyl)-N-(5-(cyclobutanecarbonyl)-4,5,6,7-tetrahydrothiazolo[5,4-c]pyridin-2-yl)-6-methylnicotinamide | 488 | $^1$H NMR (400 MHZ, DMSO-$d_6$) δ 8.68 (s, 1H), 8.04-7.60 (m, 2H), 7.38 (s, 1H), 7.17 (d, J = 8.8 Hz, 1H), 4.57-4.48 (m, 2H), 3.77 (t, J = 5.8 Hz, 1H), 3.69 (s, 1H), 3.57 (d, J = 1.5 Hz, 3H), 3.44 (t. J = 8.6 Hz, 1H), 2.80-2.65 (m, 2H), 2.58 (s, 3H), 2.20-2.12 (m, 4H), 2.01-1.84 (m, 1H), 1.78-1.7 (m, 1H) |
| 773‡ | 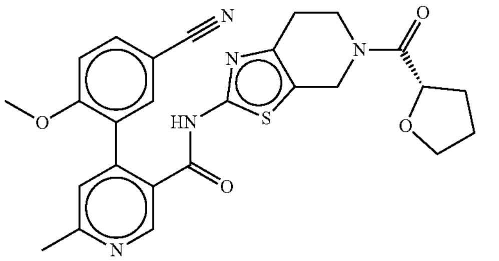 | (S)-4-(5-cyano-2-methoxyphenyl)-6-methyl-N-(5-(tetrahydrofuran-2-carbonyl)-4,5,6,7-tetrahydrothiazolo[5,4-c]pyridin-2-yl)nicotinamide | 504 | $^1$H NMR (400 MHZ, DMSO-$d_6$) δ 12.48 (s, 1H), 8.69 (s, 1H), 7.95-7.80 (m, 2H), 7.38 (s, 1H), 7.18-7.15 (m, 1H), 4.84-4.68 (m, 2H), 4.65-4.53 (m, 1H), 3.91-3.69 (m, 4H), 3.57 (d, J = 3.9 Hz, 3H), 2.74 (s. 1H), 2.68-2.66 (m, 1H), 2.57 (s, 3H), 2.11-1.99 (m, 2H), 1.87-1.81 (m, 2H) |
| 774‡ | 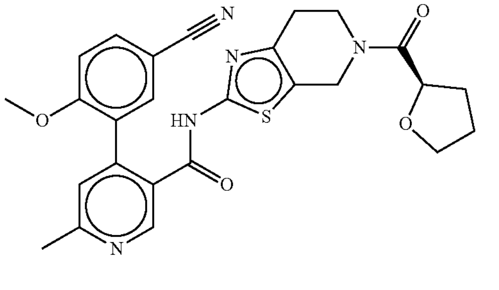 | (R)-4-(5-cyano-2-methoxyphenyl)-6-methyl-N-(5-(tetrahydrofuran-2-carbonyl)-4,5,6,7-tetrahydrothiazolo[5,4-c]pyridin-2-yl)nicotinamide | 504 | $^1$H NMR (300 MHZ, DMSO-$d_6$) δ 12.5 (s, 1H), 8.72 (s, 1H), 7.92-7.85 (m, 2H), 7.42 (s, 1H), 7.19-7.16 (m, 1H), 4.80-4.52 (m, 3H), 3.93-3.70 (m, 4H), 3.57 (s, 3H), 2.75-2.64 (m, 1H), 2.59-2.56 (m, 1H), 2.52-2.50 (m, 3H), 2.14-1.83 (m, 4H) |

TABLE S-continued

| The following examples were prepared using a similar procedure to that described for Example 233 | | | | |
|---|---|---|---|---|
| Ex. No. | Structure | Compound Name | LCMS $[M + H]^+$ | NMR |
| 775‡ | 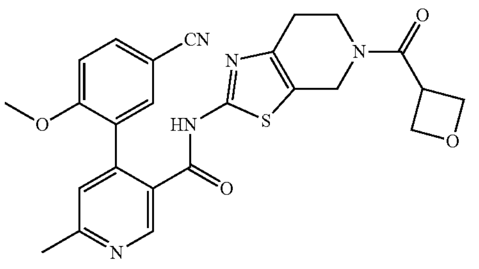 [SMILES: COc1ccc(C#N)cc1-c1cc(C)ncc1C(=O)Nc1nc2c(s1)CN(C(=O)C1COC1)CC2] | 4-(5-cyano-2-methoxyphenyl)-6-methyl-N-(5-(oxetane-3-carbonyl)-4,5,6,7-tetrahydrothiazolo[5,4-c] pyridin-2-yl)nicotinamide | 490 | $^1$H NMR (300 MHZ, DMSO-$d_6$) δ 12.51 (s, 1H), 8.70 (s, 1H), 7.91-7.90 (m, 1H), 7.84 (d, J = 2.1 Hz, 1H), 7.39 (s, 1H), 7.17 (dd, J = 8.7, 1.9 Hz, 1H), 4.76-4.71 (m, 3H), 4.69-4.57 (m, 2H), 4.37 (s, 1H), 4.27-4.19 (m, 1H), 3.82 (t, J = 5.8 Hz, 1H), 3.57 (d, J = 1.2 Hz, 3H), 3.49 (d, J = 5.7 Hz, 1H), 2.66 (d. J = 6.6 Hz, 2H), 2.58 (s, 3H) |
| 776‡ | 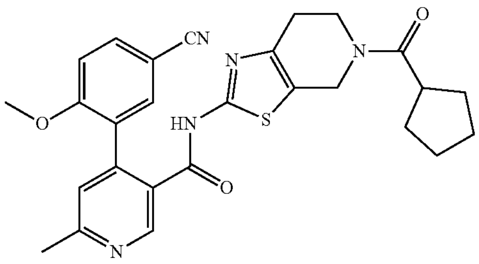 [SMILES: COc1ccc(C#N)cc1-c1cc(C)ncc1C(=O)Nc1nc2c(s1)CN(C(=O)C1CCCC1)CC2] | 4-(5-cyano-2-methoxyphenyl)-N-(5-(cyclopentanecarbonyl)-4,5,6,7-tetrahydrothiazolo[5,4-c] pyridin-2-yl)-6-methylnicotinamide | 502 | $^1$H NMR (400 MHZ, DMSO-$d_6$) δ 12.47 (s, 1H), 8.69 (s, 1H), 7.90-7.83 (m, 2H), 7.38 (s, 1H), 7.18-7.15 (m, 1H), 4.69-4.59 (m, 2H), 3.82-3.77 (m, 2H), 3.57 (s, 3H), 3.08 (d, J = 8 Hz, 1H), 2.72 (s, 1H), 2.67-2.66 (m, 1H), 2.57 (s, 3H), 1.82-1.52 (m, 8H) |
| 777‡,#,i | 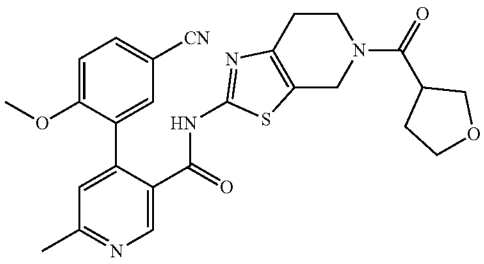 [SMILES: COc1ccc(C#N)cc1-c1cc(C)ncc1C(=O)Nc1nc2c(s1)CN(C(=O)C1CCOC1)CC2] | (R or S)-4-(5-cyano-2-methoxyphenyl)-6-methyl-N-(5-(tetrahydrofuran-3-carbonyl)-4,5,6,7-tetrahydrothiazolo[5,4-c] pyridin-2-yl)nicotinamide | 504 | $^1$H NMR (400 MHZ, Chloroform-d) δ 8.69 (d, J = 6.4 Hz, 1H), 7.73-7.70 (m, 1H), 7.54-7.43 (m, 1H), 7.18 (s, 1H), 6.99-6.96 (m, 1H), 4.68 (m, 2H), 4.04-3.98 (m, 1H), 3.94-3.81 (m, 3H), 3.84-3.69 (m, 5H), 3.29-3.21 (m, 1H), 2.68 (s, 3H), 2.23-2.20 (m, 2H), 2.11(d, J = 8.1 Hz, 2H) |
| 778 | 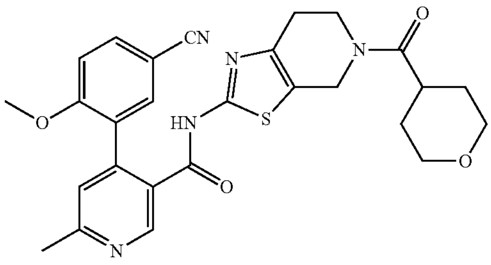 [SMILES: COc1ccc(C#N)cc1-c1cc(C)ncc1C(=O)Nc1nc2c(s1)CN(C(=O)C1CCOCC1)CC2] | 4-(5-cyano-2-methoxyphenyl)-6-methyl-N-(5-(tetrahydro-2H-pyran-4-carbonyl)-4,5,6,7-tetrahydrothiazolo[5,4-c] pyridin-2-yl)nicotinamide | 518 | $^1$H NMR (300 MHZ, DMSO-$d_6$) δ 12.51 (s, 1H), 8.73 (s, 1H), 8.02-7.75 (m, 2H), 7.45 (s, 1H), 7.18 (d, J = 8.5 Hz, 1H), 4.66 (m, 2H), 3.83 (s, 4H), 3.57 (s, 3H), 3.40 (m, 2H), 2.98 (s, 1H), 2.74 (s, 1H), 2.59 (s, 4H), 1,55 (m, 4H) |

TABLE S-continued

| The following examples were prepared using a similar procedure to that described for Example 233 | | | | |
|---|---|---|---|---|
| Ex. No. | Structure | Compound Name | LCMS $[M + H]^+$ | NMR |
| 779[‡,#,i] | 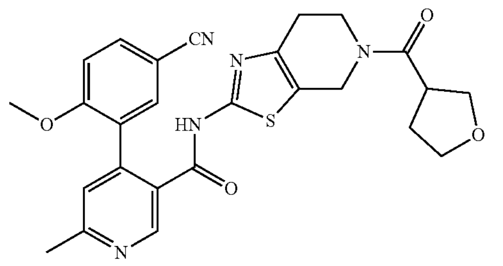 [SMILES: COc1ccc(C#N)cc1-c1cc(C)ncc1C(=O)Nc1nc2c(s1)CN(C(=O)C1CCOC1)CC2] | (S or R)-4-(5-cyano-2-methoxyphenyl)-6-methyl-N-(5-(tetrahydrofuran-3-carbonyl)-4,5,6,7-tetrahydrothiazolo[5,4-c] pyridin-2-yl)nicotinamide | 504 | $^1$H NMR (400 MHZ, Chloroform-d) δ 8.73 (s, 1H), 7.73 (d, J = 8.0 Hz, 1H), 7.54-7.46 (m, 1H), 7.20 (d, J = 3,7 Hz, 1H), 7.00-6.96 (m, 1H), 4.68 (m, 2H), 4.00-3.90 (m, 1H), 3.94-3.82 (m, 3H), 3.76-3.70 (m, 5H), 3.28-3.25 (m, 1H), 2.70 (s, 3H), 2.29-2.23 (m,1H), 2.18-2.14 (m, 2H), 2.13-2.06 (m, 1H) |

[#] Single unknown enantiomer

[c] Separation conditions for Examples 730 and 731: column, C18 gel; mobile phase, ACN in water (0.1% FA), 10% to 50% gradient in 10 min; detector, UV 254 nm.

‡Compounds were made using DCM as solvent instead of DMF

[d] Separation conditions for Examples 762 and 768: Chiral HPLC Chiralpak IC-3 Column 4.6 x 200 mm, 3 μm; mobile phase 70%/30% 1:1 MTBE:hexane with 0.1% DEA modifier/MeOH; 1.67 mL/min flow rate to give two peaks: Peak 1:1.80 min (Example 768), Peak 2:2.56 min (Example 762)

[e] Chiral separation conditions for Examples 763 and 769: Prep-chiral-HPLC CHIRALPAK ID-3 column, 4.6 x 50 mm, 3 μm; Mobile Phase 70%/30% MTBE with 0.1% DEA modifier/MeOH; Flow rate: 1 mL/min; Injection Volume: 5 ul; Peak 1:2.06 min (Example 769), Peak 2:3.24 min (Example 763)

[f] Chiral separation conditions for Example 764 and 765: Prep-chiral-HPLC CHIRALPAK IE-3 column, 4.6 x 50 mm, 3 μm; Mobile Phase 60%/40% MTBE with 0.1% DEA modifier/MeOH; Flow rate: 1 mL/min; Injection Volume 5 uL, Peak 1:1.02 min (Example 764), Peak 2:2.16 min (Example 765)

[g] Examples 766 and 767 are either each single isomers (cis or trans), or one example is a mixture of cis isomers and the other example is a mixture of trans isomers. Chiral separation conditions for Examples 766 and 767: prep-chiral-HPLC CHIRALPAK IE-3 column, 4.6 x 50 mm 3 μm; Mobile Phase 60%/40% 1:1 MTBE:Hexane with 0.1% TFA modifier/MeOH; Flow rate 1 mL/min; Injection Volume: 5 ul mL, Peak 1:2.15 min (Example 766), Peak 2:3.76 min (Example 767)

[h] Chiral separation conditions for Examples 770 and 771: prep-chiral-HPLC CHIRALPAK IC column, 2 x 25 cm, 5 μm; Mobile Phase 60%/40% MTBE with 10 mM $NH_3$-MeOH/EtOH; Flow rate: 20 mL/min; wave length: 236/212 nm, Peak 1:10 min (Example 771), Peak 2:19 min (Example 770)

[i] Chiral separation conditions for Examples 777 and 779: prep-chiral-HPLC CHIRAL ART Cellulose-SC column, 2 x 25 cm, 5 μm; Mobile Phase 70%/30% MTBE with 10 mM $NH_3$-MeOH modifier/MeOH; Flow rate: 20 mL/min; wave length: 212/236 nm; Peak 1:9.3 min (Example 779), Peak 2:12.6 min (Example 777)

Example 299: Synthesis of 4-(2-methoxyphenyl)-6-methyl-N-{5-[2-(1H-pyrazol-1-yl)acetyl]-4H,5H,6H-pyrrolo[3,4-d][1,3]thiazol-2-yl}pyridine-3-carboxamide

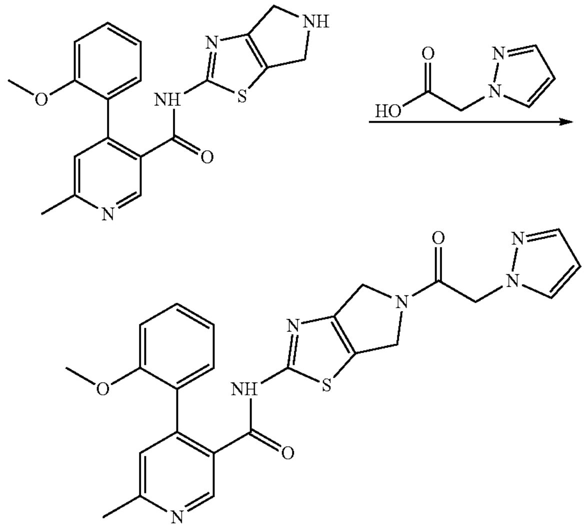

To a mixture of N-(5,6-dihydro-4H-pyrrolo[3,4-d]thiazol-2-yl)-4-(2-methoxyphenyl)-6-methylnicotinamide (37 mg, 0.10 mmol) in DMF (1 mL) was added 2-(1H-pyrazol-1-yl) acetic acid (19 mg, 0.15 mmol) and DIPEA (65 mg, 0.50 mmol). HATU (46 mg, 0.12 mmol) was added, and the reaction mixture was stirred for 16 h at 80° C. The mixture was concentrated, and the crude product was purified directly by prep-HPLC (40-60% ACN (1% $NH_3$)-water (0.1% formic acid) to afford 4-(2-methoxyphenyl)-6-methyl-N-{5-[2-(1H-pyrazol-1-yl)acetyl]-4H,5H,6H-pyrrolo[3,4-d][1,3]thiazol-2-yl}pyridine-3-carboxamide as a tan solid. LCMS: m/z=475 $[M+H]^+$. $^1H$ NMR (400 MHz, DMSO-$d_6$) δ 12.66-12.64 (m, 1H), 8.68 (s, 1H), 7.69-7.68 (m, 1H), 7.45-7.44 (m, 1H), 7.40-7.35 (m, 3H), 7.10-7.06 (m, 1H), 6.99-6.97 (m, 1H), 6.29-6.28 (m, 1H). 5.16-5.15 (m, 2H), 4.90 (s, 1H), 4.76 (s, 1H), 4.61 (s, 1H), 4.48 (s, 1H), 3.50 (s, 3H), 2.58 (s, 3H).

TABLE T

The following examples were prepared using a similar procedure to that described for Example 299

| Ex. No. | Structure | Compound Name | LCMS [M+H]+ |
|---|---|---|---|
| 300 | 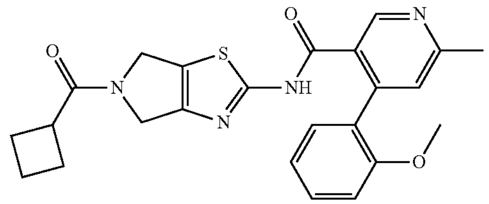 [SMILES: COc1ccccc1-c1cc(C)ncc1C(=O)Nc1nc2c(s1)CN(C(=O)C1CCC1)C2] | N-{5-cyclobutanecarbonyl-4H,5H,6H-pyrrolo[3,4-d][1,3]thiazol-2-yl}-4-(2-methoxyphenyl)-6-methylpyridine-3-carboxamide | 449 |
| 301 | 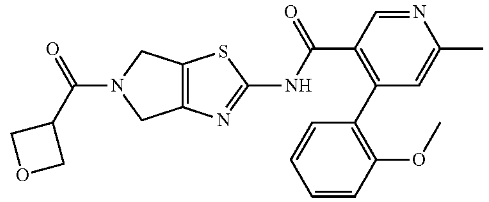 [SMILES: COc1ccccc1-c1cc(C)ncc1C(=O)Nc1nc2c(s1)CN(C(=O)C1COC1)C2] | 4-(2-methoxyphenyl)-6-methyl-N-[5-(oxetane-3-carbonyl)-4H,5H,6H-pyrrolo[3,4-d][1,3]thiazol-2-yl]pyridine-3-carboxamide | 451 |
| 302 | 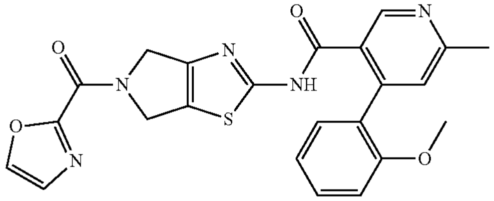 [SMILES: COc1ccccc1-c1cc(C)ncc1C(=O)Nc1nc2c(s1)CN(C(=O)c1ncco1)C2] | 4-(2-methoxyphenyl)-6-methyl-N-[5-(1,3-oxazole-2-carbonyl)-4H,5H,6H-pyrrolo[3,4-d][1,3]thiazol-2-yl]pyridine-3-carboxamide | 462 |
| 303 | 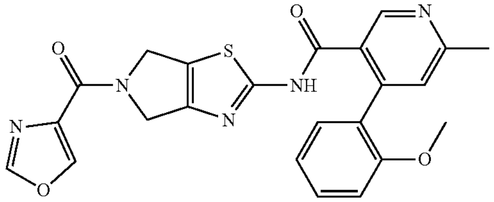 [SMILES: COc1ccccc1-c1cc(C)ncc1C(=O)Nc1nc2c(s1)CN(C(=O)c1cocn1)C2] | 4-(2-methoxyphenyl)-6-methyl-N-[5-(1,3-oxazole-4-carbonyl)-4H,5H,6H-pyrrolo[3,4-d][1,3]thiazol-2-yl]pyridine-3-carboxamide | 462 |
| 304 | 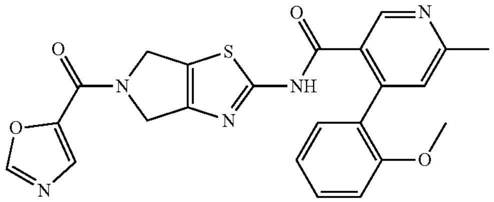 [SMILES: COc1ccccc1-c1cc(C)ncc1C(=O)Nc1nc2c(s1)CN(C(=O)c1cnco1)C2] | 4-(2-methoxyphenyl)-6-methyl-N-[5-(1,3-oxazole-5-carbonyl)-4H,5H,6H-pyrrolo[3,4-d][1,3]thiazol-2-yl]pyridine-3-carboxamide | 462 |
| 305 | 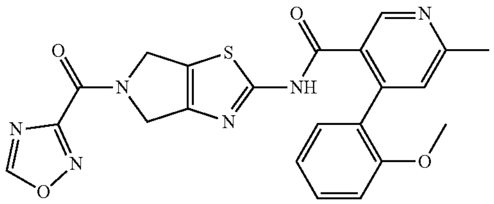 [SMILES: COc1ccccc1-c1cc(C)ncc1C(=O)Nc1nc2c(s1)CN(C(=O)c1ncon1)C2] | 4-(2-methoxyphenyl)-6-methyl-N-[5-(1,2,4-oxadiazole-3-carbonyl)-4H,5H,6H-pyrrolo[3,4-d][1,3]thiazol-2-yl]pyridine-3-carboxamide | 463 |

TABLE T-continued

The following examples were prepared using a similar procedure to that described for Example 299

| Ex. No. | Structure | Compound Name | LCMS [M+H]+ |
| --- | --- | --- | --- |
| 306 | 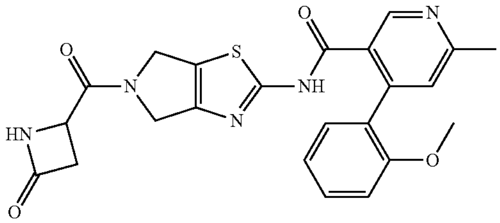 [SMILES: COc1ccccc1-c1cc(C)ncc1C(=O)Nc1nc2c(s1)CN(C(=O)C1CC(=O)N1)C2] | (Racemic)-4-(2-methoxyphenyl)-6-methyl-N-[5-(4-oxoazetidine-2-carbonyl)-4H,5H,6H-pyrrolo[3,4-d][1,3]thiazol-2-yl]pyridine-3-carboxamide | 464 |
| 307 | 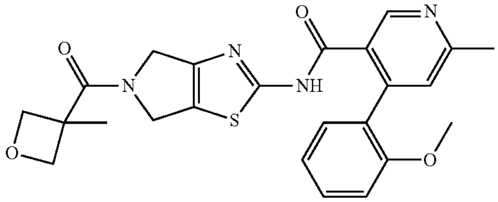 [SMILES: COc1ccccc1-c1cc(C)ncc1C(=O)Nc1nc2c(s1)CN(C(=O)C1(C)COC1)C2] | 4-(2-methoxyphenyl)-6-methyl-N-[5-(3-methyloxetane-3-carbonyl)-4H,5H,6H-pyrrolo[3,4-d][1,3]thiazol-2-yl]pyridine-3-carboxamide | 465 |
| 308 | 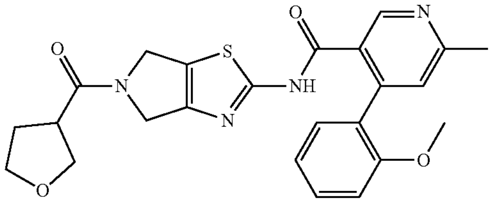 [SMILES: COc1ccccc1-c1cc(C)ncc1C(=O)Nc1nc2c(s1)CN(C(=O)C1CCOC1)C2] | (Racemic)-4-(2-methoxyphenyl)-6-methyl-N-[S-(oxolane-3-carbonyl)-4H,5H,6H-pyrrolo[3,4-d][1,3]thiazol-2-yl]pyridine-3-carboxamide | 465 |
| 309 | 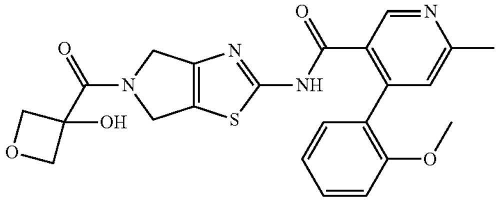 [SMILES: COc1ccccc1-c1cc(C)ncc1C(=O)Nc1nc2c(s1)CN(C(=O)C1(O)COC1)C2] | N-[5-(3-hydroxyoxetane-3-carbonyl)-4H,5H,6H-pyrrolo[3,4-d][1,3]thiazol-2-yl]-4-(2-methoxyphenyl)-6-methylpyridine-3-carboxamide | 467 |
| 310 | 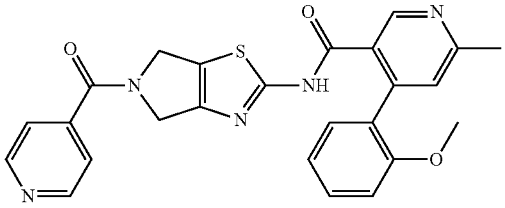 [SMILES: COc1ccccc1-c1cc(C)ncc1C(=O)Nc1nc2c(s1)CN(C(=O)c1ccncc1)C2] | 4-(2-methoxyphenyl)-6-methyl-N-[5-(pyridine-4-carbonyl)-4H,5H,6H-pyrrolo[3,4-d][1,3]thiazol-2-yl]pyridine-3-carboxamide | 472 |
| 311 | 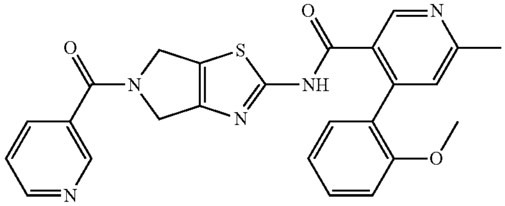 [SMILES: COc1ccccc1-c1cc(C)ncc1C(=O)Nc1nc2c(s1)CN(C(=O)c1cccnc1)C2] | 4-(2-methoxyphenyl)-6-methyl-N-[5-(pyridine-3-carbonyl)-4H,5H,6H-pyrrolo[3,4-d][1,3]thiazol-2-yl]pyridine-3-carboxamide | 472 |
| 312 | 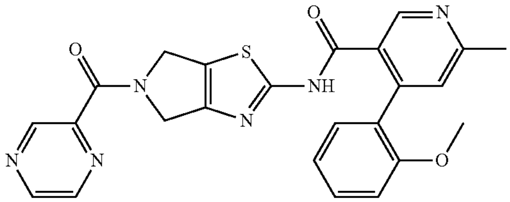 [SMILES: COc1ccccc1-c1cc(C)ncc1C(=O)Nc1nc2c(s1)CN(C(=O)c1cnccn1)C2] | 4-(2-methoxyphenyl)-6-methyl-N-[5-(pyrazine-2-carbonyl)-4H,5H,6H-pyrrolo[3,4-d][1,3]thiazol-2-yl]pyridine-3-carboxamide | 473 |

TABLE T-continued

| Ex. No. | Structure | Compound Name | LCMS [M+H]+ |
|---|---|---|---|
| The following examples were prepared using a similar procedure to that described for Example 299 | | | |
| 313 | 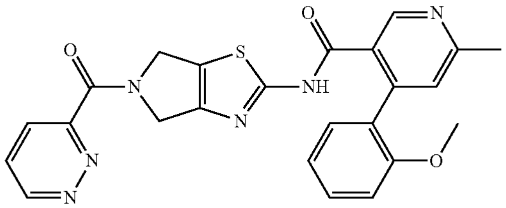 | 4-(2-methoxyphenyl)-6-methyl-N-[5-(pyridazine-3-carbonyl)-4H,5H,6H-pyrrolo[3,4-d][1,3]thiazol-2-yl]pyridine-3-carboxamide | 473 |
| 314 | 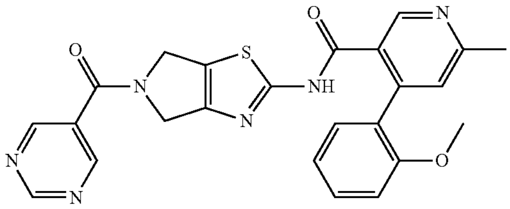 [SMILES: COc1ccccc1-c1cc(C)ncc1C(=O)Nc1nc2c(s1)CN(C(=O)c1cncnc1)C2] | 4-(2-methoxyphenyl)~6-methyl-N-[5-(pyrimidine-5-carbonyl)-4H,5H,6H-pyrrolo[3,4-d][1,3]thiazol-2-yl]pyridine-3-carboxamide | 473 |
| 315 | 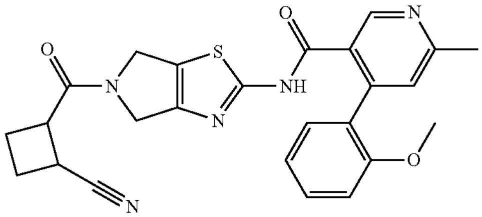 [SMILES: COc1ccccc1-c1cc(C)ncc1C(=O)Nc1nc2c(s1)CN(C(=O)C1CCC1C#N)C2] | (Racemic)-N-[5-(2-cyanocyclobutanecarbonyl)-4H,5H,6H-pyrrolo[3,4-d][1,3]thiazol-2-yl]-4-(2-methoxyphenyl)-6-methylpyridine-3-carboxamide | 474 |
| 316 | 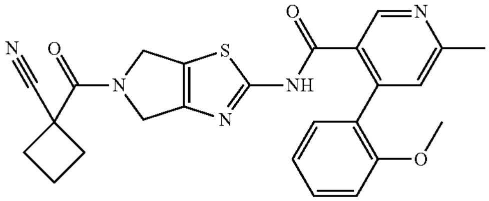 [SMILES: COc1ccccc1-c1cc(C)ncc1C(=O)Nc1nc2c(s1)CN(C(=O)C1(C#N)CCC1)C2] | N-[5-(1-cyanocyclobutanecarbonyl)-4H,5H,6H-pyrrolo[3,4-d][1,3]thiazol-2-yl]-4-(2-methoxyphenyl)-6-methylpyridine-3-carboxamide | 474 |
| 317 | 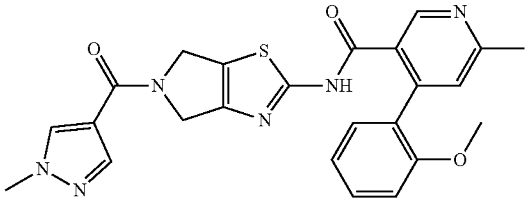 | 4-(2-methoxyphenyl)-6-methyl-N-[5-(1-methyl-1H-pyrazole-4-carbonyl)-4H,5H,6H-pyrrolo[3,4-d][1,3]thiazol-2-yl]pyridine-3-carboxamide | 475 |
| 318 | 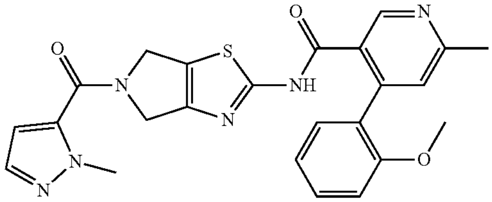 [SMILES: COc1ccccc1-c1cc(C)ncc1C(=O)Nc1nc2c(s1)CN(C(=O)c1ccnn1C)C2] | 4-(2-methoxyphenyl)-6-methyl-N-[5-(1-methyl-1H-pyrazole-5-carbonyl)-4H,5H,6H-pyrrolo[3,4-d][1,3]thiazol-2-yl]pyridine-3-carboxamide | 475 |
| 319 | 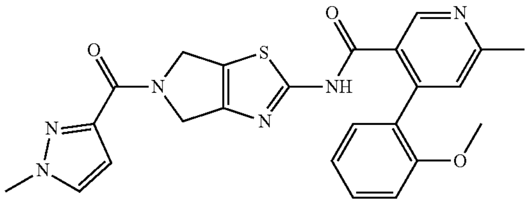 | 4-(2-methoxyphenyl)-6-methyl-N-[5-(1-methyl-1H-pyrazole-3-carbonyl)-4H,5H,6H-pyrrolo[3,4-d][1,3]thiazol-2-yl]pyridine-3-carboxamide | 475 |

TABLE T-continued

The following examples were prepared using a similar procedure to that described for Example 299

| Ex. No. | Structure | Compound Name | LCMS [M+H]+ |
|---|---|---|---|
| 320 | 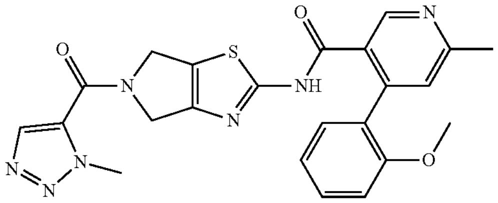 [SMILES: COc1ccccc1-c1cc(C)ncc1C(=O)Nc1nc2c(s1)CN(C(=O)c1cnnn1C)C2] | 4-(2-methoxyphenyl)-6-methyl-N-[5-(1-methyl-1H-1,2,3-triazole-5-carbonyl)-4H,5H,6H-pyrrolo[3,4-d][1,3]thiazol-2-yl]pyridine-3-carboxamide | 476 |
| 321 | 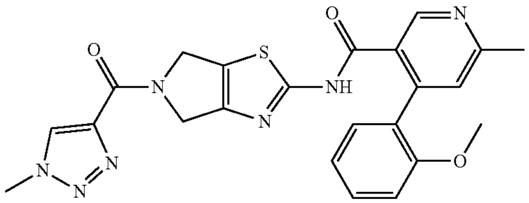 | 4-(2-methoxyphenyl)-6-methyl-N-[5-(1-methyl-1H-1,2,3-triazole-4-carbonyl)-4H,5H,6H-pyrrolo[3,4-d][1,3]thiazol-2-yl]pyridine-3-carboxamide | 476 |
| 322 | 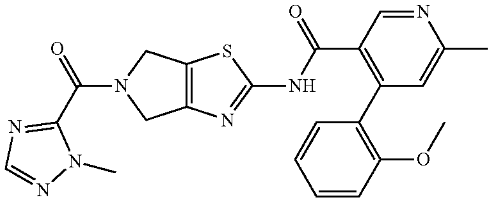 [SMILES: COc1ccccc1-c1cc(C)ncc1C(=O)Nc1nc2c(s1)CN(C(=O)c1ncnn1C)C2] | 4-(2-methoxyphenyl)-6-methyl-N-[5-(1-methyl-1H-1,2,4-triazole-5-carbonyl)-4H,5H,6H-pyrrolo[3,4-d][1,3]thiazol-2-yl]pyridine-3-carboxamide | 476 |
| 323 | 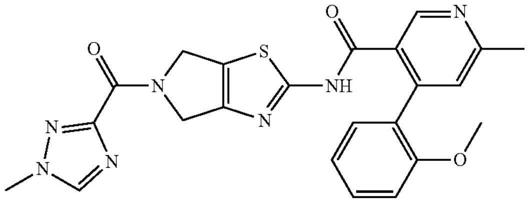 | 4-(2-methoxyphenyl)-6-methyl-N-[5-(1-methyl-1H-1,2,4-triazole-3-carbonyl)-4H,5H,6H-pyrrolo[3,4-d][1,3]thiazol-2-yl]pyridine-3-carboxamide | 476 |
| 324 | 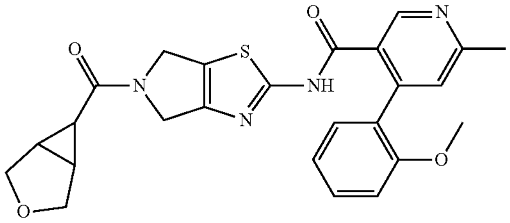 [SMILES: COc1ccccc1-c1cc(C)ncc1C(=O)Nc1nc2c(s1)CN(C(=O)C1C3COCC31)C2] | 4-(2-methoxyphenyl)~6-methyl-N-(5-{3-oxabicyclo[3.1.0]hexane-6-carbonyl}-4H,5H,6H-pyrrolo[3,4-d][1,3]thiazol-2-yl)pyridine-3-carboxamide | 477 |
| 325 | 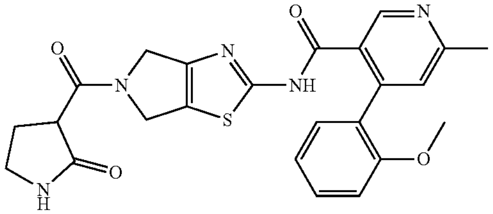 [SMILES: COc1ccccc1-c1cc(C)ncc1C(=O)Nc1nc2c(s1)CN(C(=O)C1CCNC1=O)C2] | (Racemic)-4-(2-methoxyphenyl)-6-methyl-N-[5-(2-oxopyrrolidine-3-carbonyl)-4H,5H,6H-pyrrolo[3,4-d][1,3]thiazol-2-yl]pyridine-3-carboxamide | 478 |
| 326 | 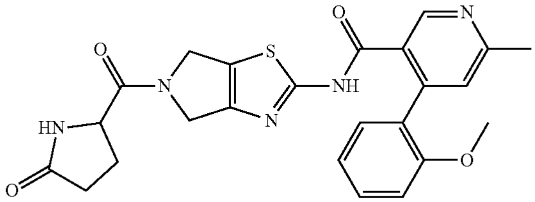 [SMILES: COc1ccccc1-c1cc(C)ncc1C(=O)Nc1nc2c(s1)CN(C(=O)C1CCC(=O)N1)C2] | (Racemic)-4-(2-methoxyphenyl)-6-methyl-N-[5-(5-oxopyrrolidine-2-carbonyl)-4H,5H,6H-pyrrolo[3,4-d][1,3]thiazol-2-yl]pyridine-3-carboxamide | 478 |

TABLE T-continued

The following examples were prepared using a similar procedure to that described for Example 299

| Ex. No. | Structure | Compound Name | LCMS [M+H]+ |
|---|---|---|---|
| 327 | 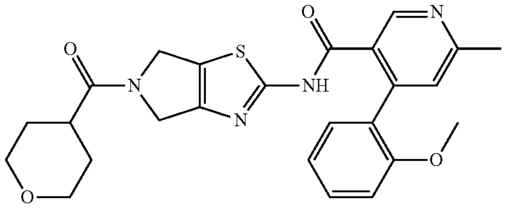 | 4-(2-methoxyphenyl)-6-methyl-N-[5-(oxane-4-carbonyl)-4H,5H,6H-pyrrolo[3,4-d][1,3]thiazol-2-yl]pyridine-3-carboxamide | 479 |
| 328 | 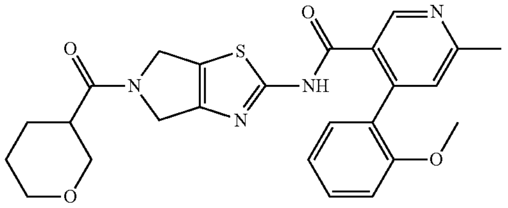 [SMILES: COc1ccccc1-c1cc(C)ncc1C(=O)Nc1nc2c(s1)CN(C(=O)C1CCCOC1)C2] | (Racemic)-4-(2-methoxyphenyl)-6-methyl-N-[S-(oxane-3-carbonyl)-4H,5H,6H-pyrrolo[3,4-d][1,3]thiazol-2-yl]pyridine-3-carboxamide | 479 |
| 329 | 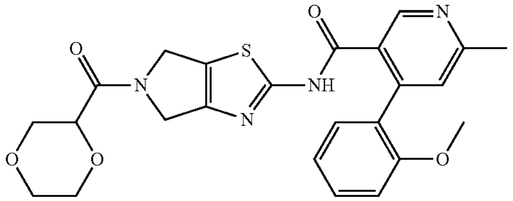 [SMILES: COc1ccccc1-c1cc(C)ncc1C(=O)Nc1nc2c(s1)CN(C(=O)C1COCCO1)C2] | (Racemic)-N-[5-(1,4-dioxane-2-carbonyl)-4H,5H,6H-pyrrolo[3,4-d][1,3]thiazol-2-yl]-4-(2-methoxyphenyl)-6-methylpyridine-3-carboxamide | 481 |
| 330 | 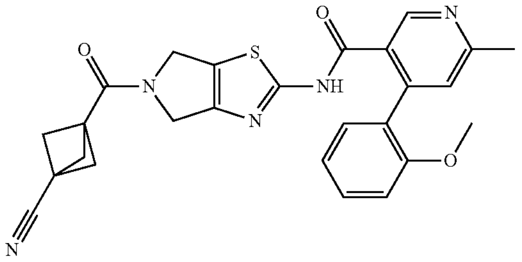 [SMILES: COc1ccccc1-c1cc(C)ncc1C(=O)Nc1nc2c(s1)CN(C(=O)C13CC(C#N)(C1)C3)C2] | N-(5-{3-cyanobicyclo[1.1.1]pentane-1-carbonyl}-4H,5H,6H-pyrrolo[3,4-d][1,3]thiazol-2-yl)-4-(2-methoxyphenyl)-6-methylpyridine-3-carboxamide | 486 |
| 331 | 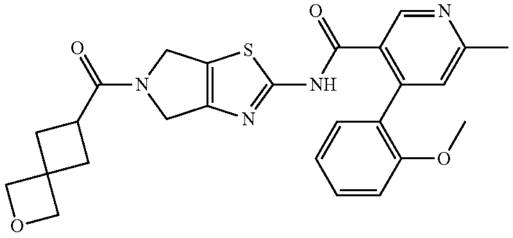 [SMILES: COc1ccccc1-c1cc(C)ncc1C(=O)Nc1nc2c(s1)CN(C(=O)C1CC3(COC3)C1)C2] | 4-(2-methoxyphenyl)-6-methyl-N-(5-{2-oxaspiro[3.3]heptane-6-carbonyl}-4H,5H,6H-pyrrolo[3,4-d][1,3]thiazol-2-yl)pyridine-3-carboxamide | 491 |
| 332 | 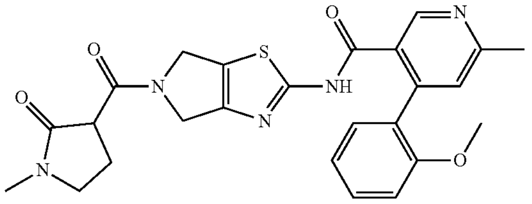 | (Racemic)-4-(2-methoxyphenyl)-6-methyl-N-[5-(1-methyl-2-oxopyrrolidine-3-carbonyl)-4H,5H,6H-pyrrolo[3,4-d][1,3]thiazol-2-yl]pyridine-3-carboxamide | 492 |

TABLE T-continued

The following examples were prepared using a similar procedure to that described for Example 299

| Ex. No. | Structure | Compound Name | LCMS [M+H]+ |
|---|---|---|---|
| 333 | 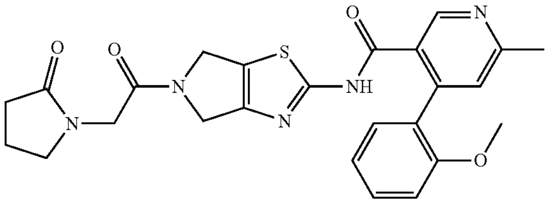 [SMILES: COc1ccccc1-c1cc(C)ncc1C(=O)Nc1nc2c(s1)CN(C(=O)CN1CCCC1=O)C2] | 4-(2-methoxyphenyl)-6-methyl-N-{5-[2-(2-oxopyrrolidin-1-yl)acetyl]-4H,5H,6H-pyrrolo[3,4-d][1,3]thiazol-2-yl}pyridine-3-carboxamide | 492 |
| 334 | 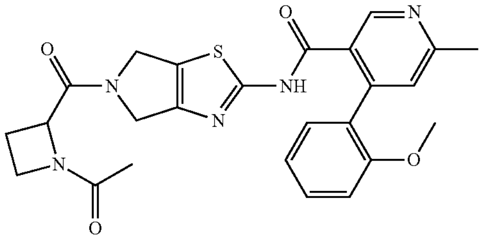 [SMILES: COc1ccccc1-c1cc(C)ncc1C(=O)Nc1nc2c(s1)CN(C(=O)C1CCN1C(C)=O)C2] | (Racemic)-N-[5-(1-acetylazetidine-2-carbonyl)-4H,5H,6H-pyrrolo[3,4-d][1,3]thiazol-2-yl]-4-(2-methoxyphenyl)-6-methylpyridine-3-carboxamide | 492 |
| 335 | 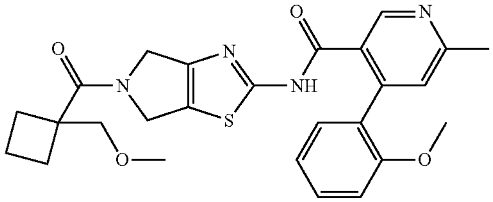 [SMILES: COCC1(C(=O)N2Cc3nc(NC(=O)c4cnc(C)cc4-c4ccccc4OC)sc3C2)CCC1] | N-{5-[1-(methoxymethyl)cyclobutanecarbonyl]-4H,5H,6H-pyrrolo[3,4-d][1,3]thiazol-2-y]}-4-(2-methoxyphenyl)-6-methylpyridine-3-carboxamide | 493 |
| 336 | 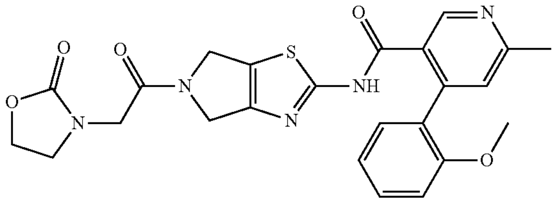 [SMILES: COc1ccccc1-c1cc(C)ncc1C(=O)Nc1nc2c(s1)CN(C(=O)CN1CCOC1=O)C2] | 4-(2-methoxyphenyl)-6-methyl-N-{5-[2-(2-oxo-1,3-oxazolidin-3-yl)acetyl]-4H,5H,6H-pyrrolo[3,4-d][1,3]thiazol-2-yl}pyridine-3-carboxamide | 494 |
| 337 | 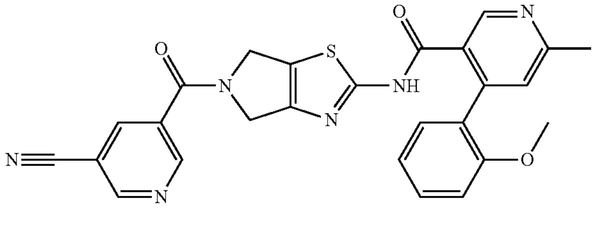 [SMILES: COc1ccccc1-c1cc(C)ncc1C(=O)Nc1nc2c(s1)CN(C(=O)c1cncc(C#N)c1)C2] | N-[5-(5-cyanopyridine-3-carbony])-4H,5H,6H-pyrrolo[3,4-d][1,3]thiazol-2-yl]-4-(2-methoxyphenyl)-6-methylpyridine-3-carboxamide | 497 |
| 338 | 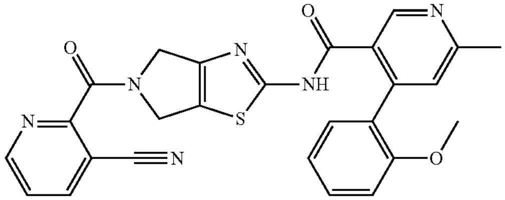 [SMILES: COc1ccccc1-c1cc(C)ncc1C(=O)Nc1nc2c(s1)CN(C(=O)c1ncccc1C#N)C2] | N-[5-(3-cyanopyridine-2-carbonyl)-4H,5H,6H-pyrrolo[3,4-d][1,3]thiazol-2-yl]-4-(2-methoxyphenyl)-6-methylpyridine-3-carboxamide | 497 |

TABLE T-continued

The following examples were prepared using a similar procedure to that described for Example 299

| Ex. No. | Structure | Compound Name | LCMS [M+H]+ |
|---|---|---|---|
| 339 | 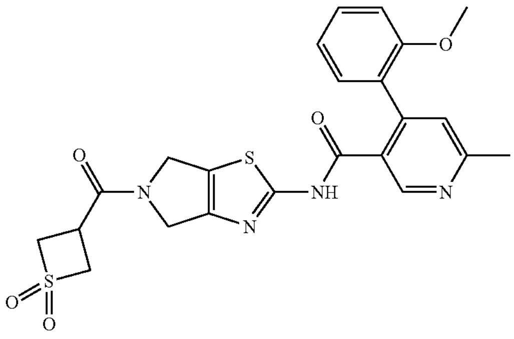 [SMILES: COc1ccccc1-c1cc(C)ncc1C(=O)Nc1nc2c(s1)CN(C(=O)C1CS(=O)(=O)C1)C2] | N-(5-(1,1-dioxidothietane-3-carbonyl)-5,6-dihydro-4H-pyrrolo[3,4-d]thiazol-2-yl)-4-(2-methoxyphenyl)-6-methylnicotinamide | 499 |
| 340 | 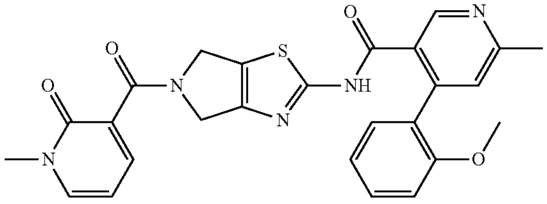 | 4-(2-methoxyphenyl)-6-methyl-N-[5-(1-methyl-2-oxo-1,2-dihydropyridine-3-carbonyl)-4H,5H,6H-pyrrolo[3,4-d][1,3]thiazol-2-yl]pyridine-3-carboxamide | 502 |
| 341 | 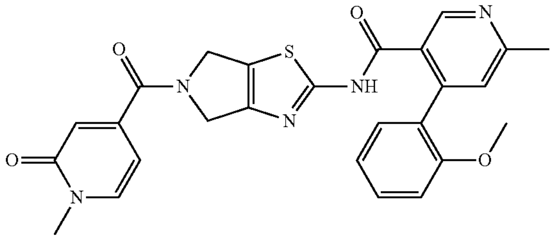 [SMILES: COc1ccccc1-c1cc(C)ncc1C(=O)Nc1nc2c(s1)CN(C(=O)c1ccn(C)c(=O)c1)C2] | 4-(2-methoxyphenyl)-6-methyl-N-[5-(1-methyl-2-oxo-1,2-dihydropyridine-4-carbonyl)-4H,5H,6H-pyrrolo[3,4-d][1,3]thiazol-2-yl]pyridine-3-carboxamide | 502 |
| 342 | 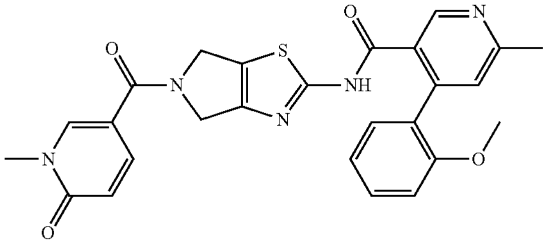 | 4-(2-methoxyphenyl)~6-methyl-N-[5-(1-methyl-6-oxo-1,6-dihydropyridine-3-carbonyl)-4H,5H,6H-pyrrolo[3,4-d][1,3]thiazol-2-yl]pyridine-3-carboxamide | 502 |
| 343 | 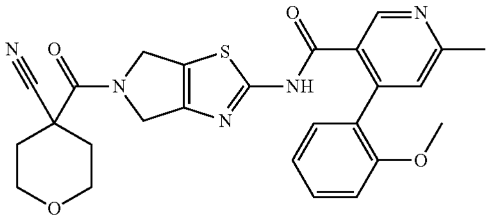 [SMILES: COc1ccccc1-c1cc(C)ncc1C(=O)Nc1nc2c(s1)CN(C(=O)C1(C#N)CCOCC1)C2] | N-[5-(4-cyanooxane-4-carbonyl)-4H,5H,6H-pyrrolo[3,4-d][1,3]thiazol-2-yl]-4-(2-methoxyphenyl)-6-methylpyridine-3-carboxamide | 504 |
| 344 | 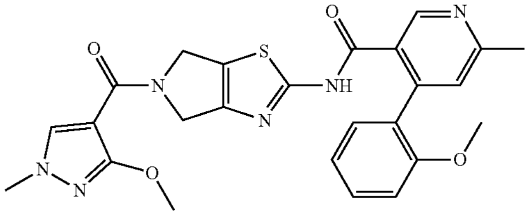 | N-[5-(3-methoxy-1-methyl-1H-pyrazole-4-carbonyl)-4H,5H,6H-pyrrolo[3,4-d][1,3]thiazol-2-yl]-4-(2-methoxyphenyl)-6-methylpyridine-3-carboxamide | 505 |

TABLE T-continued

The following examples were prepared using a similar procedure to that described for Example 299

| Ex. No. | Structure | Compound Name | LCMS [M+H]+ |
|---|---|---|---|
| 345 | 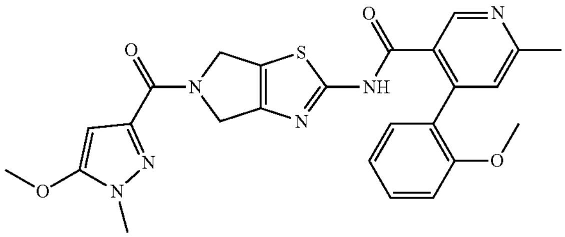 | N-[5-(5-methoxy-1-methyl-1H-pyrazole-3-carbonyl)-4H,5H,6H-pyrrolo[3,4-d][1,3]thiazol-2-yl]-4-(2-methoxyphenyl)-6-methylpyridine-3-carboxamide | 505 |
| 346 | 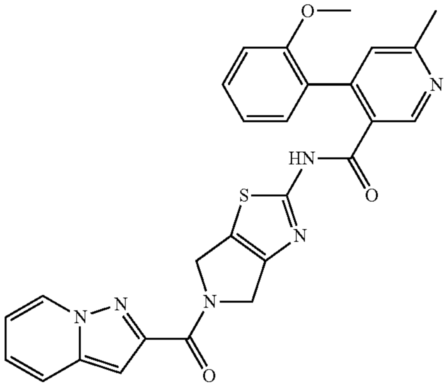 [SMILES: COc1ccccc1-c1cc(C)ncc1C(=O)Nc1nc2c(s1)CN(C(=O)c1cc3ccccn3n1)C2] | 4-(2-methoxyphenyl)-6-methyl-N-(5-{pyrazolo[1,5-a]pyridine-2-carbonyl}-4H,5H,6H-pyrrolo[3,4-d][1,3]thiazol-2-yl)pyridine-3-carboxamide | 511 |
| 347 | 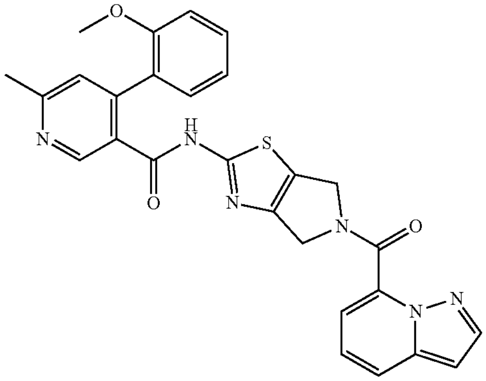 [SMILES: COc1ccccc1-c1cc(C)ncc1C(=O)Nc1nc2c(s1)CN(C(=O)c1cccc3ccnn13)C2] | 4-(2-methoxyphenyl)-6-methyl-N-(5-{pyrazolo[1,5-a]pyridine-7-carbonyl}-4H,5H,6H-pyrrolo[3,4-d][1,3]thiazol-2-yl)pyridine-3-carboxamide | 511 |
| 348 | 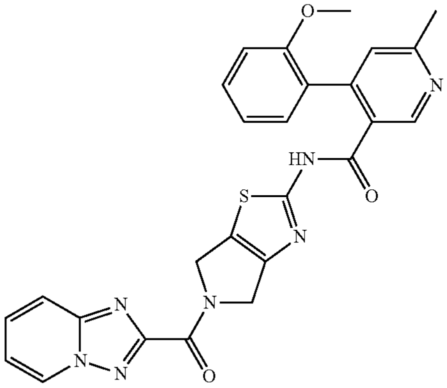 [SMILES: COc1ccccc1-c1cc(C)ncc1C(=O)Nc1nc2c(s1)CN(C(=O)c1nc3ccccn3n1)C2] | 4-(2-methoxyphenyl)-6-methyl-N-(5-{[1,2,4]triazolo[1,5-a]pyridine-2-carbonyl}-4H,5H,6H-pyrrolo[3,4-d][1,3]thiazol-2-yl)pyridine-3-carboxamide | 512 |

TABLE T-continued

| The following examples were prepared using a similar procedure to that described for Example 299 | | | |
|---|---|---|---|
| Ex. No. | Structure | Compound Name | LCMS [M+H]+ |
| 349 | 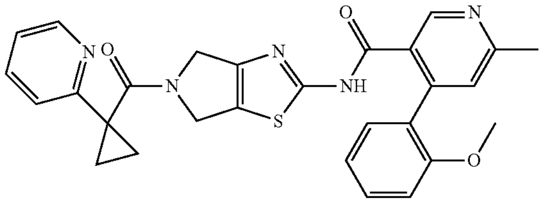 [SMILES: COc1ccccc1-c1cc(C)ncc1C(=O)Nc1nc2c(s1)CN(C(=O)C1(c3ccccn3)CC1)C2] | 4-(2-methoxyphenyl)-6-methyl-N-{5-[1-(pyridin-2-yl)cyclopropanecarbonyl]-4H,5H,6H-pyrrolo[3,4-d][1,3]thiazol-2-yl}pyridine-3-carboxamide | 512 |
| 350 | 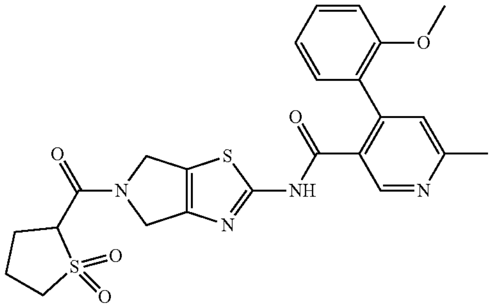 [SMILES: COc1ccccc1-c1cc(C)ncc1C(=O)Nc1nc2c(s1)CN(C(=O)C1CCCS1(=O)=O)C2] | (Racemic)-N-(5-(1,1-dioxidotetrahydrothiophene-2-carbonyl)-5,6-dihydro-4H-pyrrolo[3,4-d]thiazol-2-yl)-4-(2-methoxyphenyl)-6-methylnicotinamide | 513 |
| 351 | 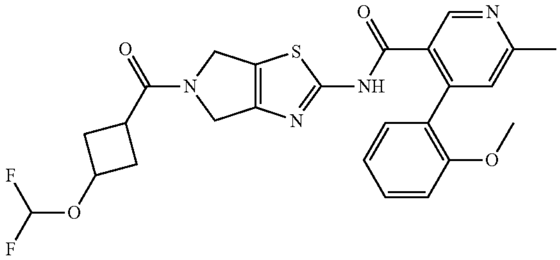 [SMILES: COc1ccccc1-c1cc(C)ncc1C(=O)Nc1nc2c(s1)CN(C(=O)C1CC(OC(F)F)C1)C2] | (Cis and Trans)-N-{5-[3-(difluoromethoxy)cyclobutanecarbonyl]-4H,5H,6H-pyrrolo[3,4-d][1,3]thiazol-2-yl}-4-(2-methoxyphenyl)-6-methylpyridine-3-carboxamide | 515 |

Example 732: Synthesis of 4-(6-Methoxy-1H-indazol-5-yl)-N-(5-(2-methoxynicotinoyl)-5,6-dihydro-4H-pyrrolo[3,4-d]thiazol-2-yl)-6-methylnicotinamide

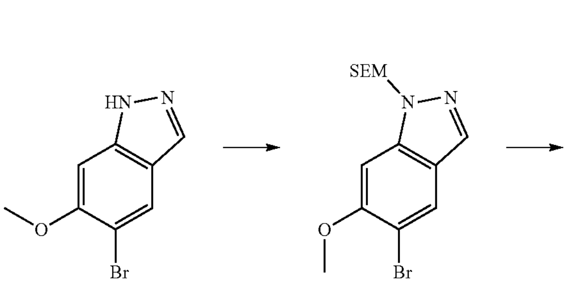

-continued

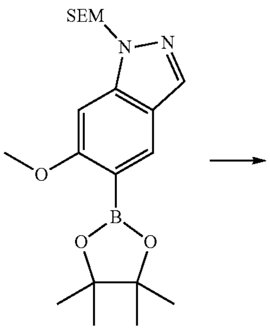

-continued

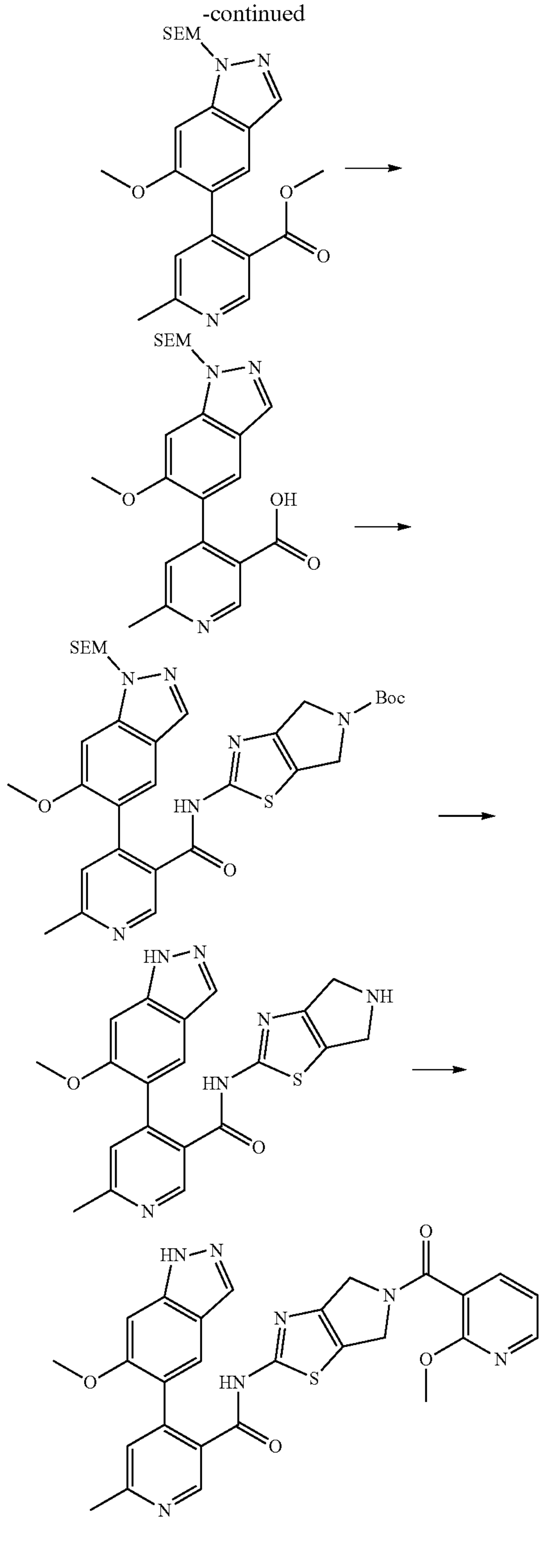

Step 1: To a solution of 5-bromo-6-methoxy-1H-indazole (100 mg, 0.44 mmol) in THF (8 mL) at 0° C. under a $N_2$ atmosphere was added NaH (60% w/w in oil, 26 mg, 0.66 mmol) and the mixture was stirred at 0° C. for 1 h. SEM-Cl (293 mg, 1.76 mmol) was then added dropwise and the mixture was stirred at 0° C. for a further 1 h. The mixture was diluted with water (20 mL), extracted with EtOAc (40 mL-3), and the combined organic layers were washed with brine (20 mL×2), dried over $Na_2SO_4$, filtered, and concentrated under reduced pressure. The residue was purified by prep-TLC (DCM/MeOH=50/1, v/v) to give 5-bromo-6-methoxy-1-((2-(trimethylsilyl)ethoxy)methyl)-1H-indazole (100 mg, 63%) as colorless oil. LCMS: m/z=357 $[M+H]^+$; $^1H$ NMR (400 MHz, DMSO-$d_6$) δ 8.03 (s, 1H), 7.99 (s, 1H), 7.38 (s, 1H), 5.73 (s, 2H), 3.93 (s, 3H), 3.53 (t, J=7.8 Hz, 2H), 0.80 (t, J=7.8 Hz, 2H), −0.11 (s, 9H).

Step 2: A solution of 5-bromo-6-methoxy-1-((2-(trimethylsilyl)ethoxy)methyl)-1H-indazole (500 mg, 1.40 mmol), $Pin_2B_2$ (888 mg, 3.50 mmol), KOAc (231 mg, 4.20 mmol), and Pd(dppf)$Cl_2$ (101 mg, 0.104 mmol) in dioxane (10 mL) was heated at 100° C. under a $N_2$ atmosphere overnight. The mixture was filtered and the filtrate concentrated under reduced pressure to give 6-methoxy-5-(4,4,5,5-tetramethyl-1,3,2-dioxaborolan-2-yl)-1-((2-(trimethylsilyl)ethoxy)methyl)-1H-indazole (1 g) as a black solid, which was used directly in the next step without further purification. LCMS: m/z=405 $[M+H]^+$.

Step 3: A mixture of 6-methoxy-5-(4,4,5,5-tetramethyl-1,3,2-dioxaborolan-2-yl)-1-((2-(trimethylsilyl)ethoxy)methyl)-1H-indazole (1 g), methyl 4-chloro-6-methylnicotinate (518 mg, 2.79 mmol), $K_2CO_3$ (579 mg, 4.19 mmol) and Pd(dtbpf)$Cl_2$ (180 mg, 0.28 mmol) in dioxane (20 mL) and water (5 mL) was heated at 100° C. under a $N_2$ atmosphere overnight. The mixture was filtered and the filtrate concentrated under reduced pressure. The residue was purified by prep-TLC (DCM/MeOH=10/1, v/v) to give methyl 4-(6-methoxy-1-((2-(trimethylsilyl)ethoxy)methyl)-1H-indazol-5-yl)-6-methylnicotinate (390 mg, 65% over two steps) as a yellow solid. LCMS: m/z=428 $[M+H]^+$; $^1H$ NMR (400 MHz, DMSO-$d_6$) δ 8.75 (s, 1H), 8.06 (s, 1H), 7.68 (s, 1H), 7.32 (s, 1H), 7.27 (s, 1H), 5.75 (s, 2H), 3.73 (s, 3H), 3.60 (s, 3H), 3.57 (t, J=8.2 Hz, 2H), 2.56 (s, 3H), 0.84 (t, J=8.0 Hz, 2H), −0.08 (s, 9H).

Step 4: A solution of methyl 4-(6-methoxy-1-((2-(trimethylsilyl)ethoxy)methyl)-1H-indazol-5-yl)-6-methylnicotinate (390 mg, 0.91 mmol) and NaOH (109 mg, 2.74 mmol) in MeOH (10 mL) and water (10 mL) was heated at 50° C. for 3 h. The mixture was adjusted to pH 5 with 2 M aqueous HCl and concentrated under reduced pressure. The residue was washed with a mixture of DCM (30 mL) and MeOH (3 mL) to give 4-(6-methoxy-1-((2-(trimethylsilyl)ethoxy)methyl)-1H-indazol-5-yl)-6-methylnicotinic acid (347 mg, 92%) as a yellow solid. LCMS: m/z=414 $[M+H]^+$.

Step 5: To a solution of 4-(6-methoxy-1-((2-(trimethylsilyl)ethoxy)methyl)-1H-indazol-5-yl)-6-methylnicotinic acid (200 mg, 0.48 mmol), tert-butyl 2-amino-4,6-dihydro-5H-pyrrolo[3,4-d]thiazole-5-carboxylate (163 mg, 0.67 mmol) and TCFH (203 mg, 0.72 mmol) in MeCN (10 mL) was added NMI (158 mg, 1.93 mmol) and the mixture was heated at 80° C. overnight. The mixture was diluted with water (30 mL), extracted with EtOAc (50 mL×3), and the combined organic layers were washed with brine (20 mL×2), dried over $Na_2SO_4$, filtered, and concentrated under reduced pressure. The residue was purified by prep-TLC (Pet. ether/EtOAc=1/2, v/v) to give tert-butyl 2-(4-(6-methoxy-1-((2-(trimethylsilyl)ethoxy)methyl)-1H-indazol-5-yl)-6-methylnicotinamido)-4,6-dihydro-5H-pyrrolo[3,4-d]thiazole-5-carboxylate (160 mg, 52%) as a brown solid. LCMS: m/z=637 $[M+H]^+$; $^1H$ NMR (400 MHz, DMSO-$d_6$) δ 8.65 (s, 1H), 8.09 (s, 1H), 7.75 (s, 1H), 7.37 (s, 1H), 7.19 (s, 1H), 5.72 (s, 2H), 4.51 (d, J=11.4 Hz, 2H), 4.38 (dd, J=8.8, 3.8 Hz, 2H), 3.56 (d, J=2.4 Hz, 5H), 2.58 (s, 3H), 1.44 (s, 9H), 0.83 (t, J=8.0 Hz, 2H), −0.10 (s, 9H).

Step 6: A mixture of tert-butyl 2-(4-(6-methoxy-1-((2-(trimethylsilyl)ethoxy)methyl)-1H-indazol-5-yl)-6-methylnicotinamido)-4,6-dihydro-5H-pyrrolo[3,4-d]thiazole-5-carboxylate (50 mg, 0.08 mmol) and a 4 M HCl in MeOH solution (5 mL) was stirred at room temperature for 1 h then concentrated under reduced pressure to give N-(5,6-dihydro-4H-pyrrolo[3,4-d]thiazol-2-yl)-4-(6-methoxy-1H-indazol-5-yl)-6-methylnicotinamide hydrochloride (40 mg), which was used directly in the next step. LCMS: m/z=407.20 $[M+H]^+$.

Step 7: To a solution of N-(5,6-dihydro-4H-pyrrolo[3,4-d]thiazol-2-yl)-4-(6-methoxy-1H-indazol-5-yl)-6-methylnicotinamide hydrochloride (40 mg), 2-methoxynicotinic acid (30 mg, 0.20 mmol), and DIPEA (63 mg, 0.49 mmol) in DMF (2 mL) at 0° C. under a $N_2$ atmosphere was added T3P (50% in DMF, 93 mg, 0.14 mmol) and the mixture was stirred at room temperature overnight. The mixture was diluted with water (10 mL), extracted with EtOAc (30 mL×3), and the combined organic layers were washed with brine (20 mL×3), dried over $Na_2SO_4$, filtered and, concentrated under reduced pressure. The residue was purified by prep-TLC (DCM/MeOH=10/1, v/v) to give 4-(6-methoxy-1H-indazol-5-yl)-N-(5-(2-methoxynicotinoyl)-5,6-dihydro-4H-pyrrolo[3,4-d]thiazol-2-yl)-6-methylnicotinamide (20 mg, 38%) as a white solid. LCMS: m/z=542 $[M+H]^+$; $^1H$ NMR (400 MHz, DMSO-$d_6$) δ 12.9 (s, 1H), 12.5 (s, 1H), 8.64 (d, J=4.0 Hz, 1H), 8.30-8.25 (m, 1H), 8.02 (s, 1H), 7.80-7.76 (m, 1H), 7.72 (s, 1H), 7.36 (d, J=2.4 Hz, 1H), 7.13-7.07 (m, 1H), 6.89 (d, J=2.8 Hz, 1H), 4.76 (s, 1H), 4.61 (s, 1H), 4.47 (s, 1H), 4.35 (s, 1H), 3.91 (d, J=1.8 Hz, 3H), 3.53 (s, 3H), 2.57 (d, J=2.6 Hz, 3H).

Example 733: Synthesis of 5-Cyano-N-(5-(5-(difluoromethyl)picolinoyl)-5,6-dihydro-4H-pyrrolo[3,4-d]thiazol-2-yl)-2-methoxy-6'-methyl-[3,4'-bipyridine]-3'-carboxamide

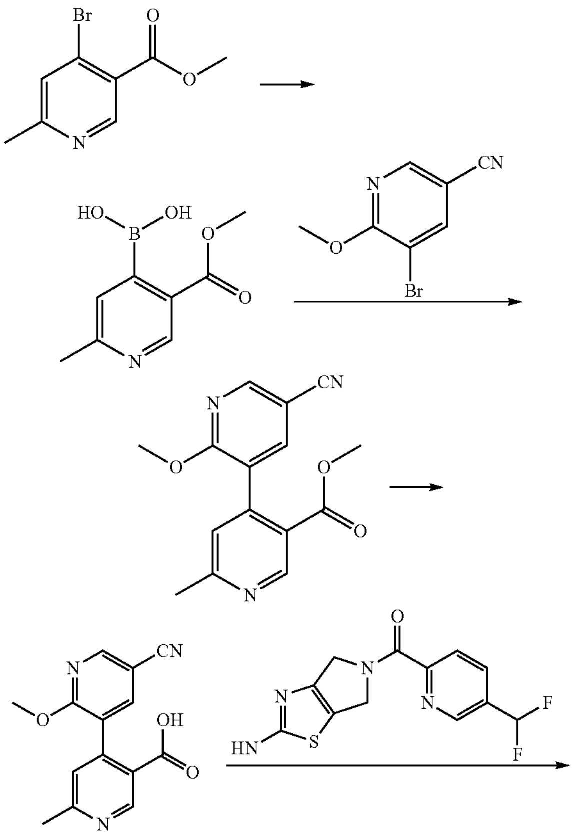

-continued

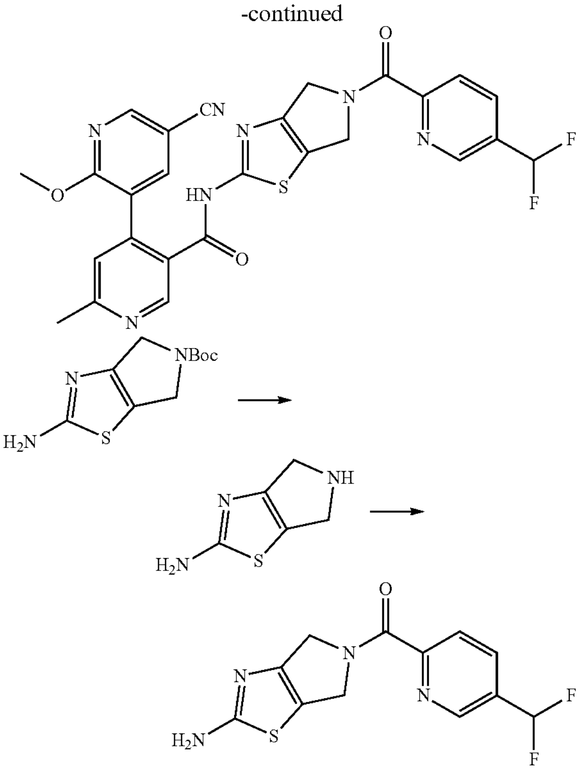

Step 1: To a solution of methyl 4-bromo-6-methylnicotinate (300) mg, 1.30 mmol) in 1,4-dioxane (10 mL) was added KOAc (384 mg, 3.91 mmol), Pd(dppf)$Cl_2$ (191 mg, 0.261 mmol), and bis(pinacolato)diboron (993 mg, 3.91 mmol). The mixture was heated at 100° C. for 16 h under $N_2$. The mixture was filtered, washed with DCM (30 mL), and the filtrate was concentrated under reduced pressure to afford (5-(methoxycarbonyl)-2-methylpyridin-4-yl)boronic acid (229 mg, 90%) as a black solid. LCMS: m/z=196 $[M+H]^+$.

Step 2: A mixture of (5-(methoxycarbonyl)-2-methylpyridin-4-yl)boronic acid (229 mg, 1.17 mmol), 5-bromo-6-methoxynicotinonitrile (250 mg, 1.17 mmol), 1,1'-bis(di-t-butylphosphino)ferrocene palladium dichloride (76.5 mg, 0.117 mmol) and $K_2CO_3$ (487 mg, 3.52 mmol) in water (2 mL) and 1,4-dioxane (8 mL) was heated at 100° C. under $N_2$ for 16 h. The mixture was diluted with water (50 mL), extracted with DCM (3×20 mL), and the combined organic layers were washed with brine (50 mL), dried over $Na_2SO_4$, filtered, and concentrated under reduced pressure. The residue was purified by prep-TLC (Pet. ether/EtOAc=2/1, v/v) to afford methyl 5-cyano-2-methoxy-6'-methyl-[3,4'-bipyridine]-3'-carboxylate (100 mg, 31%) as a yellow solid. LCMS: m/z=284 $[M+H]^+$; $^1H$ NMR (400 MHz, DMSO-$d_6$) δ 8.89 (s, 1H), 8.77 (d, J=2.2 Hz, 1H), 8.25 (d, J=2.2 Hz, 1H), 7.41 (s, 1H), 3.85 (s, 3H), 3.68 (s, 3H), 2.57 (s, 3H).

Step 3: To a solution of methyl 5-cyano-2-methoxy-6'-methyl-[3,4'-bipyridine]-3'-carboxylate (40 mg, 0.14 mmol) in MeOH (2 mL) and water (2 mL) was added NaOH (17 mg, 0.42 mmol) and the mixture was heated at 50° C. for 16 h. The mixture was adjusted to pH 3 with 2 M aqueous HCl then diluted with water (20 mL) and extracted with EtOAc (3×10 mL). The combined organic layers were washed with brine (30 mL), dried over $Na_2SO_4$, filtered, and concentrated under reduced pressure to give 5-cyano-2-methoxy-6'-methyl-[3,4'-bipyridine]-3'-carboxylic acid (36 mg, 95%) as a brown solid. LCMS: m/z=270 [M+H]$^+$; $^1$H NMR (400 MHz, DMSO-$d_6$) δ 8.91 (s, 1H), 8.75 (d, J=2.4 Hz, 1H), 8.21 (d, J=2.2 Hz, 1H), 7.45 (s, 1H), 3.85 (s, 3H), 2.59 (s, 3H). 7.94 (m, 1H), 7.46 (s, 1H), 7.25 (t, J=55.2 Hz, 1H), 5.01 (s, 1H), 4.91 (s, 1H), 4.87 (s, 1H), 4.73 (s, 1H), 3.66 (s, 3H), 2.59 (s, 3H).

TABLE AE

The following example was prepared using a similar procedure to that described for Example 733

| Ex. No. | Structure | Compound Name | LCMS [M + H]$^+$ | NMR |
|---|---|---|---|---|
| 734 | 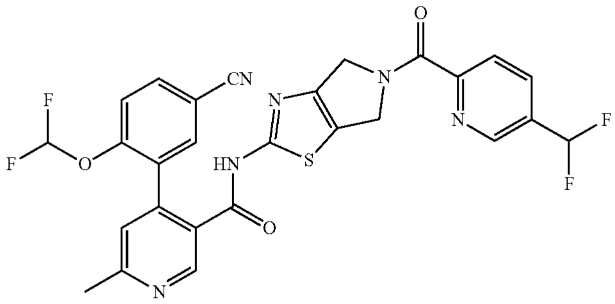 [SMILES: Cc1cc(-c2cc(C#N)ccc2OC(F)F)c(C(=O)Nc2nc3c(s2)CN(C(=O)c2ccc(C(F)F)cn2)C3)cn1] | 4-(5-Cyano-2-(difluoromethoxy)phenyl)-N-(5-(5-(difluoromethyl)picolinoyl)-5,6-dihydro-4H-pyrrolo[3,4-d]thiazol-2-yl)-6-methylnicotinamide | 583 | $^1$H NMR (400 MHZ, DMSO-$d_6$) δ 12.8 (s, 1H), 8.90-8.83 (m, 2H), 8.19 (d, J = 8.4 Hz, 1H), 8.08-7.94 (m, 3H), 7.43-7.36 (m, 2H), 7.24 (t, J = 54.8 Hz, 1H), 7.21 (t, J = 72.4 Hz, 1H), 5.00 (s, 1H), 4.91 (s, 1H), 4.86 (s, 1H), 4.72 (s, 1H), 2.59 (s, 3H) |

Step 4: A mixture of tert-butyl 2-amino-4,6-dihydro-5H-pyrrolo[3,4-d]thiazole-5-carboxylate (1.0 g, 4.1 mmol) and a 4 M HCl in MeOH solution (20 mL) was stirred at 25° C. for 2 h then concentrated under reduced pressure to afford 5,6-dihydro-4H-pyrrolo[3,4-d]thiazol-2-amine hydrochloride (600 mg), which was used in next step directly. LCMS: m/z 142 [M+H]$^+$.

Step 5: To a solution of 5,6-dihydro-4H-pyrrolo[3,4-d]thiazol-2-amine hydrochloride (600 mg), 5-(difluoromethyl)picolinic acid (1.18 g, 6.80 mmol), and DIPEA (2.75 g, 21.2 mmol) in DMF (10 mL) at 0° C. under $N_2$ was added T3P (50% in DMF, 4.06 g, 6.37 mmol) and the mixture was stirred at 25° C. for 16 h. The mixture was diluted with water (40 mL), extracted with EtOAc (4×40 mL), and the combined organic layers were washed with brine (100 mL), dried over $Na_2SO_4$, filtered, and concentrated under reduced pressure. The residue was purified by silica gel chromatography (DCM/MeOH=80/1, v/v) to afford (2-amino-4,6-dihydro-5H-pyrrolo[3,4-d]thiazol-5-yl)(5-(difluoromethyl)pyridin-2-yl)methanone (810 mg, 67% over two steps) as a yellow solid. LCMS: m/z=297 [M+H]$^+$; $^1$H NMR (400 MHz, DMSO-$d_6$) δ 8.88-8.83 (m, 1H), 8.18 (d, J=8.2 Hz, 1H), 7.96 (dd, J=8.0, 2.2 Hz, 1H), 7.39-7.08 (m, 3H), 4.83 (t, J=2.8 Hz, 1H), 4.69 (q, J=3.4 Hz, 2H), 4.52 (t, J=2.8 Hz, 1H).

Step 6: To a solution of 5-cyano-2-methoxy-6'-methyl-[3,4'-bipyridine]-3'-carboxylic acid (30 mg, 0.11 mmol) in MeCN (2 mL) was added N,N,N',N'-tetramethylchloroformamidinium-hexafluorophosphate (47 mg, 0.17 mmol), 1-methylimidazole (37 mg, 0.45 mmol) and (2-amino-4,6-dihydro-5H-pyrrolo[3,4-d]thiazol-5-yl)(5-(difluoromethyl)pyridin-2-yl)methanone (33 mg, 0.11 mmol) and the mixture was heated at 80° C. for 16 h. The mixture was diluted with water (30 mL), extracted with EtOAc (3×10 mL), and the combined organic layers were washed with brine (30 mL), dried over $Na_2SO_4$, filtered, and concentrated under reduced pressure. The residue was purified by prep-TLC (DCM/MeOH=15/1, v/v) to afford 5-cyano-N-(5-(5-(difluoromethyl)picolinoyl)-5,6-dihydro-4H-pyrrolo[3,4-d]thiazol-2-yl)-2-methoxy-6'-methyl-[3,4'-bipyridine]-3'-carboxamide (6.2 mg, 10%) as a yellow solid. LCMS: m/z=548 [M+H]$^+$; $^1$H NMR (400 MHz, DMSO-$d_6$) δ 12.8 (s, 1H), 8.92-8.72 (m, 3H), 8.50-8.29 (m, 1H), 8.20 (d, J=8.6 Hz, 1H), 8.02-

Example 735: Synthesis of 5-Chloro-2-(difluoromethoxy)-N-(5-(5-(difluoromethyl)picolinoyl)-5,6-dihydro-4H-pyrrolo[3,4-d]thiazol-2-yl)-6'-methyl-[3,4'-bipyridine]-3'-carboxamide

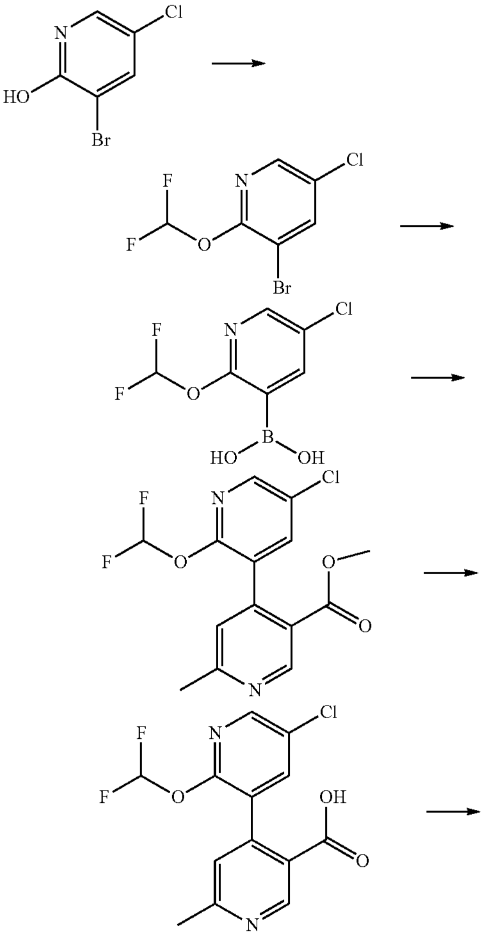

-continued

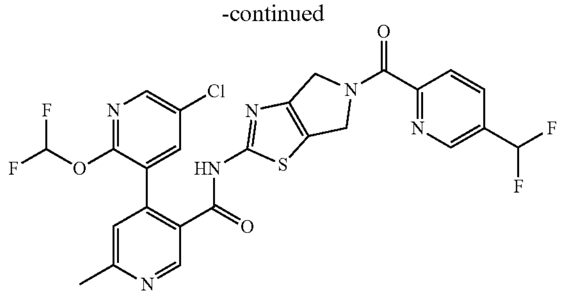

Step 1: Completed as described in Intermediate 74: 5-(Difluoromethoxy)-6-methylpyrazine-2-carboxylic acid step 3 from 3-bromo-5-chloropyridin-2-ol to afford 3-bromo-5-chloro-2-(difluoromethoxy)pyridine (1.30 g, 52%) as a colorless oil. $^1$H NMR (400 MHz, Chloroform-d) δ 8.10-8.07 (m, 1H), 7.96-7.94 (m, 1H), 7.38 (t, J=72.0 Hz, 1H).

Step 2: To a solution of 3-bromo-5-chloro-2-(difluoromethoxy)pyridine (740 mg, 2.86 mmol) and tris(prop-2-yl) borate (1.62 g, 8.59 mmol) in THF (40 mL) at −78° C. under a nitrogen atmosphere was added n-BuLi (2.5 M in hexanes, 1.72 mL, 4.29 mmol) and the mixture was stirred at −78° C. for 2 h. The reaction was quenched with 7% phosphoric acid (30 mL), then allowed to warm to room temperature, diluted with DCM (60 mL), and extracted with a 5% aqueous NaOH solution (60 mL×2). The combined aqueous layers were adjusted to pH 4-5 with 85% phosphoric acid and extracted with DCM (100 mL-2). The combined organic layers were dried over $Na_2SO_4$, filtered, and concentrated under reduced pressure to give (5-chloro-2-(difluoromethoxy)pyridin-3-yl)boronic acid (330 mg, 51%) as a yellow solid. LCMS: m/z: =224 [M+H]; $^1$H NMR (400 MHz, DMSO-$d_6$) δ 8.48 (s, 2H), 8.29 (d, J=2.8 Hz, 1H), 7.98 (d 0.1=2.8 Hz, 1H), 7.59 (t, J=72.6 Hz, 1H).

Step 3: A mixture of methyl 4-bromo-6-methylnicotinate (100 mg, 0.435 mmol), (5-chloro-2-(difluoromethoxy)pyridin-3-yl)boronic acid (150 mg, 0.673 mmol), $K_2CO_3$ (180 mg, 1.30 mmol), and Pd(dppf)$Cl_2$ (56.1 mg, 0.076 mmol) in 1,4-dioxane (2 mL) and water (0.4 mL) was heated at 100° C. under $N_2$ for 4 h. The mixture was filtered and the filtrate concentrated under reduced pressure. The residue was purified by prep-TLC (DCM/MeOH=50/1, v/v) to give methyl 5-chloro-2-(difluoromethoxy)-6'-methyl-[3,4'-bipyridine]-3'-carboxylate (80 mg, 56%) as a yellow solid. LCMS: m/z=329 $[M+H]^+$; $^1$H NMR (400 MHz, DMSO-$d_6$) δ 8.96 (s, 1H), 8.41 (d, J=2.6 Hz, 1H), 8.16 (d, J=2.6 Hz, 1H), 7.82-7.44 (m, 2H), 3.69 (s, 3H), 2.59 (s, 3H).

Step 4: A solution of methyl 5-chloro-2-(difluoromethoxy)-6'-methyl-[3,4'-bipyridine]-3'-carboxylate (50 mg, 0.15 mmol) and NaOH (18 mg, 0.46 mmol) in MeOH (2 mL) and water (2 mL) was heated at 50° C. for 1 h. The mixture was acidified to pH 5 with 2 M aqueous HCl and concentrated under reduced pressure. The residue was suspended in a mixture of DCM (10 mL) and MeOH (1 mL), filtered, and the filtrate was concentrated under reduced pressure to give 5-chloro-2-(difluoromethoxy)-6'-methyl-[3,4'-bipyridine]-3'-carboxylic acid (40 mg, 84%) as a yellow solid. LCMS: m/z=315 $[M+H]^+$; H NMR (400 MHz, DMSO-$d_6$) δ 9.28 (s, 1H), 9.15-9.09 (m, 1H), 8.98-8.31 (m, 3H), 2.69 (s, 3H).

Step 5: A solution of (2-amino-4,6-dihydro-5H-pyrrolo[3,4-d]thiazol-5-yl)(5-(difluoromethyl)pyridin-2-yl)methanone (30 mg, 0.10 mmol), 5-chloro-2-(difluoromethoxy)-6'-methyl-[3,4'-bipyridine]-3'-carboxylic acid (38 mg, 0.12 mmol), N,N,N',N'-tetramethylchloroformamidinium-hexafluorophosphate (43 mg, 0.15 mmol) and 1-methylimidazole (33 mg, 0.40 mmol) in MeCN (2 mL) was heated at 80° C. overnight. The mixture was diluted with water (10 mL), extracted with EtOAc (3×20 mL), and the combined organic layers were washed with brine (2×20 mL), dried over $Na_2SO_4$, filtered, and concentrated under reduced pressure. The residue was purified by prep-TLC (DCM/MeOH=50/1, v/v) and prep-HPLC to give 5-chloro-2-(difluoromethoxy)-N-(5-(5-(difluoromethyl)picolinoyl)-5,6-dihydro-4H-pyrrolo[3,4-d]thiazol-2-yl)-6'-methyl-[3,4'-bipyridine]-3'-carboxamide (25 mg, 41%) as a white solid. LCMS: m/z=593 $[M+H]^+$; $^1$H NMR (400 MHz, DMSO-$d_6$) δ 12.9 (s, 1H), 8.91-8.85 (M, 2H), 8.40-8.35 (m, 1H), 8.23-8.15 (m, 2H), 8.02-7.96 (m, 1H), 7.52 (t, J=71.6 Hz, 1H), 7.48 (s, 1H), 7.25 (t, J=55.2 Hz, 1H), 5.00 (s, 1H), 4.91 (s, 1H), 4.86 (s, 1H), 4.73 (s, 1H), 2.60 (s, 3H).

TABLE AF

The following example was prepared using a similar procedure to that described for Example 735

| Ex. No. | Structure | Compound Name | LCMS $[M + H]^+$ | NMR |
|---|---|---|---|---|
| 736 | 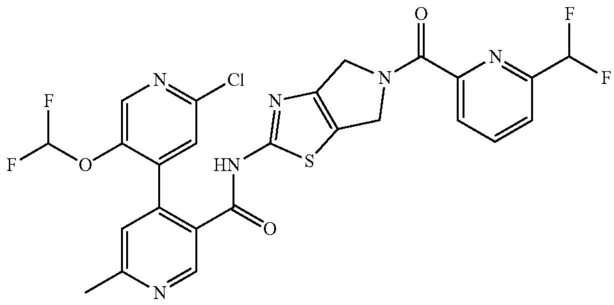 [SMILES: Cc1cc(-c2cc(Cl)ncc2OC(F)F)c(C(=O)Nc2nc3c(s2)CN(C(=O)c2cccc(C(F)F)n2)C3)cn1] | 2'-Chloro-5'-(difluoromethoxy)-N-(5-(6-(difluoromethyl)picolinoyl)-5,6-dihydro-4H-pyrrolo[3,4-d]thiazol-2-yl)-6-methyl-[4,4'-bipyridine]-3-carboxamide | 593 | $^1$H NMR (400 MHZ, DMSO-$d_6$) 8 12.9 (d, J = 18.0 Hz, 1H). 8.93 (d, J = 3.8 Hz, 1H), 8.33 (d. J = 2.4 Hz, 1H), 8.19 (t, J = 7.8 Hz, 1H), 8.05-7.98 (m, 1H), 7.87 (d, J = 7.8 Hz, 1H), 7.72 (d, ) = 2.0 Hz, 1H), 7.46 (s, 1H), 7.11 (td, J = 72.4, 2.4 Hz, 1H), 7.08 (td, J = 54.8, 14.8 Hz, 1H), 5.02 (s, 1H), 4.94 (s, 1H), 4.86 (s, 1H), 4.74 (s, 1H), 2.60 (s, 3H) |

Example 737A &737B: Synthesis of 4-(6-Chloro-3-methoxypyridazin-4-yl)-6-methyl-N-(5-(5-(trifluoromethyl)pyrazine-2-carbonyl)-5,6-dihydro-4H-pyrrolo[3,4-d]thiazol-2-yl)nicotinamide (737A) & 4-(6-Chloro-3-oxo-2,3-dihydropyridazin-4-yl)-6-methyl-N-(5-(5-(trifluoromethyl)pyrazine-2-carbonyl)-5,6-dihydro-4H-pyrrolo[3,4-d]thiazol-2-yl)nicotinamide (737B)

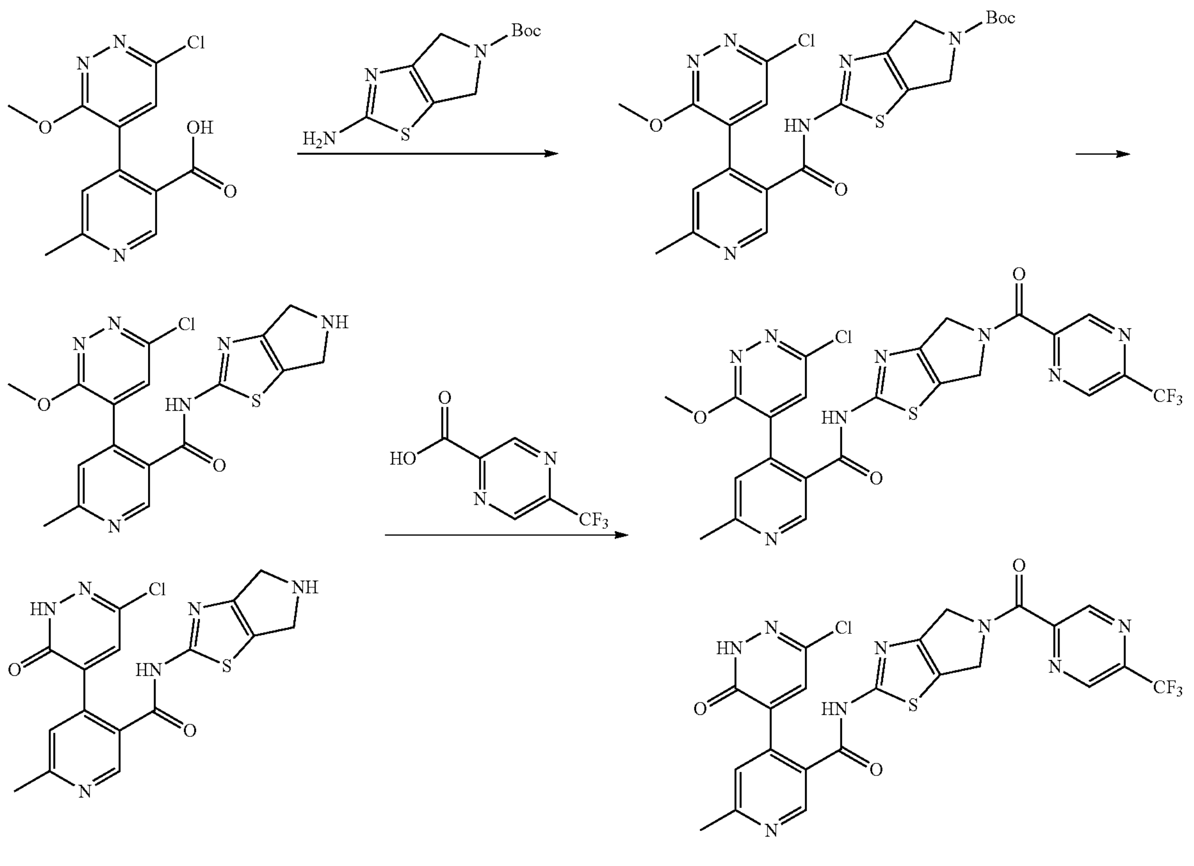

Step 1: To a solution of 4-(6-chloro-3-methoxypyridazin-4-yl)-6-methylnicotinic acid (300 mg, 1.07 mmol), tert-butyl 2-amino-4,6-dihydro-5H-pyrrolo[3,4-d]thiazole-5-carboxylate (259 mg, 1.07 mmol) and N,N,N',N'-tetramethylchloroformamidinium-hexafluorophosphate (451 mg, 1.61 mmol) in ACN (12 mL) was added 1-methylimidazole (352 mg, 4.29 mmol) and the mixture was heated at 80° C. for 20 h. The mixture was concentrated under reduced pressure and the residue diluted with water (50 mL) and extracted with EtOAc (50 mL). The organic layer was washed with water (50 mL), brine (50 mL), dried over $Na_2SO_4$, filtered, and concentrated under reduced pressure. The residue was purified by silica gel chromatography (Pet. ether/EtOAc=1/1, v/v) and prep-TLC (DCM/MeOH=15/1, v/v) to afford tert-butyl 2-(4-(6-chloro-3-methoxypyridazin-4-yl)-6-methylnicotinamido)-4,6-dihydro-5H-pyrrolo[3,4-d]thiazole-5-carboxylate (230 mg, 43%) as an off-white solid. LCMS: m/z=503 $[M+H]^+$; $^1H$ NMR (400 MHz, DMSO-$d_6$) δ58.89 (s, 1H), 8.00 (d, J=1.0 Hz, 1H), 7.53 (s, 1H), 4.54 (d, J=12.6 Hz, 2H), 4.42 (d, J=11.4 Hz, 2H), 3.75 (s, 3H), 2.60 (s, 3H), 1.45 (d, J=1.2 Hz, 9H).

Step 2: A mixture of tert-butyl 2-(4-(6-chloro-3-methoxypyridazin-4-yl)-6-methylnicotinamido)-4,6-dihydro-5H-pyrrolo[4-d]thiazole-5-carboxylate (50 mg, 0.099 mmol), MeOH (0.2 mL), and a 4 M HCl in dioxane solution (1 mL) was stirred at 25° C. for 10 mi then concentrated under reduced pressure to give a 3:2 mixture of 4-(6-chloro-3-methoxypyridazin-4-yl)-N-(5,6-dihydro-4H-pyrrolo[3,4-d]thiazol-2-yl)-6-methylnicotinamide and 4-(6-chloro-3-oxo-2,3-dihydropyridazin-4-yl)-N-(5,6-dihydro-4H-pyrrolo[3,4-d]thiazol-2-yl)-6-methylnicotinamide (40 mg) as a green solid. LCMS: m/z=403 and 389 $[M+H]^+$.

Step 3: To a solution of a 3:2 mixture of 4-(6-chloro-3-methoxypyridazin-4-yl)-N-(5,6-dihydro-4H-pyrrolo[34-d]thiazol-2-yl)-6-methylnicotinamide and 4-(6-chloro-3-oxo-2,3-dihydropyridazin-4-yl)-N-(5,6-dihydro-4H-pyrrolo[3,4-d]thiazol-2-yl)-6-methylnicotinamide (40 mg) in DMF (3 mL) at 0° C. was added 5-(trifluoromethyl)pyrazine-2-carboxylic acid (25 mg, 0.13 mmol), DIPEA (0.10 g, 0.79 mmol), and T3P (50% in DMF, 95 mg, 0.15 mmol) and the mixture was stirred at 25° C. for 20 h. The mixture was diluted with water (20 mL), extracted with EtOAc (20 mL×2), and the combined organic layers washed with water (20 mL), brine (20 mL), dried over $Na_2SO_4$, filtered, and concentrated under reduced pressure. The residue was purified by prep-TLC (DCM/MeOH=15/1, v/v) to afford two products:

Example 737A: 4-(6-chloro-3-methoxypyridazin-4-yl)-6-methyl-N-(5-(5-(trifluoromethyl)pyrazine-2-carbonyl)-5,6-dihydro-4H-pyrrolo[3,4-d]thiazol-2-yl)nicotinamide (11 mg, 19% over two steps) as an off-white solid. LCMS: m/z=577 $[M+H]^+$, $^1H$ NMR (400 MHz, DMSO-$d_6$) δ 13.0 (s, 1H), 9.29 (d, J=10.0 Hz, 1H), 9.23 (s, 1H), 8.91 (d, J=3.0 Hz, 1H), 7.99 (s, 1H), 7.52 (s, 1H), 5.05 (s, 1H), 4.93 (s, 1H), 4.91 (s, 1H), 4.78 (s, 1H), 3.75 (s, 3H), 2.60 (d, J=1.6 Hz, 3H)

Example 737B: 4(6-Chloro-3-oxo-2,3-dihydropyridazin-4-yl)-6-methyl-N-(5-(5-(trifluoromethyl)pyrazine-2-carbonyl)-5,6-dihydro-4H-pyrrolo[3,4-d]thiazol-2-yl)nicotinamide (4 mg, 7% over two steps) was also obtained as a yellow solid. LCMS: m/z=563 [M+H]1; $^1H$ NMR (400 MHz, DMSO-$d_6$) δ 13.3 (s, 1H), 12.9 (s, 1H), 9.29 (d, J=9.0 Hz, 1H), 9.24 (s, 1H), 8.84 (s, 1H), 7.76 (s, 1H), 7.44 (s, 1H), 5.05 (s, 1H), 4.92 (s, 2H), 4.76 (s, 1H), 2.58 (s, 3H).

TABLE AG

The following examples were prepared using a similar procedure to that described for Examples 737A and 737B

| Ex. No. | Structure | Compound Name | LCMS $[M + H]^+$ | NMR |
|---|---|---|---|---|
| 738 | 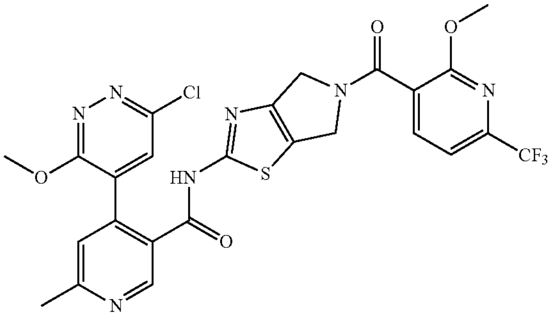 [SMILES: COc1nc(C(F)(F)F)ccc1C(=O)N1Cc2nc(NC(=O)c3cnc(C)cc3-c3cc(Cl)nnc3OC)sc2C1] | 4-(6-Chloro-3-methoxypyridazin-4-yl)-N-(5-(2-methoxy-6-(trifluoromethyl) nicotinoyl)-5,6-dihydro-4H-pyrrolo[3,4-d]thiazol-2-yl)-6-methylnicotinamide | 606 | $^1H$ NMR (400 MHZ, DMSO-$d_6$) δ 13.0 (s. 1H), 8.89 (d, J = 4.6 Hz, 1H), 8.09 (d, J = 7.4 Hz, 1H), 8.00 (s, 1H), 7.62 (dd, J = 7.6, 3.0 Hz, 1H), 7.54 (s, 1H), 4.80 (s, 1H), 4.68 (s, 1H), 4.52 (s, 1H), 4.43 (s, 1H), 3.98 (d, J = 1.4 Hz, 3H), 3.74 (d, J = 1.6 Hz, 3H), 2.60 (d, J = 2.4 Hz, 3H) |
| 739 | 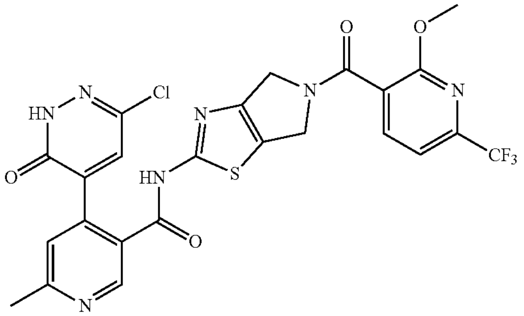 [SMILES: COc1nc(C(F)(F)F)ccc1C(=O)N1Cc2nc(NC(=O)c3cnc(C)cc3-c3cc(Cl)n[nH]c3=O)sc2C1] | 4-(6-Chloro-3-oxo-2,3-dihydropyridazin-4-yl)-N-(5-(2-methoxy-6-(trifluoromethyl)nicotinoyl)-5,6-dihydro-4H-pyrrolo[3,4-d]thiazol-2-yl)-6-methylnicotinamide | 592 | $^1H$ NMR (400 MHZ, DMSO-$d_6$) δ 13.3 (s, 1H), 12.9 (s, 1H), 8.81 (d, J = 3.0 Hz, 1H), 8.09 (dd, J = 7.6, 4.4 Hz, 1H), 7.78 (s, 1H), 7.62 (dd, J = 7.4, 4.8 Hz, 1H), 7.46 (s, 1H), 4.81 (s, 1H), 4.67 (s, 1H), 4.52 (s, 1H), 4.42 (s, 1H), 3.98 (s, 3H), 2.59 (d, J = 2.4 Hz, 3H) |
| 740 | 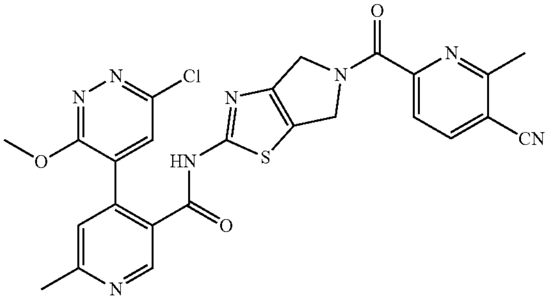 [SMILES: COc1nnc(Cl)cc1-c1cc(C)ncc1C(=O)Nc1nc2c(s1)CN(C(=O)c1ccc(C#N)c(C)n1)C2] | 4-(6-Chloro-3-methoxypyridazin-4-yl)-N-(5-(5-cyano-6-methylpicolinoyl)-5,6-dihydro-4H-pyrrolo[3,4-d]thiazol-2-yl)-6-methylnicotinamide | 547 | $^1H$ NMR (400 MHZ, DMSO-$d_6$) δ 13.0 (s, 1H), 8.90 (d, J = 3.6 Hz, 1H), 8.42 (d, J = 8.0 Hz, 1H), 8.00 (s, 1H), 7.80 (dd, J = 8.0, 5.0 Hz, 1H), 7.53 (s, 1H), 4.97 (s, 1H), 4.86 (s, 2H), 4.72 (s, 1H), 3.75 (s, 3H), 2.76 (d, J = 5.0 Hz, 3H), 2.60 (s, 3H) |
| 741 | 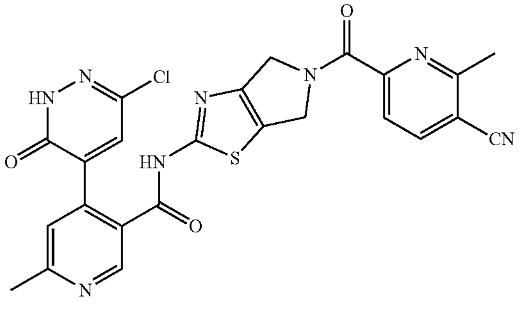 [SMILES: Cc1cc(-c2cc(Cl)n[nH]c2=O)c(C(=O)Nc2nc3c(s2)CN(C(=O)c2ccc(C#N)c(C)n2)C3)cn1] | 4-(6-Chloro-3-oxo-2,3-dihydropyridazin-4-yl)-N-(5-(5-cyano-6-methylpicolinoyl)-5,6-dihydro-4H-pyrrolo[3,4-d]thiazol-2-yl)-6-methylnicotinamide | 533 | $^1H$ NMR (400 MHZ, DMSO-$d_6$) δ 13.3 (s, 1H). 12.9 (s. 1H), 8.82 (d, J = 4.2 Hz, 1H), 8.42 (d, J = 8.0 Hz, 1H), 7.85-7.73 (m, 2H), 7.45 (s, 1H), 4.98 (s, 1H), 4.86 (s, 2H), 4.71 (s, 1H), 2.77 (d, J = 2.8 Hz, 3H), 2.59 (s, 3H) |

TABLE AG-continued

The following examples were prepared using a similar procedure to that described for Examples 737A and 737B

| Ex. No. | Structure | Compound Name | LCMS $[M + H]^+$ | NMR |
|---|---|---|---|---|
| 742 | 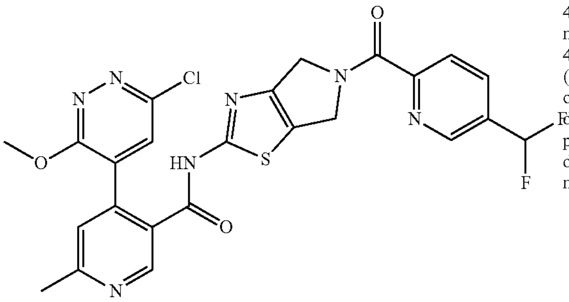 [SMILES: COc1nnc(Cl)cc1-c1cc(C)ncc1C(=O)Nc1nc2c(s1)CN(C(=O)c1ccc(C(F)F)cn1)C2] | 4-(6-chloro-3-methoxypyridazin-4-yl)-N-(5-(5-(difluoromethyl)picolinoyl)-5,6-dihydro-4H-pyrrolo[3,4-d]thiazol-2-yl)-6-methylnicotinamide | 558 | $^1$H NMR (400 MHZ, DMSO-$d_6$) δ 12.97 (s, 1H), 8.93-8.80 (m, 2H), 8.20 (d. J = 8.2 Hz, 1H), 8.04-7.94 (m, 2H), 7.54 (s, 1H), 7.25 (t, J = 54.7 Hz, 1H), 5.02 (s, 1H), 4.90 (d. J = 19.5 Hz, 2H), 4.75 (s, 1H), 3.75 (s, 3H), 2.60 (d, J = 1.6 Hz. 3H) |
| 697 | 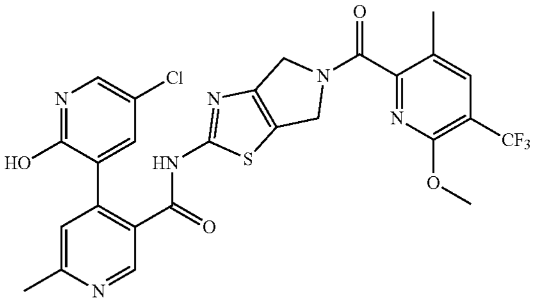 [SMILES: COc1nc(C(=O)N2Cc3nc(NC(=O)c4cnc(C)cc4-c4cc(Cl)cnc4O)sc3C2)c(C)cc1C(F)(F)F] | 5-Chloro-2-hydroxy-N-(5-(6-methoxy-3-methyl-5-(trifluoromethyl)picolinoyl)-5,6-dihydro-4H-pyrrolo[3,4-d]thiazol-2-yl)-6'-methyl-[3,4'-bipyridine]-3'-carboxamide | 605 | $^1$H NMR (400 MHZ, DMSO-$d_6$) δ 12.7-12.6 (m, 1H), 12.1 (s, 1H), 8.68-8.63 (m, 1H), 8.16-8.12 (m, 1H), 7.75-7.62 (m, 2H), 7.37 (s, 1H), 4.85 (s, 1H), 4.70 (s, 1H), 4.61 (s, 1H), 4.51-4.47 (m, 1H), 3.98 (d, J = 3.6 Hz, 3H), 2.57-2.55 (m, 3H), 2.29 (s, 3H). |

Example 743: Synthesis of 2'-Chloro-N-(5-(3-fluoro-6-methyl-5-(trifluoromethyl)picolinoyl)-5,6-dihydro-4H-pyrrolo[3,4-d]thiazol-2-yl)-5'-methoxy-6-methyl-[4,4'-bipyridine]-3-carboxamide

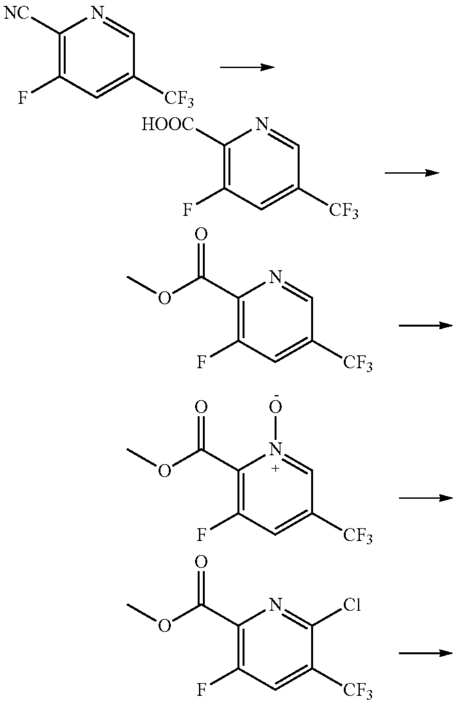

-continued

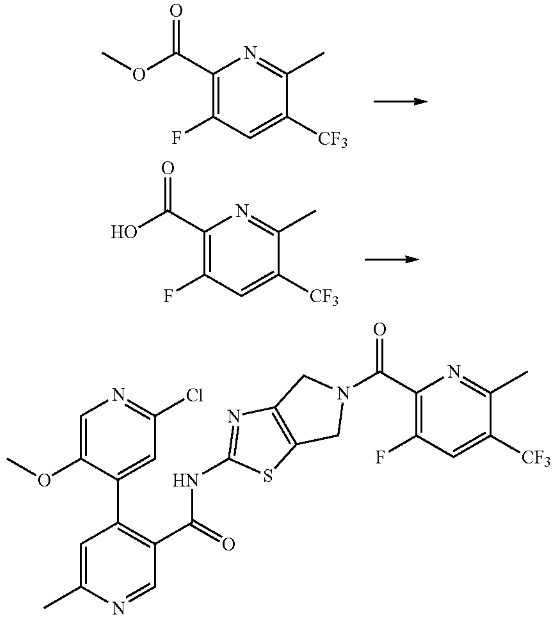

Step 1: A solution of 3-fluoro-5-(trifluoromethyl)picolinonitrile (1.00 g, 5.00 mmol) in conc. $H_2SO_4$ (10 mL) was heated at 110° C. for 3 days. The mixture was allowed to cool, poured into ice-water, diluted with water (30 mL), and extracted with DCM (60 mL×2). The combined organic layers were washed with brine (2×40 mL), dried over $Na_2SO_4$, filtered, and concentrated under reduced pressure to give 3-fluoro-5-(trifluoromethyl)picolinic acid (1.05 g, 100%) as a white solid. LCMS: m/z: =210 $[M+H]^+$, $^1H$ NMR (400 MHz, DMSO-$d_6$) δ 8.94 (s, 1H), 8.54-8.48 (m, 1H).

Step 2: To a solution of 3-fluoro-5-(trifluoromethyl)picolinic acid (100 mg, 0.478 mmol) and $K_2CO_3$ (66.1 mg, 0.478 mmol) in DMF (2 mL) at 0° C. was added methyl iodide (67.9 mg, 0.478 mmol) and the mixture was stirred at room temperature overnight. The mixture was diluted with water (20 mL), extracted with EtOAc (3×40 mL), and the combined organic layers were washed with brine (2×20 mL), dried over $Na_2SO_4$, filtered, and concentrated under reduced pressure. The residue was purified by prep-TLC (DCM/MeOH=20/1, v/v) to give methyl 3-fluoro-5-(trifluoromethyl)picolinate (36 mg, 33%) as a yellow solid. LCMS: m/z=224 $[M+H]^+$, $^1H$ NMR (400 MHz, DMSO-$d_6$) δ 8.98 (s, 1H), 8.59-8.54 (m, 1H), 3.94 (s, 3H).

Step 3: Completed as described in Intermediate 62: 6-Chloro-5-methoxy-3-methylpyrazine-2-carboxylic acid step 1 from methyl 3-fluoro-5-(trifluoromethyl)picolinate to afford 3-fluoro-2-(methoxycarbonyl)-5-(trifluoromethyl) pyridine 1-oxide (346 mg, 64%) as a white solid. LCMS: m/z=240 $[M+H]^+$; $^1H$ NMR (400 MHz, DMSO-46) δ 8.92 (s, 1H), 8.14 (d, J=7.8 Hz, 1H), 3.98 (s, 3H).

Step 4: Completed as described in Intermediate 62: 6-Chloro-5-methoxy-3-methylpyrazine-2-carboxylic acid step 2 from 3-fluoro-2-(methoxycarbonyl)-5-(trifluoromethyl)pyridine 1-oxide to afford methyl 6-chloro-3-fluoro-5-(trifluoromethyl)picolinate (248 mg, 67%) as a yellow oil. LCMS: m/z=258 $[M+H]^+$; $^1H$ NMR (400 MHz, DMSO-$d_6$) δ 8.67 (d, J=9.4 Hz, 1H), 3.94 (s, 3H).

Step 5: Completed as described in Intermediate 68: 3,4-Dimethyl-5-(trifluoromethyl)picolinic acid step 3 starting from methyl 6-chloro-3-fluoro-5-(trifluoromethyl)picolinate to afford methyl 3-fluoro-6-methyl-5-(trifluoromethyl)picolinate (14 mg, 30%) as a yellow oil. LCMS: m/z=238 $[M+H]^+$; $^1H$ NMR (400 MHz, Chloroform-d) δ 7.77 (d, J=9.6 Hz, 1H), 4.03 (s, 3H), 2.75 (s, 3H).

Step 6: A solution of methyl 3-fluoro-6-methyl-5-(trifluoromethyl)picolinate (30 mg, 0.13 mmol) and LiOH (9.1 mg, 0.38 mmol) in THF (1 mL) and water (1 mL) was stirred at room temperature for 1 h. The mixture was adjusted to pH 3 with 2 M aqueous HCl, extracted with DCM (3×20 mL), and the combined organic layers were washed with brine (2×10 mL), dried over $Na_2SO_4$, filtered, and concentrated under reduced pressure to give 3-fluoro-6-methyl-5-(trifluoromethyl)picolinic acid (17 mg, 60%) as a yellow solid. LCMS: m/z=224 $[M+H]^+$.

Step 7: A solution of 3-fluoro-6-methyl-5-(trifluoromethyl)picolinic acid (17 mg, 0.076 mmol), 2'-chloro-N-(5,6-dihydro-4H-pyrrolo[3,4-d]thiazol-2-yl)-5'-methoxy-6-methyl-[4,4'-bipyridine]-3-carboxamide (30 mg, 0.076 mmol), HATU (43 mg, 0.11 mmol), and DIPEA (29 mg, 0.23 mmol) in DCM (5 mL) was stirred at room temperature overnight. The mixture was diluted with water (10 mL), extracted with DCM (3×20 mL), and the combined organic layers were washed with brine (2×20 mL), dried over $Na_2SO_4$, filtered, and concentrated under reduced pressure. The residue was purified by prep-TLC (DCM/MeOH=20/1, v/v) to give 2'-chloro-N-(5-(3-fluoro-6-methyl-5-(trifluoromethyl)picolinoyl)-5,6-dihydro-4H-pyrrolo[3,4-d]thiazol-2-yl)-5'-methoxy-6-methyl-[4,4'-bipyridine]-3-carboxamide (20 mg, 44%) as a yellow solid. LCMS: m/z=607 $[M+H]^+$; $^1H$ NMR (400 MHz, DMSO-$d_6$) δ 12.8 (s, 1H), 8.78 (d, J=4.4 Hz, 1H), 8.41-8.34 (m, 1H), 8.17 (s, 1H), 7.54 (s, 1H), 7.43 (s, 1H), 4.86 (s, 1H), 4.72 (s, 2H), 4.60 (s, 1H), 3.60 (s, 3H), 2.66 (s, 3H), 2.59 (s, 3H).

Example 744: Synthesis of 2'-chloro-N-(5-((1s,4s)-4-(difluoromethyl)cyclohexane-1-carbonyl)-5,6-dihydro-4H-pyrrolo[3,4-d]thiazol-2-yl)-5'-methoxy-6-methyl-[4,4'-bipyridine]-3-carboxamide

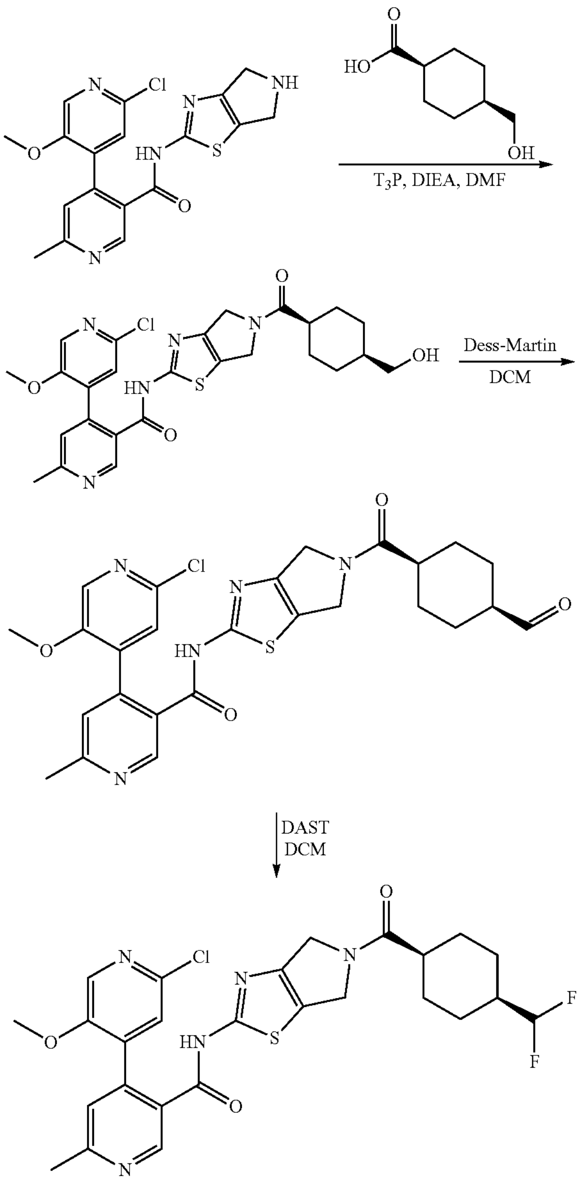

Step 1: A solution of (1s,4s)-4-(hydroxymethyl)cyclohexane-1-carboxylic acid (197 mg 1.2 mmol) in DMF (2 mL) was treated with T3P (792 mg, 2.5 mmol) and 2'-chloro-N-(5,6-dihydro-4H-pyrrolo[3,4-d]thiazol-2-yl)-5'-methoxy-6-methyl-[4,4'-bipyridine]-3-carboxamide (500 mg, 1.2 mmol) at 25° C. under a nitrogen atmosphere followed by the addition of DIEA (804 mg, 6.2 mmol) dropwise at 25° C. The reaction mixture was stirred at 25° C. for 12 h under a nitrogen atmosphere. The mixture was purified directly by reverse-phase flash chromatography (10-50% MeCN in water with 0.1% formic acid modifier) to afford 2'-chloro- N-(5-((1s,4s)-4-(hydroxymethyl)cyclohexane-1-carbonyl)-5,6-dihydro-4H-pyrrolo[3,4-d]thiazol-2-yl)-5'-methoxy-6-methyl-[4,4'-bipyridine]-3-carboxamide (180.0 mg, 26.7% yield) as a white solid. LCMS: m/z=542[M+H]$^+$.

Step 2: A solution of 2'-chloro-N-(5-((1s,4s)-4-(hydroxymethyl)cyclohexane-1-carbonyl)-5,6-dihydro-4H-pyrrolo[3,4-d]thiazol-2-yl)-5'-methoxy-6-methyl-[4,4'-bipyridine]-3-carboxamide (160 mg, 3.0 mmol) in DCM (20 mL) was treated with Dess-Martin periodinane (150 mg, 3.5 mmol) in portions at 25° C. under a nitrogen atmosphere. The reaction mixture was stirred at 25° C. for 12 hours under a nitrogen atmosphere. The reaction mixture was concentrated under reduced pressure. The mixture was purified directly by reverse-phase flash chromatography (10-50% MeCN in water with 0.1% formic acid modifier) to afford 2'-chloro-N-(5-((1s,4s)-4-formylcyclohexane-1-carbonyl)-5,6-dihydro-4H-pyrrolo[3,4-d]thiazol-2-yl)-5'-methoxy-6-methyl-[4,4'-bipyridine]-3-carboxamide (110.0 mg, 69.0% yield) as a white solid. LCMS: m/z=540 [M+H]$^+$.

Step 3: A solution of 2'-chloro-N-(5-((1s,4s)-4-formylcyclohexane-1-carbonyl)-5,6-dihydro-4H-pyrrolo[3,4-d]thiazol-2-yl)-5'-methoxy-6-methyl-[4,4'-bipyridine]-3-carboxamide (120 mg, 2.1 mmol) in DCM (10 mL) was treated with BAST (98 mg, 4.4 mmol) dropwise at 0° C. under a nitrogen atmosphere. The reaction mixture was warmed to 25° C. and stirred at 25° C. for 2 h under a nitrogen atmosphere. The reaction mixture was quenched with water (1 mL) and concentrated under reduced pressure. The residue was purified by prep-TLC (DCM/MeOH, 15/1) to afford the crude product. The crude product was purified by prep-HPLC (46-64% MeOH in water with 0.1% formic acid modifier) to afford 2'-chloro-N-(5-((1s,4s)-4-(difluoromethyl)cyclohexane-1-carbonyl)-5,6-dihydro-4H-pyrrolo[3,4-d]thiazol-2-yl)-5'-methoxy-6-methyl-[4,4'-bipyridine]-3-carboxamide (14.0 mg, 11.2% yield) as a white solid. LCMS: m/z=562 [M+H]$^+$, $^1$H NMR (300 MHz, Methanol-$d_4$) δ 8.78 (d, J=1.7 Hz, 1H), 8.08 (s, 1H), 7.52 (s, 1H), 7.45 (s, 1H), 5.67 (d, J=4.2 Hz, 1H), 4.95-4.92 (m, 1H), 4.79-4.75 (m, 1H), 4.73-4.67 (m, 1H), 4.58-4.50 (m, 1H), 3.70 (s, 3H), 2.84-2.74 (m, 1H), 2.69 (s, 3H), 2.64-2.53 (m, 1H), 2.03-1.70 (m, 6H), 1.58-1.47 (m, 1H), 1.38-1.25 (m, 1H).

Example 746: Synthesis of 2'-chloro-N-(5-(3-(difluoromethoxy)cyclohexane-1-carbonyl)-5,6-dihydro-4H-pyrrolo[3,4-d]thiazol-2-yl)-5'-methoxy-6-methyl-[4,4'-bipyridine]-3-carboxamide

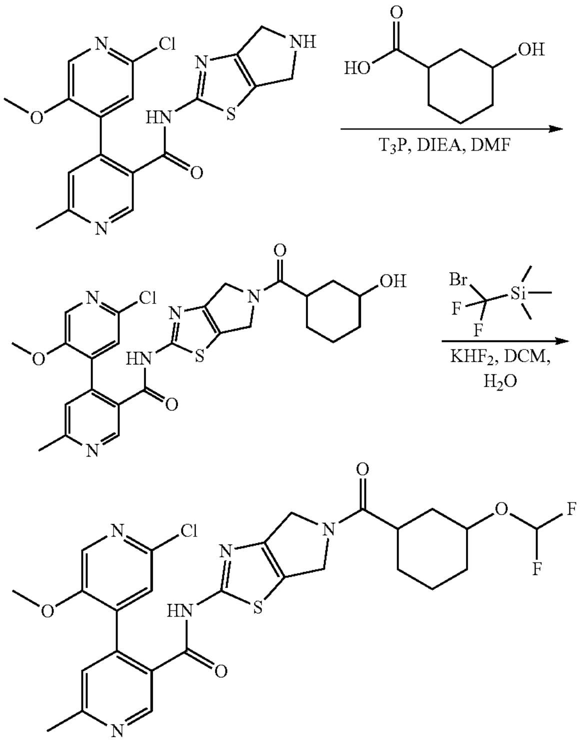

Step 1: A solution of 2'-chloro-N-(5,6-dihydro-4H-pyrrolo[3,4-d]thiazol-2-yl)-5'-methoxy-6-methyl-[4,4'-bipyridine]-3-carboxamide (500 mg, 1.2 mmol) in DMF (6 mL) was treated with DIEA (1.6 g, 12.4 mmol) at 25° C. under a nitrogen atmosphere followed by the addition of 3-hydroxycyclohexane-1-carboxylic acid (215 mg, 1.5 mmol) and T3P (1.2 g, 3.7 mmol) in portions at 25° C. The reaction mixture was charged with $N_2$ three times at 25° C. and stirred at 25° C. for 2 h under a nitrogen atmosphere. The resulting mixture was purified by reverse-phase flash chro-

TABLE AH

The following example was prepared using a similar procedure to that described for Example 744

| Ex. No. | Structure | Compound Name | LCMS [M + H]$^+$ | NMR |
|---|---|---|---|---|
| 745 | 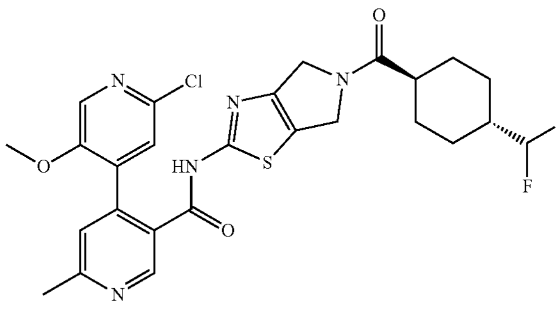 | 2'-chloro-N-(5-((1r,4r)-4-(difluoromethyl)cyclohexane-1-carbonyl)-5,6-dihydro-4H-pyrrolo[3,4-d]thiazol-2-yl)-5'-methoxy-6-methyl-[4,4'-bipyridine]-3-carboxamide | 562 | $^1$H NMR (300 MHZ, DMSO-$d_6$) δ 12.79 (s, 1H), 8.79 (s, 1H), 8.20-8.14 (m, 1H), 7.54 (s, 1H), 7.43 (s, 1H), 6.08-5.64 (m, 1H), 4.81 (d, J = 38.1 Hz, 2H), 4.50 (d, J = 39.0 Hz, 2H), 3.60 (s, 3H), 2.59 (s, 3H), 2.49-2.45 (m, 1H), 1.83 (t, J = 14.7 Hz, 5H), 1.42-1.13 (m, 4H) |

matography (20-40% MeCN in water with 0.1% formic acid modifier) to afford 2'-chloro-N-(5-(3-hydroxycyclohexane-1-carbonyl)-5,6-dihydro-4H-pyrrolo[3,4-d]thiazol-2-yl)-5'-methoxy-6-methyl-[4,4'-bipyridine]-3-carboxamide (321 mg, 49% yield) as a white solid. LCMS: m/z 528 $[M+H]^+$.

Step 2: To a solution of 2'-chloro-N-(5-(3-hydroxycyclohexane-1-carbonyl)-5,6-dihydro-4H-pyrrolo[3,4-d]thiazol-2-yl)-5'-methoxy-6-methyl-[4,4'-bipyridine]-3-carboxamide (320 mg, 0.6 mmol) in DCM (8 mL) and water (8 mL) was added $KHF_2$ (237 mg, 3.0 mmol) and (bromodifluoromethyl)trimethylsilane (739 mg, 3.6 mmol) in one portion at 0° C. The reaction mixture was stirred at 25° C. for 16 h. The resulting mixture was concentrated under reduced pressure. The residue was purified by reverse-phase flash chromatography (10-60% MeCN in water with 0.1% formic acid modifier) to afford the crude product. The crude product was purified by prep-TLC (DCM/MeOH 10/1) to afford crude product. The crude product was purified by reversed-phase flash chromatography (20-40% MeCN in water with 0.1% formic acid modifier) to afford 2'-chloro-N-(5-(3-(difluoromethoxy)cyclohexane-1-carbonyl)-5,6-dihydro-4H-pyrrolo[3,4-d]thiazol-2-yl)-5'-methoxy-6-methyl-[4,4'-bipyridine]-3-carboxamide (5.8 mg, 1.6% yield) as a white solid. LCMS: m/z 578 $[M+H]^+$, $^1H$ NMR (40) MHz, DMSO-$d_6$) δ 9.27 (d, J=4.7 Hz, 1H), 8.16 (d, J=3.3 Hz, 1H), 7.94 (d, J=1.9 Hz, 1H), 7.45 (s, 1H), 7.29 (s, 1H), 4.88 (t, J=3.5 Hz, 1H), 4.73 (t, J=3.6 Hz, 1H), 4.66-4.52 (m, 2H), 4.44 (t, J=3.6 Hz, 1H), 3.63 (d, J=1.6 Hz, 3H), 3.52-3.42 (m, 1H), 2.58 (s, 3H), 1.93-1.78 (m, 2H), 1.78-1.61 (m, 2H), 1.42-1.10 (m, 3H), 1.08-1.05 (m, 1H).

Example 747: Synthesis of 2'-chloro-N-(5-(4,5-dimethyloxazole-2-carbonyl)-5,6-dihydro-4H-pyrrolo[3,4-d]thiazol-2-yl)-5'-methoxy-6-methyl-[4,4'-bipyridine]-3-carboxamide

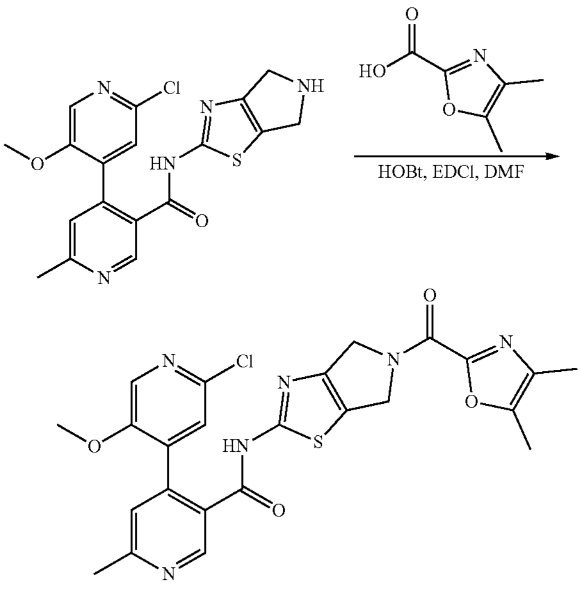

A solution of 2'-chloro-N-(5,6-dihydro-4H-pyrrolo[3,4-d]thiazol-2-yl)-5'-methoxy-6-methyl-[4,4'-bipyridine]-3-carboxamide (50 mg, 0.1 mmol) in DMF (1 mL) was treated with EDCI (48 mg, 0.3 mmol) and 4,5-dimethyloxazole-2-carboxylic acid (18 mg, 0.1 mmol) at 25° C. under a nitrogen atmosphere followed by the addition of HOBt (34 mg, 0.3 mmol) in portions at 25° C. The reaction mixture was charged with $N_2$ three times at 25° C. and stirred for 12 h at 25° C. under a nitrogen atmosphere. The mixture was purified by reverse-phase flash chromatography (10-50% MeCN in water with 0.1% formic acid modifier) to afford 2'-chloro-N-(5-(4,5-dimethyloxazole-2-carbonyl)-5,6-dihydro-4H-pyrrolo[3,4-d]thiazol-2-yl)-5'-methoxy-6-methyl-[4,4'-bipyridine]-3-carboxamide (1.5 mg, 2.3% yield) as a white solid. LCMS: m/z=525 $[M+H]^+$, $^1H$ NMR (300 MHz, Methanol-$d_4$) δ 8.78 (s, 1H), 8.08 (s, 1H), 7.52 (s, 1H), 7.45 (s, 1H), 5.36 (s, 1H), 5.16 (s, 1H), 4.98 (s, 1H), 4.74 (s, 1H), 3.71 (s, 3H), 2.69 (s, 3H), 2.38 (s, 3H), 2.19 (d, J=2.0 Hz, 3H).

Example 748: Synthesis of 2'-chloro-5'-methoxy-6-methyl-N-(5-(3-methyl-5-(trifluoromethyl)pyrazine-2-carbonyl)-5,6-dihydro-4H-pyrrolo[3,4-d]thiazol-2-yl)-[4,4'-bipyridine]-3-carboxamide

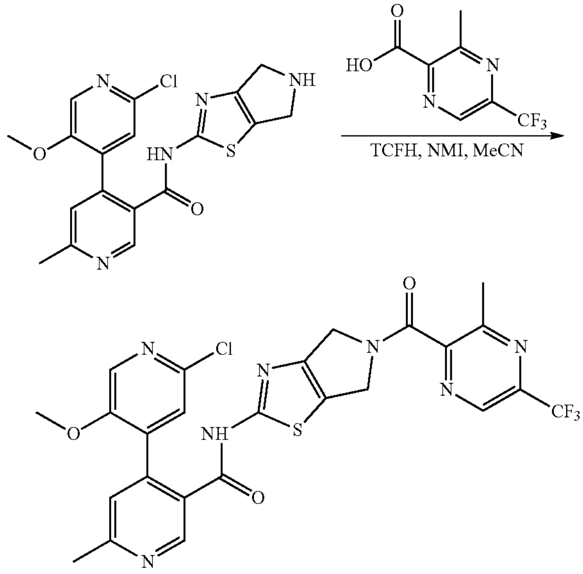

To a stirred solution of 3-methyl-5-(trifluoromethyl)pyrazine-2-carboxylic acid (150 mg, 0.73 mmol) and 2'-chloro-N-(5,6-dihydro-4H-pyrrolo[3,4-d]thiazol-2-yl)-5'-methoxy-6-methyl-[4,4'-bipyridine]-3-carboxamide (292 mg, 0.73 mmol) in MeCN (8 mL) was added TCFH (1.23 g, 4.37 mmol) and 1-methylimidazole (359 mg, 4.37 mmol) at room temperature. The resulting mixture was stirred for 1 hour at 60° C. under a nitrogen atmosphere. The resulting mixture was diluted with water (20 mL) and extracted with EtOAc (3×20 mL). The combined organic layers were washed with brine (2×20 mL) and dried over anhydrous $Na_2SO_4$. After filtration, the filtrate was concentrated under reduced pressure. The residue was purified by reverse-phase flash chromatography (10-50% MeOH in water with 0.1% formic acid modifier) to afford 2'-chloro-5'-methoxy-6-methyl-N-(5-(3-methyl-5-(trifluoromethyl)pyrazine-2-carbonyl)-5,6-dihydro-4H-pyrrolo[3,4-d]thiazol-2-yl)-[4,4'-bipyridine]-3-carboxamide (127 mg, 38% over two steps) as an off white solid. LCMS: m/z=590 $[M+H]^+$, $^1H$ NMR (300 MHz, DMSO-$d_6$) δ 12.85 (s, 1H), 9.10 (d, J=2.7 Hz, 1H), 8.79 (d, J=3.4 Hz, 1H), 8.18 (d, J=1.5 Hz, 1H), 7.56 (s, 1H), 7.44 (d, J=2.1 Hz, 1H), 4.97-4.52 (m, 4H), 3.60 (s, 3H), 2.67 (d, J=1.6 Hz, 3H), 2.59 (d, J=2.2 Hz, 3H).

TABLE AI

| The following example was prepared using a similar procedure to that described for Example 748 | | | | |
|---|---|---|---|---|
| Ex. No. | Structure | Compound Name | LCMS $[M + H]^+$ | NMR |
| 749 | 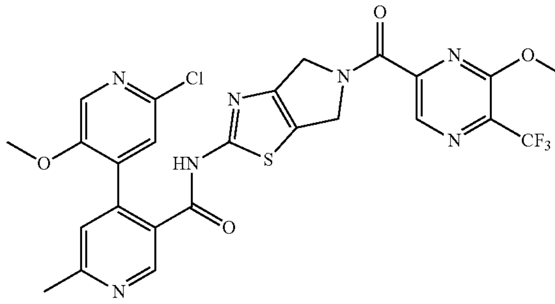 | 2'-chloro-5'-methoxy-N-(5-(6-methoxy-5-(trifluoromethyl) pyrazine-2-carbonyl)-5,6-dihydro-4H-pyrrolo[3,4-d]thiazol-2-yl)-6-methyl-[4,4'-bipyridine]-3-carboxamide | 606 | $^1H$ NMR (300 MHZ, DMSO-$d_6$) δ 12.81 (d, J = 12.4 Hz, 1H), 8.79 (d. J = 3.6 Hz, 1H), 8.77 (s, 1H), 8.18 (d, J = 1.7 Hz, 1H), 7.56 (s, 1H), 7.45 (s, 1H), 5.17 (s, 1H), 5.03 (s, 1H), 4.90 (s, 1H), 4.76 (s, 1H), 4.14 (d, J = 1.7 Hz, 3H), 3.61 (s, 3H), 2.60 (s, 3H) |

Example 750: Synthesis of 2'-Chloro-5'-methoxy-N-(5-(2-methoxy-6-(trifluoromethyl)nicotinoyl)-4-methyl-5,6-dihydro-4H-pyrrolo[3,4-d]thiazol-2-yl)-6-methyl-[4,4'-bipyridine]-3-carboxamide

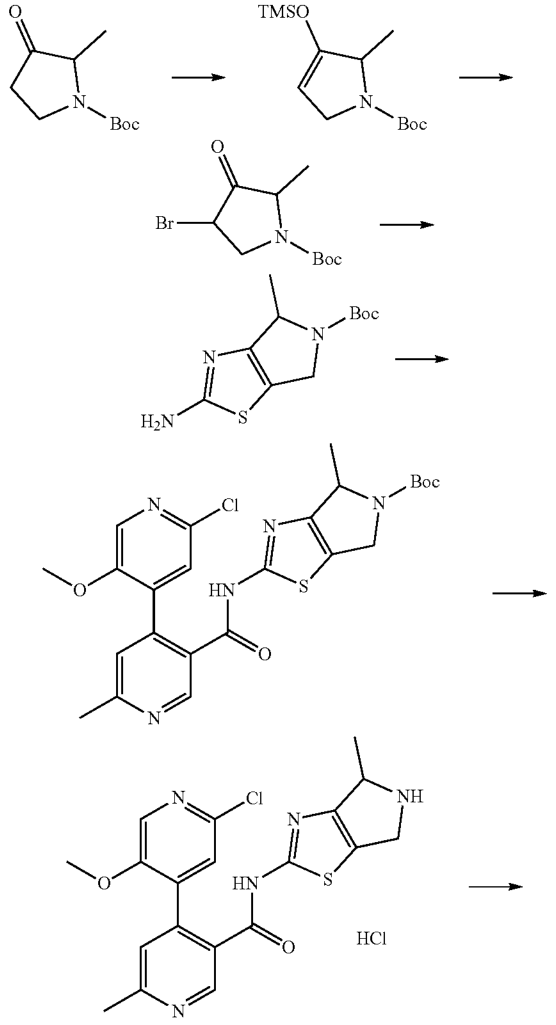

-continued

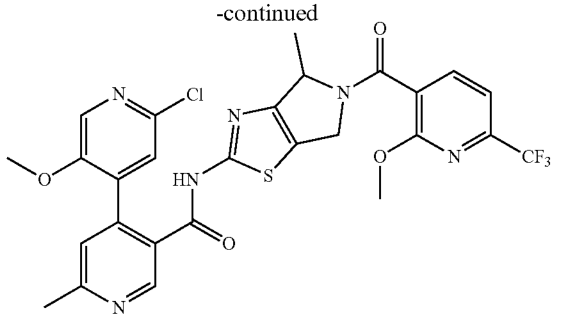

Step 1: To a solution of tert-butyl 2-methyl-3-oxopyrrolidine-1-carboxylate (400 mg, 2.01 mmol) in dry THF (10 mL) at −78° C. under $N_2$ was added lithium bis(trimethylsilyl)amide (1 M in THF, 4.02 mL, 4.02 mmol) and the mixture was stirred at −78° C. for 30 mm. $Et_3N$ (406 mg, 4.02 mmol) was added followed by chlorotrimethylsilane (436 mg, 4.02 mmol) and the mixture was stirred at −78° C. for 1 h. The mixture was diluted with water (30 mL), extracted with EtOAc (3×30 mL), and the combined organic layers were washed with brine (30 mL), dried over $Na_2SO_4$, filtered, and concentrated under reduced pressure to afford tert-butyl 2-methyl-3-((trimethylsilyl)oxy)-2,5-dihydro-1H-pyrrole-1-carboxylate (400 mg) as a yellow oil, which was used directly in the next step without further purification.

Step 2: To a solution of tert-butyl 2-methyl-3-((trimethylsilyl)oxy)-2,5-dihydro-1H-pyrrole-1-carboxylate (400 mg) in THF (10 mL) at 0° C. was added pyridinium perbromide (707 mg, 2.21 mmol) and the mixture was stirred at 0° C. for 0.5 h. The reaction was quenched at 0° C. with a saturated aqueous $Na_2S_2O_3$ solution (30 mL) and extracted with EtOAc (3×30 mL). The combined organic layers were washed with brine, dried over $Na_2SO_4$, filtered, and concentrated under reduced pressure to afford tert-butyl 4-bromo-2-methyl-3-oxopyrrolidine-1-carboxylate (500 mg) as a yellow oil. $^1H$ NMR (400 MHz, DMSO-$d_6$) δ64.47 (d, J=13.8 Hz, 1H), 4.42-4.36 (m, 1H), 4.06-3.92 (m, 2H), 1.42 (s, 9H), 1.37 (d, J=7.0 Hz, 3H).

Step 3: To a solution of tert-butyl 4-bromo-2-methyl-3-oxopyrrolidine-1-carboxylate (500 mg) in THF (3 mL) was added $NaHCO_3$ (453 mg, 5.39 mmol) and thiourea (547 mg, 7.19 mmol) and the mixture was heated at 70° C. for 5 h. The mixture was diluted with water (30 mL), extracted with EtOAc (2×30 mL), and the combined organic layers washed with a dilute aqueous $NaHCO_3$ solution (20 mL), brine (10 mL), dried over $Na_2SO_4$, filtered, and concentrated under reduced pressure. The residue was purified by prep-TLC (DCM/MeOH=20/1, v/v) to afford tert-butyl 2-amino-4-methyl-4,6-dihydro-5H-pyrrolo[3,4-d]thiazole-5-carboxylate (150 mg, 29% over three steps) as a yellow solid. LCMS: m/z=256 $[M+H]^+$. $^1H$ NMR (400 MHz, DMSO-$d_6$) δ 7.06 (d, J=5.8 Hz, 2H), 4.59-4.49 (m, 1H), 4.42-4.23 (m, 2H), 1.43 (d, J=4.0 Hz, 9H), 1.34-1.29 (m, 3H).

Step 4: To a solution of 2'-chloro-5'-methoxy-6-methyl-[4,4'-bipyridine]-3-carboxylic acid (0.20 g, 0.70 mmol) in MeCN (6 mL) was added TCFH (0.30 g, 1.1 mmol), tert-butyl 2-amino-4-methyl-4,6-dihydro-5H-pyrrolo[3,4-d]thiazole-5-carboxylate (90 mg, 0.35 mmol) and 1-methyl-1H-imidazole (0.12 g, 1.4 mmol) and the mixture was heated at 80° C. for 16 h. The mixture was diluted with water (30 mL), extracted with EtOAc (3×30 mL), and the combined organic layers were washed with a dilute aqueous $NaHCO_3$ solution (20 mL), brine (30 mL), dried over $Na_2SO_4$, filtered, and concentrated under reduced pressure. The residue was purified by prep-TLC (DCM/MeOH=20/1, v/v) to afford tert-butyl 2-(2'-chloro-5'-methoxy-6-methyl-[4,4'-bipyridine]-3-carboxamido)-4-methyl-4,6-dihydro-5H-pyrrolo[3,4-d]thiazole-5-carboxylate (100 mg, 55%) as a white solid. LCMS: m/z=516 $[M+H]^+$; $^1H$ NMR (400 MHz, DMSO-$d_6$) δ 12.8 (s, 1H), 8.78 (s, 1H), 8.15 (s, 1H), 7.51 (s, 1H), 7.41 (s, 1H), 4.81-4.73 (m, 1H), 4.62-4.40 (m, 2H), 3.59 (s, 3H), 2.58 (s, 3H), 1.45 (d, J=4.0 Hz, 9H), 1.41 (d, J=5.8 Hz, 3H).

Step 5: To a solution of tert-butyl 2-(2'-chloro-5'-methoxy-6-methyl-[4,4'-bipyridine]-3-carboxamido)-4-methyl-4,6-dihydro-5H-pyrrolo[3,4-d]thiazole-5-carboxylate (100 mg, 0.194 mmol) in MeOH (0 mL) was added a 4 M HCl in dioxane solution (2 mL) and the mixture was stirred at 25° C. for 1 h. The mixture was concentrated under reduced pressure to give 2'-chloro-5'-methoxy-6-methyl-N-(4-methyl-5,6-dihydro-4H-pyrrolo[3,4-d]thiazol-2-yl)-[4,4'-bipyridine]-3-carboxamide hydrochloride (100 mg, >100%) as a black solid. LCMS: m/z=416 $[M+H]^+$; $^1H$ NMR (400 MHz, DMSO-$d_6$) δ 13.0 (s, 1H), 10.3 (s, 1H), 9.83 (s, 1H), 8.80 (s, 1H), 8.16 (s, 1H), 7.53 (s, 1H), 7.47 (s, 1H), 4.87-4.69 (m, 1H), 4.51-4.43 (m, 2H), 3.59 (s, 3H), 2.59 (s, 3H), 1.52 (d, J=6.6 Hz, 3H).

Step 6: To a solution of 2'-chloro-5'-methoxy-6-methyl-N-(4-methyl-5,6-dihydro-4H-pyrrolo[3,4-d]thiazol-2-yl)-[4,4'-bipyridine]-3-carboxamide hydrochloride (80 mg, 0.18 mmol) and 2-methoxy-6-(trifluoromethyl)nicotinic acid (43 mg, 0.19 mmol) in DMF (3 mL) at 0° C. was added DIPEA (0.12 g, 0.96 mmol) and T3P (50% in DMF, 0.18 g, 0.29 mmol) and the mixture was stirred at 25° C. for 16 h. The mixture was diluted with water (40 mL), extracted with EtOAc (3×30 mL), and the combined organic layers washed with a dilute aqueous $NaHCO_3$ solution (10 mL), water (10 mL), brine (20 mL), dried over $Na_2SO_4$, filtered, and concentrated under reduced pressure. The residue was purified by prep-TLC (DCM/MeOH=20/1, v/v) to afford 2'-chloro-5'-methoxy-N-(5-(2-methoxy-6-(trifluoromethyl)nicotinoyl)-4-methyl-5,6-dihydro-4H-pyrrolo[3,4-d]thiazol-2-yl)-6-methyl-[4,4'-bipyridine]-3-carboxamide (50 mg, 45%) as a white solid. LCMS: m/z=619 $[M+H]^+$. $^1H$ NMR (400 MHz, DMSO-$d_6$) δ 12.9 (s, 1H), 8.78 (d, J=4.2 Hz, 1H), 8.18-8.04 (m, 2H), 7.62-7.59 (m, 1H), 7.53 (d, J=1.6 Hz, 1H), 7.43 (s, 1H), 5.21-5.13 (m, 0.7H), 4.89 (d, J=15.1 Hz, 0.3H), 4.84-4.77 (m, 0.3H), 4.70 (dd, J=15.3, 3.4 Hz, 0.3H), 4.54 (dd, J=13.2, 3.6 Hz, 0.7H), 4.40 (d, J=13.3 Hz, 0.7H), 3.96 (d, J=3.2 Hz, 3H), 3.60 (d, J=7.2 Hz, 3H), 2.58 (s, 3H), 1.54 (d, J=6.2 Hz, 2H), 1.05 (d, J=6.2 Hz, 1H).

TABLE AJ

The following example was prepared from tert-butyl 2-methyl-4-oxopyrrolidine-1-carboxylate and tert-butyldimethylsilyl chloride using a similar procedure to that described for Example 750

| Ex. No. | Structure | Compound Name | LCMS $[M + H]^+$ | NMR |
|---|---|---|---|---|
| 751 | 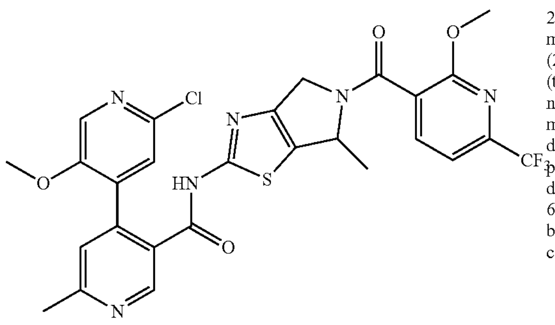 | 2'-Chloro-5'-methoxy-N-(5-(2-methoxy-6-(trifluoromethyl)nicotinoyl)-6-methyl-5,6-dihydro-4H-pyrrolo[3,4-d]thiazol-2-yl)-6-methyl-[4,4'-bipyridine]-3-carboxamide | 619 | $^1H$ NMR (400 MHZ, DMSO-$d_6$) δ 12.9 (s, 1H), 8.78 (d, J = 6.8 Hz, 1H), 8.17 (s, 1H), 8.15-8.03 (m, 1H), 7.64-7.57 (m, 1H), 7.53 (s, 1H), 7.42 (d, J = 3.2 Hz, 1H), 5.48-5.38 (m, 0.7H), 5.05-4.97 (m, 0.3H), 4.77 (d, J = 14.9 Hz, 0.3H), 4.60 (dd, J = 14.8, 3.2 Hz, 0.3H), 4.49 (dd, J = 13.0, 3.4 Hz, 0.7H), 4.32 (d, J = 12.9 Hz, 0.7H), 3.96 (d. J = 5.2 Hz, 3H), 3.61 (d, J = 5.2 Hz, 3H), 2.58 (d, J = 3.4 Hz, 3H), 1.55 (d, J = 6.2 Hz, 2H), 1.08 (d, J = 6.2 Hz, 1H). |

Example 752A & 752B: Synthesis of (R or S)-2'-chloro-5'-methoxy-N-(5-(2-methoxy-6-(trifluoromethyl)nicotinoyl)-4-methyl-5,6-dihydro-4H-pyrrolo[3,4-d]thiazol-2-yl)-& methyl-[4,4'-bipyridine]-3-carboxamide (752A) & (S or R)-2'-chloro-5'-methoxy-N-(5-(2-methoxy-6-(trifluoromethyl)nicotinoyl)-4-methyl-5,6-dihydro-4H-pyrrolo[3,4-d]thiazol-2-yl)-6-methyl-[4,4'-bipyridine]-3-carboxamide (752B) with arbitrarily assigned stereochemistry

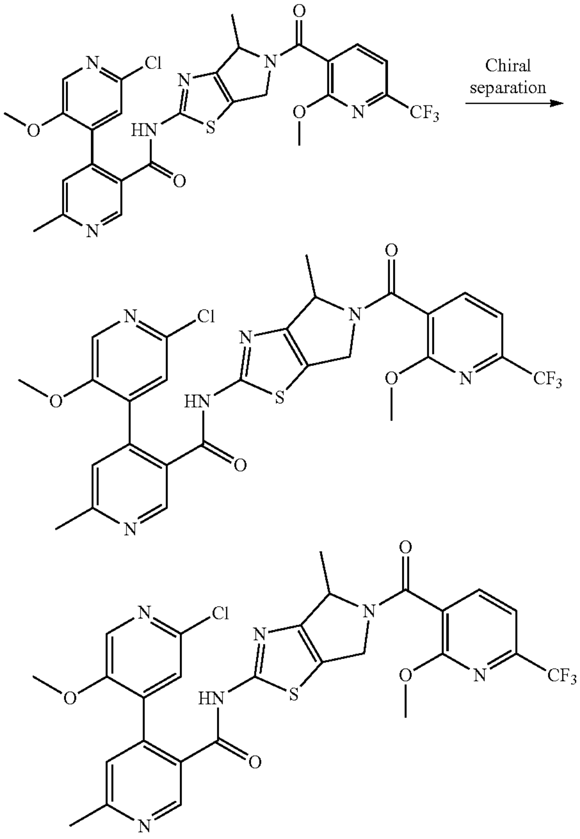

2'-chloro-5'-methoxy-N-(5-(2-methoxy-6-(trifluoromethyl)nicotinoyl)-4-methyl-5,6-dihydro-4H-pyrrolo[3,4-d]thiazol-2-yl)-6-methyl-[4,4'-bipyridine]-3-carboxamide (65 mg) was purified by chiral SFC (Column: Daicel IG, 30×250 mm, 10 μm; Mobile Phase: 55% $CO_2$/45% iPrOH; Flow rate: 60 mL/min) to afford two peaks:

Example 752A: Peak 1, retention time 1.96 min. LCMS: m/z=619 $[M+H]^+$; $^1$H NMR (400 MHz, DMSO-$d_6$) δ 12.9 (s, 1H), 8.78 (d, J=4.2 Hz, 1H), 8.19-8.04 (m, 2H), 7.62-7.59 (m, 1H), 7.53 (d, J=1.6 Hz, 1H), 7.42 (s, 1H), 5.21-5.13 (m, 0.7H), 4.89 (d, J=15.1 Hz, 0.3H), 4.84-4.77 (m, 0.3H), 4.70 (dd, =15.3, 3.4 Hz, 0.3H), 4.54 (dd, J=13.2, 3.6 Hz, 0.7H), 4.40 (d, J=13.3 Hz, 0.7H), 3.96 (d, J=3.2 Hz, 3H), 3.60 (d, J=7.2 Hz, 3H), 2.58 (s, 3H), 1.54 (d, J=6.2 Hz, 2H), 1.05 (d, J=6.2 Hz, 1H).

Example 752B: Peak 2, retention time 2.68 min. LCMS: m/z=619 $[M+H]^+$; $^1$H NMR (400 MHz, DMSO-$d_6$) δ 12.9 (s, 1H), 8.78 (d, J=4.2 Hz, 1H), 8.19-8.04 (m, 2H), 7.62-7.59 (m, 1H), 7.53 (d, J=1.6 Hz, 1H), 7.42 (s, 1H), 5.21-5.13 (m, 0.7H), 4.89 (d, J=15.1 Hz, 0.3H), 4.84-4.77 (m, 0.3H), 4.70 (dd, =15.3, 3.4 Hz, 0.3H), 4.54 (dd, J=13.2, 3.6 Hz, 0.7H), 4.40 (d, J=13.3 Hz, 0.7H), 3.96 (d, J=3.2 Hz, 3H), 3.60 (d, J=7.2 Hz, 3H), 2.58 (s, 3H), 1.54 (d, J=6.2 Hz, 2H), 1.05 (d, J=6.2 Hz, 1H).

Example 753A & 753B: Synthesis of (S or R)-2'-chloro-5'-methoxy-N-(5-(2-methoxy-6-(trifluoromethyl)nicotinoyl)-6-methyl-5,6-dihydro-4H-pyrrolo[3,4-d]thiazol-2-yl)-6-methyl-[4,4'-bipyridine]-3-carboxamide (753A) & (R or S)-2'-chloro-5'-methoxy-N-(5-(2-methoxy-6-(trifluoromethyl)nicotinoyl)-6-methyl-5,6-dihydro-4H-pyrrolo[3,4-d]thiazol-2-yl)-6-methyl-[4,4'-bipyridine]-3-carboxamide (753B) with arbitrarily assigned stereochemistry

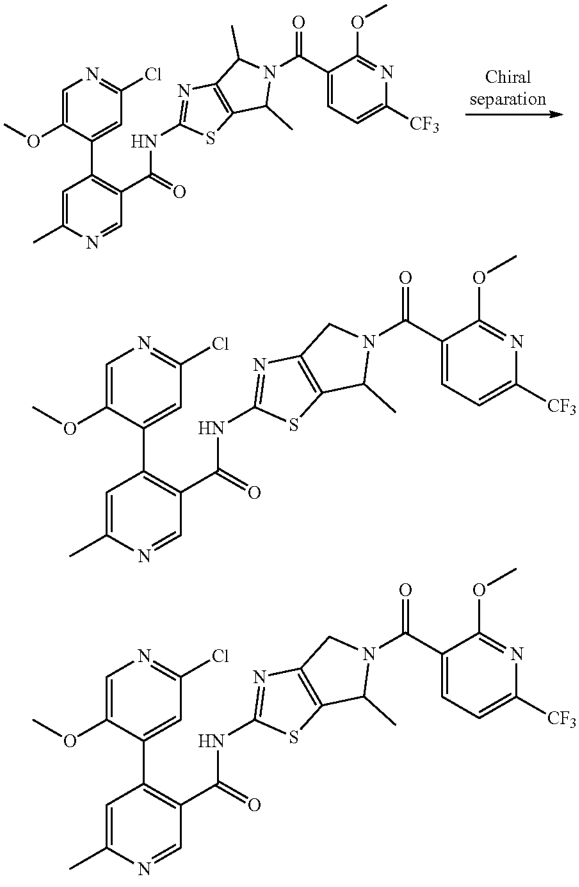

2'-Chloro-5'-methoxy-N-(5-(2-methoxy-6-(trifluoromethyl)nicotinoyl)-6-methyl-5,6-dihydro-4H-pyrrolo[3,4-d]thiazol-2-yl)-6-methyl-[4,4'-bipyridine]-3-carboxamide (40 mg) was purified by chiral SFC (Column: Daicel AS, 30×250 mm, 10 μm; Mobile Phase: 70% $CO_{230}$% MeOH; Flow rate: 60 mL/min) to afford two peaks:

Example 753A: Peak 1, retention time 1.17 min. LCMS: m/z=619 $[M+H]^+$; 1H NMR (400 MHz, DMSO-$d_6$) δ 12.9 (s, 1H), 8.78 (d, J=6.8 Hz, 1H), 8.17 (s, 1H), 8.15-8.03 (m, 1H), 7.64-7.57 (m, 1H), 7.53 (s, 1H), 7.42 (d, J=3.2 Hz, 1H), 5.48-5.38 (m, 0.7H), 5.05-4.97 (m, 0.3H), 4.77 (d, J=14.9 Hz, 0.3H), 4.60 (dd, J=14.8, 3.2 Hz, 0.3H), 4.49 (dd, J=13.0, 3.4 Hz, 0.7H), 4.32 (d, J=12.9 Hz, 0.7H), 3.96 (d, J=5.2 Hz, 3H), 3.61 (d, J=5.2 Hz, 3H), 2.58 (d, J=3.4 Hz, 3H), 1.55 (d, J=6.2 Hz, 2H), 1.08 (d, J=6.2 Hz, 1H).

Example 753B: Peak 2, retention time 1.83 min. LCMS: m/z=619 $[M+H]^+$; 1H NMR (400 MHz, DMSO-$d_6$) δ 12.9 (s, 1H), 8.78 (d, J=6.8 Hz, 1H), 8.17 (s, 1H), 8.15-8.03 (m, 1H), 7.64-7.57 (m, 1H), 7.53 (s, 1H), 7.42 (d, J=3.2 Hz, 1H), 5.48-5.38 (m, 0.7H), 5.05-4.97 (m, 0.3H), 4.77 (d, J=14.9 Hz, 0.3H), 4.60 (dd, J=14.8, 3.2 Hz, 0.3H), 4.49 (dd, J=13.0, 3.4 Hz, 0.7H), 4.32 (d, J=12.9 Hz, 0.7H), 3.96 (d, J=5.2 Hz, 3H), 3.61 (d, J=5.2 Hz, 3H), 2.58 (d, J=3.4 Hz, 3H), 1.55 (d, J=6.2 Hz, 2H), 1.08 (d, J=6.2 Hz, 1H).

Example 780A & 780B: Synthesis of (Z)-4-((2-((2'-chloro-5'-methoxy-6-methyl-[4,4'-bipyridine]-3-carbonyl)imino)-5(5-(difluoromethyl)picolinoyl)-5,6-dihydro-2H-pyrrolo[3,4-d]thiazol-3(4H)-yl)methoxy)-4-oxobutanoic acid (780A) & 4-((2'-chloro-N-(5-(5-(difluoromethyl)picolinoyl)-5,6-dihydro-4H-pyrrolo[3,4-d]thiazol-2-yl)-5'-methoxy-6-methyl-[4,4'-bipyridine]-3-carboxamido)methoxy)-4-oxobutanoic acid (780B)

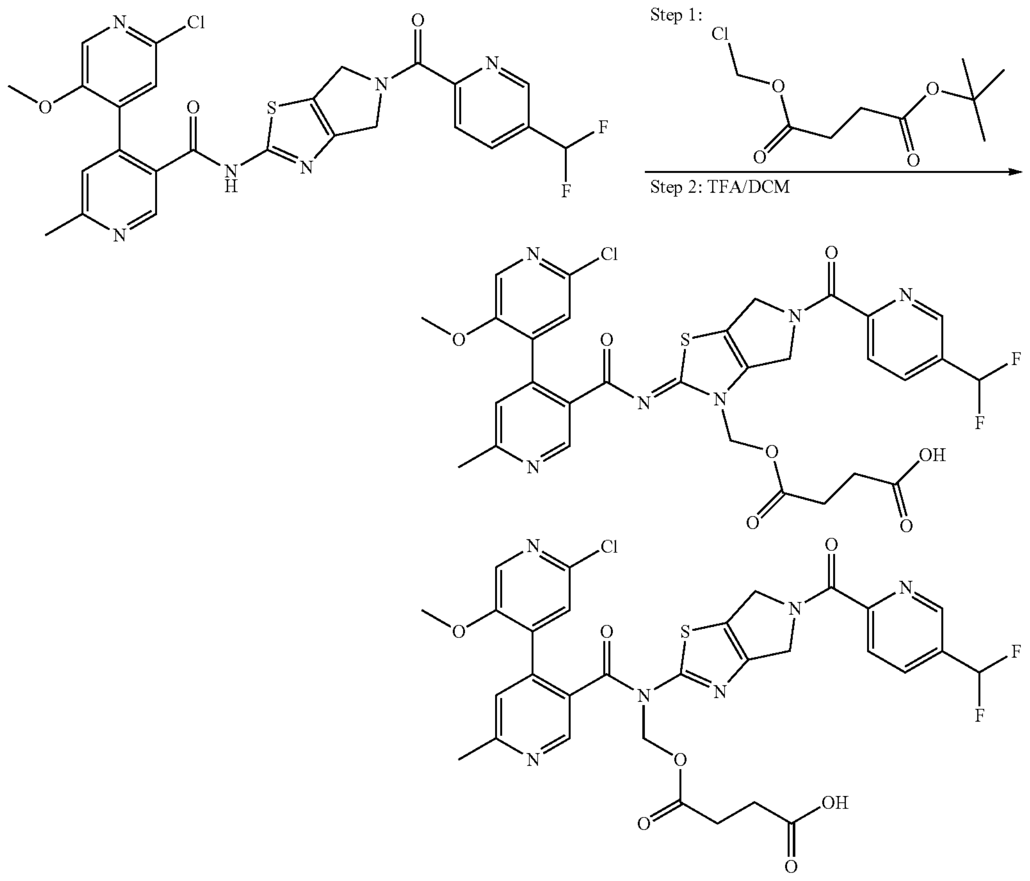

Step 1: To a stirred mixture of 2'-chloro-N-(5-(5-(difluoromethyl)picolinoyl)-5,6-dihydro-4H-pyrrolo[3,4-d]thiazol-2-yl)-5'-methoxy-6-methyl-[4,4'-bipyridine]-3-carboxamide (Example 53, 290 mg, 0.52 mmol) and 1-tert-butyl 4-chloromethyl butanedioate (290 mg, 1.30 mmol) in DMF (10 mL) were added $K_2CO_3$ (216 mg, 1.56 mmol) and $K_1$ (86 mg, 0.52 mmol) at room temperature under a nitrogen atmosphere. The resulting mixture was stirred at 50° C. for 16 h under a nitrogen atmosphere. The reaction was cooled to room temperature and filtered. The filter cake was washed with DMF (2×2 mL) and the filtrate was concentrated under reduced pressure. The residue was purified by reverse-phase flash chromatography ($C_{18}$ gel column; 40-60% MeCN in water with 0.1% formic acid modifier) to give a mixture of two products. The mixture (250 mg) was purified by Prep-HPLC (XSelect CSH Fluoro Phenyl column 30×150 mm, 5 μm; 39-56% MeCN in water with 0.05% TFA modifier; 60 mL/min flow rate; wave length: 254 nm/220 nm) to afford two peaks:

Peak 1 retention time 6 min: (Z)-tert-butyl ((2-((2'-chloro-5'-methoxy-6-methyl-[4,4'-bipyridine]-3-carbonyl)imino)-5-(5-(difluoromethyl)picolinoyl)-5,6-dihydro-2H-pyrrolo[3, 4-d]thiazol-3(4H)-yl)methyl) succinate (150 mg, 39% yield) as a white solid. LCMS: m/z=743 [M+H]+; 1 H NMR (400 MHz, DMSO-$d_6$) δ 9.19 (d, J=2.4 Hz, 1H), 8.87 (dd, J=7.3, 1.9 Hz, 1H), 8.22 (ddd, J=7.5, 4.2, 1.9 Hz, 1H), 8.17 (d, 0.1=3.7 Hz, 1H), 8.01 (dd, J=8.1, 6.3 Hz, 1H), 7.43 (d, J=14.9 Hz, 2H), 7.39-7.09 (m, 1H), 5.85 (d, J=35.6 Hz, 2H), 5.12 (t, J=3.0 Hz, 1H), 5.00-4.95 (m, 1H), 4.90 (t, J=3.2 Hz, 1H), 4.78 (t, J=3.0 Hz, 1H), 3.64 (s, 3H), 2.61 (s, 4H), 2.58-2.51 (m, 2H), 2.45 (dt, J=8.4, 3.7 Hz, 1H), 1.30 (d, J=20.4 Hz, 9H).

Peak 2 retention time 8.6 min: tert-butyl ((2'-chloro-N-(5-(5-(difluoromethyl)picolinoyl)-5,6-dihydro-4H-pyrrolo[3,4-d]thiazol-2-yl)-5'-methoxy-6-methyl-[4,4'-bipyridine]-3-carboxamido)methyl) succinate (50 mg, 13% yield) as a white solid. LCMS: m/z=743 [M+H]+; $^1$H NMR (400 MHz, DMSO-$d_6$) δ 8.87 (dt, J=2.4, 1.3 Hz, 1H), 8.74 (d, J=2.6 Hz, 1H), 8.25-8.18 (m, 2H), 8.00 (t, J=7.4 Hz, 1H), 7.53 (s, 2H), 7.25 (td, J=55.1, 3.9 Hz, 1H), 5.95 (s, 2H), 5.05 (d, J=2.7 Hz, 1H), 4.98-4.92 (m, 1H), 4.89 (t, J=2.5 Hz, 1H), 4.75 (d, J=2.7 Hz, 1H), 3.71 (s, 3H), 2.60 (s, 3H), 2.58-2.52 (m, 2H), 2.48-2.42 (m, 2H), 1.35 (d, J=18.1 Hz, 9H).

Step 2: A mixture of (Z)-tert-butyl ((2-((2'-chloro-5'-methoxy-6-methyl-[4,4'-bipyridine]-3-carbonyl)imino)-5-(5-(difluoromethyl)picolinoyl)-5,6-dihydro-2H-pyrrolo[3,4-d]thiazol-3(4H)-yl)methyl) succinate (100 mg, 0.12 mmol) and TFA (2 mL) in $CH_{212}$ (4 mL) was stirred for 2 h at 20° C. The resulting mixture was concentrated under reduced pressure and the residue was purified by Prep-HPLC (XBridge Prep OBD C18 column 30×150 mm, 5 μm; 39-55% MeCN in water with 0.1% formic acid modifier; wave length: 254 nm/220 nm nm) to afford (Z)-4-((2-((2'-chloro-5'-methoxy-6-methyl-[4,4'-bipyridine]-3-carbonyl)imino)-5-(5-(difluoromethyl)picolinoyl)-5,6-dihydro-2H-pyrrolo[3,4-d]thiazol-3(4H)-yl)methoxy)-4-oxobutanoic acid (39 mg) as off-white solid. LCMS: m/z=687 [M+H]+; $^1$H NMR (400 MHz, Acetonitrile-$d_3$) δ 9.20 (s, 1H), 8.81 (d, J=12.6 Hz, 1H), 8.08 (d, J=6.4 Hz, 1H), 8.04 (d, J=1.4 Hz, 1H), 8.00 (dd, J=8.1, 3.1 Hz, 1H), 7.28 (s, 1H), 7.14 (s, 1H), 6.96 (td, J=55.3, 9.3 Hz, 1H), 5.78 (s, 1H), 5.69 (s, 1H), 5.08 (d, J=3.2 Hz, 1H), 5.00 (d, J=3.2 Hz, 1H), 4.86 (s, 1H), 4.78 (d, J=3.4 Hz, 1H), 3.66 (s, 3H), 2.65-2.50 (m, 7H).

Example 352. Biological Activity of the Compounds of the Present Disclosure

The biological activity of the compounds of the present disclosure was determined utilizing the assay described herein.

ATPase Assay

POLθ-mediated ATP hydrolysis was measured using the ADP-Glo Kinase Assay (Promega Corporation, Madison, WI). Reactions were performed in white 384-well small-volume microplates (Greiner Bio-One, Frickenhausen, Germany) using a total volume of 15 μL. The ATPase reaction consisted of 1 nM biotinylated Avi-POLθ[2-894], 5 nM of a 50 nucleotide poly-thymine repeat single-stranded DNA (PolyT(50) ssDNA), and 100 μM ATP in 5 μL of assay buffer (50 mM Tris, pH 7.5, 80 mM KCl, 10 $MgCl_2$, 1 mM DTT, 5% glycerol, 0.01% BSA, 0.01% Tween-20). Inhibition of POLΘATPase activity was determined by preparing 11-point serial dilutions of the test compounds in 100% DMSO, then transferring 30 nL of the compounds into the ATPase reaction using an Echo acoustic liquid handler (Beckman Coulter, Brea, CA). DMSO-treated wells containing either all of the reaction components (1 nM biotinylated Avi-POLθ[2-894], 5 nM PolyT(50) ssDNA, 100 μM ATP) or with assay buffer substituted for the biotinylated Avi-POLθ[2-894](0 nM biotinylated Avi-POLθ[2-894], 5 nM PolyT(50) ssDNA, 100 μM ATP) were used to define the maximum and minimum response in the assay. Following a one-hour incubation at ambient temperature, 5 μL of ADP-Glo Reagent was added to the ATPase reaction, and this mixture was allowed to incubate at ambient temperature for an additional hour. Lastly, 5 μL of Kinase Detection Reagent was added, followed by a third one-hour incubation at ambient temperature. The reagent concentrations listed represent the amounts only in the 5 μL ATPase reaction volume. Luminescence signal was measured using the EnVision multimode plate reader (Perkin Elmer. Waltham. MA). To determine the inhibitory potency ($AC_{50}$) of the test compounds, the luminescence signal was normalized to percent activity using the median value of the maximum signal wells (corresponding to 0% activity) and the median value of the minimum signal wells (corresponding to −100% activity). Non-linear regression analysis using the four-parameter logistic equation was conducted on the percent activity

TABLE AK

The following example was prepared using a similar procedure to that described for Example 780A:

| Ex. No. | Structure | Compound Name | LCMS | NMR |
|---|---|---|---|---|
| 780 B | 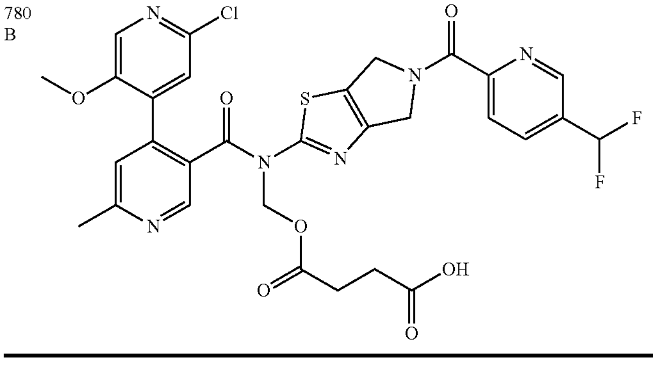 | 4-((2'-chloro-N-(5-(5-(difluoromethyl)picolinoyl)-5,6-dihydro-4H-pyrrolo[3,4-d]thiazol-2-yl)-5'-methoxy-6-methyl-[4,4'-bipyridine]-3-carboxamido)methoxy)-4-oxobutanoic acid | 687 | $^1$H NMR (400 MHZ, DMSO-$d_6$) δ 12.23 (s, 1H), 8.91-8.83 (m, 1H), 8.73 (s, 1H), 8.21 (d, J = 13.1 Hz, 2H), 8.00 (t, J = 8.8 Hz, 1H), 7.52 (s, 2H), 7.25 (td, J = 55.2, 2.9 Hz, 1H), 5.92 (s, 2H), 5.04 (s, 1H), 4.96 (s, 1H), 4.89 (s, 1H), 4.75 (s, 1H), 3.71 (s, 3H), 2.64-2.53 (m, 5H), 2.46 (t, J = 7.0 Hz, 2H) |

values of the compound dose-responses, yielding the $AC_{50}$ value for each compound. Genedata Screener (Genedata. Basel, Switzerland) was used for the data analysis.

Measurement of Cell Proliferation in Human Cell Lines DLD1 Parental (WT) and DLD1 BRCA2 (−/−) in a 7-Day Cell Viability Assay Cell lines DLD1 WT and DLD1 BRCA2 (−/−) (Horizon Discovery Cat No. HD PAR-008 and HD-105-007) were plated in 384-well culture plates at seeding densities of 100 cells/50 ul/well and 200 cells/50 uL/well respectively. The seeding densities are pre-determined from the growth curve kinetics performed to ensure log linear phase of cell growth for these 2 cell lines. These assay plates are then placed in the incubator at 37° C., 5% CO2, relative humidity >90% for a few hours before addition of test compounds. Compounds are dispensed using the Tecan HPD300 or Echo based on the plate map in the appropriate wells of the 384-well plates. The cells are treated with nine-point dose response with 3-fold serial dilutions of test compounds starting at 10 uM top concentration. After addition of the test compounds, the plates are incubated at 37° C., 5% $CO_2$, relative humidity >90% for 7 days. CellTiter-Glo (Promega Cat. No. G7573), ATP detection reagent is prepared according to manufacturer's specifications. Cell assay plates are removed from incubator and bring to room temperature (RT) by letting them sit at bench top for at least 15 min. Using the MultiDrop liquid handler or a multichannel pipette, 35 µL/well of CTG is added and the plates are then placed shakes for 5 seconds, RT. These plates are then incubated for 30 minutes in the dark at RT before measuring luminescence using Spectramax/Enspire/Ensight/Envision/PheraSTAR Data is analyzed using the DMSO control wells as the 0% inhibition control (high signal) and the 10 uM Doxorubicin control wells as the 100% inhibition control (low signal) control to calculate percent inhibition and $IC_{50}$s for the test compound dose responses.

The inhibitory activity values $IC_{50}$ of each compound is shown in Table AA below (n=2).

Values of Biochemical ATPase ADPGlo $IC_{50}$ in Table AA are presented in ranges, in which 0.001 µM≤"+"<0.015 µM, 0.015 µM≤"++"≤0.050 µM, 0.050 µM "+++"<0.150 µM, 0.150 µM≤"++++"<0.900 µM, and 0.900 µM≤"+++++."

Values of Viability $IC_{50}$ (µM) DLD1 BRCA2 null in Table AA are presented in ranges, in which 0.001 µM≤"*"<0.100 µM, 0.100 µM≤""<0.250 µM 0.250 µM≤"*"<0.500 µM, 0.500 µM≤"**"<2.000 µM, and 2.000 µM≤"***."

Values of Viability $IC_{50}$ (µM) DLD1 WT in Table AA are presented in ranges, in which 0.001 µM≤"#"<0.500 µM, 0.500 µM≤"##"<2.000 µM≤"###"≤5.000 µM, 5.000 µM≤"####"<10.00 µM, and 10.00 µM≤"#####."

TABLE AA

| Compound No. | Example No. | Biochemical ATPase ADPGlo $IC_{50}$ (uM) | Viability $IC_{50}$ (uM) DLD1 BRCA2 null | Viability $IC_{50}$ (uM) DLD1 WT |
|---|---|---|---|---|
| 18 | 1 | + | * | #### |
| 304 | 2 | + | ** | ##### |
| 278 | 3 | + | ** | ##### |
| 221 | 4 | ++ | | |
| 166 | 5 | + | *** | ##### |
| 189 | 6 | + | | |
| 219 | 7 | ++ | | |
| 220 | 8 | + | | |
| 231 | 9 | + | ** | ##### |
| 179 | 10 | + | * | ##### |
| 199 | 11 | + | ** | #### |

TABLE AA-continued

| Compound No. | Example No. | Biochemical ATPase ADPGlo $IC_{50}$ (uM) | Viability $IC_{50}$ (uM) DLD1 BRCA2 null | Viability $IC_{50}$ (uM) DLD1 WT |
|---|---|---|---|---|
| 170 | 12 | + | ** | ##### |
| 197 | 13 | + | *** | ##### |
| 182 | 14 | + | | |
| 192 | 15 | + | | |
| 206 | 16 | + | *** | ##### |
| 178 | 17 | + | * | ##### |
| 204 | 18 | + | | |
| 195 | 19 | + | | |
| 202 | 20 | + | | |
| 191 | 21 | + | | |
| 205 | 22 | ++ | | |
| 181 | 23 | + | | |
| 184 | 24 | + | | |
| 186 | 25 | + | | |
| 216 | 26 | + | ** | ##### |
| 183 | 27 | + | | |
| 198 | 28 | + | **** | ##### |
| 194 | 29 | + | * | ##### |
| 171 | 30 | + | ** | ##### |
| 187 | 31 | + | | |
| 185 | 32 | + | | |
| 193 | 33 | + | | |
| 190 | 34 | + | *** | ##### |
| 201 | 35 | + | ** | ##### |
| 177 | 36 | + | * | ##### |
| 180 | 37 | + | | |
| 173 | 38 | + | | |
| 196 | 39 | + | * | ##### |
| 169 | 40 | + | ** | ##### |
| 168 | 41 | + | ** | ##### |
| 172 | 42 | + | * | ##### |
| 157 | 43 | + | *** | ##### |
| 146 | 44 | + | * | ##### |
| 118 | 45 | + | * | ### |
| 98 | 46 | ++++ | | |
| 108 | 47 | ++ | | |
| 163 | 48 | + | | |
| 153 | 49 | + | | |
| 151 | 50 | + | | |
| 155 | 51 | + | **** | ##### |
| 158 | 52 | + | ** | ##### |
| 9 | 53 | + | * | ##### |
| 145 | 54 | + | * | ##### |
| 148 | 55 | + | ** | ##### |
| 140 | 56 | + | * | #### |
| 161 | 57 | + | **** | ##### |
| 152 | 58 | + | ** | ##### |
| 156 | 59 | + | * | ##### |
| 143 | 60 | + | | |
| 131 | 61 | + | | |
| 139 | 62 | + | * | # |
| 159 | 63 | + | ** | ##### |
| 137 | 64 | + | | |
| 138 | 65 | + | * | ##### |
| 160 | 66 | + | ** | ##### |
| 164 | 67 | + | ** | ##### |
| 120 | 68 | ++ | | |
| 24 | 69 | ++ | | |
| 119 | 70 | + | | |
| 132 | 71 | + | * | #### |
| 121 | 72 | + | * | ##### |
| 127 | 73 | + | * | ##### |
| 122 | 74 | + | * | #### |
| 123 | 75 | + | * | ##### |
| 124 | 76 | + | | |
| 117 | 77 | + | * | ##### |
| 125 | 78 | + | ** | ##### |
| 97 | 79 | + | | |
| 22 | 80 | ++ | | |
| 30 | 81 | ++ | | |
| 23 | 82 | ++ | | |
| 20 | 83 | + | * | ##/\ |
| 21 | 84 | + | * | ##### |
| 28 | 85 | + | * | ## |
| 19 | 86 | + | * | ##### |

TABLE AA-continued

| Compound No. | Example No. | Biochemical ATPase ADPGlo $IC_{50}$ (uM) | Viability $IC_{50}$ (uM) DLD1 BRCA2 null | Viability $IC_{50}$ (uM) DLD1 WT |
|---|---|---|---|---|
| 32 | 87 | + | * | ### |
| 33 | 88 | + | | |
| 34 | 89 | + | | |
| 35 | 90 | + | * | ### |
| 37 | 91 | + | * | ##### |
| 38 | 92 | + | * | ##### |
| 39 | 93 | + | * | ##### |
| 40 | 94 | + | * | #### |
| 41 | 95 | + | | |
| 42 | 96 | + | * | ##### |
| 11 | 97 | + | * | ### |
| 12 | 98 | + | * | ##### |
| 13 | 99 | + | * | ##### |
| 14 | 100 | + | * | ##### |
| 15 | 101 | + | * | #### |
| 16 | 102 | + | * | ##### |
| 100 | 103 | + | | |
| 3 | 104 | + | * | ### |
| 103 | 105 | ++ | | |
| 104 | 106 | ++ | | |
| 128 | 107 | + | * | ##### |
| 141 | 108 | + | * | ##### |
| 142 | 109 | ++ | | |
| 335 | 110 | ++++ | | |
| 377 | 111 | +++++ | ***** | ##### |
| 374 | 112 | +++++ | | |
| 372 | 113 | +++++ | **** | ## |
| 358 | 114 | +++++ | ***** | ##### |
| 357 | 115 | +++++ | ***** | ##### |
| 369 | 116 | +++++ | **** | ## |
| 362 | 117 | +++++ | | |
| 344 | 118 | +++++ | ***** | ## |
| 213 | 119 | ++++ | | |
| 226 | 120 | +++ | | |
| 238 | 121 | ++++ | | |
| 247 | 122 | ++++ | | |
| 248 | 123 | ++++ | | |
| 249 | 124 | +++ | | |
| 373 | 125 | +++++ | | |
| 321 | 127 | +++ | | |
| 338 | 128A | ++++ | | |
| 325 | 128B | ++++ | | |
| 328 | 129 | ++++ | | |
| 375 | 130 | +++++ | ***** | ##### |
| 361 | 131 | +++++ | | |
| 378 | 132 | +++++ | | |
| 367 | 134 | +++++ | | |
| 356 | 135 | +++++ | | |
| 352 | 136 | +++++ | | |
| 318 | 137 | +++ | | |
| 135 | 138 | + | **** | #### |
| 133 | 139 | + | ** | ##### |
| 99 | 140 | +++++ | | |
| 111 | 141 | +++++ | | |
| 134 | 142 | ++++ | | |
| 312 | 143A | +++ | ***** | ##### |
| 366 | 143B | +++++ | | |
| 353 | 144 | +++++ | | |
| 376 | 145 | +++++ | | |
| 314 | 146 | +++ | **** | ### |
| 368 | 147 | +++++ | | |
| 355 | 148 | +++++ | | |
| 323 | 149 | ++++ | | |
| 332 | 150 | ++++ | | |
| 324 | 151 | ++++ | | |
| 305 | 152 | + | ** | ##### |
| 300 | 153 | +++++ | | |
| 333 | 154 | ++++ | | |
| 340 | 155 | ++++ | ***** | ##### |
| 371 | 156 | +++++ | | |
| 351 | 157 | +++++ | | |
| 337 | 158 | ++++ | | |
| 331 | 159 | ++++ | | |
| 316 | 160 | +++ | | |
| 311 | 161 | +++ | | |

TABLE AA-continued

| Compound No. | Example No. | Biochemical ATPase ADPGlo $IC_{50}$ (uM) | Viability $IC_{50}$ (uM) DLD1 BRCA2 null | Viability $IC_{50}$ (uM) DLD1 WT |
|---|---|---|---|---|
| 310 | 162 | ++ | | |
| 308 | 163 | ++ | ***** | ##### |
| 281 | 164 | +++ | | |
| 246 | 165 | ++ | | |
| 233 | 166 | ++ | | |
| 303 | 167 | +++ | | |
| 280 | 168 | +++ | | |
| 269 | 169 | + | ***** | ##### |
| 301 | 170 | +++ | | |
| 302 | 171 | + | **** | ##### |
| 275 | 172 | + | ***** | ##### |
| 309 | 173 | ++ | | |
| 299 | 174 | + | **** | ##### |
| 240 | 175 | + | ***** | ##### |
| 230 | 176 | + | | |
| 272 | 177 | + | ***** | ##### |
| 270 | 178 | + | **** | ##### |
| 274 | 179 | ++ | ***** | ##### |
| 217 | 180 | +++ | | |
| 279 | 181 | ++ | | |
| 266 | 182 | +++ | | |
| 263 | 183 | ++ | | |
| 264 | 184 | + | | |
| 262 | 185 | + | ***** | ##### |
| 257 | 186 | + | **** | ##### |
| 273 | 187 | + | **** | ##### |
| 218 | 188 | + | | |
| 242 | 189 | + | | |
| 259 | 190 | + | ***** | ##### |
| 265 | 191 | + | **** | ##### |
| 260 | 192 | + | **** | ##### |
| 203 | 193 | ++++ | | |
| 234 | 194 | + | | |
| 261 | 195 | ++ | | |
| 276 | 196 | + | ***** | ##### |
| 307 | 197 | + | **** | ##### |
| 277 | 198 | + | **** | ##### |
| 258 | 199 | + | **** | ##### |
| 241 | 200 | + | **** | ##### |
| 235 | 201 | + | | |
| 243 | 202 | + | ***** | ##### |
| 245 | 203 | ++ | | |
| 267 | 204 | + | ***** | ##### |
| 268 | 205 | +++ | | |
| 232 | 206 | + | *** | ##### |
| 244 | 207 | + | **** | ##### |
| 282 | 208 | + | **** | ##### |
| 271 | 209 | + | ***** | ##### |
| 165 | 210 | +++ | | |
| 200 | 211 | +++ | | |
| 188 | 212 | ++++ | | |
| 167 | 213 | +++ | | |
| 162 | 214A | ++ | | |
| 154 | 214B | ++++ | | |
| 109 | 215 | ++++ | | |
| 110 | 216 | +++++ | | |
| 149 | 217 | +++ | | |
| 150 | 218 | ++ | | |
| 129 | 219 | + | | |
| 126 | 220 | + | | |
| 136 | 221 | ++++ | | |
| 130 | 222 | ++++ | | |
| 144 | 223 | ++++ | | |
| 147 | 224 | ++++ | | |
| 10 | 225 | + | * | ##### |
| 25 | 226 | + | * | ##∧ |
| 26 | 227 | + | * | #### |
| 27 | 228 | ++ | | |
| 29 | 229 | ++++ | | |
| 32 | 230 | + | | |
| 36 | 231 | + | * | ##### |
| 60 | 232 | + | | |
| 67 | 233 | + | * | ## |
| 86 | 234 | + | | |
| 88 | 235 | ++ | | |

TABLE AA-continued

| Compound No. | Example No. | Biochemical ATPase ADPGlo $IC_{50}$ (uM) | Viability $IC_{50}$ (uM) DLD1 BRCA2 null | Viability $IC_{50}$ (uM) DLD1 WT |
|---|---|---|---|---|
| 45 | 236 | + | * | ### |
| 50 | 237 | + | | |
| 71 | 238 | + | | |
| 17 | 240 | + | * | # |
| 49 | 241 | + | * | ##### |
| 87 | 242 | ++ | | |
| 65 | 243 | + | | |
| 81 | 244 | + | * | ##### |
| 69 | 245 | + | | |
| 116 | 246 | + | | |
| 62 | 247 | ++ | | |
| 8 | 248 | + | * | #### |
| 92 | 249 | ++ | | |
| 79 | 250 | + | * | ## |
| 43 | 251 | ++++ | | |
| 96 | 252 | + | | |
| 115 | 253 | ++ | | |
| 63 | 254 | + | * | #### |
| 4 | 255 | + | * | # |
| 80 | 257 | + | | |
| 57 | 258 | + | * | ##### |
| 58 | 259 | + | * | ##### |
| 75 | 260 | + | | |
| 76 | 262 | + | | |
| 85 | 263 | + | | |
| 77 | 264 | ++ | | |
| 90 | 265 | + | * | ##### |
| 7 | 266 | + | * | ### |
| 78 | 267 | + | * | #### |
| 66 | 268 | + | * | #### |
| 113 | 269 | + | | |
| 48 | 270 | + | * | ##### |
| 73 | 271 | + | * | # |
| 53 | 272 | + | * | ##### |
| 47 | 273 | + | * | #### |
| 54 | 274 | + | * | ##/\ |
| 95 | 275 | + | * | ##### |
| 94 | 277 | + | * | ##### |
| 5 | 278 | + | * | ##### |
| 74 | 279 | + | * | # |
| 114 | 280 | + | ** | ##### |
| 52 | 281 | + | * | ##### |
| 91 | 282 | + | | |
| 51 | 283 | + | | |
| 64 | 284 | + | * | #### |
| 56 | 285 | + | * | ##/\ |
| 70 | 286 | + | * | ##/\ |
| 72 | 287 | + | | |
| 93 | 288 | + | * | # |
| 6 | 289 | + | * | ##### |
| 59 | 290 | + | | |
| 44 | 291 | + | * | ##### |
| 61 | 292 | + | | |
| 84 | 293 | + | * | ##### |
| 46 | 294 | + | | |
| 83 | 295 | ++ | | |
| 55 | 296 | + | | |
| 89 | 297 | + | * | ##### |
| 112 | 298 | + | | |
| 292 | 299 | +++++ | | |
| 317 | 300 | +++ | | |
| 256 | 301 | ++++ | | |
| 294 | 302 | +++ | | |
| 283 | 303 | ++++ | | |
| 295 | 304 | ++++ | | |
| 250 | 305 | +++ | | |
| 350 | 306 | ++++ | | |
| 354 | 307 | +++++ | | |
| 336 | 308 | ++++ | | |
| 251 | 309 | ++++ | | |
| 313 | 310 | +++ | | |
| 319 | 311 | +++ | | |
| 327 | 312 | +++ | | |
| 342 | 313 | ++++ | | |
| 341 | 314 | ++++ | | |

TABLE AA-continued

| Compound No. | Example No. | Biochemical ATPase ADPGlo $IC_{50}$ (uM) | Viability $IC_{50}$ (uM) DLD1 BRCA2 null | Viability $IC_{50}$ (uM) DLD1 WT |
|---|---|---|---|---|
| 346 | 315 | ++++ | | |
| 347 | 316 | ++++ | | |
| 293 | 317 | ++++ | | |
| 287 | 318 | +++ | | |
| 289 | 319 | +++ | | |
| 284 | 320 | ++++ | | |
| 296 | 321 | ++++ | | |
| 286 | 322 | ++++ | | |
| 255 | 323 | +++ | | |
| 330 | 324 | ++++ | | |
| 345 | 325 | ++++ | | |
| 348 | 326 | ++++ | | |
| 326 | 327 | +++ | | |
| 329 | 328 | ++++ | | |
| 339 | 329 | ++++ | | |
| 349 | 330 | ++++ | | |
| 320 | 331 | +++ | | |
| 364 | 332 | +++++ | | |
| 363 | 333 | +++++ | | |
| 365 | 334 | +++++ | | |
| 334 | 335 | ++++ | | |
| 359 | 336 | +++++ | | |
| 322 | 337 | +++ | | |
| 290 | 338 | +++ | | |
| 343 | 339 | ++++ | | |
| 254 | 340 | ++++ | | |
| 285 | 341 | ++++ | | |
| 288 | 342 | ++++ | | |
| 360 | 343 | +++++ | | |
| 291 | 344 | ++ | | |
| 297 | 345 | ++++ | | |
| 298 | 346 | +++ | | |
| 253 | 347 | ++ | | |
| 252 | 348 | +++ | | |
| 315 | 349 | +++ | | |
| 370 | 350 | +++++ | | |
| 306 | 351 | + | *** | ##### |
| 101 | 754 | + | | |
| 1 | 755 | + | * | ##### |
| 102 | 756 | + | | |
| 2 | 757 | + | * | ##### |
| 105 | 758 | ++ | | |
| 106 | 759 | + | | |
| 107 | 760 | +++ | | |
| 174 | 239 | + | ** | ##### |
| 175 | 276 | + | ***** | ##### |
| 176 | 761 | +++ | | |
| 207 | 762 | ++ | | |
| 208 | 763 | ++++ | | |
| 209 | 764 | +++ | | |
| 210 | 765 | ++++ | | |
| 211 | 766 | ++ | | |
| 212 | 767 | + | | |
| 214 | 768 | ++++ | | |
| 215 | 769 | +++++ | | |
| 222 | 770 | +++++ | | |
| 223 | 771 | ++++ | | |
| 224 | 772 | ++++ | | |
| 225 | 773 | ++++ | | |
| 227 | 774 | ++++ | | |
| 228 | 775 | ++++ | | |
| 229 | 776 | ++++ | | |
| 236 | 777 | ++++ | | |
| 237 | 778 | ++++ | | |
| 239 | 779 | ++++ | | |
| 408 | 570 | + | * | ##### |
| 402 | 571 | + | * | ##### |
| 409 | 572 | + | * | ##### |
| 439 | 573 | + | * | ##### |
| 466 | 574 | + | * | ##### |
| 394 | 575 | + | * | ##### |
| 658 | 576 | + | | |
| 659 | 577 | + | | |
| 412 | 729 | + | * | ##### |
| 452 | 578 | + | * | ##### |

TABLE AA-continued

| Compound No. | Example No. | Biochemical ATPase ADPGlo $IC_{50}$ (uM) | Viability $IC_{50}$ (uM) DLD1 BRCA2 null | Viability $IC_{50}$ (uM) DLD1 WT |
|---|---|---|---|---|
| 420 | 579 | + | ** | ##### |
| 399 | 580 | + | * | ##### |
| 664 | 717 | ++++ | | |
| 665 | 708 | ++++ | | |
| 666 | 711 | ++ | | |
| 667 | 732 | + | | |
| 668 | 707 | ++++ | | |
| 669 | 714 | ++++ | | |
| 478 | 360 | + | * | ##### |
| 474 | 363 | + | * | ##### |
| 391 | 358 | + | * | #### |
| 535 | 367 | ++ | | |
| 674 | 710 | +++ | | |
| 533 | 721 | + | | |
| 676 | 712 | +++ | | |
| 677 | 713 | +++++ | | |
| 447 | 359 | + | * | #### |
| 486 | 362 | + | * | ##### |
| 515 | 581 | + | | |
| 681 | 718 | ++++ | | |
| 682 | 715 | ++++ | | |
| 683 | 720A | ++++ | | |
| 460 | 361 | + | * | #### |
| 685 | 716 | ++++ | | |
| 686 | 719 | ++++ | | |
| 434 | 375 | + | * | ### |
| 442 | 364 | + | * | ##### |
| 689 | 709 | ++++ | | |
| 524 | 366 | + | | |
| 473 | 369 | + | * | ##### |
| 692 | 720B | ++++ | | |
| 476 | 353 | + | | |
| 546 | 355 | +++ | | |
| 430 | 582 | + | * | ##### |
| 542 | 583 | ++ | | |
| 495 | 584 | + | | |
| 429 | 585 | + | * | ##### |
| 443 | 586 | + | * | ##### |
| 506 | 587 | + | | |
| 393 | 588 | + | * | ##### |
| 477 | 589 | + | * | ##### |
| 483 | 590 | + | | |
| 491 | 591 | + | * | ##### |
| 458 | 723 | + | | |
| 436 | 724 | + | | |
| 459 | 725 | + | | |
| 435 | 726 | + | | |
| 523 | 727 | + | | |
| 513 | 728 | + | | |
| 530 | 592 | + | | |
| 512 | 593 | + | | |
| 481 | 594 | + | * | ##### |
| 507 | 705 | + | | |
| 461 | 595 | + | * | #### |
| 479 | 596 | + | * | ##### |
| 490 | 597 | + | * | ##### |
| 514 | 598 | + | | |
| 421 | 378 | + | * | ### |
| 498 | 380 | + | * | ##### |
| 496 | 377 | + | * | ##### |
| 532 | 368 | + | | |
| 505 | 381 | + | * | #### |
| 427 | 376 | + | * | ##### |
| 449 | 383 | + | * | ##### |
| 497 | 379 | + | * | #### |
| 418 | 370 | + | * | #### |
| 489 | 698 | + | * | #### |
| 534 | 356 | + | | |
| 390 | 599 | + | * | #### |
| 485 | 600 | + | * | ##### |
| 493 | 601 | + | | |
| 448 | 602 | + | * | ##### |
| 734 | 731 | + | | |
| 397 | 603 | + | * | ##### |
| 736 | 730 | + | | |

TABLE AA-continued

| Compound No. | Example No. | Biochemical ATPase ADPGlo $IC_{50}$ (uM) | Viability $IC_{50}$ (uM) DLD1 BRCA2 null | Viability $IC_{50}$ (uM) DLD1 WT |
|---|---|---|---|---|
| 395 | 386 | + | * | ##### |
| 456 | 371 | + | * | ##### |
| 379 | 109A | + | * | ##### |
| 526 | 409 | + | | |
| 525 | 365 | + | | |
| 450 | 400 | + | * | ##### |
| 520 | 412 | + | | |
| 437 | 414 | + | * | ##### |
| 464 | 408 | + | * | ### |
| 543 | 357 | ++ | | |
| 528 | 403 | + | | |
| 417 | 407 | + | * | ##### |
| 389 | 387 | + | * | ##### |
| 416 | 410 | + | * | ##### |
| 510 | 402 | + | | |
| 475 | 391 | + | * | ##### |
| 522 | 413 | + | | |
| 411 | 388 | + | * | ##### |
| 431 | 384 | + | * | ##### |
| 756 | 604 | + | | |
| 547 | 746 | ++++ | | |
| 462 | 606 | + | | |
| 406 | 569 | + | * | ##### |
| 424 | 607 | + | * | ##### |
| 761 | 605 | + | | |
| 392 | 390 | | ** | ##### |
| 404 | 411 | | ** | ##### |
| 388 | 428 | | * | ### |
| 387 | 426 | | * | ##### |
| 537 | 373 | | ***** | ##### |
| 396 | 431 | | * | ##### |
| 386 | 424 | | * | ##### |
| 536 | 389 | | * | ##### |
| 413 | 425 | | * | ##### |
| 518 | 382 | | * | #### |
| 410 | 430 | | * | ##### |
| 407 | 427 | | * | ##### |
| 484 | 608 | + | | |
| 414 | 609 | + | | |
| 451 | 610 | + | | |
| 455 | 611 | + | | |
| 444 | 436 | + | ** | ##### |
| 480 | 441 | + | * | ##### |
| 467 | 437 | + | * | ##### |
| 465 | 374 | + | * | ##### |
| 438 | 435 | + | * | ##### |
| 422 | 439 | + | * | ##### |
| 470 | 438 | + | * | #### |
| 385 | 429 | + | * | #### |
| 516 | 440 | + | | |
| 503 | 434 | + | * | ##### |
| 529 | 747 | + | | |
| 469 | 612 | + | * | ##### |
| 508 | 742 | + | * | ##### |
| 482 | 613 | + | | |
| 499 | 614 | + | * | ##### |
| 432 | 615 | + | * | ##### |
| 440 | 413 | + | * | ##### |
| 539 | 445 | ++ | | |
| 527 | 354 | + | | |
| 538 | 444 | ++ | | |
| 541 | 401 | ++ | | |
| 445 | 385 | + | * | ##### |
| 446 | 446 | + | * | ### |
| 425 | 372 | + | * | ##### |
| 504 | 616 | + | * | ##### |
| 457 | 617 | + | | |
| 472 | 618 | + | * | ### |
| 400 | 619 | + | * | ##### |
| 544 | 620 | ++ | | |
| 545 | 621 | ++ | | |
| 517 | 416 | + | * | ##### |
| 487 | 443 | + | * | ##### |
| 398 | 472 | + | * | ##### |
| 419 | 432 | + | * | ##### |

TABLE AA-continued

| Compound No. | Example No. | Biochemical ATPase ADPGlo $IC_{50}$ (uM) | Viability $IC_{50}$ (uM) DLD1 BRCA2 null | Viability $IC_{50}$ (uM) DLD1 WT |
|---|---|---|---|---|
| 403 | 466 | + | * | #### |
| 402 | 571 | + | * | ##### |
| 428 | 464 | + | * | ##### |
| 511 | 405 | + | | |
| 463 | 478 | + | * | ##### |
| 519 | 442 | + | * | ##### |
| 423 | 622 | + | | |
| 405 | 623 | + | ** | ##### |
| 384 | 624 | + | * | ##### |
| 501 | 625 | + | | |
| 415 | 626 | + | * | ##### |
| 502 | 627 | + | | |
| 454 | 628 | + | | |
| 521 | 629 | + | | |
| 383 | 470 | + | * | #### |
| 441 | 482 | + | | |
| 382 | 467 | + | * | ##### |
| 540 | 733 | ++ | | |
| 494 | 487 | + | | |
| 381 | 468 | + | | |
| 531 | 456 | + | | |
| 433 | 484 | + | | |
| 380 | 475 | + | | |
| 468 | 452 | + | * | |
| 598 | 630 | | * | ##### |
| 597 | 631 | | * | ##### |
| 596 | 632 | | * | ##### |
| 595 | 633 | + | | |
| 840 | 634 | | * | ##### |
| 841 | 635 | | * | ##### |
| 842 | 636 | | * | ##### |
| 843 | 469 | | * | ##### |
| 846 | 417 | | * | ##### |
| 848 | 450 | | * | #### |
| 849 | 453 | | * | ##### |
| 850 | 447 | | * | ##### |
| 851 | 498 | | * | ##### |
| 852 | 415 | | ** | ##### |
| 853 | 476 | | * | ##### |
| 856 | 492 | | * | #### |
| 859 | 461 | | * | ##### |
| 863 | 448 | | * | ##### |
| 865 | 455 | | * | ##### |
| 866 | 521 | | * | ##### |
| 872 | 520 | | * | ##### |
| 873 | 519 | | * | ##### |
| 874 | 516 | | * | ##### |
| 875 | 460 | | * | ##### |
| 879 | 505 | | * | ##### |
| 880 | 637 | | * | ##### |
| 881 | 638 | | * | ##### |
| 882 | 639 | | * | #### |
| 886 | 643 | | * | ##### |
| 887 | 496 | | * | ##### |
| 888 | 499 | | **** | ##### |
| 889 | 462 | | * | #### |
| 890 | 457 | | *** | ##### |
| 892 | 451 | | * | ##### |
| 893 | 506 | | * | ##### |
| 894 | 513 | | ** | ##### |
| 895 | 499 | | *** | ##### |
| 896 | 449 | | * | ##### |
| 897 | 497 | | * | ##### |
| 898 | 644 | | *** | ##### |
| 902 | 701 | | * | ##### |
| 903 | 463 | | * | ##### |
| 904 | 502 | | * | ##### |
| 905 | 420 | | * | ##### |
| 907 | 647 | | * | ##### |
| 908 | 745 | | * | ##### |
| 909 | 744 | | * | ##### |
| 910 | 648 | | * | ##### |
| 911 | 649 | | * | ##### |
| 912 | 531 | | ** | ##### |
| 914 | 458 | | * | ##### |

TABLE AA-continued

| Compound No. | Example No. | Biochemical ATPase ADPGlo $IC_{50}$ (uM) | Viability $IC_{50}$ (uM) DLD1 BRCA2 null | Viability $IC_{50}$ (uM) DLD1 WT |
|---|---|---|---|---|
| 915 | 508 | | * | ##### |
| 917 | 526 | | * | ##### |
| 918 | 532 | | * | ##### |
| 920 | 527 | | ** | ##### |
| 922 | 650 | | * | ##### |
| 923 | 651 | | * | ##### |
| 925 | 653 | | * | #### |
| 926 | 466 | | * | ##### |
| 927 | 518 | | * | ##### |
| 928 | 509 | | * | ##### |
| 929 | 524 | | * | ##### |
| 930 | 654 | | * | ##### |
| 932 | 656 | | * | ##### |
| 933 | 657 | | * | ##### |
| 935 | 517 | | * | ##### |
| 936 | 542 | | * | ##### |
| 937 | 543 | | * | ##### |
| 938 | 735 | | * | ##### |
| 939 | 507 | | * | ##### |
| 940 | 511 | | * | ##### |
| 945 | 663 | | * | ##### |
| 947 | 665 | | * | ##### |
| 949 | 541 | | * | ##### |
| 950 | 504 | | * | ##### |
| 951 | 537 | | * | ##### |
| 952 | 544 | | * | ##### |
| 953 | 510 | | * | ##### |
| 954 | 535 | | * | ## |
| 956 | 667 | | * | ##### |
| 957 | 668 | | * | ##### |
| 959 | 553 | | * | ##### |
| 961 | 538 | | * | ##### |
| 962 | 670 | | * | #### |
| 964 | 702 | | * | ##### |
| 965 | 545 | | * | ##### |
| 966 | 539 | | * | ##### |
| 968 | 536 | | * | ##### |
| 969 | 671 | | * | ##### |
| 970 | 672 | | * | ##### |
| 971 | 533 | | * | ##### |
| 972 | 418 | | * | ##### |
| 973 | 547 | | * | ##### |
| 974 | 546 | | * | ##### |
| 975 | 703 | | * | ##### |
| 976 | 540 | | * | ##### |
| 977 | 512 | | * | #### |
| 980 | 529 | | * | ##### |
| 981 | 740 | | * | ##### |
| 985 | 558 | | * | ##### |
| 986 | 749 | | * | ##### |
| 987 | 562 | | * | ##### |
| 988 | 706 | | * | ##### |
| 989 | 563 | | * | ##### |
| 990 | 557 | | * | ##### |
| 991 | 525 | | * | ##### |
| 992 | 530 | | * | ##### |
| 994 | 674 | | * | ##### |
| 995 | 555 | | * | ##### |
| 996 | 738 | | * | ##### |
| 997 | 556 | | * | ##### |
| 999 | 675 | | * | ##### |
| 1001 | 522 | | * | ##### |
| 1002 | 528 | | * | ##### |
| 1003 | 566 | | * | ##### |
| 1004 | 568 | | * | ##### |
| 1005 | 564 | | * | ##### |
| 1006 | 548 | | * | ##### |
| 1007 | 560 | | * | ##### |
| 1008 | 554 | | * | ##### |
| 1009 | 561 | | * | ##### |
| 1010 | 722 | | * | ##### |
| 1011 | 676 | | * | ##### |
| 1012 | 677 | | * | ##### |
| 1013 | 565 | | * | ##### |
| 1014 | 743 | | * | ##### |

TABLE AA-continued

| Compound No. | Example No. | Biochemical ATPase ADPGlo $IC_{50}$ (uM) | Viability $IC_{50}$ (uM) DLD1 BRCA2 null | Viability $IC_{50}$ (uM) DLD1 WT |
|---|---|---|---|---|
| 1015 | 551 | | * | ##### |
| 1016 | 699 | | * | ##### |
| 1017 | 534 | | * | ##### |
| 1018 | 559 | | * | ##### |
| 1019 | 704 | | * | ##### |
| 1020 | 523 | | * | ##### |
| 1022 | 682 | | * | ##### |
| 1023 | 683 | | * | ##### |
| 1024 | 678 | | * | ##### |
| 1025 | 679 | | * | ##### |
| 1026 | 680 | | * | ##### |
| 1027 | 684 | | * | ##### |
| 1028 | 685 | | * | ##### |
| 1029 | 686 | | * | ##### |
| 1030 | 687 | | * | ##### |
| 1032 | 689 | | * | ##### |
| 1033 | 750 | | * | ##### |
| 1034 | 690 | | * | ##### |
| 1035 | 691 | | * | ##### |
| 1036 | 692 | + | * | ##### |
| 1037 | 752A | ++ | | |
| 1038 | 694 | | ** | ##### |
| 1039 | 693 | | * | ##### |
| 1040 | 751 | + | * | ##### |
| 1041 | 752B | + | * | ##### |
| 1042 | 695 | + | * | ##### |
| 1043 | 697 | +++++ | | |
| 1044 | 696 | | * | ##### |
| 1045 | 567 | +++++ | | |
| 1046 | 753B | + | * | ##### |
| 1047 | 753A | ++++ | | |
| 1048 | 700 | | * | ##### |

/\ indicates an $IC_{50}$ wherein the highest concentration run was 1 μM

EQUIVALENTS

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

The foregoing description has been presented only for the purposes of illustration and is not intended to limit the disclosure to the precise form disclosed, but by the claims appended hereto.

The invention claimed is:

1. A compound of Formula (I-F):

(I-F)

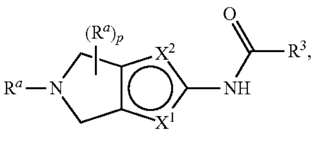

or a pharmaceutically acceptable salt, solvate, hydrate, stereoisomer, or tautomer thereof, wherein:

$X^1$ is N and $X^2$ is S, or $X^1$ is S and $X^2$ is N;

each $R^a$ independently is oxo, halo, cyano, —$OR^{a1}$, —$N(R^{a1})_2$, —$C(O)R^{a1}$, —$C(O)N(R^{a1})_2$, —$C(O)OR^{a1}$, —$S(O)_2N(R^{a1})_2$, —$S(O)_2(R^{a1})$, $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, $C_6$-$C_{10}$ aryl, 5- to 10-membered heteroaryl, or 3- to 10-membered heterocycloalkyl, wherein the $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, $C_6$-$C_{10}$ aryl, 5- to 10-membered heteroaryl, or 3- to 10-membered heterocycloalkyl is optionally substituted with one or more $R^{a1}$;

p is 0 to 4;

each $R^{a1}$ independently is H, oxo, halo, cyano, —OH, —$NH_2$, —$C(O)(C_1$-$C_6$ alkyl), —$C(O)(C_3$-$C_{10}$ cycloalkyl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_{10}$ cycloalkyl, 3- to 10-membered heterocycloalkyl, $C_6$-$C_{10}$ aryl, or 5- to 10-membered heteroaryl, wherein the —$C(O)(C_3$-$C_{10}$ cycloalkyl), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_3$-$C_{10}$ cycloalkyl, 3- to 10-membered heterocycloalkyl, $C_6$-$C_{10}$ aryl, or 5- to 10-membered heteroaryl is optionally substituted with one or more $R^{a2}$;

each $R^{a2}$ independently is oxo, halo, cyano, —OH, —$NH_2$, —$NH(C_1$-$C_6$ alkyl), —$N(C_1$-$C_6$ alkyl$)_2$, $C_1$-$C_6$ alkyl optionally substituted with $C_1$-$C_6$ alkoxy or —OH, $C_3$-$C_{10}$ cycloalkyl, $C_1$-$C_6$ haloalkoxy, $C_1$-$C_6$ haloalkyl, $C_1$-$C_6$ alkoxy, 3- to 10-membered heterocycloalkyl optionally substituted with oxo, or 5- to 10-membered heteroaryl;

$R^3$ is $C_6$-$C_{10}$ aryl or 5- to 10-membered heteroaryl, wherein the $C_6$-$C_{10}$ aryl or 5- to 10-membered heteroaryl is substituted with one or more $R^{3a}$;

each $R^{3a}$ independently is halo, cyano, —OH, —$NH_2$, $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, 3- to 10-membered heterocycloalkyl, $C_6$-$C_{10}$ aryl, or 5- to 10-membered heteroaryl, wherein the $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, 3- to 10-membered heterocycloalkyl, $C_6$-$C_{10}$ aryl, or 5- to 10-membered heteroaryl is optionally substituted with one or more $R^{3a1}$; and each $R^{3a1}$ independently is oxo, halo, cyano, —OH, —$C(O)(C_1$-$C_6$ alkyl), —$C(O)(O$—$(C_1$-$C_6$ alkyl)), $C_1$-$C_6$ alkyl optionally substituted with $C_3$-$C_{10}$ cycloalkyl, $C_2$-$C_6$ alkenyl, $C_2$-$C_6$ alkynyl, $C_1$-$C_6$ haloalkyl, $C_1$-$C_6$ haloalkoxy, $C_1$-$C_6$ alkoxy, —$O(C_1$-$C_6$ haloalkyl), $C_3$-$C_{10}$ cycloalkyl, $C_6$-$C_{10}$ aryl, or 5- to 10-membered heteroaryl.

2. The compound of claim 1, wherein $R^3$ is 5- to 6-membered heteroaryl substituted with one or more $R^{3a}$.

3. The compound of claim 1, wherein each $R^{3a}$ independently is $C_1$-$C_6$ alkyl or 5- to 10-membered heteroaryl, wherein the $C_1$-$C_6$ alkyl or 5- to 10-membered heteroaryl is optionally substituted with one or more $R^{3a1}$.

4. The compound of claim 1, wherein each $R^{3a1}$ independently is halo or $C_1$-$C_6$ alkoxy.

5. The compound of claim 1, wherein $R^3$ is

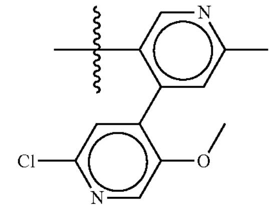

or

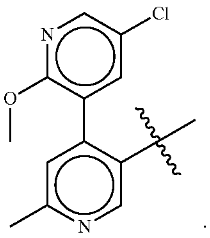

.

6. The compound of claim 1, wherein each $R^a$ independently is —C(O)$R^{a1}$.

7. The compound of claim 1, wherein each $R^{a1}$ is 5- to 6-membered heteroaryl substituted with one or more $R^{a2}$.

8. The compound of claim 1, wherein each $R^{a2}$ independently is $C_1$-$C_6$ haloalkyl or $C_1$-$C_6$ alkoxy.

9. The compound of claim 1, wherein p is 0.

10. The compound of claim 1, wherein the compound is of Formula (I-Fa), (I-Fb), (I-Fb'), (I-Fc), or (I-Fc'):

(I-Fa)

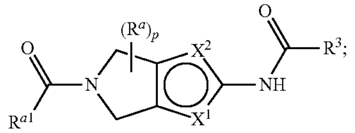

(I-Fb)

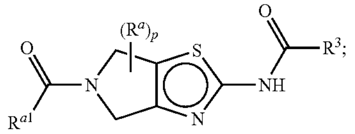

(I-Fb')

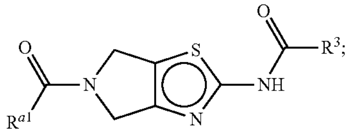

(I-Fc)

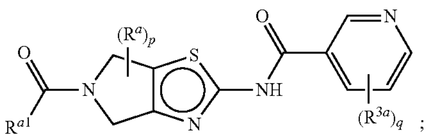

or (I-Fc')

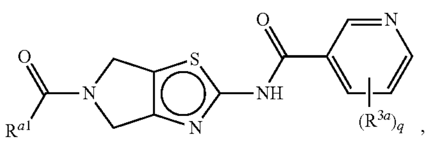

or a pharmaceutically acceptable salt, solvate, hydrate, stereoisomer, or tautomer thereof.

11. The compound of claim 1, wherein the compound is selected from:

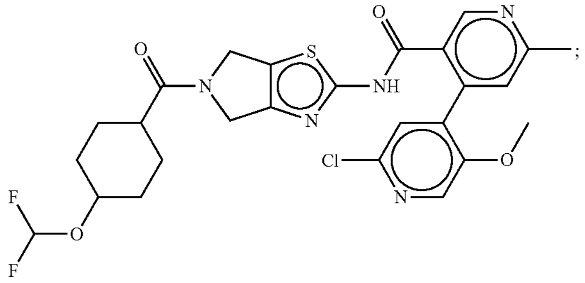

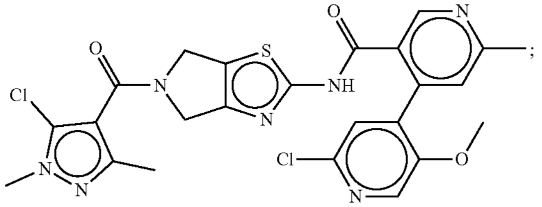

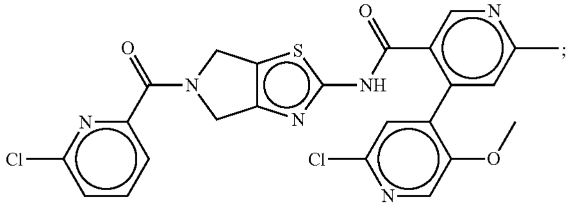

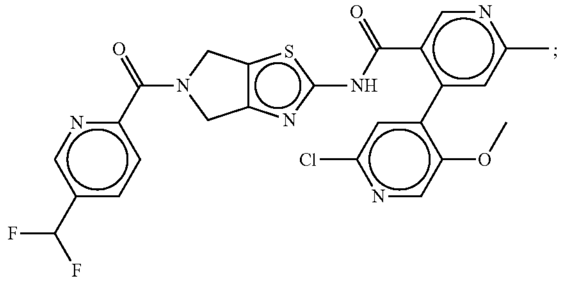

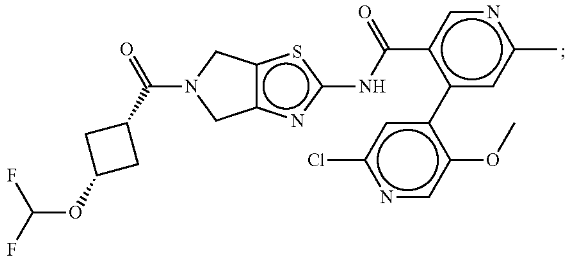

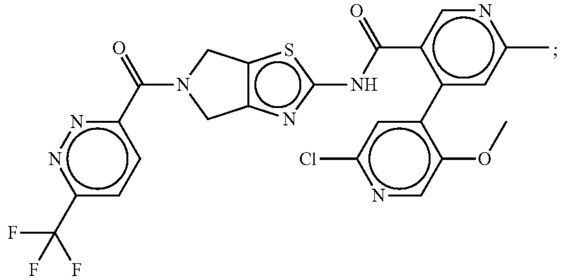

-continued
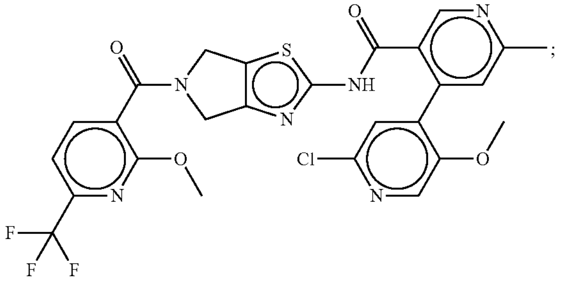
;
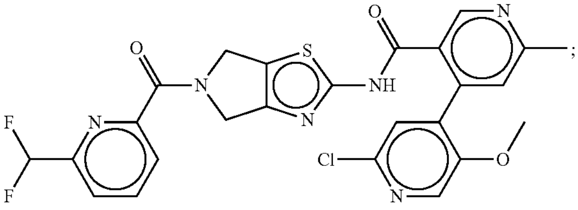
;
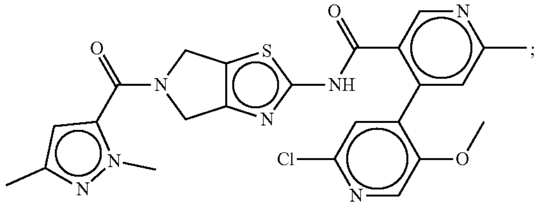
;
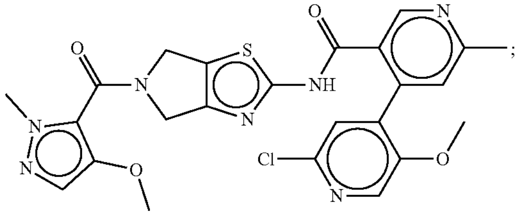
;
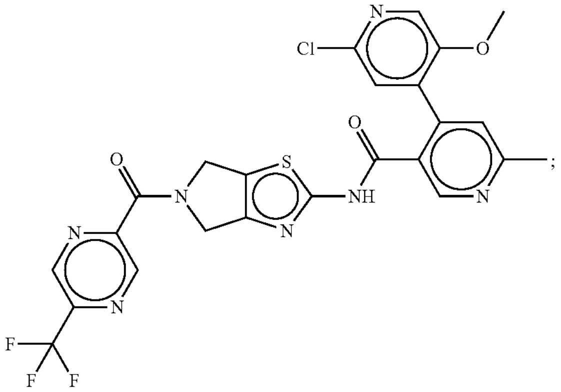
;
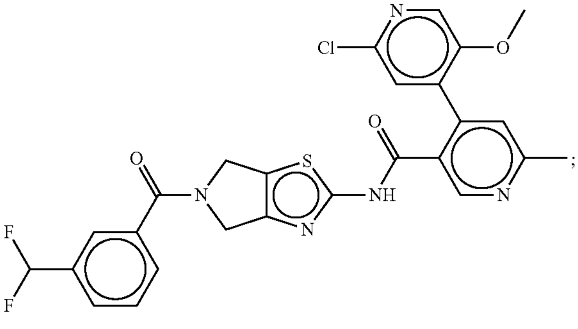
;
-continued
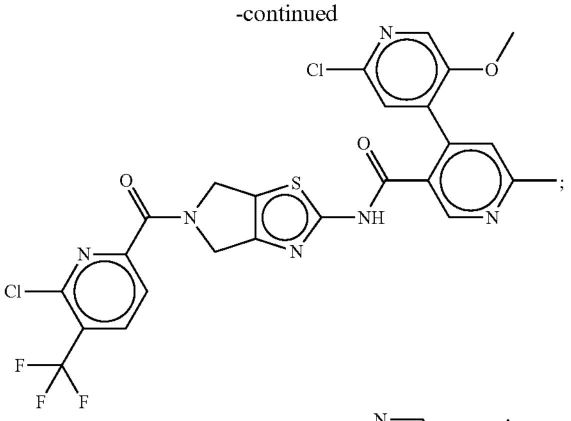
;
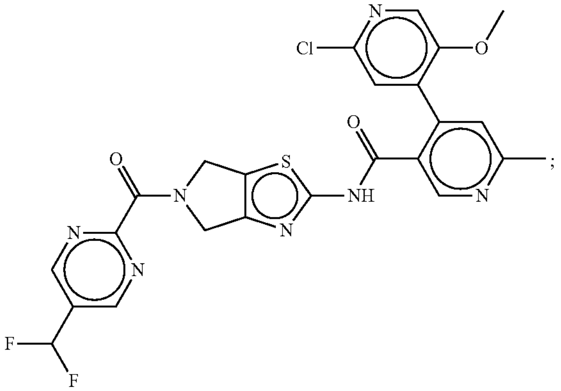
;
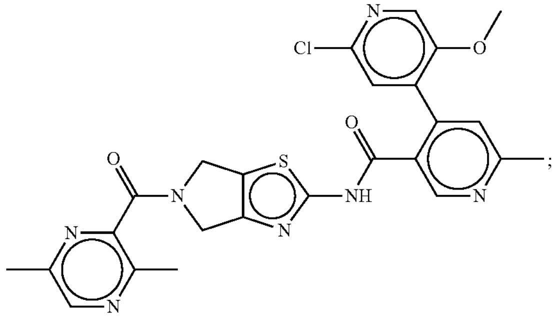
;
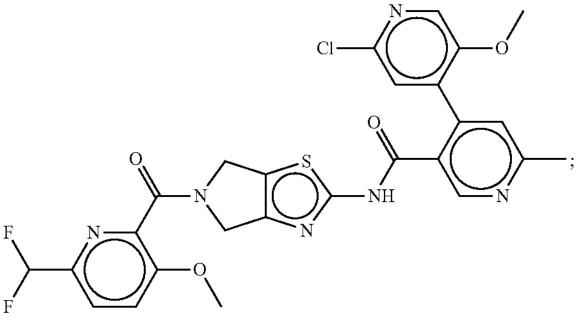
;
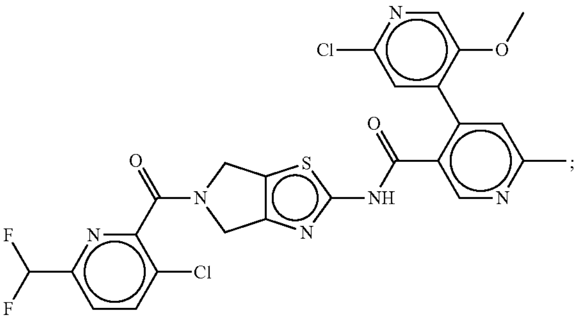
;

-continued
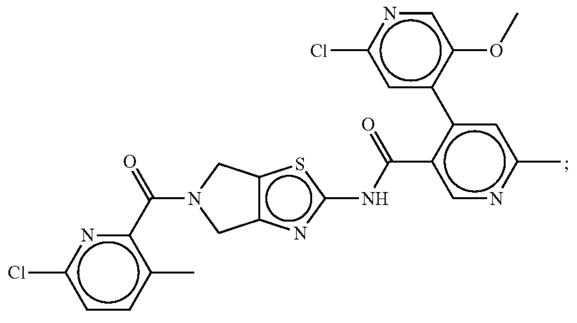
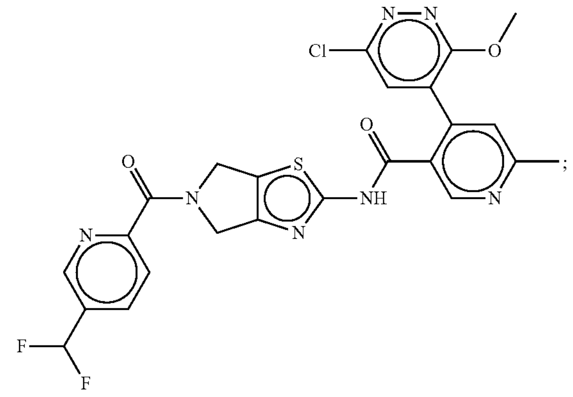
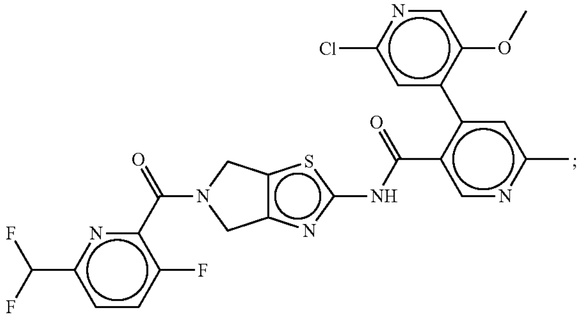
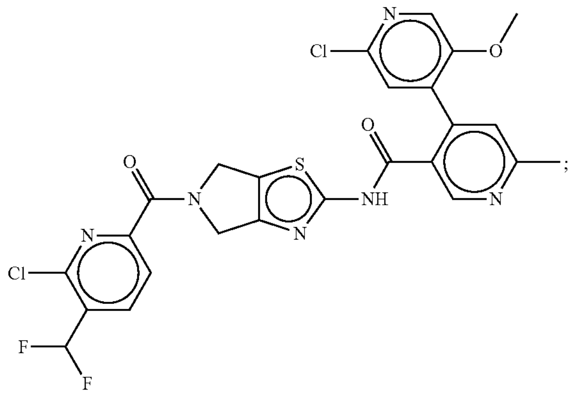
-continued
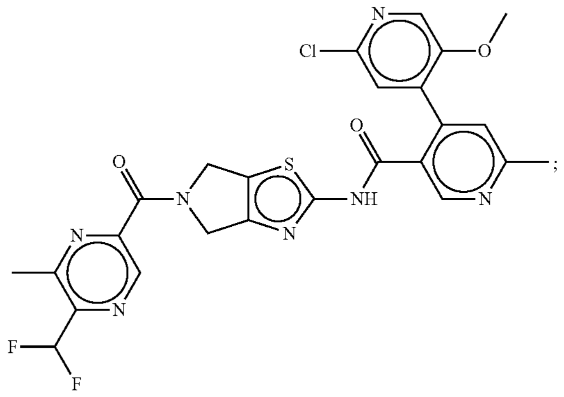
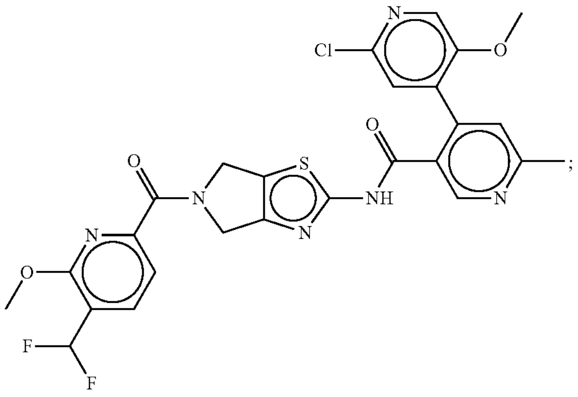
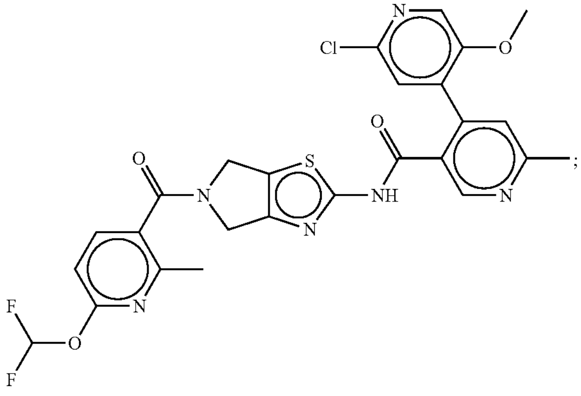
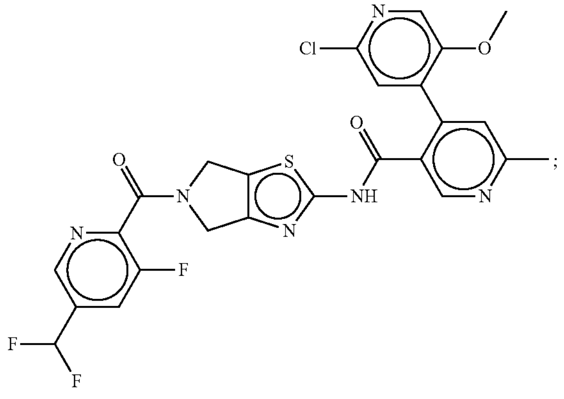

-continued
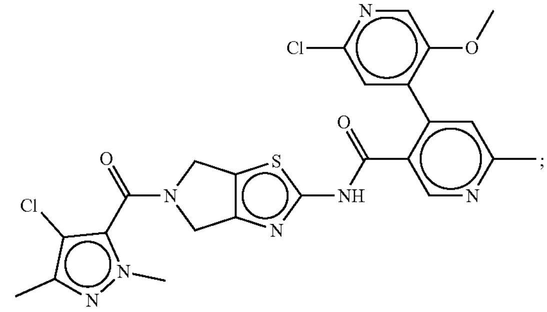
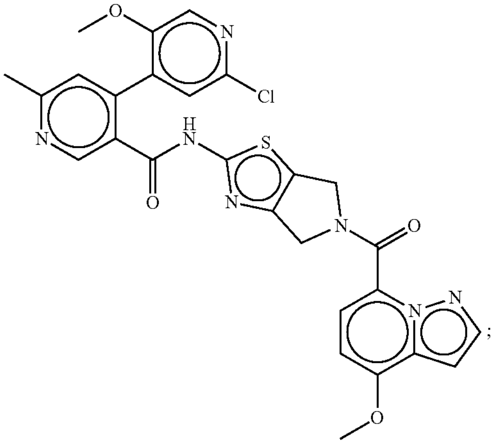
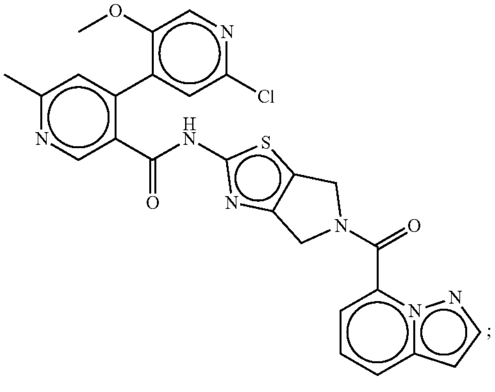
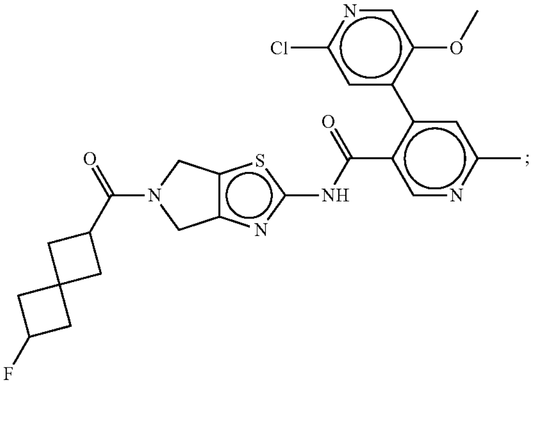
-continued
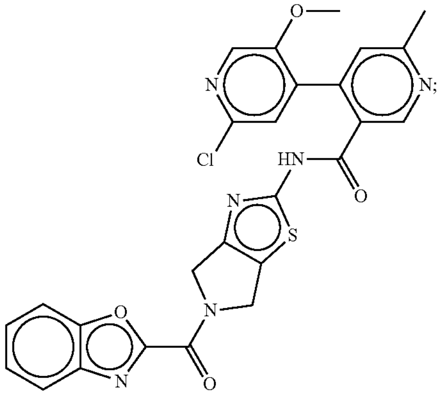
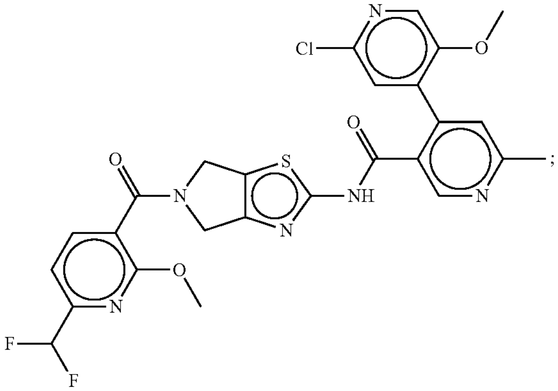
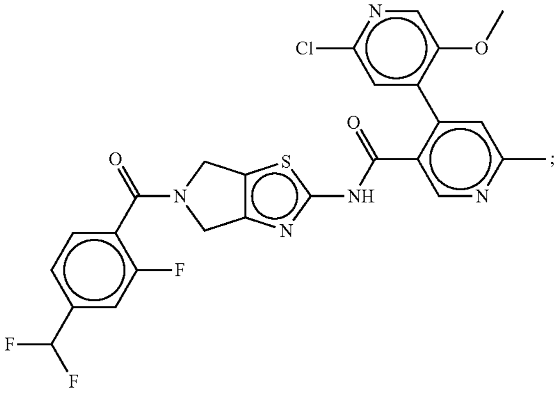
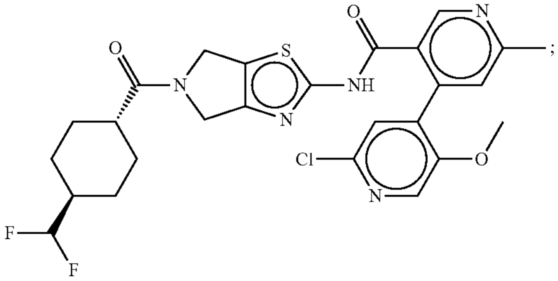
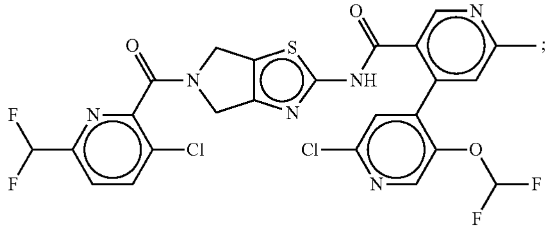

-continued
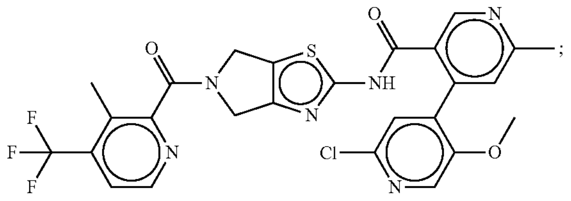
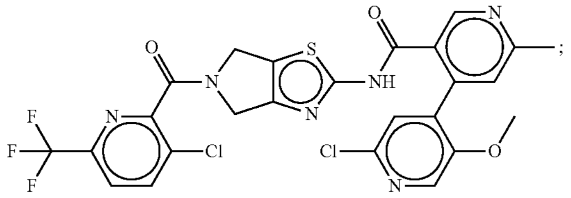
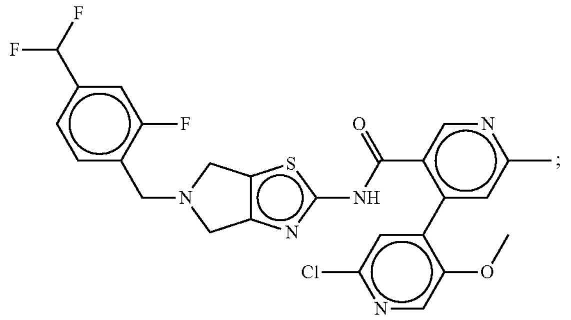
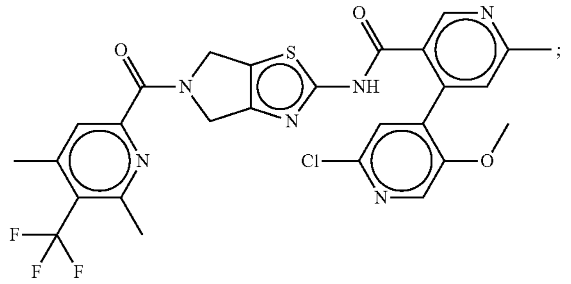
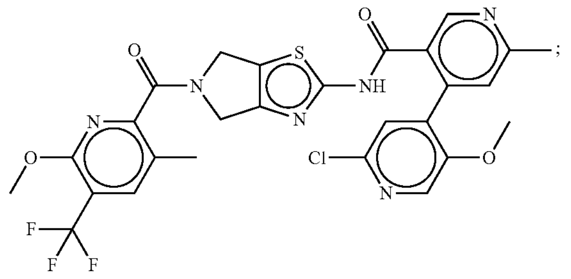
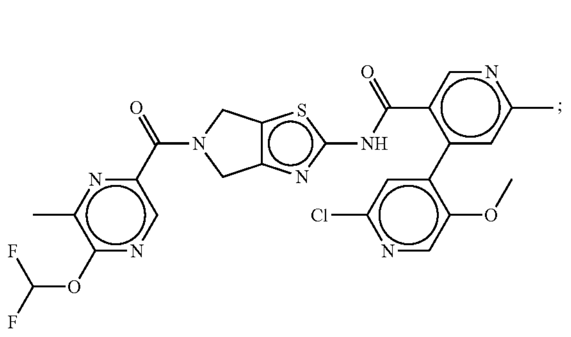
-continued
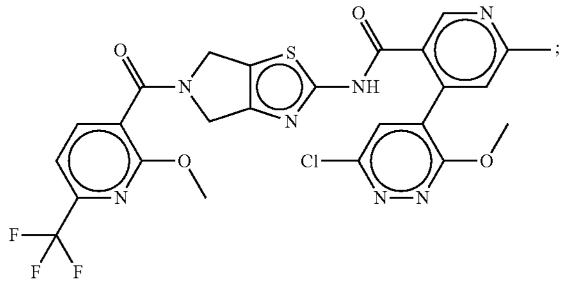
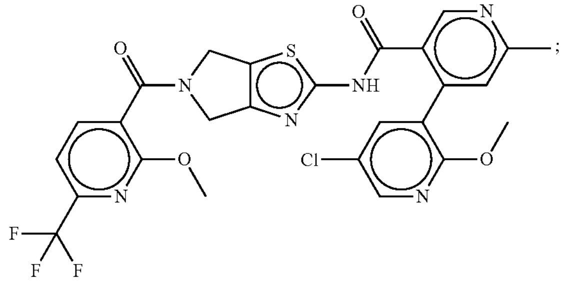
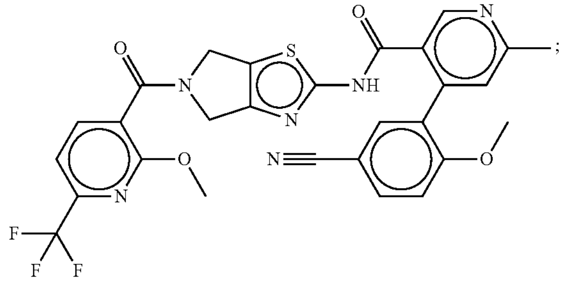
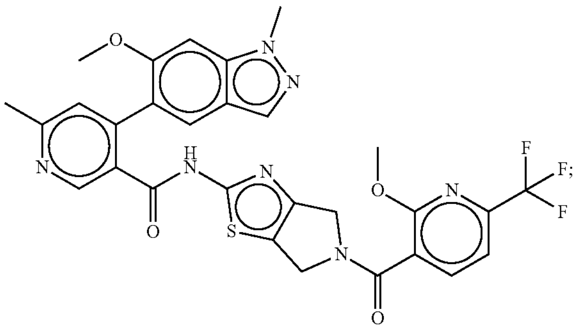
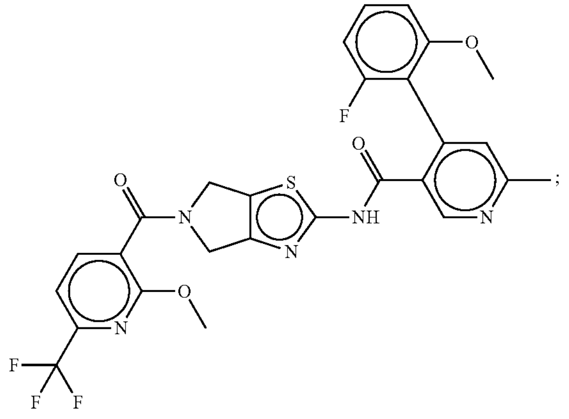

-continued
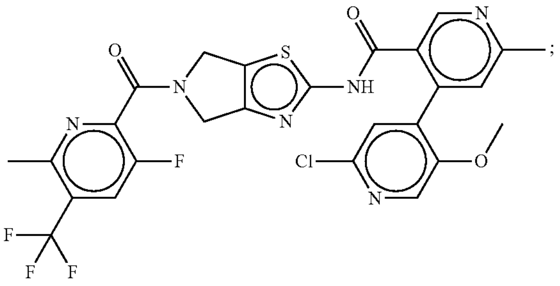
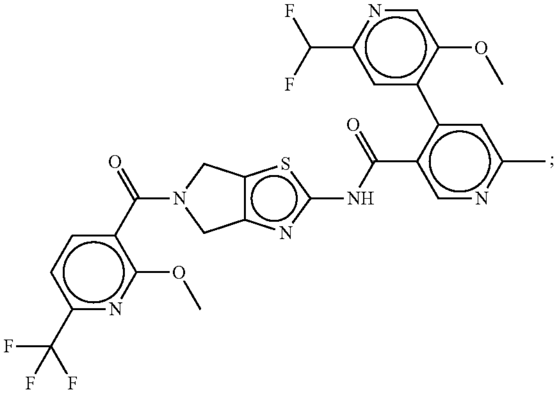
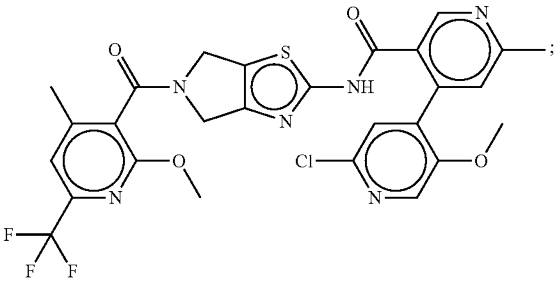
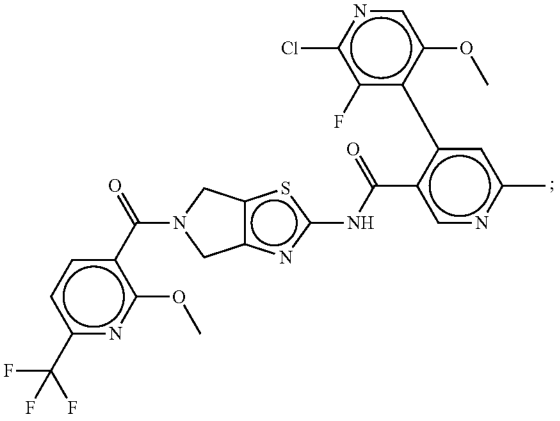
-continued
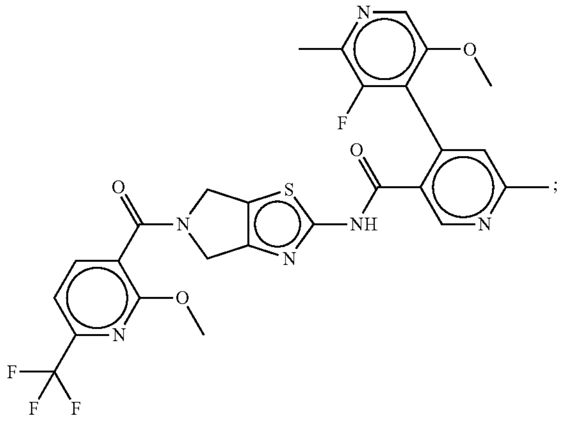
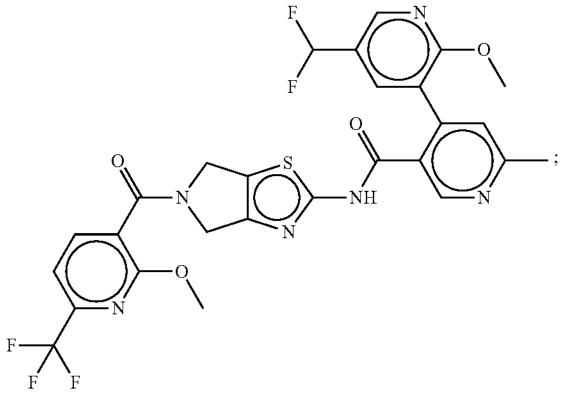
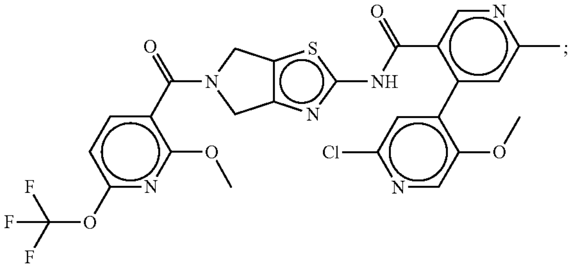
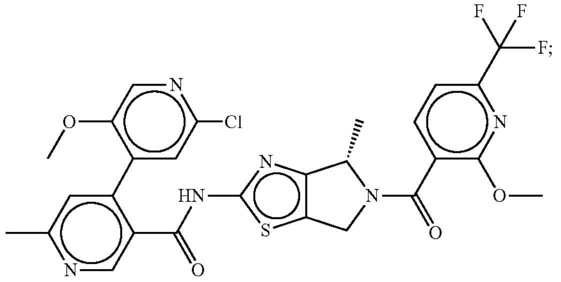
and -continued
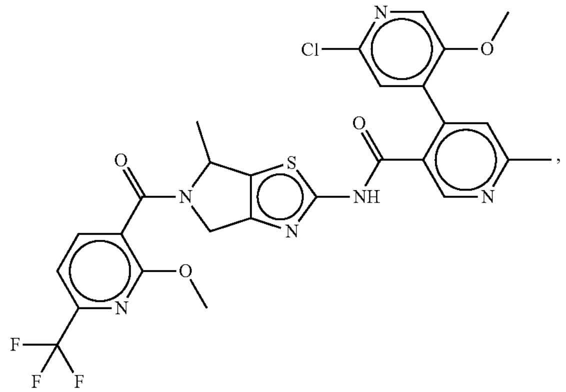
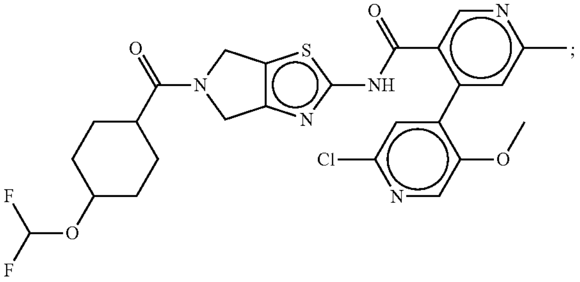
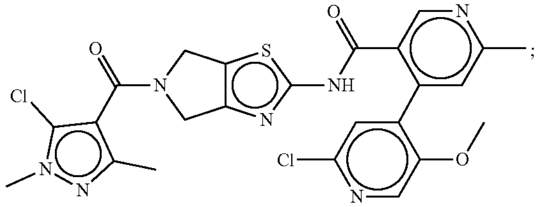
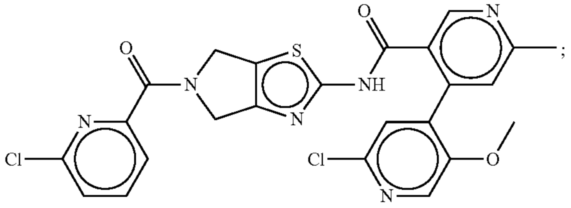
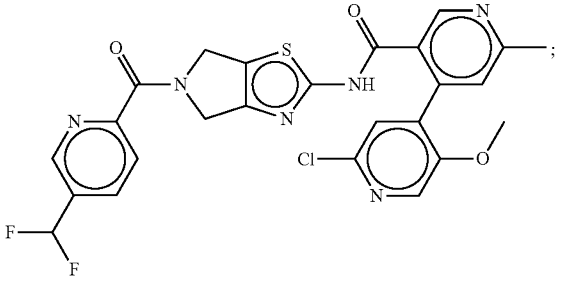
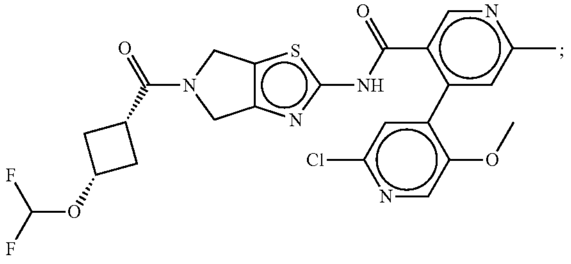
-continued
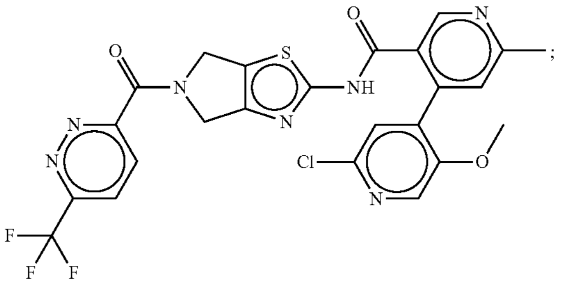
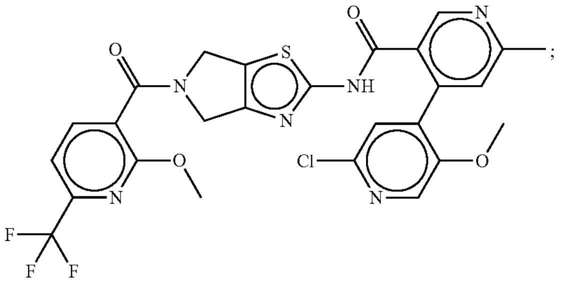
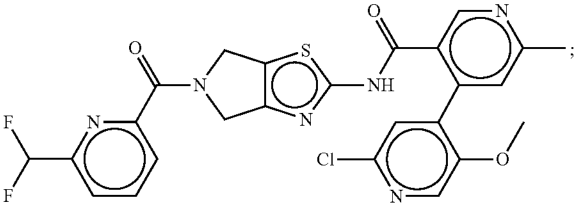
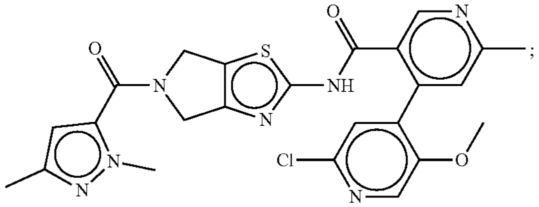
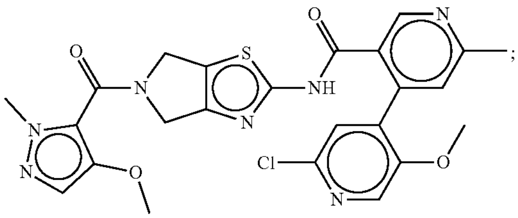
or a pharmaceutically acceptable salt thereof.
12. The compound of claim 1, wherein the compound is selected from:
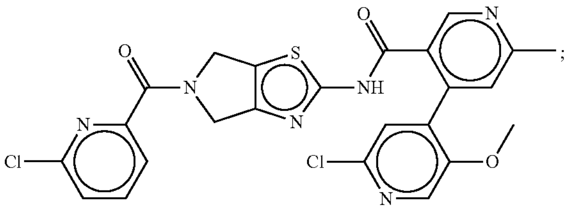

-continued
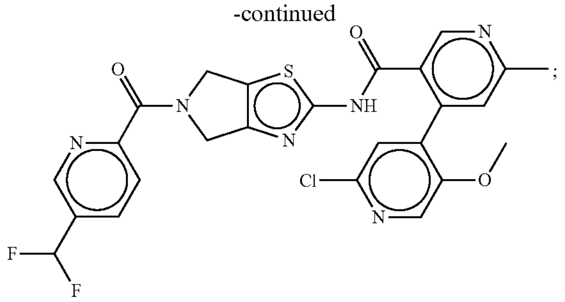
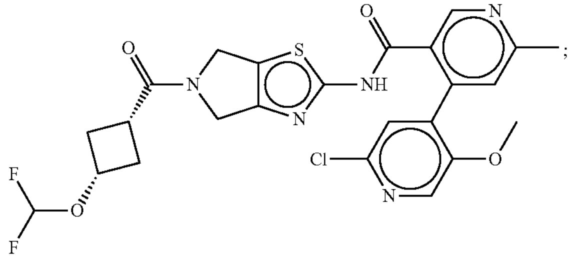
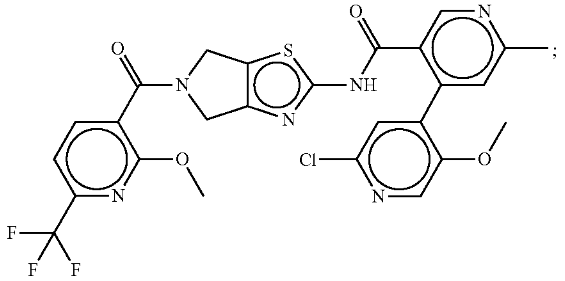
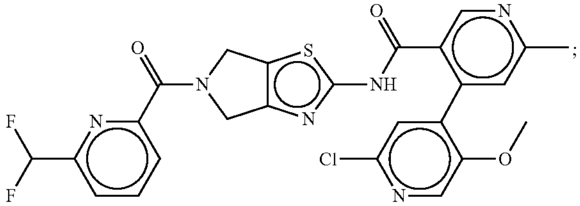
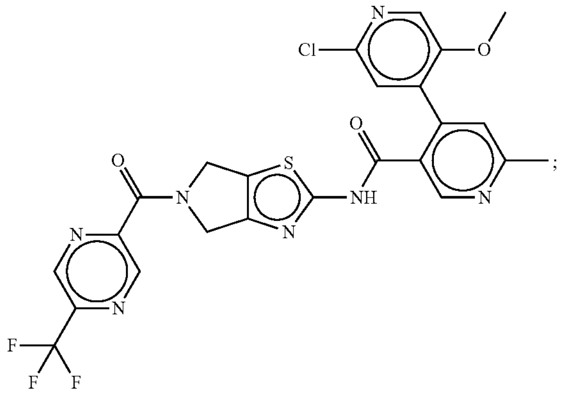
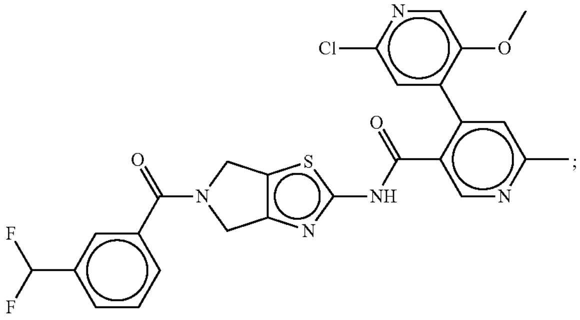
-continued
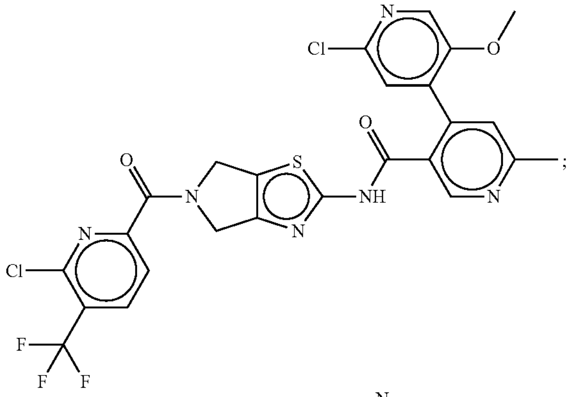
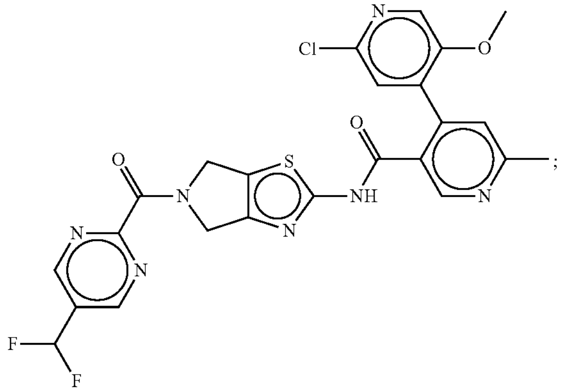
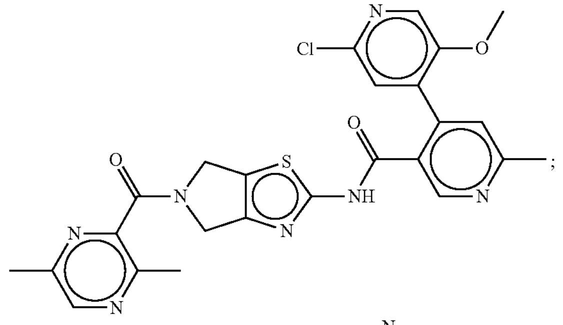
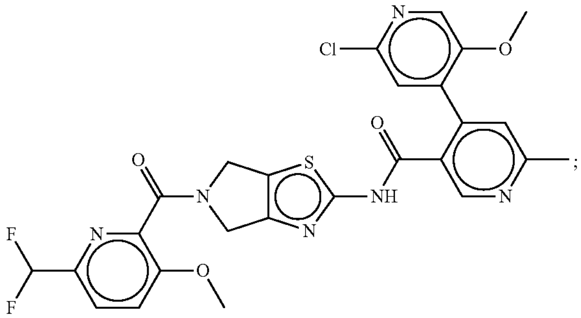
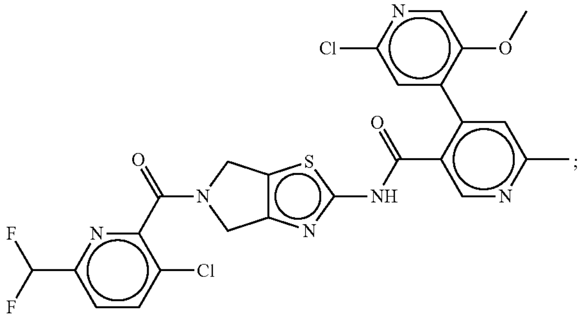

-continued
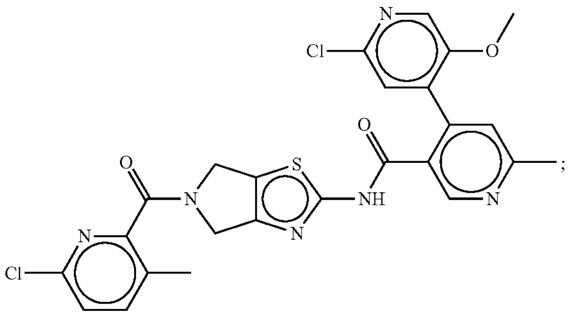
;
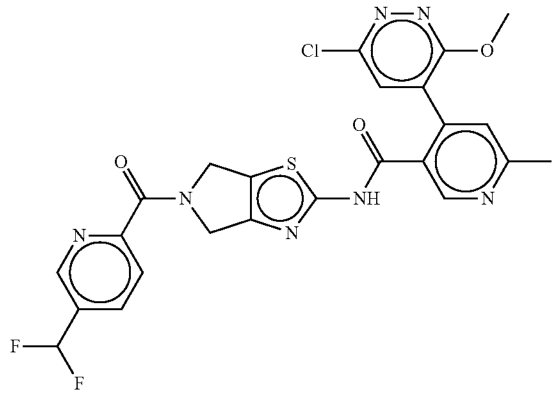
;
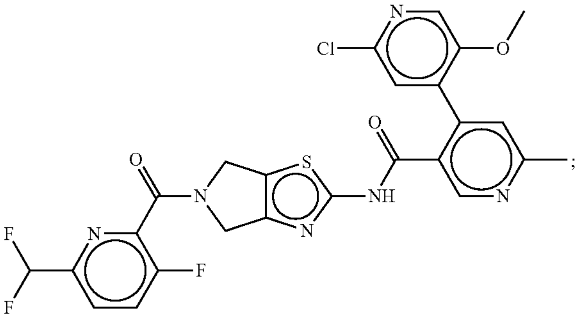
;
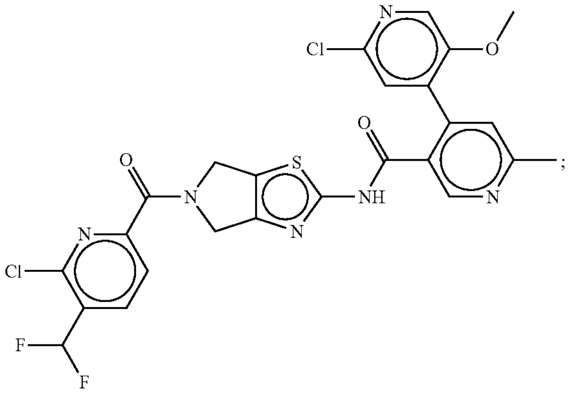
;
-continued
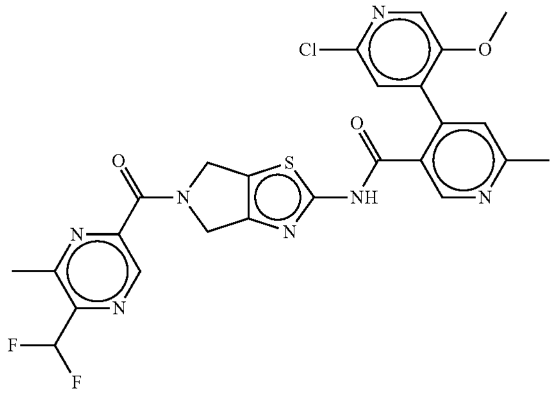
;
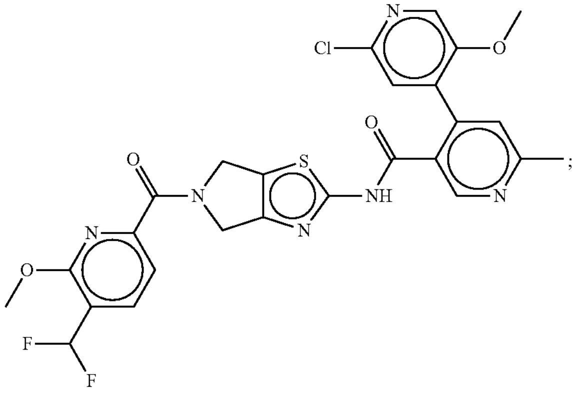
;
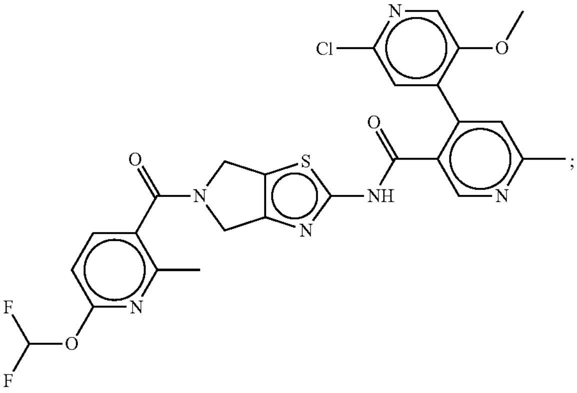
;
and
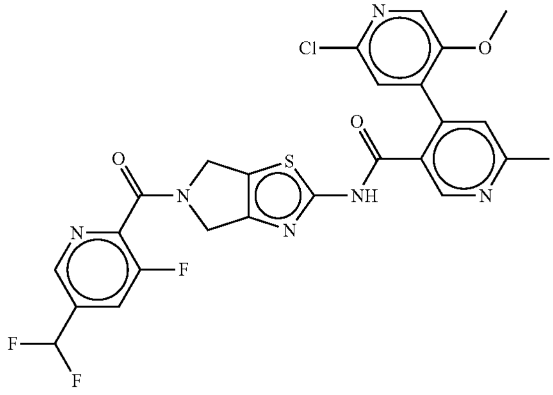
, -continued

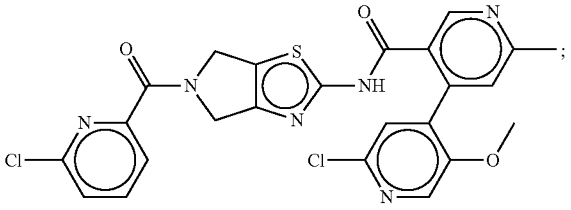

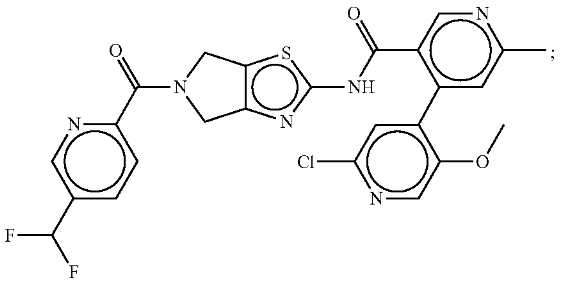

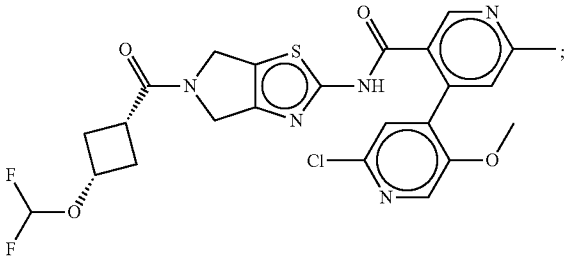

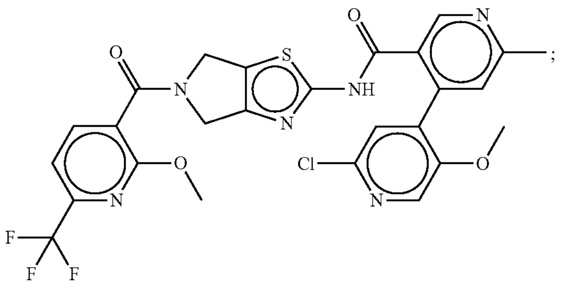

-continued

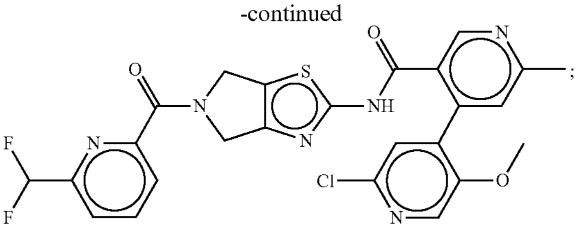

or a pharmaceutically acceptable salt thereof.

13. A pharmaceutical composition comprising the compound of claim 1, or a pharmaceutically acceptable salt thereof, and one or more of a diluent, a carrier, an excipient, an adjuvant, and a binder.

14. A pharmaceutical composition comprising the compound of claim 11, or a pharmaceutically acceptable salt thereof, and one or more of a diluent, a carrier, an excipient, an adjuvant, and a binder.

15. A pharmaceutical composition comprising the compound of claim 12, or a pharmaceutically acceptable salt thereof, and one or more of a diluent, a carrier, an excipient, an adjuvant, and a binder.

16. The compound of claim 1, wherein each $R^{a1}$ independently is 5- to 6-membered heteroaryl optionally substituted with one or more $R^{a2}$.

17. The compound of claim 1, wherein each $R^{a2}$ independently is $—OCH_3$ or $—CF_3$.

18. The compound of claim 1, wherein each $R^a$ independently is

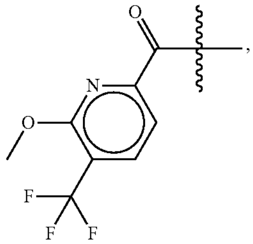,

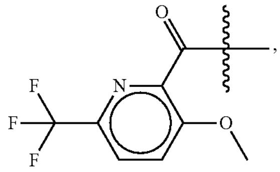, or

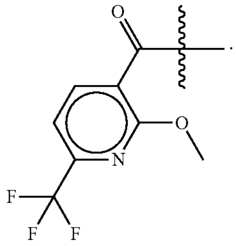.

19. The compound of claim 1, wherein each $R^{3a}$ independently is methyl or 5- to 6-membered heteroaryl substituted with one or more $R^{3a1}$.

20. The compound of claim 1, wherein each $R^{3a1}$ independently is —Cl or $—OCH_3$.

* * * * *